(12) United States Patent
Haddach et al.

(10) Patent No.: US 8,575,177 B2
(45) Date of Patent: Nov. 5, 2013

(54) PYRAZOLOPYRIMIDINES AND RELATED HETEROCYCLES AS CK2 INHIBITORS

(75) Inventors: Mustapha Haddach, San Diego, CA (US); Joe A. Tran, San Marcos, CA (US); Fabrice Pierre, La Jolla, CA (US); Collin F. Regan, Encinitas, CA (US); Nicholas B. Raffaele, San Diego, CA (US); Suchitra Ravula, San Diego, CA (US); David M. Ryckman, San Diego, CA (US)

(73) Assignee: Senhwa Biosciences, Inc., New Taipei (TW)

( * ) Notice: Subject to any disclaimer, the term of this patent is extended or adjusted under 35 U.S.C. 154(b) by 67 days.

(21) Appl. No.: 12/946,759

(22) Filed: Nov. 15, 2010

(65) Prior Publication Data

US 2011/0152240 A1    Jun. 23, 2011

Related U.S. Application Data

(60) Provisional application No. 61/266,801, filed on Dec. 4, 2009, provisional application No. 61/354,165, filed on Jun. 11, 2010.

(51) Int. Cl.
*A01N 43/90* (2006.01)
*A61K 31/519* (2006.01)
*C07D 487/00* (2006.01)

(52) U.S. Cl.
USPC ........................................ 514/259.3; 544/281

(58) Field of Classification Search
None
See application file for complete search history.

(56) References Cited

U.S. PATENT DOCUMENTS 7,205,308 B2    4/2007  Guzi et al.
2006/0122176 A1  6/2006  Rueckle et al.

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Vippagunta et. al. Advanced Drug Delivery Reviews 48 (2001) 3-26.*
Niefind et al., Crystal Structure of Human Protein Kinase CK2: Insight into Basic Properties of the CK2 Holoenzyme. EMBO Journal 2001, 20:5320-5331.
International Search Report based on International Patent Application No. PCT/US2010/056712, mailed on Apr. 5, 2011.
Written Opinion of the International Searching Authority based on International Patent Application No. PCT/US2010/056712, mailed on Apr. 5, 2011.

* cited by examiner

*Primary Examiner* — Jeffrey Murray
(74) *Attorney, Agent, or Firm* — Cooley LLP

(57) ABSTRACT

The invention provides compounds that inhibit protein kinase CK2 activity (CK2 activity), and compositions containing such compounds. These compounds and compositions are useful for treating proliferative disorders such as cancer, as well as other kinase-associated conditions including inflammation, pain, and certain immunological disorders, and have the following general formula:

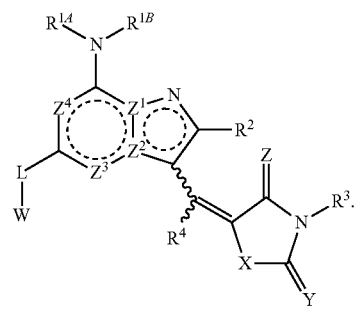

40 Claims, 12 Drawing Sheets

CK2, IC50 = 7 nM
PIM1, IC50 = 351 nM

SEQUENCE LISTING

```
<160> NUMBER OF SEQ ID NOS: 6

<210> SEQ ID NO 1
<211> LENGTH: 391
<212> TYPE: PRT
<213> ORGANISM: Homo sapiens

<400> SEQUENCE: 1

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270
```

```
Leu Gly Arg His Ser Arg Lys Arg Trp Glu Arg Phe Val His Ser Glu
            275                 280                 285

Asn Gln His Leu Val Ser Pro Glu Ala Leu Asp Phe Leu Asp Lys Leu
        290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Ala Asn Pro Leu Gly Met Pro Val Pro
    370                 375                 380

Ala Ala Ala Gly Ala Gln Gln
385                 390

<210> SEQ ID NO 2
<211> LENGTH: 391
<212> TYPE: PRT
<213> ORGANISM: Homo sapiens

<400> SEQUENCE: 2

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255
```

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
    290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Ala Asn Pro Leu Gly Met Pro Val Pro
    370                 375                 380

Ala Ala Ala Gly Ala Gln Gln
385                 390

<210> SEQ ID NO 3
<211> LENGTH: 255
<212> TYPE: PRT
<213> ORGANISM: Homo sapiens

<400> SEQUENCE: 3

Met Tyr Glu Ile Leu Lys Ala Leu Asp Tyr Cys His Ser Met Gly Ile
1               5                   10                  15

Met His Arg Asp Val Lys Pro His Asn Val Met Ile Asp His Glu His
            20                  25                  30

Arg Lys Leu Arg Leu Ile Asp Trp Gly Leu Ala Glu Phe Tyr His Pro
        35                  40                  45

Gly Gln Glu Tyr Asn Val Arg Val Ala Ser Arg Tyr Phe Lys Gly Pro
    50                  55                  60

Glu Leu Leu Val Asp Tyr Gln Met Tyr Asp Tyr Ser Leu Asp Met Trp
65                  70                  75                  80

Ser Leu Gly Cys Met Leu Ala Ser Met Ile Phe Arg Lys Glu Pro Phe
                85                  90                  95

Phe His Gly His Asp Asn Tyr Asp Gln Leu Val Arg Ile Ala Lys Val
            100                 105                 110

Leu Gly Thr Glu Asp Leu Tyr Asp Tyr Ile Asp Lys Tyr Asn Ile Glu
        115                 120                 125

Leu Asp Pro Arg Phe Asn Asp Ile Leu Gly Arg His Ser Arg Lys Arg
    130                 135                 140

Trp Glu Arg Phe Val His Ser Glu Asn Gln His Leu Val Ser Pro Glu
145                 150                 155                 160

Ala Leu Asp Phe Leu Asp Lys Leu Leu Arg Tyr Asp His Gln Ser Arg
                165                 170                 175

Leu Thr Ala Arg Glu Ala Met Glu His Pro Tyr Phe Tyr Thr Val Val
            180                 185                 190

Lys Asp Gln Ala Arg Met Gly Ser Ser Ser Met Pro Gly Gly Ser Thr
        195                 200                 205

Pro Val Ser Ser Ala Asn Met Met Ser Gly Ile Ser Ser Val Pro Thr
    210                 215                 220

Pro Ser Pro Leu Gly Pro Leu Ala Gly Ser Pro Val Ile Ala Ala Ala
225                 230                 235                 240

```
Asn Pro Leu Gly Met Pro Val Pro Ala Ala Ala Gly Ala Gln Gln
            245                 250                 255

<210> SEQ ID NO 4
<211> LENGTH: 10
<212> TYPE: PRT
<213> ORGANISM: Unknown
<220> FEATURE:
<223> OTHER INFORMATION: CK2 Assay substrate peptide

<400> SEQUENCE: 4

Arg Arg Arg Asp Asp Asp Ser Asp Asp Asp
1               5                   10

<210> SEQ ID NO 5
<211> LENGTH: 9
<212> TYPE: PRT
<213> ORGANISM: Unknown
<220> FEATURE:
<223> OTHER INFORMATION: Pim-1 Assay substrate peptide

<400> SEQUENCE: 5

Lys Lys Arg Asn Arg Thr Leu Thr Lys
1               5

<210> SEQ ID NO 6
<211> LENGTH: 10
<212> TYPE: PRT
<213> ORGANISM: Unknown
<220> FEATURE:
<223> OTHER INFORMATION: PIM-2 Assay substrate peptide

<400> SEQUENCE: 6

Arg Ser Arg Ser Ser Tyr Pro Ala Gly Thr
1               5                   10
```

PYRAZOLOPYRIMIDINES AND RELATED HETEROCYCLES AS CK2 INHIBITORS

CROSS-REFERENCE TO RELATED APPLICATIONS

This application claims the benefit of U.S. Provisional Application No. 61/266,801, filed Dec. 4, 2009 and entitled "PYRAZOLOPYRIMIDINES AND RELATED HETEROCYCLES AS KINASE INHIBITORS"; and U.S. Provisional Application No. 61/354,165, filed Jun. 11, 2010 and entitled "PYRAZOLOPYRIMIDINES AND RELATED HETEROCYCLES AS CK2 INHIBITORS"; the contents of which are hereby incorporated by references in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (file-name: CYLE_060_02US_SeqList_ST25.txt, date recorded: Mar. 7, 2011, file size 10 kilobytes).

FIELD OF THE INVENTION

The invention relates in part to molecules having certain biological activities that include, but are not limited to, inhibiting cell proliferation, and modulating certain protein kinase activities. Molecules of the invention modulate, e.g., Protein Kinase CK2 (called CK2 herein) and are useful to treat conditions associated directly or indirectly with CK2 activities, e.g., cancers, inflammatory conditions, infectious disorders, pain, immunological disorders, a neurodegenerative disorder (such as Alzheimer's disease and Parkinson's disease), etc. The invention also relates in part to methods for using such compounds, and pharmaceutical compositions containing these compounds.

BACKGROUND

Protein kinase CK2 (formerly called Casein kinase H, referred to herein as "CK2") is a ubiquitous and highly conserved protein serine/threonine kinase. The holoenzyme is typically found in tetrameric complexes consisting of two catalytic (alpha and/or alpha') subunits and two regulatory (beta) subunits. CK2 has a number of physiological targets and participates in a complex series of cellular functions including the maintenance of cell viability. The level of CK2 in normal cells is tightly regulated, and it has long been considered to play a role in cell growth and proliferation. Inhibitors of CK2 that are useful for treating certain types of cancers are described in PCT/US2007/077464, PCT/US2008/074820, PCT/US2009/35609.

The prevalence and importance of CK2, as well as an evolutionary analysis of its sequence, suggest it is an ancient enzyme on the evolutionary scale; its longevity may explain why it has become important in so many biochemical processes, and why CK2 from hosts have even been co-opted by infectious pathogens (e.g., viruses, protozoa) as an integral part of their survival and life cycle biochemical systems. These same characteristics explain why inhibitors of CK2 are believed to be useful in a variety of medical treatments as discussed herein. Because CK2 is central to many biological processes, as summarized by Guerra & Issinger, *Curr. Med. Chem.*, 2008, 15:1870-1886, inhibitors of CK2, including the compounds described herein, should be useful in the treatment of a variety of diseases and disorders.

Cancerous cells show an elevation of CK2, and recent evidence suggests that CK2 exerts potent suppression of apoptosis in cells by protecting regulatory proteins from caspase-mediated degradation. The anti-apoptotic function of CK2 may contribute to its ability to participate in transformation and tumorigenesis. In particular, CK2 has been shown to be associated with acute and chronic myelogenous leukemia, lymphoma and multiple myeloma. In addition, enhanced CK2 activity has been observed in solid tumors of the colon, rectum and breast, squamous cell carcinomas of the lung and of the head and neck (SCCHN), adenocarcinomas of the lung, colon, rectum, kidney, breast, and prostate. Inhibition of CK2 by a small molecule is reported to induce apoptosis of pancreatic cancer cells, and hepatocellular carcinoma cells (HegG2, Hep3, HeLa cancer cell lines); and CK2 inhibitors dramatically sensitized RMS (Rhabdomyosarcoma) tumors toward apoptosis induced by TRAIL. Thus an inhibitor of CK2 alone, or in combination with TRAIL or a ligand for the TRAIL receptor, would be useful to treat RMS, the most common soft-tissue sarcoma in children. In addition, elevated CK2 has been found to be highly correlated with aggressiveness of neoplasias, and treatment with a CK2 inhibitor of the invention should thus reduce tendency of benign lesions to advance into malignant ones, or for malignant ones to metastasize.

Unlike other kinases and signaling pathways, where mutations are often associated with structural changes that cause loss of regulatory control, increased CK2 activity level appears to be generally caused by upregulation or overexpression of the active protein rather than by changes that affect activation levels. Guerra and Issinger postulate this may be due to regulation by aggregation, since activity levels do not correlate well with mRNA levels. Excessive activity of CK2 has been shown in many cancers, including SCCHN tumors, lung tumors, breast tumors, and others. Id.

Elevated CK2 activity in colorectal carcinomas was shown to correlate with increased malignancy. Aberrant expression and activity of CK2 have been reported to promote increase nuclear levels of NF-kappaB in breast cancer cells. CK2 activity is markedly increased in patients with AML and CML during blast crisis, indicating that an inhibitor of CK2 should be particularly effective in these conditions. Multiple myeloma cell survival has been shown to rely on high activity of CK2, and inhibitors of CK2 were cytotoxic to MM cells.

The literature provides clear evidence that inhibition of CK2 correlates with efficacy against tumor cells. For example, a CK2 inhibitor inhibited growth of murine p190 lymphoma cells. Its interaction with Bcr/Abl has been reported to play an important role in proliferation of Bcr/Abl expressing cells, indicating inhibitors of CK2 may be useful in treatment of Bcr/Abl-positive leukemias. Inhibitors of CK2 have been shown to inhibit progression of skin papillomas, prostate and breast cancer xenografts in mice, and to prolong survival of transgenic mice that express prostate-promoters. Id. The role of CK2 in various non-cancer disease processes has been recently reviewed.

See Guerra & Issinger, *Curr. Med. Chem.*, 2008, 15:1870-1886. Increasing evidence indicates that CK2 is involved in critical diseases of the central nervous system, including, for example, Alzheimer's disease, Parkinson's disease, and rare neurodegenerative disorders such as Guam-Parkinson dementia, chromosome 18 deletion syndrome, progressive supranuclear palsy, Kuf's disease, or Pick's disease. It is suggested that selective CK2-mediated phosphorylation of tau proteins may be involved in progressive neurodegeneration of Alzheimer's disease. In addition, recent studies suggest that CK2 plays a role in memory impairment and brain ischemia, the latter effect apparently being mediated by CK2's regulatory effect on the PI3K survival pathways.

CK2 has also been shown to be involved in the modulation of inflammatory disorders, for example, acute or chronic inflammatory pain, glomerulonephritis, and autoimmune diseases, including, e.g., multiple sclerosis (MS), systemic lupus erythematosus, rheumatoid arthritis, and juvenile arthritis. It positively regulates the function of the serotonin 5-HT3 receptor channel, activates heme oxygenase type 2, and enhances the activity of neuronal nitric oxide synthase. A selective CK2 inhibitor was reported to strongly reduce pain response of mice when administered to spinal cord tissue prior to pain testing. It phosphorylates secretory type IIA phospholipase A2 from synovial fluid of RA patients, and modulates secretion of DEK (a nuclear DNA-binding protein), which is a proinflammatory molecule found in synovial fluid of patients with juvenile arthritis. Thus, inhibition of CK2 is expected to control progression of inflammatory pathologies such as those described here, and the inhibitors disclosed herein have been shown to effectively treat pain in animal models.

Protein kinase CK2 has also been shown to play a role in disorders of the vascular system, such as, e.g., atherosclerosis, laminar shear stress, and hypoxia. CK2 has also been shown to play a role in disorders of skeletal muscle and bone tissue, such as cardiomyocyte hypertrophy, impaired insulin signaling and bone tissue mineralization. In one study, inhibitors of CK2 were effective at slowing angiogenesis induced by growth factor in cultured cells. Moreover, in a retinopathy model, a CK2 inhibitor combined with octreotide (a somatostatin analog) reduced neovascular tufts; thus, the CK2 inhibitors described herein would be effective in combination with a somatostatin analog to treat retinopathy.

CK2 has also been shown to phosphorylate GSK, troponin and myosin light chain; thus, CK2 is important in skeletal muscle and bone tissue physiology, and is linked to diseases affecting muscle tissue.

Evidence suggests that CK2 is also involved in the development and life cycle regulation of protozoal parasites, such as, for example, *Theileria parva, Trypanosoma cruzi, Leishmania donovani, Herpetomonas muscarum muscarum, Plasmodium falciparum, Trypanosoma brucei, Toxoplasma gondii* and *Schistosoma mansoni*. Numerous studies have confirmed the role of CK2 in regulation of cellular motility of protozoan parasites, essential to invasion of host cells. Activation of CK2 or excessive activity of CK2 has been shown to occur in hosts infected with *Leishmania donovani, Herpetomonas muscarum muscarum, Plasmodium falciparum, Trypanosoma brucei, Toxoplasma gondii* and *Schistosoma mansoni*. Indeed, inhibition of CK2 has been shown to block infection by *T. cruzi*.

CK2 has also been shown to interact with and/or phosphorylate viral proteins associated with human immunodeficiency virus type 1 (HIV-1), human papilloma virus, and herpes simplex virus, in addition to other virus types (e.g. human cytomegalovirus, hepatitis C and B viruses, Borna disease virus, adenovirus, coxsackievirus, coronavirus, influenza, and varicella zoster virus). CK2 phosphorylates and activates HIV-1 reverse transcriptase and proteases in vitro and in vivo, and promotes pathogenicity of simian-human immunodeficiency virus (SHIV), a model for HIV. Inhibitors of CK2 are thus able to reduce pathogenic effects of a model of HIV infection. CK2 also phosphorylates numerous proteins in herpes simplex virus and numerous other viruses, and some evidence suggests viruses have adopted CK2 as a phosphorylating enzyme for their essential life cycle proteins. Inhibition of CK2 is thus expected to deter infection and progression of viral infections, which rely upon the host's CK2 for their own life cycles.

CK2 is unusual in the diversity of biological processes that it affects, and it differs from most kinases in other ways as well: it is constitutively active, it can use ATP or GTP, and it is elevated in most tumors and rapidly proliferating tissues. In addition, while many kinase inhibitors affect multiple kinases, increasing the likelihood of off-target effects or variability between individual subjects, CK2's unique structural features enable discovery of highly CK2-specific inhibitors. For all of these reasons, CK2 is a particularly interesting target for drug development, and the invention provides highly effective inhibitors of CK2 that are useful in treating a variety of different diseases and disorders mediated by or associated with excessive, aberrant or undesired levels of CK2 activity.

Compounds of Formula I have been found to be active on CK2 as well as on one or more Pim proteins. It has now been found that compounds of Formula (II) and (II') are typically more active on CK2, and also have less activity on Pim kinases. Without being bound by the theory, it is believed that their physiological activities derive from their activity on CK2.

The current invention provides novel compounds of Formula (II) and (II'), as well as Formulae IIa, IIa', II-Th and II-Th', and pharmaceutical compositions containing these compounds. The novel compounds of Formula II, which are related to the compounds of Formula I, show surprisingly greater activity on CK2 and reduced Pim activity, and thus are advantageously used to treat conditions sensitive to CK2 inhibition such as those described herein. Compounds of Formula II are therefore useful to treat conditions mediated by or associated with excessive activity of CK2, with reduced likelihood of off-target effects caused by inhibition of other kinases.

DISCLOSURE OF THE INVENTION

The present invention in part provides chemical compounds having certain biological activities that include, but are not limited to, inhibiting cell proliferation, inhibiting angiogenesis, and modulating protein kinase activities. These molecules modulate protein kinase CK2 (CK2) and/or PIM activity, and are typically more selective for CK2 activity over other kinases than similar compounds that lack the amine group shown in Formula (II) or (II'). These compounds affect biological functions that include but are not limited to, inhibiting gamma phosphate transfer from ATP to a protein or peptide substrate, inhibiting angiogenesis, inhibiting cell proliferation and inducing cell apoptosis, for example. The present invention also in part provides methods for preparing novel chemical compounds, and analogs thereof, and methods of using these compounds. Also provided are compositions comprising these molecules in combination with other materials, including other therapeutic agents, and methods for using such compositions.

Compounds of the general formula (I) have been shown to inhibit Pim and CK2 (PCT/US2010/035657):

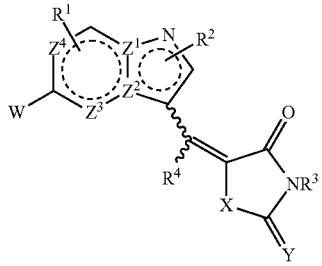

(I)

wherein the bicyclic ring system containing $Z^1$-$Z^4$ is aromatic;
one of $Z^1$ and $Z^2$ is C, the other of $Z^1$ and $Z^2$ is N;
$Z^3$ and $Z^4$ are independently $CR^5$ or N,
where $R^5$ can be H or $R^1$;
$R^1$ is H, halo, CN, optionally substituted C1-C4 alkyl, optionally substituted C2-C4 alkenyl, optionally substituted C2-C4 alkynyl, optionally substituted C1-C4 alkoxy, or —$NR^7R^8$,
where $R^7$ and $R^8$ are each independently selected from H, optionally substituted C1-C10 alkyl, optionally substituted aryl, optionally substituted arylalkyl, optionally substituted heteroaryl, and optionally substituted heteroarylalkyl,
or $R^7$ and $R^8$ taken together with the N of —$NR^7R^8$ form an optionally substituted 5-8 membered ring that optionally contains an additional heteroatom selected from N, O and S as a ring member;
$R^2$ is H, halo, CN, or an optionally substituted group selected from C1-C4 alkyl, C2-C4 alkenyl, and C2-C4 alkynyl;
$R^3$ and $R^4$ are independently selected from H and optionally substituted C1-C10 alkyl;
X is $NR^6$, O, or S, where $R^6$ is H or an optionally substituted group selected from C1-C4 alkyl, C2-C4 alkenyl, and C2-C4 alkynyl;
Y is O or S;
W is optionally substituted aryl, optionally substituted heteroaryl, or —$NR^9R^{10}$, —$OR^9$, $S(O)_nR^9$, optionally substituted carbon-linked heterocyclyl, optionally substituted C3-C8 cycloalkyl, or $CR^9R^{10}R^{11}$,
wherein n is 0, 1 or 2, and
$R^9$ and $R^{10}$ are each independently selected from H, optionally substituted C1-C10 alkyl, optionally substituted aryl, optionally substituted arylalkyl, optionally substituted heteroaryl, and optionally substituted heteroarylalkyl,
or $R^9$ and $R^{10}$ taken together with the N of —$NR^9R^{10}$ form an optionally substituted 5-8 membered ring that optionally contains an additional heteroatom selected from N, O and S as a ring member, and
$R^{11}$ is selected from H, optionally substituted C1-C10 alkyl, optionally substituted aryl, optionally substituted arylalkyl, optionally substituted heteroaryl, and optionally substituted heteroarylalkyl.

The compounds of Formula I inhibit Pim and CK2, and often inhibit other kinases as well. For use as pharmaceuticals, it can be advantageous to select compounds that inhibit one primary target enzyme or receptor with minimal affect on other pathways or targets, because off-target biochemical effects can cause unpredictable side effects. It has now been found that compounds of Formula (II) and (II'), which are related to the compounds of Formula I, retain high levels of CK2 activity, and indeed are often more potent on CK2 than other compounds like Formula I, yet they are typically selective for CK2 over Pim kinases. In addition, their selectivity for CK2 over other kinases in a broad array of kinases is also improved over that of the compounds of Formula I generally. Therefore, compounds of Formula (II) or (II') represent a particularly useful class of compounds for the methods of treatment described herein, because they are selective for CK2 and inhibit fewer other kinases, resulting in a reduced risk of side-effects.

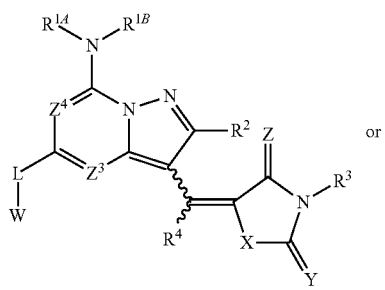

(II)


(II')

wherein:
$Z^3$ and $Z^4$ each independently represent N or $CR^5$, or CH;
each $R^5$ is independently selected from halo, CN, R, —OR, —$S(O)_nR$, COOR, $CONR^2$, and $NR_2$,
wherein each R is independently selected from H and optionally substituted C1-C4 alkyl, and the two R groups of $NR_2$ can be linked together to form a 5-6 membered heterocyclic ring that is optionally substituted and can include an additional heteroatom selected from N, O and S as a ring member;
$R^2$, $R^3$ and $R^4$ are each independently selected from H and optionally substituted C1-C10 alkyl;
X represents O, S, or $NR^2$;
Y is O or S or $NR^{10}$;
where $R^{10}$ is selected from H, CN, optionally substituted C1-C4 alkyl, optionally substituted C2-C4 alkenyl, optionally substituted C2-C4 alkynyl, optionally substituted C1-C4 alkoxy, and —$NR^7R^8$,
Z is O or S;
L can be a bond, —$CR^7$=$CR^8$—, —C≡C—, —$NR^7$—, —O—, —$S(O)_n$—, or $(CR^7R^8)_m$, —$(CR^7R^8)_m$—$NR^7$—, —$(CR^7R^8)_m$—O—, or —$(CR^7R^8)_m$—$S(O)_n$—;
W is optionally substituted C1-C10 alkyl, optionally substituted aryl, optionally substituted heteroaryl, —$NR^7R^8$, —$OR^7$, $S(O)_nR^7$, $CONR^7R^8$, optionally substituted heterocyclyl, optionally substituted C3-C8 cycloalkyl, optionally substituted C2-C10 alkenyl, optionally substituted C2-C10 alkynyl, or $CR^7R^8R^9$, where each $R^7$ and $R^8$ and $R^9$ is independently selected from H, optionally substituted C1-C6 alkoxy, optionally substituted C1-C6 alkylamino, optionally substituted C1-C6 dialkylamino, optionally substituted heterocyclyl, optionally substituted C1-C10 alkyl, optionally substituted C3-C8 cycloalkyl, optionally substituted C4-C10 cycloalkylalkyl, optionally substituted aryl, optionally substituted arylalkyl, optionally substituted heteroaryl, and optionally substituted heteroarylalkyl;

or $R^8$ and $R^9$ taken together can be =O (oxo) or =N—$OR^7$ or =N—CN;

or $R^7$ and $R^8$ taken together with the N of —$NR^7R^8$ can form an optionally substituted 5-10 membered heterocyclic or heteroaromatic ring system that optionally contains an additional heteroatom selected from N, O and S as a ring member;

provided that no more than one of or $R^7$ and $R^8$ in —$NR^7R^8$ is selected from the group consisting of alkoxy, alkylamino, dialkylamino and heterocyclyl;

each n is independently is 0, 1 or 2;

each m is independently 1, 2, 3 or 4;

$R^{1A}$ and $R^{1B}$ are each independently selected from H, optionally substituted C1-C10 alkyl, optionally substituted heterocyclyl, optionally substituted cycloalkyl, optionally substituted cycloalkylalkyl, optionally substituted heterocyclylalkyl, optionally substituted arylalkyl, or an optionally substituted 5-6 membered aryl ring containing up to two heteroatoms as ring members;

or $R^{1A}$ and $R^{1B}$ in —$NR^{1A}R^{1B}$ can be taken together to form an optionally substituted 5-8 membered monocyclic or 5-10 membered bicyclic heteroaryl or heterocyclic group containing up to two additional heteroatoms selected from N, O and S as ring members;

and pharmaceutically acceptable salts of these compounds.

A favored class of compounds of Formula II are those of Formula (IIa) or (IIa'):

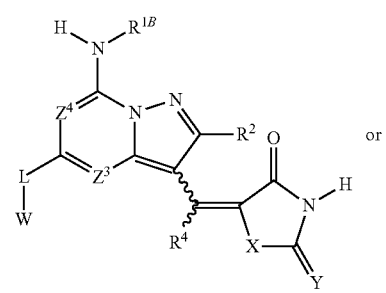

(IIa)

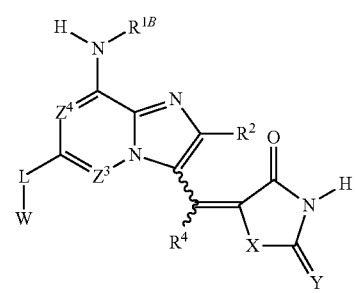

(IIa')

where $R^2$ is H, Me or $CF_3$; $R^4$ is H, Me or $CF_3$; X is O, S or NH; Y is O or S; $R^{1B}$ is as described for Formula II; L is a bond, —$NR^7$—, —O—, or —$S(O)_n$—, $(CR^7R^8)_m$, or it can be —$(CR^7R^8)_m$—$NR^7$—; m is 1-4 and n is 0-2; and W is selected from optionally substituted aryl, optionally substituted heteroaryl, and —$NR^7R^8$, where $R^7$ and $R^8$ are as defined for Formula II.

Particular embodiments of the compounds of the invention include thiophene-containing compounds of Formula (II-Th) and (II-Th'):

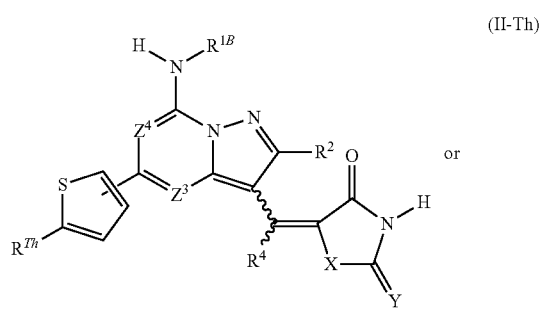

(II-Th)

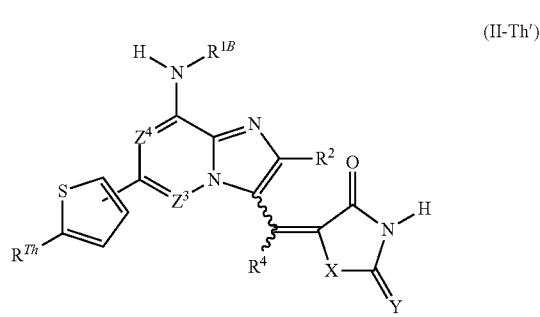

(II-Th')

where $R^{Th}$ is selected from H, halo, optionally substituted C1-C6 alkyl, CN, $S(O)_{0-2}R$, —$SO_2NR_2$, COOR, $CONR_2$, and C(O)R, where each R is independently H, halo, CN, or an optionally substituted member selected from the group consisting of C1-C6 alkyl, C1-C6 alkoxy, C1-C6 alkylamino, di(C1-C6)alkylamino, C3-C8 cycloalkyl, C4-C10 cycloalkylalkyl, C5-C8 heterocyclyl, C6-C10 heterocyclylalkyl, aryl, arylalkyl, C5-C6 heteroalkyl, and C6-C10 heteroalkylalkyl;

and two R on the same atom or adjacent atoms can form an optionally substituted heterocyclic ring that can contain an additional heteroatom selected from N, O and S; and other structural features are as defined for Formula IIa above.

The invention includes pharmaceutically acceptable salts of compounds of Formula II, II', IIa, IIa', II-Th, and II-Th' as well as the neutral compounds.

The invention also provides pharmaceutical compositions containing such compounds plus one or more pharmaceutically acceptable carriers or excipients, and methods of using these compounds and compositions for the treatment of specified conditions as further described herein.

In addition, the invention provides intermediates of Formula (III), which are useful for preparation of compounds described above, and methods of using these intermediates to make compounds of Formula (II):

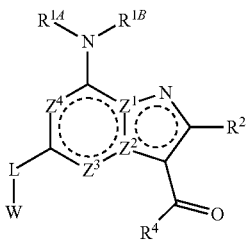

(III)

where $R^{1A}$, $R^{1B}$, $R^2$, $R^4$, $Z^3$, $Z^4$, L and W are as defined for Formula (II) above, or in certain embodiments, these are the same as the corresponding features defined for Formula (IIa) above;

one of $Z^1$ and $Z^2$ represents N, and the other of $Z^1$ and $Z^2$ represents C;

and the circles inside the two rings indicate that the rings are both aromatic.

The method comprises reacting a compound of Formula (III) with a hydantoin or similar 5-membered heterocyclic compound of Formula (IV):

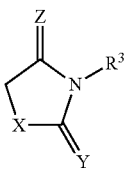

(IV)

where $R^3$, X, Y and Z are as defined for Formula (II) or (II'), under conditions that promote condensation of the two compounds.

Typically, the reaction conditions will include a suitable solvent and a base, optionally a catalytic amount of base, but stoichiometric or larger amounts of base can be used. Suitable bases are those capable of deprotonating the compound of Formula (IV) to promote condensation with the compound of Formula (III), and secondary amines that are capable of reacting with aldehydes of Formula (III) to form an iminium species. Suitable bases include C1-C4 alkoxides, metal hydrides, tertiary amines such as triethylamine or diisopropyl ethylamine, DABCO, DBU and the like; and suitable secondary amine bases include piperidine, morpholine, piperazine, N-methylpiperazine, pyrrolidine, and the like. Suitable solvents include polar aprotic solvents such as NMP, DMF, DMSO, DMA, and dioxane; as well as protic solvents such as C1-C10 alcohols and diols, e.g., ethanol, propanol, isopropanol, ethylene glycol, propylene glycol, methoxyethanol, and the like. Mixtures of such solvents can also be used, as can mixtures of one or more of these solvents with a less polar organic solvent to promote solubility of the reactants. Selection of suitable solvents and bases for these reactions are well within the level of skill of an ordinary practitioner.

In some embodiments of the compounds of Formula (III), -L-W represents a group of the formula —S(O)$_{1-2}$R, where R is an alkyl, cycloalkyl, aryl, heteroaryl or similar group, and the product is a compound of Formula (II) or (II') having the same -L-W group. Such compounds are conveniently used for the preparation of other compounds of formula (II) or (II'), because the moiety of formula —S(O)$_{1-2}$R is a good leaving group, and can readily be displaced by nucleophiles such as primary or secondary amines, to introduce other -L-W groups. Thus another method for synthesizing the compounds of the invention is to react a compound of Formula (V),

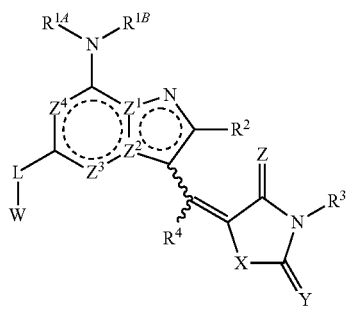

(V)

wherein -L-W represents a group of the formula —S(O)$_{1-2}$R, where R is an optionally substituted group selected from C1-C6 alkyl, C3-C8 cycloalkyl, C4-C10 cycloalkylalkyl, C6-C10 aryl, C5-C6 heteroaryl, C7-C12 arylalkyl, and C6-C12 heteroarylalkyl;

and other variables are as defined for formulas (III) and (IV) above; with a nucleophilic compound of formula

W'-L'-H wherein L' is selected from NR$^7$, O and S; and

W' is optionally substituted aryl, optionally substituted heteroaryl optionally substituted heterocyclyl, optionally substituted C3-C8 cycloalkyl, optionally substituted C2-C10 alkenyl, optionally substituted C2-C10 alkynyl, or CR$^7$R$^8$R$^9$, where R$^7$, R$^8$ and R$^9$ are as defined above for Formula II under suitable conditions as described herein to provide a compound of Formula (V'):

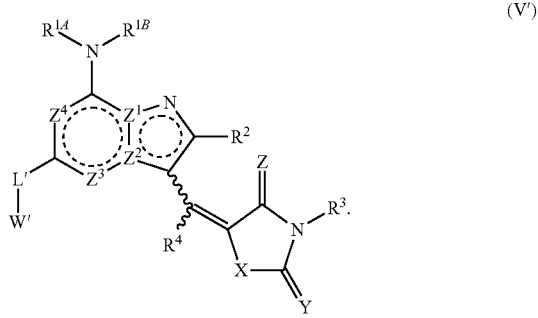

(V')

Also provided herein are pharmaceutical compositions comprising a compound of Formula I or II as described herein and at least one pharmaceutically acceptable carrier or excipient, or two or more pharmaceutically acceptable carriers and/or excipients. Pharmaceutical compositions comprising at least one of these compounds can be utilized in methods of treatment such as those described herein.

The compounds of Formulae I and II as described herein bind to and inhibit certain kinase proteins, which is believed to be the basis for their pharmaceutical activity. In certain embodiments, the protein is a CK2 protein, such as a CK2 protein comprising the amino acid sequence of SEQ ID NO:1, 2 or 3 or a substantially identical variant thereof, for example.

```
(NP_001886; casein kinase II alpha 1 subunit isoform a [Homo sapiens])
                                                      SEQ ID NO: 1
    msgpvpsrar vytdvnthrp reywdyeshv vewgnqddyq lvrklgrgky sevfeainit nnekvvvkil kpvkkkkikr eikilenlrg gpniitladi vkdpvsrtpa lvfehvnntd 121 fkqlyqtltd ydirfymyei lkaldychsm gimhrdvkph nvmidhehrk lrlidwglae 181 fyhpgqeynv rvasryfkgp ellvdyqmyd ysldmwslgc mlasmifrke pffhghdnyd 241 qlvriakvlg tedlydyidk ynieldprfn dilgrhsrkr werfvhsenq hlvspealdf 301 ldkllrydhq srltareame hpyfytvvkd qarmgsssmp ggstpvssan mmsgissvpt 361 psplgplags pviaaanplg mpvpaaagaq q (NP_808227; casein kinase II alpha 1 subunit isoform a [Homo sapiens])
                                                      SEQ ID NO: 2
    msgpvpsrar vytdvnthrp reywdyeshv vewgnqddyq lvrklgrgky sevfeainit nnekvvvkil kpvkkkkikr eikilenlrg gpniitladi vkdpvsrtpa lvfehvnntd 121 fkqlyqtltd ydirfymyei lkaldychsm gimhrdvkph nvmidhehrk lrlidwglae 181 fyhpgqeynv rvasryfkgp ellvdyqmyd ysldmwslgc mlasmifrke pffhghdnyd 241 qlvriakvlg tedlydyidk ynieldprfn dilgrhsrkr werfvhsenq hlvspealdf 301 ldkllrydhq srltareame hpyfytvvkd qarmgsssmp ggstpvssan mmsgissvpt 361 psplgplags pviaaanplq mpvpaaagaq q (NP_808228; casein kinase II alpha 1 subunit isoform b [Homo sapiens])
                                                      SEQ ID NO: 3
    myeilkaldy chsmgimhrd vkphnvmidh ehrklrlidw glaefyhpgq eynvrvasry fkgpellvdy qmydysldmw slgcmlasmi frkepffhgh dnydqlvria kvlgtedlyd 121 yidkynield prfndilgrh srkrwerfvh senqhlvspe aldfldkllr ydhqsrltar 181 eamehpyfyt vvkdqarmgs ssmpggstpv ssanmmsgis svptpsplgp lagspviaaa 241 nplgmpvpaa agaqq
```

Substantially identical variants of these include proteins having at least 90% sequence homology with one of these, preferably at least 90% sequence identity; and having at least 50% of the level of in vitro kinase activity of the specified sequence under typical assay conditions.

The invention includes methods to modulate the activity of CK2 protein, either in vitro or ex vivo. Suitable methods comprise contacting a system comprising the protein with a compound described herein in an amount effective for modulating the activity of the protein. In certain embodiments the activity of the protein is inhibited, and sometimes the protein is a CK2 protein comprising the amino acid sequence of SEQ ID NO:1, SEQ ID NO:2 or SEQ ID NO:3 or a substantially identical variant thereof, for example. In certain embodiments the CK2 is in a cell or tissue; in other embodiments, it can be in a cell-free system.

Provided also are methods for inhibiting cell proliferation, which comprise contacting cells with a compound described herein in an amount effective to inhibit proliferation of the cells. The cells sometimes are in a cell line, such as a cancer cell line (e.g., breast cancer, prostate cancer, pancreatic cancer, lung cancer, hemopoietic cancer, colorectal cancer, skin cancer, ovary cancer cell line), for example. In some embodiments, the cancer cell line is a breast cancer, prostate cancer or pancreatic cancer cell line. The cells sometimes are in a tissue, can be in a subject, at times are in a tumor, and sometimes are in a tumor in a subject. In certain embodiments, the method further comprises inducing cell apoptosis. Cells sometimes are from a subject having macular degeneration.

Also provided are methods for treating a condition related to aberrant cell proliferation, which comprise administering a compound described herein to a subject in need thereof in an amount effective to treat the cell proliferative condition. In certain embodiments the cell proliferative condition is a tumor-associated cancer, e.g., a solid or circulating tumor. The cancer sometimes is cancer of the breast, prostate, pancreas, lung, colorectum, skin, or ovary. In some embodiments, the cell proliferative condition is a non-tumor cancer, such as a hematopoietic cancer, for example, including leukemias, e.g., multiple myeloma and lymphomas. The cell proliferative condition is macular degeneration in some embodiments.

The invention also includes methods for treating cancer or an inflammatory disorder or other disorders described herein that are mediated by excessive activity of one or more of these kinases, in a subject in need of such treatment, comprising: administering to the subject a therapeutically effective amount of a therapeutic agent useful for treating such disorder; and administering to the subject a molecule described herein , e.g., a compound inhibits CK2 in an amount that is effective to enhance a desired effect of the therapeutic agent. In certain embodiments, the molecule that inhibits CK2 is a compound of Formula I or Formula II, or Formula II' or (IIa) or (IIa'), or a pharmaceutically acceptable salt thereof. In certain embodiments, the desired effect of the therapeutic agent that is enhanced by the molecule that inhibits CK2 is an increase in apoptosis in at least one type of cell. In certain embodiments, the cell is a cancer cell and the compound is a compound of Formula (II) or (IIa) that is a potent inhibitor (IC-50 less than about 100 nM, for example) of CK2. Preferably, the compound has an IC-50 on Pim of less than about 30 nM, and is selective for CK2 over Pim kinases. In certain embodiments, the IC-50 for inhibition of CK2 is lower by at least a factor of ten than activity on Pim; in preferred embodiments, the compound has an IC-50 for CK2 that is lower than its IC-50 for at least one of Pim-1, Pim-2 and Pim-3 by about 100-fold or more.

In some embodiments, the therapeutic agent and the molecule that inhibits CK2 are administered at substantially the same time. The therapeutic agent and molecule that inhibits CK2 sometimes are used concurrently by the subject. The therapeutic agent and the molecule that inhibits CK2 can be combined into one pharmaceutical composition in certain embodiments; in other embodiments that are admistered as separate compositions.

Also provided are compositions of matter comprising a compound described herein and an isolated protein. The protein sometimes is a CK2 protein, such as a CK2 protein comprising the amino acid sequence of SEQ ID NO:1, SEQ ID NO:2 or SEQ ID NO:3 or a substantially identical variant thereof, for example. In some embodiments, the protein is a Pim protein. Certain compositions comprise a compound described herein in combination with a cell. The cell may be from a cell line, such as a cancer cell line. In the latter embodiments, the cancer cell line is sometimes a breast cancer, prostate cancer, pancreatic cancer, lung cancer, hematopoietic cancer, colorectal cancer, skin cancer, of ovary cancer cell line.

These and other embodiments of the invention are described in the description that follows.

MODES OF CARRYING OUT THE INVENTION

Figure 1:
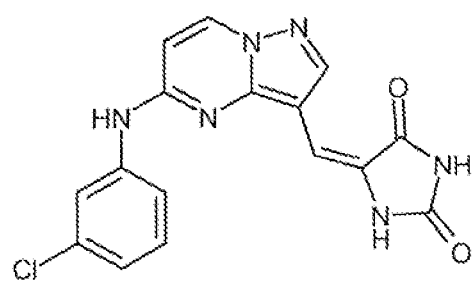
FIG. 1 depicts a compound of Formula I as described herein, and shows its IC50 on CK2 (7 nM) and on PIM1 (351 nM), and also shows a plot of inhibition of a panel of 108 kinases to illustrate its selectivity for these kinases relative to other kinases.
Figure 1:
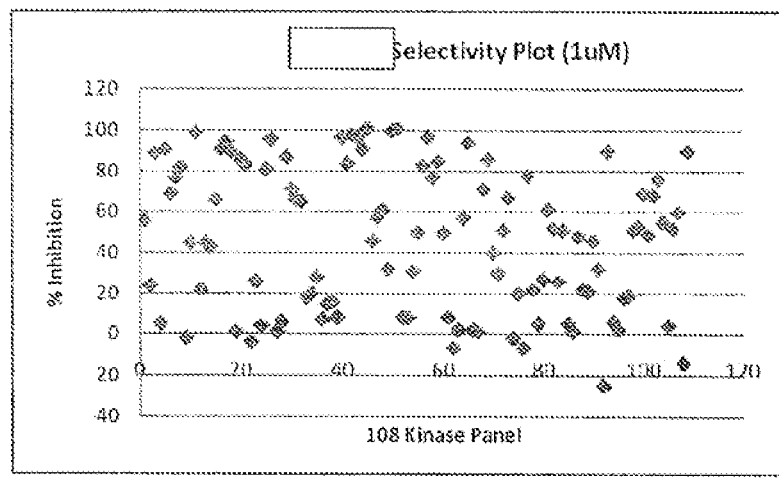

Compounds of the present invention exert biological activities that include, but are not limited to, inhibiting cell proliferation, reducing angiogenesis, preventing or reducing inflammatory responses and pain, and modulating certain immune responses. Such compounds modulate CK2 activity, as demonstrated by the data herein. Such compounds therefore can be utilized in multiple applications by a person of ordinary skill in the art. For example, compounds described herein can be used, for example, for (i) modulation of protein kinase activity (e.g., CK2 activity), (ii) modulation of cell proliferation, (iii) modulation of apoptosis, and/or (iv) treatments of cell proliferation related disorders (e.g., administration alone or co-administration with another molecule). In particular, the compounds of Formula (II) and (IIa) can be used to modulate CK2 activity, in vitro or in vivo, and to treat disorders associated with excessive or undesirable levels of CK2 activity, including cancers, certain inflammatory disorders, vascular disorders, certain skeletal and muscle disorders, and infections such as protozoal parasite infections and some viral infections.

Definitions

The terms "a" and "an" do not denote a limitation of quantity, but rather denote the presence of at least one of the referenced item. The terms "a" and "an" are used interchangeable with "one or more" or "at least one". The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

The terms "compound(s) of the invention", "these compounds", "such compound(s)", "the compound(s)", and "the present compound(s)" refer to compounds encompassed by structural formulae disclosed herein, e.g., Formula (I), (II), (II'), (IIa), (IIa'), (IIb'), (IIc), (II-Th), and (II-Th'), includes any specific compounds within these formulae whose structure is disclosed herein. Compounds may be identified either by their chemical structure and/or chemical name. When the chemical structure and chemical name conflict, the chemical structure is determinative of the identity of the compound. Furthermore, the present compounds can modulate, i.e., inhibit or enhance, the biological activity of a CK2 protein, a Pim protein or both, and thereby is also referred to herein as a "modulator(s)" or "CK2 and/or Pim modulator(s)". Compounds of Formula (I), (II), (II'), (IIa), (IIa'), (IIb), (IIb'), (IIc), (II-Th), and (II-Th'), including any specific compounds, i.e., species, described herein are exemplary "modulators".

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and etc.) as well as mixtures of stereoisomers in varying degrees of chiral purity or percetange of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted olefin isomer. When the chemical name does not specify the isomeric form of the compound, it denotes any one of the possible isomeric forms or a mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium. For example, ketone and enol are two tautomeric forms of one compound. In another example, a substituted 1,2,4-triazole derivative may exist in at least three tautomeric forms as shown below:

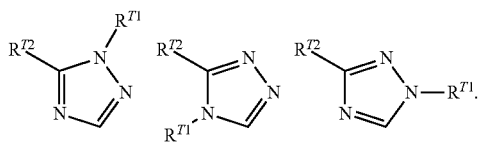

$R^{T1}$ is H or optionally substituted alkyl,
$R^{T2}$ is an optionally substituted aryl.

The descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The compounds of the invention often have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge. Standard methods for the preparation of pharmaceutically acceptable salts and their formulations are well known in the art, and are disclosed in various references, including for example, "*Remington: The Science and Practice of Pharmacy*", A. Gennaro, ed., 20th edition, Lippincott, Williams & Wilkins, Philadelphia, Pa.

"Solvate", as used herein, means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate". Examples of hydrate include, but are not limited to, hemihydrate, monohydrate, dihydrate, trihydrate, hexahydrate, etc. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

The term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolysable esters of the present compounds are the compounds whose carboxyls are present in the form of hydrolysable ester groups. That is, these esters are pharmaceutically acceptable and can be hydrolyzed to the corresponding carboxyl acid in vivo. These esters may be conventional ones, including lower alkanoyloxyalkyl esters, e.g. pivaloyloxymethyl and 1-pivaloyloxyethyl esters; lower alkoxycarbonylalkyl esters, e.g., methoxycarbonyloxymethyl, 1-ethoxycarbonyloxyethyl, and 1-isopropylcarbonyloxyethyl esters; lower alkoxymethyl esters, e.g., methoxymethyl esters, lactonyl esters, benzofuran keto esters, thiobenzofuran keto esters; lower alkanoylaminomethyl esters, e.g., acetylaminomethyl esters. Other esters can also be used, such as benzyl esters and cyano methyl esters. Other examples of these esters include: (2,2-dimethyl-1-oxypropyloxy)methyl esters; (1RS)-1-acetoxyethyl esters, 2-[(2-methylpropyloxy)carbonyl]-2-pentenyl esters, 1-[[(1-methylethoxy)carbonyl]-oxy]ethyl esters; isopropyloxycarbonyloxyethyl esters, (5-methyl-2-oxo-1,3-dioxole-4-yl)methyl esters, 1-[[(cyclohexyloxy)carbonyl]oxy]ethyl esters; 3,3-dimethyl-2-oxobutyl esters. It is obvious to those skilled in the art that hydrolysable esters of the compounds of the present invention can be formed at free carboxyls of said compounds by using conventional methods. Representative esters include pivaloyloxymethyl esters, isopropyloxycarbonyloxyethyl esters and (5-methyl-2-oxo-1,3-dioxole-4-yl)methyl esters.

The term "prodrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug can be an ester, ether, or amide form of a pharmaceutically active compound. Various types of prodrug have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these prodrugs with commonly employed techniques of organic synthesis.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Excipient" refers to a diluent, adjuvant, vehicle, or carrier with which a compound is administered.

An "effective amount" or "therapeutically effective amount" is the quantity of the present compound in which a beneficial outcome is achieved when the compound is administered to a patient or alternatively, the quantity of compound that possesses a desired activity in vivo or in vitro. In the case of proliferative disorders, a beneficial clinical outcome includes reduction in the extent or severity of the symptoms associated with the disease or disorder and/or an increase in the longevity and/or quality of life of the patient compared with the absence of the treatment. For example, for a subject with cancer, a "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the patient, such as general health, age, sex, body weight and tolerance to drugs. It will also depend on the degree, severity and type of proliferative disorder. The skilled artisan will be able to determine appropriate dosages depending on these and other factors.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10 C or as C1-C10 or C1-C10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described. Where a ring is included, it is understood that the group contains at least three carbon atoms as a 3-membered ring is the smallest size for a ring.

Typically, the alkyl, alkenyl and alkynyl substituents of the invention contain 1-10 C (alkyl) or 2-10 C (alkenyl or alkynyl), or 3-10 C when a ring is included. Preferably they contain 1-8 C (alkyl) or 2-8 C (alkenyl or alkynyl) or 3-8 C when a ring is included. Sometimes they contain 1-4 C (alkyl) or 2-4 C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond; provided, however, that the presence of multiple bonds does not produce an aromatic ring.

Alkyl, alkenyl and alkynyl groups are often optionally substituted to the extent that such substitution makes sense chemically.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Substituted," when used to modify a specified group or radical, means that one or more hydrogen atoms of the specified group or radical are each, independently of one another, replaced with the same or different substituent(s).

Substituent groups useful for substituting saturated carbon atoms in the specified group or radical include, but are not limited to —$R^a$, =O, —$OR^b$, —$SR^b$, =$S^-$, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, $OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-$C(O)OR^b$, -alkylene-$C(O)NR^bR^b$, and —$CH_2$—$CH_2$—$C(O)$—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^-$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Alkyl, alkenyl and alkynyl groups can alternatively or in addition be substituted by C1-C8 acyl, C2-C8 heteroacyl, C6-C10 aryl, C3-C8 cycloalkyl, C3-C8 heterocyclyl, or C5-C10 heteroaryl, each of which can be substituted by one or more R, halo, =O, =N—CN, =N—OR, =NR, OR, $NR_2$, SR, $SO_2R$, $SO_2NR_2$, $NRSO_2R$, $NRCONR_2$, $NRCSNR_2$, $NRC(=NR)NR_2$, NRCOOR, NRCOR, CN, C≡CR, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, or C5-C10 heteroaryl, and each R is optionally substituted with one or more (typically up to three) halo, =O, =N—CN, =N—OR', =NR', OR', $NR'_2$, SR', $SO_2R'$, $SO_2NR'_2$, NR'$SO_2R'$, NR'$CONR'_2$, NR'$CSNR'_2$, NR'C(=NR')$NR'_2$, NR'COOR', NR'COR', CN, C≡CR', COOR', $CONR'_2$, OOCR', COR', and $NO_2$, wherein each $R^1$ is independently H, C1-C8 alkyl, C2-C8 heteroalkyl, C1-C8 acyl, C3-C8 heterocyclyl, C2-C8 heteroacyl, C6-C10 aryl or C5-C10 heteroaryl.

Where any of these substituents contains two R or R' groups on the same or adjacent atoms (e.g., —$NR_2$, or —NR—C(O)R), the two R or R' groups can optionally be taken together with the atom(s) in the substituent group to which they are attached to form a ring having 5-8 ring members, which can include another heteroatom as a ring member (N, O or S) and can be substituted with one or more halo, =O, =N—CN, =N—OR, =NR, OR, $NR_2$, SR, $SO_2R$, $SO_2NR_2$, $NRSO_2R$, $NRCONR_2$, $NRCSNR_2$, $NRC(=NR)NR_2$, NRCOOR, NRCOR, CN, C≡CR, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, NR'$SO_2R'$, NR'$CONR'_2$, NR'$CSNR'_2$, NR'C(=NR')$NR'_2$, NR'COOR', NR'COR', CN, C≡CR', COOR', $CONR'_2$, OOCR', COR', and $NO_2$, wherein each $R^1$ is independently H, C1-C8 alkyl, C2-C8 heteroalkyl, C1-C8 acyl, C3-C8 heterocyclyl, C2-C8 heteroacyl, C6-C10 aryl or C5-C10 heteroaryl, and each of the substitutable groups on R' can be substituted with one or more (e.g., up to three) halo, piperidinyl, pyrrolidinyl, piperazinyl, morpholinyl, CN, C1-C4 alkoxy, OH, OAc, $NH_2$, C1-C4 alkyl amine, di(C1-C4 alkyl)amine, NHAc, NHCOOMe, NHCOOEt, NHCOOtBu, $NHSO_2Me$, SMe, $SO_2Me$, $SO_2NH_2$, $SO_2NMe_2$, COOH, $CONH_2$, COOMe, COOEt, CONHMe, or $CONMe_2$.

"Acetylene" substituents are 2-10 C alkynyl groups that contain at least one carbon-carbon triple bond and are optionally substituted with the groups described herein as suitable for alkyl groups; in some embodiments, the alkynyl groups are of the formula —C≡C—$R^a$, wherein $R^a$ is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl.

Each $R^a$ group is optionally substituted with one or more substituents selected from halo, =O, =N—CN, =N—OR', =NR', OR', $NR'_2$, SR', $SO_2R'$, $SO_2NR'_2$, NR'$SO_2R'$, NR'$CONR'_2$, NR'$CSNR'_2$, NR'C(=NR')$NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, CN, C1-C4 alkyl, C2-C4 heteroalkyl, C1-C6 acyl, C1-C6 heteroacyl, C1-C4 alkoxy, C1-C4 alkylamino, di(C1-C4 alkyl)amino, hydroxy, amino, and =O; and wherein two R' can be linked to form a 3-7 membered ring optionally containing up to three heteroatoms selected from N, O and S. In some embodiments, $R^a$ of —C≡C—$R^a$ is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

Like alkyl groups, the cycloalkyl and heterocyclyl groups described herein can be substituted to the extent permitted by their valence and stability considerations, which are well understood by those of skill in the art. Substituents for the cycloalkyl and heterocyclyl rings or ring systems include those described herein as suitable for placement on alkyl groups.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such'groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms and up to four heteroatoms selected from N, O and S. Frequently, the monocyclic heteroaryls contain 5-6 ring members and up to three such heteroatoms, and the bicyclic heteroaryls contain 8-10 ring members and up to four such heteroatoms. The number and placement of heteroatoms in such rings is in accordance with the well-known limitations of aromaticity and stability, where stability requires the heteroaromatic group to be stable enough to be exposed to water without rapid degradation.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRC-SNR$_2$, NRC(=NR)NR$_2$, NRCOOR, NRCOR, CN, C=CR, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups. Where a substituent group contains two R groups on the same or adjacent atoms (e.g., —NR$_2$, or —NR—C(O)R), the two R groups can optionally be taken together with the atom(s) in the substituent group to which the are attached to form a ring having 5-8 ring members, which can be substituted as allowed for the R itself, and can contain an additional heteroatom (N, O or S) as a ring member.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these subtituents is similar to those recited with regard to the primary substituents themselves if the substituents are not otherwise described. Thus, where an embodiment of, for example, $R^x$ is alkyl, this alkyl may optionally be substituted by the remaining substituents listed as embodiments for $R^x$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Halo", as used herein includes fluoro, chloro, bromo and iodo. Fluoro and chloro are often preferred.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are taken together with the N to which they are attached to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle", "carbocyclyl", or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but nonaromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described; for example, where W represents 1,2,3,4-tetrahydronaphth-1-yl, the group would be encompassed by an optionally substituted cycloalkyl or carbocyclic group, while the group 1,2,3,4-tetrahydronaphth-6-yl would be included within optionally substituted aromatic groups.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

Illustrative examples of heterocycles and heteroaryls include but are not limited to tetrahydropyran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4b]pyridine, piperazine, pyrazine, morpholine, thiomorpholine, imidazole, imidazolidine 2,4-dione, 1,3-dihydrobenzimidazol-2-one, indole, thiazole, benzothiazole, thiadiazole, thiophene, tetrahydro thiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

Embodiments of the Compounds

In one embodiment, the compounds of the invention have the general formula (I):

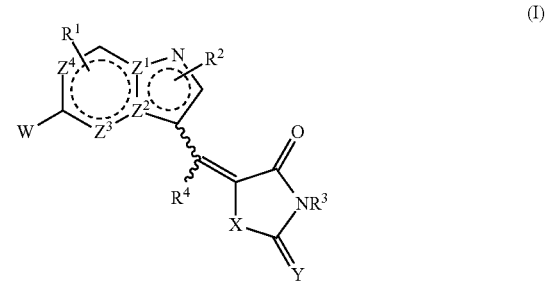

(I)

wherein the bicyclic ring system containing $Z^1$ to $Z^4$ is aromatic;

one of $Z^1$ and $Z^2$ is C, the other of $Z^1$ and $Z^2$ is N;

$Z^3$ and $Z^4$ are independently $CR^5$ or N,
where $R^5$ can be H or $R^1$;

$R^1$ is H, halo, CN, optionally substituted C1-C4 alkyl, optionally substituted C2-C4 alkenyl, optionally substituted C2-C4 alkynyl, optionally substituted C1-C4 alkoxy, or —$NR^7R^8$,
where $R^7$ and $R^8$ are each independently selected from H, optionally substituted C1-C10 alkyl, optionally substituted aryl, optionally substituted arylalkyl, optionally substituted heteroaryl, and optionally substituted heteroarylalkyl,
or $R^7$ and $R^8$ taken together with the N of —$NR^7R^8$ form an optionally substituted 5-8 membered ring that optionally contains an additional heteroatom selected from N, O and S as a ring member;

$R^2$ is H, halo, CN, or an optionally substituted group selected from C1-C4 alkyl, C2-C4 alkenyl, and C2-C4 alkynyl;

$R^3$ and $R^4$ are each independently selected from H and optionally substituted C1-C10 alkyl;

X is $NR^6$, O, or S, where $R^6$ is H or an optionally substituted group selected from C1-C4 alkyl, C2-C4 alkenyl, and C2-C4 alkynyl;

Y is O or S;

W is H, optionally substituted aryl, optionally substituted heteroaryl, or —$NR^9R^{10}$, —$OR^9$, $S(O)_nR^9$, optionally substituted carbon-linked heterocyclyl, optionally substituted C3-C8 cycloalkyl, or $CR^9R^{10}R^{11}$,
wherein n is 0, 1 or 2, $R^9$ and $R^{10}$ are each independently selected from H, optionally substituted C1-C10 alkyl, optionally substituted aryl, optionally substituted arylalkyl, optionally substituted heteroaryl, optionally substituted heteroarylalkyl, and optionally substituted heterocyclyl,
or $R^9$ and $R^{10}$ taken together with the N of —$NR^9R^{10}$ form an optionally substituted 5-8 membered ring that optionally contains an additional heteroatom selected from N, O and S as a ring member, and $R^{11}$ is selected from H, optionally substituted C1-C10 alkyl, optionally substituted aryl, optionally substituted arylalkyl, optionally substituted heteroaryl, and optionally substituted heteroarylalkyl;

or pharmaceutically acceptable salts, solvates, and/or prodrugs of these compounds.

The compounds of the invention are characterized by a bicyclic aromatic heterocyclic ring system containing two or more nitrogen atoms: one N atom is shown, and one of $Z^1$ and $Z^2$ is also N. In certain embodiments of interest, $Z^1$ is N and $Z^2$ is C; in other embodiments, $Z^1$ is C and $Z^2$ is N.

Optionally, $Z^3$ and/or $Z^4$ can also be N. In certain embodiments, they are both C; in other embodiments $Z^3$ is N and $Z^4$ is C; and in other embodiments $Z^4$ is N and $Z^3$ is C; while in other embodiments, $Z^3$ and $Z^4$ are both N.

In addition, the compounds of the invention contain another heterocyclic group linked to the bicyclic group, and the additional heterocyclic group contains an amide linkage within the ring, plus an additional carbonyl or thiocarbonyl (C=O or C=S). The additional heterocyclic group is linked to the bicyclic group through an exocyclic methylene group (an $sp^2$ carbon) that is connected to the five-membered ring of the bicyclic group.

This additional heterocyclic group contains X, which can be NR6, O or S. In certain embodiments, it is NR6, and R6 is often H or a small alkyl group, such as Me. Preferably, NR6 is NH. In other embodiments, X is O. In certain embodiments, X is S.

This additional heterocyclic group is substituted with =Y; in some embodiments, Y is O and in some embodiments Y is S.

The additional heterocyclic group also contains $NR^3$, and $R^3$ in this group can be H or a small alkyl such as Me. In some embodiments, it is a substituted alkyl group such as formyl, acetyl, propionyl, benzoyl, and the like. Preferably, $R^3$ is H.

The $sp^2$ carbon connecting the two heterocyclic groups is $CR^4$, where $R^4$ can be H or a small alkyl; in preferred embodiments, it is H.

The five-membered ring of the bicyclic group is substituted by $R^2$. This can be H, halo or a small alkyl, such as Me, Et, $CF_3$, —$CH_2OMe$, vinyl, or acetylene. In preferred embodiments, $R^2$ is H.

The six-membered ring of the bicyclic group is substituted by $R^1$. This can be a variety of groups, including H, halo or an optionally substituted alkyl, amine or alkoxy group. In some embodiments, it is H, halo, or a small alkyl, such as Me, Et, $CF_3$, —$CH_2OMe$, vinyl, or acetylene. In certain embodiments, $R^1$ is H, halo, Me, NHMe, $NMe_2$, $CF_3$, or CN. In other embodiments, $R^1$ is —$NR^7R^8$. In other embodiments, $R^8$ is a C3-6 cycloalkyl.

The six-membered ring of the bicyclic group is also substituted by a group W. This can represent a range of different features while retaining the desired protein kinase modulatory activities. In certain embodiments, W is an optionally substituted aryl or heteroaryl group, often selected from phenyl, pyridyl, pyrimidinyl, and pyrazinyl. In particular, it can be an optionally substituted phenyl group. In specific embodiments, W is phenyl substituted with up to two substituents; in certain embodiments, the phenyl group is substituted by at least one group other than H, such as F, Cl, Me, $CF_3$, CN, OMe, COOH, or COOMe, at the ortho or meta position relative to the point at which the phenyl is connected to the bicyclic group.

Specific embodiments of the substituted phenyl that can be W include 2-fluorophenyl, 3-fluorophenyl, 3-carboxyphenyl, and 3-(COOMe)-phenyl.

In other embodiments, W can be a group of the formula —$NR^9R^{10}$, where $R^9$ and $R^{10}$ are as described above. Typically, $R^9$ and $R^{10}$ are not both H. In certain of these embodiments, $R^9$ is H, Me, or an acyl group such as formyl, acetyl, methoxyacetyl, benzoyl, or trifluoroacetyl; such acylated compounds may be active as kinase inhibitors, or they can serve as prodrugs for compounds wherein $R^9$ is H. In these embodiments, $R^{10}$ can be an optionally substituted alkyl group, or an aryl or heteroaryl group, such as phenyl, pyridinyl, pyrimidinyl, pyrazinyl, and the like, which can be optionally substituted. Suitable optionally substituted alkyl groups include C1-C6 alkyls, e.g., methyl, ethyl, butyl, propyl, isopropyl, t-butyl, fluoroethyl, methoxyethyo, isobutyl, and the like. In certain embodiments, the aryl or heteroaryl group is substituted by at least one non-H substituent group. $R^{10}$ can also be such an aryl or heteroaryl group that is connected to $NR^9$ through a C1-C4 alkylene chain; e.g., it can be imidazolylmethyl, phenylethyl, and the like. In specific embodiments, the aryl is phenyl, and is substituted by at least one non-H substituent, often at the position that is meta or para to the point where the phenyl is connected to the N of $NR^9R^{10}$.

The substituent(s) on this aryl or heteroaryl group can be halo, C1-C4 alkyl, or C1-C4 alkoxy groups, or aryl or heteroaryl groups such as imidazole, phenyl, pyridyl, pyrazolyl, triazolyl, and the like; or they can be C5-C8 heterocyclic groups such as morpholine, piperidine, piperazine, and the like. In some embodiments, the aryl ring (e.g., phenyl) represented by $R^{10}$ is substituted with a group of the formula R'2N—(CH2)p-L-, where p is 0-3, L is a bond, O, S, or NR" (R" is H or C1-C4 alkyl), and each $R^1$ is independently H or C1-C6 alkyl that is optionally substituted, and wherein the two R' groups can optionally cyclize to form a ring, which can include an additional heteroatom (N, O or S) as a ring member. Representative examples of this version of R10 include dimethylamino; 4-methylpiperazinyl; 4-morpholinyl; 4-morpholinomethyl; 4-Me-piperazinoethyl; dimethylaminomethyl; diethylaminomethyl; dimethylaminoethoxy, and the like.

Alternatively, $R^{10}$ can be an arylalkyl or heteroarylalkyl group, such as an optionally substituted benzyl group. In certain embodiments of Formula I, $R^{10}$ is an optionally substituted carbon-linked heterocyclyl.

Alternatively, W can be —$NR^9R^{10}$, where $R^9$ and $R^{10}$ taken together with N form a ring, which in some embodiments is an optionally substituted 5-8 membered ring that can optionally contain N, O or S as an additional ring member. Exemplary rings include piperidine, piperazine, homopiperazine, morpholine, thiomorpholine, pyrrolidine, pyrrolidinone, and the like. In certain embodiments, substituents on such rings are C1-4 alkyl or heteroaryl.

In certain embodiments of Formula I, W is H.

In Formula I, X and Y each represent a heteroatom, and they can be the same or they can be different. In some embodiments, Y is O, while X is S or NH or NMe or O; in other embodiments, Y is S, while X is S, or NH, or NMe or O. Where X is NR6, R6 can be H, methyl, ethyl, methoxyethyl, and the like; in preferred embodiments, R6 is H or it is Me.

The compounds of the invention include compounds of Formulae I that contain the features specifically described below, or any combination of these features.

In certain embodiments of Formulae I, $Z^1$ is N and $Z^2$ is C.

In certain embodiments of Formulae I, $Z^3$ is N.

In certain embodiments of Formulae I, $Z^4$ is $CR^5$.

In certain embodiments of Formulae I, X is $NR^6$ or S.

In certain embodiments of Formulae I, $R^2$ is H or Me.

In certain embodiments of Formulae I, $R^3$ and $R^4$ are both H.

In certain embodiments of Formulae I, $R^1$ is H, Me, halo, OMe, or $CF_3$.

In certain embodiments of Formula I, $R^1$ is —$NR^7R^8$, wherein $R^8$ is C3-6 cycloalkyl.

In certain embodiments of Formulae I, Y is O.

In certain embodiments of Formulae I, Y is S.

In certain embodiments of Formulae I, W is —NH-A, wherein A is optionally substituted phenyl. In alternative embodiments of the above compounds, W is optionally substituted aryl or optionally substituted heteroaryl. In specific embodiments of this type, W can be optionally substituted phenyl. In certain embodiments of Formula I, W is H. In other embodiments of Formula I, W is —$N^9R^{10}$ wherein $R^{10}$ is an optionally substituted heterocyclyl.

In another embodiment, the compounds of Formula (I) have structural Formula (II) or (II') as shown below (including IIa', IIb, IIb', II-TH, and II-TH'). These compounds are typically more selective for CK2, and are highly potent on CK2.

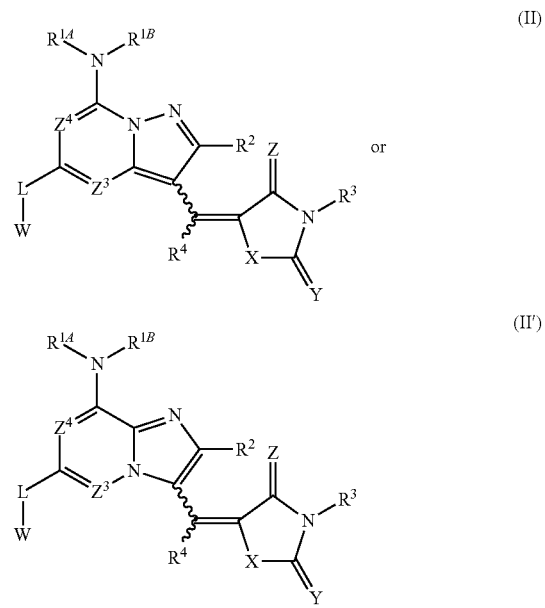

wherein:
$Z^3$ and $Z^4$ each independently represent N or $CR^5$, or CH;
each $R^5$ is independently selected from halo, —CN, —R, —OR, —S(O)$_n$R, —COOR, —$CONR_2$, and —$NR_2$,
wherein each R is independently selected from H and optionally substituted C1-C4 alkyl, or alternatively, the two R groups, taken together with the nitrogen atom to which they are attached, form an optionally substituted 5 or 6 membered heterocyclic ring that optionally contains one or more additional heteroatom selected from N, O and S as a ring member;
$R^2$, $R^3$ and $R^4$ are each independently selected from H and optionally substituted C1-C10 alkyl;
X represents O, S, or $NR^2$;
Y is O or S or $NR^{10}$;
where $R^{10}$ is selected from H, CN, optionally substituted C1-C4 alkyl, optionally substituted C2-C4 alkenyl, optionally substituted C2-C4 alkynyl, optionally substituted C1-C4 alkoxy, and —$NR^7R^8$,
Z is O or S;
L is a bond, —$CR^7$=$CR^8$—, —C≡C—, —$NR^7$—, —O—, —S(O)$_n$—, —$(CR^7R^8)_m$—, $NR^7$—, —$(CR^7R^8)_m$—O—, or —$(CR^7R^8)_m$—S(O)$_n$—;
W is optionally substituted C1-C10 alkyl, optionally substituted C1-C10 heteroalkyl, optionally substituted aryl, optionally substituted heteroaryl, —$NR^7R^8$, —$OR^7$, —S(O)$_n R^7$, —$CONR^7R^8$, optionally substituted heterocyclyl, optionally substituted carbocyclyl, optionally substituted C2-C10 alkenyl, optionally substituted C2-C10 alkynyl, or —$CR^7R^8R^9$;
where each $R^7$ and $R^8$ and $R^9$ is independently selected from H, optionally substituted C1-C10 alkyl, optionally substituted heteroalkyl, optionally substituted carbocyclyl, optionally substituted heterocyclyl, optionally substituted carbocyclylalkyl, optionally substituted heterocyclylalkyl, optionally substituted aryl, optionally substituted arylalkyl, optionally substituted heteroaryl, and optionally substituted heteroarylalkyl;
or $R^8$ and $R^9$, taken together with the carbon atom to which they are attached, form =O (oxo) or =N—$OR^7$ or =N—CN;

or $R^7$ and $R^8$, taken together on a single carbon atom or on adjacent connected carbon atoms of $(CR^7R^8)_m$ whether alone or as part of another group, form a 3 to 8 membered carbocyclic ring or heterocyclic ring;

or $R^7$ and $R^8$, taken together with the nitrogen atom to which they are attached, form an optionally substituted 5 to 10 membered heterocyclic or heteroaryl ring that optionally contains one or more additional heteroatom selected from N, O and S as a ring member;

provided that no more than one of or $R^7$ and $R^8$ in —$NR^7R^8$ is selected from the group consisting of alkoxy, alkylamino, dialkylamino and heterocyclyl;

each n is independently is 0, 1 or 2;

each m is independently 1, 2, 3 or 4; and $R^{1A}$ and $R^{1B}$ are each independently selected from H, optionally substituted C1-C10 alkyl, optionally substituted heteroalkyl, optionally substituted heterocyclyl, optionally substituted carbocyclyl, optionally substituted carbocyclylalkyl, optionally substituted heterocyclylalkyl, optionally substituted aryl, optionally substituted arylalkyl, optionally substituted heteroaryl, or optionally substituted heteroarylalkyl;

or $R^{1A}$ and $R^{1B}$, taken together with the nitrogen atom to which they are attached, form an optionally substituted 5- to 8-membered monocyclic or 5- to 10-membered bicyclic heteroaryl or heterocyclic ring containing up to two additional heteroatoms selected from N, O and S as ring members;

and pharmaceutically acceptable salts, solvates, and/or prodrugs of these compounds.

In one embodiment of Formula (II) or (II'), the optionally substituted carbocyclyl is an optionally substituted C3-C8 cycloalkyl; the optionally substituted carbocyclylalkyl is an optionally substituted C4-C10 cycloalkylalkyl; and the optionally substituted heteroalkyl is an optionally substituted C1-C6 alkoxy, optionally substituted C1-C6 alkylamino, or optionally substituted C1-C6 dialkylamino.

In one embodiment of Formula (II) or (II'), -L-M is —$NHR^7$, —$OR^7$, or —$S(O)_nR^7$; n is 0, 1, or 2; and $R^7$ is optionally substituted C1-C10 alkyl, optionally substituted heteroalkyl, optionally substituted aryl, optionally substituted heteroaryl, optionally substituted arylalkyl, optionally substituted heteroarylalkyl, optionally substituted carbocyclyl, optionally substituted heterocyclyl, optionally substituted carbocyclylalkyl, or optionally substituted heterocyclylalkyl.

In one embodiment of Formula (II) or (II'), -L-M is —$NR^7R^8$; and $R^7$ and $R^8$, taken together with the nitrogen atom to which they are attached, form an optionally substituted heterocyclyl which optionally contains one or more additional heteroatom as ring members.

In one embodiment of Formula (II) or (II'), -L-M is optionally substituted aryl, optionally substituted heteroaryl, optionally substituted carbocycyl, or optionally substituted heterocyclyl.

In one embodiment of Formula (II) or (II'), $R^{1A}$ and $R^{1B}$ are independently selected from H, optionally substituted C1-C10 alkyl, optionally substituted heterocyclyl, optionally substituted cycloalkyl, optionally substituted cycloalkylalkyl, optionally substituted heterocyclylalkyl, optionally substituted arylalkyl, or an optionally substituted 5-6 membered aryl ring containing up to two heteroatoms as ring members. Preferably the amine group —$NR^{1A}R^{1B}$ in compounds of Formulas (II) or (IIa) and II' or IIa' is not —$NH_2$, —NHMe, or —$NMe_2$.

Suitably, $R^{1A}$ can be selected from H, C1-C4 alkyl, and C1-C6 acyl, where the alkyl and acyl are optionally substituted. In many embodiments, $R^{1A}$ is H; in other embodiments, it is sometimes Me, or an optionally substituted C1-C4 alkyl. In some embodiments, $R^{1A}$ is an optionally substituted C1-C6 acyl group, particularly one that can readily be cleaved under mild conditions, such as methoxyacetyl, hydroxyacetyl, or an alpha-amino acyl group, which can act as pro-drugs for the compounds where $R^{1A}$ is H.

Often, $R^{1A}$ in this amine group —$NR^{1A}R^{1B}$ is H, and $R^{1B}$ is a substituted or unsubstituted group selected from C2-C8 alkyl, C3-C8 cycloalkyl, aryl, arylalkyl, heteroaryl, heteroarylalkyl, heterocyclyl, and heterocyclylalkyl. Typically, this aryl is phenyl; heteroaryl refers to, a 5-6 membered ring containing up to three heteroatoms selected from N, O and S as ring members; and heterocyclyl refers to a 3-8 membered ring containing at least one heteroatom, and optionally two heteroatoms for 6-8 membered rings, as ring members, where the heteroatoms are selected from N, O and S; and the -alkyl- versions of these (arylalkyl, heteroarylalkyl, and heterocyclylalkyl) typically comprise the specified cyclic group linked via an alkylene linker such as $(CH_2)_{1-4}$ to the nitrogen atom of $NR^{1A}R^{1B}$. In certain embodiments, $R^{1B}$ comprises at least one ring having 3-8 ring members.

Examples of suitable $R^{1B}$ groups include ethyl, isopropyl, t-butyl, cyclopropyl, cyclobutyl, cyclopentyl, tetrahydrofuranyl, piperidinyl, pyrrolidinyl, cyclopropylmethyl, cyclobutylmethyl, phenyl, and the like, each of which can be unsubstituted or substituted with up to three substituents. Some preferred embodiments include cyclopropyl, isopropyl, t-butyl, and cyclobutyl.

Specific examples of substituted $R^{1B}$ groups include 2,2,2-trifluoroethyl, 2-methoxy-ethyl, 2-ethoxyethyl, methoxymethyl, 2-aminoethyl, 2-(N-morpholino)ethyl, 3-hydroxypropyl, 3-dimethylaminopropyl, 3-methoxypropyl, 2-hydroxyethyl, 2-hydroxypropyl, acetyl, benzoyl, phenyl substituted with —COOH, —COOMe, —COOEt, —$CONMe_2$, and

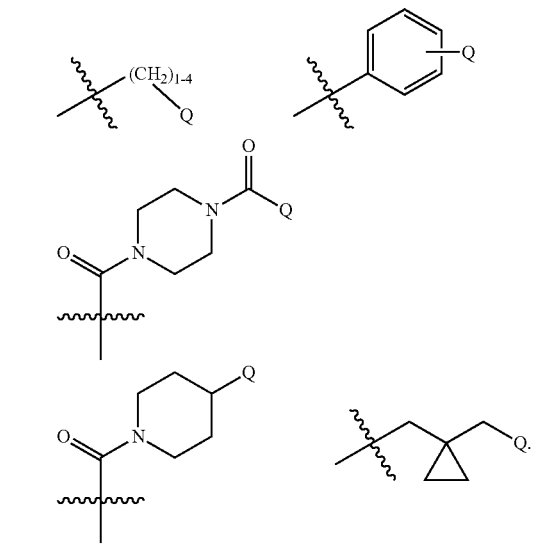

where Q represents a functional group such as —OH, —OR, —COOH, —COOR, —$NH_2$, —NHR, —$NR_2$, —$CONH_2$, —CONHR, —$CONR_2$, —SR, —S(O)R, —$SO_2R$, —$SONR_2$, —C(O)R, —NRC(O)R, —NRC(O)OR, —OC(O)OR, —OC(O)$NR_2$, wherein each R is independently H or an optionally substituted C1-C4 alkyl group, and two R present on the same functional group can be taken together to form a 5-8 membered optionally substituted ring, which can contain up to two heteroatoms selected from N, O and S as ring members.

Where one or more substituents are present on these R, $R^{1A}$, or $R^{1B}$ groups, often the substituents are selected from halo, OR", N(R")$_2$, S(O)$_m$,R", COOR", CON(R")$_2$, CN, phenyl, pyridinyl, pyrrolidinyl, and the like, where each R" is independently selected from H and C1-C4 alkyl, optionally substituted with one or more groups selected from OH, C1-C4 alkoxy, halo, NH$_2$, C1-C4 alkylamine, and di(C1-C4) alkyl amine, and piperidine, pyrrolidine, morpholine, or furan; and m is 0-2. Frequently, $R^{1B}$ comprises at least one ring, such as a heterocylyl or cycloalkyl or aryl ring. A preferred embodiment of $R^{1B}$ in the amine group —NR$^{1A}$R$^{1B}$ in Formulas (II) and (II') is cyclopropyl, and a preferred embodiment of $R^{1A}$ is H.

In compounds of Formula (II) and (II') and (IIa) or (IIa'), L can be a bond, —CR$^7$=CR$^8$—, —C≡C—, —NR$^7$—, —O—, —S(O)$_n$—, or (CR$^7$R$^8$)$_n$, or it can be —(CR$^7$R$^8$)$_m$—NR$^7$—, —(CR$^7$R$^8$)$_m$—O—, or —(CR$^7$R$^8$)$_n$—S(O)$_n$. Typically, where L is attached to W at a heteroatom of W, L will be a bond or one of the hydrocarbon linkers, such as (CR$^7$R$^8$)$_m$. However, embodiments of the invention include compounds wherein -L-W is a group of the formula —NR$^7$—NR$^7$R$^8$ as well. Some examples of suitable groups for L include —CH=CH—, —C≡C—, —NH—, NMe, —O—, —S—, —S(O)$_2$—, and —CH$_2$NH—. Where L is attached to W at a heteroatom of W, L is often CH$_2$ or (CH$_2$)$_2$.

Figure 2:
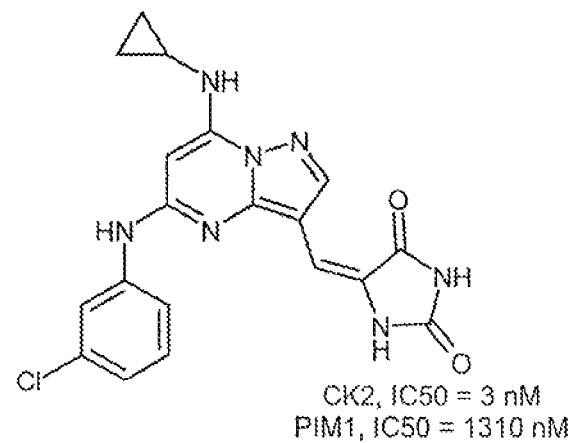
FIG. 2 depicts a compound of Formula II as described herein, and shows that it is more potent on CK2 (3 nM), less potent on PIM1 (1310 nM), and generally more selective towards various kinases than is the compound in FIG. 1.
Figure 2:
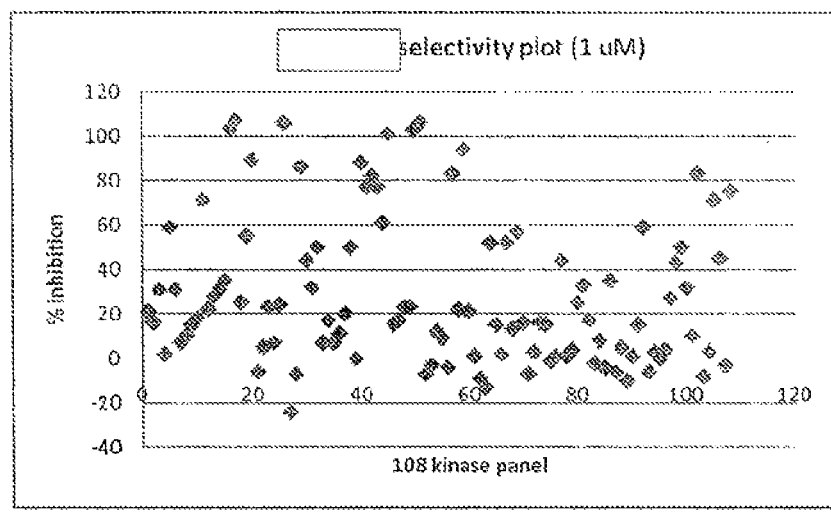

FIGS. 1 and 2 illustrate the improved selectivity found for compounds of Formula II. FIG. 1 depicts a compound of Formula I that is a potent inhibitor of CK2. In assays for inhibition of a panel of 108 kinases, this compound at a comcentration of 1 micromolar is a potent inhibitor of many of the various kinases. By comparison, FIG. 2 shows a similar compound of Formula II, having a substituted amine group as an additional substituent on the six-membered ring of the bicyclic core. This compound is more potent as an inhibitor of CK2 than the similar-looking compound in FIG. 1; it is less potent as an inhibitor of PIM1; and as the kinase panel assay shows, it is less potent on many other kinases than the compound of FIG. 1 is. Relatively few kinases are inhibited by more than 80% with the amine-substituted compound of Formula II, when compared to the proportion of kinase inhibitors showing similar levels of inhibition by the non-aminated compound of Formula I. This improved selectivity is observed for a wide array of amine substituent groups, as the data in Tables 1 and 2 and additional data throughout the application demonstrate.

Specific embodiments of the compounds of the invention include compounds of Formula IIa and/or IIa':

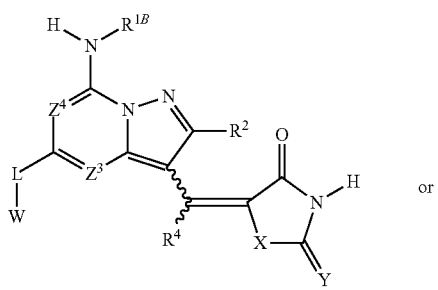

(IIa)

or

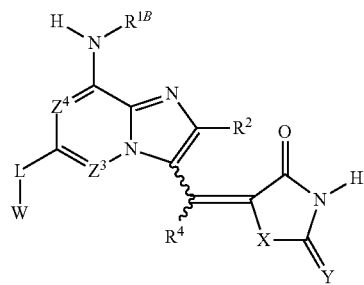

(IIa')

wherein,
$R^2$ is H, CH$_3$ or CF$_3$;
$Z^3$ and $Z^4$ each independently represent N or CR$^5$, or CH;
where each R$^5$ is independently selected from halo, —CN, —R, —OR, —S(O)$_n$R, —COOR, —CONR$^2$, and —NR$_2$,
wherein each R is independently selected from H and optionally substituted C1-C4 alkyl, or the two R groups, taken together with the nitrogen atom to which they are attached, form an optionally substituted 5- or 6-membered heterocyclic ring which contains one or more additional heteroatom selected from N, O and S as a ring member;
$R^4$ is H, CH$_3$ or CF$_3$;
X is O, S or NH;
Y is O or S;
$R^{1B}$ is selected from H, optionally substituted C1-C10 alkyl, optionally substituted heteroalkyl, optionally substituted heterocyclyl, optionally substituted cycloalkyl, optionally substituted cycloalkylalkyl, optionally substituted heterocyclylalkyl, optionally substituted arylalkyl, or an optionally substituted heteroaryl;
L is a bond, —NR$^7$—, —O—, —S(O)$_n$—, (CR$^7$R$^8$)$_m$, or —(CR$^7$R$^8$)$_m$—NR$^7$—;
m is 1, 2, 3, or 4;
n is 0, 1, or 2;
W is selected from optionally substituted aryl, optionally substituted heteroaryl, and —NR$^7$R$^8$,
where each R$^7$ and R$^8$ is independently selected from H, optionally substituted C1-C6 alkoxy, optionally substituted C1-C6 alkylamino, optionally substituted C1-C6 dialkylamino, optionally substituted heterocyclyl, optionally substituted C1-C10 alkyl, optionally substituted C3-C8 cycloalkyl, optionally substituted C4-C10 cycloalkylalkyl, optionally substituted aryl, optionally substituted arylalkyl, optionally substituted heteroaryl, and optionally substituted heteroarylalkyl;
and R$^7$ and R$^8$, taken together on a single carbon atom or on adjacent connected carbon atoms of (CR$^7$R$^8$)$_m$, whether alone or as part of another group, form a 3- to 8-membered ring that contains one or more heteroatoms as ring members;
or R$^7$ and R$^8$, taken together with the nitrogen atom to which they are attached, form an optionally substituted 5- to 10-membered heterocyclic or heteroaryl ring system that optionally contains an additional heteroatom selected from N, O and S as a ring member; and
provided that no more than one of or R$^7$ and R$^8$ in —NR$^7$R$^8$ is selected from the group consisting of alkoxy, alkylamino, dialkylamino and heterocyclyl.

In the foregoing compounds of Formula (IIa) or (IIa'), $R^2$ and $R^4$ are selected from H, CH$_3$ and CF$_3$. In some embodiments $R^2$ is H. In some embodiments, $R^4$ is H.

In the foregoing compounds of Formula (IIa) or (IIa'), Y is O or S. In preferred embodiments, Y is O.

In the foregoing compounds of Formula (IIa) or (IIa'), X can be S, O or NH. Frequently, X is NH or S. In certain embodiments, X is NH.

In the foregoing compounds of Formula (IIa) or (IIa'), $Z^3$ and $Z^4$ are often selected from N and CH. In some embodiments, one of these ring members is N and the other is CH. In alternative embodiments, both $Z^3$ and $Z^4$ are N. In still other embodiments, $Z^3$ and $Z^4$ are both CH.

In certain compounds of Formula IIa, $Z^3$ can be N while $Z^4$ is CH; or $Z^3$ can be N while $Z^4$ is also N. In certain compounds of Formula II', $Z^3$ can be CH while $Z^4$ is N;

alternatively, $Z^3$ can be N while $Z^4$ is N or CH.

In the foregoing compounds of Formula (IIa) or (IIa'), $R^3$, when present, can be H or optionally substituted alkyl. Often, $R^3$ is H.

Z can be O or S; in preferred embodiments, Z is O.

When present, m is frequently 1 or 2.

In these compounds of Formula IIa and/or IIa', $R^2$ and $R^4$ are frequently both H.

In the foregoing compounds of Formula IIa and/or IIa', $R^{1B}$ can be optionally substituted C1-C10 alkyl, optionally substituted heterocyclyl, optionally substituted cycloalkyl, optionally substituted cycloalkylalkyl, optionally substituted heterocyclylalkyl, optionally substituted arylalkyl, or an optionally substituted 5-6 membered aryl ring containing up to two heteroatoms as ring members. In some embodiments, $R^{1B}$ is a C3-C6 cycloalkyl or a 3-6 membered heterocyclic group such as piperidine or a C1-C3 alkyl group substituted with one of these rings, and it is optionally substituted. Specific embodiments of $R^{1B}$ include cyclopropyl, cyclopropylmethyl, 4-piperidinyl, and substituted 4-piperidinyl, e.g. 4-piperidinyl substituted with an acyl group, such as acetyl, at N-1. Other embodiments include optionally substituted phenyl.

In the foregoing compounds of Formula (IIa) or (IIa'), -L-M is —$NHR^7$, —$OR^7$, or —$S(O)_nR^7$; n is 0, 1, or 2; and $R^7$ is optionally substituted C1-C10 alkyl, optionally substituted heteroalkyl, optionally substituted aryl, optionally substituted heteroaryl, optionally substituted arylalkyl, optionally substituted heteroarylalkyl, optionally substituted carbocyclyl, optionally substituted heterocyclyl, optionally substituted carbocyclylalkyl, or optionally substituted heterocyclylalkyl.

In the foregoing compounds of Formula (IIa) or (II'), -L-M is —$NR^7R^8$; and $R^7$ and $R^8$, taken together with the nitrogen atom to which they are attached, form an optionally substituted heterocyclyl which optionally contains one or more additional heteroatom as ring members.

In the foregoing compounds of Formula (IIa) or (IIa'), -L-M is optionally substituted aryl, optionally substituted heteroaryl, optionally substituted carbocycyl, or optionally substituted heterocyclyl.

In the foregoing compounds of Formula IIa and/or IIa', L is typically a bond or NH. When L is NH, W can be an optionally substituted group selected from phenyl, phenylalkyl, heterocyclyl, cycloalkyl and cycloalkylalkyl.

In the foregoing compounds of Formula IIa and/or IIa', W is frequently an optionally substituted phenyl, arylalkyl, cycloalkyl, heteroaryl, cycloalkylalkyl, or heterocyclic group. Specific examples include optionally substituted phenyl; optionally substituted phenylmethyl; optionally substituted 1-phenylethyl; cyclopropylmethyl; 1-cyclopropylethyl; piperidinyl; and morpholinyl. Some preferred substituents for the pheyl groups of W include halo, CN, Me, $CF_3$, OMe, $OCF_3$, and heteroaryl groups such as pyrazole or pyrrole or imidazole.

When L is a bond, W is frequently an optionally substituted aryl, heteroaryl or heterocyclyl group. Surprisingly high flexibility has been demonstrated among the groups that can be represented by W in Formula II, II', and (IIa) or (IIa'). Aryl and heteroaryl groups are suitable for W, and can be unsubstituted or substituted. Examples of suitable aromatic groups include phenyl, pyridinyl, pyrimidinyl, thienyl (thiophene ring), furanyl, oxazole, isoxazole, thiazole, isothiazole, oxadiazole, thiadiazole, triazole, and the like, as well as indole, benzimidazole, benzofuran, benzopyrazole, imidazole, pyrrole, pyrazole, and the like. Note that the latter group (indole, benzimidazole, benzofuran, benzopyrazole, imidazole, pyrrole, pyrazole) contain a 5-membered nitrogen heterocycle, and can be linked to L through either C or N as a result. In some embodiments, W represents one of these aromatic groups that comprises a 5-membered ring, and W is attached via N of the 5-membered ring to L, and L is a bond so that W is effectively attached directly to the ring containing $Z^3$ and $Z^4$. Suitable substituents for all of these aryl or heteroaryl groups include those described herein as suitable for such aromatic groups.

When W is an aromatic group, L is sometimes a bond, NH, or O. A particular embodiment of interest is a compound of Formula II, II', (IIa) or (IIa'), wherein L is a bond or NH, and W is an optionally substituted phenyl or optionally substituted thienyl ring. In embodiments where L is a bond, it is often desirable for the position of each ring atom of the aryl ring that is adjacent to the attachment point for L to be unsubstituted (i.e., any adjacent carbon(s) would be CH), so the optional substituents on W in such compounds are often, when present, located at positions 3, 4, or 5 of a phenyl ring (assuming position 1 attaches to L), or to positions 4 or 5 of a thienyl ring when L attaches to position 2, and at position 5 of the thienyl group when L attaches at position 3. Examples of these W groups include:

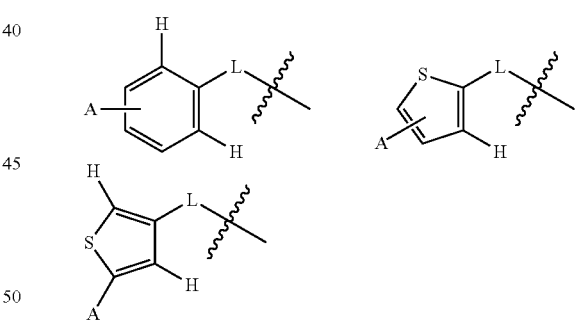

where each A represents the presence of an optional substituent (or more than one where the ring valence permits more) on a carbon not having an explicit H attached.

Where W is an aromatic group, a wide array of substituents are well tolerated and provide high levels of kinase activity. Suitable substituents include those described herein as suitable for placement on aromatic groups in general. Some of the suitable substituents for these aromatic group W' s include halo (especially F or Cl), alkyl (e.g., C1-C4 alkyl, such as methyl, ethyl, isopropyl or cyclopropyl); alkoxy (especially C1-C4 alkyloxy); haloalkyl (e.g., $CF_3$, —$CH_2CF_3$); haloalkoxy (e.g. —$OCF_3$, —$OCF_2H$, $OCH_2CF_3$, and the like); CN, —OH, alkynyl —CCH, CCMe, and the like); heterocyclylmethyl (e.g., N-piperidinylmethyl, N-pyrrolidinylmethyl, N-morpholinylmethyl, etc.); hydroxymethyl, aminomethyl, dimethylaminomethyl, methylaminomethyl; substituted C1-C4 alkoxy such as methoxyethoxy, ethoxymethoxy, trifluoroethoxy, 2-(N-morpholino)ethoxy, 2-(N-pyrrolidinyl)ethoxy, 2-(piperidinyl)ethoxy, and the like; acyl groups of the formula —C(O)—X, where X represents —OR, —NR$_2$, or —R, where each R is independently selected from H or an optionally substituted member selected from C1-C4 alkyl, 3-8 membered cycloalkyl or heterocyclyl, and 5-6 membered aryl or heteroaryl containing up to 3 heteroatoms selected from N, O and S as ring members, and where two R on one group (e.g., two R's of —NR$_2$) can be taken together to form an optionally substituted 5-8 membered ring containing up to two heteroatoms selected from N, O and S as ring members; heterocyclic groups such as morpholine, tetrahydrofuran, piperidine, pyrrolidine, 4-Me-N-piperazinyl, N-piperazinyl, 4-acetyl-N-piperazinyl, and the like.

Commonly, an aromatic group W will have 1-2 substituents, or it will be unsubstituted; and commonly the substituents, when present, are positioned as described above, so that the ring carbon(s) adjacent to where L is attached are unsubstituted (CH). When L is other than a bond, the substituents on W can be at any position, and often will be at the positions ortho and/or para to the point of attachment of W to L.

Alternatively, W can be a heterocyclic group such as piperidinyl, morpholinyl, pyrrolidinyl, tetrahydrofuranyl, tetrahydropyranyl, thiomorpholinyl, piperazinyl, thiolanyl, and the like, each of which can be unsubstituted or substituted with up to four substituents. Suitable substituents for these groups include those described herein as suitable for heterocyclic groups. Note that even when L is NR or NH, W can be a heterocyclic groups such as 1-piperidinyl or 4-morpholinyl where L links to a heteroatom (N) of the heterocyclic group as well as at C of the heterocyclic group.

Where L is NH, W can also be arylalkyl or cycloalkylalkyl or heterocyclylalkyl, and the alkyl portion of W can be e.g. C1-C4. Where L comprises an alkyl portion, it can be a straight chain (e.g., ethylene, propylene, butylene), or it can be a substituted alkylene chain, resulting in formation of a potentially chiral carbon linker. Where L is a chiral group of this type, e.g. when L is —CH(R)— or —CH$_2$—CH(R)— where R is not H (e.g., R is Methyl or ethyl, L can be either in an R configuration or an S configuration, where those terms are used in their conventional stereochemical sense, or it can be present as a mixture of isomers, including a racemic mixture. In some embodiments, such a chiral center present in L will be in the S configuration. In other embodiments, it can be in the R configuration.

Alternatively, W can be a group of the formula or —NR$^7$R$^8$, —OR$^7$, S(O)$_n$R$^7$, CONR$^7$R$^8$, or CR$^7$R$^8$R$^9$, where each R$^7$ and R$^8$ and R$^9$ is independently selected from H, optionally substituted C1-C10 alkyl, optionally substituted aryl, optionally substituted arylalkyl, optionally substituted heteroaryl, and optionally substituted heteroarylalkyl; or R$^7$ and R$^8$ taken together with the N of —NR$^7$R$^8$ can form an optionally substituted 5-10 membered heterocyclic or heteroaromatic ring system that optionally contains an additional heteroatom selected from N, O and S as a ring member.

In embodiments where W is —NR$^7$R$^8$, L is frequently a bond, and R$^7$ and R$^8$ taken together with the N of —NR$^7$R$^8$ can form an optionally substituted 5-10 membered heterocyclic or heteroaromatic ring system that optionally contains an additional heteroatom selected from N, O and S as a ring member. Suitable such rings include e.g., pyrrolidinyl, piperidinyl, piperazinyl, thiomorpholinyl, diazepinyl, and morpholinyl, each of which can be substituted to the extent substitution forms relatively water-stable structures. Suitable substituents include, for example, oxo (═O), C1-C4 alkyl, —OH, —CN, halo (especially F or Cl), COOR, CONR$_2$, SR, —S(O)R, —SO$_2$R, —NR$_2$, hydroxyalkyl, —OR, methoxyalkyl (e.g., methoxymethyl), where each R is independently H or optionally substituted C1-C4 alkyl, and where two R on one group can be taken together to form an optionally substituted 5-8 membered ring containing up to two heteroatoms selected from N, O and S as ring members.

In some embodiments of the compounds of Formula (II) and (II') and (IIa) or (IIa'), -L-W is a group of the formula —NH—Ar, where Ar represents an optionally substituted aromatic group. Suitable aromatic rings for this group include phenyl, naphthyl, pyridinyl, pyrimidinyl, thienyl (thiophene ring), furanyl, indolyl, benzofuranyl, benzothienyl, benzopyrazolyl, benzimidazolyl, benzoxazole, benzothiazole, and the like. Suitable substituents for these aryl or heteroaryl groups include those described herein as suitable for such aromatic groups.

In some embodiments, W is an optionally substituted cycloalkyl group, typically containing 3-8 ring atoms in a monocyclic structure, or 8-10 ring atoms in a bicyclic structure. Examples include 1,2,3,4-tetrahydronaphth-1-yl, cyclopropyl, cyclobutyl, cyclopentyl, cyclohexyl, decalin, and the like. These groups are optionally substituted as described herein; in some embodiments, the cycloalkyl ring will be substituted with one or more (e.g., up to three) groups selected from halo, hydroxy, oxo (═O), COOR, CONR$_2$, SR, —S(O)R, —SO$_2$R, —NR$_2$, hydroxyalkyl, —OR, methoxyalkyl (e.g., methoxymethyl), C1-C4 alkyl, where each R is independently H or optionally substituted C1-C4 alkyl, and where two R on one group can be taken together to form an optionally substituted 5-8 membered ring containing up to two heteroatoms selected from N, O and S as ring members.

Particular embodiments of the compounds of the invention include thiophene-containing compounds of Formula (II-Th) and (II-Th'):

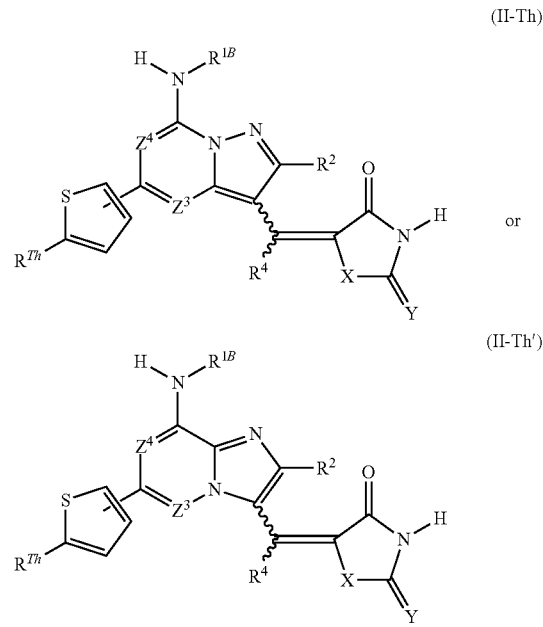

where R$^{Th}$ is selected from H, halo, optionally substituted C1-C6 alkyl, CN, S(O)$_{0-2}$R, —SO$_2$NR$_2$, COOR, CONR$_2$, and C(O)R, where each R is independently H, halo, CN, or an optionally substituted member selected from the group consisting of C1-C6 alkyl, C1-C6 alkoxy, C1-C6 alkylamino, di(C1-C6)alkylamino, C3-C8 cycloalkyl, C4-C10 cycloalkylalkyl, C5-C8 heterocyclyl, C6-C10 heterocyclylalkyl, aryl, arylalkyl, C5-C6 heteroalkyl, and C6-C10 heteroalkylalkyl;

and two R on the same atom or adjacent connected atoms can form an optionally substituted heterocyclic ring that can contain an additional heteroatom selected from N, O and S as a ring member;

and other structural features are as defined for Formula IIa above.

The thienyl (thiophene) ring in Formulas II-Th and II-Th' can be attached to the bicyclic core at either position 2 or position 3 of the thiophene ring, when the position substituted with $R^{Th}$ is defined as position 5, and the ring sulfur is position 1. In some embodiments, connection is at position 2 of the thienyl group, and in alternative embodiments, connection is at position 3 of the thienyl group.

In these compounds of Formulas II-Th and II-Th', $R^2$ and $R^4$ are frequently both H.

In the foregoing compounds of Formulas II-Th and II-Th', X is preferably NH.

In the foregoing compounds of Formulas II-Th and II-Th', Y is frequently O.

In the foregoing compounds of Formulas II-Th and II-Th', $Z^3$ is often N.

In the foregoing compounds of Formulas II-Th and II-Th', $Z^4$ can be CH or N.

In the foregoing compounds of Formulas II-Th and II-Th', $R^{1B}$ can be optionally substituted C1-C10 alkyl, optionally substituted heterocyclyl, optionally substituted cycloalkyl, optionally substituted cycloalkylalkyl, optionally substituted heterocyclylalkyl, optionally substituted arylalkyl, or an optionally substituted 5-6 membered aryl ring containing up to two heteroatoms as ring members. In some embodiments, $R^{1B}$ is a C3-C6 cycloalkyl or a 3-6 membered heterocyclic group such as piperidine or a C1-C3 alkyl group substituted with one of these rings, and it is optionally substituted. Specific embodiments of $R^{1B}$ include cyclopropyl, cyclopropylmethyl, 4-piperidinyl, and substituted 4-piperidinyl, e.g. 4-piperidinyl substituted with an acyl group, such as acetyl, at N-1. Other embodiments include optionally substituted phenyl.

In these compounds, $R^{TH}$ can be halo (F, Cl, Br), $CF_3$, CN, C1-C6 alkyl, C1-C3 alkyl substituted with heterocyclyl or heterocyclylamino, COOR, or $COONR_2$.

In one embodiment of the present invention, the compounds of Formula (IIa) or (IIa') have structural Formula (IIb) or (IIb'):

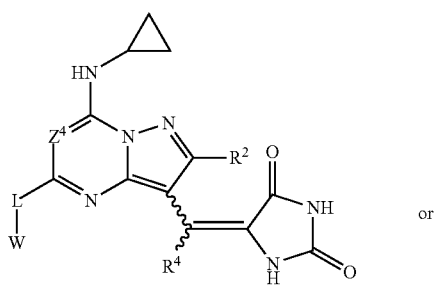

(IIb)

or

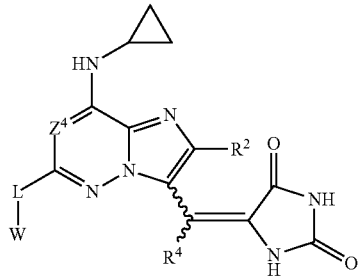

(IIb')

wherein $R^2$ and $R^4$ are independently H, $CH_3$ or $CF_3$;

$Z^4$ is N or CH;

-L-M is $-NR^{8A}R^7$, $-NHR^7$, $-OR^7$, or $-S(O)_nR^7$;

n is 0, 1, or 2; and $R^7$ is optionally substituted C1-C10 alkyl, optionally substituted heteroalkyl, optionally substituted aryl, optionally substituted heteroaryl, optionally substituted arylalkyl, optionally substituted heteroarylalkyl, optionally substituted carbocyclyl, optionally substituted heterocyclyl, optionally substituted carbocyclylalkyl, or optionally substituted heterocyclylalkyl, optionally substituted aryl, optionally substituted heteroaryl, optionally substituted carbocycyl, or optionally substituted heterocyclyl; or $R^7$ and $R^{8A}$, taken together with the nitrogen atom to which they are attached, form an optionally substituted heterocyclyl which optionally contains one or more additional heteroatom as ring members.

In one embodiment of the present invention, the compounds of Formula (II) have structural Formula (IIc):

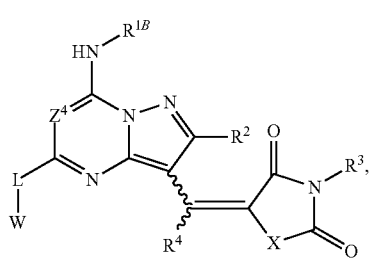

(IIc)

wherein,

X is O, S, or $NR^2$;

$R^3$ is $-(CH_2)-X^C$;

$X^C$ is hydroxyl or a group having structural formula (a), (b), (c), or (d):

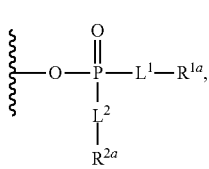

(a)

-continued

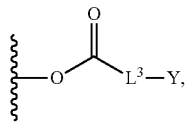

(b)

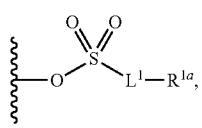

(c)

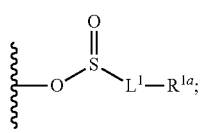

(d)

$L^1$ and $L^2$ are each independently a covalent bond, —O—, or —NR$^{3a}$—;

R$^{1a}$ and R$^{2a}$ are each independently hydrogen, alkyl, heteroalkyl, heteroaryl, heterocyclyl, alkenyl, alkynyl, arylalkyl, heteroarylalkyl, heterocyclylalkyl, -alkylene-C(O)—O—R$^{4a}$, or -alkylene-O—C(O)—O—R$^{4a}$; and R$^{3a}$ and R$^{4a}$ are each independently hydrogen, alkyl, heteroalkyl, cyclylalkyl, heterocyclyl, aryl, heteroaryl, alkenyl, alkynyl, arylalkyl, heterocyclylalkyl, or heteroarylalkyl;

$L^3$ is a covalent bond or alkylene;

Y is OR$^{5a}$, NR$^{5a}$R$^{6a}$, or C(O)OR$^{7a}$, provided that when Y is C(O)OR$^{7a}$, then L$^3$ is not a covalent bond; and R$^{5a}$, R$^{6a}$, and R$^{7a}$ are each independently hydrogen, alkyl, arylalkyl, aryl, heteroalkyl, alkylheteroaryl, heterocyclyl, or heteroaryl; or alternatively, R$^{5a}$ and R$^{6a}$, taken together with the nitrogen atom to which they are attached, form a heterocyclyl ring optionally containing one o more additional heteroatom independently selected from N, O, and S.

In one embodiment of Formula (IIc), X is NR$^2$; R$^3$ is —(CH$_2$)—X$^C$; and X$^C$ is hydroxyl or a group having structural formula (b):

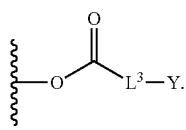

In one embodiment of Formula (IIc), R$^2$ and R$^4$ are hydrogen.

In one embodiment of Formula (IIc), R$^{1B}$ is an optionally substituted C1-C10 alkyl, cycloalkyl, or cycloalkylalkyl.

In one embodiment of Formula (IIc), -L-W is —OR$^7$ or —NR$^7$R$^8$.

In one embodiment of Formula (IIc), R$^7$ is optionally substituted aryl or optionally substituted heteroaryl; and R$^8$ is H.

In one embodiment of Formula (IIc), R$^8$ is optionally substituted phenyl.

In one embodiment of Formula (IIc), L$^3$ is a covalent bond; and Y is OR$^{5a}$ or NR$^{5a}$R$^{6a}$.

The compounds of the invention also include those enriched in isotopes of the atoms involved in the structures described herein. For example, the compounds as described are intended to include versions wherein one or more H atoms is preferentially enriched in a heavier hydrogen isotope (deuterium or tritium). In particular, where any of the foregoing compounds contains a methyl group (Me), an enriched methyl group containing deuterium at levels far above natural abundance can be used. For example, —CH$_3$ could be replaced by —CH$_2$D or —CHD$_2$ or —CD$_3$, where each D represents deuterium present in place of $^1$H, and indicates that D is present instead of $^1$H in at least about 50% of the molecules of a sample of the compound. Of particular interest are compounds comprising —N(R)Me or —NMe$_2$, where Me can be present as CD$_3$. This variation of the compounds described herein is particularly interesting because the presence of CD$_3$ in place of CH$_3$ can have a significant effect on rates of metabolism of an N-methyl group, thus a compound comprising CD$_3$ can have improved pharmacokinetic properties over a non-enriched compound. Accordingly, the alkyl groups described herein are intended to include ones enriched in deuterium, and compounds containing a methyl group on N are specifically considered to include a deuterium-enriched methyl group on N.

The compounds of the invention often have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge.

Utilities of the Compounds:

In another aspect, the invention provides a pharmaceutical composition comprising any of the above-described compounds, admixed with a pharmaceutically acceptable excipient.

In another aspect, the invention provides a method to treat cancer, a vascular disorder, inflammation, infection, pain, or an immunological disorder comprising administering to a subject in need of such treatment, an effective amount of any of the above-described compounds.

The compounds of the invention are useful as medicaments, and are useful for the manufacture of medicaments, including medicaments to treat conditions disclosed herein, such as cancers, inflammatory conditions, infections, pain, and immunological disorders.

The terms "treat" and "treating" as used herein refer to ameliorating, alleviating, lessening, and removing symptoms of a disease or condition. A candidate molecule or compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor).

These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganisms include but are not limited to virus, bacterium and fungus.

The compounds of the invention have activities to modulate protein kinases, in particular CK2 activity and/or Pim activity. In some embodiments, the compounds of the invention specifically inhibit the activity of CK2, but not Pim, e.g., more than 100, 90, 80, 70, 60, 50, 40, 30, 20, or 10 fold difference between CK2 inhibition vs. Pim inhibition. In some embodiments, the compounds of the invention specifically inhibit the activity of Pim, but not Ck2, e.g., more than 100, 90, 80, 70, 60, 50, 40, 30, 20, or 10 fold difference between Pim inhibition vs. CK2 inhibition. In some embodiments, the compounds of the invention inhibit the activity of CK2 as well as Pim.

The compounds of the invention can be used to modulate the activity of CK2 and/or Pim, e.g., inhibit the activity of CK2 and/or Pim in a cell, e.g., in vivo or in vitro. In some embodiments, compounds of the invention can be used to modulate the activity of CK2, e.g., inhibit the activity of CK2 without substantially interfering or changing the activity of Pim. In some embodiments, compounds of the invention can be used to modulate the activity of Pim, e.g., inhibit the activity of Pim without substantially interfering or changing the activity of CK2. In some embodiments, compounds of the invention can be used to modulate the activity of CK2 and Pim, e.g., inhibit the activity of CK2 and Pim.

The compounds of the invention are thus useful to treat infections by certain pathogens, including protozoans and viruses. The invention thus provides methods for treating protozoal disorders such as protozoan parasitosis, including infection by parasitic protozoa responsible for neurological disorders such as schizophrenia, paranoia, and encephalitis in immunocompromised patients, as well as Chagas' disease. It also provides methods to treat various viral diseases, including human immunodeficiency virus type 1 (HIV-1), human papilloma viruses (HPVs), herpes simplex virus (HSV), Epstein-Barr virus (EBV), human cytomegalovirus, hepatitis C and B viruses, influenza virus, Borna disease virus, adenovirus, coxsackievirus, coronavirus and varicella zoster virus. The methods for treating these disorders comprise administering to a subject in need thereof an effective amount of a compound of Formula II or Formula II'.

As used herein, the term "apoptosis" refers to an intrinsic cell self-destruction or suicide program. In response to a triggering stimulus, cells undergo a cascade of events including cell shrinkage, bleeding of cell membranes and chromatic condensation and fragmentation. These events culminate in cell conversion to clusters of membrane-bound particles (apoptotic bodies), which are thereafter engulfed by macrophages.

The invention in part provides pharmaceutical compositions comprising at least one compound within the scope of the invention as described herein, and methods of using compounds described herein.

In addition, the invention in part provides methods for identifying a candidate molecule that interacts with a CK2, which comprises contacting a composition containing a CK2 protein and a molecule described herein with a candidate molecule and determining whether the amount of the molecule described herein that interacts with the protein is modulated, whereby a candidate molecule that modulates the amount of the molecule described herein that interacts with the protein is identified as a candidate molecule that interacts with the protein.

Also provided by the invention are methods for modulating certain protein kinase activities. Protein kinases catalyze the transfer of a gamma phosphate from adenosine triphosphate to a serine or threonine amino acid (serine/threonine protein kinase), tyrosine amino acid (tyrosine protein kinase), tyrosine, serine or threonine (dual specificity protein kinase) or histidine amino acid (histidine protein kinase) in a peptide or protein substrate. Thus, included herein are methods which comprise contacting a system comprising a protein kinase protein with a compound described herein in an amount effective for modulating (e.g., inhibiting) the activity of the protein kinase. In some embodiments, the activity of the protein kinase is the catalytic activity of the protein (e.g., catalyzing the transfer of a gamma phosphate from adenosine triphosphate to a peptide or protein substrate). In certain embodiments, provided are methods for identifying a candidate molecule that interacts with a protein kinase, which comprise: contacting a composition containing a protein kinase and a compound described herein with a candidate molecule under conditions in which the compound and the protein kinase interact, and determining whether the amount of the compound that interacts with the protein kinase is modulated relative to a control interaction between the compound and the protein kinase without the candidate molecule, whereby a candidate molecule that modulates the amount of the compound interacting with the protein kinase relative to the control interaction is identified as a candidate molecule that interacts with the protein kinase. Systems in such embodiments can be a cell-free system or a system comprising cells (e.g., in vitro). The protein kinase, the compound or the molecule in some embodiments is in association with a solid phase. In certain embodiments, the interaction between the compound and the protein kinase is detected via a detectable label, where in some embodiments the protein kinase comprises a detectable label and in certain embodiments the compound comprises a detectable label. The interaction between the compound and the protein kinase sometimes is detected without a detectable label.

Provided also are compositions of matter comprising a protein kinase and a compound described herein. In some embodiments, the protein kinase in the composition is a serine-threonine protein kinase. In some embodiments, the protein kinase in the composition is, or contains a subunit (e.g., catalytic subunit, SH2 domain, SH3 domain) of, CK2. In certain embodiments the composition is cell free and sometimes the protein kinase is a recombinant protein.

The protein kinase can be from any source, such as cells from a mammal, ape or human, for example. Examples of serine-threonine protein kinases that can be inhibited, or may potentially be inhibited, by compounds disclosed herein include without limitation human versions of CK2, or CK2α2. A serine-threonine protein kinase sometimes is a member of a sub-family containing one or more of the following amino acids at positions corresponding to those listed in human CK2: leucine at position 45, methionine at position 163 and isoleucine at position 174. Nucleotide and amino acid sequences for protein kinases and reagents are publicly available (e.g., World Wide Web URLs www.ncbi.nlm.nih.gov/sites/entrez/and www.Invitrogen.com, each last visited Dec. 2, 2009).

The invention also in part provides methods for treating a condition related to aberrant cell proliferation. For example, provided are methods of treating a cell proliferative condition in a subject, which comprises administering a compound described herein to a subject in need thereof in an amount effective to treat the cell proliferative condition. The subject may be a research animal (e.g., rodent, dog, cat, monkey), optionally containing a tumor such as a xenograft tumor (e.g., human tumor), for example, or may be a human. A cell proliferative condition sometimes is a tumor, e.g., solid or circulating tumor or non-tumor cancer, including but not limited to, cancers of the colorectum, breast, lung, liver, pancreas, lymph node, colon, prostate, brain, head and neck, skin, liver, kidney, blood and heart (e.g., leukemia, lymphoma, carcinoma).

Compounds and compositions of the invention may be used alone or in combination with anticancer or other agents, such as a palliative agents, that are typically administered to a patient being treated for cancer, as further described herein.

Also provided are methods for treating a condition related to inflammation or pain. For example, methods are provided for treating pain in a subject, which comprise administering a compound described herein to a subject in need thereof in an amount effective to treat the pain. Provided also are methods of treating inflammation in a subject, which comprise administering a compound described herein to a subject in need thereof in an amount effective to treat the inflammation. The subject may be a research animal (e.g., rodent, dog, cat, monkey), for example, or may be a human. Conditions associated with inflammation and pain include without limitation acid reflux, heartburn, acne, allergies and allergen sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, glomerulonephritis (GN), juvenile cystic kidney disease, and type I nephronophthisis (NPHP), osteoporosis, Parkinson's disease, Guam-Parkinson dementia, supranuclear palsy, Kuf's disease, and Pick's disease, as well as memory impairment, brain ischemia, and schizophrenia, periodontal disease, polyarteritis, polychondritis, psoriasis, scleroderma, sinusitis, Sjögren's syndrome, spastic colon, systemic candidiasis, tendonitis, urinary track infections, vaginitis, inflammatory cancer (e.g., inflammatory breast cancer) and the like.

Methods for determining and monitoring effects of compounds herein on pain or inflammation are known. For example, formalin-stimulated pain behaviors in research animals can be monitored after administration of a compound described herein to assess treatment of pain (e.g., Li et al., *Pain* 115(1-2): 182-90 (2005)). Also, modulation of pro-inflammatory molecules (e.g., IL-8, GRO-alpha, MCP-1, TNFalpha and iNOS) can be monitored after administration of a compound described herein to assess treatment of inflammation (e.g., Parhar et al., *Int J Colorectal Dis.* 22(6): 601-9 (2006)), for example. Thus, also provided are methods for determining whether a compound herein reduces inflammation or pain, which comprise contacting a system with a compound described herein in an amount effective for modulating (e.g., inhibiting) the activity of a pain signal or inflammation signal.

Provided also are methods for identifying a compound that reduces inflammation or pain, which comprise: contacting a system with a compound of Formula II or Formula II'; and detecting a pain signal or inflammation signal, whereby a compound that modulates the pain signal relative to a control molecule is identified as a compound that reduces inflammation of pain. Non-limiting examples of pain signals are formalin-stimulated pain behaviors and examples of inflammation signals include without limitation a level of a pro-inflammatory molecule. The invention thus in part pertains to methods for modulating angiogenesis in a subject, and methods for treating a condition associated with aberrant angiogenesis in a subject proliferative diabetic retinopathy.

CK2 has also been shown to play a role in the pathogenesis of atherosclerosis, and may prevent atherogenesis by maintaining laminar shear stress flow. CK2 plays a role in vascularization, and has been shown to mediate the hypoxia-induced activation of histone deacetylases (HDACs). CK2 is also involved in diseases relating to skeletal muscle and bone tissue, including, e.g., cardiomyocyte hypertrophy, heart failure, impaired insulin signaling and insulin resistance, hypophosphatemia and inadequate bone matrix mineralization.

Thus in one aspect, the invention provides methods to treat each of these conditions, comprising administering to a subject in need of such treatment an effect amount of a CK2 inhibitor, such as a compound of Formula II or Formula II' as described herein.

The invention also in part pertains to methods for modulating an immune response in a subject, and methods for treating a condition associated with an aberrant immune response in a subject. Thus, provided are methods for determining whether a compound herein modulates an immune response, which comprise contacting a system with a compound described herein in an amount effective for modulating (e.g., inhibiting) an immune response or a signal associated with an immune response. Signals associated with immunomodulatory activity include, e.g., stimulation of T-cell proliferation, suppression or induction of cytokines, including, e.g., interleukins, interferon-γ and TNF. Methods of assessing immunomodulatory activity are known in the art.

Also provided are methods for treating a condition associated with an aberrant immune response in a subject, which comprise administering a compound described herein to a subject in need thereof in an amount effective to treat the condition. Conditions characterized by an aberrant immune response include without limitation, organ transplant rejection, asthma, autoimmune disorders, including rheumatoid arthritis, multiple sclerosis, myasthenia gravis, systemic lupus erythematosus, scleroderma, polymyositis, mixed connective tissue disease (MCTD), Crohn's disease, and ulcerative colitis. In certain embodiments, an immune response may be modulated by administering a compound herein in combination with a molecule that modulates (e.g., inhibits) the biological activity of an mTOR pathway member or member of a related pathway (e.g., mTOR, PI3 kinase, AKT). In certain embodiments the molecule that modulates the biological activity of an mTOR pathway member or member of a related pathway is rapamycin. In certain embodiments, provided herein is a composition comprising a compound described herein in combination with a molecule that modulates the biological activity of an mTOR pathway member or member of a related pathway, such as rapamycin, for example.

Compositions and Routes of Administration

In another aspect, the invention provides pharmaceutical compositions (i.e., formulations). The pharmaceutical compositions can comprise a compound of any of Formulae (I), (II), (II'), (IIa), (IIa'), (IIb), (IIb'), (II-Th), and (II-Th'), as described herein which is admixed with at least one pharmaceutically acceptable excipient or carrier. Frequently, the composition comprises at least two pharmaceutically acceptable excipients or carriers.

While the compositions and methods of the present invention will typically be used in therapy for human patients, they may also be used in veterinary medicine to treat similar or identical diseases. The compositions may, for example, be used to treat mammals, including, but not limited to, primates and domesticated mammals. The compositions may, for example be used to treat herbivores. The compositions of the present invention include geometric and optical isomers of one or more of the drugs, wherein each drug is a racemic mixture of isomers or one or more purified isomers.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

The compounds of the present invention may exist as pharmaceutically acceptable salts. The present invention includes such salts. The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, for example, acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof, including racemic mixtures), succinates, benzoates and salts with amino acids such as glutamic acid. These salts may be prepared by methods known to those skilled in art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

The pharmaceutically acceptable esters in the present invention refer to non-toxic esters, preferably the alkyl esters such as methyl, ethyl, propyl, isopropyl, butyl, isobutyl or pentyl esters, of which the methyl ester is preferred. However, other esters such as phenyl-$C_{1-5}$ alkyl may be employed if desired. Ester derivatives of certain compounds may act as prodrugs which, when absorbed into the bloodstream of a warm-blooded animal, may cleave in such a manner as to release the drug form and permit the drug to afford improved therapeutic efficacy.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

When used as a therapeutic the compounds described herein often are administered with a physiologically acceptable carrier. A physiologically acceptable carrier is a formulation to which the compound can be added to dissolve it or otherwise facilitate its administration. Examples of physiologically acceptable carriers include, but are not limited to, water, saline, physiologically buffered saline.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention. The compounds of the present invention may also contain unnatural proportions of atomic isotopes at one or more of atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are encompassed within the scope of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

A compound of the present invention can be formulated as a pharmaceutical composition. Such a pharmaceutical composition can then be administered orally, parenterally, by inhalation spray, rectally, or topically in dosage unit formulations containing conventional nontoxic pharmaceutically acceptable carriers, adjuvants, and vehicles as desired. The amount of active ingredient that can be combined with the carrier materials to produce a single dosage form varies depending upon the mammalian host treated and the particular mode of administration. Topical administration can also involve the use of transdermal administration such, as transdermal patches or iontophoresis devices. The term parenteral as used herein includes subcutaneous injections, intravenous, intramuscular, infrasternal injection, or infusion techniques. Formulation of drugs is discussed in, for example, Hoover, John E., REMINGTON'S PHARMACEUTICAL SCIENCES, Mack Publishing Co., Easton, Pa.; 1975. Other examples of drug formulations can be found in Liberman, H. A. and Lachman, L., Eds., PHARMACEUTICAL DOSAGE FORMS, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a compound of the invention can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A compound of the invention can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The dosage regimen utilizing the compounds of the present invention in combination with an anticancer agent is selected in accordance with a variety of factors including type, species, age, weight, sex and medical condition of the patient; the severity of the condition to be treated; the route of administration; the renal and hepatic function of the patient; and the particular compound or salt or ester thereof employed. A consideration of these factors is well within the purview of the ordinarily skilled clinician for the purpose of determining the therapeutically effective dosage amounts to be given to a person in need of the instant combination therapy.

[I believe these paragraphs are repeats of paragraph 0184-0187] In certain embodiments of the present invention, the compound is a compound of Formula (I)a, and in certain embodiments it is a compound of Formula (I)b.

Any suitable formulation of a compound described above can be prepared for administration by methods known in the art. Selection of useful excipients or carriers can be achieved without undue experimentation, based on the desired route of administration and the physical properties of the compound to be administered.

Any suitable route of administration may be used, as determined by a treating physician, including, but not limited to, oral, parenteral, intravenous, intramuscular, transdermal, topical and subcutaneous routes. Depending on the subject to be treated, the mode of administration, and the type of treatment desired—e.g., prevention, prophylaxis, therapy; the compounds are formulated in ways consonant with these parameters. Preparation of suitable formulations for each route of administration are known in the art. A summary of such formulation methods and techniques is found in *Remington's Pharmaceutical Sciences*, latest edition, Mack Publishing Co., Easton, Pa. The formulation of each substance or of the combination of two substances will frequently include a diluent as well as, in some cases, adjuvants, buffers, preservatives and the like. The substances to be administered can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised, and can be applied to compounds of the invention. See, for example, U.S. Pat. No. 5,624,677, the methods of which are incorporated herein by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the appropriate dosage of a compound described above often is 0.01-15 mg/kg, and sometimes 0.1-10 mg/kg. In some embodiments, a suitable dosage of the compound of the invention for an adult patient will be between 1 and 1000 mg per dose, frequently between 10 and 300 mg, and the dosage may be administered 1-4 times per day. Dosage levels are dependent on the nature of the condition, drug efficacy, the condition of the patient, the judgment of the practitioner, and the frequency and mode of administration; optimization of such parameters is within the ordinary level of skill in the art.

Therapeutic Combinations:

Compounds of the invention may be used alone or in combination with another therapeutic agent. The invention provides methods to treat conditions such as cancer, inflammation and immune disorders by administering to a subject in need of such treatment a therapeutically effective amount of a therapeutic agent useful for treating said disorder and administering to the same subject a therapeutically effective amount of a modulator of the present invention, i.e., a compound of the invention. The therapeutic agent and the modulator may be "co-administered", i.e, administered together, either as separate pharmaceutical compositions or admixed in a single pharmaceutical composition. By "administered together", the therapeutic agent and the modulator may also be administered separately, including at different times and with different frequencies. The modulator may be administered by any known route, such as orally, intravenously, intramuscularly, nasally, and the like; and the therapeutic agent may also be administered by any conventional route. In many embodiments, at least one and optionally both of the modulator and the therapeutic agent may be administered orally. Preferably, the modulator is an inhibitor, and it may inhibit either one of CK2 and Pim, or both of them to provide the treatment effects described herein.

In certain embodiments, a "modulator" as described above may be used in combination with a therapeutic agent that can act by binding to regions of DNA that can form certain quadruplex structures. In such embodiments, the therapeutic agents have anticancer activity on their own, but their activity is enhanced when they are used in combination with a modulator. This synergistic effect allows the therapeutic agent to be administered in a lower dosage while achieving equivalent or higher levels of at least one desired effect.

A modulator may be separately active for treating a cancer. For combination therapies described above, when used in combination with a therapeutic agent, the dosage of a modulator will frequently be two-fold to ten-fold lower than the dosage required when the modulator is used alone to treat the same condition or subject. Determination of a suitable amount of the modulator for use in combination with a therapeutic agent is readily determined by methods known in the art.

Compounds and compositions of the invention may be used in combination with anticancer or other agents, such as palliative agents, that are typically administered to a patient being treated for cancer. Such "anticancer agents" include, e.g., classic chemotherapeutic agents, as well as molecular targeted therapeutic agents, biologic therapy agents, and radiotherapeutic agents.

When a compound or composition of the invention is used in combination with an anticancer agent to another agent, the present invention provides, for example, simultaneous, staggered, or alternating treatment. Thus, the compound of the invention may be administered at the same time as an anticancer agent, in the same pharmaceutical composition; the compound of the invention may be administered at the same time as the anticancer agent, in separate pharmaceutical compositions; the compound of the invention may be administered before the anticancer agent, or the anticancer agent may be administered before the compound of the invention, for example, with a time difference of seconds, minutes, hours, days, or weeks.

In examples of a staggered treatment, a course of therapy with the compound of the invention may be administered, followed by a course of therapy with the anticancer agent, or the reverse order of treatment may be used, and more than one series of treatments with each component may also be used. In certain examples of the present invention, one component, for example, the compound of the invention or the anticancer agent, is administered to a mammal while the other component, or its derivative products, remains in the bloodstream of the mammal. For example, the present compound may be administered while the anticancer agent or its derivative products remains in the bloodstream, or the anticancer agent may be administered while the present compound or its derivatives remains in the bloodstream. In other examples, the second component is administered after all, or most of the first component, or its derivatives, have left the bloodstream of the mammal.

The compound of the invention and the anticancer agent may be administered in the same dosage form, e.g., both administered as intravenous solutions, or they may be administered in different dosage forms, e.g., one compound may be administered topically and the other orally. A person of ordinary skill in the art would be able to discern which combinations of agents would be useful based on the particular characteristics of the drugs and the cancer involved.

Anticancer agents useful in combination with the compounds of the present invention may include agents selected from any of the classes known to those of ordinary skill in the art, including, but not limited to, antimicrotubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; nonreceptor tyrosine kinase angiogenesis inhibitors; immunotherapeutic agents; pro-apoptotic agents; and cell cycle signaling inhibitors; and other agents described below.

Anti-microtubule or anti-mitotic agents are phase specific agents that are typically active against the microtubules of tumor cells during M or the mitosis phase of the cell cycle. Examples of anti-microtubule agents include, but are not limited to, diterpenoids and vinca alkaloids.

Plant alkaloid and terpenoid derived agents include mitotic inhibitors such as the vinca alkaloids vinblastine, vincristine, vindesine, and vinorelbine; and microtubule polymer stabilizers such as the taxanes, including, but not limited to paclitaxel, docetaxel, larotaxel, ortataxel, and tesetaxel.

Diterpenoids, which are derived from natural sources, are phase specific anti-cancer agents that are believed to operate at the G2/M phases of the cell cycle. It is believed that the diterpenoids stabilize the p-tubulin subunit of the microtubules, by binding with this protein. Disassembly of the protein appears then to be inhibited with mitosis being arrested and cell death following.

Examples of diterpenoids include, but are not limited to, taxanes such as paclitaxel, docetaxel, larotaxel, ortataxel, and tesetaxel. Paclitaxel is a natural diterpene product isolated from the Pacific yew tree *Taxus brevifolia* and is commercially available as an injectable solution TAXOL®. Docetaxel is a semisynthetic derivative of paclitaxel q. v., prepared using a natural precursor, 10-deacetyl-baccatin III, extracted from the needle of the European Yew tree. Docetaxel is commercially available as an injectable solution as TAXOTERE®.

Vinca alkaloids are phase specific anti-neoplastic agents derived from the periwinkle plant. Vinca alkaloids that are believed to act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, vindesine, and vinorelbine. Vinblastine, vincaleukoblastine sulfate, is commercially available as VELBAN® as an injectable solution. Vincristine, vincaleukoblastine 22-oxo-sulfate, is commercially available as ONCOVIN® as an injectable solution. Vinorelbine, is commercially available as an injectable solution of vinorelbine tartrate (NAVELBINE®), and is a semisynthetic vinca alkaloid derivative.

Platinum coordination complexes are non-phase specific anti-cancer agents, which are interactive with DNA. The platinum complexes are believed to enter tumor cells, undergo, aquation and form intra- and interstrand crosslinks with DNA causing adverse biological effects to the tumor. Platinum-based coordination complexes include, but are not limited to cisplatin, carboplatin, nedaplatin, oxaliplatin, satraplatin, and (SP-4-3)-(cis)-amminedichloro-[2-methylpyridine] platinum(II). Cisplatin, cis-diamminedichloroplatinum, is commercially available as PLATINOL® as an injectable solution. Carboplatin, platinum, diammine [1,1-cyclobutane-dicarboxylate(2-)-0,0'] is commercially available as PARAPLATIN® as an injectable solution.

Alkylating agents are generally non-phase specific agents and typically are strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, alkyl sulfonates such as busulfan; ethyleneimine and methylmelamine derivatives such as altretamine and thiotepa; nitrogen mustards such as chlorambucil, cyclophosphamide, estramustine, ifosfamide, mechlorethamine, melphalan, and uramustine; nitrosoureas such as carmustine, lomustine, and streptozocin; triazenes and imidazotetrazines such as dacarbazine, procarbazine, temozolamide, and temozolomide. Cyclophosphamide, 2-[bis(2-chloroethyl)-amino] tetrahydro-2H-1,3,2-oxazaphosphorine 2-oxide monohydrate, is commercially available as an injectable solution or tablets as CYTOXAN®. Melphalan, 4-[bis(2-chloroethyl) amino]-L-phenylalanine, is commercially available as an injectable solution or tablets as ALKERAN®. Chlorambucil, 4-[bis(2-chloroethyl)amino]-benzenebutanoic acid, is commercially available as LEUKERAN® tablets. Busulfan, 1,4-butanediol dimethanesulfonate, is commercially available as MYLERAN® TABLETS. Carmustine, 1,3-[bis(2-chloroethyl)-1-nitrosourea, is commercially available as single vials of lyophilized material as BiCNU®, 5-(3,3-dimethyl-1-triazeno)-imidazole-4-carboxamide, is commercially available as single vials of material as DTIC-Dome®. Furthermore, alkylating agents include (a) alkylating-like platinum-based chemotherapeutic agents such as cisplatin, carboplatin, nedaplatin, oxaliplatin, satraplatin, and (SP-4-3)-(cis)-amminedichloro-[2-methylpyridine] platinum(II); (b) alkyl sulfonates such as busulfan; (c) ethyleneimine and methylmelamine derivatives such as altretamine and thiotepa; (d) nitrogen mustards such as chlorambucil, cyclophosphamide, estramustine, ifosfamide, mechlorethamine, trofosamide, prednimustine, melphalan, and uramustine; (e) nitrosoureas such as carmustine, lomustine, fotemustine, nimustine, ranimustine and streptozocin; (f) triazenes and imidazotetrazines such as dacarbazine, procarbazine, temozolamide, and temozolomide.

Anti-tumor antibiotics are non-phase specific agents which are believed to bind or intercalate with DNA. This may result in stable DNA complexes or strand breakage, which disrupts ordinary function of the nucleic acids, leading to cell death. Examples of anti-tumor antibiotic agents include, but are not limited to, anthracyclines such as daunorubicin (including liposomal daunorubicin), doxorubicin (including liposomal doxorubicin), epirubicin, idarubicin, and valrubicin; streptomyces-related agents such as bleomycin, actinomycin, mithramycin, mitomycin, porfiromycin; and mitoxantrone. Dactinomycin, also know as Actinomycin D, is commercially available in injectable form as COSMEGEN®. Daunorubicin, (8S-cis-)-8-acetyl-10-[(3-amino-2,3,6-trideoxy-a-L-lyxohexopyranosyl)oxy]-7,8,9,10-tetrahydro-6,8,11-trihydroxy-1-methoxy-5,12-naphthacenedione hydrochloride, is commercially available as a liposomal injectable form as DAUNOXOME® or as an injectable as CERUBIDINE®. Doxorubicin, (8S, 10S)-10-[(3-amino-2,3,6-trideoxy-α-L-lyxohexopyranosyl)oxy]-8-glycoloyl, 7,8,9,10-tetrahydro-6, 8,11-trihydroxy-1-methoxy-5,12-naphthacenedione hydrochloride, is commercially available in an injectable form as RUBEX® or ADRIAMYCIN RDF®. Bleomycin, a mixture of cytotoxic glycopeptide antibiotics isolated from a strain of *Streptomyces verticillus*, is commercially available as BLENOXANE®.

Topoisomerase inhibitors include topoisomerase I inhibitors such as camptothecin, topotecan, irinotecan, rubitecan, and belotecan; and topoisomerase II inhibitors such as etoposide, teniposide, and amsacrine.

Topoisomerase II inhibitors include, but are not limited to, epipodophyllotoxins, which are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide, teniposide, and amsacrine. Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Teniposide, 4'-demethyl-epipodophyllotoxin 9[4,6-0-(R)-thenylidene-β-D-glucopyranoside], is commercially available as an injectable solution as VUMON® and is commonly known as VM-26.

Topoisomerase I inhibitors including, camptothecin and camptothecin derivatives. Examples of topoisomerase I inhibitors include, but are not limited to camptothecin, topotecan, irinotecan, rubitecan, belotecan and the various optical forms (i.e., (R), (S) or (R,S)) of 7-(4-methylpiperazino-methylene)-10,11-ethylenedioxy-camptothecin, as described in U.S. Pat. Nos. 6,063,923; 5,342,947; 5,559,235; 5,491,237 and pending U.S. patent application Ser. No. 08/977,217 filed Nov. 24, 1997. Irinotecan HCl, (4S)-4,11-diethyl-4-hydroxy-9-[(4-piperidinopiperidino)-carbonyloxy]-1 H-yrano[3',4',6, 7]indolizino[1,2-b]quinoline-3, 14(4H, 12H)-dione hydrochloride, is commercially available as the injectable solution CAMPTOSAR®. Irinotecan is a derivative of camptothecin which binds, along with its active metabolite 8N-38, to the topoisomerase I-DNA complex. Topotecan HCl, (S)-10-[(dimethylamino)methyl]-4-ethyl-4,9-dihydroxy-1H-pyrano [3',4',6,7]indolizino[1,2-b]quinoline-3,14-(4H, 12H)-dione monohydrochloride, is commercially available as the injectable solution HYCAMTIN®.

Anti-metabolites include (a) purine analogs such as fludarabine, cladribine, chlorodeoxyadenosine, clofarabine, mercaptopurine, pentostatin, and thioguanine; (b) pyrimidine analogs such as fluorouracil, gemcitabinc, capecitabine, cytarabine, azacitidine, edatrexate, floxuridine, and troxacitabine; (c) antifolates, such as methotrexate, pemetrexed, raltitrexed, and trimetrexate. Anti-metabolites also include thymidylate synthase inhibitors, such as fluorouracil, raltitrexed, capecitabine, floxuridine and pemetrexed; and ribonucleotide reductase inhibitors such as claribine, clofarabine and fludarabine. Antimetabolite neoplastic agents are phase specific anti-neoplastic agents that typically act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Anti-metabolites, include purine analogs, such as fludarabine, cladribine, chlorodeoxyadenosine, clofarabine, mercaptopurine, pentostatin, erythrohydroxynonyladenine, fludarabine phosphate and thioguanine; pyrimidine analogs such as fluorouracil, gemcitabine, capecitabine, cytarabine, azacitidine, edatrexate, floxuridine, and troxacitabine; antifolates, such as methotrexate, pemetrexed, raltitrexed, and trimetrexate. Cytarabine, 4-amino-1-p-D-arabinofuranosyl-2(1H)-pyrimidinone, is commercially available as CYTOSAR-U® and is commonly known as Ara-C. Mercaptopurine, 1,7-dihydro-6H-purine-6-thione monohydrate, is commercially available as PURINETHOL®. Thioguanine, 2-amino-1,7-dihydro-6H-purine-6-thione, is commercially available as TABLOID®. Gemcitabine, 2'-deoxy-2',2'-difluorocytidine monohydrochloride (p-isomer), is commercially available as GEMZAR®.

Hormonal therapies include (a) androgens such as fluoxymesterone and testolactone; (b) antiandrogens such as bicalutamide, cyproterone, flutamide, and nilutamide; (c) aromatase inhibitors such as aminoglutethimide, anastrozole, exemestane, formestane, and letrozole; (d) corticosteroids such as dexamethasone and prednisone; (e) estrogens such as diethylstilbestrol; (f) antiestrogens such as fulvestrant, raloxifene, tamoxifen, and toremifine; (g) LHRH agonists and antagonists such as buserelin, goserelin, leuprolide, and triptorelin; (h) progestins such as medroxyprogesterone acetate and megestrol acetate; and (i) thyroid hormones such as levothyroxine and liothyronine. Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, androgens such as fluoxymesterone and testolactone; antiandrogens such as bicalutamide, cyproterone, flutamide, and nilutamide; aromatase inhibitors such as aminoglutethimide, anastrozole, exemestane, formestane, vorazole, and letrozole; corticosteroids such as dexamethasone, prednisone and prednisolone; estrogens such as diethylstilbestrol; antiestrogens such as fulvestrant, raloxifene, tamoxifen, toremifine, droloxifenc, and iodoxyfene, as well as selective estrogen receptor modulators (SERMS) such those described in U.S. Pat. Nos. 5,681,835, 5,877,219, and 6,207,716; 5α-reductases such as finasteride and dutasteride; gonadotropin-releasing hormone (GnRH) and analogues thereof which stimulate the release of leutinizing hormone (LH) and/or follicle stimulating hormone (FSH), for example LHRH agonists and antagonists such as buserelin, goserelin, leuprolide, and triptorelin; progestins such as medroxyprogesterone acetate and megestrol acetate; and thyroid hormones such as levothyroxine and liothyronine.

Signal transduction pathway inhibitors are those inhibitors, which block or inhibit a chemical process which evokes an intracellular change, such as cell proliferation or differentiation. Signal tranduction inhibitors useful in the present invention include, e.g., inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Molecular targeted agents include (a) receptor tyrosine kinase ('RTK') inhibitors, such as inhibitors of EGFR, including erlotinib, gefitinib, and neratinib; inhibitors of VEGFR including vandetanib, semaxinib, and cediranib; and inhibitors of PDGFR; further included are RTK inhibitors that act at multiple receptor sites such as lapatinib, which inhibits both EGFR and HER2, as well as those inhibitors that act at each of C-kit, PDGFR and VEGFR, including but not limited to axitinib, sunitinib, sorafenib and toceranib; also included are inhibitors of BCR-ABL, c-kit and PDGFR, such as imatinib; (b) FKBP binding agents, such as an immunosuppressive macrolide antibiotic, including bafilomycin, rapamycin (sirolimus) and everolimus; (c) gene therapy agents, antisense therapy agents, and gene expression modulators such as the retinoids and rexinoids, e.g. adapalene, bexarotene, trans-retinoic acid, 9-cis-retinoic acid, and N-(4-hydroxyphenyl)retinamide; (d) phenotype-directed therapy agents, including monoclonal antibodies such as alemtuzumab, bevacizumab, cetuximab, ibritumomab tiuxetan, rituximab, and trastuzumab; (e) immunotoxins such as gemtuzumab ozogamicin; (f) radioimmunoconjugates such as 131I-tositumomab; and (g) cancer vaccines.

Several protein tyrosine kinases catalyse the phosphorylation of specific tyrosyl residues in various proteins involved in the regulation of cell growth. Such protein tyrosine kinases can be broadly classified as receptor or non-receptor kinases. Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed, growth factor receptors.

Inappropriate or uncontrolled activation of many of these kinases, for example by over-expression or mutation, has been shown to result in uncontrolled cell growth. Accordingly, the aberrant activity of such kinases has been linked to malignant tissue growth. Consequently, inhibitors of such kinases could provide cancer treatment methods.

Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I(IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene.

Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., *Exp. Opin. Ther. Patents* (2000) 10(6):803-818; Shawver et al., *Drug Discov. Today* (1997), 2(2):50-63; and Lofts, F. J. et al., "Growth factor receptors as targets", New Molecular Targets for Cancer Chemotherapy, ed. Workman, Paul and Kerr, David, CRC press 1994, London. Specific examples of receptor tyrosine kinase inhibitors include, but are not limited to, sunitinib, erlotinib, gefitinib, and imatinib.

Tyrosine kinases which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Bruton tyrosine kinase, and Bcr-Abl. Such non-receptor kinases and agents which inhibit non-receptor tyrosine kinase function are described in Sinh, S, and Corey, S. J., *J. Hematotherapy & Stem Cell Res*. (1999) 8(5): 465-80; and Bolen, L B., Brugge, J. S., *Annual Review of Immunology*. (1997) 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E., *J. Pharmacol. Toxicol. Methods*. (1995), 34(3): 125-32. Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., *J. Biochemistry*. (1999) 126 (5): 799-803; Brodt, P, Samani, A, & Navab, R, *Biochem. Pharmacol*. (2000) 60:1101-1107; Massague, J., Weis-Garcia, F., *Cancer Surv*. (1996) 27:41-64; Philip, P. A, and Harris, A L, *Cancer Treat. Res*. (1995) 78: 3-27; Lackey, K. et al. *Bioorg. Med. Chem. Letters*, (2000) 10(3): 223-226; U.S. Pat. No. 6,268, 391; and Martinez-Lacaci, I., et al., *Int. J. Cancer* (2000), 88(1): 44-52. Inhibitors of Phosphotidyl inositol-3 Kinase family members including blockers of PI3-kinase, ATM, DNA-PK, and Ku are also useful in the present invention. Such kinases are discussed in Abraham, R T. *Current Opin. Immunol*. (1996), 8(3): 412-8; Canman, C. E., Lim, D. S., Oncogene (1998) 17(25): 3301-8; Jackson, S. P., *Int. J. Biochem. Cell Biol*. (1997) 29(7):935-8; and Zhong, H. et al., *Cancer Res*. (2000) 60(6):1541-5. Also useful in the present invention are Myo-inositol signaling inhibitors such as phospholipase C blockers and Myoinositol analogues. Such signal inhibitors are described in Powis, G., and Kozikowski A, (1994) New Molecular Targets for Cancer Chemotherapy, ed., Paul Workman and David Kerr, CRC Press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R, Gervasoni, S I, Matar, P., *J. Biomed. Sci*. (2000) 7(4): 292-8; Ashby, M. N., *Curr. Opin. Lipidol*. (1998) 9(2): 99-102; and Oliff, A., *Biochim. Biophys. Acta*, (1999) 1423 (3):C19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al., *Cancer Treat. Rev.*, (2000) 26(4): 269-286); Herceptin® erbB2 antibody (see Stern, D F, *Breast Cancer Res*. (2000) 2(3):176-183); and 2CB VEGFR2 specific antibody (see Brekken, R. A. et al., *Cancer Res*. (2000) 60(18): 5117-24).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alphav beta3) that will inhibit angiogenesis; endostatin and angiostatin (non-RTK) may also prove useful in combination with the disclosed erb family inhibitors. (See Bruns, C J et al., *Cancer Res*. (2000), 60(11): 2926-2935; Schreiber A B, Winkler M E, & Derynck R., *Science* (1986) 232(4755):1250-53; Yen L. et al., Oncogene (2000) 19(31): 3460-9).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T, et al., *Cancer Res*. (2000) 60(13): 3569-76; and Chen Y, et al., *Cancer Res*. (1998) 58(9):1965-71.

Agents used in pro-apoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family. Therefore, strategies designed to downregulate the expression of bcl-2 in tumors have demonstrated clinical benefit and are now in Phase II/III trials, namely Genta's G3139 bcl-2 antisense oligonucleotide. Such pro-apoptotic strategies using the antisense oligonucleotide strategy for bcl-2 are discussed in Waters J S, et al., *J. Clin. Oncol*. (2000) 18(9): 1812-23; and Kitada S, et al. *Antisense Res. Dev*. (1994) 4(2): 71-9.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania G R & Chang Y-T., *Exp. Opin. Ther. Patents* (2000) 10(2):215-30.

Other molecular targeted agents include FKBP binding agents, such as the immunosuppressive macrolide antibiotic, rapamycin; gene therapy agents, antisense therapy agents, and gene expression modulators such as the retinoids and rexinoids, e.g. adapalene, bexarotene, trans-retinoic acid, 9-cisretinoic acid, and N-(4 hydroxyphenyl)retinamide; phenotype-directed therapy agents, including: monoclonal antibodies such as alemtuzumab, bevacizumab, cetuximab, ibritumomab tiuxetan, rituximab, and trastuzumab; immunotoxins such as gemtuzumab ozogamicin, radioimmunoconjugates such as 131-tositumomab; and cancer vaccines.

Anti-tumor antibiotics include (a) anthracyclines such as daunorubicin (including liposomal daunorubicin), doxorubicin (including liposomal doxorubicin), epirubicin, idarubicin, and valrubicin; (b) streptomyces-related agents such as bleomycin, actinomycin, mithramycin, mitomycin, porfiromycin; and (c) anthracenediones, such as mitoxantrone and pixantrone. Anthracyclines have three mechanisms of action: intercalating between base pairs of the DNA/RNA strand; inhibiting topoisomerase II enzyme; and creating iron-mediated free oxygen radicals that damage the DNA and cell membranes. Anthracyclines are generally characterized as topoisomerase II inhibitors.

Monoclonal antibodies include, but are not limited to, murine, chimeric, or partial or fully humanized monoclonal antibodies. Such therapeutic antibodies include, but are not limited to antibodies directed to tumor or cancer antigens either on the cell surface or inside the cell. Such therapeutic antibodies also include, but are not limited to antibodies directed to targets or pathways directly or indirectly associated with CK2. Therapeutic antibodies may further include, but are not limited to antibodies directed to targets or pathways that directly interact with targets or pathways associated with the compounds of the present invention. In one variation, therapeutic antibodies include, but are not limited to anticancer agents such as Abagovomab, Adecatumumab, Afutuzumab, Alacizumab pegol, Alemtuzumab, Altumomab pentetate, Anatumomab mafenatox, Apolizumab, Bavituximab, Belimumab, Bevacizumab, Bivatuzumab mertansine, Blinatumomab, Brentuximab vedotin, Cantuzumab mertansine, Catumaxomab, Cetuximab, Citatuzumab bogatox, Cixutumumab, Clivatuzumab tetraxetan, Conatumumab, Dacetuzumab, Detumomab, Ecromeximab, Edrecolomab, Elotuzumab, Epratuzumab, Ertumaxomab, Etaracizumab, Farletuzumab, Figiturmumab, Fresolimumab, Galiximab, Glembatumumab vedotin, Ibritumomab tiuxetan, Intetumumab, Inotuzumab ozogamicin, Ipilimumab, Iratumumab, Labetuzurnab, Lexatumumab, Lintuzumab, Lucatumumab, Lumiliximab, Mapatumumab, Matuzumab, Milatuzumab, Mitumomab, Nacolomab tafenatox, Naptumomab estafenatox, Necitumumab, Nimotuzumab, Ofatumumab, Olaratumab, Oportuzumab monatox, Oregovomab, Panitumumab, Pemtumomab, Pertuzumab, Fintumomab, Pritumumab, Ramucirumab, Rilotumumab, Rituximab, Robatumumab, Sibrotuzumab, Tacatuzumab tetraxetan, Taplitumomab paptox, Tenatumomab, Ticilimumab, Tigatuzumab, Tositumomab, Trastuzumab, Tremelimumab, Tucotuzumab celmoleukin, Veltuzumab, Volociximab, Votumumab, Zalutumumab, and Zanolimumab. In some embodiments, such therapeutic antibodies include, alemtuzumab, bevacizumab, cetuximab, daclizumab, gemtuzumab, ibritumomab tiuxetan, pantitumumab, rituximab, tositumomab, and trastuzumab; in other embodiments, such monoclonal antibodies include alemtuzumab, bevacizumab, cetuximab, ibritumomab tiuxetan, rituximab, and trastuzumab; alternately, such antibodies include daclizumab, gemtuzumab, and pantitumumab. In yet another embodiment, therapeutic antibodies useful in the treatment of infections include but are not limited to Afelimomab, Efungumab, Exbivirumab, Felvizumab, Foravirumab, Ibalizumab, Libivirumab, Motavizumab, Nebacumab, Pagibaximab, Palivizumab, Panobacumab, Rafivirumab, Raxibacumab, Regavirumab, Sevirumab, Tefibazumab, Tuvirumab, and Urtoxazumab. In a further embodiment, therapeutic antibodies can be useful in the treatment of inflammation and/or autoimmune disorders, including, but are not limited to, Adalimumab, Atlizumab, Atorolimumab, Aselizumab, Bapineuzumab, Basiliximab, Benralizumab, Bertilimumab, Besilesomab, Briakinumab, Canakinumab, Cedelizumab, Certolizumab pegol, Clenoliximab, Daclizumab, Denosumab, Eculizumab, Edobacomab, Efalizumab, Erlizumab, Fezakinumab, Fontolizumab, Fresolimumab, Gantenerumab, Gavilimomab, Golimumab, Gomiliximab, Infliximab, Inolimomab, Keliximab, Lebrikizumab, Lerdelimumab, Mepolizumab, Metelimumab, Muromonab-CD3, Natalizumab, Ocrelizumab, Odulimomab, Omalizumab, Otelixizumab, Pascolizumab, Priliximab, Reslizumab, Rituximab, Rontalizumab, Rovelizumab, Ruplizumab, Sifalimumab, Siplizumab, Solanezumab, Stamulumab, Talizumab, Tanezumab, Teplizumab, Tocilizumab, Toralizumab, Ustekinumab, Vedolizumab, Vepalimomab, Visilizumab, Zanolimumab, and Zolimomab aritox. In yet another embodiment, such therapeutic antibodies include, but are not limited to adalimumab, basiliximab, certolizumab pegol, eculizumab, efalizumab, infliximab, muromonab-CD3, natalizumab, and omalizumab. Alternately the therapeutic antibody can include abciximab or ranibizumab. Generally a therapeutic antibody is non-conjugated, or is conjugated with a radionuclide, cytokine, toxin, drug-activating enzyme or a drug-filled liposome.

Akt inhibitors include 1L6-Hydroxymethyl-chiro-inositol-2-(R)-2-O-methyl-3-O-octadecyl-sn-glycerocarbonate, SH-5 (Calbiochem Cat. No. 124008), SH-6 (Calbiochem Cat. No. Cat. No. 124009), Calbiochem Cat. No. 124011, Triciribine (NSC 154020, Calbiochem Cat. No. 124012), 10(4'-(N-diethylamino)butyl)-2-chlorophenoxazine, $Cu(II)Cl_2$(3-Formylchromone thiosemicarbazone), 1,3-dihydro-1-(1-((4-(6-phenyl-1H-imidazo[4,5-g]quinoxalin-7-yl)phenyl)methyl)-4-piperidinyl)-2H-benzimidazol-2-one, GSK690693 (4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol), SR 13668 ((2,10-dicarbethoxy-6-methoxy-5,7-dihydro-indolo[2,3-b]carbazole), GSK2141795, Perifosine, GSK21110183, XL418, XL147, PF-04691502, BEZ-235 [2-Methyl-2-[4-(3-methyl-2-oxo-8-quinolin-3-yl-2,3-dihydro-imidazo[4,5-c]quinolin-1-yl)-phenyl]-propionitrile], PX-866 ((acetic acid (1S,4E,10R,11R,13S,14R)-[4-diallylaminomethylene-6-hydroxy-1-methoxymethyl-10,13-dimethyl-3,7,17-trioxo-1,3,4,7,10,11,12,13,14,15,16,17-dodecahydro-2-oxa-cyclopenta[a]phenanthren-11-yl ester)), D-106669, CAL-101, GDC0941 (2-(1H-indazol-4-yl)-6-(4-methanesulfonyl-piperazin-1-yl-methyl)-4-morpholin-4-yl-thieno[3,2-d]pyrimidine), SF1126, SF1188, SF2523, TG100-115 [3-[2,4-damino-6-(3-hydroxyphenyl)pteridin-7-yl]phenol]. A number of these inhibitors, such as, for example, BEZ-235, PX-866, D 106669, CAL-101, GDC0941, SF1126, SF2523 are also identified in the art as PI3K/mTOR inhibitors; additional examples, such as PI-103 [3-[4(4-morpholinylpyrido[3',2':4,5]furo[3,2-d]pyrimidin-2-yl]phenol hydrochloride] are well-known to those of skill in the art. Additional well-known PI3K inhibitors include LY294002 [2-(4-morpholinyl)-8-phenyl-4H-1-benzopyran-4-one] and wortmannin. mTOR inhibitors known to those of skill in the art include temsirolimus, deforolimus, sirolimus, everolimus, zotarolimus, and biolimus A9. A representative subset of such inhibitors includes temsirolimus, deforolimus, zotarolimus, and biolimus A9.

HDAC inhibitors include (i) hydroxamic acids such as Trichostatin A, vorinostat (suberoylanilide hydroxamic acid (SAHA)), panobinostat (LBH589) and belinostat (PXD101) (ii) cyclic peptides, such as trapoxin B, and depsipeptides, such as romidepsin (NSC 630176), (iii) benzamides, such as MS-275 (3-pyridylmethyl-N-{4-[(2-aminophenyl)-carbamoyl]-benzyl}-carbamate), CI994 (4-acetylamino-N-(2-aminophenyl)-benzamide) and MGCDO103 (N-(2-aminophenyl)-4-((4-(pyridin-3-yl)pyrimidin-2-ylamino)methyl)benzamide), (iv) electrophilic ketones, (v) the aliphatic acid compounds such as phenylbutyrate and valproic acid.

Hsp90 inhibitors include benzoquinone ansamycins such as geldanamycin, 17-DMAG (17-Dimethylamino-ethylamino-17-demethoxygeldanamycin), tanespimycin (17-AAG, 17-allylamino-17-demethoxygeldanamycin), ECS, retaspimycin (IPI-504, 18,21-didehydro-17-demethoxy-18,21-dideoxo-18,21-dihydroxy-17-(2-propenylamino)-geldanamycin), and herbimycin; pyrazoles such as CCT 018159 (4-[4-(2,3-dihydro-1,4-benzodioxin-6-yl)-5-methyl-1H-pyrazol-3-yl]-6-ethyl-1,3-benzenediol); macrolides, such as radicocol; as well as BIIB021 (CNF2024), SNX-5422, STA-9090, and AUY922.

Miscellaneous agents include altretamine, arsenic trioxide, gallium nitrate, hydroxyurea, levamisole, mitotane, octreotide, procarbazine, suramin, thalidomide, lenalidomide, photodyl)amic compounds such as methoxsalen and sodium porfimer, and proteasome inhibitors such as bortezomib.

Biologic therapy agents include: interferons such as interferon-α2a and interferon-α2b, and interleukins such as aldesleukin, denileukin diftitox, and oprelvekin.

In addition to these anticancer agents intended to act against cancer cells, combination therapies including the use of protective or adjunctive agents, including: cytoprotective agents such as armifostine, dexrazonxane, and mesna, phosphonates such as pamidronate and zoledronic acid, and stimulating factors such as epoetin, darbepoetin, filgrastim, PEG-filgrastim, and sargramostim, are also envisioned.

EXAMPLES

The following examples illustrate and do not limit the invention.

Example 1

Synthesis of 5-chloropyrazolo[1,5-a]pyrimidin-7-amine

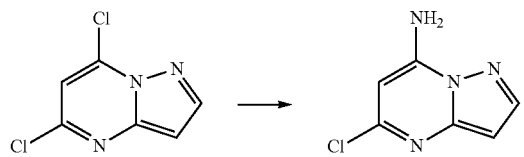 [SMILES: Clc1cc(Cl)n2nccc2n1 ; Nc1cc(Cl)nc2ccnn12]

To the reaction flask, 5,7-dichloropyrazolo[1,5-a]pyrimidine (3 g, 16 mmol) was added along with ammonium hydroxide solution (48 mL). The heterogeneous reaction was refluxed at 85° C. for 12 hours. After cooling to room temperature, the mixture was filtered, washed with water, and dried under vacuum overnight. The product, 5-chloropyrazolo[1,5-a]pyrimidin-7-amine, was collected as an off-white solid in 88% yield. LCMS (M+1=169)

Example 2

Synthesis of tert-butyl 5-chloropyrazolo[1,5-a]pyrimidin-7-ylcarbamate

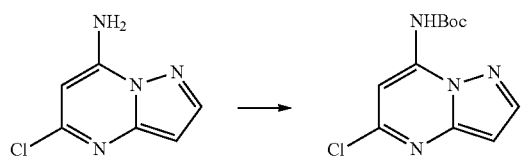 [SMILES: Nc1cc(Cl)nc2ccnn12 ; CC(C)(C)OC(=O)Nc1cc(Cl)nc2ccnn12]

To the reaction flask, 5-chloropyrazolo[1,5-a]pyrimidin-7-amine (2.4 g, 14.1 mmol) was added to dichloromethane (35 mL) along with di-tert-butyl dicarbonate (3.7 g, 17 mmol), triethylamine (2.4 mL, 17 mmol) and DMAP (100 mg, 0.8 mmol). The reaction was stirred at room temperature for 6 hours then diluted with DCM, washed with saturated NaHCO3 solution (3×) followed by washing with brine. The organic layer was isolated, dried over anhydrous MgSO4, filtered, and evaporated to dryness. The product, tert-butyl 5-chloropyrazolo[1,5-a]pyrimidin-7-ylcarbamate, was collected as an off-white solid in 98% yield. LCMS (M-t-Butyl=213)

Example 3

Synthesis of tert-butyl 5-chloro-3-formylpyrazolo[1,5-a]pyrimidin-7-ylcarbamate

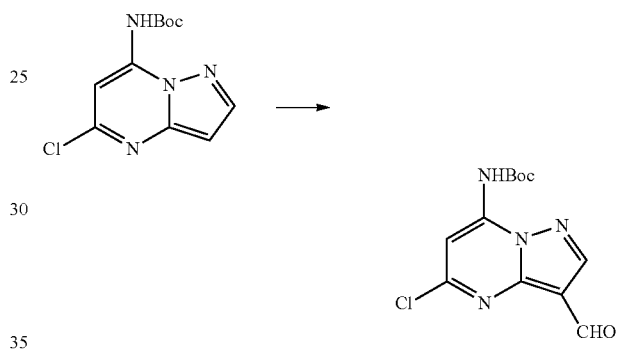

To tert-butyl 5-chloropyrazolo[1,5-a]pyrimidin-7-ylcarbamate (3.7 g, 13.8 mmol) in DMF (36 mL), POCl3 (7.7 mL, 82.9 mmol) was added dropwise at 0° C. After the addition was complete, the reaction was allowed to warm to room temperature and stirred for 8 hours. Then, the reaction was quenched by slow addition to ice cold 6N NaOH. The mixture was diluted with water then the solid was collected by filtration. The solid was washed several more times with water and dried under vacuum overnight. The product, tert-butyl 5-chloro-3-formylpyrazolo[1,5-a]pyrimidin-7-ylcarbamate, was collected as a solid in 27% yield. The product did not ionize on LCMS unless first deprotected using TFA/DCM (1:1). LCMS (M+1=197)

Example 4

Synthesis of 7-amino-5-(3-chlorophenylamino)pyrazolo[1,5-a]pyrimidine-3-carbaldehyde

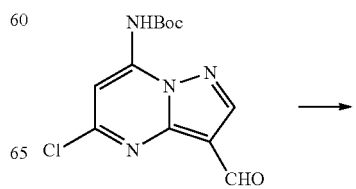

-continued

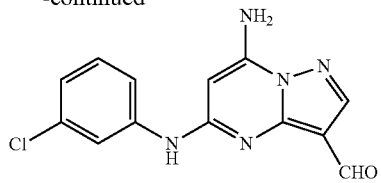

Tert-butyl 5-chloro-3-formylpyrazolo[1,5-a]pyrimidin-7-ylcarbamate (1.1 g, 3.8 mmol) was added to 1,4-dioxane (15 mL) along with 3-chloroaniline (2.4 mL, 22.6 mmol) and p-toluenesulfonic acid monohydrate (73 mg, 0.4 mmol). The reaction was heated at 95° C. for 12 hours then cooled to room temperature, diluted with water and filtered. Analysis of the recovered solid by LCMS showed product mass (M+1=288), as well as, product with chloro aniline imine mass (M+1=397). To completely convert this mixture to the desired product, the solid was dissolved in 6 mL of MeOH/conc. HCl solution (1:1) and heated at 60° C. for 1.5 hours. The reaction was quenched by slow addition to ice cold 6N NaOH. The mixture was diluted with water then the solid was collected by filtration. The solid was washed several more times with water then dried under vacuum overnight. The product, 7-amino-5-(3-chlorophenylamino)pyrazolo[1,5-a]pyrimidine-3-carbaldehyde, was collected as orange-red solid in 38% yield. LCMS (M+1=288)

Example 5

Synthesis of 5-((7-amino-5-(3-chlorophenylamino)pyrazolo[1,5-a]pyrimidin-3-yl)methylene)imidazolidine-2,4-dione

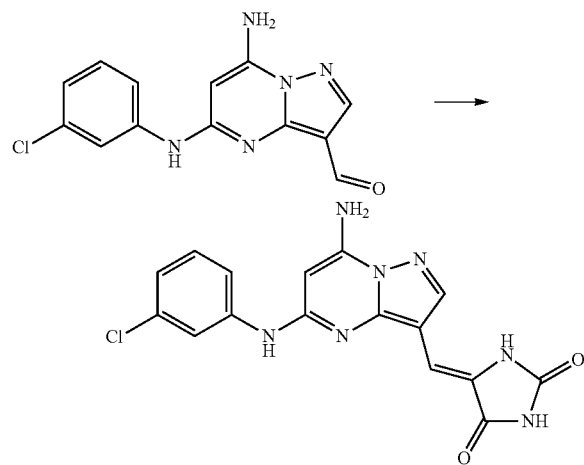

To the reaction vial, 7-amino-5-(3-chlorophenylamino)pyrazolo[1,5-a]pyrimidine-3-carbaldehyde (411 mg, 1.4 mmol) was added to ethanol (5.2 mL) along with hydantoin (143 mg, 1.4 mmol) and piperidine (141 µL, 1.4 mmol). The reaction was heated at 80° C. for 60 minutes in the microwave. The reaction was then cooled to room temperature and diluted with water. The solid was collected by filtration, washed with water and cold ethanol. The material was dried under vacuum overnight. The product, 5-((7-amino-5-(3-chlorophenylamino)pyrazolo[1,5-a]pyrimidin-3-yl)methyl-ene)imidazolidine-2,4-dione, was recovered as a red solid in 54% yield. LCMS (M+1=370)

Example 6

Synthesis of N-(5-(3-chlorophenylamino)-3(2,5-dioxoimidazolidin-4-ylidene)methyl)pyrazolo[1,5-a]pyrimidin-7-yl)piperidine-4-carboxamide

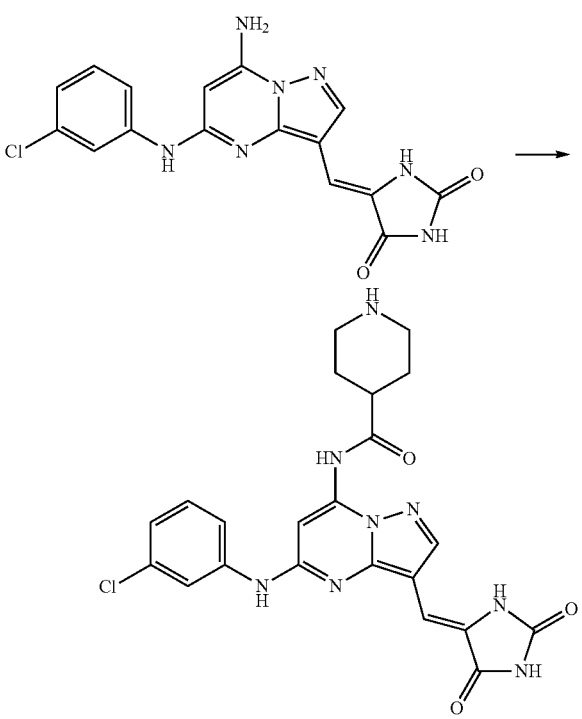

To the reaction vial, 5-((7-amino-5-(3-chlorophenylamino)pyrazolo[1,5-a]pyrimidin-3-yl)methylene)imidazolidine-2,4-dione (15 mg, 0.04 mmol) was added to DMF (0.2 mL) along with HBTU (30 mg, 0.08 mmol), DIEA (28 µL, 0.16 mmol) and 1-(tert-butoxycarbonyl)piperidine-4-carboxylic acid (18 mg, 0.08 mmol). The reaction was stirred at room temperature for 8 hours then heated at 95° C. for 4 hours. The reaction was then cooled to room temperature and diluted with water. The solid was collected by filtration, washed with water, 1N HCl solution, and more water. The material was then dissolved in 5% DCM/MeOH and purified by prep HPLC. The isolated fractions were combined and evaporated to dryness. The material was dissolved in 1 mL of TFA/DCM (1:1) and stirred at room temperature for 1 hour. The solvent was removed by evaporation under a stream of nitrogen and the crude material was washed with 1N NaOH followed by water. The solid was collected by filtration and dried under vacuum overnight. The product, N-(5-(3-chlorophenylamino)-3-((2,5-dioxoimidazolidin-4-ylidene)methyl)pyrazolo[1,5-a]pyrimidin-7-yl)piperidine-4-carboxamide, was recovered as a solid in 2% yield. LCMS (M+1=481).

Table 1 below shows the biological activities of Examples 5 and 6 as listed as Compounds A1 and B1.

TABLE 1

| Compound | CK2: IC50 (μM) | PIM2: IC50 (5 μM ATP) | AB: MDAMB453 (μM) | AB: BxPC3 (μM) |
|---|---|---|---|---|
| A1 | <0.1 | 1.1779 | 2.464 | 16.599 |
| B1 | <1.0 | 2.5000 | | |

Example 7

Synthesis of 5-chloro-N-cyclopropylpyrazolo[1,5-a]pyrimidin-7-amine

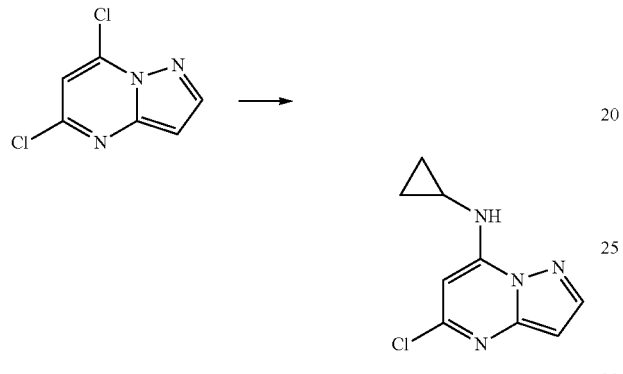

To 5,7-dichloropyrazolo[1,5-a]pyrimidine (200 mg, 1.06 mmol) in ACN was added Et₃N (148 μl, 1.06 mmol) and cyclopropylamine (75 μl, 1.06 mmol). The reaction was refluxed at 80° C. overnight. The mixture was concentrated under reduced pressure, dissolved in DCM, and washed with water. The resulting organic layer was dried over Na₂SO₄ and concentrated under reduced pressure to afford 156 mg of 5-chloro-N-cyclopropylpyrazolo[1,5-a]pyrimidin-7-amine (70% yield). LCMS (M+1=209)

Example 8

Synthesis of 5-chloro-7-(cyclopropylamino)pyrazolo[1,5-a]pyrimidine-3-carbaldehyde

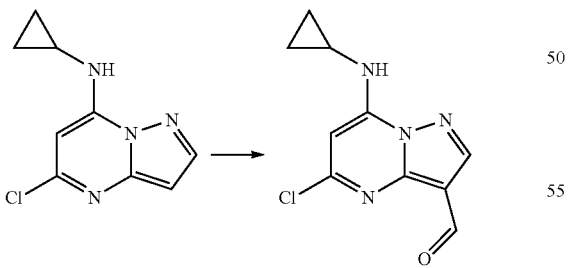

To 5-chloro-N-cyclopropylpyrazolo[1,5-a]pyrimidin-7-amine (156 mg, 0.75 mmol) in DMF was added POCl₃ (205 μl, 2.25 mmol). The mixture was stirred at room temperature for 3 hours. Ice was added to quench excess POCl₃ then the mixture was neutralized with 1M NaOH. DCM was added and the product was extracted three times. The organic layer was dried over Na₂SO₄ and concentrated under reduced pressure to yield 5-chloro-7-(cyclopropylamino)pyrazolo[1,5-a]pyrimidine-3-carbaldehyde. Some residual DMF could not be removed. LCMS (M+1=237)

Example 9

Synthesis of 5-(3-chlorophenylamino)-7-(cyclopropylamino)pyrazolo[1,5-a]pyrimidine-3-carbaldehyde

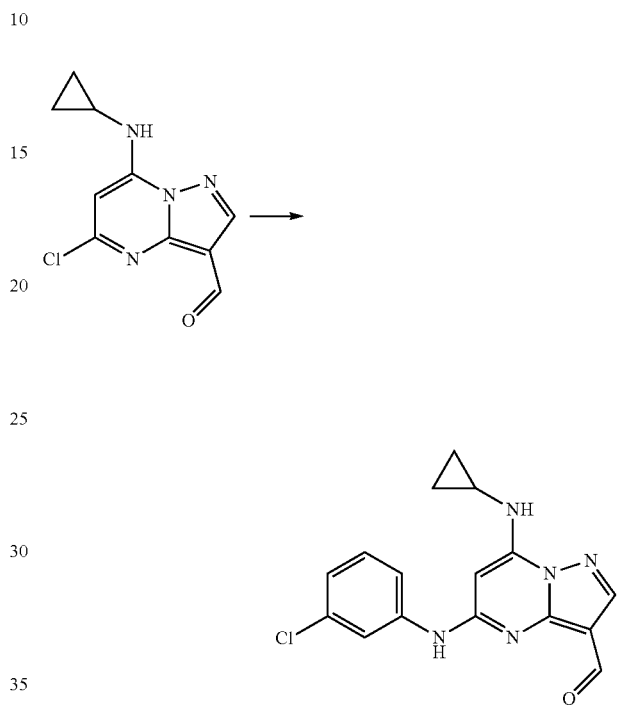

To 5-chloro-7-(cyclopropylamino)pyrazolo[1,5-a]pyrimidine-3-carbaldehyde (177 mg, 0.75 mmol) in 1,4-dioxane was added 3-chloroaniline (397 3.75 mmol). The mixture was heated in microwave at 120° C. for 60 minutes. The precipitate was filtered off, and the filtrate was purified by prep TLC (1% MeOH/DCM) to yield 26 mg (11% yield) of 5-(3-chlorophenylamino)-7-(cyclopropylamino)pyrazolo[1,5-a]pyrimidine-3-carbaldehyde. LCMS (M+1=328)

Example 10

Synthesis of 5-((5-(3-chlorophenylamino)-7-(cyclopropylamino)pyrazolo[1,5-a]pyrimidin-3-yl)methylene)imidazolidine-2,4-dione

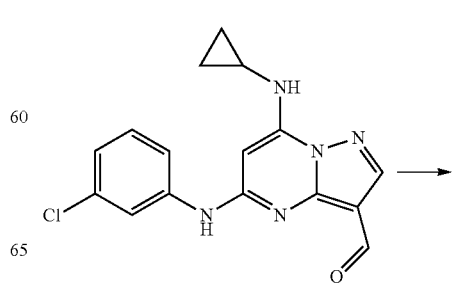

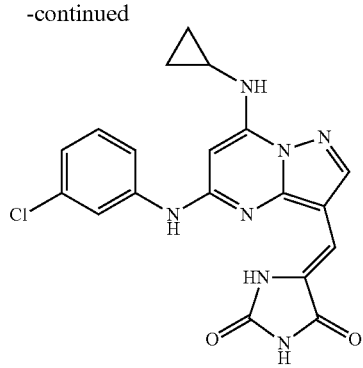

To 5-(3-chlorophenylamino)-7-(cyclopropylamino)pyrazolo[1,5-a]pyrimidine-3-carbaldehyde (26 mg, 0.08 mmol) in EtOH was added hydantoin (8 mg, 0.08 mmol) and piperidine (8 μl, 0.08 mmol). The mixture was stirred at 70° C. over the weekend. Insolubilities were filtered off, and filtrate was concentrated under reduced pressure. Filtrate was then dissolved in MeOH and, isolated by prep HPLC to yield 5-((5-(3-chlorophenylamino)-7-(cyclopropylamino)pyrazolo[1,5-a]pyrimidin-3-yl)methylene)imidazolidine-2,4-dione. LCMS (M+1=410)

Example 11

Synthesis of 7-(cyclopropylamino)-5-(3-fluorophenylamino)pyrazolo[1,5-a]pyrimidine-3-carbaldehyde

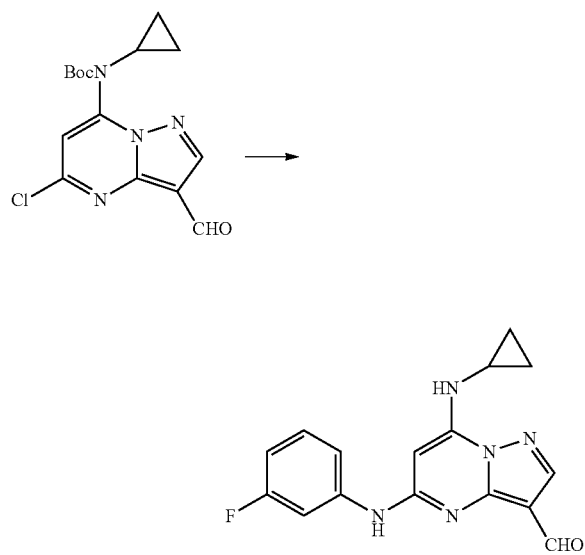

Tert-butyl 5-chloro-3-formylpyrazolo[1,5-a]pyrimidin-7-yl(cyclopropyl)carbamate (0.2 g, 0.59 mmol) was suspended in ethanol (2 mL). 3-fluoroaniline (189 mg, 1.48 mmol) was added, followed by 4M HCl/dioxane (0.3 mL, 1.18 mmol). The reaction was heated to 80° C. for 6 h, and then the volatiles were removed in vacuo. The residue was diluted with water (10 mL) and the pH was adjusted to 12 by the addition of 6M NaOH. The solution was stirred for 0.5 h, then the precipitate, which is a mixture of tert-butyl cyclopropyl (5-(3-fluorophenylamino)-3-formylpyrazolo[1,5-a]pyrimidin-7-yl)carbamate and the corresponding imine, were isolated by filtration and dried in vacuo. The imine was hydrolyzed by dissolving in methanol (9 mL), 1,4-dioxane (3.6 mL) and 6M HCl (9 mL) and heating at 60° C. for 5 h. The solution was poured onto ice (50 mL) and the pH was adjusted to 12 by addition of 6M NaOH. The precipitate was isolated by filtration and dried in vacuo to provide tert-butyl cyclopropyl(5-(3-fluorophenylamino)-3-formylpyrazolo[1,5-a]pyrimidin-7-yl)carbamate (172 mg, 93%). LCMS (M+1=312)

Example 12

Synthesis of 5-((7-(cyclopropylamino)-5-(3-fluorophenylamino)pyrazolo[1,5-a]pyrimidin-3-yl)methylene)imidazolidine-2,4-dione

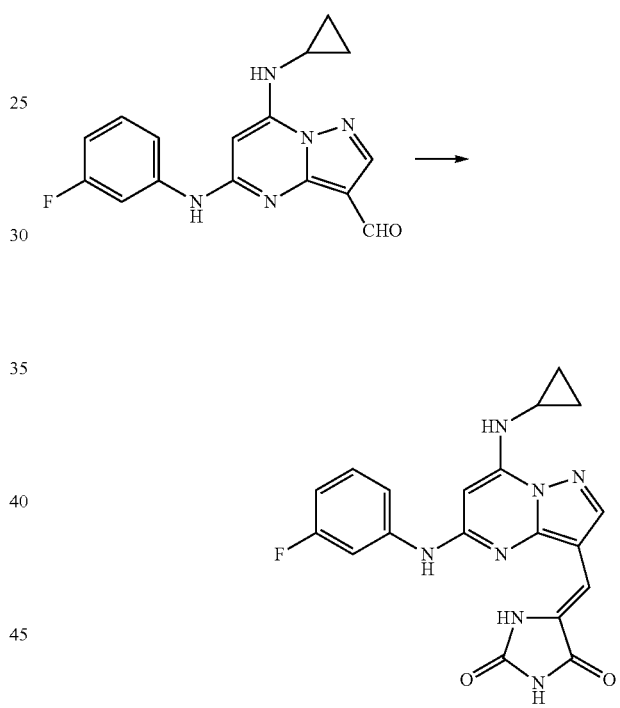

Hydantoin (69 mg, 0.69 mmol) and piperidine (69 μL, 0.69 mmol) were added to 7-(cyclopropylamino)-5-(3-fluorophenylamino)pyrazolo[1,5-a]pyrimidine-3-carbaldehyde (72 mg, 0.23 mmol) dissolved in ethanol (1.1 mL). The reaction was heated at 80° C. After 15 h, the reaction was cooled to r.t., diluted with water (5 mL), and the precipitate was collected and washed with 1:1 ethanol:water (5 mL). The bright yellow solid was dried in vacuo to give (Z)-5-((7-(cyclopropylamino)-5-(3-fluorophenylamino)pyrazolo[1,5-a]pyrimidin-3-yl)methylene)imidazolidine-2,4-dione (25 mg, 10% over 3 steps). LCMS (M+1=507)

The compounds described in the following Table 2A were prepared using chemistries similar to those exemplified in Example 11 and Example 12. All compounds were characterized by LCMS. Table 2B shows the biological activities of the compounds listed in Table 2A.

TABLE 2A
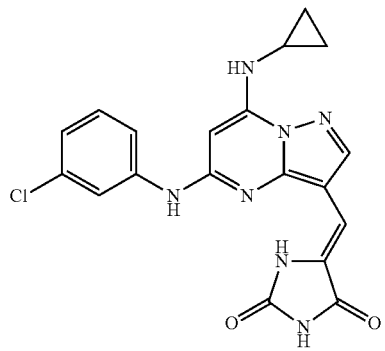
TABLE 2A-continued
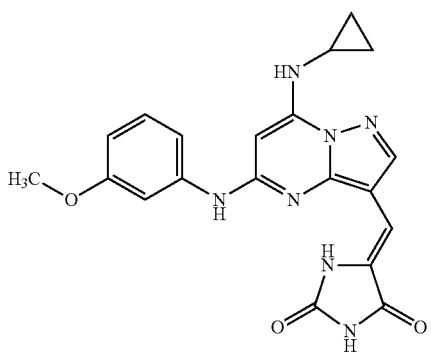 [SMILES: COc1cccc(Nc2cc(NC3CC3)n3ncc(/C=C4\NC(=O)NC4=O)c3n2)c1]
TABLE 2B
| Com-pound | CK2: IC50 (μM) | PIM2: IC50 (μM) | PIM2: IC50 (5 μM ATP) | AB: MDAMB453 (μM) | AB: BxPC3 (μM) |
|---|---|---|---|---|---|
| C1 | <0.01 | 1.3 | >2.5000 | 1.038 | 15.029 |
| D1 | <0.01 | | 2.2002 | 1.34 | 4.067 |
| E1 | <0.01 | | >2.5000 | 17.713 | 16.835 |
| F1 | <0.01 | | >2.5000 | 2.037 | 5.763 |
TABLE 2A-continued
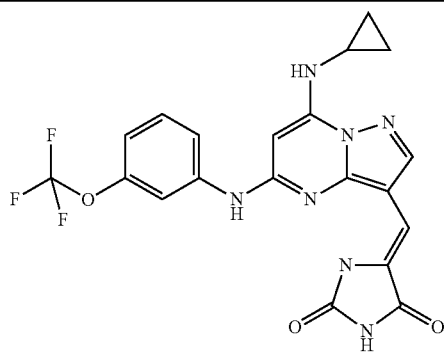
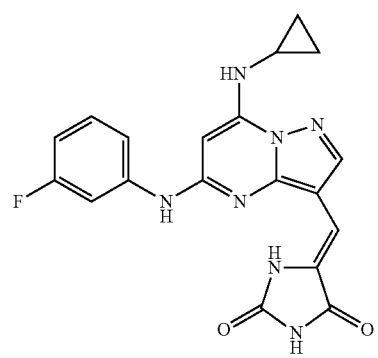
Example 13
Synthesis of 7-(cyclopropylamino)-5-(3,5-difluorophenylamino)pyrazolo[1,5-a]pyrimidine-3-carbaldehyde
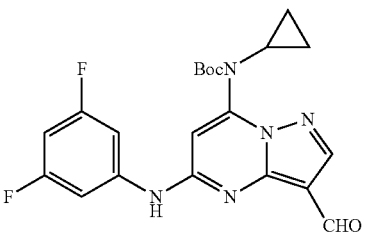

-continued

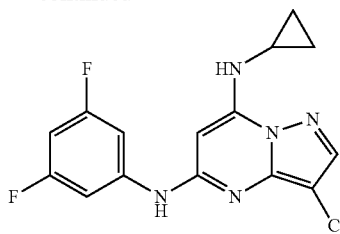

3,5-Difluoroaniline (29 mg, 0.22 mmol), Cs₂CO₃ (67 mg, 0.21 mmol) were added to Ten-butyl 5-chloro-3-formylpyrazolo[1,5-a]pyrimidin-7-yl(cyclopropyl)carbamate (50 mg, 0.15 mmol) dissolved in 1,4-dioxane (1 mL). Racemic BINAP (6 mg, 0.06 mmol) and palladium(II) acetate (4 mg, 0.04 mmol) were then added. The mixture was sealed and irradiated at 110° C. for 20 min in the microwave. Et₂O (3 mL) was added and the solution was filtered. The filtrate was concentrated in vacuo. The crude residue was dissolved in dichloromethane (1.5 mL) and trifluoroacetic acid (1.5 mL). After 1 h, the solution was concentrated under a stream of air. The residue was triturated with 20% 2-propanol/hexanes. The product was filtered to yield 7-(cyclopropylamino)-5-(3,5-difluorophenylamino)pyrazolo[1,5-a]pyrimidine-3-carbaldehyde (39 mg, 80%). LCMS (M+1=330)

The compounds described in the following Table 3 were prepared using chemistries similar to those exemplified in Example 13. All compounds were characterized by LCMS.

TABLE 3

| Structure | MW | LCMS m/z [M + 1]+ |
|---|---|---|
| 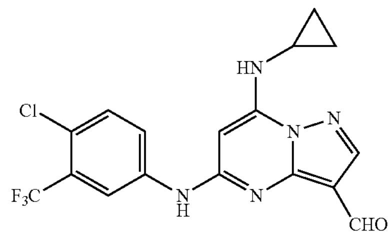 [SMILES: O=Cc1cnn2c(NC3CC3)cc(Nc3ccc(Cl)c(C(F)(F)F)c3)nc12] | 395.7 | 396 |
| 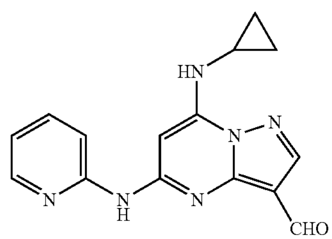 [SMILES: O=Cc1cnn2c(NC3CC3)cc(Nc3ccccn3)nc12] | 294.3 | 295 |
| 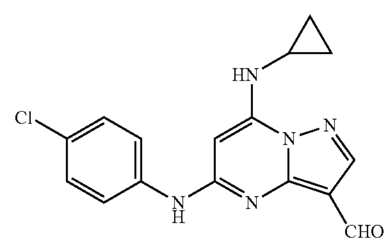 [SMILES: O=Cc1cnn2c(NC3CC3)cc(Nc3ccc(Cl)cc3)nc12] | 327.7 | 328 |
| 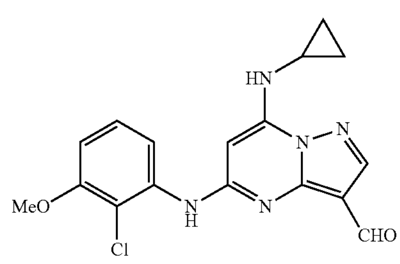 [SMILES: COc1cccc(Nc2cc(NC3CC3)n3ncc(C=O)c3n2)c1Cl] | 357.7 | 358 |
| 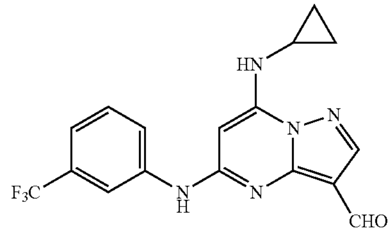 [SMILES: O=Cc1cnn2c(NC3CC3)cc(Nc3cccc(C(F)(F)F)c3)nc12] | 361.3 | 362 |

TABLE 3-continued
| Structure | MW | LCMS m/z [M + 1]+ |
|---|---|---|
| 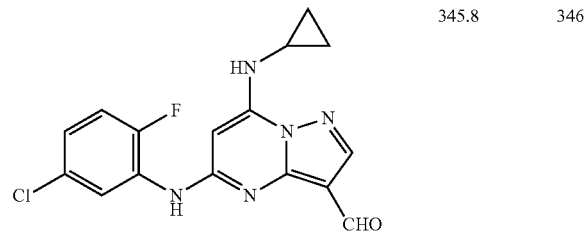 | 345.8 | 346 |
| 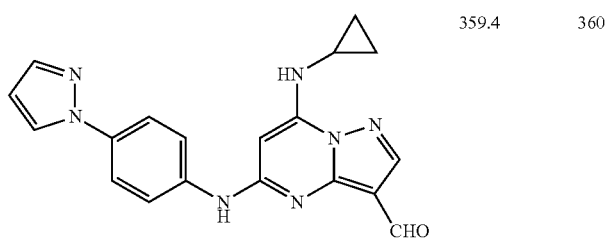 | 359.4 | 360 |
| 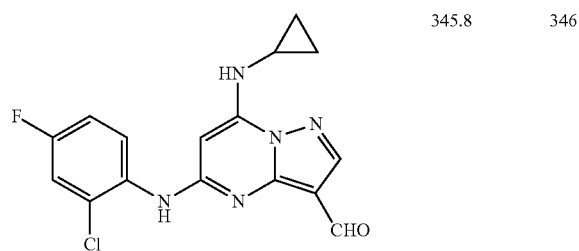 | 345.8 | 346 |
| 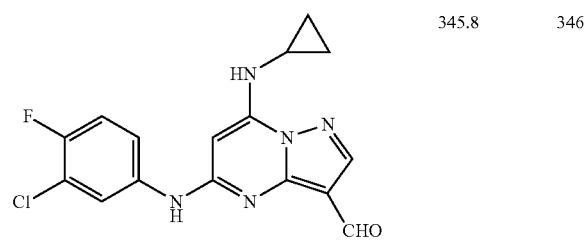 | 345.8 | 346 |
| 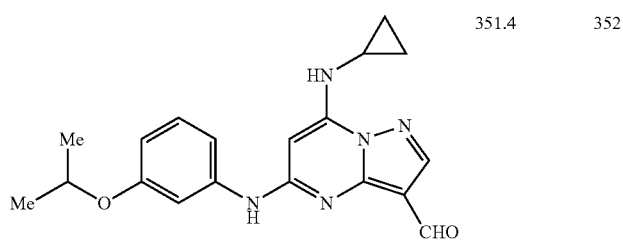 | 351.4 | 352 |
| 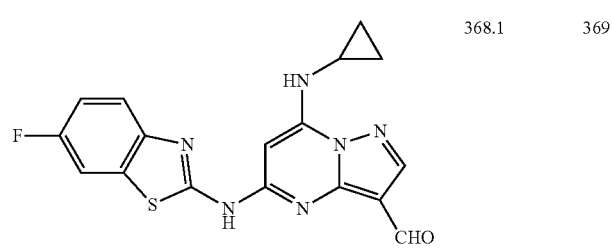 | 368.1 | 369 |

TABLE 3-continued

| Structure | MW | LCMS m/z [M + 1]+ |
|---|---|---|
| (cyclopropylamino-pyridylamino-pyrazolopyrimidine-carbaldehyde) | 294.3 | 295 |
| (cyclopropylamino-methoxyindolyl-pyrazolopyrimidine-carbaldehyde) | 347.4 | 348 |
| (cyclopropylamino-pyrrolyl-pyrazolopyrimidine-carbaldehyde) | 267.3 | 268 |

Example 14

Synthesis of (Z)-5-((7-(cyclopropylamino)-5-(3,5-difluorophenylamino)pyrazolo[1,5-a]pyrimidin-3-yl)methylene)imidazolidine-2,4-dione

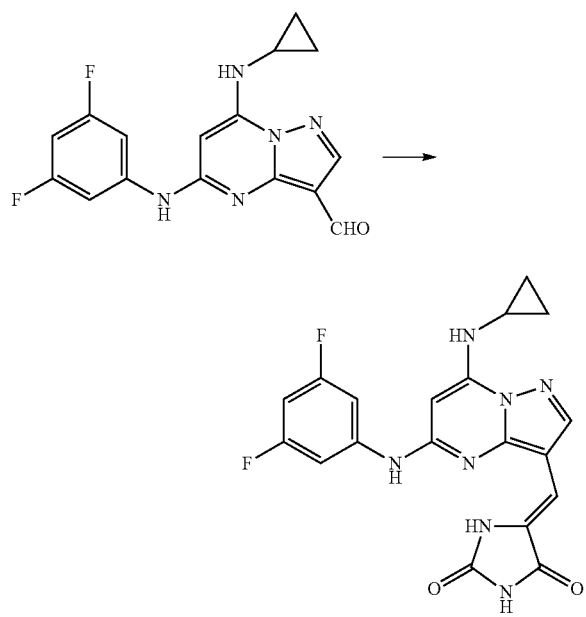

Hydantoin (28 mg, 0.28 mmol) and piperidine (42 μL, 0.42 mmol) were added to 7-(cyclopropylamino)-5-(3,5-difluorophenylamino)pyrazolo[1,5-a]pyrimidine-3-carbaldehyde (52 mg, 0.16 mmol) dissolved in ethanol (1 mL). The reaction was heated at 80° C. After 12 h, the reaction was cooled to r.t., diluted with water (2 mL), and the precipitate was collected and washed with 1:1 ethanol:water (5 mL). The solid was dried in vacuo to give (Z)-5-((7-(cyclopropylamino)-5-(3,5-difluorophenylamino)pyrazolo[1,5-a]pyrimidin-3-yl)methylene)imidazolidine-2,4-dione (18 mg, 28% over 3 steps). LCMS (M+1=440)

The compounds described in the following tables were prepared using chemistries similar to those exemplified in Example 14. All compounds were characterized by LCMS. Table 4B shows the biological activities of the compounds listed in Table 4A.

TABLE 4A
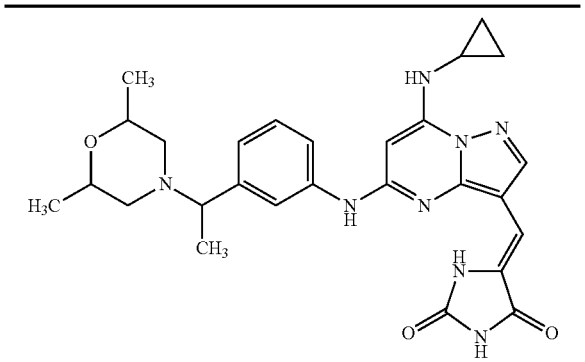
TABLE 4A-continued
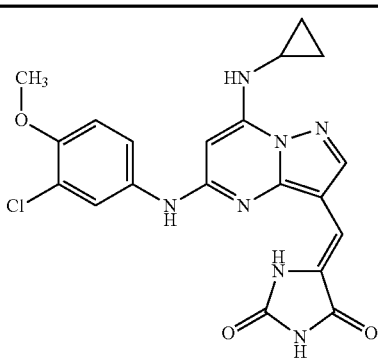

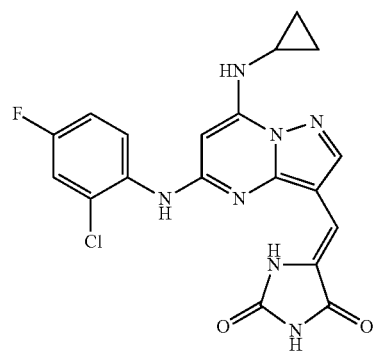

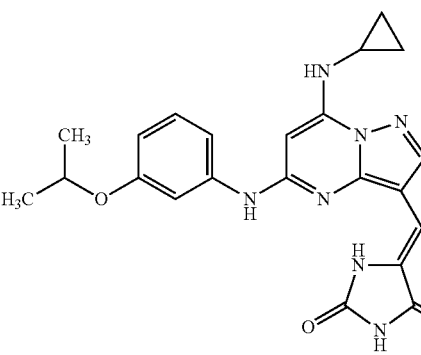
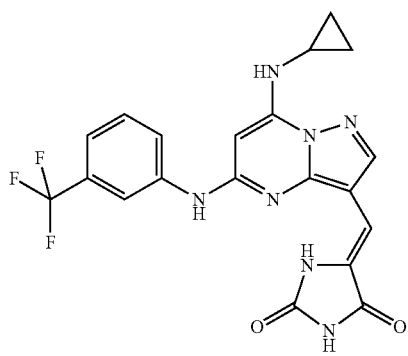 [SMILES: O=C1NC(=O)/C(=C/c2cnn3c(NC4CC4)cc(Nc4cccc(C(F)(F)F)c4)nc23)N1]
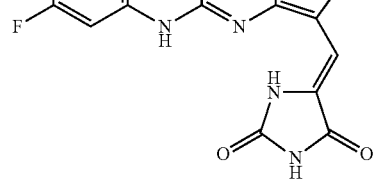

TABLE 4A-continued
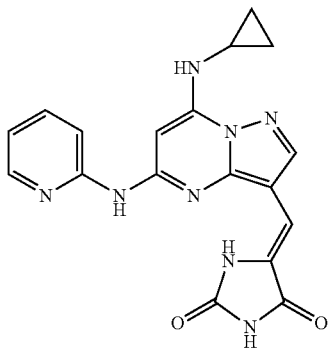 [SMILES: O=C1NC(=O)/C(=C/c2cnn3c(NC4CC4)cc(Nc4ccccn4)nc23)N1]
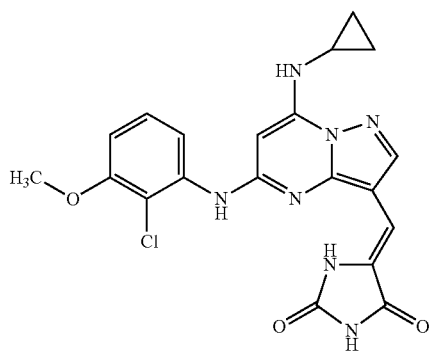 [SMILES: COc1cccc(Nc2cc(NC3CC3)n3ncc(/C=C4\NC(=O)NC4=O)c3n2)c1Cl]
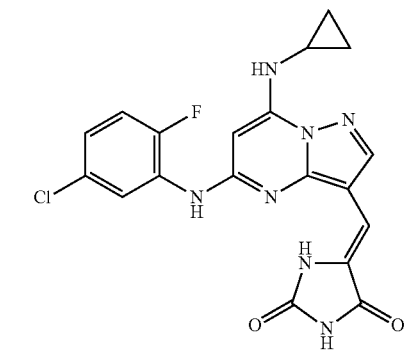 [SMILES: O=C1NC(=O)/C(=C/c2cnn3c(NC4CC4)cc(Nc4cc(Cl)ccc4F)nc23)N1]
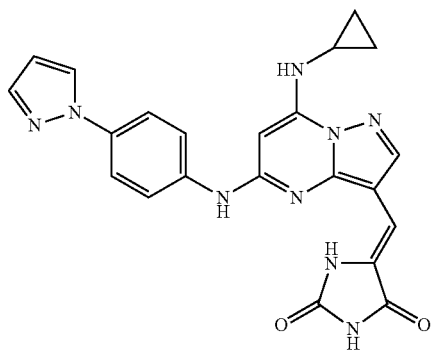 [SMILES: O=C1NC(=O)/C(=C/c2cnn3c(NC4CC4)cc(Nc4ccc(-n5cccn5)cc4)nc23)N1]
TABLE 4A-continued
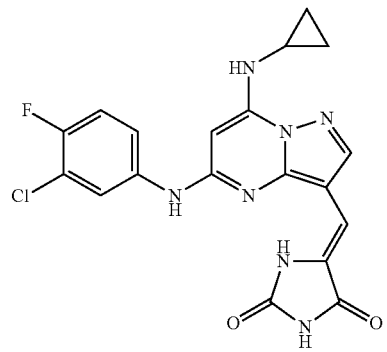 [SMILES: O=C1NC(=O)/C(=C/c2cnn3c(NC4CC4)cc(Nc4ccc(F)c(Cl)c4)nc23)N1]
TABLE 4B
| Compound | CK2: IC50 (μM) | PIM2: IC50 (5 μM ATP) | AB: MDAMB453 (μM) | AB: BxPC3 (μM) |
|---|---|---|---|---|
| G1 | <0.01 | >2.5000 | 10.006 | >30 |
| H1 | <0.01 | >2.5000 | 0.991 | 3.209 |
| I1 | <0.01 | >2.5000 | 11.121 | 15.148 |
| J1 | <0.01 | 2.4799 | 7.116 | 3.924 |
| K1 | <0.01 | >2.5000 | 7.711 | 5.66 |
| L1 | <0.01 | >2.5000 | 0.5 | 1.354 |
| M1 | <0.01 | >2.5000 | | |
| N1 | <0.01 | 1.9706 | | |
| O1 | <0.01 | >2.5000 | | |
| P1 | <0.01 | >2.5000 | | |
| Q1 | <0.01 | >2.5000 | | |
| R1 | <0.01 | >2.5000 | | |
| S1 | <0.01 | 2.041 | | |
The compounds described in the following Table 5 were prepared following the general scheme below using chemistries similar to Example 13 and Example 14.
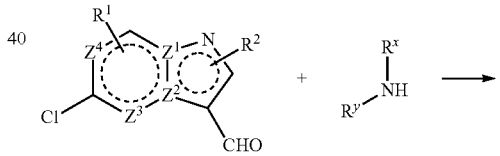
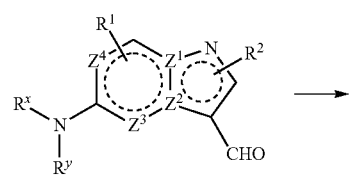
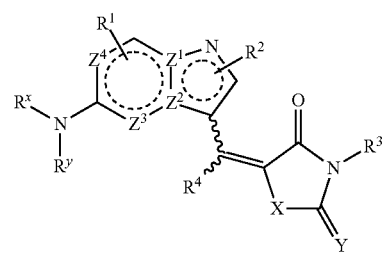

TABLE 5
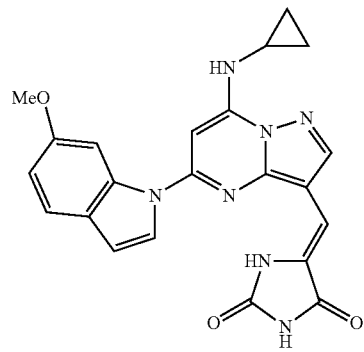 [SMILES: COc1ccc2ccn(-c3cc(NC4CC4)n4ncc(/C=C5\NC(=O)NC5=O)c4n3)c2c1]
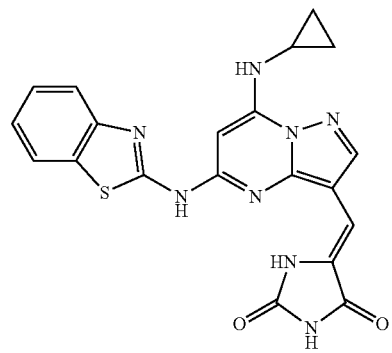 [SMILES: O=C1NC(=O)/C(=C/c2cnn3c(NC4CC4)cc(Nc4nc5ccccc5s4)nc23)N1]
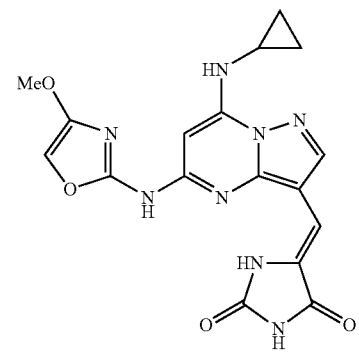 [SMILES: COc1coc(Nc2cc(NC3CC3)n3ncc(/C=C4\NC(=O)NC4=O)c3n2)n1]
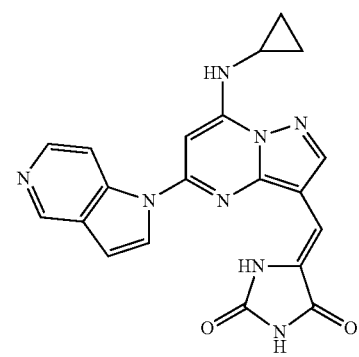 [SMILES: O=C1NC(=O)/C(=C/c2cnn3c(NC4CC4)cc(-n4ccc5cnccc54)nc23)N1]
TABLE 5-continued
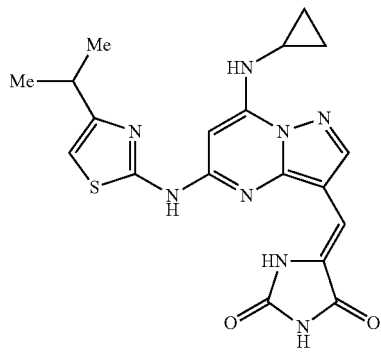 [SMILES: CC(C)c1csc(Nc2cc(NC3CC3)n3ncc(/C=C4\NC(=O)NC4=O)c3n2)n1]
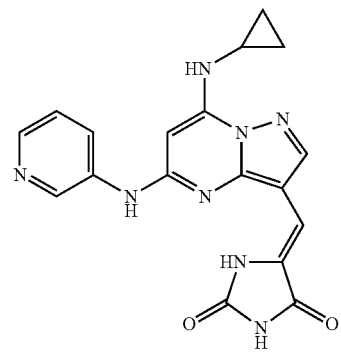 [SMILES: O=C1NC(=O)/C(=C/c2cnn3c(NC4CC4)cc(Nc4cccnc4)nc23)N1]
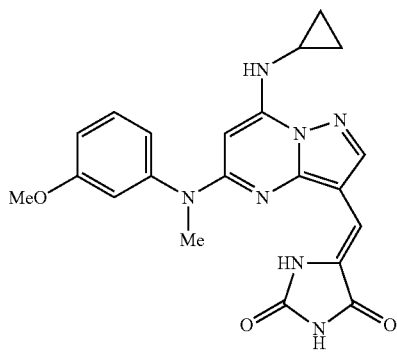 [SMILES: COc1cccc(N(C)c2cc(NC3CC3)n3ncc(/C=C4\NC(=O)NC4=O)c3n2)c1]
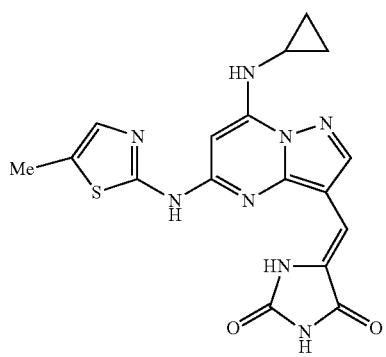 [SMILES: Cc1cnc(Nc2cc(NC3CC3)n3ncc(/C=C4\NC(=O)NC4=O)c3n2)s1]

TABLE 5-continued

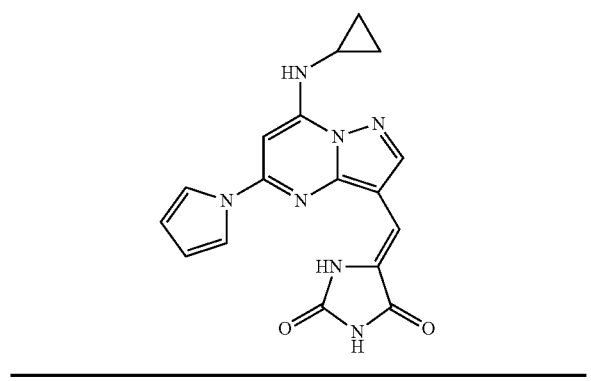

Example 15

Synthesis of 5-(3-chloro-4-fluorophenylamino)-7-(cyclopropylmethylamino)pyrazolo[1,5-a]pyrimidine-3-carbaldehyde

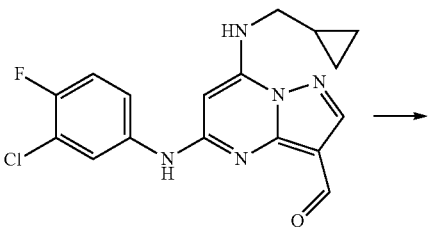

To tert-butyl 5-chloro-3-formylpyrazolo[1,5-a]pyrimidin-7-yl(cyclopropylmethyl) carbamate (50 mg, 0.14 mmol) in 1 mL of 1,4 dioxane was added cesium carbonate (65 mg, 0.2 mmol), Pd (OAc)$_2$ (4 mg, 0.006 mmol), (±)-BINAP (5 mg, 0.009 mmol), 3-chloro-4-fluoroaniline (31 mg, 0.21 mmol). The reaction mixture was heated in microwave at 110° C. for 20 minutes. The mixture was then cooled to room temperature, water was added, and the product was extracted with ether. The organic layer was then concentrated under reduced pressure and the crude product was dissolved in 1:1 mixture of dichloromethane and trifluoroacetic acid at room temperature for 1 hour. The reaction mixture was concentrated with 10 mL of dichloromethane. To the reaction mixture, ether/hexanes (1:1) was added and the flask was sonicated for 10 minutes then filtered to obtain the yellow precipitate. The precipitate was washed with hexane to yield 5-(3-chloro-4-fluorophenylamino)-7-(cyclopropylmethylamino)pyrazolo[1,5-a]pyrimidine-3-carbaldehyde. LCMS (M+1=-460)

Example 16

Synthesis of 5-((5-(3-chloro-4-fluorophenylamino)-7-(cyclopropylmethylamino)pyrazolo[1,5-a]pyrimidin-3-yl)methylene)imidazolidine-2,4-dione

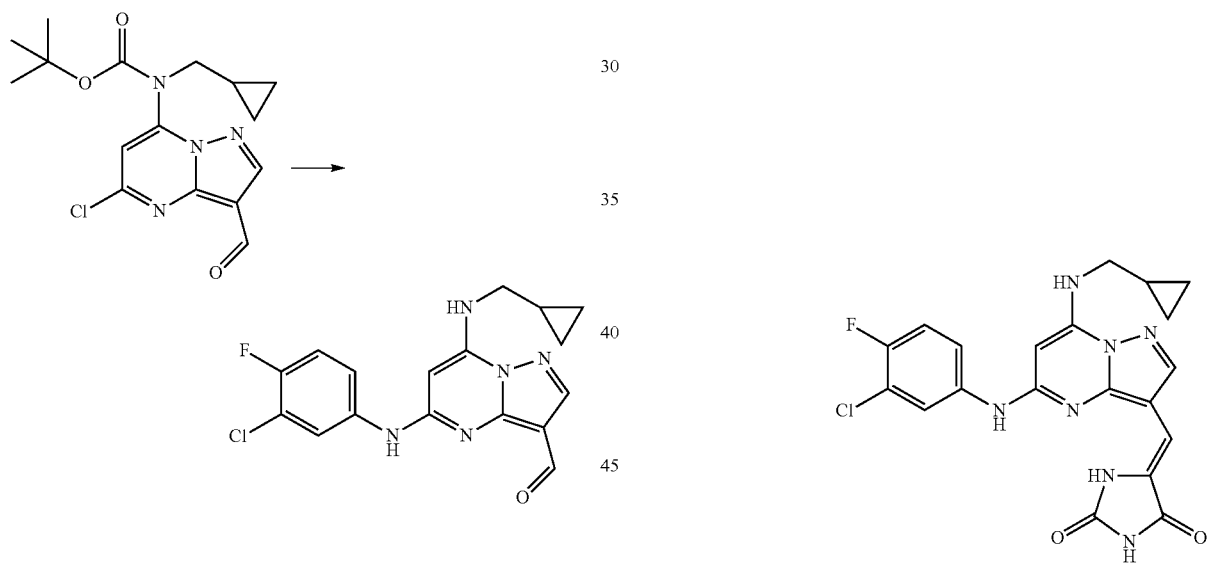

To 5-(3-chloro-4-fluorophenylamino)-7-(cyclopropylmethylamino)pyrazolo[1,5-a]pyrimidine-3-carbaldehyde (40 mg, 0.09 mmol) in 1.0 mL of ethanol was added hydantoin (9 mg, 0.09 mmol) and piperidine (8 ul). The reaction was heated at 80° C. overnight, cooled to room temperature, filtered, and washed with ethanol to yield 20 mg (31% yield) (Z)-5-((5-(3-chloro-4-fluorophenylamino)-7-(cyclopropylmethylamino) pyrazolo[1,5-a]pyrimidin-3-yl) methylene) imidazolidine-2,4-dione as a yellow powder. LCMS (M+1=442)

The compounds described in the following tables were prepared using chemistries similar to those exemplified in Example 15 and Example 16. All compounds were characterized by LCMS. Table 6B shows the biological activities of the compounds listed in Table 6A.

TABLE 6A
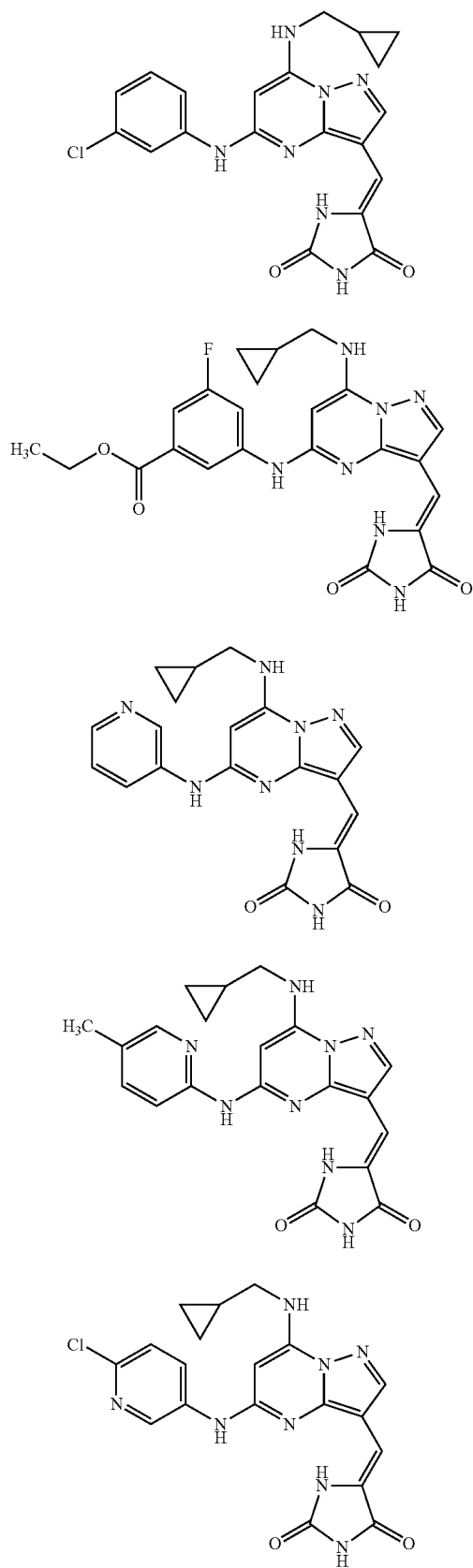
TABLE 6A-continued
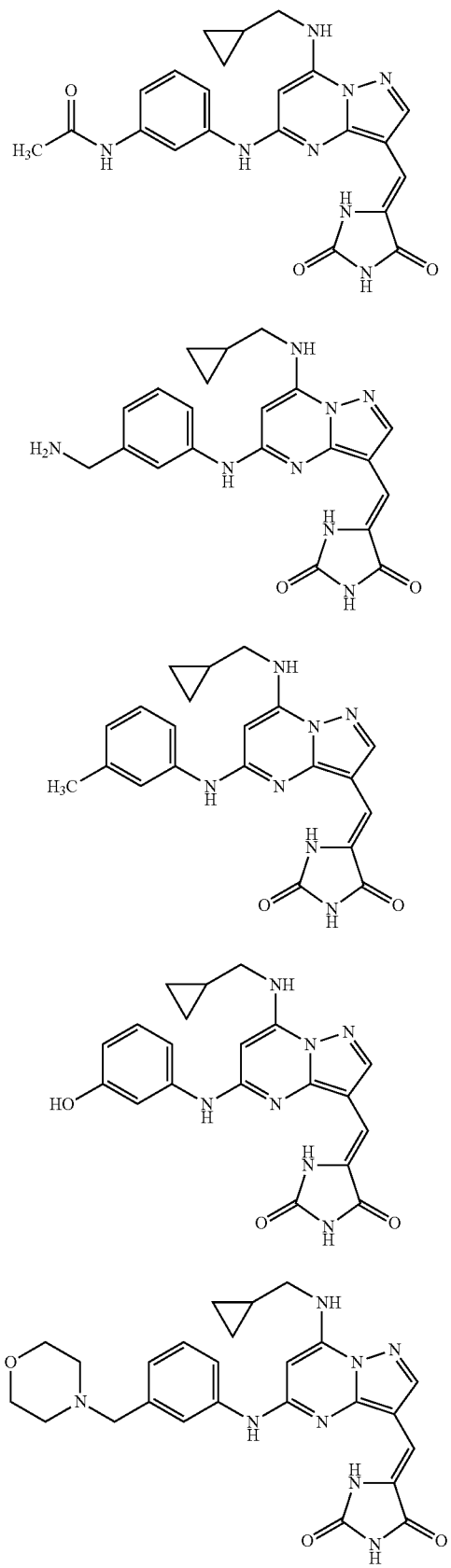

TABLE 6A-continued
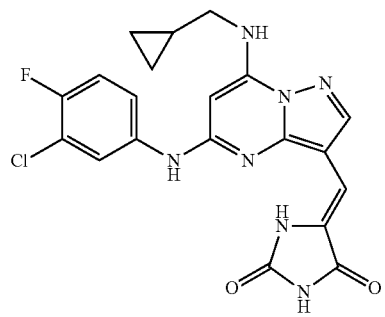 [SMILES: O=C1NC(=O)/C(=C/c2cnn3c(NCC4CC4)cc(Nc4ccc(F)c(Cl)c4)nc23)N1]
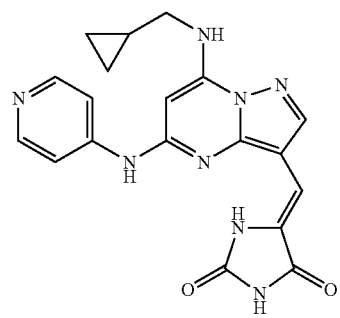 [SMILES: O=C1NC(=O)/C(=C/c2cnn3c(NCC4CC4)cc(Nc4ccncc4)nc23)N1]
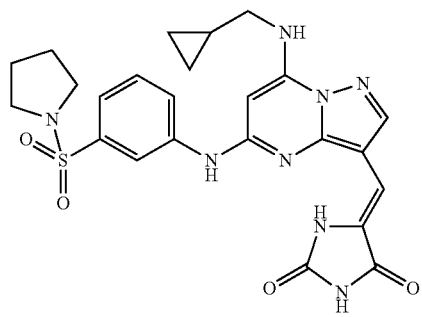 [SMILES: O=C1NC(=O)/C(=C/c2cnn3c(NCC4CC4)cc(Nc4cccc(S(=O)(=O)N5CCCC5)c4)nc23)N1]
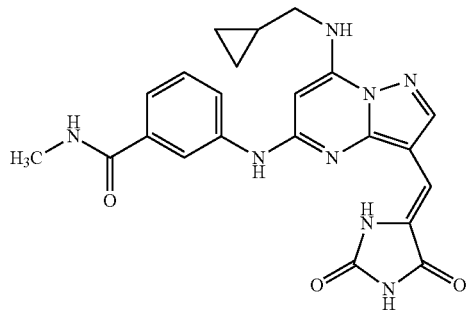 [SMILES: CNC(=O)c1cccc(Nc2cc(NCC3CC3)n3ncc(/C=C4\NC(=O)NC4=O)c3n2)c1]
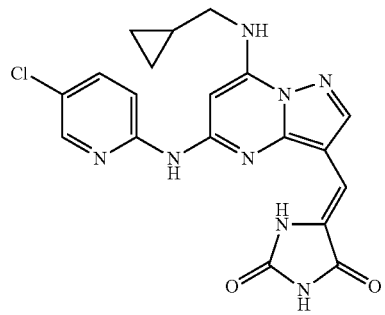 [SMILES: O=C1NC(=O)/C(=C/c2cnn3c(NCC4CC4)cc(Nc4ccc(Cl)cn4)nc23)N1]
TABLE 6A-continued
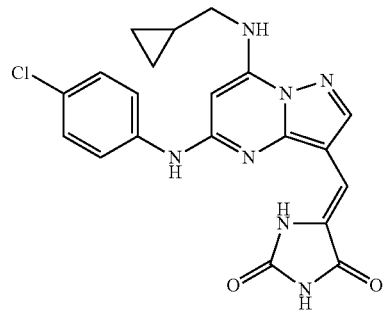 [SMILES: O=C1NC(=O)/C(=C/c2cnn3c(NCC4CC4)cc(Nc4ccc(Cl)cc4)nc23)N1]
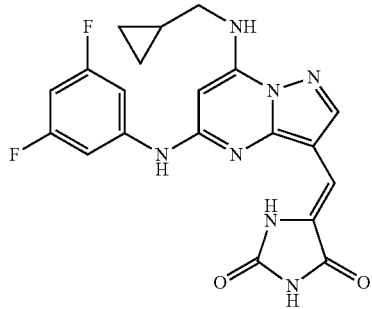 [SMILES: O=C1NC(=O)/C(=C/c2cnn3c(NCC4CC4)cc(Nc4cc(F)cc(F)c4)nc23)N1]
TABLE 6B
| Compound | CK2: IC50 (μM) | PIM2: IC50 (5 μM ATP) | AB: MDAMB453 (μM) | AB: BxPC3 (μM) |
| --- | --- | --- | --- | --- |
| T1 | <0.01 | 0.5087 | 2.196 | 12.315 |
| U1 | <0.1 | >2.5000 | | |
| V1 | <0.1 | >2.5000 | 5.086 | 6.188 |
| W1 | <0.1 | >2.5000 | 7.424 | 9.207 |
| X1 | <0.1 | >2.5000 | 6.935 | 7.986 |
| Y1 | <0.1 | >2.5000 | | |
| Z1 | <0.1 | | | |
| A2 | <0.1 | | | |
| B2 | <0.1 | | | |
| C2 | <0.1 | | | |
| D2 | <0.1 | | | |
| E2 | <0.01 | | | |
| F2 | <0.1 | | | |
| G2 | <0.01 | | | |
| H2 | <0.01 | | | |
| I2 | <0.1 | | | |
Example 17
Synthesis of tert-butyl 5-azido-3-formylpyrazolo[1,5-a]pyrimidin-7-yl(cyclopropyl)carbamate
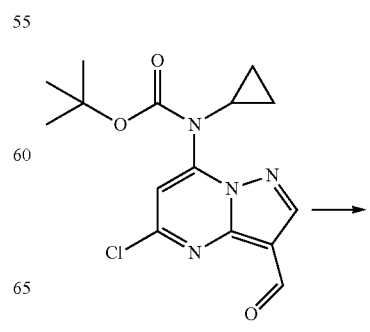

87

-continued

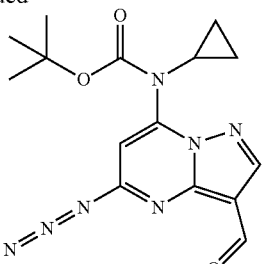

To tert-butyl 5-chloro-3-formylpyrazolo[1,5-a]pyrimidin-7-yl (cyclopropyl) carbamate (500 mg, 1.5 mmol) in dimethylformamide was added sodium azide (150 mg, 2.3 mmol) then the reaction mixture was stirred at room temperature for 30 minutes. The reaction mixture was then partitioned between ethyl acetate/water. The organic layer was collected, dried over sodium sulfate, filtered, and concentrated under high vacuum to yield tert-butyl 5-azido-3-formylpyrazolo[1,5-a]pyrimidin-7-yl(cyclopropyl)carbamate. The crude product was taken to next step without further purification. LCMS (M+1=344)

Example 18
Synthesis of 5-amino-7-(cyclopropylamino)pyrazolo[1,5-a]pyrimidine-3-carbaldehyde

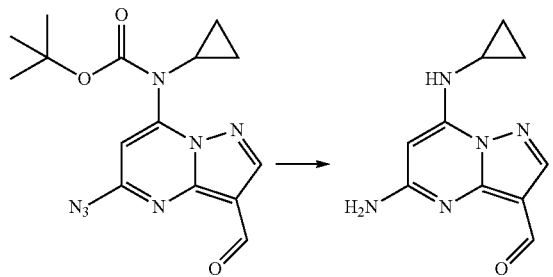 [SMILES: CC(C)(C)OC(=O)N(c1cc(N=[N+]=[N-])nc2c(C=O)cnn12)C1CC1 ; Nc1cc(NC2CC2)n2ncc(C=O)c2n1]

The crude product, tert-butyl 5-azido-3-formylpyrazolo[1,5-a]pyrimidin-7-yl (cyclopropyl) carbamate was subjected to hydrogenation using 10% wt palladium on carbon in ethanol. The reaction was stirred under hydrogen for 3 hours. The mixture was filtered through celite and sonicated with 1:1 mixture of ethyl acetate and hexane. The yellow solid was filtered and dried under reduced pressure and was dissolved in (1:1) DCM/TFA at room temperature for 1 hour. The reaction mixture was washed with aqueous sodium bicarbonate solution and extracted with dichloromethane. The organic layer was concentrated and dried under high vacuum to yield 5-amino-7-(cyclopropylamino) pyrazolo[1,5-a]pyrimidine-3-carbaldehyde as product 310 mg (95% yield on three steps). LCMS (M+1=218)

Example 19
Synthesis of (Z)-5-(5-amino-7-(cyclopropylamino)pyrazolo[1,5-a]pyrimidin-3-yl)methylene)imidazolidine-2,4-dione

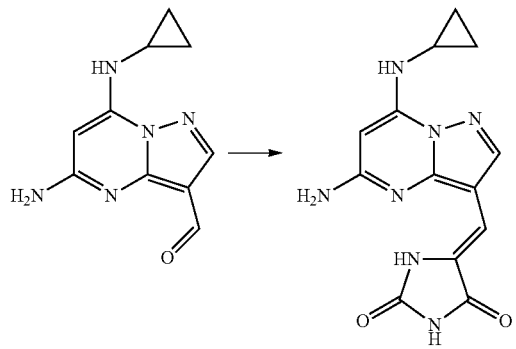 [SMILES: Nc1cc(NC2CC2)n2ncc(C=O)c2n1 ; Nc1cc(NC2CC2)n2ncc(/C=C3\NC(=O)NC3=O)c2n1]

88

To 5-amino-7-(cyclopropylamino) pyrazolo[1,5-a]pyrimidine-3-carbaldehyde (75 mg, 0.34 mmol) in 1.0 mL ethanol was added hydantoin (34 mg, 0.34 mmol) and piperidine (33 ul). The reaction was heated at 80° C. overnight. The reaction mixture was cooled to room temperature and yellow precipitate was filtered, washed with ethanol to yield 45 mg (44% yield) Z)-5-(5-amino-7-(cyclopropylamino)pyrazolo[1,5-a]pyrimidin-3-yl)methylene)imidazolidine-2,4-dione. LCMS (M+1=300)

Example 20

Synthesis of methyl 7-(cyclopropylamino)-3-formylpyrazolo[1,5-a]pyrimidin-5-ylcarbamate

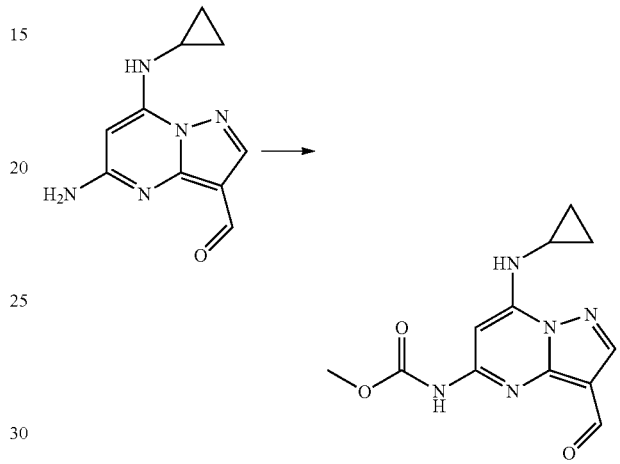

To 5-amino-7-(cyclopropylamino) pyrazolo[1,5-a]pyrimidine-3-carbaldehyde (50 mg, 0.23 mmol) in 1.0 mL tetrahydrofuran was added methyl chloroformate (35 ul, 0.46 mmol) and DIEA (39 ul). The reaction mixture was heated at 60° C. for one hour. The reaction was partitioned between ethyl acetate/water. The organic layer was collected, dried over sodium sulfate, and concentrated under high vacuum to yield methyl 7-(cyclopropylamino)-3-formylpyrazolo[1,5-a]pyrimidin-5-ylcarbamate. The crude product was taken to next step without further purification. LCMS (M+1=276)

Example 21

Synthesis of (Z)-methyl 7-(cyclopropylamino)-3-((2,5-dioxoimidazolidin-4-ylidene)methyl)pyrazolo[1,5-a]pyrimidin-5-ylcarbamate

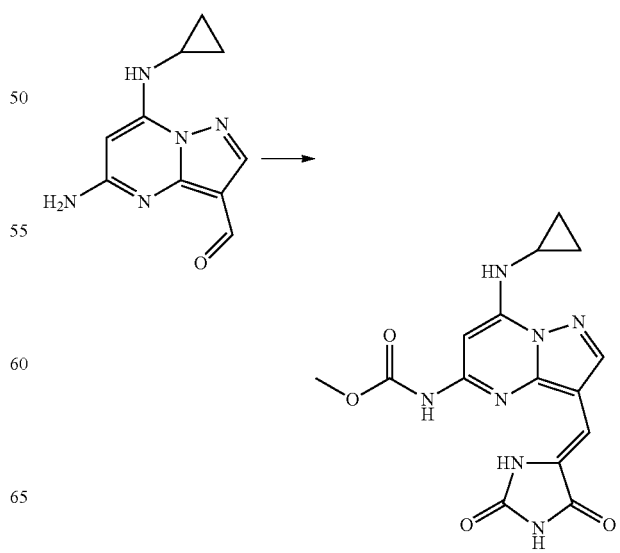

To methyl 7-(cyclopropylamino)-3-formylpyrazolo[1,5-a]pyrimidin-5-ylcarbamate (33 mg, 0.12 mmol) in 1.0 mL ethanol was added hydantoin (12 mg, 0.12 mmol) and piperidine (11 ul). The reaction was heated at 80° C. for two hours. The reaction was cooled to room temperature, the yellow precipitate was filtered, and washed with ethanol to yield 15 mg (40% yield) (Z)-methyl 7-(cyclopropylamino)-3-((2,5-dioxoimidazolidin-4-ylidene) methyl)pyrazolo [1,5-a]pyrimidin-5-ylcarbamate. LCMS (M+1=358)

Example 22

Synthesis of N-(7-(cyclopropylamino)-3-formylpyrazolo[1,5-a]pyrimidin-5-yl)cyclopropanecarboxamide

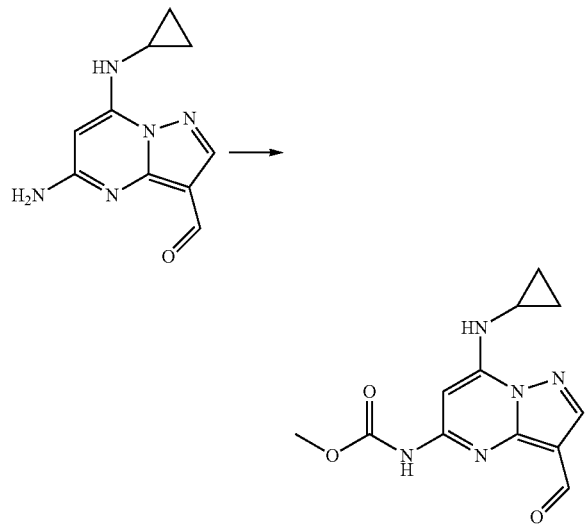

To 5-amino-7-(cyclopropylamino)pyrazolo[1,5-a]pyrimidine-3-carbaldehyde (step b) (58 mg, 0.266 mmol) in 1.0 mL tetrahydrofuran was added cyclopropane carbonyl chloride (38 ul, 0.419 mmol) and DIPEA (39.0 ul). The reaction mixture was heated at 60° C. for one hour. The reaction was partitioned between ethyl acetate and water, the organic layer was dried under sodium sulfate concentrated on high vac to yield N-(7-(cyclopropylamino)-3-formylpyrazolo[1,5-a]pyrimidin-5-yl)cyclopropanecarboxamide. The crude product was taken to next step without further purification. LCMS (M+1=286)

Example 23

Synthesis of (Z)-N-(7-(cyclopropylamino)-3-((2,5-dioxoimidazolidin-4-ylidene)methyl)pyrazolo[1,5-a]pyrimidin-5-yl)cyclopropanecarboxamide

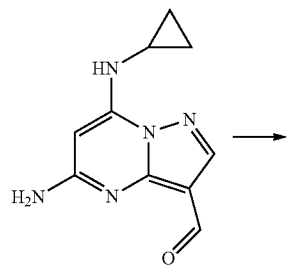

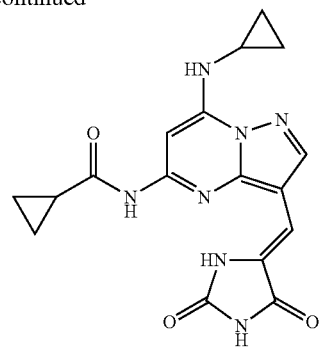

To N-(7-(cyclopropylamino)-3-formylpyrazolo[1,5-a]pyrimidin-5-yl) cyclopropanecarboxamide (74 mg, 0.26 mmol) in 1.0 mL ethanol was added hydantoin (26 mg, 0.26 mmol) and piperidine (24 ul). The reaction was heated at 80° C. for two hours. The reaction mixture was cooled to room temperature, concentrated and diluted with MeOH. The product was purified by prep HPLC to yield 14 mg (20% yield) (Z)-N-(7-(cyclopropylamino)-3-((2,5-dioxoimidazolidin-4-ylidene) methyl)pyrazolo[1,5-a]pyrimidin-5-yl)cyclopropanecarboxamide. LCMS (M+1=368)

The compounds described in the following table were prepared using chemistries similar to those exemplified in Example 20 and Example 16. All compounds were characterized by LCMS. Table 7B shows the biological activities of the compounds listed in Table 7A.

TABLE 7A

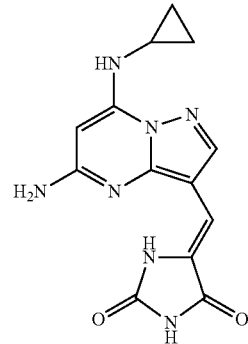 [SMILES: Nc1cc(NC2CC2)n2ncc(/C=C3\NC(=O)NC3=O)c2n1]

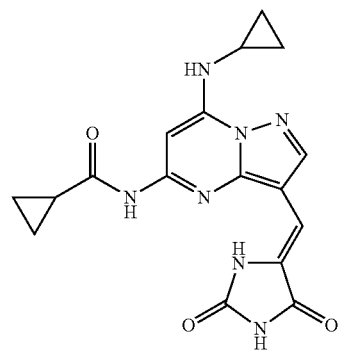 [SMILES: O=C1NC(=O)/C(=C/c2cnn3c(NC4CC4)cc(NC(=O)C4CC4)nc23)N1]

TABLE 7A-continued

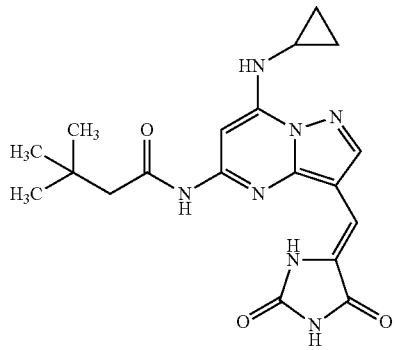 [SMILES: CC(C)(C)CC(=O)Nc1cc(NC2CC2)n2ncc(/C=C3\NC(=O)NC3=O)c2n1]

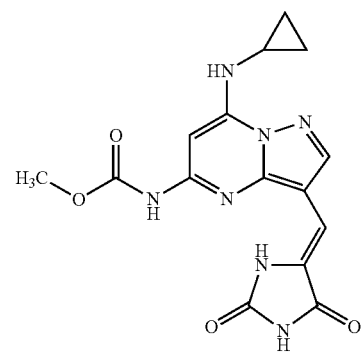 [SMILES: COC(=O)Nc1cc(NC2CC2)n2ncc(/C=C3\NC(=O)NC3=O)c2n1]

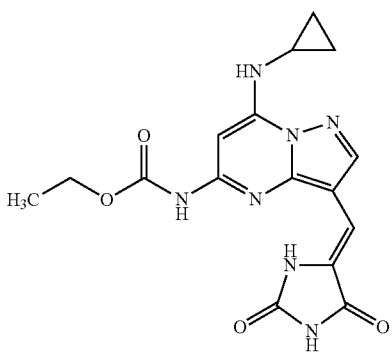 [SMILES: CCOC(=O)Nc1cc(NC2CC2)n2ncc(/C=C3\NC(=O)NC3=O)c2n1]

TABLE 7B

| Compound | CK2: IC50 (µM) | PIM2: IC50 (5 µM ATP) | AB: MDAMB453 (µM) | AB: BxPC3 (µM) |
|---|---|---|---|---|
| J2 | <0.1 | >2.5000 | | |
| K2 | <0.01 | >2.5000 | 11.768 | 9.93 |
| L2 | <0.01 | | 4.17 | 10.986 |

Example 24

Synthesis of 5-((5-(chloro-7-(cyclopropylamino) pyrazolo[1,5-a]pyrimidin-3-yl)methylene)imidazolidine-2,4-dione

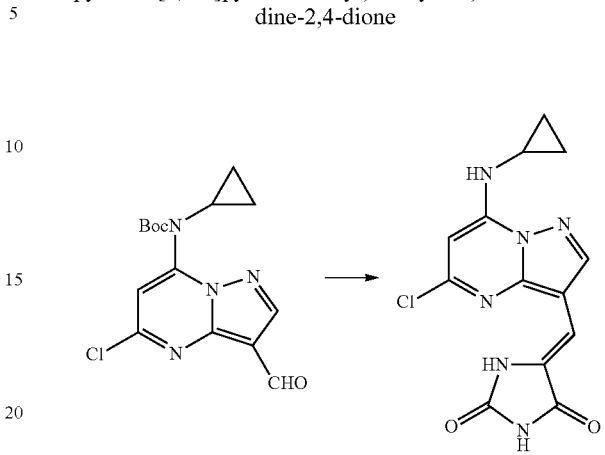

Tert-butyl 5-chloro-3-formylpyrazolo[1,5-a]pyrimidin-7-yl(cyclopropyl)carbamate (0.5 g, 1.48 mmol) was dissolved in glacial acetic acid (5 mL). NaOAc (1.21 g, 14.8 mmol) and hydantoin (356 mg, 3.56 mmol) were added and the reaction was placed in a 110° C. bath for 4 d. The solution was cooled to r.t. and water (15 mL) was added. The precipitate was filtered and then triturated with ethanol (5 mL) and then CH$_2$Cl$_2$ (5 mL) to give (Z)-5-(5-(chloro-7-(cyclopropylamino)pyrazolo[1,5-a]pyrimidin-3-yl)methylene)imidazolidine-2,4-dione (202 mg, 43%). LCMS (ES): >85% pure, m/z 319 [M+1]$^+$.

Example 25

Synthesis of 547-(cyclopropylamino)-5-(4,4-difluoropiperidin-1-yl)pyrazolo[1,5-a]pyrimidin-3-yl)methylene)imidazolidine-2,4-dione

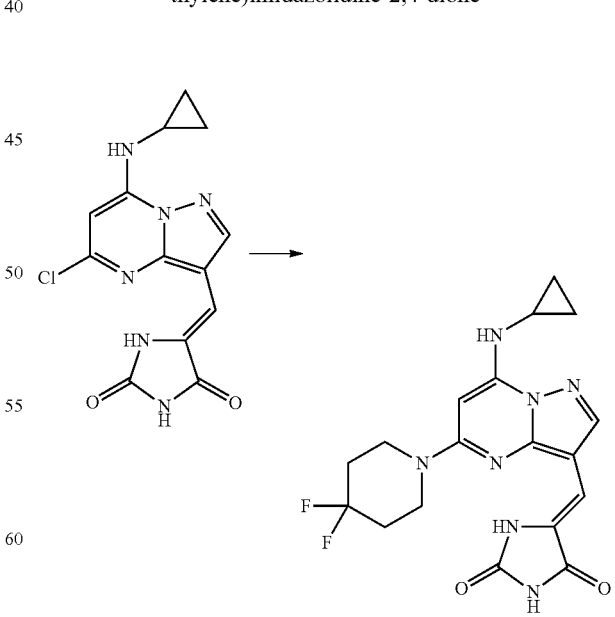

(Z)-5-(5-(Chloro-7-(cyclopropylamino)pyrazolo[1,5-a] pyrimidin-3-yl)methylene)imidazolidine-2,4-dione (25 mg, 0.08 mmol) was suspended in NMP (0.2 mL). 4,4-difluoropiperidine hydrochloride (60 mg, 0.38 mmol) and diisopropylethylamine (67 μL, 0.38 mmol) were added and the reaction was irradiated in the microwave at 140° C. for 20 min. The product was purified by preparative HPLC to afford (Z)-5-((7-(cyclopropylamino)-5-(4,4-difluoropiperidin-1-yl)pyrazolo[1,5-a]pyrimidin-3-yl)methylene)imidazolidine-2,4-dione (5.9 mg, 14%). LCMS (ES): >95% pure, m/z 404 [M+1]⁺.

Example 26

Synthesis of 5-(cyclopentylamino)-7-(cyclopropylamino)pyrazolo[1,5-a]pyrimidine-3-carbaldehyde

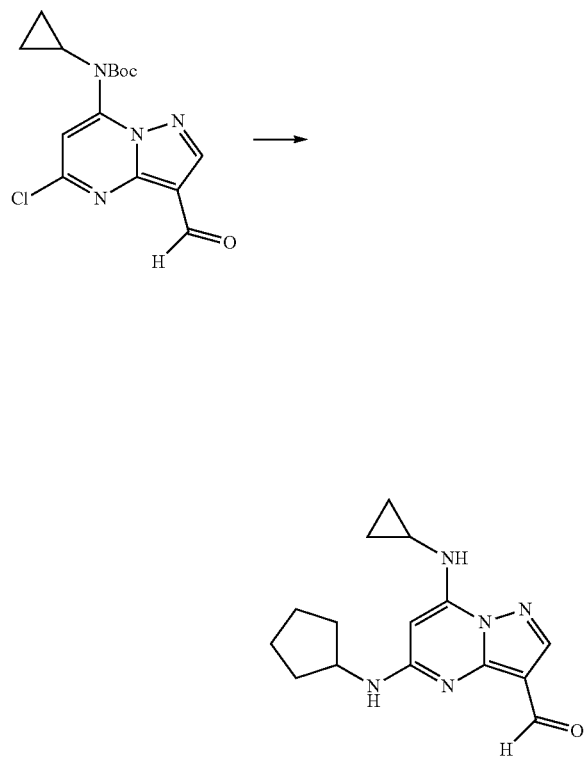

Tert-butyl 5-chloro-3-formylpyrazolo[1,5-a]pyrimidin-7-yl(cyclopropyl)carbamate (1.0 eq, 105 mg, 0.312 mmol) was dissolved in DMF (1 ml) in a vial. K₂CO₃ (1.5 eq, 64 mg, 0.463 mmol) and cyclopentylamine (1.5 eq, 46 ul, 0.465 mmol) were added and the mixture was stirred at 50° C. for one hour. An additional amount of cyclopentylamine (1.5 eq, 46 ul, 0.465 mmol) was added and the mixture stirred at 70° C. for 2 hours. Water was added and the resulting precipitate was filtered and dried to provide 130 mg of solid. This solid was stirred in HCl 4N in dioxane (4 ml) at room temperature for 4 hours. Methanol (1 ml) and aqueous 6N HCl (2 ml) were added and the mixture stirred at room temperature overnight. The reaction was subsequently stirred overnight at 60° C. to complete the imine hydrolysis. The reaction was neutralized with 6N NaOH and the compound extracted with methylene chloride. After drying over Na₂SO₄, and evaporation of the volatiles, the material was triturated in ethylacetate to form a solid. 5-(cyclopentylamino)-7-(cyclopropylamino)pyrazolo[1,5-a]pyrimidine-3-carbaldehyde was isolated as a solid by filtration (21 mg). LCMS (ES):>95% pure, m/z 286 [M+H]⁺.

Example 27

Synthesis of 5-((5-(cyclopentylamino)-7-(cyclopropylamino)pyrazolo[1,5-a]pyrimidin-3-yl)methylene)imidazolidine-2,4-dione

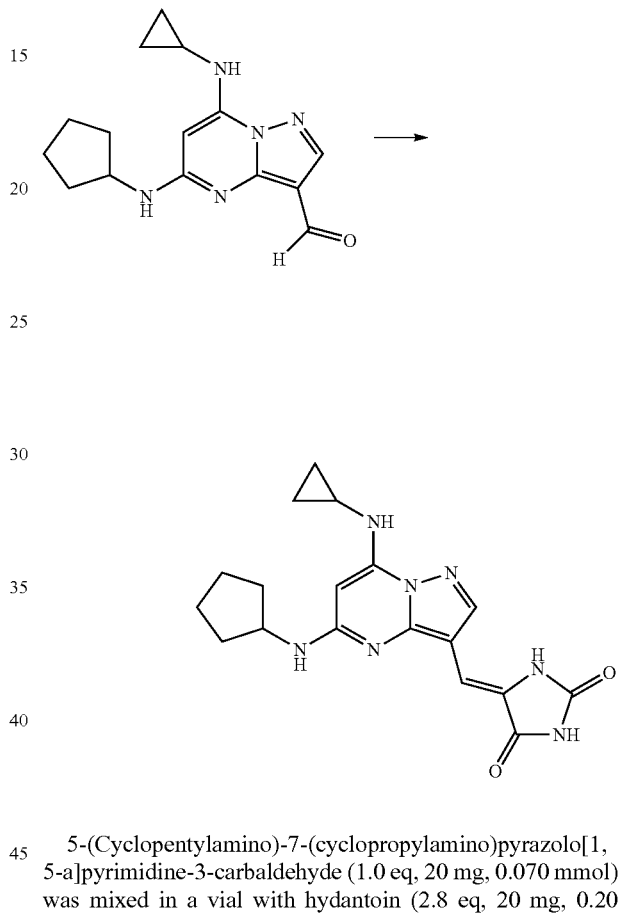

5-(Cyclopentylamino)-7-(cyclopropylamino)pyrazolo[1,5-a]pyrimidine-3-carbaldehyde (1.0 eq, 20 mg, 0.070 mmol) was mixed in a vial with hydantoin (2.8 eq, 20 mg, 0.20 mmol) in Ethanol (0.3 ml). Piperidine (2.9 eq, 20 ul, 0.202 mmol) was added and the mixture was stirred at 90° C. for 3 hours. The mixture was cooled down, the precipitate was filtered, washed with ethanol and dried. (Z)-5-((5-(cyclopentylamino)-7-(cyclopropylamino)pyrazolo[1,5-a]pyrimidin-3-yl)methylene)imidazolidine-2,4-dione was isolated as a solid (25 mg, 100%). LCMS (ES):>95% pure, m/z 368 [M+H]⁺.

The compounds listed in the following Table 6 are Example 25, Example 26, and Example 27.

TABLE 8

| Compound | CK2: IC50 (μM) | PIM2: IC50 (5 μM ATP) | AB: MDAMB453 (μM) | AB: BxPC3 (μM) |
| --- | --- | --- | --- | --- |
| M2 | <0.01 | 0.359 | 6.676 | 4.872 |
| N2 | <0.01 | 0.8453 | 3.042 | 9.185 |
| O2 | <0.01 | >2.5000 | 4.514 | 10.417 |

Example 28

Synthesis of (R,Z)-5-(7-(cyclopropylamino)-5-(3-fluoropyrrolidin-1-yl)pyrazolo[1,5-a]pyrimidin-3-yl)methylene)imidazolidine-2,4-dione

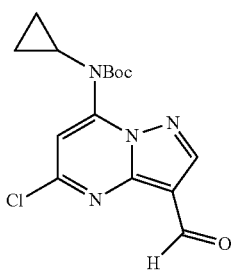

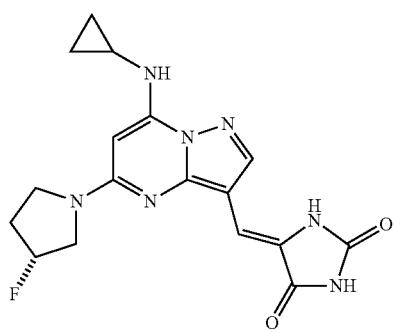

(R,Z)-5-((7-(Cyclopropylamino)-5-(3-fluoropyrrolidin-1-yl)pyrazolo[1,5-a]pyrimidin-3-yl)methylene)imidazolidine-2,4-dione was prepared using chemistries similar to the ones used to prepare (Z)-5-((5-(cyclopentylamino)-7-(cyclopropylamino)pyrazolo[1,5-a]pyrimidin-3-yl)methylene)imidazolidine-2,4-dione. The compound was isolated as a solid (84 mg, 75% yield). LCMS (ES):>95% pure, m/z 372 [M+H]$^+$.

Example 29

Synthesis (Z)-5-((5-(((1r,4r)-4-aminocyclohexylamino)-7-(cyclopropylamino)pyrazolo[1,5-a]pyrimidin-3-yl)methylene)imidazolidine-2,4-dione 2,2,2-trifluoroacetate

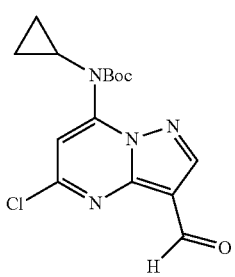

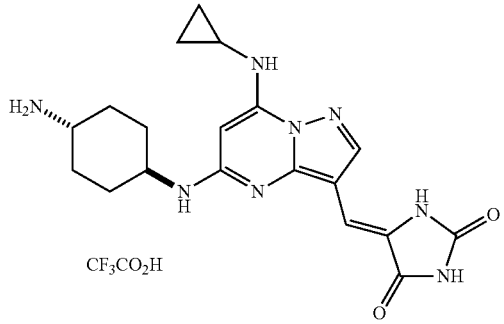

5-Chloro-3-formylpyrazolo[1,5-a]pyrimidin-7-yl(cyclopropyl)carbamate (1.0 eq, 113 mg, 0.335 mmol) was mixed in a vial with trans-tert-butyl 4-aminocyclohexylcarbamate (1.0 eq, 81 mg, 0.335 mmol) and K$_2$CO$_3$ (5.0 eq, 232 mg, 1.68 mmol) in DMF (1 ml). The mixture was stirred at 70° C. for 2.5 hours. Water was added, the solid was filtered and dried. The compound was treated with hydantoin (3.0 eq, 100 mg), piperidine (3.0 eq, 100 ul) in ethanol (2 ml) at 85-90° C. for 4.5 hours. Water was added and the solid was filtered and dried. The crude solid was suspended in methylene chloride (5 ml) and trifluoroacetic acid (1 ml) and the mixture was stirred at room temperature for 1 hour. The volatiles were evaporated. The residue was dissolved in methanol and water and subjected to purification by preparative HPLC. After genevac evaporation (Z)-5-((5-((1r,4r)-4-aminocyclohexylamino)-7-(cyclopropylamino)pyrazolo[1,5-a]pyrimidin-3-yl)methylene)imidazolidine-2,4-dione 2,2,2-trifluoroacetate was isolated a yellow solid (96 mg, 56% yield). LCMS (ES): >99% pure, m/z 397 [M+H]$^+$. Two isomers detected (ratio: 97.5% and 2.5%).

The following compounds were prepared using chemistries similar to the one used in Example 26, Example 27, Example 28 and Example 29. Compounds were characterized by LCMS. Table 9B shows the biological activities of the compounds listed in Table 9A.

TABLE 9A

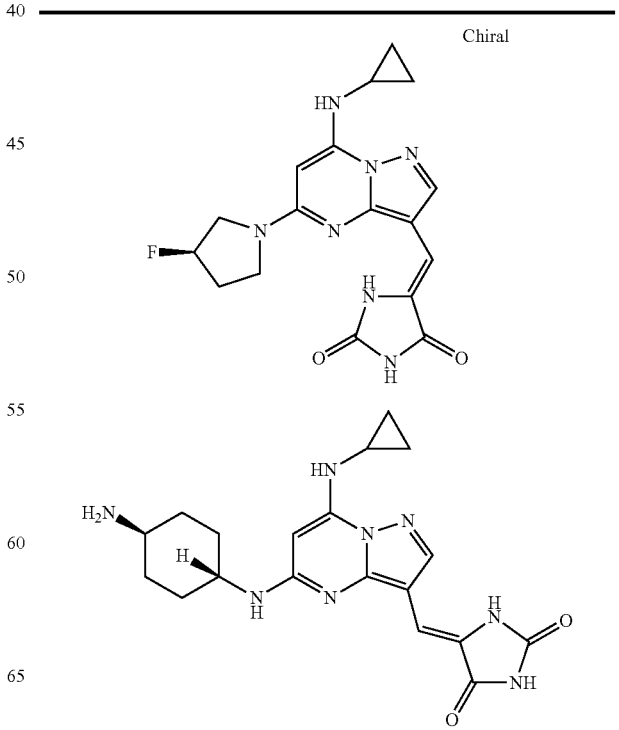

TABLE 9A-continued
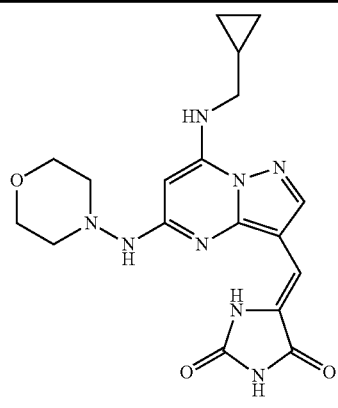
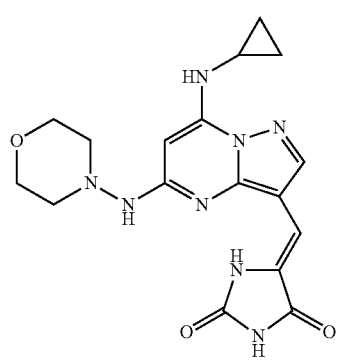 [SMILES: O=C1NC(=O)/C(=C/c2cnn3c(NC4CC4)cc(NN4CCOCC4)nc23)N1]
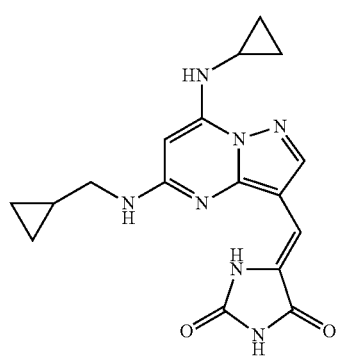 [SMILES: O=C1NC(=O)/C(=C/c2cnn3c(NC4CC4)cc(NCC4CC4)nc23)N1]
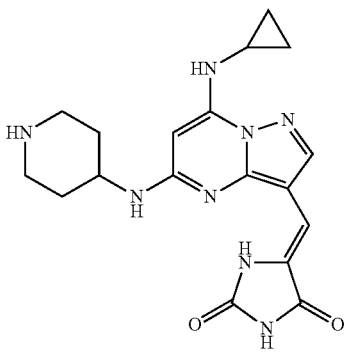 [SMILES: O=C1NC(=O)/C(=C/c2cnn3c(NC4CC4)cc(NC4CCNCC4)nc23)N1]
TABLE 9A-continued
Chiral
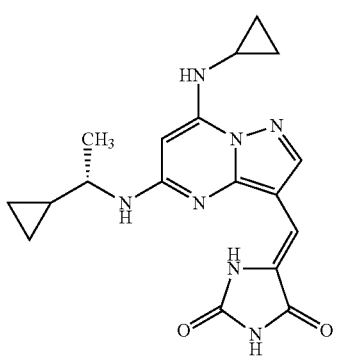
Chiral
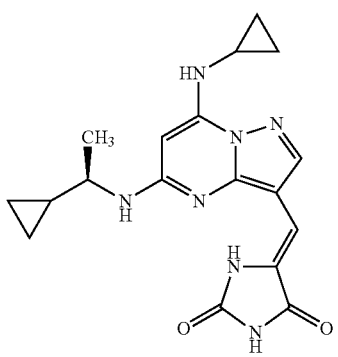
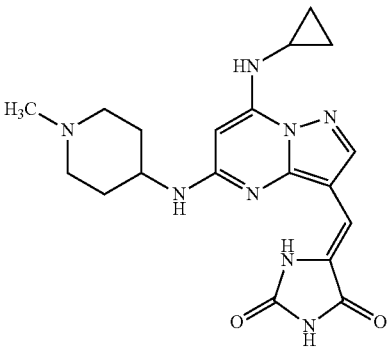 [SMILES: CN1CCC(Nc2cc(NC3CC3)n3ncc(/C=C4\NC(=O)NC4=O)c3n2)CC1]
TABLE 9B
| Com- pounds | CK2: IC50 (μM) | PIM2: IC50 (5 μM ATP) | AB: MDAMB453 (μM) | AB: BxPC3 (μM) |
|---|---|---|---|---|
| P2 | <0.01 | 0.7076 | 0.66 | 2.12 |
| Q2 | <0.01 | 0.2841 | 0.154 | 5.371 |
| R2 | <0.1 | 0.8783 | | |
| S2 | <0.01 | 1.2984 | 3.507 | 3.876 |
| T2 | <0.01 | 0.9978 | 2.494 | 6.901 |
| U2 | <0.01 | 0.7659 | 12.773 | >30 |
| V2 | <0.01 | 1.3652 | 1.483 | 1.626 |
| W2 | <0.01 | 0.8771 | | |
| X2 | <0.01 | 1.952 | | |

Example 30

Scheme Synthesis of N-((1r,4r)-4-(7-(cyclopropylamino)-3-(Z)-(2,5-dioxoimidazolidin-4-ylidene)methyl)pyrazolo[1,5-a]pyrimidin-5-ylamino)cyclohexyl)acetamide

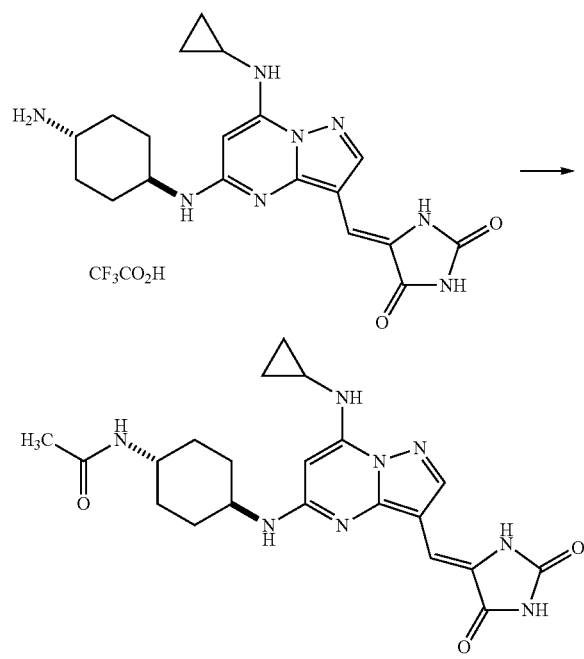

(Z)-5-((5-((1r,4r)-4-Aminocyclohexylamino)-7-(cyclopropylamino)pyrazolo[1,5-a]pyrimidin-3-yl)methylene)imidazolidine-2,4-dione 2,2,2-trifluoroacetate (1.0 eq, 10 mg, 0.0196 mmol) and DIEA (1.2 eq, 4 ul, 0.0229 mmol) were dissolved in NMP (0.1 ml). Acetic anhydride (1.0 eq, 2 ul, 0.0211 mmol) was added and the mixture stirred at room temperature overnight. Water was added and the resulting precipitate was filtered and dried to provide N-((1r,4r)-4-(7-(cyclopropylamino)-3-(Z)-(2,5-dioxoimidazolidin-4-ylidene)methyl)pyrazolo[1,5-a]pyrimidin-5-ylamino)cyclohexyl)acetamide as a solid (8 mg). LCMS (ES):>95% pure, m/z 439 [M+H]$^+$.

Example 31

Synthesis of 3-((1r,4r)-4-(7-(cyclopropylamino)-3-((Z)-(2,5-dioxoimidazolidin-4-ylidene)methyl)pyrazolo[1,5-a]pyrimidin-5-ylamino)cyclohexyl)-1,1-dimethylurea 2,2,2-trifluoroacetate

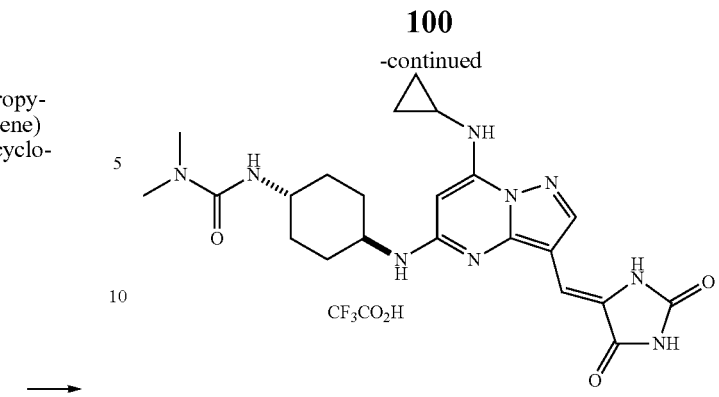

(Z)-5-((5-((1r,4r)-4-Aminocyclohexylamino)-7-(cyclopropylamino)pyrazolo[1,5-a]pyrimidin-3-yl)methylene)imidazolidine-2,4-dione 2,2,2-trifluoroacetate (10 mg) and DIEA (1.2 eq, 4.1 ul) were mixed in dry NMP (0.1 ml). Dimethylcarbamic chloride (1.0 eq, 1.8 ul) was added and the mixture stirred at room temperature overnight. The reaction was diluted with NMP (1.5 ml) and a few drops of water. The compound was purified by preparative HPLC and was isolated after evaporation at the genevac. 3-((1r,4r)-4-(7-(cyclopropylamino)-3-(Z)-(2,5-dioxoimidazolidin-4-ylidene)methyl)pyrazolo[1,5-a]pyrimidin-5-ylamino)cyclohexyl)-1,1-dimethylurea 2,2,2-trifluoroacetate. LCMS (ES):>95% pure, m/z 468 [M+H]$^+$. Z:E ratio: 86:13

The following molecules were prepared using similar chemistries to the ones described in Example 30 and Example 31 using the appropriate amines and anhydrides or acyl chlorides, sulfamoyl chlorides, sulfonyl chlorides or chloroformates. Compounds were purified by preparative HPLC, isolated after genevac evaporation, and characterized by LCMS. Table 10B shows the biological activities of the compounds listed in Table 10A.

TABLE 10A

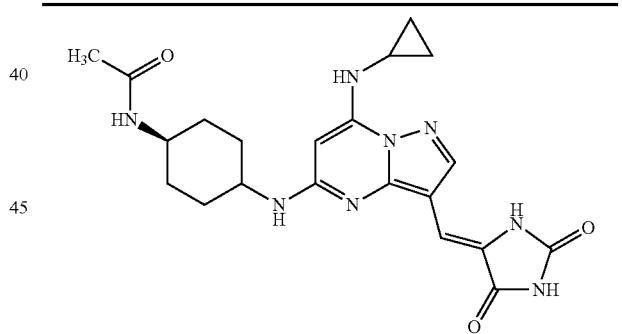

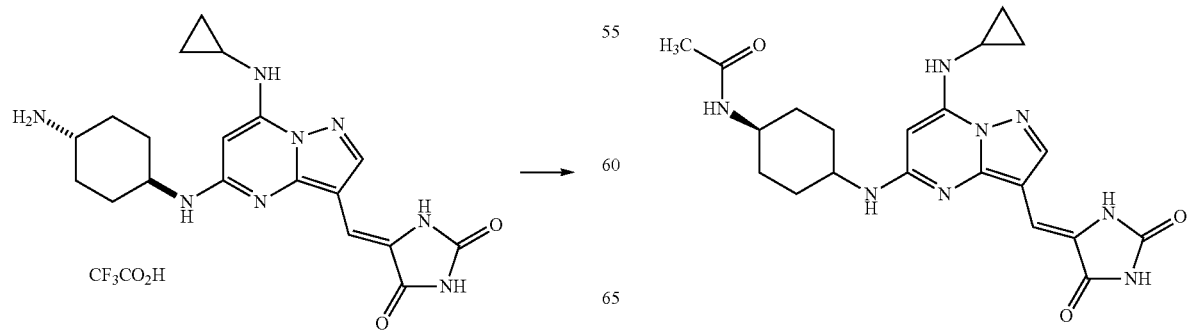

TABLE 10A-continued
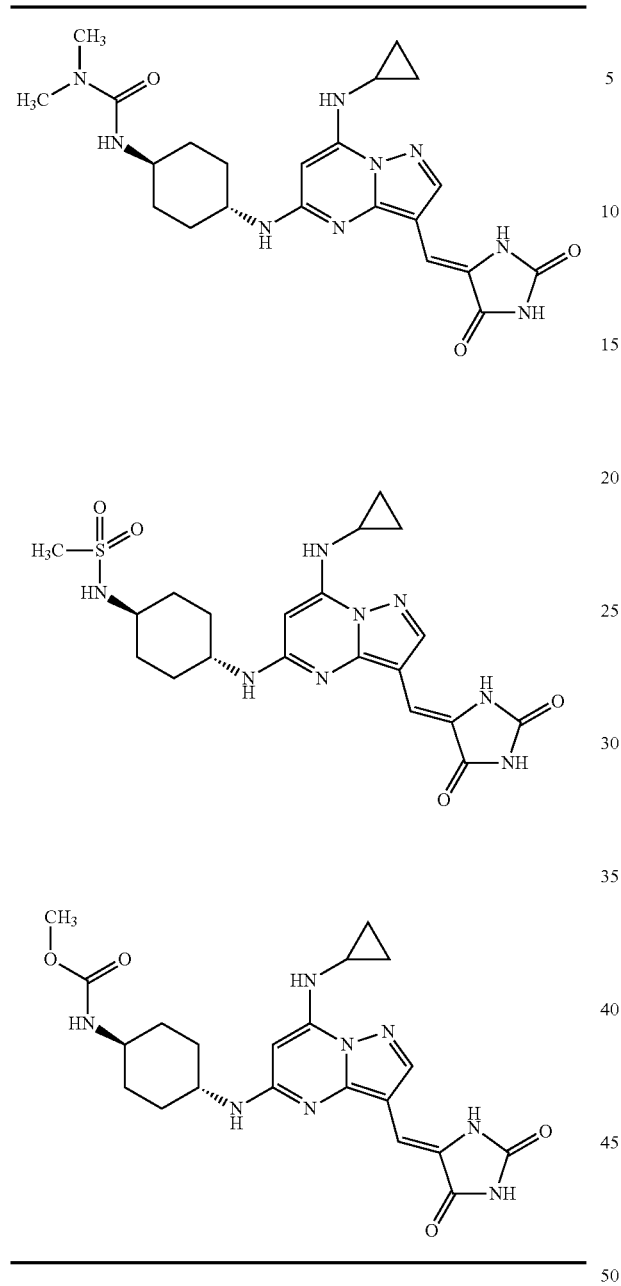
TABLE 10B
| Compound | CK2: IC50 (μM) | PIM2: IC50 (5 μM ATP) | AB: MDAMB453 (μM) | AB: BxPC3 (μM) |
|---|---|---|---|---|
| A3 | <0.01 | >2.5000 | >30 | >30 |
| B3 | <0.1 | 0.5385 | | |
| C3 | <0.01 | 0.6791 | | |
| D3 | <0.01 | 0.476 | | |
| E3 | <0.01 | >2.5000 | | |
The following molecules in Table 10 were prepared using chemistries similar to the ones in Example 26, Example 27, Example 28 and Example 29.
TABLE 10
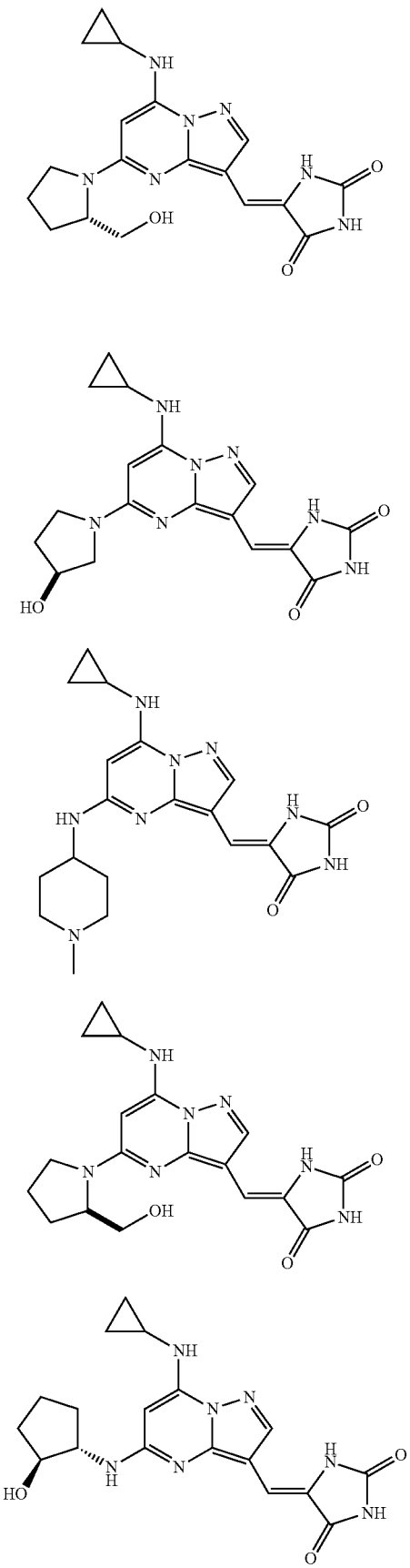

TABLE 10-continued

TABLE 10-continued
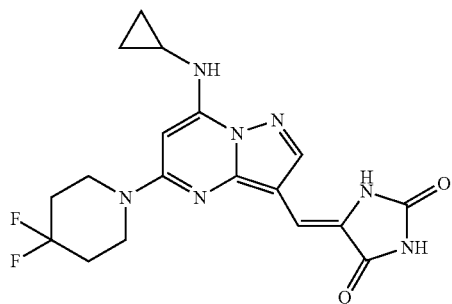 [SMILES: O=C1NC(=O)/C(=C/c2cnn3c(NC4CC4)cc(N4CCC(F)(F)CC4)nc23)N1]
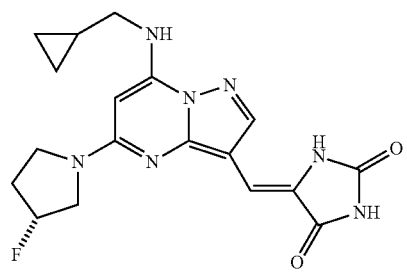 [SMILES: O=C1NC(=O)/C(=C/c2cnn3c(NCC4CC4)cc(N4CC[C@@H](F)C4)nc23)N1]
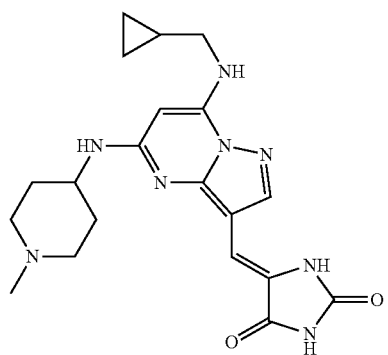 [SMILES: CN1CCC(Nc2cc(NCC3CC3)n3ncc(/C=C4\NC(=O)NC4=O)c3n2)CC1]
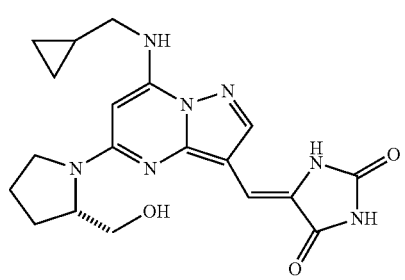 [SMILES: O=C1NC(=O)/C(=C/c2cnn3c(NCC4CC4)cc(N4CCC[C@H]4CO)nc23)N1]
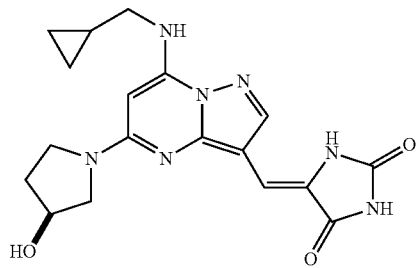 [SMILES: O=C1NC(=O)/C(=C/c2cnn3c(NCC4CC4)cc(N4CC[C@H](O)C4)nc23)N1]
TABLE 10-continued
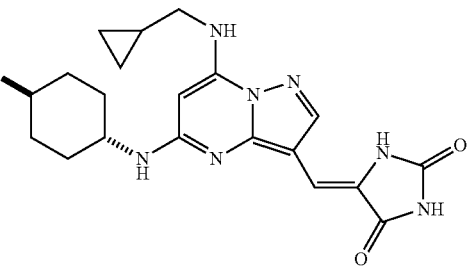
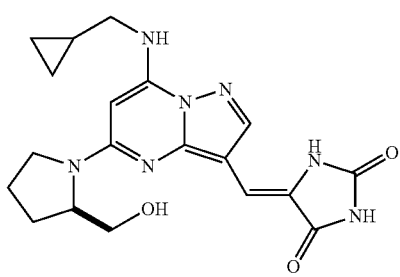 [SMILES: O=C1NC(=O)/C(=C/c2cnn3c(NCC4CC4)cc(N4CCC[C@@H]4CO)nc23)N1]
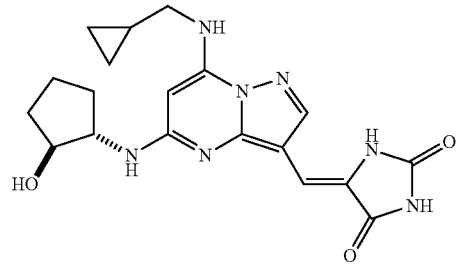
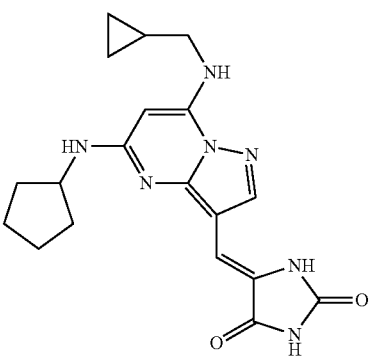 [SMILES: O=C1NC(=O)/C(=C/c2cnn3c(NCC4CC4)cc(NC4CCCC4)nc23)N1]
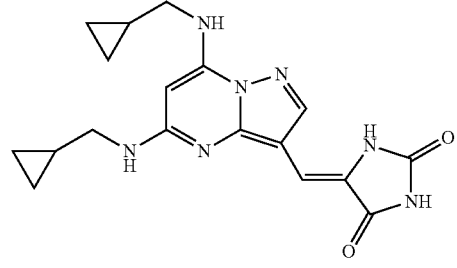 [SMILES: O=C1NC(=O)/C(=C/c2cnn3c(NCC4CC4)cc(NCC4CC4)nc23)N1]

TABLE 10-continued
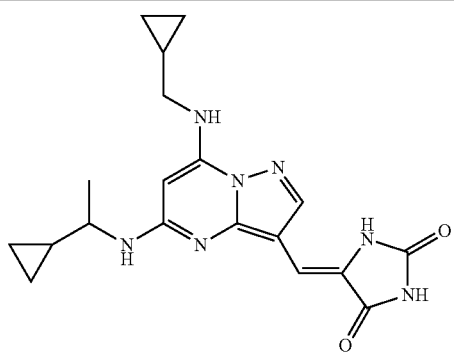 [SMILES: CC(Nc1cc(NCC2CC2)n2ncc(/C=C3\NC(=O)NC3=O)c2n1)C1CC1]
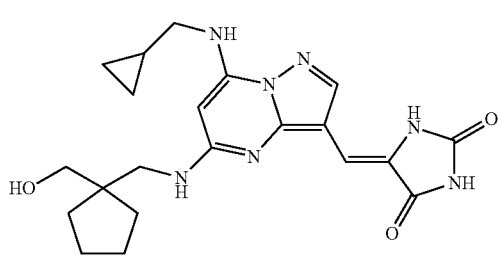 [SMILES: O=C1NC(=O)/C(=C/c2cnn3c(NCC4CC4)cc(NCC4(CO)CCCC4)nc23)N1]
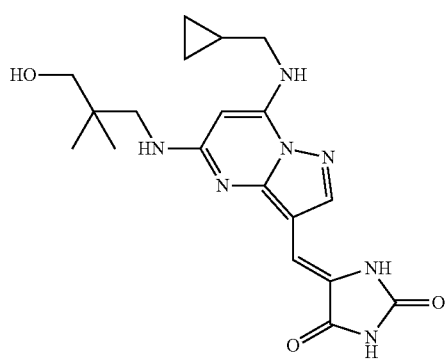 [SMILES: CC(C)(CO)CNc1cc(NCC2CC2)n2ncc(/C=C3\NC(=O)NC3=O)c2n1]
TABLE 10-continued
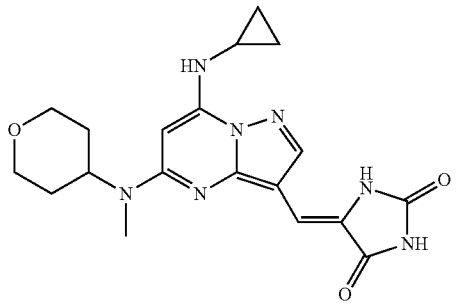 [SMILES: CN(c1cc(NC2CC2)n2ncc(/C=C3\NC(=O)NC3=O)c2n1)C1CCOCC1]
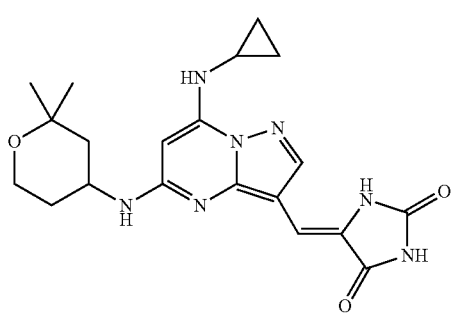 [SMILES: CC1(C)CC(Nc2cc(NC3CC3)n3ncc(/C=C4\NC(=O)NC4=O)c3n2)CCO1]
Example 32
Synthesis of tert-butyl 5-(benzylthio)-3-formylpyrazolo[1,5-a]pyrimidin-7-yl(cyclopropyl)carbamate
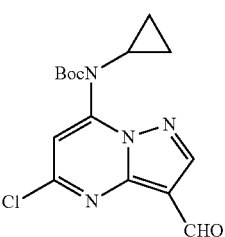
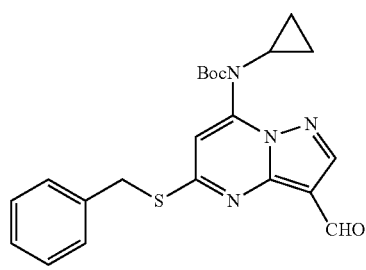

Diisopropylethylamine (256 μL, 1.48 mmol) was added to tert-butyl 5-chloro-3-formylpyrazolo[1,5-a]pyrimidin-7-yl (cyclopropyl)carbamate (250 mg, 0.74 mmol) suspended in ethanol (2.5 mL). Benzyl mercaptan (191 μL, 1.48 mmol) was added and the reaction was homogeneous after ~2 min. After 10 min, the reaction was diluted with ethanol (3 mL) and the precipitate was filtered and washed with ethanol (10 mL) to yield tert-butyl 5-(benzylthio)-3-formylpyrazolo[1,5-a]pyrimidin-7-yl(cyclopropyl)carbamate (148 mg, 47%). LCMS (ES): >95% pure, m/z 425 [M+1]$^+$.

Example 33

Synthesis of 5-((5-(benzylthio)-7-(cyclopropylamino)pyrazolo[1,5-a]pyrimidin-3-yl)methylene)imidazolidine-2,4-dione

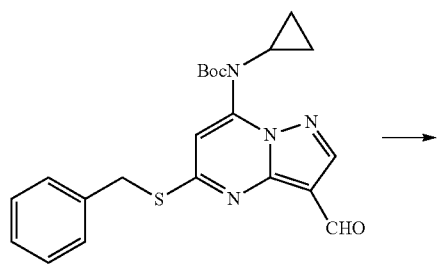

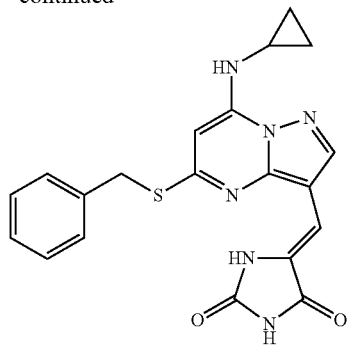

Hydantoin (67 mg, 0.67 mmol) and piperidine (66 μL, 0.67 mmol) were added to tert-butyl 5-(benzylthio)-3-formylpyrazolo[1,5-a][1,5-a]pyrimidin-7-yl(cyclopropyl)carbamate (95 mg, 0.22 mmol) dissolved in ethanol (1.1 mL). The reaction was heated at 80° C. After 15 h, the reaction was cooled to r.t., diluted with water (5 mL), and the precipitate was collected and washed with 1:1 ethanol:water (10 mL) and then ethanol (3 mL). The bright yellow solid was dried in vacuo to give (Z)-5-(5-(benzylthio)-7-(cyclopropylamino)pyrazolo[1,5-a]pyrimidin-3-yl)methylene)imidazolidine-2,4-dione (75 mg, 66%). LCMS (ES): >95% pure, m/z 507 [M+1]$^+$.

5-((5-(Benzylthio)-7-(cyclopropylamino)pyrazolo[1,5-a]pyrimidin-3-yl)methylene)imidazolidine-2,4-dione (60 mg, 0.15 mmol) was dissolved in dichloromethane (1 mL) and trifluoroacetic acid (1 mL). After 1 h, the solution was concentrated under a stream of air. The residue was triturated with Et$_2$O (3 mL) and the precipitate was collected to provide (Z)-5((5-(benzylthio)-7-(cyclopropylamino)pyrazolo[1,5-a]pyrimidin-3-yl)methylene)imidazolidine-2,4-dione (59 mg, 98%). LCMS (ES): >95% pure, m/z 407 [M+1]$^+$.

TABLE 11

| Structure | LCMS m/z [M + 1]+ | CK2: IC50 (uM) | PIM2: IC50 (Sum ATP) | AB: MDAMB453 (uM) | AB: BxPC3 (uM) |
| --- | --- | --- | --- | --- | --- |
| 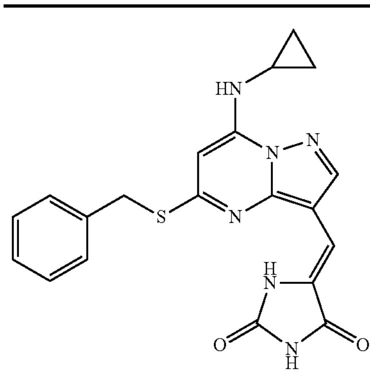 | 407 | <0.01 | >2.5000 | >30 | 11.037 |

Example 34

Synthesis of 5-((5-chloro-7-(cyclopropylamino)pyrazolo[1,5-a]pyrimidin-3-yl)methylene)thiazolidine-2,4-dione

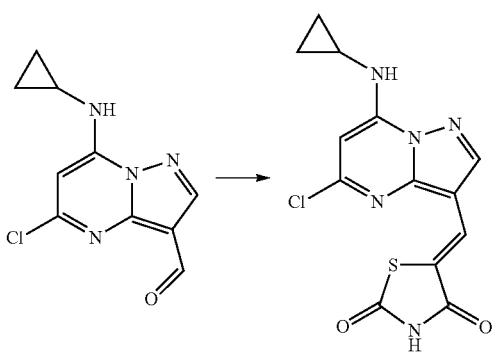 [SMILES: O=Cc1cnn2c(NC3CC3)cc(Cl)nc12 ; O=C1NC(=O)/C(=C/c2cnn3c(NC4CC4)cc(Cl)nc23)S1]

To 5-chloro-7-(cyclopropylamino)pyrazolo[1,5-a]pyrimidine-3-carbaldehyde (440 mg, 1.86 mmol) in EtOH was added thiazolidine-2,4-dione (458 mg, 3.91 mmol) and piperidine (208 μl, 2.05 mmol). The reaction was heated at 80° C. overnight. To the reaction mixture, isopropanol (3 mL) was added in the along with 218 mg thiazolidine-2,4-dione and 94 μL of piperidine. The temperature was increased to 90° C. and the reaction was stirred at that temperature overnight. The precipitate was filtered while hot and dissolved in MeOH. To the reaction mixture, 1M HCl (1 mL) was added and the mixture sonicated. The precipitate was filtered and washed with MeOH to yield 340 mg (54% yield) 5-((5-chloro-7-(cyclopropylamino)pyrazolo[1,5-a]pyrimidin-3-yl)methylene)thiazolidine-2,4-dione as a yellow powder. LCMS (M+1=336)

Example 35

Synthesis of 5-((5-(3-chlorophenylamino)-7-(cyclopropylamino)pyrazolo[1,5-a]pyrimidin-3-yl)methylene)thiazolidine-2,4-dione

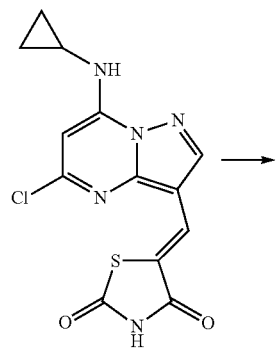

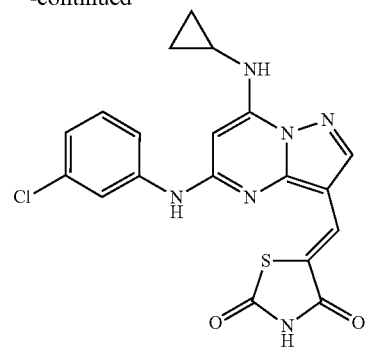

To 5-((5-chloro-7-(cyclopropylamino)pyrazolo[1,5-a]pyrimidin-3-yl)methylene)thiazolidine-2,4-dione (20 mg, 0.06 mmol) in NMP was added 3-chloroaniline (38 μL, 0.36 mmol) and a few granules of p-toluenesulfonic acid. The reaction was heated in microwave at 180° C. 1.5 hours. The reaction mixture was filtered and purified by prep HPLC then prep TLC (1% MeOH/DCM) to yield 5-((5-(3-chlorophenylamino)-7-(cyclopropylamino)pyrazolo[1,5-a]pyrimidin-3-yl)methylene)thiazolidine-2,4-dione as a yellow solid. LCMS (M+1=427)

Example 36

Synthesis of 5-((7-(cyclopropylamino)-5-(isobutylamino)pyrazolo[1,5-a]pyrimidin-3-yl)methylene)thiazolidine-2,4-dione

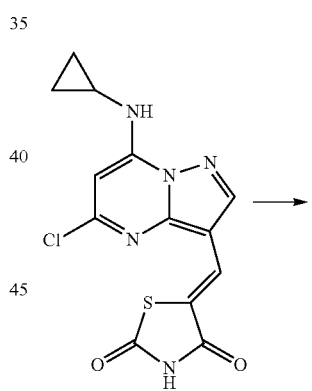

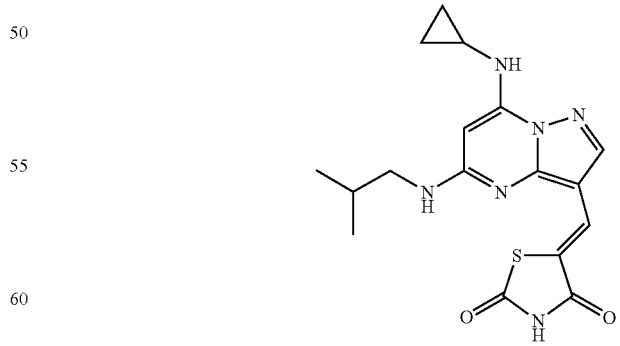

To 5-((5-chloro-7-(cyclopropylamino)pyrazolo[1,5-a]pyrimidin-3-yl)methylene)thiazolidine-2,4-dione (30 mg, 0.09 mmol) in NMP was added 2-methylpropan-1-amine (20 mg, 0.268 mmol). The reaction was heated at 130° C. overnight.

The reaction mixture was diluted with MeOH and purified by prep HPLC to yield 5-((7-(cyclopropylamino)-5-(isobutylamino)pyrazolo[1,5-a]pyrimidin-3-yl)methylene)thiazolidine-2,4-dione. LCMS (M+1=373)

The compounds described in the following table were prepared using chemistries similar to those exemplified in Example 36. All compounds were characterized by LCMS. Table 12B shows the biological activities of the compounds listed in Table 12A.

TABLE 12A

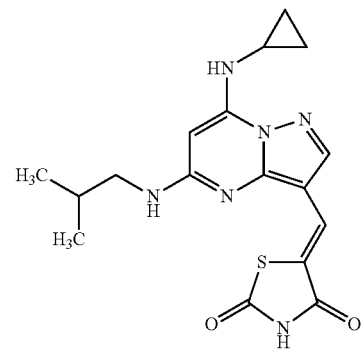 [SMILES: CC(C)CNc1cc(NC2CC2)n2ncc(/C=C3\SC(=O)NC3=O)c2n1]

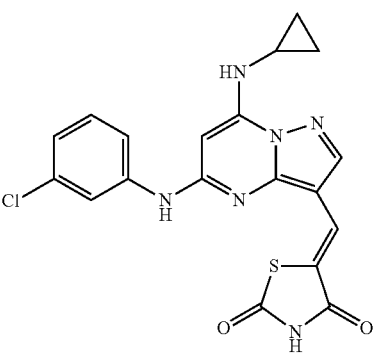

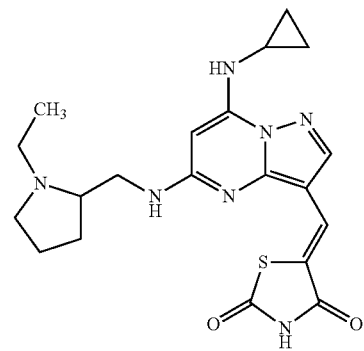 [SMILES: CCN1CCCC1CNc1cc(NC2CC2)n2ncc(/C=C3\SC(=O)NC3=O)c2n1]

TABLE 12A-continued

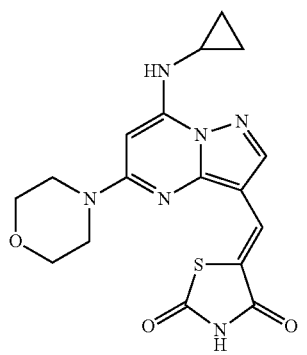 [SMILES: O=C1NC(=O)/C(=C/c2cnn3c(NC4CC4)cc(N4CCOCC4)nc23)S1]

TABLE 12A-continued
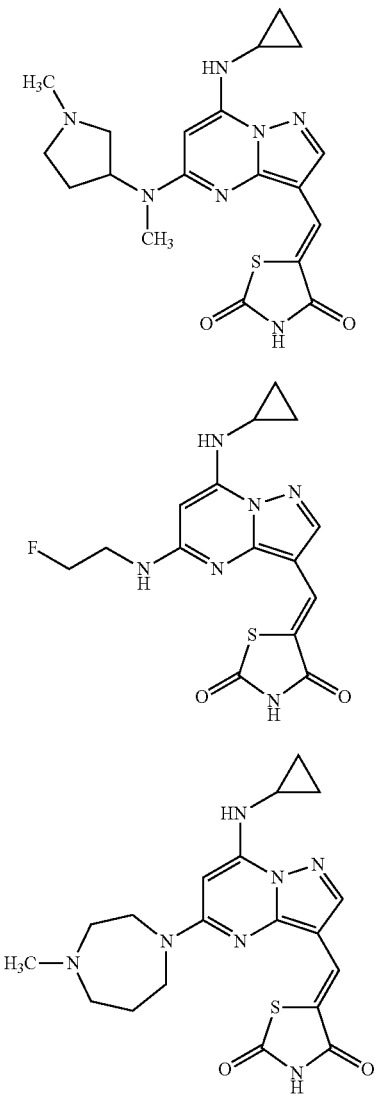
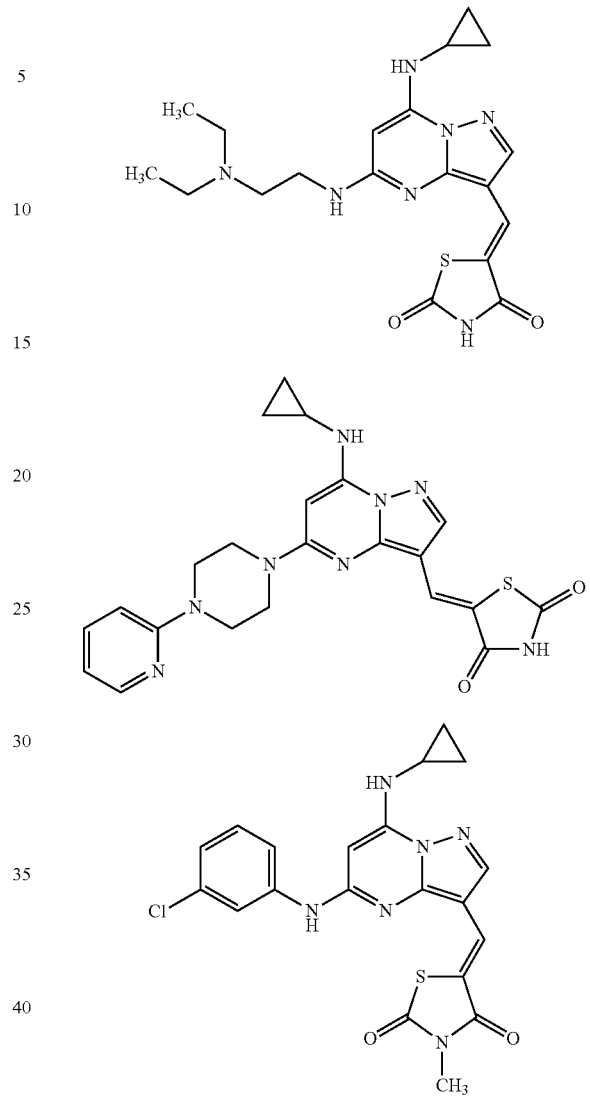
TABLE 12B
| Compound | CK2: IC50 (μM) | PIM1: IC50 (30 μM ATP) | PIM2: IC50 (5 μM ATP) | AB: MDAMB453 (μM) | AB: BxPC3 (μM) |
|---|---|---|---|---|---|
| F3 | <1.0 | 2.0638 | 1.6438 | | |
| G3 | <0.1 | 2.0575 | 1.8456 | 7.7 | 9.45 |
| H3 | <1.0 | 2.3875 | >2.5000 | | |
| I3 | <0.1 | >2.5000 | 0.8759 | | |
| J3 | <1.0 | >2.5000 | >2.5000 | | |
| K3 | <1.0 | 0.9177 | 1.3934 | | |
| L3 | <1.0 | >2.5000 | 1.4327 | | |
| M3 | <0.1 | 1.4455 | 1.4379 | | |
| N3 | <1.0 | >2.5000 | >2.5000 | | |
| O3 | <0.1 | 1.2533 | >2.5000 | | |
| P3 | <1.0 | >2.5000 | >2.5000 | | |
| Q3 | <0.1 | | 2.0461 | | |
| R3 | <1.0 | | 1.82 | | |

Example 37

Synthesis of tert-butyl 5-chloro-3-formylpyrazolo[1,5-a]pyrimidin-7-yl(cyclopropyl)carbamate

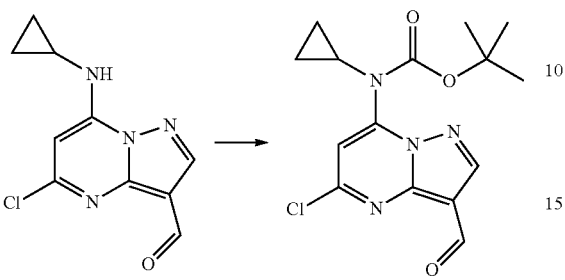

To 5-chloro-7-(cyclopropylamino)pyrazolo[1,5-a]pyrimidine-3-carbaldehyde (4.52 g, 19.15 mmol) in methylene chloride (80 mL) was added triethylamine (3.2 mL, 23 mmol), dimethylaminopyridine (350 mg, 2.87 mmol), and di-t-butyldicarbonate (12.53 g, 57.44 mmol) The mixture was stirred at room temperature for 60 minutes. The reaction mixture was transferred to a separatory funnel, washed 1× with $H_2O$, 2× with brine, dried over $MgSO_4$, filtered, and evaporated to dryness to provide an oily residue. The crude material was purified by silica gel chromatography (0%-20% ethyl acetate/hexanes) to yield 5.68 g (88% yield) of tert-butyl 5-chloro-3-formylpyrazolo[1,5-a]pyrimidin-7-yl (cyclopropyl)carbamate. LCMS (M+1=337)

Example 38

Synthesis of tert-butyl cyclopropyl(3-hydroxyphenyl)pyrazolo[1,5-a]pyrimidin-7-yl)carbamate

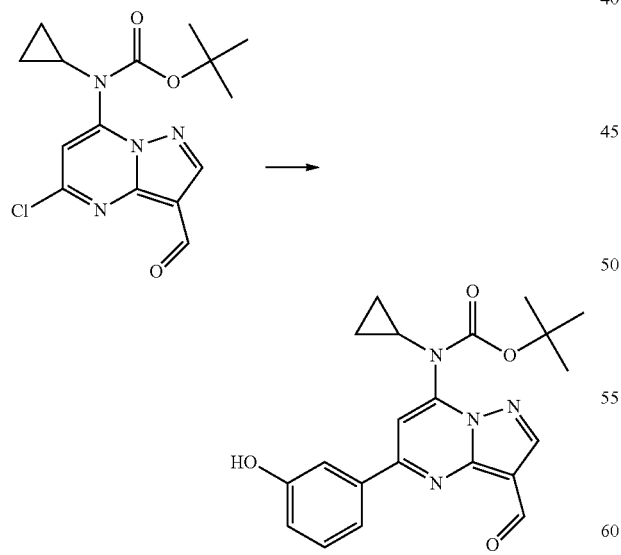

To 5 tert-butyl 5-chloro-3-formylpyrazolo[1,5-a]pyrimidin-7-yl (cyclopropyl)carbamate (650 mg, 1.93 mmol) in 14 mL of a 2:1 mixture of 1,2-dimethoxyethane/EtOH was added 3-hydroxyphenyl boronic acid (399 mg, 2.89 mmol), tetrakis(triphenylphosphine)palladium(0) (112 mg, 0.096 mmol), and 2M aqueous solution of $Na_2CO_3$ (2.9 mL, 5.79 mmol). The mixture was stirred at 85° C. for 1 h. The volatiles were removed by rotary evaporation and the residue was purified by silica gel chromatography (0%-30% EtOAc/Hexanes) to provide 400 mg of tert-butyl cyclopropyl(3-formyl-5-(3-hydroxyphenyl)pyrazolo[1,5-a]pyrimidin-7-yl)carbamate. (52%). LCMS (M+1=395)

Example 39

Synthesis of 7-(cyclopropylamino)-5-(3-hydroxyphenyl)pyrazolo[1,5-a]pyrimidine-3-carbaldehyde

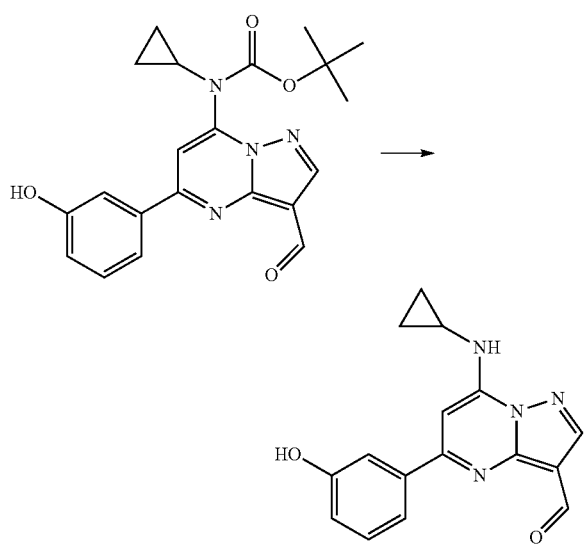

To tert-butyl cyclopropyl(3-formyl-5-(3-hydroxyphenyl)pyrazolo[1,5-a]pyrimidin-7-yl)carbamate (400 mg, 1.01 mmol) in methylene chloride (20 mL) was added TFA (10 mL). The reaction mixture was stirred at room temperature for 2 hours. The volatiles were removed by rotary evaporation and the residue was purified by silica gel chromatography (0%-40% EtOAc/hexanes) to provide 103 mg of 7-(cyclopropylamino)-5-(3-hydroxyphenyl)pyrazolo[1,5-a]pyrimidine-3-carbaldehyde. (35%). LCMS (M+1=295)

Example 40

Synthesis of 5-7-(cyclopropylamino)-5(3-hydroxyphenyl)pyrazolo[1,5-a]pyrimidin-3-yl)methylene)imidazolidine-2,4-dione

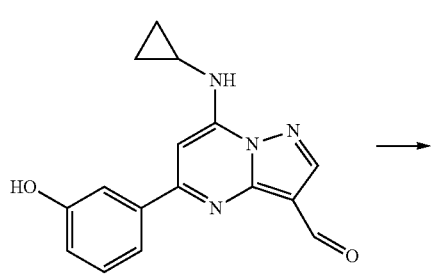

-continued

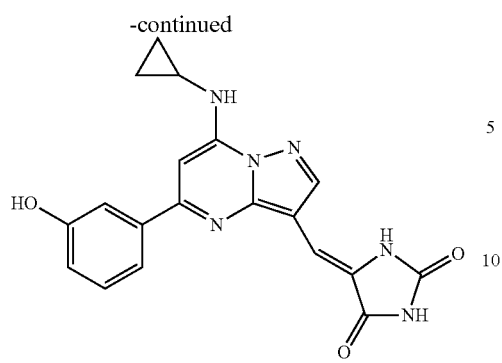

To 7-(cyclopropylamino)-5-(3-hydroxyphenyl)pyrazolo[1,5-a]pyrimidine-3-carbaldehyde (100 mg, 0.340 mmol) in EtOH (2 mL) was added piperidine (67 μL, 0.680 mmol), and hydantoin (34 mg, 0.34 mmol). The reaction was stirred at 50° C. overnight. The solid formed was isolated by filtration to provide 70 mg of 5-((7-(cyclopropylamino)-5-(3-hydroxyphenyl)pyrazolo[1,5-a]pyrimidin-3-yl)methylene)imidazolidine-2,4-dione. (55%). LCMS (M+1=377)

The compounds described in the following table were prepared using chemistries similar to those exemplified in Example 38, Example 39, and Example 40. All compounds were characterized by LCMS. Table 13B shows the biological activities of the compounds listed in Table 13A.

TABLE 13A

TABLE 13A-continued

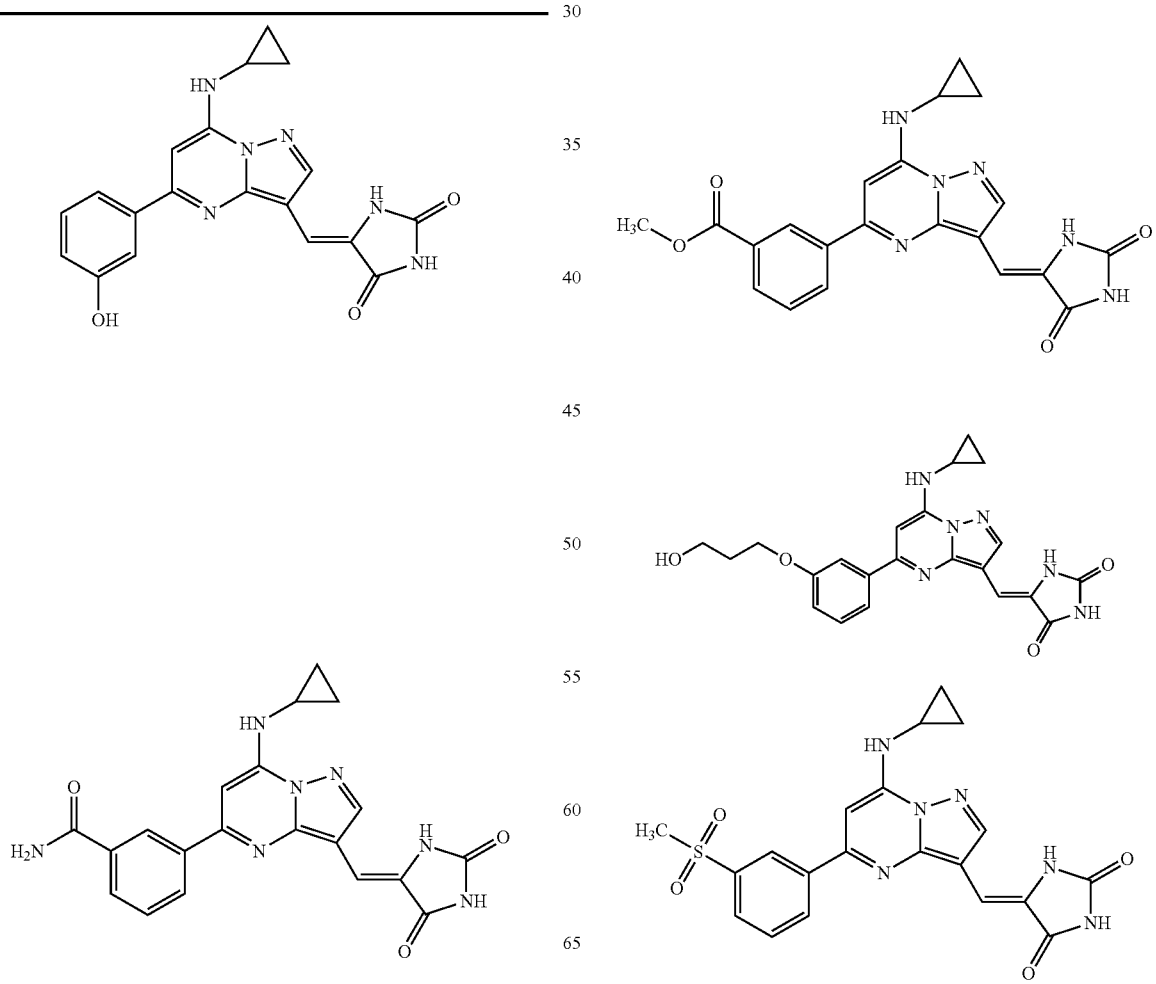

TABLE 13A-continued
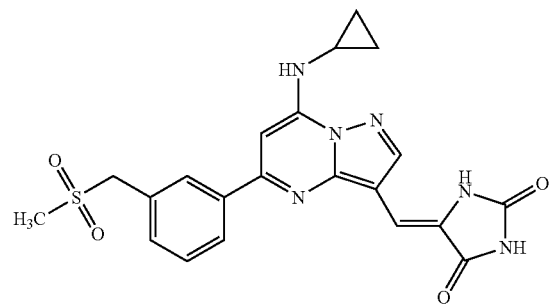 [SMILES: CS(=O)(=O)Cc1cccc(-c2cc(NC3CC3)n3ncc(/C=C4\NC(=O)NC4=O)c3n2)c1]
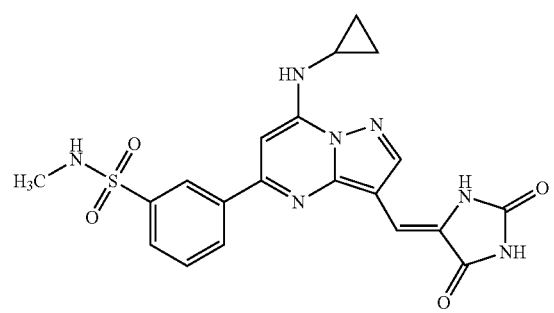 [SMILES: CNS(=O)(=O)c1cccc(-c2cc(NC3CC3)n3ncc(/C=C4\NC(=O)NC4=O)c3n2)c1]
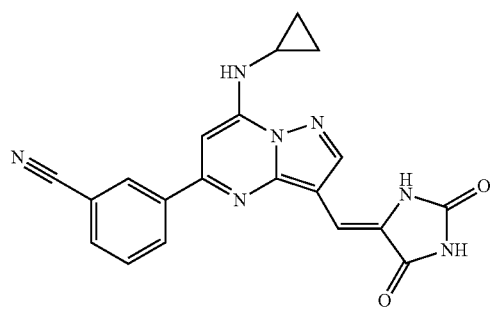 [SMILES: N#Cc1cccc(-c2cc(NC3CC3)n3ncc(/C=C4\NC(=O)NC4=O)c3n2)c1]
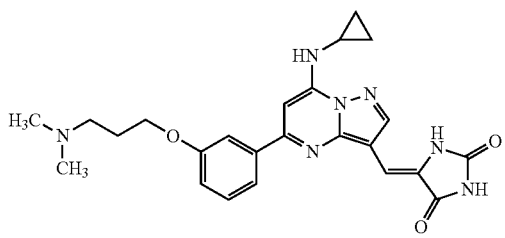 [SMILES: CN(C)CCCOc1cccc(-c2cc(NC3CC3)n3ncc(/C=C4\NC(=O)NC4=O)c3n2)c1]
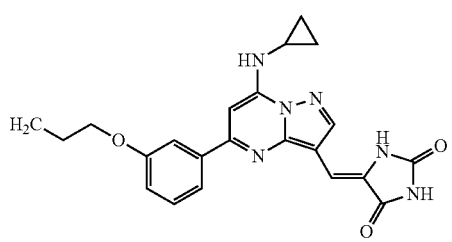 [SMILES: CCCOc1cccc(-c2cc(NC3CC3)n3ncc(/C=C4\NC(=O)NC4=O)c3n2)c1]
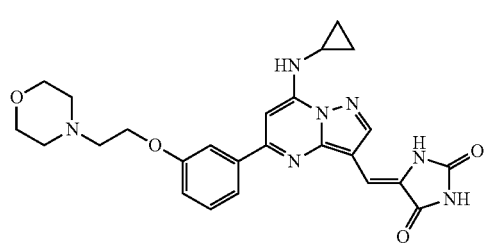 [SMILES: O=C1NC(=O)/C(=C/c2cnn3c(NC4CC4)cc(-c4cccc(OCCN5CCOCC5)c4)nc23)N1]
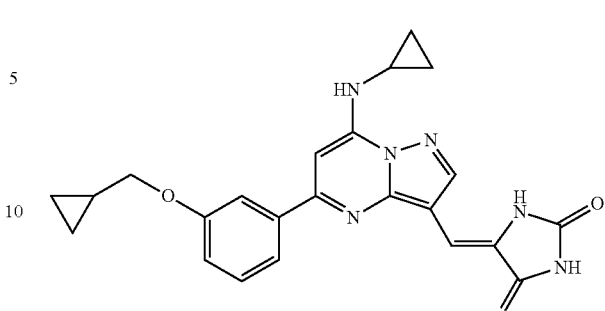
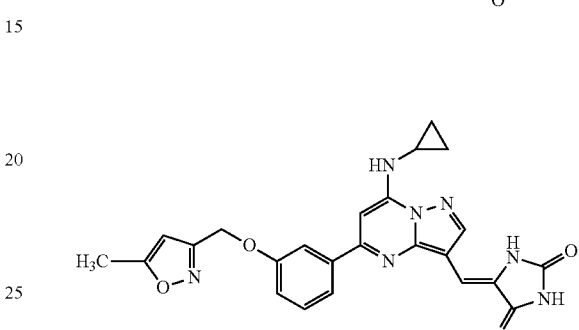
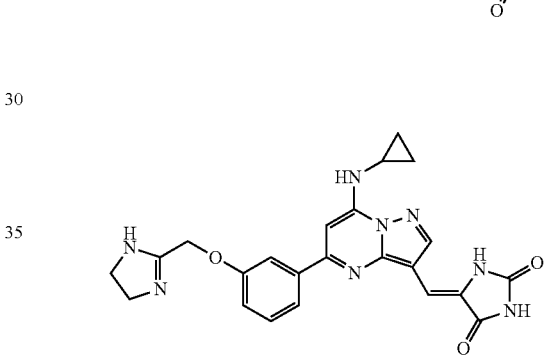
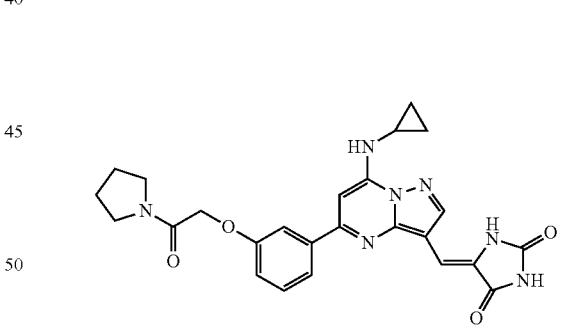
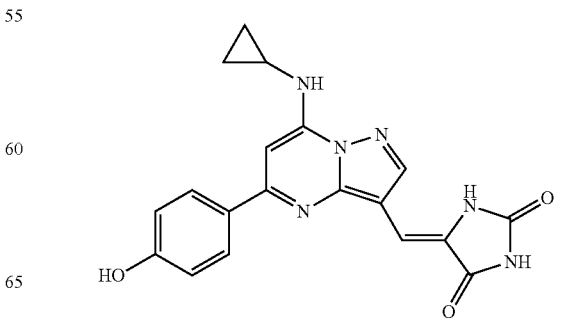

TABLE 13A-continued
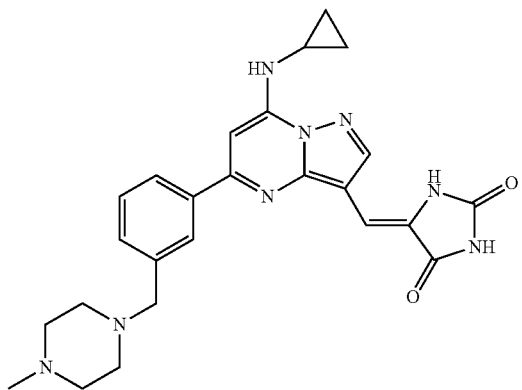 [SMILES: CN1CCN(Cc2cccc(-c3cc(NC4CC4)n4ncc(/C=C5\NC(=O)NC5=O)c4n3)c2)CC1]
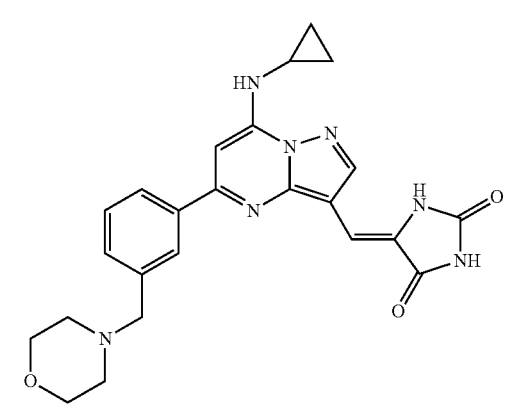 [SMILES: O=C1NC(=O)/C(=C/c2cnn3c(NC4CC4)cc(-c4cccc(CN5CCOCC5)c4)nc23)N1]
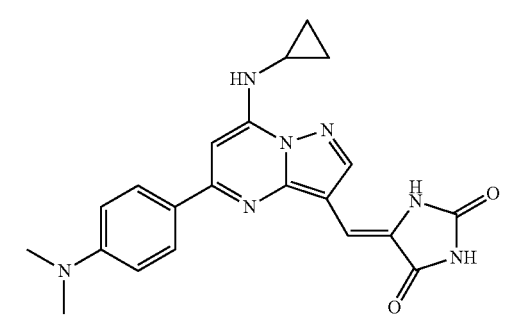 [SMILES: CN(C)c1ccc(-c2cc(NC3CC3)n3ncc(/C=C4\NC(=O)NC4=O)c3n2)cc1]
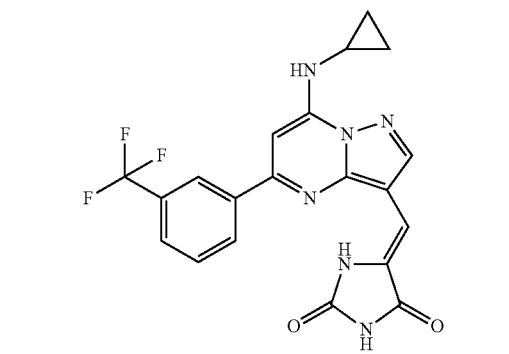 [SMILES: O=C1NC(=O)/C(=C/c2cnn3c(NC4CC4)cc(-c4cccc(C(F)(F)F)c4)nc23)N1]
TABLE 13A-continued
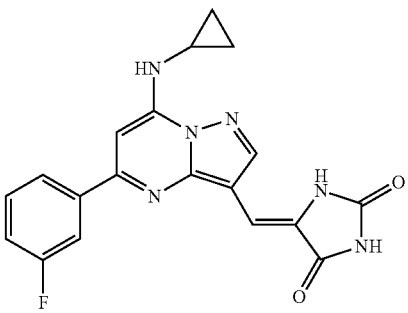 [SMILES: O=C1NC(=O)/C(=C/c2cnn3c(NC4CC4)cc(-c4cccc(F)c4)nc23)N1]
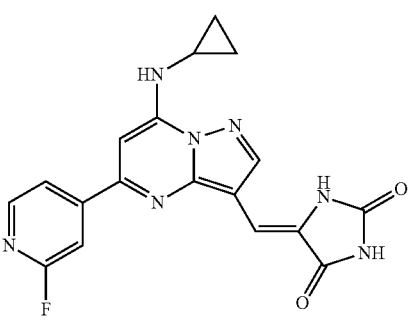 [SMILES: O=C1NC(=O)/C(=C/c2cnn3c(NC4CC4)cc(-c4ccnc(F)c4)nc23)N1]
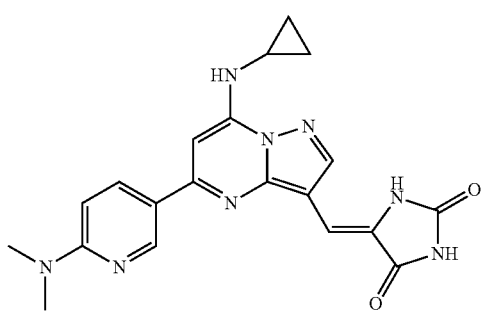
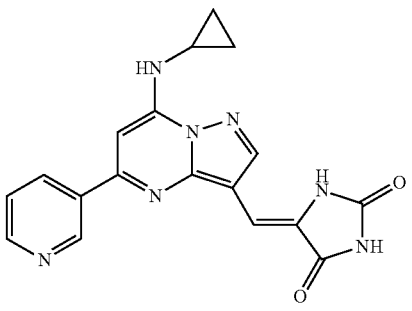 [SMILES: O=C1NC(=O)/C(=C/c2cnn3c(NC4CC4)cc(-c4cccnc4)nc23)N1]
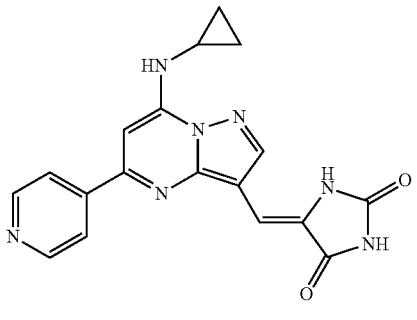 [SMILES: O=C1NC(=O)/C(=C/c2cnn3c(NC4CC4)cc(-c4ccncc4)nc23)N1]

TABLE 13A-continued
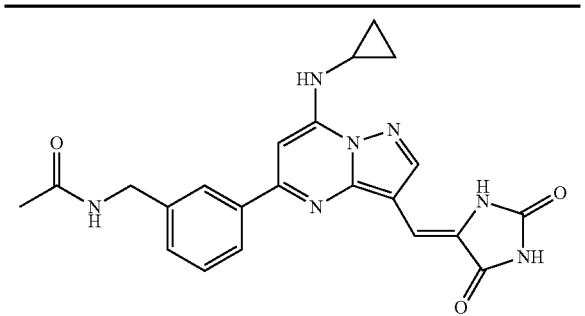
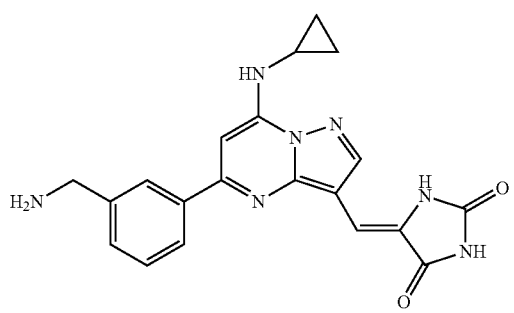 [SMILES: NCc1cccc(-c2cc(NC3CC3)n3ncc(/C=C4\NC(=O)NC4=O)c3n2)c1]
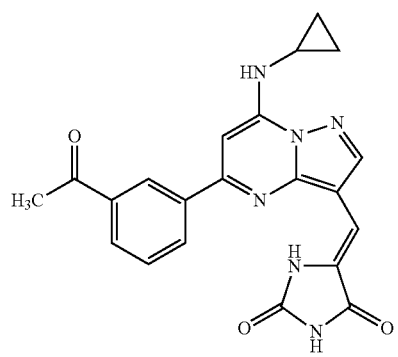 [SMILES: CC(=O)c1cccc(-c2cc(NC3CC3)n3ncc(/C=C4\NC(=O)NC4=O)c3n2)c1]
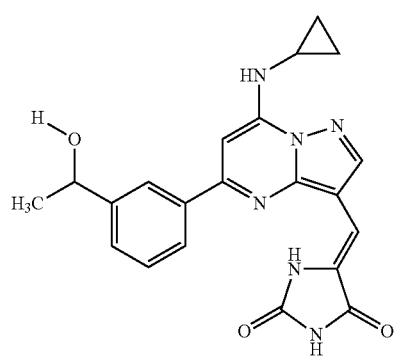 [SMILES: CC(O)c1cccc(-c2cc(NC3CC3)n3ncc(/C=C4\NC(=O)NC4=O)c3n2)c1]
TABLE 13A-continued
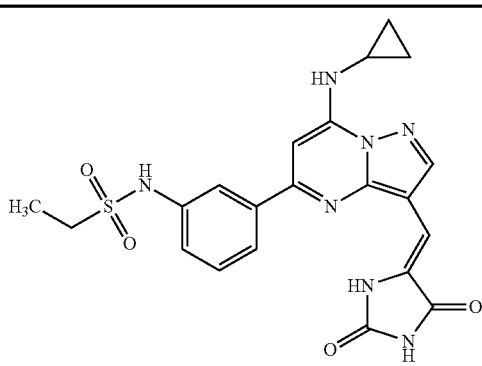
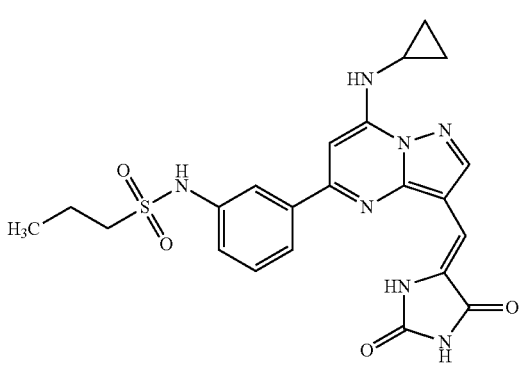 [SMILES: CCCS(=O)(=O)Nc1cccc(-c2cc(NC3CC3)n3ncc(/C=C4\NC(=O)NC4=O)c3n2)c1]
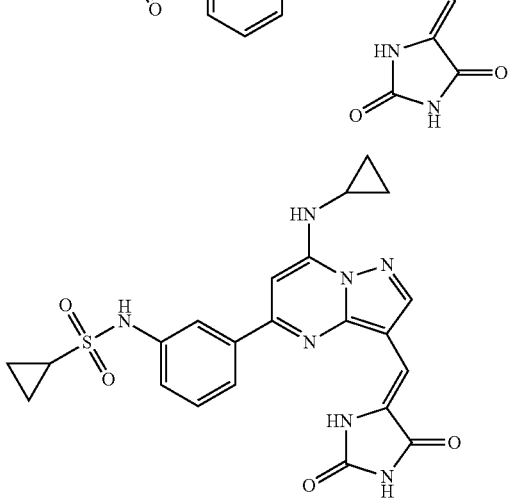

TABLE 13A-continued
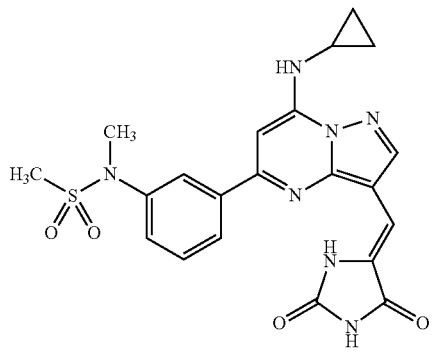 [SMILES: CN(c1cccc(-c2cc(NC3CC3)n3ncc(/C=C4\NC(=O)NC4=O)c3n2)c1)S(C)(=O)=O]
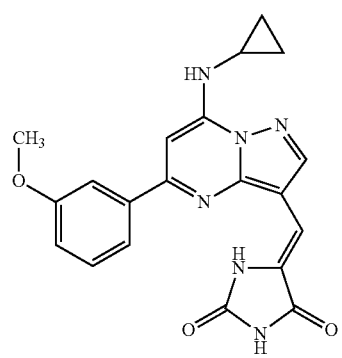 [SMILES: COc1cccc(-c2cc(NC3CC3)n3ncc(/C=C4\NC(=O)NC4=O)c3n2)c1]
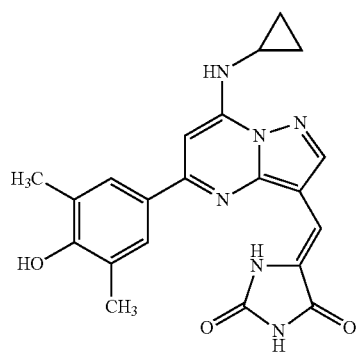 [SMILES: Cc1cc(-c2cc(NC3CC3)n3ncc(/C=C4\NC(=O)NC4=O)c3n2)cc(C)c1O]
TABLE 13B
| Compound | CK2: IC50 (µM) | PIM2: IC50 (5 µM ATP) | AB: MDAMB453 (µM) | AB: BxPC3 (µM) |
|---|---|---|---|---|
| S3 | <0.01 | 0.6135 | 0.33 | 10.627 |
| T3 | <0.01 | 0.8908 | 0.402 | 1.541 |
| U3 | <0.01 | >2.5000 | 3.743 | 3.68 |
| V3 | <0.01 | 0.6492 | 0.477 | 5.171 |
| W3 | <0.01 | >2.5000 | 1.709 | 2.054 |
| X3 | <0.01 | >2.5000 | 0.517 | 13.111 |
| Y3 | <0.01 | >2.5000 | | |
| Z3 | <0.01 | 2.2144 | 0.284 | 2.916 |
| A4 | <0.01 | >2.5000 | >30 | >30 |
TABLE 13B-continued
| Compound | CK2: IC50 (µM) | PIM2: IC50 (5 µM ATP) | AB: MDAMB453 (µM) | AB: BxPC3 (µM) |
|---|---|---|---|---|
| B4 | <0.01 | 2.1685 | 7.866 | 7.907 |
| C4 | <0.1 | 2.4032 | 1.494 | 3.279 |
| D4 | <0.01 | >2.5000 | 1.054 | 23.617 |
| E4 | <0.01 | >2.5000 | 1.174 | 11.78 |
| F4 | <0.01 | >2.5000 | 1.298 | 6.592 |
| G4 | <0.01 | >2.5000 | 1.153 | 1.191 |
| H4 | <0.01 | >2.5000 | 1.964 | 14.486 |
| I4 | <0.1 | >2.5000 | 0.683 | 1.898 |
| J4 | <0.01 | 0.867 | 4.746 | >30 |
| K4 | <0.1 | 1.3082 | 1.938 | 2.578 |
| L4 | <0.01 | 1.4748 | 1.79 | 0.725 |
| M4 | <0.01 | 1.2497 | >30 | 14.437 |
| N4 | <0.01 | >2.5000 | >30 | 12.535 |
| O4 | <0.01 | >2.5000 | 17.123 | 1.232 |
| P4 | <0.01 | 0.0754 | 5.276 | 0.549 |
| Q4 | <0.01 | 0.2562 | 1.068 | 0.745 |
| R4 | <0.01 | 0.0487 | 14.882 | 10.61 |
| S4 | <0.01 | >2.5000 | 20.012 | 4.608 |
| T4 | <0.1 | >2.5000 | 1.706 | 2.744 |
| U4 | <0.01 | >2.5000 | 1.263 | 8.129 |
| V4 | <0.1 | >2.5000 | 12.417 | >30 |
| W4 | <0.01 | 2.084 | 12.278 | >30 |
| X4 | <0.01 | 1.7271 | >30 | >30 |
| Y4 | <0.01 | >2.5000 | 1.979 | 2.253 |
| Z4 | <0.01 | >2.5000 | 15.69 | 29.035 |
| A5 | <0.01 | | 0.948 | 1.742 |
| B5 | <0.01 | >2.5000 | 26.74 | 5.426 |
| C5 | <1.0 | >2.5000 | | |
Synthesis of 5-(7-(tert-butoxycarbonyl(cyclopropyl)amino)-3-formylpyrazolo[1,5-a]pyrimidin-5-yl)-2-fluorobenzoic acid
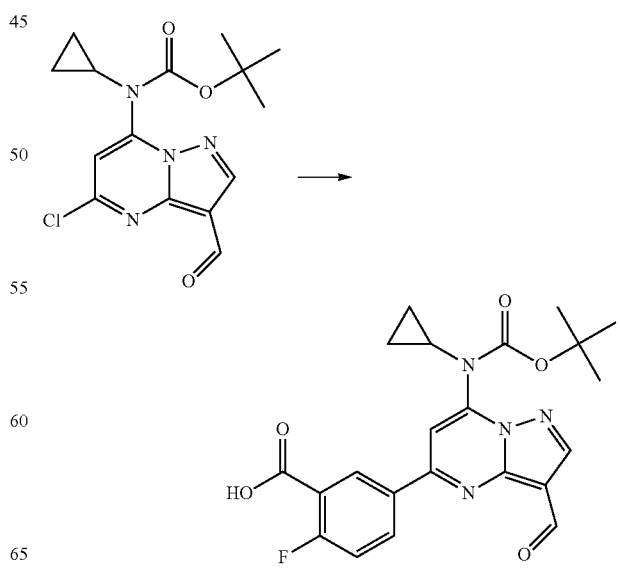

Same procedure as [Example 38]. LCMS (M+1=441)

Example 41

Synthesis of 5-(7-(cyclopropylamino)-3-formylpyrazolo[1,5-a]pyrimidin-5-yl)-2-fluorobenzoic acid

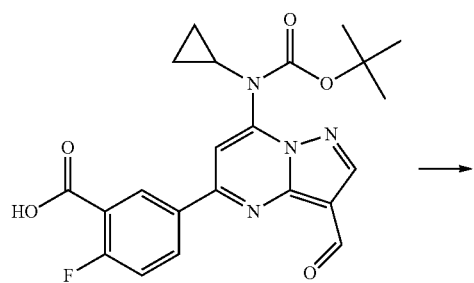

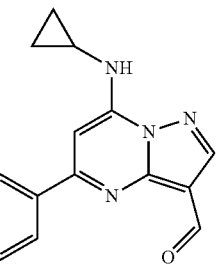

To 5-(7-(cyclopropyl amino)-3-formylpyrazolo[1,5-a]pyrimidin-5-yl)-2-fluorobenzoic acid (75 mg, 0.22 mmol 0 in DMF (3 mL) was added EDCI (46 mg, 0.24 mmol), HOBt (33 mg, 0.24 mmol), and morpholine (21 mg, 0.24 mmol). The reaction mixture was stirred at room temperature for 2 hours. The reaction mixture was diluted with ethyl acetate and washed 1× with saturated sodium bicarbonate, 2× with brine, dried over MgSO$_4$, filtered and evaporated to dryness to provide 92 mg of 7-(cyclopropylamino)-5-(4-fluoro-3-(morpholine-4-carbonyl)phenyl)pyrazolo[1,5-a]pyrimidine-3-carbaldehyde. LCMS (M+1=410)

Example 43

Synthesis of 547-(cyclopropylamino)-5-(4-fluoro-3-(morpholine-4-carbonyl)phenyl)pyrazolo[1,5-a]pyrimidin-3-yl)methylene)imidazolidine-2,4-dione

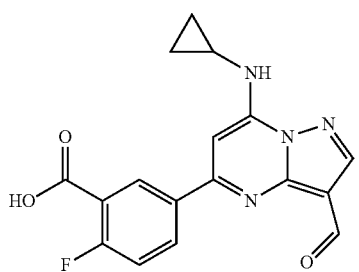

Same procedure as [Example 39]. LCMS (M+1=341)

Example 42

Synthesis of 7-(cyclopropylamino)-5-(4-fluoro-3-(morpholine-4-carbonyl)phenyl)pyrazolo[1,5-a]pyrimidine-3-carbaldehyde

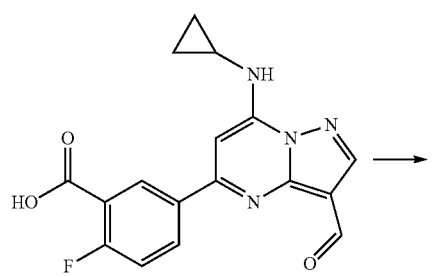

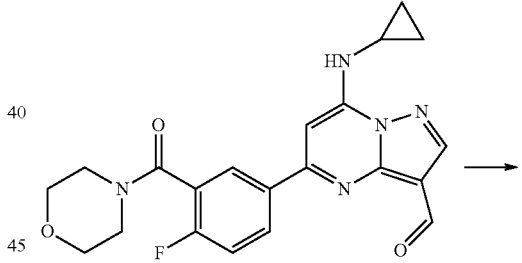

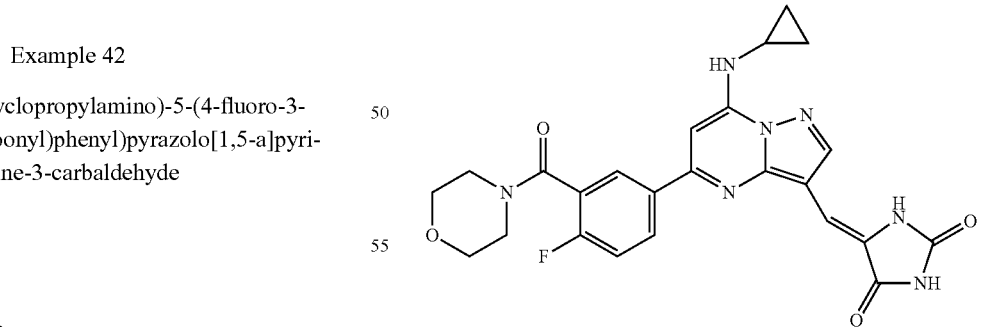

Same procedure as [Example 40]. LCMS (M+1=492)

The compounds described in the following table were prepared using chemistries similar to those exemplified in Example 42 and Example 43. All compounds were characterized by LCMS. Table 14B shows the biological activities of the compounds listed in Table 14A.

TABLE 14A

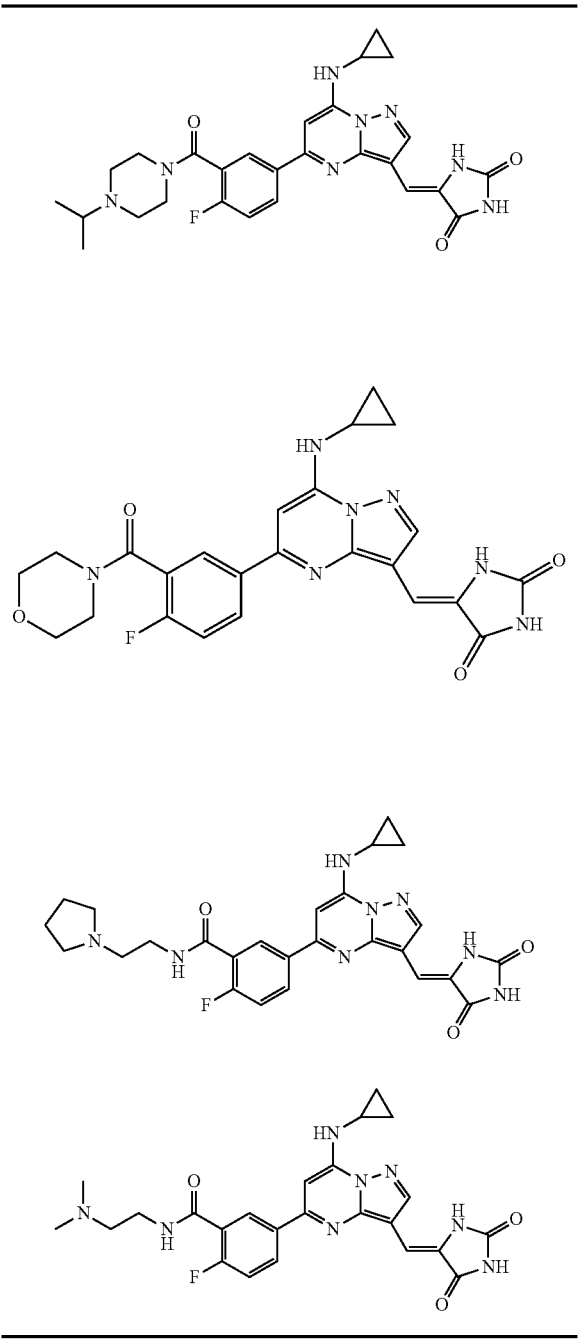

Example 44

Synthesis of tert-butyl cyclopropyl(5-(2-fluoropyridin-4-yl)-3-formylpyrazolo[1,5-a]pyrimidin-7-yl)carbamate

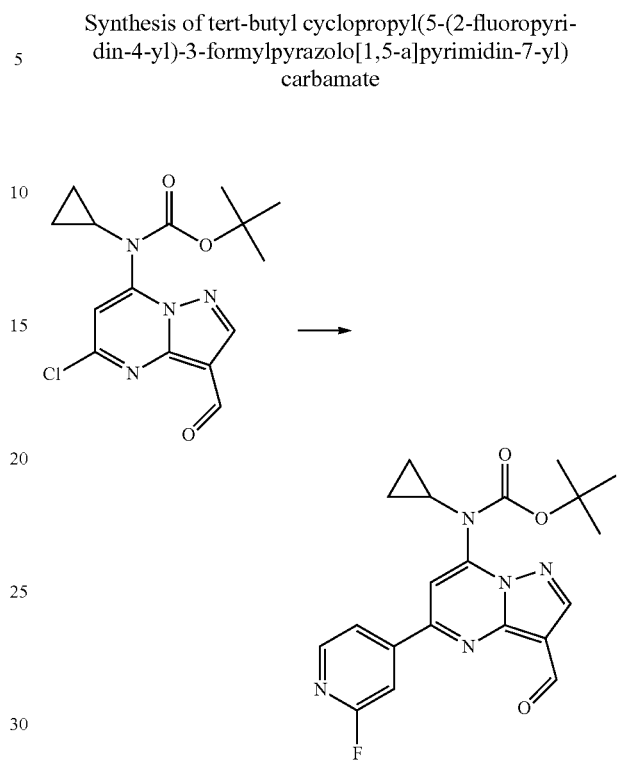

To tert-butyl 5-chloro-3-formylpyrazolo[1,5-a]pyrimidin-7-yl(cyclopropyl)carbamate (1 g, 3 mmol) in 29 mL of a 2:1 mixture of 1,2-dimethoxyethane/EtOH was added 2-Fluoropyridine-4-boronic acid (500 mg, 3.55 mmol), tetrakis(triphenylphosphine)palladium(0) (173 mg, 0.15 mmol), and 2M aqueous solution of $Na_2CO_3$ (4.4 mL, 8.9 mmol). The mixture was stirred at 85° C. for 8 hours. The volatiles were removed by rotary evaporation and the residue was purified by silica gel chromatography (35% EtOAc/Hexanes) to provide 324 mg tert-butyl cyclopropyl(5-(2-fluoropyridin-4-yl)-3-formylpyrazolo[1,5-a]pyrimidin-7-yl)carbamate (28% yield). LCMS (M+1=398)

Example 45

Synthesis of 7-(cyclopropylamino)-5-(2-fluoropyridin-4-yl)pyrazolo[1,5-a]pyrimidine-3-carbaldehyde

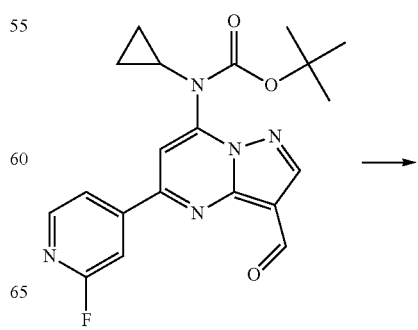

TABLE 14B

| Compound | CK2: IC50 (µM) | PIM2: IC50 (5 µM ATP) | AB: MDAMB453 (µM) | AB: BxPC3 (µM) |
|---|---|---|---|---|
| D5 | <0.1 | >2.5000 | 2.443 | 1.208 |
| E5 | <0.1 | >2.5000 | | |
| F5 | <0.01 | >2.5000 | 0.948 | 1.808 |
| G5 | <0.01 | >2.5000 | 0.435 | 1.841 |

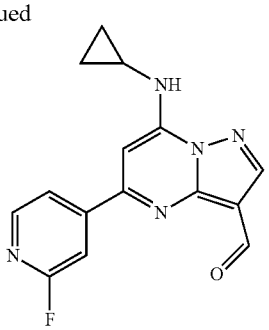

To tert-butyl cyclopropyl(5-(2-fluoropyridin-4-yl)-3-formylpyrazolo[1,5-a]pyrimidin-7-yl)carbamate (320 mg, 0.82 mmol) in methylene chloride (3 mL) was added TFA (3 mL). The reaction mixture was stirred at room temperature for 1.5 hours. The volatiles were removed by rotary evaporation and 1N NaOH was added to the residue to make basic. The precipitate was collected by filtration, washed with water, and dried under vacuum to provide 180 mg of 7-(cyclopropylamino)-5-(2-fluoropyridin-4-yl)pyrazolo[1,5-a]pyrimidine-3-carbaldehyde (74%). LCMS (M+1=298)

Example 46

Synthesis of 5-((7-(cyclopropylamino)-5-(2-fluoropyridin-4-pyrazolo[1,5-a]pyrimidin-3-yl)methylene)thiazolidine-2,4-dione

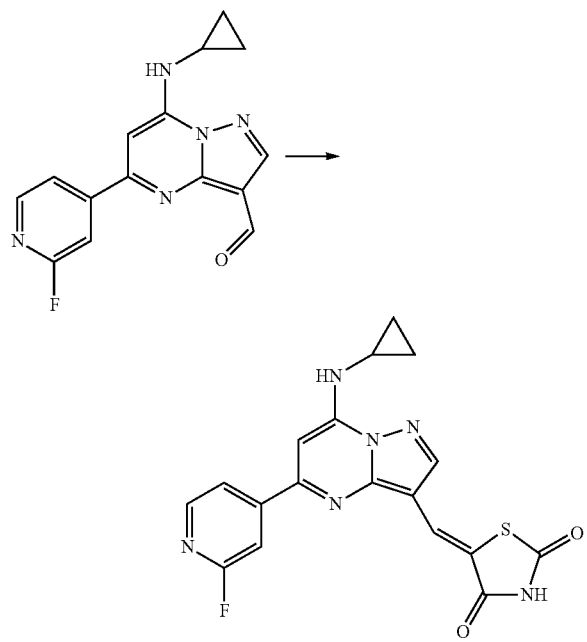

To 7-(cyclopropylamino)-5-(2-fluoropyridin-4-yl)pyrazolo[1,5-a]pyrimidine-3-carbaldehyde 30 mg, 0.1 mmol) in EtOH (1 mL) was added piperidine (13 μL, 0.1 mmol), and thiazolidine-2,4-dione (12 mg, 0.1 mmol). The reaction was stirred at 80° C. for 2 hours. The solid formed was isolated by filtration, washed with water then ethanol. The recovered solid was further purified by washing with 20% methanol/dichloromethan to provide 9 mg of 5-((7-(cyclopropy-lamino)-5-(2-fluoropyridin-4-pyrazolo[1,5-a]pyrimidin-3-yl)methylene)thiazolidine-2,4-dione (23%). LCMS (M+1=397)

The compounds described in the following table were prepared using chemistries similar to those exemplified in Example 44, Example 45, and Example 46. All compounds were characterized by LCMS. Table 15B shows the biological activities of the compounds listed in Table 15A.

TABLE 15A

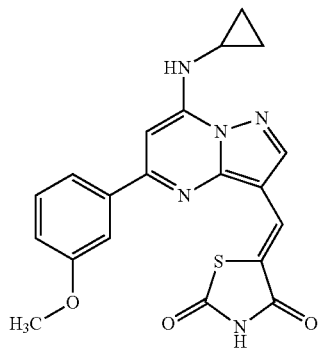 [SMILES: COc1cccc(-c2cc(NC3CC3)n3ncc(/C=C4\SC(=O)NC4=O)c3n2)c1]

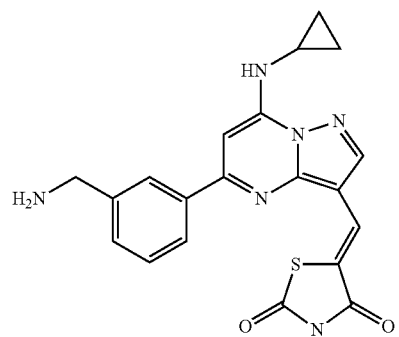

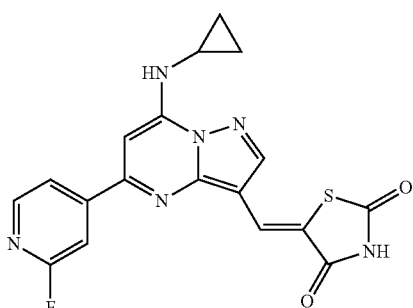

TABLE 15B

| Compound | CK2: IC50 (μM) | PIM2: IC50 (5 μM ATP) | AB: MDAMB453 (μM) | AB: BxPC3 (μM) |
|---|---|---|---|---|
| H5 | <0.1 | 0.8152 | | |
| I5 | <1.0 | 0.2176 | | |
| J5 | <1.0 | 0.1978 | >30 | 18.951 |

Example 47

Synthesis of 5-((7-(cyclopropylamino)-5-(2-fluoro-pyridin-4yl)pyrazolo[1,5-a]pyrimidin-3-yl)methyl-ene)-2-thioxothiazolidin-4-one

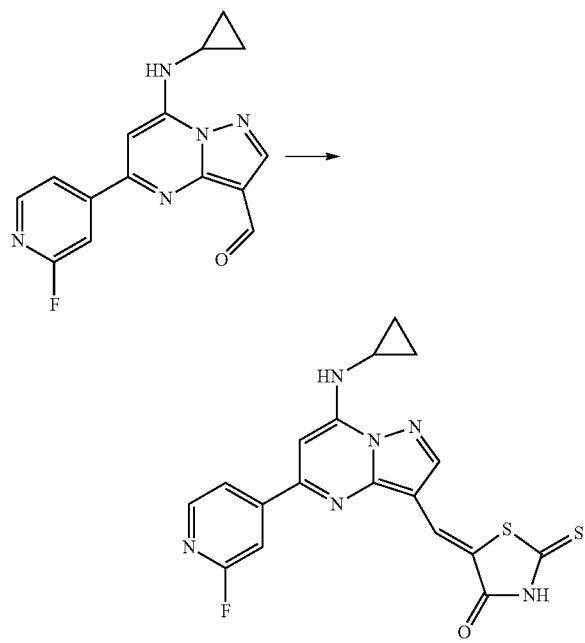

To 7-(cyclopropylamino)-5-(2-fluoropyridin-4-yl)pyrazolo[1,5-a]pyrimidine-3-carbaldehyde 30 mg, 0.1 mmol) in EtOH (1 mL) was added piperidine (13 µL, 0.1 mmol), and rhodanine (13 mg, 0.1 mmol). The reaction was stirred at 80° C. for 2 hours. The solid formed was isolated by filtration, washed with water then ethanol. The recovered solid was further purified by washing with 20% methanol/dichloromethan to provide 15 mg of 5-((7-(cyclopropylamino)-5-(2-fluoropyridin-4-yl)pyrazolo[1,5-a]pyrimidin-3-yl)methylene)-2-thioxothiazolidin-4-one (35%). LCMS (M+1=413)

Example 48

Synthesis of tert-butyl 4-(5-chloropyrazolo[1,5-a]pyrimidin-7-ylamino)piperidine-1-carboxylate

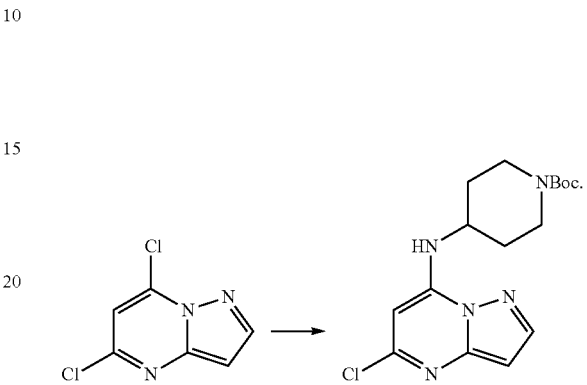

To the reaction flask, 5,7-dichloropyrazolo[1,5-a]pyrimidine (896 mg, 4.8 mmol) was added along with tert-butyl 4-aminopiperidine-1-carboxylate (954 mg, 4.8 mmol), triethylamine (664 µL, 4.8 mmol), and acetonitrile (16 mL). The reaction was heated at 100° C. for 12 hours then cooled to room temperature, diluted with water, filtered and washed with water. The product, tert-butyl 4-(5-chloropyrazolo[1,5-

TABLE 16

| Structure | LCMS m/z [M + 1]+ | CK2: IC50 (uM) | PIM2: IC50 (5um ATP) | AB: MDAMB453 (uM) | AB: BxPC3 (uM) |
|---|---|---|---|---|---|
| 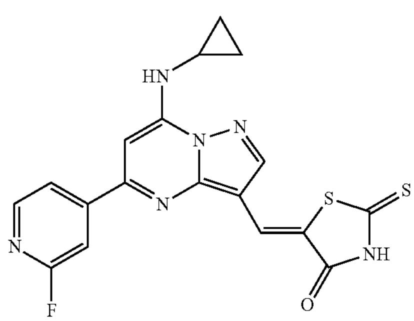 [SMILES: O=C1NC(=S)S/C1=C\c1cnn2c(NC3CC3)cc(-c3ccnc(F)c3)nc12] | 413 | <1.0 | 1.5908 | >30 | 22.671 |

Example 49

Synthesis of tert-butyl 4-(5-chloro-3-formylpyrazolo[1,5-a]pyrimidin-7-ylamino)piperidine-1-carboxylate

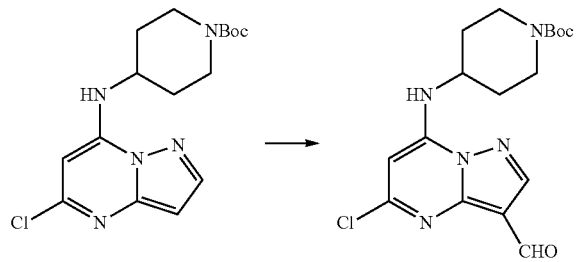 [SMILES: CC(C)(C)OC(=O)N1CCC(Nc2cc(Cl)nc3ccnn23)CC1 ; CC(C)(C)OC(=O)N1CCC(Nc2cc(Cl)nc3c(C=O)cnn23)CC1]

To tert-butyl 4-(5-chloropyrazolo[1,5-a]pyrimidin-7-ylamino)piperidine-1-carboxylate (1.7 g, 4.8 mmol) in DMF (36 mL), POCl$_3$ (7.7 mL, 82.9 mmol) was added dropwise at room temperature. After the addition was complete, the reaction was stirred for 8 hours. Then, the reaction was quenched by slow addition to ice cold 6N NaOH. The mixture was diluted with water and the solid was collected by filtration. The solid was washed several more times with water then dried under vacuum overnight. The product, tert-butyl 4-(5-chloro-3-formylpyrazolo[1,5-a]pyrimidin-7-ylamino)piperidine-1-carboxylate, was collected as a solid in 48% yield. LCMS (M+1=380)

Example 50

Synthesis of tert-butyl 4-(5-(3-chlorophenylamino)-3-formylpyrazolo[1,5-a]pyrimidin-7-ylamino)piperidine-1-carboxylate

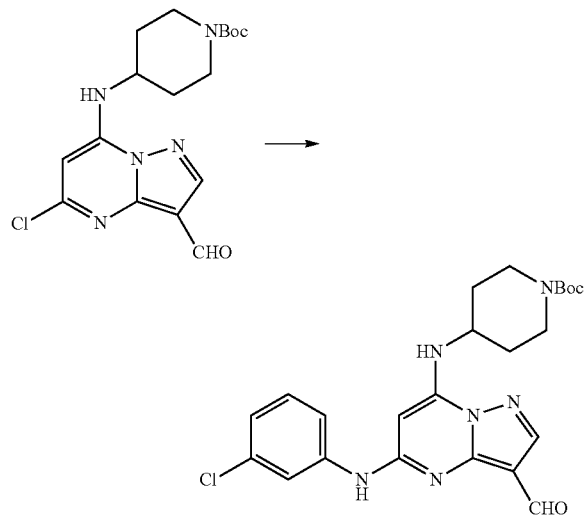

Tert-butyl 4-(5-chloro-3-formylpyrazolo[1,5-a]pyrimidin-7-ylamino)piperidine-1-carboxylate (876 mg, 2.3 mmol) was added to 1,4-dioxane (6 mL) along with 3-chloroaniline (1.5 mL, 13.9 mmol) and p-toluenesulfonic acid monohydrate (44 mg, 0.23 mmol). The reaction was heated at 95° C. for 12 hours then cooled to room temperature, diluted with water, and filtered. The solid was washed with 1N NaOH followed with water then dried under vacuum overnight. The product, tert-butyl 4-(5-(3-chlorophenylamino)-3-formylpyrazolo[1,5-a]pyrimidin-7-ylamino)piperidine-1-carboxylate, was collected after further purification by recrystallization from ethyl acetate/hexanes (74% yield). LCMS (M+1=471)

Example 51

Synthesis tert-butyl 4-(5-(3-chlorophenylamino)-3-((2,5-dioxoimidazolidin-4-ylidene)methyl)pyrazolo[1,5-a]pyrimidin-7-ylamino)piperidine-1-carboxylate

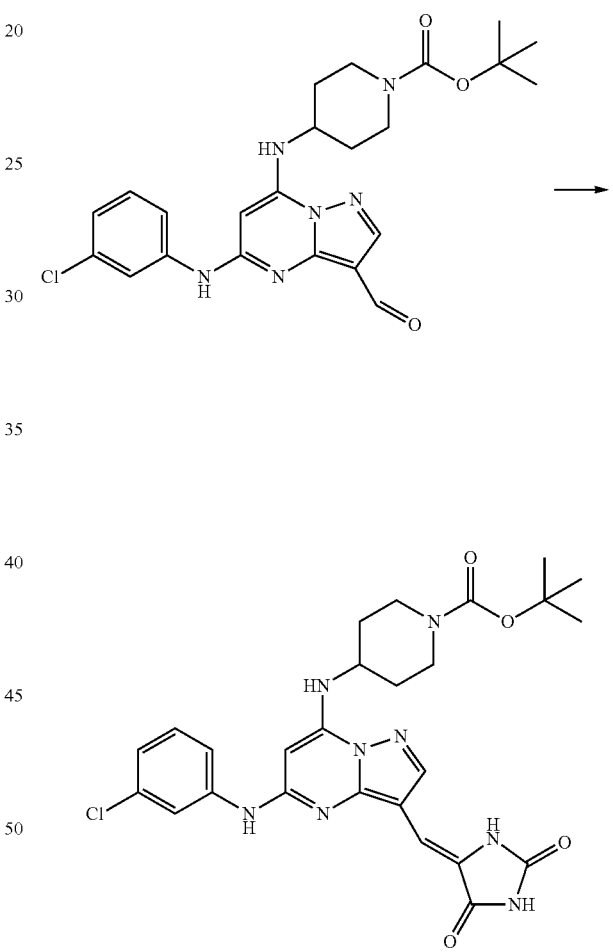

To the reaction flask, tert-butyl 445-(3-chlorophenylamino)-3-formylpyrazolo[1,5-a]pyrimidin-7-ylamino)piperidine-1-carboxylate (811 mg, 1.7 mmol) was added to ethanol (6.3 mL) along with hydantoin (172 mg, 1.7 mmol) and piperidine (170 μL, 1.7 mmol). The reaction was heated at 80° C. for 12 hours then cooled to room temperature and diluted with water. The solid was collected by filtration, washed with water and cold ethanol. The material was dried under vacuum overnight. The product, tert-butyl 4-(5-(3-chlorophenylamino)-3-(2,5-dioxoimidazolidin-4-ylidene)methyl)pyrazolo[1,5-a]pyrimidin-7-ylamino)piperidine-1-carboxylate, was recovered as a red solid in 67% yield after further purification by recrystallization from ethyl acetate/hexanes. LCMS (M+1=553)

Example 52

Synthesis 5-((5-(3-chlorophenylamino)-7-(piperidin-4-ylamino)pyrazolo[1,5-a]pyrimidin-3-yl)methylene)imidazolidine-2,4-dione

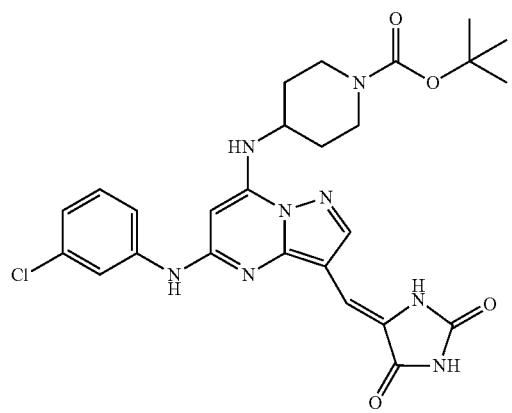

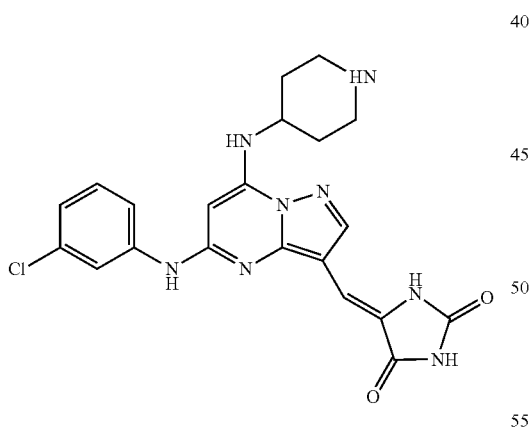

Tert-butyl 4-(5-(3-chlorophenylamino)-3-((2,5-dioxoimidazolidin-4-ylidene)methyl)pyrazolo[1,5-a]pyrimidin-7-ylamino)piperidine-1-carboxylate (640 mg, 1.2 mmol) was dissolved in 10 mL of TFA/DCM (1:1) and stirred at room temperature for 1 hour then quenched by addition to ice cold 6N NaOH. The mixture was diluted with water then the aqueous layer was decanted. The organic layer was diluted with hexanes and filtered. The product, 5-((5-(3-chlorophenylamino)-7-(piperidin-4-ylamino)pyrazolo[1,5-a]pyrimidin-3-yl)methylene)imidazolidine-2,4-dione, was collected as a solid in quantitative yield. LCMS (M+1=453)

Example 53

Synthesis of 5-((5-(3-chlorophenylamino)-7-(1-(cyclopropanecarbonyl)piperidin-4-ylamino)pyrazolo[1,5-a]pyrimidin-3-yl)methylene)imidazolidine-2,4-dione

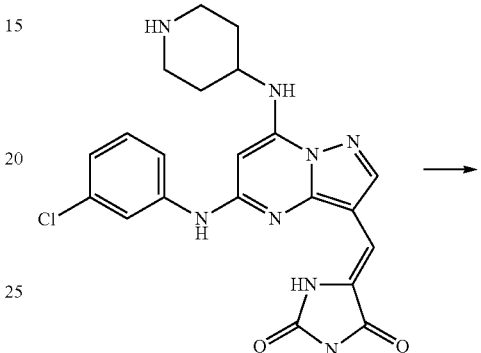

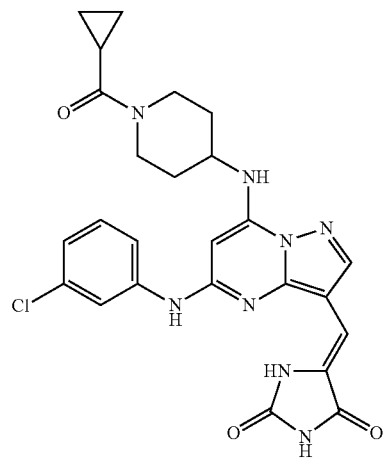

To 5-((5-(3-chlorophenylamino)-7-(piperidin-4-ylamino)pyrazolo[1,5-a]pyrimidin-3-yl)methylene) imidazolidine-2,4-dione (30 mg, 0.066 mmol) in THF was added cyclopropyl carbonyl chloride (5 µL, 0.04 mmol). The mixture was stirred at room temperature for ten minutes. The reaction mixture was then concentrated, diluted with MeOH, and purified by prep HPLC to yield 5-((5-(3-chlorophenylamino)-7-(1-(cyclopropanecarbonyl)piperidin-4-ylamino)pyrazolo[1,5-a]pyrimidin-3-yl)methylene)imidazolidine-2,4-dione. LCMS (M+1=521)

Example 54

Synthesis of 5-((5-(3-chlorophenylamino)-7-(1-pivaloylpiperidin-4-ylamino)pyrazolo[1,5-a]pyrimidin-3-yl)methylene)imidazolidine-2,4-dione

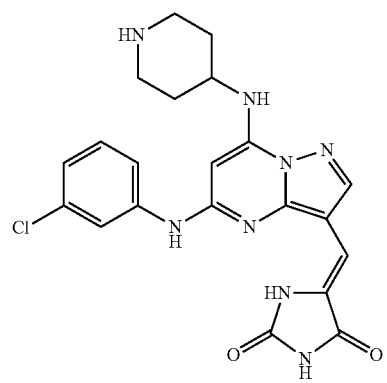

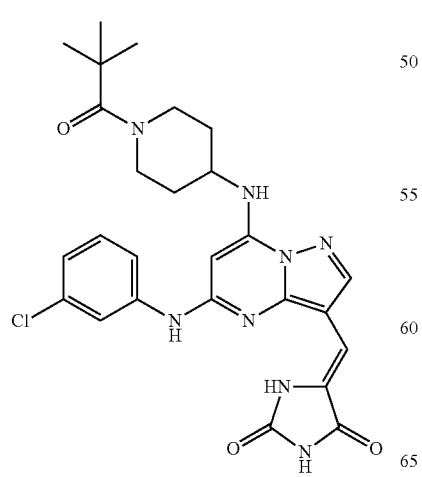

Same procedure as [Example 53]. LCMS (M+1=537)

Example 55

Synthesis of 5-((5-(3-chlorophenylamino)-7-(1-(3,3-dimethylbutanoyl)piperidin-4-ylamino)pyrazolo[1,5-a]pyrimidin-3-yl)methylene)imidazolidine-2,4-dione

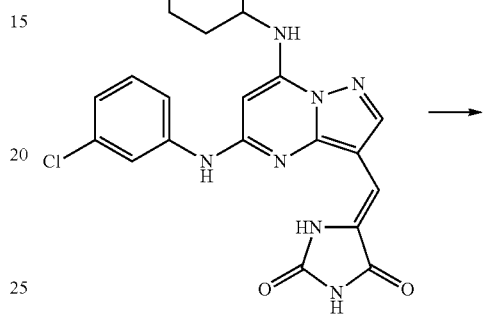

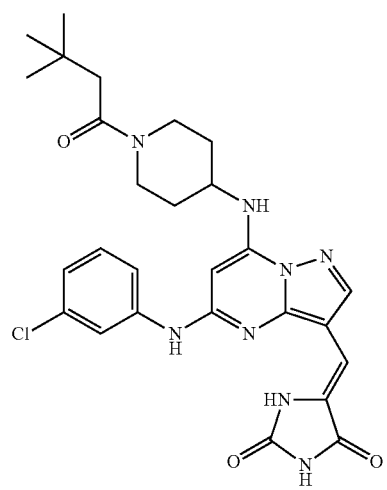

143
Same procedure as [Example 53]. LCMS (M+1=551)
Example 56
Synthesis of 4-(5-(3-chlorophenylamino)-3-(2,5-dioxoimidazolidin-4-ylidene)methyl)pyrazolo[1,5-a]pyrimidin-7-ylamino)-N,N-dimethylpiperidine-1-carboxamide
144
Same procedure as [Example 53]. LCMS (M+1=524)
Example 57
Synthesis of methyl 4-(5-(3-chlorophenylamino)-3-((2,5-dioxoimidazolidin-4-ylidene)methyl)pyrazolo[1,5-a]pyrimidin-7-ylamino)piperidine-1-carboxylate
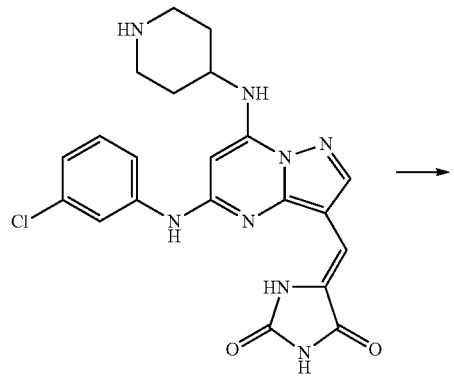
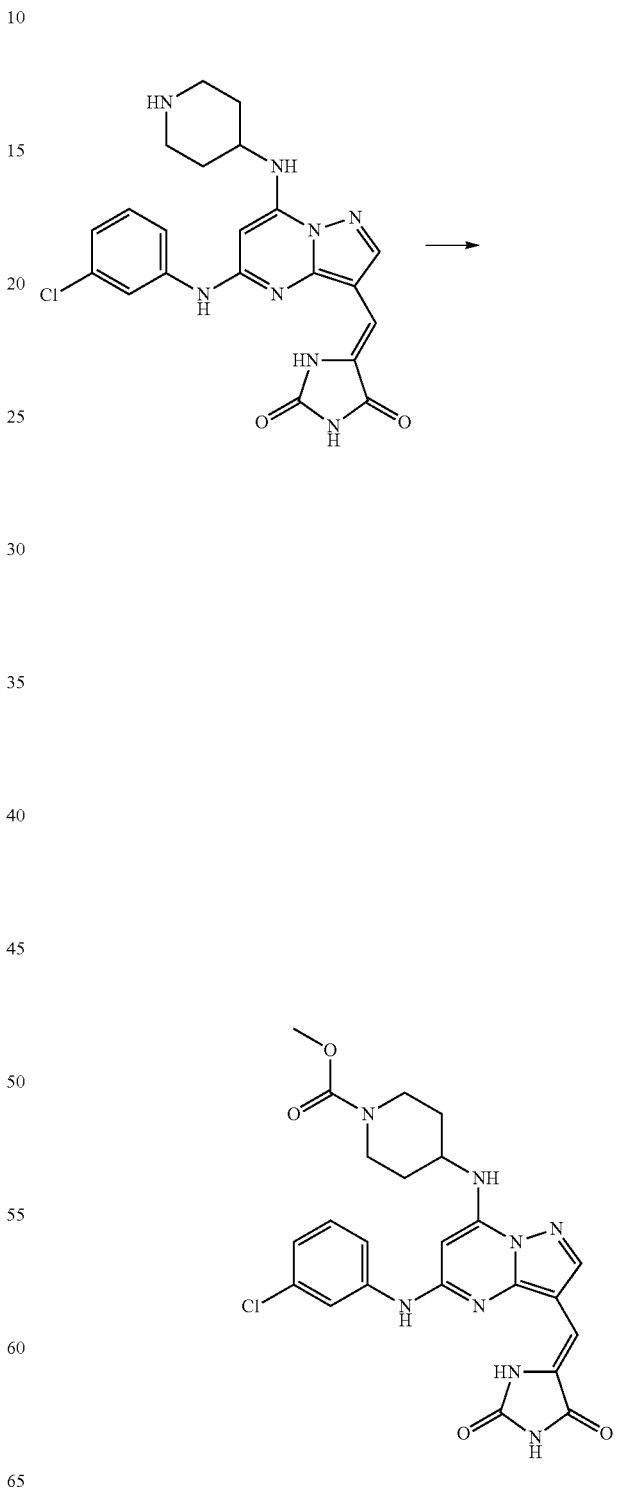

145

Same procedure as [Example 53] except DMF is used as solvent. LCMS (M+1=511)

Example 58

Synthesis of methyl 2-(4-(5-(3-chlorophenylamino)-3-(2,5-dioxoimidazolidin-4-ylidene)methyl)pyrazolo[1,5-a]pyrimidin-7-ylamino)piperidin-1-yl)acetate

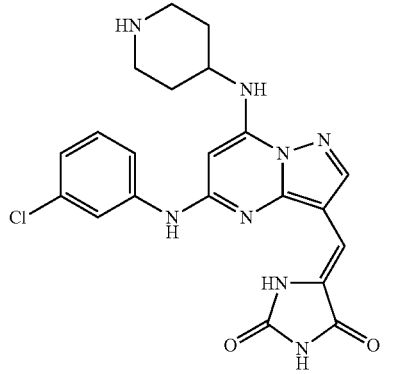

146

Same procedure as [Example 53] except DMF is used as solvent. LCMS (M+1=525)

Example 59

Synthesis of 5-((5-(3-chlorophenylamino)-7-(1-(2-hydroxypropyl)piperidin-4-ylamino)pyrazolo[1,5-a]pyrimidin-3-yl)methylene)imidazolidine-2,4-dione

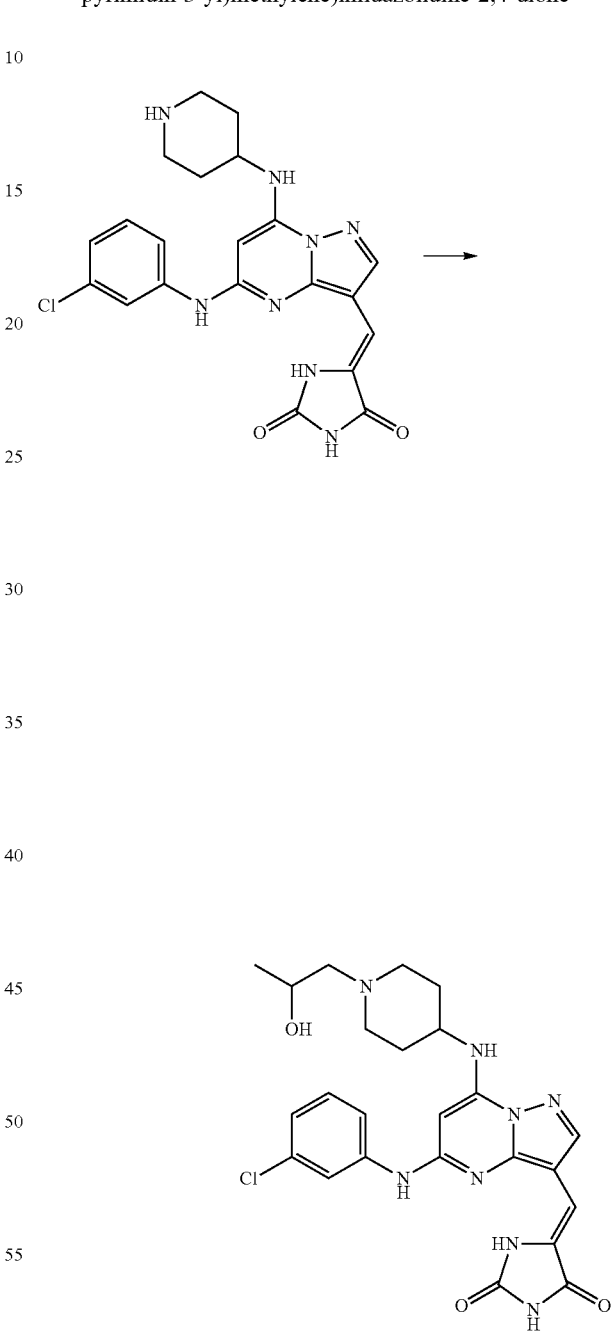

To 5((5(3-chlorophenylamino)-7-(piperidin-4-ylamino)pyrazolo[1,5-a]pyrimidin-3-yl)methylene)imidazolidine-2,4-dione (30 mg, 0.066 mmol) in DMF was added 1-chloro2-propanol (7 μL, 0.13 mmol) and potassium iodide (11.0 mg, 0.066 mmol). The mixture was heated to 120° C. and stirred for overnight. The reaction mixture was concentrated, diluted with MeOH, and purified by prep HPLC to yield 5-((5-(3-chlorophenylamino)-7-(2-hydroxypropyl)piperidin-4- ylamino)pyrazolo[1,5-a]pyrimidin-3-yl)methylene)imidazolidine-2,4-dione. LCMS (M+1=511)

Example 60

Synthesis of 5-((5-(3-chlorophenylamino)-7-(1-(2-hydroxyethyl)piperidin-4-ylamino)pyrazolo[1,5-a]pyrimidin-3-yl)methylene)imidazolidine-2,4-dione

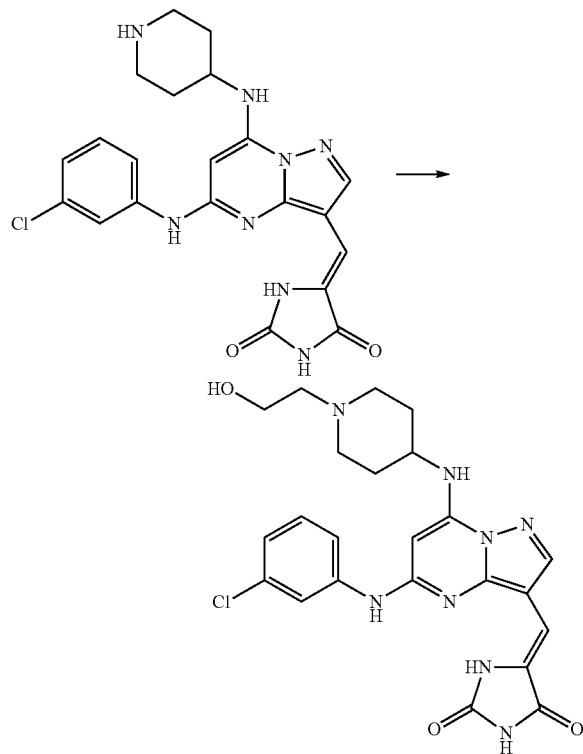

Same procedure as [Example 59]. LCMS (M+1=497)

Example 61

Synthesis of 5-((5-(3-chlorophenylamino)-7-(1-(pyridin-2-ylmethyl)piperidin-4-ylamino)pyrazolo[1,5-a]pyrimidin-3-yl)methylene)imidazolidine-2,4-dione

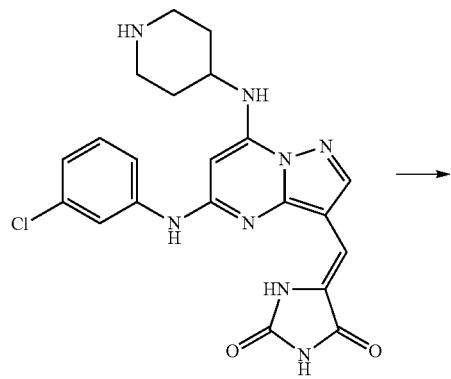

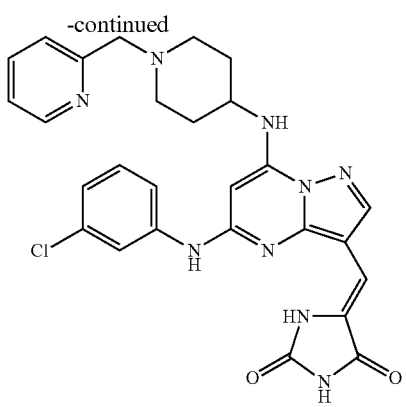

To 5-((5-(3-chlorophenylamino)-7-(piperidin-4-ylamino) pyrazolo[1,5-a]pyrimidin-3-yl)methylene) imidazolidine-2,4-dione (30 mg, 0.066 mmol) in DMF was added 2-(bromomethyl)pyridine hydrogen bromide (26.0 mg, 0103 mmol). The mixture was stirred at room temperature for 0.5 hour. The reaction mixture was concentrated, diluted with MeOH, and purified by prep HPLC to yield 5-((5-(3-chlorophenylamino)-7-(1-(pyridin-2-ylmethyl)piperidin-4-ylamino) pyrazolo[1,5-a]pyrimidin-3-yl)methylene)imidazolidine-2,4-dione. LCMS (M+1=544)

Example 62

Synthesis of 5-((5(3-chlorophenylamino)-7-(1-isopropylpiperidin-4-ylamino)pyrazolo[1,5-a]pyrimidin-3-yl)methylene)imidazolidine-2,4-dione

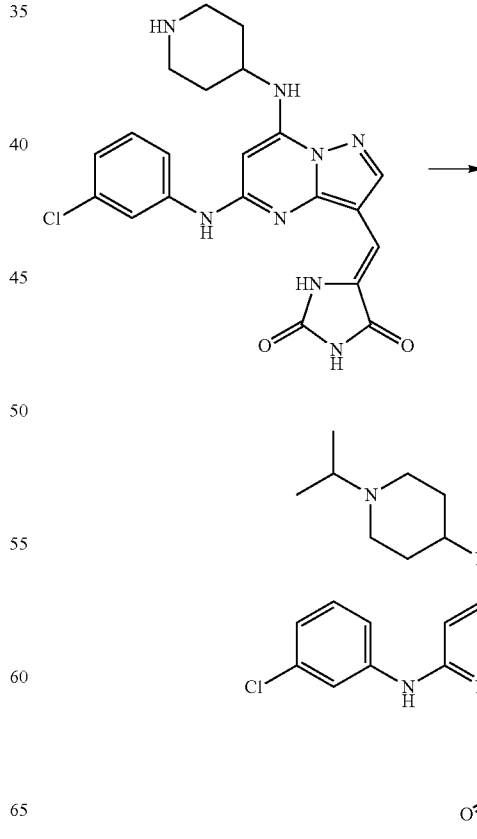

To 5-((5-(3-chlorophenylamino)-7-(piperidin-4-ylamino) pyrazolo[1,5-a]pyrimidin-3-yl)methylene) imidazolidine-2,4-dione (20 mg, 0.04 mmol) in THF and AcOH (4.8 mg, 0.08 mmol) was added acetone (2.0 mL, 0.2 mmol) and sodium triacetoxy borohydride (85.0 mg, 0.4 mmol). The mixture was heated at 60° C. for one hour. Saturated sodium bicarbonate solution was added to the reaction mixture. The mixture was extracted with ethyl acetate and dried over sodium sulfate. Then the mixture was, diluted with MeOH, and purified by prep HPLC to yield 5-((5-(3-chlorophenylamino)-7-(1-isopropylpiperidin-4-ylamino) pyrazolo[1,5-a]pyrimidin-3-yl)methylene) imidazolidine-2,4-dione. LCMS (M+1=495)

Example 63

Synthesis of 5-((5-(3-chlorophenylamino)-7-(1-ethylpiperidin-4-ylamino)pyrazolo[1,5-a]pyrimidin-3-yl)methylene)imidazolidine-2,4-dione

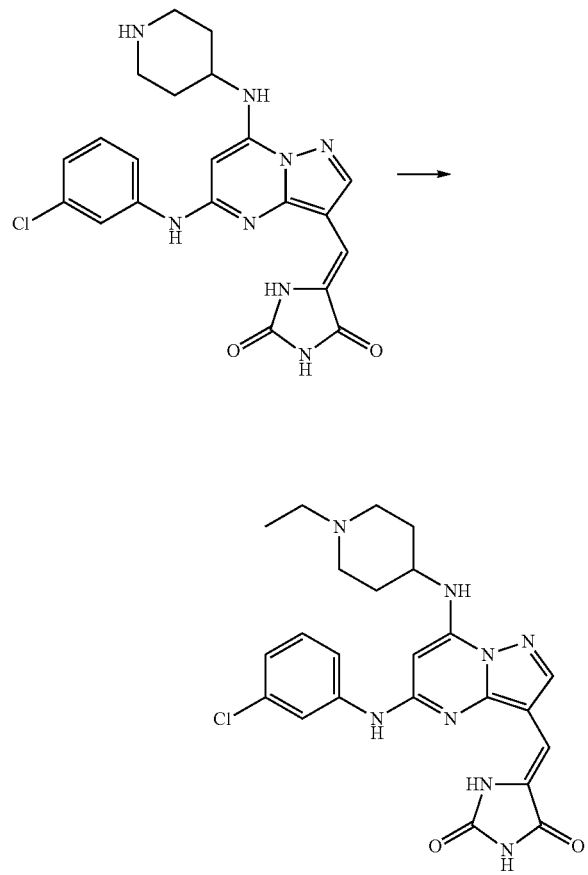

To 5-((5-(3-chlorophenylamino)-7-(piperidin-4-ylamino) pyrazolo[1,5-a]pyrimidin-3-yl)methylene) imidazolidine-2,4-dione (30 mg, 0.06 mmol) in THF and AcOH (4.8 mg, 0.08 mmol) was added acetaldehyde (2.0 mL, 0.2 mmol) and sodium triacetoxy borohydride (85.0 mg, 0.4 mmol). The mixture was stirred at room temperature for 0.5 hour. The reaction mixture was concentrated, diluted with MeOH, and purified by prep HPLC to yield 5-((5-(3-chlorophenylamino)-7-(1-ethylpiperidin-4-ylamino) pyrazolo[1,5-a]pyrimidin-3-yl)methylene) imidazolidine-2,4-dione. LCMS (M+1=481)

Example 64

Synthesis of 5-((5-(3-chlorophenylamino)-7-(1-isobutylpiperidin-4-ylamino)pyrazolo[1,5-a]pyrimidin-3-yl)methylene)imidazolidine-2,4-dione

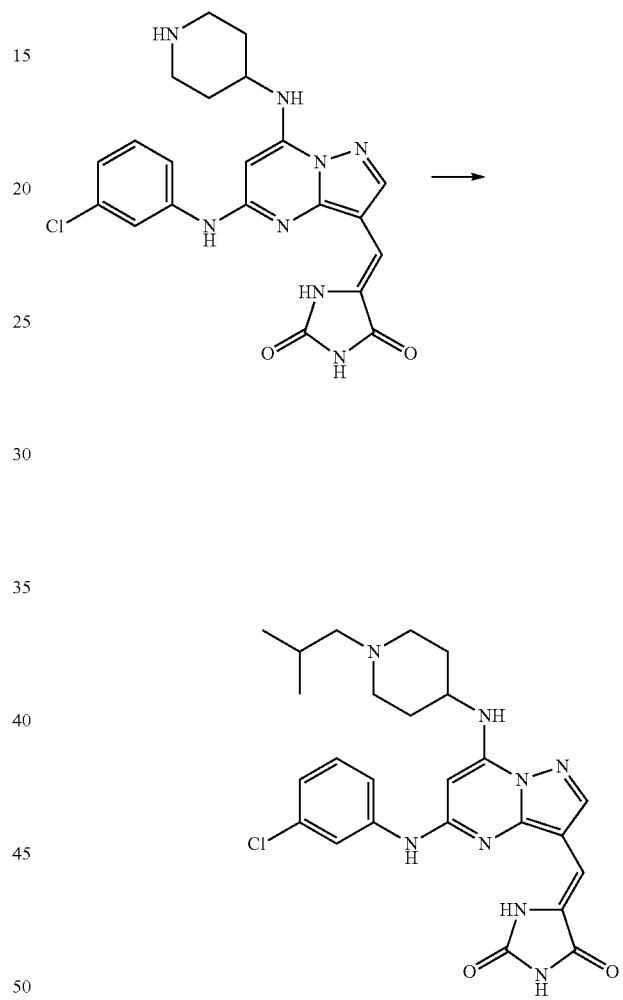

To 5-((5-(3-chlorophenylamino)-7-(piperidin-4-ylamino) pyrazolo[1,5-a]pyrimidin-3-yl)methylene) imidazolidine-2,4-dione (30 mg, 0.06 mmol) in THF and AcOH (4.8 mg, 0.08 mmol) was added isobutryldehyde (2.2 mL, 0.2 mmol) and sodium triacetoxy borohydride (85.0 mg, 0.4 mmol). The mixture was stirred at room temperature for 0.5 hour. The mixture was concentrated, diluted with MeOH, and purified by prep HPLC to yield 5-((5-(3-chlorophenylamino)-7-(1-isobutylpiperidin-4-ylamino) pyrazolo[1,5-a]pyrimidin-3-yl) methylene) imidazolidine-2,4-dione. LCMS (M+1=509)

The compounds described in the following table were prepared using chemistries similar to those exemplified in the Examples described above. All compounds were characterized by LCMS. Table 17B shows the biological activities of the compounds listed in Table 17A.

TABLE 17A
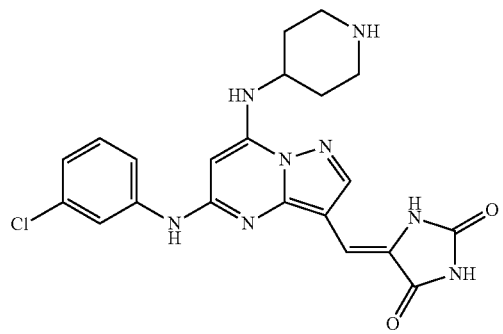 [SMILES: O=C1NC(=O)/C(=C/c2cnn3c(NC4CCNCC4)cc(Nc4cccc(Cl)c4)nc23)N1]
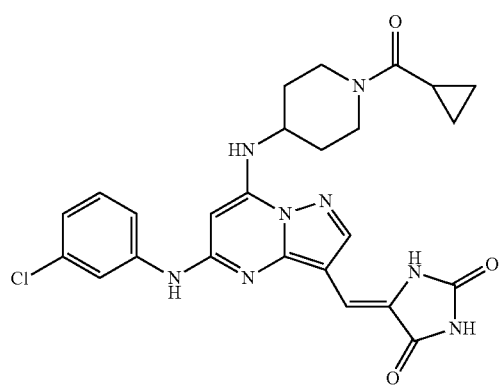 [SMILES: O=C1NC(=O)/C(=C/c2cnn3c(NC4CCN(C(=O)C5CC5)CC4)cc(Nc4cccc(Cl)c4)nc23)N1]
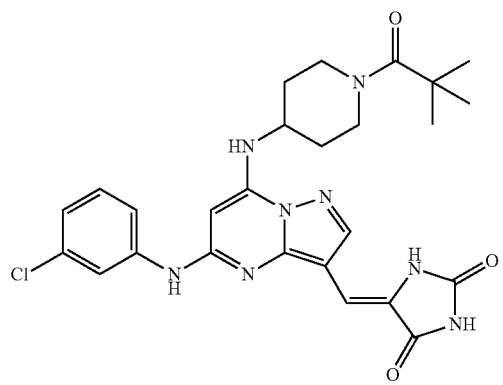 [SMILES: CC(C)(C)C(=O)N1CCC(Nc2cc(Nc3cccc(Cl)c3)nc3c(/C=C4\NC(=O)NC4=O)cnn23)CC1]
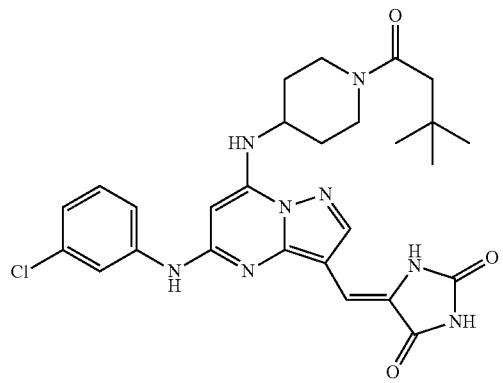 [SMILES: CC(C)(C)CC(=O)N1CCC(Nc2cc(Nc3cccc(Cl)c3)nc3c(/C=C4\NC(=O)NC4=O)cnn23)CC1]
TABLE 17A-continued
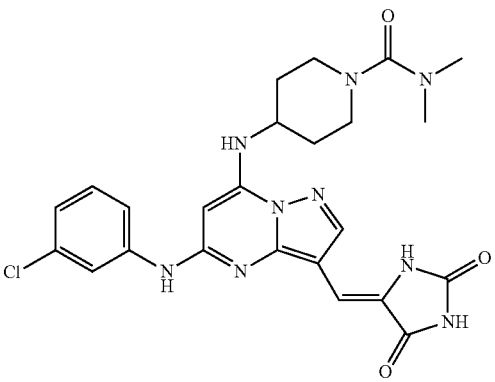 [SMILES: CN(C)C(=O)N1CCC(Nc2cc(Nc3cccc(Cl)c3)nc3c(/C=C4\NC(=O)NC4=O)cnn23)CC1]
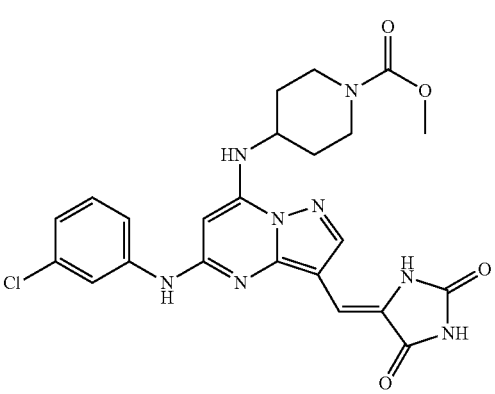 [SMILES: COC(=O)N1CCC(Nc2cc(Nc3cccc(Cl)c3)nc3c(/C=C4\NC(=O)NC4=O)cnn23)CC1]
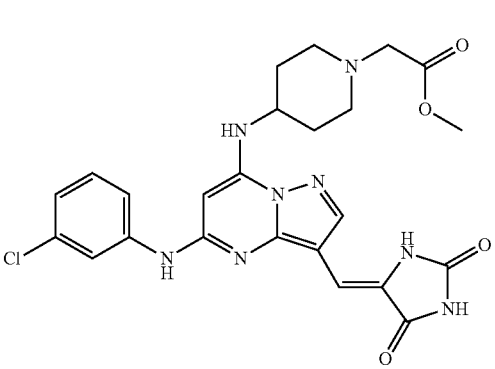 [SMILES: COC(=O)CN1CCC(Nc2cc(Nc3cccc(Cl)c3)nc3c(/C=C4\NC(=O)NC4=O)cnn23)CC1]
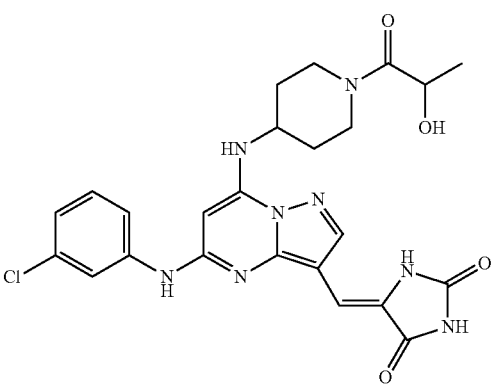 [SMILES: CC(O)C(=O)N1CCC(Nc2cc(Nc3cccc(Cl)c3)nc3c(/C=C4\NC(=O)NC4=O)cnn23)CC1]

TABLE 17A-continued

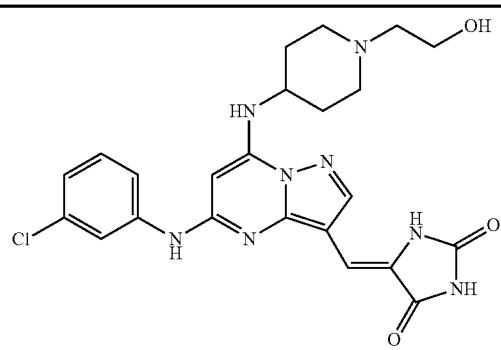

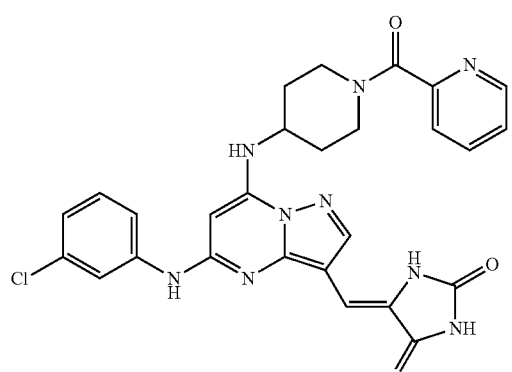

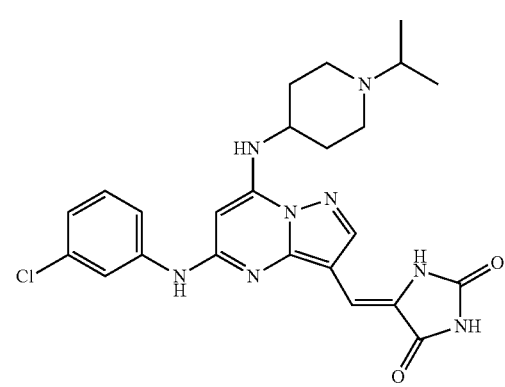 [SMILES: CC(C)N1CCC(Nc2cc(Nc3cccc(Cl)c3)nc3c(/C=C4\NC(=O)NC4=O)cnn23)CC1]

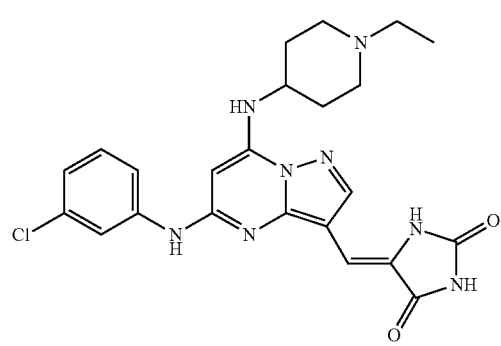 [SMILES: CCN1CCC(Nc2cc(Nc3cccc(Cl)c3)nc3c(/C=C4\NC(=O)NC4=O)cnn23)CC1]

TABLE 17A-continued

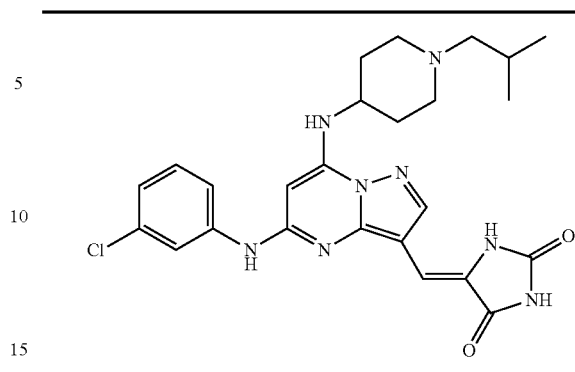

TABLE 17B

| Compound | CK2: IC50 (μM) | PIM2: IC50 (5 μM ATP) | AB: MDAMB453 (μM) | AB: BxPC3 (μM) |
|---|---|---|---|---|
| K5 | <0.1 | 2.4491 | 1.078 | 10.984 |
| L5 | <0.01 | >2.5000 | 0.993 | 2.399 |
| M5 | <0.1 | >2.5000 | 0.874 | 10.023 |
| N5 | <0.1 | >2.5000 | 1.569 | 17.368 |
| O5 | <0.1 | 2.4076 | 1.115 | 4.263 |
| P5 | <0.1 | >2.5000 | 0.825 | 16.513 |
| Q5 | <0.1 | >2.5000 | | |
| R5 | <0.1 | 2.2046 | | |
| S5 | <0.1 | >2.5000 | | |
| T5 | <0.1 | >2.5000 | | |
| U5 | <1.0 | >2.5000 | | |
| V5 | <1.0 | >2.5000 | | |
| W5 | <1.0 | >2.5000 | | |

Example 65

Synthesis of 7-(benzylthio)-5-chloropyrazolo[1,5-a]pyrimidine

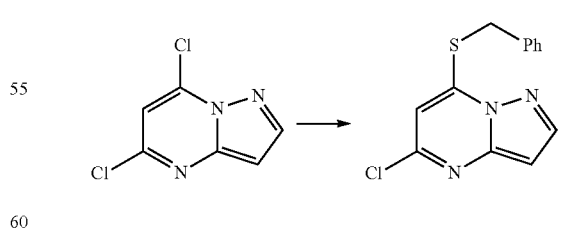

To the reaction flask, 5,7-dichloropyrazolo[1,5-a]pyrimidine (4.1 g, 22 mmol) was added along with benzyl mercaptan (2.8 mL, 22 mmol), triethylamine (3.1 mL, 22 mmol), and acetonitrile (71 mL). The reaction was stirred at room temperature for 3 hours then diluted with water, filtered and washed with water. The product, 7-(benzylthio)-5-chloropyrazolo[1,5-a]pyrimidine, was collected as a solid in 96% yield after drying under vacuum overnight. LCMS (M+1=276)

Example 66

Synthesis of 7-(benzylthio)-N-(3-chlorophenyl)pyrazolo[1,5-a]pyrimidin-5-amine

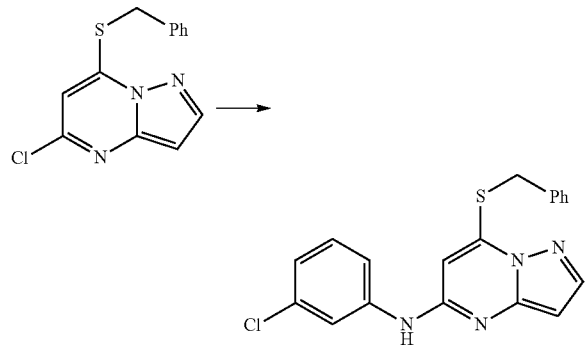

To the reaction flask, 7-(benzylthio)-5-chloropyrazolo[1,5-a]pyrimidine (3.45 g, 12.5 mmol) was added along with 3-chloroaniline (3.3 mL, 31.3 mmol), 4N HCl in dioxane (3.1 mL, 12.5 mmol), and ethanol (42 mL). The reaction was stirred at reflux for 12 hours then cool to room temperature. Excess solvent was removed under vacuum and the residue was diluted with water. The mixture was made basic with 3N NaOH, filtered and washed with water. The product, 7-(benzylthio)-N-(3-chlorophenyl)pyrazolo[1,5-a]pyrimidin-5-amine, was collected as a solid in 90% yield after drying under vacuum overnight. LCMS (M+1=376)

Example 67

Synthesis of 7-(benzylthio)-5-(3-chlorophenylamino)pyrazolo[1,5-a]pyrimidine-3-carbaldehyde

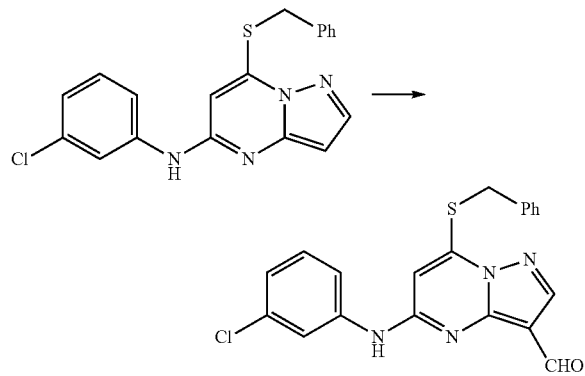

To 7-(benzylthio)-N-(3-chlorophenyl)pyrazolo[1,5-a]pyrimidin-5-amine (4.1 g, 11.3 mmol) in DMF (42 mL), POCl$_3$ (6.3 mL, 67.6 mmol) was added dropwise at room temperature. After the addition was complete, the reaction was stirred for 3 hours at room temperature. Then, the reaction was quenched by slow addition to ice cold 6N NaOH. The mixture was diluted with water and the solid was collected by filtration. The solid was washed several more times with water then dried under vacuum overnight. The product, 7-(benzylthio)-5-(3-chlorophenylamino)pyrazolo[1,5-a]pyrimidine-3-carbaldehyde, was collected as a solid in 83% yield. LCMS (M+1=395)

Example 68

Synthesis 5-((7-(benzylthio)-5-(3-chlorophenylamino)pyrazolo[1,5-a]pyrimidin-3-yl)methylene)imidazolidine-2,4-dione

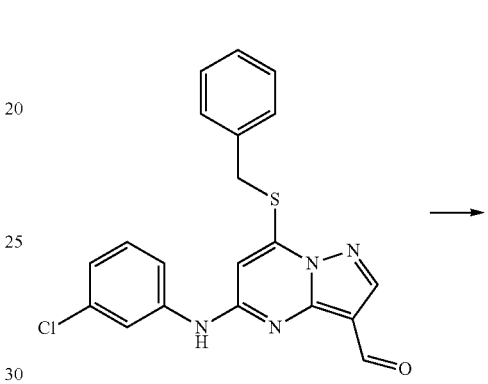

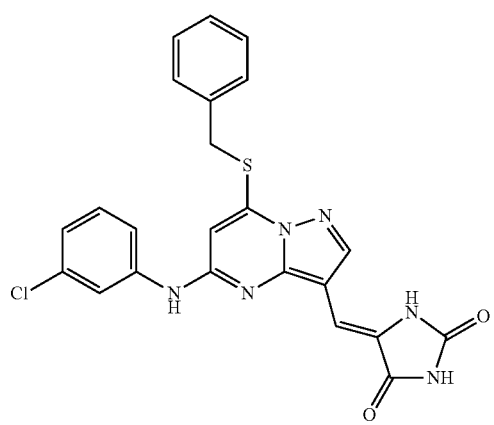

To the reaction flask, 7-(benzylthio)-5-(3-chlorophenylamino)pyrazolo[1,5-a]pyrimidine-3-carbaldehyde (3.7 g, 9.3 mmol) was added to ethanol (31 mL) along with hydantoin (933 mg, 9.3 mmol) and piperidine (920 µL, 9.3 mmol). The reaction was heated at 80° C. for 3 days then cooled to room temperature and diluted with water. The solid was collected by filtration, washed with water, 50% ethanol/water, and then 100% ethanol. The material was dried under vacuum overnight. The product, 5-((7-(benzylthio)-5-(3-chlorophenylamino)pyrazolo[1,5-a]pyrimidin-3-yl)methylene)imidazolidine-2,4-dione, was recovered as a yellow solid in 92% yield. LCMS (M+1=477)

Example 69

Synthesis of 5-((7-(benzylsulfinyl)-5-(3-chlorophenylamino)pyrazolo[1,5-a]pyrimidin-3-yl)methylene)imidazolidine-2,4-dione

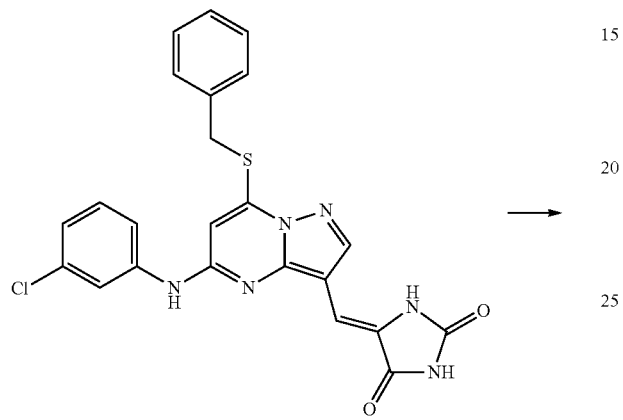

→

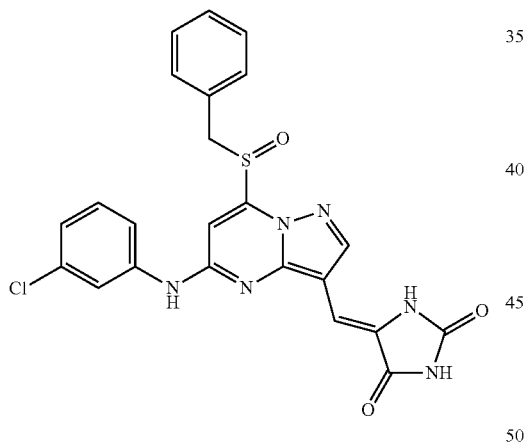

To the reaction flask, 5-((7-(benzylthio)-5-(3-chlorophenylamino)pyrazolo[1,5-a]pyrimidin-3-yl)methylene)imidazolidine-2,4-dione (4.1 g, 8.6 mmol) was added to dichloromethane (86 mL) along with m-chloroperbenzoic acid (5.9 g, 34.4 mmol). The mixture was allowed to stir at room temperature for 12 hours. The solid was collected by filtration, washed with dichloromethane then dried under vacuum overnight. The product, 5-((7-(benzylsulfinyl)-5-(3-chlorophenylamino)pyrazolo[1,5-a]pyrimidin-3-yl)methylene) imidazolidine-2,4-dione, was recovered as a bright yellow solid in quantitative yield. LCMS (M+1=493)

The compounds described in the following table were prepared using chemistries similar to those exemplified in the Examples described above. All compounds were characterized by LCMS. Table 18B shows the biological activities of the compounds listed in Table 18A.

TABLE 18A

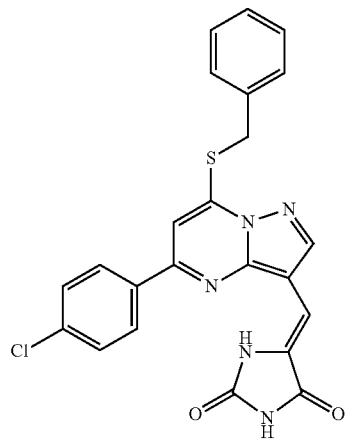 [SMILES: O=C1NC(=O)/C(=C/c2cnn3c(SCc4ccccc4)cc(-c4ccc(Cl)cc4)nc23)N1]

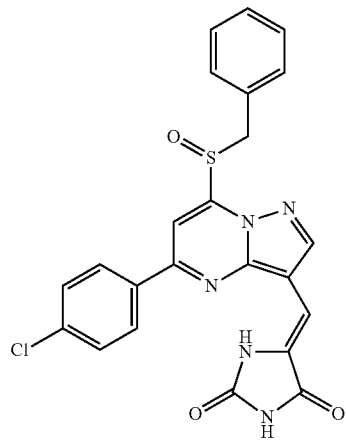 [SMILES: O=C1NC(=O)/C(=C/c2cnn3c(S(=O)Cc4ccccc4)cc(-c4ccc(Cl)cc4)nc23)N1]

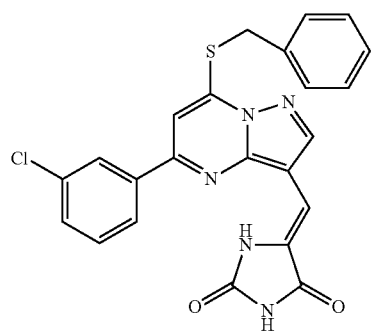 [SMILES: O=C1NC(=O)/C(=C/c2cnn3c(SCc4ccccc4)cc(-c4cccc(Cl)c4)nc23)N1]

TABLE 18A-continued

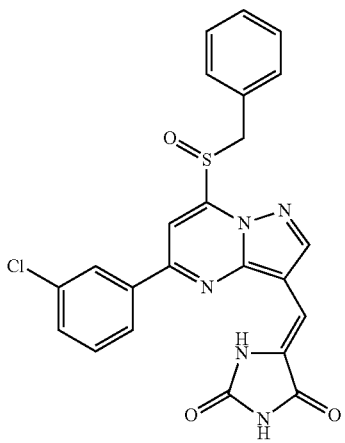 [SMILES: O=C1NC(=O)/C(=C/c2cnn3c(S(=O)Cc4ccccc4)cc(-c4cccc(Cl)c4)nc23)N1]

TABLE 18B

| Compound | CK2: IC50 (μM) | PIM2: IC50 (5 μM ATP) | AB: MDAMB453 (μM) | AB: BxPC3 (μM) |
|---|---|---|---|---|
| X5 | <1.0 | 2.2449 | | |
| Y5 | <1.0 | 0.2913 | | |
| Z5 | <1.0 | 0.2968 | | |
| A6 | <0.1 | 0.209 | | |

Example 70

Synthesis of 5-((5-(3-chlorophenylamino)-7-(2-hydroxyethyl amino)pyrazolo[1,5-a]pyrimidin-3-yl)methylene)imidazolidine-2,4-dione

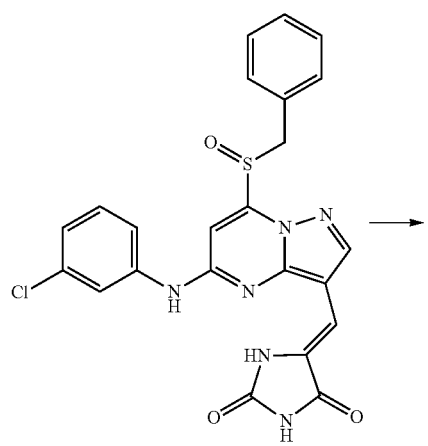

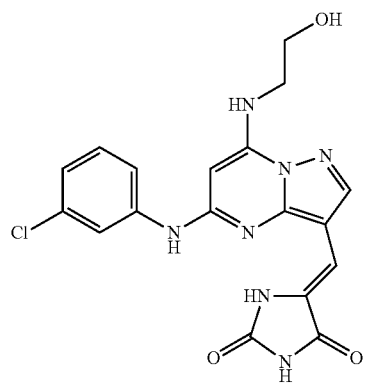

To 5-((7-(benzylsulfinyl)-5-(3-chlorophenylamino) pyrazolo[1,5-a]pyrimidin-3-yl) methylene) imidazolidine-2,4-dione (15 mg, 0.0304 mmol) in NMP was added 2-aminoethanol (14.6 μL, 0.242 mmol). The mixture was heated in the microwave at 120° C. for 20 minutes. Water was added to the reaction mixture and the precipitate was collected by filtration. The precipitate was washed with methanol to yield 5-((5-(3-chlorophenylamino)-7-(2-hydroxyethylamino) pyrazolo[1,5-a]pyrimidin-3-yl)methylene) imidazolidine-2,4-dione LCMS (M+1=414). Similar products (shown below) were also obtained as precipitates by addition of water while other reactions were purified by prep HPLC to yield corresponding products.

Example 71

Synthesis of 5-((5-(3-chlorophenylamino)-7-(pyridin-3-ylmethylamino)pyrazolo[1,5-a]pyrimidin-3-yl)methylene)imidazolidine-2,4-dione

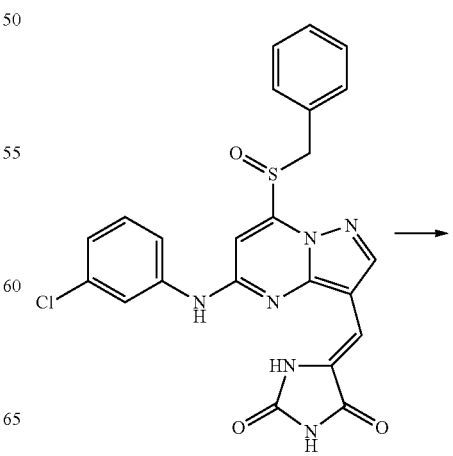

-continued
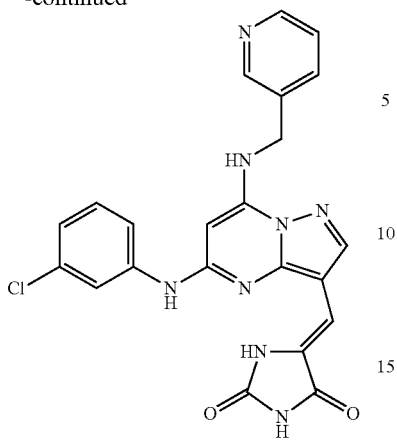
Same procedure as [Example 70]. LCMS (M+1=461)
Example 72
Synthesis 5-((5-(3-chlorophenylamino)-7-(pyridin-4-ylmethylamino)pyrazolo[1,5-a]pyrimidin-3-yl)methylene)imidazolidine-2,4-dione
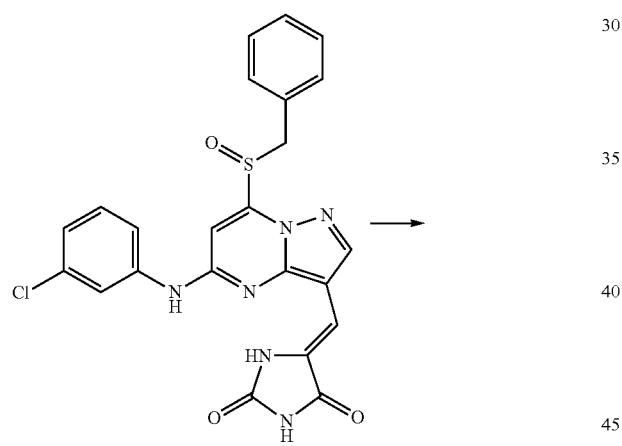
Same procedure as [Example 70]. LCMS (M+1=461)
Example 73
Synthesis 5-((5-(3-chlorophenylamino)-7-(2-(dimethylamino)ethyl amino)pyrazolo[1,5-a]pyrimidin-3-yl)methylene)imidazolidine-2,4-dione
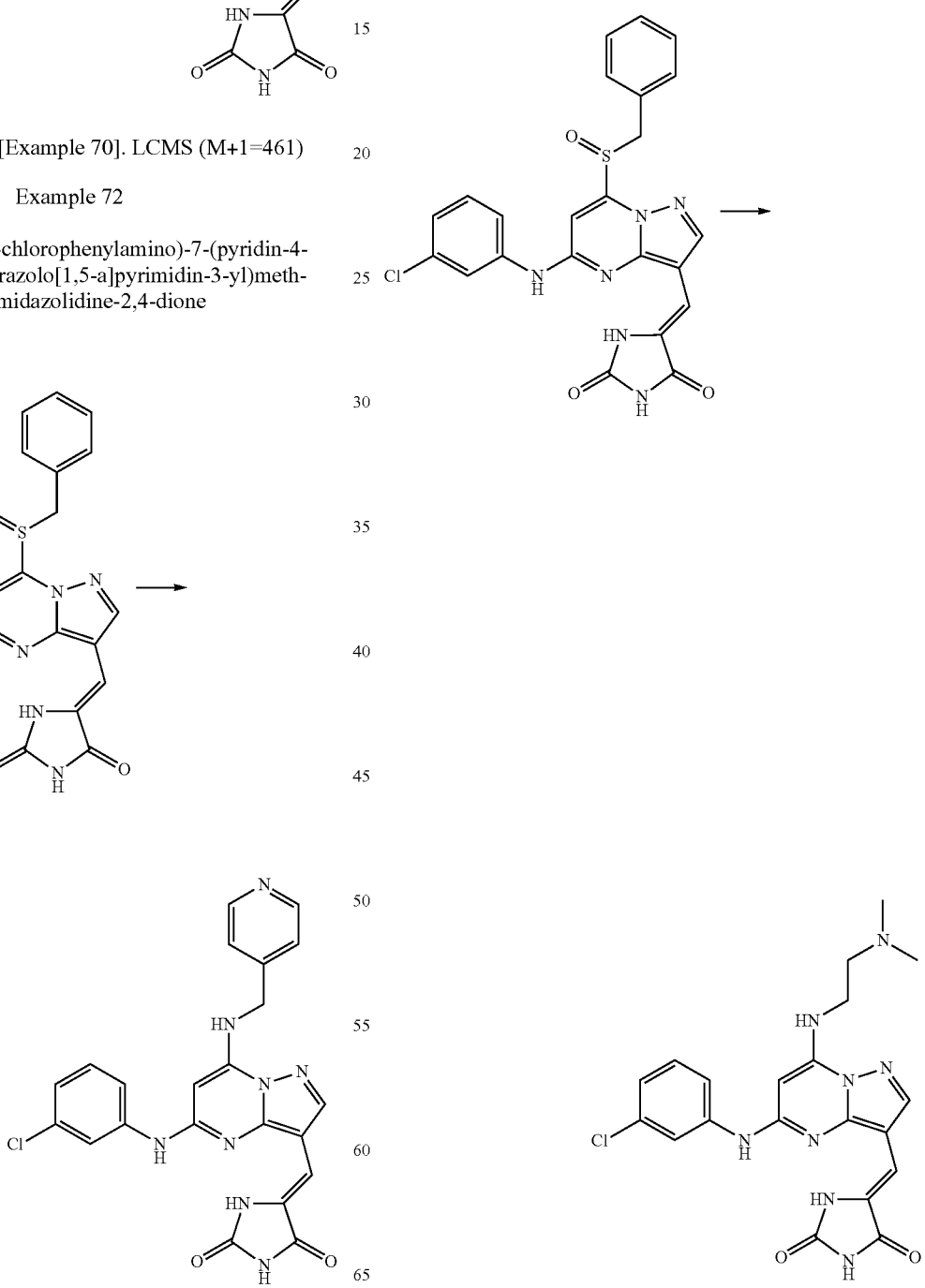

163
Same procedure as [Example 70]. LCMS (M+1=441)
Example 74
Synthesis of 5-((5-(3-chlorophenylamino)-7-(isopropyl amino)pyrazolo[1,5-a]pyrimidin-3-yl)methylene)imidazolidine-2,4-dione
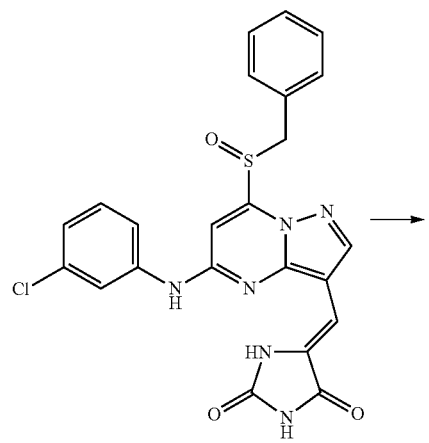
164
Same procedure as [Example 70]. LCMS (M+1=412)
Example 75
Synthesis of 5-((5(3-chlorophenylamino)-7-(2-hydroxy propylamino)pyrazolo[1,5-a]pyrimidin-3-yl)methylene)imidazolidine-2,4-dione
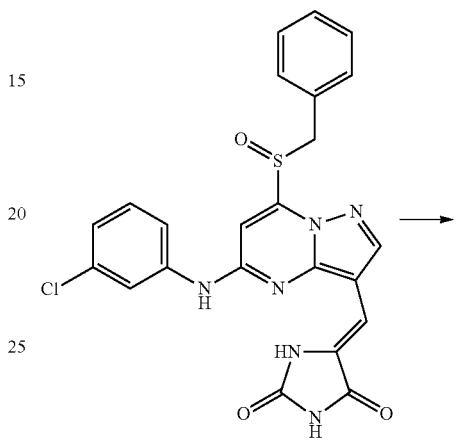
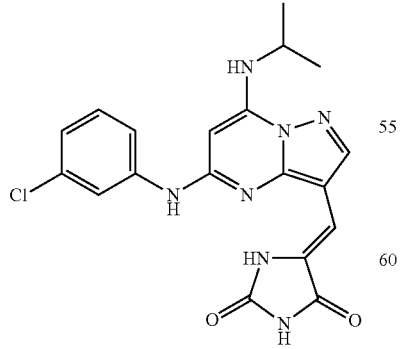
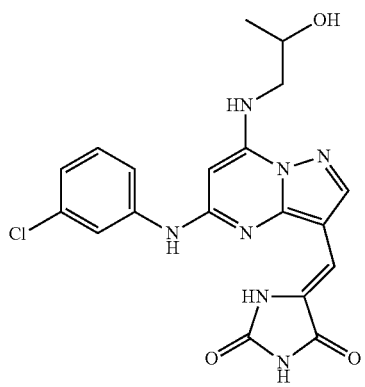

165
Same procedure as [Example 70]. LCMS (M+1=428)
Example 76
Synthesis of 5-((5-(3-chlorophenylamino)-7-(cyclobutyl amino)pyrazolo[1,5-a]pyrimidin-3-yl)methylene)imidazolidine-2,4-dione
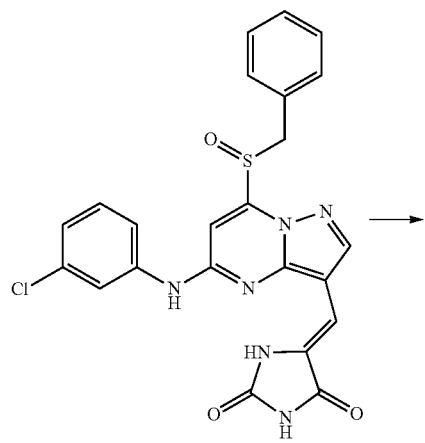
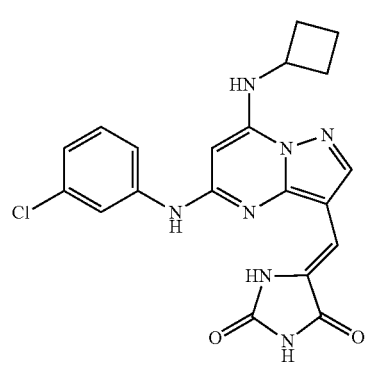
166
Same procedure as [Example 70]. LCMS (M+1=424)
Example 77
Synthesis of 5-((5-(3-chlorophenylamino)-7-(2-morpholinoethyl amino)pyrazolo[1,5-a]pyrimidin-3-yl)methylene)imidazolidine-2,4-dione
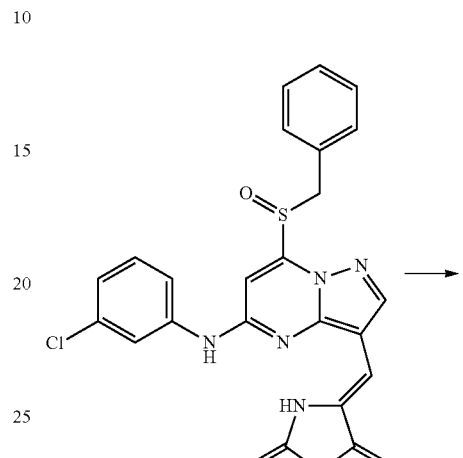
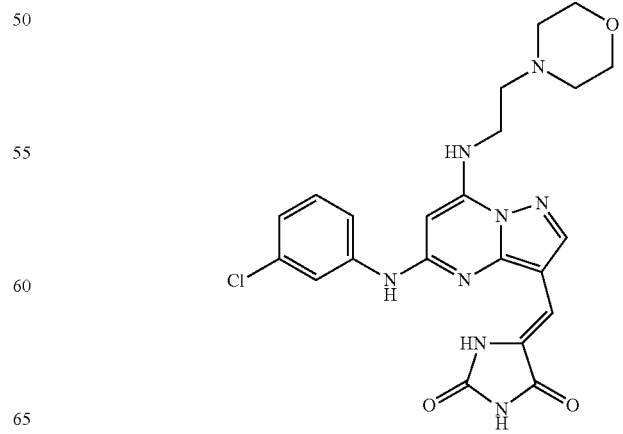

167
Same procedure as [Example 70]. LCMS (M+1=483)
Example 78
Synthesis 5-((5-(3-chlorophenylamino)-7-(pyridin-2-ylmethyl amino)pyrazolo[1,5-a]pyrimidin-3-yl)methylene)imidazolidine-2,4-dione
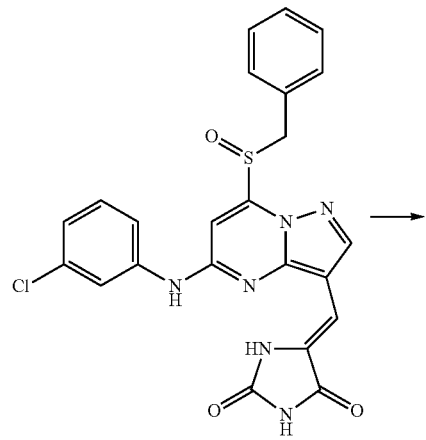
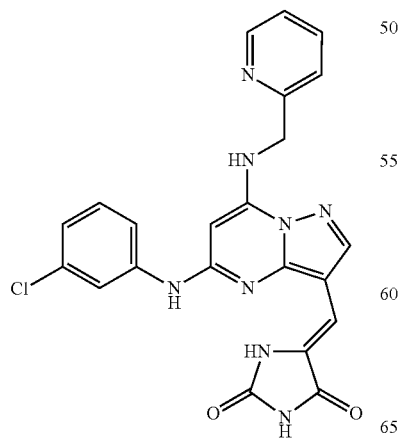
168
Same procedure as [Example 70]. LCMS (M+1=461)
Example 79
Synthesis of 5-((5-(3-chlorophenylamino)-7-(3-(dimethylamino)-2,2-dimethylpropylamino)pyrazolo[1,5-a]pyrimidin-3-yl)methylene)imidazolidine-2,4-dione
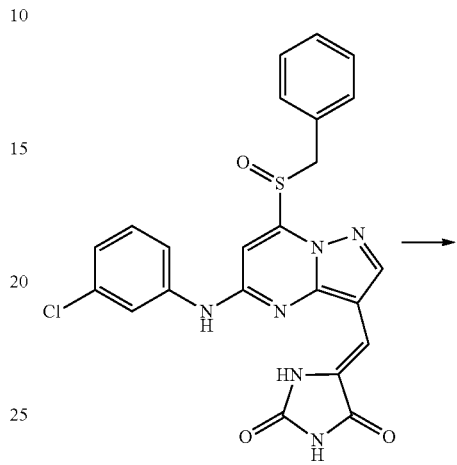
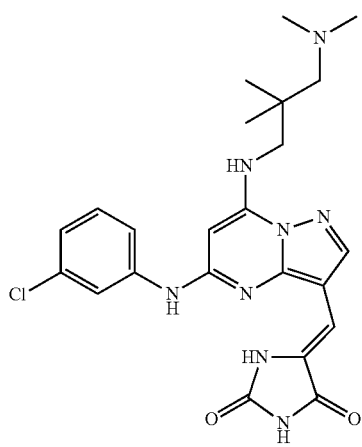

169

Same procedure as [Example 70]. LCMS (M+1=483)

Example 80

Synthesis tert-butyl 2-((5-(3-chlorophenylamino)-3-((2,5-dioxoimidazolidin-4-ylidene)methyl)pyrazolo[1,5-a]pyrimidin-7-ylamino)methyl)pyrrolidine-1-carboxylate

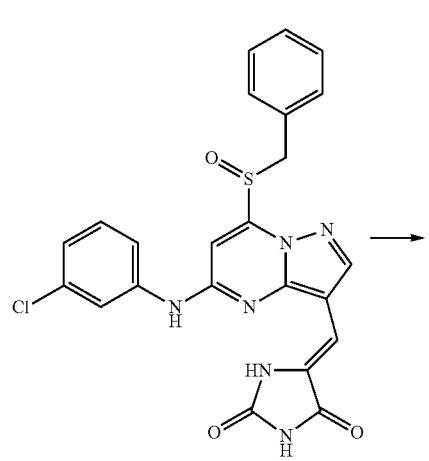

170

Same procedure as [Example 70]. LCMS (M+1=553)

Example 81

Synthesis of tert-butyl 4-((5-(3-chlorophenylamino)-3-(2,5-dioxoimidazolidin-4-ylidene)methyl)pyrazolo[1,5-a]pyrimidin-7-ylamino)methyl)piperidine-1-carboxylate

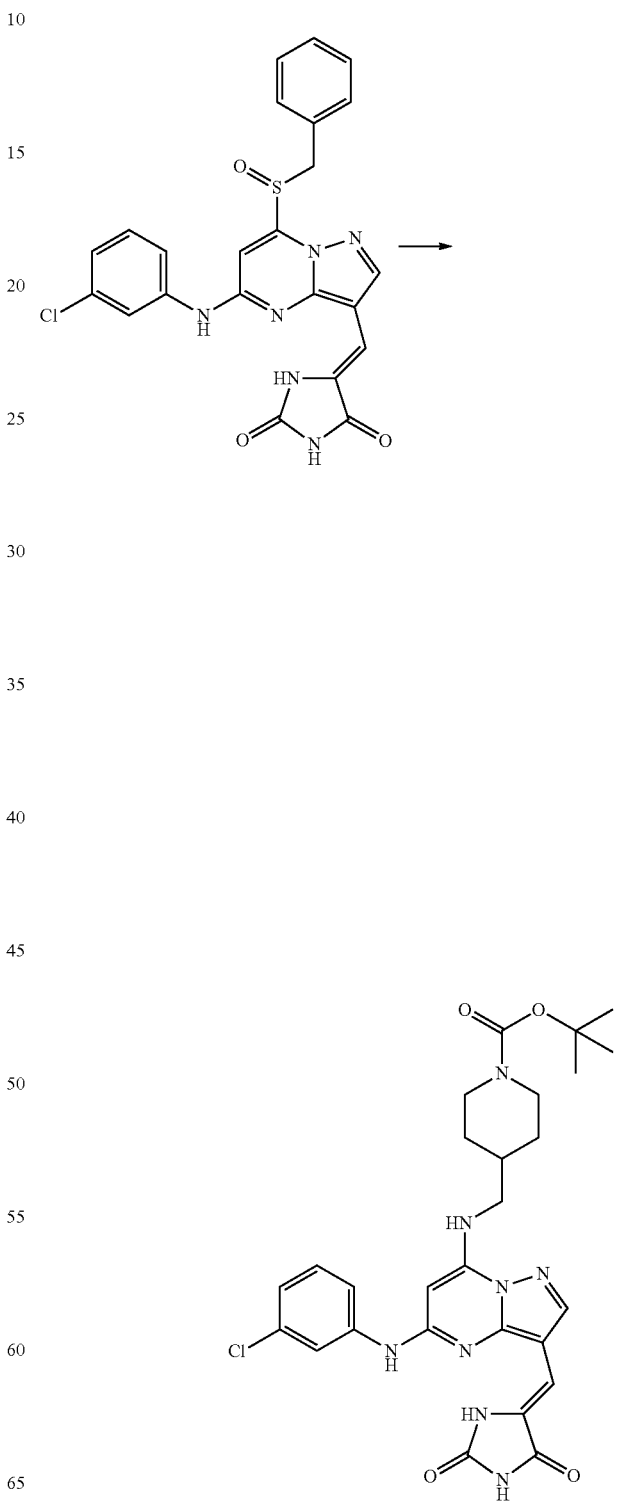

171
Same procedure as [Example 70]. LCMS (M+1-568)
Example 82
Synthesis of 5-((5-(3-chlorophenylamino)-7-(2,2,2-trifluoroethyl amino)pyrazolo[1,5-a]pyrimidin-3-yl)methylene)imidazolidine-2,4-dione
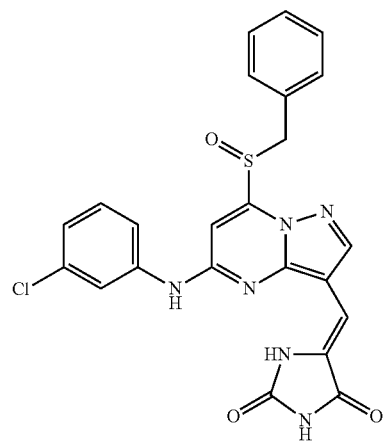
172
Same procedure as [Example 70]. LCMS (M+1=452)
Example 83
Synthesis of 5-((7-(1H-pyrazol-3-ylamino)-5-(3-chlorophenyl amino)pyrazolo[1,5-a]pyrimidin-3-yl)methylene)imidazolidine-2,4-dione
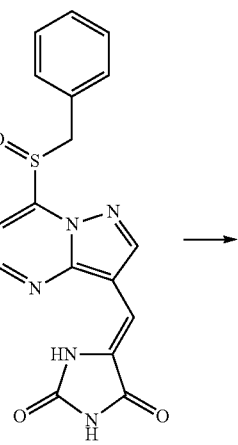
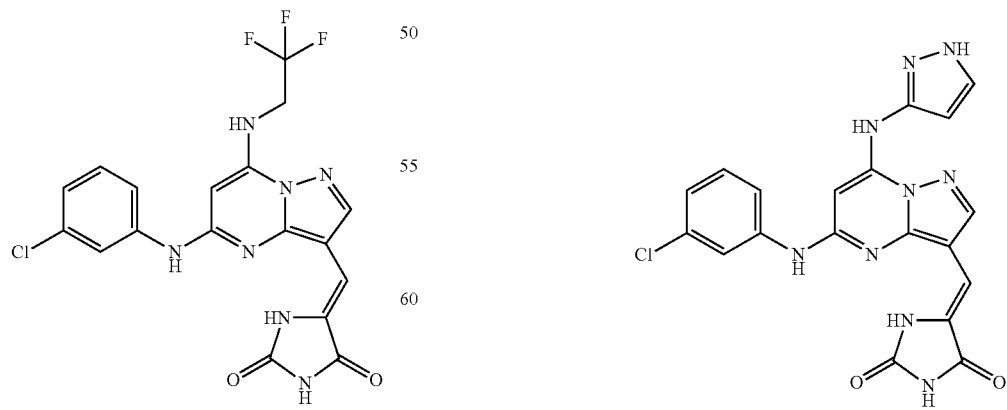

Same procedure as [Example 70]. LCMS (M+1=436)

Example 84

Synthesis 5-((5-(3-chlorophenylamino)-7-(pyrrolidin-3-yl amino)pyrazolo[1,5-a]pyrimidin-3-yl)methylene)imidazolidine-2,4-dione

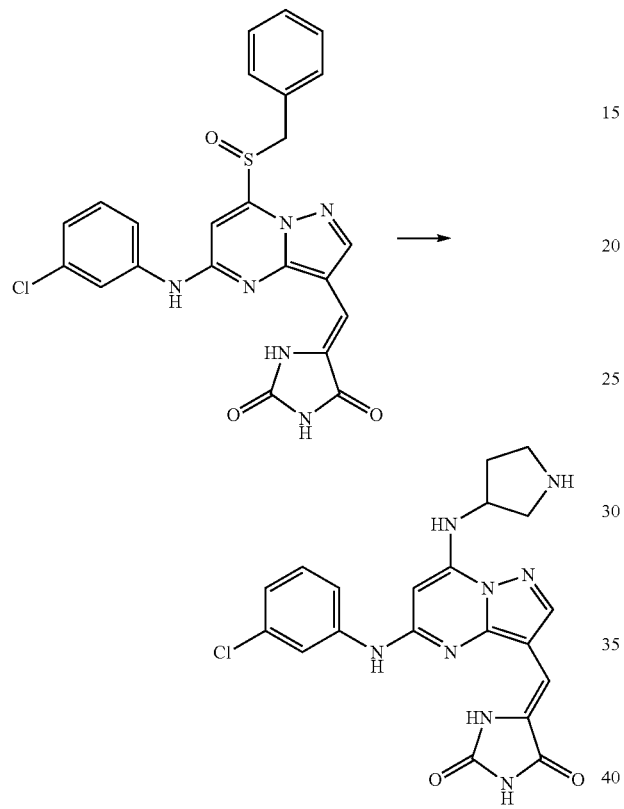

Same procedure as Example 70. LCMS (M+1=439)

The compounds described in the following table were prepared using chemistries similar to those exemplified in Example 70. All compounds were characterized by LCMS.

Table 19B shows the biological activities of the compounds listed in Table 19A.

TABLE 19A

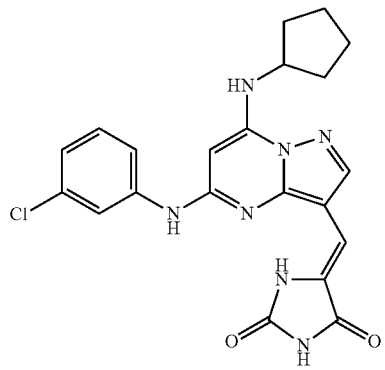 [SMILES: O=C1NC(=O)/C(=C/c2cnn3c(NC4CCCC4)cc(Nc4cccc(Cl)c4)nc23)N1]

TABLE 19A-continued

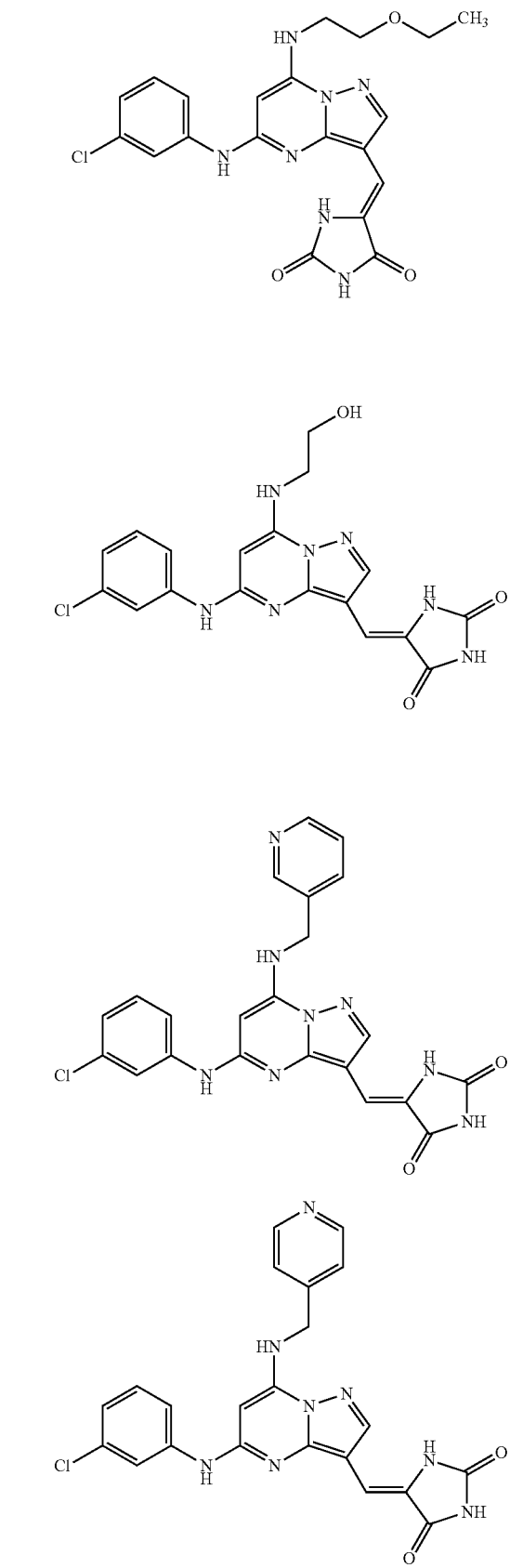

TABLE 19A-continued
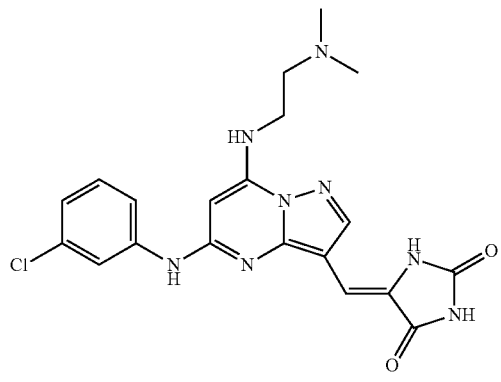 [SMILES: CN(C)CCNc1cc(Nc2cccc(Cl)c2)nc2c(/C=C3\NC(=O)NC3=O)cnn12]
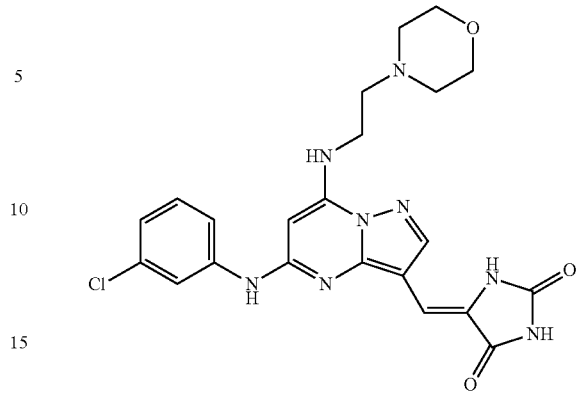
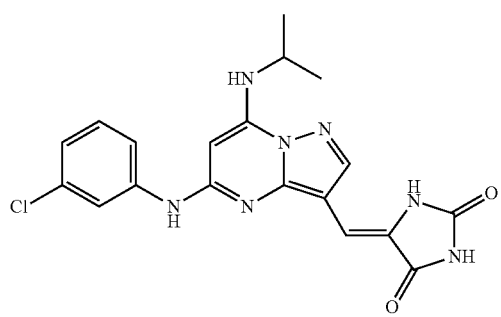 [SMILES: CC(C)Nc1cc(Nc2cccc(Cl)c2)nc2c(/C=C3\NC(=O)NC3=O)cnn12]
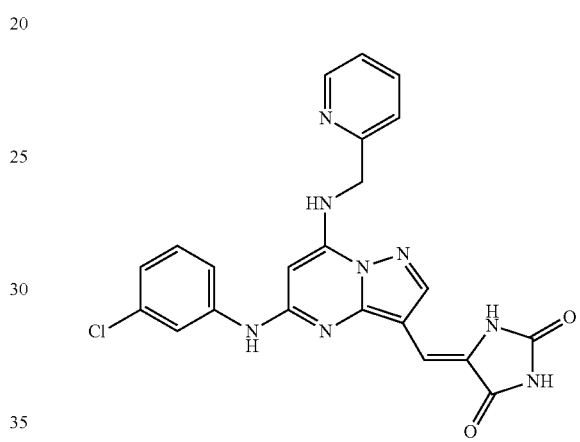
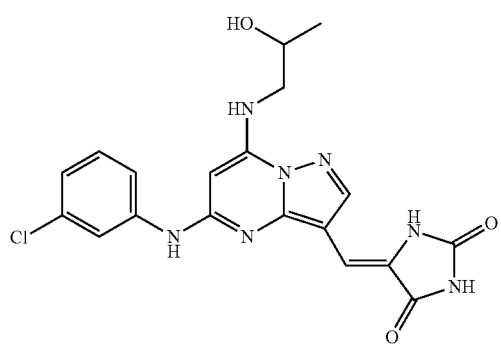 [SMILES: CC(O)CNc1cc(Nc2cccc(Cl)c2)nc2c(/C=C3\NC(=O)NC3=O)cnn12]
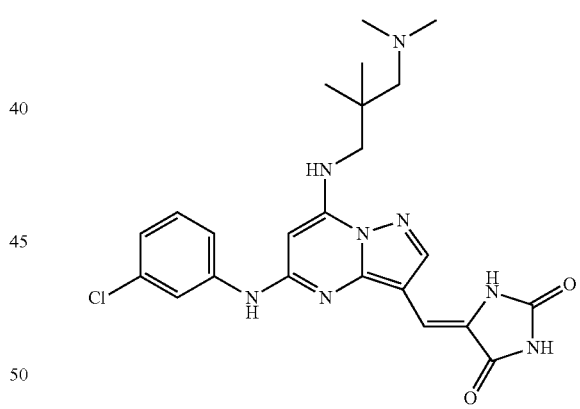
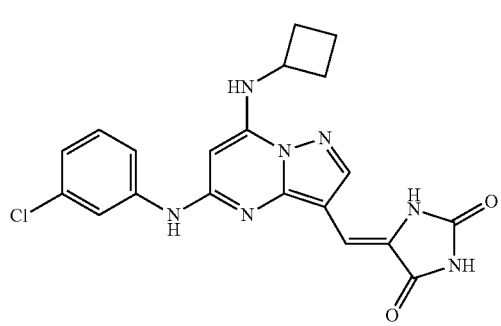 [SMILES: O=C1NC(=O)/C(=C/c2cnn3c(NC4CCC4)cc(Nc4cccc(Cl)c4)nc23)N1]
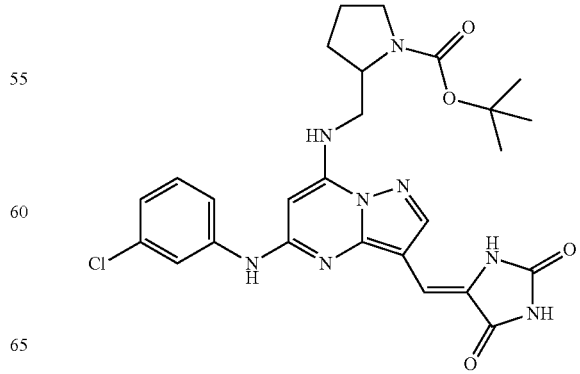

TABLE 19A-continued
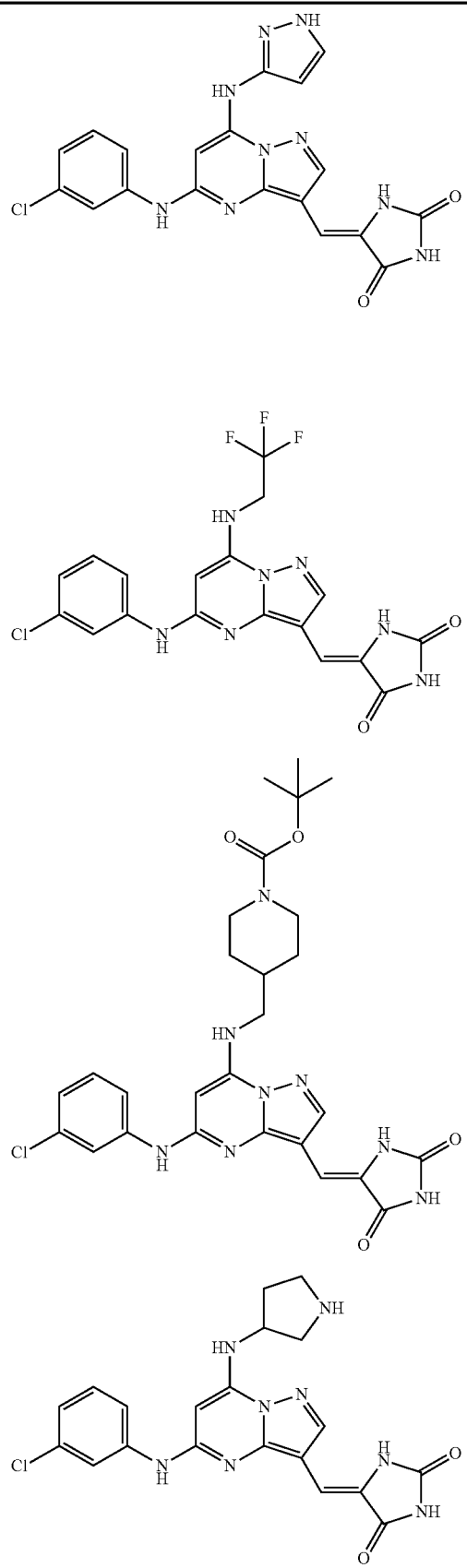
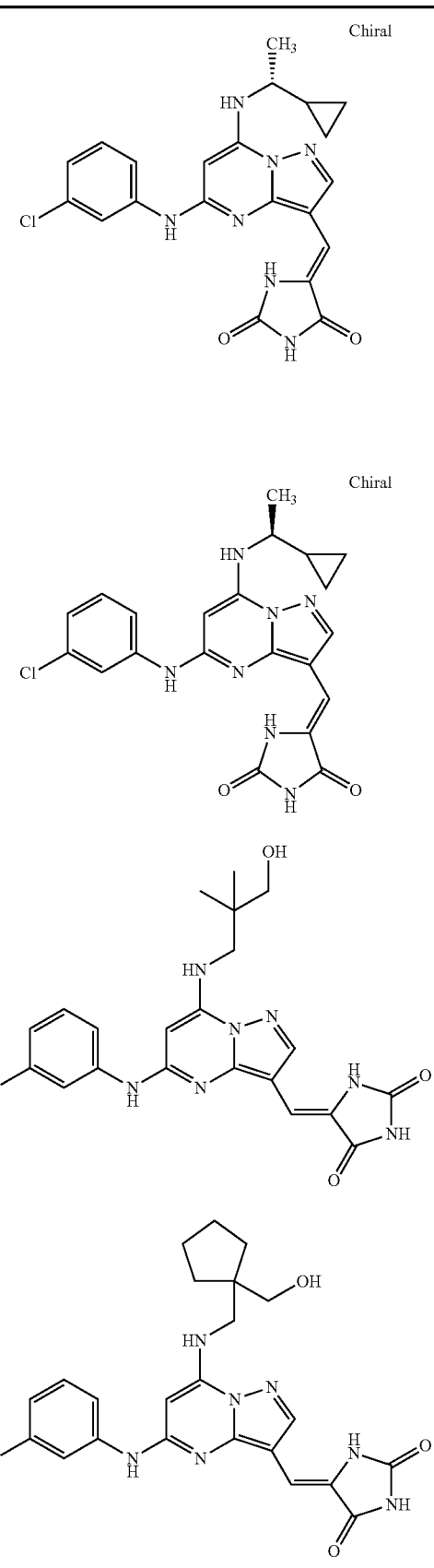

TABLE 19A-continued
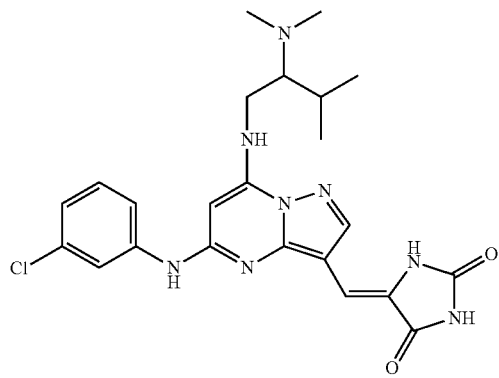 [SMILES: CC(C)C(CNc1cc(Nc2cccc(Cl)c2)nc2c(/C=C3\NC(=O)NC3=O)cnn12)N(C)C]
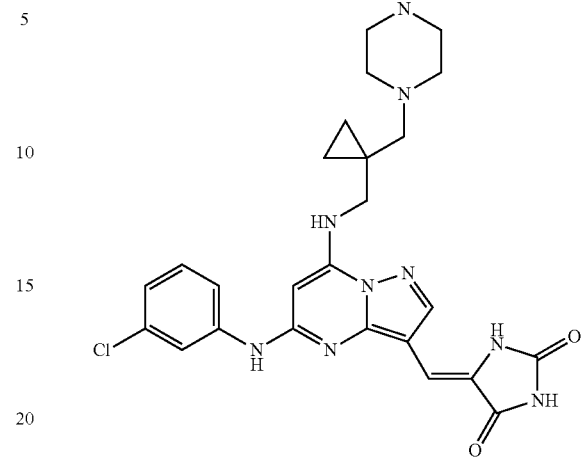
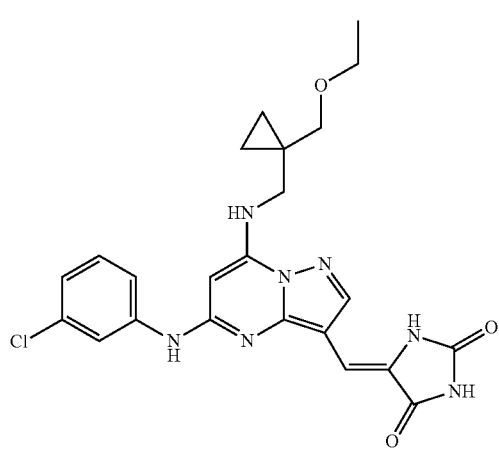 [SMILES: CCOCC1(CNc2cc(Nc3cccc(Cl)c3)nc3c(/C=C4\NC(=O)NC4=O)cnn23)CC1]
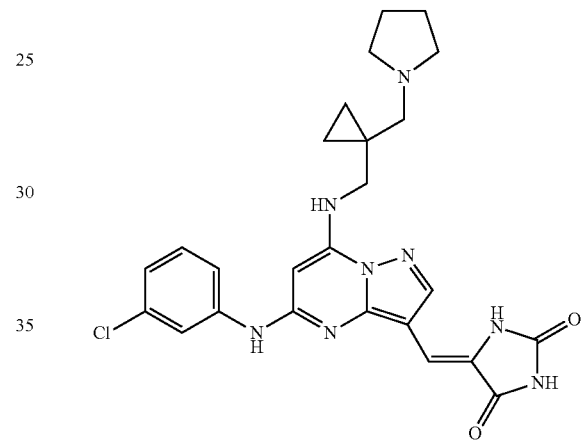
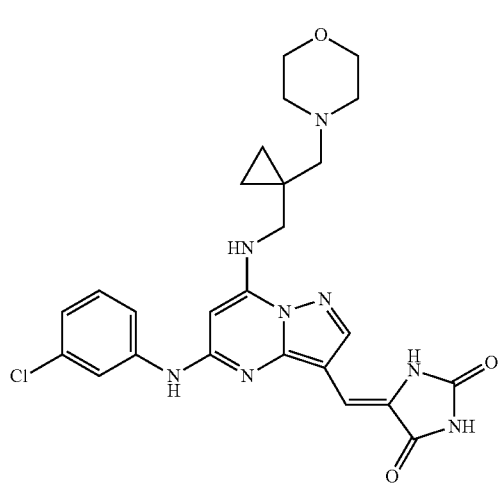 [SMILES: O=C1NC(=O)/C(=C/c2cnn3c(NCC4(CN5CCOCC5)CC4)cc(Nc4cccc(Cl)c4)nc23)N1]
TABLE 19B
| Compound | CK2: IC50 (μM) | PIM2: IC50 (5 μM ATP) | AB: MDAMB453 (μM) | AB: BxPC3 (μM) |
|---|---|---|---|---|
| B6 | <1.0 | 0.3426 | 10.519 | >30 |
| C6 | <1.0 | 0.469 | 1.144 | 3.803 |
| D6 | <1.0 | 0.4747 | 0.717 | 1.923 |
| E6 | <1.0 | 1.3345 | | |
| F6 | <0.1 | >2.5000 | | |
| G6 | <1.0 | >2.5000 | | |
| H6 | <1.0 | 0.4211 | | |
| I6 | <1.0 | 0.7041 | 0.708 | 2.559 |
| J6 | <1.0 | >2.5000 | | |
| K6 | <1.0 | 0.3165 | 0.936 | 3.159 |
| L6 | <2.0 | 2.1905 | | |
| M6 | <1.0 | >2.5000 | | |
| N6 | <0.1 | >2.5000 | | |
| O6 | <0.01 | >2.5000 | 1.145 | >30 |
| P6 | <1.0 | 0.7008 | 0.569 | 1.618 |
| Q6 | <1.0 | 1.2876 | | |
| R6 | <1.0 | 1.1213 | | |
| S6 | <0.1 | | | |
| T6 | <0.1 | | | |
| U6 | <1.0 | 0.5149 | | |
| V6 | <0.1 | | | |
| W6 | <1.0 | | | |
| X6 | <1.0 | | | |
| Y6 | <0.1 | | | |

TABLE 19B-continued

| Compound | CK2: IC50 (μM) | PIM2: IC50 (5 μM ATP) | AB: MDAMB453 (μM) | AB: BxPC3 (μM) |
|---|---|---|---|---|
| Z6 | <0.1 | | | |
| A7 | <0.1 | | | |

Example 85

Synthesis of tert-butyl 3-(5-chloropyrazolo[1,5-a]pyrimidin-7-ylamino)benzoate

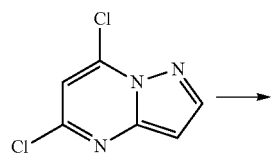

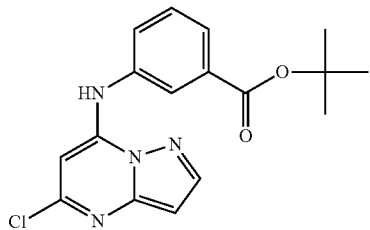

To the reaction flask, 5,7-dichloropyrazolo[1,5-a]pyrimidine (1.6 g, 8.2 mmol) was added along with tert-butyl 3-aminobenzoate (1.7 g, 8.7 mmol), triethylamine (1.2 mL, 8.6 mmol), and t-butyl alcohol (22 mL). The reaction was heated at 100° C. for 6 hours then diluted with water, filtered and washed with water. The product, tert-butyl 3-(5-chloropyrazolo[1,5-a]pyrimidin-7-ylamino)benzoate, was collected as a solid in quantitative yield after drying under vacuum overnight. LCMS (M+1=345)

Example 86

Synthesis of tert-butyl 3-(5-(3-chlorophenylamino)pyrazolo[1,5-a]pyrimidin-7-ylamino)benzoate

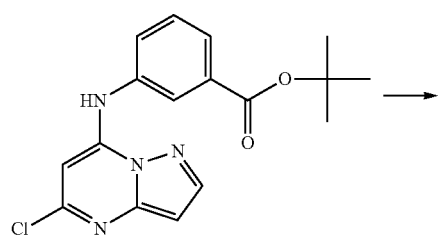

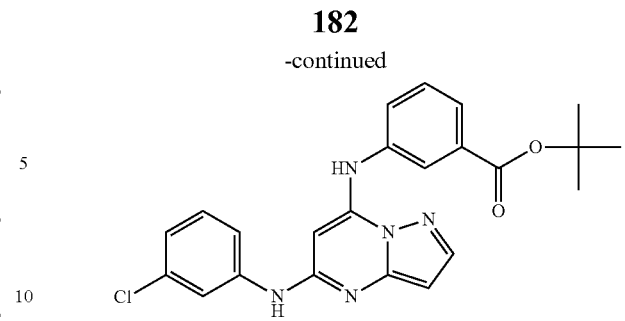

To the reaction flask, tert-butyl 3-(5-chloropyrazolo[1,5-a]pyrimidin-7-ylamino)benzoate (2.9 g, 8.2 mmol) was added along with 3-chloroaniline (2.2 mL, 20.6 mmol), 4N HCl in dioxane (2.6 mL, 10.4 mmol), and t-butyl alcohol (41 mL). The reaction was stirred at 100° C. for 2 days then cooled to room temperature. The mixture was diluted with water, made basic with 3N NaOH, filtered and washed with water. The product, tert-butyl 3-(5-(3-chlorophenylamino)pyrazolo[1,5-a]pyrimidin-7-ylamino)benzoate, was collected as a solid in 55% yield after drying under vacuum overnight. LCMS (M+1=436)

Example 87

Synthesis of tert-butyl 3-(5-(3-chlorophenylamino)-3-formylpyrazolo[1,5-a]pyrimidin-7-ylamino)benzoate

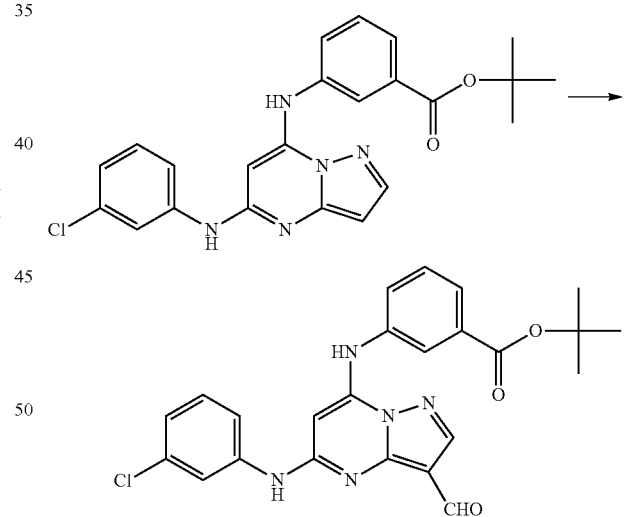

To tert-butyl 3-(5-(3-chlorophenylamino)pyrazolo[1,5-a]pyrimidin-7-ylamino)benzoate (965 mg, 2.2 mmol) in DMF (8.2 mL), POCl$_3$ (1.2 mL, 13.3 mmol) was added dropwise at room temperature. After the addition was complete, the reaction was stirred for 3 days at room temperature. Then, the reaction was quenched by slow addition to ice cold 6N NaOH. The mixture was diluted with water and the solid was collected by filtration. The solid was washed several more times with water then dried under vacuum overnight. The product, tert-butyl 3-(5-(3-chlorophenylamino)-3-formylpyrazolo[1,5-a]pyrimidin-7-ylamino)benzoate, was collected as a solid in 12% yield after purification by column chromatography on silica using 5% acetone/dichloromethane as the eluent. LCMS (M+1=464)

Example 88

Synthesis of tert-butyl 3-(5-(3-chlorophenylamino)-3-((2,5-dioxoimidazolidin-4-ylidene)methyl)pyrazolo[1,5-a]pyrimidin-7-ylamino)benzoate

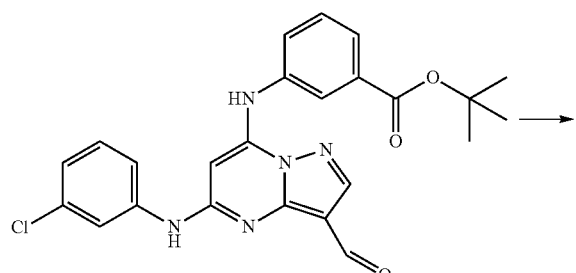

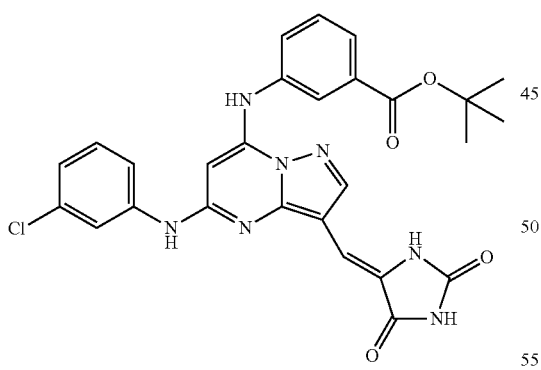

To the reaction flask, tert-butyl 3-(5-(3-chlorophenylamino)-3-formylpyrazolo[1,5-a]pyrimidin-7-ylamino)benzoate (122 mg, 0.3 mmol) was added to ethanol (1.3 mL) along with hydantoin (26 mg, 0.3 mmol) and piperidine (26 µL, 0.3 mmol). The reaction was heated at 80° C. for 2 hours in the microwave then cooled to room temperature and diluted with water. The solid was collected by filtration, washed with water, 50% ethanol/water, and then 100% ethanol. The material was dried under vacuum overnight. The product, tert-butyl 3-(5-(3-chlorophenylamino)-3-((2,5-dioxoimidazolidin-4-ylidene)methyl)pyrazolo[1,5-a]pyrimidin-7-ylamino)benzoate, was recovered as a solid in 69% yield. LCMS (M+1=546)

Example 89

Synthesis of 3-(5-(3-chlorophenylamino)-3-(2,5-dioxoimidazolidin-4-ylidene)methyl)pyrazolo[1,5-a]pyrimidin-7-ylamino)benzoic acid

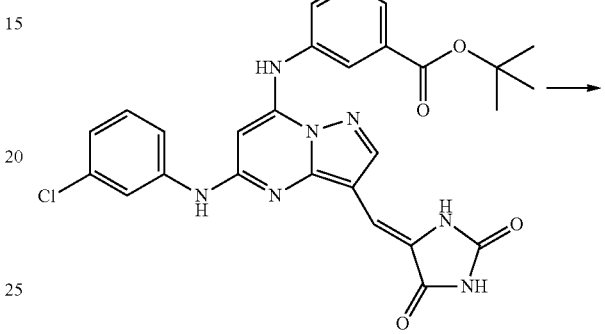

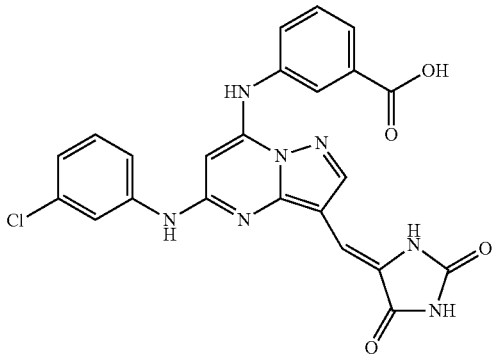

Tert-butyl 3-(5-(3-chlorophenylamino)-3-((2,5-dioxoimidazolidin-4-ylidene)methyl)pyrazolo[1,5-a]pyrimidin-7-ylamino)benzoate (97 mg, 0.2 mmol) was dissolved in 2 mL of TFA/DCM (1:1) and stirred at room temperature for 1 hour. Excess solvent and TFA were removed by evaporation under a stream of nitrogen. The residue was diluted with water then the mixture was filtered. The product, 3-(5-(3-chlorophenylamino)-3-((2,5-dioxoimidazolidin-4-ylidene)methyl)pyrazolo[1,5-a]pyrimidin-7-ylamino)benzoic acid, was collected as a solid in 85% yield. LCMS (M+1=490)

Example 90

Synthesis of tert-butyl 4-(3-(5-(3-chlorophenylamino)-3-((2,5-dioxoimidazolidin-4-ylidene)methyl)pyrazolo[1,5-a]pyrimidin-7-ylamino)benzoyl)piperazine-1-carboxylate

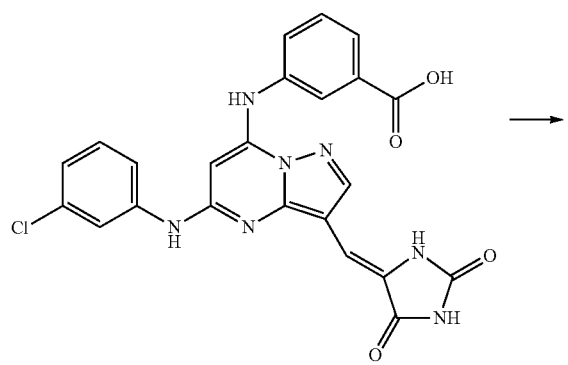

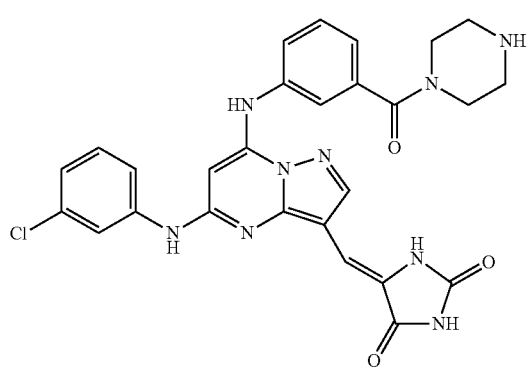

To the reaction flask, 3-(5-(3-chlorophenylamino)-3-((2,5-dioxoimidazolidin-4-ylidene)methyl)pyrazolo[1,5-a]pyrimidin-7-ylamino)benzoic acid (30 mg, 0.06 mmol) was added to DMF (0.5 mL) along with HOBt (9.2 mg, 0.06 mmol), triethylamine (8.4 µL, 0.06 mmol) and tert-butyl piperazine-1-carboxylate (11.2 mg, 0.06 mmol). The reaction mixture was stirred at room temperature for 5 minutes then EDC (11.5 mg, 0.06 mmol) was added. The reaction was allowed to stir for an additional hour then diluted with water and filtered. The recovered solid was washed with more water followed by ethanol. The product, tert-butyl 4-(3-(5-(3-chlorophenylamino)-3-((2,5-dioxoimidazolidin-4-ylidene)methyl)pyrazolo[1,5-a]pyrimidin-7-ylamino)benzoyl)piperazine-1-carboxylate, was collected as a solid in 73% yield. LCMS (M+1=658)

Example 91

Synthesis of 5-((5-(3-chlorophenylamino)-7-(3-(piperazine-1-carbonyl)phenylamino)pyrazolo[1,5-a]pyrimidin-3-yl)methylene)imidazolidine-2,4-dione

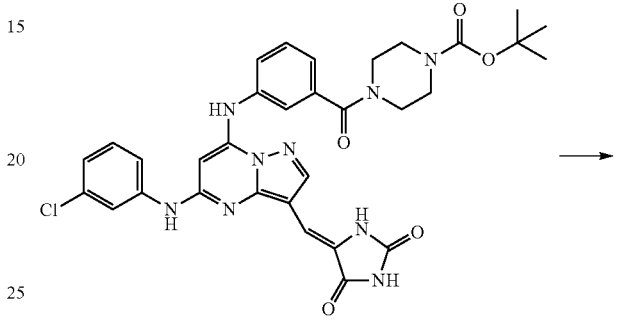

Tert-butyl 4-(3-(5-(3-chlorophenylamino)-3-((2,5-dioxoimidazolidin-4-ylidene)methyl)pyrazolo[1,5-a]pyrimidin-7-ylamino)benzoyl)piperazine-1-carboxylate (27 mg, 0.04 mmol) was dissolved in 2 mL of TFA/DCM (1:1) and stirred at room temperature for 1 hour. Excess solvent and TFA were removed by evaporation under a stream of nitrogen. The residue was diluted with water then the mixture was filtered. The recovered solid was washed with water followed by 50% ethanol. The product, 5-((5-(3-chlorophenylamino)-7-(3-(piperazine-1-carbonyl)phenylamino)pyrazolo[1,5-a]pyrimidin-3-yl)methylene)imidazolidine-2,4-dione, was collected as a solid in 21% yield. LCMS (M+1=558)

Example 92

Synthesis of 5-((5-(3-chlorophenylamino)-7-(3-(3-(dimethylamino)pyrrolidine-1-carbonyl)phenylamino)pyrazolo[1,5-a]pyrimidin-3-yl)methylene)imidazolidine-2,4-dione

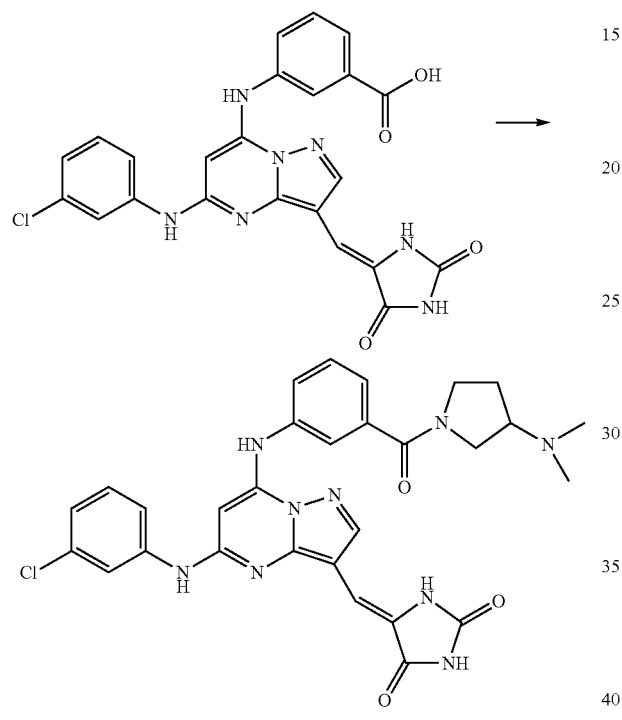

Same procedure as [Example 90]. LCMS (M+1=586)

The compounds described in the following table were prepared using chemistries similar to those exemplified in the Examples described above. All compounds were characterized by LCMS. Table 20B shows the biological activities of the compounds listed in Table 20A.

TABLE 20A

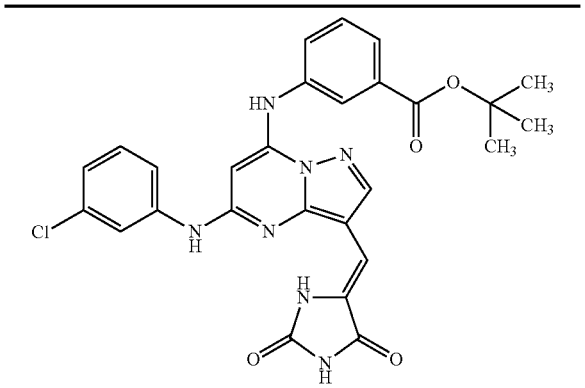

TABLE 20A-continued

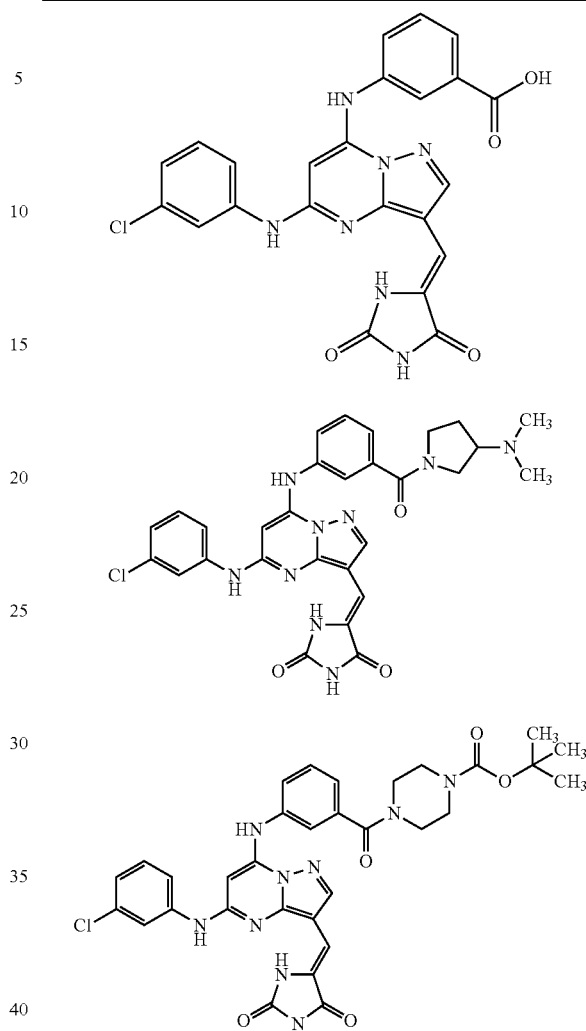

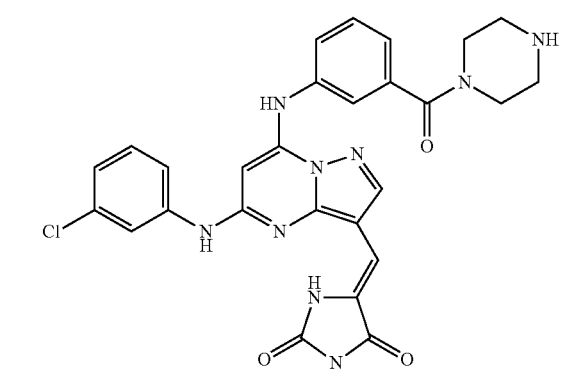

TABLE 20B

| Compound | CK2: IC50 (μM) | PIM2: IC50 (5 μM ATP) | AB: MDAMB453 (μM) | AB: BxPC3 (μM) |
|---|---|---|---|---|
| B7 | <0.01 | >2.5000 | 7.773 | 10.204 |
| C7 | <0.01 | 1.4446 | 6.435 | >30 |
| D7 | <0.1 | >2.5000 | 14.229 | >30 |

TABLE 20B-continued

| Compound | CK2: IC50 (µM) | PIM2: IC50 (5 µM ATP) | AB: MDAMB453 (µM) | AB: BxPC3 (µM) |
|---|---|---|---|---|
| E7 | <0.01 | 2.0193 | 0.364 | 3.006 |
| F7 | <0.01 | 1.2348 | 1.587 | 13.969 |

Example 93

Synthesis of 3-((7-chloropyrazolo[1,5-a]pyrimidin-5-yl)methyl)benzonitrile

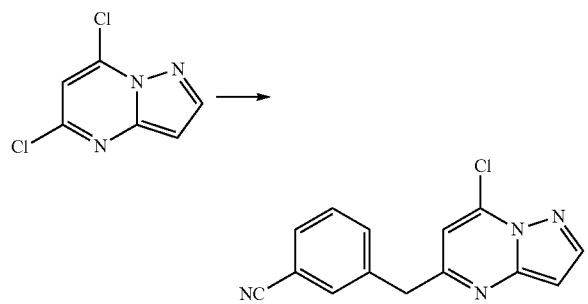

To the reaction flask, 5,7-dichloropyrazolo[1,5-a]pyrimidine (452 mg, 2.4 mmol) was added along with (3-cyanobenzyl)zinc(II) bromide (6 mL, 3.75 mmol, 0.625M in DMF), Pd(PPh$_3$)$_4$ (110 mg, 0.1 mmol), and DMF (10 mL). The reaction was heated at 60° C. for 4 hours then cooled to room temperature. The reaction mixture was poured into saturated aqueous NH$_4$Cl solution and ice and extracted with ethyl acetate. The combined extracts were washed with water, saturated NaCl solution, and then dried over Na$_2$SO$_4$. The solvent was removed in vacuo and the residue was purified by column chromatography on silica using 35% ethyl acetate/hexanes as the eluent. The product, 347-chloropyrazolo[1,5-a]pyrimidin-5-yl)methyl)benzonitrile, was recovered in 64% yield. LCMS (M+1=269)

Example 94

Synthesis of 3-((7-(cyclopropylamino)pyrazolo[1,5-a]pyrimidin-5-ylethyl)benzonitrile

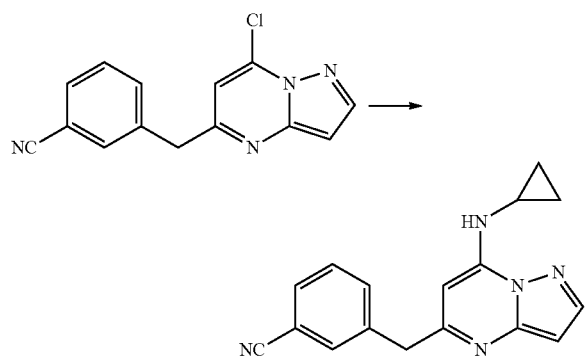

To the reaction flask, 3((7-chloropyrazolo[1,5-a]pyrimidin-5-yl)methyl)benzonitrile (400 mg, 1.5 mmol) was added along with cyclopropylamine (115 µL, 1.6 mmol), triethylamine (230 µL, 1.6 mmol), and acetonitrile (3 mL). The reaction was stirred at room temperature for 8 hours at 80° C. then cooled to room temperature, diluted with water, filtered and washed with water. The product, 3-((7-(cyclopropylamino)pyrazolo[1,5-a]pyrimidin-5-yl)methyl)benzonitrile, was collected as a solid in 83% yield after drying under vacuum overnight. LCMS (M+1=290)

Example 95

Synthesis of 3-((7-(cyclopropylamino)-3-formylpyrazolo[1,5-a]pyrimidin-5-yl)methyl)benzonitrile

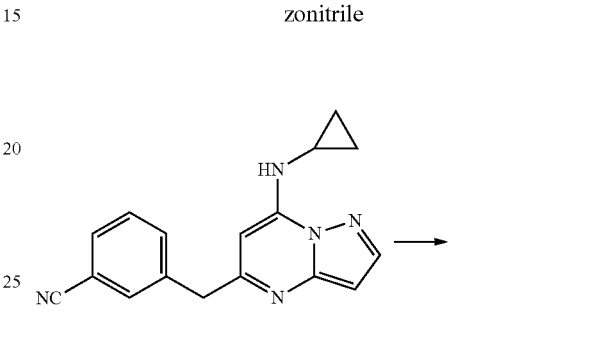

To 3-((7-(cyclopropylamino)pyrazolo[1,5-a]pyrimidin-5-yl)methyl)benzonitrile (69 mg, 0.24 mmol) in DMF (0.6 mL), POCl$_3$ (130 µL, 1.4 mmol) was added at room temperature. After the addition was complete, the reaction was stirred for 1 hour at room temperature. Then, the reaction was quenched by addition to ice cold 6N NaOH. The mixture was diluted with water and the solid was collected by filtration. The solid was washed several more times with water then dried under vacuum overnight. The product, 3-((7-(cyclopropylamino)-3-formylpyrazolo[1,5-a]pyrimidin-5-yl)methyl)benzonitrile, was collected as a solid in 37% yield. LCMS (M+1=318)

Example 96

Synthesis of 3-((7-(cyclopropylamino)-3-(2,5-dioxoimidazolidin-4-ylidene)methyl)pyrazolo[1,5-a]pyrimidin-5-yl)methyl)benzonitrile

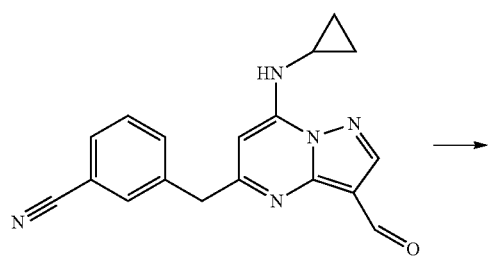

→

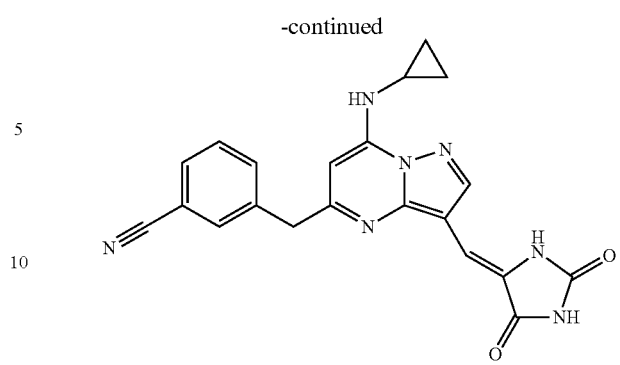

To the reaction flask, 3-((7-(cyclopropylamino)-3-formylpyrazolo[1,5-a]pyrimidin-5-yl)methyl)benzonitrile (28 mg, 0.09 mmol) was added to ethanol (0.5 mL) along with hydantoin (9 mg, 0.09 mmol) and piperidine (9 μL, 0.09 mmol). The reaction was heated at 80° C. for 30 minutes in the microwave then cooled to room temperature and diluted with water. The solid was collected by filtration, washed with water, 50% ethanol/water, and then 100% ethanol. The material was dried under vacuum overnight. The product, 3-((7-(cyclopropylamino)-3-((2,5-dioxoimidazolidin-4-ylidene)methyl)pyrazolo[1,5-a]pyrimidin-5-yl)methyl)benzonitrile, was recovered as a solid in 34% yield. LCMS (M+1=400)

TABLE 21

| Structure | LCMS m/z [M + 1]+ | CK2: IC50 (uM) | PIM2: IC50 (5 um ATP) | AB: MDAMB453 (uM) | AB: BxPC3 (uM) |
| --- | --- | --- | --- | --- | --- |
| 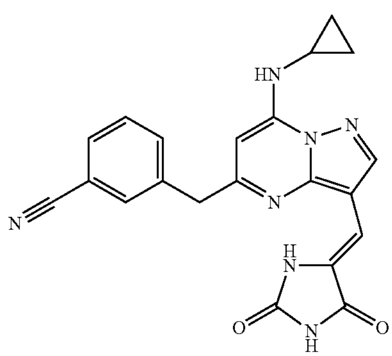 [SMILES: N#Cc1cccc(Cc2cc(NC3CC3)n3ncc(/C=C4\NC(=O)NC4=O)c3n2)c1] | 400 | <0.01 | >2.5000 | >30 | 19.66 |

Example 97

Synthesis of tert-butyl cyclopropyl(3-formyl-5-(3-hydroxyphenyl)pyrazolo[1,5-a]pyrimidin-7-yl)carbamate

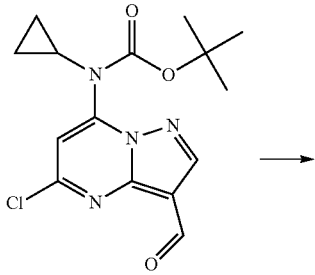

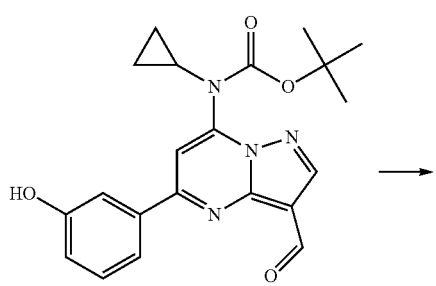

To tert-butyl 5-chloro-3-formylpyrazolo[1,5-a]pyrimidin-7-yl (cyclopropyl)carbamate (650 mg, 1.93 mmol) in 14 mL of a 2:1 mixture of 1,2-dimethoxyethane/EtOH was added 3-hydroxyphenyl boronic acid (399 mg, 2.89 mmol), tetrakis(triphenylphosphine)palladium(0) (112 mg, 0.096 mmol), and 2M aqueous solution of $Na_2CO_3$ (2.9 mL, 5.79 mmol). The mixture was stirred at 85° C. for 1 h. The volatiles were removed by rotary evaporation and the residue was purified by silica gel chromatography (0%-30% EtOAc/Hexanes) to provide 400 mg of tert-butyl cyclopropyl(3-formyl-5-(3-hydroxyphenyl)pyrazolo[1,5-a]pyrimidin-7-yl)carbamate. (52%). LCMS (M+1=395)

Example 98

Synthesis of 7-(cyclopropylamino)-5-(3-hydroxyphenyl)pyrazolo[1,5-a]pyrimidine-3-carbaldehyde

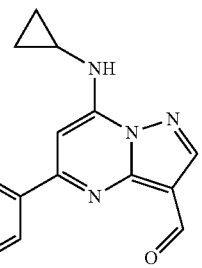

To tert-butyl cyclopropyl(3-formyl-5-(3-hydroxyphenyl)pyrazolo[1,5-a]pyrimidin-7-yl)carbamate (400 mg, 1.01 mmol) in methylene chloride (20 mL) was added TFA (10 mL). The reaction mixture was stirred at room temperature for 2 h. The volatiles were removed by rotary evaporation and the residue was purified by silica gel chromatography (0%-40% EtOAc/hexanes) to provide 103 mg of 7-(cyclopropylamino)-5-(3hydroxyphenyl)pyrazolo[1,5-a]pyrimidine-3-carbaldehyde. (35%). LCMS (M+1=295)

Example 99

Synthesis of 5((7-(cyclopropylamino)-5-(3-hydroxyphenyl)pyrazolo[1,5-a]pyrimidin-3-yl)methylene)imidazolidine-2,4-dione

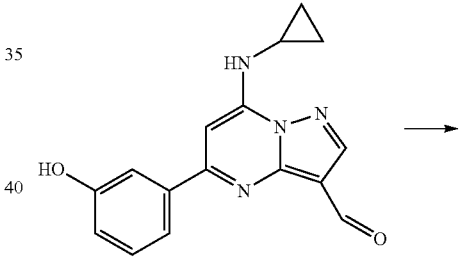

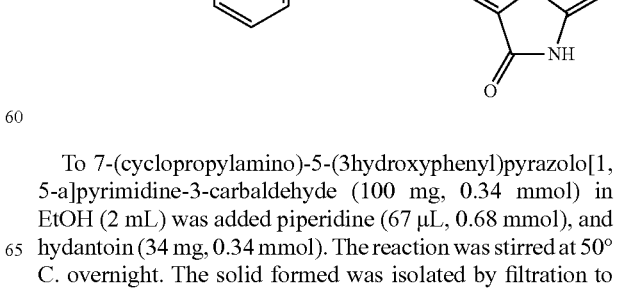

To 7-(cyclopropylamino)-5-(3hydroxyphenyl)pyrazolo[1,5-a]pyrimidine-3-carbaldehyde (100 mg, 0.34 mmol) in EtOH (2 mL) was added piperidine (67 μL, 0.68 mmol), and hydantoin (34 mg, 0.34 mmol). The reaction was stirred at 50° C. overnight. The solid formed was isolated by filtration to provide 70 mg of 5-((7-(cyclopropylamino)-5-(3-hydroxyphenyl)pyrazolo[1,5-a]pyrimidin-3-yl)methylene)imidazolidine-2,4-dione (55%). LCMS (M+1=377)

Example 100

Synthesis of tert-butyl cyclopropyl(3-formyl-5-(3-(trifluoromethoxy)phenyl)pyrazolo[1,5-a]pyrimidin-7-yl)carbamate

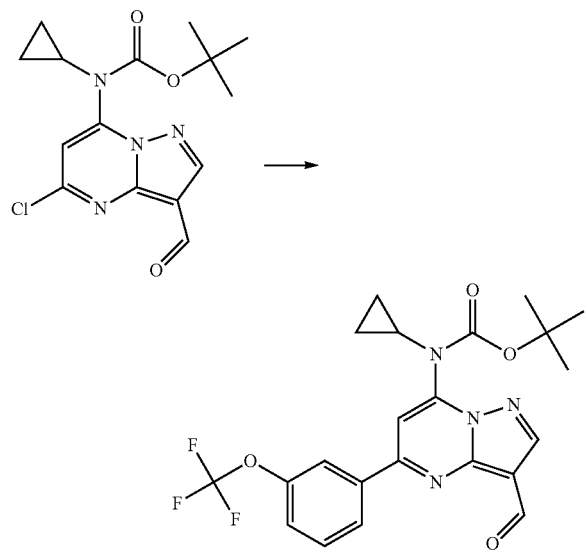

Same procedure as [Example 97]. LCMS (M+1=463)

Example 101

Synthesis of 7-(cyclopropylamino)-5-(3-(trifluoromethoxy)phenyl)pyrazolo[1,5-a]pyrimidine-3-carbaldehyde

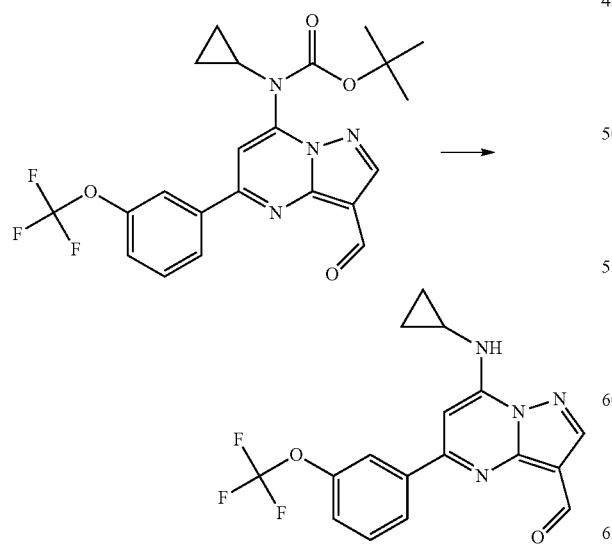

Same procedure as [Example 98]. LCMS (M+1=363)

Example 102

Synthesis of 5-((7-(cyclopropylamino)-5-(3-(trifluoromethoxy)phenyl)pyrazolo[1,5-a]pyrimidin-3-yl)methylene)imidazolidine-2,4-dione

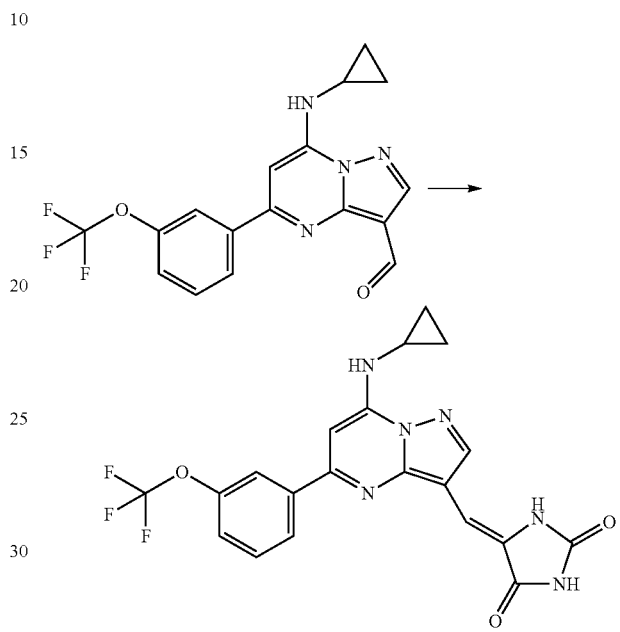

Same procedure as [Example 99]. LCMS (M+1=445)

Example 103

Synthesis of tert-butyl cyclopropyl(3-formyl-5-(3-(hydroxymethyl)phenyl)pyrazolo[1,5-a]pyrimidin-7-yl)carbamate

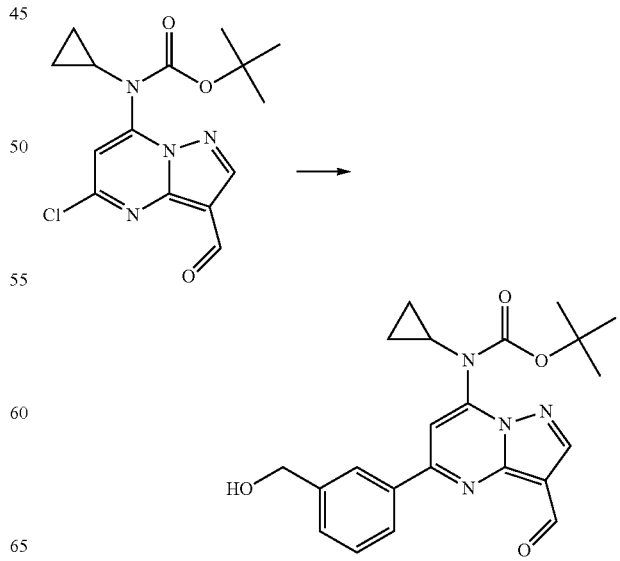

197

Same procedure as [Example 97]. LCMS (M+1=409)

Example 104

Synthesis of 7-(cyclopropylamino)-5-(3-(hydroxymethyl)phenyl)pyrazolo[1,5-a]pyrimidine-3-carbaldehyde

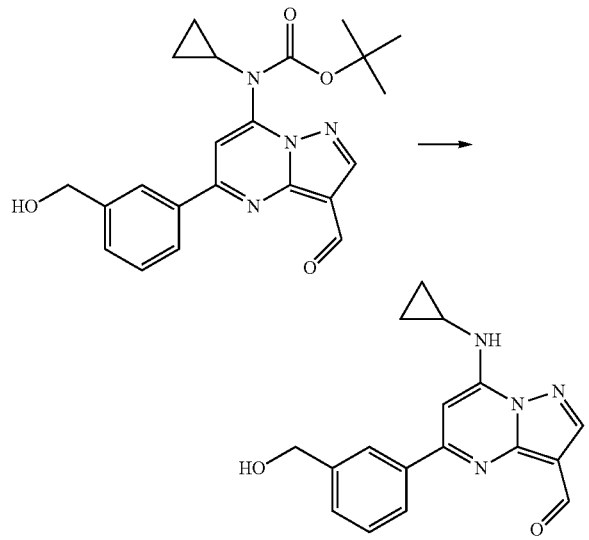

Same procedure as [Example 98]. LCMS (M+1=309)

Example 105

Synthesis of 5-((7-(cyclopropylamino)-5-(3-(hydroxymethyl)phenyl)pyrazolo[1,5-a]pyrimidin-3-yl)methylene)imidazolidine-2,4-dione

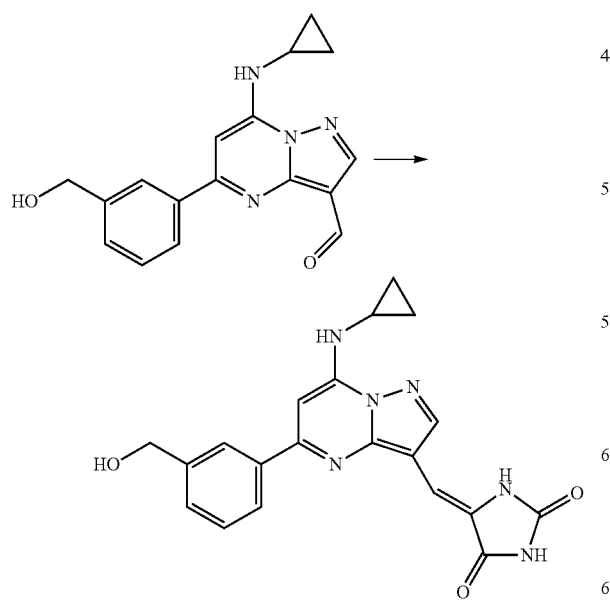

198

Same procedure as [Example 99]. LCMS (M+1=391)

Example 106

Synthesis of methyl 3-(7-(tert-butoxycarbonyl(cyclopropyl)amino)-3-formylpyrazolo[1,5-a]pyrimidin-5-yl)benzoate

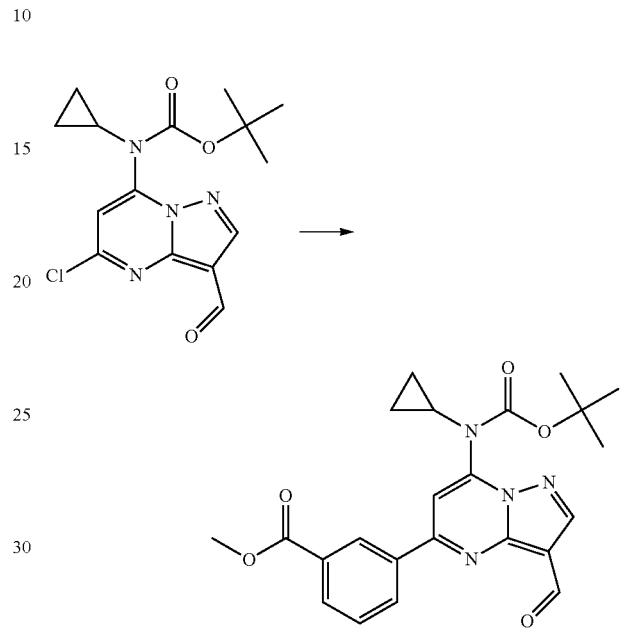

Same procedure as [Example 97]. LCMS (M+1=437)

Example 107

Synthesis of methyl 3-(7-(cyclopropylamino)-3-formylpyrazolo[1,5-a]pyrimidin-5-yl)benzoate

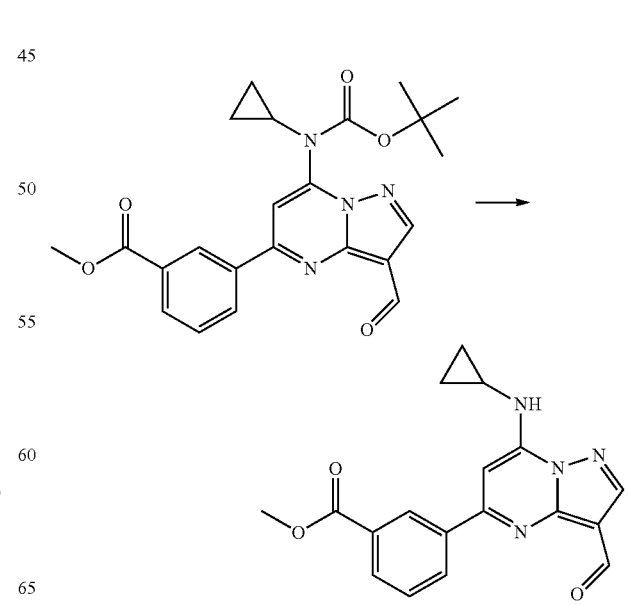

199

Same procedure as [Example 98]. LCMS (M+1=337)

Example 108

Synthesis of methyl 3-(7-(cyclopropylamino)-3-((2,5-dioxoimidazolidin-4-ylidene)methyl)pyrazolo[1,5-a]pyrimidin-5-yl)benzoate

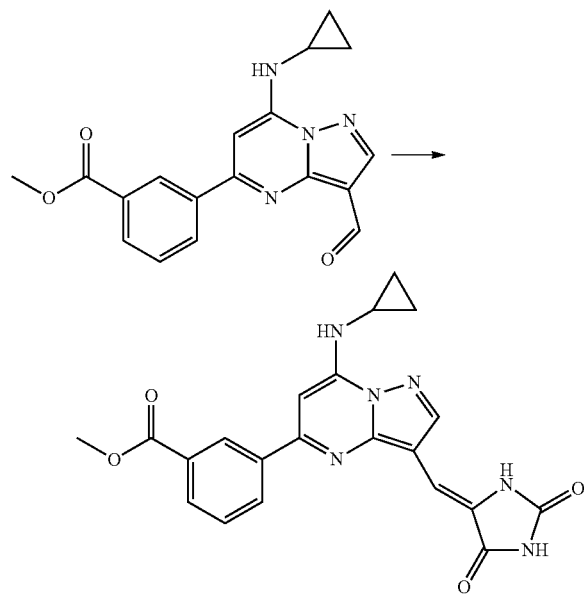

Same procedure as [Example 99]. LCMS (M+1=419)

Example 109

Synthesis of methyl tert-butyl cyclopropyl(3-formyl-5-(3-(methylsulfonyl)phenyl)pyrazolo[1,5-a]pyrimidin-7-yl)carbamate

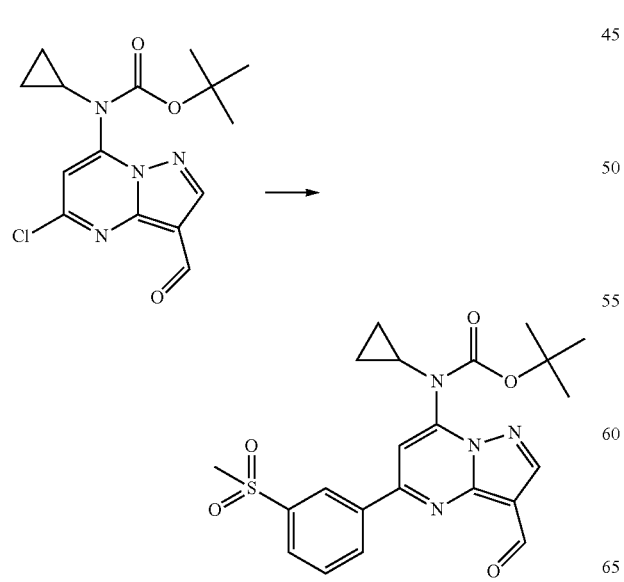

200

Same procedure as [Example 97]. LCMS (M+1=457)

Example 110

Synthesis of 7-(cyclopropylamino)-5-(3-(methylsulfonyl)phenyl)pyrazolo[1,5-a]pyrimidine-3-carbaldehyde

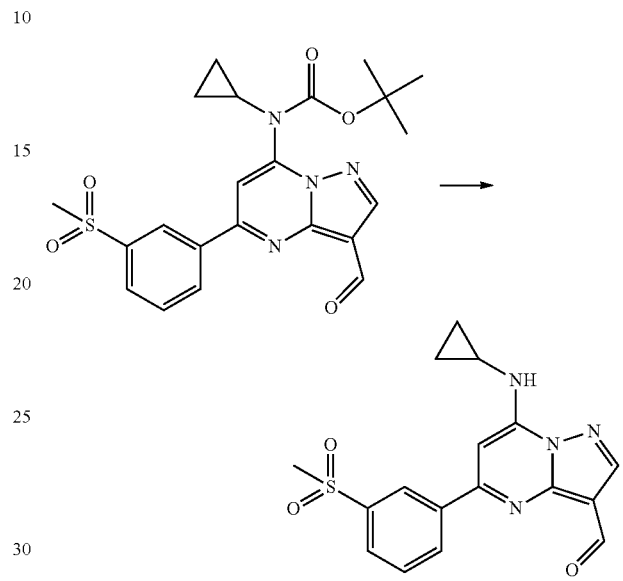

Same procedure as [Example 98]. LCMS (M+1=357)

Example 111

Synthesis of 5-((7-(cyclopropylamino)-5-(3-(methylsulfonyl)phenyl)pyrazolo[1,5-a]pyrimidin-3-yl)methylene)imidazolidine-2,4-dione

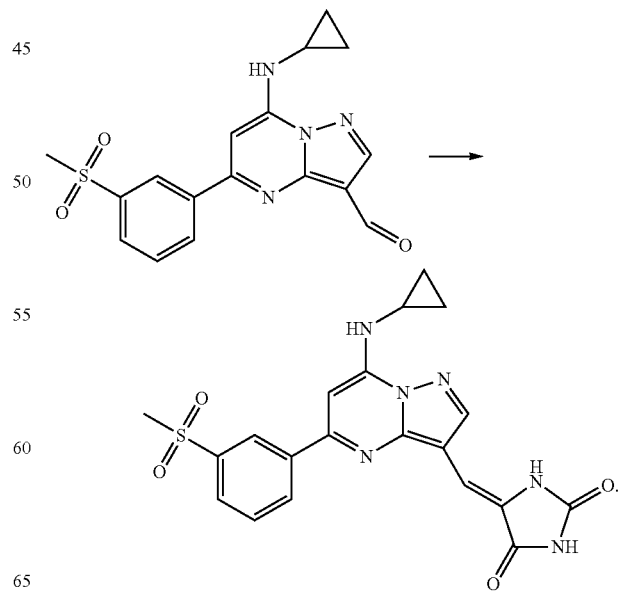

201

Same procedure as [Example 99]. LCMS (M+1=439)

Example 112

Synthesis of tert-butyl cyclopropyl(3-formyl-5-(3-(N-methylsulfamoyl)phenyl)pyrazolo[1,5-a]pyrimidin-7-yl)carbamate

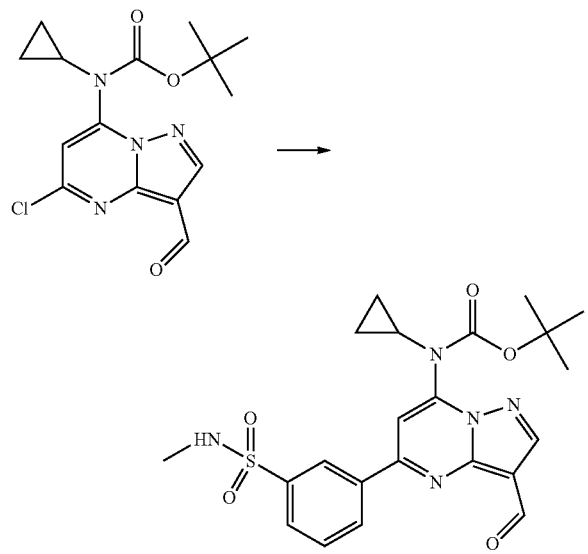 [SMILES: CC(C)(C)OC(=O)N(c1cc(Cl)nc2c(C=O)cnn12)C1CC1 ; CNS(=O)(=O)c1cccc(-c2cc(N(C(=O)OC(C)(C)C)C3CC3)n3ncc(C=O)c3n2)c1]

Same procedure as [Example 97]. LCMS (M+1=472)

Example 113

Synthesis of 3-(7-(cyclopropylamino)-3-formylpyrazolo[1,5-a]pyrimidin-5-yl)-N-methylbenzenesulfonamide

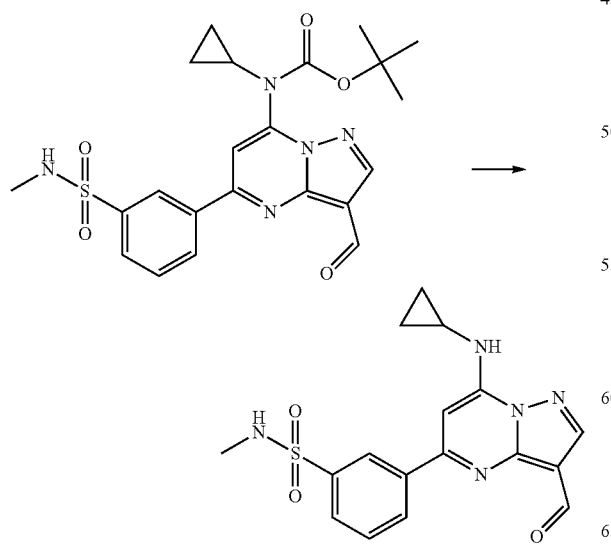

202

Same procedure as [Example 98]. LCMS (M+1=372)

Example 114

Synthesis of 3-(7-(cyclopropylamino)-3-((2,5-dioxoimidazolidin-4-ylidene)methyl)pyrazolo[1,5-a]pyrimidin-5-yl)-N-methylbenzenesulfonamide

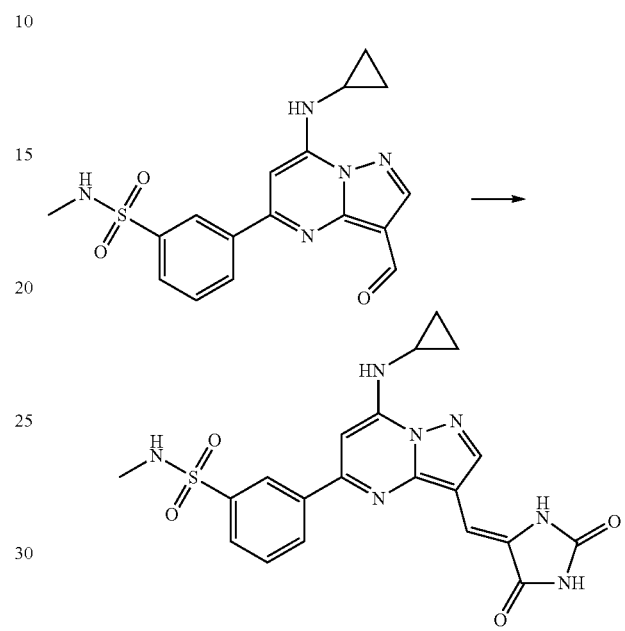

Same procedure as [Example 99]. LCMS (M+1=454)

Example 115

Synthesis of tert-butyl cyclopropyl(3-formyl-5-(3-(methylsulfonamido)phenyl)pyrazolo[1,5-a]pyrimidin-7-yl)carbamate

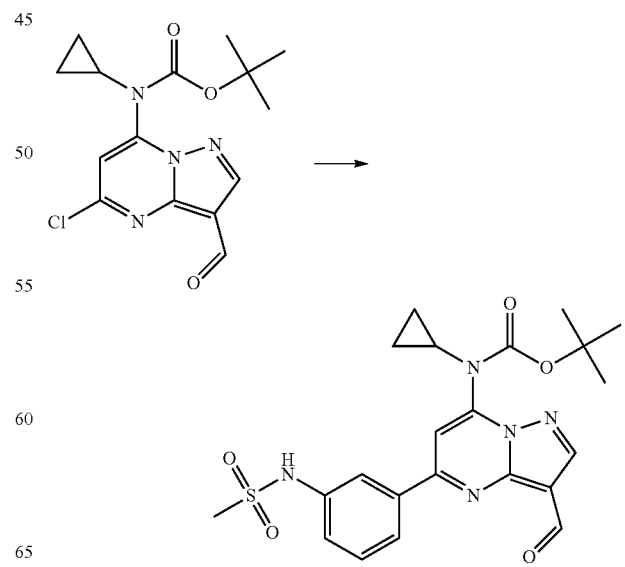

Same procedure as [Example 97]. LCMS (M+1=472)

Example 116

Synthesis of N-(3-(7-(cyclopropylamino)-3-formylpyrazolo[1,5-a]pyrimidin-5-yl)phenyl)methanesulfonamide

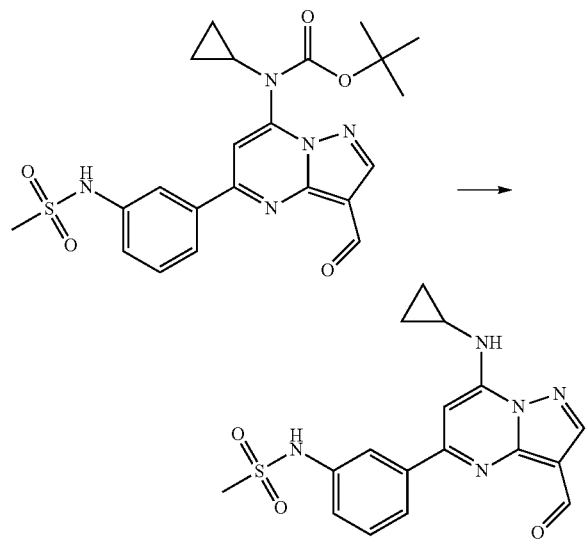

Same procedure as [Example 98]. LCMS (M+1=372)

Example 117

Synthesis of N-(3-(7-(cyclopropylamino)-3-((2,5-dioxoimidazolidin-4-ylidene)methyl)pyrazolo[1,5-a]pyrimidin-5-yl)phenyl)methanesulfonamide

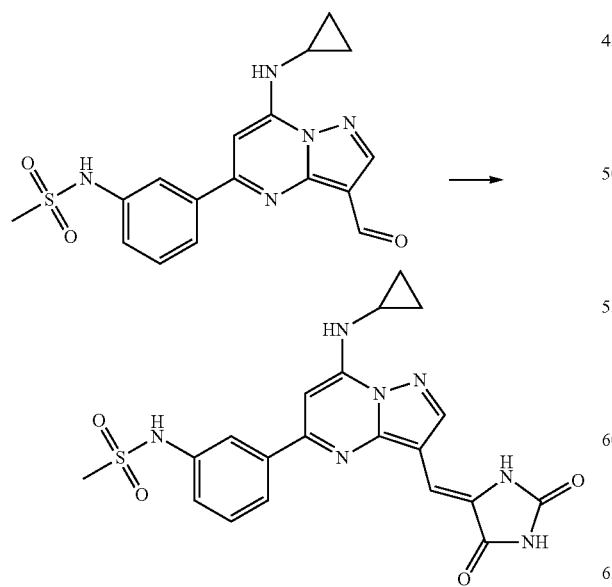

Same procedure as [Example 99]. LCMS (M+1=454)

Example 118

Synthesis of tert-butyl cyclopropyl(5-(3-(dimethylamino)phenyl)-3-formylpyrazolo[1,5-a]pyrimidin-7-yl)carbamate

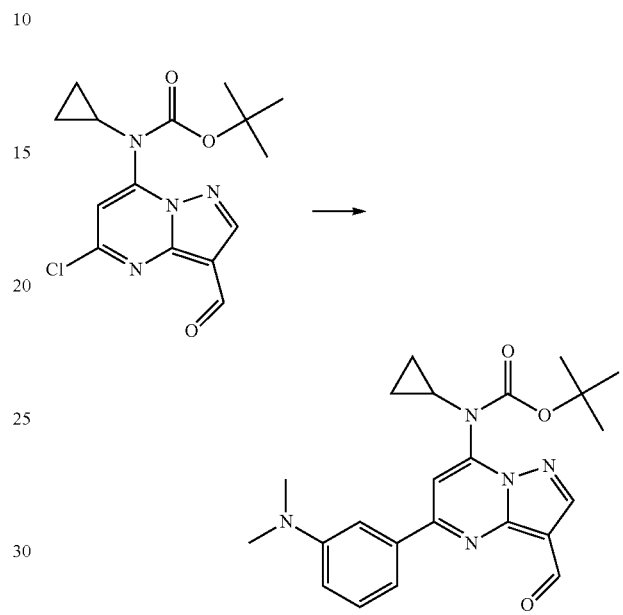

Same procedure as [Example 97]. LCMS (M+1=422)

Example 119

Synthesis of 7-(cyclopropylamino)-5-(3-(dimethylamino)phenyl)pyrazolo[1,5-a]pyrimidine-3-carbaldehyde

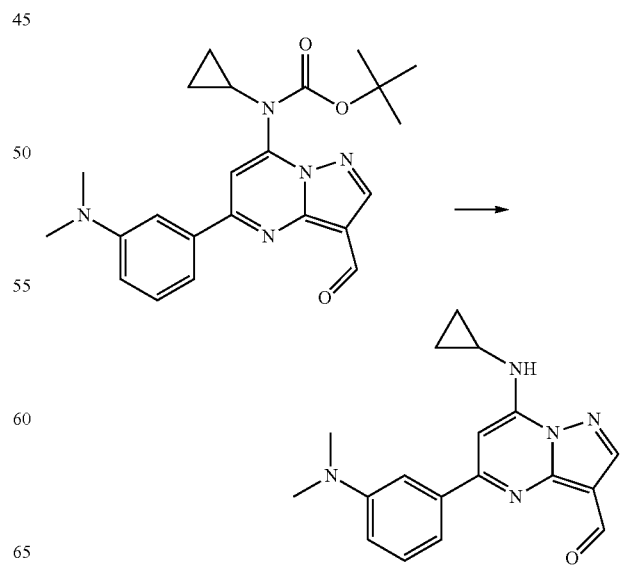

Same procedure as [Example 98]. LCMS (M+1=322)

Example 120

Synthesis of 5((7-(cyclopropylamino)-5-(3-(dimethylamino)phenyl)-pyrazolo[1,5-a]pyrimidin-3-yl)methylene)imidazolidine-2,4-dione

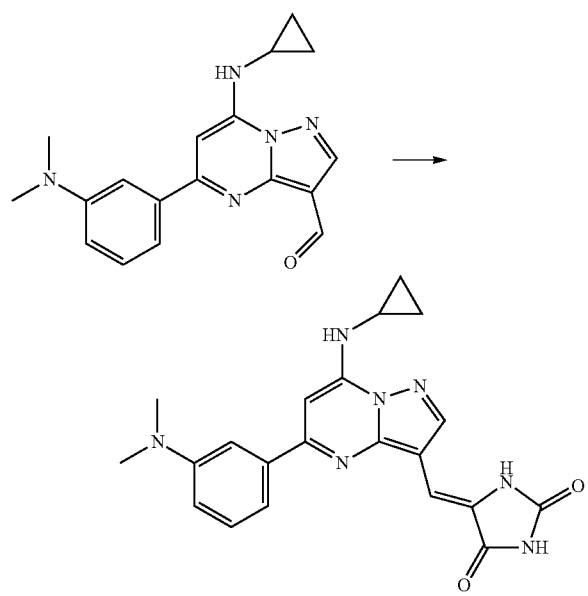

Same procedure as [Example 99]. LCMS (M+1=404)

Example 121

Synthesis of tert-butyl 5-(3-cyanophenyl)-3-formylpyrazolo[1,5-a]pyrimidin-7-yl(cyclopropyl)carbamate

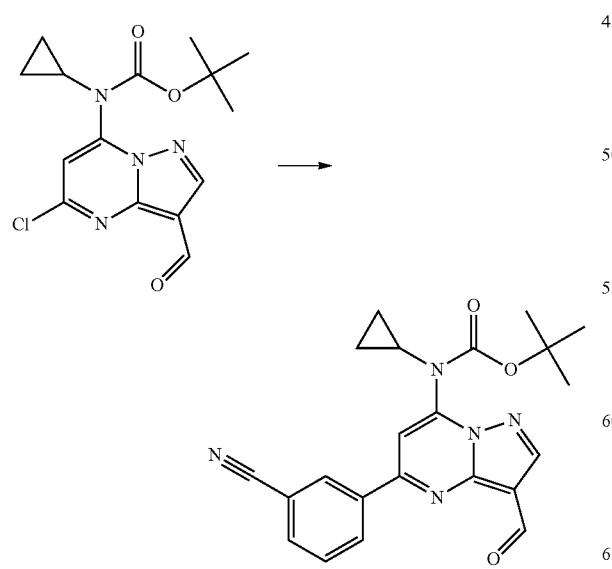

Same procedure as [Example 97]. LCMS (M+1=404)

Example 122

Synthesis of 3-(7-(cyclopropylamino)-3-formylpyrazolo[1,5-a]pyrimidin-yl)benzonitrile

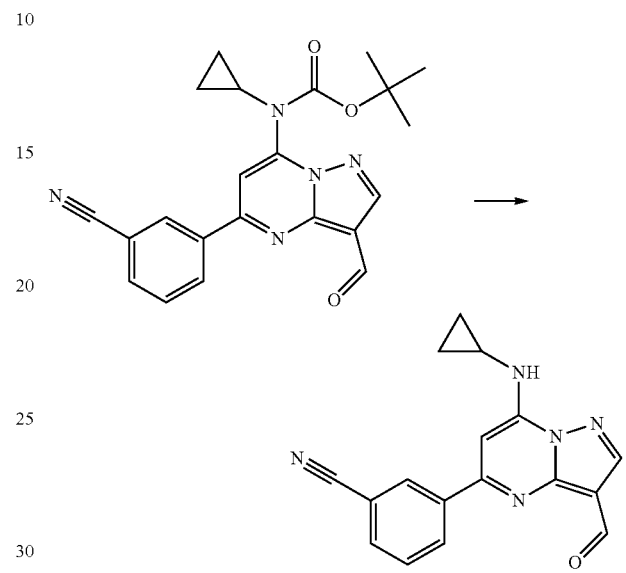

Same procedure as [Example 98]. LCMS (M+1=304)

Example 123

Synthesis of 3-(7-(cyclopropylamino)-3-((2,5-dioxoimidazolidin-4-ylidene)methyl)pyrazolo[1,5-a]pyrimidin-5-yl)benzonitrile

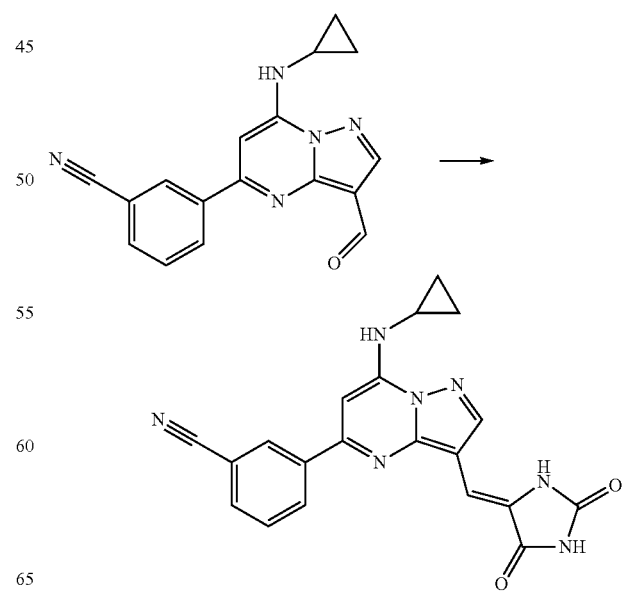

207

Same procedure as [Example 99]. LCMS (M+1=386)

Example 124

Synthesis of tert-butyl cyclopropyl(5-(3-fluorophenyl)-3-formylpyrazolo[1,5-a]pyrimidin-7-yl)carbamate

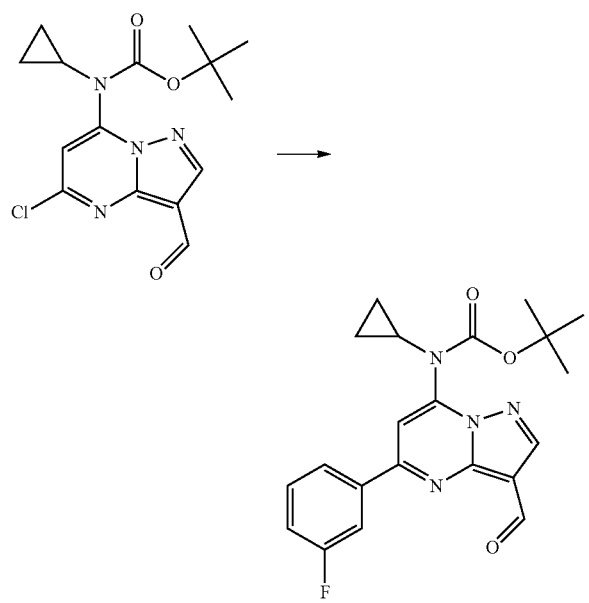 [SMILES: CC(C)(C)OC(=O)N(c1cc(Cl)nc2c(C=O)cnn12)C1CC1 ; CC(C)(C)OC(=O)N(c1cc(-c2cccc(F)c2)nc2c(C=O)cnn12)C1CC1]

Same procedure as [Example 99]. LCMS (M+1=397)

Example 125

Synthesis of 7-(cyclopropylamino)-5-(3-fluorophenyl)pyrazolo[1,5-a]pyrimidine-3-carbaldehyde

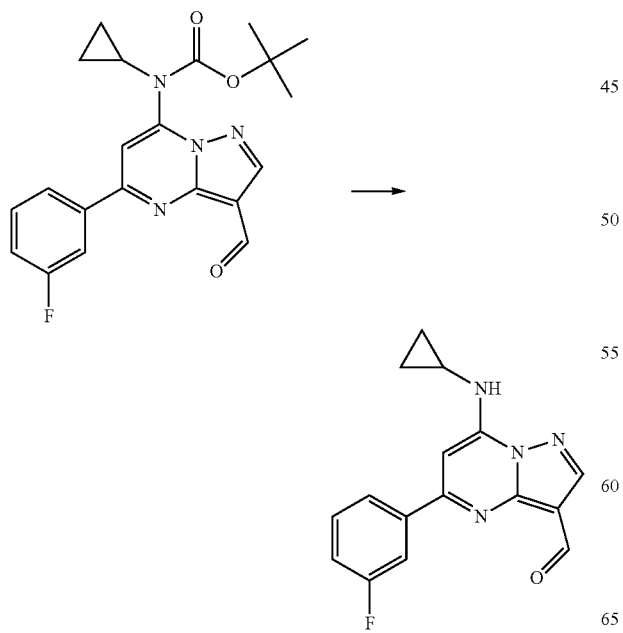

208

Same procedure as [Example 98]. LCMS (M+1=297)

Example 126

Synthesis of 5-((7-(cyclopropylamino)-5-(3-fluorophenyl)pyrazolo[1,5-a]pyrimidin-3-yl)methylene)imidazolidine-2,4-dione

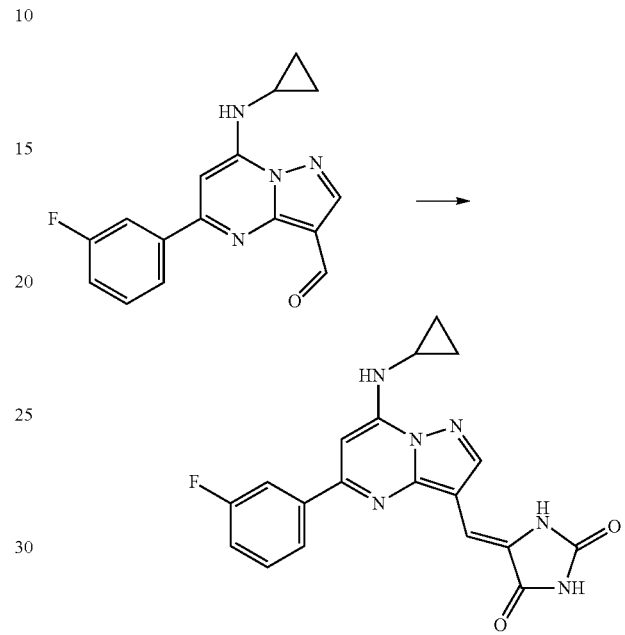

Same procedure as [Example 99]. LCMS (M+1=379)

Example 127

Synthesis of tert-butyl cyclopropyl(3-formyl-5-(pyridin-3-yl)pyrazolo[1,5-a]pyrimidin-7-yl)carbamate

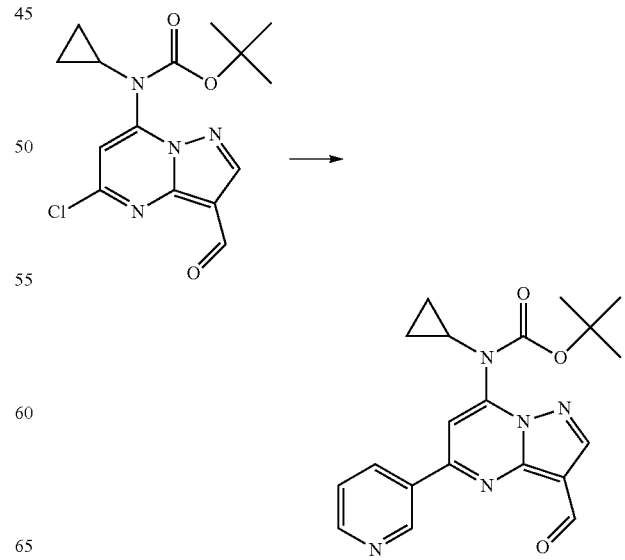

209

Same procedure as [Example 97]. LCMS (M+1=380)

Example 128

Synthesis of 7-(cyclopropylamino)-5-(pyridin-3-yl)pyrazolo[1,5-a]pyrimidine-3-carbaldehyde

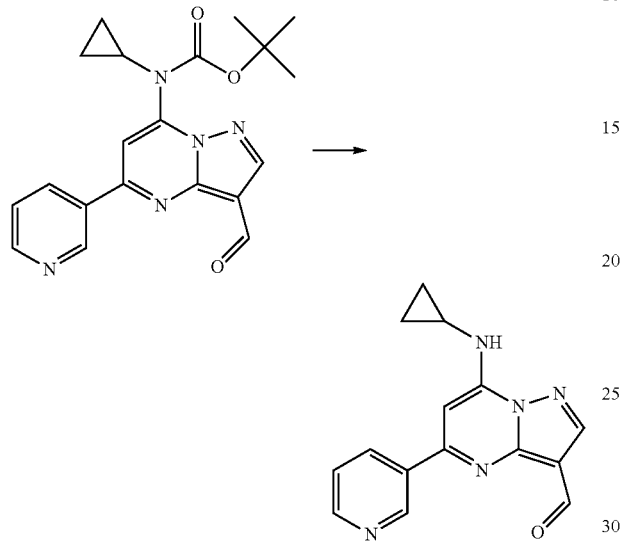

Same procedure as [Example 98]. LCMS (M+1=280)

Example 129

Synthesis of 5-((7-(cyclopropylamino)-5-(pyridin-3-yl)pyrazolo[1,5-a]pyrimidin-3-yl)methylene)imidazolidine-2,4-dione

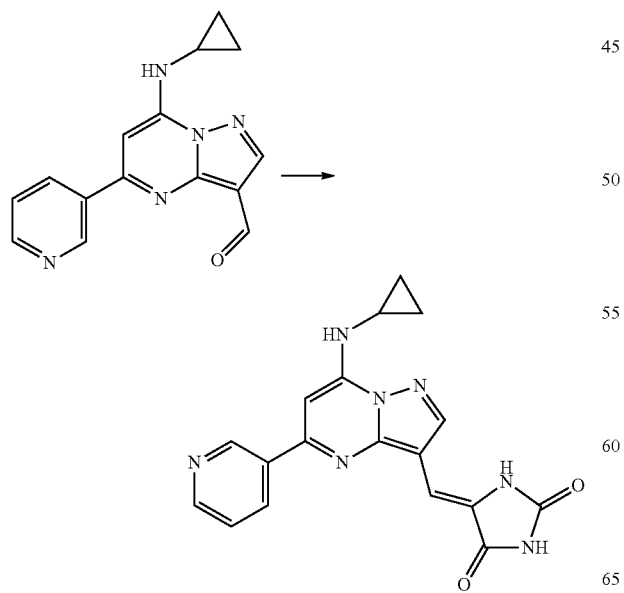

210

Same procedure as [Example 99]. LCMS (M+1=362)

Example 130

Synthesis of tert-butyl cyclopropyl(3-formyl-5-(pyridin-4-yl)pyrazolo[1,5-a]pyrimidin-7-yl)carbamate

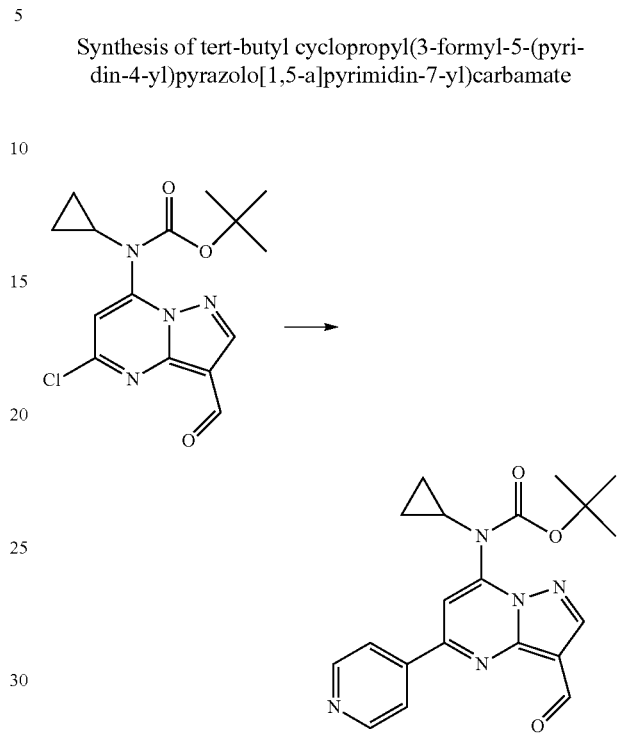

Same procedure as [Example 97]. LCMS (M+1=380)

Example 131

Synthesis of 7-(cyclopropylamino)-5-(pyridin-4-yl)pyrazolo[1,5-a]pyrimidine-3-carbaldehyde

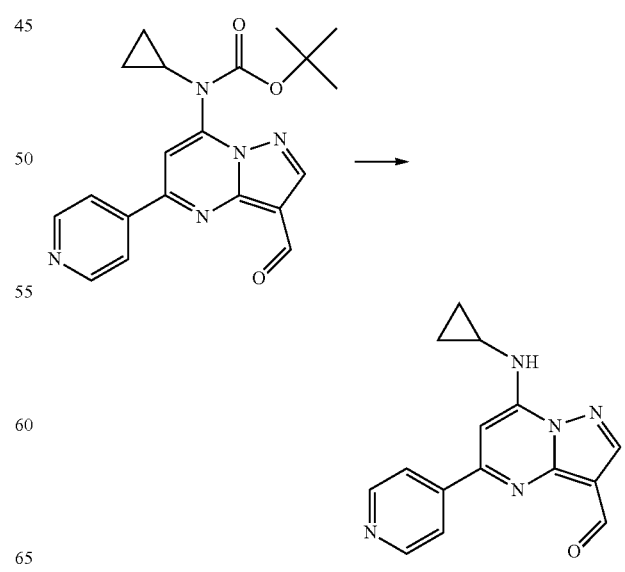

211

Same procedure as [Example 98]. LCMS (M+1=280)

Example 132

Synthesis of 5-((7-(cyclopropylamino)-5-(pyridin-4-yl)pyrazolo[1,5-a]pyrimidin-3-yl)methylene)imidazolidine-2,4-dione

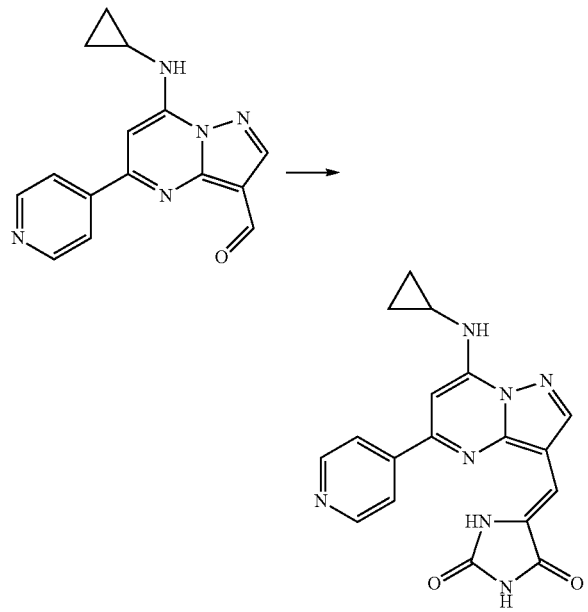

Same procedure as [Example 99]. LCMS (M+1=362)

Example 133

Synthesis of tert-butyl cyclopropyl(5-(2-fluoropyridin-4-yl)-3-formylpyrazolo[1,5-a]pyrimidin-7-yl)carbamate

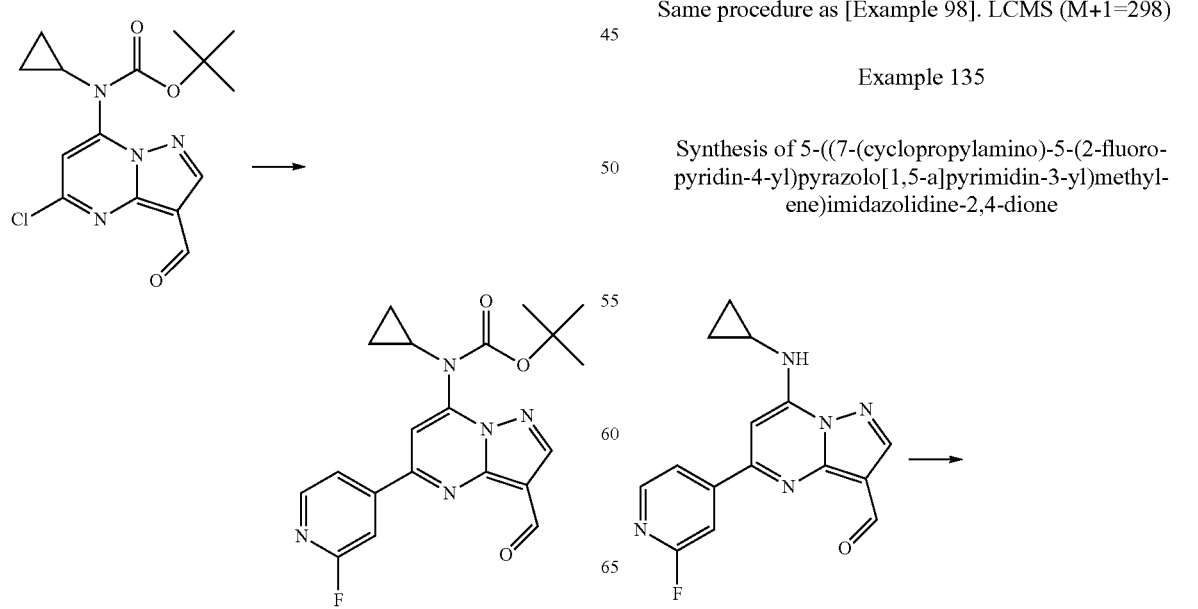

212

Same procedure as [Example 97]. LCMS (M+1=398)

Example 134

Synthesis of 7-(cyclopropylamino)-5-(2-fluoropyridin-4-yl)pyrazolo[1,5-a]pyrimidine-3-carbaldehyde

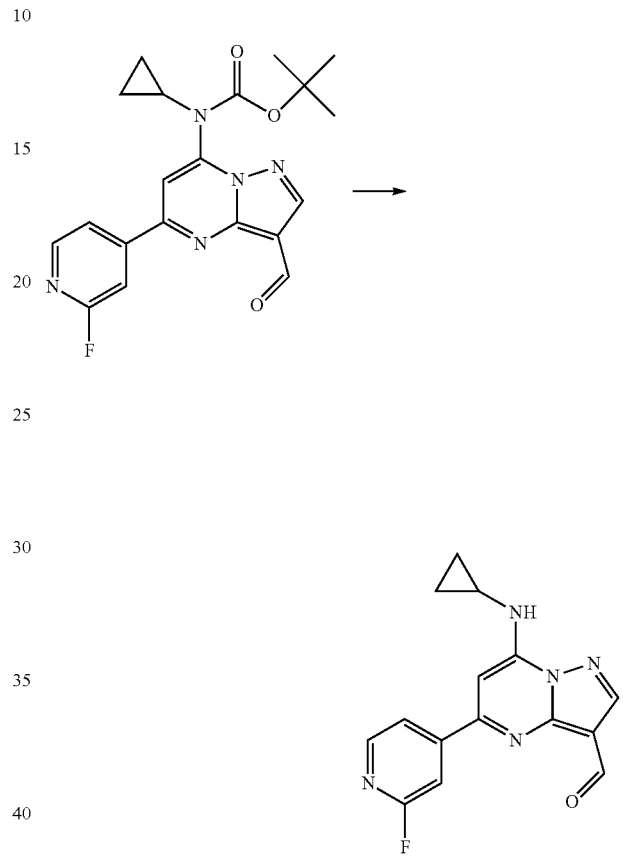

Same procedure as [Example 98]. LCMS (M+1=298)

Example 135

Synthesis of 5-((7-(cyclopropylamino)-5-(2-fluoropyridin-4-yl)pyrazolo[1,5-a]pyrimidin-3-yl)methylene)imidazolidine-2,4-dione -continued

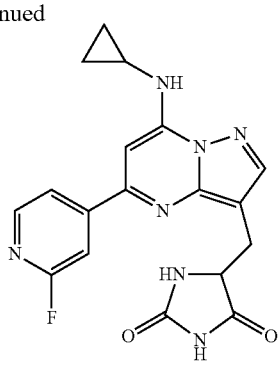

Same procedure as [Example 99]. LCMS (M+1=380)

Example 136

Synthesis of tert-butyl cyclopropyl(3-formyl-5-(4-hydroxyphenyl)pyrazolo[1,5-a]pyrimidin-7-yl)carbamate

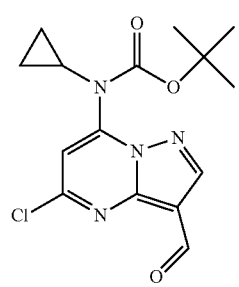

Same procedure as [Example 97]. LCMS (M+1=395)

Example 137

Synthesis of 7-(cyclopropylamino)-5-(4-hydroxyphenyl)pyrazolo[1,5-a]pyrimidine-3-carbaldehyde

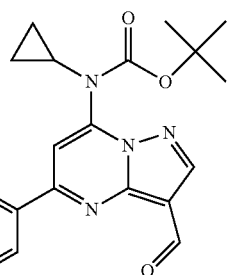

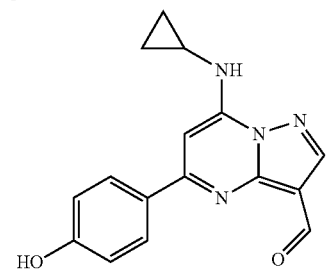

Same procedure as [Example 98]. LCMS (M+1=295)

Example 138

Synthesis of 5((7-(cyclopropylamino)-5-(4-hydroxyphenyl)pyrazolo[1,5-a]pyrimidin-3-yl)methylene)imidazolidine-2,4-dione

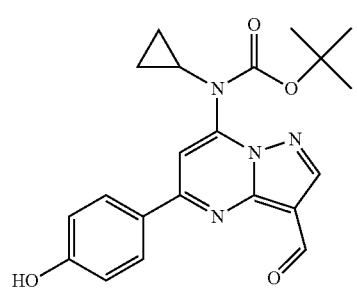

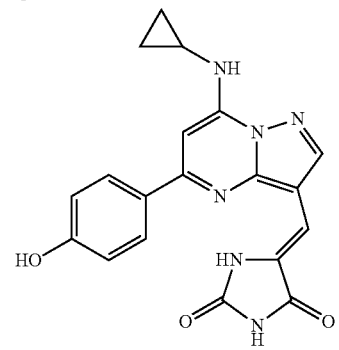

Same procedure as [Example 99]. LCMS (M+1=377)

Example 139

Synthesis of tert-butyl cyclopropyl(3-formyl-5-(3-(morpholinomethyl)phenyl)pyrazolo[1,5-a]pyrimidin-7-yl)carbamate

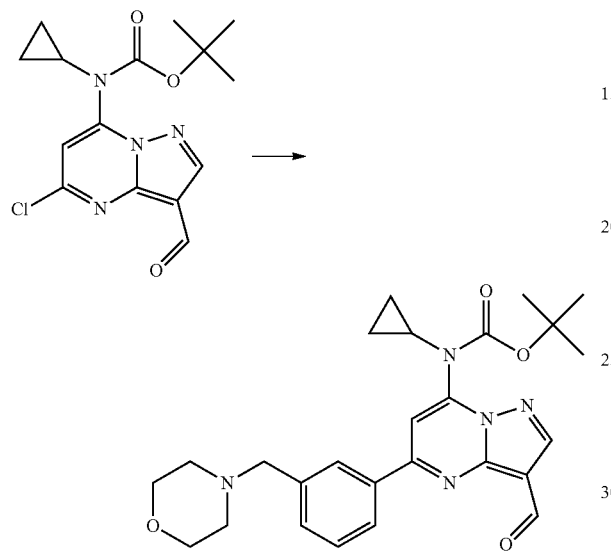

Same procedure as [Example 97]. LCMS (M+1=478)

Example 140

Synthesis of 7-(cyclopropylamino)-5-(3-(morpholinomethyl)phenyl)pyrazolo[1,5-a]pyrimidine-3-carbaldehyde

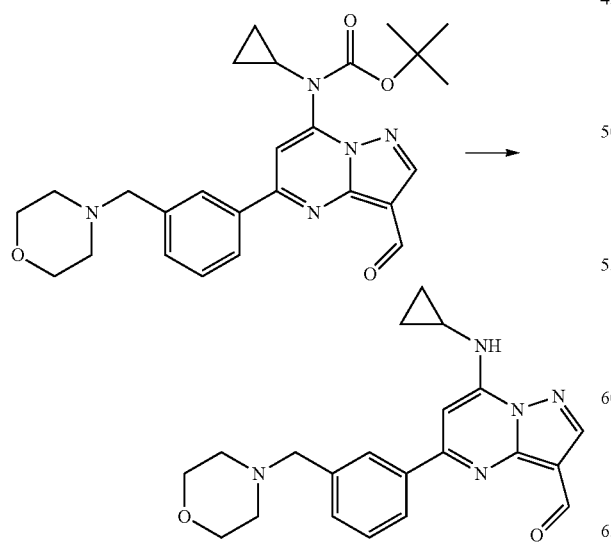

Same procedure as [Example 98]. LCMS (M+1=378)

Example 141

Synthesis of 5-((7-(cyclopropylamino)-5-(3-(morpholinomethyl)phenyl)pyrazolo[1,5-a]pyrimidin-3-yl)methylene)imidazolidine-2,4-dione

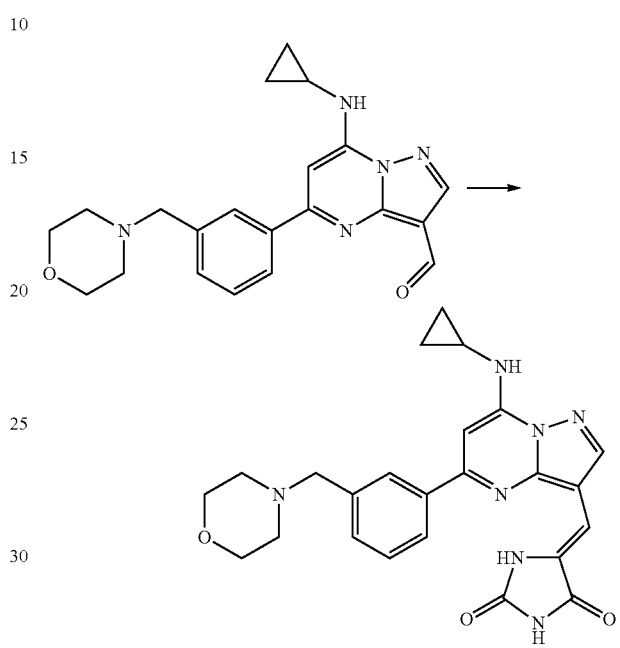

Same procedure as [Example 99]. LCMS (M+1=460)

Example 142

Synthesis of tert-butyl cyclopropyl(3-formyl-5-(3-((4-methylpiperazin-1-yl)methyl)phenyl)pyrazolo[1,5-a]pyrimidin-7-yl)carbamate

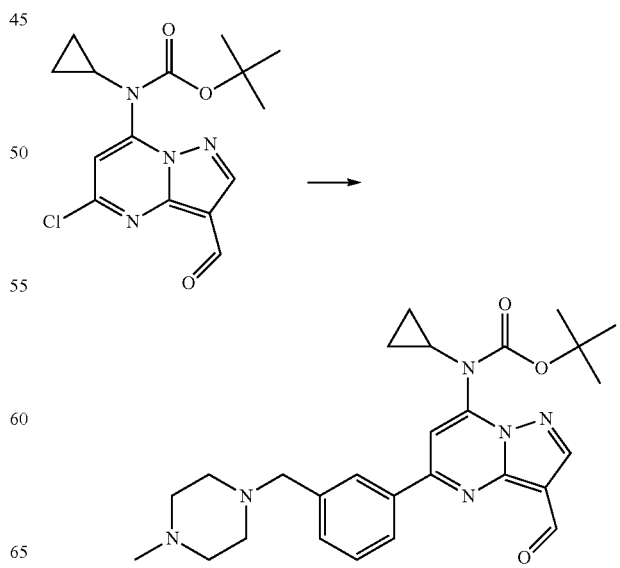

217

Same procedure as [Example 97]. LCMS (M+1=491)

Example 143

Synthesis of 7-(cyclopropylamino)-5-(3-((4-methylpiperazin-1-yl)methyl)phenyl)pyrazolo[1,5-a]pyrimidine-3-carbaldehyde

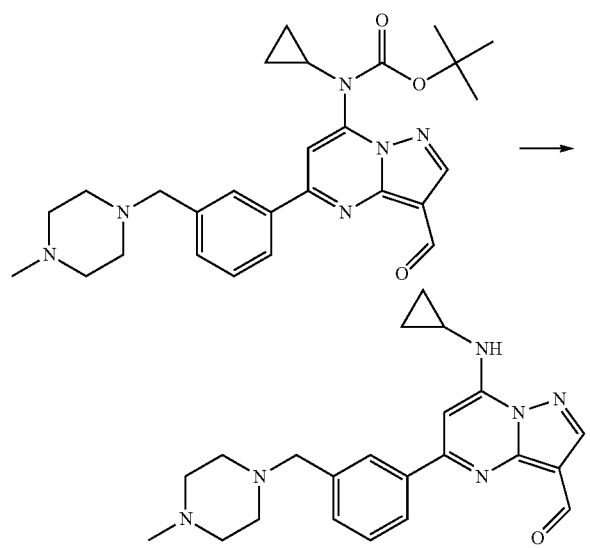

Same procedure as [Example 98]. LCMS (M+1=391)

Example 144

Synthesis of 5-((7-(cyclopropylamino)-5-(3-((4-methylpiperazin-1-yl)methyl)phenyl)pyrazolo[1,5-a]pyrimidin-3-yl)methylene)imidazolidine-2,4-dione

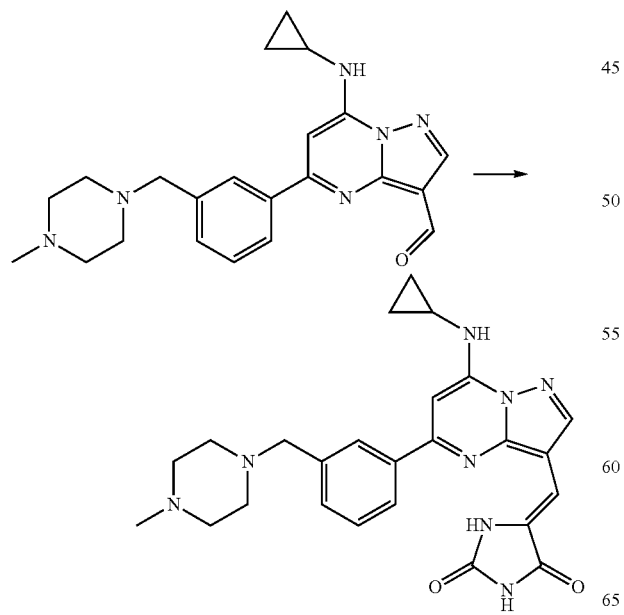

218

Same procedure as [Example 99]. LCMS (M+1=473)

Example 145

Synthesis of tert-butyl 5-(3-(acetamidomethyl)phenyl)-3-formylpyrazolo[1,5-a]pyrimidin-7-yl(cyclopropyl)carbamate

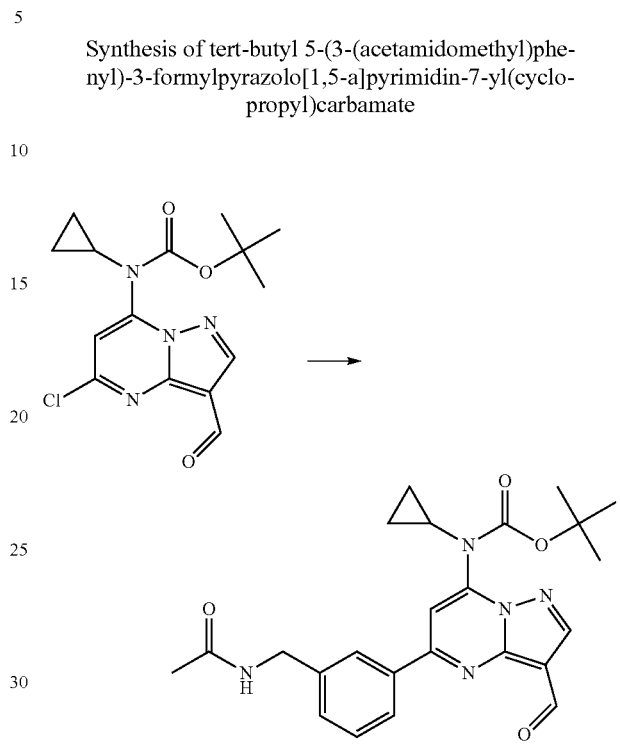

Same procedure as [Example 97]. LCMS (M+1=450)

Example 146

Synthesis of N-(3-(7-(cyclopropylamino)-3-formylpyrazolo[1,5-a]pyrimidin-5-yl)benzyl)acetamide

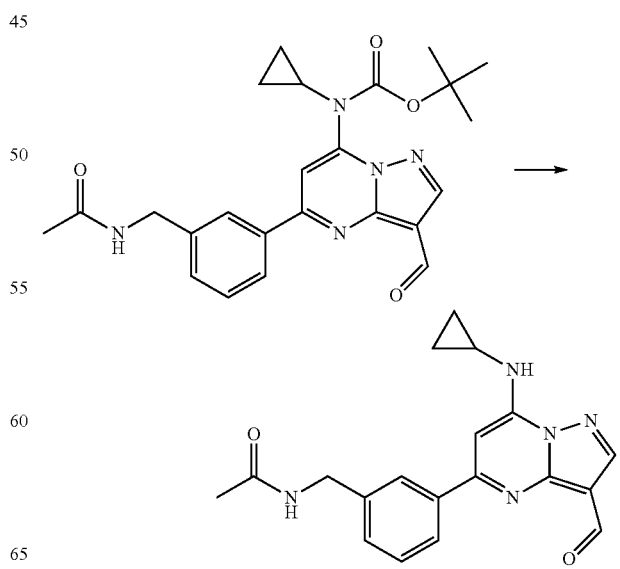

Same procedure as [Example 98]. LCMS (M+1=350)

Example 147

Synthesis of N-(3-(7-(cyclopropylamino)-3-((2,5-dioxoimidazolidin-4-ylidene)methyl)pyrazolo[1,5-a]pyrimidin-5-yl)benzyl)acetamide

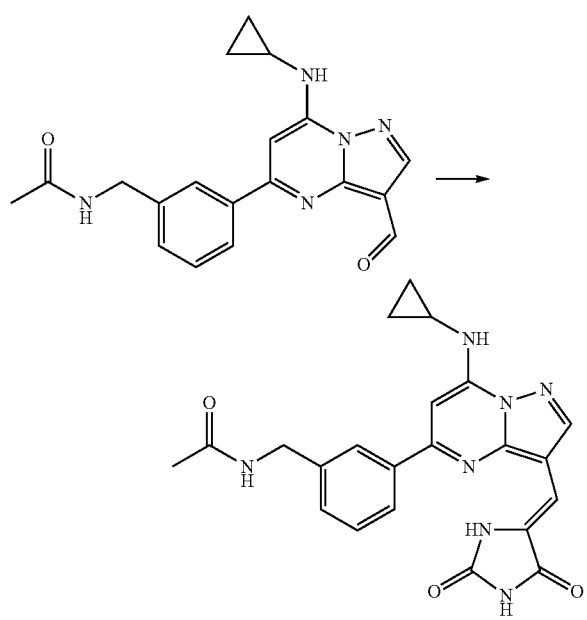

Same procedure as [Example 99]. LCMS (M+1=432)

Example 148

Synthesis of 5-(3-(aminomethyl)phenyl)-7-(cyclopropylamino)pyrazolo[1,5-a]pyrimidine-3-carbaldehyde

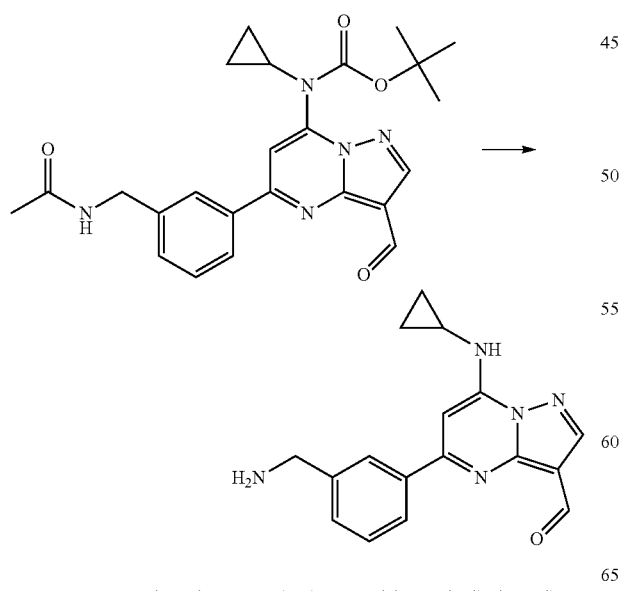

To tert-butyl 5-(3-(acetamidomethyl)phenyl)-3-formylpyrazolo[1,5-a]pyrimidin-7-yl(cyclopropyl)carbamate (50 mg, 0.111 mmol) was added 1 mL of 4M HCl in 1,4-dioxane and 1 mL of $H_2O$. The reaction mixture was stirred at 80° C. for 16 hours then cooled to room temperature and diluted with $H_2O$. To the reaction mixture, 5M NaOH was added to adjust pH to >10 then the mixture was extracted with $CH_2Cl_2$. The organic layer was collected, dried over $MgSO_4$, filtered and evaporated to dryness to provide 24 mg of 5-(3-(aminomethyl)phenyl)-7-(cyclopropylamino)pyrazolo[1,5-a]pyrimidine-3-carbaldehyde (70%). LCMS (M+1=308)

Example 149

Synthesis of 5-((5-(3-(aminomethyl)phenyl)-7-(cyclopropylamino)pyrazolo[1,5-a]pyrimidin-3-yl)methylene)imidazolidine-2,4-dione

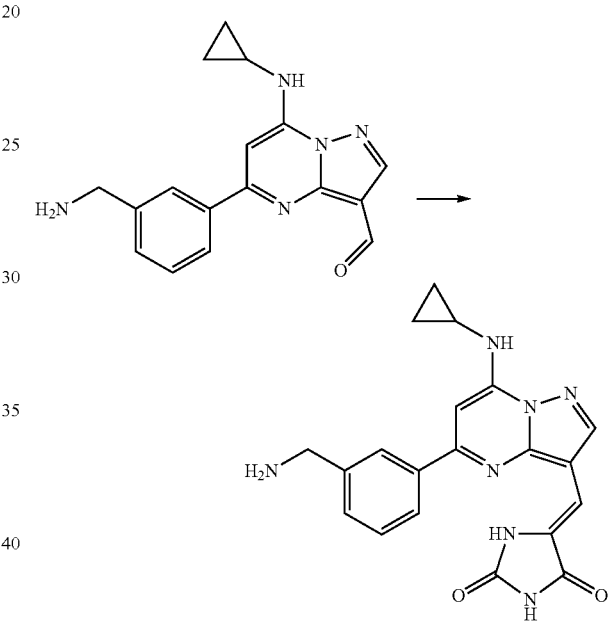

Same procedure as [Example 99]. LCMS (M+1=390)

The compounds described in the following table were prepared using chemistries similar to those exemplified in Example 98 and Example 99. All compounds were characterized by LCMS. Table 22B shows the biological activities of the compounds listed in Table 22A.

TABLE 22A

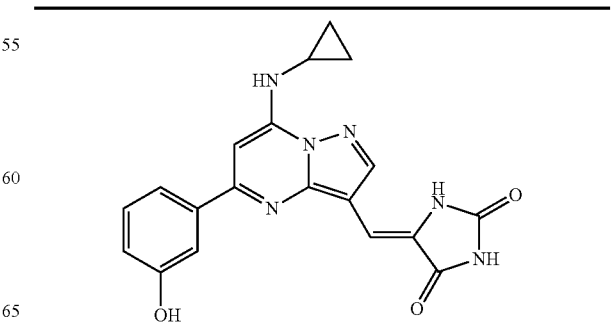

TABLE 22A-continued
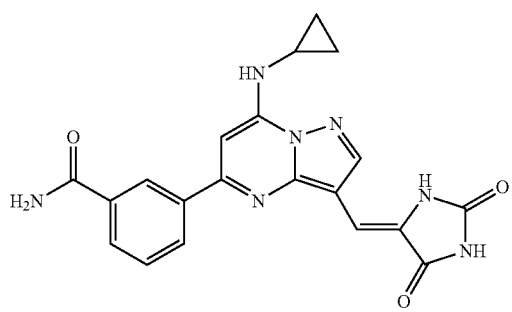 [SMILES: NC(=O)c1cccc(-c2cc(NC3CC3)n3ncc(/C=C4\NC(=O)NC4=O)c3n2)c1]
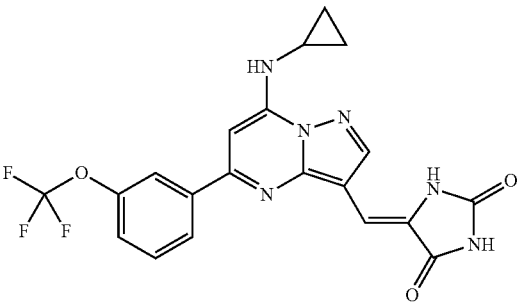 [SMILES: O=C1NC(=O)/C(=C/c2cnn3c(NC4CC4)cc(-c4cccc(OC(F)(F)F)c4)nc23)N1]
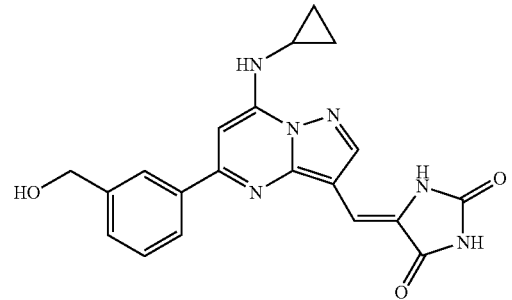 [SMILES: O=C1NC(=O)/C(=C/c2cnn3c(NC4CC4)cc(-c4cccc(CO)c4)nc23)N1]
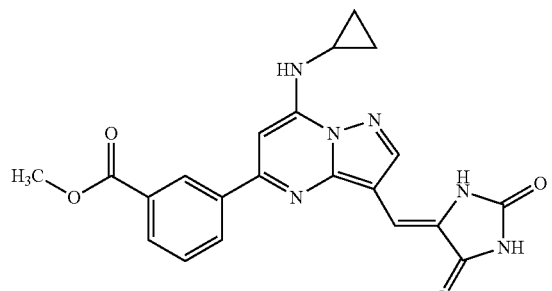
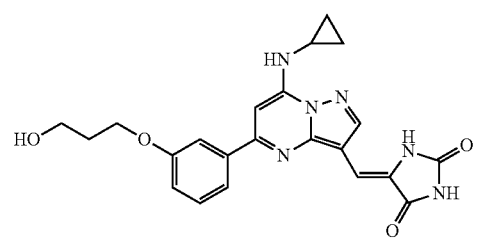 [SMILES: O=C1NC(=O)/C(=C/c2cnn3c(NC4CC4)cc(-c4cccc(OCCCO)c4)nc23)N1]
TABLE 22A-continued
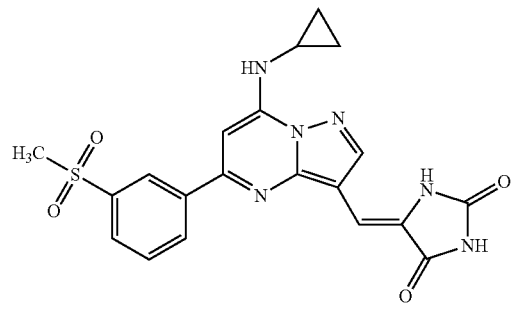 [SMILES: CS(=O)(=O)c1cccc(-c2cc(NC3CC3)n3ncc(/C=C4\NC(=O)NC4=O)c3n2)c1]
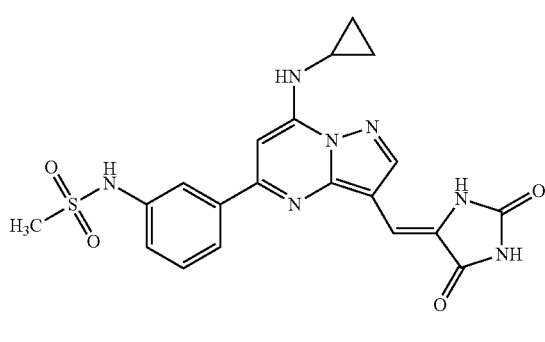 [SMILES: CS(=O)(=O)Nc1cccc(-c2cc(NC3CC3)n3ncc(/C=C4\NC(=O)NC4=O)c3n2)c1]
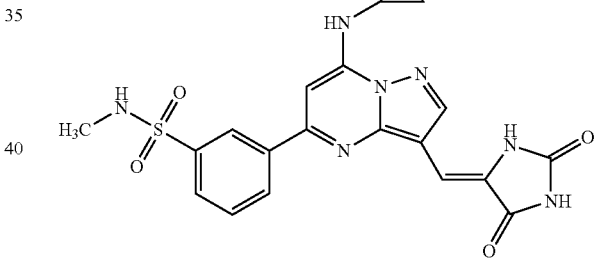
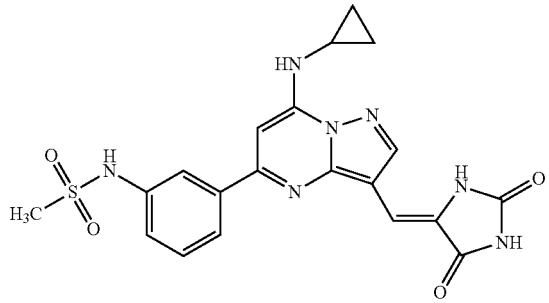 [SMILES: CS(=O)(=O)Nc1cccc(-c2cc(NC3CC3)n3ncc(/C=C4\NC(=O)NC4=O)c3n2)c1]
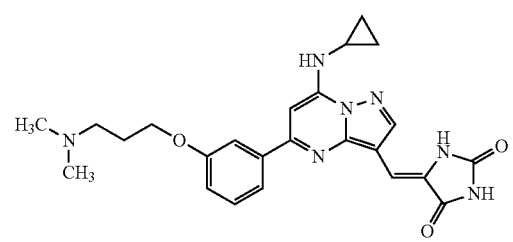 [SMILES: CN(C)CCCOc1cccc(-c2cc(NC3CC3)n3ncc(/C=C4\NC(=O)NC4=O)c3n2)c1]

TABLE 22A-continued
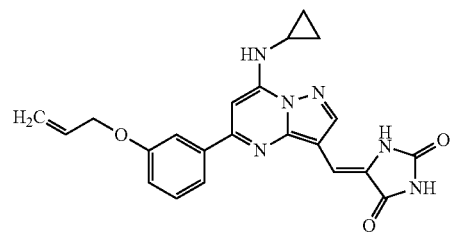 [SMILES: C=CCOc1cccc(-c2cc(NC3CC3)n3ncc(/C=C4\NC(=O)NC4=O)c3n2)c1]
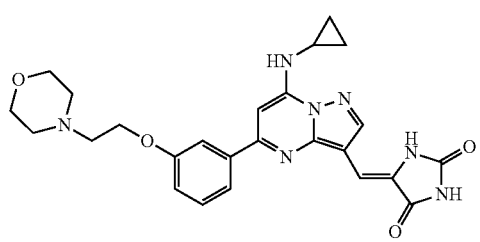 [SMILES: O=C1NC(=O)/C(=C/c2cnn3c(NC4CC4)cc(-c4cccc(OCCN5CCOCC5)c4)nc23)N1]
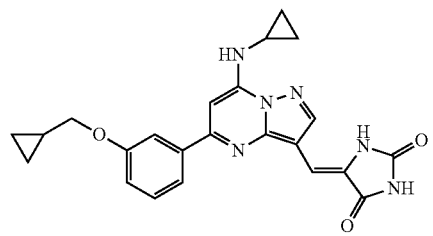 [SMILES: O=C1NC(=O)/C(=C/c2cnn3c(NC4CC4)cc(-c4cccc(OCC5CC5)c4)nc23)N1]
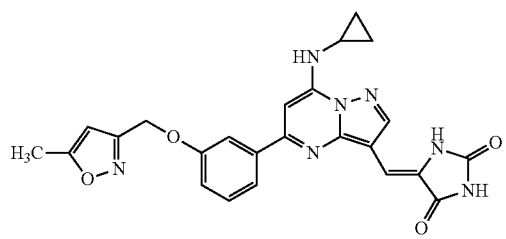 [SMILES: Cc1cc(COc2cccc(-c3cc(NC4CC4)n4ncc(/C=C5\NC(=O)NC5=O)c4n3)c2)no1]
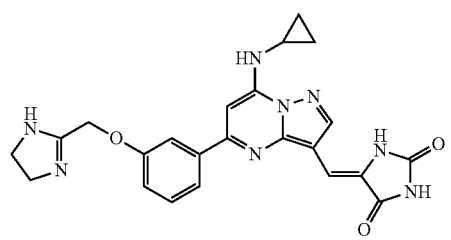 [SMILES: O=C1NC(=O)/C(=C/c2cnn3c(NC4CC4)cc(-c4cccc(OCC5=NCCN5)c4)nc23)N1]
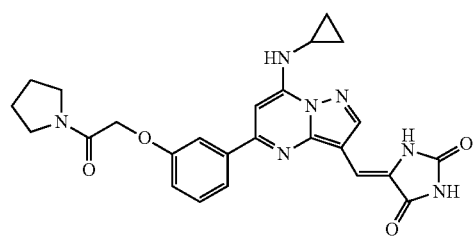 [SMILES: O=C1NC(=O)/C(=C/c2cnn3c(NC4CC4)cc(-c4cccc(OCC(=O)N5CCCC5)c4)nc23)N1]
TABLE 22A-continued
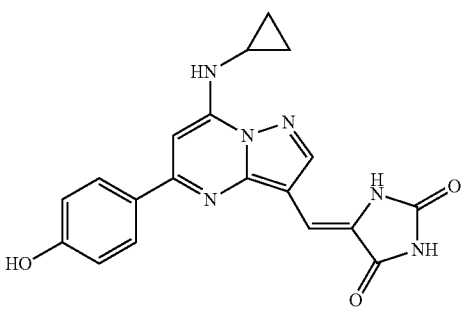 [SMILES: O=C1NC(=O)/C(=C/c2cnn3c(NC4CC4)cc(-c4ccc(O)cc4)nc23)N1]
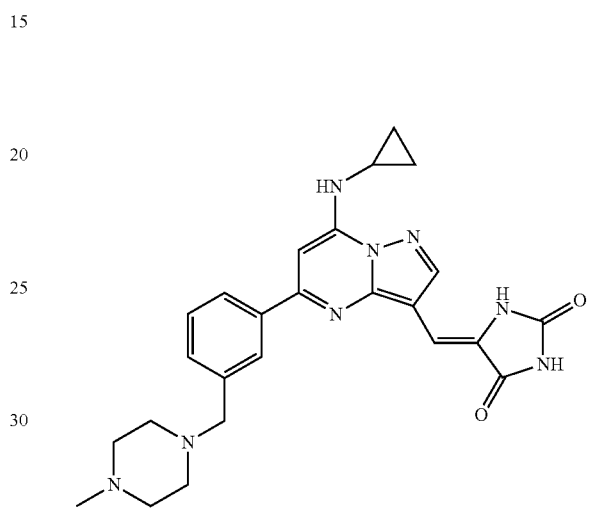
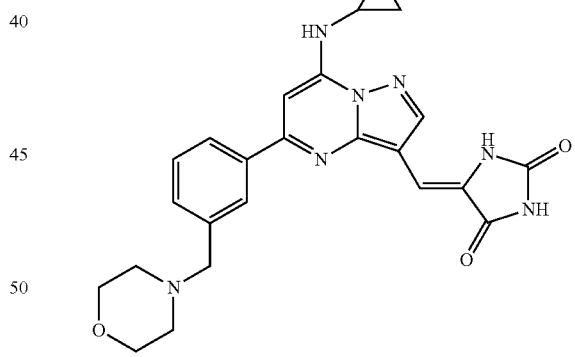
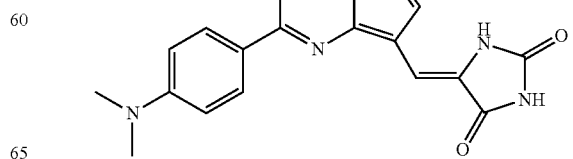

TABLE 22A-continued
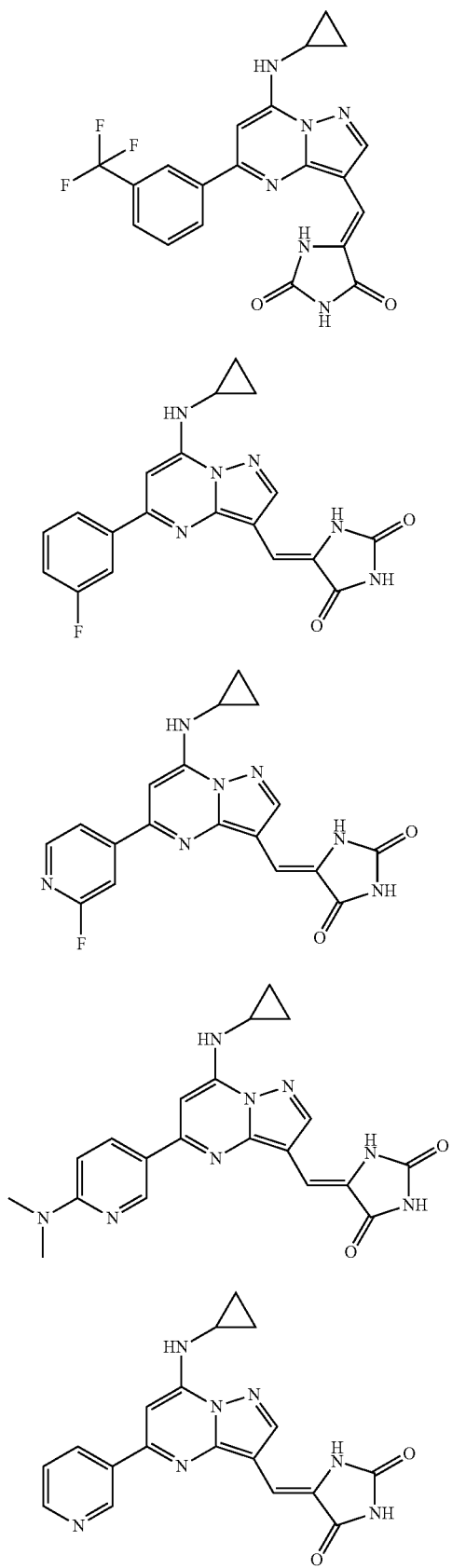
TABLE 22A-continued
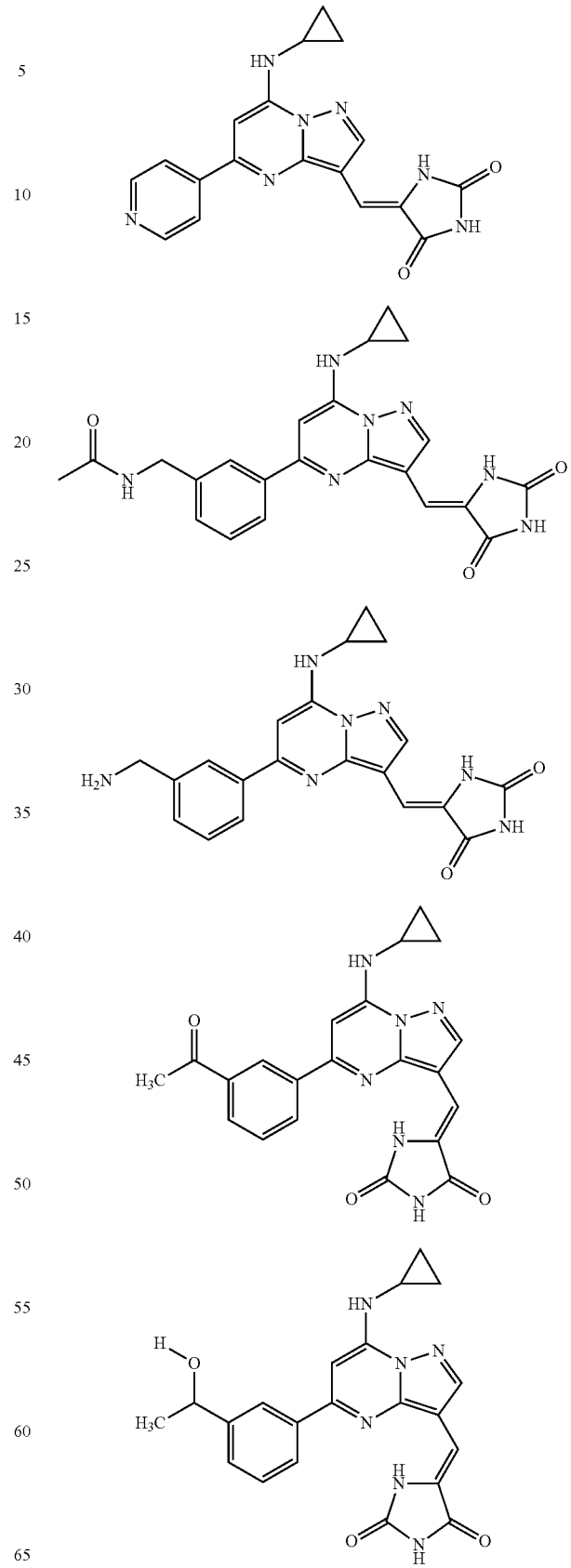

TABLE 22A-continued
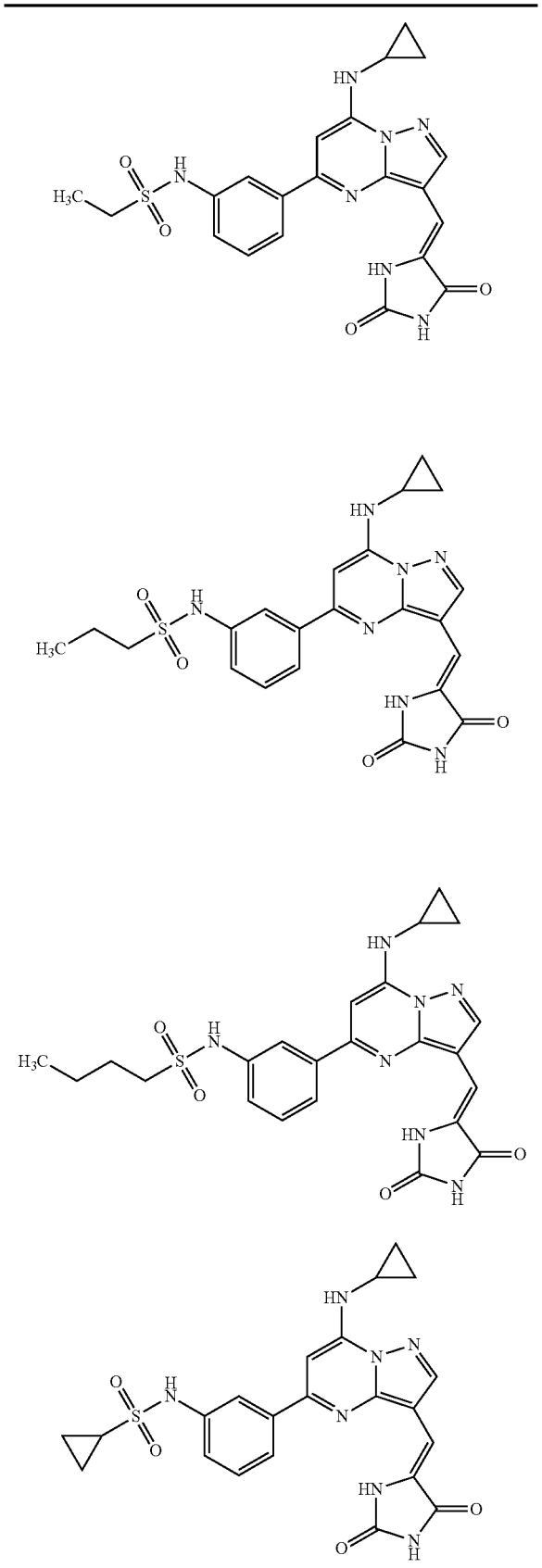
TABLE 22A-continued
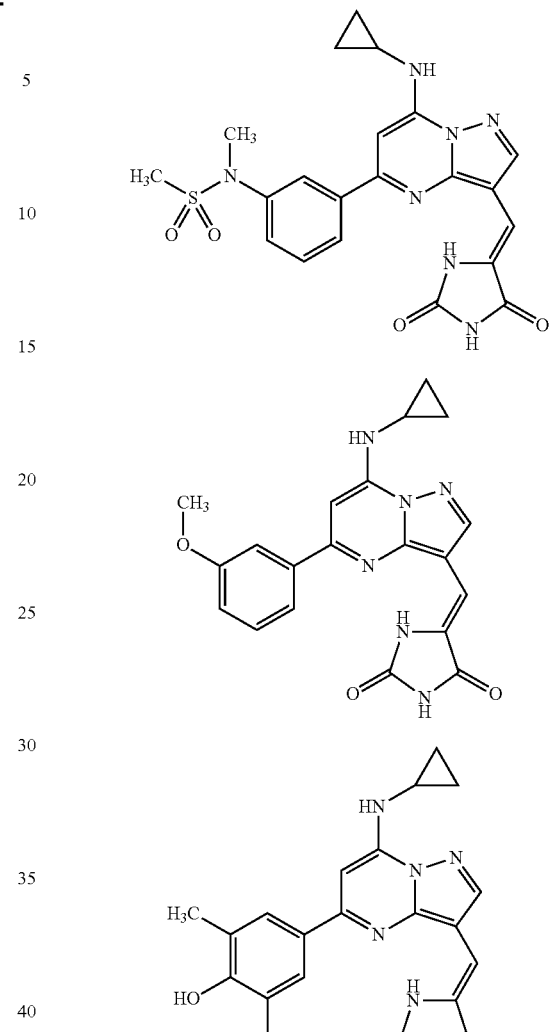
TABLE 22B
| Compound | CK2: IC50 (µM) | PIM2: IC50 (5 µM ATP) | AB: MDAMB453 (µM) | AB: BxPC3 (µM) |
| --- | --- | --- | --- | --- |
| G7 | <0.01 | 0.6135 | 0.33 | 10.627 |
| H7 | <0.01 | 0.8908 | 0.402 | 1.541 |
| I7 | <0.01 | >2.5000 | 3.743 | 3.68 |
| J7 | <0.01 | 0.6492 | 0.477 | 5.171 |
| K7 | <0.01 | >2.5000 | 1.709 | 2.054 |
| L7 | <0.01 | >2.5000 | 0.517 | 13.111 |
| M7 | <0.1 | >2.5000 | | |
| N7 | <0.01 | 2.2144 | 0.284 | 2.916 |
| O7 | <0.01 | >2.5000 | >30 | >30 |
| P7 | <0.01 | 2.1685 | 7.866 | 7.907 |
| Q7 | <0.1 | 2.4032 | 1.494 | 3.279 |
| R7 | <0.01 | >2.5000 | 1.054 | 23.617 |
| S7 | <0.01 | >2.5000 | 1.174 | 11.78 |
| T7 | <0.01 | >2.5000 | 1.298 | 6.592 |
| U7 | <0.01 | >2.5000 | 1.153 | 1.191 |
| V7 | <0.01 | >2.5000 | 1.964 | 14.486 |
| W7 | <0.1 | >2.5000 | 0.683 | 1.898 |
| X7 | <0.01 | 0.867 | 4.746 | >30 |
| Y7 | <0.1 | 1.3082 | 1.938 | 2.578 |
| Z7 | <0.01 | 1.4748 | 1.79 | 0.725 |

TABLE 22B-continued

| Compound | CK2: IC50 (μM) | PIM2: IC50 (5 μM ATP) | AB: MDAMB453 (μM) | AB: BxPC3 (μM) |
|---|---|---|---|---|
| A8 | <0.01 | 1.2497 | >30 | 14.347 |
| B8 | <0.01 | >2.5000 | >30 | 12.535 |
| C8 | <0.01 | >2.5000 | 17.123 | 1.232 |
| D8 | <0.01 | 0.0754 | 5.276 | 0.549 |
| E8 | <0.01 | >2.5000 | 11.733 | >30 |
| F8 | <0.01 | 0.2562 | 1.068 | 0.745 |
| G8 | <0.01 | 0.0487 | 14.882 | 10.61 |
| H8 | <0.01 | >2.5000 | 20.012 | 4.608 |
| I8 | <0.1 | >2.5000 | 1.706 | 2.744 |
| J8 | <0.01 | >2.5000 | 1.263 | 8.129 |
| K8 | <0.1 | >2.5000 | 12.417 | >30 |
| L8 | <0.01 | 2.084 | 12.278 | >30 |
| M8 | <0.01 | 1.7271 | >30 | >30 |
| N8 | <0.01 | >2.5000 | 1.979 | 2.253 |
| O8 | <0.01 | >2.5000 | 15.69 | 29.035 |
| P8 | <0.01 | | 0.948 | 1.742 |
| Q8 | <0.01 | >2.5000 | 26.74 | 5.426 |
| R8 | <1.0 | >2.5000 | | |

Example 150

Synthesis of methyl 5-(7-(tert-butoxycarbonyl(cyclopropyl)amino)-3-formylpyrazolo[1,5-a]pyrimidin-5-yl)thiophene-2-carboxylate

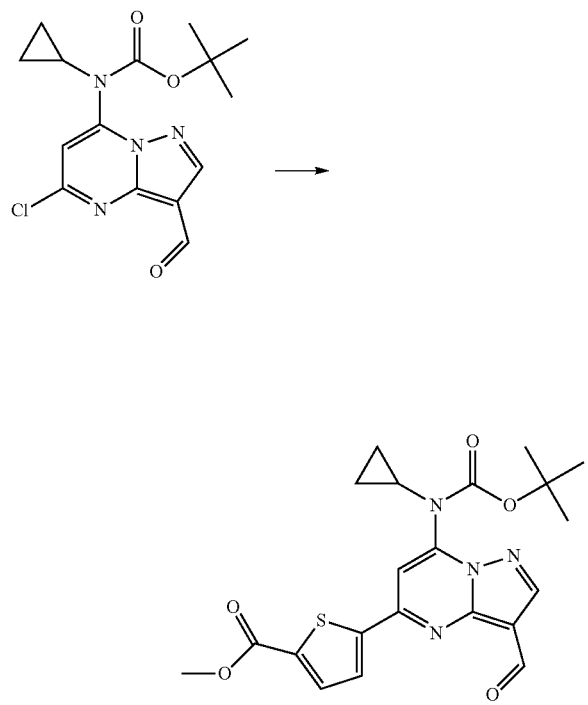

Same procedure as [Example 97]. LCMS (M+1=443)

Example 151

Synthesis of methyl 5-(7-(cyclopropylamino)-3-formylpyrazolo[1,5-a]pyrimidin-5-yl)thiophene-2-carboxylate

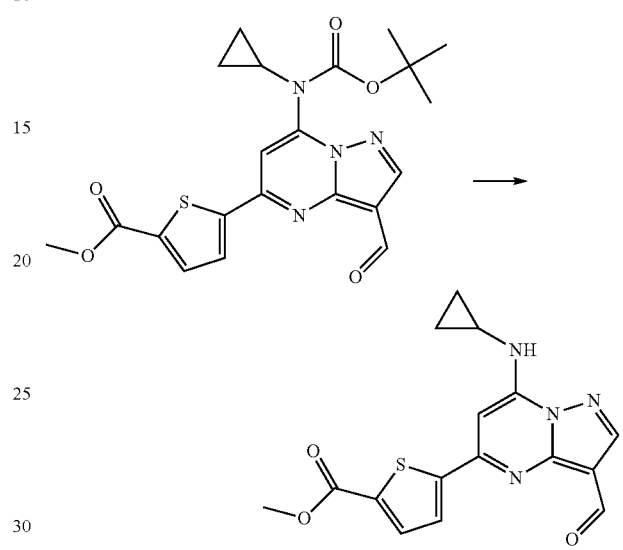

Same procedure as [Example 98]. LCMS (M+1=343)

Example 152

Synthesis of methyl 5-(7-(cyclopropylamino)-3-((2,5-dioxoimidazolidin-4-ylidene)methyl)pyrazolo[1,5-a]pyrimidin-5-yl)thiophene-2-carboxylate

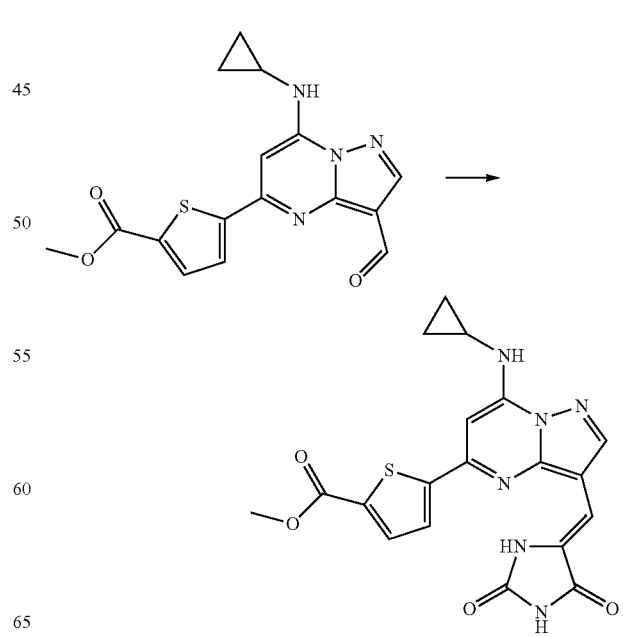

231

Same procedure as [Example 99]. LCMS (M+1=425)

Example 153

Synthesis of tert-butyl 5-(5-cyanothiophen-2-yl)-3-formylpyrazolo[1,5-a]pyrimidin-7-yl(cyclopropyl)carbamate

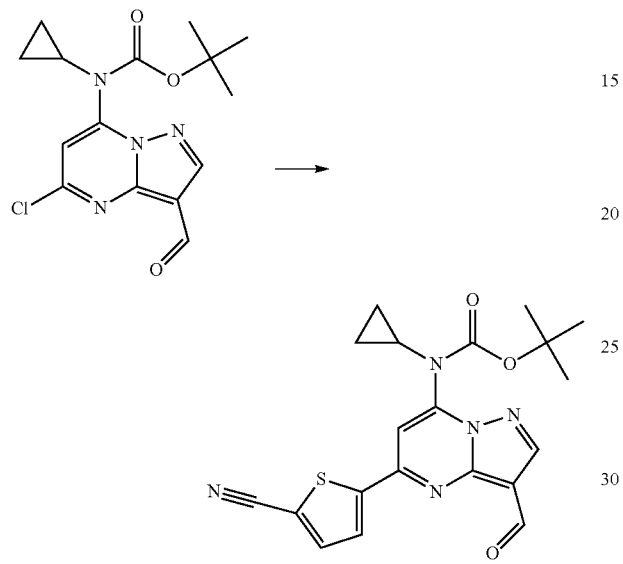

Same procedure as [Example 97]. LCMS (M+1=410)

Example 154

Synthesis of 5-(7-(cyclopropylamino)-3-formylpyrazolo[1,5-a]pyrimidin-5-yl)thiophene-2-carbonitrile

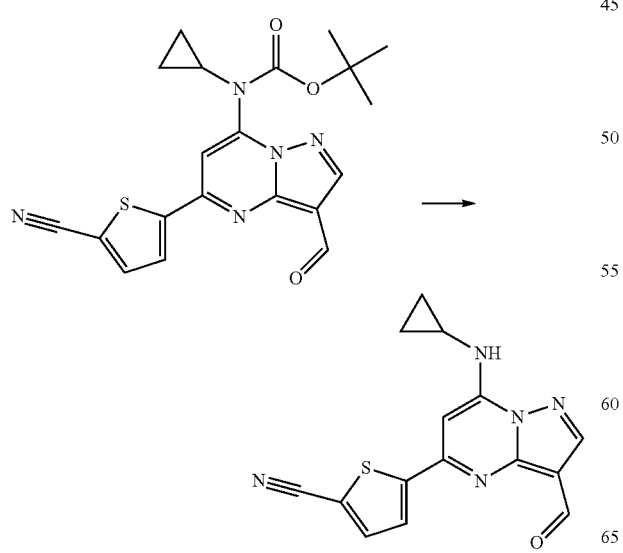

232

Same procedure as [Example 98]. LCMS (M+1=310)

Example 155

Synthesis of 5-(7-(cyclopropylamino)-3-((2,5-dioxoimidazolidin-4-ylidene)methyl)pyrazolo[1,5-a]pyrimidin-5-yl)thiophene-2-carbonitrile

Same procedure as [Example 99]. LCMS (M+1=392)

Example 156

Synthesis of 5-(7-(tert-butoxycarbonyl(cyclopropyl)amino)-3-formylpyrazolo[1,5-a]pyrimidin-5-yl)thiophene-2-carboxylic acid

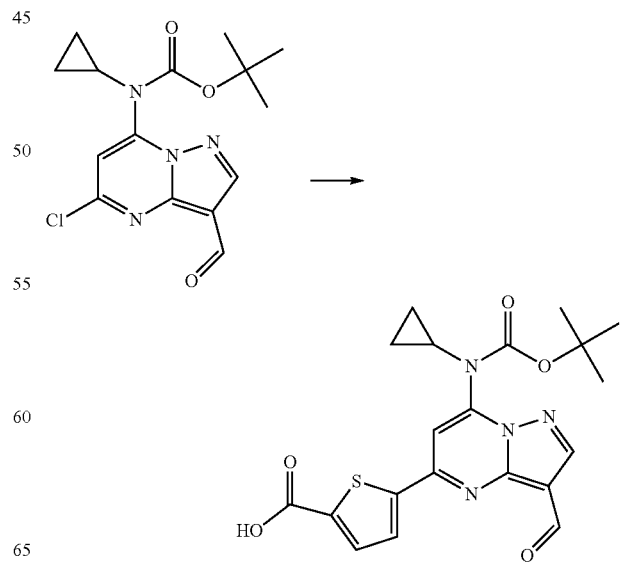

233

To tert-butyl 5-chloro-3-formylpyrazolo[1,5-a]pyrimidin-7-yl (cyclopropyl)carbamate (1 g, 2.97 mmol) in 30 mL of a 2:1 mixture of 1,2-dimethoxyethane/EtOH was added 2-carboxythiophene-5-boronic acid (766 mg, 4.45 mmol), tetrakis(triphenylphosphine)palladium(0) (171 mg, 0.148 mmol), and 2M aqueous solution of $Na_2CO_3$ (4.45 mL, 8.91 mmol). The mixture was stirred at 95° C. for 3 hours then cooled to room temperature and partitioned between 2N NaOH and ethyl acetate. The layers were separated and the aqueous layer was acidified to pH<3 with conc. HCl. The aqueous layer was extracted (3×) with methylene chloride. The combined organic layers was washed with brine, dried over $MgSO_4$, filtered, and evaporated to dryness to provide 450 mg of 5-(7-(tert-butoxycarbonyl(cyclopropyl)amino)-3-formylpyrazolo[1,5-a]pyrimidin-5-yl)thiophene-2-carboxylic acid. Some additional material which was in the first ethyl acetate layer was purified by silica gel chromatography (0%-20% $MeOH/CH_2Cl_2$) to provide another 550 mg of 5-(7-(tert-butoxycarbonyl(cyclopropyl)amino)-3-formylpyrazolo[1,5-a]pyrimidin-5-yl)thiophene-2-carboxylic acid (79%). LCMS (M+1=429)

Example 157

Synthesis of 5-(7-(cyclopropylamino)-3-formylpyrazolo[1,5-a]pyrimidin-5-yl)thiophene-2-carboxylic acid

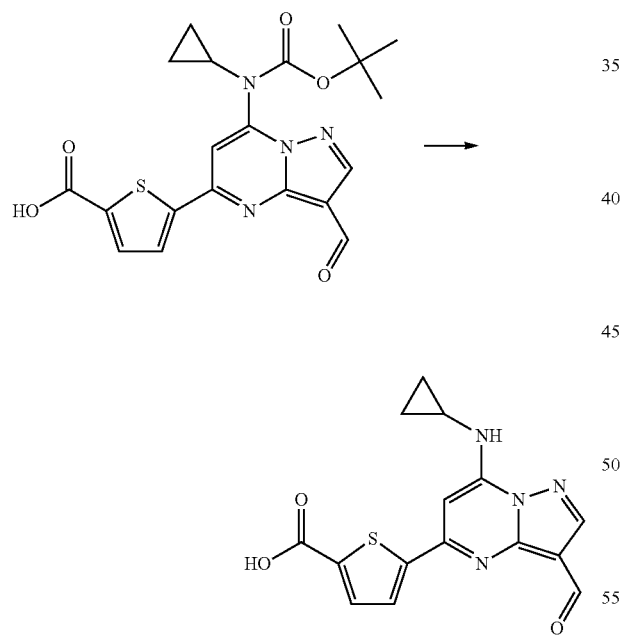

To 5-(7-(tert-butoxycarbonyl(cyclopropyl)amino)-3-formylpyrazolo[1,5-a]pyrimidin-5-yl)thiophene-2-carboxylic acid (1 g, 2.33 mmol) was added 8 mL of 4M HCl in dioxane and another 5 mL of dioxane. The reaction mixture was stirred at 80° C. for 2 hours, cooled to room temperature and partitioned between $CH_2Cl_2$ and $H_2O$. The emulsion that formed between the layers was filtered off and rinsed with $H_2O$. The recovered solid was dried under vacuum to provide 627 mg of 5-(7-(cyclopropylamino)-3-formylpyrazolo[1,5-a]pyrimidin-5-yl)thiophene-2-carboxylic acid as a red solid (82%). LCMS (M+1=329)

Example 158

Synthesis of 5-(7-(cyclopropylamino)-3-formylpyrazolo[1,5-a]pyrimidin-5-yl)-N-(3-methoxypropyl)thiophene-2-carboxamide

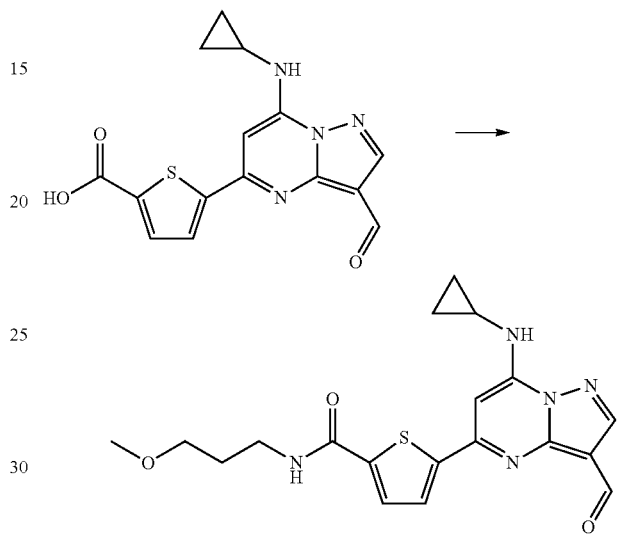

To 5-(7-(cyclopropylamino)-3-formylpyrazolo[1,5-a]pyrimidin-5-yl)thiophene-2-carboxylic acid (30 mg, 0.091 mmol), EDCI (19 mg, 0.10 mmol), $Et_3N$ (14 µL, 0.10 mmol), and HOBt (14 mg, 0.10 mmol) in 2 mL of DMF pre-stirred for 5 minutes was added 3-methoxypropylamine (10 µL, 0.10 mmol). The reaction mixture was stirred at room temperature for 1 hour. The reaction was diluted with ethyl acetate, washed with $H_2O$, brine, dried over $MgSO_4$, filtered, and evaporated to dryness to provide 30 mg of 547-(cyclopropylamino)-3-formylpyrazolo[1,5-a]pyrimidin-5-yl)-N-(3-methoxypropyl)thiophene-2-carboxamide (83%). LCMS (M+1=400)

Example 159

Synthesis of 5-(7-(cyclopropylamino)-3-((2,5-dioxoimidazolidin-4-ylidene)methyl)pyrazolo[1,5-a]pyrimidin-5-yl)-N-(3-methoxypropyl)thiophene-2-carboxamide

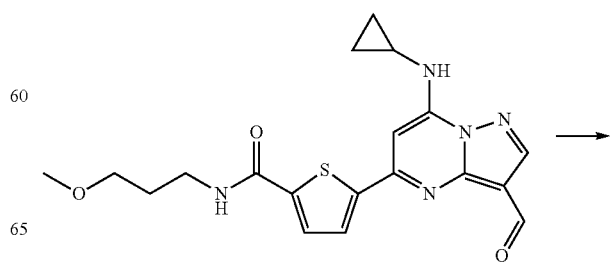

-continued

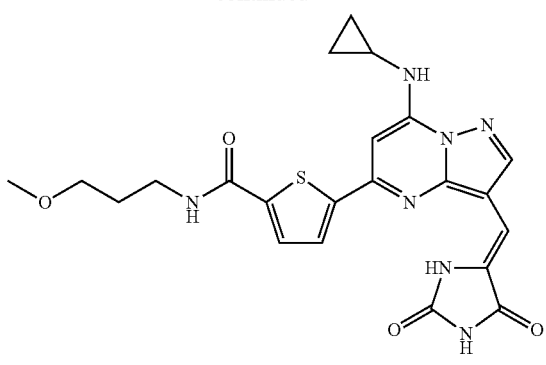

To 5-(7-(cyclopropylamino)-3-formylpyrazolo[1,5-a]pyrimidin-5-yl)-N-(3-methoxypropyl)thiophene-2-carboxamide (30 mg, 0.075 mmol) in EtOH (1 mL) was added piperidine (20 µL, 0.150 mmol), and hydantoin (10 mg, 0.075 mmol). The reaction mixture was stirred at 85° C. for 3 hours. The solid formed was isolated by filtration to provide 5-(7-(cyclopropylamino)-3-((2,5-dioxoimidazolidin-4-ylidene)methyl)pyrazolo[1,5-a]pyrimidin-5-yl)-N-(3-methoxypropyl)thiophene-2-carboxamide. LCMS (M+1=482)

Example 160

Synthesis of 5-(7-(cyclopropylamino)-3-formylpyrazolo[1,5-a]pyrimidin-5-yl)thiophene-2-carboxamide

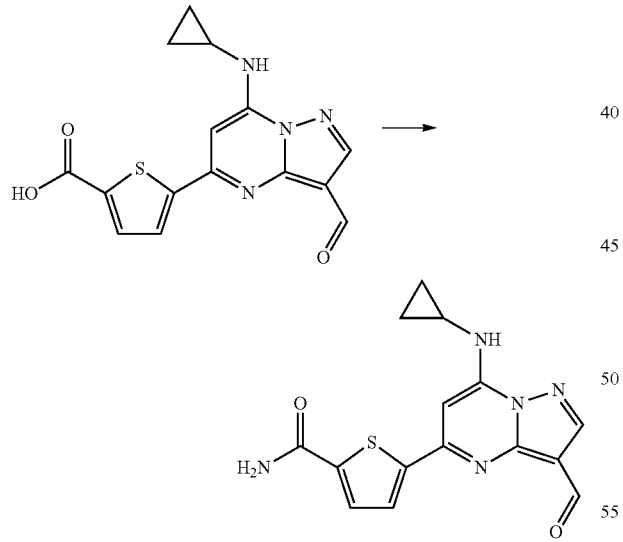

To 5-(7-(cyclopropylamino)-3-formylpyrazolo[1,5-a]pyrimidin-5-yl)thiophene-2-carboxylic acid (40 mg, 0.122 mmol), HATU (70 mg, 0.183 mmol), HOBt (4 mg, 0.024 mmol) and DIEA (85 µL, 0.488 mmol) in 2 mL of DMF was added ammonium chloride (20 mg, 0.366 mmol). The reaction mixture was stirred at room temperature for 1 hour. The reaction mixture was diluted with ethyl acetate washed with saturated NaHCO₃ solution, brine, dried over MgSO4, filtered, and evaporated to dryness to provide 42 mg of 5-(7-(cyclopropylamino)-3-formylpyrazolo[1,5-a]pyrimidin-5-yl)thiophene-2-carboxamide (100%). LCMS (M+1=328).

Example 161

Synthesis of 5-(7-(cyclopropylamino)-3-((2,5-dioxoimidazolidin-4-ylidene)methyl)pyrazolo[1,5-a]pyrimidin-5-yl)thiophene-2-carboxamide

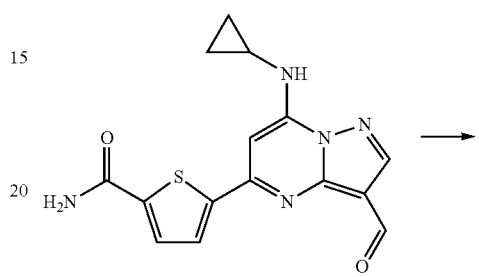

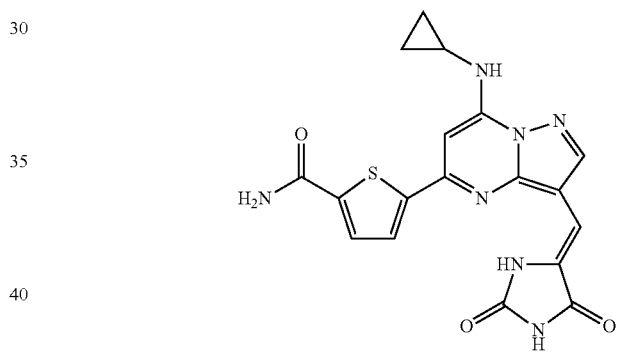

Same procedure as [Example 159]. LCMS (M+1=410)

The compounds described in the following table were prepared using chemistries similar to those exemplified in Example 158 and Example 159. All compounds were characterized by LCMS. Table 23B shows the biological activities of the compounds listed in Table 23A.

TABLE 23A

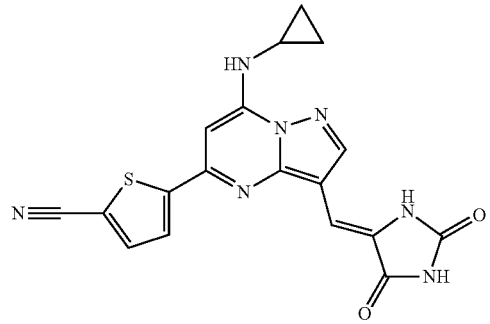 [SMILES: N#Cc1ccc(-c2cc(NC3CC3)n3ncc(/C=C4\NC(=O)NC4=O)c3n2)s1]

TABLE 23A-continued
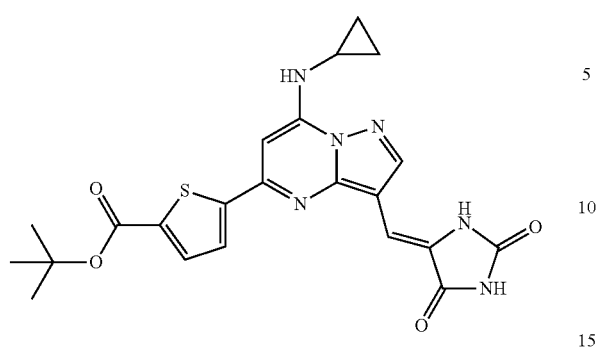
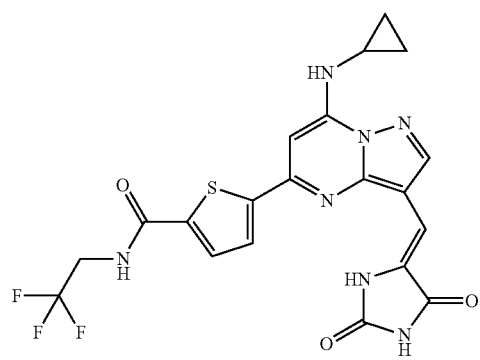 [SMILES: O=C1NC(=O)/C(=C/c2cnn3c(NC4CC4)cc(-c4ccc(C(=O)NCC(F)(F)F)s4)nc23)N1]
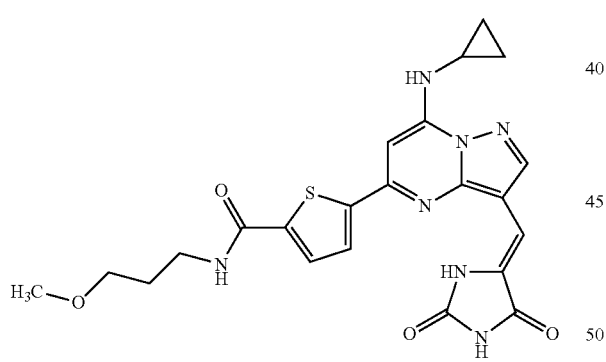
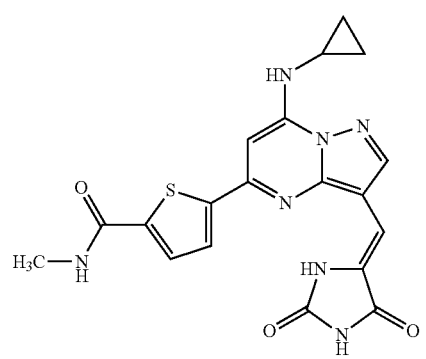 [SMILES: CNC(=O)c1ccc(-c2cc(NC3CC3)n3ncc(/C=C4\NC(=O)NC4=O)c3n2)s1]
TABLE 23A-continued
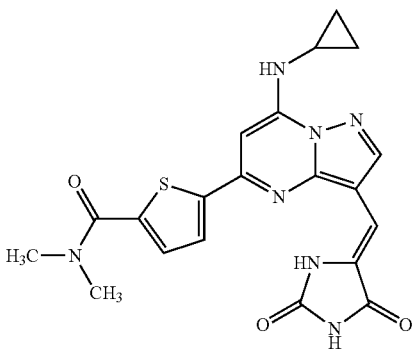
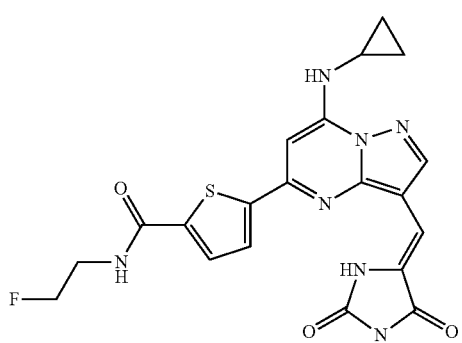
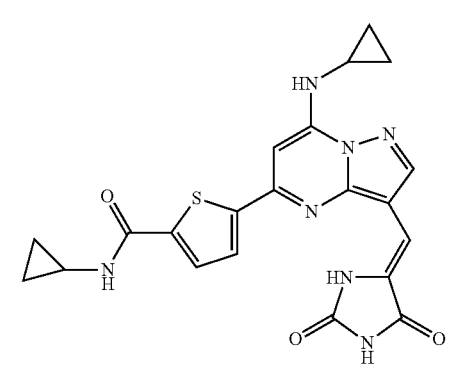 [SMILES: O=C1NC(=O)/C(=C/c2cnn3c(NC4CC4)cc(-c4ccc(C(=O)NC5CC5)s4)nc23)N1]
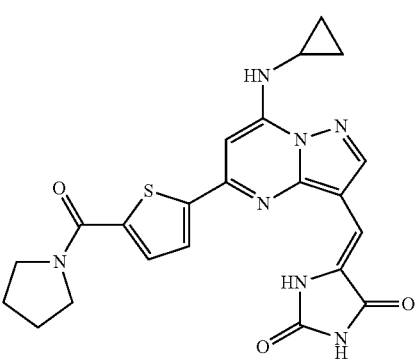 [SMILES: O=C1NC(=O)/C(=C/c2cnn3c(NC4CC4)cc(-c4ccc(C(=O)N5CCCC5)s4)nc23)N1]

TABLE 23A-continued
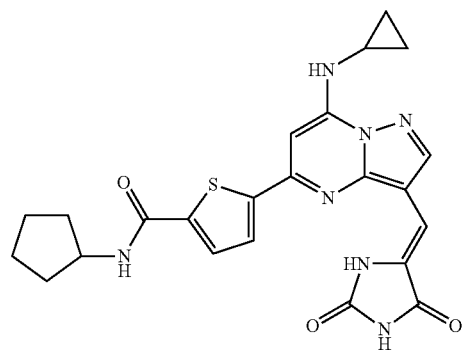 [SMILES: O=C1NC(=O)/C(=C/c2cnn3c(NC4CC4)cc(-c4ccc(C(=O)NC5CCCC5)s4)nc23)N1]
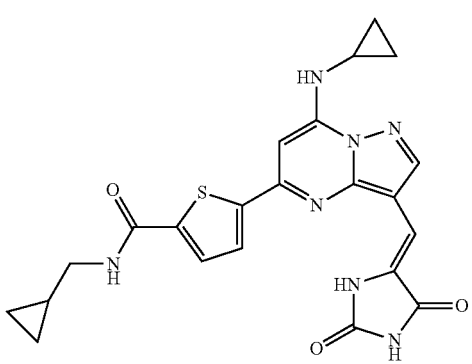 [SMILES: O=C1NC(=O)/C(=C/c2cnn3c(NC4CC4)cc(-c4ccc(C(=O)NCC5CC5)s4)nc23)N1]
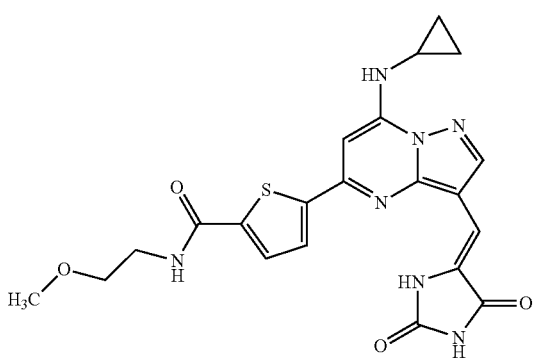 [SMILES: COCCNC(=O)c1ccc(-c2cc(NC3CC3)n3ncc(/C=C4\NC(=O)NC4=O)c3n2)s1]
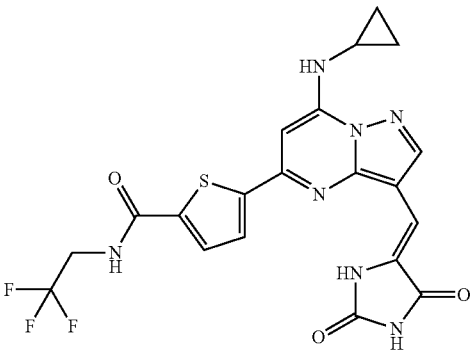 [SMILES: O=C1NC(=O)/C(=C/c2cnn3c(NC4CC4)cc(-c4ccc(C(=O)NCC(F)(F)F)s4)nc23)N1]
TABLE 23A-continued
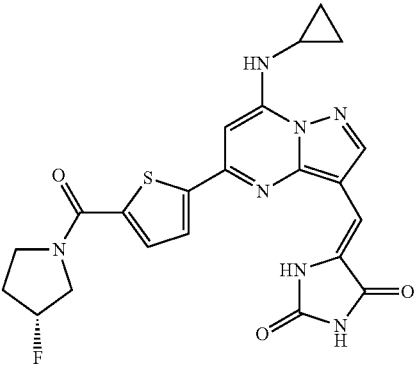
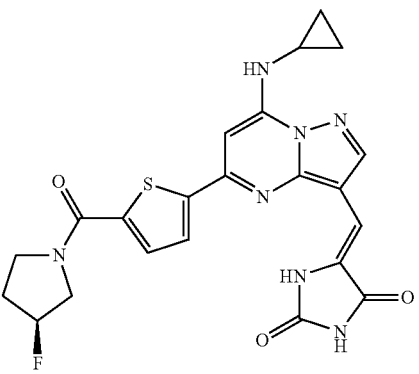
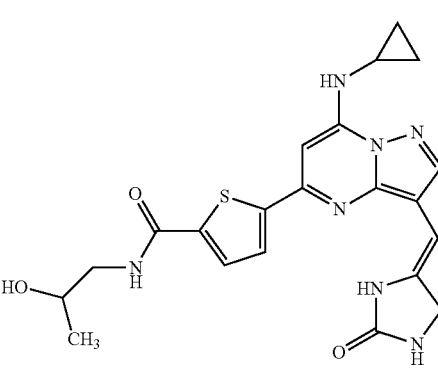
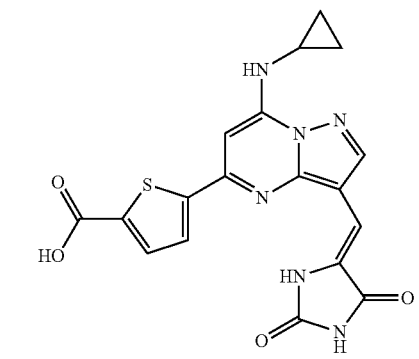 [SMILES: O=C1NC(=O)/C(=C/c2cnn3c(NC4CC4)cc(-c4ccc(C(=O)O)s4)nc23)N1]

TABLE 23A-continued
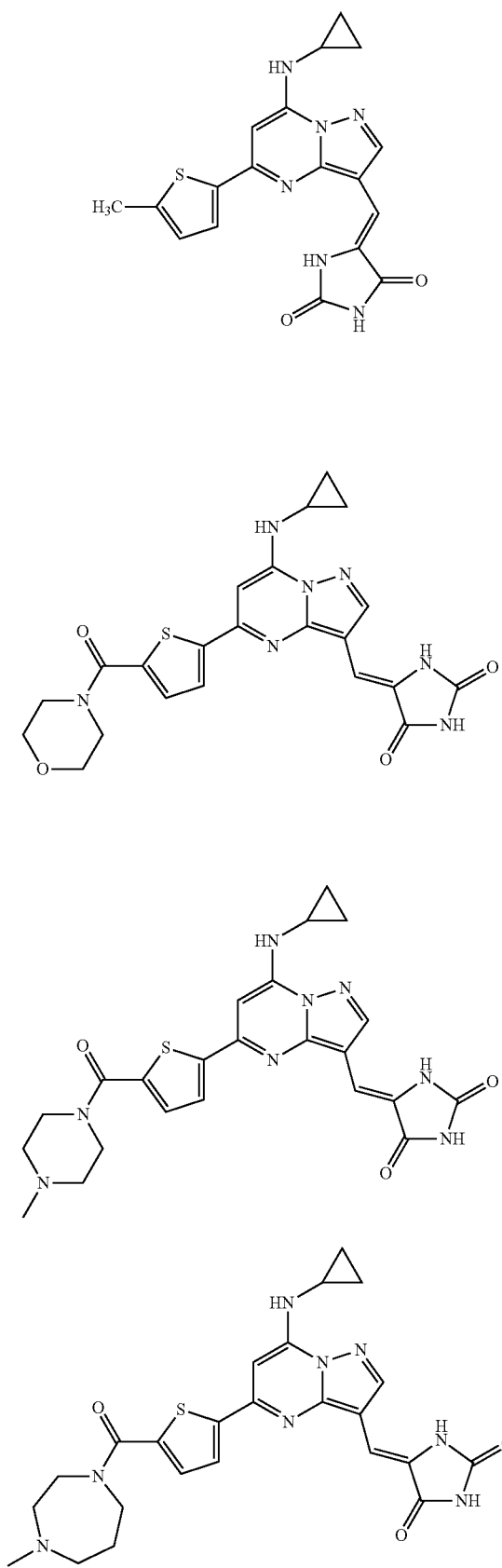
TABLE 23A-continued
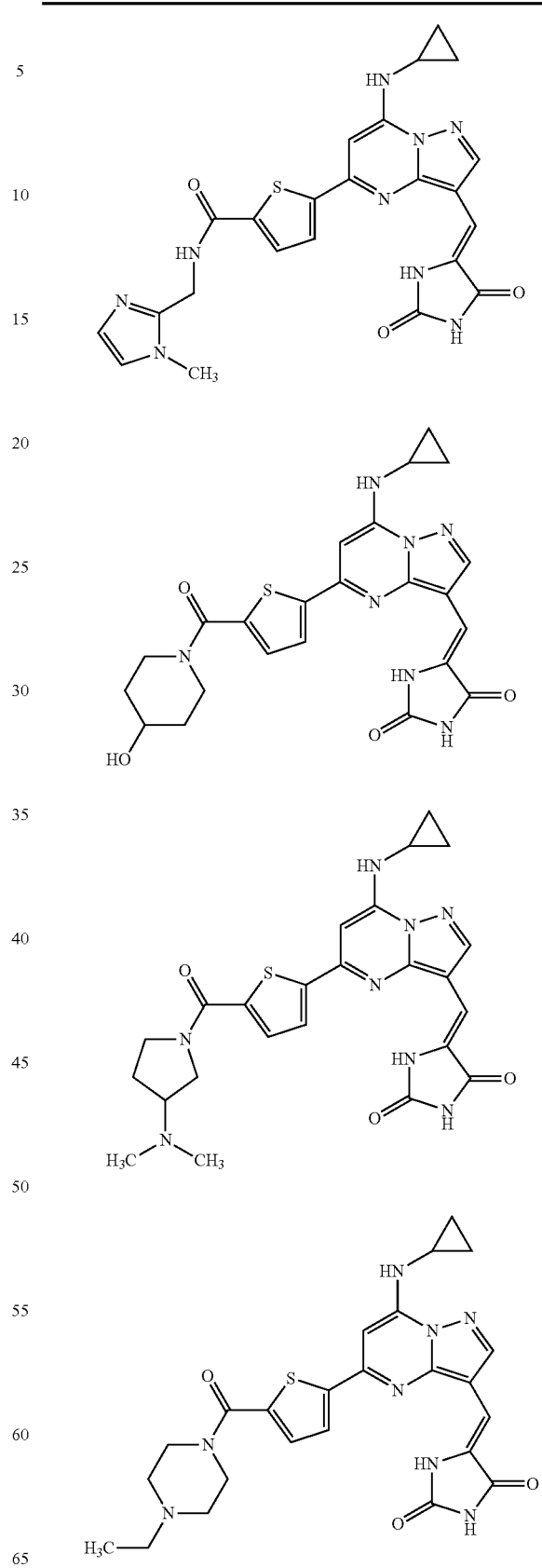

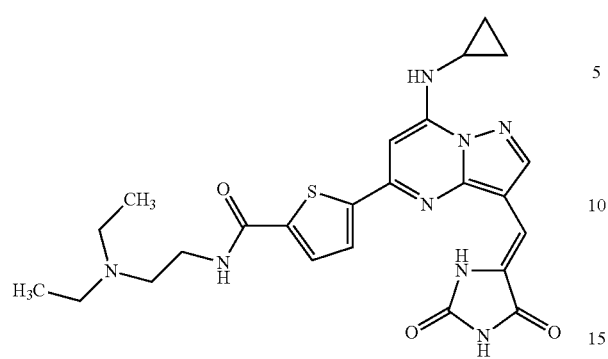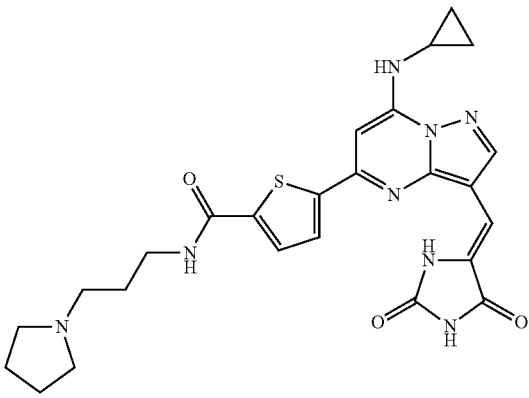 [SMILES: O=C1NC(=O)/C(=C/c2cnn3c(NC4CC4)cc(-c4ccc(C(=O)NCCCN5CCCC5)s4)nc23)N1]

TABLE 23A-continued
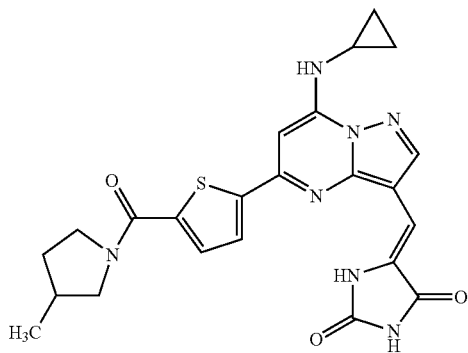 [SMILES: CC1CCN(C(=O)c2ccc(-c3cc(NC4CC4)n4ncc(/C=C5\NC(=O)NC5=O)c4n3)s2)C1]
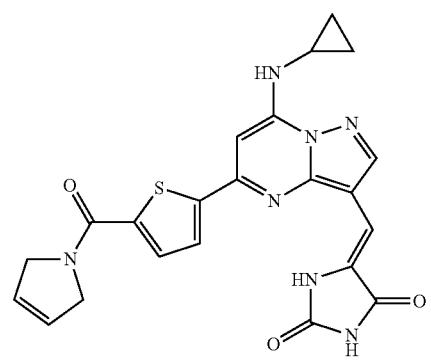 [SMILES: O=C1NC(=O)/C(=C/c2cnn3c(NC4CC4)cc(-c4ccc(C(=O)N5CC=CC5)s4)nc23)N1]
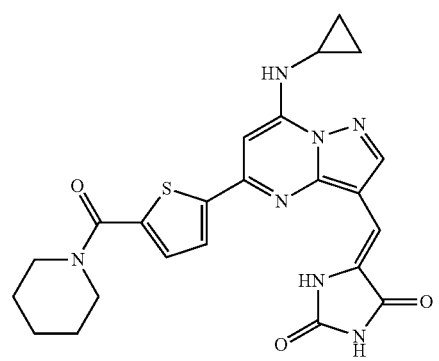 [SMILES: O=C1NC(=O)/C(=C/c2cnn3c(NC4CC4)cc(-c4ccc(C(=O)N5CCCCC5)s4)nc23)N1]
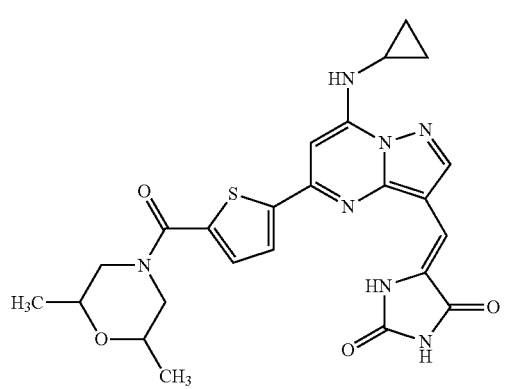 [SMILES: CC1CN(C(=O)c2ccc(-c3cc(NC4CC4)n4ncc(/C=C5\NC(=O)NC5=O)c4n3)s2)CC(C)O1]
TABLE 23A-continued
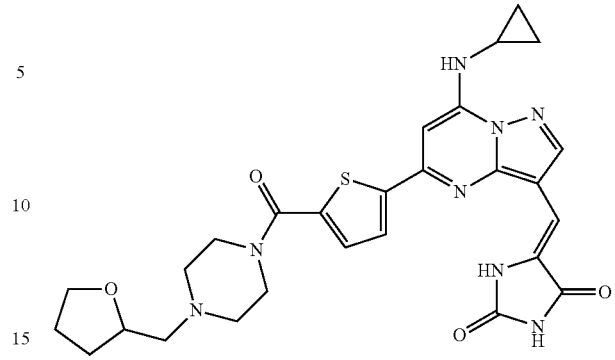
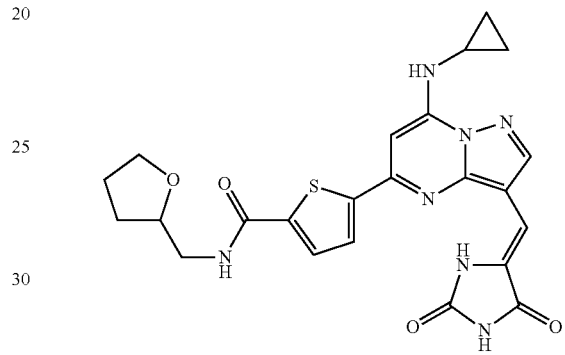
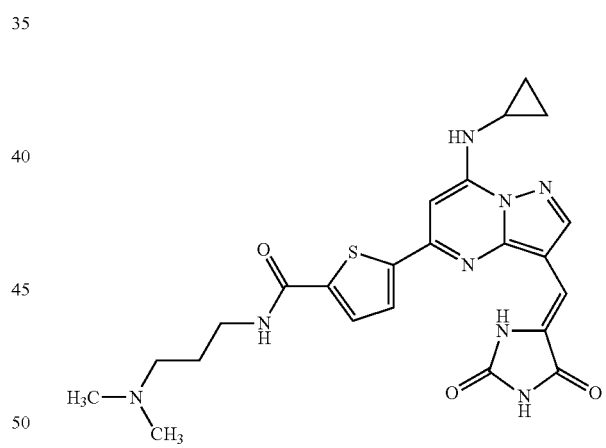
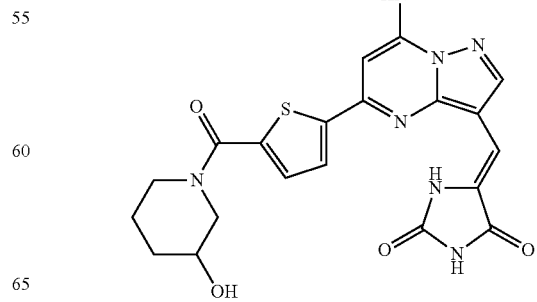

TABLE 23A-continued
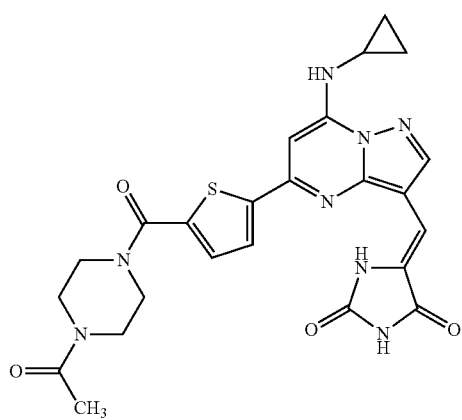 [SMILES: CC(=O)N1CCN(C(=O)c2ccc(-c3cc(NC4CC4)n4ncc(/C=C5\NC(=O)NC5=O)c4n3)s2)CC1]
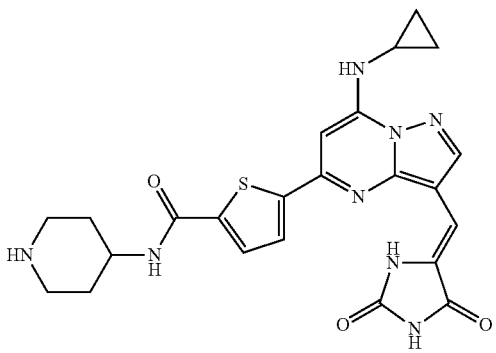 [SMILES: O=C1NC(=O)/C(=C/c2cnn3c(NC4CC4)cc(-c4ccc(C(=O)NC5CCNCC5)s4)nc23)N1]
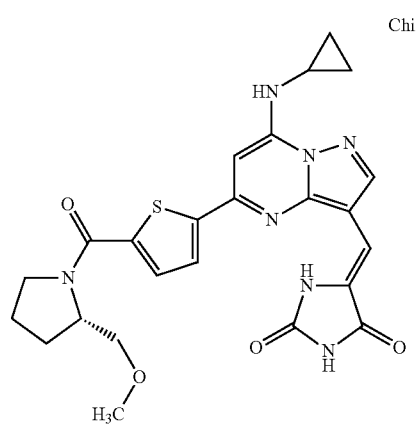
Chiral
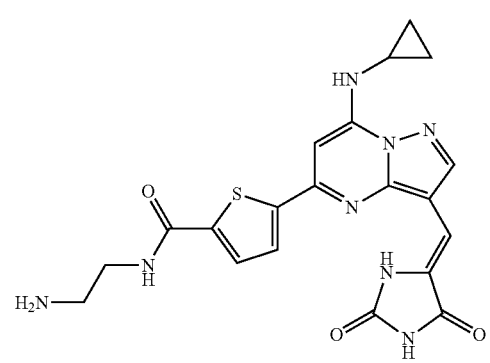 [SMILES: NCCNC(=O)c1ccc(-c2cc(NC3CC3)n3ncc(/C=C4\NC(=O)NC4=O)c3n2)s1]
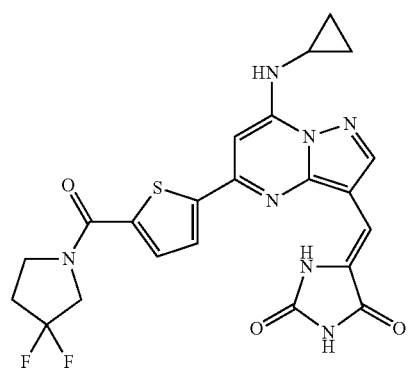
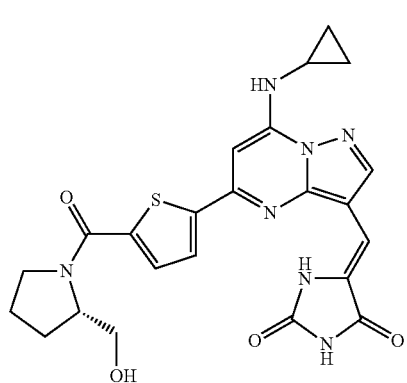 [SMILES: O=C1NC(=O)/C(=C/c2cnn3c(NC4CC4)cc(-c4ccc(C(=O)N5CCC[C@H]5CO)s4)nc23)N1]
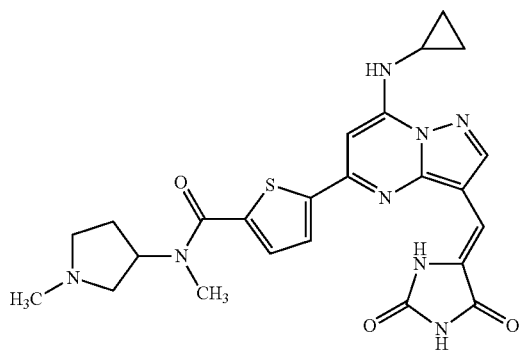
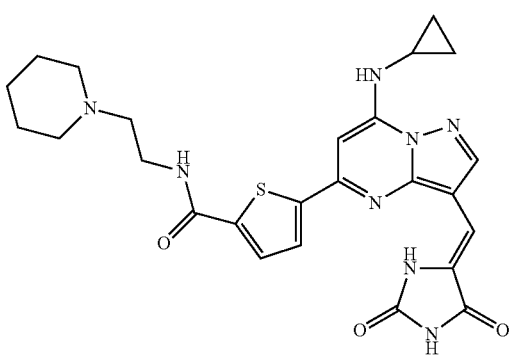 [SMILES: O=C1NC(=O)/C(=C/c2cnn3c(NC4CC4)cc(-c4ccc(C(=O)NCCN5CCCCC5)s4)nc23)N1]

TABLE 23A-continued
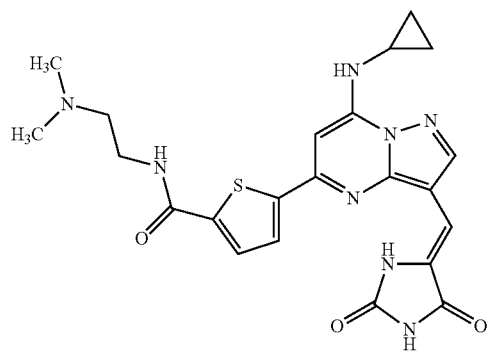 [SMILES: CN(C)CCNC(=O)c1ccc(-c2cc(NC3CC3)n3ncc(/C=C4\NC(=O)NC4=O)c3n2)s1]
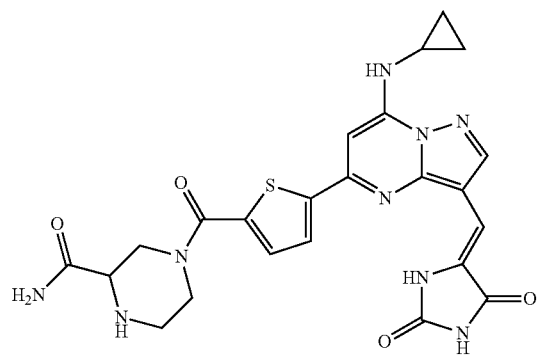
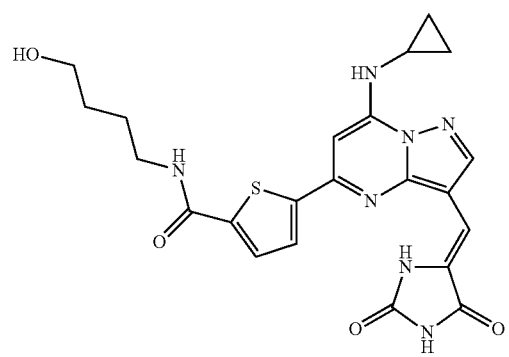 [SMILES: O=C1NC(=O)/C(=C/c2cnn3c(NC4CC4)cc(-c4ccc(C(=O)NCCCCO)s4)nc23)N1]
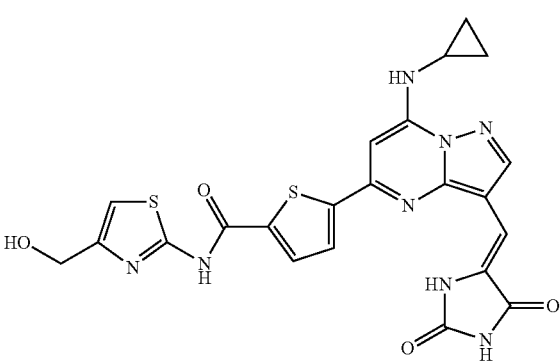
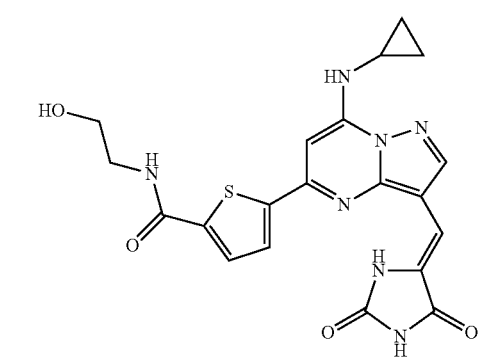 [SMILES: O=C1NC(=O)/C(=C/c2cnn3c(NC4CC4)cc(-c4ccc(C(=O)NCCO)s4)nc23)N1]
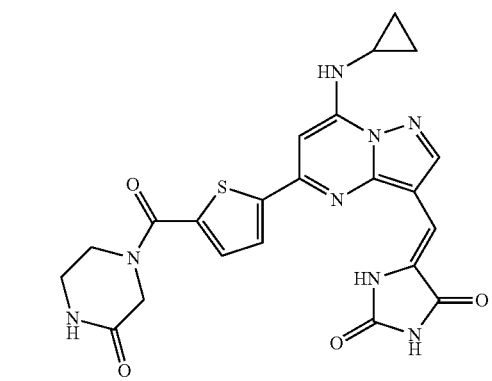
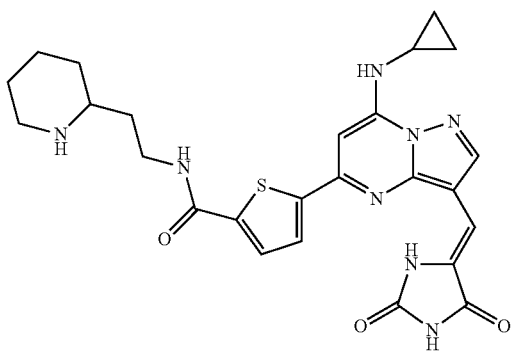 [SMILES: O=C1NC(=O)/C(=C/c2cnn3c(NC4CC4)cc(-c4ccc(C(=O)NCCC5CCCCN5)s4)nc23)N1]
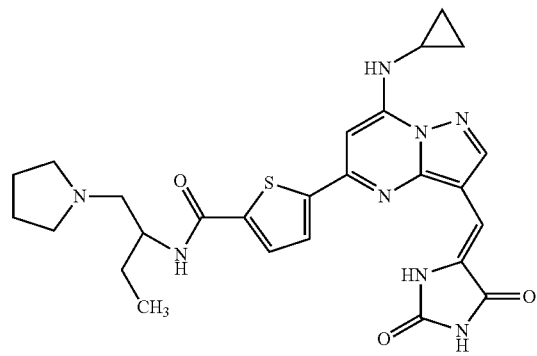 [SMILES: CCC(CN1CCCC1)NC(=O)c1ccc(-c2cc(NC3CC3)n3ncc(/C=C4\NC(=O)NC4=O)c3n2)s1]

TABLE 23A-continued
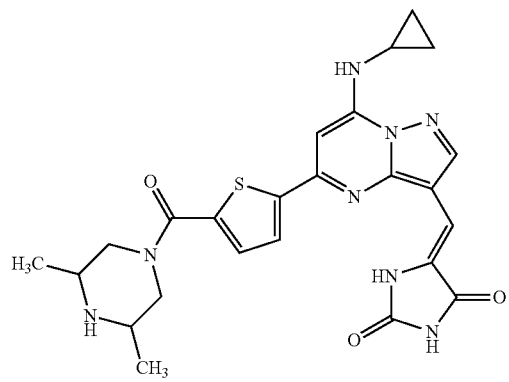 [SMILES: CC1CN(C(=O)c2ccc(-c3cc(NC4CC4)n4ncc(/C=C5\NC(=O)NC5=O)c4n3)s2)CC(C)N1]
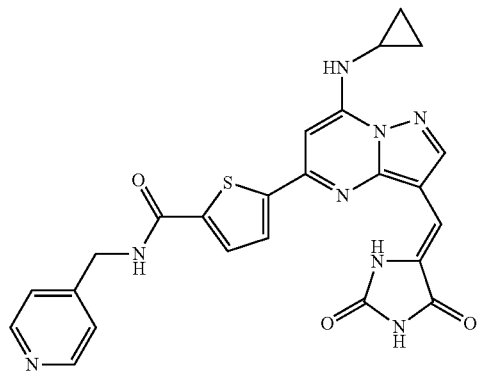
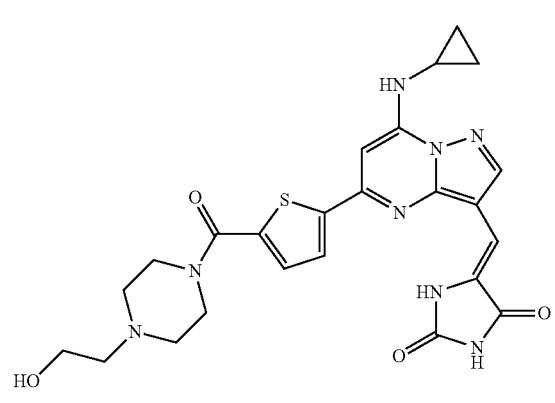 [SMILES: O=C1NC(=O)/C(=C/c2cnn3c(NC4CC4)cc(-c4ccc(C(=O)N5CCN(CCO)CC5)s4)nc23)N1]
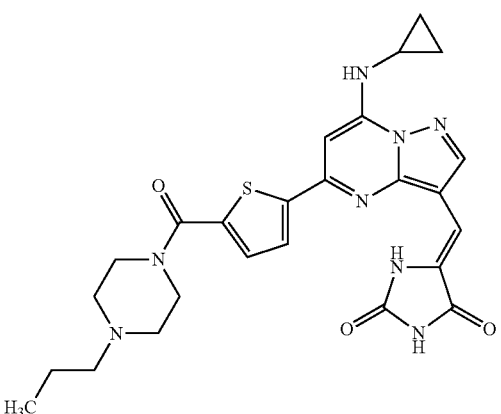
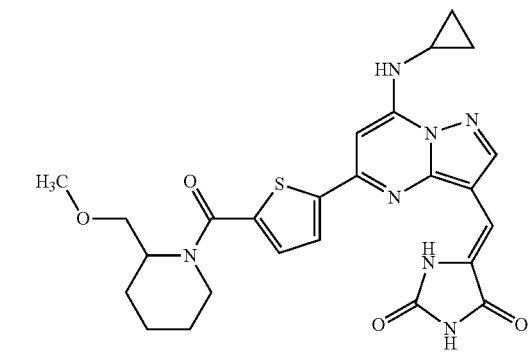 [SMILES: COCC1CCCCN1C(=O)c1ccc(-c2cc(NC3CC3)n3ncc(/C=C4\NC(=O)NC4=O)c3n2)s1]
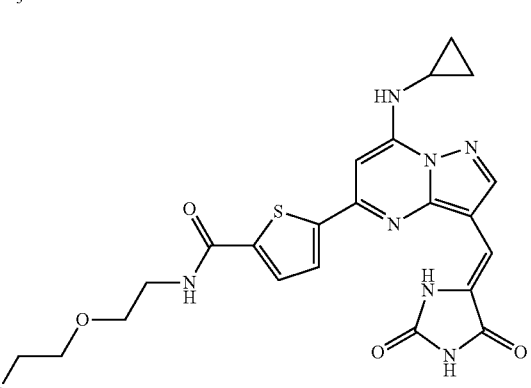
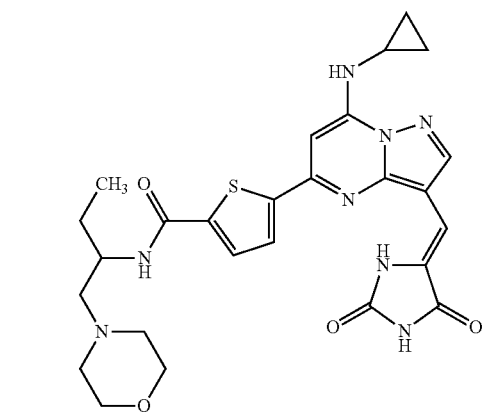 [SMILES: CCC(CN1CCOCC1)NC(=O)c1ccc(-c2cc(NC3CC3)n3ncc(/C=C4\NC(=O)NC4=O)c3n2)s1]
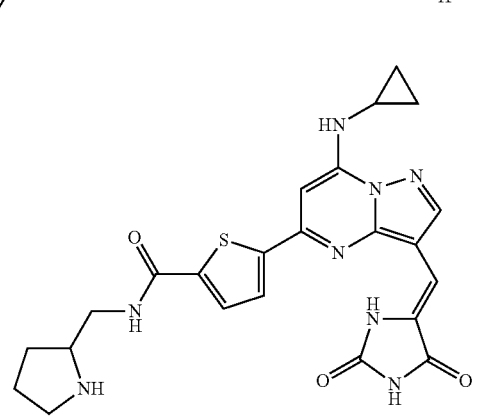

TABLE 23A-continued
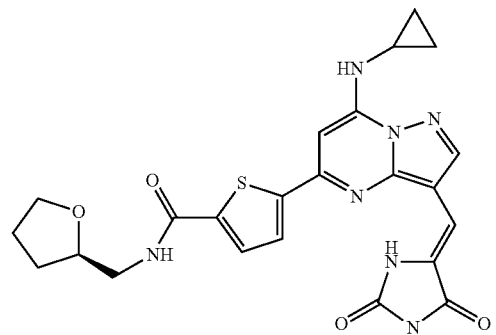
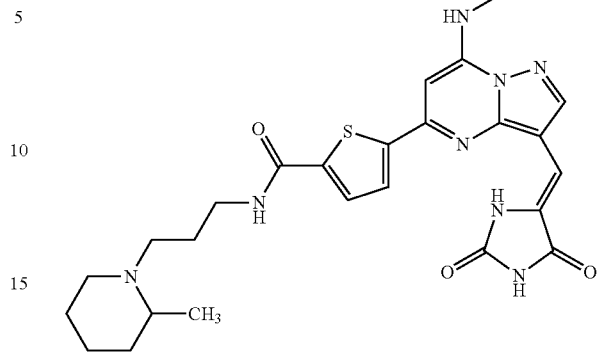
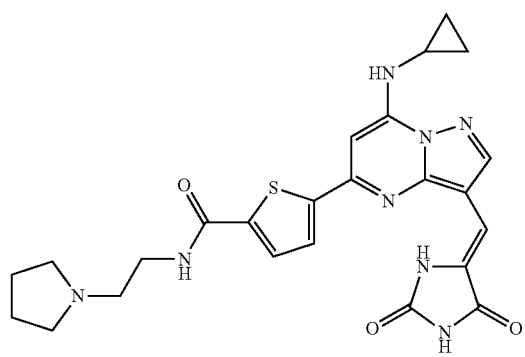 [SMILES: O=C1NC(=O)/C(=C/c2cnn3c(NC4CC4)cc(-c4ccc(C(=O)NCCN5CCCC5)s4)nc23)N1]
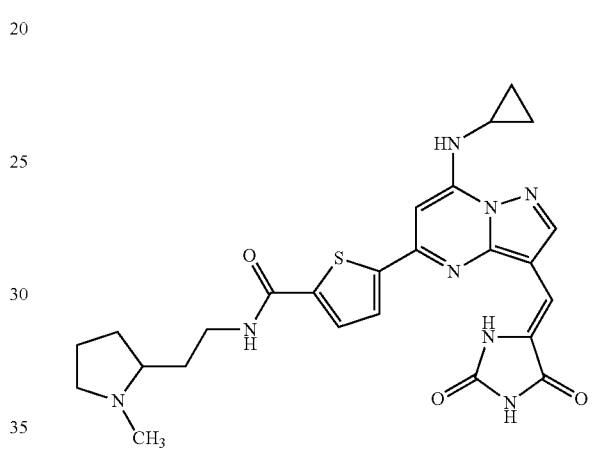
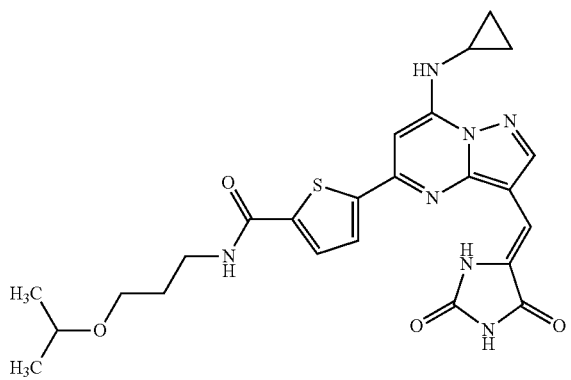 [SMILES: CC(C)OCCCNC(=O)c1ccc(-c2cc(NC3CC3)n3ncc(/C=C4\NC(=O)NC4=O)c3n2)s1]
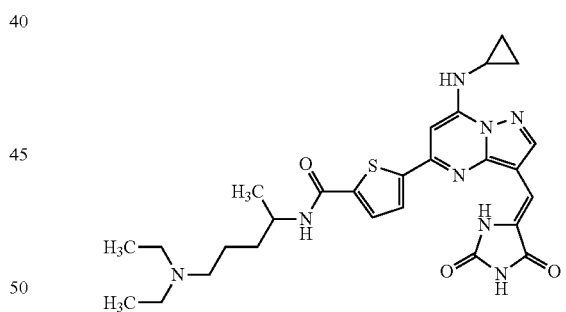
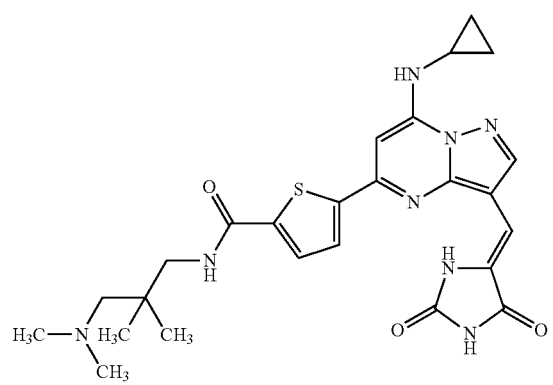 [SMILES: CN(C)CC(C)(C)CNC(=O)c1ccc(-c2cc(NC3CC3)n3ncc(/C=C4\NC(=O)NC4=O)c3n2)s1]

TABLE 23A-continued
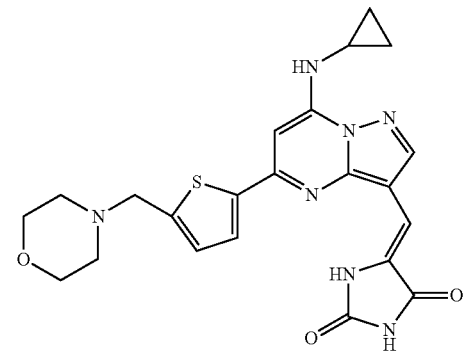 [SMILES: O=C1NC(=O)/C(=C/c2cnn3c(NC4CC4)cc(-c4ccc(CN5CCOCC5)s4)nc23)N1]
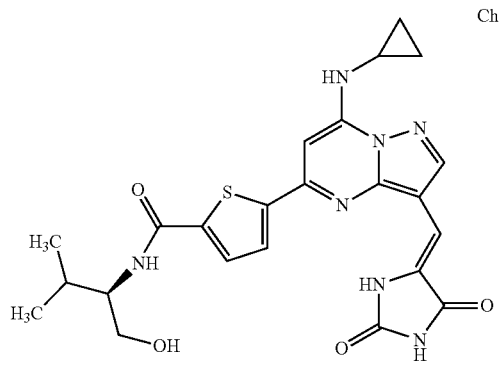
Chiral
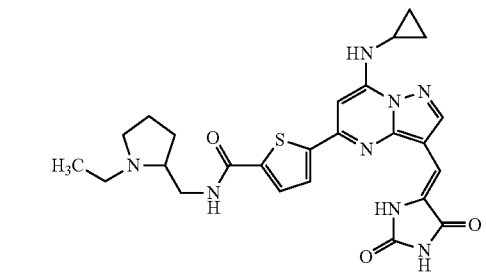 [SMILES: CCN1CCCC1CNC(=O)c1ccc(-c2cc(NC3CC3)n3ncc(/C=C4\NC(=O)NC4=O)c3n2)s1]
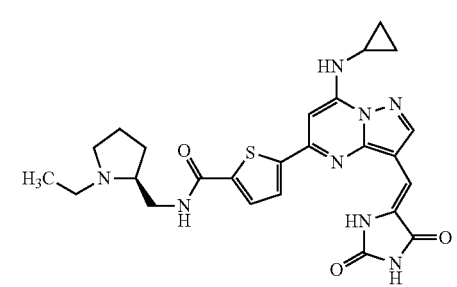
Chiral
TABLE 23A-continued
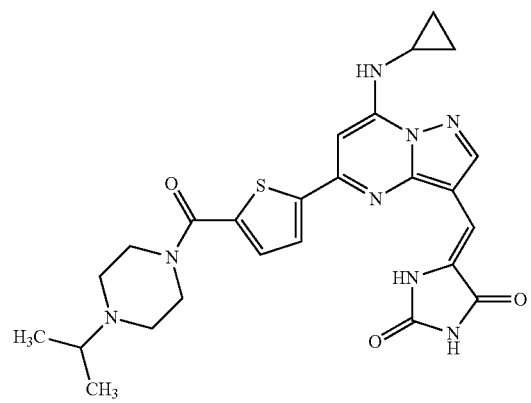 [SMILES: CC(C)N1CCN(C(=O)c2ccc(-c3cc(NC4CC4)n4ncc(/C=C5\NC(=O)NC5=O)c4n3)s2)CC1]
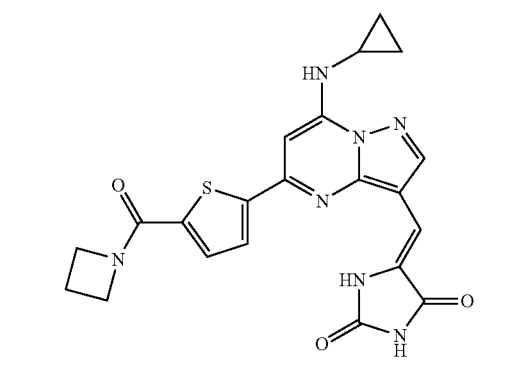 [SMILES: O=C1NC(=O)/C(=C/c2cnn3c(NC4CC4)cc(-c4ccc(C(=O)N5CCC5)s4)nc23)N1]
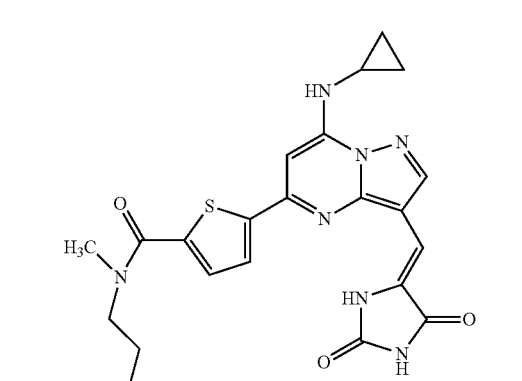

TABLE 23A-continued
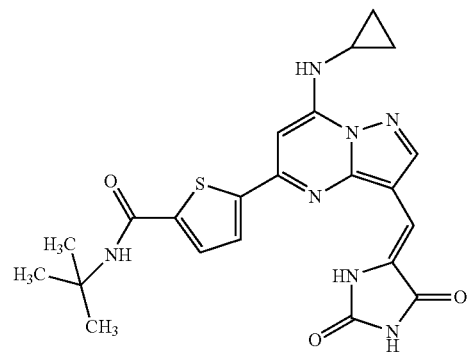 [SMILES: CC(C)(C)NC(=O)c1ccc(-c2cc(NC3CC3)n3ncc(/C=C4\NC(=O)NC4=O)c3n2)s1]
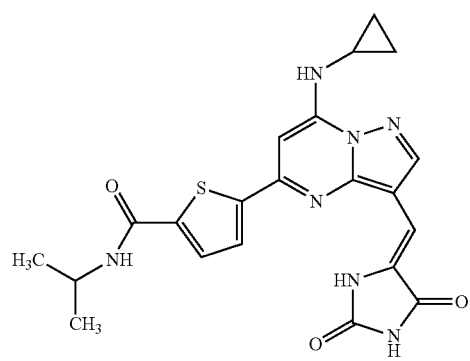 [SMILES: CC(C)NC(=O)c1ccc(-c2cc(NC3CC3)n3ncc(/C=C4\NC(=O)NC4=O)c3n2)s1]
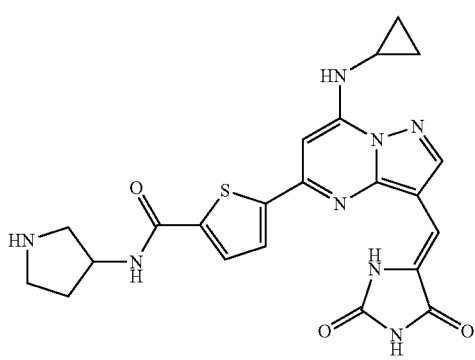 [SMILES: O=C1NC(=O)/C(=C/c2cnn3c(NC4CC4)cc(-c4ccc(C(=O)NC5CCNC5)s4)nc23)N1]
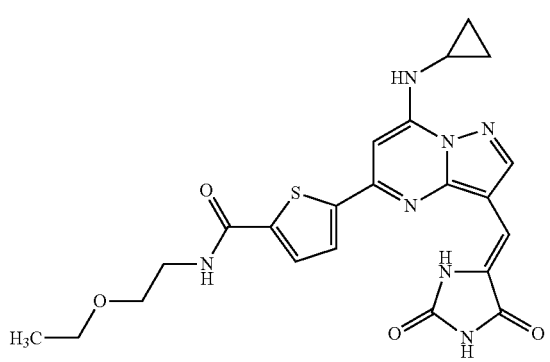 [SMILES: CCOCCNC(=O)c1ccc(-c2cc(NC3CC3)n3ncc(/C=C4\NC(=O)NC4=O)c3n2)s1]
TABLE 23A-continued
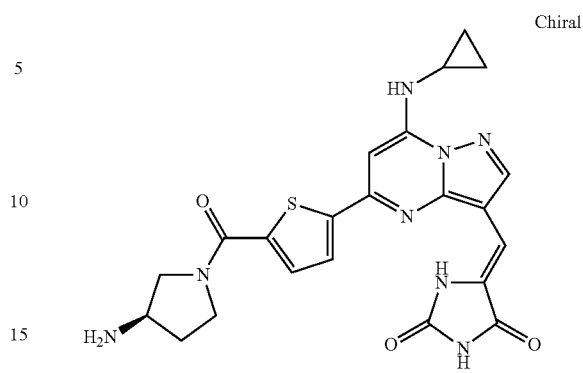
Chiral
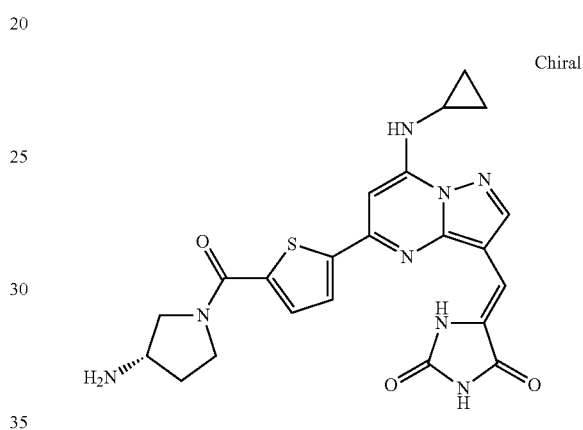
Chiral
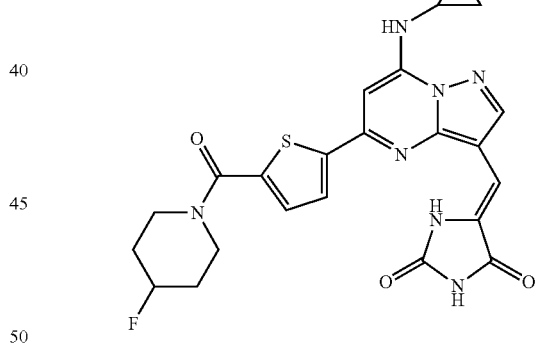
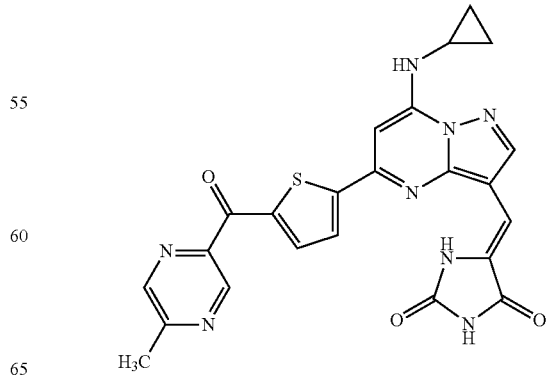

TABLE 23A-continued
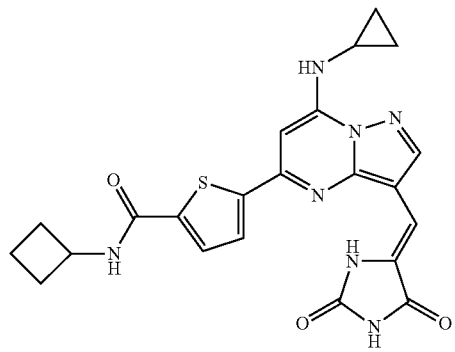 [SMILES: O=C1NC(=O)/C(=C/c2cnn3c(NC4CC4)cc(-c4ccc(C(=O)NC5CCC5)s4)nc23)N1]
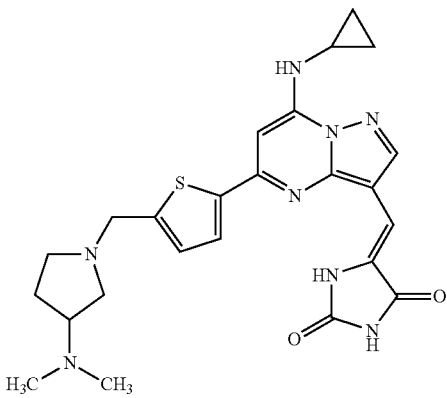
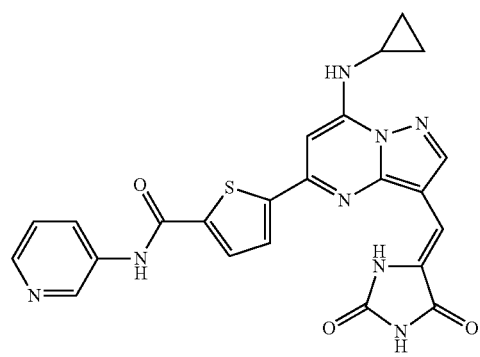 [SMILES: O=C1NC(=O)/C(=C/c2cnn3c(NC4CC4)cc(-c4ccc(C(=O)Nc5cccnc5)s4)nc23)N1]
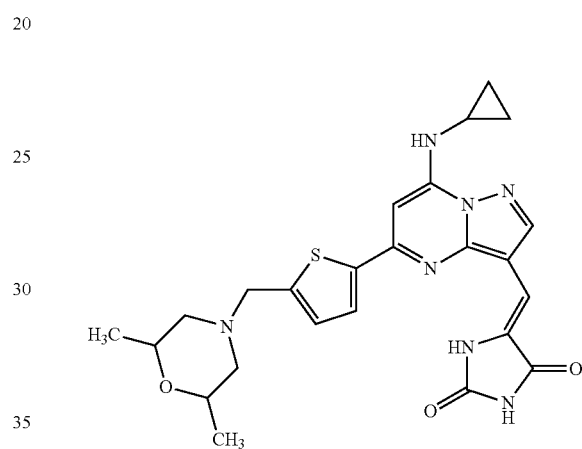
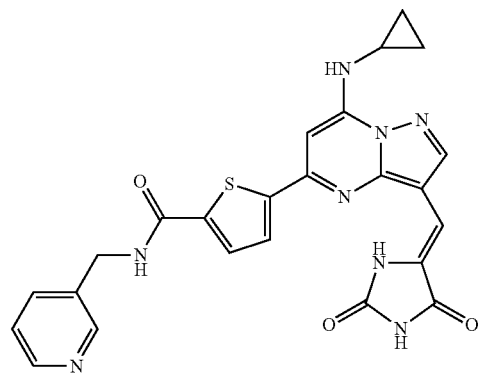 [SMILES: O=C1NC(=O)/C(=C/c2cnn3c(NC4CC4)cc(-c4ccc(C(=O)NCc5cccnc5)s4)nc23)N1]
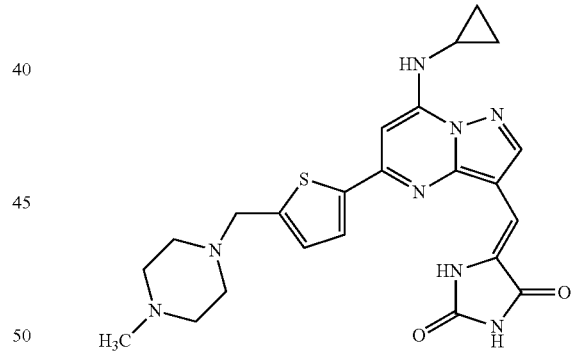
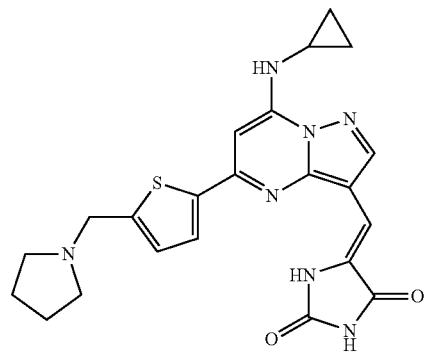 [SMILES: O=C1NC(=O)/C(=C/c2cnn3c(NC4CC4)cc(-c4ccc(CN5CCCC5)s4)nc23)N1]
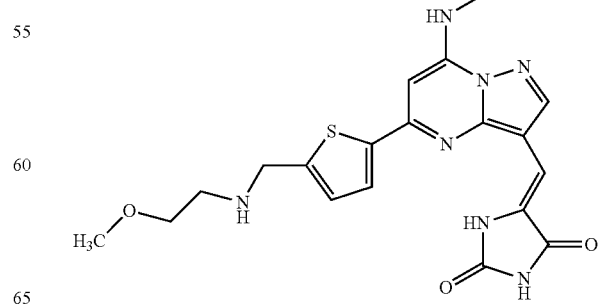

TABLE 23A-continued
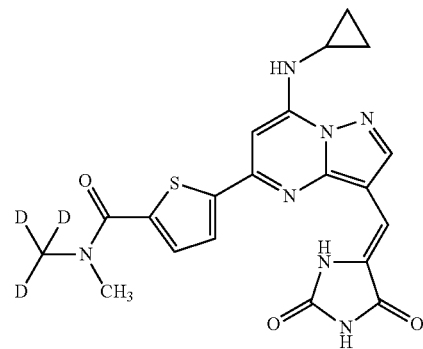 [SMILES: [2H]C([2H])([2H])N(C)C(=O)c1ccc(-c2cc(NC3CC3)n3ncc(/C=C4\NC(=O)NC4=O)c3n2)s1]
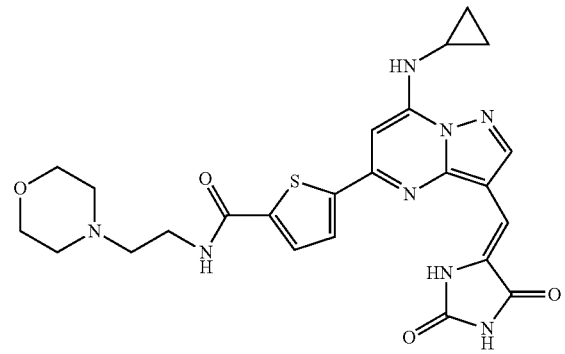
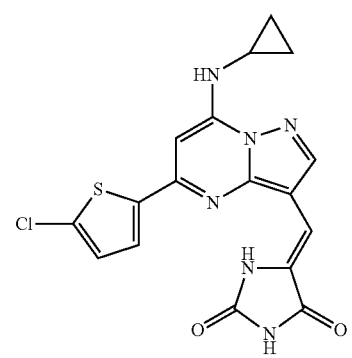 [SMILES: O=C1NC(=O)/C(=C/c2cnn3c(NC4CC4)cc(-c4ccc(Cl)s4)nc23)N1]
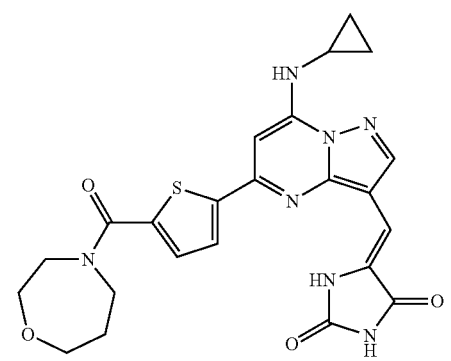
Chiral
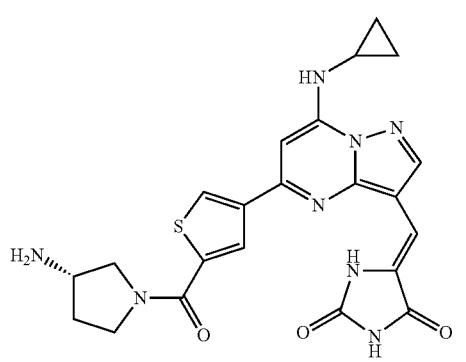
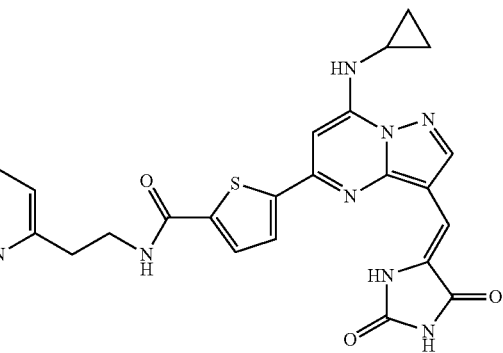
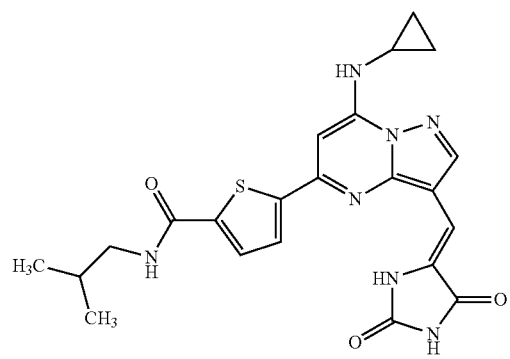 [SMILES: CC(C)CNC(=O)c1ccc(-c2cc(NC3CC3)n3ncc(/C=C4\NC(=O)NC4=O)c3n2)s1]
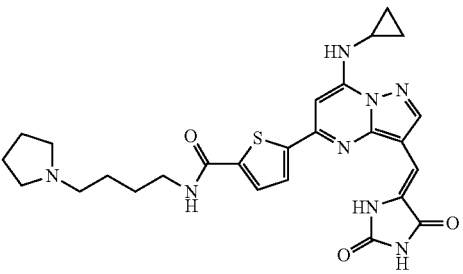 [SMILES: O=C1NC(=O)/C(=C/c2cnn3c(NC4CC4)cc(-c4ccc(C(=O)NCCCCN5CCCC5)s4)nc23)N1]

TABLE 23A-continued
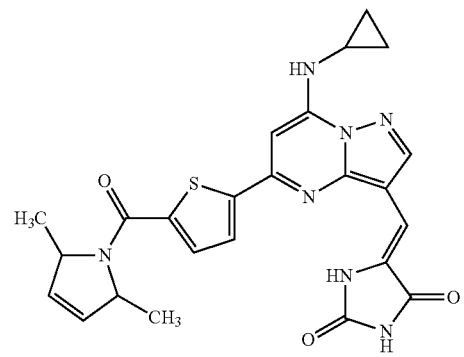 [SMILES: CC1C=CC(C)N1C(=O)c1ccc(-c2cc(NC3CC3)n3ncc(/C=C4\NC(=O)NC4=O)c3n2)s1]
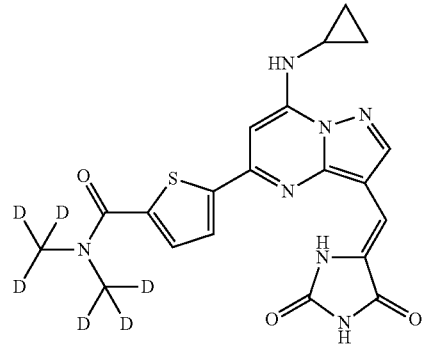
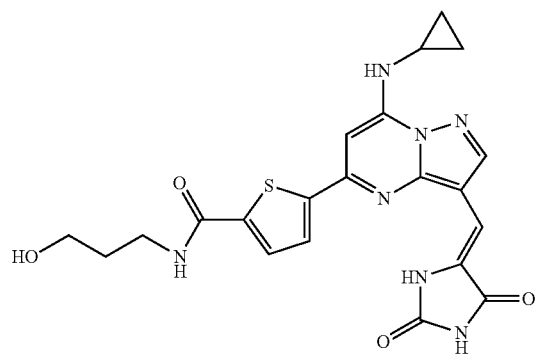 [SMILES: O=C1NC(=O)/C(=C/c2cnn3c(NC4CC4)cc(-c4ccc(C(=O)NCCCO)s4)nc23)N1]
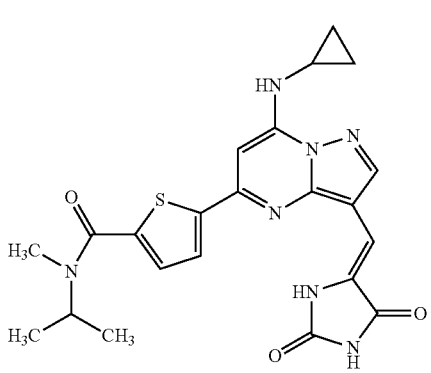
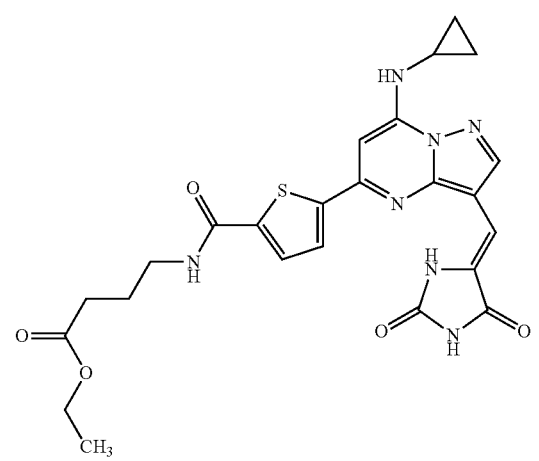 [SMILES: CCOC(=O)CCCNC(=O)c1ccc(-c2cc(NC3CC3)n3ncc(/C=C4\NC(=O)NC4=O)c3n2)s1]
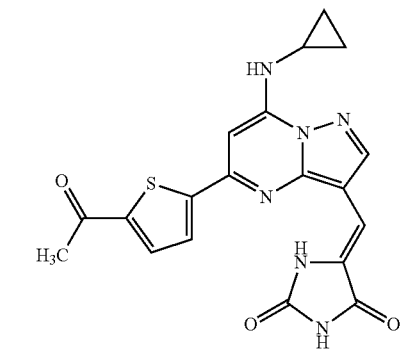
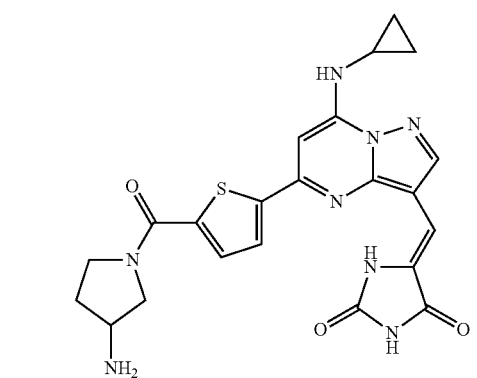 [SMILES: NC1CCN(C(=O)c2ccc(-c3cc(NC4CC4)n4ncc(/C=C5\NC(=O)NC5=O)c4n3)s2)C1]
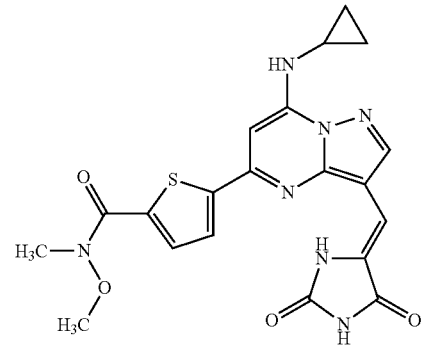 [SMILES: CON(C)C(=O)c1ccc(-c2cc(NC3CC3)n3ncc(/C=C4\NC(=O)NC4=O)c3n2)s1]

TABLE 23A-continued

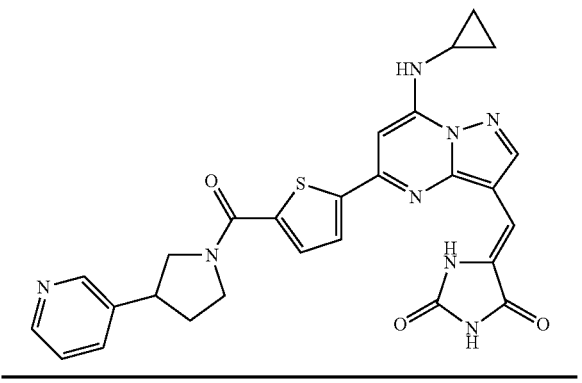

TABLE 23B

| Compound | CK2: IC50 (μM) | PIM2: IC50 (5 μM ATP) | AB: MDAMB453 (μM) | AB: BxPC3 (μM) |
|---|---|---|---|---|
| S8 | <0.01 | 1.1336 | 0.648 | 0.99 |
| T8 | <0.01 | >2.5000 | 0.141 | 0.837 |
| U8 | <0.01 | 1.0091 | 10.145 | 6.668 |
| V8 | <0.01 | >2.5000 | 0.416 | >30 |
| W8 | <0.01 | >2.5000 | 0.425 | 0.417 |
| X8 | <0.01 | >2.5000 | 0.689 | >30 |
| Y8 | <0.01 | >2.5000 | 0.358 | 0.642 |
| Z8 | <0.01 | >2.5000 | 0.162 | 1.15 |
| A9 | <0.01 | >2.5000 | 0.542 | 1 |
| B9 | <0.01 | >2.5000 | 0.49 | 3.925 |
| C9 | <0.01 | >2.5000 | 0.171 | 0.822 |
| D9 | <0.01 | >2.5000 | 0.869 | 1.983 |
| E9 | <0.01 | >2.5000 | 0.397 | 0.496 |
| F9 | <0.01 | >2.5000 | 0.312 | 0.643 |
| G9 | <0.01 | >2.5000 | 0.31 | 0.657 |
| H9 | <0.01 | >2.5000 | 0.251 | 10.512 |
| I9 | <0.01 | 0.7137 | >30 | >30 |
| J9 | <0.01 | >2.5000 | 0.795 | 1.736 |
| K9 | <0.01 | >2.5000 | 9.378 | 11.666 |
| L9 | <0.01 | >2.5000 | 2.066 | 3.829 |
| M9 | <0.01 | >2.5000 | 1.266 | 1.469 |
| N9 | <0.01 |  | 1.134 | 5.413 |
| O9 | <0.01 |  | 0.621 | 12.558 |
| P9 | <0.01 |  | 0.596 | 0.5 |
| Q9 | <0.01 |  | 1.044 | 2.134 |
| R9 | <0.01 |  | 1.554 | 1.555 |
| S9 | <0.01 |  | 5.882 | 5.532 |
| T9 | <0.01 |  | 0.444 | 0.956 |
| U9 | <0.01 |  | 1.479 | 4.863 |
| V9 | <0.01 |  | 1.567 | 2.905 |
| W9 | <0.01 |  | 1.145 | 0.885 |
| X9 | <0.01 | >2.5000 | 1.391 | >30 |
| Y9 | <0.01 | >2.5000 | 0.389 | 0.438 |
| Z9 | <0.01 | >2.5000 | 0.762 | 1.337 |
| A10 | <0.01 | >2.5000 | 0.408 | 2.115 |
| B10 | <0.01 | >2.5000 | 0.895 | 1.167 |
| C10 | <0.01 | 0.7939 | 0.66 | 2.399 |
| D10 | <0.01 | >2.5000 | 1.529 | 6.508 |
| E10 | <0.01 | >2.5000 | 0.557 | 0.624 |
| F10 | <0.01 | >2.5000 | 0.251 | 0.323 |
| G10 | <0.01 | >2.5000 | 1.038 | 0.995 |
| H10 | <0.01 | >2.5000 | 0.294 | 2.968 |
| I10 | <0.01 | >2.5000 | 0.813 | 1.386 |
| J10 | <0.01 | >2.5000 | 0.613 | 0.324 |
| K10 | <0.01 | >2.5000 | 0.579 | 0.451 |
| L10 | <0.01 | >2.5000 | 2.275 | 0.792 |
| M10 | <0.01 | 1.7758 | 5.94 | 0.677 |
| N10 | <0.01 | >2.5000 | 0.958 | 0.455 |
| O10 | <0.01 | 1.8944 | 0.537 | 0.297 |
| P10 | <0.01 | >2.5000 | 0.394 | 0.451 |
| Q10 | <0.01 | >2.5000 | 1.782 | 16.637 |
| R10 | <0.01 | >2.5000 | 1.641 | 5.729 |
| S10 | <0.01 | >2.5000 | 10.053 | 18.645 |
| T10 | <0.1 | >2.5000 | >30 | >30 |

TABLE 23B-continued

| Compound | CK2: IC50 (μM) | PIM2: IC50 (5 μM ATP) | AB: MDAMB453 (μM) | AB: BxPC3 (μM) |
|---|---|---|---|---|
| U10 | <0.01 | >2.5000 | 13.297 | 21.203 |
| V10 | <0.01 | 2.1321 | >30 | >30 |
| W10 | <0.01 | 1.3653 | 0.236 | 0.63 |
| X10 | <0.01 | >2.5000 | 0.937 | 0.917 |
| Y10 | <0.01 | >2.5000 | 0.79 | >30 |
| Z10 | <0.01 | >2.5000 | 2.336 | 22.798 |
| A11 | <0.01 | >2.5000 | 0.458 | 0.724 |
| B11 | <0.01 | >2.5000 | >30 | 1.262 |
| C11 | <0.01 | >2.5000 | 27.783 | 3.302 |
| D11 | <0.01 | >2.5000 | 1.445 | 2.265 |
| E11 | <0.01 | >2.5000 | 1.298 | 2.948 |
| F11 | <0.01 | >2.5000 | 0.567 | 0.903 |
| G11 | <0.01 | 2.0441 | 0.231 | 0.494 |
| H11 | <0.01 | >2.5000 | 1.11 | 2.705 |
| I11 | <0.01 | >2.5000 | 1.232 | 0.591 |
| J11 | <0.01 | >2.5000 | 0.833 | 1.234 |
| K11 | <0.01 | >2.5000 | 0.546 | 1.257 |
| L11 | <0.01 | >2.5000 | 1.004 | 0.816 |
| M11 | <0.01 | >2.5000 | 1.016 | 0.745 |
| N11 | <0.01 | >2.5000 | 1.266 | 2.261 |
| O11 | <0.01 | >2.5000 | 0.887 | 4.986 |
| P11 | <0.01 | >2.5000 | 0.487 | 0.517 |
| Q11 | <0.01 | >2.5000 | 0.621 | 0.564 |
| R11 | <0.01 | >2.5000 | 0.845 | 2.309 |
| S11 | <0.01 | >2.5000 | 1.935 | >30 |
| T11 | <0.01 | >2.5000 | 0.193 | >30 |
| U11 | <0.01 | >2.5000 | 0.618 | 5.349 |
| V11 | <0.01 | >2.5000 | 0.892 | 1.6 |
| W11 | <0.01 | >2.5000 | 0.156 | 3.435 |
| X11 | <0.01 | 1.7245 | 3.806 | 0.225 |
| Y11 | <0.01 | >2.5000 | 1.402 | 0.352 |
| Z11 | <0.01 | 1.2434 | 2.251 | 0.355 |
| A12 | <0.01 | 1.4396 | 1.151 | 0.445 |
| B12 | <0.01 | >2.5000 | 0.399 | 2.764 |
| C12 | <0.01 | >2.5000 | >30 | >30 |
| D12 | <0.01 | >2.5000 | 0.683 | 0.854 |
| E12 | <0.01 | >2.5000 | 29.518 | 2.348 |
| F12 | <0.01 | >2.5000 | >30 | >30 |
| G12 | <0.01 | 0.8106 | 0.658 | 0.352 |
| H12 | <0.01 | >2.5000 | 0.449 | 0.418 |
| I12 | <0.01 | >2.5000 | 1.282 | 1.516 |
| J12 | <0.01 | >2.5000 | 0.52 | 0.94 |
| K12 | <0.01 | 1.872 | 1.338 | 0.379 |
| L12 | <0.01 | >2.5000 | 0.498 | >30 |
| M12 | <0.01 | 1.2604 | 7.403 | 8.736 |
| N12 | <0.01 |  | 3.52 | >30 |
| O12 | <0.01 | >2.5000 | 1.077 | 2.509 |
| P12 | <0.01 | >2.5000 | 1.014 | 3.421 |
| Q12 | <0.01 | >2.5000 | 0.942 | 7.084 |
| R12 | <0.01 | >2.5000 | 0.846 | 14.096 |
| S12 | <0.01 | >2.5000 | 1.034 | 4.897 |
| T12 | <0.01 | >2.5000 | 0.767 | 2.662 |
| U12 | <0.01 | >2.5000 | 0.525 | >30 |
| V12 | <0.01 |  | 1.759 | >30 |
| W12 | <0.01 |  | 1.041 | 1.184 |
| X12 | <0.01 |  | 7.54 | >30 |
| Y12 | <0.01 |  | 0.692 | 1.706 |
| Z12 | <0.01 |  | 2.17 | 9.892 |
| A13 | <0.01 | >2.5000 | 0.534 | 0.996 |
| B13 | <0.01 | >2.5000 | 0.388 | 2.584 |

Example 162

Synthesis of 4-(7-(tert-butoxycarbonyl(cyclopropyl)amino)-3-formylpyrazolo[1,5-a]pyrimidin-5-yl)thiophene-2-carboxylic acid

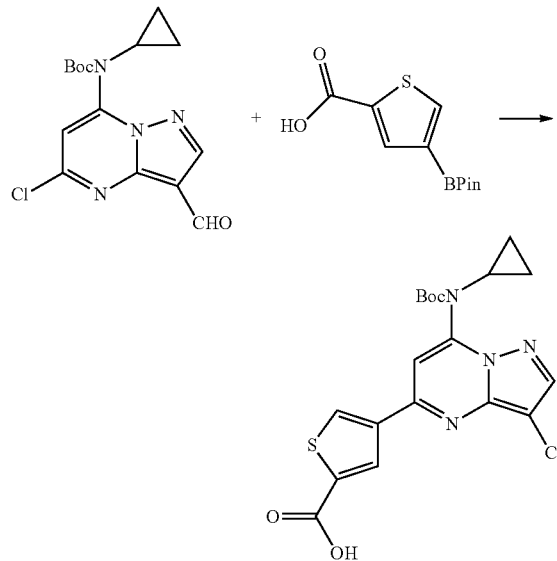

Tert-butyl 5-chloro-3-formylpyrazolo[1,5-a]pyrimidine-7-yl)(cyclopropyl)carbamate (0.5 g, 1.48 mmol) and commercially available (Combi-Blocks) 2-carboxythiophene-4-boronic acid pinacol ester (754 mg, 2.97 mmol) were dissolved in acetonitrile. 2M Na$_2$CO$_3$ (1 mL) was added and the solution was degassed with a stream of N$_2$ for 10 min. PdCl$_2$dppf·CH$_2$Cl$_2$ (60 mg, 0.07 mmol) was added and the reaction was heated to 100° C. for 1.5 h. The solution was diluted with 1.5N NaOH (80 mL) and filtered over celite. The pH of the filtrate was adjusted to pH=3 by the addition of 6M HCl. The resulting precipitate was filtered and dried in vacuo to afford 4-(7-(tert-butoxycarbonyl(cyclopropyl)amino)-3-formylpyrazolo[1,5-a]pyrimidin-5-yl)thiophene-2-carboxylic acid (473 mg, 74%) as a tan solid. LCMS (ES): >90% pure, m/z 429 [M+1]$^+$.

Example 163

Synthesis of 4-(7-(cyclopropyl)amino)-3-formylpyrazolo[1,5-a]pyrimidin-5-yl)thiophene-2-carboxylic acid

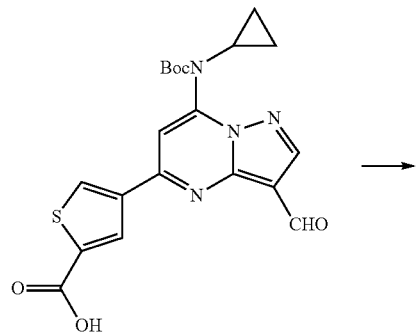

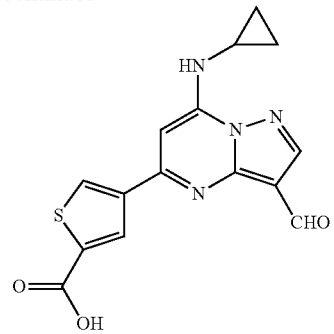

4-(7-(Tert-butoxycarbonyl(cyclopropyl)amino)-3-formylpyrazolo[1,5-a]pyrimidin-5-yl)thiophene-2-carboxylic acid (473 mg, 1.10 mmol) was dissolved in dichloromethane (5 mL) and trifluoroacetic acid (3 mL). After 1 h, the dark red solution was concentrated under a stream of air. The red oil was triturated with Et$_2$O (5 mL) and the precipitate was filtered to provide 4-(7-(cyclopropyl)amino)-3-formylpyrazolo[1,5-a]pyrimidin-5-yl)thiophene-2-carboxylic acid (321 mg, 88%). LCMS (ES): >95% pure, m/z 329 [M+1]$^+$.

Example 164

Synthesis of (Z)-4-(7-(cyclopropyl)amino)-3-((2,5-dioxoimidazolidin-4-ylidene)methyl)pyrazolo[1,5-a]pyrimidin-5-yl)thiophene-2-carboxylic acid

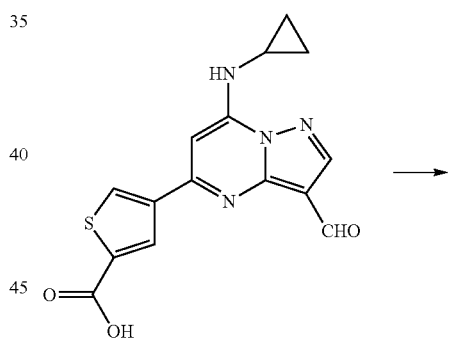

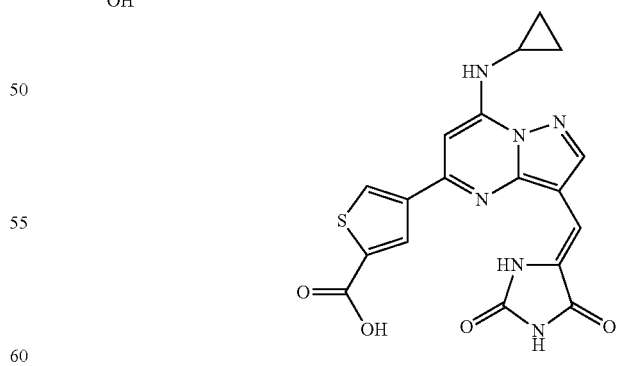

Hydantoin (292 mg, 2.92 mmol) and piperidine (285 µL, 2.89 mmol) were added to 4-(7-(cyclopropyl)amino)-3-formylpyrazolo[1,5-a]pyrimidin-5-yl)thiophene-2-carboxylic acid (315 mg, 0.96 mmol) dissolved in ethanol (5 mL). The reaction was heated at 80° C. After 15 h, the reaction was cooled to r.t., then diluted with water (10 mL). The pH was adjusted to pH=3 by addition of 1N HCl. The yellow precipitate was collected and washed with 1:1 ethanol:water (10 mL) and then ethanol (10 mL). The solid was dried in vacuo to give (Z)-4-(7-(cyclopropyl)amino)-3-((2,5-dioxoimidazolidin-4-ylidene)methyl)pyrazolo[1,5-a]pyrimidin-5-yl)thiophene-2-carboxylic acid (362 mg, 92%). LCMS (ES): >95% pure, m/z 411 [M+1]+.

Example 165

Synthesis of (Z)-5-((7-(cyclopropylamino)-5-(5-(2,6-dimethylmorpholine-4-carbonyl)thiophen-3-yl)pyrazolo[1,5-a]pyrimidin-3-yl)methylene)imidazolidine-2,4-dione

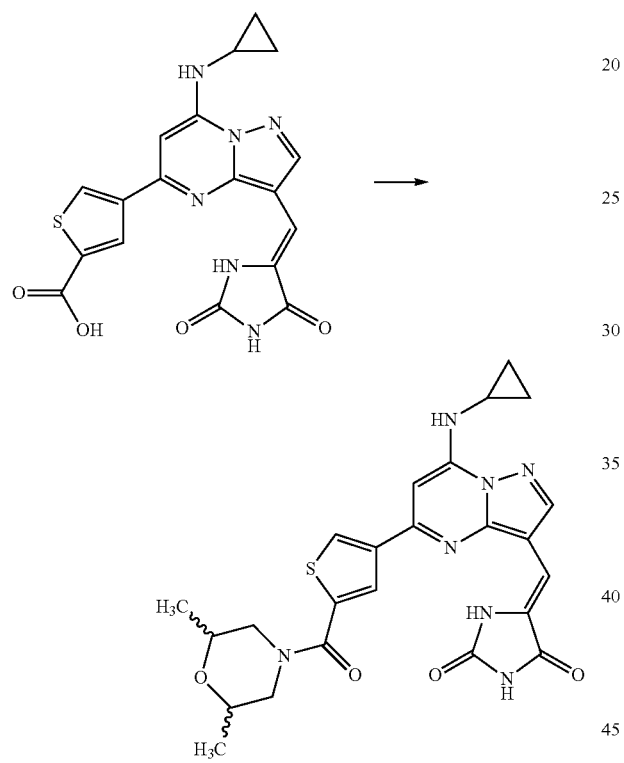

(Z)-4-(7-(cyclopropyl)amino)-3-(2,5-dioxoimidazolidin-4-ylidene)methyl)pyrazolo[1,5-a]pyrimidin-5-yl)thiophene-2-carboxylic acid (1.0 eq, 34 mg, 0.0828 mmol) was mixed in a vial with HOBt.H₂O (2.0 eq, 22 mg, 0.163 mmol), 2,6 dimethylmorpholine (isomer mixture, 4.0 eq, 41 ul, 0.333 mmol), DIEA (2.0 eq, 29 ul, 0.166 mmol) in NMP (0.5 ml). EDCI (2.0 eq, 32 mg, 0.166 mmol) was added and the mixture was stirred at 70° C. for 1 hour. Water was added and the resulting precipitate was filtered and dried. The material was triturated in a mixture of ethyl acetate and hexanes, filtered and dried in vacuo to give (Z)-5-(7-(cyclopropylamino)-5-(5-(2,6-dimethylmorpholine-4-carbonyl)thiophen-3-yl)pyrazolo[1,5-a]pyrimidin-3-yl)methylene)imidazolidine-2,4-dione as a yellow solid (26 mg, 62% yield). LCMS (ES): >95% pure, m/z 508 [M+1]+.

The following compounds were prepared using conditions similar to the chemistries described in Example 165. All compounds were characterized by LCMS. Table 24B shows the biological activities of the compounds listed in Table 24A.

TABLE 24A

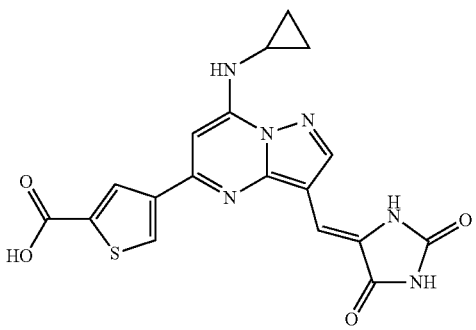 [SMILES: O=C1NC(=O)/C(=C/c2cnn3c(NC4CC4)cc(-c4csc(C(=O)O)c4)nc23)N1]

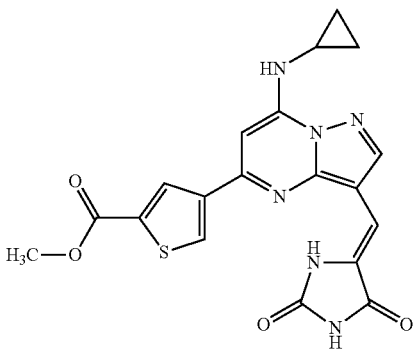 [SMILES: COC(=O)c1cc(-c2cc(NC3CC3)n3ncc(/C=C4\NC(=O)NC4=O)c3n2)cs1]

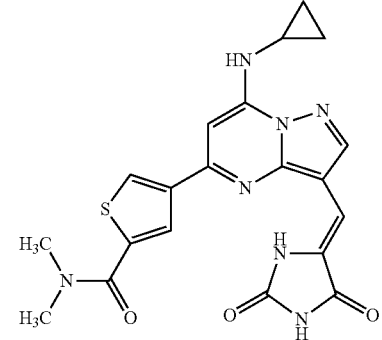 [SMILES: CN(C)C(=O)c1cc(-c2cc(NC3CC3)n3ncc(/C=C4\NC(=O)NC4=O)c3n2)cs1]

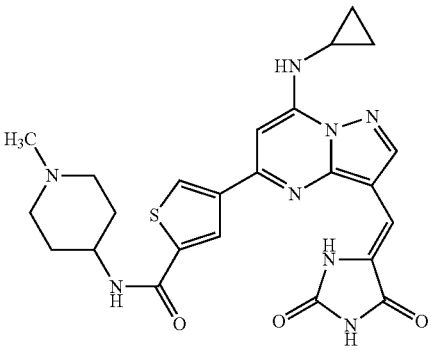 [SMILES: CN1CCC(NC(=O)c2cc(-c3cc(NC4CC4)n4ncc(/C=C5\NC(=O)NC5=O)c4n3)cs2)CC1]

TABLE 24A-continued
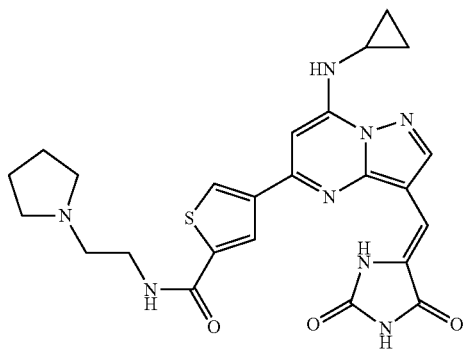 [SMILES: O=C1NC(=O)/C(=C/c2cnn3c(NC4CC4)cc(-c4csc(C(=O)NCCN5CCCC5)c4)nc23)N1]
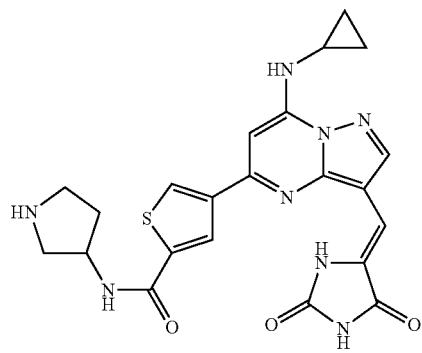 [SMILES: O=C1NC(=O)/C(=C/c2cnn3c(NC4CC4)cc(-c4csc(C(=O)NC5CCNC5)c4)nc23)N1]
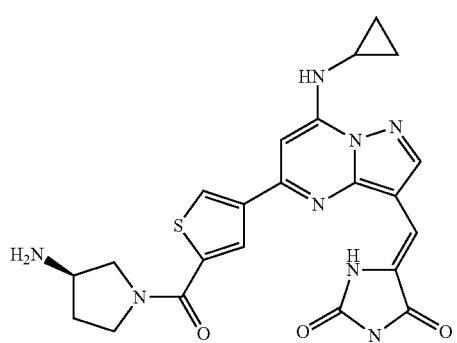
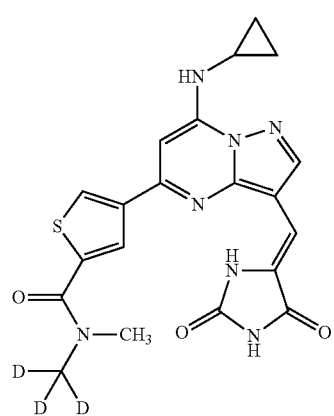 [SMILES: [2H]C([2H])([2H])N(C)C(=O)c1cc(-c2cc(NC3CC3)n3ncc(/C=C4\NC(=O)NC4=O)c3n2)cs1]
TABLE 24A-continued
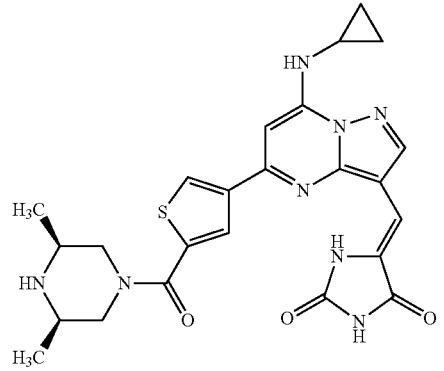
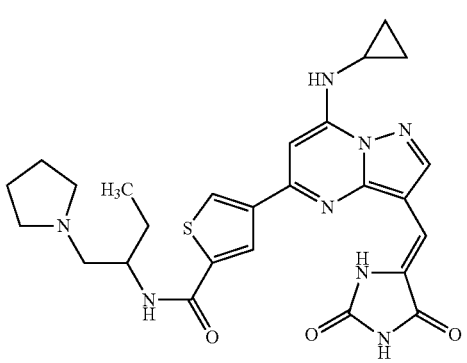 [SMILES: CCC(CN1CCCC1)NC(=O)c1cc(-c2cc(NC3CC3)n3ncc(/C=C4\NC(=O)NC4=O)c3n2)cs1]
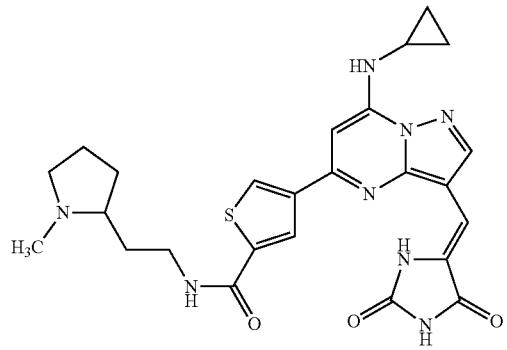 [SMILES: CN1CCCC1CCNC(=O)c1cc(-c2cc(NC3CC3)n3ncc(/C=C4\NC(=O)NC4=O)c3n2)cs1]
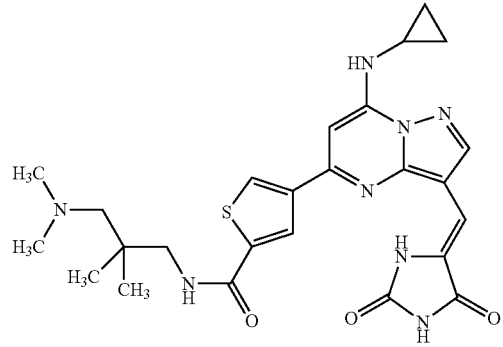 [SMILES: CN(C)CC(C)(C)CNC(=O)c1cc(-c2cc(NC3CC3)n3ncc(/C=C4\NC(=O)NC4=O)c3n2)cs1]

TABLE 24A-continued

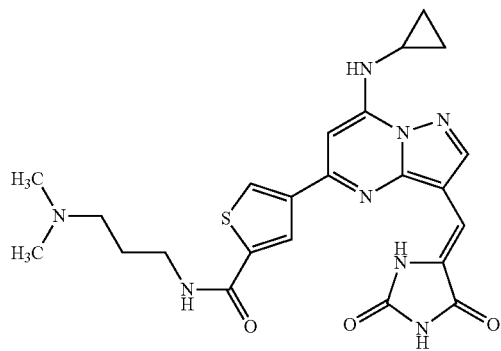 [SMILES: CN(C)CCCNC(=O)c1cc(-c2cc(NC3CC3)n3ncc(/C=C4\NC(=O)NC4=O)c3n2)cs1]

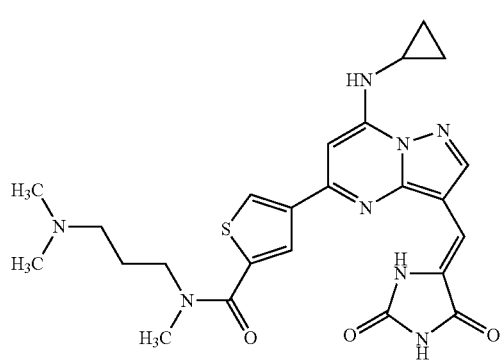 [SMILES: CN(C)CCCN(C)C(=O)c1cc(-c2cc(NC3CC3)n3ncc(/C=C4\NC(=O)NC4=O)c3n2)cs1]

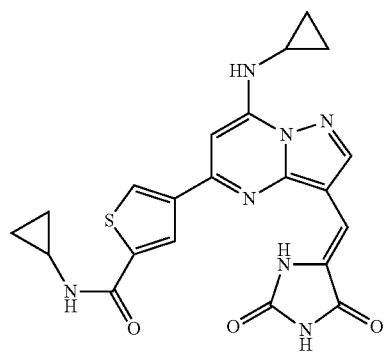 [SMILES: O=C1NC(=O)/C(=C/c2cnn3c(NC4CC4)cc(-c4csc(C(=O)NC5CC5)c4)nc23)N1]

TABLE 24B

| Compound | CK2: IC50 (μM) | PIM2: IC50 (5 μM ATP) | AB: MDAMB453 (μM) | AB: BxPC3 (μM) |
|---|---|---|---|---|
| C13 | <0.01 | 2.382 | >30 | >30 |
| D13 | <0.01 | >2.5000 | 0.605 | 0.591 |
| E13 | <0.01 | 0.982 | 1.469 | 3.466 |
| F13 | <0.01 | 0.6084 | 1.641 | 0.943 |
| G13 | <0.01 | 0.888 | 0.845 | 1.251 |
| H13 | <0.01 | 0.654 | 3.98 | 10.149 |
| I13 | <0.01 | 1.8781 | 15.19 | >30 |
| J13 | <0.01 | 0.548 | 0.266 | 1.348 |
| K13 | <0.01 | >2.5000 | 4.31 | 9.291 |
| L13 | <0.01 | 1.9547 | 1.548 | 0.767 |
| M13 | <0.01 | >2.5000 | 10.179 | 4.429 |
| N13 | <0.01 | 1.9848 | 3.335 | 4.142 |
| O13 | <0.01 | >2.5000 | 6.095 | 19.358 |
| P13 | <0.01 | 0.8133 | 2.772 | 8.499 |
| Q13 | <0.01 |  | >30 | 6.578 |
| R13 | <0.01 | >2.5000 | 1.657 | 2.293 |

Example 166

Synthesis of 5-(hydroxymethyl)thiophen-2-boronic acid

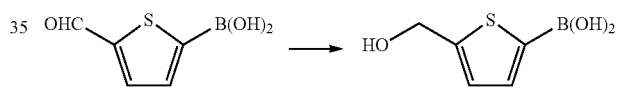

5-(Hydroxymethyl)thiophen-2-boronic acid was prepared from the commercially available 5-formylthiophen-2-boronic acid (Combi-Blocks) according to the procedure described in patent application WO2007/118137.

Example 167

Synthesis of tert-butyl cyclopropyl(3-formyl-5-(5-(hydroxymethyl)thiophen-2-yl)pyrazolo[1,5-a]pyrimidine-7-yl)carbamate

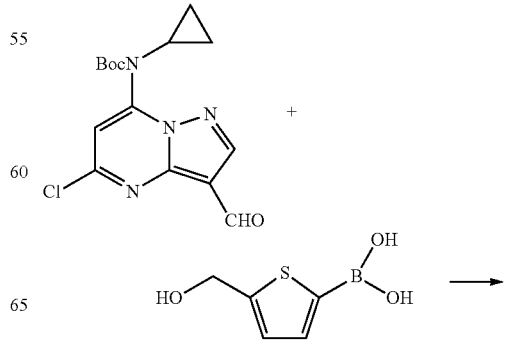

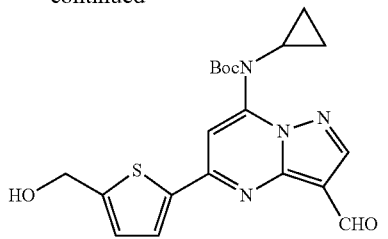

Note: DME and 2M Na₂CO₃ were degassed with a stream of N₂ in separate flasks prior to addition. Tert-butyl 5-chloro-3-formylpyrazolo[1,5-a]pyrimidine-7-yl)(cyclopropyl)carbamate (1.5 g, 4.45 mmol) was dissolved in DME (40 mL). Crude 5-(hydroxymethyl)thiophene-3-boronic acid (1.4 g, 8.9 mmol) was added, followed by Pd(PPh₃)₄ (510 mg, 0.45 mmol) and finally 2M Na₂CO₃ (6.7 mL, 13.3 mmol). The reaction was heated to 90° C. for 2 h. The solution was partitioned between EtOAc (100 mL) and 0.5N HCl (100 mL). The aqueous layer was extracted with EtOAc (2×75 mL). The organics were washed with brine (250 mL), dried over MgSO₄, filtered and concentrated in vacuo. The residue was purified via flash column chromatography (30-45% EtOAc/hexanes) and then triturated with hexanes (3×10 mL) to yield tert-butyl cyclopropyl(3-formyl-5-(5-(hydroxymethyl)thiophen-2-yl)pyrazolo[1,5-a]pyrimidine-7-yl)carbamate (984 mg, 53%) as an off white solid. LCMS (ES): >95% pure, m/z 415 [M+1]⁺.

Example 168

Synthesis of 5-(5-(bromomethyl)thiophen-2-yl)-7-(cyclopropylamino)pyrazolo[1,5-a]pyrimidine-3-carbaldehyde

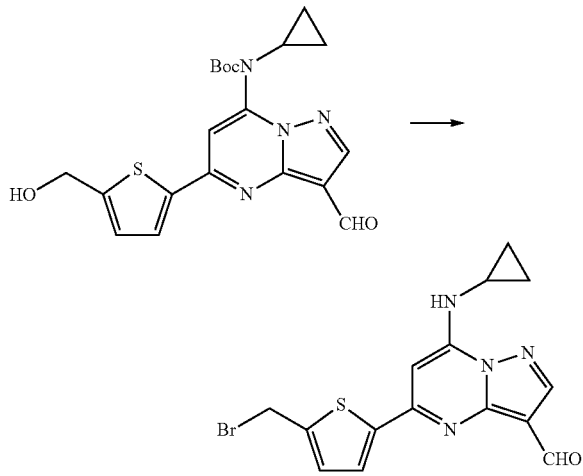

Hydrogen bromide (48% in water, 5 mL) was added dropwise to tert-butyl cyclopropyl(3-formyl-5-(5-(hydroxymethyl)thiophen-2-yl)pyrazolo[1,5-a]pyrimidine-7-yl)carbamate (980 mg, 2.4 mmol) suspended in dichloromethane (5 mL). The solution immediately became dark brown and homogeneous upon addition. The reaction was heated to 40° C. for 4 hours, then diluted with dichloromethane (10 mL). The liquid was decanted and the gummy residue was washed with dichloromethane (3×10 mL). The combined liquids were washed successively with sat. NaHCO₃ (20 mL) and brine (20 mL), and then dried over MgSO₄, filtered and concentrated in vacuo: The residue was triturated with hexanes and then purified via flash column chromatography (10-20% EtOAc/hexanes) to provide 5-(5-(bromomethyl)thiophen-2-yl)-7-(cyclopropylamino)pyrazolo[1,5-a]pyrimidine-3-carbaldehyde (300 mg, 34%) as a yellow solid. LCMS (ES): >95% pure, m/z 378 [M+1]⁺.

Example 169

Synthesis of (Z)-5-((7-(cyclopropylamino)-5-(5-pyrrolidin-1-ylmethyl)thiophen-2-yl)pyrazolo[1,5-a]pyrimidin-3-yl)methylene)imidazolidine-2,4-dione

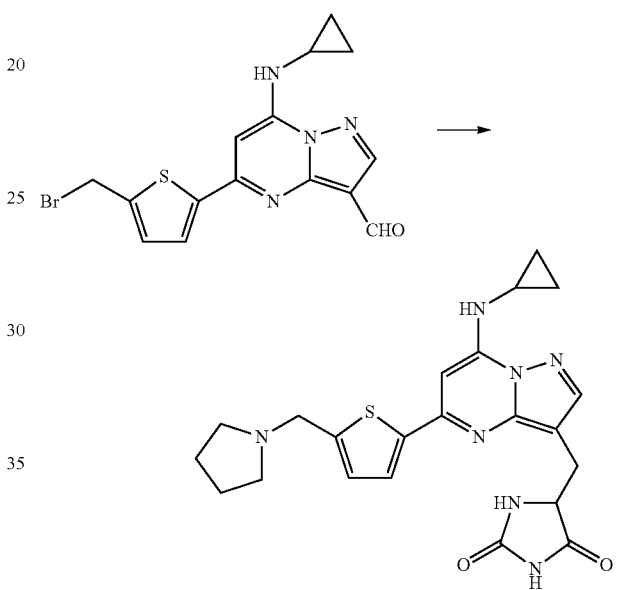

Potassium carbonate (30 mg, 0.20 mmol) was added to 5-(5-(bromomethyl)thiophen-2-yl)-7-(cyclopropylamino)pyrazolo[1,5-a]pyrimidine-3-carbaldehyde (25 mg, 0.07 mmol) dissolved in DMF (0.7 mL). Pyrrolidine (6µL, 0.07 mmol) was added and the reaction was heated to 60° C. for 4 h. Water (3 mL) was added and the orange precipitate was filtered and dried in vacuo to give 7-(cyclopropylamino)-5-(5-(pyrrolidin-1-ylmethyl)thiophen-2-yl)pyrazolo[1,5-a]pyrimidine-3-carbaldehyde (13 mg, 54%) which was used without further purification. LCMS (ES): >85% pure, m/z 368 [M+1]⁺.

Hydantoin (3 mg, 0.03 mmol) and piperidine (3 µL, 0.03 mmol) were added to 7-(cyclopropylamino)-5-(5-(pyrrolidin-1-ylmethyl)thiophen-2-yl)pyrazolo[1,5-a]pyrimidine-3-carbaldehyde (12 mg, 0.03 mmol) dissolved in ethanol (0.5 mL). The reaction was heated at 80° C. After 15 h, the reaction was cooled to room temperature then diluted with water (3 mL). The precipitate was collected and washed with 1:1 ethanol:water (3 mL) and dried in vacuo to furnish (Z)-5-((7-(cyclopropylamino)-5-(5-pyrrolidin-1-ylmethyl)thiophen-2-yl)pyrazolo[1,5-a]pyrimidin-3-yl)methylene)imidazolidine-2,4-dione (2.8 mg, 9% over two steps). LCMS (ES): >95% pure, m/z 450 [M+1]⁺.

The compounds described in the following table were prepared using chemistries similar to those exemplified in Example 168 and Example 169. All compounds were characterized by LCMS. Table 25B shows the biological activities of the compounds listed in Table 25A.
TABLE 25A
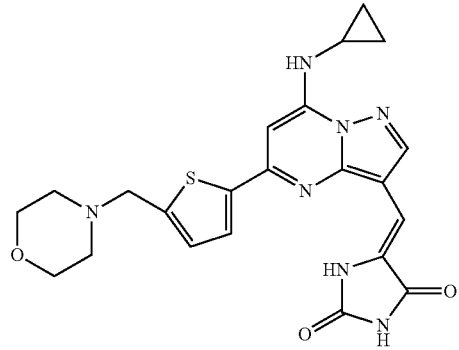 [SMILES: O=C1NC(=O)/C(=C/c2cnn3c(NC4CC4)cc(-c4ccc(CN5CCOCC5)s4)nc23)N1]
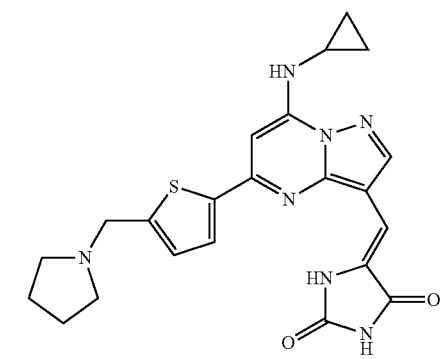 [SMILES: O=C1NC(=O)/C(=C/c2cnn3c(NC4CC4)cc(-c4ccc(CN5CCCC5)s4)nc23)N1]
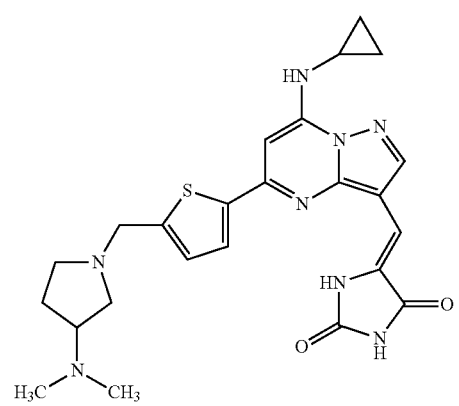 [SMILES: CN(C)C1CCN(Cc2ccc(-c3cc(NC4CC4)n4ncc(/C=C5\NC(=O)NC5=O)c4n3)s2)C1]
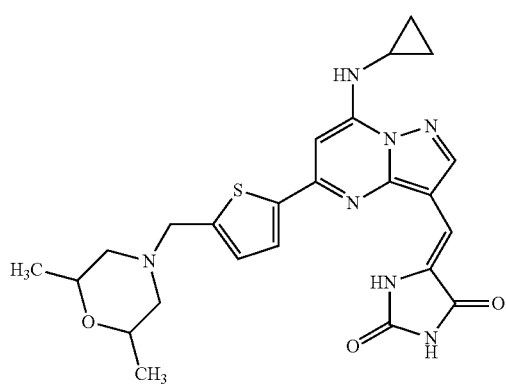 [SMILES: CC1CN(Cc2ccc(-c3cc(NC4CC4)n4ncc(/C=C5\NC(=O)NC5=O)c4n3)s2)CC(C)O1]
TABLE 25A-continued
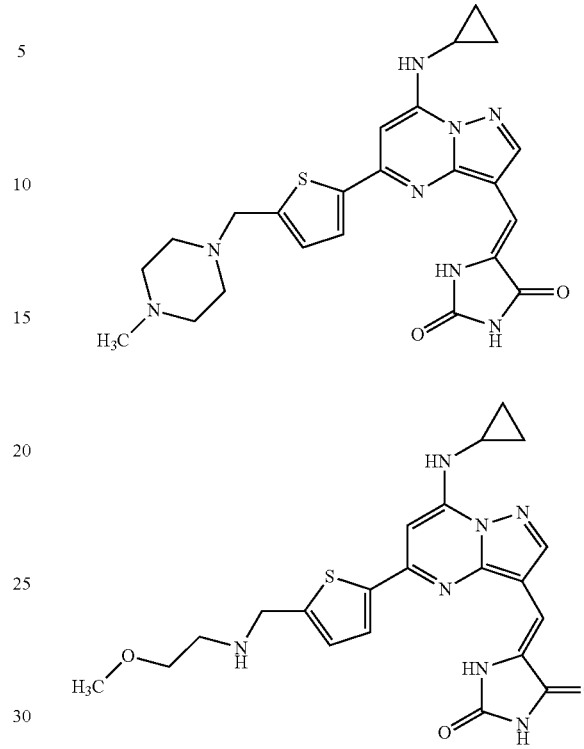
TABLE 25B
| Compound | CK2: IC50 (µM) | PIM2: IC50 (5 µM ATP) | AB: MDAMB453 (µM) | AB: BxPC3 (µM) |
|---|---|---|---|---|
| S13 | <0.01 | >2.5000 | 1.266 | 2.261 |
| T13 | <0.01 | 0.8106 | 0.658 | 0.352 |
| U13 | <0.01 | >2.5000 | 0.449 | 0.418 |
| V13 | <0.01 | >2.5000 | 1.282 | 1.516 |
| W13 | <0.01 | >2.5000 | 0.52 | 0.94 |
| X13 | <0.01 | 1.872 | 1.338 | 0.379 |
Example 170
Synthesis of 5-(hydroxymethyl)thiophen-3-boronic acid
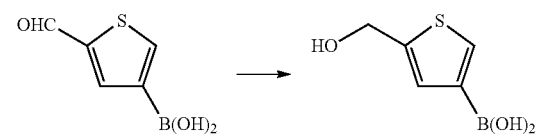 [SMILES: O=Cc1cc(B(O)O)cs1 ; OCc1cc(B(O)O)cs1]
5-(Hydroxymethyl)thiophen-3-boronic acid was prepared from the commercially available 5-formylthiophen-3-bo-

Example 171

Synthesis of tert-butyl cyclopropyl(3-formyl-5-(5-(hydroxymethyl)thiophen-3-yl)pyrazolo[1,5-a]pyrimidine-7-yl)carbamate

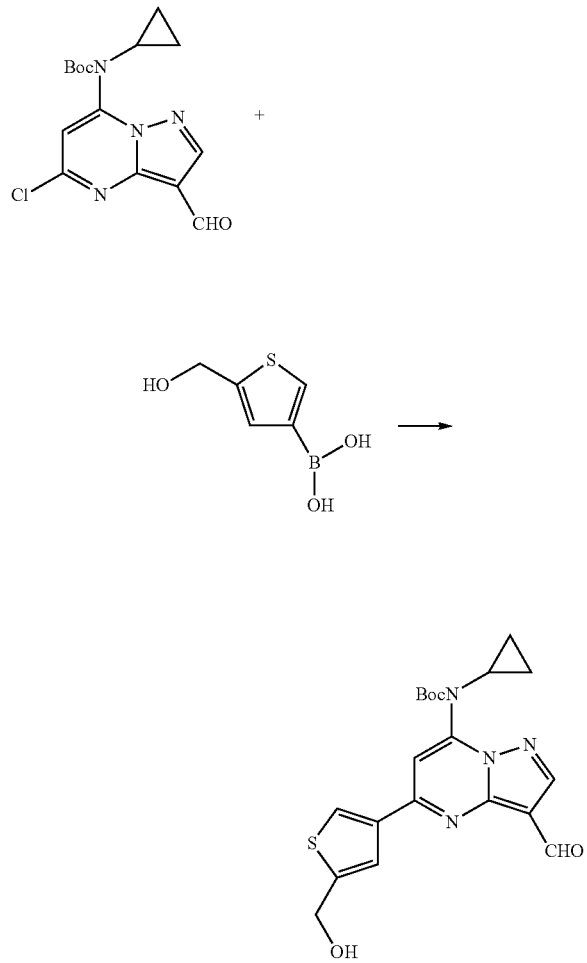

Note: DME and 2M $Na_2CO_3$ were degassed with a stream of $N_2$ in separate flasks prior to addition. Tert-butyl 5-chloro-3-formylpyrazolo[1,5-a]pyrimidine-7-yl)(cyclopropyl)carbamate (750 mg, 2.22 mmol) was dissolved in DME (22 mL). Crude 5-(hydroxymethyl)thiophen-3-boronic acid (880 mg, 5.57 mmol) was added, followed by $Pd(PPh_3)_4$ (256 mg, 0.22 mmol) and finally 2M $Na_2CO_3$ (3.3 mL, 6.60 mmol). The reaction was heated to 90° C. for 2 h. The solution was partitioned between EtOAc (100 mL) and 0.5N HCl (100 mL). The aqueous layer was extracted with EtOAc (2×75 mL). The organics were washed with brine (250 mL), dried over $MgSO_4$, filtered and concentrated in vacuo. The residue was purified via flash column chromatography (30-45% EtOAc/hexanes) and then triturated with hexanes (3×10 mL) to yield tert-butyl cyclopropyl(3-formyl-5-(5-(hydroxymethyl)thiophen-3-yl)pyrazolo[1,5-a]pyrimidine-7-yl)carbamate (638 mg, 69%) as an off white solid. $^1$H NMR ($CDCl_3$, 400 MHz) δ: 10.34 (s, 1H), 8.55 (s, 1H), 8.11 (d, 1'-1, J=1.6 Hz), 7.76 (d, 1H, J=1.6 Hz), 7.18 (s, 1H), 4.93 (bs, 2H), 3.30 (dddd, 1H, J=6.8, 6.8, 3.6, 3.6 Hz), 2.15 (bs, 1H), 1.42 (s, 9H), 0.85-0.92 (m, 2H), 0.63-0.70 (m, 2H). LCMS (ES): >95% pure, m/z 415 [M+1]$^+$.

Example 172

Synthesis of 7-(cyclopropylamino)-5-(5-(hydroxymethyl)thiophen-3-yl)pyrazolo[1,5-a]pyrimidine-3-carbaldehyde 2,2,2-trifluoroacetate

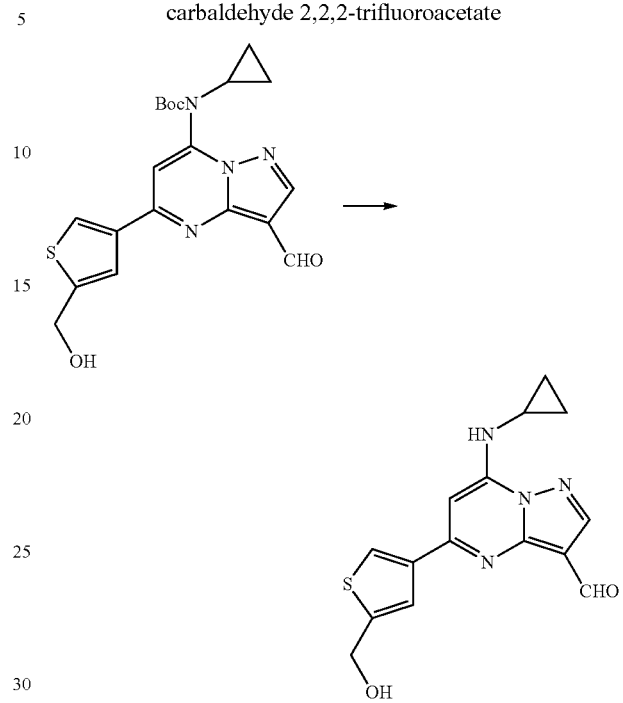

Tert-butyl cyclopropyl(3-formyl-5-(5-(hydroxymethyl) thiophen-3-yl)pyrazolo[1,5-a]pyrimidine-7-yl)carbamate (20 mg, 0.05 mmol) was dissolved in dichloromethane (0.5 mL) and trifluoroacetic acid (0.5 mL). After 1 h, the solution was concentrated under a stream of air. The residue was purified via preparative HPLC to furnish 7-(cyclopropylamino)-5-(5-(hydroxymethyl)thiophen-3-yl)pyrazolo[1,5-a]pyrimidine-3-carbaldehyde 2,2,2-trifluoroacetate (4.8 mg, 23%).

Example 173

Synthesis of 5-(5-(bromomethyl)thiophen-3-yl)-7-(cyclopropylamino)pyrazolo[1,5-a]pyrimidine-3-carbaldehyde

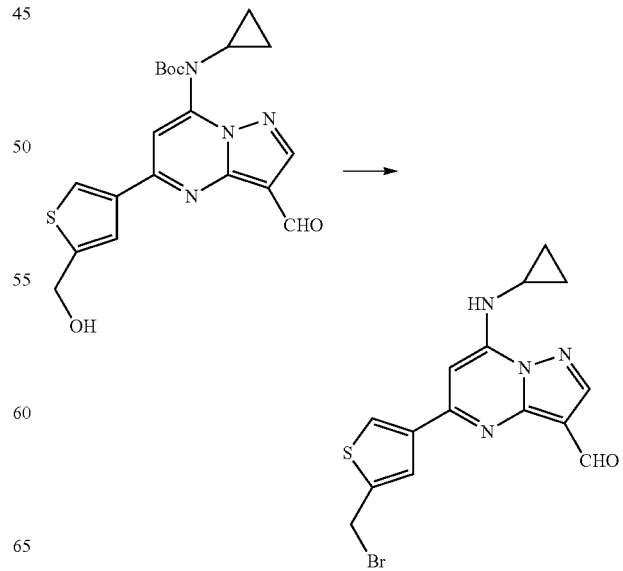

Hydrogen bromide (48% in water, 2.5 mL) was added dropwise to tert-butyl cyclopropyl(3-formyl-5-(5-(hydroxymethyl)thiophen-3-yl)pyrazolo[1,5-a]pyrimidine-7-yl)carbamate (561 mg, 1.35 mmol) suspended in dichloromethane (3.5 mL). The solution immediately became dark brown and homogeneous upon addition. The reaction was heated to 40° C. for 3 h, then diluted with dichloromethane (10 mL). The liquid was decanted and the gummy residue was washed with dichloromethane (3×10 mL). The combined liquids were washed successively with sat. NaHCO$_3$ (20 mL) and brine (20 mL), and then dried over MgSO$_4$, filtered and concentrated in vacuo. The residue was triturated with hexanes and then purified via flash column chromatography (15-40% EtOAc/hexanes) to provide 5-(5-(bromomethyl) thiophen-3-yl)-7-(cyclopropylamino)pyrazolo[1,5-a] pyrimidine-3-carbaldehyde (105 mg, 20%) as a yellow solid. $^1$H NMR (CDCl$_3$, 400 MHz) δ: 10.26 (s, 1H), 8.44 (s, 1H), 8.12 (d, 1H, J=1.6 Hz), 7.80 (s, 1H), 6.73 (s, 1H), 6.65 (bs, 1H), 4.80 (s, 2H), 2.81 (m, 1H), 1.03-1.09 (m, 2H), 0.84-0.89 (m, 2H). LCMS (ES): >95% pure, m/z 378 [M+1]$^+$.

Example 174

Synthesis of (Z)-5-((7-(cyclopropylamino)-5-(5-pyrrolidin-1-ylmethyl)thiophen-3-yl)pyrazolo[1,5-a] pyrimidin-3-yl)methylene)imidazolidine-2,4-dione

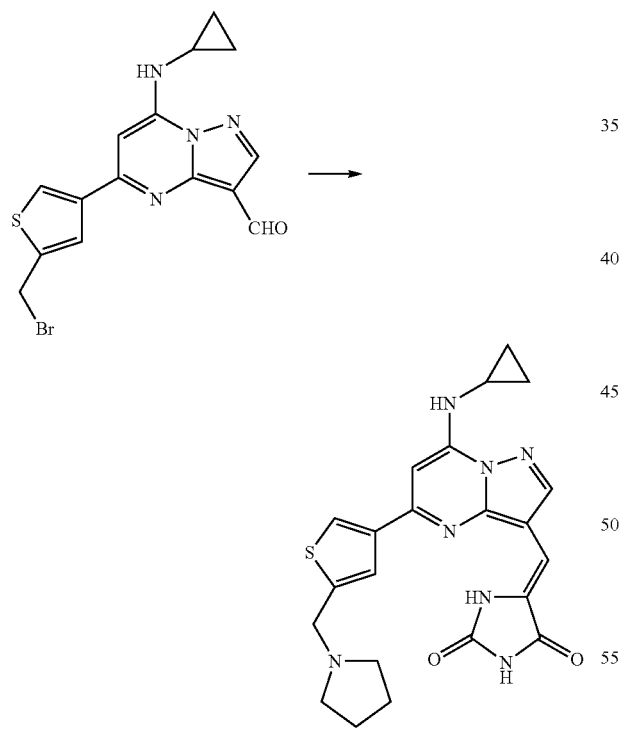

Potassium carbonate (30 mg, 0.20 mmol) was added to 5-(5-(bromomethyl)thiophen-3-yl)-7-(cyclopropylamino) pyrazolo[1,5-a]pyrimidine-3-carbaldehyde (25 mg, 0.07 mmol) dissolved in DMF (0.7 mL). Pyrrolidine (6 μL, 0.07 mmol) was added and the reaction was heated to 50° C. for 1.25 h. Water (3 mL) was added and the orange precipitate was filtered and dried in vacuo to give 7-(cyclopropylamino)-5-(5-(pyrrolidin-1-ylmethyl)thiophen-3-yl)pyrazolo[1,5-a] pyrimidine-3-carbaldehyde (13 mg, 54%) which was used without further purification. LCMS (ES): >85% pure, m/z 368 [M+1]$^+$.

Hydantoin (3 mg, 0.03 mmol) and piperidine (3 μL, 0.03 mmol) were added to 7-(cyclopropyl amino)-5-(5-(pyrrolidin-1-ylmethyl)thiophen-3-yl)pyrazolo[1,5-a]pyrimidine-3-carbaldehyde (12 mg, 0.03 mmol) dissolved in ethanol (0.5 mL). The reaction was heated at 80° C. After 15 h, the reaction was cooled to r.t., then diluted with water (3 mL). The precipitate was collected and washed with 1:1 ethanol:water (3 mL) and dried in vacuo to furnish (Z)-5-((7-(cyclopropylamino)-5-(5-pyrrolidin-1-ylmethyl)thiophen-3-yl)pyrazolo [1,5-a]pyrimidin-3-yl)methylene)imidazolidine-2,4-dione (2.8 mg, 9% over two steps). LCMS (ES): >95% pure, m/z 450 [M+1]$^+$.

The compounds described in the following table were prepared using chemistries similar to those exemplified in Example 174. All compounds were characterized by LCMS. Table 26B shows the biological activities of the compounds listed in Table 26A.

TABLE 26A

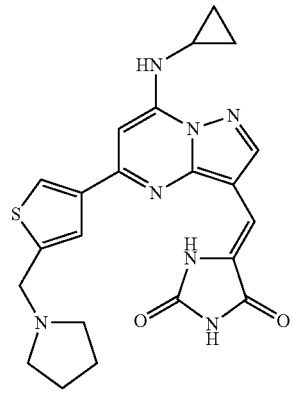 [SMILES: O=C1NC(=O)/C(=C/c2cnn3c(NC4CC4)cc(-c4csc(CN5CCCC5)c4)nc23)N1]

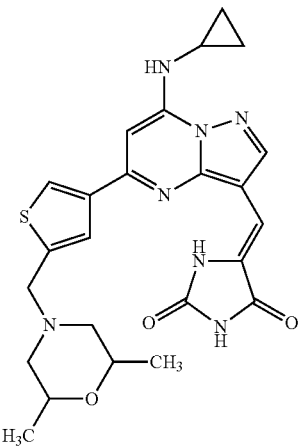 [SMILES: CC1CN(Cc2cc(-c3cc(NC4CC4)n4ncc(/C=C5\NC(=O)NC5=O)c4n3)cs2)CC(C)O1]

TABLE 26A-continued

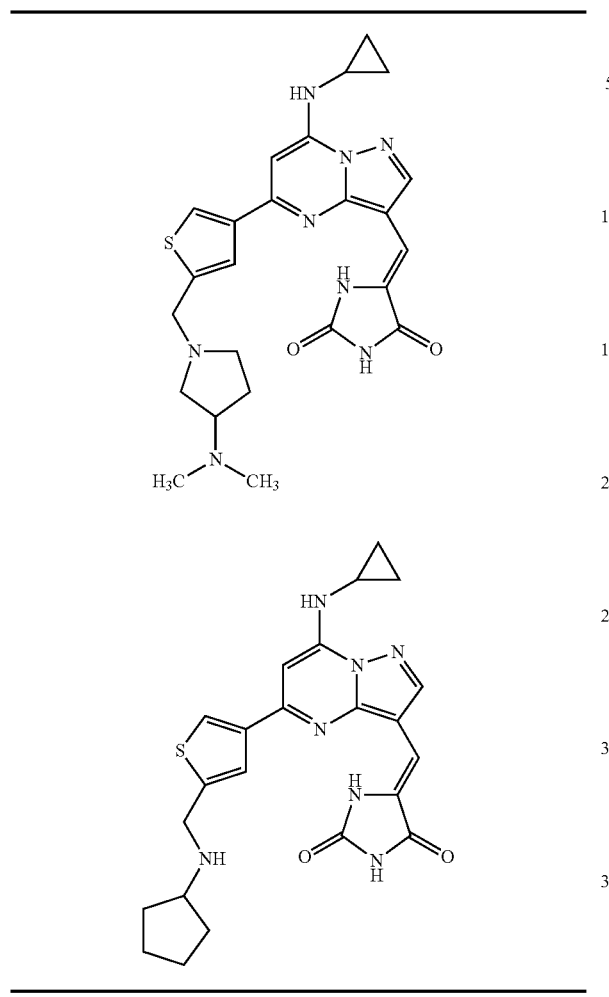

TABLE 26B

| Compound | CK2: IC50 (µM) | PIM2: IC50 (5 µM ATP) | AB: MDAMB453 (µM) | AB: BxPC3 (µM) |
|---|---|---|---|---|
| Y13 | <0.01 | >2.5000 | 1.386 | 0.929 |
| Z13 | <0.01 | >2.5000 | 2.498 | 10.153 |
| A14 | <0.01 | 1.5722 | 1.614 | 1.758 |
| B14 | <0.01 | 1.4451 | 1.614 | 1.003 |

Figure 3:
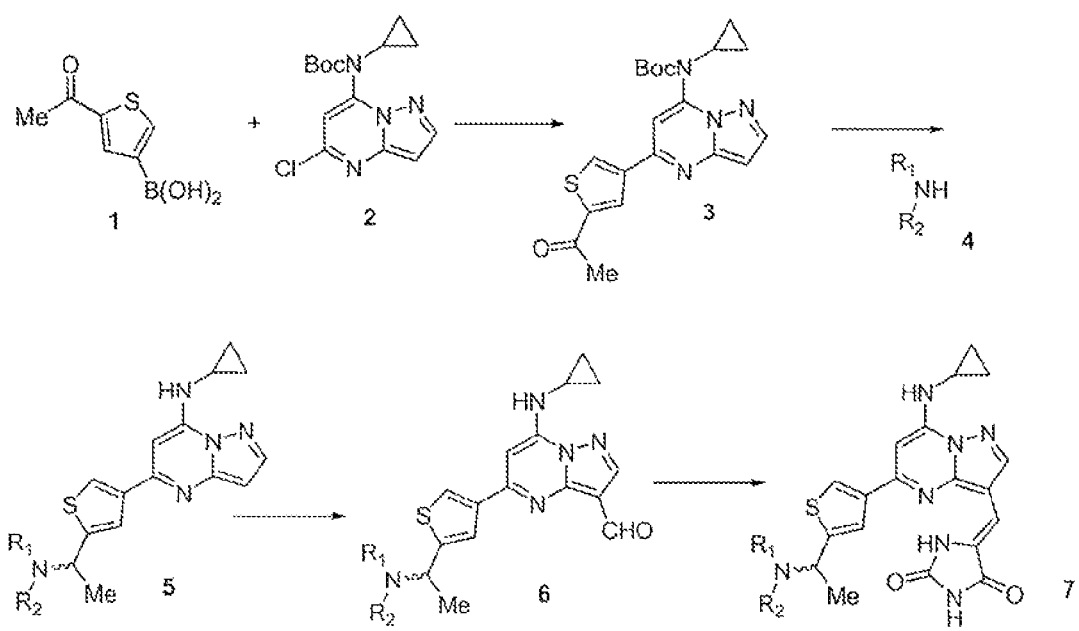
FIG. 3 shows a synthesis scheme for preparing certain compounds of the invention containing a thiophene ring.

The chemistry depicted in FIG. 3 can be used to prepare analogs 7 substituted by a methyl group. Commercially available boronic acid 1 can be reacted with tert-butyl 5-chloropyrazolo[1,5-a]pyrimidin-7-yl(cyclopropyl)carbamate 2 under Suzuki reaction conditions to for methyl ketone 3. This compound 3 can be reacted with various substituted amines 4 under reductive amination conditions such as the conditions described in US2007/244094 or reaction conditions described in *European Journal of Medicinal Chemistry*, vol 32, 1997, 143-150 to prepare compounds 5. Compound 5 can be converted to aldehyde 6 under Vilsmeier conditions. Compound 6 can be converted to compound 7 by reacting with hydantoin and piperidine in ethanol.

The molecules in the following Table 27 can be prepared using similar chemistries.

TABLE 27

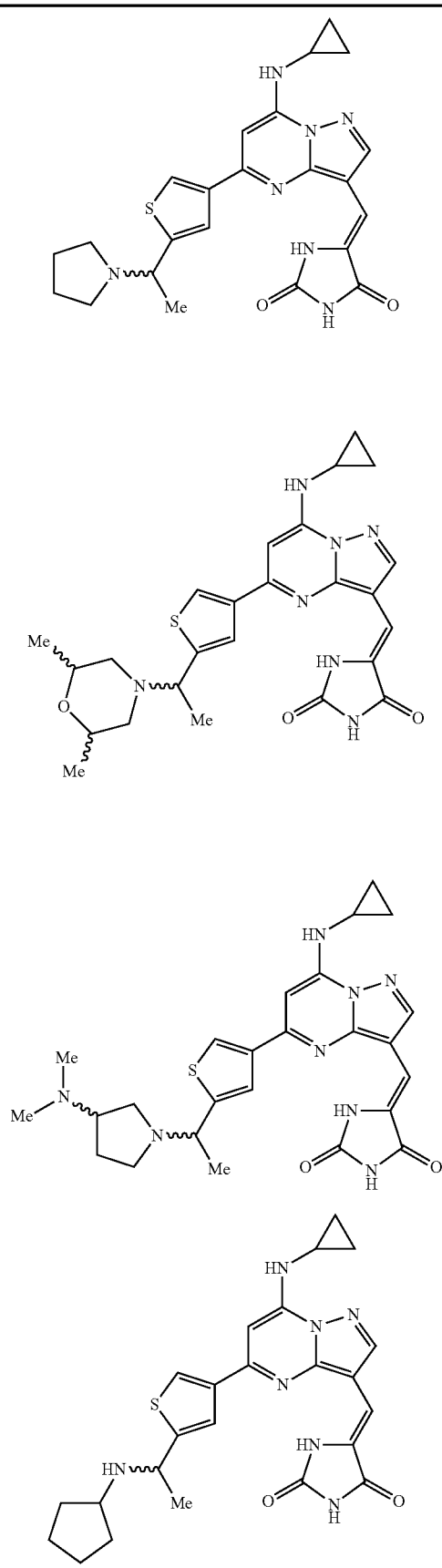

TABLE 27-continued

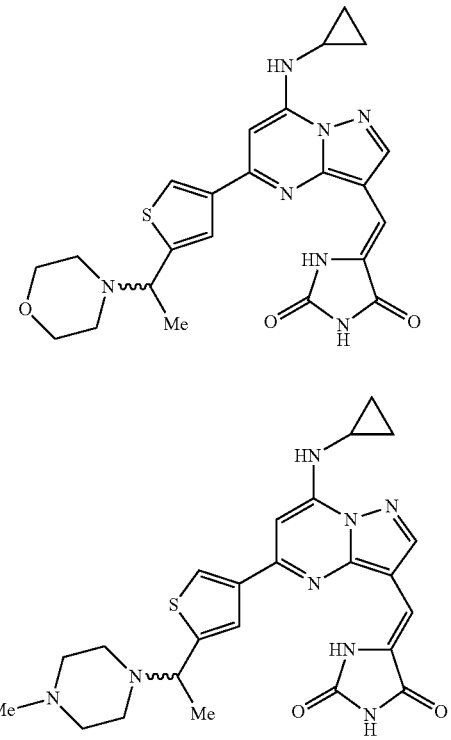

Example 175

Synthesis of 6-bromo-N-cyclopropylimidazo[1,2-a]pyrazin-8-amine

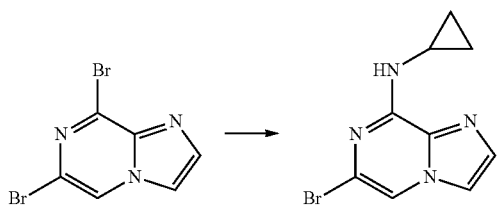 [SMILES: Brc1cn2ccnc2c(Br)n1 ; Brc1cn2ccnc2c(NC2CC2)n1]

Diisopropylethylamine (2.4 mL, 13.62 mmol) and cyclopropylamine (943 μL, 13.62 mmol) were added to commercially available (Ark Pharm, Inc.) 6,8-dibromoimidazo[1,2-a]pyrazine (2.51 g, 9.08 mmol) dissolved in 2-propanol (9 mL). The solution was placed in an 80° C. oil bath. After 4.5 h, the volatiles were removed in vacuo. The brown residue was partitioned between dichloromethane (50 mL) and water (50 mL). The organic layer was washed further with water (50 mL) and then brine (50 mL). The organic layer was dried over MgSO$_4$, filtered and concentrated in vacuo. The residue was purified via a filtration over a short plug of silica gel (40% EtOAc/hexanes) and the filtrate was concentrated in vacuo to afford 6-bromo-N-cyclopropylimidazo[1,2-a]pyrazin-8-amine (2.19 g, 95%) as a light brown solid. $^1$H NMR (CDCl$_3$, 400 MHz) δ: 7.61 (s, 1H), 7.46 (d, 1H, J=1.2 Hz), 7.44 (d, 1H, J=1.2 Hz), 6.26 (bs, 1H), 3.02 (dddd, 1H, J=7.2, 7.2, 7.2, 3.6 Hz), 0.89-0.95 (m, 2H), 0.64-0.69 (m, 2H). LCMS (ES): >95% pure, m/z 254 [M+1]$^+$.

Example 176

Synthesis of tert-butyl 6-bromoimidazo[1,2-a]pyrazin-8-yl(cyclopropyl) carbamate

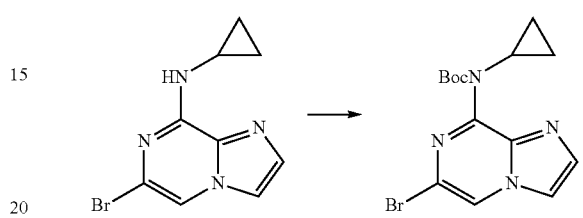

6-Bromo-N-cyclopropylimidazo[1,2-a]pyrazin-8-amine (0.5 g, 1.98 mmol) was dissolved in dichloromethane (8 mL). Di-tert-butyl dicarbonate (733 mg, 3.35 mmol), DMAP (5 mg, 0.02 mmol) and pyridine (0.4 mL) were added sequentially. After 12 h, the solution was diluted with EtOAc (50 mL) and then washed sequentially with 1N HCl (50 mL), 1N NaOH (50 mL), and brine (50 mL). The organic layer was dried over MgSO$_4$, filtered and concentrated in vacuo. The residue was triturated with hexanes (5 mL) to yield tert-butyl 6-bromoimidazo[1,2-a]pyrazin-8-yl(cyclopropyl) carbamate (337 mg, 48%) as an off white solid. $^1$H NMR (CDCl$_3$, 400 MHz) δ: 8.18 (s, 1H), 7.78 (d, 1H, J=0.8 Hz), 7.67 (d, 1H, J=0.8 Hz), 3.25 (dddd, 1H, J=6.8, 6.8, 3.6, 3.6 Hz), 1.20 (s, 9H), 0.78-0.86 (m, 2H), 0.71-0.77 (m, 2H). LCMS (ES): >90% pure, m/z 354 [M+1]$^+$.

Example 177

Synthesis of 6-bromo-8-(cyclopropylamino)imidazo[1,2-a]pyrazine-3-carbaldehyde

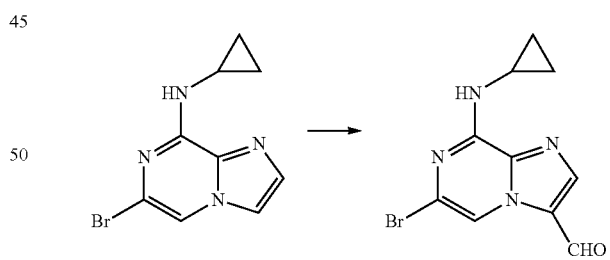

Phosphorus(V) oxychloride (3.9 mL, 42.68 mmol) was added dropwise to anhydrous DMF (16 mL) at 0° C. 6-bromo-N-cyclopropylimidazo[1,2-a]pyrazin-8-amine (900 mg, 3.56 mmol) was dissolved in anhydrous DMF (24 mL) and added over two minutes. The solution was place in an 85° C. oil bath for 5 h. The solution was cooled to 0° C. and conc. HCl (30 mL) was added. The mixture was basified to pH=10 w/3N NaOH (~175 mL). The mixture was extracted with dichloromethane (3×250 mL), and the organics were washed with brine (500 mL). The organic layer was dried over MgSO$_4$, filtered and concentrated in vacuo. The residue was purified via flash column chromatography (30% EtOAc/hexanes) to furnish 6-bromo-8-(cyclopropylamino)imidazo[1,2-a]pyrazine-3-carbaldehyde (490 mg, 49%). LCMS (ES): >95% pure, m/z 282 [M+1]+.

Example 178

Synthesis of tert-butyl 6-bromo-3-formylimidazo[1,2-a]pyrazine-8-yl(cyclopropyl)carbamate

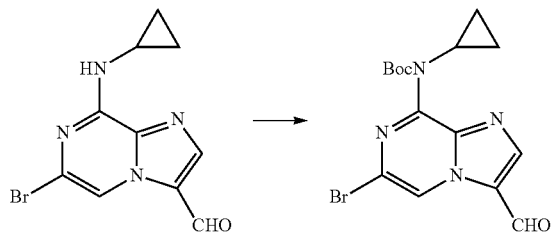 [SMILES: O=Cc1cnc2c(NC3CC3)nc(Br)cn12 ; CC(C)(C)OC(=O)N(c1nc(Br)cn2c(C=O)cnc12)C1CC1]

Di-tert-butyl dicarbonate (1.16 g, 5.30 mmol) and DMAP (21 mg, 0.18 mmol) were added to a solution of 6-bromo-8-(cyclopropylamino)imidazo[1,2-a]pyrazine-3-carbaldehyde (994 mg, 3.50 mmol) in dichloromethane (15 mL). After 2.5 h, the solution was partitioned between EtOAc (100 mL) and water (100 mL). The aqueous layer was further extracted with EtOAc (2×75 mL). The organics were washed with brine (250 mL), dried over MgSO4, filtered and concentrated in vacuo. The residue was purified via flash column chromatography (30% EtOAc/hexanes) to provide tert-butyl 6-bromo-3-formylimidazo[1,2-a]pyrazine-8-yl(cyclopropyl)carbamate (1.17 g, 87%) as a brown foam. $^1$H NMR (CDCl3, 400 MHz) δ: 10.05 (s, 1H), 9.42 (s, 1H), 8.37 (s, 1H), 3.25 (dddd, 1H, J=6.8, 6.8, 4.0, 4.0 Hz), 1.22 (s, 9H), 0.85-0.90 (m, 2H), 0.69-0.75 (m, 2H). LCMS (ES): >95% pure, m/z 382 [M+1]+.

Example 179

Synthesis of tert-butyl cyclopropyl(3-formyl-6-(3-trifluoromethoxy)phenyl)imidazo[1,2-a]pyrazin-8-yl)carbamate

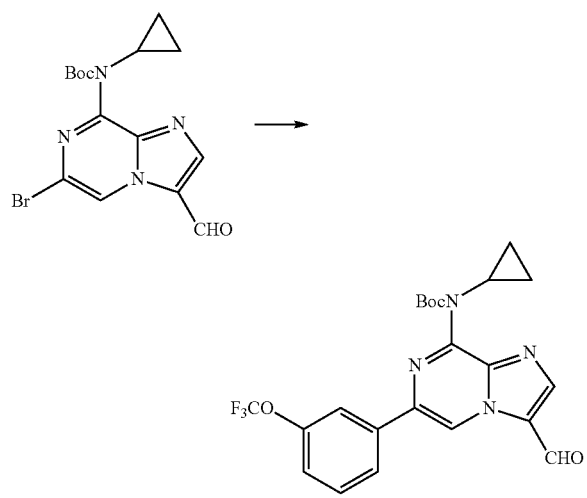

Tert-butyl 6-bromo-3-formylimidazo[1,2-a]pyrazine-8-yl(cyclopropyl)carbamate (130 mg, 0.34 mmol), 3-(trifluoromethoxy)phenyl boronic acid (105 mg, 0.51 mmol), 3M Na2CO3 (1.1 mL, 3.4 mmol) and DME (4.5 mL) were combined. The solution was degassed with a stream of N2 for 10 min. Pd(PPh3)4 was added and the solution was refluxed for 2 h. The solution was partitioned between dichloromethane (25 mL) and water (25 mL). The aqueous layer was further extracted with dichloromethane (2×25 mL). The organics were washed with brine (50 mL), dried over MgSO4, filtered and concentrated in vacuo. The residue was purified via flash column chromatography (30-45% EtOAc/hexanes) to provide tert-butyl cyclopropyl(3-formyl-6-(3-trifluoromethoxy)phenyl)imidazo[1,2-a]pyrazin-8-yl)carbamate (96 mg, 61%) as a bright yellow solid. LCMS (ES): >95% pure, m/z 463 [M+1]+.

Example 180

Synthesis of tert-butyl cyclopropyl(6-(3-trifluoromethoxy)phenyl)imidazo[1,2-a]pyrazin-8-yl)carbamate

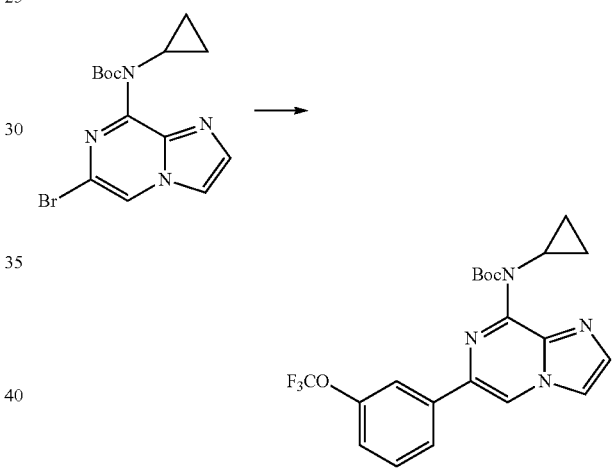

Tert-butyl cyclopropyl(6-(3-trifluoromethoxy)phenyl)imidazo[1,2-a]pyrazin-8-yl)carbamate (77%) was synthesized in a manner analogous to Example 179. LCMS (ES): >95% pure, m/z 435 [M+1]+.

Example 181

Synthesis of tert-butyl cyclopropyl(6-(3-fluorophenyl)-3-formylimidazo[1,2-a]pyrazin-8-yl)carbamate

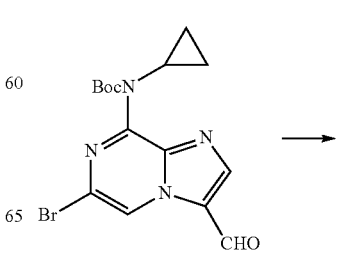

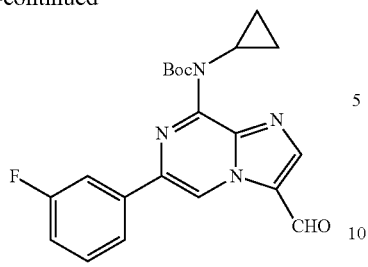

Tert-butyl cyclopropyl(6-(3-fluorophenyl)-3-formylimidazo[1,2-a]pyrazin-8-yl)carbamate (28%) was synthesized in a manner analogous to Example 183. LCMS (ES): >95% pure, m/z 435 [M+1]$^+$.

Example 182

Synthesis of tert-butyl cyclopropyl(3-formyl-6-(3-(morpholinomethyl)phenyl)imidazo[1,2-a]pyrazin-8-yl)carbamate

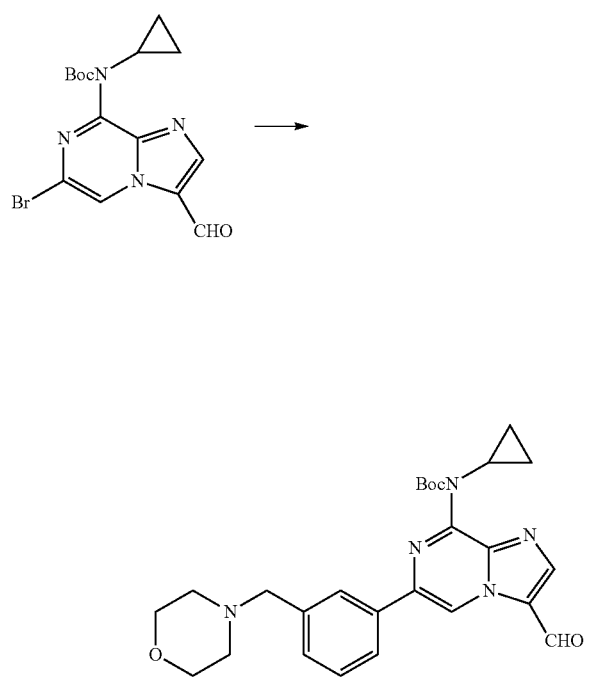

Tert-butyl 6-bromo-3-formylimidazo[1,2-a]pyrazine-8-yl (cyclopropyl)carbamate (100 mg, 0.26 mmol), 4-[3-(4,4,5,5-tetramethyl-1,3,2-dioxaborolan-2-yl)benzyl]morpholine (118 mg, 0.39 mmol), 3M Na$_2$CO$_3$ (1.3 mL, 2.60 mmol) and DME (3.5 mL) were combined. The solution was degassed with a stream of N$_2$ for 10 min. Pd(PPh$_3$)$_4$ was added and the solution was refluxed for 2 h. The solution was partitioned between dichloromethane (25 mL) and water (25 mL). The aqueous layer was further extracted with dichloromethane (2×25 mL). The organics were washed with brine (50 mL), dried over MgSO$_4$, filtered and concentrated in vacuo. The residue was purified via preparative TLC (5% MeOH/dichloromethane) to afford tert-butyl cyclopropyl(3-formyl-6-(3-(morpholinomethyl)phenyl)imidazo[1,2-a]pyrazin-8-yl)carbamate (60 mg, 48%). LCMS (ES): >95% pure, m/z 478 [M+1]$^+$.

Example 183

Synthesis of tert-butyl cyclopropyl(3-formyl-6-((trimethylsilyl)ethynyl)imidazo[1,2-a]pyrazin-8-yl)carbamate

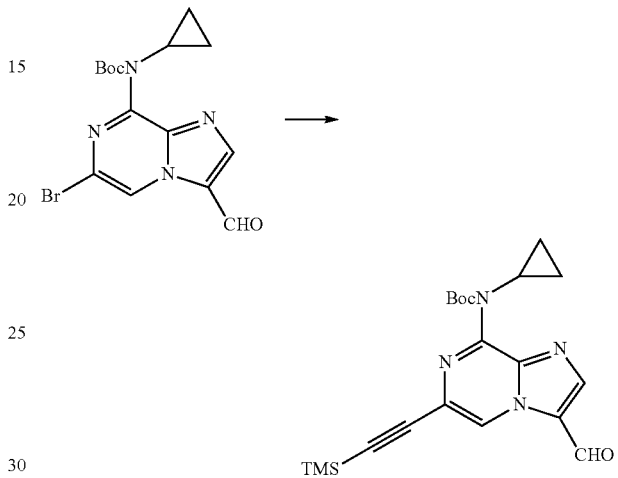

Triethylamine (912 μL, 6.56 mmol) was added to tert-butyl 6-bromo-3-formylimidazo[1,2-a]pyrazine-8-yl(cyclopropyl)carbamate (250 mg, 0.66 mmol) dissolved in anhydrous DMF (2.2 mL) in a 15 mL pressure tube. The solution was degassed with a stream of N$_2$ for 10 min. Trimethylsilylacetylene (927 μL, 6.56 mmol), Pd(PPh$_3$)$_4$ (76 mg, 0.07 mmol), and copper(I) iodide (25 mg, 0.13 mmol) were added and the reaction was sealed and heated to 65° C. for 24 h. The reaction was diluted with EtOAc (50 mL) and then washed with 10% brine (4×50 mL) and brine (50 mL). The organics were dried over MgSO$_4$, filtered and concentrated in vacuo. The residue was purified via flash column chromatography (30% EtOAc/hexanes) to give tert-butyl cyclopropyl(3-formyl-6-((trimethylsilyl)ethynyl)imidazo[1,2-a]pyrazin-8-yl)carbamate (186 mg, 71%) as a brown foamy solid. LCMS (ES): >95% pure, m/z 400 [M+1]$^+$.

Example 184

Synthesis of tert-butyl cyclopropyl(3-formyl-6-((phenylethynyl)imidazo[1,2-a]pyrazin-8-yl)carbamate

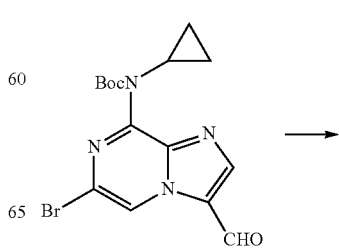

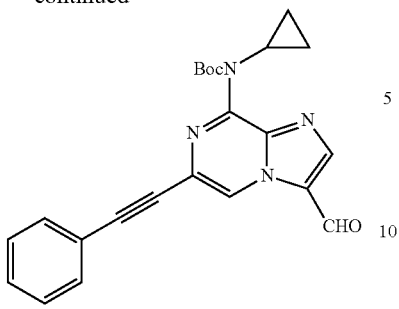

Tert-butyl cyclopropyl(3-formyl-6-((phenylethynyl)imidazo[1,2-a]pyrazin-8-yl)carbamate (64%) was synthesized in a manner analogous to Example 183. LCMS (ES): >95% pure, m/z 403 [M+1]⁺.

Example 185

Synthesis of tert-butyl cyclopropyl(6-ethynyl-3-formylimidazo[1,2-a]pyrazin-8-yl)carbamate

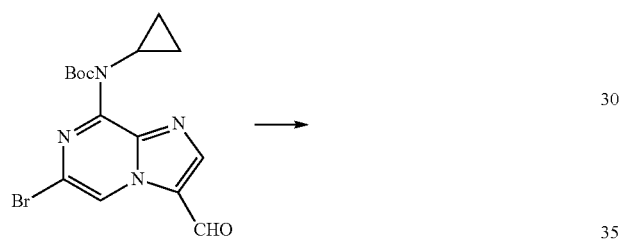

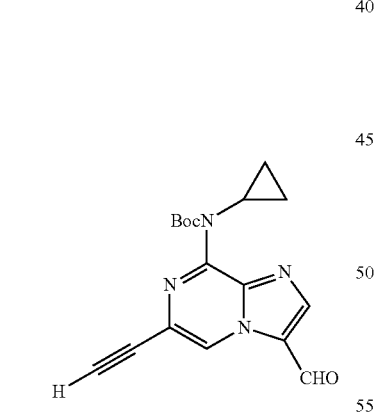

Potassium carbonate (86 mg, 0.63 mmol) was added to tert-butyl cyclopropyl(3-formyl-6-(((trimethylsilyl)ethynyl)imidazo[1,2-a]pyrazin-8-yl)carbamate (50 mg, 0.13 mmol) dissolved in methanol (2.5 mL). After 2 h, the volatiles were removed in vacuo. The residue was partitioned between dichloromethane (10 mL) and water (10 mL). The aqueous layer was further extracted with dichloromethane (2×10 mL). The organics were washed with brine (30 mL), dried over MgSO₄, filtered and concentrated in vacuo. The residue was purified via flash column chromatography (30% EtOAc/hexanes) to provide tert-butyl cyclopropyl(6-ethynyl-3-formylimidazo[1,2-a]pyrazin-8-yl)carbamate (20 mg, 50%) as a yellow foamy solid. LCMS (ES): >95% pure, m/z 327 [M+1]⁺.

Example 186

Synthesis of tort-butyl cyclopropyl(3-((2,5-dioxoimidazolidin-4-ylidene)methyl)-6-(3-trifluoromethoxy)phenyl)imidazo[1,2-a]pyrazin-8-yl)carbamate

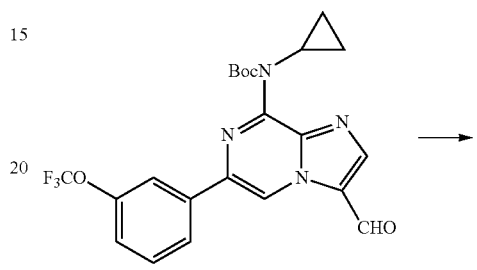

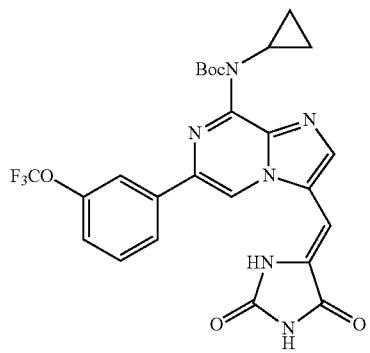

Hydantoin (33 mg, 0.33 mmol) and piperidine (33 µL, 0.33 mmol) were added to tert-butyl cyclopropyl(3-formyl-6-(3-trifluoromethoxy)phenyl)imidazo[1,2-a]pyrazin-8-yl)carbamate (50 mg, 0.11 mmol) suspended in ethanol (0.5 mL). The reaction was sealed and irradiated in the microwave at 80° C. for 12 h. The precipitate was filtered off and washed with ethanol (3 mL) to give (Z)-tert-butyl cyclopropyl(3-((2, 5-dioxoimidazolidin-4-ylidene)methyl)-6-(3-trifluoromethoxy)phenyl)imidazo[1,2-a]pyrazin-8-yl)carbamate (18 mg, 30%) as a bright yellow solid. LCMS (ES): >90% pure, m/z 545 [M+1]+.

Example 187

Synthesis of 5((8-cyclopropylamino)-6-(3-(trifluoromethoxy)phenyl) imidazo[1,2-a]pyrazin-3-yl)methylene)imidazolidine-2,4-dione

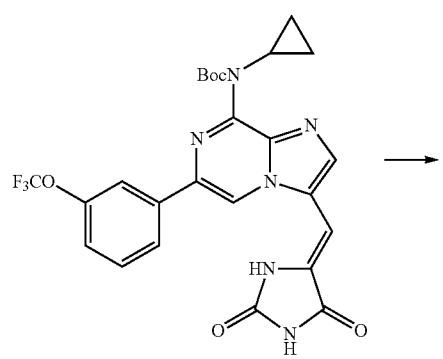

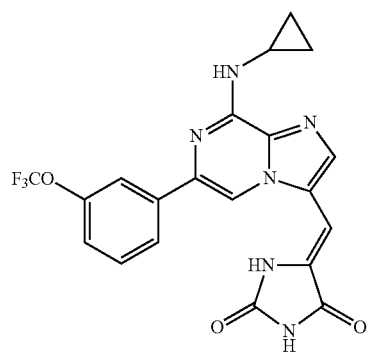

Tert-butyl cyclopropyl(3-((2,5-dioxoimidazolidin-4-ylidene)methyl)-6-(3-trifluoromethoxy)phenyl)imidazo[1,2-a]pyrazin-8-yl)carbamate (15 mg, 0.03 mmol) was dissolved in dichloromethane (0.5 mL) and trifluoroacetic acid (0.5 mL). After 1 h, the solution was concentrated under a stream of air. The residue was purified via preparative HPLC to furnish (Z)-5-((8-cyclopropylamino)-6-(3-(trifluoromethoxy)phenyl) imidazo[1,2-a]pyrazin-3-yl)methylene) imidazolidine-2,4-dione (0.9 mg, 8%).

Example 188

Synthesis of tert-butyl cyclopropyl(3-((2,5-dioxoimidazolidin-4-ylidene)methyl)-6-(phenylethnyl)imidazo[1,2-a]pyrazin-8-yl)carbamate

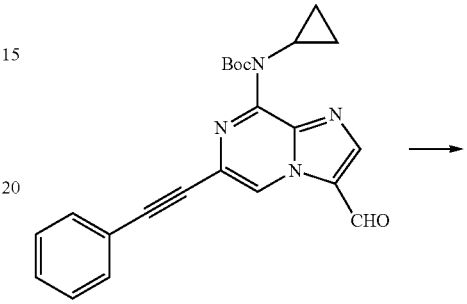

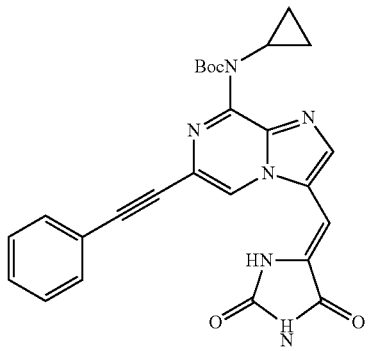

Hydantoin (24 mg, 0.24 mmol) and piperidine (24 µL, 0.24 mmol) were added to tert-butyl cyclopropyl(3-formyl-6-((phenylethynyl)imidazo[1,2-a]pyrazin-8-yl)carbamate (24 mg, 0.06 mmol) dissolved in ethanol (1 mL). The reaction was heated at 80° C. for 12 h, and then cooled to r.t. The precipitate was filtered off and washed with ethanol (3 mL) to give (Z)-tert-butyl cyclopropyl(3-((2,5-dioxoimidazolidin-4-ylidene)methyl)-6-(phenylethynyl)imidazo[1,2-a]pyrazin-8- yl)carbamate (12 mg, 43%) as an orange/yellow solid. LCMS (ES): >90% pure, m/z 485 [M+1]+.

Example 189

Synthesis of (Z)-5((8-(cyclopropylamino)-6-(phenylethynyl)imidazo[1,2-a]pyrazin-3-yl)methylene)imidazolidine-2,4-dione

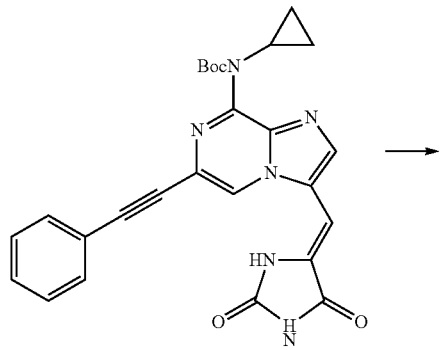

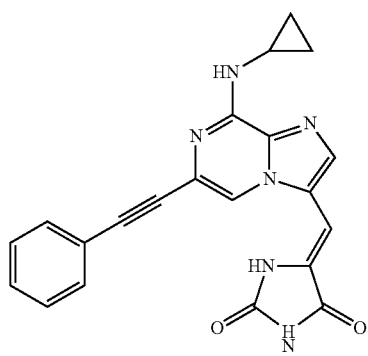

(Z)-Tert-butyl cyclopropyl(3-((2,5-dioxoimidazolidin-4-ylidene)methyl)-6-(phenylethynyl)imidazo[1,2-a]pyrazin-8-yl)carbamate (12 mg, 0.03 mmol) was dissolved in dichloromethane (0.3 mL) and trifluoroacetic acid (0.3 mL). After 1 h, the solution was concentrated under a stream of air. The residue was triturated with Et₂O and filtered to yield (Z)-5-((8-(cyclopropylamino)-6-(phenylethynyl)imidazo[1,2-a]pyrazin-3-yl)methylene)imidazolidine-2,4-dione (6 mg, 63%) as a bright yellow solid.

Example 190

Synthesis of (Z)-5-((8-(cyclopropylamino)-6-(3-morpholinomethyl)phenyl)imidazo[1,2-a]pyrazin-3-yl)methylene)imidazolidine-2,4-dione 2,2,2-trifluoroacetate

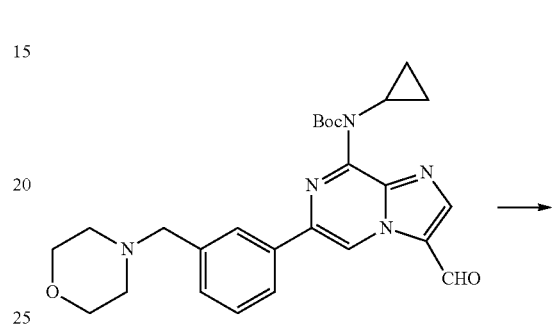

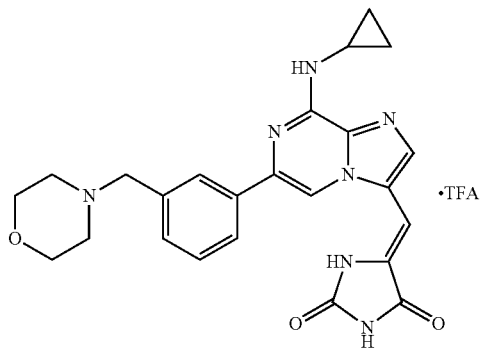

Hydantoin (152 mg, 1.50 mmol) and piperidine (150 μL, 1.50 mmol) were added to tert-butyl cyclopropyl(3-formyl-6-(3-(morpholinomethyl)phenyl)imidazo[1,2-a]pyrazin-8-yl)carbamate (60 mg, 0.13 mmol) dissolved in ethanol (1 mL). The reaction was heated at 80° C. for 4 d, and then diluted with water (10 mL). The supernatant was decanted and extracted with dichloromethane (2×15 mL). The organics were washed with brine (30 mL), dried over MgSO₄, filtered and concentrated in vacuo to a yellow solid. LCMS (ES): >95% pure, m/z 560 [M+1]+.

The crude solid was dissolved in dichloromethane (0.5 mL) and trifluoroacetic acid (0.5 mL). After 1 h, the solution was concentrated under a stream of air. The residue was purified via preparative HPLC to furnish (Z)-5-((8-(cyclopropylamino)-6-(3-morpholinomethyl)phenyl)imidazo[1,2-a]

pyrazin-3-yl)methylene)imidazolidine-2,4-dione 2,2,2-trifluoroacetate (5.5 mg, 8% over two steps).

Example 191

Synthesis of (Z)-548-cyclopropylamino)-6-(3-fluorophenyl)imidazo[1,2-a]pyrazin-3-yl)methylene)imidazolidine-2,4-dione

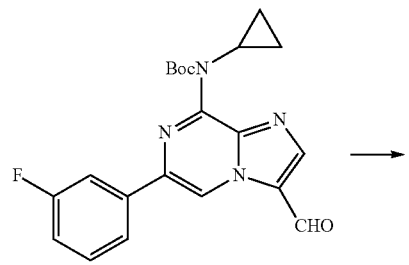

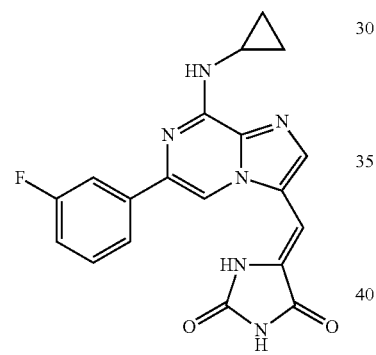

Hydantoin (18 mg, 0.17 mmol) and piperidine (17 μL, 0.17 mmol) were added to tert-butyl cyclopropyl(6-(3-fluorophenyl)-3-formylimidazo[1,2-a]pyrazin-8-yl)carbamate (23 mg, 0.06 mmol) dissolved in ethanol (0.3 mL). The reaction was heated at 80° C. for 18 h, and then concentrated in vacuo to a yellow solid. The crude solid was dissolved in dichloromethane (0.5 mL) and trifluoroacetic acid (1.5 mL). After 1 h, the solution was concentrated under a stream of air. The residue was triturated with ethanol and filtered to provide (Z)-5-((8-cyclopropylamino)-6-(3-fluorophenyl)imidazo[1,2-a]pyrazin-3-yl)methylene)imidazolidine-2,4-dione as an orange/yellow solid (2.4 mg, 10% over two steps).

Example 192

Synthesis of Related Compounds

The compounds in the following table were prepared by the methods described above, by selecting appropriate starting materials as is apparent to the person of ordinary skill. Table 28B shows the biological activities of the compounds listed in Table 28A.

TABLE 28A

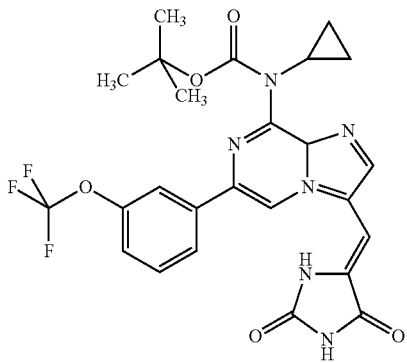

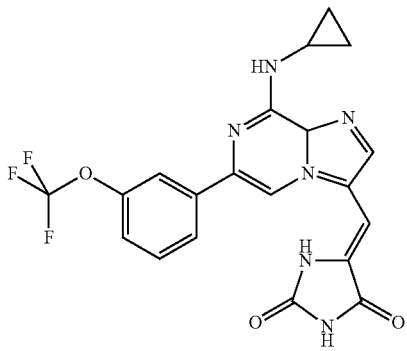

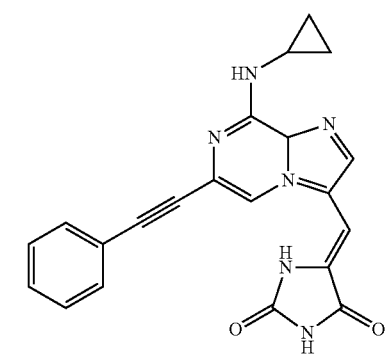

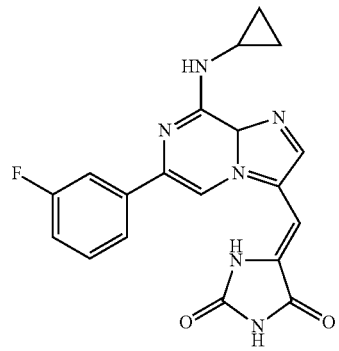

TABLE 28A-continued

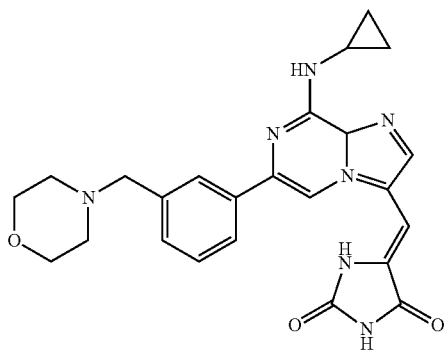

TABLE 28B

| Compound | CK2: IC50 (µM) | PIM2: IC50 (5 µM ATP) | AB: MDAMB453 (µM) | AB: BxPC3 (µM) |
| --- | --- | --- | --- | --- |
| C14 | >5.0000 | >2.5000 | | |
| D14 | <0.1 | >2.5000 | 4.531 | 3.69 |
| E14 | >5.0000 | >2.5000 | | |
| F14 | >5.0000 | >2.5000 | | |
| G14 | >5.0000 | >2.5000 | | |

Figure 7:
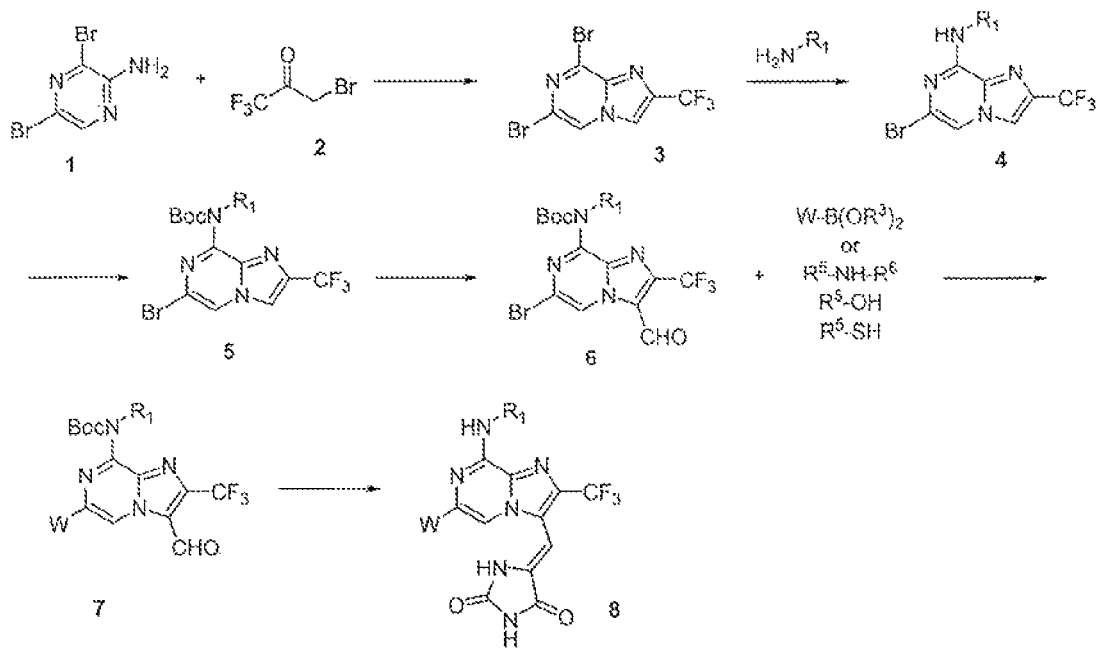
FIG. 7 shows a general synthetic method for making various imidazo-pyrazine ring systems andfor making certain compounds of the invention.

The chemistries described on FIG. 7 can be used to prepare analogs substituted by a trifluoromethyl group. Commercially available 2-amino-3,5-dibromopyrazine and commercially available 3-bromo-1,1,1-trifluoroacetone can be reacted together at 50° C. in a solvent such as dioxin (conditions previously described in WO2003/82817), to prepare compound 3 Compound 3 can be reacted with amine $R_1NH_2$ to obtain 4. This material can be protected by a boc group by reacting 4 with a reagent like $Boc_2O$ to obtain 5. This material can be further transformed into 6 under vilsmeir conditions in the presence of $POCl_3$. Compound 6 can be reacted with various reagents such as boronic acids or esters $W-B(OR_3)_2$ under Suzuki conditions to form molecule 7.

Other analogs of 7 can be prepared by heating 6 with amines or anilines $R_5R_6NH$, alcohols or phenols $R_5OH$, thiols or thiophenols $R_5SH$, in the presence of a base or an acid. Compound 8 can be prepared by heating 7 with hydantoin in ethanol in the presence of a base such as piperidine.

General Methods

Unless otherwise specified, the various substituents of the compounds are defined in the same manner as the formula II/II' compound of the invention.

Figure 4:
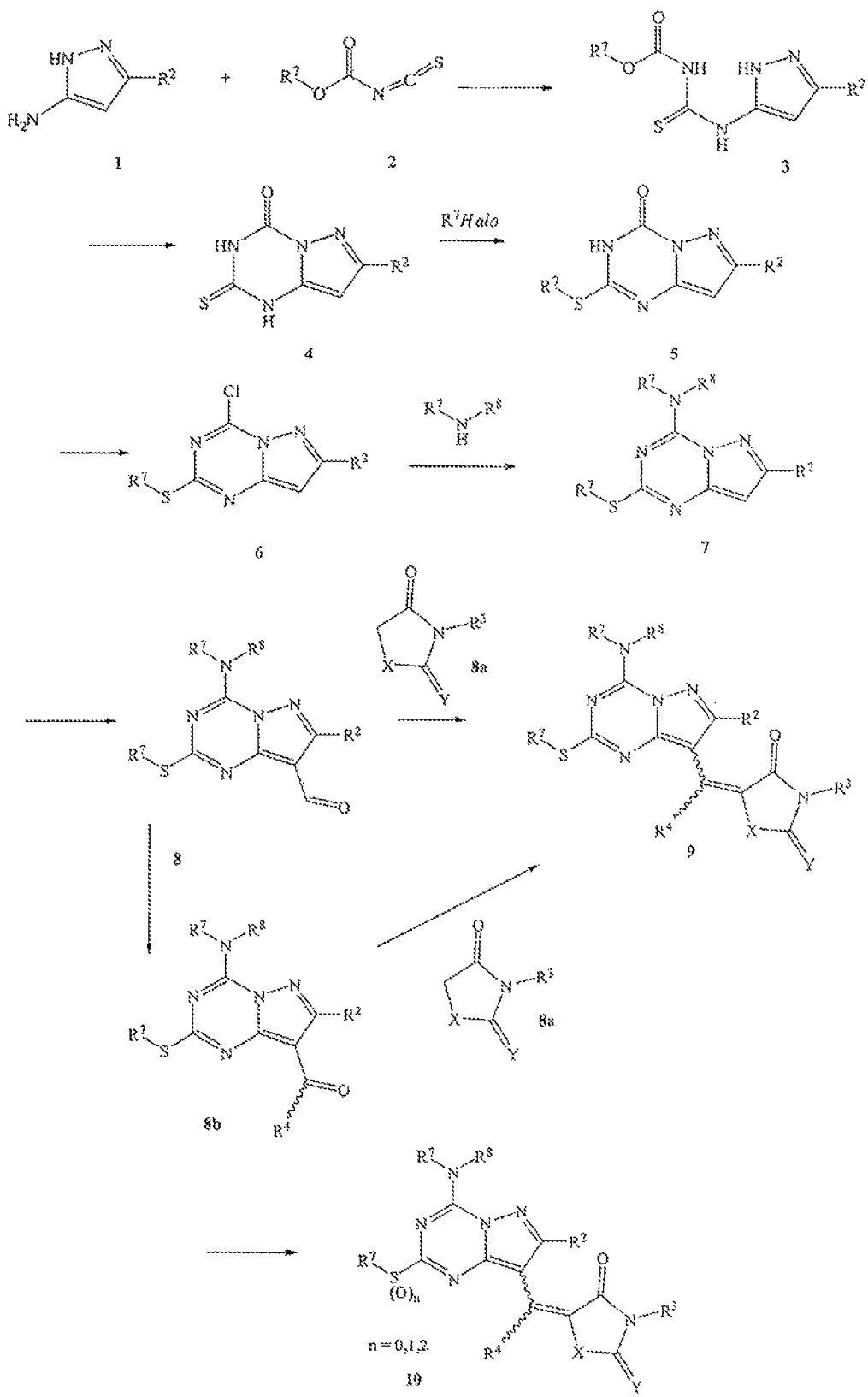
FIG. 4 illustrates the syntheses of certain pyrazolotriazines of the invention.
Figure 5:
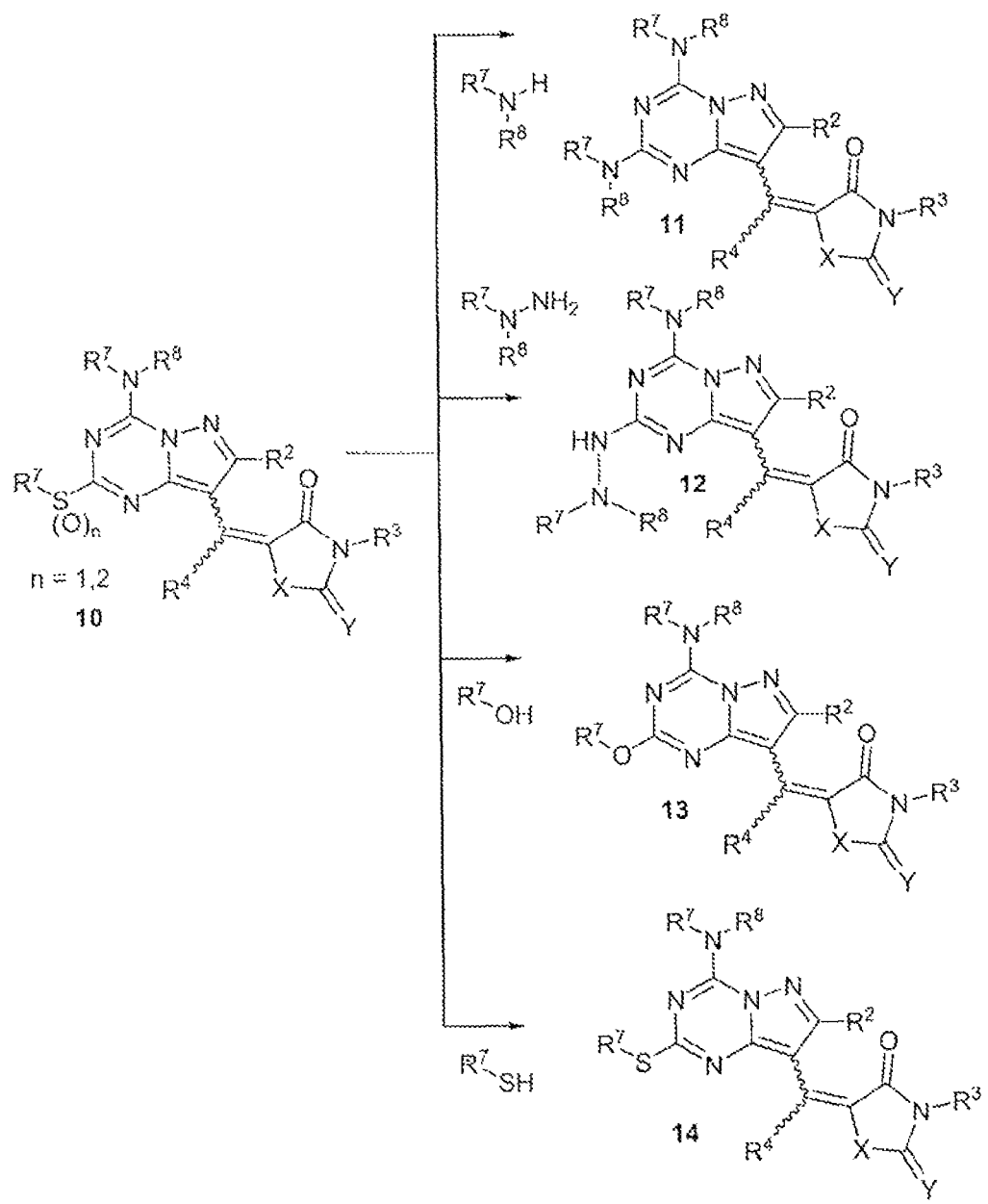
FIG. 5 illustrates synthesis methods for introducing various nucleophilic groups onto a pyrazolo-triazine ring system for preparing compounds of the invention.

The chemistry described in FIG. 4 and FIG. 5 can be used to prepare various substituted compounds of formula II.

Substituted aminopyrazole 1 can react with isothiocyanate 2 to form intermediate 3.

Compound 3 can be cyclized to 4 in the presence of a base such as sodium hydroxide. Compound 4 can be alkylated by with R7Halo in the presence of a base. Compound 5 can be converted to compound 6 using phosphorus oxychloride. Molecule 7 can be prepared by addition of amine $R_7R_8NH$ to molecule 6 in a solvent like NMP or DMF. Compound 8 can be obtained by reacting compound 7 with DMF and Phosphorus oxychloride under Vilsmeier reaction conditions. Aldehyde 8 can be converted in two steps to substituted ketone 8b by reacting with a Grignard reagent $R_4MgX$, followed by reaction with an oxidant such as DCC or using Swern reaction conditions.

Compound 8 and 8a, or 8b and 8a can react upon heating in a solvent such as ethanol and in the presence of a base such as piperidine to form compound 9. Oxidation of 9 by an oxidant such as meta-chloroperbenzoic acid or oxone can provide compound 10, which can contain variable quantities of sulfide (n=0), sulfoxide (n=1) or sulfone (n=2).

The chemistry depicted in FIG. 5 can be used to prepare various substituted analogs of formula II compounds.

Compound 10 can be mixed at room temperature or heated with amines $R_7R_8NH$ to form compound 11. Compound 10 can be reacted with hydrazines $R_7R_8N$—$NH_2$ to form compound 12. Compound 10 can be reacted with alcohols or phenols $R_7OH$ in the presence of a base such as NaH or $K_2CO_3$ to form compound 13. Compound 10 can be reacted with thiols or thiophenols $R_7SH$ with or without a base to form compound 14.

Figure 6:
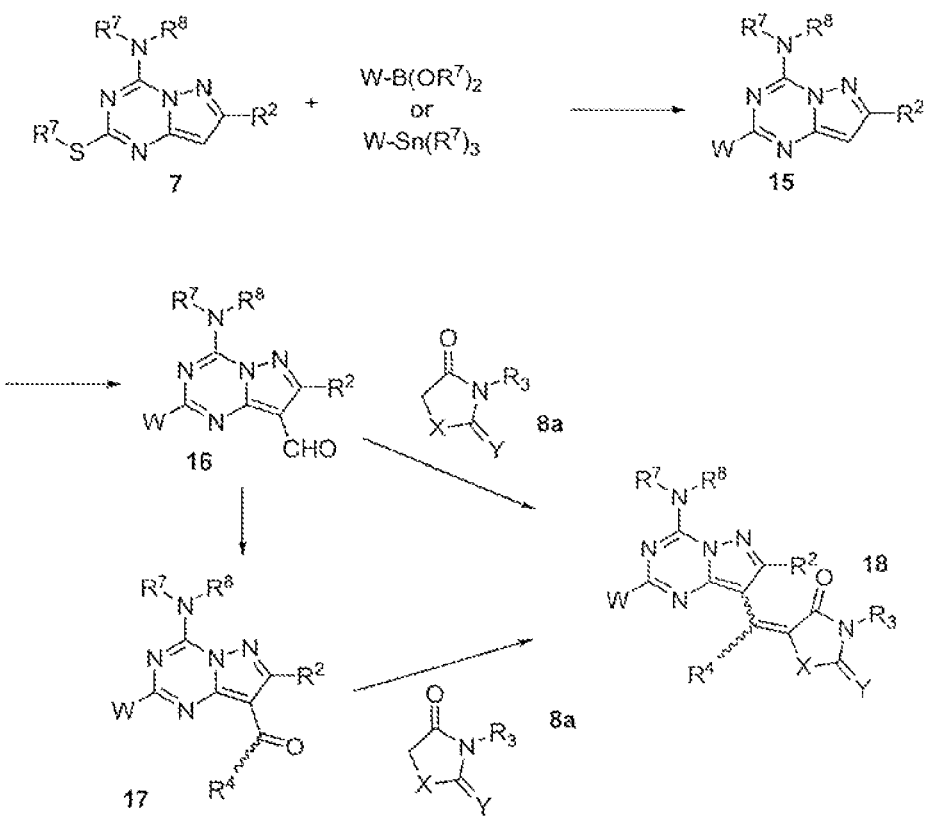
FIG. 6 illustrates general synthesis routes for making certain pyrazolo-triazine compounds of the invention.

The chemistry described in FIG. 6 can be used to prepare analogs substituted by aryl or heteroaryls groups. Compound 7 can be reacted with boronic esters or acids $W-B(OR^7)_2$ or organo tin compounds $W$—$Sn(R^7)_3$ in the presence of tri(2-furyl)phosphine, copper(I)thiophene-2-carboxylate and $Pd_2 dba_3$ or using conditions previously described in Organic Letters 2002, vol 4(6), pp. 979-981. Compound 15 can be converted to compound 18 using chemistries similar to the one described in FIG. 4.

Example 193

Synthesis of 2-(methylthio)pyrazolo[1,5-a][1,3,5]-triazin-4(3H)-one

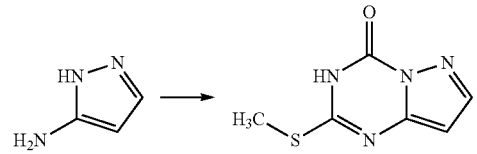

The material was prepared according to a procedure published in patent U.S. Pat. No. 3,846,423. Characterized by LCMS (ES):>95% pure, m/z 183 [M+H]+.

Example 194

Synthesis of 4-chloro-2-(methylthio)pyrazolo[1,5-a][1,3,5]triazine

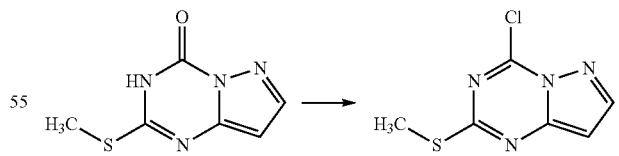

In a round bottom flask equipped with a magnetic stirbar, 2-(methylthio)pyrazolo[1,5-a][1,3,5]triazin-4(3H)-one (1.0 eq, 10.43 g, 57.24 mmol) was suspended in acetonitrile (100 ml). Phosphorus oxychloride (4.0 eq, 21 ml, 229.4 mmol) and triethylamine (1.05 eq, 8.4 ml, 60.27 mmol) were added and the mixture stirred at reflux for 3.5 hours, at which time LCMS indicated completion of the reaction. The mixture was cooled down and slowly poured into crushed ice (final total volume of about 600 ml). The solid was filtered, washed with water and dried in a vacuum oven to afford 4-chloro-2-(methylthio)pyrazolo[5-a][1,3,5]triazine as a tan solid (8.15 g, 71% yield). LCMS (ES):>97% pure, m/z 201 [M+H]⁺.

Example 195

Synthesis of N-cyclopropyl-2-(methylthio)pyrazolo[1,5-a][1,3,5]-triazin-4-amine

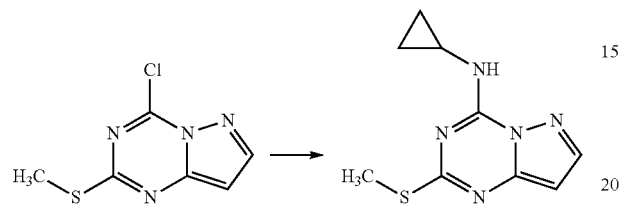

4-Chloro-2-(methylthio)pyrazolo[1,5-a][1,3,5]triazine (1.0 eq, 6.26 g, 31.19 mmol) was suspended in anhydrous NMP (50 ml). Cyclopropylamine (1.5 eq, 3.2 ml, 46.26 mmol) was added through syringe dropwise. Internal temperature rose to 47° C. The mixture was stirred without any external cooling for one hour. An additional amount of cypropylamine (1 ml) was added and the mixture stirred for another 1.5 hours. The mixture was slowly poured into water (500 ml) under stirring. The resulting solid was filtered, washed with water and dried in a vacuum oven to give N-cyclopropyl-2-(methylthio)pyrazolo[1,5-a][1,3,5]triazin-4-amine as a tan solid (5.44 g, 79% yield). LCMS (ES):>95% pure, m/z 222 [M+H]⁺.

The following molecules were prepared using chemistries similar to Example 195. Compounds were characterized by LCMS.

TABLE 29

| Structure | MW | LCMS m/z [M + 1]+ |
|---|---|---|
| HN-CH₂-CH₂-O-CH₂-CH₃ on core | 253.32 | 254 |
| H₃C-N(phenyl) on core | 271.34 | 272 |

TABLE 29-continued

| Structure | MW | LCMS m/z [M + 1]+ |
|---|---|---|
| HN-CH₂-CF₃ with extra F on core | 263.24 | 264 |
| HN-CH₂-cyclopropyl on core | 235.31 | 236 |

Example 196

Synthesis of 4-(cyclopropylamino)-2-(methylthio)pyrazolo[1,5-a][1,3,5]triazine-8-carbaldehyde

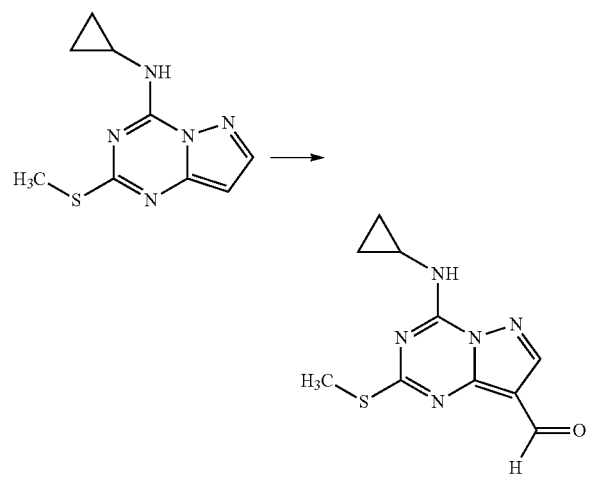

N-Cyclopropyl-2-(methylthio)pyrazolo[1,5-a][1,3,5]triazin-4-amine (1.0 eq, 3.10 g, 14.00 mmol) was dissolved in anhydrous DMF (50 ml) under nitrogen atmosphere. Phosphorus oxychloride (5.0 eq, 6.4 ml, 69.9 mmol) was added dropwise over 5 minutes. Internal temperature rose to 45° C. The reaction was stirred in an oil bath at 70° C. for 4.5 hours. The mixture was cooled down and added dropwise into a solution of 6N NaOH (150 ml) chilled with an ice bath. The rate of addition was adjusted to maintain the internal temperature of the aqueous NaOH below 16° C. At the end of the addition, the mixture was neutralized by slow addition of 6N HCl to reach pH=5-6. The resulting solid was filtered, washed with water and dried in a vacuum oven overnight. 4-(cyclopropylamino)-2-(methylthio)pyrazolo[1,5-a][1,3,5]triazine-8-carbaldehyde was isolated as tan solid (9.26 g, 93%). LCMS (ES):>95% pure, m/z 250 [M+H]⁺.

The following molecules were prepared using chemistries similar to Example 196. Compounds were characterized by LCMS.

TABLE 30

| Structure | MW | LCMS m/z [M + 1]+ |
|---|---|---|
| 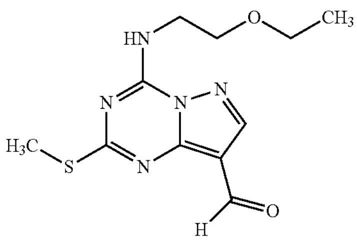 [SMILES: CCOCCNc1nc(SC)nc2c(C=O)cnn12] | 281.3341 | 282 |
| 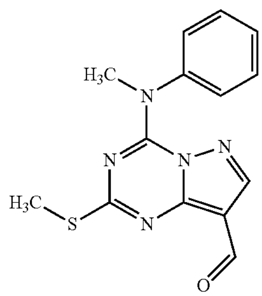 [SMILES: CSc1nc(N(C)c2ccccc2)n2ncc(C=O)c2n1] | 299.3509 | 300 |
| 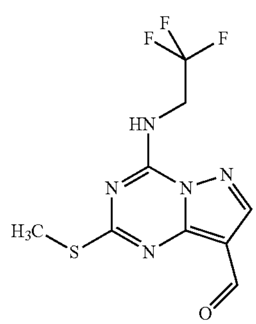 [SMILES: CSc1nc(NCC(F)(F)F)n2ncc(C=O)c2n1] | 291.26 | 292 |
| 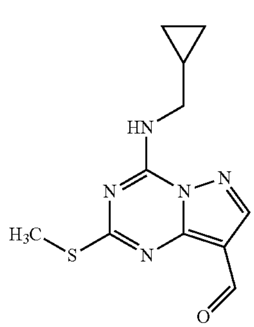 [SMILES: CSc1nc(NCC2CC2)n2ncc(C=O)c2n1] | 263.32 | 264 |

Example 197

Synthesis of (Z)-5-((4-(cyclopropylamino)-2-(methylthio)pyrazolo[1,5-a][1,3,5]-triazin-8-yl)methylene)imidazolidine-2,4-dione

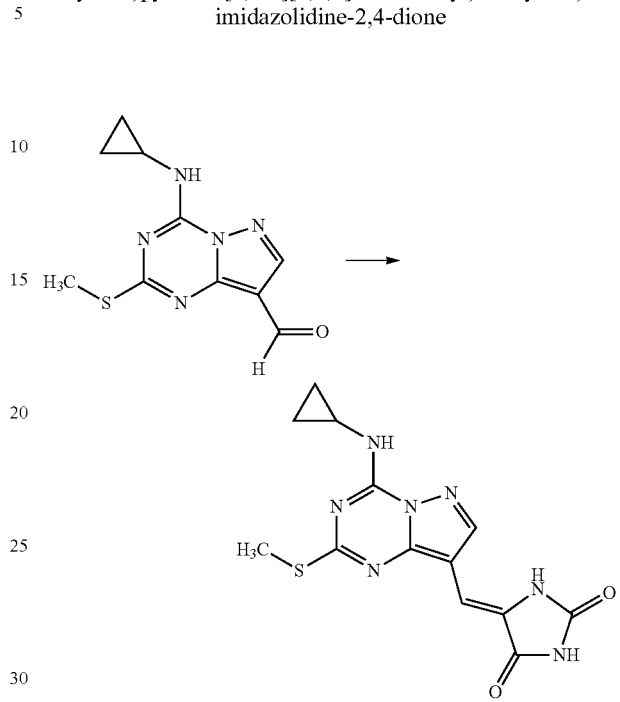

4-(Cyclopropylamino)-2-(methylthio)pyrazolo[1,5-a][1,3,5]triazine-8-carbaldehyde (1.0 eq, 3.00 g, 12.03 mmol) was suspended in ethanol (40 ml). Hydantoin (1.5 eq, 1.81 g, 18.08 mmol) and piperidine (1.5 eq, 1.78 ml, 18.01 mmol) were added. The mixture was heated at reflux under vigorous magnetic stirring for 3 hours. After cooling of the reaction mixture, the precipitate was filtered, washed with ethanol, then with a mixture of ethanol and water (1:1). After drying in vacuo, (Z)-5-((4-(cyclopropylamino)-2-(methylthio)pyrazolo[1,5-a][1,3,5]triazin-8-yl)methylene)imidazolidine-2,4-dione was isolated as a yellow solid (3.80 g, 95%). LCMS (ES):>85% pure, m/z 332 [M+H]+.

The following molecules were prepared using chemistries similar to Example 197. Compounds were characterized by LCMS.

TABLE 31

| Structure | MW | LCMS m/z [M + 1]+ |
|---|---|---|
| 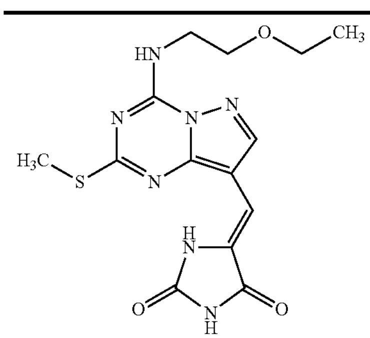 | 363.39 | 364 |

TABLE 31-continued

| Structure | MW | LCMS m/z [M + 1]+ |
|---|---|---|
| (structure with CF3, HN, H3C-S, pyrazolo-triazine, imidazolidine-2,4-dione) | 373.32 | 374 |
| (structure with N-methyl-N-phenyl, H3C-S, pyrazolo-triazine, imidazolidine-2,4-dione) | 381.42 | 382 |

Example 198

Synthesis of (Z)-5-((4-(cyclopropylamino)-2-methylsulfonyl)pyrazolo [1,5-a][1,3,5]triazin-8-yl)methylene)imidazolidine-2,4-dione and (Z)-5-((4-cyclopropylamino-2-(methylsulfinyl)pyrazolo[1,5-a][1,3,5]triazin-8-yl)methylene)imidazolidine-2,4-dione

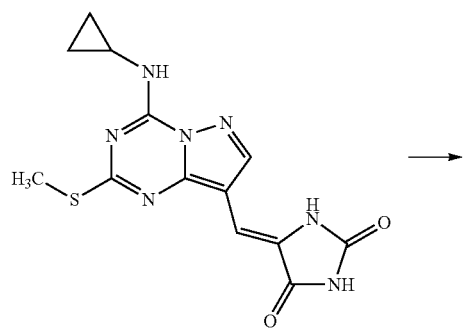

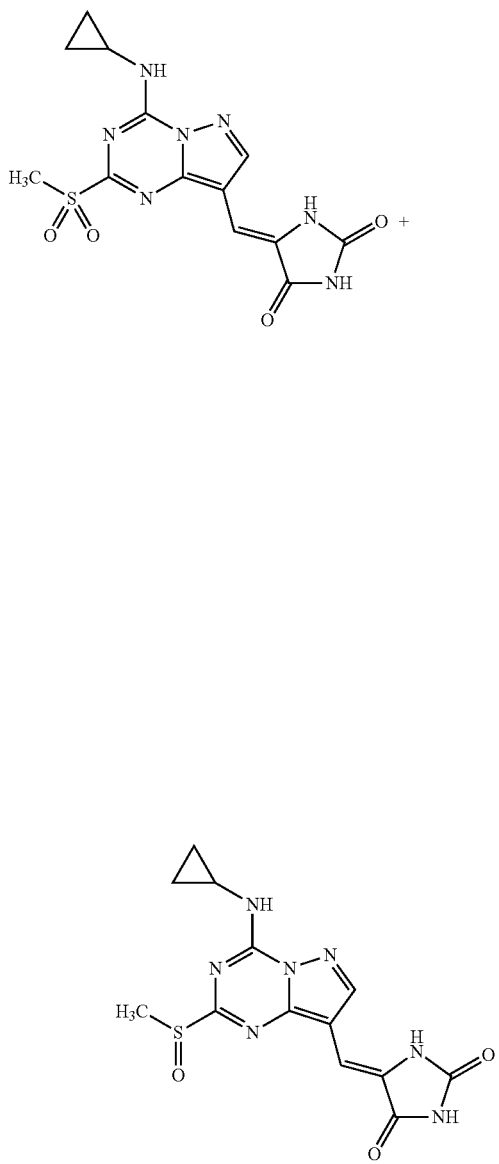

(Z)-5-(4-(Cyclopropylamino)-2-(methylthio)pyrazolo[1,5-a][1,3,5]triazin-8-yl)methylene)imidazolidine-2,4-dione (1.0 eq, 3.00 g, 9.05 mmol) was suspended in dichloromethane (150 ml). m-cpba (77% purity grade, 5.0 eq, 10.1 g, 45.06 mmol) was added and the mixture stirred at room temperature for 4 hours. The reaction was diluted by addition of dichloromethane (500 ml). The solid was filtered and washed with dichloromethane. After drying a (1:1) mixture of (Z)-5-((4-(cyclopropylamino)-2-(methylsulfonyl)pyrazolo [1,5-a][1,3,5]triazin-8-yl)methylene)imidazolidine-2,4-dione and (Z)-5-(4-(cyclopropylamino)-2-(methylsulfinyl) pyrazolo[1,5-a][1,3,5]triazin-8-yl)methylene)imidazolidine-2,4-dione was isolated as a yellow solid (2.67 g, 81%). LCMS (ES):>85% pure, m/z 364 [M+H]+ and m/z 398 [M+H]+. The mixture was used for next step without any separation of the molecules.

The following mixtures of sulfones and sulfoxides were prepared using chemistries similar to Example 198. Compounds were characterized by LCMS.

TABLE 32
| Structure | MW | LCMS m/z [M + 1]+ |
|---|---|---|
| 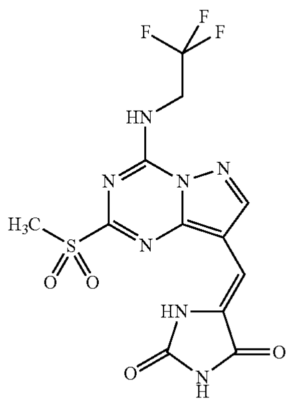 [SMILES: CS(=O)(=O)c1nc(NCC(F)(F)F)n2ncc(/C=C3\NC(=O)NC3=O)c2n1] | 405.32 | 406 |
| 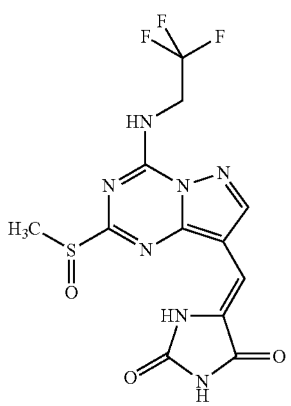 [SMILES: CS(=O)c1nc(NCC(F)(F)F)n2ncc(/C=C3\NC(=O)NC3=O)c2n1] | 389.32 | 390 |
| 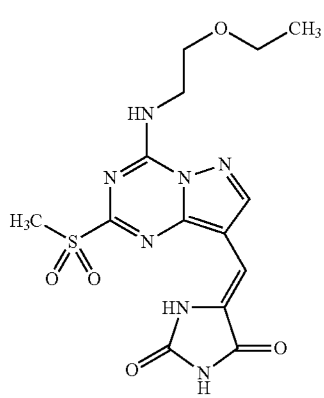 [SMILES: CCOCCNc1nc(S(C)(=O)=O)nc2c(/C=C3\NC(=O)NC3=O)cnn12] | 395.4 | 396 |
TABLE 32-continued
| Structure | MW | LCMS m/z [M + 1]+ |
|---|---|---|
| 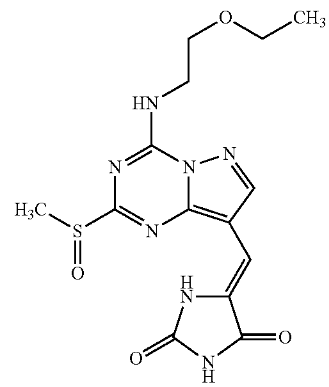 [SMILES: CCOCCNc1nc(S(C)=O)nc2c(/C=C3\NC(=O)NC3=O)cnn12] | 379.4 | 380 |
Example 199
Synthesis of (Z)-5-((2-(3-chlorophenylamino)-4-(cyclopropylamino)-pyrazolo[1,5-a][1,3,5]triazin-8-yl)methylene)imidazolidine-2,4-dione
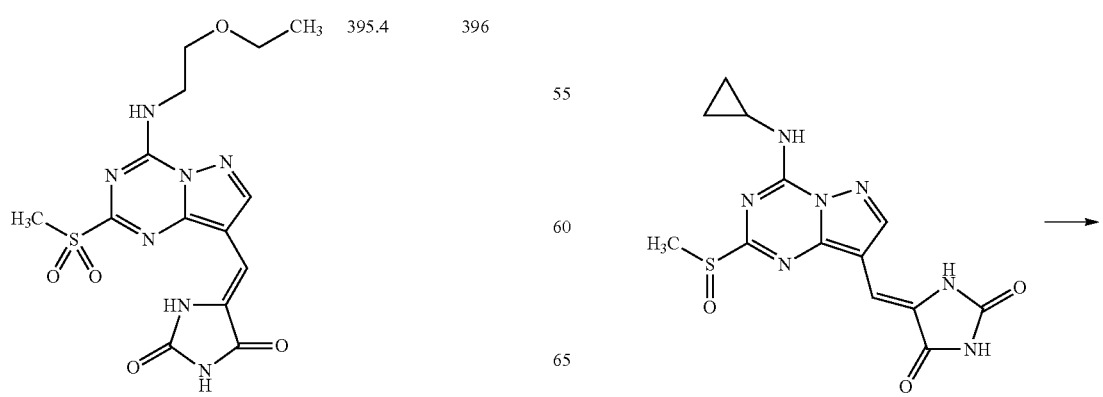

-continued

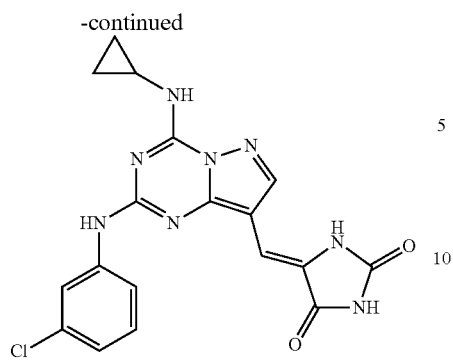

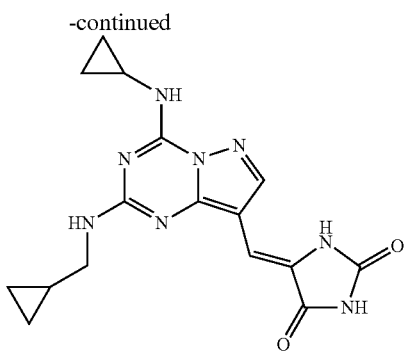

A (1:1) mixture of (Z)-5-((4-(cyclopropylamino)-2-(methylsulfonyl)pyrazolo[1,5-a][1,3,5]triazin-8-yl)methylene)imidazolidine-2,4-dione and (Z)-5((4-(cyclopropylamino)-2-(methylsulfinyl)pyrazolo[1,5-a][1,3,5]triazin-8-yl)methylene)imidazolidine-2,4-dione (15 mg) was mixed with 3-chloroaniline (0.1 ml) in NMP (0.2 ml) and the mixture heated in a microwave oven at 120° C. for 15 min. Methanol was added and the resulting solid filtered and dried to provide (Z)-5-(2-(3-chlorophenylamino)-4-(cyclopropylamino)pyrazolo[1,5-a][1,3,5]triazin-8-yl)methylene)imidazolidine-2,4-dione as a solid (7 mg). LCMS (ES):>95% pure, m/z 411 [M+H]$^+$.

Example 200

Synthesis of (Z)-5-((4-(cyclopropylamino)-2-(cyclopropylmethylamino)-pyrazolo[1,5-a][1,3,5]triazin-8-yl)methylene) imidazolidine-2,4-dione A (1:1) mixture of (Z)-5-((4-(cyclopropylamino)-2-(methylsulfonyl)pyrazolo[1,5-a][1,3,5]triazin-8-yl)methylene)imidazolidine-2,4-dione and (Z)-5-((4-(cyclopropylamino)-2-(methylsulfinyl)pyrazolo[1,5-a][1,3,5]triazin-8-yl)methylene)imidazolidine-2,4-dione (36 mg) was suspended in NMP (0.2 ml). Cyclopropylmethylamine (88 uL) was added and the mixture stirred at room temperature for 15 minutes. Water and methylene chloride were added and the resulting precipitate was filtered. After triturating in a mixture of ethyl acetate and hexanes, (Z)-5-((4-(cyclopropylamino)-2-(cyclopropylmethylamino)pyrazolo[1,5-a][1,3,5]triazin-8-yl) methylene)imidazolidine-2,4-dione was isolated as a yellow solid.). LCMS (ES):>95% pure, m/z 355 [M+H]$^+$.

Example 201

Synthesis of (Z)-5-((2-(3-chlorophenoxy)-4-(cyclopropylamino)pyrazolo[1,5-a][1,3,5]-triazin-8-yl)methylene)imidazolidine-2,4-dione

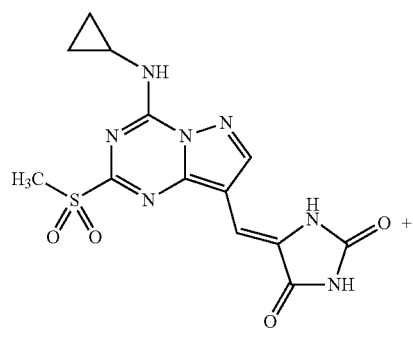

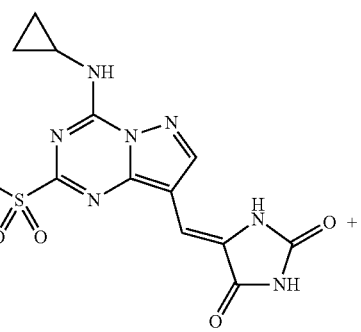

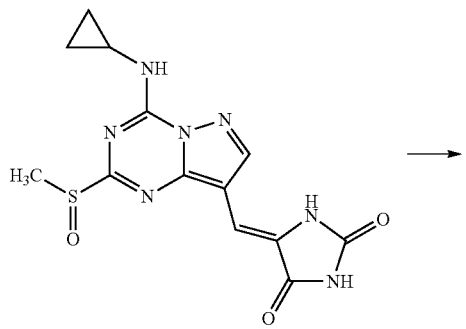

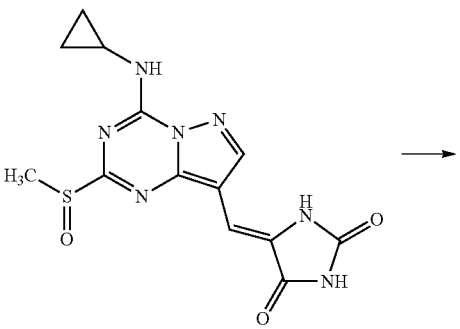

-continued

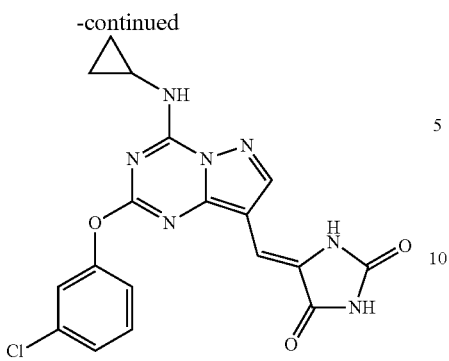

A (1:1) mixture of (Z)-5-((4-(cyclopropylamino)-2-(methylsulfonyl)pyrazolo[1,5-a][1,3,5]triazin-8-yl)methylene)imidazolidine-2,4-dione and (Z)-5-((4-(cyclopropylamino)-2-(methylsulfinyl)pyrazolo[1,5-a][1,3,5]triazin-8-yl)methylene)imidazolidine-2,4-dione (1.0 eq, 25 mg, 0.0704 mmol) was combined in a vial with 3-chlorophenol (5.0 eq, 45 mg, 0.35 mmol) and $K_2CO_3$ (5.0 eq, 48 mg, 0.347 mmol) in NMP (0.2 ml). The mixture was stirred at 90° C. for 1 hour. Water was added and the resulting solid was filtered and dried. Trituration in a mixture of ethyl acetate and hexanes followed by filtration provided (Z)-5-((2-(3-chlorophenoxy)-4-(cyclopropylamino)pyrazolo[1,5-a][1,3,5]triazin-8-yl)methylene)imidazolidine-2,4-dione as a tan solid (20 mg, 69%). LCMS (ES):>95% pure, m/z 412 [M+H]$^+$.

Example 202

Synthesis of (1r,4r)-4-(4-(cyclopropylamino)-8-((Z)-(2,5-dioxoimidazolidin-4-ylidene)methyl)pyrazolo[1,5-a][1,3,5]triazin-2-ylamino)-N-methylcyclohexanecarboxamide

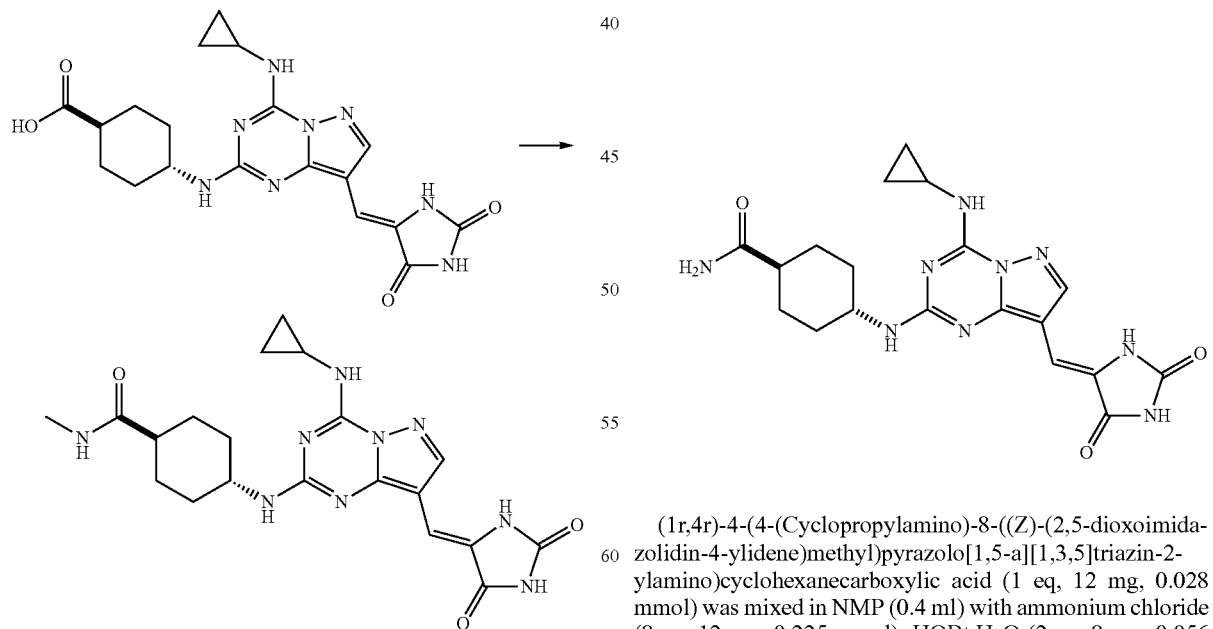

(1r,4r)-4-(4-(Cyclopropylamino)-8-((Z)-(2,5-dioxoimidazolidin-4-ylidene)methyl)pyrazolo[1,5-a][1,3,5]triazin-2-ylamino)cyclohexanecarboxylic acid (1 eq, 12 mg, 0.028 mmol) was mixed in NMP (0.4 ml) with methyl amine hydrochloride (8 eq, 15 mg, 0.225 mmol), HOBt.H$_2$O (2 eq, 8 mg, 0.056 mmol), DIEA (4 eq, 14 uL, 0.113 mmol) and EDCI (4 eq, 22 mg, 0.113 mmol). The mixture was stirred at 70° C. for 2.5 hours. Water was added and the precipitate filtered to afford (1r,4r)-4-(4-(cyclopropylamino)-8-((Z)-(2,5-dioxoimidazolidin-4-ylidene)methyl)pyrazolo[1,5-a][1,3,5]triazin-2-ylamino)-N-methylcyclohexanecarboxamide. LCMS (ES):>95% pure, m/z 440 [M+H]$^+$.

Example 203

Synthesis of (1r,4r)-4-(4-(cyclopropylamino)-8-((Z)-(2,5-dioxoimidazolidin-4-ylidene)methyl)pyrazolo-[1,5-a][1,3,5]triazin-2-ylamino)cyclohexanecarboxamide

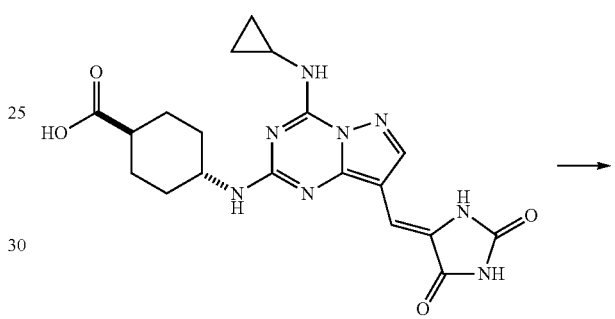

(1r,4r)-4-(4-(Cyclopropylamino)-8-((Z)-(2,5-dioxoimidazolidin-4-ylidene)methyl)pyrazolo[1,5-a][1,3,5]triazin-2-ylamino)cyclohexanecarboxylic acid (1 eq, 12 mg, 0.028 mmol) was mixed in NMP (0.4 ml) with ammonium chloride (8 eq, 12 mg, 0.225 mmol), HOBt.H$_2$O (2 eq, 8 mg, 0.056 mmol), DIEA (4 eq, 14 uL, 0.113 mmol) and EDCI (4 eq, 22 mg, 0.113 mmol). The mixture was stirred at 70° C. for 2.5 hours. Water was added and the precipitate filtered to afford (1r,4r)-4-(4-(cyclopropylamino)-8-((Z)-(2,5-dioxoimidazolidin-4-ylidene)methyl)pyrazolo[1,5-a][1,3,5]triazin-2-ylamino)cyclohexanecarboxamide. LCMS (ES):>95% pure, m/z 426 [M+H]⁺.

Example 204

Synthesis of (Z)-5-((2-((1r,4r)-4-aminocyclohexylamino)-4-(cyclopropylamino)pyrazolo[1,5-a][1,3,5]-triazin-8-yl)methylene)imidazolidine-2,4-dione

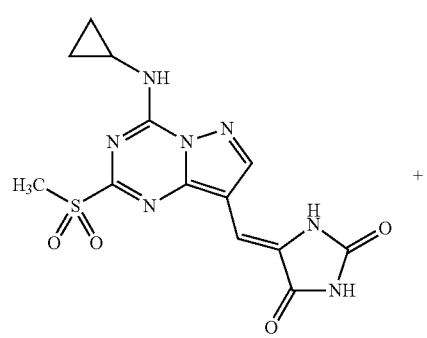

+

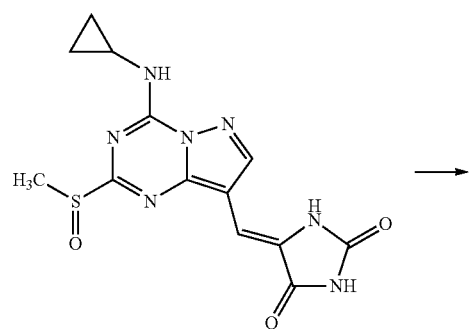

↓

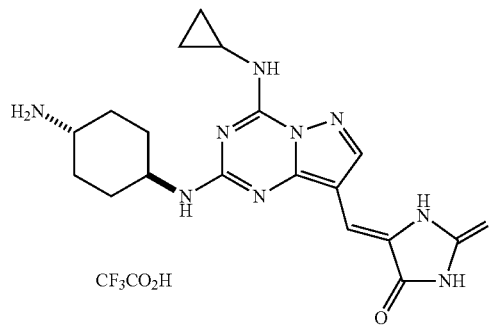

A (1:1) mixture of (Z)-5-((4-(cyclopropylamino)-2-(methylsulfonyl)pyrazolo[1,5-a][1,3,5]triazin-8-yl)methylene)imidazolidine-2,4-dione and (Z)-5-((4-(cyclopropylamino)-2-(methylsulfinyl)pyrazolo[1,5-a][1,3,5]triazin-8-yl)methylene)imidazolidine-2,4-dione (1.0 eq, 16 mg, 0.0451 mmol) was reacted with trans-1,4-diaminocyclohexane (20.0 eq, 103 mg, 0.902 mmol) in NMP (0.4 ml) at room temperature for 3 hours. Water and methanol was added and the material was purified by preparative HPLC. Genevac evaporation provided (Z)-5-((2-((1r,4r)-4-aminocyclohexylamino)-4-(cyclopropylamino)pyrazolo[1,5-a][1,3,5]triazin- 8-yl)methylene)imidazolidine-2,4-dione 2,2,2-trifluoroacetate (15 mg). LCMS (ES):>95% pure, m/z 398 [M+H]⁺.

Example 205

Synthesis of tert-butyl cyclopropyl(2-(3-(trifluoromethoxy)phenyl)pyrazolo[1,5-a][1,3,5]triazin-4-yl)carbamate Di-tert-butyl dicarbonate (327 mg, 1.50 mmol) and DMAP (6 mg, 0.05 mmol) were added to N-cyclopropyl2-(methylthio)pyrazolo[1,5-a][1,3,5]triazin-4-amine (221 mg, 1 mmol) dissolved in dichloromethane (4 mL). After 15 h, the solution was diluted with EtOAc (100 mL) and washed successively with water (3×100 mL) and brine (100 mL). The organic layer was dried over MgSO₄, filtered and concentrated in vacuo to an orange oil. The residue was purified via flash column chromatography (10% EtOAc/hexanes) to afford tert-butyl cyclopropyl(2-(methylthio)pyrazolo[1,5-a][1,3,5]triazin-4-yl)carbamate (368 mg, 79%). LCMS (ES): >95% pure, m/z 322 [M+1]⁺.

Example 206

Synthesis of tort-butyl cyclopropyl(2-(3-(trifluoromethoxy)phenyl)pyrazolo[1,5-a][1,3,5]triazin-4-yl)carbamate Note: THF was degassed with a stream of N₂ for 10 min. in a separate flask. Tert-butyl cyclopropyl(2-(methylthio)pyrazolo[1,5-a][1,3,5]triazin-4-yl)carbamate (100 mg, 0.31 mmol), 3-(trifluoromethoxy)phenyl boronic acid (154 mg, 0.74 mmol), tri(2-furyl)phosphine (86 mg, 0.37 mmol), copper(I) thiophene-2-carboxylate (167 mg, 0.88 mmol), Pd₂ dba₃ (24 mg, 0.03 mmol) were combined. The flask was evacuated and backfilled with N₂. THF (3.7 mL) was added and the reaction was heated to 50° C. for 5 d. The solution was diluted with Et₂O (40 mL) and washed with 10% NH₄OH (3×30 mL). The organic layer was dried over MgSO₄, filtered and concentrated in vacuo. The solid residue was triturated with Et₂O and filtered. The filtrate was concentrated in vacuo and purified via flash column chromatography (2.5-5% EtOAc/hexanes) to afford tert-butyl cyclopropyl(2-(3-(trifluoromethoxy)phenyl)pyrazolo[1,5-a][1,3,5]triazin-4-yl)carbamate (116 mg, 85%). LCMS (ES): >95% pure, m/z 436 [M+1]⁺.

Example 207

Synthesis of 4-(cyclopropylamino)-2-(3-(trifluoromethoxy)phenyl)pyrazolo[1,5a][1,3,5]triazine-8-carbaldehyde

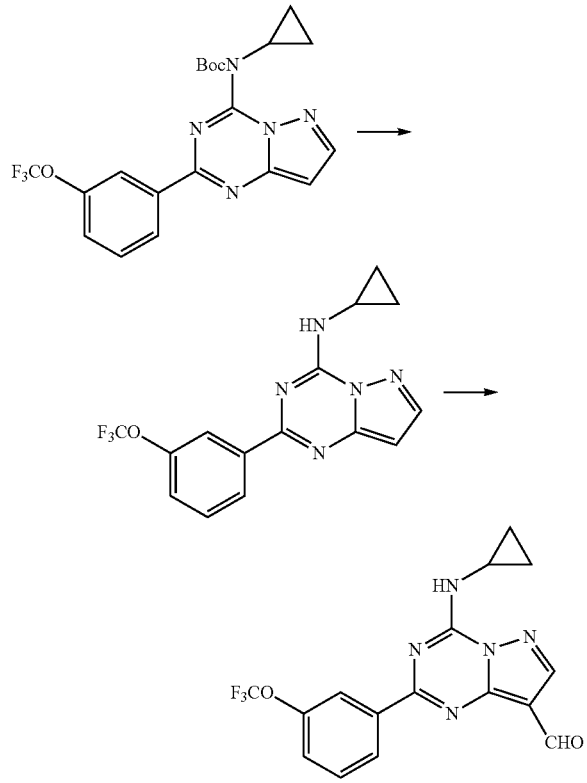

Tert-butyl cyclopropyl(2-(3-(trifluoromethoxy)phenyl)pyrazolo[1,5-a][1,3,5]triazin-4-yl)carbamate was dissolved in dichloromethane (0.7 mL) and trifluoroacetic acid (0.7 mL). After 1 h, the solution was concentrated under a stream of air to give crude 4-(cyclopropylamino)-2-(3-(trifluoromethoxy)phenyl)pyrazolo[1,5-a][1,3,5] triazine-8-carbaldehyde which was used without further purification. LCMS (ES): >90% pure, m/z 336 [M+1]⁺. 4-(cyclopropylamino)-2-(3-(trifluoromethoxy)phenyl)pyrazolo[1,5-a][1,3,5]triazine-8-carbaldehyde (87 mg, 0.26 mmol) was dissolved in DMF (0.8 mL). Phosphorus(V) oxychloride (318 μL, 3.47 mmol) was added was added dropwise and the reaction was heated to 70° C. After 6 h, the solution was added dropwise to 6M NaOH (~10 mL) cooled to 0° C. The pH was adjusted to 7 by the addition of 12N HCl. The precipitate was filtered off and dried in vacuo to furnish 4-(cyclopropylamino)-2-(3-(trifluoromethoxy)phenyl)pyrazolo[1,5-a][1,3,5]triazine-8-carbaldehyde (71 mg, 75%) as a tan solid. LCMS (ES): >95% pure, m/z 364 [M+1]⁺.

Example 208

Synthesis of (Z)-5-((4-(cyclopropylamino)-2-(3-(trifluoromethoxy)phenyl)pyrazolo[1,5-a][1,3,5]triazine-8-yl)methylene)imidazolidine-2,4-dione

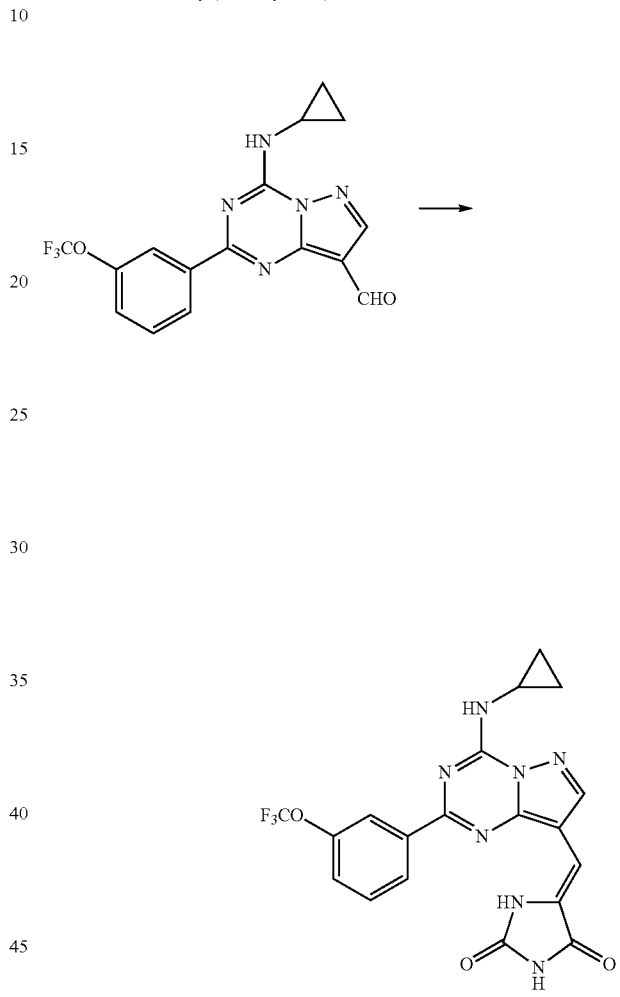

(Z)-5-((4-(cyclopropylamino)-2-(3-(trifluoromethoxy)phenyl)pyrazolo[1,5-a][1,3,5]triazine-8-yl)methylene)imidazolidine-2,4-dione was prepared using chemistries similar to those exemplified in Example 197. LCMS (ES): >90% pure, m/z 446 [M+1]⁺.

The following compounds were prepared using chemistries described in Example 199, Example 200, Example 201, Example 202, Example 203, Example 204, Example 205, Example 206, Example 207 and Example 208; using appropriate reagents. General methods for preparation of such compounds are included in FIGS. 3-14 herein. Reagents bearing two reactive amino groups were generally used as mono-Boc protected. The protecting group was removed by reaction with trifluoroacetic acid in methylene chloride prior to purification. Compounds were isolated by filtration after addition of water or methanol. Some compounds were purified by preparative HPLC and isolated as TFA salts after evaporation at the Genevac. Compounds were characterized by LCMS. Table 33B shows the biological activities of the compounds listed in Table 33A.

TABLE 33A
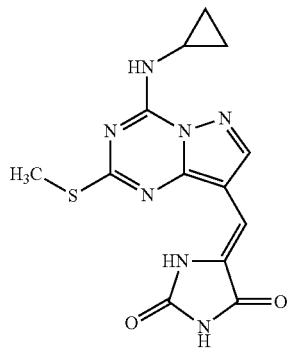 [SMILES: CSc1nc(NC2CC2)n2ncc(/C=C3\NC(=O)NC3=O)c2n1]
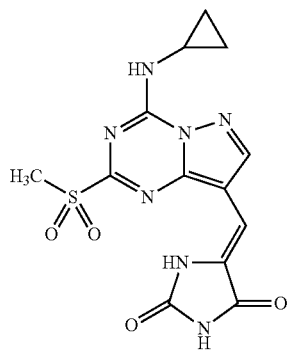 [SMILES: CS(=O)(=O)c1nc(NC2CC2)n2ncc(/C=C3\NC(=O)NC3=O)c2n1]
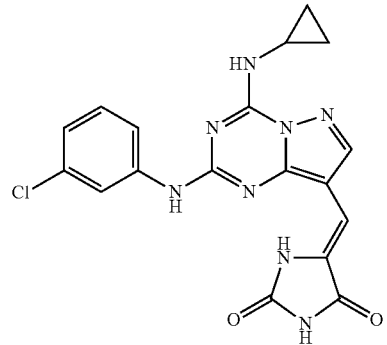 [SMILES: O=C1NC(=O)/C(=C/c2cnn3c(NC4CC4)nc(Nc4cccc(Cl)c4)nc23)N1]
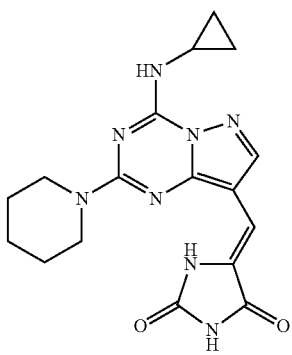 [SMILES: O=C1NC(=O)/C(=C/c2cnn3c(NC4CC4)nc(N4CCCCC4)nc23)N1]
TABLE 33A-continued
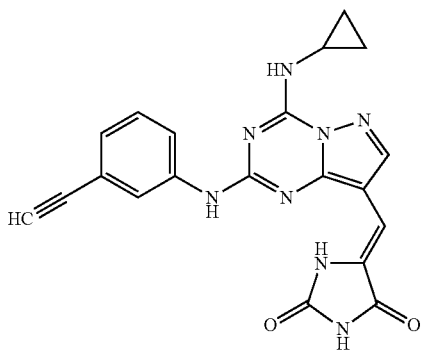 [SMILES: C#Cc1cccc(Nc2nc(NC3CC3)n3ncc(/C=C4\NC(=O)NC4=O)c3n2)c1]
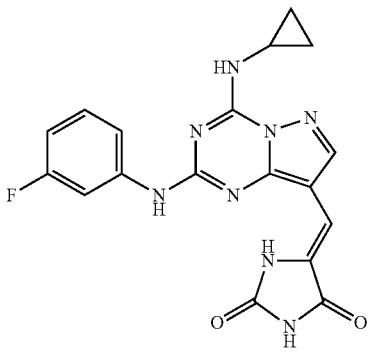 [SMILES: O=C1NC(=O)/C(=C/c2cnn3c(NC4CC4)nc(Nc4cccc(F)c4)nc23)N1]
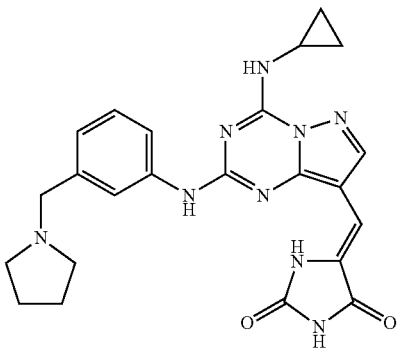 [SMILES: O=C1NC(=O)/C(=C/c2cnn3c(NC4CC4)nc(Nc4cccc(CN5CCCC5)c4)nc23)N1]
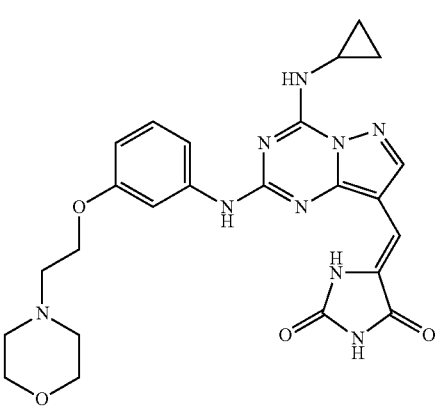 [SMILES: O=C1NC(=O)/C(=C/c2cnn3c(NC4CC4)nc(Nc4cccc(OCCN5CCOCC5)c4)nc23)N1]

TABLE 33A-continued
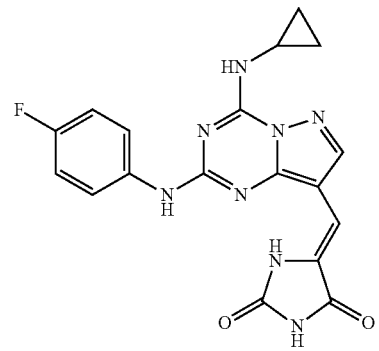 [SMILES: O=C1NC(=O)/C(=C/c2cnn3c(NC4CC4)nc(Nc4ccc(F)cc4)nc23)N1]
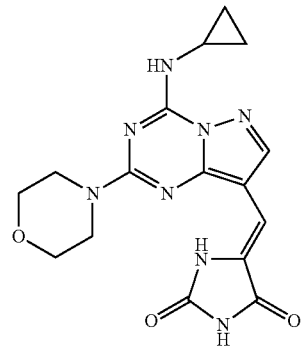
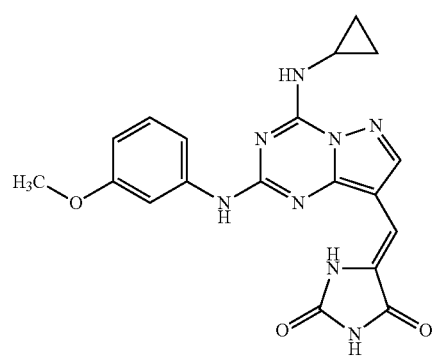 [SMILES: COc1cccc(Nc2nc(NC3CC3)n3ncc(/C=C4\NC(=O)NC4=O)c3n2)c1]
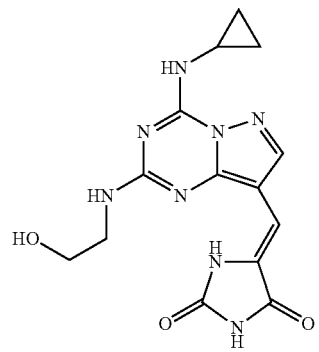
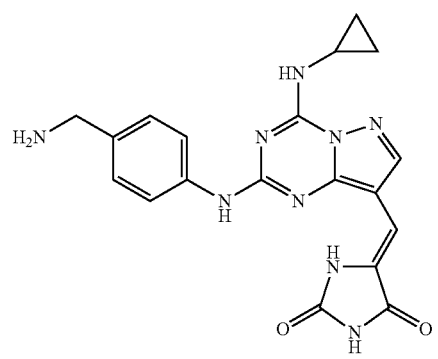 [SMILES: NCc1ccc(Nc2nc(NC3CC3)n3ncc(/C=C4\NC(=O)NC4=O)c3n2)cc1]
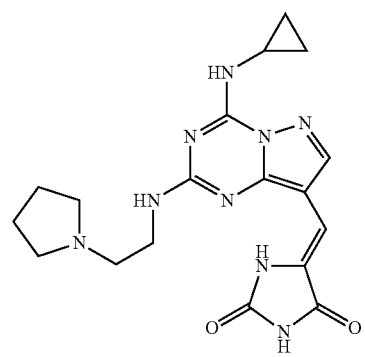
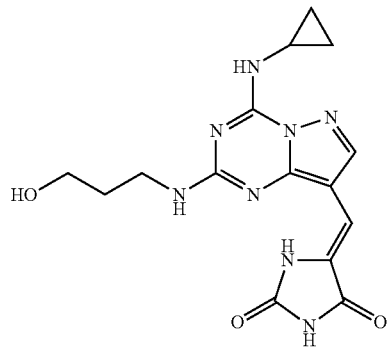 [SMILES: O=C1NC(=O)/C(=C/c2cnn3c(NC4CC4)nc(NCCCO)nc23)N1]
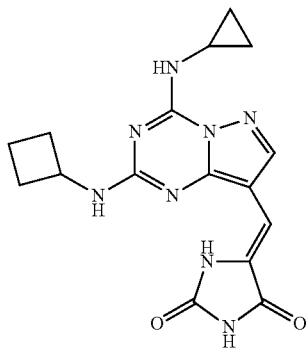 [SMILES: O=C1NC(=O)/C(=C/c2cnn3c(NC4CC4)nc(NC4CCC4)nc23)N1]

TABLE 33A-continued
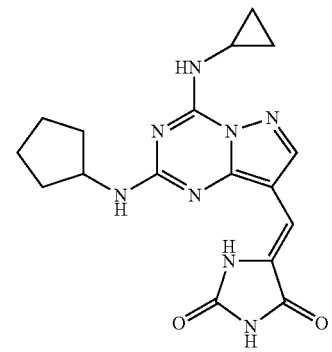 [SMILES: O=C1NC(=O)/C(=C/c2cnn3c(NC4CC4)nc(NC4CCCC4)nc23)N1]
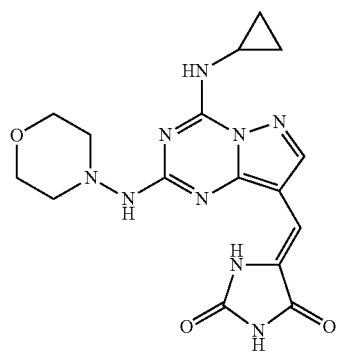 [SMILES: O=C1NC(=O)/C(=C/c2cnn3c(NC4CC4)nc(NN4CCOCC4)nc23)N1]
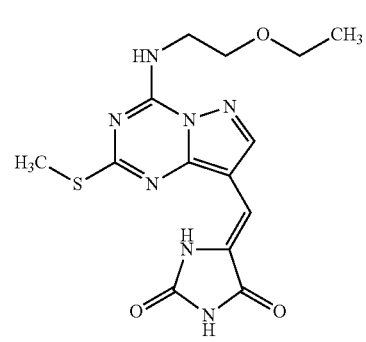 [SMILES: CCOCCNc1nc(SC)nc2c(/C=C3\NC(=O)NC3=O)cnn12]
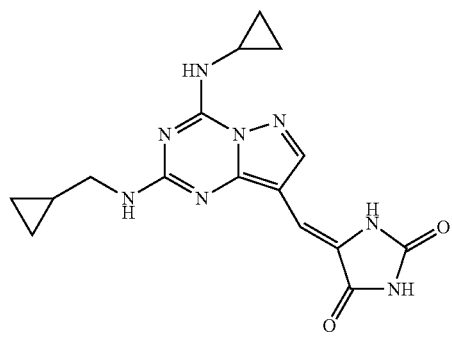 [SMILES: O=C1NC(=O)/C(=C/c2cnn3c(NC4CC4)nc(NCC4CC4)nc23)N1]
TABLE 33A-continued
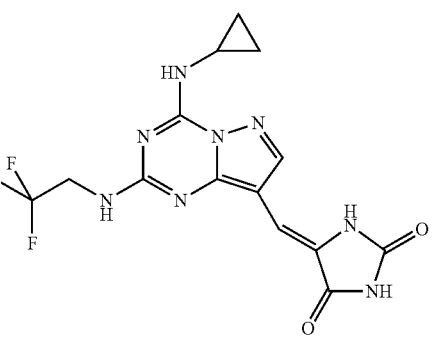
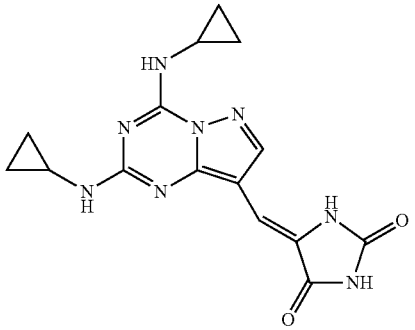 [SMILES: O=C1NC(=O)/C(=C/c2cnn3c(NC4CC4)nc(NC4CC4)nc23)N1]
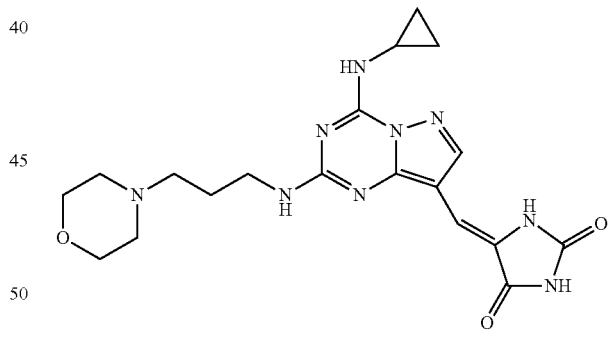
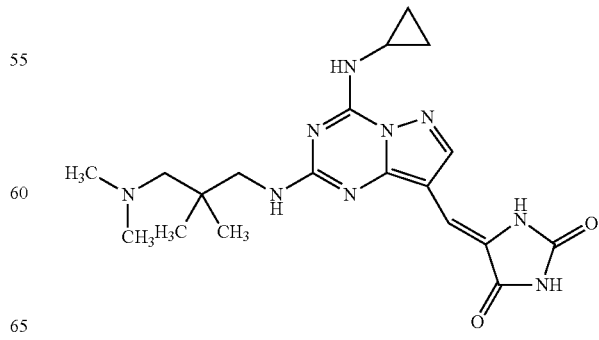

TABLE 33A-continued
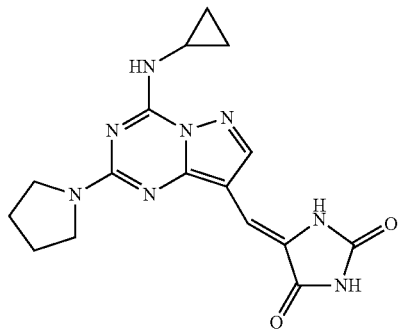 [SMILES: O=C1NC(=O)/C(=C/c2cnn3c(NC4CC4)nc(N4CCCC4)nc23)N1]
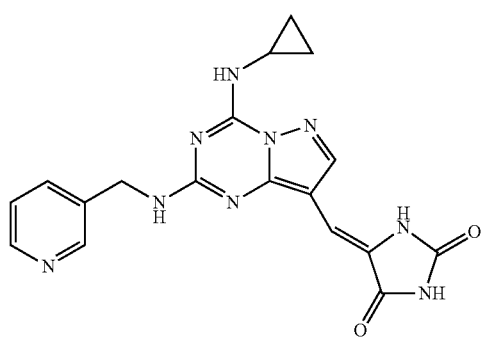 [SMILES: O=C1NC(=O)/C(=C/c2cnn3c(NC4CC4)nc(NCc4cccnc4)nc23)N1]
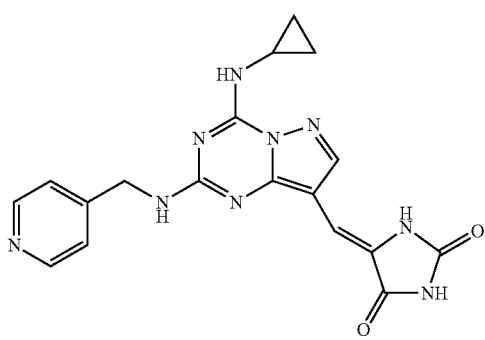 [SMILES: O=C1NC(=O)/C(=C/c2cnn3c(NC4CC4)nc(NCc4ccncc4)nc23)N1]
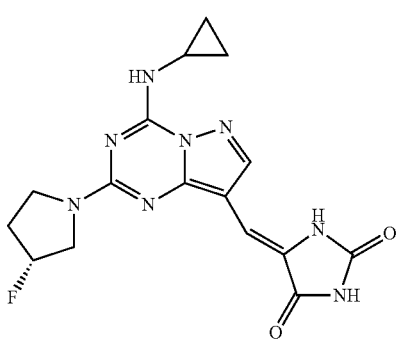 [SMILES: O=C1NC(=O)/C(=C/c2cnn3c(NC4CC4)nc(N4CC[C@@H](F)C4)nc23)N1]
TABLE 33A-continued
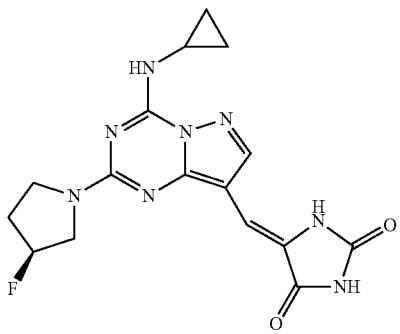 [SMILES: O=C1NC(=O)/C(=C/c2cnn3c(NC4CC4)nc(N4CC[C@H](F)C4)nc23)N1]
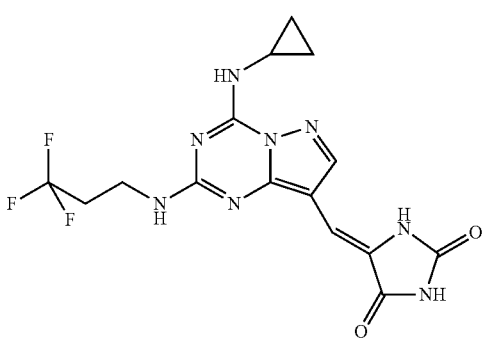 [SMILES: O=C1NC(=O)/C(=C/c2cnn3c(NC4CC4)nc(NCCC(F)(F)F)nc23)N1]
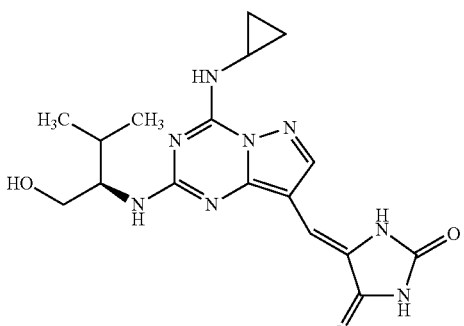
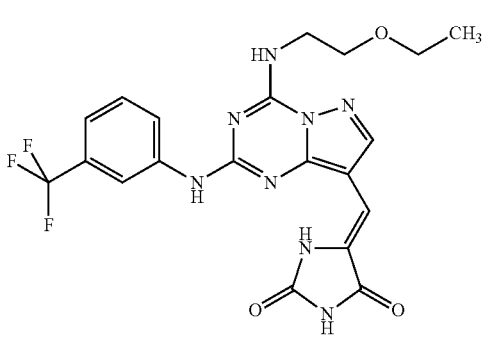 [SMILES: CCOCCNc1nc(Nc2cccc(C(F)(F)F)c2)nc2c(/C=C3\NC(=O)NC3=O)cnn12]

TABLE 33A-continued
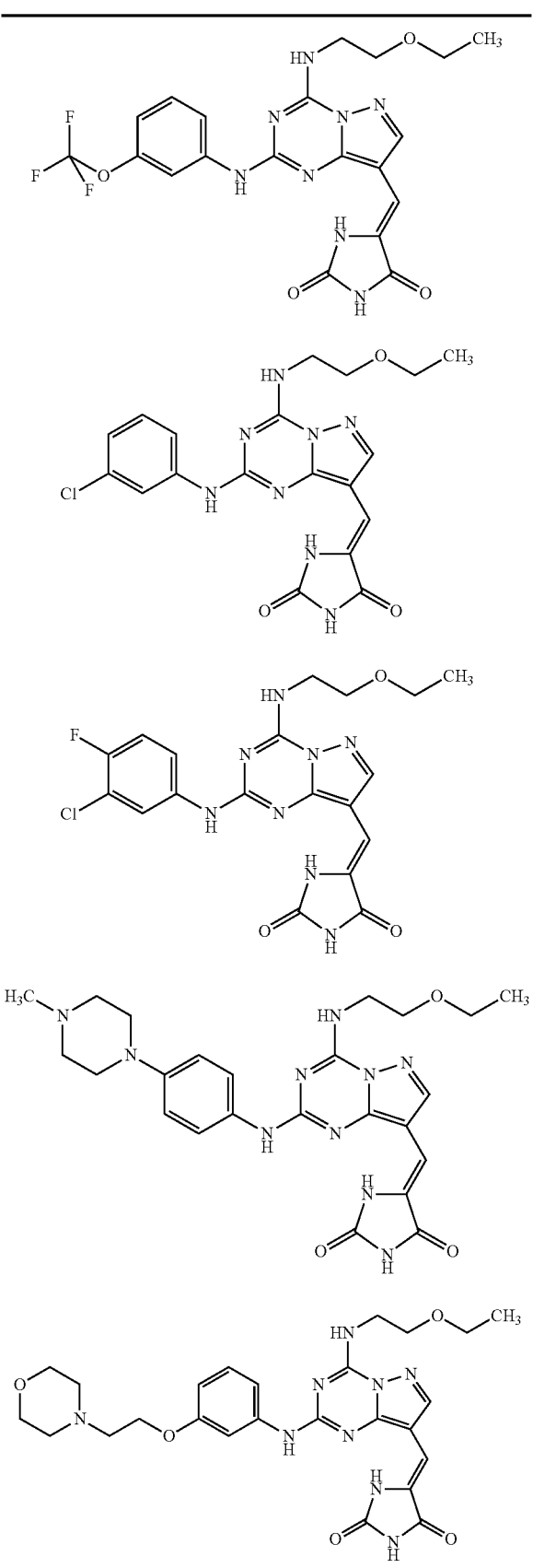
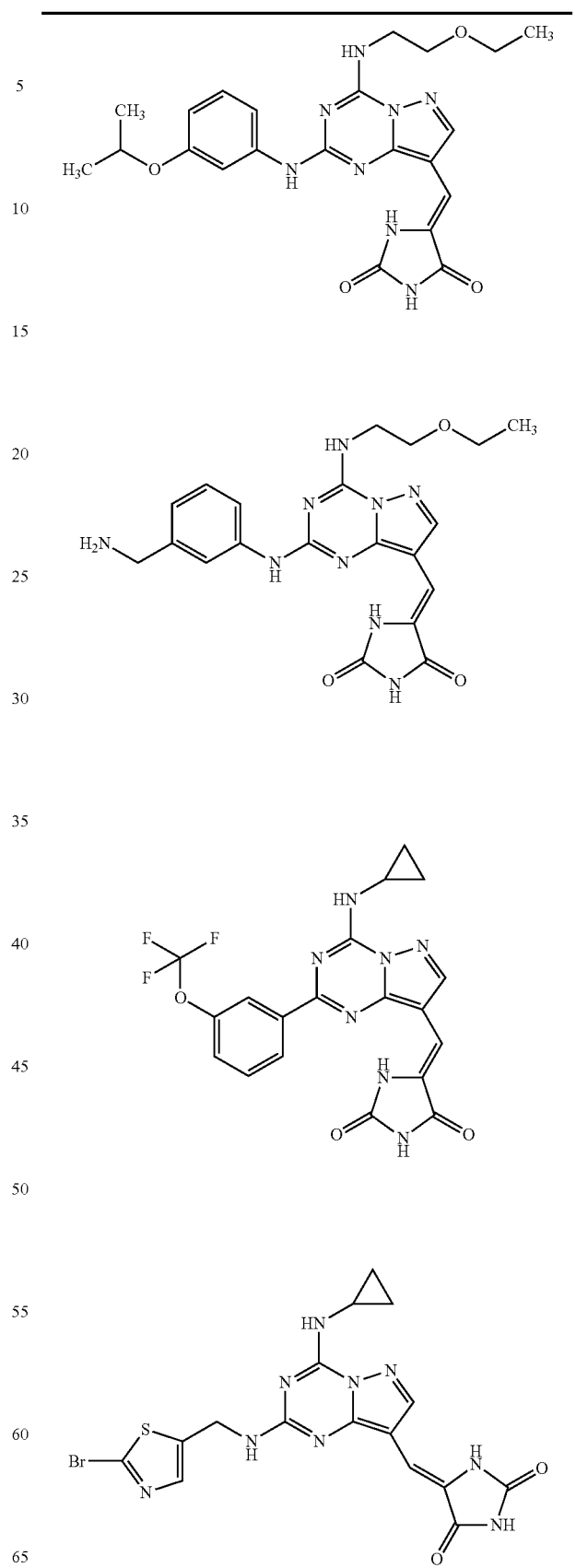

TABLE 33A-continued
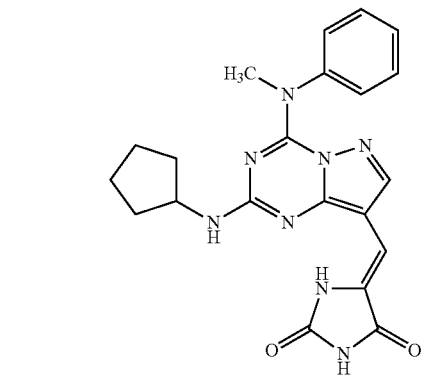 [SMILES: CN(c1ccccc1)c1nc(NC2CCCC2)nc2c(/C=C3\NC(=O)NC3=O)cnn12]
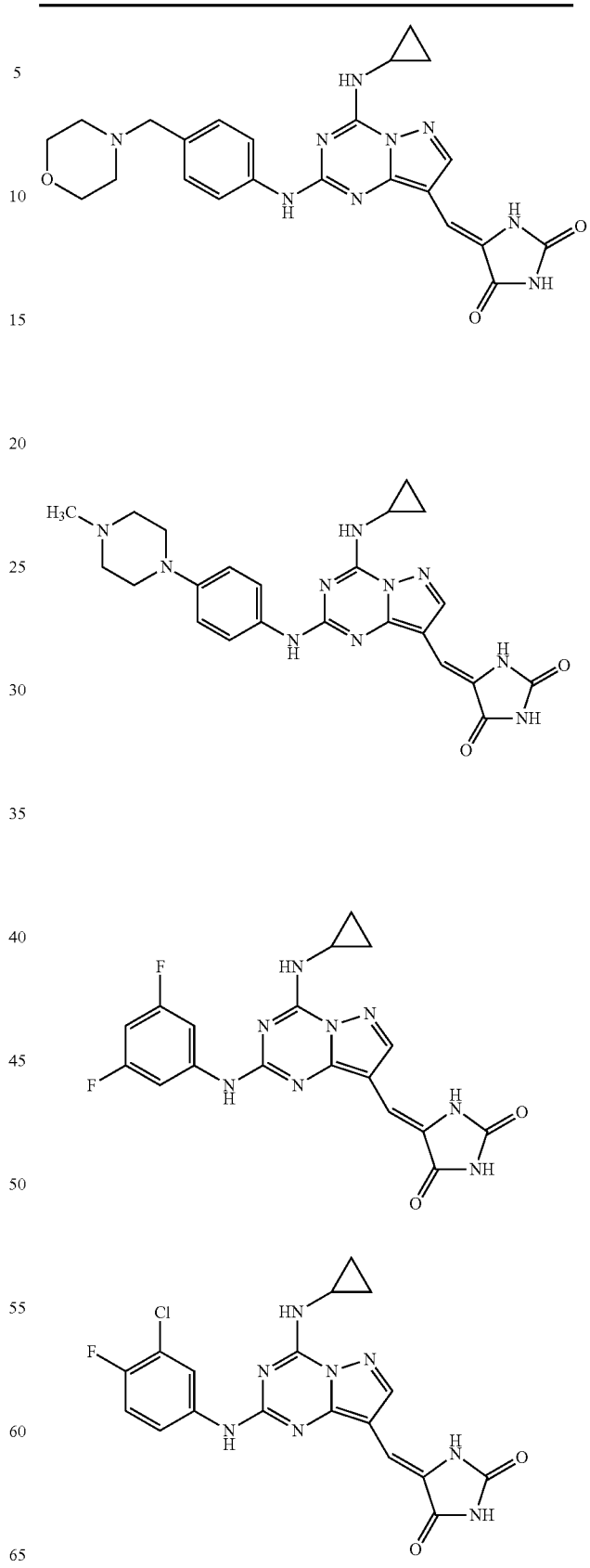

TABLE 33A-continued
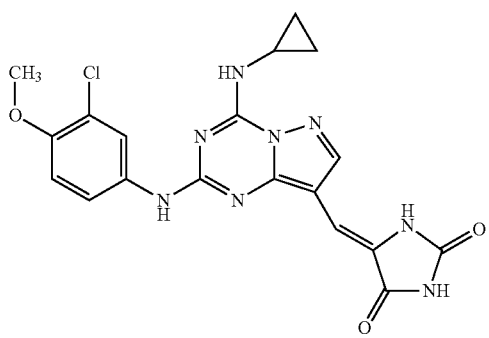 [SMILES: COc1ccc(Nc2nc(NC3CC3)n3ncc(/C=C4\NC(=O)NC4=O)c3n2)cc1Cl]
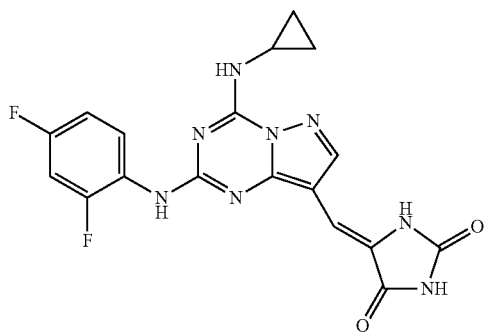 [SMILES: O=C1NC(=O)/C(=C/c2cnn3c(NC4CC4)nc(Nc4ccc(F)cc4F)nc23)N1]
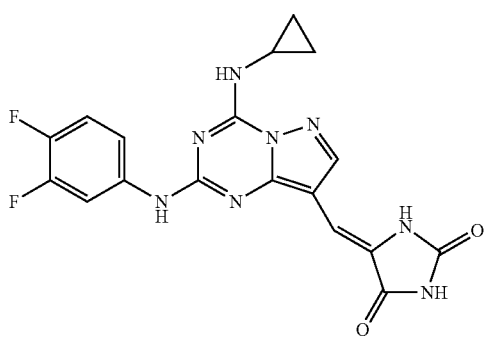 [SMILES: O=C1NC(=O)/C(=C/c2cnn3c(NC4CC4)nc(Nc4ccc(F)c(F)c4)nc23)N1]
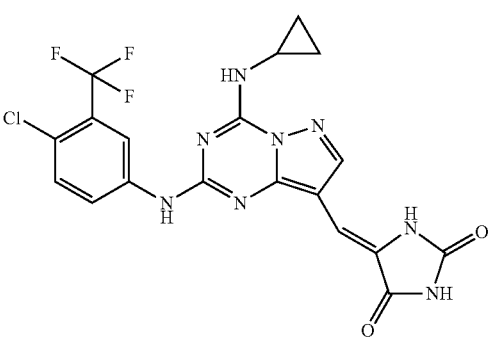 [SMILES: O=C1NC(=O)/C(=C/c2cnn3c(NC4CC4)nc(Nc4ccc(Cl)c(C(F)(F)F)c4)nc23)N1]
TABLE 33A-continued
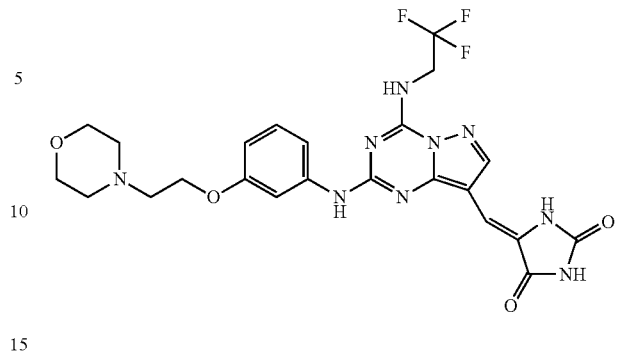
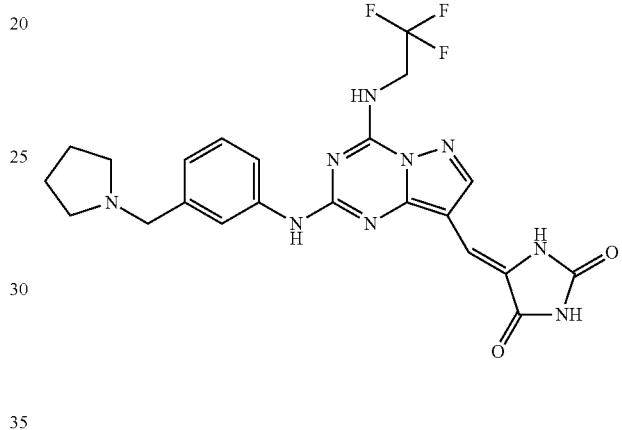
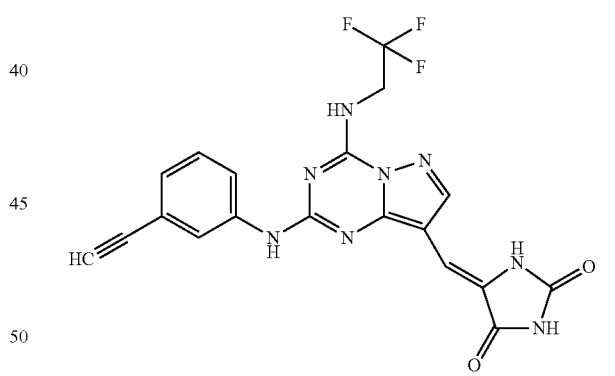
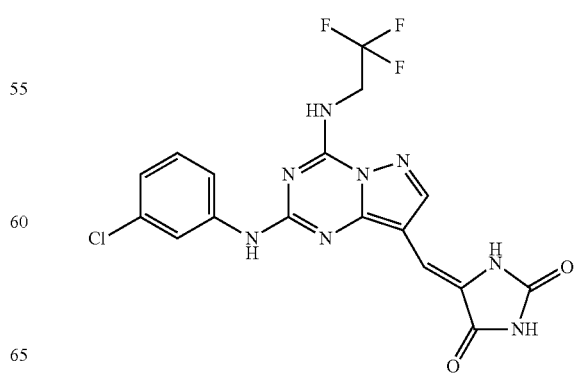

TABLE 33A-continued
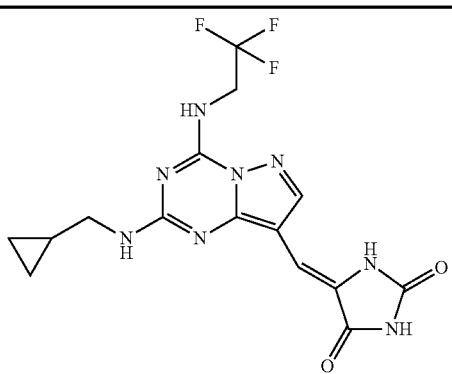
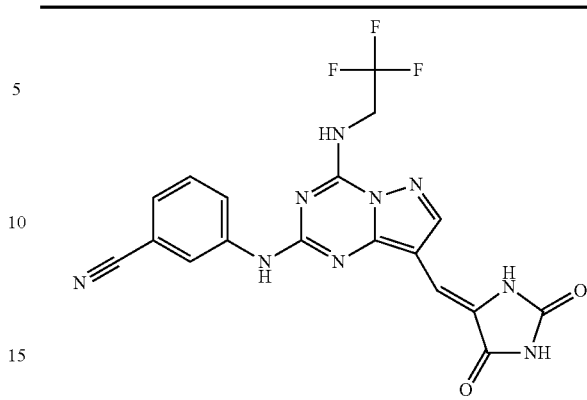
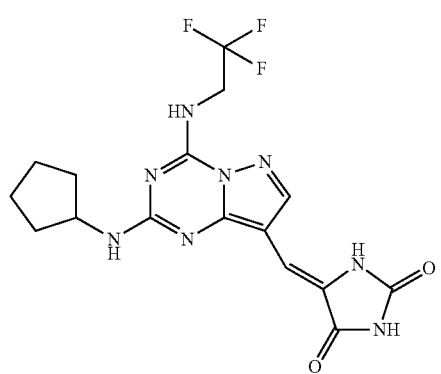 [SMILES: O=C1NC(=O)/C(=C/c2cnn3c(NCC(F)(F)F)nc(NC4CCCC4)nc23)N1]
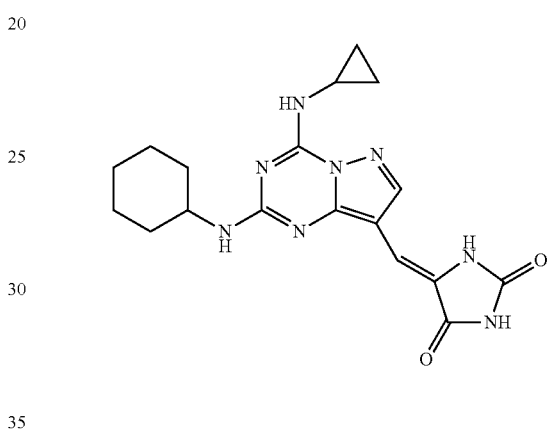
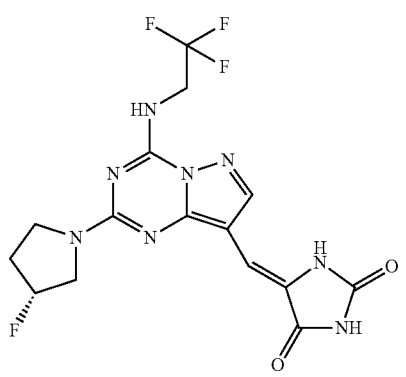 [SMILES: O=C1NC(=O)/C(=C/c2cnn3c(NCC(F)(F)F)nc(N4CC[C@@H](F)C4)nc23)N1]
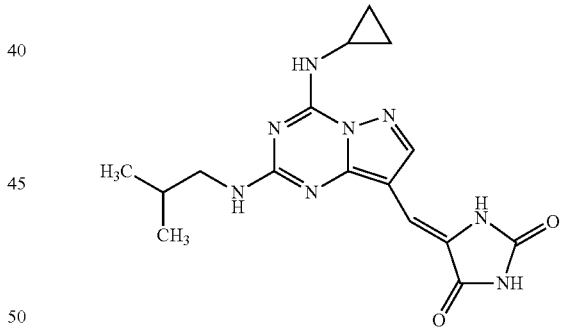

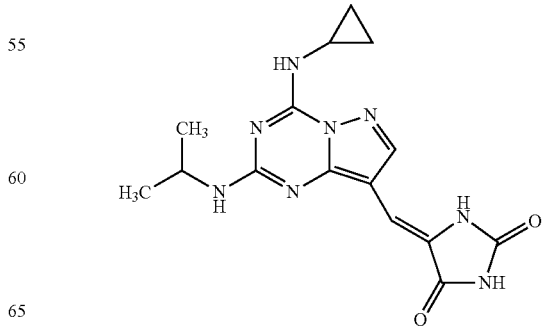

TABLE 33A-continued
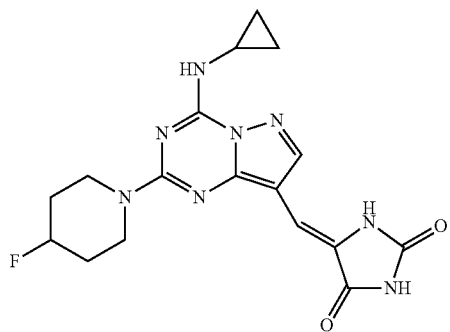 [SMILES: O=C1NC(=O)/C(=C/c2cnn3c(NC4CC4)nc(N4CCC(F)CC4)nc23)N1]
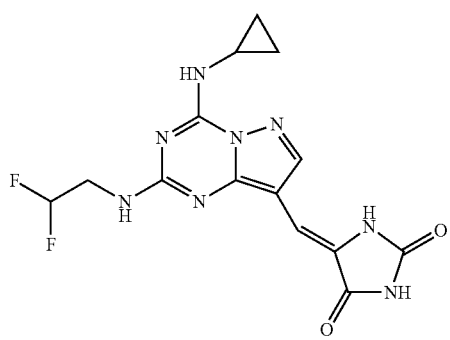 [SMILES: O=C1NC(=O)/C(=C/c2cnn3c(NC4CC4)nc(NCC(F)F)nc23)N1]
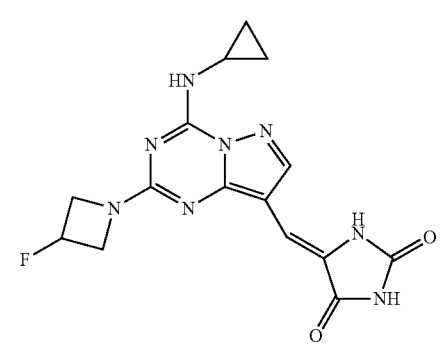 [SMILES: O=C1NC(=O)/C(=C/c2cnn3c(NC4CC4)nc(N4CC(F)C4)nc23)N1]
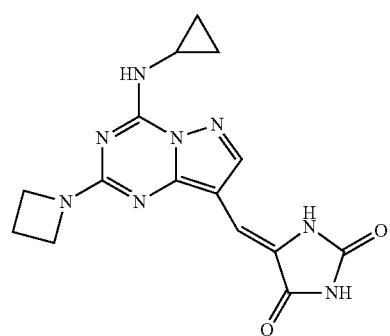 [SMILES: O=C1NC(=O)/C(=C/c2cnn3c(NC4CC4)nc(N4CCC4)nc23)N1]
TABLE 33A-continued
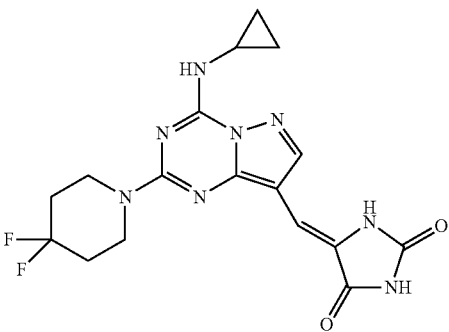 [SMILES: O=C1NC(=O)/C(=C/c2cnn3c(NC4CC4)nc(N4CCC(F)(F)CC4)nc23)N1]
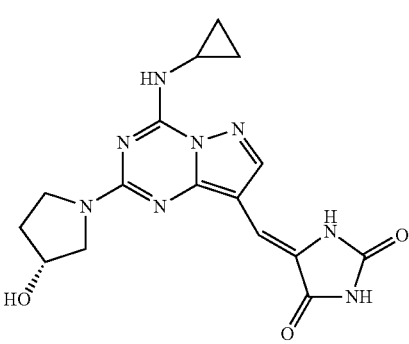 [SMILES: O=C1NC(=O)/C(=C/c2cnn3c(NC4CC4)nc(N4CC[C@@H](O)C4)nc23)N1]
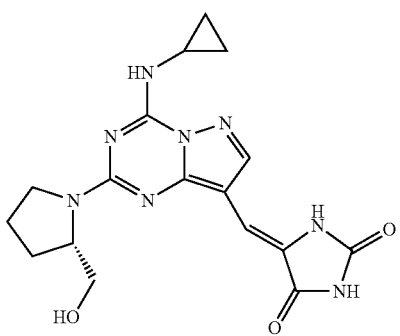 [SMILES: O=C1NC(=O)/C(=C/c2cnn3c(NC4CC4)nc(N4CCC[C@H]4CO)nc23)N1]

| 335 | 336 |
|---|---|
| TABLE 33A-continued | TABLE 33A-continued |
| 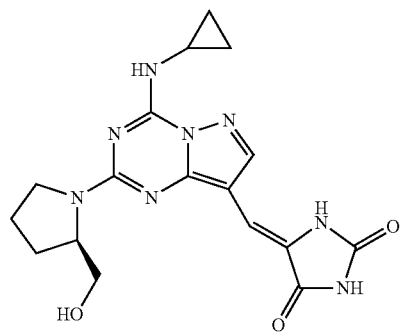 [SMILES: O=C1NC(=O)/C(=C/c2cnn3c(NC4CC4)nc(N4CCC[C@@H]4CO)nc23)N1] | 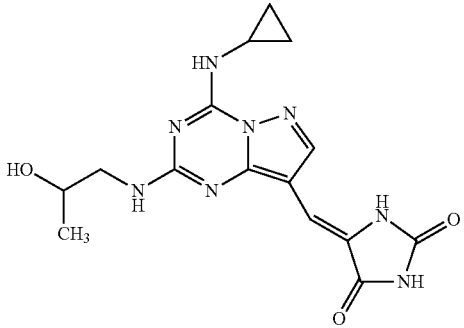 |
| 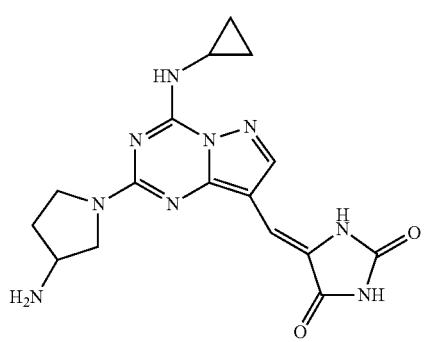 [SMILES: NC1CCN(c2nc(NC3CC3)n3ncc(/C=C4\NC(=O)NC4=O)c3n2)C1] | 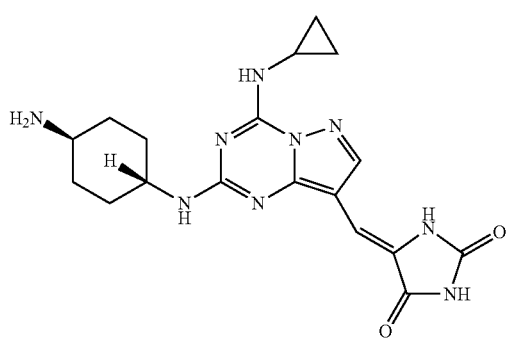 |
| 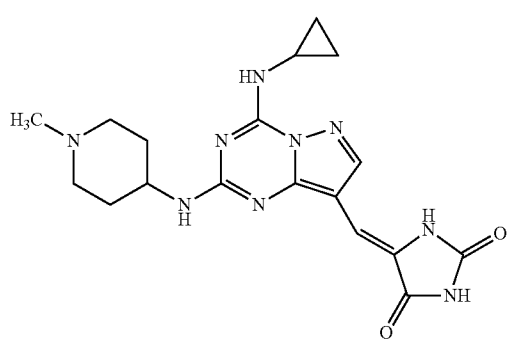 [SMILES: CN1CCC(Nc2nc(NC3CC3)n3ncc(/C=C4\NC(=O)NC4=O)c3n2)CC1] | 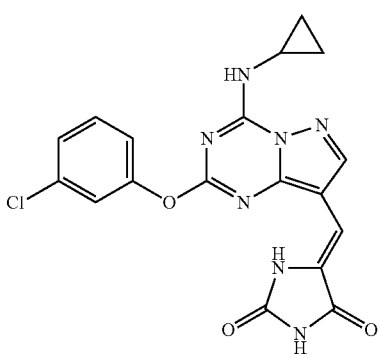 |
| 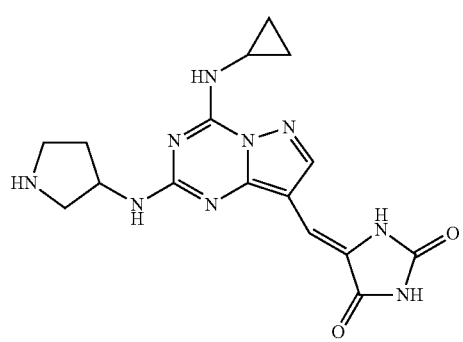 [SMILES: O=C1NC(=O)/C(=C/c2cnn3c(NC4CC4)nc(NC4CCNC4)nc23)N1] | 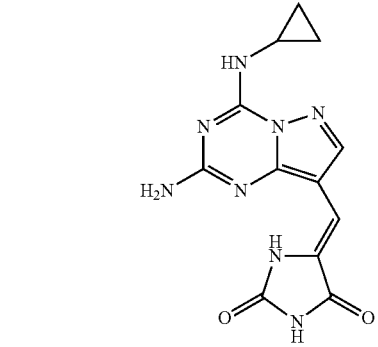 [SMILES: Nc1nc(NC2CC2)n2ncc(/C=C3\NC(=O)NC3=O)c2n1] |

TABLE 33A-continued
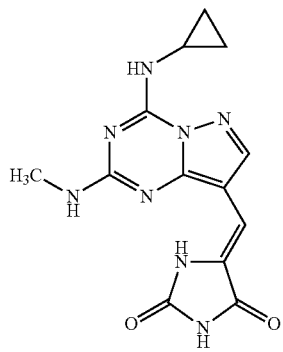 [SMILES: CNc1nc(NC2CC2)n2ncc(/C=C3\NC(=O)NC3=O)c2n1]
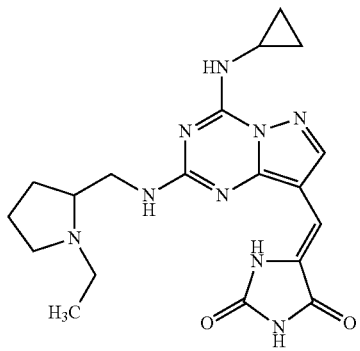
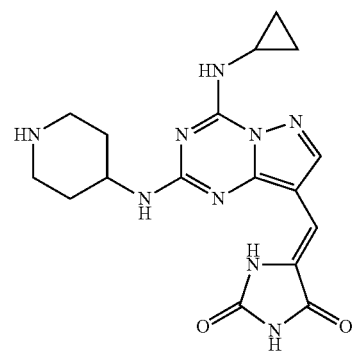 [SMILES: O=C1NC(=O)/C(=C/c2cnn3c(NC4CC4)nc(NC4CCNCC4)nc23)N1]
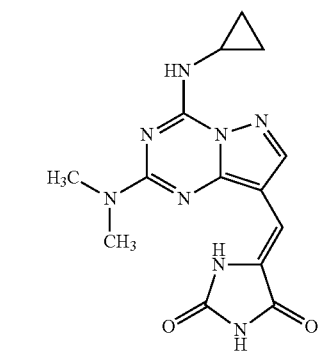
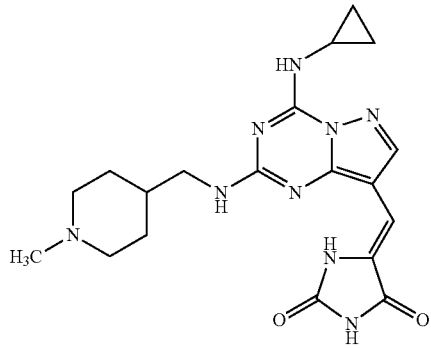 [SMILES: CN1CCC(CNc2nc(NC3CC3)n3ncc(/C=C4\NC(=O)NC4=O)c3n2)CC1]
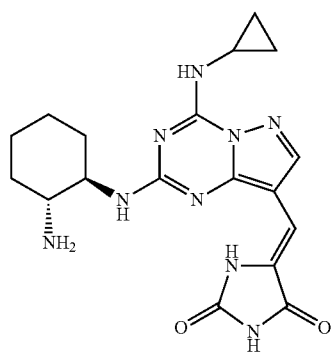
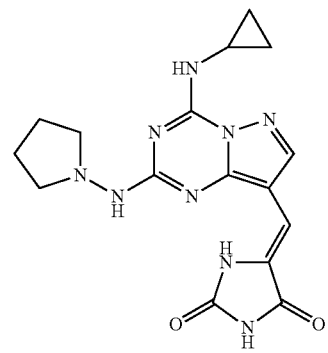 [SMILES: O=C1NC(=O)/C(=C/c2cnn3c(NC4CC4)nc(NN4CCCC4)nc23)N1]
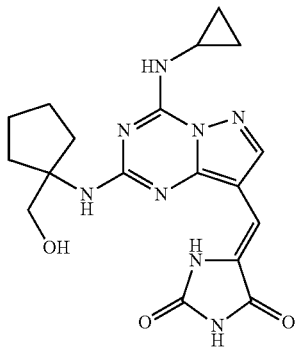 [SMILES: O=C1NC(=O)/C(=C/c2cnn3c(NC4CC4)nc(NC4(CO)CCCC4)nc23)N1]

TABLE 33A-continued
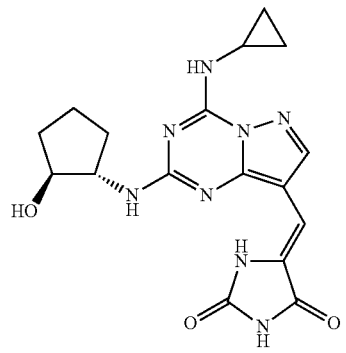 [SMILES: O=C1NC(=O)/C(=C/c2cnn3c(NC4CC4)nc(N[C@H]4CCC[C@@H]4O)nc23)N1]
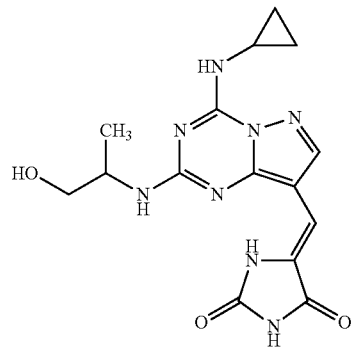
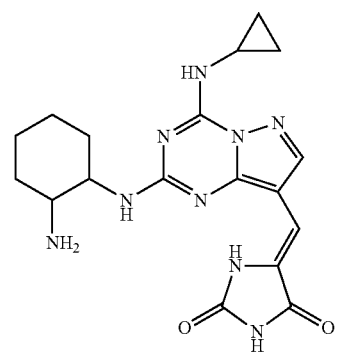 [SMILES: NC1CCCCC1Nc1nc(NC2CC2)n2ncc(/C=C3\NC(=O)NC3=O)c2n1]
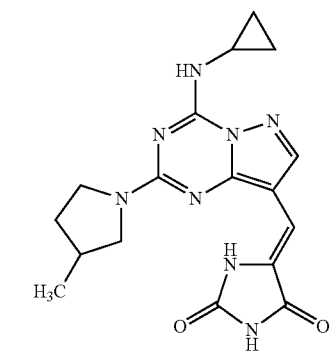
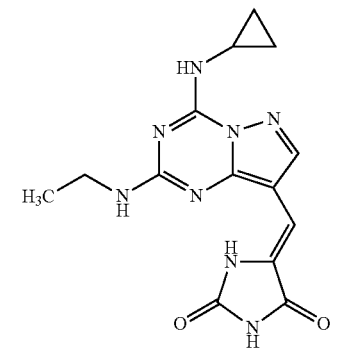 [SMILES: CCNc1nc(NC2CC2)n2ncc(/C=C3\NC(=O)NC3=O)c2n1]
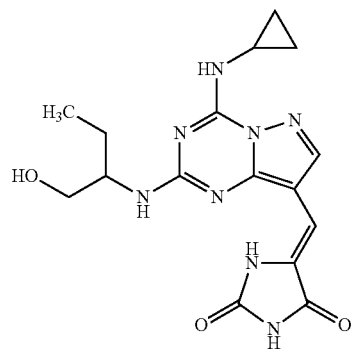
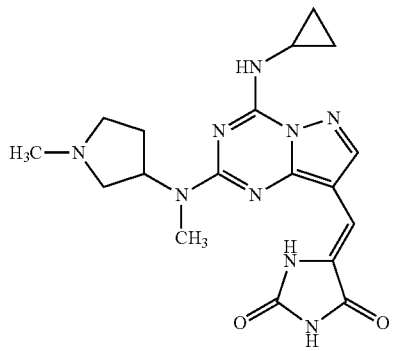 [SMILES: CN1CCC(N(C)c2nc(NC3CC3)n3ncc(/C=C4\NC(=O)NC4=O)c3n2)C1]
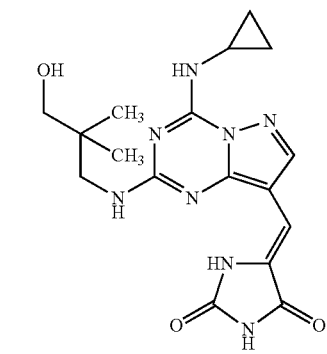 [SMILES: CC(C)(CO)CNc1nc(NC2CC2)n2ncc(/C=C3\NC(=O)NC3=O)c2n1]

TABLE 33A-continued
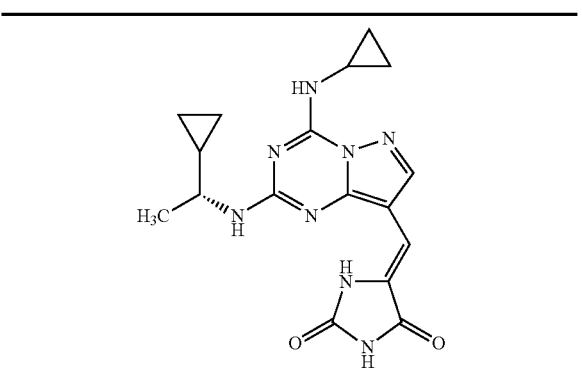
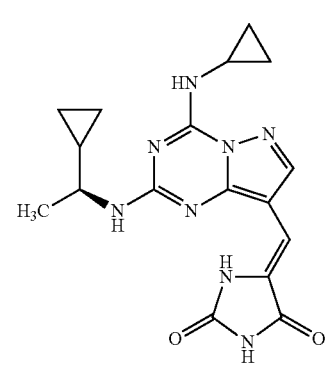 [SMILES: C[C@H](Nc1nc(NC2CC2)n2ncc(/C=C3\NC(=O)NC3=O)c2n1)C1CC1]
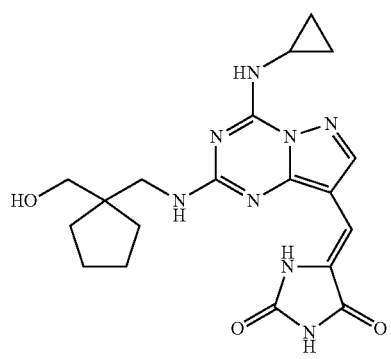 [SMILES: O=C1NC(=O)/C(=C/c2cnn3c(NC4CC4)nc(NCC4(CO)CCCC4)nc23)N1]
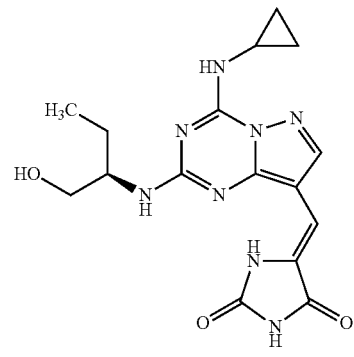 [SMILES: CC[C@H](CO)Nc1nc(NC2CC2)n2ncc(/C=C3\NC(=O)NC3=O)c2n1]
TABLE 33A-continued
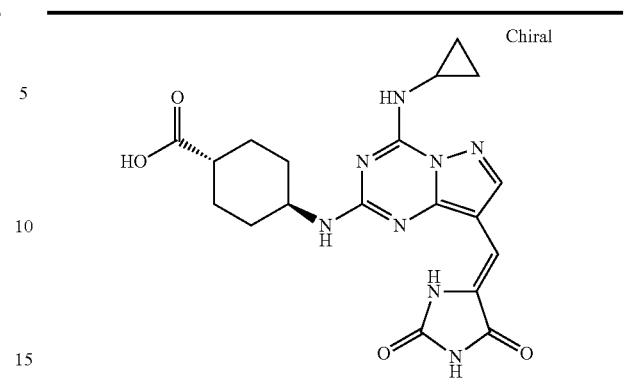
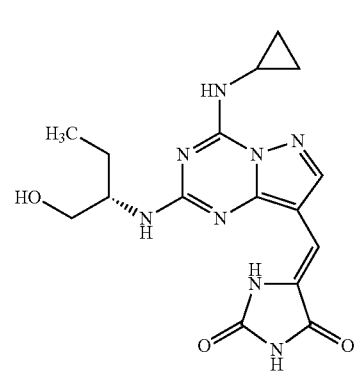 [SMILES: CC[C@@H](CO)Nc1nc(NC2CC2)n2ncc(/C=C3\NC(=O)NC3=O)c2n1]
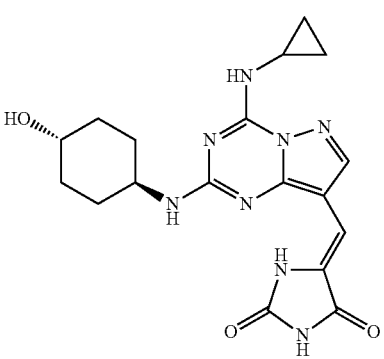 [SMILES: O=C1NC(=O)/C(=C/c2cnn3c(NC4CC4)nc(N[C@H]4CC[C@H](O)CC4)nc23)N1]
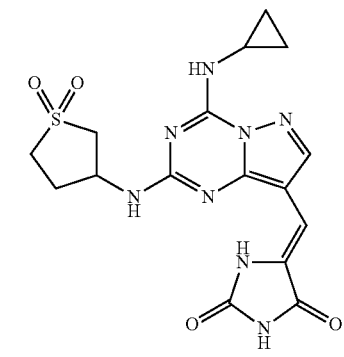 [SMILES: O=C1NC(=O)/C(=C/c2cnn3c(NC4CC4)nc(NC4CCS(=O)(=O)C4)nc23)N1]

TABLE 33A-continued
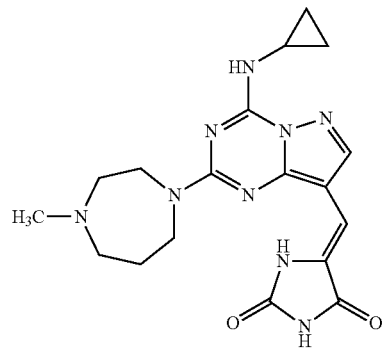 [SMILES: CN1CCCN(c2nc(NC3CC3)n3ncc(/C=C4\NC(=O)NC4=O)c3n2)CC1]
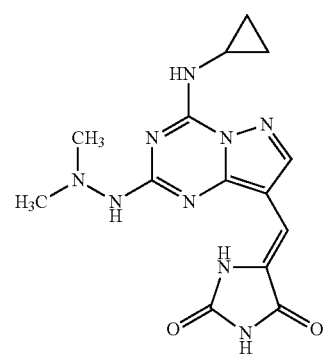 [SMILES: CN(C)Nc1nc(NC2CC2)n2ncc(/C=C3\NC(=O)NC3=O)c2n1]
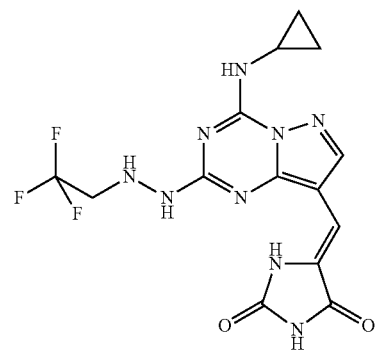 [SMILES: O=C1NC(=O)/C(=C/c2cnn3c(NC4CC4)nc(NNCC(F)(F)F)nc23)N1]
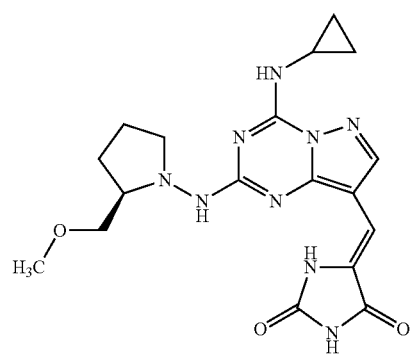 [SMILES: COC[C@H]1CCCN1Nc1nc(NC2CC2)n2ncc(/C=C3\NC(=O)NC3=O)c2n1]
TABLE 33A-continued
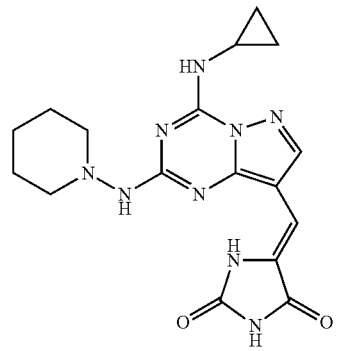 [SMILES: O=C1NC(=O)/C(=C/c2cnn3c(NC4CC4)nc(NN4CCCCC4)nc23)N1]
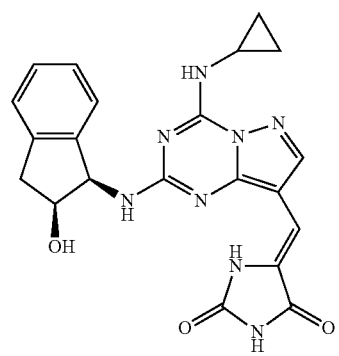 [SMILES: O=C1NC(=O)/C(=C/c2cnn3c(NC4CC4)nc(N[C@@H]4c5ccccc5C[C@@H]4O)nc23)N1]
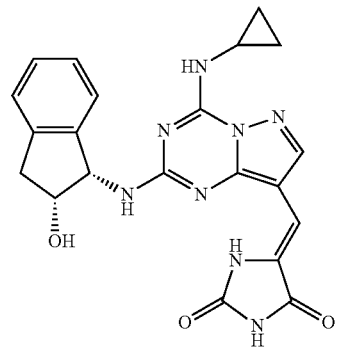 [SMILES: O=C1NC(=O)/C(=C/c2cnn3c(NC4CC4)nc(N[C@H]4c5ccccc5C[C@H]4O)nc23)N1]
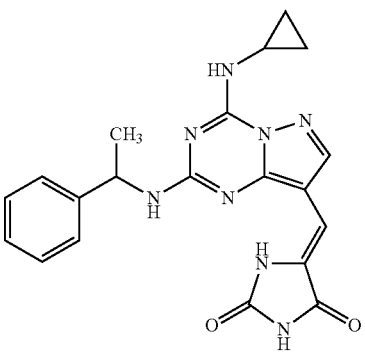

TABLE 33A-continued
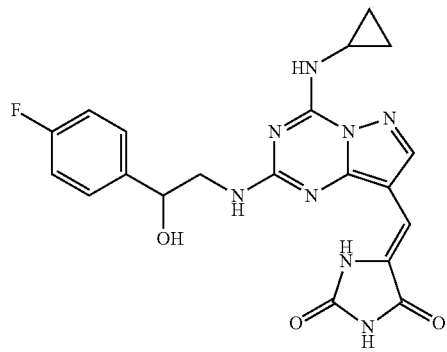 [SMILES: O=C1NC(=O)/C(=C/c2cnn3c(NC4CC4)nc(NCC(O)c4ccc(F)cc4)nc23)N1]
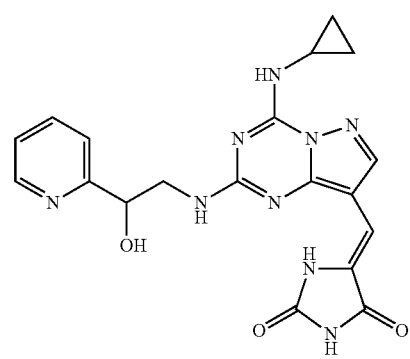 [SMILES: O=C1NC(=O)/C(=C/c2cnn3c(NC4CC4)nc(NCC(O)c4ccccn4)nc23)N1]
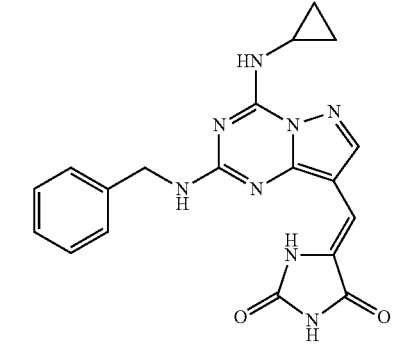 [SMILES: O=C1NC(=O)/C(=C/c2cnn3c(NC4CC4)nc(NCc4ccccc4)nc23)N1]
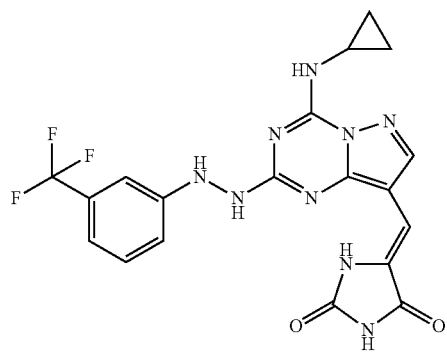 [SMILES: O=C1NC(=O)/C(=C/c2cnn3c(NC4CC4)nc(NNc4cccc(C(F)(F)F)c4)nc23)N1]
TABLE 33A-continued
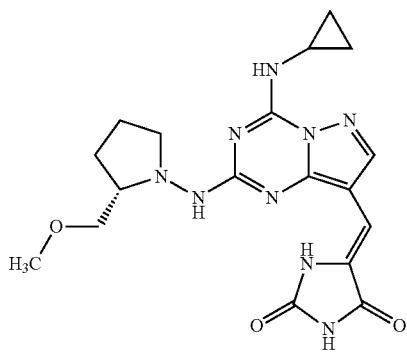 [SMILES: COC[C@@H]1CCCN1Nc1nc(NC2CC2)n2ncc(/C=C3\NC(=O)NC3=O)c2n1]
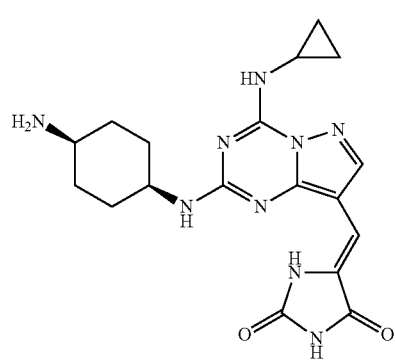 [SMILES: N[C@H]1CC[C@@H](Nc2nc(NC3CC3)n3ncc(/C=C4\NC(=O)NC4=O)c3n2)CC1]
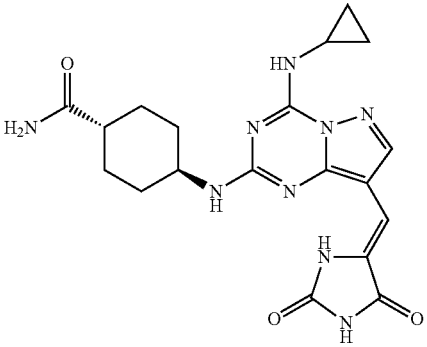 [SMILES: NC(=O)[C@H]1CC[C@H](Nc2nc(NC3CC3)n3ncc(/C=C4\NC(=O)NC4=O)c3n2)CC1]
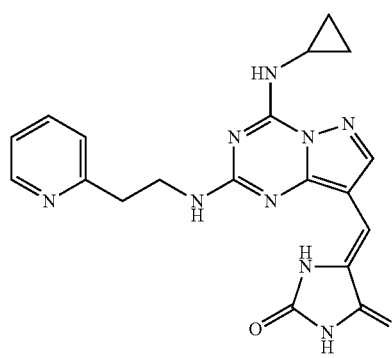

TABLE 33A-continued
347
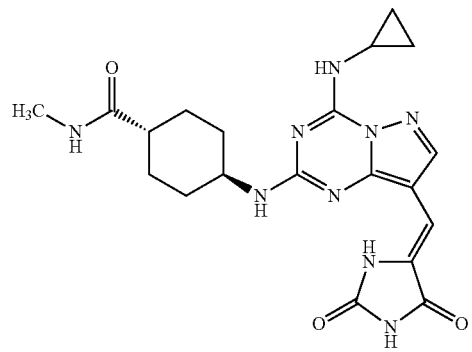 [SMILES: CNC(=O)[C@H]1CC[C@H](Nc2nc(NC3CC3)n3ncc(/C=C4\NC(=O)NC4=O)c3n2)CC1]
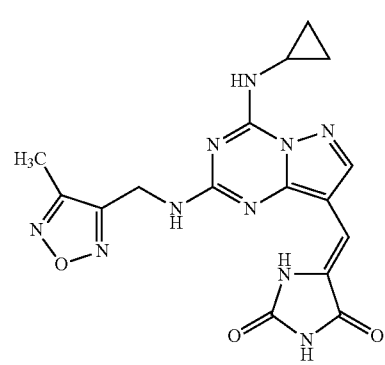 [SMILES: Cc1nonc1CNc1nc(NC2CC2)n2ncc(/C=C3\NC(=O)NC3=O)c2n1]
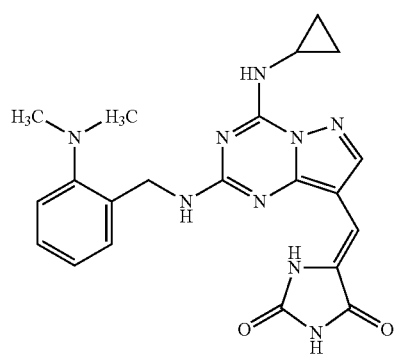 [SMILES: CN(C)c1ccccc1CNc1nc(NC2CC2)n2ncc(/C=C3\NC(=O)NC3=O)c2n1]
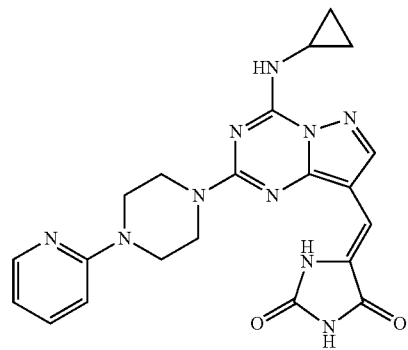 [SMILES: O=C1NC(=O)/C(=C/c2cnn3c(NC4CC4)nc(N4CCN(c5ccccn5)CC4)nc23)N1]
348
TABLE 33A-continued
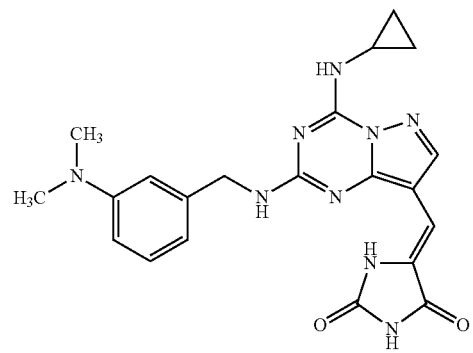 [SMILES: CN(C)c1cccc(CNc2nc(NC3CC3)n3ncc(/C=C4\NC(=O)NC4=O)c3n2)c1]
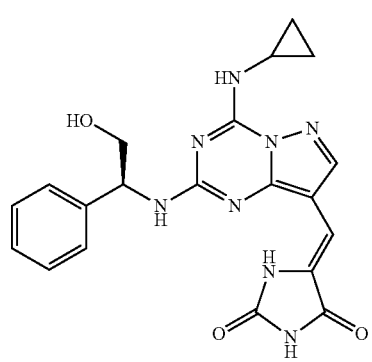 [SMILES: O=C1NC(=O)/C(=C/c2cnn3c(NC4CC4)nc(N[C@H](CO)c4ccccc4)nc23)N1]
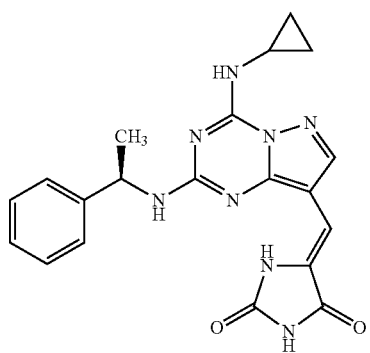 [SMILES: C[C@@H](Nc1nc(NC2CC2)n2ncc(/C=C3\NC(=O)NC3=O)c2n1)c1ccccc1]
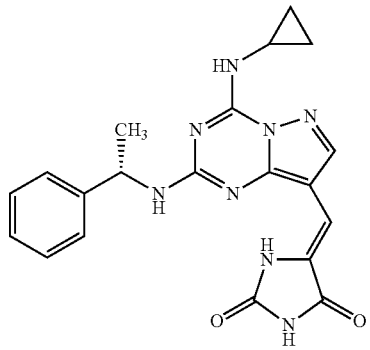 [SMILES: C[C@H](Nc1nc(NC2CC2)n2ncc(/C=C3\NC(=O)NC3=O)c2n1)c1ccccc1]

US 8,575,177 B2
349
TABLE 33A-continued
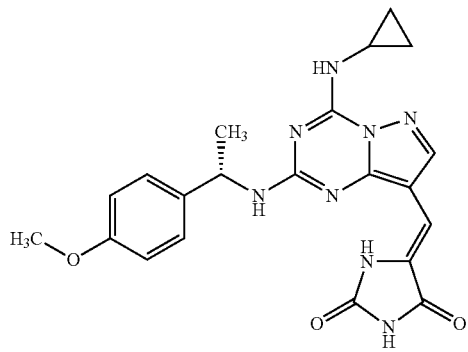 [SMILES: COc1ccc([C@H](C)Nc2nc(NC3CC3)n3ncc(/C=C4\NC(=O)NC4=O)c3n2)cc1]
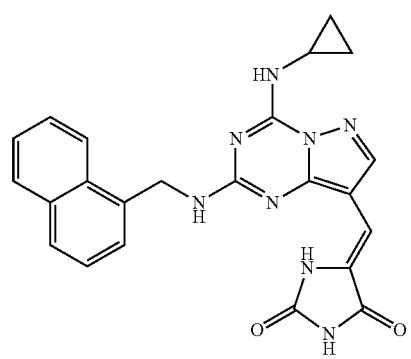 [SMILES: O=C1NC(=O)/C(=C/c2cnn3c(NC4CC4)nc(NCc4cccc5ccccc45)nc23)N1]
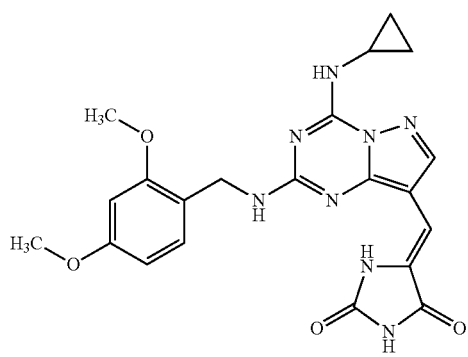 [SMILES: COc1ccc(CNc2nc(NC3CC3)n3ncc(/C=C4\NC(=O)NC4=O)c3n2)c(OC)c1]
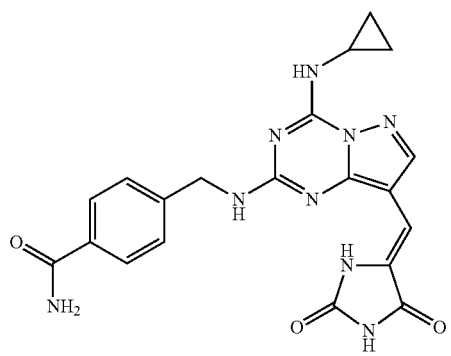 [SMILES: NC(=O)c1ccc(CNc2nc(NC3CC3)n3ncc(/C=C4\NC(=O)NC4=O)c3n2)cc1]
350
TABLE 33A-continued
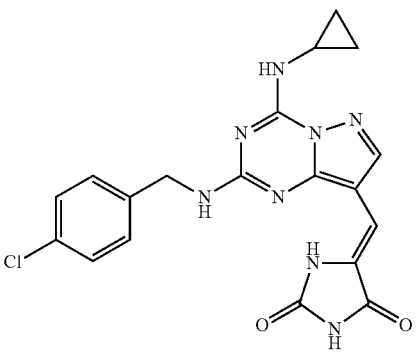 [SMILES: O=C1NC(=O)/C(=C/c2cnn3c(NC4CC4)nc(NCc4ccc(Cl)cc4)nc23)N1]
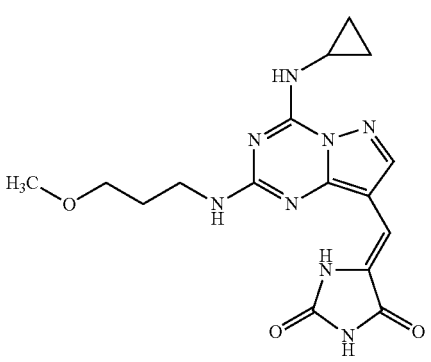 [SMILES: COCCCNc1nc(NC2CC2)n2ncc(/C=C3\NC(=O)NC3=O)c2n1]
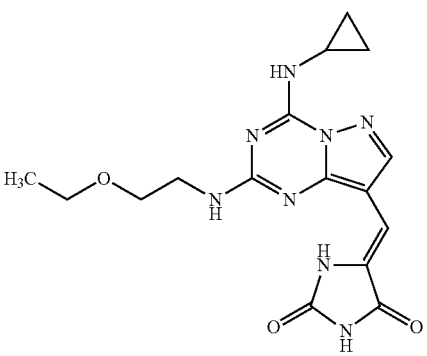 [SMILES: CCOCCNc1nc(NC2CC2)n2ncc(/C=C3\NC(=O)NC3=O)c2n1]
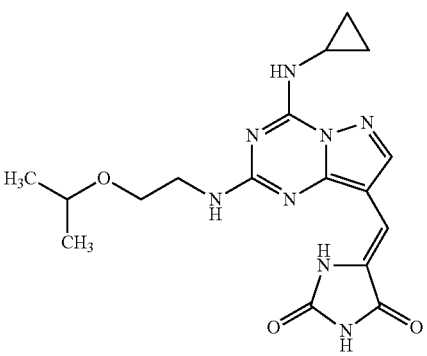 [SMILES: CC(C)OCCNc1nc(NC2CC2)n2ncc(/C=C3\NC(=O)NC3=O)c2n1]

TABLE 33A-continued
351
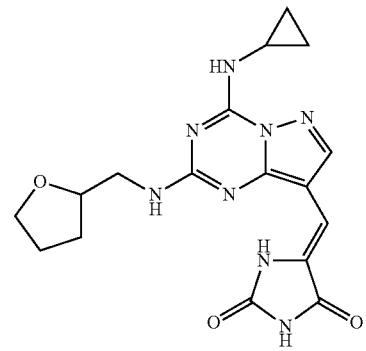 [SMILES: O=C1NC(=O)/C(=C/c2cnn3c(NC4CC4)nc(NCC4CCCO4)nc23)N1]
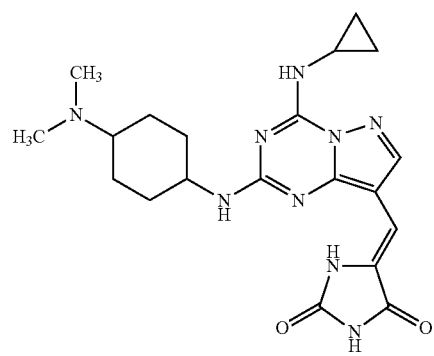 [SMILES: CN(C)C1CCC(Nc2nc(NC3CC3)n3ncc(/C=C4\NC(=O)NC4=O)c3n2)CC1]
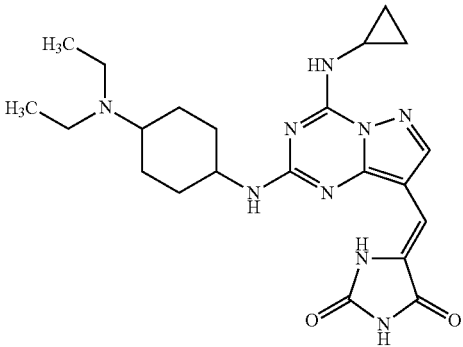 [SMILES: CCN(CC)C1CCC(Nc2nc(NC3CC3)n3ncc(/C=C4\NC(=O)NC4=O)c3n2)CC1]
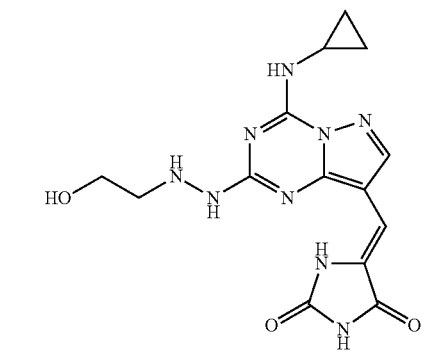 [SMILES: O=C1NC(=O)/C(=C/c2cnn3c(NC4CC4)nc(NNCCO)nc23)N1]
TABLE 33A-continued
352
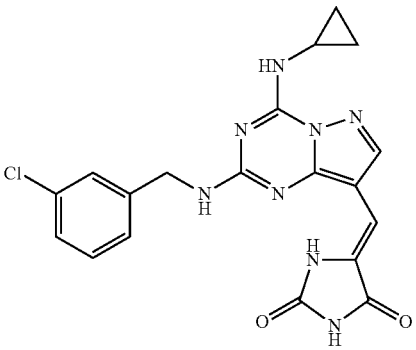 [SMILES: O=C1NC(=O)/C(=C/c2cnn3c(NC4CC4)nc(NCc4cccc(Cl)c4)nc23)N1]
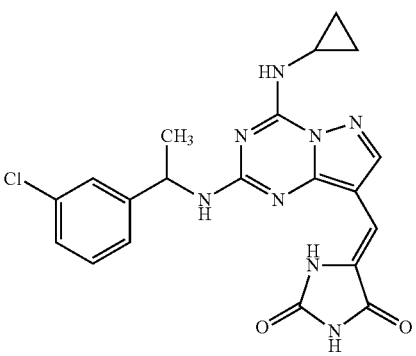 [SMILES: CC(Nc1nc(NC2CC2)n2ncc(/C=C3\NC(=O)NC3=O)c2n1)c1cccc(Cl)c1]
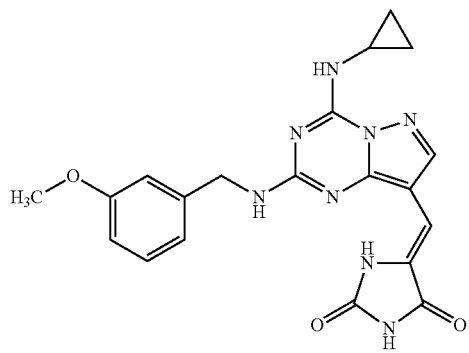 [SMILES: COc1cccc(CNc2nc(NC3CC3)n3ncc(/C=C4\NC(=O)NC4=O)c3n2)c1]
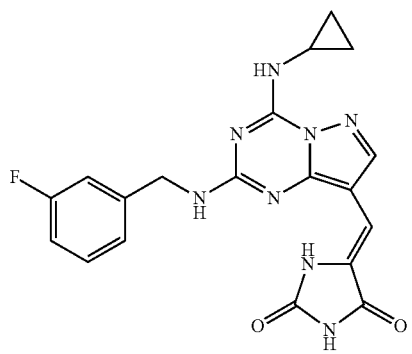 [SMILES: O=C1NC(=O)/C(=C/c2cnn3c(NC4CC4)nc(NCc4cccc(F)c4)nc23)N1]

TABLE 33A-continued
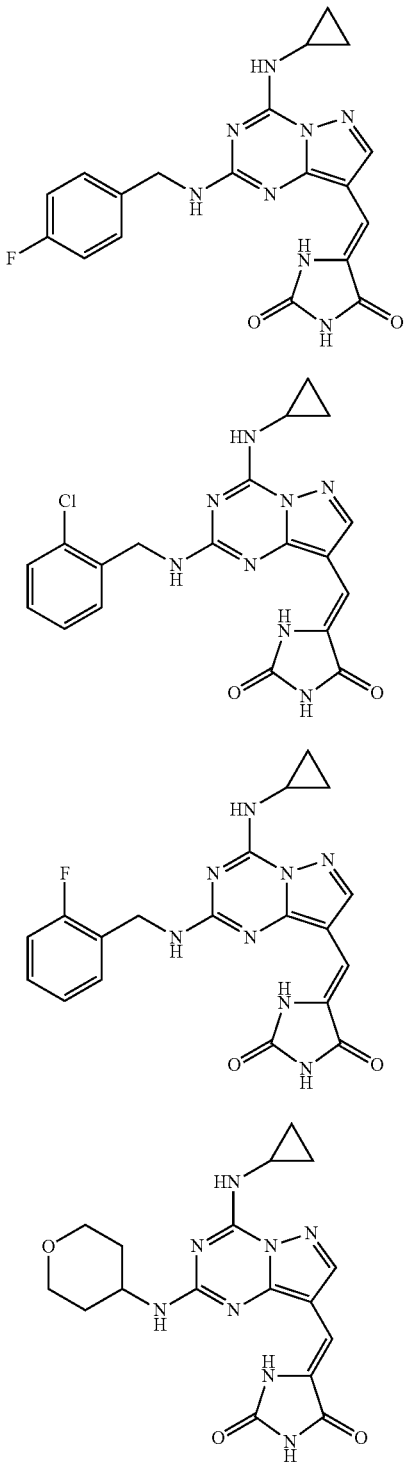
TABLE 33B
| Compound | CK2: IC50 (μM) | PIM2: IC50 (5 μM ATP) | AB: MDAMB453 (μM) | AB: BxPC3 (μM) |
|---|---|---|---|---|
| H14 | <1.0 | 1.3064 | 25.377 | 22.762 |
| I14 | <0.01 | >2.5000 | >30 | >30 |
TABLE 33B-continued
| Compound | CK2: IC50 (μM) | PIM2: IC50 (5 μM ATP) | AB: MDAMB453 (μM) | AB: BxPC3 (μM) |
|---|---|---|---|---|
| J14 | <0.01 | >2.5000 | 1.193 | 5.747 |
| K14 | <0.1 | >2.5000 | | |
| L14 | <0.01 | >2.5000 | 1.003 | 11.197 |
| M14 | <0.01 | >2.5000 | 0.77 | 2.905 |
| N14 | <0.01 | 2.3344 | 1.998 | 1.766 |
| O14 | <0.01 | >2.5000 | 0.753 | 2.178 |
| P14 | <0.01 | >2.5000 | 3.129 | >30 |
| Q14 | <0.01 | >2.5000 | 1.06 | 2.671 |
| R14 | <0.01 | 2.4058 | 1.602 | 15.41 |
| S14 | <0.1 | >2.5000 | 11.279 | 11.668 |
| T14 | <0.1 | 1.25 | | |
| U14 | <0.1 | >2.5000 | | |
| V14 | <1.0 | >2.5000 | | |
| W14 | <0.1 | >2.5000 | 6.386 | 23.384 |
| X14 | <0.01 | 1.1205 | 0.559 | 1.517 |
| Y14 | <0.01 | >2.5000 | 3.325 | 6.748 |
| A15 | >1 | >2.5000 | | |
| B15 | <0.01 | >2.5000 | 2.214 | 3.394 |
| C15 | <1.0 | >2.5000 | | |
| D15 | <0.1 | 1.5464 | | |
| E15 | <1.0 | >2.5000 | | |
| F15 | <1.0 | >2.5000 | | |
| G15 | <0.1 | >2.5000 | | |
| H15 | <0.1 | >2.5000 | | |
| I15 | <0.1 | >2.5000 | | |
| J15 | <0.01 | >2.5000 | 1.936 | 11.99 |
| K15 | <0.1 | 1.6558 | 5.319 | 23.688 |
| L15 | <0.1 | >2.5000 | | |
| M15 | >1 | >2.5000 | | |
| N15 | >1 | >2.5000 | | |
| O15 | >1 | >2.5000 | | |
| P15 | <1.0 | >2.5000 | | |
| Q15 | <1.0 | >2.5000 | | |
| R15 | <1.0 | >2.5000 | | |
| S15 | >1 | >2.5000 | | |
| T15 | <1.0 | >2.5000 | | |
| U15 | <1.0 | >2.5000 | | |
| V15 | <1.0 | >2.5000 | | |
| W15 | <1.0 | >2.5000 | | |
| X15 | <1.0 | | 18.336 | 14.152 |
| Y15 | <0.1 | >2.5000 | 6.603 | 10.731 |
| Z15 | <0.01 | >2.5000 | 6.283 | 15.114 |
| A16 | <0.1 | >2.5000 | 17.82 | >30 |
| B16 | <0.01 | >2.5000 | 2.627 | 5.528 |
| C16 | <0.1 | 1.7695 | 1.859 | 1.841 |
| D16 | <0.1 | >2.5000 | 5.03 | 17.83 |
| E16 | <0.01 | >2.5000 | 7.856 | 11.797 |
| F16 | <0.01 | >2.5000 | 3.545 | 17.187 |
| G16 | <0.01 | >2.5000 | 5.177 | 19.446 |
| H16 | <0.1 | >2.5000 | 18.952 | >30 |
| I16 | <0.1 | >2.5000 | 12.508 | 12.673 |
| J16 | <0.1 | >2.5000 | 11.685 | 18.88 |
| K16 | <1.0 | >2.5000 | 9.2 | 12.494 |
| L16 | <0.1 | >2.5000 | 9.964 | 11.216 |
| M16 | <0.01 | | 5.059 | 9.052 |
| N16 | <1.0 | | 25.644 | >30 |
| O16 | <0.1 | | 7.829 | >30 |
| P16 | <0.1 | | 10.353 | >30 |
| Q16 | <0.1 | | 17.611 | >30 |
| R16 | <0.1 | | 13.114 | 19.2 |
| S16 | <0.01 | >2.5000 | 4.697 | 8.049 |
| T16 | <0.01 | 1.9391 | 2.491 | 1.712 |
| U16 | <0.01 | >2.5000 | 4.313 | 8.232 |
| V16 | <0.01 | 2.438 | 5.738 | 5.492 |
| W16 | <0.1 | >2.5000 | 27.524 | 9.27 |
| X16 | <1.0 | >2.5000 | 17.619 | 9.053 |
| Y16 | <0.1 | >2.5000 | | |
| Z16 | <0.01 | <1.0 | 14.666 | 2.909 |
| A17 | <0.1 | 1.8629 | 12.569 | 5.872 |
| B17 | <0.01 | >2.5000 | 12.517 | 6.862 |
| C17 | <0.1 | >2.5000 | 11.841 | 2.389 |
| D17 | <0.01 | 1.884 | 3.353 | 8.144 |
| E17 | <1.0 | >2.5000 | | |
| F17 | <0.01 | >2.5000 | 3.97 | 15.62 |
| G17 | <0.1 | <1.0 | | |
| H17 | <0.1 | <1.0 | 6.919 | 6.611 |

TABLE 33B-continued
| Compound | CK2: IC50 (μM) | PIM2: IC50 (5 μM ATP) | AB: MDAMB453 (μM) | AB: BxPC3 (μM) |
|---|---|---|---|---|
| I17 | <0.01 | 1.1903 | 0.442 | 7.667 |
| J17 | <0.01 | >2.5000 | 1.416 | 9.445 |
| K17 | <0.1 | >2.5000 | | |
| L17 | <0.1 | 2.0781 | 20.449 | 5.948 |
| M17 | <0.01 | >2.5000 | 27.014 | >30 |
| N17 | <0.1 | >2.5000 | 13.419 | 19.135 |
| O17 | <0.1 | >2.5000 | 12.459 | 17.049 |
| P17 | <0.1 | >2.5000 | | |
| Q17 | <0.1 | 1.6281 | >30 | 2.009 |
| R17 | <1.0 | >2.5000 | | |
| S17 | <0.1 | >2.5000 | 2.594 | 6.849 |
| T17 | <0.01 | <1.0 | 2.751 | 4.95 |
| U17 | <0.1 | >2.5000 | 4.554 | 10.817 |
| V17 | <0.1 | >2.5000 | 13.033 | 1.55 |
| W17 | <0.1 | >2.5000 | | |
| X17 | <0.1 | >2.5000 | 2.477 | 5.229 |
| Y17 | <0.1 | >2.5000 | 8.283 | 3.409 |
| Z17 | <0.1 | >2.5000 | 4.486 | 9.071 |
| A18 | <0.01 | >2.5000 | 1.478 | 4.729 |
| B18 | <0.01 | 1.304 | 2.64 | 4.027 |
| C18 | <0.01 | >2.5000 | 1.245 | 1.388 |
| D18 | <0.01 | >2.5000 | 2.286 | 4.684 |
| E18 | <0.1 | >2.5000 | 10.575 | 9.784 |
| F18 | <0.01 | >2.5000 | >30 | >30 |
| G18 | <0.1 | >2.5000 | 13.472 | 14.435 |
| H18 | <0.01 | >2.5000 | 1.907 | 4.537 |
| I18 | <0.1 | >2.5000 | 8.221 | 14.522 |
| J18 | <0.1 | >2.5000 | | |
| K18 | <0.1 | >2.5000 | | |
| L18 | <0.1 | >2.5000 | | |
| M18 | <0.1 | >2.5000 | | |
| N18 | <0.1 | >2.5000 | 26.829 | 25.022 |
| O18 | <0.01 | >2.5000 | 13.2 | >30 |
| P18 | <0.1 | >2.5000 | 21.799 | >30 |
| Q18 | <0.1 | >2.5000 | 1.368 | 8.975 |
| R18 | <0.1 | >2.5000 | 8.555 | 13.435 |
| S18 | <0.1 | >2.5000 | | |
| T18 | <0.01 | >2.5000 | 3.136 | 4.168 |
| U18 | <0.1 | >2.5000 | | |
| V18 | <0.1 | >2.5000 | | |
| W18 | <0.01 | >2.5000 | 11.668 | >30 |
| X18 | <0.01 | >2.5000 | 13.548 | 18.585 |
| Y18 | <0.1 | >2.5000 | 18.328 | 5.013 |
| Z18 | <0.01 | >2.5000 | 11.97 | >30 |
| A19 | <0.1 | >2.5000 | | |
| B19 | <0.1 | >2.5000 | | |
| C19 | <0.01 | >2.5000 | | |
| D19 | <0.1 | >2.5000 | | |
| E19 | <0.1 | >2.5000 | | |
| F19 | <0.01 | >2.5000 | | |
| G19 | <0.01 | >2.5000 | | |
| H19 | <0.1 | >2.5000 | | |
| I19 | <0.1 | >2.5000 | | |
| J19 | <0.01 | >2.5000 | | |
| K19 | <0.1 | >2.5000 | | |
| L19 | <0.1 | >2.5000 | | |
| M19 | <0.01 | | | |
| N19 | <0.1 | | | |
| O19 | <0.1 | | | |
| P19 | <0.01 | | | |
| Q19 | <0.01 | | | |
| R19 | <0.01 | | | |
| S19 | <0.1 | | | |
Scheme 1
The compounds described in the following table can be prepared using chemistries described on FIG. 7.
TABLE 34
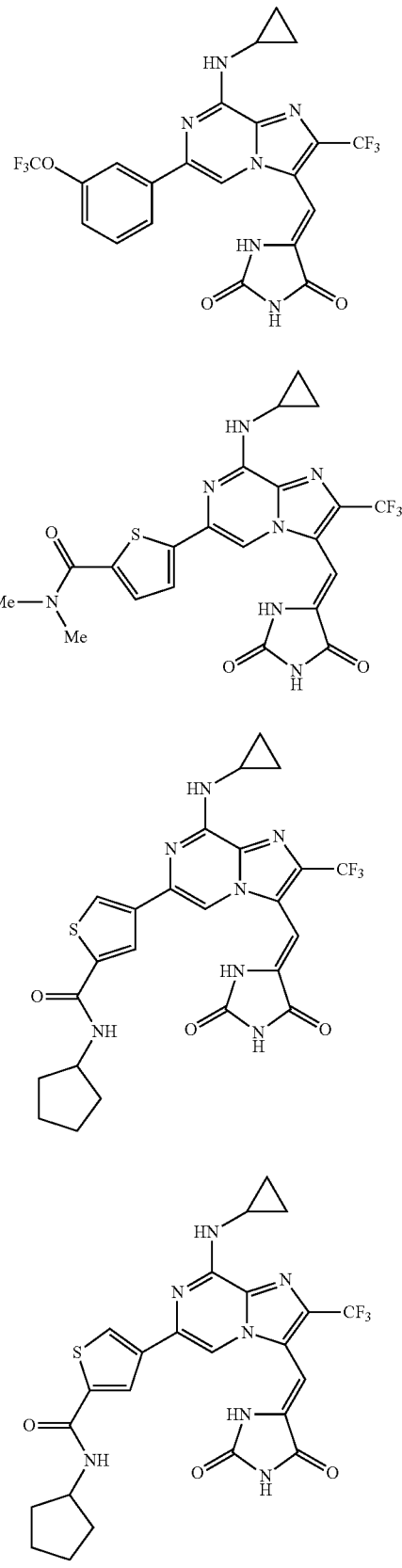

TABLE 34-continued
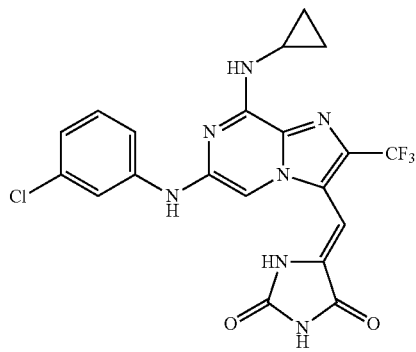 [SMILES: O=C1NC(=O)/C(=C/c2c(C(F)(F)F)nc3c(NC4CC4)nc(Nc4cccc(Cl)c4)cn23)N1]
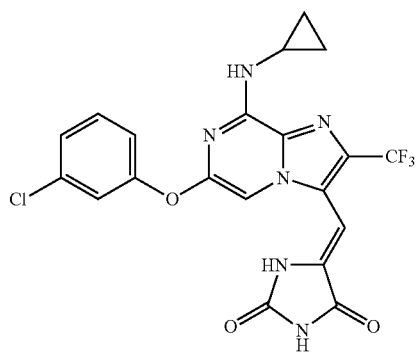 [SMILES: O=C1NC(=O)/C(=C/c2c(C(F)(F)F)nc3c(NC4CC4)nc(Oc4cccc(Cl)c4)cn23)N1]
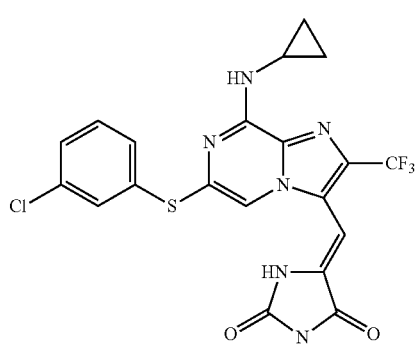
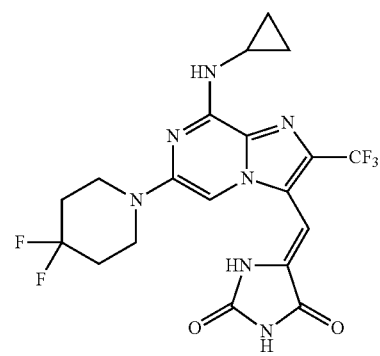 [SMILES: O=C1NC(=O)/C(=C/c2c(C(F)(F)F)nc3c(NC4CC4)nc(N4CCC(F)(F)CC4)cn23)N1]
TABLE 34-continued
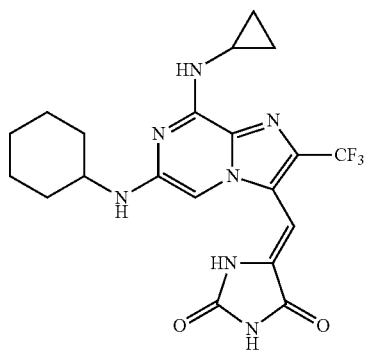 [SMILES: O=C1NC(=O)/C(=C/c2c(C(F)(F)F)nc3c(NC4CC4)nc(NC4CCCCC4)cn23)N1]
The following molecules can be prepared using chemistries similar to Example 206, Example 207 and Example 208.
TABLE 35
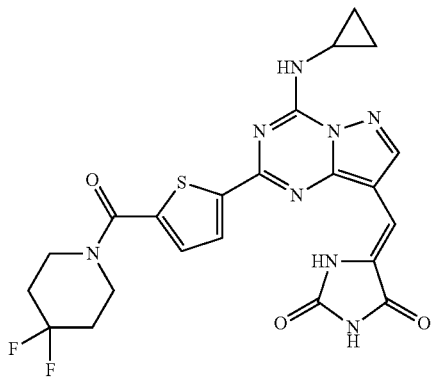 [SMILES: O=C1NC(=O)/C(=C/c2cnn3c(NC4CC4)nc(-c4ccc(C(=O)N5CCC(F)(F)CC5)s4)nc23)N1]
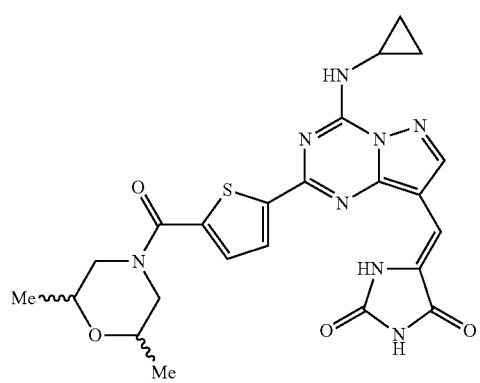
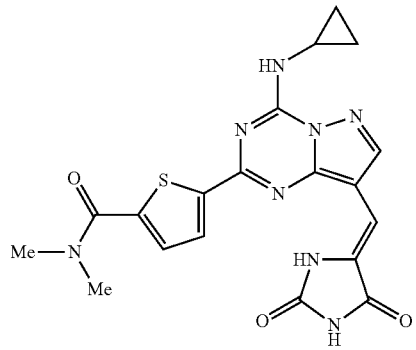 [SMILES: CN(C)C(=O)c1ccc(-c2nc(NC3CC3)n3ncc(/C=C4\NC(=O)NC4=O)c3n2)s1]

TABLE 35-continued

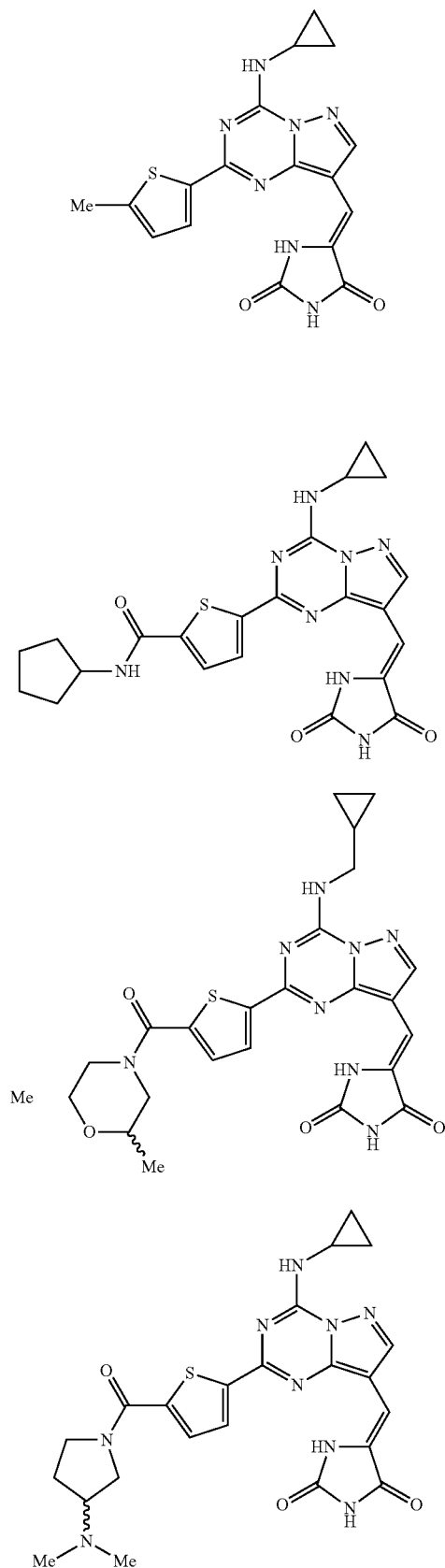

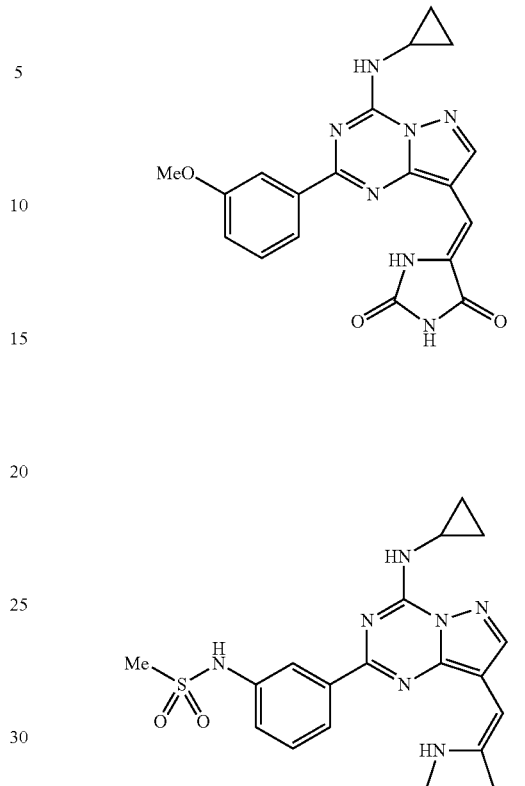

Figure 8:
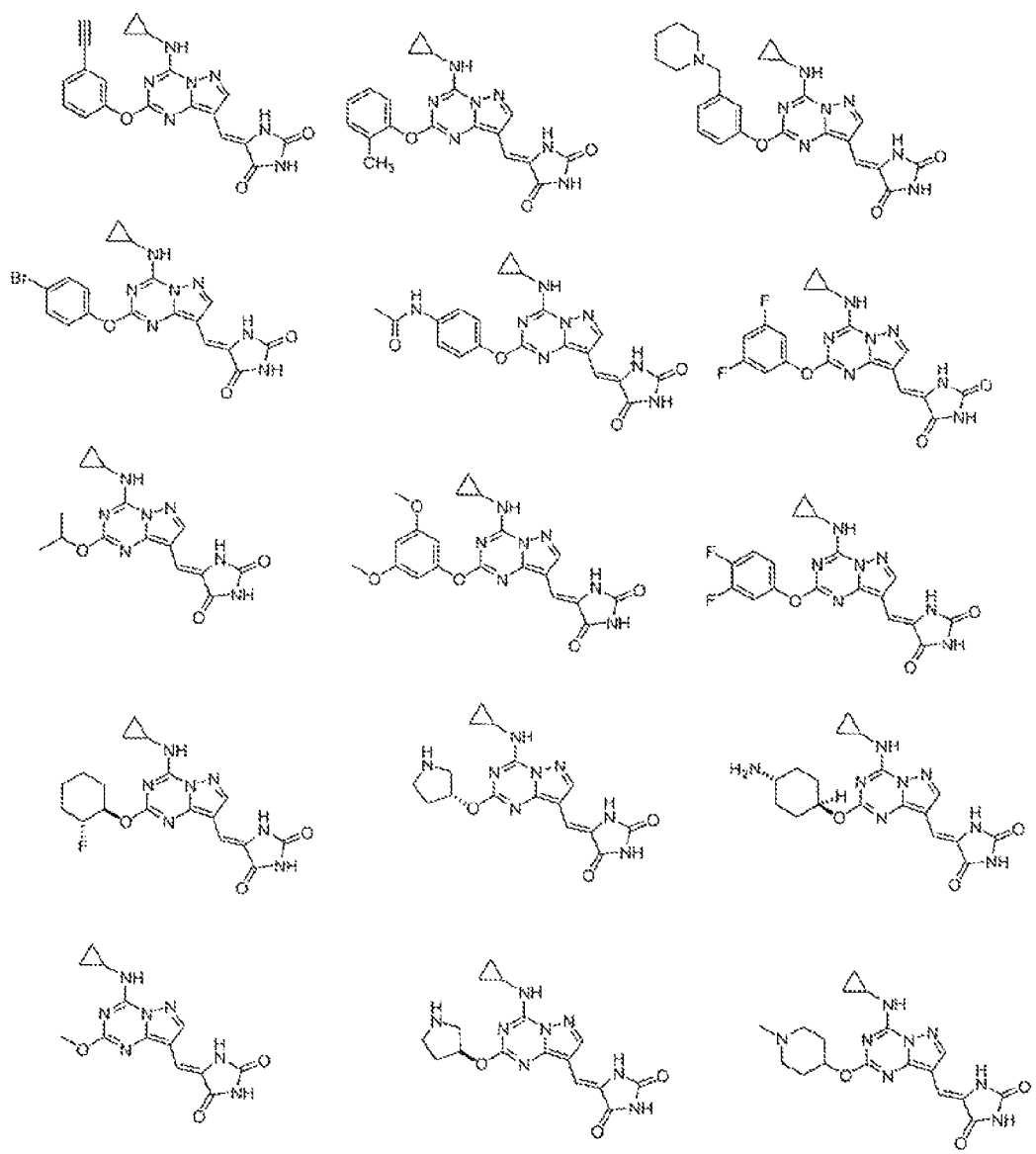
FIG. 8 depicts a number of variations of the pyrazolotriazine compounds within the scope of the invention.

The molecules described in FIG. 8 were prepared using chemistries described in Example 201, using bases such as $K_2CO_3$ or sodium hydride.

Others

Figure 9:
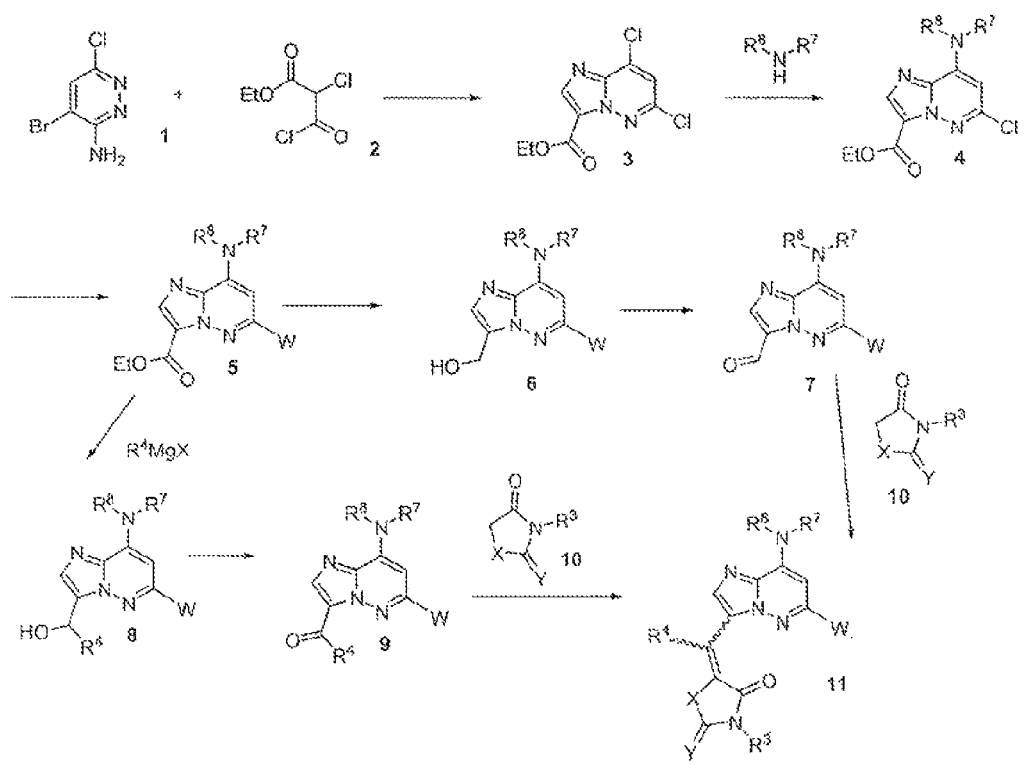
FIG. 9 depicts methods to make certain imidazo-pyridazine compounds within the scope of the invention.
Figure 10:
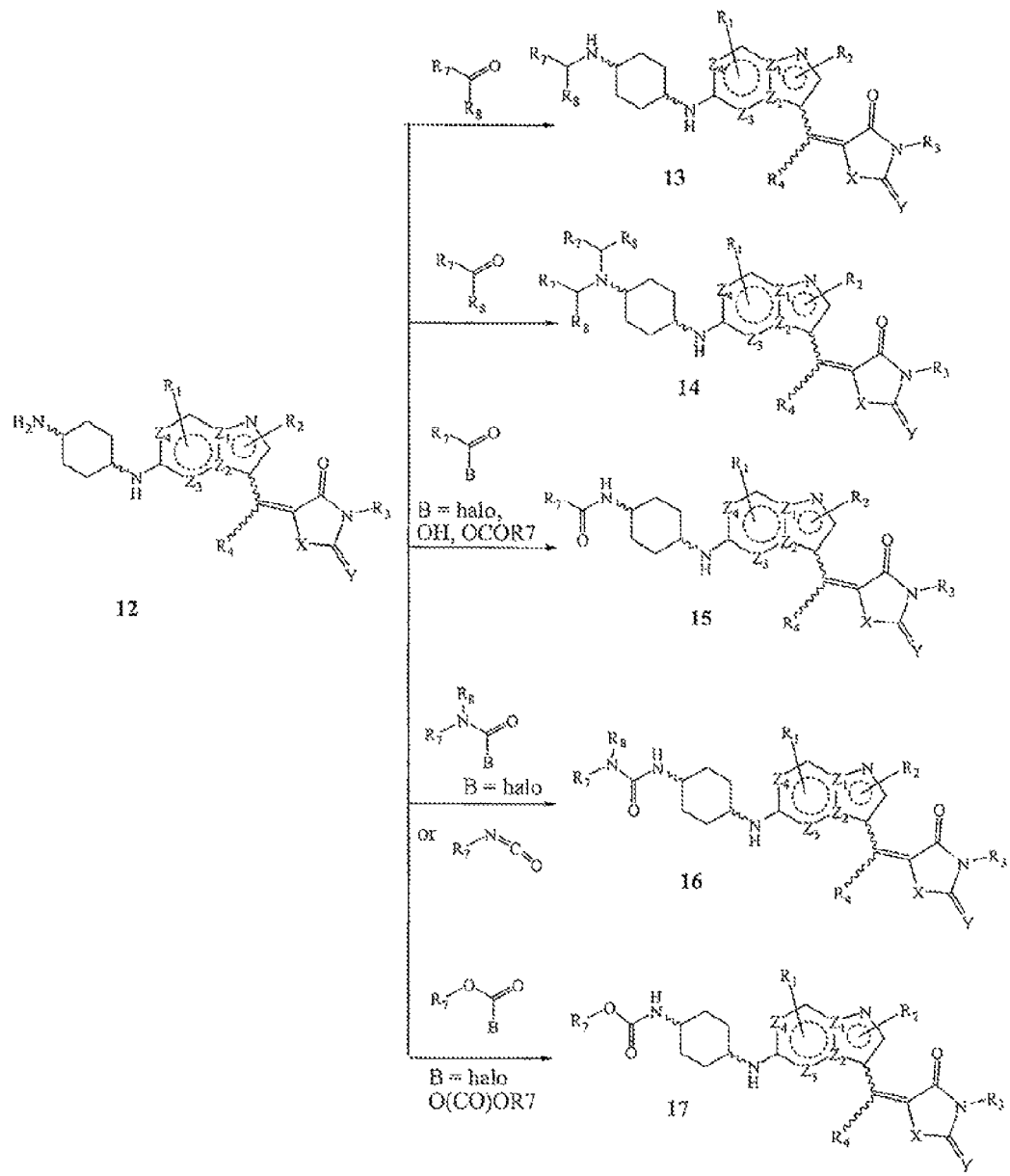
FIG. 10 illustrates a general method for modifying certain substituted compounds of the invention to introduce additional features.
Figure 11:
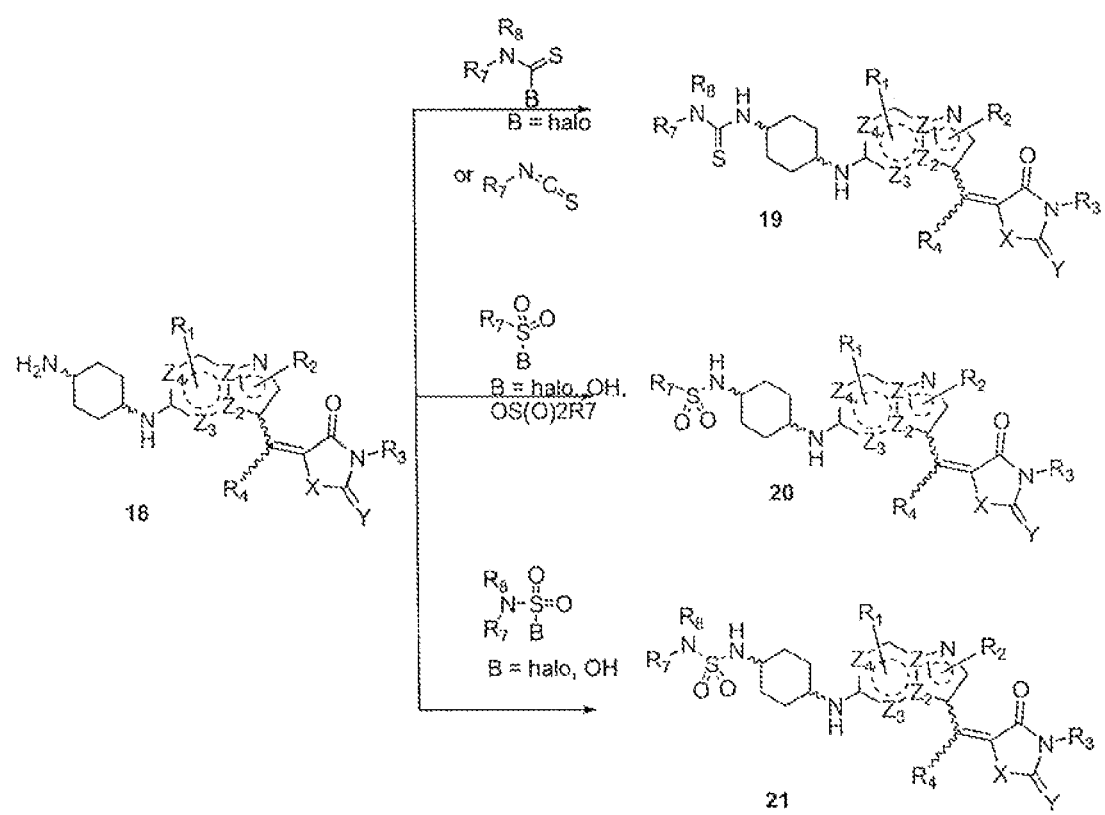
FIG. 11 depicts more methods for modifying substituents on compounds of the invention.
Figure 12:
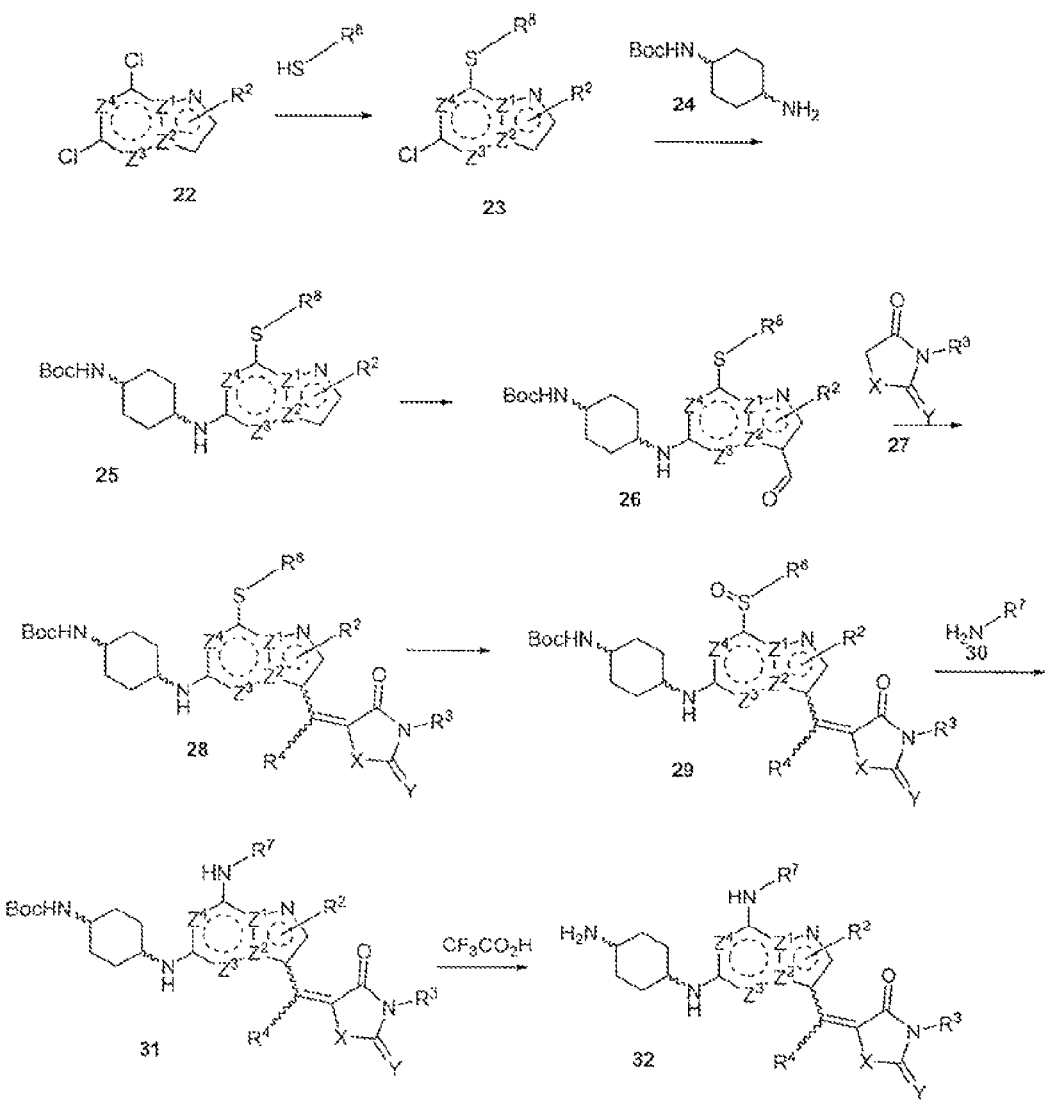
FIG. 12 illustrates alternative synthesis routes for making certain compounds of the invention.
Figure 13:
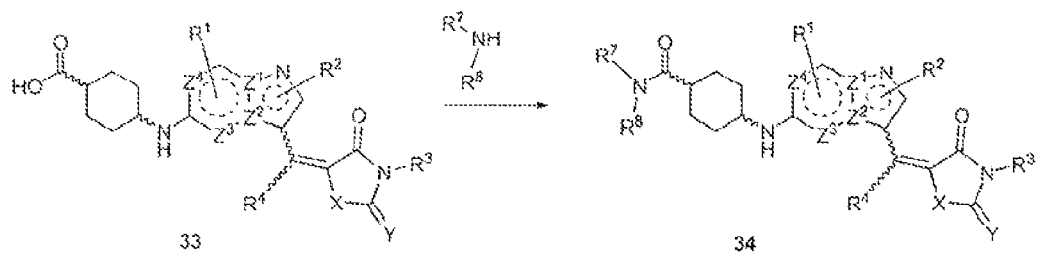
FIG. 13 depicts formation of an amide compound of the invention from a corresponding carboxylic acid compound.
Figure 14:
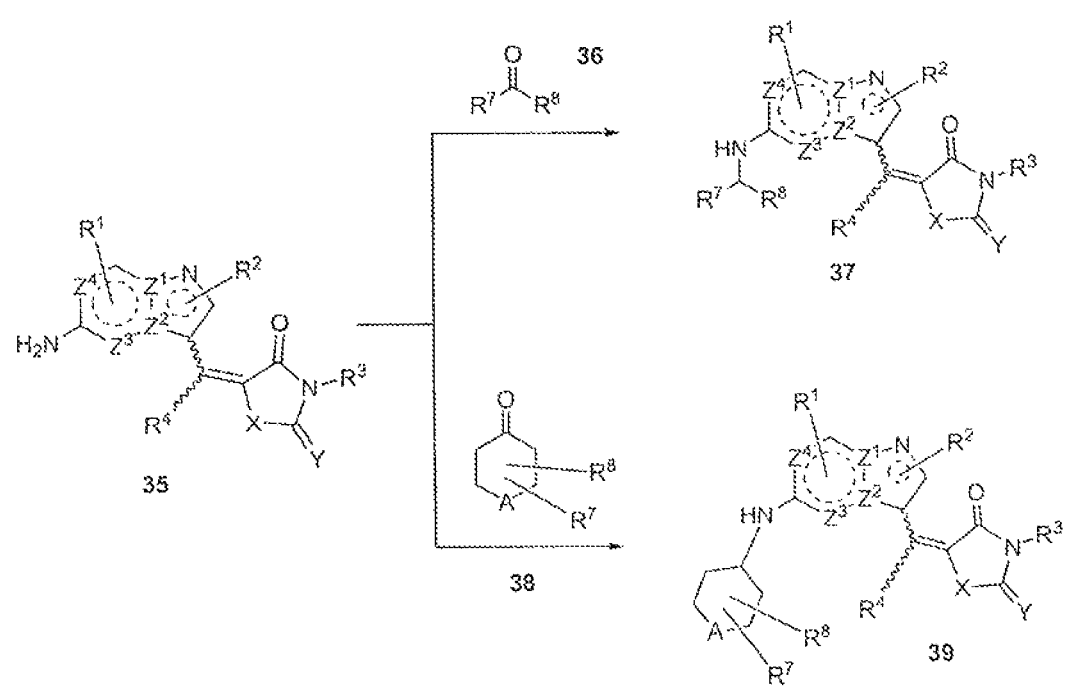
FIG. 14 depicts a reductive amination method for introducing certain groups onto the compounds of the invention.

The chemistry described on FIG. 9 can be used to prepare analogs of formula 11. 4-bromo-6-chloropyridazin-3-amine 1 can be reacted with 2 using conditions analogous to the preparation described in the patent application WO2009/100375 to form compound 3. Compound 3 can react with amine $R_8R_7NH$ to form compound 4. Compound 4 can be transformed to compound 5 by nucleophilic substitutions with amines, anilines, alcohols, phenols or thiophenols, in the presence of a base, or by transition metal catalyzed conversions such as Suzuki coupling with boronic acid or esters of formula $WB(OR)_2$. Compound 5 can be transformed to compound 6 by reduction with $LiAlH_4$. Alcohol 6 can be converted to aldehyde 7 by oxidation with DCC or under Swern conditions. Compound 5 can react with an organometallic reagent exemplified by Grignard reagent $R^4MgX$ to form secondary alcohol 8. This compound can be converted to alkylketone 9 under conditions analogous to the conditions used to convert 6 into 7. Compounds 7 and 9 can both be converted to compound 11 by condensation with 10 in a solvent such as ethanol and in the presence of a base such as piperidine.

The compounds described in the following table can be prepared using chemistry described on FIG. 9.

FIGS. 10-14 illustrate other synthesis methods that can be used to prepare compounds of the invention.

TABLE 36
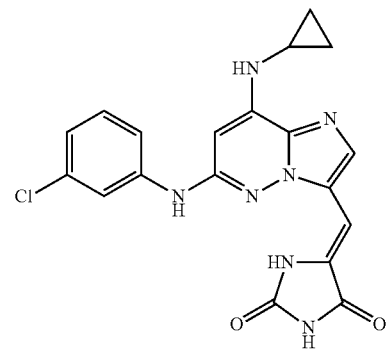 [SMILES: O=C1NC(=O)/C(=C/c2cnc3c(NC4CC4)cc(Nc4cccc(Cl)c4)nn23)N1]
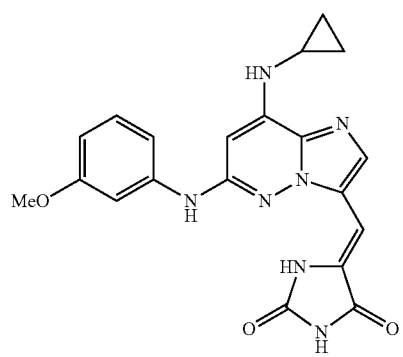 [SMILES: COc1cccc(Nc2cc(NC3CC3)c3ncc(/C=C4\NC(=O)NC4=O)n3n2)c1]
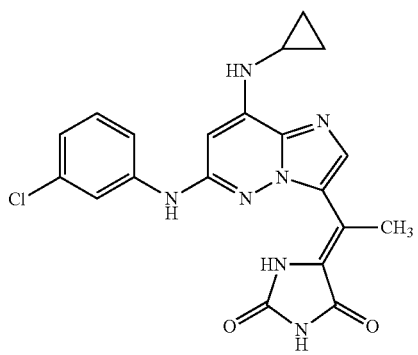 [SMILES: C/C(=C1/NC(=O)NC1=O)c1cnc2c(NC3CC3)cc(Nc3cccc(Cl)c3)nn12]
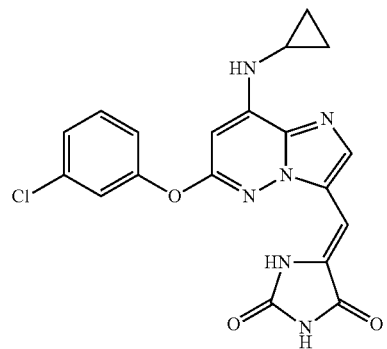 [SMILES: O=C1NC(=O)/C(=C/c2cnc3c(NC4CC4)cc(Oc4cccc(Cl)c4)nn23)N1]
TABLE 36-continued
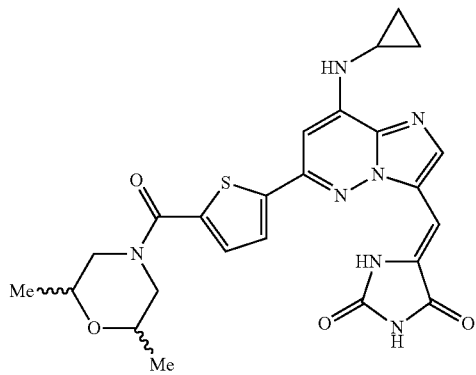
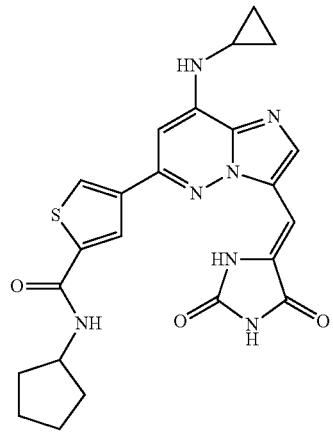 [SMILES: O=C1NC(=O)/C(=C/c2cnc3c(NC4CC4)cc(-c4csc(C(=O)NC5CCCC5)c4)nn23)N1]
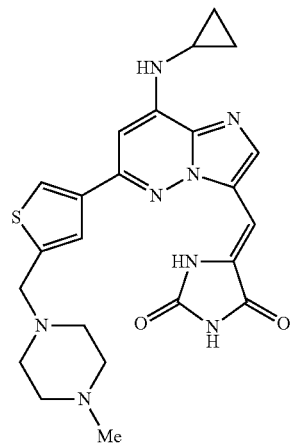 [SMILES: CN1CCN(Cc2cc(-c3cc(NC4CC4)c4ncc(/C=C5\NC(=O)NC5=O)n4n3)cs2)CC1]
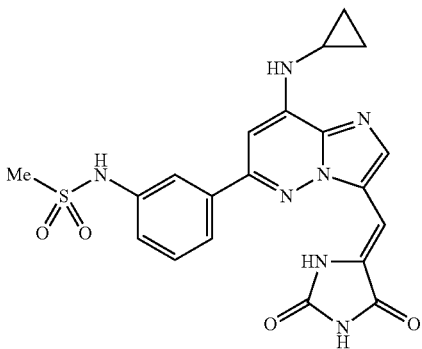 [SMILES: CS(=O)(=O)Nc1cccc(-c2cc(NC3CC3)c3ncc(/C=C4\NC(=O)NC4=O)n3n2)c1]

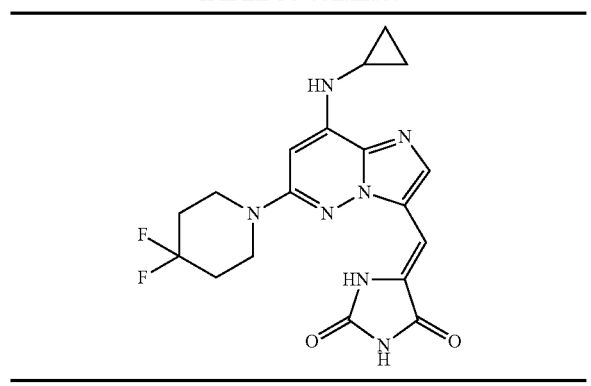

Example 209

Synthesis of 5-((5-(3-chlorophenylamino)-7-(cyclopropylamino)pyrazolo[1,5-a]pyrimidin-3-yl)methylene)imidazolidine-2,4-dione

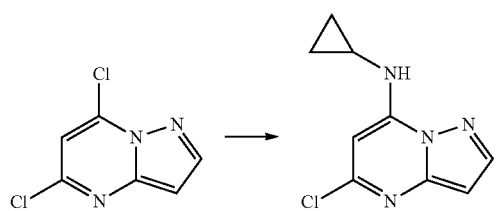 [SMILES: Clc1cc(Cl)n2nccc2n1 ; Clc1cc(NC2CC2)n2nccc2n1]

Step A. To 5,7-dichloropyrazolo[1,5-a]pyrimidine (200 mg, 1.06 mmol) in acetonitrile was added $Et_3N$ (148 μl, 1.06 mmol) and cyclopropylamine (75 μl, 1.06 mmol). The reaction was heated at 80° C. overnight. The mixture was concentrated under reduced pressure, dissolved in dichloromethane, and washed with water. The resulting organic layer was dried over $Na_2SO_4$ and concentrated under reduced pressure to afford 156 mg of 5-chloro-N-cyclopropylpyrazolo[1,5-a]pyrimidin-7-amine (70% yield). LCMS (M+1=209)

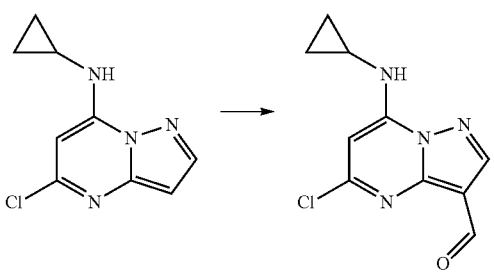 [SMILES: Clc1cc(NC2CC2)n2nccc2n1 ; O=Cc1cnn2c(NC3CC3)cc(Cl)nc12]

Step B. To 5-chloro-N-cyclopropylpyrazolo[1,5-a]pyrimidin-7-amine (156 mg, 0.75 mmol) in DMF was added $POCl_3$ (205 μl, 2.25 mmol). The mixture was stirred at room temperature for 3 hours. Ice was added to quench $POCl_3$, and then the mixture was neutralized with 1 M NaOH. Dichloromethane was added and the product was extracted three times. The organic layer was dried over $Na_2SO_4$ and concentrated under reduced pressure to yield 5-chloro-7-(cyclopropylamino)pyrazolo[1,5-a]pyrimidine-3-carbaldehyde. Some residual DMF could not be removed. LCMS (M+1=237)

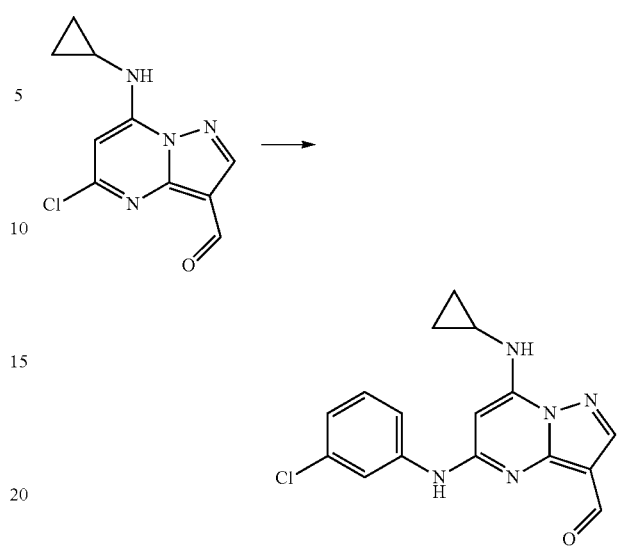

Step C. To 5-chloro-7-(cyclopropylamino)pyrazolo[1,5-a]pyrimidine-3-carbaldehyde (177 mg, 0.75 mmol) in 1,4-dioxane was added 3-chloroaniline (397 μl, 3.75 mmol). The mixture was heated in microwave at 120° C. for 60 minutes. Precipitate was filtered off, and the filtrate was prepared by TLC (1% methanol/dichloromethane) to yield 26 mg (11% yield) of 5-(3-chlorophenylamino)-7-(cyclopropylamino)pyrazolo[1,5-a]pyrimidine-3-carbaldehyde. LCMS (M+1=328)

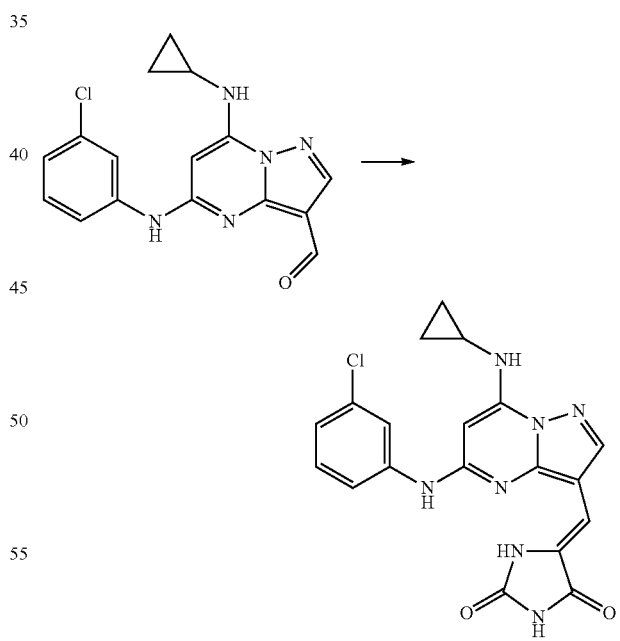

Step D. To 5-(3-chlorophenylamino)-7-(cyclopropylamino)pyrazolo[1,5-a]pyrimidine-3-carbaldehyde (26 mg, 0.08 mmol) in EtOH was added hydantoin (8 mg, 0.08 mmol) and piperidine (8 μl, 0.08 mmol). The mixture was stirred at 70° C. for 3 days. Insolubles were filtered off, and filtrate was concentrated under reduced pressure. Filtrate was then dissolved in methanol and purified by HPLC to yield 5-((5-(3- chlorophenylamino)-7-(cyclopropylamino)pyrazolo[1,5-a]pyrimidin-3-yl)methylene)imidazolidine-2,4-dione. LCMS (M+1=410)

Example 210

Synthesis of 5-((7-(cyclopropylamino)-5-(isobutylamino)pyrazolo[1,5-a]pyrimidin-3-yl)methylene)thiazolidine-2,4-dione

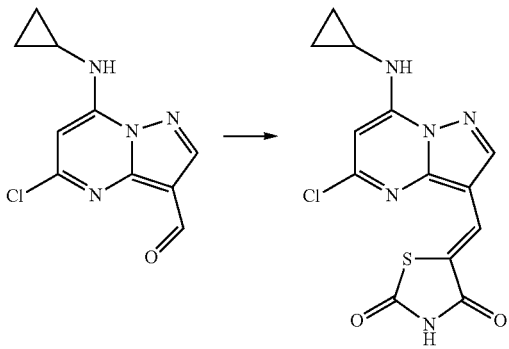 [SMILES: O=Cc1cnn2c(NC3CC3)cc(Cl)nc12 ; O=C1NC(=O)/C(=C/c2cnn3c(NC4CC4)cc(Cl)nc23)S1]

Step A. To 5-chloro-7-(cyclopropylamino)pyrazolo[1,5-a]pyrimidine-3-carbaldehyde (440 mg, 1.86 mmol) in EtOH was added thiazolidine-2,4-dione (458 mg, 3.91 mmol) and piperidine (208 pl, 2.05 mmol). The reaction was heated at 80° C. overnight. 3 mL Isopropanol was added in the morning, along with 218 mg thiazolidine-2,4-dione, 94 µL piperidine. Temperature was increased to 90° C. and left overnight. Precipitate was filtered while hot and dissolved in methanol. 1 mL of 1M HCl was added and the mixture sonicated. Precipitate was filtered and washed with methanol to yield 340 mg (54% yield) 5-((5-chloro-7-(cyclopropylamino)pyrazolo[1,5-a]pyrimidin-3-yl)methylene)thiazolidine-2,4-dione as a yellow powder. LCMS (M+1=336)

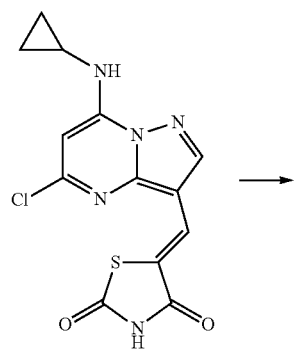

Step B. To 5-((5-chloro-7-(cyclopropylamino)pyrazolo[1,5-a]pyrimidin-3-yl)methylene)thiazolidine-2,4-dione (30 mg, 0.09 mmol) in N-methylpyrrolidinone (NMP) was added 2-methylpropan-1-amine (20 mg, 0.268 mmol). The reaction was heated at 130° C. overnight. Mixture was diluted with methanol and prepared by HPLC to yield 5-((7-(cyclopropylamino)-5-(isobutylamino)pyrazolo[1,5-a]pyrimidin-3-yl)methylene)thiazolidine-2,4-dione. LCMS (M+1=373)

Example 211

Synthesis of 5-((7-(cyclopropylamino)-5-(2-hydroxypropylamino)pyrazolo[1,5-a]pyrimidin-3-yl)methylene)thiazolidine-2,4-dione

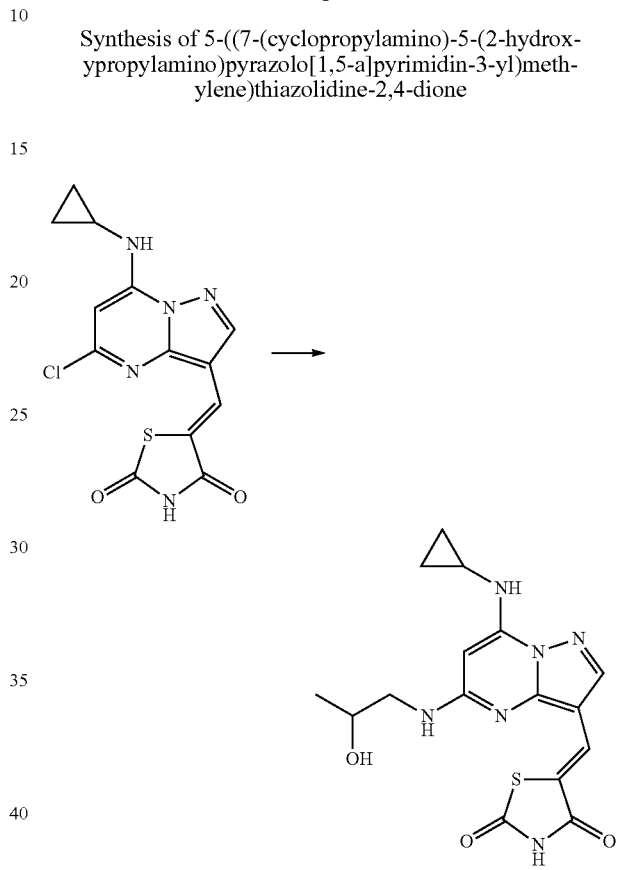

The titled compound was prepared using a method analogous to that described for Example 210. LCMS (M+1=375)

Example 212

Synthesis of 5-((7-(cyclopropylamino)-5-(diethylamino)pyrazolo[1,5-a]pyrimidin-3-yl)methylene)thiazolidine-2,4-dione

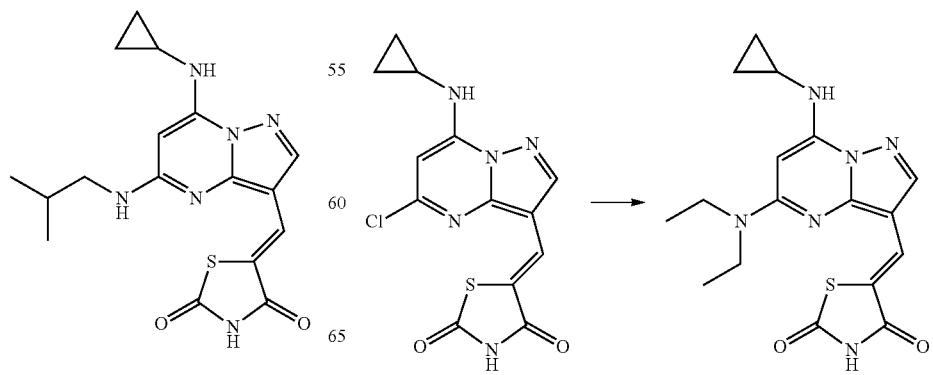

367

The titled compound was prepared using a method analogous to that described for Example 210. LCMS (M+1=373)

Example 213

Synthesis of 5((7-(cyclopropylamino)-5-(dimethylamino)pyrazolo[1,5-a]pyrimidin-3-yl)methylene)thiazolidine-2,4-dione

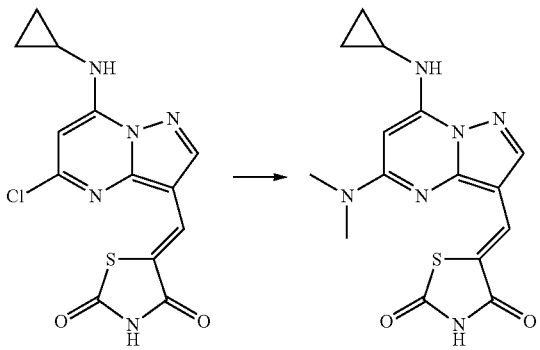 [SMILES: O=C1NC(=O)/C(=C/c2cnn3c(NC4CC4)cc(Cl)nc23)S1 ; CN(C)c1cc(NC2CC2)n2ncc(/C=C3\SC(=O)NC3=O)c2n1]

The titled compound was prepared using a method analogous to that described for Example 210. LCMS (M+1=345)

Example 214

Synthesis of 5((7-(cyclopropylamino)-5-(methyl(1-methylpyrrolidin-3-yl)amino)pyrazolo[1,5-a]pyrimidin-3-yl)methylene)thiazolidine-2,4-dione

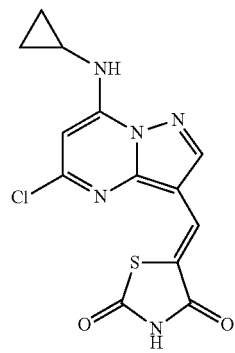

368

The titled compound was prepared using a method analogous to that described for Example 210. LCMS (M+1=414)

Example 215

Synthesis of 5-((7-(cyclopropylamino)-5-(2-fluoroethylamino)pyrazolo[1,5-a]pyrimidin-3-yl)methylene)thiazolidine-2,4-dione

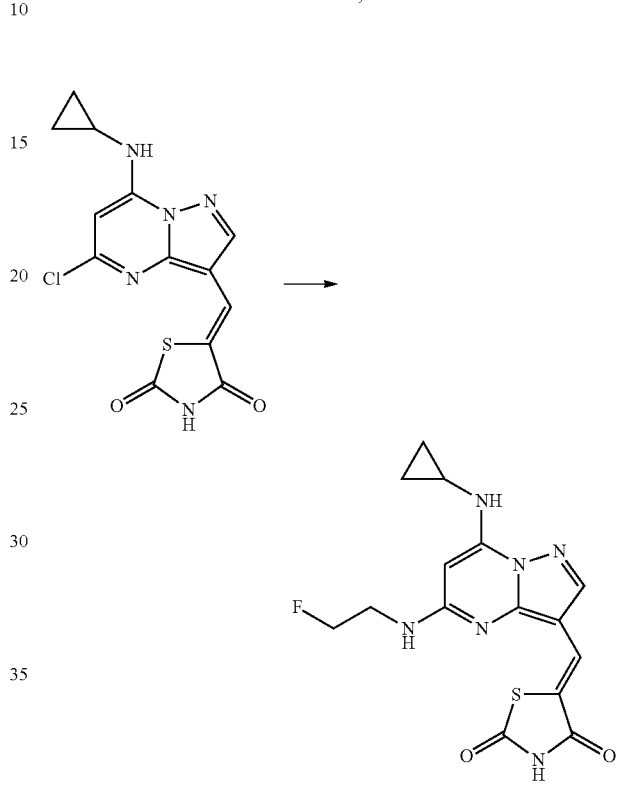

The titled compound was prepared using a method analogous to that described for Example 210. LCMS (M+1=363)

Example 216

Synthesis of 5-((7-(cyclopropylamino)-5-(4-methyl-1,4-diazepan-1-yl)pyrazolo[1,5-a]pyrimidin-3-yl)methylene)thiazolidine-2,4-dione

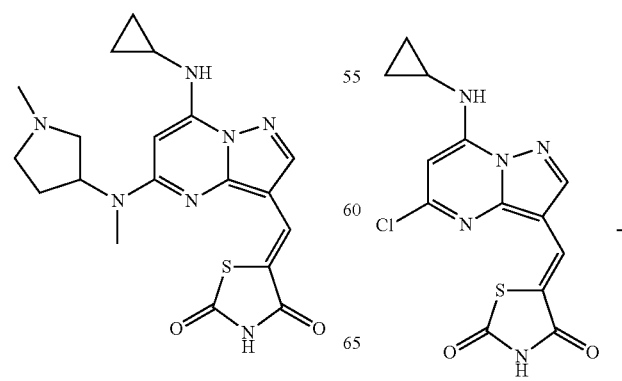

-continued

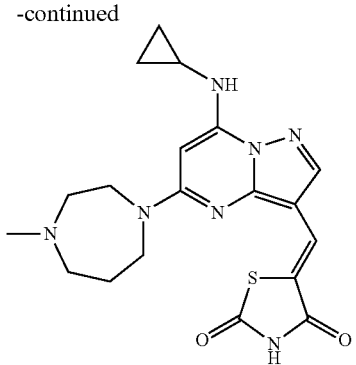

The titled compound was prepared using a method analogous to that described for Example 210. LCMS (M+1=414)

Example 217

Synthesis of 5-((7-(cyclopropylamino)-5-(2-(diethylamino)ethylamino)-pyrazolo[1,5-a]pyrimidin-3-yl)methylene)thiazolidine-2,4-dione

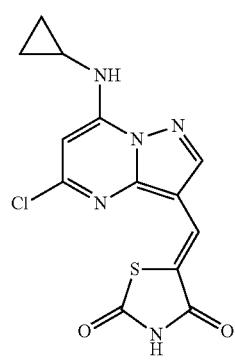

The titled compound was prepared using a method analogous to that described for Example 210. LCMS (M+1=416)

Example 218

Synthesis of 5-((5-(3-chlorophenylamino)-7-(cyclopropylamino)pyrazolo[1,5-a]pyrimidin-3-yl)methylene)thiazolidine-2,4-dione

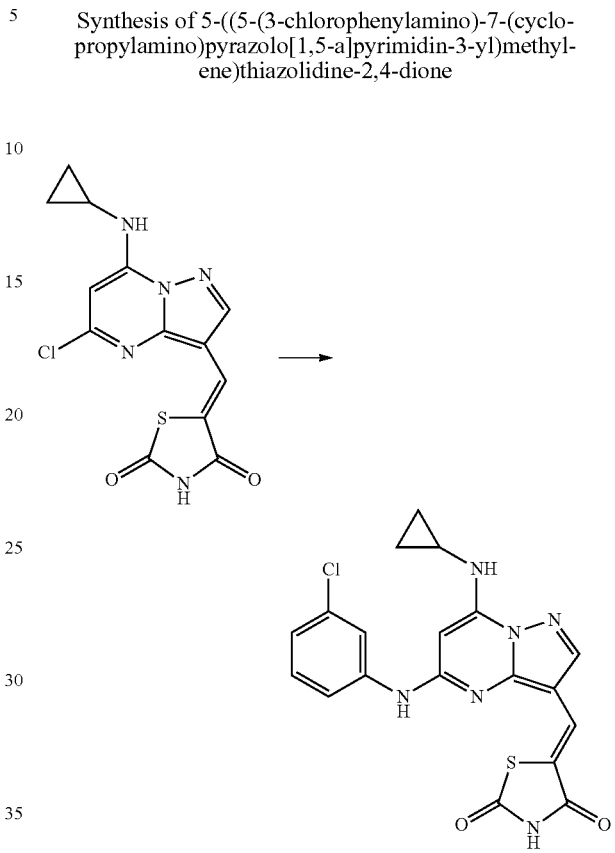

To 5-((5-chloro-7-(cyclopropylamino)pyrazolo[1,5-a]pyrimidin-3-yl)methylene)thiazolidine-2,4-dione (20 mg, 0.06 mmol) in NMP was added 3-chloroaniline (38 μL, 0.36 mmol) and few granules p-toluenesulfonic acid. The reaction was heated in microwave at 180° C. for 1.5 hours. Mixture was filtered and prepared by HPLC then preparative TLC (1% methanol/dichloromethane) to yield 5-((5-(3-chlorophenylamino)-7-(cyclopropylamino)pyrazolo[1,5-a]pyrimidin-3-yl)methylene)thiazolidine-2,4-dione as a yellow solid. LCMS (M+1=427)

Example 219

Synthesis of 5-((7-(cyclopropylamino)-2,5-dimethylpyrazolo[1,5-a]pyrimidin-3-yl)methylene)thiazolidine-2,4-dione

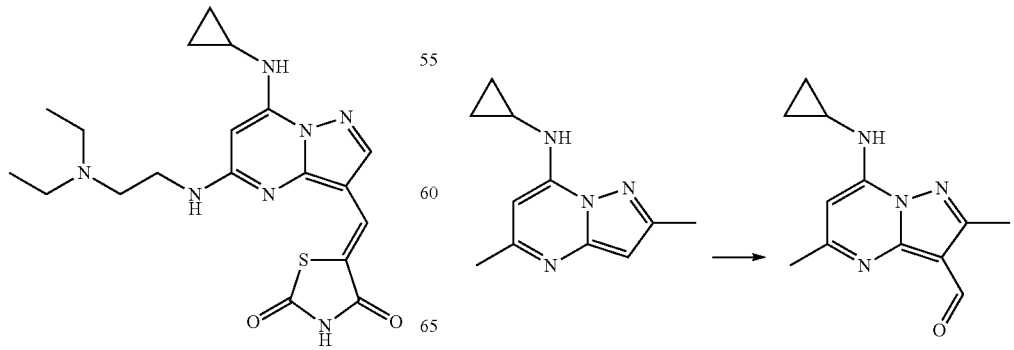

Step A. 7-(Cyclopropylamino)-2,5-dimethylpyrazolo[1,5-a]pyrimidine-3-carbaldehyde was prepared from N-cyclopropyl-2,5-dimethylpyrazolo[1,5-a]pyrimidin-7-amine using methods analogous to those described in Example 209. Step B. LCMS (M+1=231)

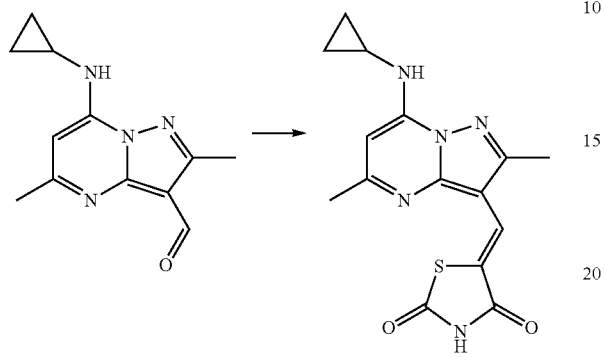

Step B. To 7-(cyclopropylamino)-2,5-dimethylpyrazolo[1,5-a]pyrimidine-3-carbaldehyde (0.25 mmol) in DMF was added thiazolidine-2,4-dione (88 mg, 0.75 mmol) and piperidine (25 µl, 0.25 mmol). The mixture was stirred at room temperature overnight. Mixture was prepared by HPLC to yield 5-((7-(cyclopropylamino)-2,5-dimethylpyrazolo[1,5-a]pyrimidin-3-yl)methylene)thiazolidine-2,4-dione. LCMS (M+1=330)

Example 220

Synthesis of 5-((7-(cyclopropylamino)pyrazolo[1,5-a]pyrimidin-3-yl)methylene)thiazolidine-2,4-dione

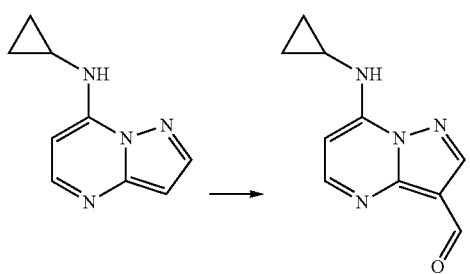 [SMILES: c1cc(NC2CC2)n2nccc2n1 ; O=Cc1cnn2c(NC3CC3)ccnc12]

Step A. 7-(Cyclopropylamino)pyrazolo[1,5-a]pyrimidine-3-carbaldehyde was prepared from N-cyclopropylpyrazolo[1,5-a]pyrimidin-7-amine using the methods described in Example 219, Step A. LCMS (M+1=203)

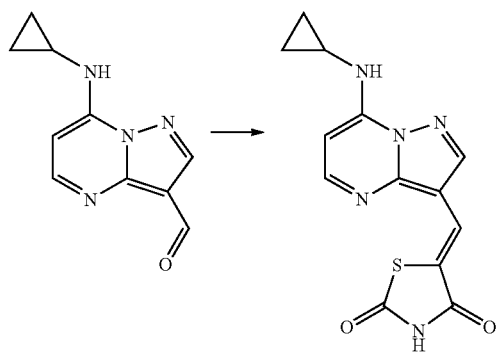 [SMILES: O=Cc1cnn2c(NC3CC3)ccnc12 ; O=C1NC(=O)/C(=C/c2cnn3c(NC4CC4)ccnc23)S1]

Step B. The titled compound was prepared from 7-(cyclopropylamino)pyrazolo[1,5-a]pyrimidine-3-carbaldehyde using methods analogous to those described in Example 219, Step B, except the product was isolated by filtration, washed with methanol, and air dried. LCMS (M+1=302)

Example 221

Synthesis of 5-((7-(cyclopropylamino)-5-(4-(pyridin-2-yl)piperazin-1-yl)pyrazolo[1,5-a]pyrimidin-3-yl)methylene)imidazolidine-2,4-dione

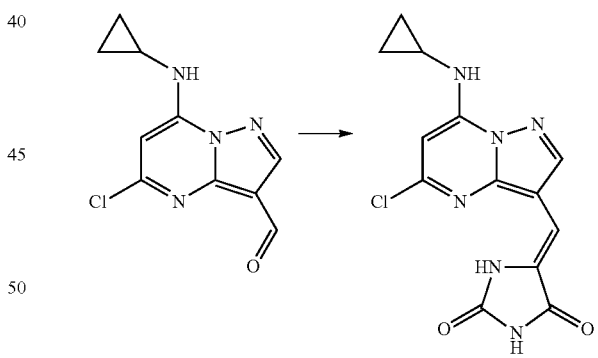

Step A. To 5-chloro-7-(cyclopropylamino)pyrazolo[1,5-a]pyrimidine-3-carbaldehyde (400 mg, 1.70 mmol) in EtOH was added hydantoin (186 mg, 1.86 mmol) and pyrrolidine (14 µL, 0.17 mmol). The reaction was stirred at 70° C. over weekend. Precipitate was filtered and air dried to yield 180 mg (33% yield) 5-((5-chloro-7-(cyclopropylamino)pyrazolo-[1,5-a]pyrimidin-3-yl)methylene)imidazolidine-2,4-dione. LCMS (M+1=319)

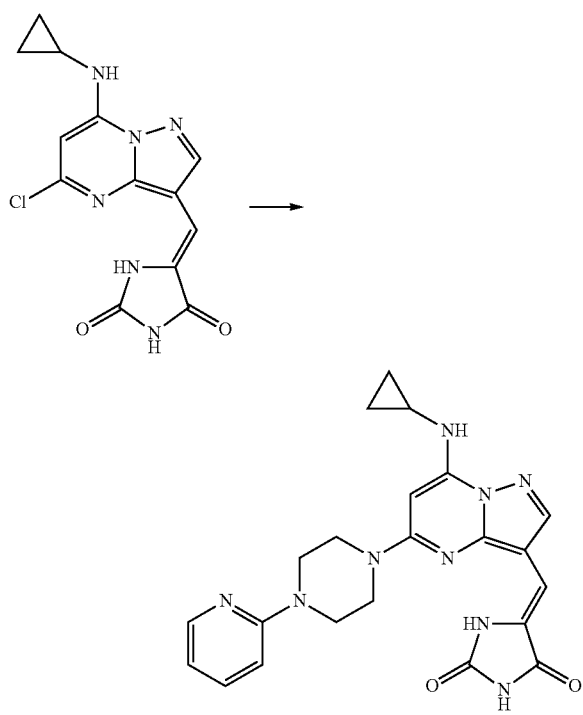

Step B. To 5-((5-chloro-7-(cyclopropylamino)pyrazolo[1,5-a]pyrimidin-3-yl)methylene)imidazolidine-2,4-dione (30 mg, 0.09 mmol) in 1,4-dioxane was added 1-(pyridin-2-yl)piperazine (58 μL, 4.10 mmol) and Et₃N (13 μL, 0.09 mmol). Reaction was then heated 120° C. for 35 minutes in microwave. Solvent was removed under reduced pressure, and mixture was dissolved in methanol. Solid was isolated by filtration, then air dried to yield 11 mg (26% yield) 5-((7-(cyclopropylamino)-5-(4-(pyridin-2-yl)piperazin-1-yl)pyrazolo[1,5-a]pyrimidin-3-yl)methylene)imidazolidine-2,4-dione. LCMS (M+1=446)

Example 222

Synthesis of 5((7-(cyclopropylamino)-5-(4-ethylpiperazin-1-yl)pyrazolo[1,5-a]pyrimidin-3-yl)methylene)imidazolidine-2,4-dione

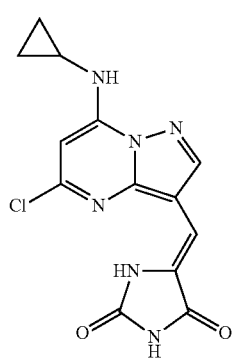

The titled compound was prepared using methods analogous to those described for Example 221, Step B, with the following alteration. The solvent was removed under reduced pressure, and the mixture was dissolved in methanol. The mixture was filtered, and the filtrate was concentrated under reduced pressure to provide 18 mg (48% yield) of the product as a yellow solid. LCMS (M+1=397)

Example 223

Synthesis of (Z)-5-((4-(cyclopropylamino)-2-(3,4-dimethylbenzylamino)pyrazolo[1,5-a][1,3,5]triazin-8-yl)methylene)imidazolidine-2,4-dione

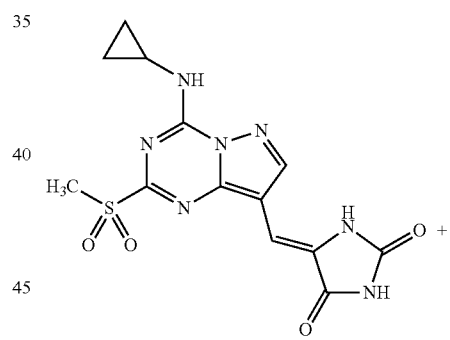

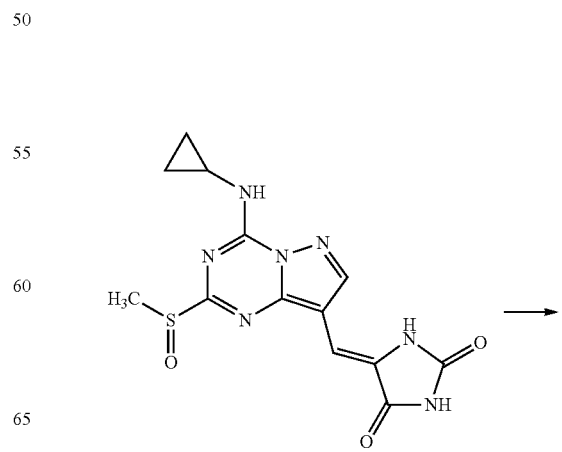

-continued

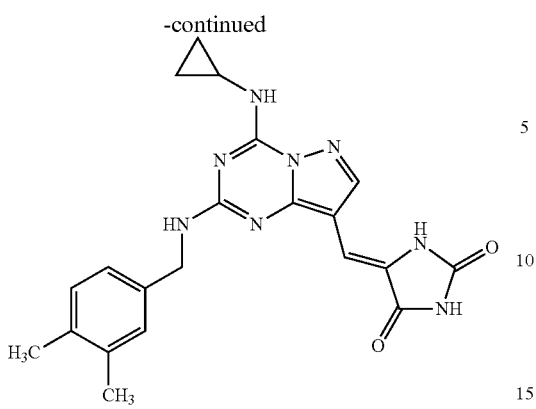

A solution of (3,4-dimethylphenyl)methanamine in NMP (106 µl, 0.4 M, 1.5 eq, 0.042 mmol) was transferred in a glass reaction vial. A solution of a (1:1) mixture of (Z)-5-((4-(cyclopropylamino)-2-(methylsulfonyl)pyrazolo[1,5-a][1,3,5]triazin-8-yl)methylene)imidazolidine-2,4-dione and (Z)-5-((4-(cyclopropylamino)-2-(methylsulfinyl)pyrazolo[1,5-a][1,3,5]triazin-8-yl)methylene)imidazolidine-2,4-dione in NMP (100 µl, 0.282M, 1.0 eq, 0.0282 mmol) was added. The mixture was heated at 80° C. for 5 hours. NMP was added (0.7 ml) and the solution subjected to preparative HPLC purification. Genevac evaporation provided (Z)-5-((4-(cyclopropylamino)-2-(3,4-dimethylbenzylamino)pyrazolo[1,5-a][1,3,5]triazin-8-yl)methylene)imidazolidine-2,4-dione as a solid (5.8 mg). LCMS (ES):>85% pure, m/z 419 [M+H]+.

Example 224

Synthesis of (Z)-5-((4-(cyclopropylamino)-2-(1-(pyridin-2-yl)ethylamino)pyrazolo[1,5][1,3,53-triazin-8-yl)methylene]imidazolidine-2,4-dione.

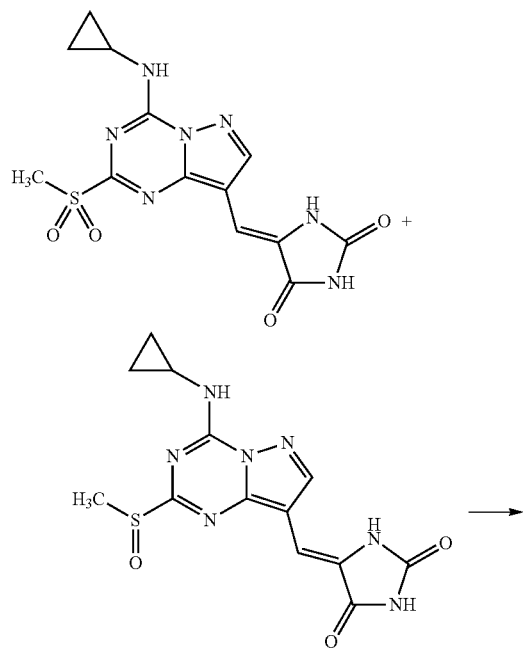

-continued

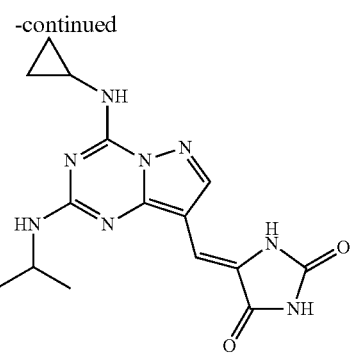

A (2:1) mixture of (Z)-5-((4-(cyclopropylamino)-2-(methylsulfonyl)pyrazolo[1,5-a][1,3,5]triazin-8-yl)methylene) imidazolidine-2,4-dione and (Z)-5-((4-(cyclopropylamino)-2-(methylsulfinyl)pyrazolo[1,5-a][1,3,5]triazin-8-yl) methylene)imidazolidine-2,4-dione (1.0 eq, 3.6 g, 10.08 mmol) was suspended in 2-propanol (40 ml). Rac-1-pyridinil-2-yl-ethylamine (2.0 eq, 2.47 g, 20.22 mmol) was added and the mixture stirred at 90° C. for 6.5 hours. The mixture was cooled down and the solid isolated by filtration. After drying in a vacuum oven, (Z)-5-((4-(cyclopropylamino)-2-(1-(pyridin-2-yl)ethylamino)pyrazolo[1,5-a][1,3,5]triazin-8-yl)methylene)imidazolidine-2,4-dione was isolated as a pale yellow solid (3.60 g, 88%). LCMS (ES):>95% pure, m/z 406 [M+H]+.

The compounds in the following table were prepared using procedures described in Example 223, Example 224, Example 199 and Example 200. When the amine reagent was used as a salt, a stoichiometric amount of DIEA was added to the reaction mixture. Table 37B shows the biological activities of the compounds listed in Table 37A.

TABLE 37A

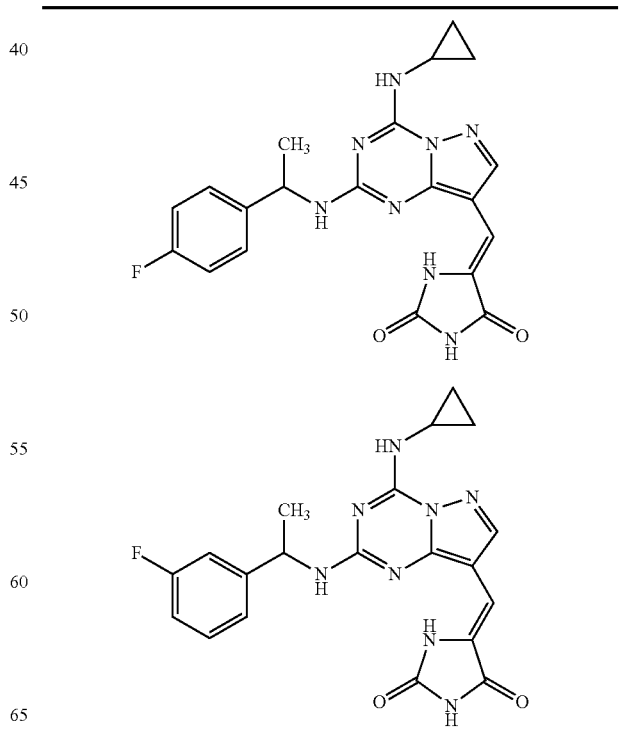

TABLE 37A-continued
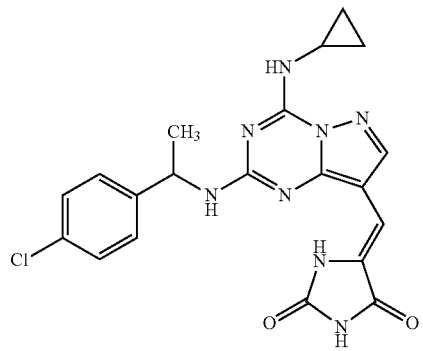 [SMILES: CC(Nc1nc(NC2CC2)n2ncc(/C=C3\NC(=O)NC3=O)c2n1)c1ccc(Cl)cc1]
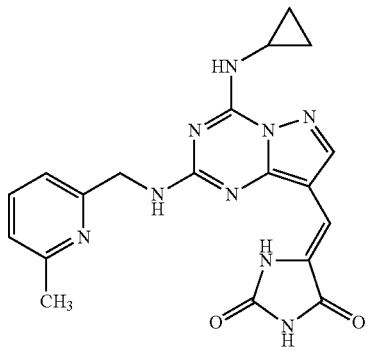
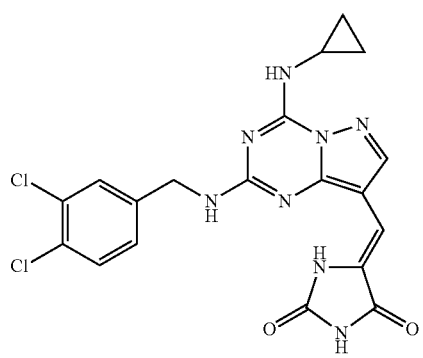 [SMILES: O=C1NC(=O)/C(=C/c2cnn3c(NC4CC4)nc(NCc4ccc(Cl)c(Cl)c4)nc23)N1]
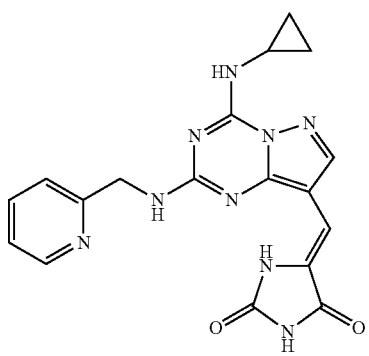
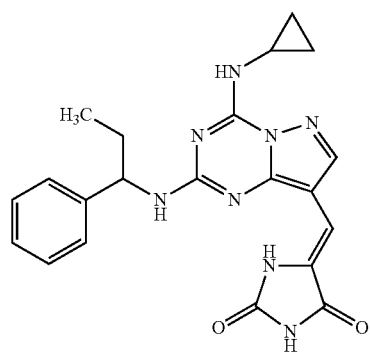 [SMILES: CCC(Nc1nc(NC2CC2)n2ncc(/C=C3\NC(=O)NC3=O)c2n1)c1ccccc1]
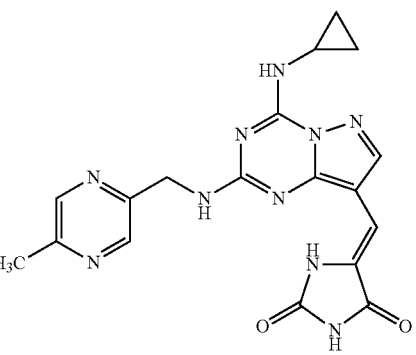
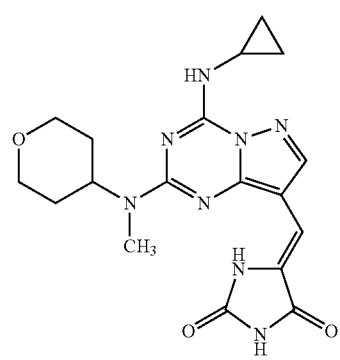 [SMILES: CN(c1nc(NC2CC2)n2ncc(/C=C3\NC(=O)NC3=O)c2n1)C1CCOCC1]
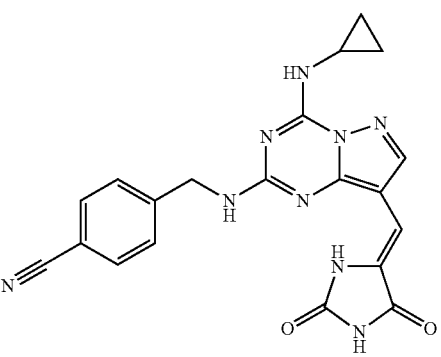 [SMILES: N#Cc1ccc(CNc2nc(NC3CC3)n3ncc(/C=C4\NC(=O)NC4=O)c3n2)cc1]

TABLE 37A-continued
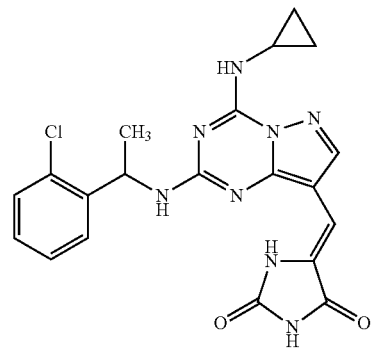 [SMILES: CC(Nc1nc(NC2CC2)n2ncc(/C=C3\NC(=O)NC3=O)c2n1)c1ccccc1Cl]
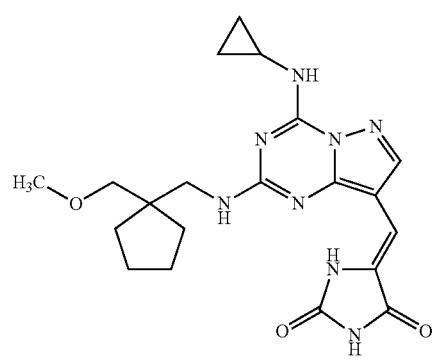 [SMILES: COCC1(CNc2nc(NC3CC3)n3ncc(/C=C4\NC(=O)NC4=O)c3n2)CCCC1]
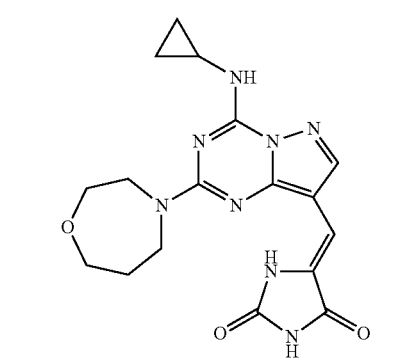 [SMILES: O=C1NC(=O)/C(=C/c2cnn3c(NC4CC4)nc(N4CCCOCC4)nc23)N1]
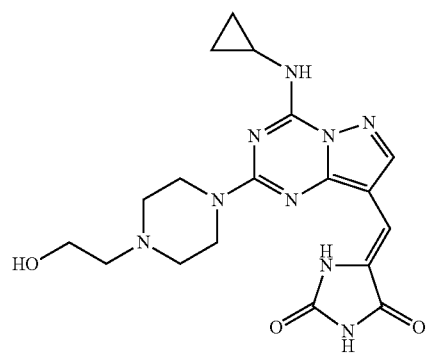 [SMILES: O=C1NC(=O)/C(=C/c2cnn3c(NC4CC4)nc(N4CCN(CCO)CC4)nc23)N1]
TABLE 37A-continued
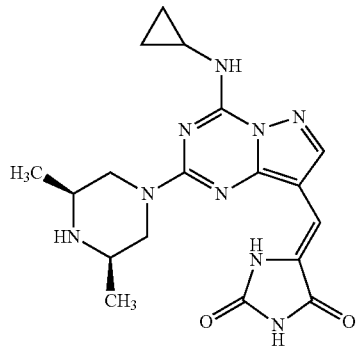 [SMILES: C[C@@H]1CN(c2nc(NC3CC3)n3ncc(/C=C4\NC(=O)NC4=O)c3n2)C[C@H](C)N1]
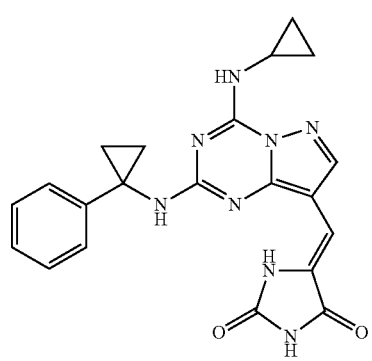 [SMILES: O=C1NC(=O)/C(=C/c2cnn3c(NC4CC4)nc(NC4(c5ccccc5)CC4)nc23)N1]
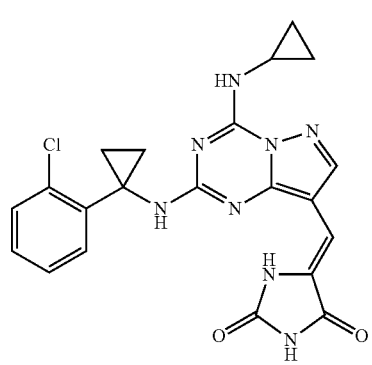 [SMILES: O=C1NC(=O)/C(=C/c2cnn3c(NC4CC4)nc(NC4(c5ccccc5Cl)CC4)nc23)N1]
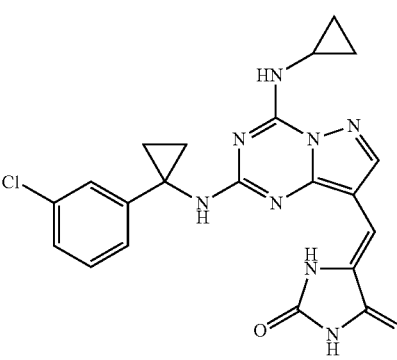

TABLE 37A-continued
| 381 | 382 |
|---|---|
| 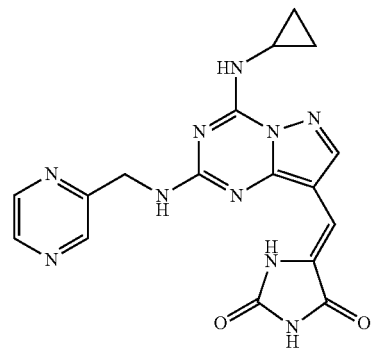 [SMILES: O=C1NC(=O)/C(=C/c2cnn3c(NC4CC4)nc(NCc4cnccn4)nc23)N1] | 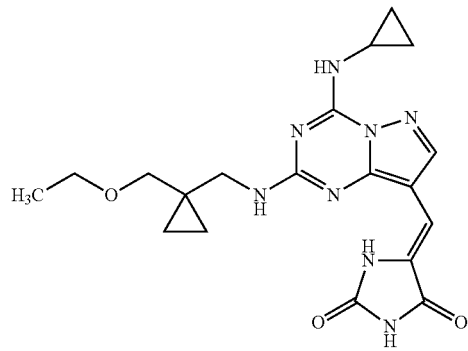 |
| 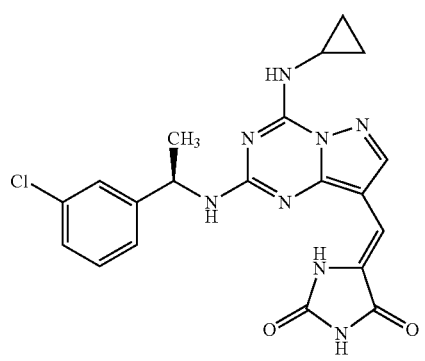 [SMILES: C[C@@H](Nc1nc(NC2CC2)n2ncc(/C=C3\NC(=O)NC3=O)c2n1)c1cccc(Cl)c1] | 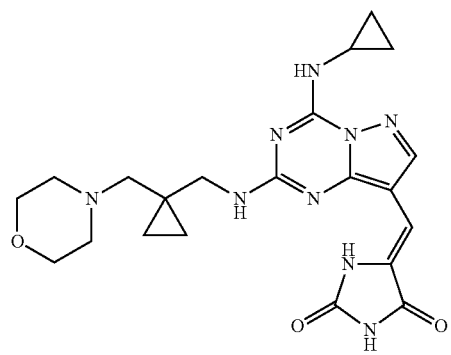 |
| 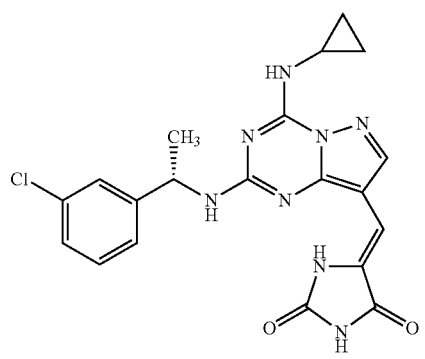 | 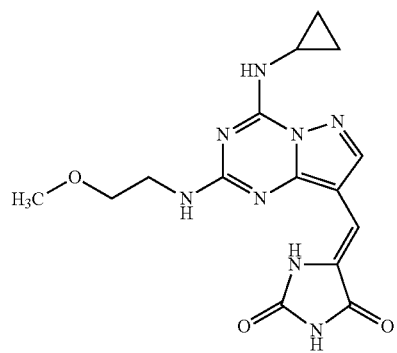 |
| 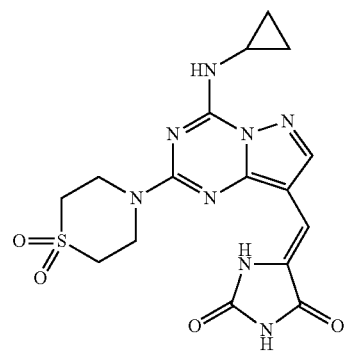 [SMILES: O=C1NC(=O)/C(=C/c2cnn3c(NC4CC4)nc(N4CCS(=O)(=O)CC4)nc23)N1] | 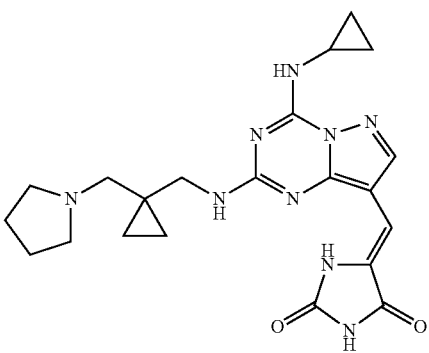 [SMILES: O=C1NC(=O)/C(=C/c2cnn3c(NC4CC4)nc(NCC4(CN5CCCC5)CC4)nc23)N1] |

TABLE 37A-continued
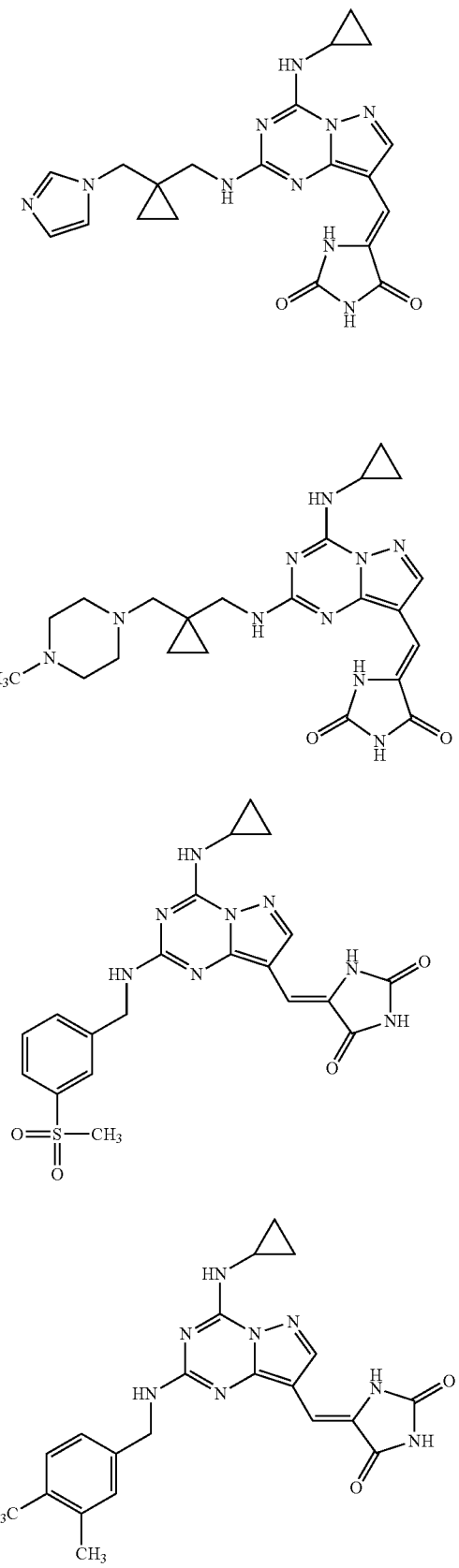
TABLE 37A-continued
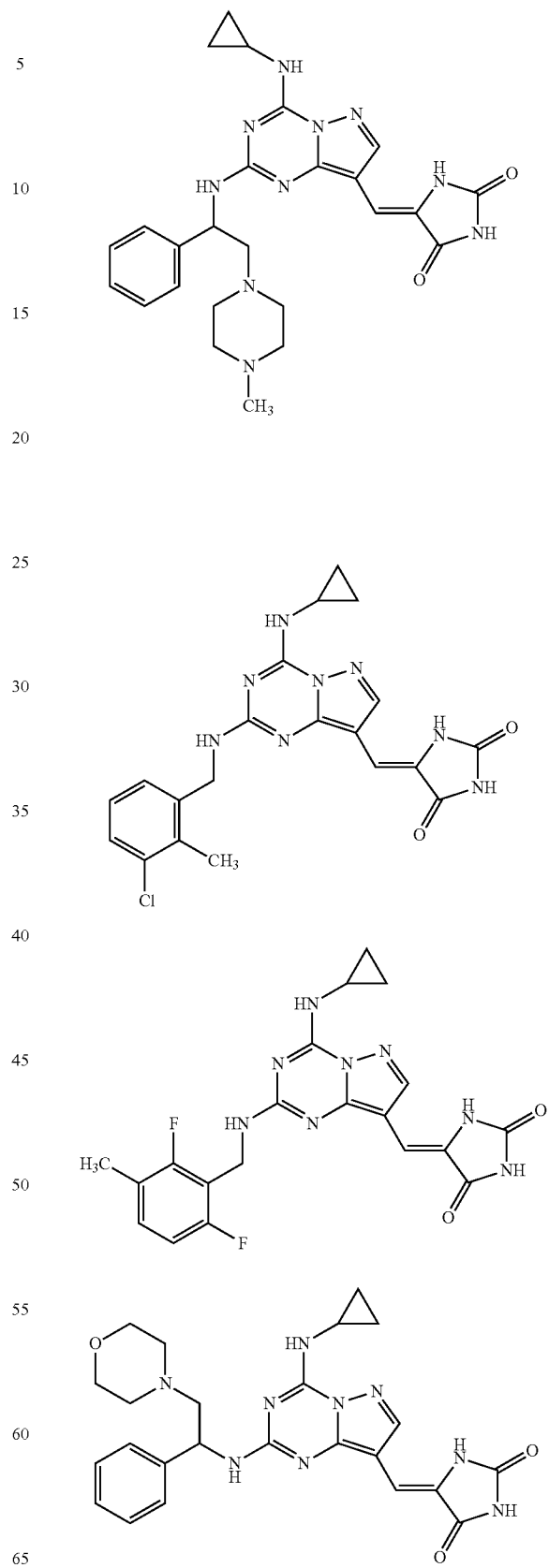

TABLE 37A-continued
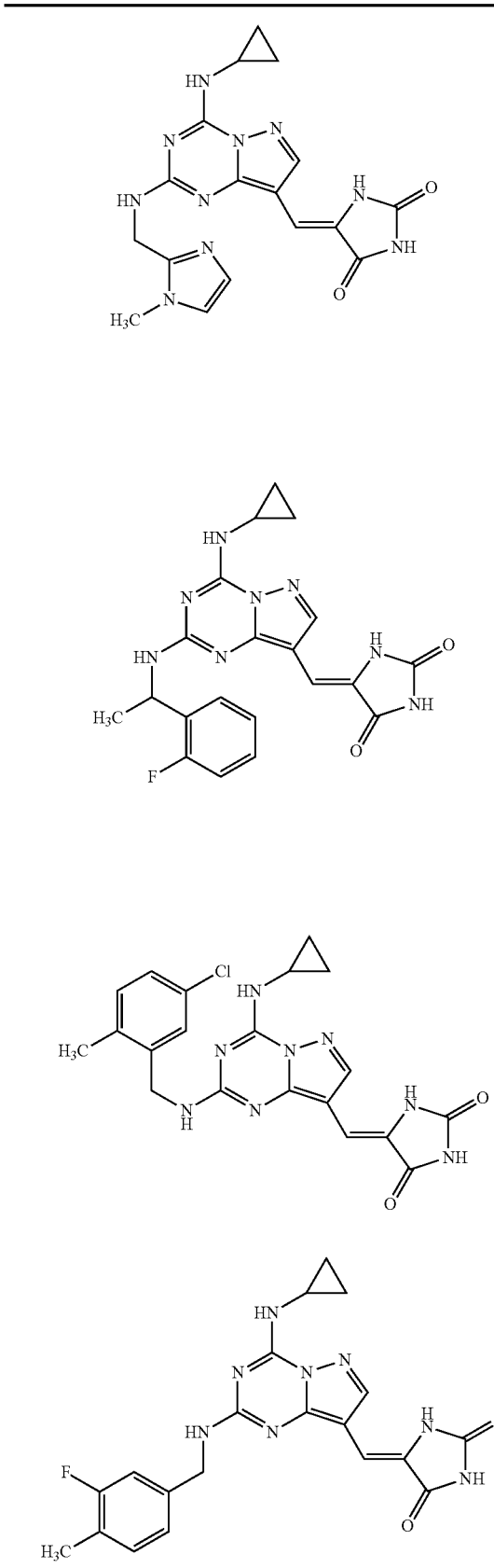
TABLE 37A-continued
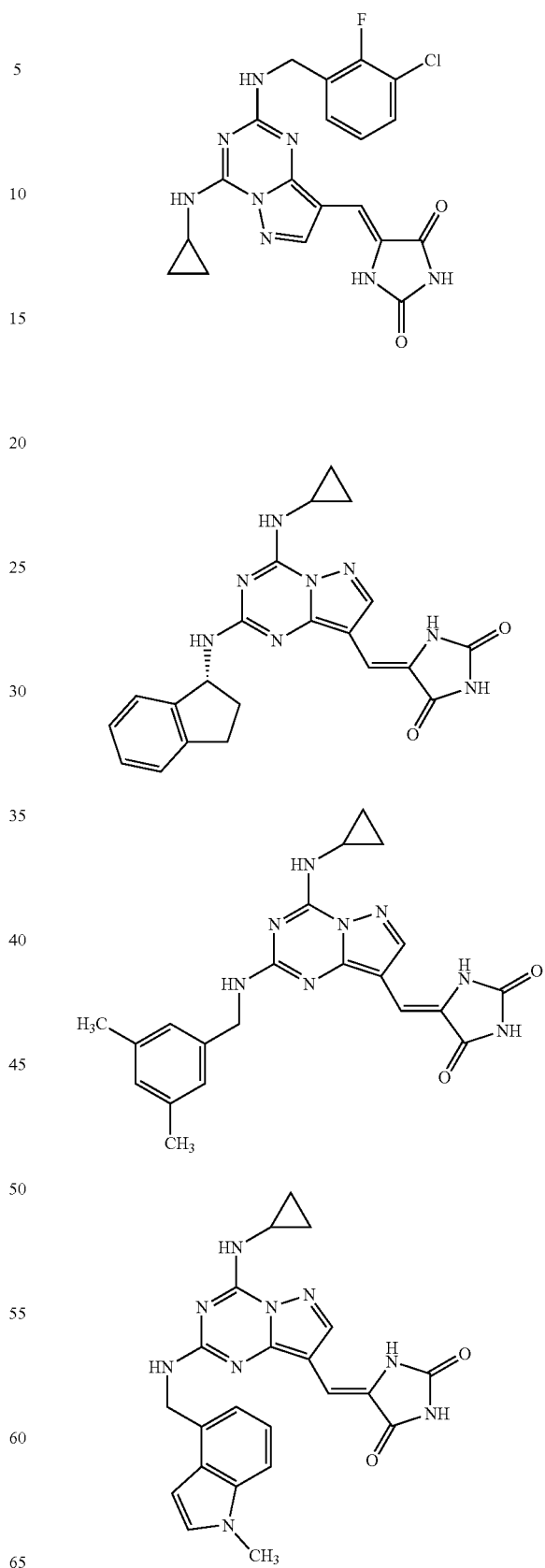

TABLE 37A-continued
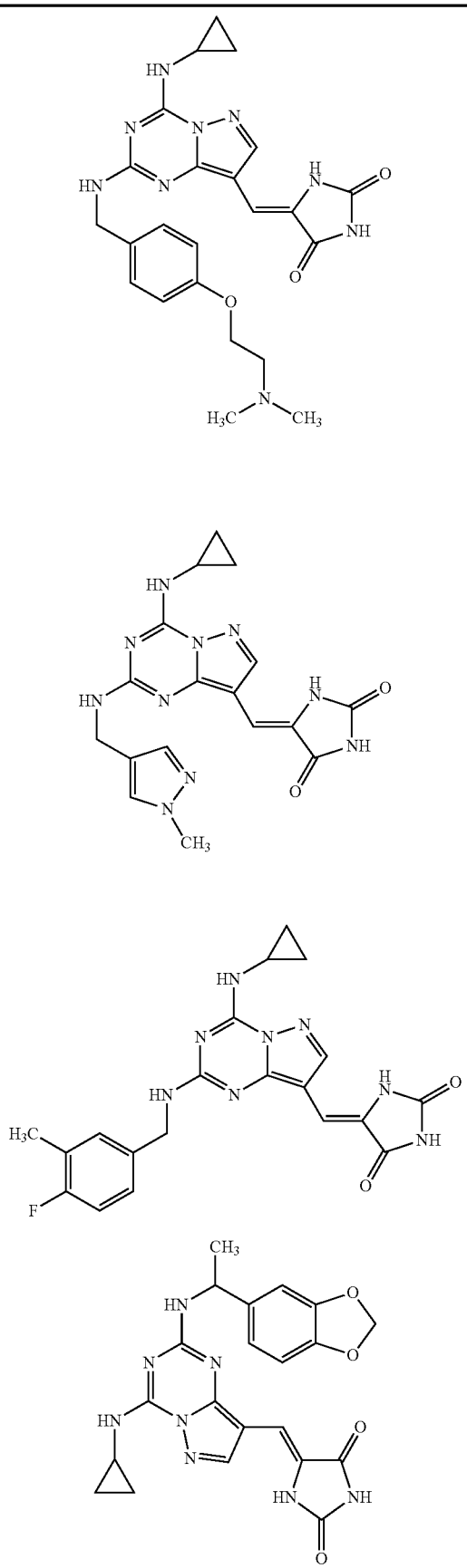
TABLE 37A-continued
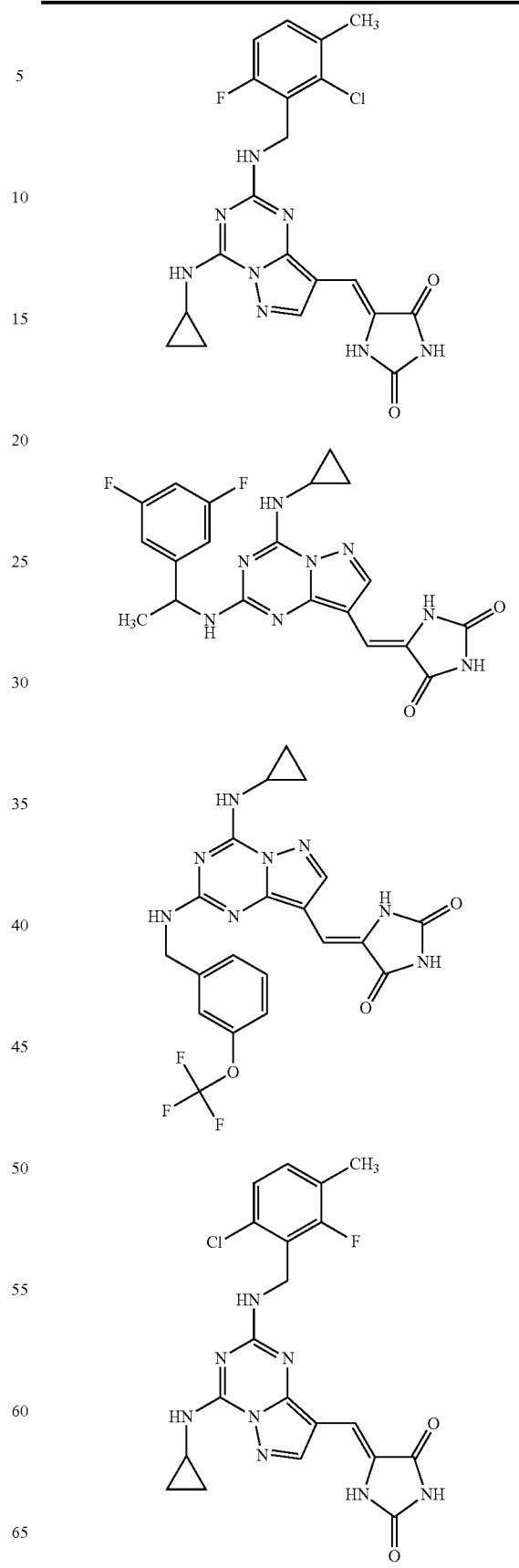

TABLE 37A-continued
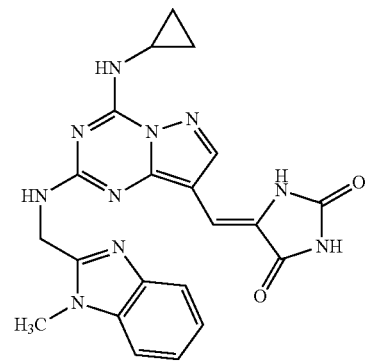 [SMILES: Cn1c(CNc2nc(NC3CC3)n3ncc(/C=C4\NC(=O)NC4=O)c3n2)nc2ccccc21]
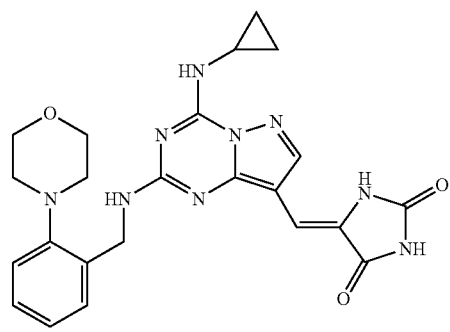 [SMILES: O=C1NC(=O)/C(=C/c2cnn3c(NC4CC4)nc(NCc4ccccc4N4CCOCC4)nc23)N1]
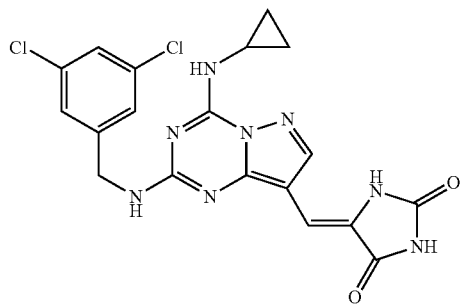 [SMILES: O=C1NC(=O)/C(=C/c2cnn3c(NC4CC4)nc(NCc4cc(Cl)cc(Cl)c4)nc23)N1]
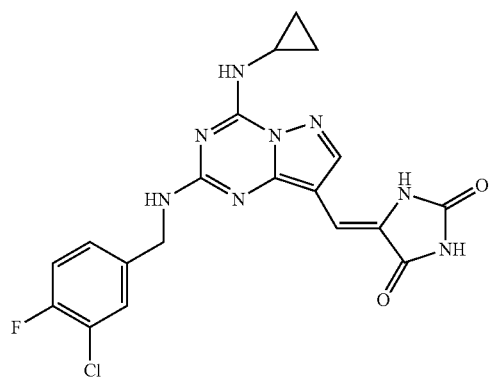 [SMILES: O=C1NC(=O)/C(=C/c2cnn3c(NC4CC4)nc(NCc4ccc(F)c(Cl)c4)nc23)N1]
TABLE 37A-continued
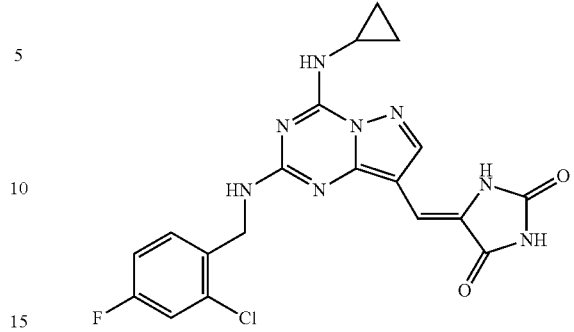
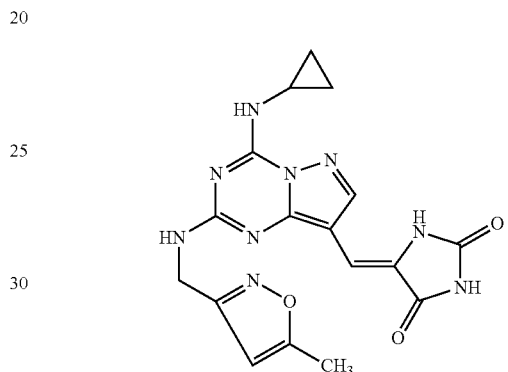
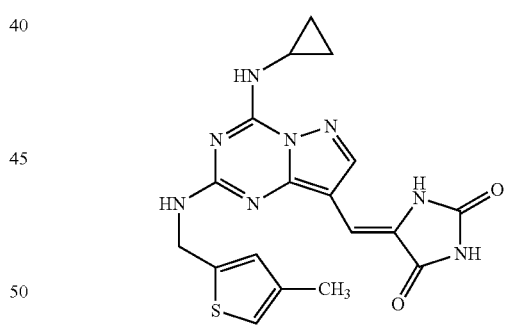
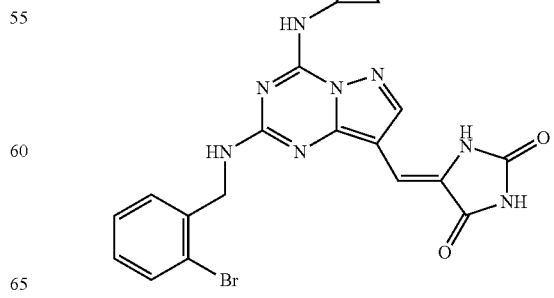

TABLE 37A-continued
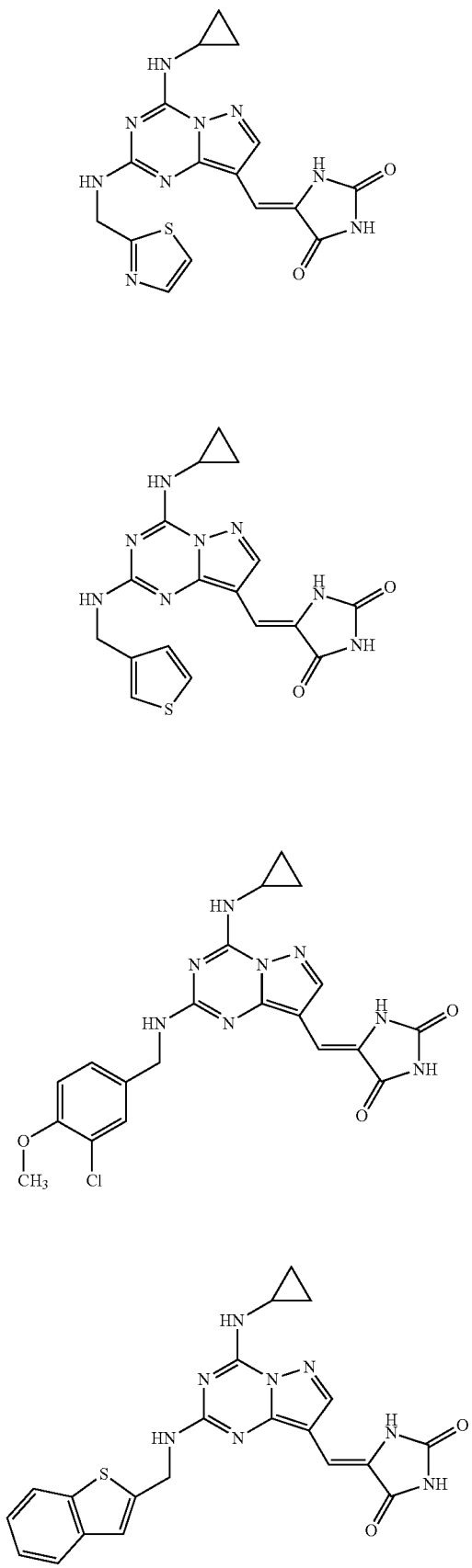
TABLE 37A-continued
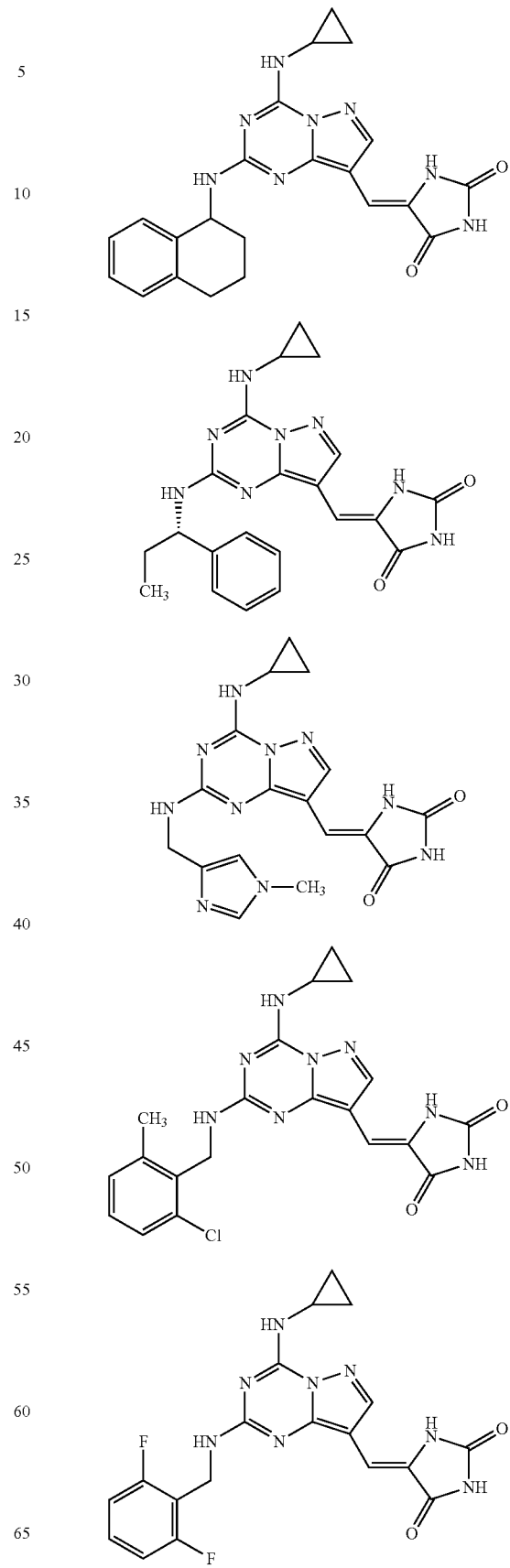

TABLE 37A-continued
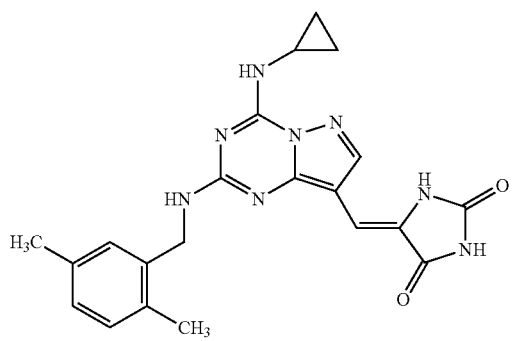 [SMILES: Cc1ccc(C)c(CNc2nc(NC3CC3)n3ncc(/C=C4\NC(=O)NC4=O)c3n2)c1]
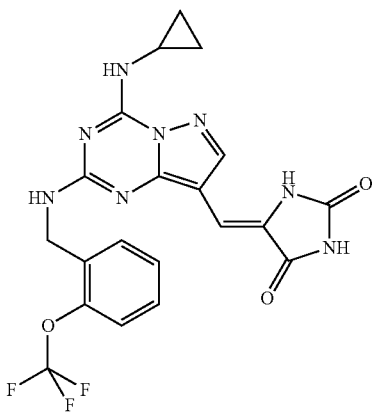 [SMILES: O=C1NC(=O)/C(=C/c2cnn3c(NC4CC4)nc(NCc4ccccc4OC(F)(F)F)nc23)N1]
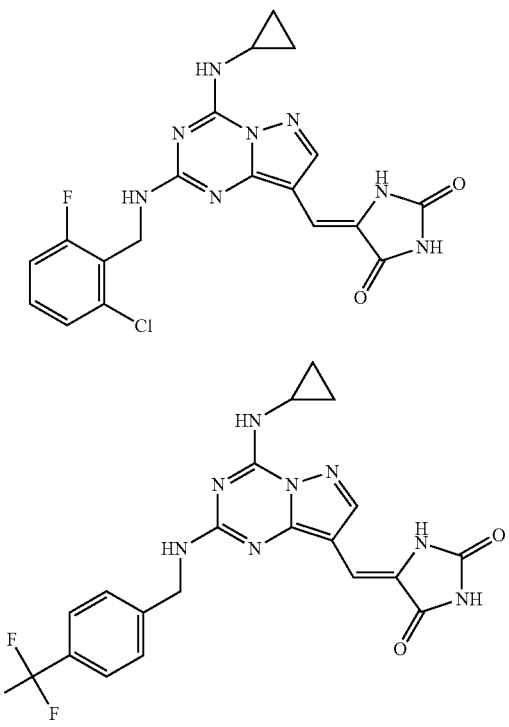
TABLE 37A-continued
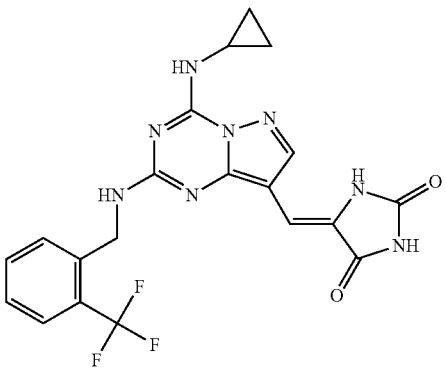 [SMILES: O=C1NC(=O)/C(=C/c2cnn3c(NC4CC4)nc(NCc4ccccc4C(F)(F)F)nc23)N1]
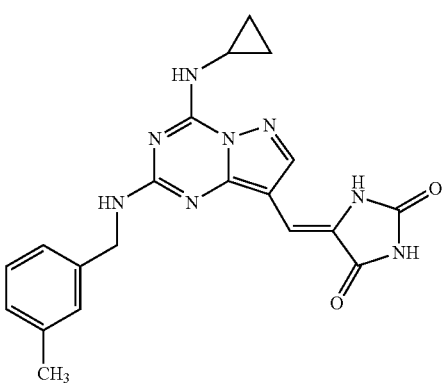 [SMILES: Cc1cccc(CNc2nc(NC3CC3)n3ncc(/C=C4\NC(=O)NC4=O)c3n2)c1]
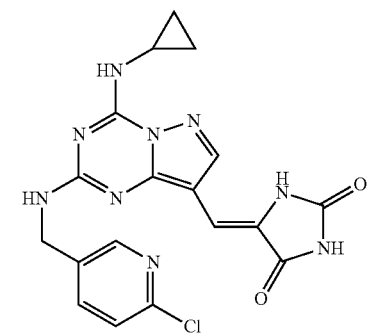 [SMILES: O=C1NC(=O)/C(=C/c2cnn3c(NC4CC4)nc(NCc4ccc(Cl)nc4)nc23)N1]
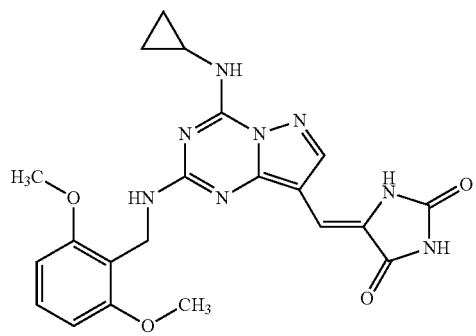 [SMILES: COc1cccc(OC)c1CNc1nc(NC2CC2)n2ncc(/C=C3\NC(=O)NC3=O)c2n1]

TABLE 37A-continued
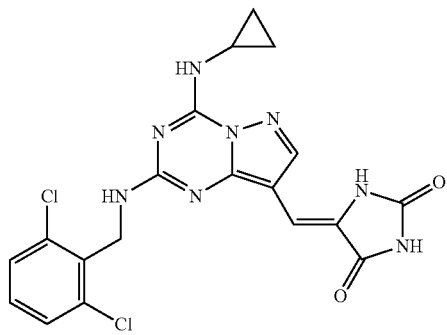
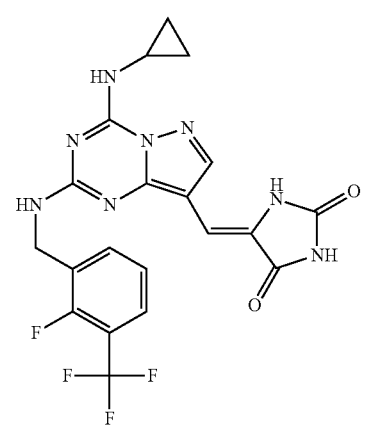 [SMILES: O=C1NC(=O)/C(=C/c2cnn3c(NC4CC4)nc(NCc4cccc(C(F)(F)F)c4F)nc23)N1]
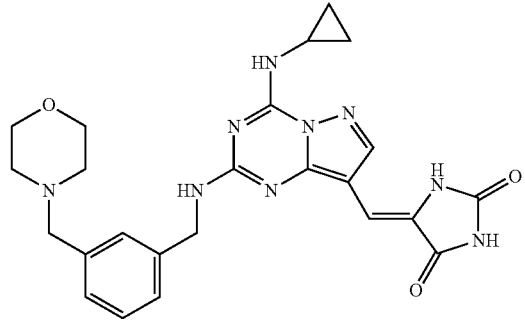 [SMILES: O=C1NC(=O)/C(=C/c2cnn3c(NC4CC4)nc(NCc4cccc(CN5CCOCC5)c4)nc23)N1]
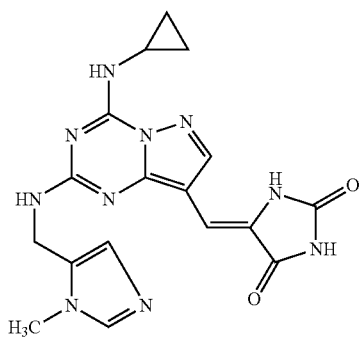 [SMILES: Cn1cncc1CNc1nc(NC2CC2)n2ncc(/C=C3\NC(=O)NC3=O)c2n1]
TABLE 37A-continued
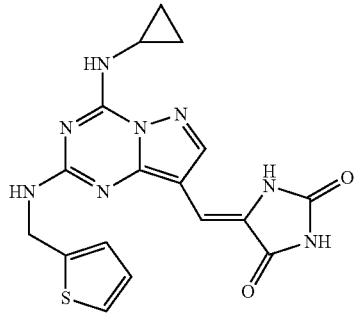 [SMILES: O=C1NC(=O)/C(=C/c2cnn3c(NC4CC4)nc(NCc4cccs4)nc23)N1]
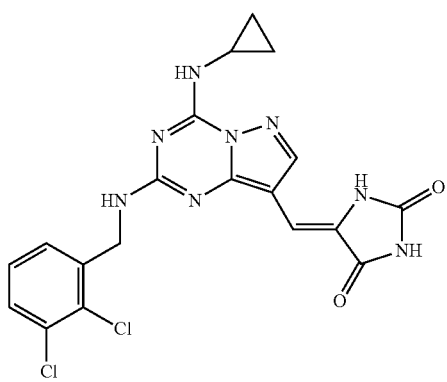 [SMILES: O=C1NC(=O)/C(=C/c2cnn3c(NC4CC4)nc(NCc4cccc(Cl)c4Cl)nc23)N1]
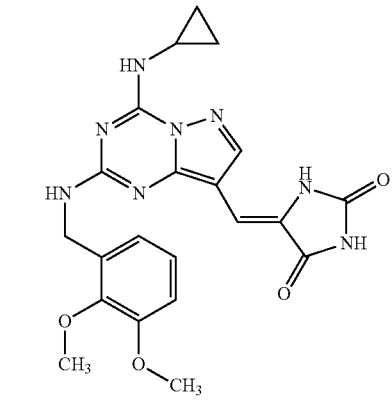 [SMILES: COc1cccc(CNc2nc(NC3CC3)n3ncc(/C=C4\NC(=O)NC4=O)c3n2)c1OC]
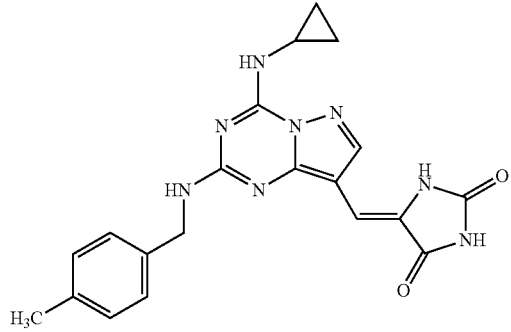 [SMILES: Cc1ccc(CNc2nc(NC3CC3)n3ncc(/C=C4\NC(=O)NC4=O)c3n2)cc1]

397
TABLE 37A-continued
398
TABLE 37A-continued
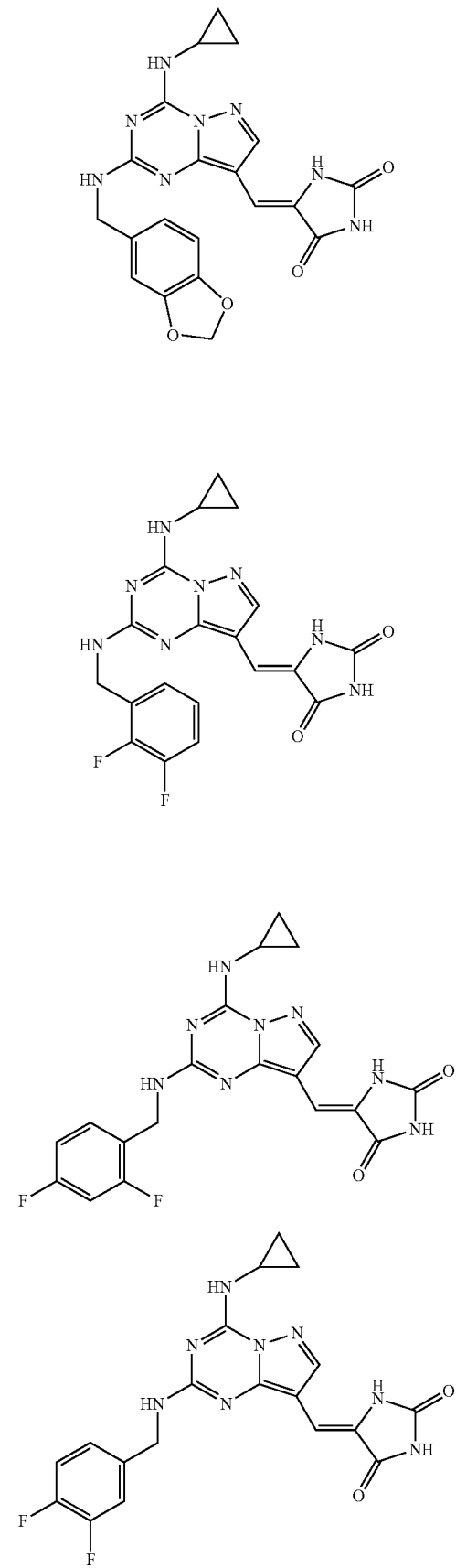
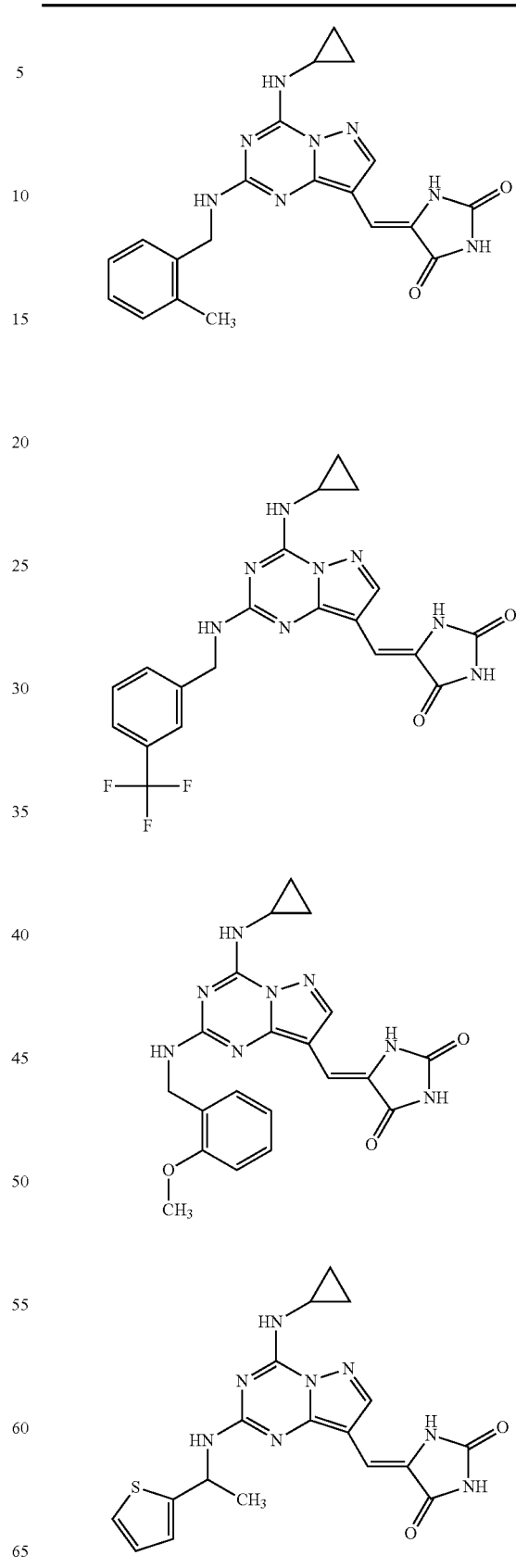

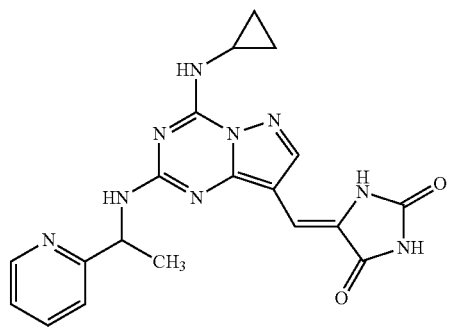 [SMILES: CC(Nc1nc(NC2CC2)n2ncc(/C=C3\NC(=O)NC3=O)c2n1)c1ccccn1]
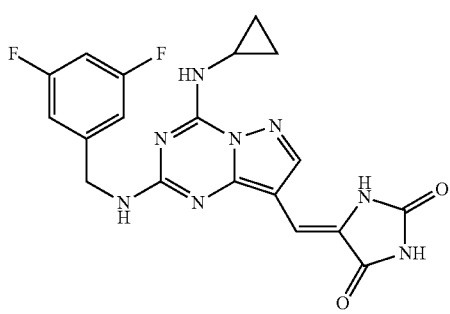 [SMILES: O=C1NC(=O)/C(=C/c2cnn3c(NC4CC4)nc(NCc4cc(F)cc(F)c4)nc23)N1]
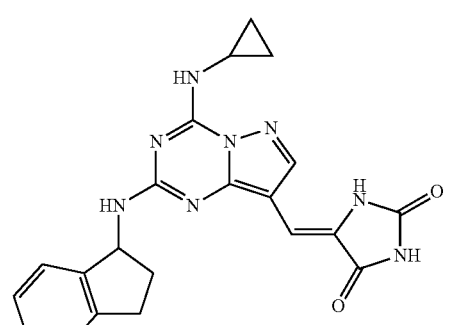
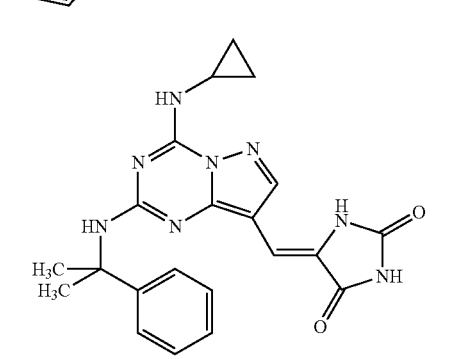
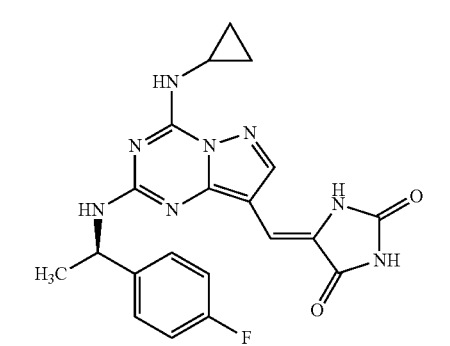 [SMILES: C[C@@H](Nc1nc(NC2CC2)n2ncc(/C=C3\NC(=O)NC3=O)c2n1)c1ccc(F)cc1]
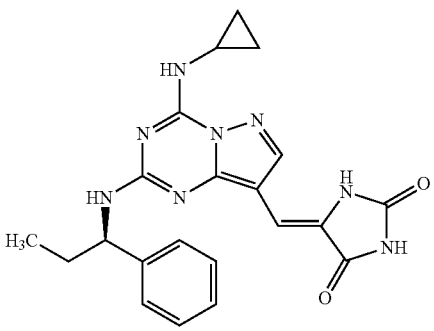 [SMILES: CC[C@@H](Nc1nc(NC2CC2)n2ncc(/C=C3\NC(=O)NC3=O)c2n1)c1ccccc1]
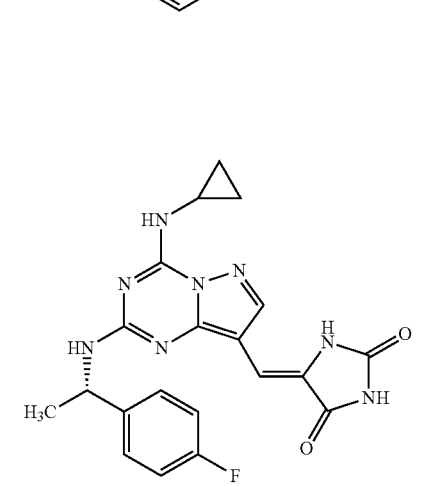
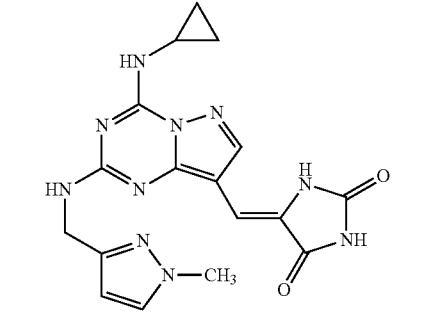 [SMILES: Cn1ccc(CNc2nc(NC3CC3)n3ncc(/C=C4\NC(=O)NC4=O)c3n2)n1]
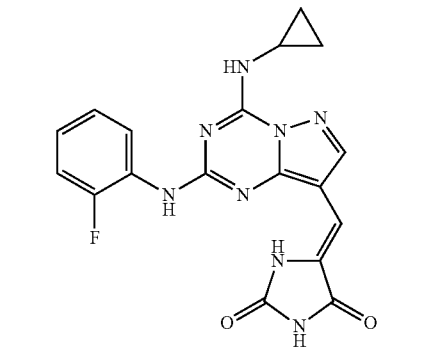

TABLE 37A-continued
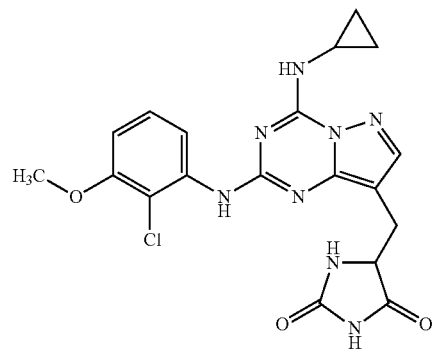 [SMILES: COc1cccc(Nc2nc(NC3CC3)n3ncc(CC4NC(=O)NC4=O)c3n2)c1Cl]
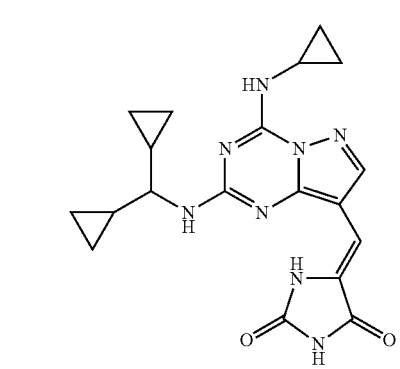 [SMILES: O=C1NC(=O)/C(=C/c2cnn3c(NC4CC4)nc(NC(C4CC4)C4CC4)nc23)N1]
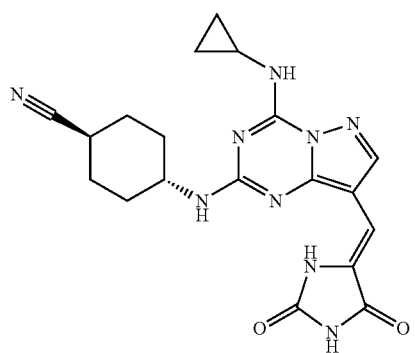 [SMILES: N#C[C@H]1CC[C@H](Nc2nc(NC3CC3)n3ncc(/C=C4\NC(=O)NC4=O)c3n2)CC1]
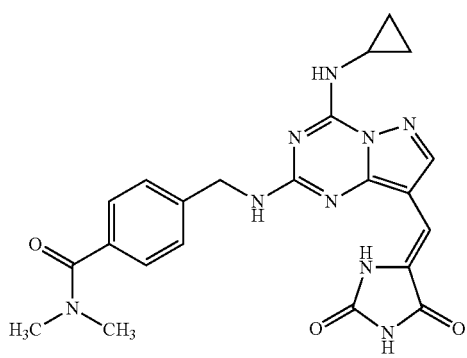 [SMILES: CN(C)C(=O)c1ccc(CNc2nc(NC3CC3)n3ncc(/C=C4\NC(=O)NC4=O)c3n2)cc1]
TABLE 37A-continued
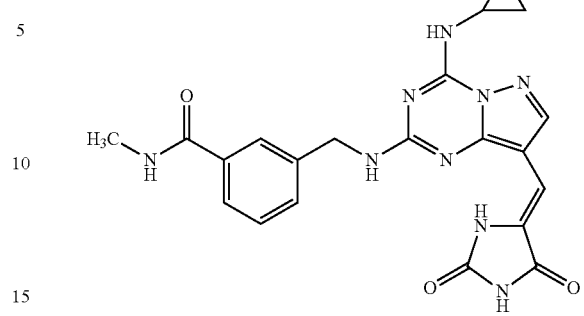
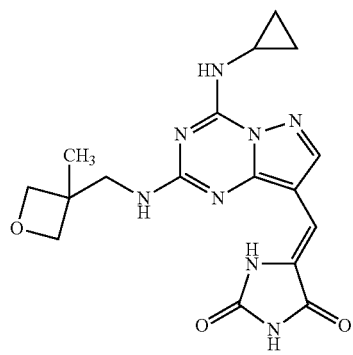 [SMILES: CC1(CNc2nc(NC3CC3)n3ncc(/C=C4\NC(=O)NC4=O)c3n2)COC1]
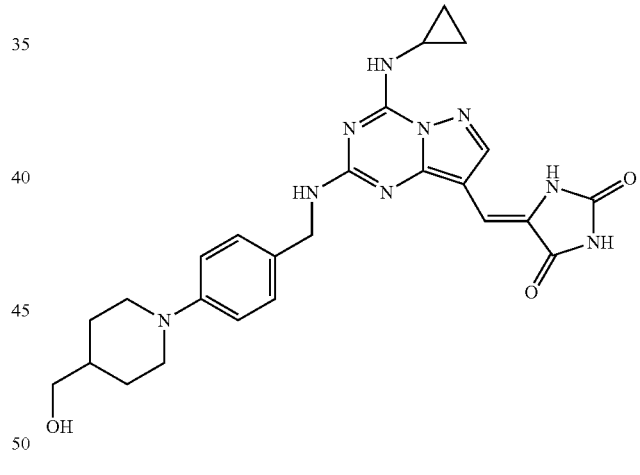

TABLE 37A-continued
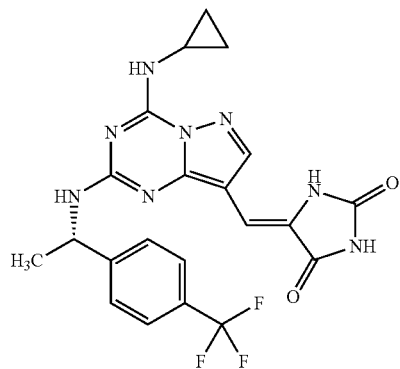 [SMILES: C[C@H](Nc1nc(NC2CC2)n2ncc(/C=C3\NC(=O)NC3=O)c2n1)c1ccc(C(F)(F)F)cc1]
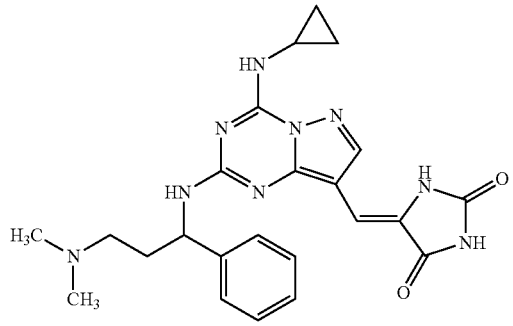
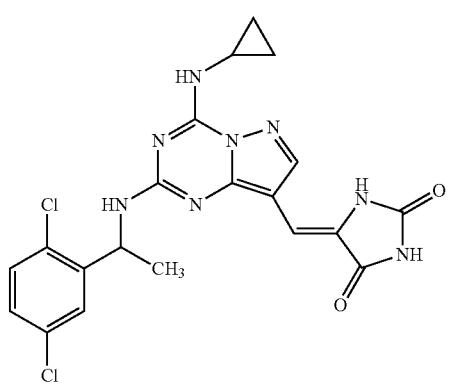 [SMILES: CC(Nc1nc(NC2CC2)n2ncc(/C=C3\NC(=O)NC3=O)c2n1)c1cc(Cl)ccc1Cl]
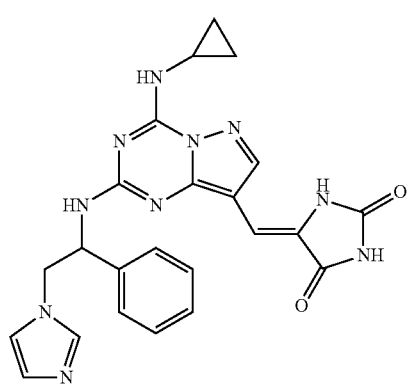
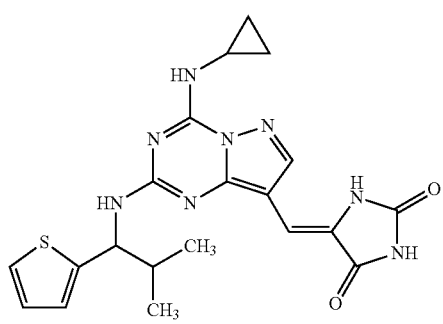 [SMILES: CC(C)C(Nc1nc(NC2CC2)n2ncc(/C=C3\NC(=O)NC3=O)c2n1)c1cccs1]
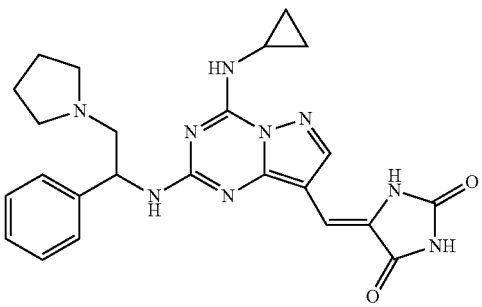
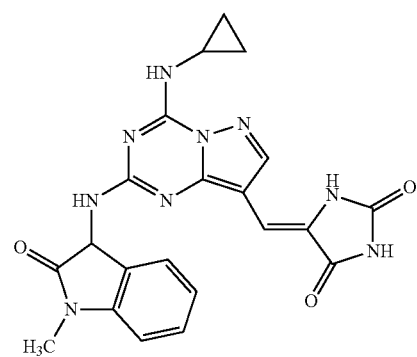 [SMILES: CN1C(=O)C(Nc2nc(NC3CC3)n3ncc(/C=C4\NC(=O)NC4=O)c3n2)c2ccccc21]
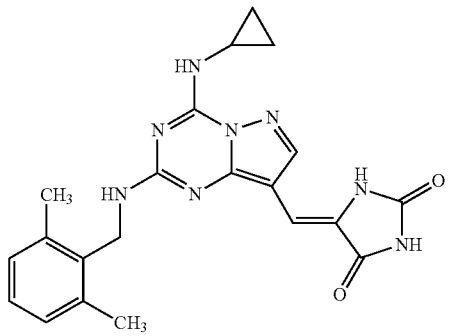 [SMILES: Cc1cccc(C)c1CNc1nc(NC2CC2)n2ncc(/C=C3\NC(=O)NC3=O)c2n1]

TABLE 37A-continued
405
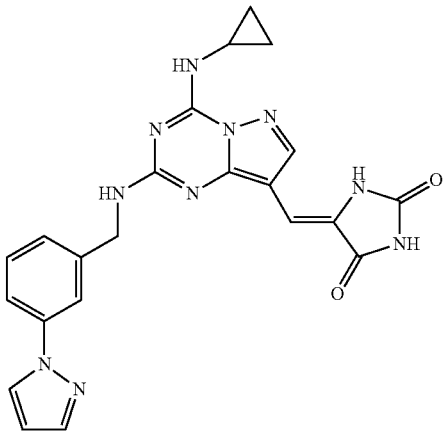 [SMILES: O=C1NC(=O)/C(=C/c2cnn3c(NC4CC4)nc(NCc4cccc(-n5cccn5)c4)nc23)N1]
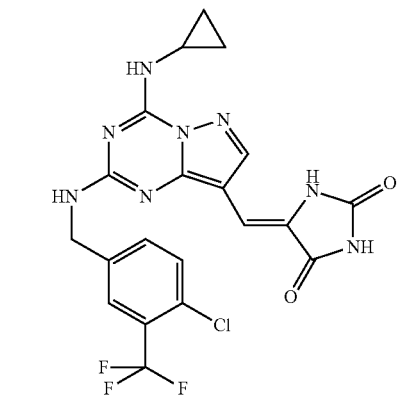 [SMILES: O=C1NC(=O)/C(=C/c2cnn3c(NC4CC4)nc(NCc4ccc(Cl)c(C(F)(F)F)c4)nc23)N1]
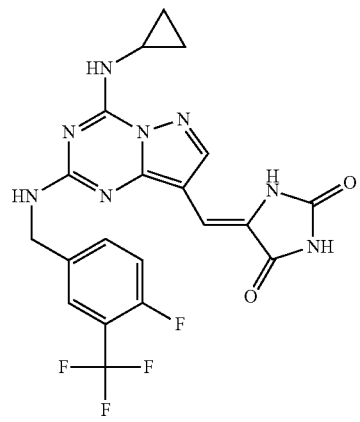 [SMILES: O=C1NC(=O)/C(=C/c2cnn3c(NC4CC4)nc(NCc4ccc(F)c(C(F)(F)F)c4)nc23)N1]
TABLE 37A-continued
406
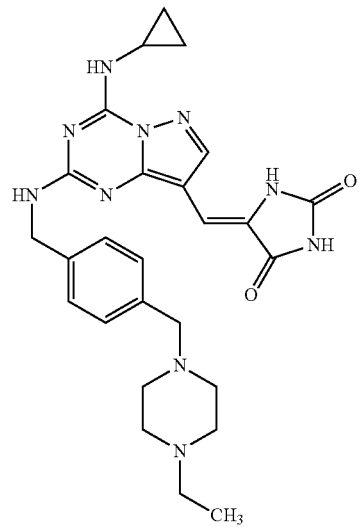 [SMILES: CCN1CCN(Cc2ccc(CNc3nc(NC4CC4)n4ncc(/C=C5\NC(=O)NC5=O)c4n3)cc2)CC1]
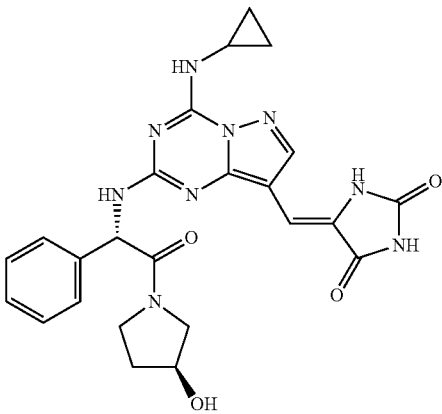 [SMILES: O=C1NC(=O)/C(=C/c2cnn3c(NC4CC4)nc(N[C@H](C(=O)N4CC[C@H](O)C4)c4ccccc4)nc23)N1]
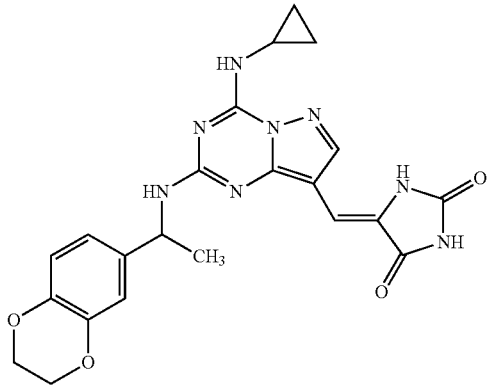 [SMILES: CC(Nc1nc(NC2CC2)n2ncc(/C=C3\NC(=O)NC3=O)c2n1)c1ccc2c(c1)OCCO2]

TABLE 37A-continued
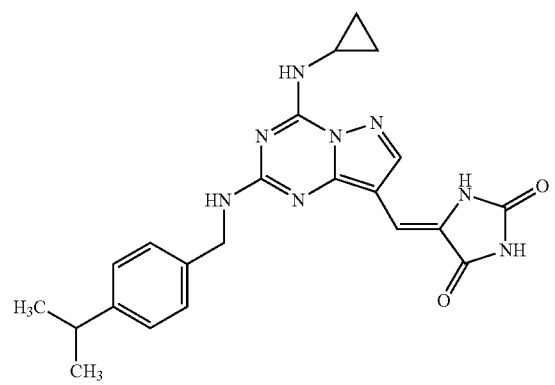 [SMILES: CC(C)c1ccc(CNc2nc(NC3CC3)n3ncc(/C=C4\NC(=O)NC4=O)c3n2)cc1]
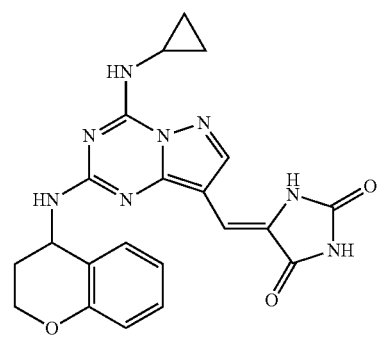 [SMILES: O=C1NC(=O)/C(=C/c2cnn3c(NC4CC4)nc(NC4CCOc5ccccc54)nc23)N1]
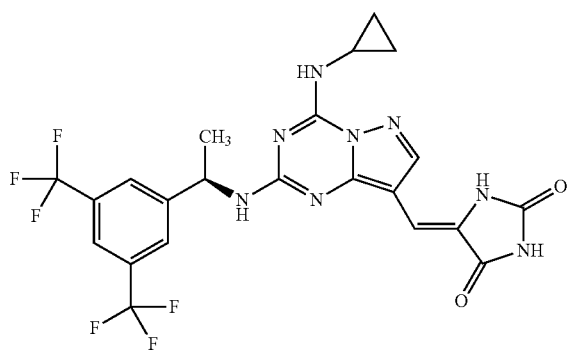 [SMILES: C[C@@H](Nc1nc(NC2CC2)n2ncc(/C=C3\NC(=O)NC3=O)c2n1)c1cc(C(F)(F)F)cc(C(F)(F)F)c1]
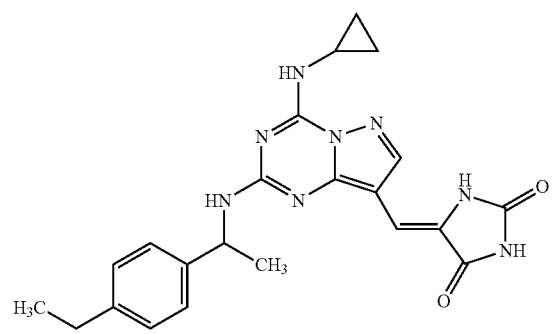 [SMILES: CCc1ccc(C(C)Nc2nc(NC3CC3)n3ncc(/C=C4\NC(=O)NC4=O)c3n2)cc1]
TABLE 37A-continued
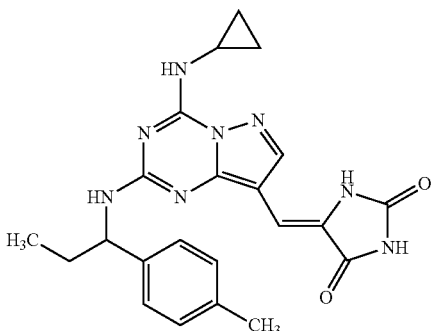
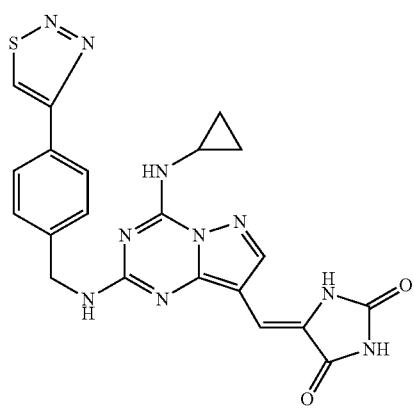 [SMILES: O=C1NC(=O)/C(=C/c2cnn3c(NC4CC4)nc(NCc4ccc(-c5csnn5)cc4)nc23)N1]
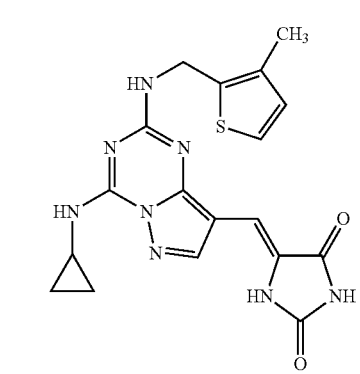 [SMILES: Cc1ccsc1CNc1nc(NC2CC2)n2ncc(/C=C3\NC(=O)NC3=O)c2n1]
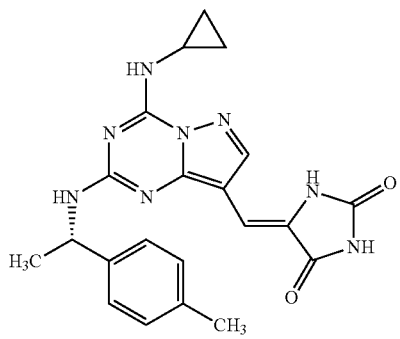 [SMILES: Cc1ccc([C@H](C)Nc2nc(NC3CC3)n3ncc(/C=C4\NC(=O)NC4=O)c3n2)cc1]

TABLE 37A-continued
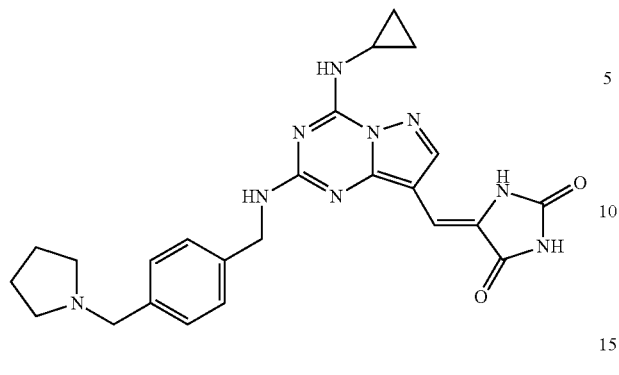
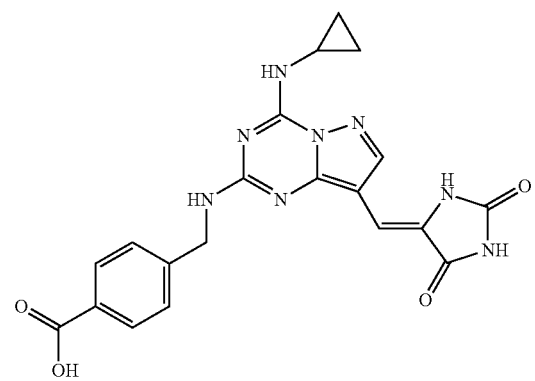 [SMILES: O=C1NC(=O)/C(=C/c2cnn3c(NC4CC4)nc(NCc4ccc(C(=O)O)cc4)nc23)N1]
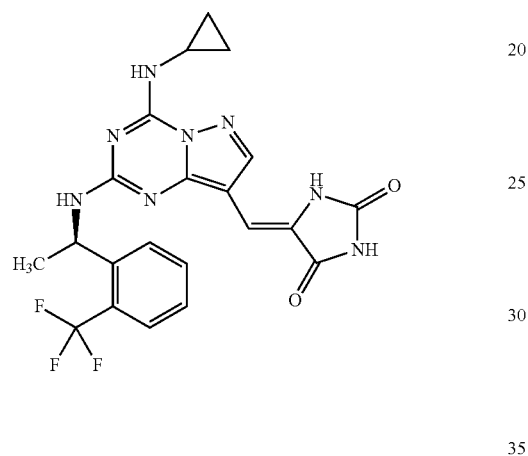
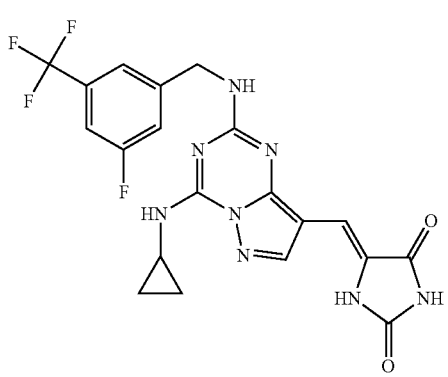 [SMILES: O=C1NC(=O)/C(=C/c2cnn3c(NC4CC4)nc(NCc4cc(F)cc(C(F)(F)F)c4)nc23)N1]
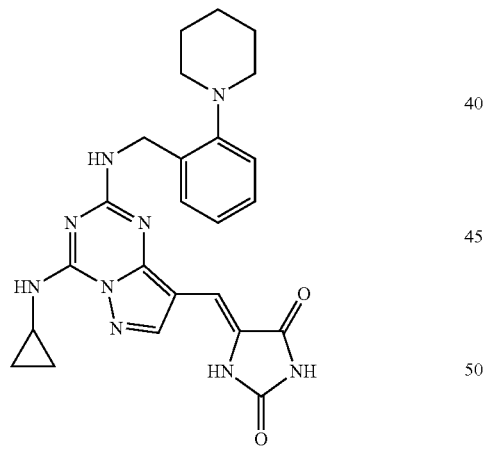
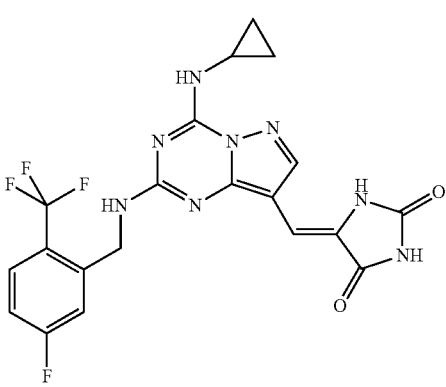 [SMILES: O=C1NC(=O)/C(=C/c2cnn3c(NC4CC4)nc(NCc4cc(F)ccc4C(F)(F)F)nc23)N1]
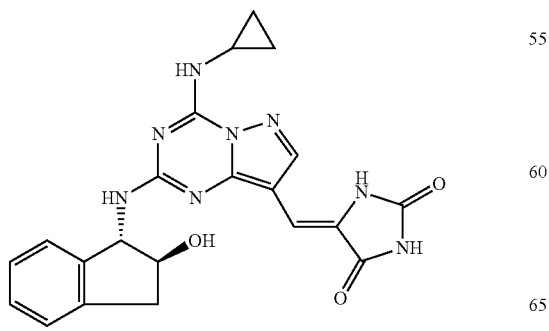
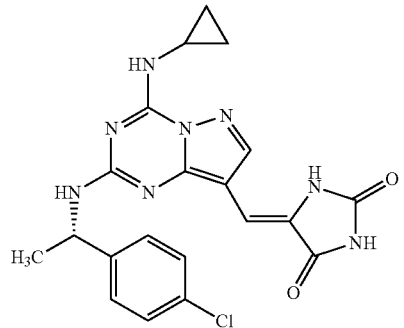 [SMILES: C[C@H](Nc1nc(NC2CC2)n2ncc(/C=C3\NC(=O)NC3=O)c2n1)c1ccc(Cl)cc1]

TABLE 37A-continued
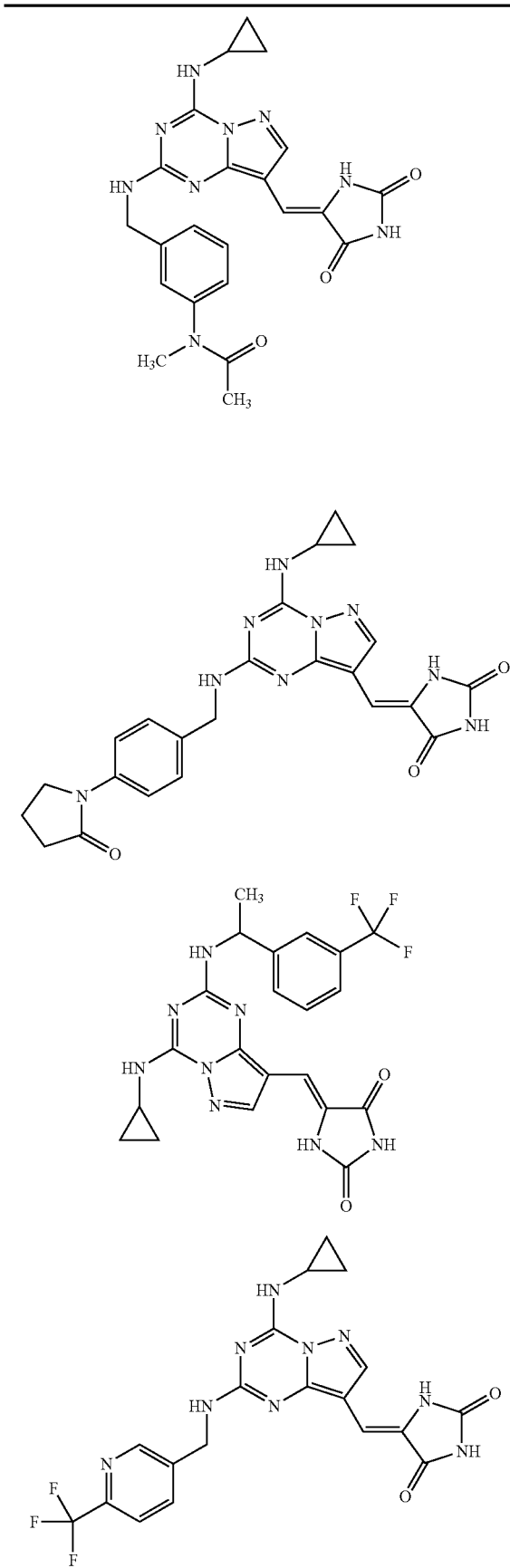
TABLE 37A-continued
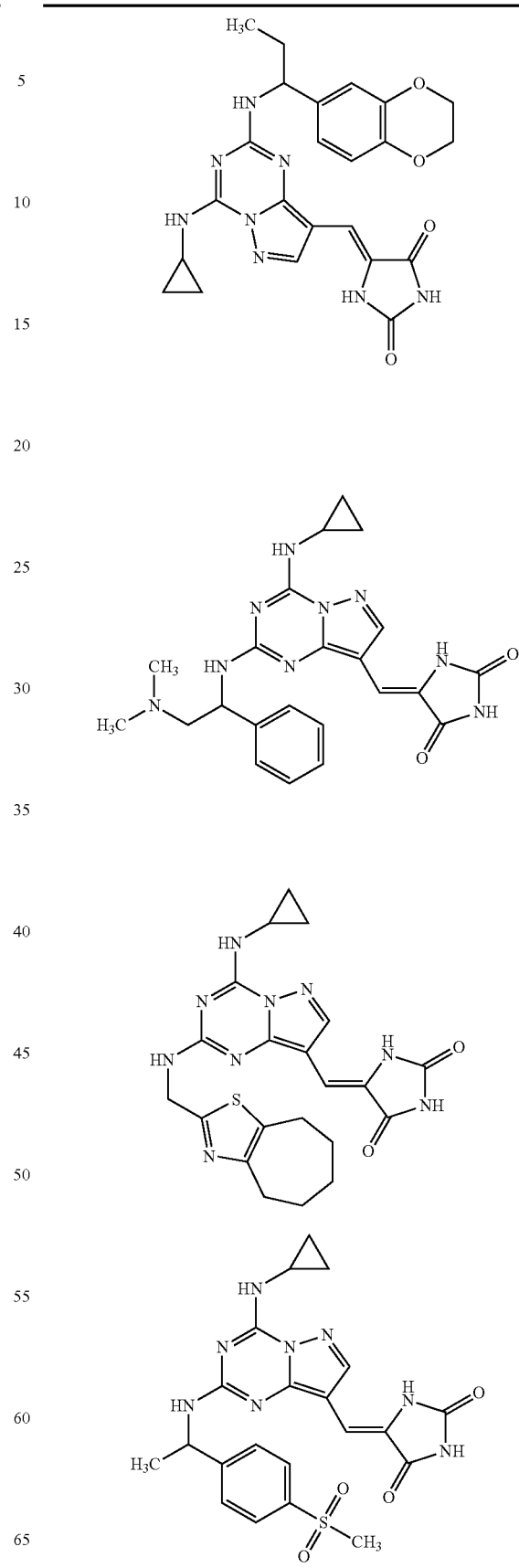

TABLE 37A-continued
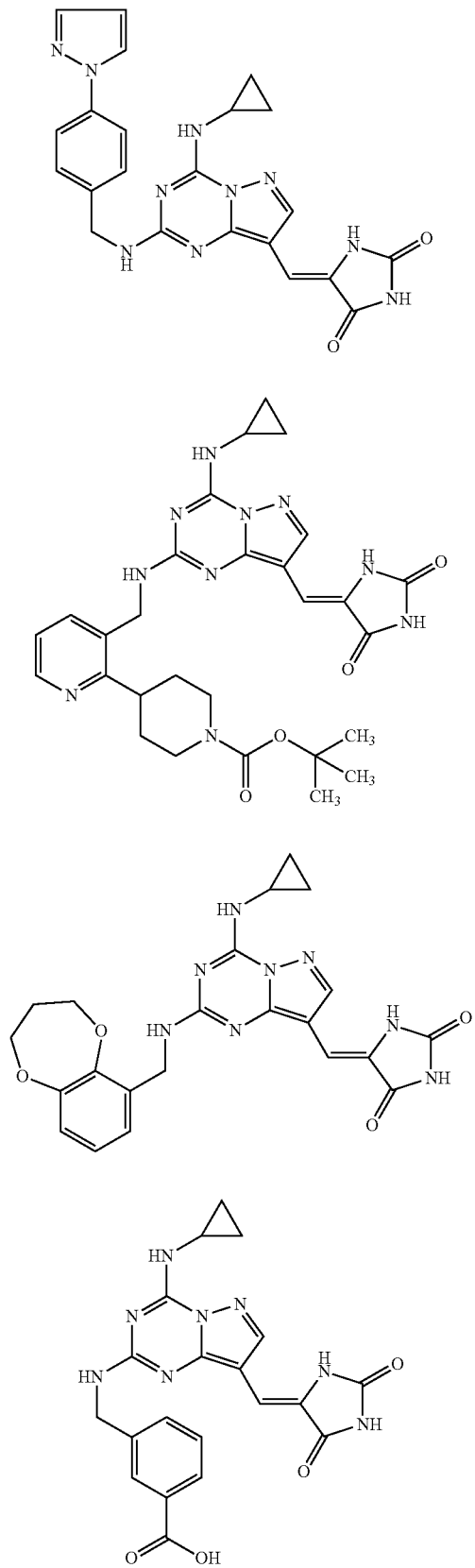
TABLE 37A-continued
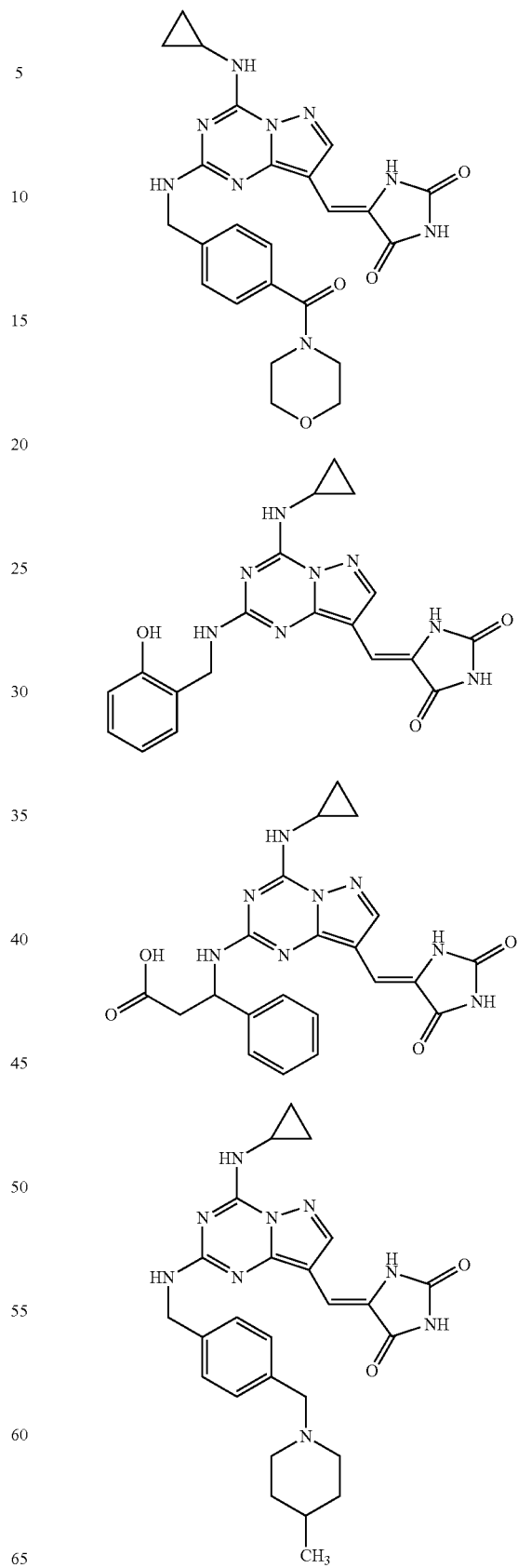

TABLE 37A-continued
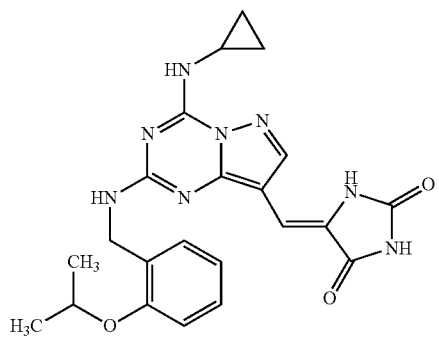 [SMILES: CC(C)Oc1ccccc1CNc1nc(NC2CC2)n2ncc(/C=C3\NC(=O)NC3=O)c2n1]
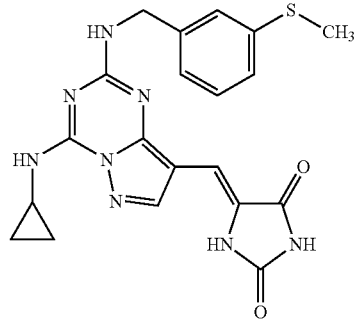
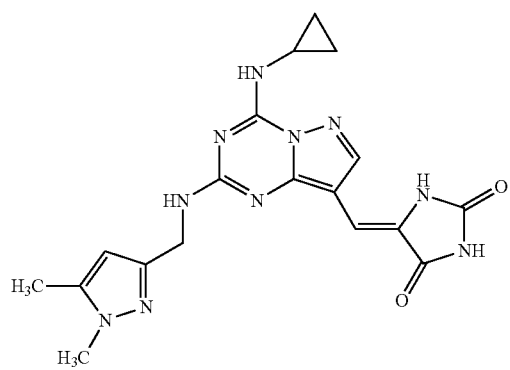 [SMILES: Cc1cc(CNc2nc(NC3CC3)n3ncc(/C=C4\NC(=O)NC4=O)c3n2)nn1C]
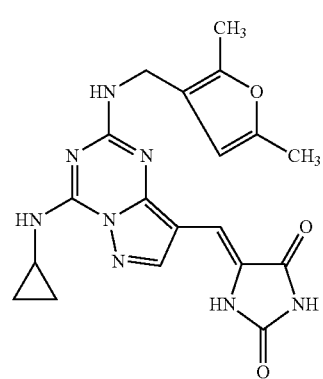
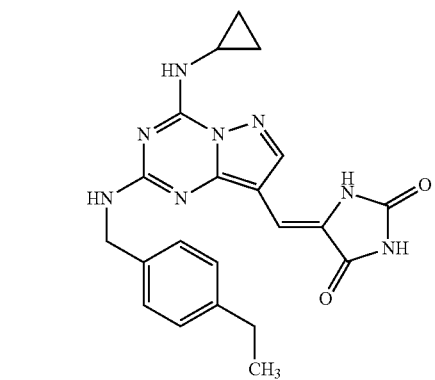 [SMILES: CCc1ccc(CNc2nc(NC3CC3)n3ncc(/C=C4\NC(=O)NC4=O)c3n2)cc1]
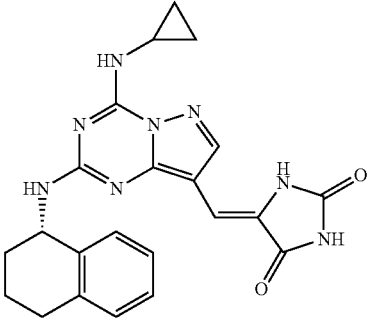
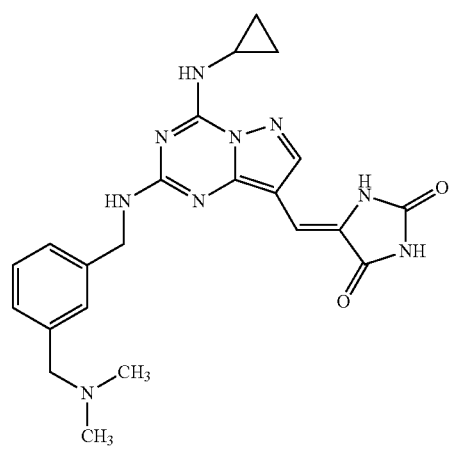 [SMILES: CN(C)Cc1cccc(CNc2nc(NC3CC3)n3ncc(/C=C4\NC(=O)NC4=O)c3n2)c1]
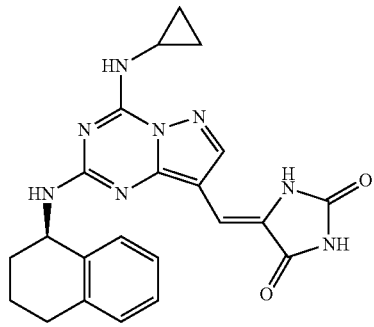 [SMILES: O=C1NC(=O)/C(=C/c2cnn3c(NC4CC4)nc(N[C@@H]4CCCc5ccccc54)nc23)N1]

TABLE 37A-continued
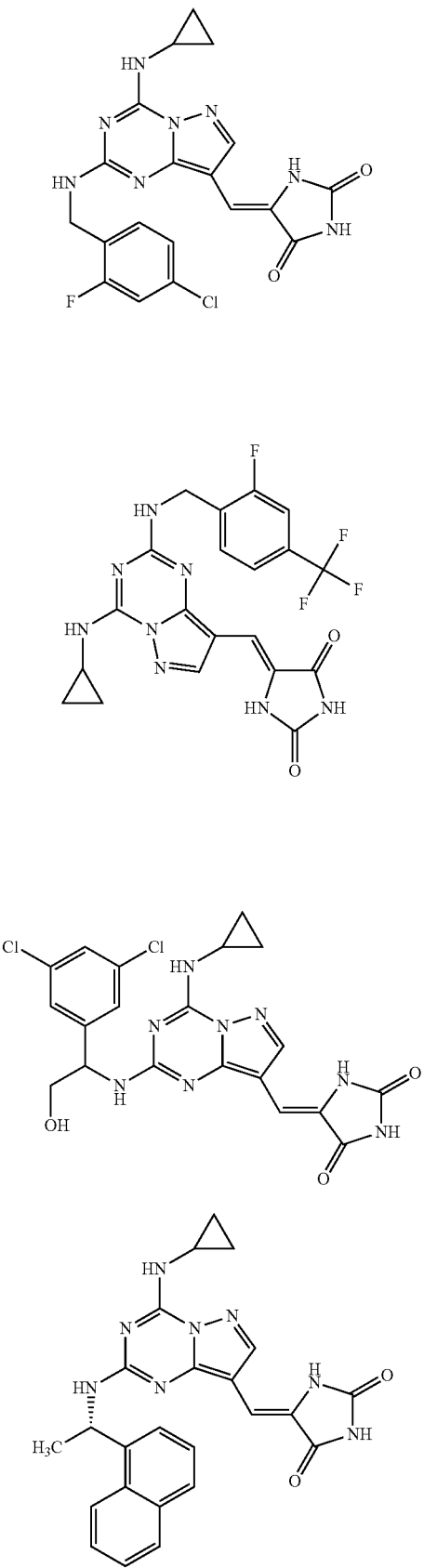
TABLE 37A-continued
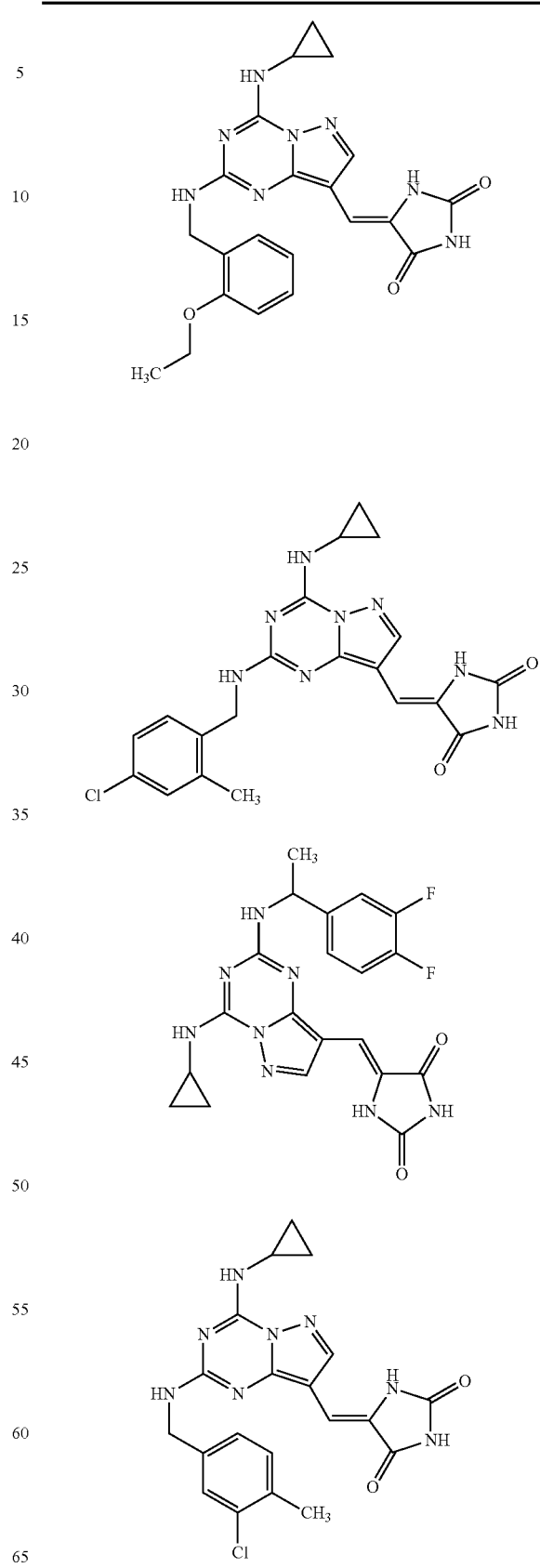

TABLE 37A-continued
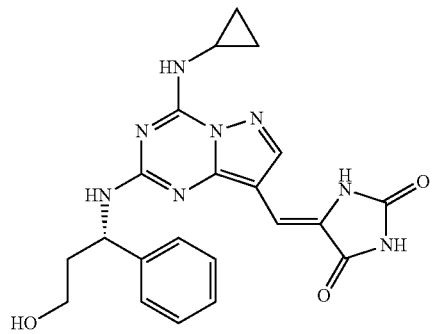
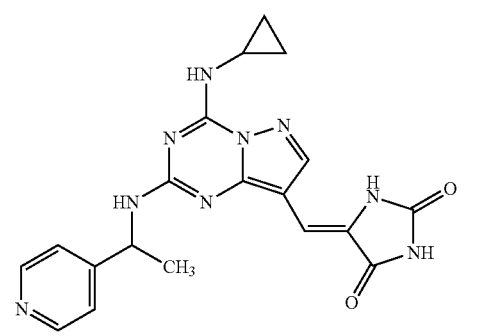 [SMILES: CC(Nc1nc(NC2CC2)n2ncc(/C=C3\NC(=O)NC3=O)c2n1)c1ccncc1]
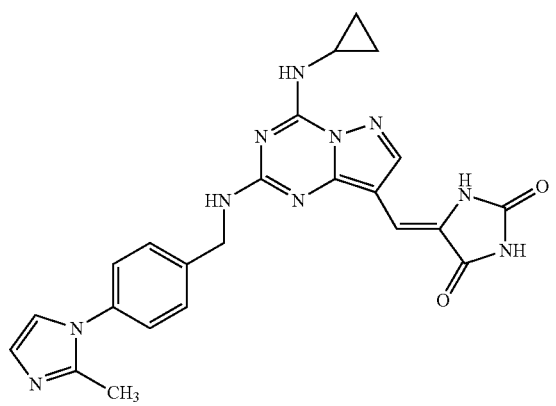 [SMILES: Cc1nccn1-c1ccc(CNc2nc(NC3CC3)n3ncc(/C=C4\NC(=O)NC4=O)c3n2)cc1]
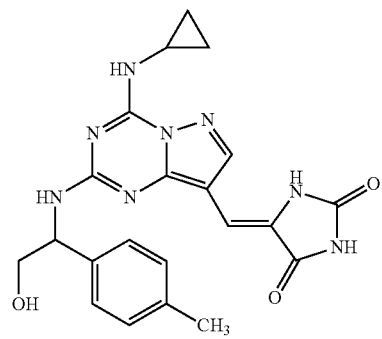 [SMILES: Cc1ccc(C(CO)Nc2nc(NC3CC3)n3ncc(/C=C4\NC(=O)NC4=O)c3n2)cc1]
TABLE 37A-continued
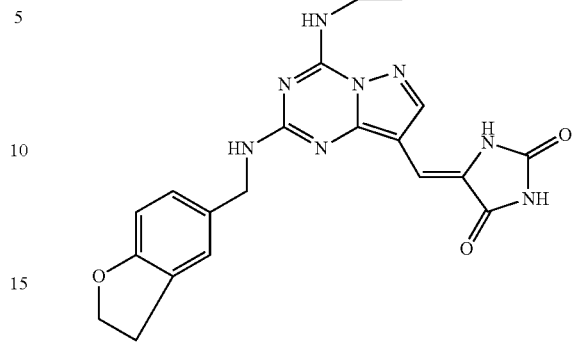
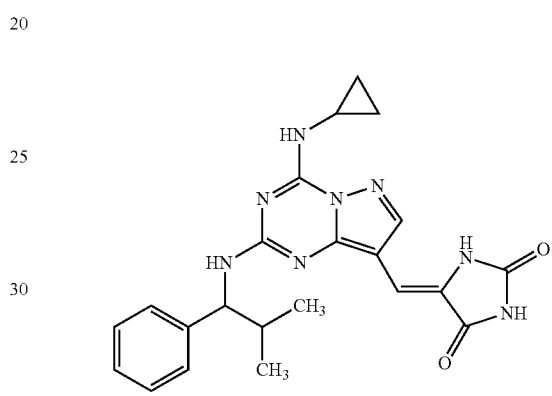
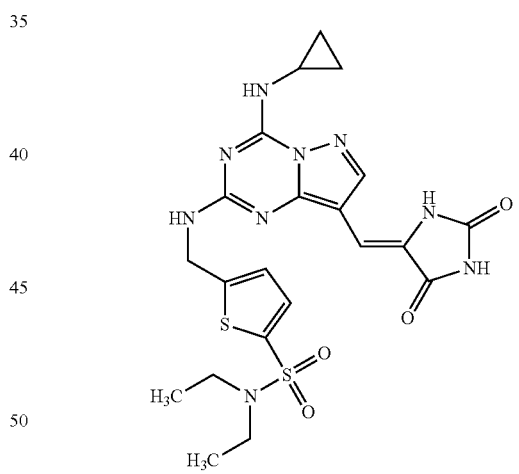
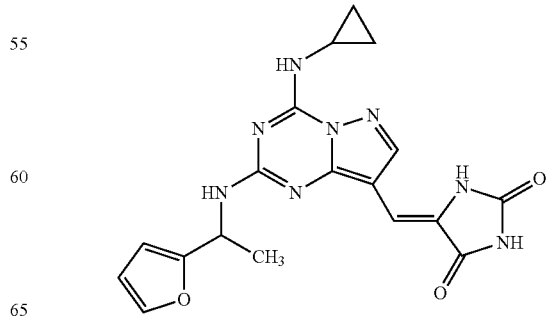

TABLE 37A-continued
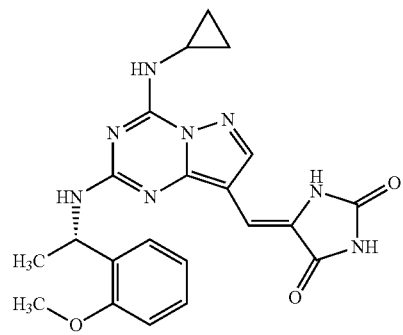 [SMILES: COc1ccccc1[C@H](C)Nc1nc(NC2CC2)n2ncc(/C=C3\NC(=O)NC3=O)c2n1]
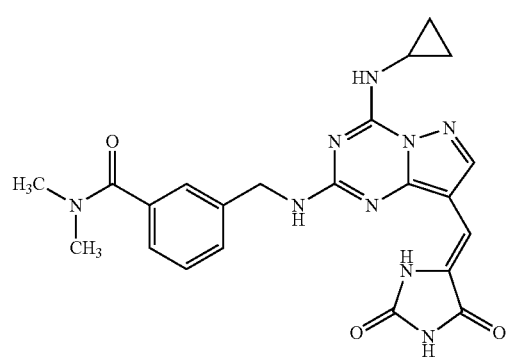 [SMILES: CN(C)C(=O)c1cccc(CNc2nc(NC3CC3)n3ncc(/C=C4\NC(=O)NC4=O)c3n2)c1]
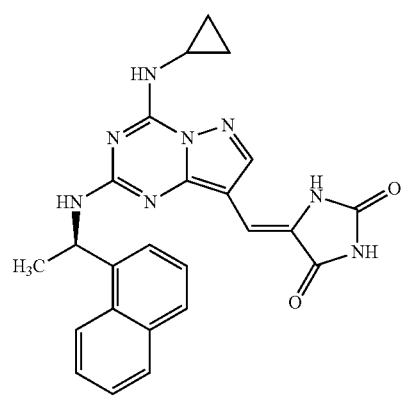 [SMILES: C[C@@H](Nc1nc(NC2CC2)n2ncc(/C=C3\NC(=O)NC3=O)c2n1)c1cccc2ccccc12]
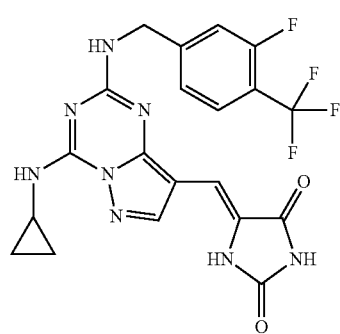 [SMILES: O=C1NC(=O)/C(=C/c2cnn3c(NC4CC4)nc(NCc4ccc(C(F)(F)F)c(F)c4)nc23)N1]
TABLE 37A-continued
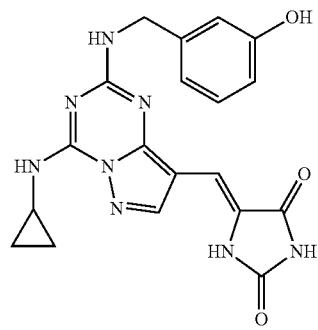 [SMILES: O=C1NC(=O)/C(=C/c2cnn3c(NC4CC4)nc(NCc4cccc(O)c4)nc23)N1]
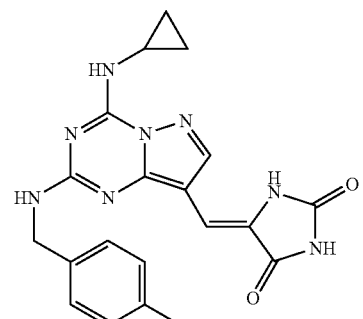
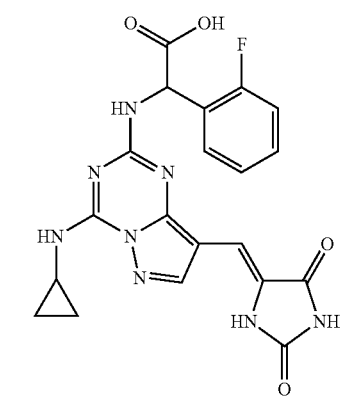 [SMILES: O=C1NC(=O)/C(=C/c2cnn3c(NC4CC4)nc(NC(C(=O)O)c4ccccc4F)nc23)N1]
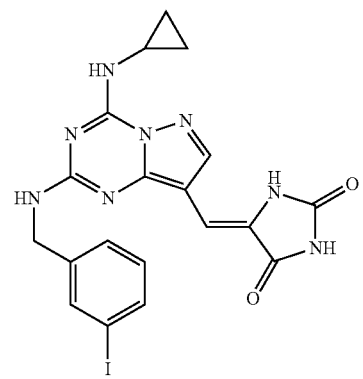 [SMILES: O=C1NC(=O)/C(=C/c2cnn3c(NC4CC4)nc(NCc4cccc(I)c4)nc23)N1]

TABLE 37A-continued
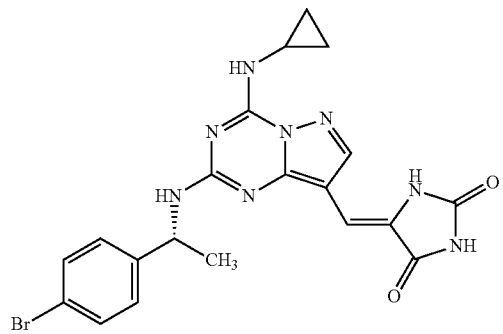
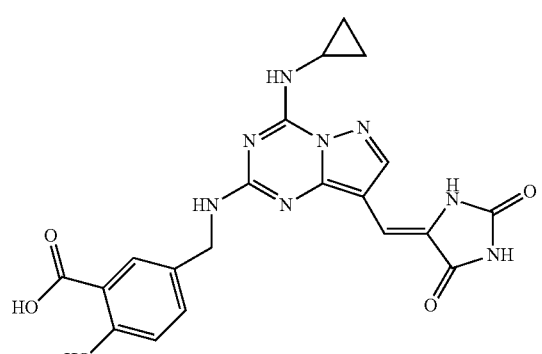
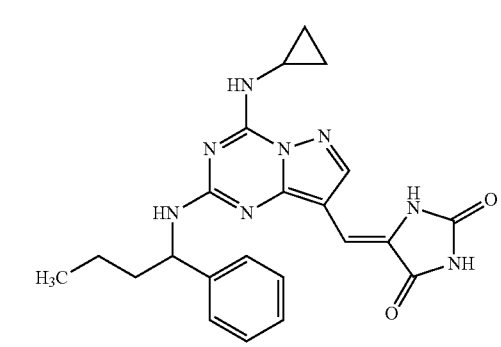 [SMILES: CCCC(Nc1nc(NC2CC2)n2ncc(/C=C3\NC(=O)NC3=O)c2n1)c1ccccc1]
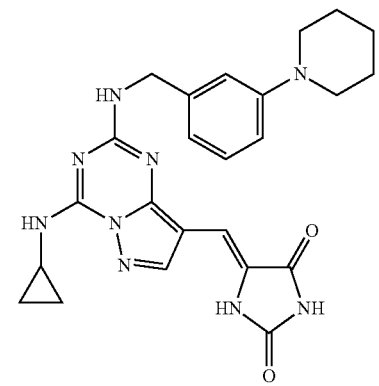 [SMILES: O=C1NC(=O)/C(=C/c2cnn3c(NC4CC4)nc(NCc4cccc(N5CCCCC5)c4)nc23)N1]
TABLE 37A-continued
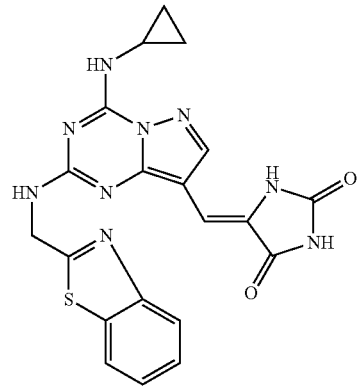 [SMILES: O=C1NC(=O)/C(=C/c2cnn3c(NC4CC4)nc(NCc4nc5ccccc5s4)nc23)N1]
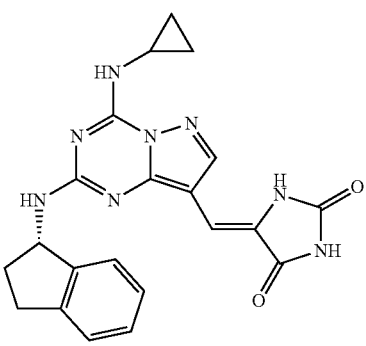 [SMILES: O=C1NC(=O)/C(=C/c2cnn3c(NC4CC4)nc(N[C@H]4CCc5ccccc54)nc23)N1]
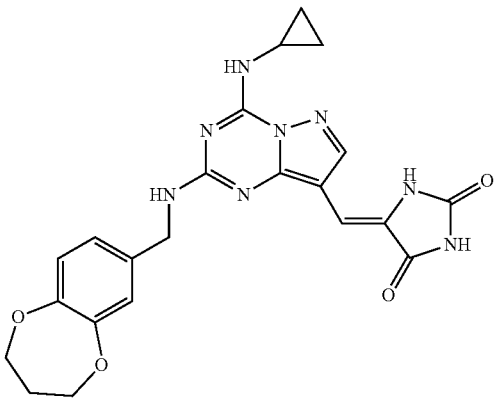 [SMILES: O=C1NC(=O)/C(=C/c2cnn3c(NC4CC4)nc(NCc4ccc5c(c4)OCCCO5)nc23)N1]
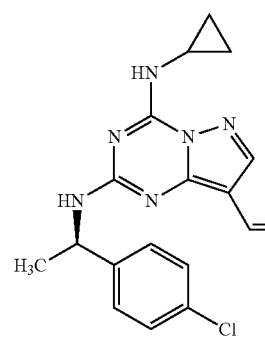

TABLE 37A-continued
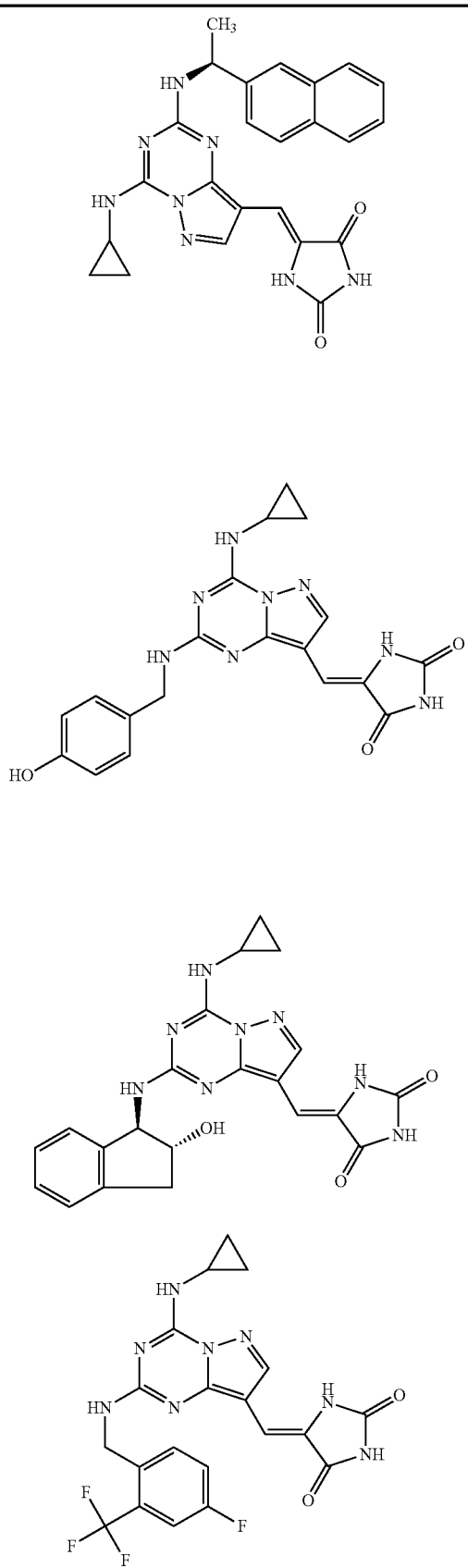
TABLE 37A-continued
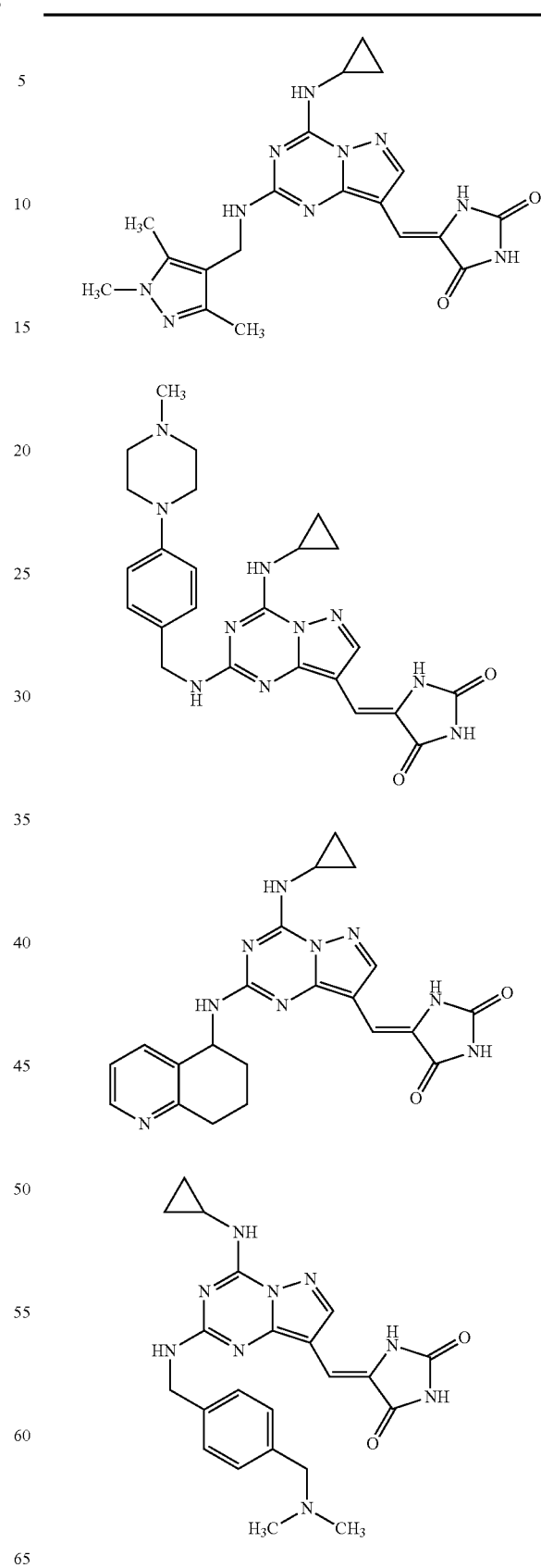

TABLE 37A-continued
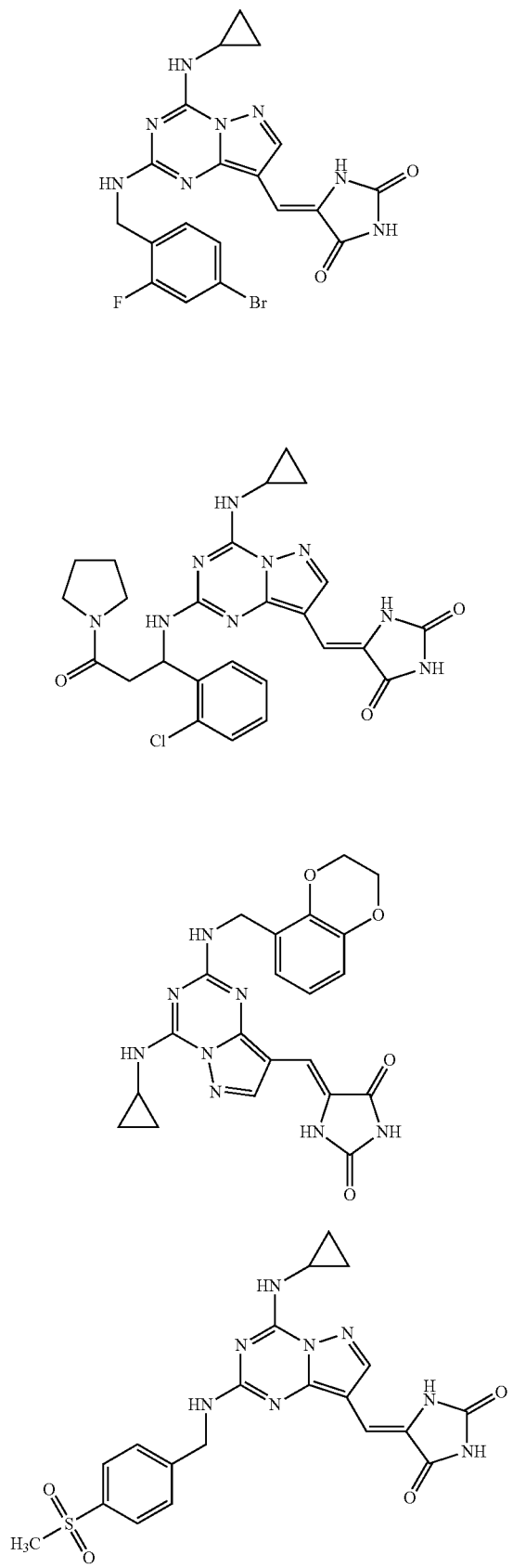
TABLE 37A-continued
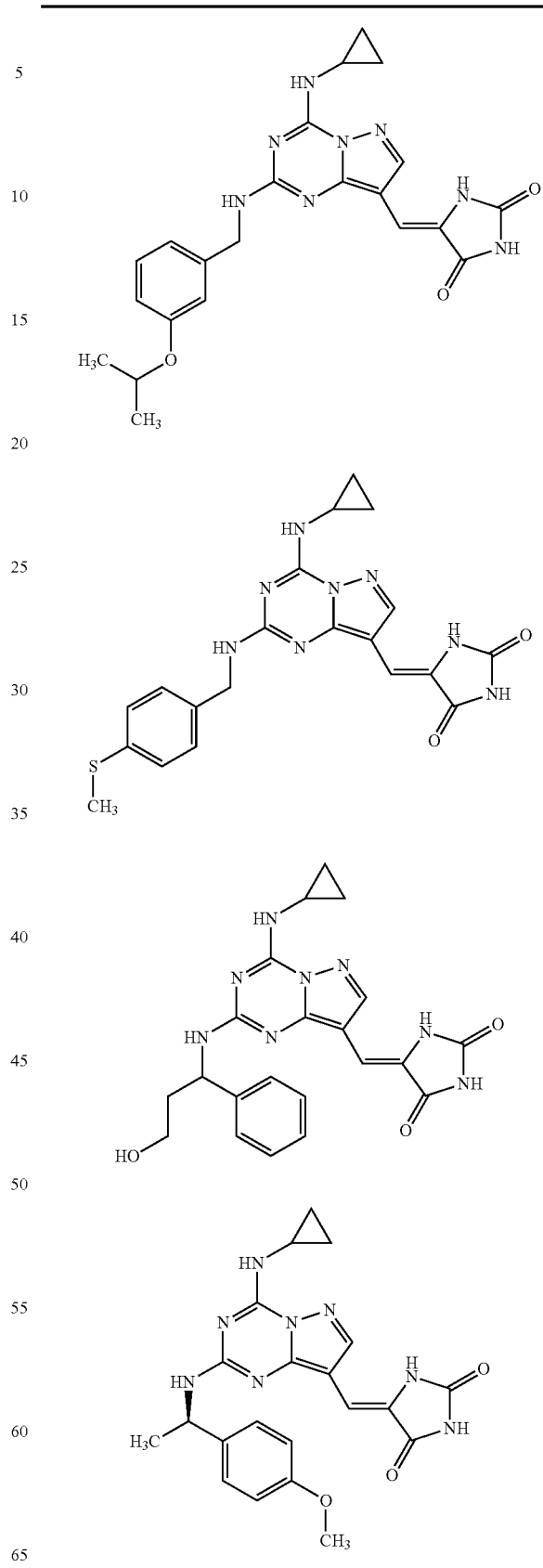

TABLE 37A-continued
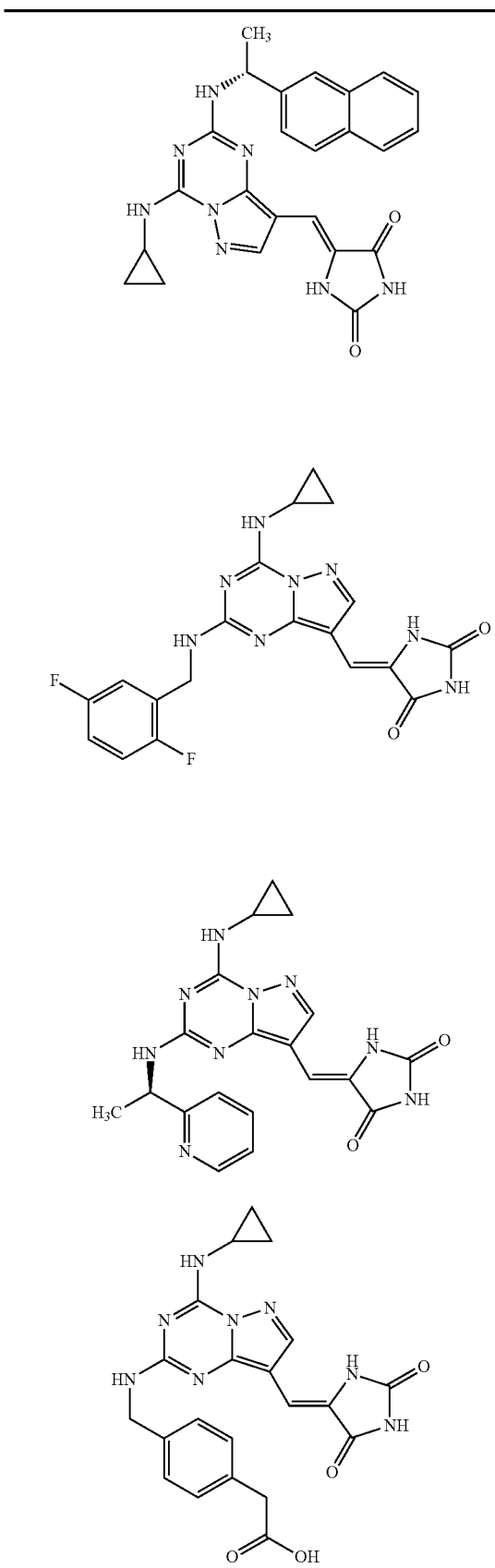
TABLE 37A-continued
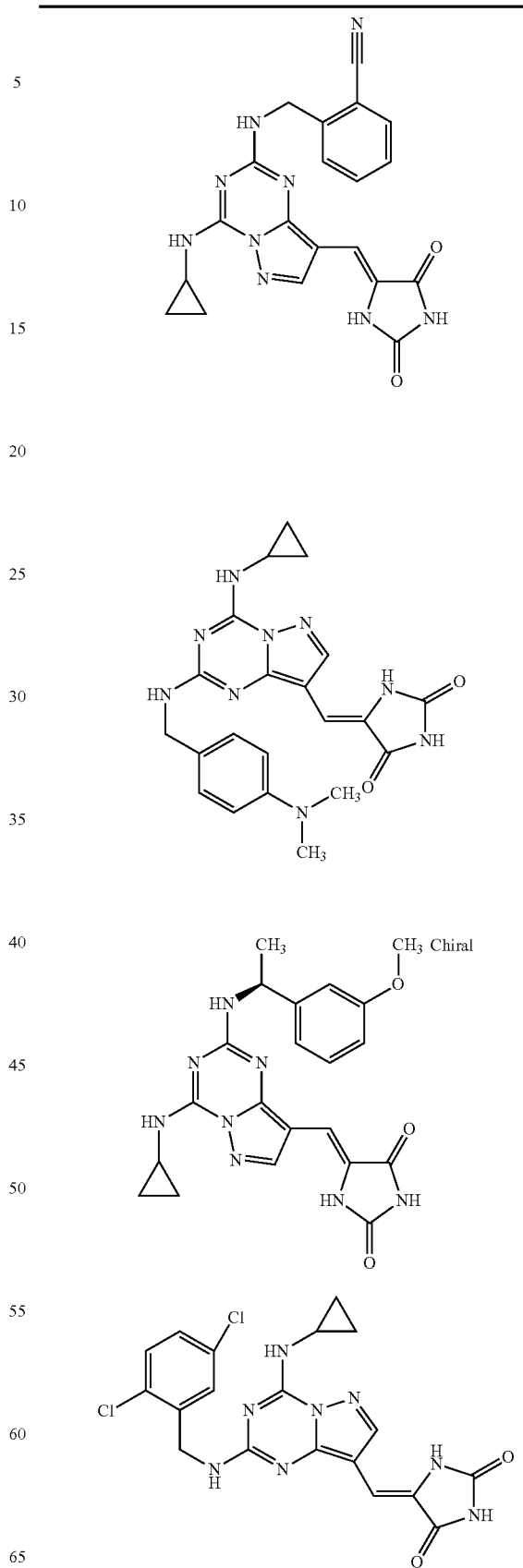

TABLE 37A-continued
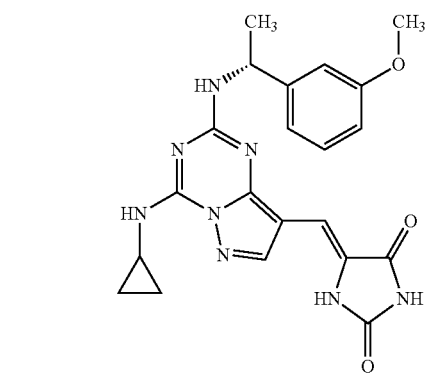 [SMILES: COc1cccc([C@@H](C)Nc2nc(NC3CC3)n3ncc(/C=C4\NC(=O)NC4=O)c3n2)c1]
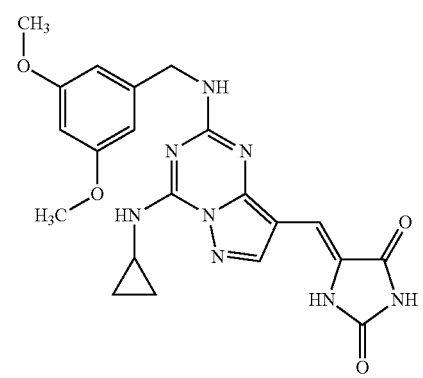 [SMILES: COc1cc(CNc2nc(NC3CC3)n3ncc(/C=C4\NC(=O)NC4=O)c3n2)cc(OC)c1]
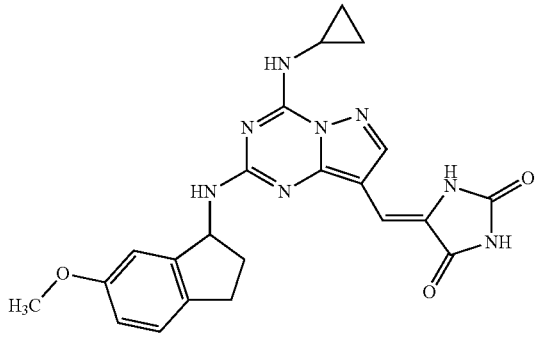 [SMILES: COc1ccc2c(c1)C(Nc1nc(NC3CC3)n3ncc(/C=C4\NC(=O)NC4=O)c3n1)CC2]
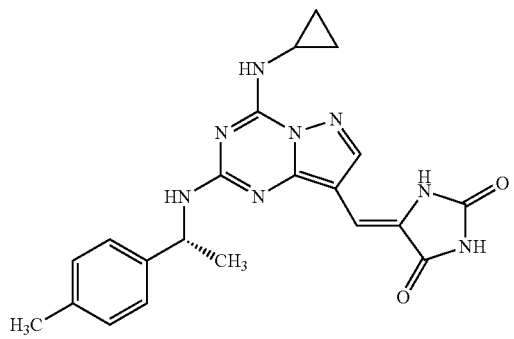 [SMILES: Cc1ccc([C@@H](C)Nc2nc(NC3CC3)n3ncc(/C=C4\NC(=O)NC4=O)c3n2)cc1]
TABLE 37A-continued
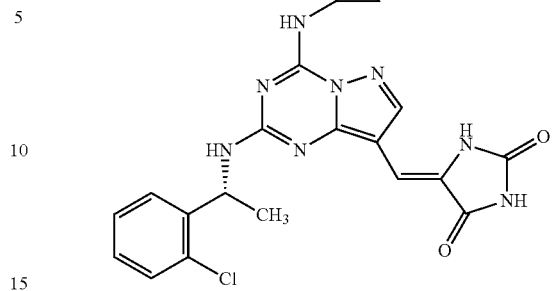
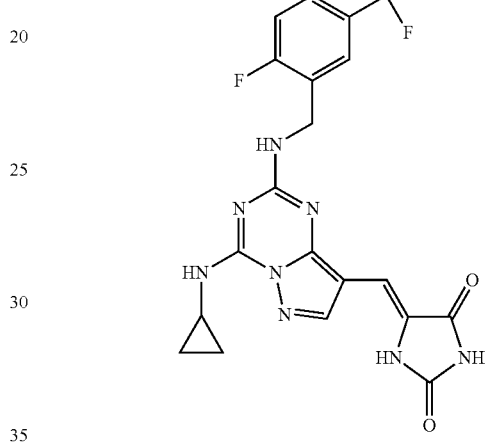
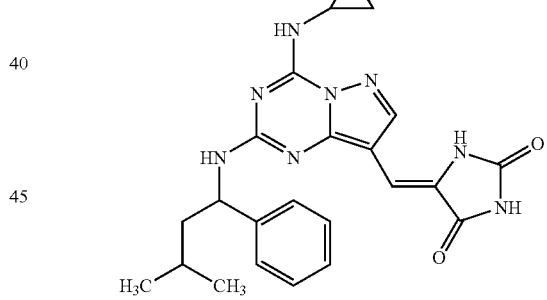
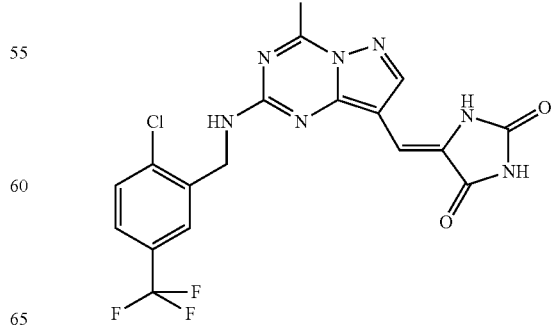

TABLE 37A-continued
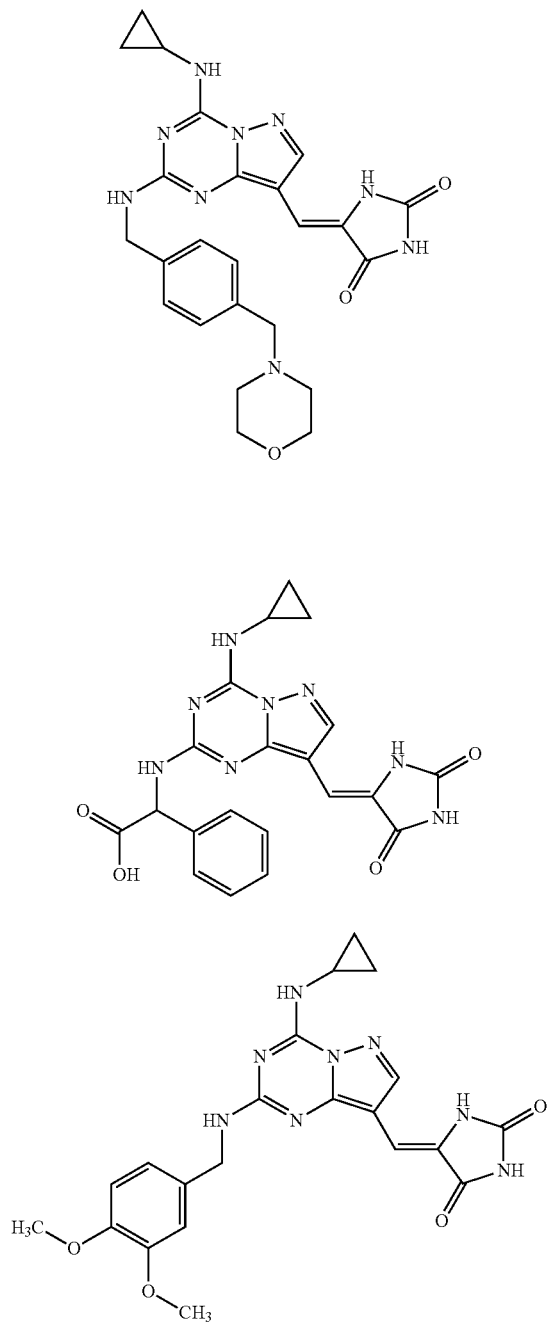
TABLE 37A-continued
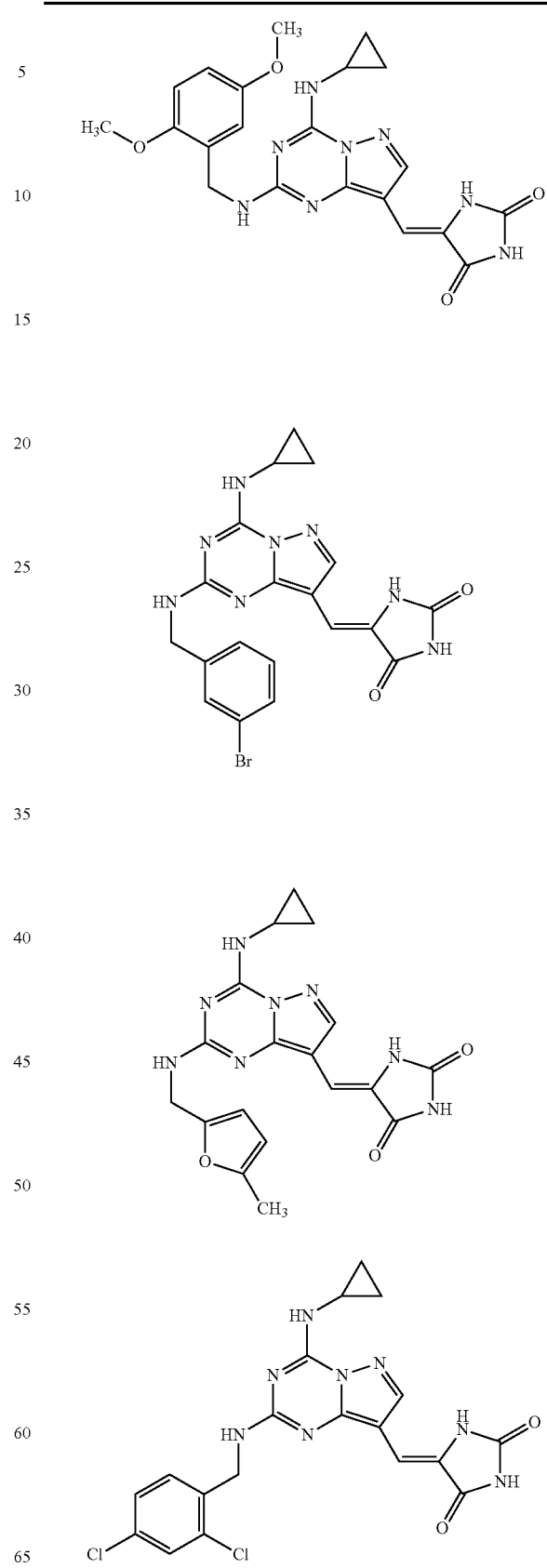

TABLE 37A-continued
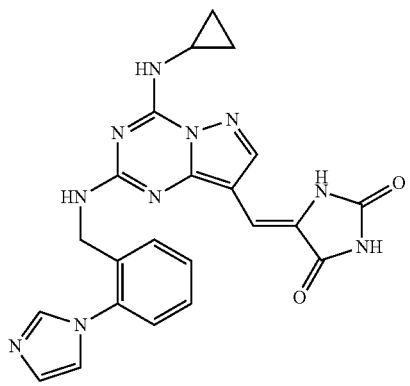 [SMILES: O=C1NC(=O)/C(=C/c2cnn3c(NC4CC4)nc(NCc4ccccc4-n4ccnc4)nc23)N1]
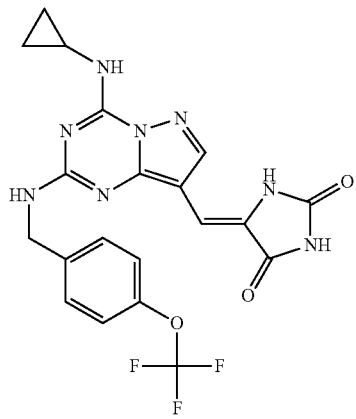
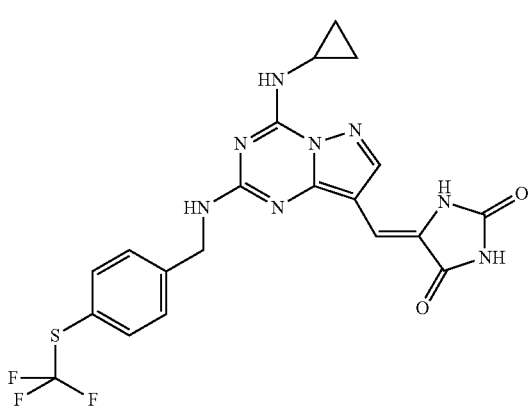 [SMILES: O=C1NC(=O)/C(=C/c2cnn3c(NC4CC4)nc(NCc4ccc(SC(F)(F)F)cc4)nc23)N1]
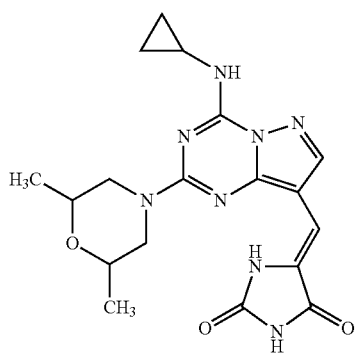
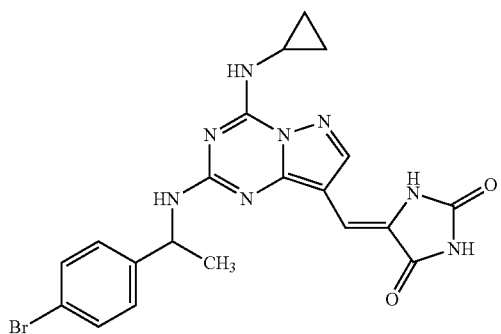 [SMILES: CC(Nc1nc(NC2CC2)n2ncc(/C=C3\NC(=O)NC3=O)c2n1)c1ccc(Br)cc1]
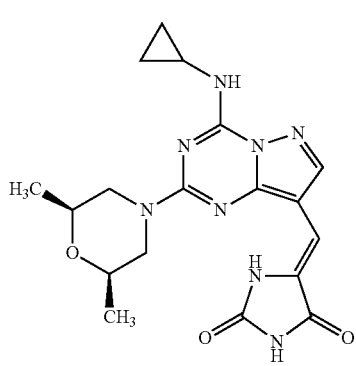
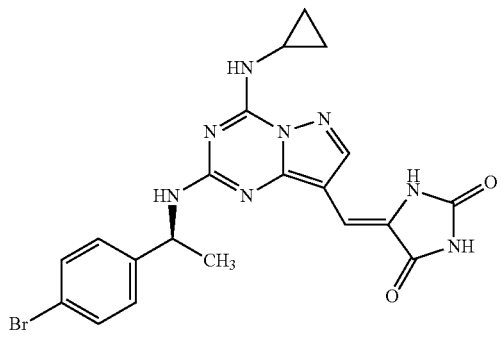 [SMILES: C[C@H](Nc1nc(NC2CC2)n2ncc(/C=C3\NC(=O)NC3=O)c2n1)c1ccc(Br)cc1]
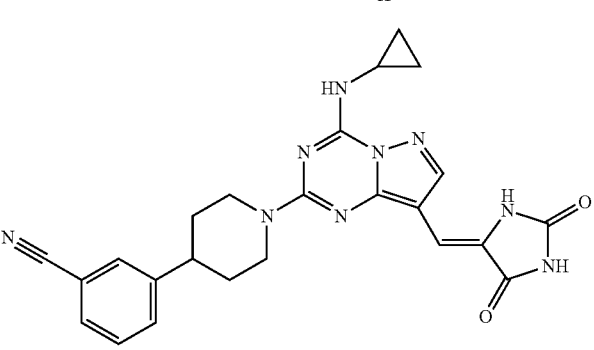

437
TABLE 37A-continued
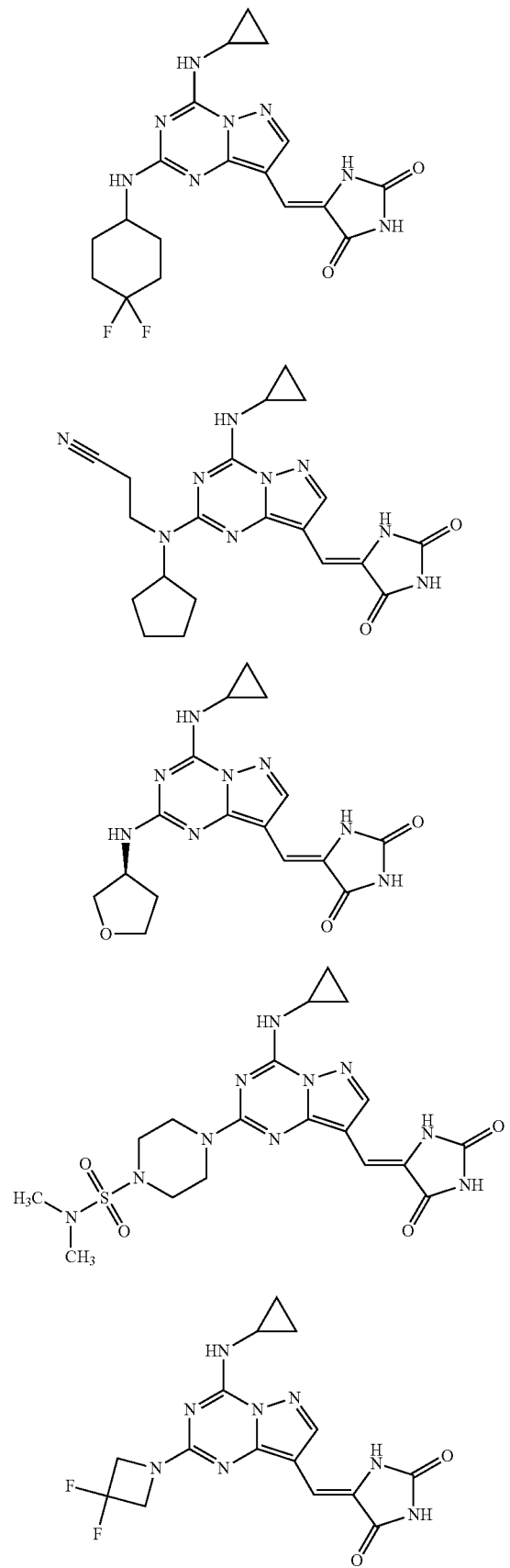
438
TABLE 37A-continued
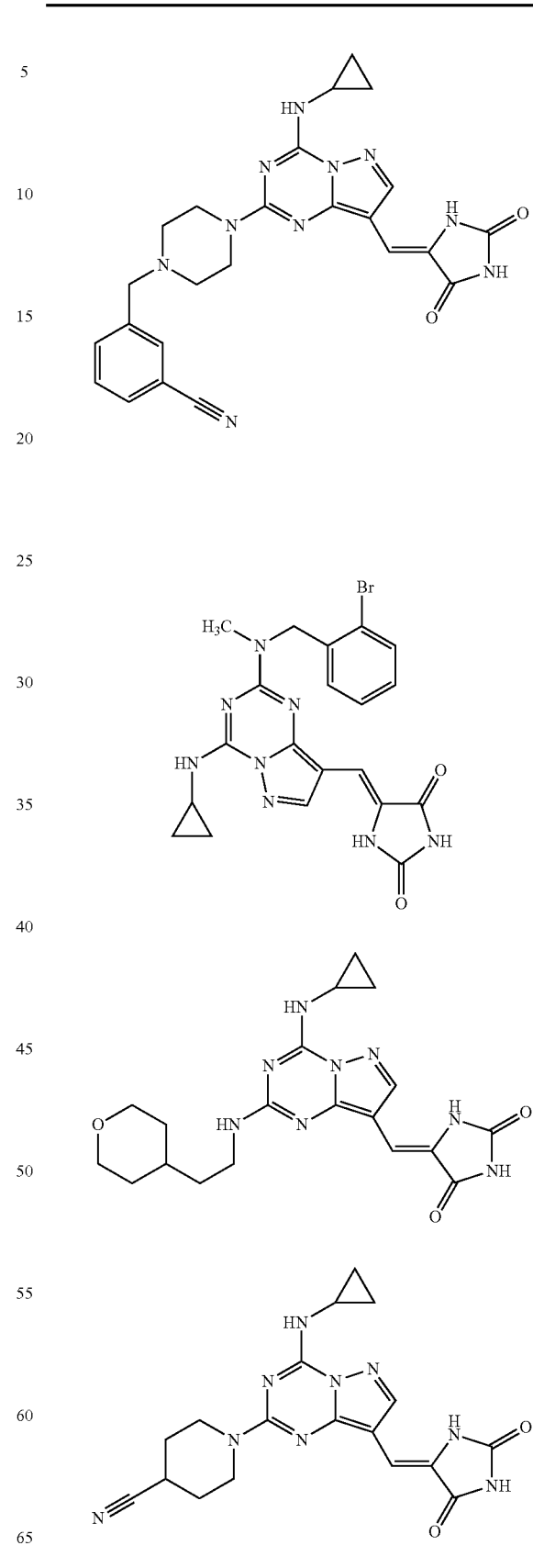

TABLE 37A-continued
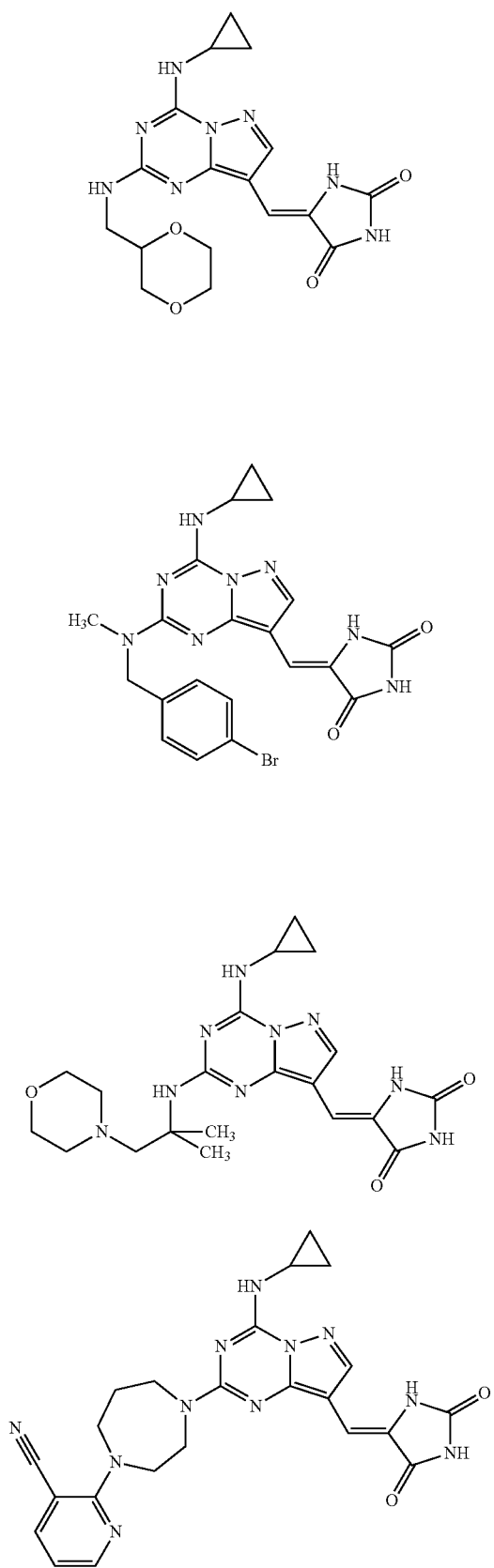
TABLE 37A-continued
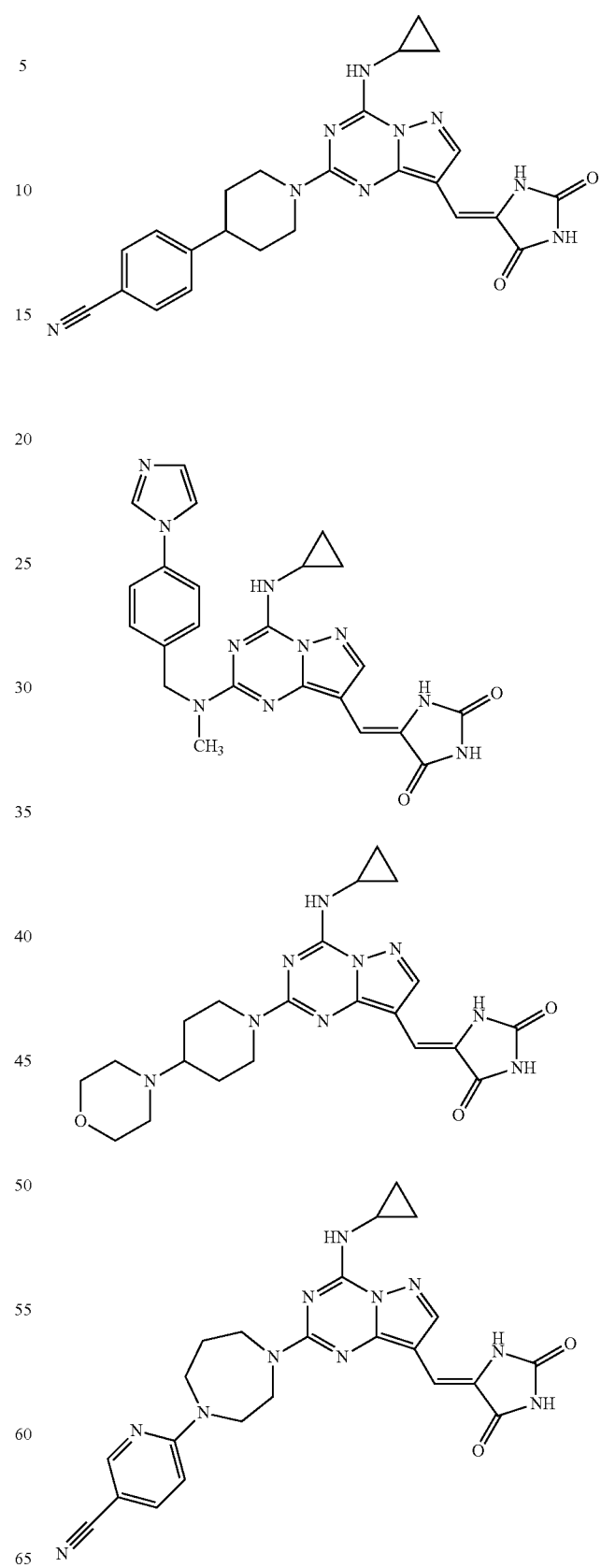

TABLE 37A-continued
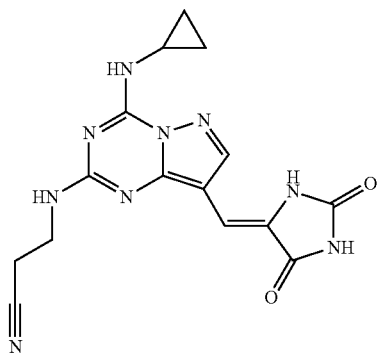 [SMILES: N#CCCNc1nc(NC2CC2)n2ncc(/C=C3\NC(=O)NC3=O)c2n1]
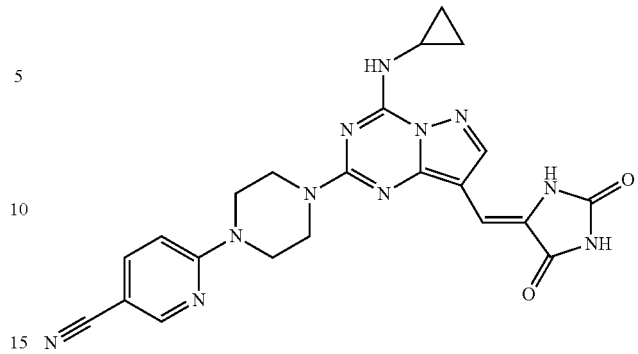
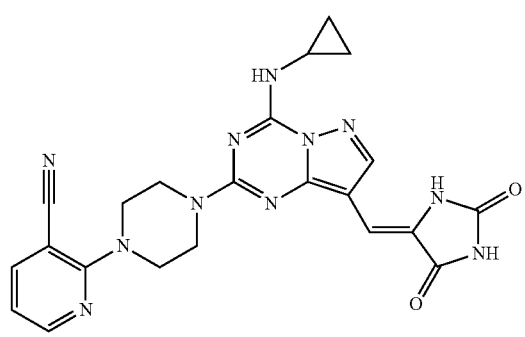 [SMILES: N#Cc1cccnc1N1CCN(c2nc(NC3CC3)n3ncc(/C=C4\NC(=O)NC4=O)c3n2)CC1]
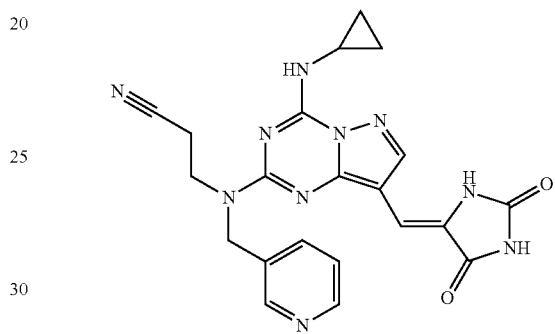
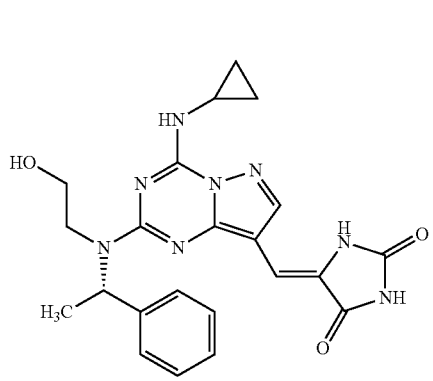 [SMILES: C[C@@H](c1ccccc1)N(CCO)c1nc(NC2CC2)n2ncc(/C=C3\NC(=O)NC3=O)c2n1]
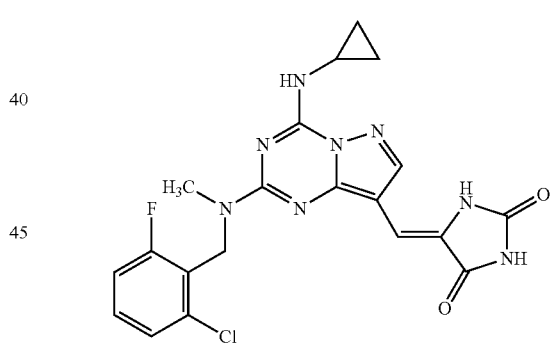
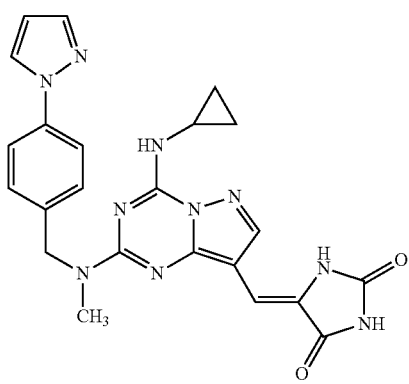 [SMILES: CN(Cc1ccc(-n2cccn2)cc1)c1nc(NC2CC2)n2ncc(/C=C3\NC(=O)NC3=O)c2n1]
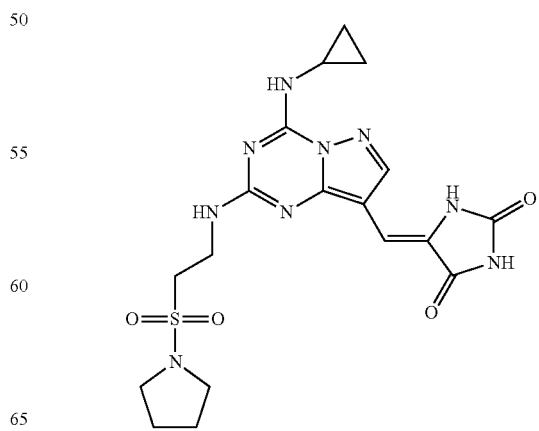

TABLE 37A-continued
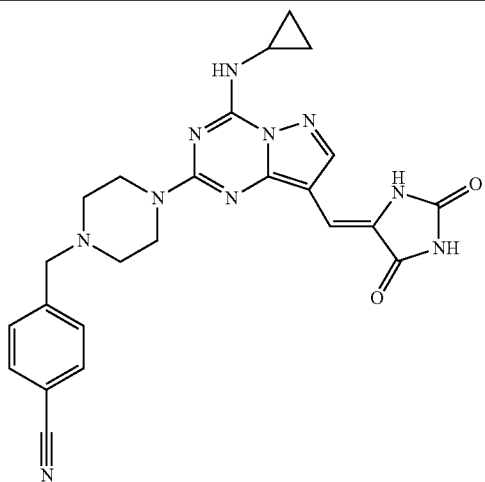
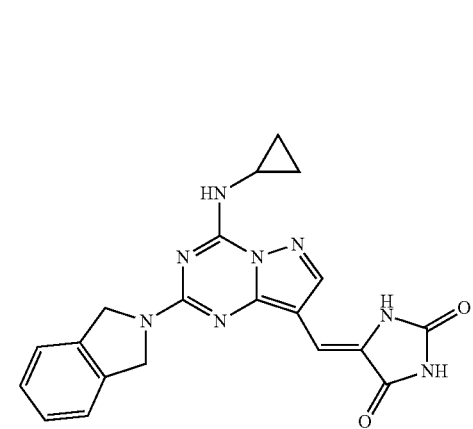 [SMILES: O=C1NC(=O)/C(=C/c2cnn3c(NC4CC4)nc(N4Cc5ccccc5C4)nc23)N1]
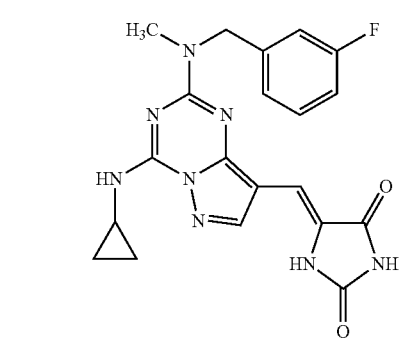 [SMILES: CN(Cc1cccc(F)c1)c1nc(NC2CC2)n2ncc(/C=C3\NC(=O)NC3=O)c2n1]
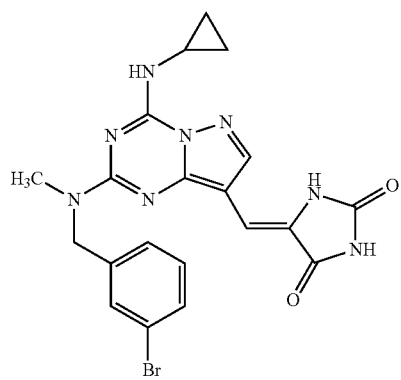 [SMILES: CN(Cc1cccc(Br)c1)c1nc(NC2CC2)n2ncc(/C=C3\NC(=O)NC3=O)c2n1]
TABLE 37A-continued
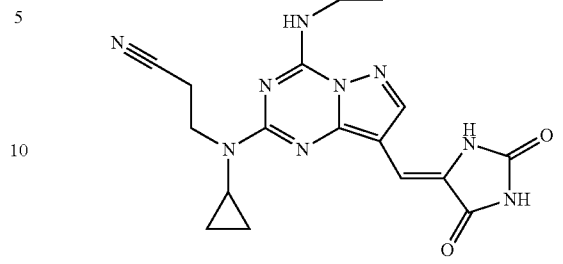
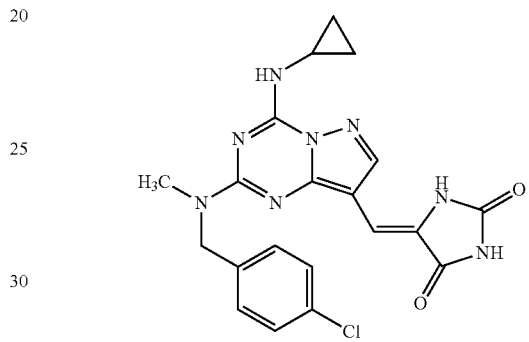
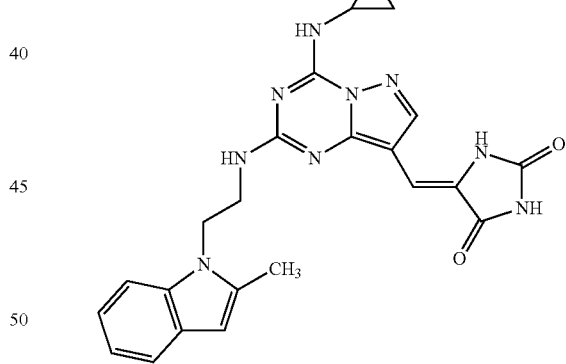
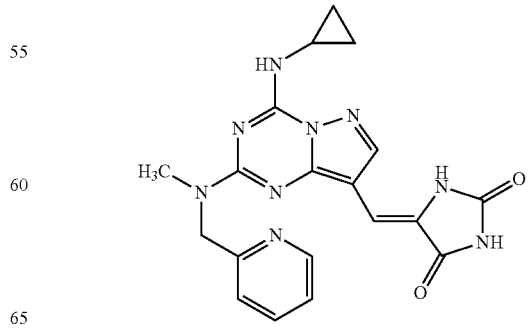

TABLE 37A-continued
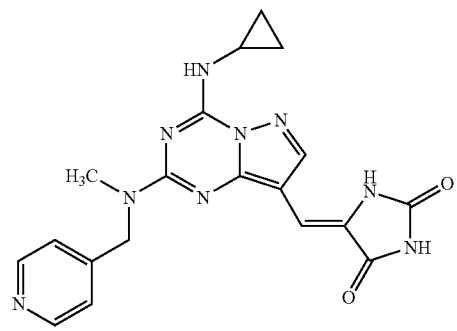 [SMILES: CN(Cc1ccncc1)c1nc(NC2CC2)n2ncc(/C=C3\NC(=O)NC3=O)c2n1]
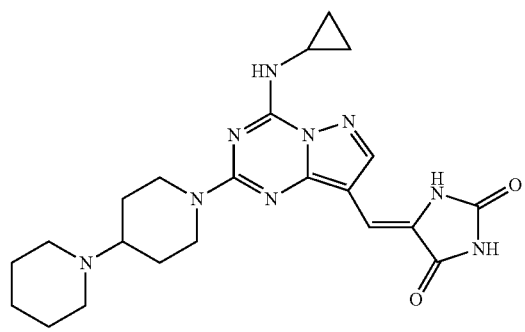 [SMILES: O=C1NC(=O)/C(=C/c2cnn3c(NC4CC4)nc(N4CCC(N5CCCCC5)CC4)nc23)N1]
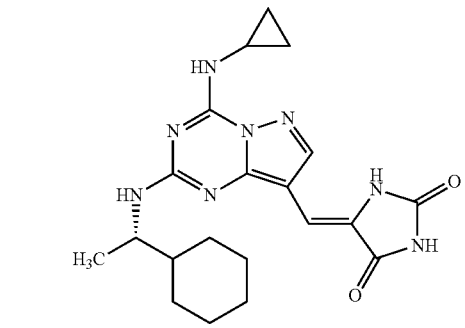 [SMILES: C[C@H](Nc1nc(NC2CC2)n2ncc(/C=C3\NC(=O)NC3=O)c2n1)C1CCCCC1]
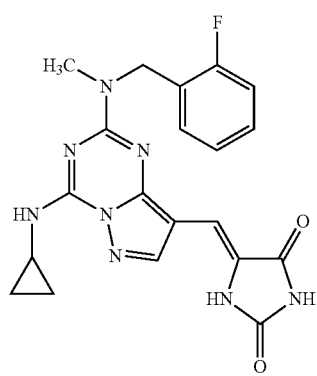 [SMILES: CN(Cc1ccccc1F)c1nc(NC2CC2)n2ncc(/C=C3\NC(=O)NC3=O)c2n1]
TABLE 37A-continued
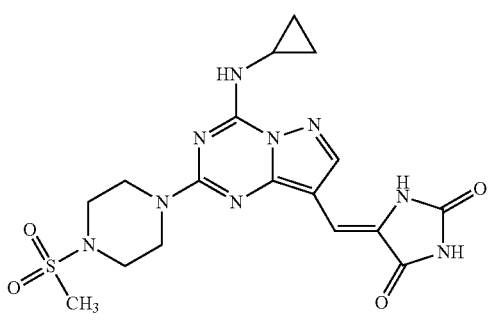 [SMILES: CS(=O)(=O)N1CCN(c2nc(NC3CC3)n3ncc(/C=C4\NC(=O)NC4=O)c3n2)CC1]
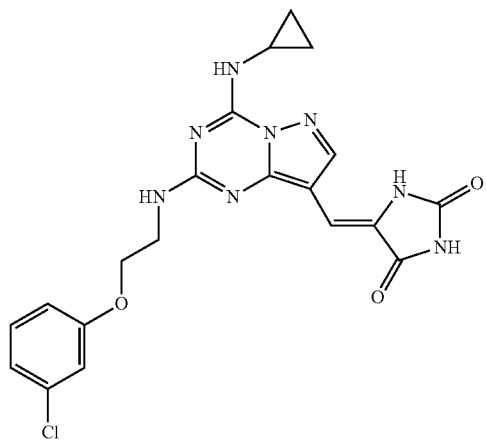 [SMILES: O=C1NC(=O)/C(=C/c2cnn3c(NC4CC4)nc(NCCOc4cccc(Cl)c4)nc23)N1]
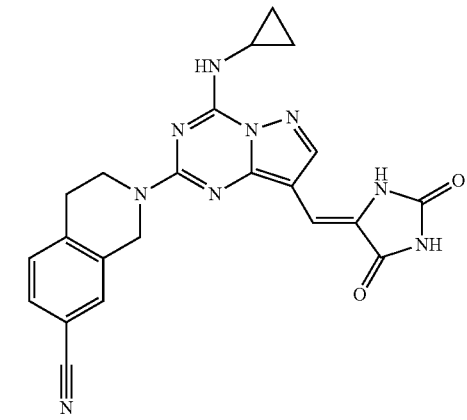 [SMILES: N#Cc1ccc2c(c1)CN(c1nc(NC3CC3)n3ncc(/C=C4\NC(=O)NC4=O)c3n1)CC2]
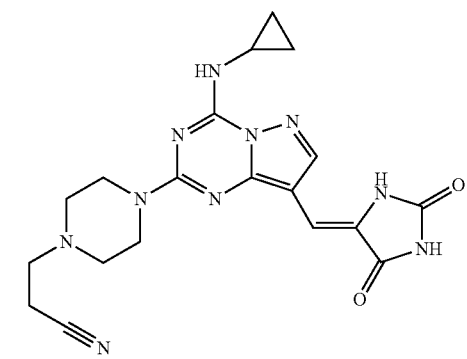 [SMILES: N#CCCN1CCN(c2nc(NC3CC3)n3ncc(/C=C4\NC(=O)NC4=O)c3n2)CC1]

TABLE 37A-continued
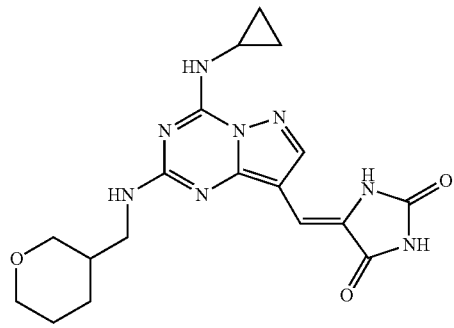 [SMILES: O=C1NC(=O)/C(=C/c2cnn3c(NC4CC4)nc(NCC4CCCOC4)nc23)N1]
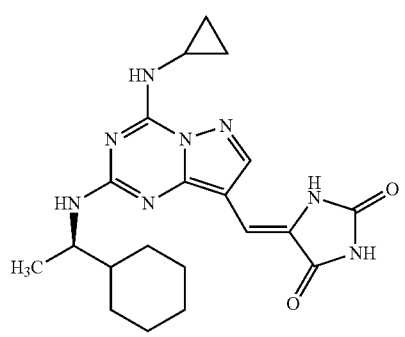 [SMILES: C[C@@H](Nc1nc(NC2CC2)n2ncc(/C=C3\NC(=O)NC3=O)c2n1)C1CCCCC1]
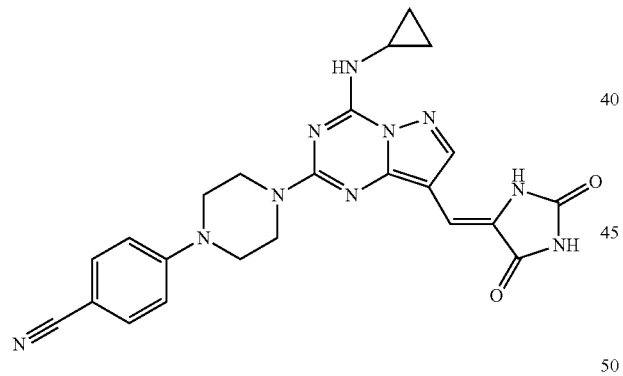
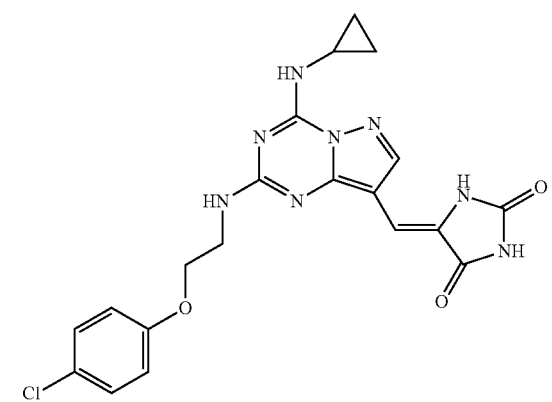 [SMILES: O=C1NC(=O)/C(=C/c2cnn3c(NC4CC4)nc(NCCOc4ccc(Cl)cc4)nc23)N1]
TABLE 37A-continued
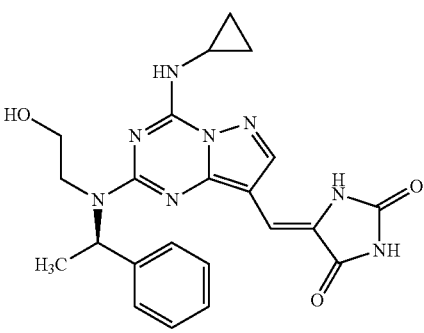 [SMILES: C[C@H](c1ccccc1)N(CCO)c1nc(NC2CC2)n2ncc(/C=C3\NC(=O)NC3=O)c2n1]
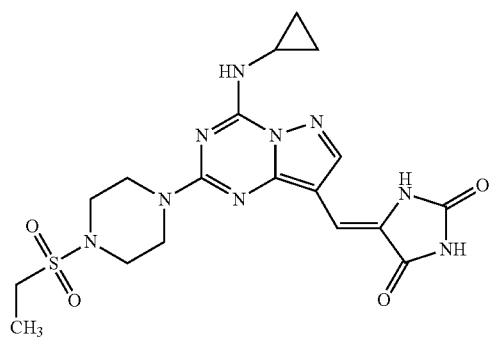 [SMILES: CCS(=O)(=O)N1CCN(c2nc(NC3CC3)n3ncc(/C=C4\NC(=O)NC4=O)c3n2)CC1]
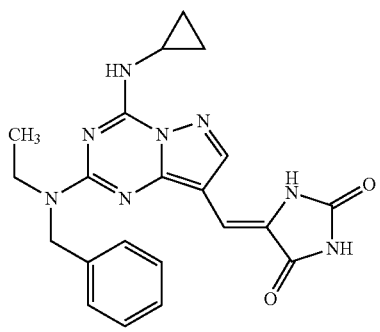 [SMILES: CCN(Cc1ccccc1)c1nc(NC2CC2)n2ncc(/C=C3\NC(=O)NC3=O)c2n1]
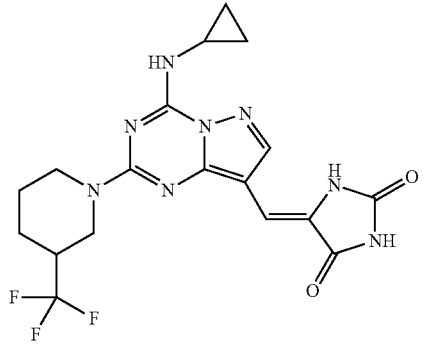 [SMILES: O=C1NC(=O)/C(=C/c2cnn3c(NC4CC4)nc(N4CCCC(C(F)(F)F)C4)nc23)N1]

TABLE 37A-continued
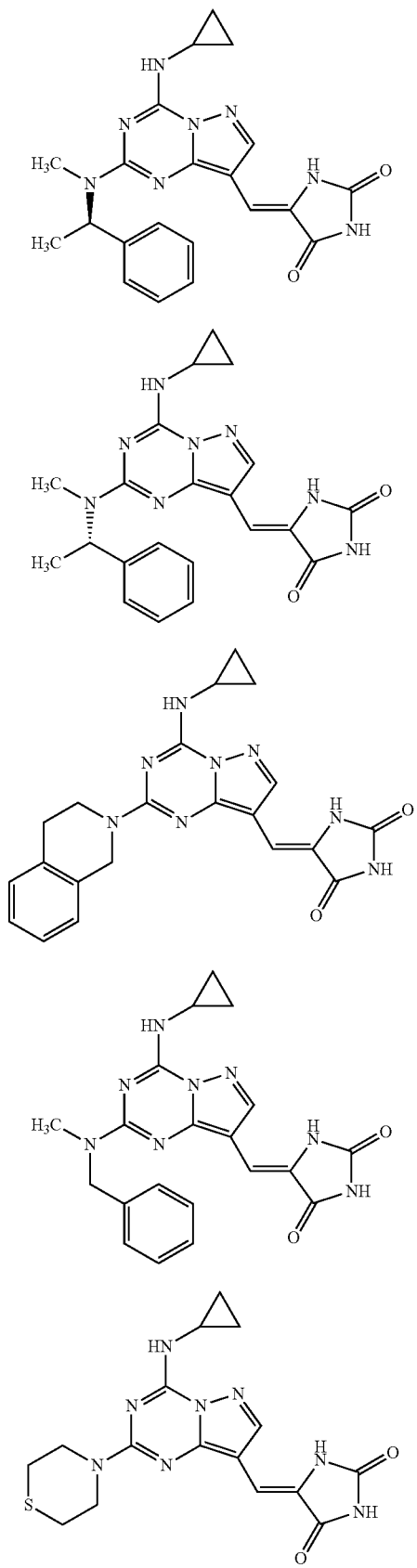
TABLE 37A-continued
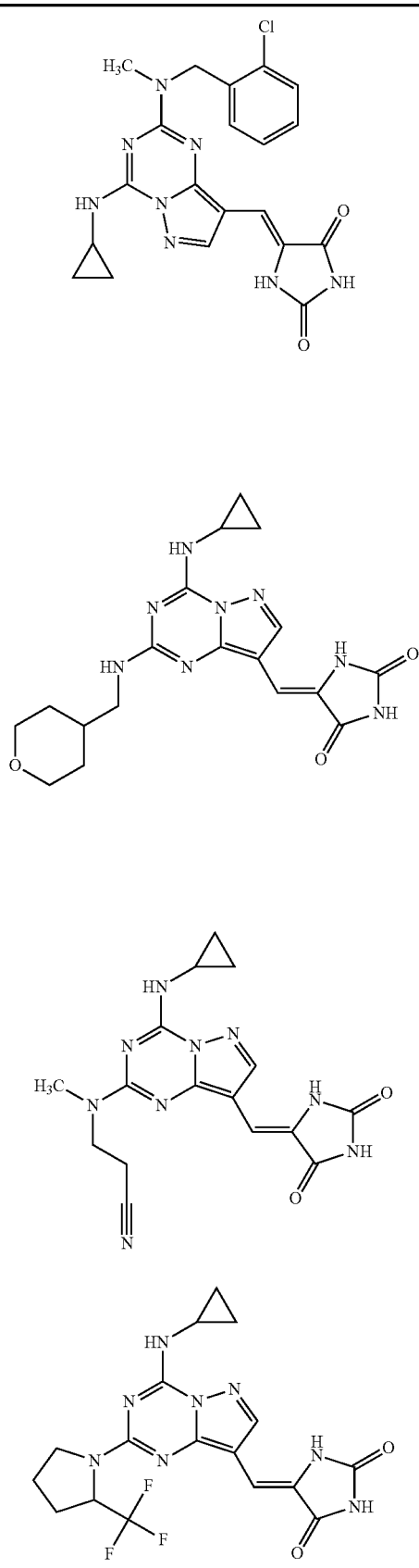

451
TABLE 37A-continued
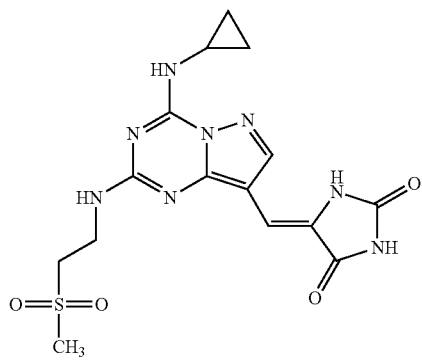 [SMILES: CS(=O)(=O)CCNc1nc(NC2CC2)n2ncc(/C=C3\NC(=O)NC3=O)c2n1]
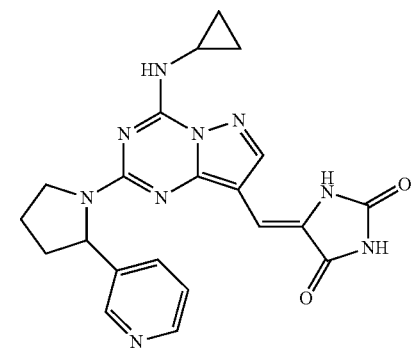 [SMILES: O=C1NC(=O)/C(=C/c2cnn3c(NC4CC4)nc(N4CCCC4c4cccnc4)nc23)N1]
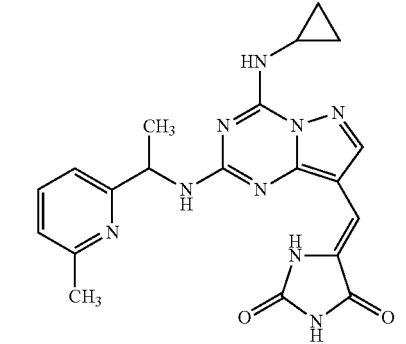 [SMILES: Cc1cccc(C(C)Nc2nc(NC3CC3)n3ncc(/C=C4\NC(=O)NC4=O)c3n2)n1]
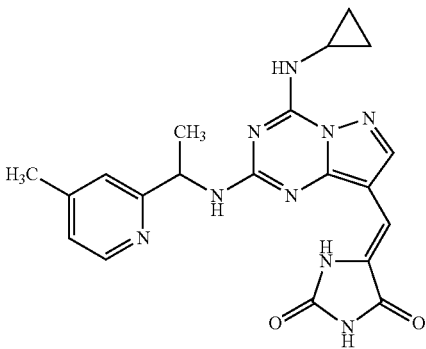 [SMILES: Cc1ccnc(C(C)Nc2nc(NC3CC3)n3ncc(/C=C4\NC(=O)NC4=O)c3n2)c1]
452
TABLE 37A-continued
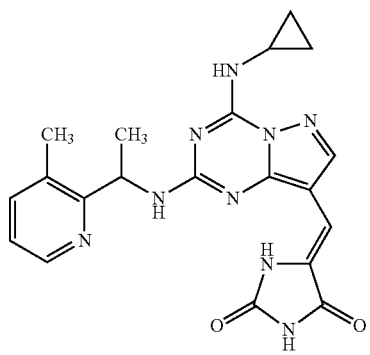 [SMILES: Cc1cccnc1C(C)Nc1nc(NC2CC2)n2ncc(/C=C3\NC(=O)NC3=O)c2n1]
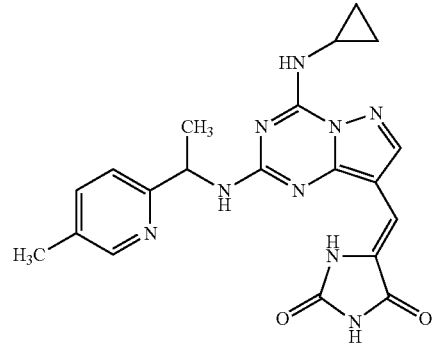 [SMILES: Cc1ccc(C(C)Nc2nc(NC3CC3)n3ncc(/C=C4\NC(=O)NC4=O)c3n2)nc1]
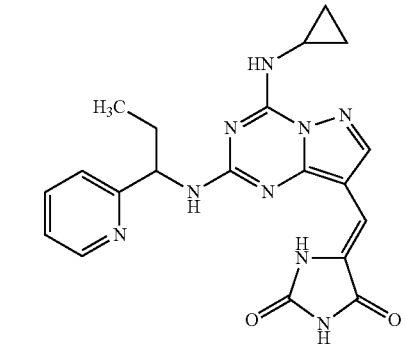 [SMILES: CCC(Nc1nc(NC2CC2)n2ncc(/C=C3\NC(=O)NC3=O)c2n1)c1ccccn1]
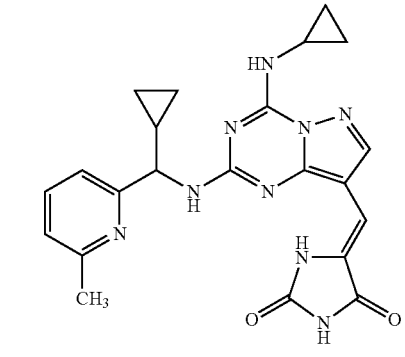 [SMILES: Cc1cccc(C(Nc2nc(NC3CC3)n3ncc(/C=C4\NC(=O)NC4=O)c3n2)C2CC2)n1]

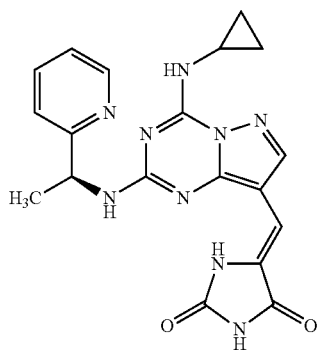 [SMILES: C[C@H](Nc1nc(NC2CC2)n2ncc(/C=C3\NC(=O)NC3=O)c2n1)c1ccccn1]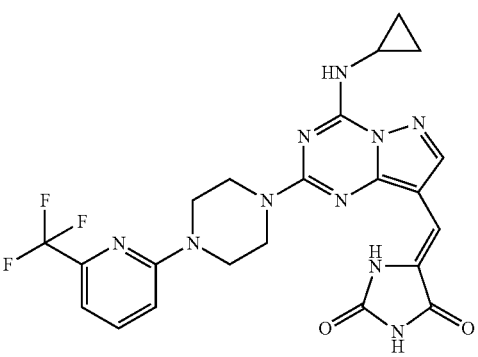 [SMILES: O=C1NC(=O)/C(=C/c2cnn3c(NC4CC4)nc(N4CCN(c5cccc(C(F)(F)F)n5)CC4)nc23)N1]

TABLE 37A-continued
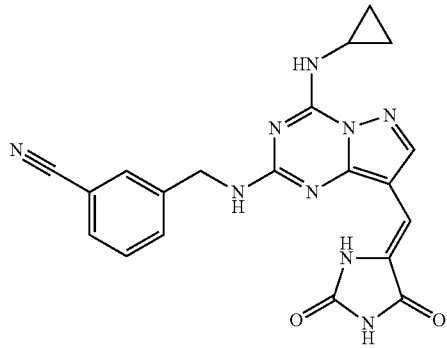 [SMILES: N#Cc1cccc(CNc2nc(NC3CC3)n3ncc(/C=C4\NC(=O)NC4=O)c3n2)c1]
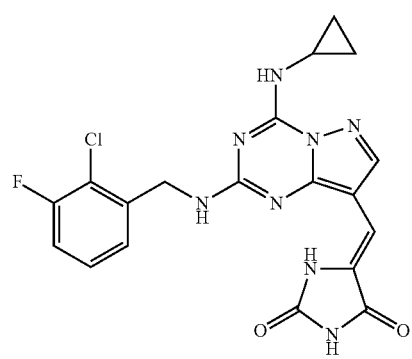 [SMILES: O=C1NC(=O)/C(=C/c2cnn3c(NC4CC4)nc(NCc4cccc(F)c4Cl)nc23)N1]
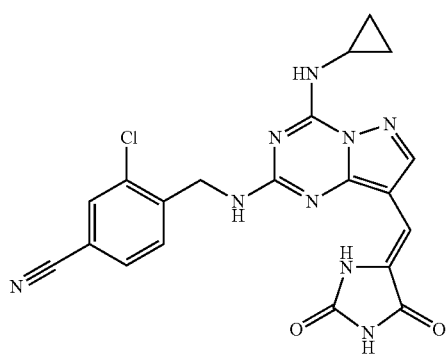 [SMILES: N#Cc1ccc(CNc2nc(NC3CC3)n3ncc(/C=C4\NC(=O)NC4=O)c3n2)c(Cl)c1]
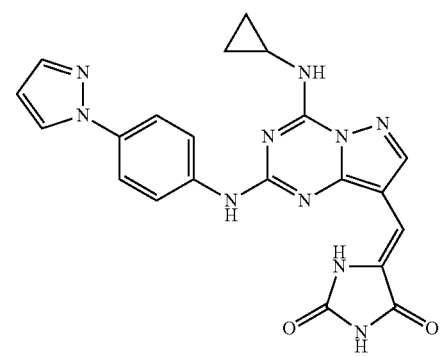 [SMILES: O=C1NC(=O)/C(=C/c2cnn3c(NC4CC4)nc(Nc4ccc(-n5cccn5)cc4)nc23)N1]
TABLE 37A-continued
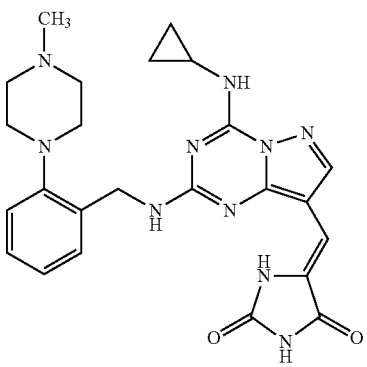 [SMILES: CN1CCN(c2ccccc2CNc2nc(NC3CC3)n3ncc(/C=C4\NC(=O)NC4=O)c3n2)CC1]
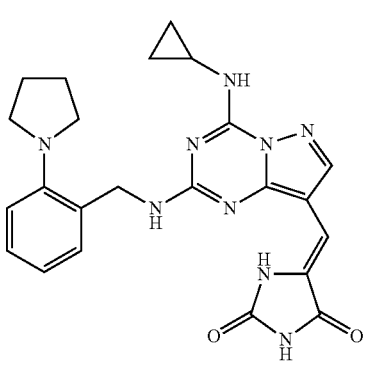 [SMILES: O=C1NC(=O)/C(=C/c2cnn3c(NC4CC4)nc(NCc4ccccc4N4CCCC4)nc23)N1]
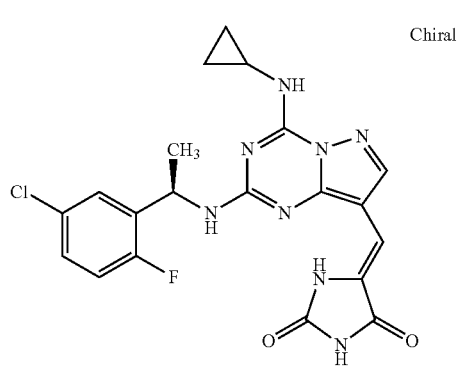 [SMILES: C[C@@H](Nc1nc(NC2CC2)n2ncc(/C=C3\NC(=O)NC3=O)c2n1)c1cc(Cl)ccc1F ; "Chiral"]
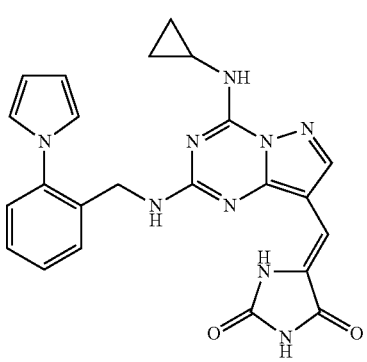 [SMILES: O=C1NC(=O)/C(=C/c2cnn3c(NC4CC4)nc(NCc4ccccc4-n4cccc4)nc23)N1]

TABLE 37A-continued
457
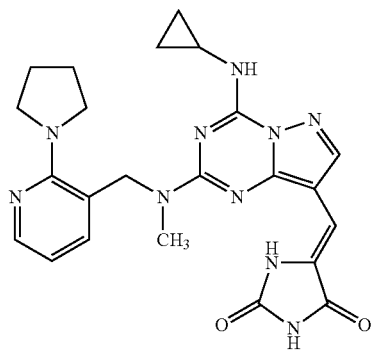 [SMILES: CN(Cc1cccnc1N1CCCC1)c1nc(NC2CC2)n2ncc(/C=C3\NC(=O)NC3=O)c2n1]
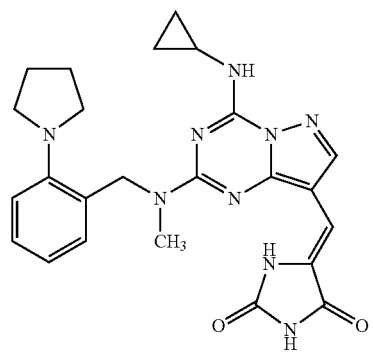 [SMILES: CN(Cc1ccccc1N1CCCC1)c1nc(NC2CC2)n2ncc(/C=C3\NC(=O)NC3=O)c2n1]
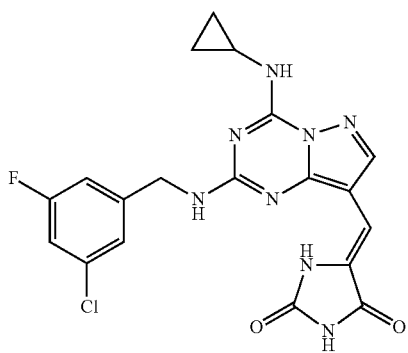 [SMILES: O=C1NC(=O)/C(=C/c2cnn3c(NC4CC4)nc(NCc4cc(F)cc(Cl)c4)nc23)N1]
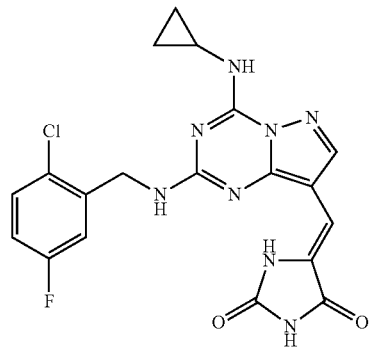 [SMILES: O=C1NC(=O)/C(=C/c2cnn3c(NC4CC4)nc(NCc4cc(F)ccc4Cl)nc23)N1]
458
TABLE 37A-continued
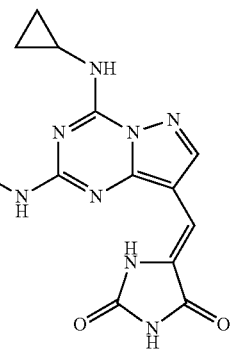
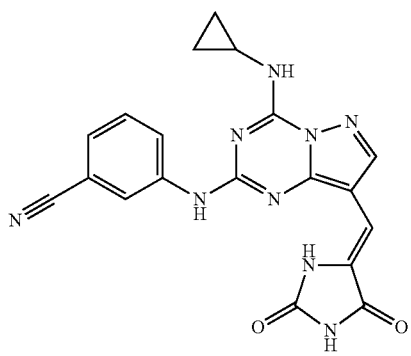 [SMILES: N#Cc1cccc(Nc2nc(NC3CC3)n3ncc(/C=C4\NC(=O)NC4=O)c3n2)c1]
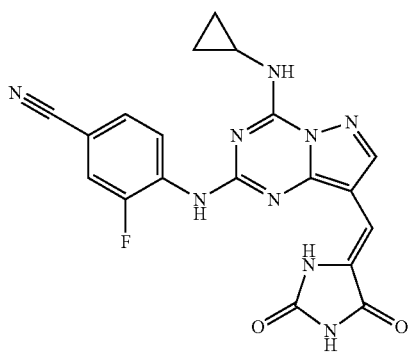 [SMILES: N#Cc1ccc(Nc2nc(NC3CC3)n3ncc(/C=C4\NC(=O)NC4=O)c3n2)c(F)c1]
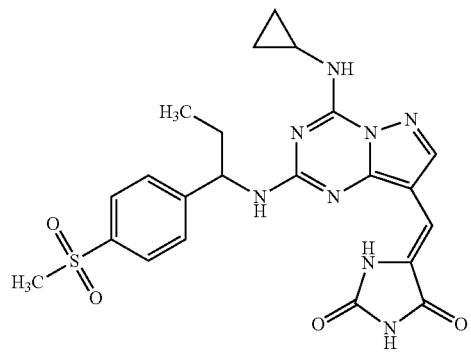 [SMILES: CCC(Nc1nc(NC2CC2)n2ncc(/C=C3\NC(=O)NC3=O)c2n1)c1ccc(S(C)(=O)=O)cc1]

TABLE 37A-continued
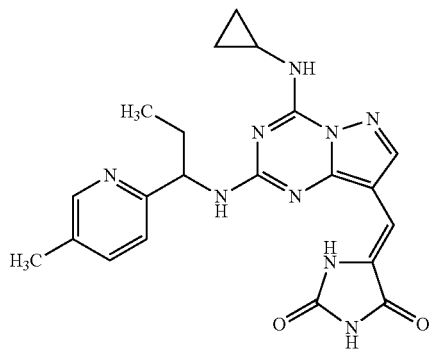 [SMILES: CCC(Nc1nc(NC2CC2)n2ncc(/C=C3\NC(=O)NC3=O)c2n1)c1ccc(C)cn1]
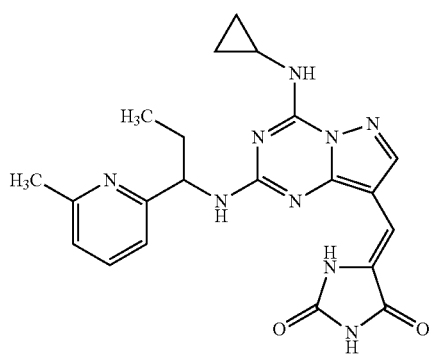 [SMILES: CCC(Nc1nc(NC2CC2)n2ncc(/C=C3\NC(=O)NC3=O)c2n1)c1cccc(C)n1]
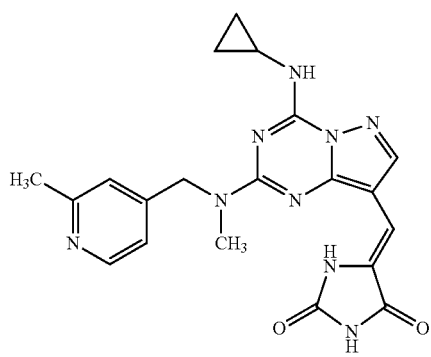 [SMILES: Cc1cc(CN(C)c2nc(NC3CC3)n3ncc(/C=C4\NC(=O)NC4=O)c3n2)ccn1]
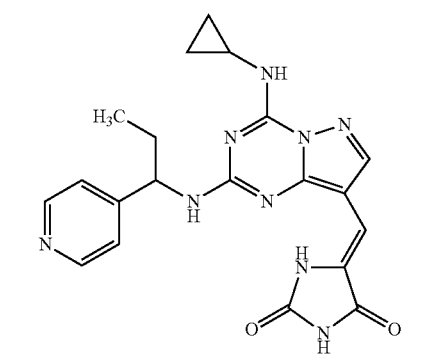 [SMILES: CCC(Nc1nc(NC2CC2)n2ncc(/C=C3\NC(=O)NC3=O)c2n1)c1ccncc1]
TABLE 37A-continued
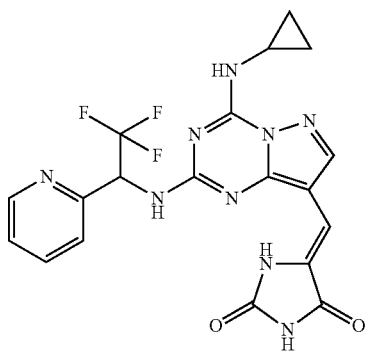 [SMILES: O=C1NC(=O)/C(=C/c2cnn3c(NC4CC4)nc(NC(c4ccccn4)C(F)(F)F)nc23)N1]
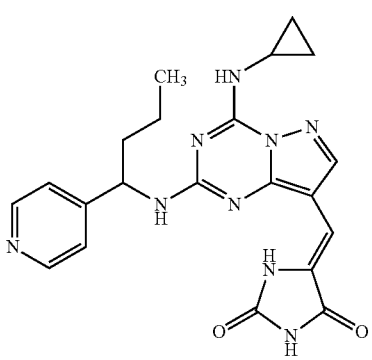 [SMILES: CCCC(Nc1nc(NC2CC2)n2ncc(/C=C3\NC(=O)NC3=O)c2n1)c1ccncc1]
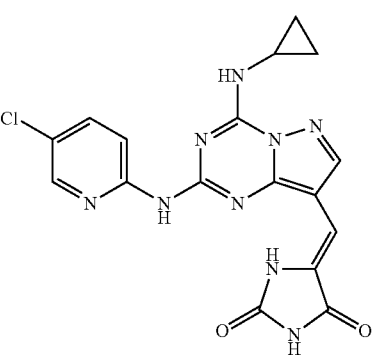 [SMILES: O=C1NC(=O)/C(=C/c2cnn3c(NC4CC4)nc(Nc4ccc(Cl)cn4)nc23)N1]
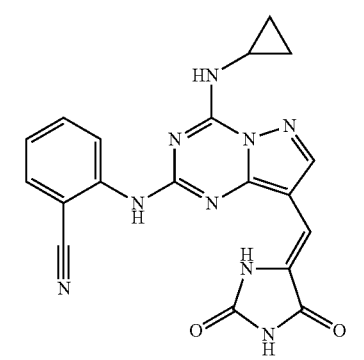 [SMILES: N#Cc1ccccc1Nc1nc(NC2CC2)n2ncc(/C=C3\NC(=O)NC3=O)c2n1]

TABLE 37A-continued
461
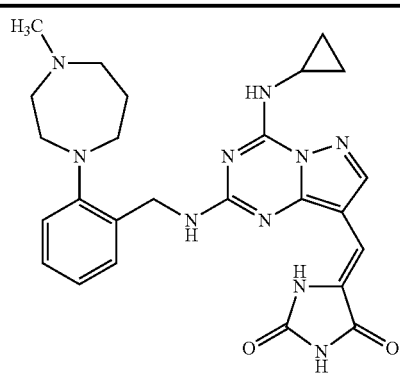
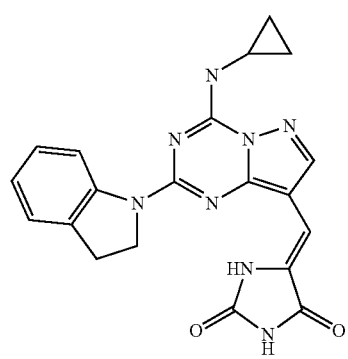 [SMILES: O=C1NC(=O)/C(=C/c2cnn3c(NC4CC4)nc(N4CCc5ccccc54)nc23)N1]
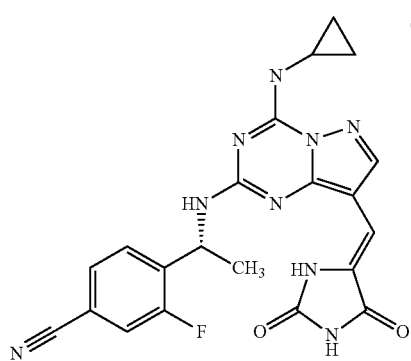
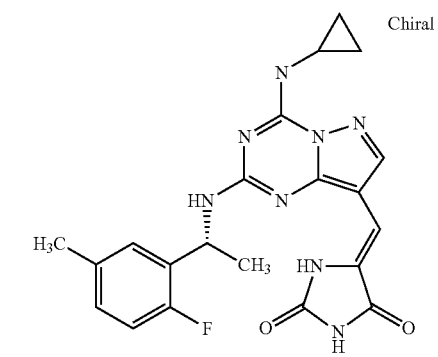 [SMILES: Cc1ccc(F)c([C@@H](C)Nc2nc(NC3CC3)n3ncc(/C=C4\NC(=O)NC4=O)c3n2)c1]
TABLE 37A-continued
462
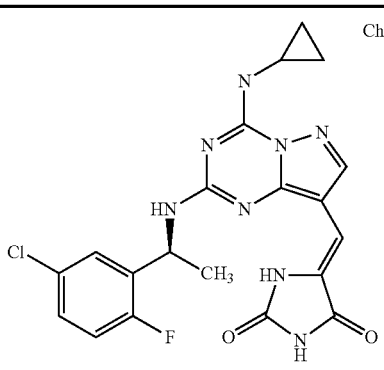
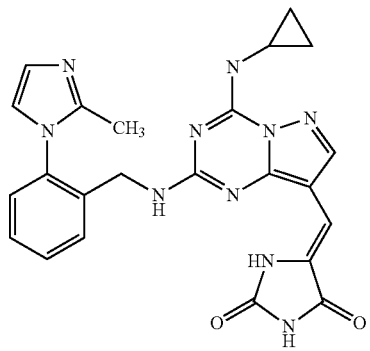 [SMILES: Cc1nccn1-c1ccccc1CNc1nc(NC2CC2)n2ncc(/C=C3\NC(=O)NC3=O)c2n1]
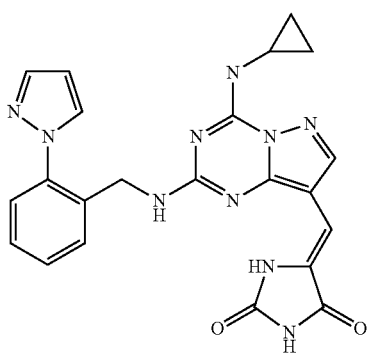 [SMILES: O=C1NC(=O)/C(=C/c2cnn3c(NC4CC4)nc(NCc4ccccc4-n4cccn4)nc23)N1]
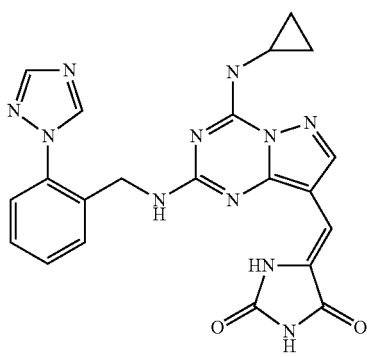 [SMILES: O=C1NC(=O)/C(=C/c2cnn3c(NC4CC4)nc(NCc4ccccc4-n4cncn4)nc23)N1]

TABLE 37A-continued
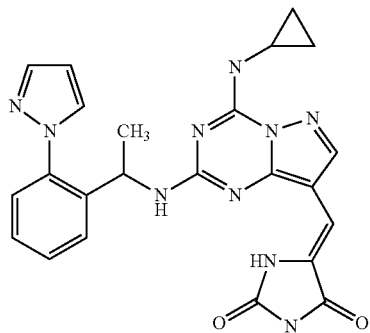
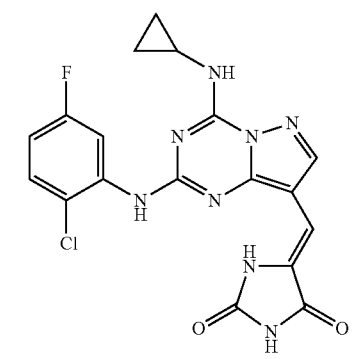 [SMILES: O=C1NC(=O)/C(=C/c2cnn3c(NC4CC4)nc(Nc4cc(F)ccc4Cl)nc23)N1]
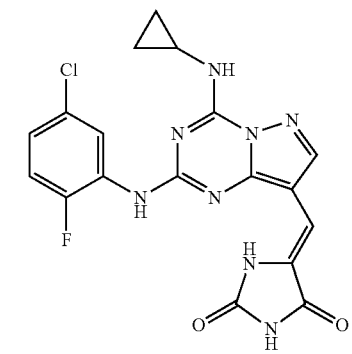
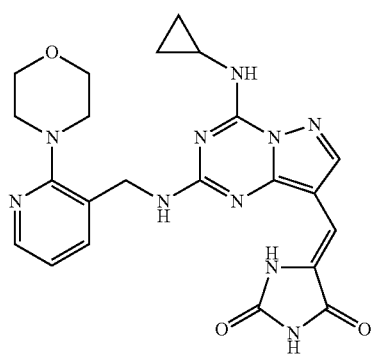 [SMILES: O=C1NC(=O)/C(=C/c2cnn3c(NC4CC4)nc(NCc4cccnc4N4CCOCC4)nc23)N1]
TABLE 37A-continued
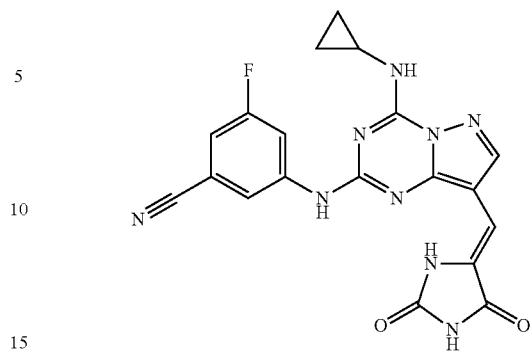
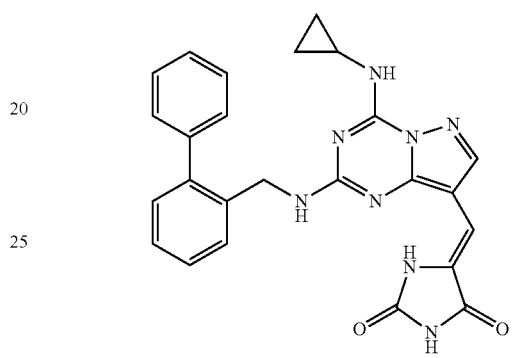
TABLE 37B
| Compound | CK2: IC50 (µM) | PIM2: IC50 (µM) | AB: MDAMB453 (µM) | AB: BxPC3 (µM) |
|---|---|---|---|---|
| A20 | <0.01 | >1.0 | 2.74 | 9.91 |
| B20 | <0.01 | >1.0 | 2.94 | 9.72 |
| C20 | <0.01 | >1.0 | 3.56 | 5.24 |
| D20 | <0.01 | >1.0 | >30 | 29.48 |
| E20 | <0.01 | >1.0 | 3.76 | 8.70 |
| F20 | <0.01 | >1.0 | 4.15 | 3.72 |
| G20 | <0.01 | >1.0 | 6.13 | 6.67 |
| H20 | <0.01 | >1.0 | 5.69 | 6.09 |
| I20 | <0.1 | >1.0 | | |
| J20 | <0.01 | >1.0 | 18.11 | 13.01 |
| K20 | <0.01 | >1.0 | 3.72 | 10.60 |
| L20 | <0.1 | >1.0 | 3.67 | 10.55 |
| M20 | <0.01 | >1.0 | 13.83 | 2.26 |
| N20 | <0.1 | >1.0 | | |
| O20 | <0.1 | >1.0 | | |
| P20 | <0.1 | >1.0 | | |
| Q20 | <0.1 | >1.0 | | |
| R20 | <0.1 | >1.0 | | |
| S20 | <0.1 | >1.0 | | |
| T20 | <0.1 | >1.0 | 3.74 | 1.25 |
| U20 | <0.01 | >1.0 | 3.50 | 6.12 |
| V20 | <0.1 | >1.0 | 19.92 | >30 |
| W20 | <0.01 | >1.0 | 1.93 | 7.97 |
| X20 | <0.1 | >1.0 | 1.16 | 1.69 |
| Y20 | <0.01 | >1.0 | 26.01 | 14.86 |
| A21 | <0.1 | >1.0 | | |
| B21 | <0.01 | >1.0 | 8.33 | 10.81 |
| C21 | <0.1 | >1.0 | | |
| D21 | <0.01 | >1.0 | 16.78 | 13.98 |
| E21 | <0.1 | >1.0 | 1.85 | 1.29 |
| F21 | <0.1 | >1.0 | | |
| G21 | <0.1 | >1.0 | 2.82 | 2.01 |
| H21 | <0.1 | >1.0 | 20.39 | 10.94 |
| I21 | <0.1 | >1.0 | | |
| J21 | <0.1 | >1.0 | | |
| K21 | <0.01 | >1.0 | 2.70 | 8.95 |
| L21 | <0.1 | >1.0 | | |

TABLE 37B-continued

| Compound | CK2: IC50 (μM) | PIM2: IC50 (μM) | AB: MDAMB453 (μM) | AB: BxPC3 (μM) |
| --- | --- | --- | --- | --- |
| M21 | <0.1 | >1.0 | | |
| N21 | <0.1 | >1.0 | 5.47 | 3.23 |
| O21 | <0.1 | >1.0 | 3.71 | 4.03 |
| P21 | <0.1 | >1.0 | 2.89 | 3.27 |
| Q21 | <0.1 | >1.0 | 5.67 | 16.70 |
| R21 | <0.1 | >1.0 | 4.13 | 10.20 |
| S21 | <0.1 | >1.0 | 2.38 | 6.25 |
| T21 | <0.1 | >1.0 | 2.58 | 2.28 |
| U21 | <0.01 | >1.0 | 6.98 | 15.57 |
| V21 | <0.01 | >1.0 | 6.20 | 5.42 |
| W21 | <0.01 | >1.0 | 3.94 | 8.72 |
| X21 | <0.1 | >1.0 | | |
| Y21 | <0.1 | >1.0 | 4.19 | 2.27 |
| Z21 | <0.01 | >1.0 | 7.61 | 22.59 |
| A22 | <0.01 | >1.0 | 0.73 | 0.59 |
| B22 | <0.1 | >1.0 | | |
| C22 | <0.1 | >1.0 | 21.24 | 17.41 |
| D22 | <0.01 | >1.0 | 11.75 | 6.88 |
| E22 | <0.1 | >1.0 | | |
| F22 | <0.1 | >1.0 | 27.68 | >30 |
| G22 | <0.1 | >1.0 | 4.20 | 8.41 |
| H22 | <0.1 | >1.0 | 20.04 | >30 |
| I22 | <0.01 | >1.0 | 2.71 | 4.06 |
| J22 | <0.1 | >1.0 | | |
| K22 | <0.1 | >1.0 | 28.97 | >30 |
| L22 | <0.1 | >1.0 | 5.96 | 10.42 |
| M22 | <0.01 | >1.0 | 1.87 | 5.95 |
| N22 | <0.1 | >1.0 | | |
| O22 | <0.01 | >1.0 | 27.15 | >30 |
| P22 | <0.01 | >1.0 | 27.00 | >30 |
| Q22 | <0.1 | >1.0 | | |
| R22 | <0.01 | >1.0 | 8.05 | 13.51 |
| S22 | <0.01 | >1.0 | 5.45 | 6.60 |
| T22 | <0.1 | >1.0 | | |
| U22 | <0.1 | >1.0 | 5.39 | 6.32 |
| V22 | <0.01 | >1.0 | 2.87 | 3.40 |
| W22 | <0.1 | >1.0 | >30 | >30 |
| X22 | <0.1 | >1.0 | 1.54 | 1.74 |
| Y22 | <0.1 | >1.0 | 4.73 | 8.69 |
| Z22 | <0.1 | >1.0 | 23.14 | >30 |
| A23 | <0.1 | >1.0 | 9.48 | 20.00 |
| B23 | <0.1 | >1.0 | 13.76 | >30 |
| C23 | <0.01 | >1.0 | 18.57 | 19.91 |
| D23 | <0.1 | >1.0 | 3.63 | 6.05 |
| E23 | <0.01 | >1.0 | 6.84 | 9.53 |
| F23 | <0.1 | >1.0 | 10.86 | 3.14 |
| G23 | <0.1 | >1.0 | 23.58 | 6.57 |
| H23 | <0.1 | >1.0 | >30 | >30 |
| I23 | <0.01 | >1.0 | >30 | >30 |
| J23 | <0.1 | >1.0 | >30 | >30 |
| K23 | <0.1 | >1.0 | 6.11 | 4.90 |
| L23 | <0.1 | >1.0 | | |
| M23 | <0.01 | >1.0 | 3.31 | 3.72 |
| N23 | <0.01 | >1.0 | 1.51 | 3.50 |
| O23 | <0.01 | >1.0 | 1.50 | 7.30 |
| P23 | <0.1 | >1.0 | >30 | >30 |
| Q23 | <0.01 | >1.0 | 3.41 | 5.50 |
| R23 | <0.1 | >1.0 | | |
| S23 | <0.01 | >1.0 | 3.14 | 7.65 |
| T23 | <0.01 | >1.0 | 4.34 | 7.98 |
| U23 | <0.01 | >1.0 | 3.15 | 8.98 |
| V23 | <0.1 | >1.0 | 7.48 | 10.27 |
| W23 | <0.01 | >1.0 | 1.70 | 5.15 |
| X23 | <0.01 | >1.0 | 0.69 | 1.15 |
| Y23 | <0.1 | >1.0 | 0.74 | 1.05 |
| Z23 | <0.01 | >1.0 | 1.97 | 7.02 |
| A24 | <0.1 | >1.0 | 11.53 | 16.87 |
| B24 | <0.01 | >1.0 | 19.35 | 7.90 |
| C24 | <0.1 | >1.0 | 6.18 | 10.36 |
| D24 | <1 | >1.0 | | |
| E24 | <0.01 | >1.0 | 1.51 | 5.11 |
| F24 | <0.1 | 0.3139 | | |
| G24 | <1 | >1.0 | | |
| H24 | <0.01 | >1.0 | 2.71 | 5.32 |
| I24 | <0.1 | >1.0 | | |
| J24 | <1 | >1.0 | | |
| K24 | <0.1 | >1.0 | 10.24 | 14.11 |
| L24 | | >1.0 | | |
| M24 | <1 | >1.0 | | |
| N24 | <0.1 | >1.0 | | |
| O24 | <0.1 | >1.0 | | |
| P24 | <0.1 | >1.0 | >30 | >30 |
| Q24 | <0.1 | >1.0 | | |
| R24 | <0.1 | >1.0 | 22.35 | >30 |
| S24 | | >1.0 | | |
| T24 | <0.1 | >1.0 | | |
| U24 | | >1.0 | | |
| V24 | <1 | >1.0 | | |
| W24 | <0.1 | >1.0 | | |
| X24 | <0.1 | >1.0 | 22.69 | 27.22 |
| Y24 | <0.1 | >1.0 | | |
| Z24 | <1 | >1.0 | | |
| A25 | <0.1 | >1.0 | | |
| B25 | <0.1 | >1.0 | | |
| C25 | <0.1 | >1.0 | 3.22 | 5.27 |
| D25 | <0.1 | >1.0 | 0.96 | 0.64 |
| E25 | <1 | >1.0 | | |
| F25 | <0.1 | >1.0 | | |
| G25 | <1 | >1.0 | | |
| H25 | <0.1 | >1.0 | | |
| I25 | <0.1 | >1.0 | 3.44 | 3.77 |
| J25 | <0.1 | >1.0 | 6.41 | 10.51 |
| K25 | <0.1 | >1.0 | 8.29 | 10.75 |
| L25 | <0.1 | >1.0 | 3.74 | 5.24 |
| M25 | <0.1 | >1.0 | >30 | >30 |
| N25 | <0.1 | >1.0 | | |
| O25 | <0.1 | >1.0 | | |
| P25 | <0.1 | >1.0 | | |
| Q25 | <0.01 | >1.0 | 1.37 | 2.36 |
| R25 | <0.1 | >1.0 | | |
| S25 | <1 | >1.0 | | |
| T25 | <0.1 | >1.0 | 6.64 | 6.40 |
| U25 | <0.1 | >1.0 | >30 | >30 |
| V25 | <0.1 | >1.0 | 26.87 | >30 |
| W25 | <0.1 | >1.0 | 5.69 | 8.74 |
| X25 | <0.01 | >1.0 | >30 | >30 |
| Y25 | <1 | >1.0 | | |
| Z25 | <0.1 | >1.0 | 2.32 | 2.49 |
| A26 | <0.1 | >1.0 | | |
| B26 | <0.1 | >1.0 | | |
| C26 | | >1.0 | | |
| D26 | | >1.0 | | |
| E26 | <0.1 | >1.0 | | |
| F26 | <0.1 | >1.0 | | |
| G26 | <0.1 | >1.0 | 14.46 | 12.56 |
| H26 | <0.1 | >1.0 | >30 | >30 |
| I26 | <0.1 | >1.0 | | |
| J26 | <0.1 | >1.0 | | |
| K26 | <0.1 | >1.0 | | |
| L26 | <0.1 | >1.0 | 3.70 | 2.98 |
| M26 | <0.1 | >1.0 | | |
| N26 | <0.1 | >1.0 | 6.88 | 10.46 |
| O26 | <0.1 | >1.0 | | |
| P26 | <0.1 | >1.0 | 2.51 | 10.63 |
| Q26 | <0.01 | >1.0 | 6.79 | 15.48 |
| R26 | <0.1 | >1.0 | | |
| S26 | <0.1 | >1.0 | | |
| T26 | <0.1 | >1.0 | 14.73 | 10.23 |
| U26 | <0.1 | >1.0 | 7.93 | 11.66 |
| V26 | <1 | >1.0 | | |
| W26 | <0.1 | >1.0 | 8.01 | 14.51 |
| X26 | <0.1 | >1.0 | | |
| Y26 | <0.1 | >1.0 | | |
| Z26 | <0.01 | >1.0 | 7.42 | 12.88 |
| A27 | <0.1 | >1.0 | | |
| B27 | <0.01 | >1.0 | 2.29 | 3.16 |
| C27 | <0.01 | >1.0 | 13.60 | 9.56 |
| D27 | <0.1 | >1.0 | | |
| E27 | <0.1 | >1.0 | >30 | >30 |
| F27 | <0.01 | >1.0 | 3.49 | 6.00 |
| G27 | <0.01 | >1.0 | >30 | >30 |
| H27 | <0.1 | >1.0 | | |

TABLE 37B-continued

| Compound | CK2: IC50 (μM) | PIM2: IC50 (μM) | AB: MDAMB453 (μM) | AB: BxPC3 (μM) |
|---|---|---|---|---|
| I27 | <0.01 | >1.0 | 13.29 | 21.63 |
| J27 | <0.01 | >1.0 | 23.48 | 28.75 |
| K27 | <0.01 | >1.0 | 3.70 | 4.28 |
| L27 | <0.1 | >1.0 | 7.37 | 9.46 |
| M27 | <0.1 | >1.0 | 12.13 | 14.19 |
| N27 | <1 | >1.0 | | |
| O27 | <0.01 | >1.0 | 3.17 | 9.00 |
| P27 | <0.01 | >1.0 | 24.48 | >30 |
| Q27 | <0.1 | >1.0 | 6.81 | 15.80 |
| R27 | <0.01 | >1.0 | 8.99 | 22.92 |
| S27 | <0.1 | >1.0 | 5.62 | 9.03 |
| T27 | <0.01 | >1.0 | 9.22 | 14.72 |
| U27 | <0.1 | >1.0 | 8.49 | 11.07 |
| V27 | <0.01 | >1.0 | >30 | >30 |
| W27 | <0.1 | >1.0 | 8.88 | 10.03 |
| X27 | <0.1 | >1.0 | 4.98 | 9.72 |
| Y27 | <0.01 | >1.0 | 23.52 | 17.78 |
| Z27 | <0.1 | >1.0 | 4.54 | 3.82 |
| A28 | <0.01 | >1.0 | 8.86 | 5.77 |
| B28 | <0.01 | >1.0 | 7.71 | 11.04 |
| C28 | <0.1 | >1.0 | 5.34 | 10.75 |
| D28 | <0.01 | >1.0 | 4.71 | 4.58 |
| E28 | <0.1 | >1.0 | >30 | >30 |
| F28 | <0.01 | >1.0 | 4.15 | 9.71 |
| G28 | <0.1 | >1.0 | | |
| H28 | <0.01 | >1.0 | 0.56 | 0.44 |
| I28 | <0.01 | >1.0 | 14.01 | 16.36 |
| J28 | <0.01 | >1.0 | 4.22 | 8.17 |
| K28 | <0.1 | >1.0 | 3.95 | 5.59 |
| L28 | <0.01 | >1.0 | 6.78 | 13.76 |
| M28 | <0.1 | >1.0 | 19.32 | 18.05 |
| N28 | <0.1 | >1.0 | | |
| O28 | <0.01 | >1.0 | 9.84 | |
| P28 | <0.1 | >1.0 | 11.59 | 18.01 |
| Q28 | <0.1 | >1.0 | | |
| R28 | <0.1 | >1.0 | | |
| S28 | <0.1 | >1.0 | | |
| T28 | <0.1 | >1.0 | | |
| U28 | <0.1 | >1.0 | | |
| V28 | <0.1 | >1.0 | >30 | >30 |
| W28 | <1 | >1.0 | | |
| X28 | <0.1 | >1.0 | 7.47 | 10.71 |
| Y28 | <0.1 | >1.0 | >30 | >30 |
| Z28 | <0.1 | >1.0 | 29.43 | >30 |
| A29 | <0.1 | >1.0 | 3.45 | 4.14 |
| B29 | <0.01 | >1.0 | 2.23 | 4.14 |
| C29 | <0.1 | >1.0 | 17.86 | 24.12 |
| D29 | <0.01 | >1.0 | 10.09 | 11.48 |
| E29 | <0.01 | >1.0 | 4.76 | 5.38 |
| F29 | <0.1 | >1.0 | 29.82 | >30 |
| G29 | <0.1 | >1.0 | 7.04 | >30 |
| H29 | <0.1 | >1.0 | 6.62 | 15.18 |
| I29 | <0.01 | >1.0 | 16.94 | 20.64 |
| J29 | <0.01 | >1.0 | 4.01 | 7.66 |
| K29 | <0.1 | >1.0 | 10.85 | 15.18 |
| L29 | <1 | >1.0 | | |
| M29 | <0.01 | >1.0 | 4.10 | 4.29 |
| N29 | <0.1 | >1.0 | 15.63 | 26.05 |
| O29 | <0.1 | >1.0 | 5.78 | >30 |
| P29 | <0.01 | >1.0 | 4.00 | 6.71 |
| Q29 | <0.1 | >1.0 | 7.70 | 22.86 |
| R29 | <0.01 | >1.0 | 5.92 | 4.53 |
| S29 | <0.1 | >1.0 | | |
| T29 | <0.1 | >1.0 | 11.56 | 13.01 |
| U29 | <0.1 | >1.0 | | |
| V29 | <0.1 | >1.0 | 8.44 | 18.96 |
| W29 | <0.01 | >1.0 | 26.85 | >30 |
| X29 | >1.0 | >1.0 | | |
| Y29 | <0.01 | >1.0 | 8.00 | 2.95 |
| Z29 | <0.1 | >1.0 | 8.38 | 5.67 |
| A30 | <0.1 | >1.0 | 29.76 | 23.57 |
| B30 | <0.01 | >1.0 | 3.24 | 2.56 |
| C30 | <0.1 | >1.0 | 18.56 | 26.35 |
| D30 | <0.1 | >1.0 | | |
| E30 | <0.01 | >1.0 | 2.19 | 9.74 |
| F30 | <0.1 | >1.0 | 18.92 | 23.77 |
| G30 | <0.01 | >1.0 | 4.79 | 10.58 |
| H30 | <0.1 | >1.0 | 15.60 | 16.24 |
| I30 | <0.01 | >1.0 | 6.83 | 5.09 |
| J30 | <0.01 | >1.0 | 2.79 | 2.15 |
| K30 | <0.1 | >1.0 | | |
| L30 | <0.1 | >1.0 | 7.00 | 4.33 |
| M30 | <0.01 | >1.0 | 27.24 | 6.01 |
| N30 | <0.1 | >1.0 | 15.00 | 16.45 |
| O30 | <0.01 | >1.0 | 24.87 | >30 |
| P30 | <0.1 | >1.0 | | |
| Q30 | <0.1 | >1.0 | | |
| R30 | <0.1 | >1.0 | 5.13 | 5.78 |
| S30 | <0.01 | >1.0 | 6.08 | 10.90 |
| T30 | <0.1 | >1.0 | | |
| U30 | <0.1 | >1.0 | | |
| V30 | <0.1 | >1.0 | | |
| W30 | <0.01 | >1.0 | 5.22 | 4.57 |
| X30 | <0.1 | >1.0 | 6.50 | 10.50 |
| Y30 | <0.01 | >1.0 | 5.29 | >30 |
| Z30 | <0.1 | >1.0 | 4.58 | 9.62 |
| A31 | <0.1 | >1.0 | 18.05 | 14.55 |
| B31 | <0.1 | >1.0 | | |
| C31 | <0.1 | >1.0 | | |
| D31 | <0.01 | >1.0 | 9.70 | 7.68 |
| E31 | | >1.0 | | |
| F31 | <0.1 | >1.0 | 5.36 | 6.37 |
| G31 | <1 | >1.0 | | |
| H31 | <1 | >1.0 | | |
| I31 | <0.1 | >1.0 | 5.18 | 7.09 |
| J31 | <1 | >1.0 | | |
| K31 | <0.1 | >1.0 | | |
| L31 | <0.1 | >1.0 | 10.06 | 10.32 |
| M31 | <0.1 | >1.0 | | |
| N31 | <0.1 | >1.0 | >30 | 14.17 |
| O31 | <0.1 | >1.0 | >30 | 21.98 |
| P31 | <1 | >1.0 | | |
| Q31 | <0.1 | >1.0 | 4.33 | 10.82 |
| R31 | <0.1 | >1.0 | | |
| S31 | <0.01 | >1.0 | 5.48 | 14.80 |
| T31 | <0.1 | >1.0 | 6.49 | 11.98 |
| U31 | <0.01 | >1.0 | 9.66 | 25.85 |
| V31 | <0.01 | >1.0 | 2.79 | 10.92 |
| W31 | <0.1 | >1.0 | 6.17 | 10.06 |
| X31 | <0.01 | >1.0 | 4.39 | 15.46 |
| Y31 | <0.1 | >1.0 | | |
| Z31 | <0.1 | >1.0 | 10.86 | >30 |
| A32 | <0.01 | >1.0 | 21.98 | >30 |
| B32 | <0.1 | >1.0 | | |
| C32 | <0.1 | >1.0 | >30 | >30 |
| D32 | <0.1 | >1.0 | | |
| E32 | <0.1 | >1.0 | | |
| F32 | <0.1 | >1.0 | >30 | >30 |
| G32 | <0.1 | >1.0 | >30 | 5.13 |
| H32 | <0.01 | >1.0 | >30 | >30 |
| I32 | <0.01 | >1.0 | 5.73 | 11.31 |
| J32 | <0.1 | >1.0 | | |
| K32 | <0.1 | >1.0 | 1.20 | 1.15 |
| L32 | <0.1 | >1.0 | 6.70 | 10.66 |
| M32 | <0.1 | >1.0 | 0.21 | 0.18 |
| N32 | <0.1 | >1.0 | 2.80 | 3.96 |
| O32 | <0.1 | >1.0 | | |
| P32 | <0.1 | >1.0 | | |
| Q32 | <0.1 | >1.0 | >30 | >30 |
| R32 | <0.01 | >1.0 | >30 | >30 |
| S32 | <0.01 | >1.0 | 3.45 | 11.90 |
| T32 | <0.01 | >1.0 | 6.79 | 25.42 |
| U32 | <0.01 | >1.0 | 4.35 | 9.97 |
| V32 | <0.1 | >1.0 | 7.38 | 11.29 |
| W32 | <0.01 | >1.0 | 2.55 | 8.92 |
| X32 | <0.1 | >1.0 | 9.82 | 17.08 |
| Y32 | <0.1 | >1.0 | 5.98 | 16.43 |
| Z32 | <0.01 | >1.0 | 4.10 | 13.91 |
| A33 | >1 | >1.0 | | |
| B33 | <0.01 | >1.0 | 4.15 | 9.63 |
| C33 | <0.1 | >1.0 | 6.35 | 11.94 |
| D33 | <0.1 | >1.0 | | |

TABLE 37B-continued

| Compound | CK2: IC50 (µM) | PIM2: IC50 (µM) | AB: MDAMB453 (µM) | AB: BxPC3 (µM) |
|---|---|---|---|---|
| E33 | <0.01 | >1.0 | 4.19 | 2.41 |
| F33 | <0.01 | >1.0 | 1.36 | 6.58 |
| G33 | <0.01 | >1.0 | 1.65 | 13.48 |
| H33 | <0.01 | >1.0 | 3.00 | 8.68 |
| I33 | <0.01 | >1.0 | 1.09 | 2.18 |
| J33 | <0.01 | >1.0 | 1.48 | 3.81 |
| K33 | <0.01 | >1.0 | 3.27 | 12.36 |
| L33 | <0.01 | >1.0 | 1.49 | 6.81 |
| M33 | <0.01 | >1.0 | 1.60 | 11.02 |
| N33 | <0.01 | >1.0 | 0.85 | 8.92 |
| O33 | <0.01 | >1.0 | 2.56 | 3.75 |
| P33 | <0.01 | >1.0 | | |
| Q33 | | >1.0 | | |

Example 225

Synthesis of (Z)-5-((4-(cyclopropylamino)-2-(1H-imidazol-1-yl)pyrazolo[1,5-a][1,3,5]triazin-8-yl)methylene)imidazolidine-2,4-dione

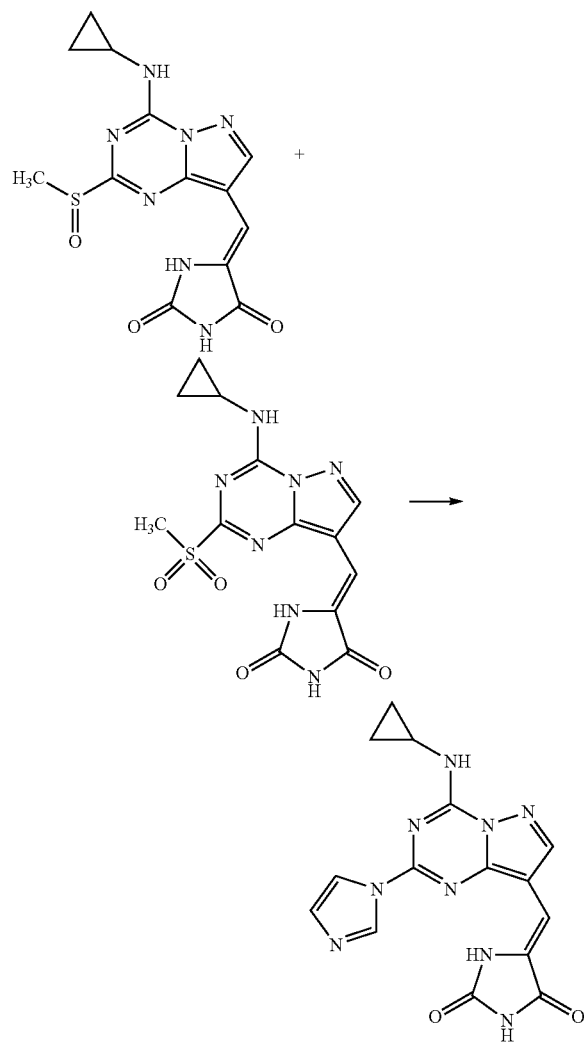

A mixture of (Z)-5-((4-(cyclopropylamino)-2-(methylsulfinyl)pyrazolo[1,5-a][1,3,5]triazin-8-yl)methylene)imidazolidine-2,4-dione and (Z)-5-((4-(cyclopropylamino)-2-(methylsulfonyl)pyrazolo[1,5-a][1,3,5]triazin-8-yl)methylene)imidazolidine-2,4-dione (10 mg, 0.028 mmol) was mixed with imidazole (6 mg, 0.084 mmol) in isopropanol (1 mL). The mixture was stirred at 80° C. for 16 h. The reaction mixture was cooled to room temperature and the resulting solid was filtered off and washed with isopropanol. The solid was dried under vacuum to provide (Z)-5-((4-(cyclopropylamino)-2-(1H-imidazol-1-yl)pyrazolo[1,5-a][1,3,5]triazin-8-yl)methylene)imidazolidine-2,4-dione as a yellow solid. LCMS (ES):>95% pure, m/z 352 [M+H]$^+$.

Example 226

Synthesis of (Z)-1-(4-(cyclopropylamino)-8-(2,5-dioxoimidazolidin-4-ylidene)methyl)pyrazolo[1,5-a][1,3,5]triazin-2-yl)-1H-benzo[d]imidazole-5-carboxylic acid

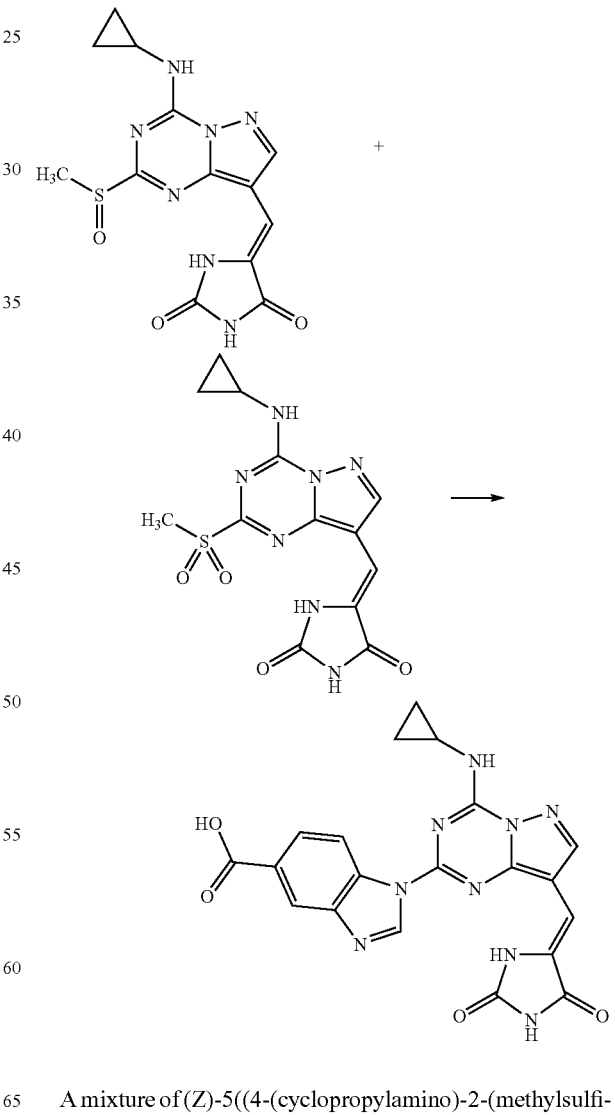

A mixture of (Z)-5((4-(cyclopropylamino)-2-(methylsulfinyl)pyrazolo[1,5-a][1,3,5]triazin-8-yl)methylene)imidazolidine-2,4-dione and (Z)-5-((4-(cyclopropylamino)-2-(methylsulfonyl)pyrazolo[1,5-a][1,3,5]triazin-8-yl)methylene)imidazolidine-2,4-dione (10 mg, 0.028 mmol) was mixed with 1H-benzo[d]imidazole-5-carboxylic acid (20 mg, 0.140 mmol) in isopropanol (1 mL). The mixture was stirred under microwave heating at 150° C. for 20 minutes. The solvent was removed to provide (Z)-1-(4-(cyclopropylamino)-8-((2,5-dioxoimidazolidin-4-ylidene)methyl)pyrazolo[1,5-a][1,3,5]triazin-2-yl)-1H-benzo[d]imidazole-5-carboxylic acid as a crude mixture which was taken on to the next step without further purification. LCMS (ES):>95% pure, m/z 446 [M+H]+

Example 227

Synthesis of (Z)-5-((4-(cyclopropylamino)-2-(5-(4-ethylpiperazine-1-carbonyl)-1H-benzo[d]imidazol-1-yl)pyrazolo[1,5-a][1,3,5]triazin-8-yl)methylene)imidazolidine-2,4-dione

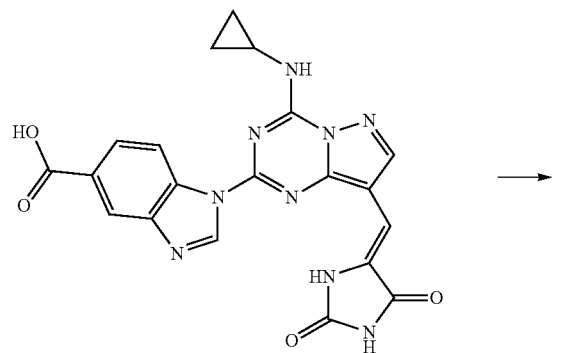

To (Z)-1-(4-(cyclopropylamino)-8-((2,5-dioxoimidazolidin-4-ylidene)methyl)pyrazolo[1,5-a][1,3,5]triazin-2-yl)-1H-benzo[d]imidazole-5-carboxylic acid (15 mg, 0.034 mmol) in DMF (2 mL) was added EDCI (65 mg, 0.34 mmol), HOBt (46 mg, 0.34 mmol), and 1-ethylpiperazine (44 µL, 0.34 mmol). The mixture was stirred at 50° C. for 1 h. The reaction mixture was cooled to room temperature, filtered through PTFE filter, and purified by mass-directed LC/MS to provide (Z)-5-((4-(cyclopropylamino)-2-(5-(4-ethylpiperazine-1-carbonyl)-1H-benzo[d]imidazol-1-yl)pyrazolo[1,5-a][1,3,5]triazin-8-yl)methylene)imidazolidine-2,4-dione as the TFA salt. LCMS (ES):>95% pure, m/z 542 [M+H]+.

Example 228

Synthesis of (Z)-1-(4-(cyclopropylamino)-8-((2,5-dioxoimidazolidin-4-ylidene)methyl)pyrazolo[1,5-a][1,3,5]-triazin-2-yl)-1H-imidazole-4-carbaldehyde

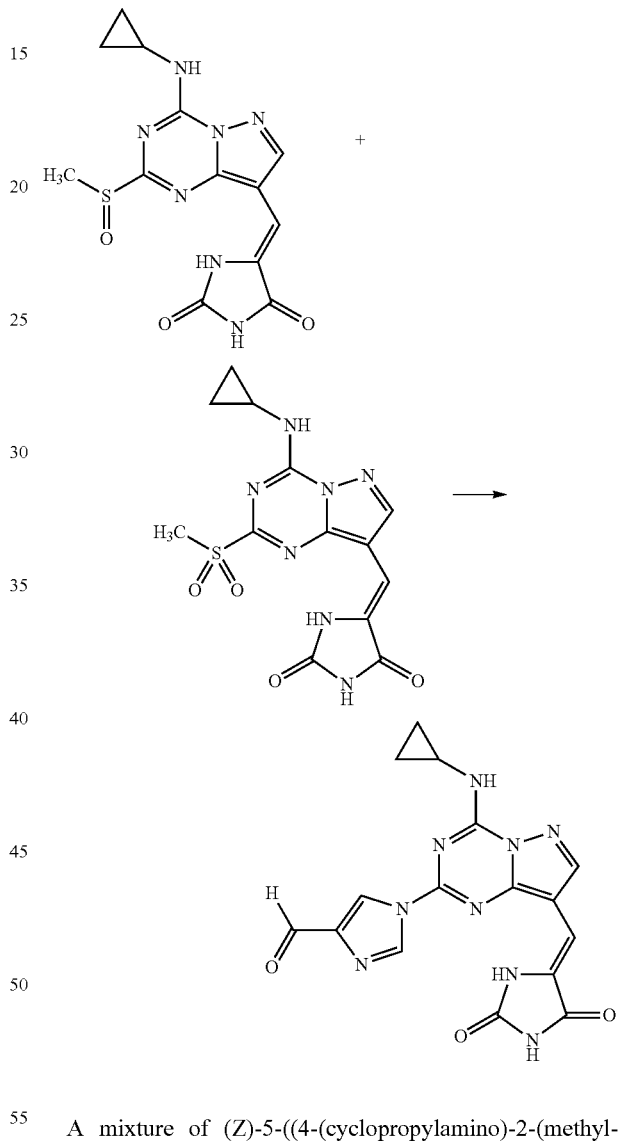

A mixture of (Z)-5-((4-(cyclopropylamino)-2-(methylsulfinyl)pyrazolo[1,5-a][1,3,5]triazin-8-yl)methylene)imidazolidine-2,4-dione and (Z)-5-((4-(cyclopropylamino)-2-(methylsulfonyl)pyrazolo[1,5-a][1,3,5]triazin-8-yl)methylene)imidazolidine-2,4-dione (20 mg, 0.056 mmol) was mixed with 1H-imidazole-4-carbaldehyde (16 mg, 0.168 mmol) in isopropanol (2 mL). The mixture was stirred under microwave heating at 150° C. for 20 minutes. The reaction mixture was cooled to room temperature and the solvent was removed by rotary evaporation to provide (Z)-1-(4-(cyclopropylamino)-8-((2,5-dioxoimidazolidin-4-ylidene)methyl)pyrazolo[1,5-a][1,3,5]triazin-2-yl)-1H-imidazole-4-carbaldehyde as a crude mixture which was taken on to the next step without further purification. LCMS (ES):>95% pure, m/z 380 [M+H]+

Example 229

Synthesis of (Z)-5-((4-(cyclopropylamino)-2-(4-(pyrrolidin-1-ylmethyl)-1H-imidazol-1-yl)pyrazolo[1,5-a][1,3,5]triazin-8-yl)methylene)imidazolidine-2,4-dione

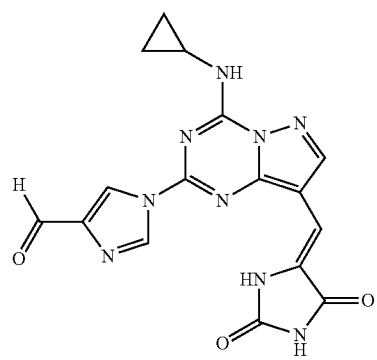

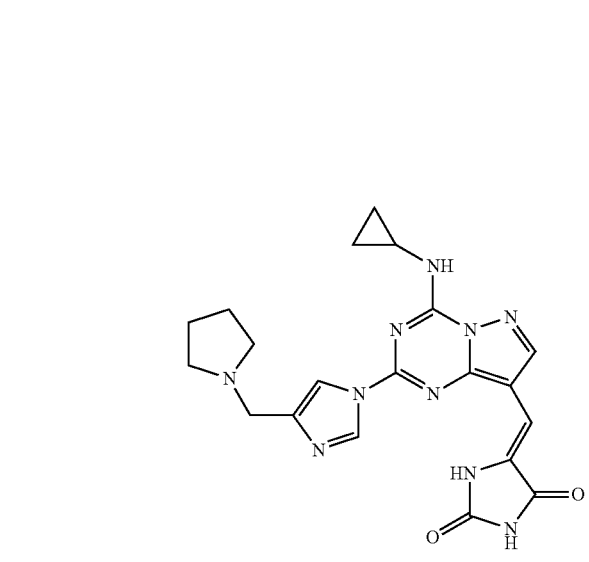

To (Z)-1-(4-(cyclopropylamino)-8-((2,5-dioxoimidazolidin-4-ylidene)methyl)pyrazolo[1,5-a][1,3,5]triazin-2-yl)-1H-imidazole-4-carbaldehyde (7 mg, 0.018 mmol) in DCE (1 mL) was added pyrrolidine (10 mg, 0.144 mmol) and sodium triacetoxyborohydride (36 mg, 0.144 mmol). The reaction mixture was stirred under microwave heating at 120° C. for 10 minutes. Dilute with DMSO (1 mL) and filter through PTFE filter. Purified by mass-directed LC/MS to provide (Z)-5-((4-(cyclopropylamino)-2-(4-(pyrrolidin-1-ylmethyl)-1H-imidazol-1-yl)pyrazolo[1,5-a][1,3,5]triazin-8-yl)methylene)imidazolidine-2,4-dione as the TFA salt. LCMS (ES): >95% pure, m/z 435 [M+H]+

The compounds in the following table were prepared using chemistries described in Examples 225 to 229. Table 38B shows the biological activities of the compounds listed in Table 38A.

TABLE 38A

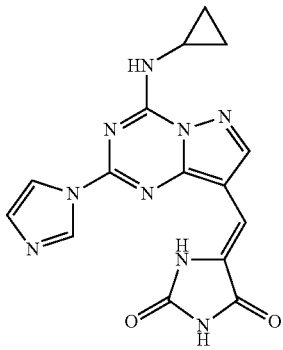 [SMILES: O=C1NC(=O)/C(=C/c2cnn3c(NC4CC4)nc(-n4ccnc4)nc23)N1]

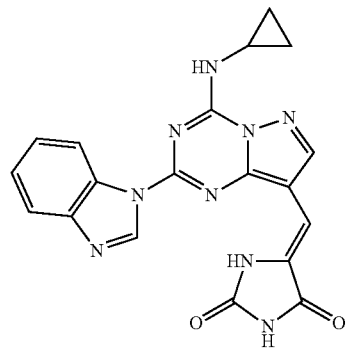 [SMILES: O=C1NC(=O)/C(=C/c2cnn3c(NC4CC4)nc(-n4cnc5ccccc54)nc23)N1]

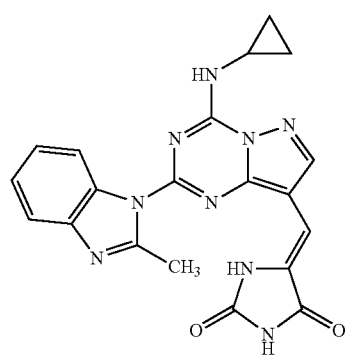 [SMILES: Cc1nc2ccccc2n1-c1nc(NC2CC2)n2ncc(/C=C3\NC(=O)NC3=O)c2n1]

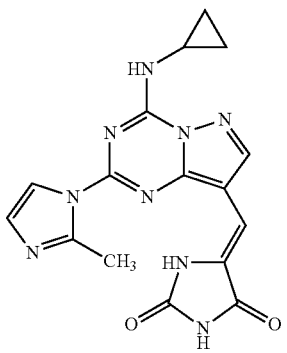 [SMILES: Cc1nccn1-c1nc(NC2CC2)n2ncc(/C=C3\NC(=O)NC3=O)c2n1]

| 475 | 476 |
|---|---|
| TABLE 38A-continued | TABLE 38A-continued |
| 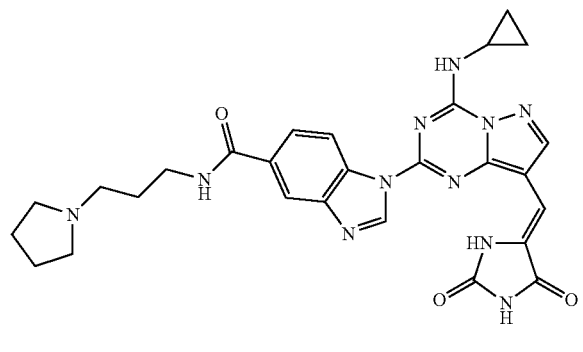 [SMILES: O=C1NC(=O)/C(=C/c2cnn3c(NC4CC4)nc(-n4cnc5cc(C(=O)NCCCN6CCCC6)ccc54)nc23)N1] | 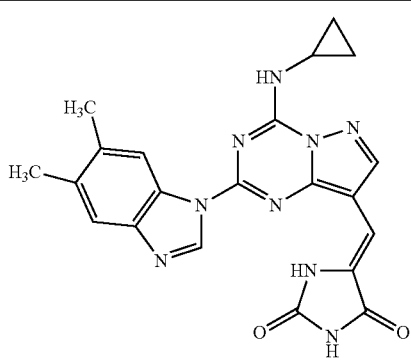 |
| 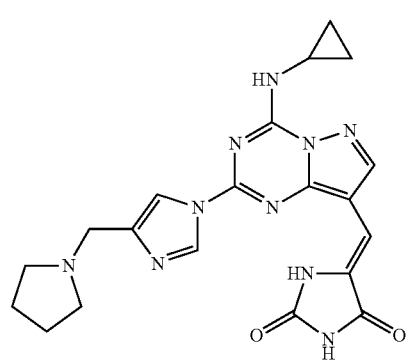 [SMILES: O=C1NC(=O)/C(=C/c2cnn3c(NC4CC4)nc(-n4cnc(CN5CCCC5)c4)nc23)N1] | 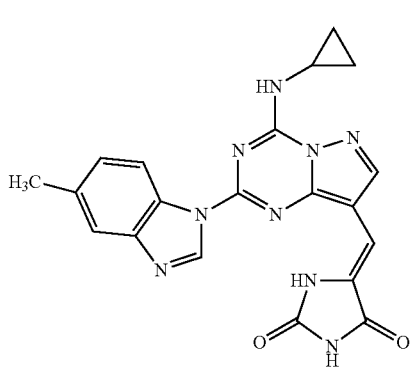 |
| 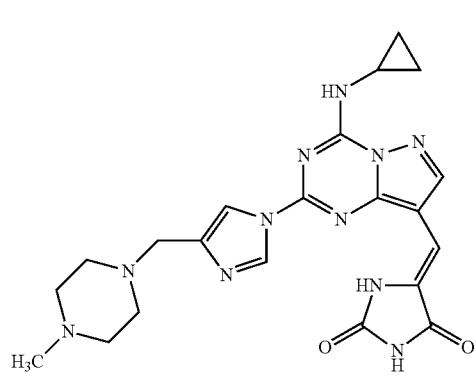 [SMILES: CN1CCN(Cc2cn(-c3nc(NC4CC4)n4ncc(/C=C5\NC(=O)NC5=O)c4n3)cn2)CC1] | 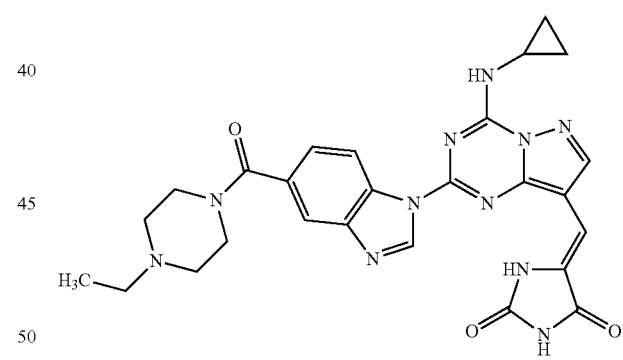 |
| 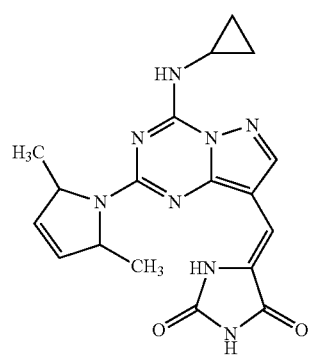 [SMILES: CC1C=CC(C)N1c1nc(NC2CC2)n2ncc(/C=C3\NC(=O)NC3=O)c2n1] | 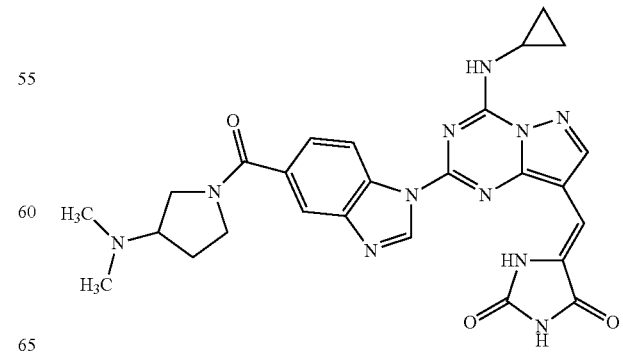 |

TABLE 38A-continued

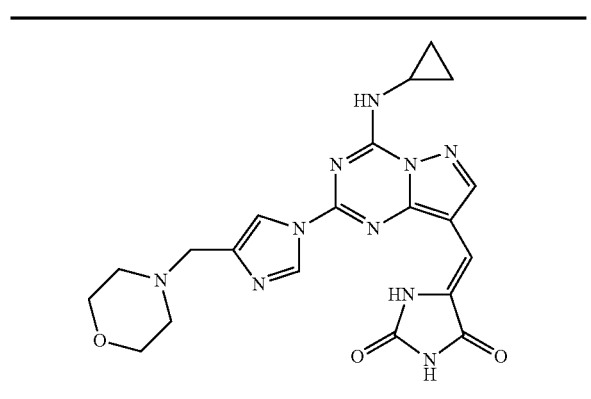

TABLE 38B

| Compound | CK2: IC50 (μM) | PIM2: IC50 (μM) | AB: MDAMB453 (μM) | AB: BxPC3 (μM) |
|---|---|---|---|---|
| R33 | <0.01 | >1.0 | 3.45 | 4.67 |
| S33 | <0.01 | >1.0 | 6.40 | 5.20 |
| T33 | <0.01 | >1.0 | 1.03 | 1.25 |
| U33 | <0.01 | >1.0 | 12.21 | 23.77 |
| V33 | <0.1 | >1.0 | | |
| W33 | <0.01 | >1.0 | 0.74 | 0.78 |
| X33 | <0.01 | >1.0 | >30 | >30 |
| Y33 | <0.1 | >1.0 | | |
| Z33 | <0.1 | >1.0 | 14.60 | 15.71 |
| A34 | <0.1 | >1.0 | | |
| B34 | <1 | >1.0 | | |
| C34 | <0.1 | >1.0 | | |
| D34 | <1 | >1.0 | | |

Example 230

Synthesis of (Z)-5-((2-(3-chlorophenoxy)-4-(cyclopropylamino)pyrazolo[1,5-a][1,3,5]triazin-8-yl)methylene)imidazolidine-2,4-dione

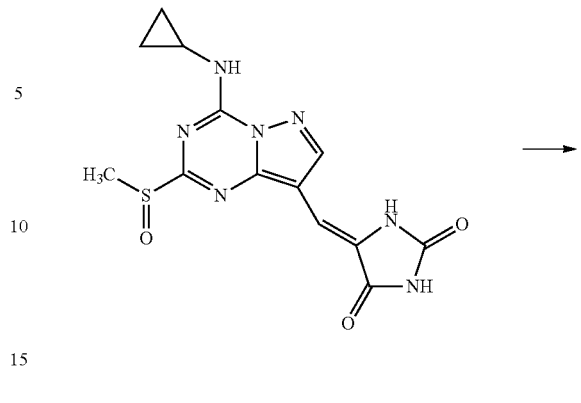

A (1:1) mixture of (Z)-5-((4-(cyclopropylamino)-2-(methylsulfonyl)pyrazolo[1,5-a][1,3,5]triazin-8-yl)methylene)imidazolidine-2,4-dione and (Z)-5-((4-(cyclopropylamino)-2-(methylsulfinyl)pyrazolo[1,5-a][1,3,5]triazin-8-yl)methylene)imidazolidine-2,4-dione (1.0 eq, 25 mg, 0.0704 mmol) was combined in a vial with 3-chlorophenol (5.0 eq, 45 mg, 0.35 mmol) and $K_2CO_3$ (5.0 eq, 48 mg, 0.347 mmol) in NMP (0.2 ml). The mixture was stirred at 90° C. for 1 hour. Water was added and the resulting solid was filtered and dried. Trituration in a mixture of ethyl acetate and hexanes followed by filtration provided (Z)-5-((2-(3-chlorophenoxy)-4-(cyclopropylamino)pyrazolo[1,5-a][1,3,5]triazin-8-yl)methylene)imidazolidine-2,4-dione as a tan solid (20 mg, 69%). LCMS (ES):>95% pure, m/z 412 [M+H]+.

The following compounds were prepared using the chemistry described in Example 230. Table 39B shows the biological activities of the compounds listed in Table 39A.

TABLE 39A

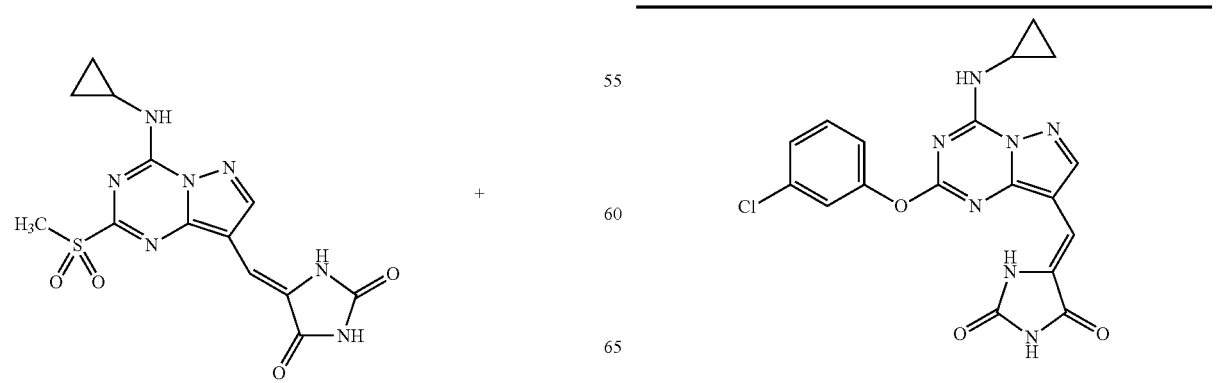

479 480
TABLE 39A-continued | TABLE 39A-continued
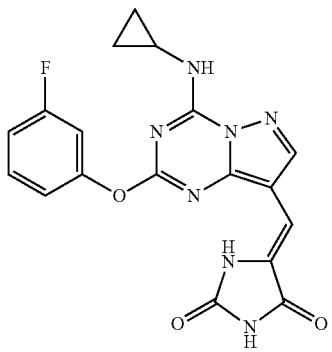 [SMILES: O=C1NC(=O)/C(=C/c2cnn3c(NC4CC4)nc(Oc4cccc(F)c4)nc23)N1]
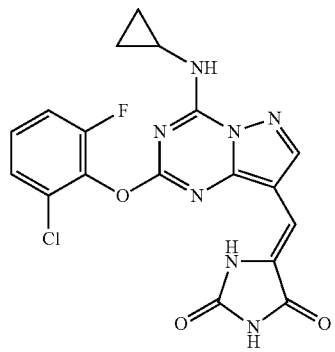
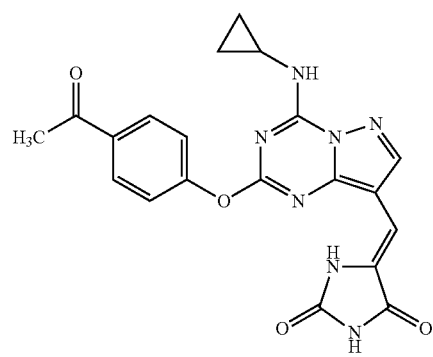 [SMILES: CC(=O)c1ccc(Oc2nc(NC3CC3)n3ncc(/C=C4\NC(=O)NC4=O)c3n2)cc1]
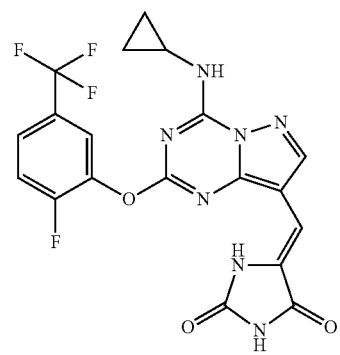 [SMILES: O=C1NC(=O)/C(=C/c2cnn3c(NC4CC4)nc(Oc4cc(C(F)(F)F)ccc4F)nc23)N1]
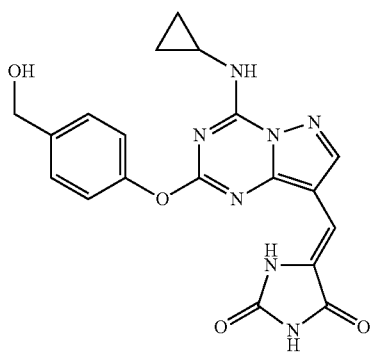
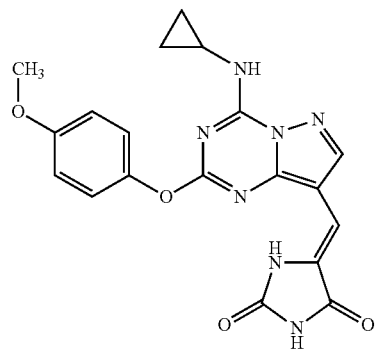 [SMILES: COc1ccc(Oc2nc(NC3CC3)n3ncc(/C=C4\NC(=O)NC4=O)c3n2)cc1]
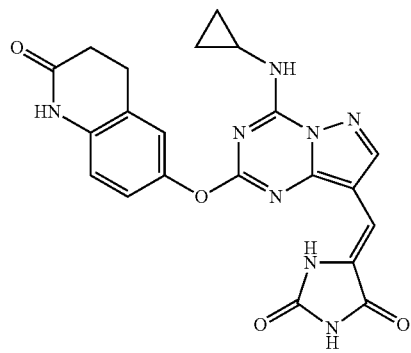 [SMILES: O=C1CCc2cc(Oc3nc(NC4CC4)n4ncc(/C=C5\NC(=O)NC5=O)c4n3)ccc2N1]

| 481 | 482 |
|---|---|
| TABLE 39A-continued | TABLE 39A-continued |
| 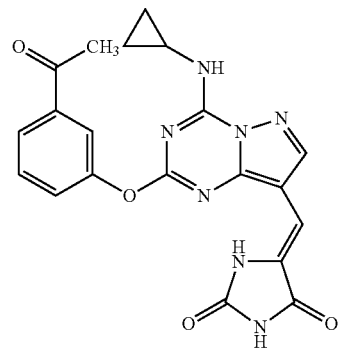 [SMILES: CC(=O)c1cccc(Oc2nc(NC3CC3)n3ncc(/C=C4\NC(=O)NC4=O)c3n2)c1] | 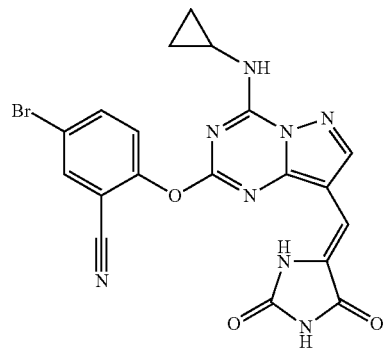 |
| 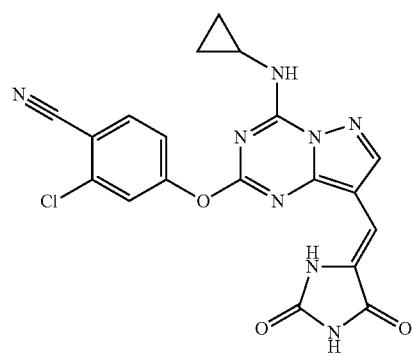 | 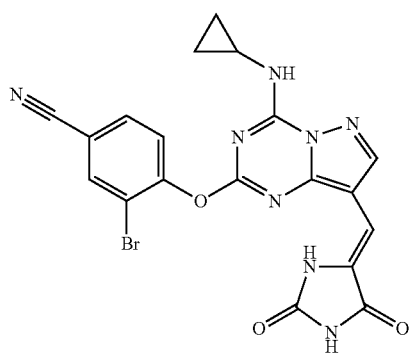 |
| 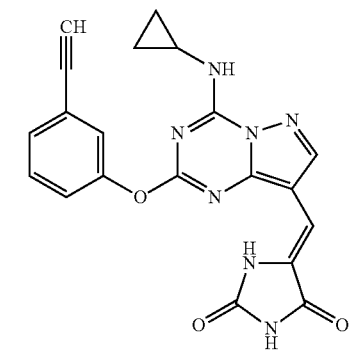 [SMILES: C#Cc1cccc(Oc2nc(NC3CC3)n3ncc(/C=C4\NC(=O)NC4=O)c3n2)c1] | 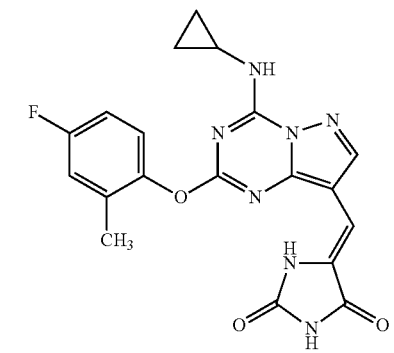 |
| 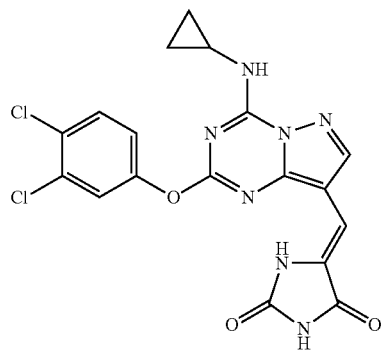 [SMILES: O=C1NC(=O)/C(=C/c2cnn3c(NC4CC4)nc(Oc4ccc(Cl)c(Cl)c4)nc23)N1] | 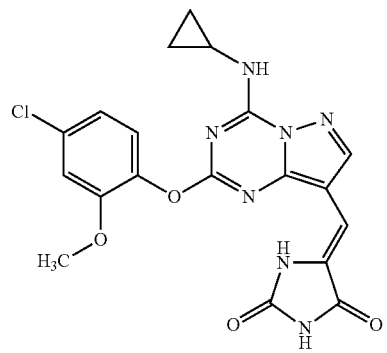 [SMILES: COc1cc(Cl)ccc1Oc1nc(NC2CC2)n2ncc(/C=C3\NC(=O)NC3=O)c2n1] |

TABLE 39A-continued
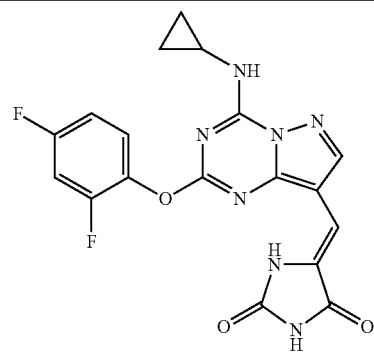
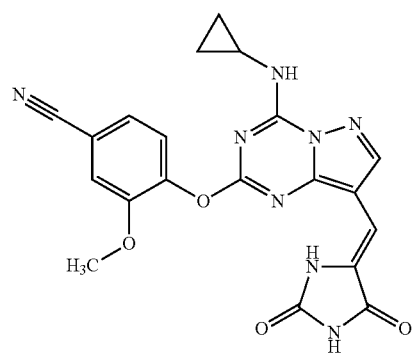
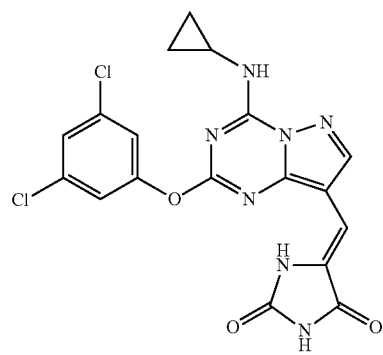 [SMILES: O=C1NC(=O)/C(=C/c2cnn3c(NC4CC4)nc(Oc4cc(Cl)cc(Cl)c4)nc23)N1]
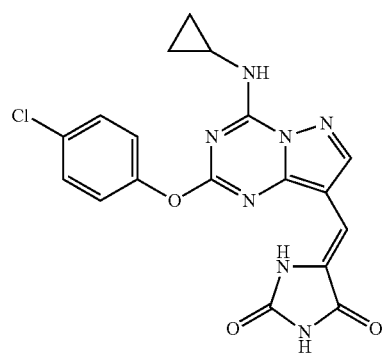 [SMILES: O=C1NC(=O)/C(=C/c2cnn3c(NC4CC4)nc(Oc4ccc(Cl)cc4)nc23)N1]
TABLE 39A-continued
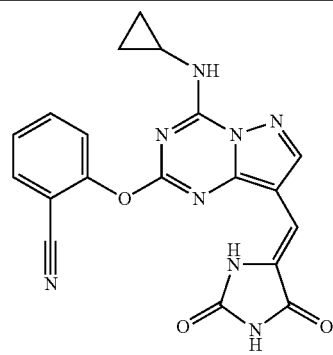
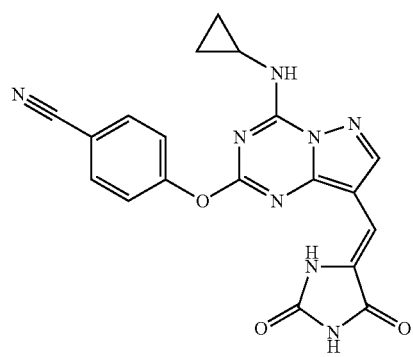
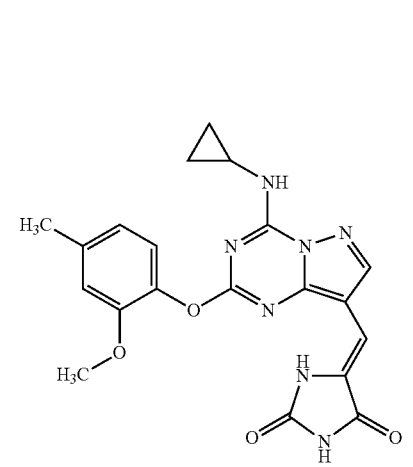 [SMILES: COc1cc(C)ccc1Oc1nc(NC2CC2)n2ncc(/C=C3\NC(=O)NC3=O)c2n1]
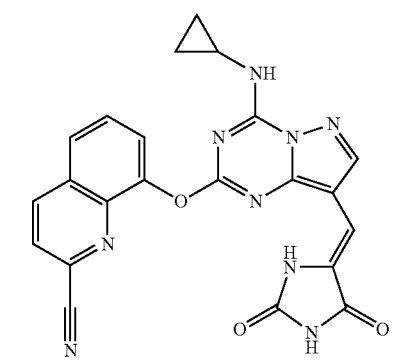 [SMILES: N#Cc1ccc2cccc(Oc3nc(NC4CC4)n4ncc(/C=C5\NC(=O)NC5=O)c4n3)c2n1]

TABLE 39A-continued
485
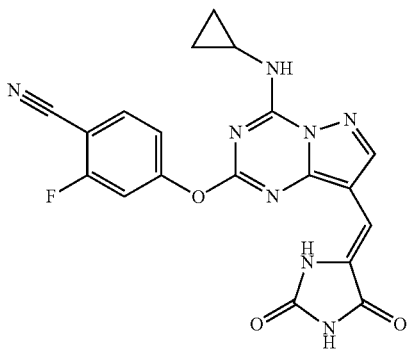
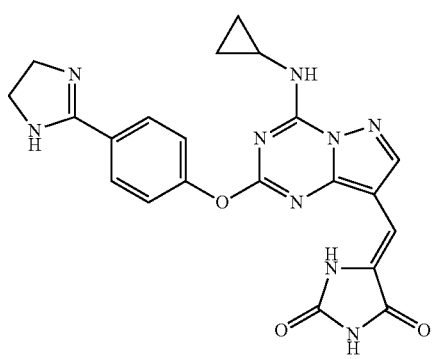 [SMILES: O=C1NC(=O)/C(=C/c2cnn3c(NC4CC4)nc(Oc4ccc(C5=NCCN5)cc4)nc23)N1]
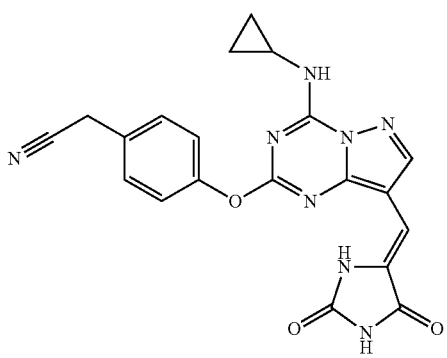 [SMILES: N#CCc1ccc(Oc2nc(NC3CC3)n3ncc(/C=C4\NC(=O)NC4=O)c3n2)cc1]
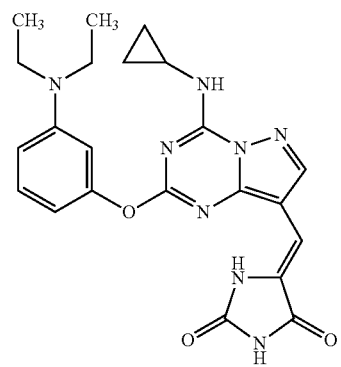 [SMILES: CCN(CC)c1cccc(Oc2nc(NC3CC3)n3ncc(/C=C4\NC(=O)NC4=O)c3n2)c1]
486
TABLE 39A-continued
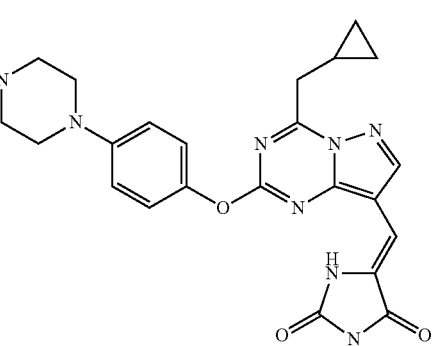
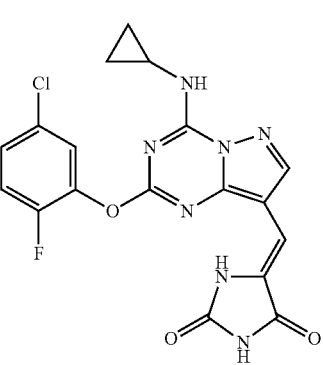 [SMILES: O=C1NC(=O)/C(=C/c2cnn3c(NC4CC4)nc(Oc4cc(Cl)ccc4F)nc23)N1]
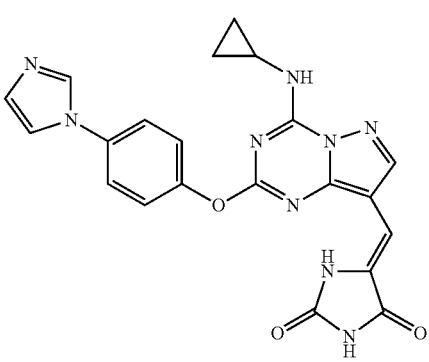
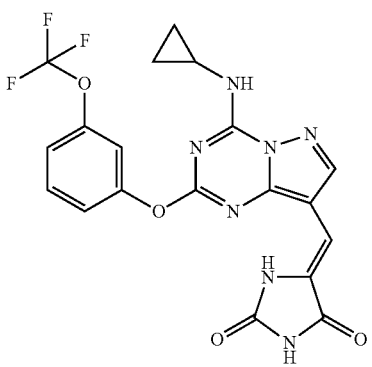 [SMILES: O=C1NC(=O)/C(=C/c2cnn3c(NC4CC4)nc(Oc4cccc(OC(F)(F)F)c4)nc23)N1]

| 487 | 488 |
|---|---|
| TABLE 39A-continued | TABLE 39A-continued |
| 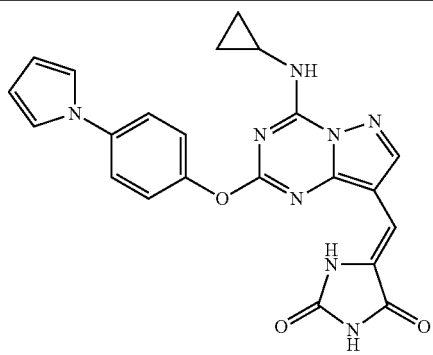 | 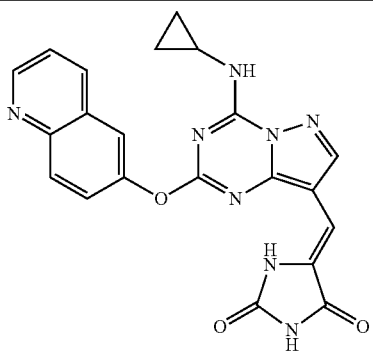 |
| 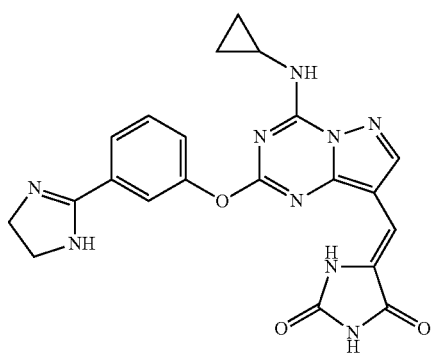 [SMILES: O=C1NC(=O)/C(=C/c2cnn3c(NC4CC4)nc(Oc4cccc(C5=NCCN5)c4)nc23)N1] | 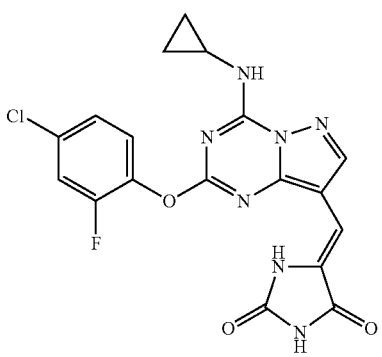 |
| 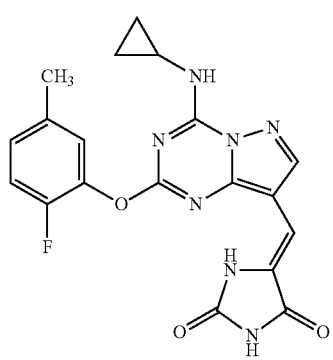 [SMILES: Cc1ccc(F)c(Oc2nc(NC3CC3)n3ncc(/C=C4\NC(=O)NC4=O)c3n2)c1] | 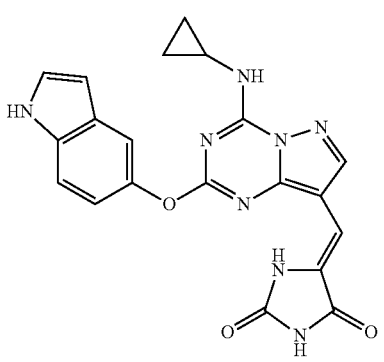 |
| 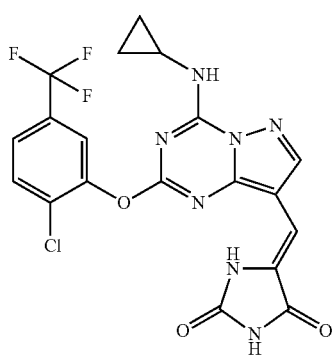 [SMILES: O=C1NC(=O)/C(=C/c2cnn3c(NC4CC4)nc(Oc4cc(C(F)(F)F)ccc4Cl)nc23)N1] | 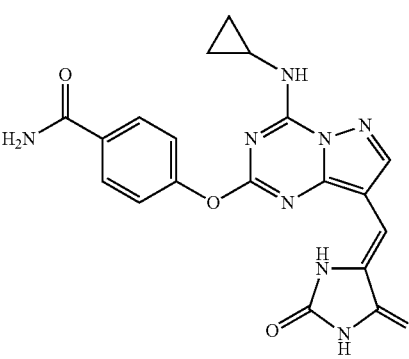 |

TABLE 39A-continued
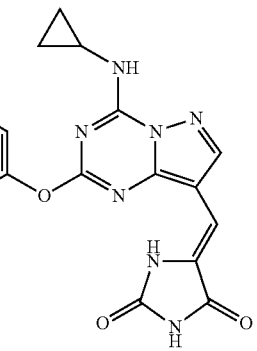
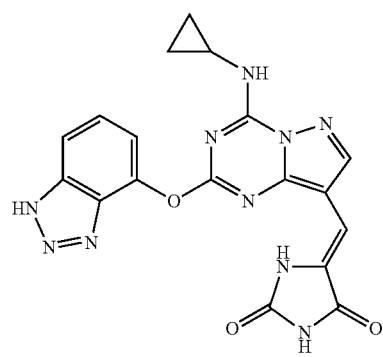 [SMILES: O=C1NC(=O)/C(=C/c2cnn3c(NC4CC4)nc(Oc4cccc5[nH]nnc45)nc23)N1]
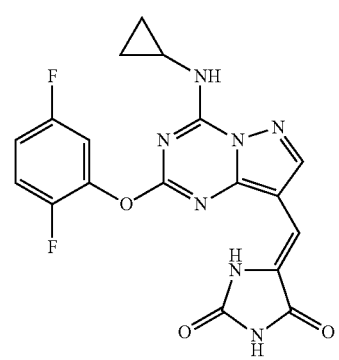 [SMILES: O=C1NC(=O)/C(=C/c2cnn3c(NC4CC4)nc(Oc4cc(F)ccc4F)nc23)N1]
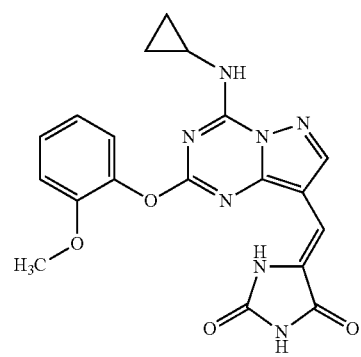 [SMILES: COc1ccccc1Oc1nc(NC2CC2)n2ncc(/C=C3\NC(=O)NC3=O)c2n1]
TABLE 39A-continued
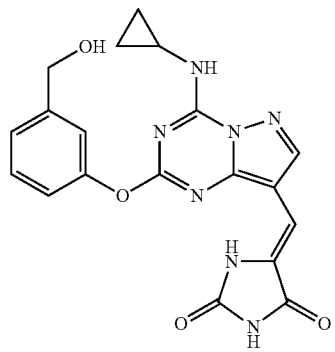 [SMILES: O=C1NC(=O)/C(=C/c2cnn3c(NC4CC4)nc(Oc4cccc(CO)c4)nc23)N1]
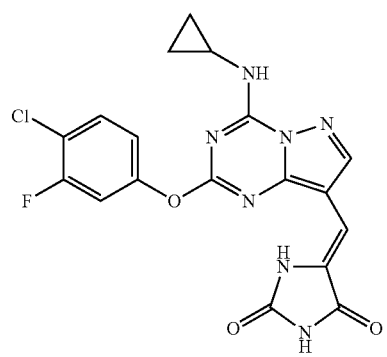 [SMILES: O=C1NC(=O)/C(=C/c2cnn3c(NC4CC4)nc(Oc4ccc(Cl)c(F)c4)nc23)N1]
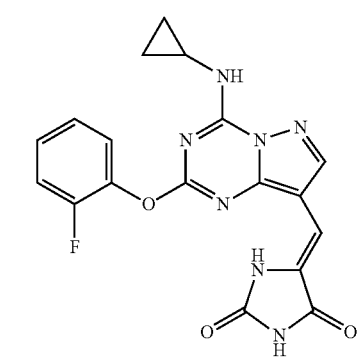 [SMILES: O=C1NC(=O)/C(=C/c2cnn3c(NC4CC4)nc(Oc4ccccc4F)nc23)N1]
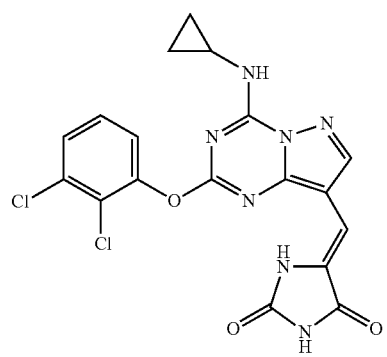 [SMILES: O=C1NC(=O)/C(=C/c2cnn3c(NC4CC4)nc(Oc4cccc(Cl)c4Cl)nc23)N1]

| 491 | 492 |
|---|---|
| 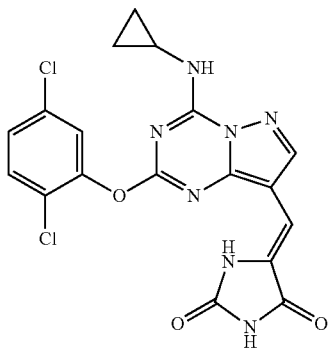 [SMILES: O=C1NC(=O)/C(=C/c2cnn3c(NC4CC4)nc(Oc4cc(Cl)ccc4Cl)nc23)N1] 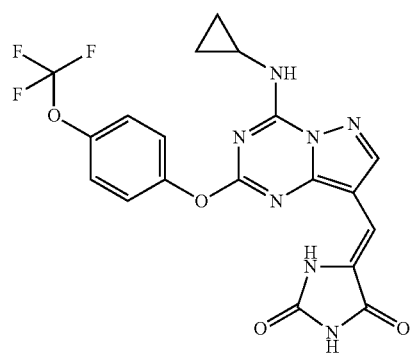 [SMILES: O=C1NC(=O)/C(=C/c2cnn3c(NC4CC4)nc(Oc4ccc(OC(F)(F)F)cc4)nc23)N1] 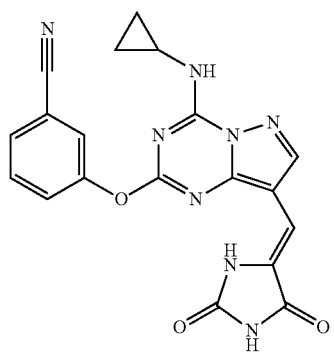 [SMILES: N#Cc1cccc(Oc2nc(NC3CC3)n3ncc(/C=C4\NC(=O)NC4=O)c3n2)c1] 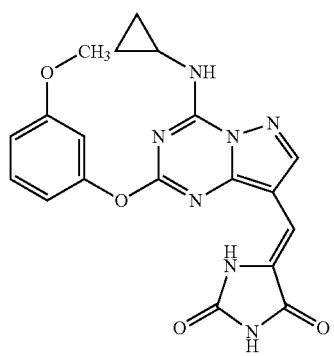 [SMILES: COc1cccc(Oc2nc(NC3CC3)n3ncc(/C=C4\NC(=O)NC4=O)c3n2)c1] | 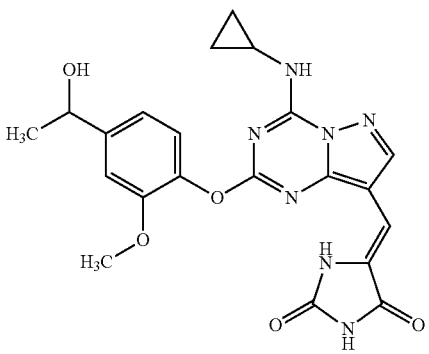 [SMILES: COc1cc(C(C)O)ccc1Oc1nc(NC2CC2)n2ncc(/C=C3\NC(=O)NC3=O)c2n1] 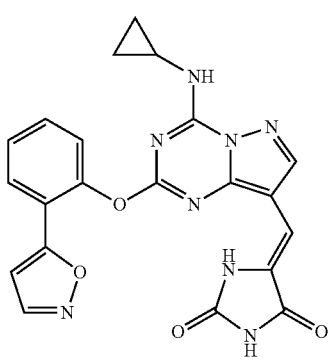 [SMILES: O=C1NC(=O)/C(=C/c2cnn3c(NC4CC4)nc(Oc4ccccc4-c4ccno4)nc23)N1] 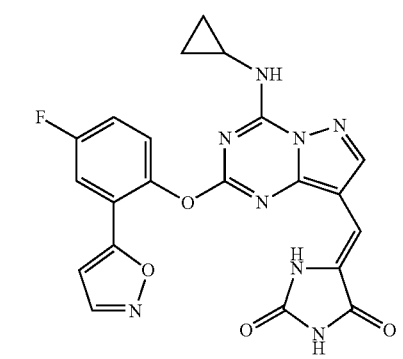 [SMILES: O=C1NC(=O)/C(=C/c2cnn3c(NC4CC4)nc(Oc4ccc(F)cc4-c4ccno4)nc23)N1] 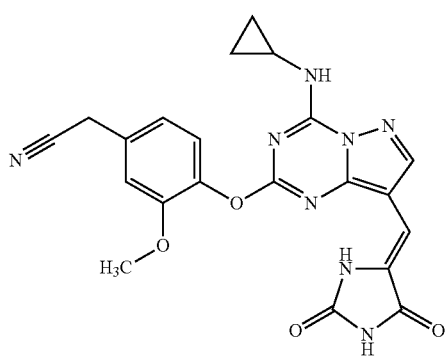 [SMILES: COc1cc(CC#N)ccc1Oc1nc(NC2CC2)n2ncc(/C=C3\NC(=O)NC3=O)c2n1] |

TABLE 39A-continued

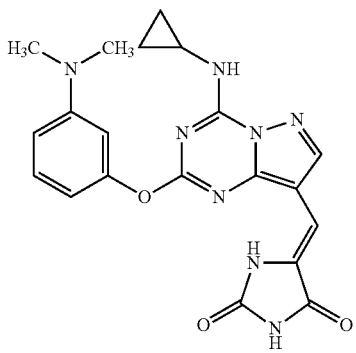 [SMILES: CN(C)c1cccc(Oc2nc(NC3CC3)n3ncc(/C=C4\NC(=O)NC4=O)c3n2)c1]

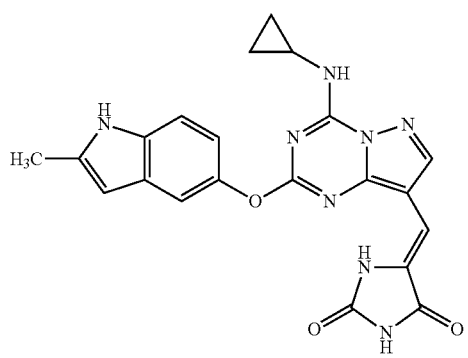 [SMILES: Cc1cc2cc(Oc3nc(NC4CC4)n4ncc(/C=C5\NC(=O)NC5=O)c4n3)ccc2[nH]1]

TABLE 39B

| Compound | CK2: IC50 (μM) | PIM2: IC50 (μM) | AB: MDAMB453 (μM) | AB: BxPC3 (μM) |
|---|---|---|---|---|
| E34 | <0.01 | >2.5000 | 1.42 | 9.45 |
| F34 | <0.01 | >1.0 | 3.27 | 9.60 |
| G34 | <0.01 | >1.0 | 2.91 | 13.64 |
| H34 | <0.01 | >1.0 | >30 | >30 |
| I34 | <0.01 | >1.0 | >30 | 8.45 |
| J34 | <0.01 | >1.0 | 5.38 | 17.57 |
| K34 | <0.1 | >1.0 | 20.53 | >30 |
| L34 | <0.1 | >1.0 | 18.30 | 28.13 |
| M34 | <0.01 | >1.0 | 26.25 | 15.88 |
| N34 | <1.0 | >1.0 | | |
| O34 | <0.01 | >1.0 | 1.44 | 2.66 |
| P34 | <0.01 | >1.0 | 17.30 | >30 |
| Q34 | <0.1 | >1.0 | | |
| R34 | <0.1 | >1.0 | | |
| S34 | <0.01 | >1.0 | 20.16 | 17.92 |
| T34 | <0.1 | >1.0 | 11.09 | >30 |
| U34 | <0.01 | >1.0 | 10.32 | >30 |
| V34 | <0.01 | >1.0 | >30 | >30 |
| W34 | <0.01 | >1.0 | >30 | 24.51 |
| X34 | <0.01 | >1.0 | 1.54 | 5.48 |
| Y34 | <0.01 | >1.0 | 14.63 | >30 |
| Z34 | <0.01 | >1.0 | >30 | >30 |
| A35 | <0.01 | >1.0 | 5.89 | 28.39 |
| B35 | <0.01 | >1.0 | >30 | >30 |
| C35 | <0.01 | >1.0 | 15.80 | >30 |
| D35 | <0.01 | >0.5 | 8.81 | 5.82 |
| E35 | <0.1 | >1.0 | | |
| F35 | <0.01 | >1.0 | 19.89 | >30 |
| G35 | <0.1 | >1.0 | | |
| H35 | <0.1 | >1.0 | | |
| I35 | <0.1 | >1.0 | | |
| J35 | <0.01 | >1.0 | 20.37 | 18.02 |
| K35 | <1.0 | >1.0 | | |
| L35 | <0.01 | >1.0 | >30 | >30 |
| M35 | <0.01 | >1.0 | >30 | >30 |
| N35 | <0.01 | >1.0 | 15.44 | >30 |
| O35 | <1.0 | >1.0 | | |

TABLE 39B-continued

| Compound | CK2: IC50 (μM) | PIM2: IC50 (μM) | AB: MDAMB453 (μM) | AB: BxPC3 (μM) |
|---|---|---|---|---|
| P35 | <0.01 | >1.0 | 7.86 | 18.37 |
| Q35 | <0.01 | >1.0 | 4.74 | 7.01 |
| R35 | <0.1 | >1.0 | >30 | >30 |
| S35 | <0.01 | >1.0 | >30 | >30 |
| T35 | <0.01 | >1.0 | 15.61 | 16.98 |
| U35 | <0.1 | >1.0 | | |
| V35 | <0.01 | >1.0 | 17.27 | 27.22 |
| W35 | <0.1 | >1.0 | | |
| X35 | <0.01 | >1.0 | 4.68 | 16.96 |
| Y35 | <0.1 | >1.0 | | |
| Z35 | <1.0 | >1.0 | | |
| A36 | <1.0 | >1.0 | | |
| B36 | <0.1 | >1.0 | | |
| C36 | <0.1 | >1.0 | 8.37 | 22.28 |
| D36 | <0.1 | >1.0 | >30 | >30 |
| E36 | <0.1 | >1.0 | 29.88 | >30 |
| F36 | <0.1 | >1.0 | | |
| G36 | <0.01 | >1.0 | 4.44 | 16.68 |
| H36 | <0.1 | >1.0 | 7.55 | >30 |
| I36 | <0.1 | >1.0 | | |
| J36 | | >1.0 | | |
| K36 | | >1.0 | | |

Example 231

Synthesis of (Z)-5-((2-(benzyloxy)-4-(cyclopropylamino)pyrazolo[1,5-a][1,3,5]triazin-8-yl)methylene)imidazolidine-2,4-dione

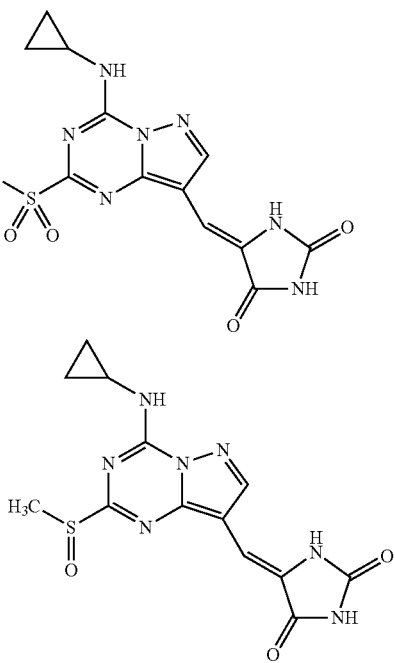

-continued

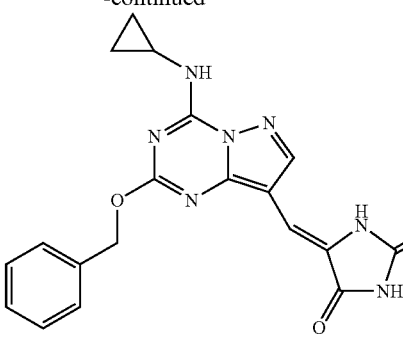

Benzyl alcohol (14.2 µL, 0.138 mmol) was dissolved in NMP (0.2 ml). Sodium Hydride (60%, 5.5 mg, 0.138 mmol) was added and the reaction stirred at room temperature for one hour. A (1:1) mixture of (Z)-5-((4-(cyclopropylamino)-2-(methylsulfonyl)pyrazolo[1,5-a][1,3,5]triazin-8-yl)methylene)imidazolidine-2,4-dione and (Z)-5-((4-(cyclopropylamino)-2-(methylsulfinyl)pyrazolo[1,5-a][1,3,5]-triazin-8-yl)methylene)imidazolidine-2,4-dione (10 mg, 0.027 mmol) was added and the mixture was stirred at room temperature for one hour. Water was added and the material was extracted with ethyl acetate. After concentration at the rotary evaporator, addition of methanol formed a precipitate that was filtered and dried. (Z)-5-((2-(benzyloxy)-4-(cyclopropylamino)pyrazolo[1,5-a][1,3,5]triazin-8-yl)methylene)imidazolidine-2,4-dione was isolated as a solid (5.6 mg). LCMS (ES):>95% pure, m/z 392 [M+H]+.

The following compounds were prepared using conditions similar to Example 231. Table 40B shows the biological activities of the compounds listed in Table 40A.

TABLE 40A

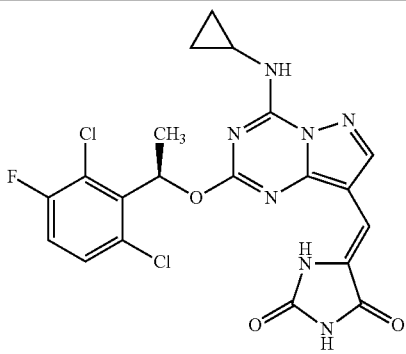 [SMILES: C[C@@H](Oc1nc(NC2CC2)n2ncc(/C=C3\NC(=O)NC3=O)c2n1)c1c(Cl)ccc(F)c1Cl]

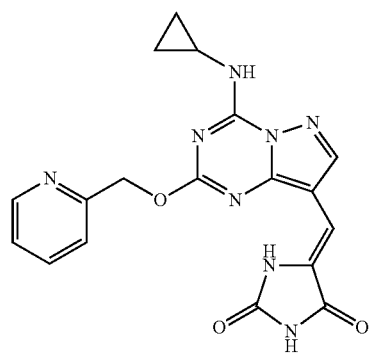 [SMILES: O=C1NC(=O)/C(=C/c2cnn3c(NC4CC4)nc(OCc4ccccn4)nc23)N1]

TABLE 40B

| Compound | CK2: IC50 (µM) | PIM2: IC50 (µM) | AB: MDAMB453 (µM) | AB: BxPC3 (µM) |
|---|---|---|---|---|
| L36 | <0.01 | >1.0 | | |
| M36 | <0.01 | >1.0 | | |
| N36 | | >1.0 | | |

Example 232

Synthesis of 3-((1r,4r)-4-(7-(cyclopropylamino)-3-((Z)-(2,5-dioxoimidazolidin-4-ylidene)methyl)pyrazolo[1,5-a]pyrimidin-5-ylamino)cyclohexyl)-1,1-dimethylurea 2,2,2-trifluoroacetate

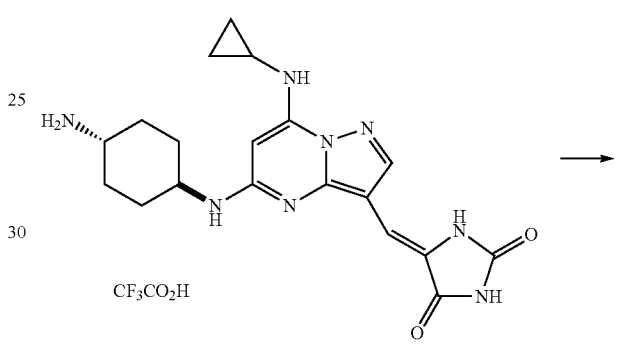

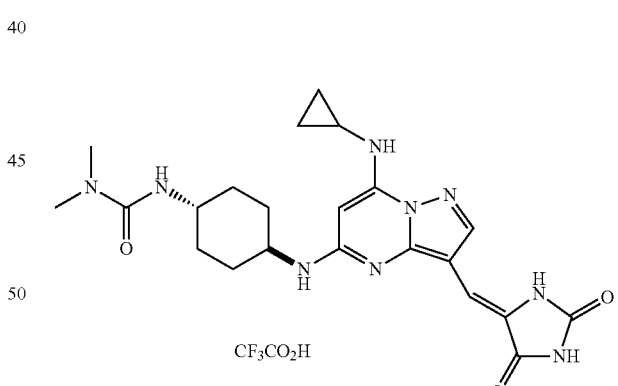

(Z)-5-((5-((1r,4r)-4-aminocyclohexylamino)-7-(cyclopropylamino)pyrazolo[1,5-a]pyrimidin-3-yl)methylene)imidazolidine-2,4-dione 2,2,2-trifluoroacetate (10 mg) and DIEA (1.2 eq, 4.1 ul) were mixed in dry NMP (0.1 ml). Dimethylcarbamic chloride (1.0 eq, 1.8 ul) was added and the mixture stirred at room temperature overnight. The reaction was diluted with NMP (1.5 ml) and a few drops of water. The compound was purified by preparative HPLC and was isolated after evaporation at the genevac. 3-((1r,4r)-4-(7-(cyclopropylamino)-3-((Z)-(2,5-dioxoimidazolidin-4-ylidene)methyl)pyrazolo[1,5-a]pyrimidin-5-ylamino)cyclohexyl)-1,1- dimethylurea 2,2,2-trifluoroacetate. LCMS (ES):>95% pure, m/z 468 [M+H]+. Z:E ratio: 86:13.

Example 233

Synthesis of N-((1r,4r)-4-(7-(cyclopropylamino)-3-((Z)-(2,5-dioxoimidazolidin-4-ylidene)methyl)pyrazolo[1,5-a]pyrimidin-5-ylamino)cyclohexyl)acetamide

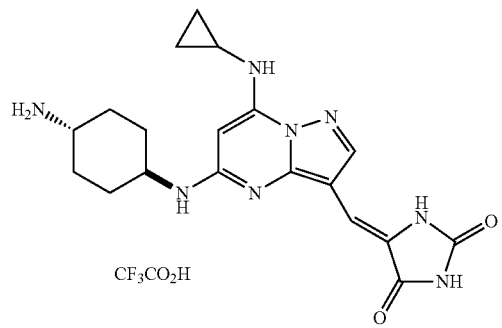

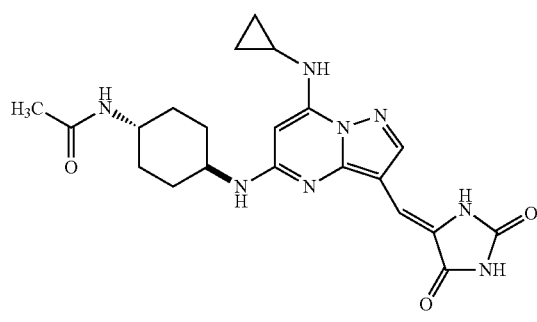

(Z)-5-((5-((1r,4r)-4-aminocyclohexylamino)-7-(cyclopropylamino)pyrazolo[1,5-a]pyrimidin-3-yl)methylene)imidazolidine-2,4-dione 2,2,2-trifluoroacetate (1.0 eq, 10 mg, 0.0196 mmol) and DIEA (1.2 eq, 4 ul, 0.0229 mmol) were dissolved in NMP (0.1 ml). Acetic anhydride (1.0 eq, 2 ul, 0.0211 mmol) was added and the mixture stirred at room temperature overnight. Water was added and the resulting precipitate was filtered and dried to provide N-((1r,4r)-4-(7-(cyclopropylamino)-3-((Z)-(2,5-dioxoimidazolidin-4-ylidene)methyl)pyrazolo[1,5-a]pyrimidin-5-ylamino)cyclohexyl)acetamide as a solid (8 mg). LCMS (ES):>95% pure, m/z 439 [M+H]+.

Example 234

Synthesis of N-((1r,4r)-4-(7-(cyclopropylamino)-3-((Z)-(2,5-dioxoimidazolidin-4-ylidene)methyl)pyrazolo[1,5-a]pyrimidin-5-ylamino)cyclohexyl)propionamide 2,2,2-trifluoroacetate

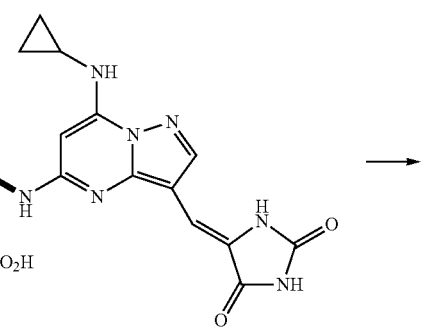

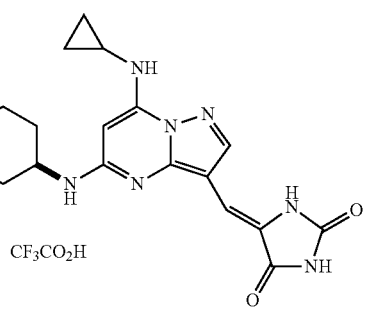

Z)-5-((5-((1r,4r)-4-aminocyclohexylamino)-7-(cyclopropylamino)pyrazolo[1,5-a]pyrimidin-3-yl)methylene)imidazolidine-2,4-dione 2,2,2-trifluoroacetate (1.0 eq, 10 mg, 0.0195 mmol) was suspended in NMP (0.05 ml). A NMP solution of propionic acid (1.2 eq, 60 uL of 0.4 M solution, 0.0234 mmol), HOBt (1.5 eq, 4 mg, 0.030 mmol), DIEA (2.5 eq, 8 uL, 0.048 mmol) and EDCI (1.5 eq, 6 mg, 0.03 mmol) were added and the mixture stirred at 70° C. for 1.5 hours. Water and NMP was added and the product was purified by preparative HPLC. Genevac evaporation provided N-((1r,4r)-4-(7-(cyclopropylamino)-3-((Z)-(2,5-dioxoimidazolidin-4-ylidene)methyl)pyrazolo[1,5-a]pyrimidin-5-ylamino)cyclohexyl)propionamide 2,2,2-trifluoroacetate (2.8 mg). LCMS (ES):>90% pure, m/z 453 [M+H]+.

Example 235

Synthesis of (Z)-5-((4-(cyclopropylamino)-2-((1r,4r)-4-(isobutylamino)cyclohexylamino)pyrazolo[1,5-a][1,3,5]triazin-8-yl)methylene)imidazolidine-2,4-dione 2,2,2-trifluoroacetate

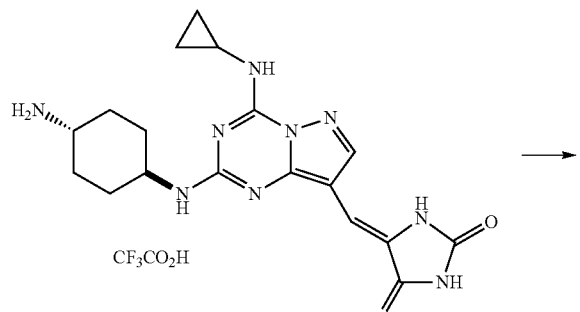

(Z)-5-((2-((1r,4r)-4-aminocyclohexylamino)-4-(cyclopropylamino)pyrazolo[1,5-a][1,3,5]triazin-8-yl)methylene)imidazolidine-2,4-dione 2,2,2-trifluoroacetate (1.0 eq, 10 mg, 0.025 mmol) was suspended in dichloroethane. Isobutyraldehyde (4 eq, 9.2 uL, 0.101 mmol), DIEA (1.0 eq, 0.025 mmol) and NaBH(OAc)$_3$ (4 eq, 21 mg, 0.101 mmol) were added and the mixture was stirred at room temperature for two hours. The mixture was diluted with water and NMP and subjected to preparative HPLC purification. Genevac evaporation provided (Z)-5-((4-(cyclopropylamino)-2-((1r,4r)-4-(isobutylamino)cyclohexylamino)pyrazolo[1,5-a][1,3,5]triazin-8-yl)methylene)imidazolidine-2,4-dione 2,2,2-trifluoroacetate as a solid (4.6 mg). LCMS (ES):>90% pure, m/z 454 [M+H]+.

The compounds in the following table were prepared using procedures described in Examples 232 to 235 and Examples 30 and 31, using the appropriate starting amines and carboxylic acids, acyl chlorides, sulfamoyl chlorides, sulfonyl chlorides, isocyanates and chloroformates. Table 41B shows the biological activities of the compounds listed in Table 41A.

TABLE 41A

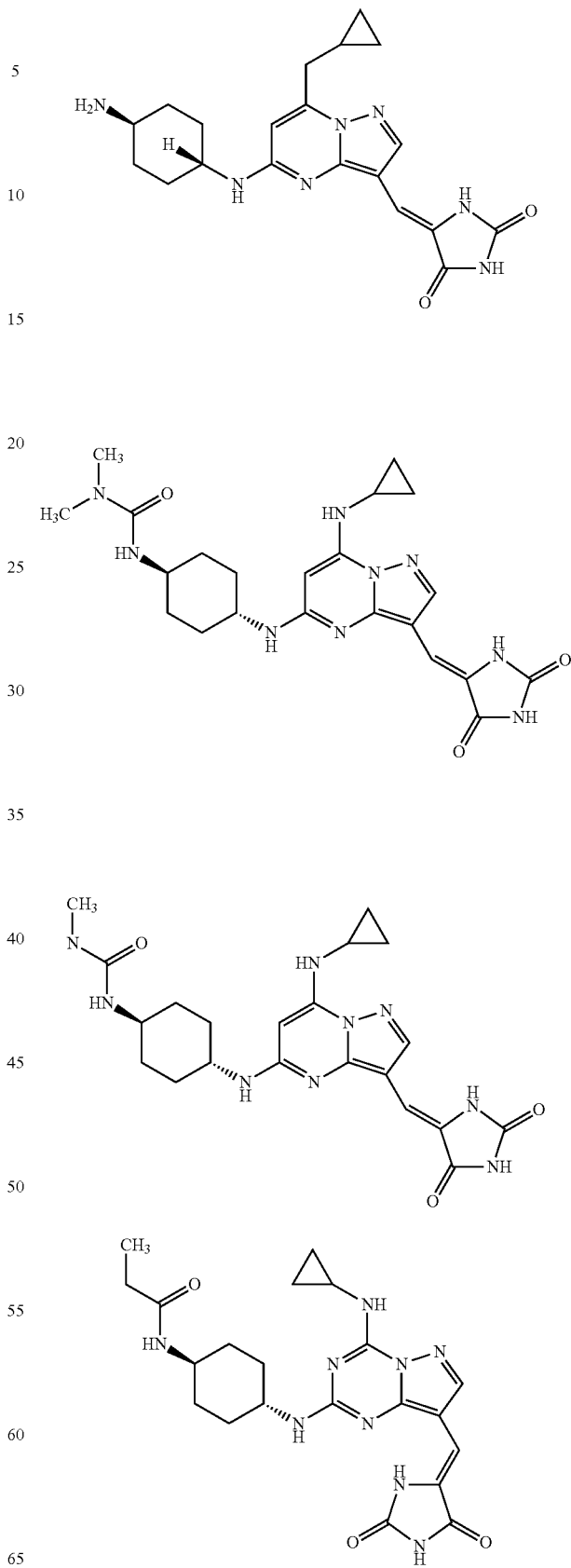

501
TABLE 41A-continued
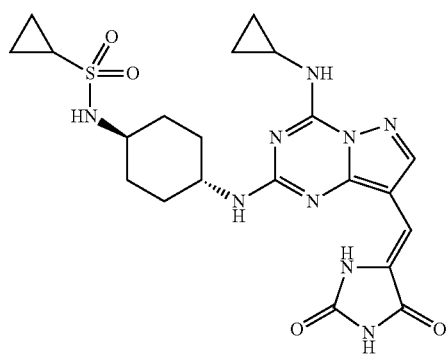 [SMILES: O=C1NC(=O)/C(=C/c2cnn3c(NC4CC4)nc(N[C@H]4CC[C@H](NS(=O)(=O)C5CC5)CC4)nc23)N1]
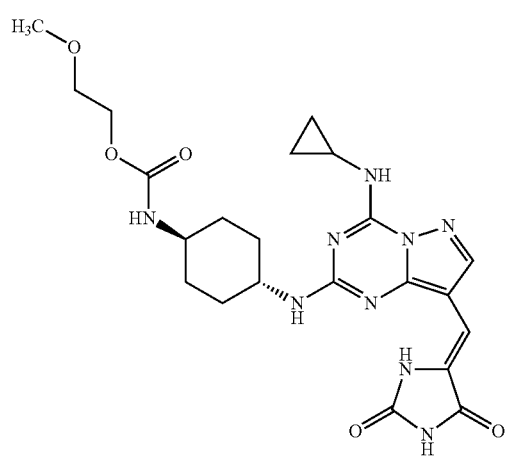 [SMILES: COCCOC(=O)N[C@H]1CC[C@H](Nc2nc(NC3CC3)n3ncc(/C=C4\NC(=O)NC4=O)c3n2)CC1]
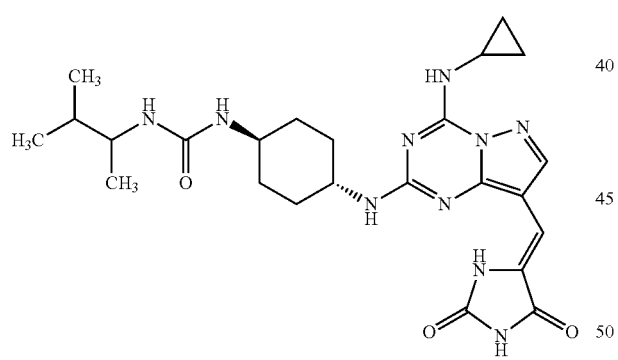
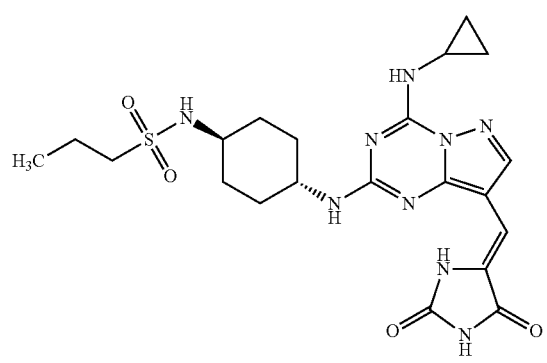 [SMILES: CCCS(=O)(=O)N[C@H]1CC[C@H](Nc2nc(NC3CC3)n3ncc(/C=C4\NC(=O)NC4=O)c3n2)CC1]
502
TABLE 41A-continued
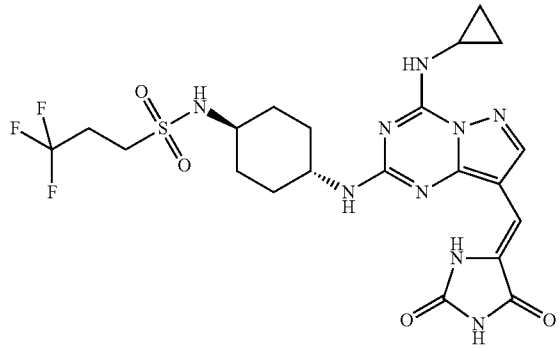 [SMILES: O=C1NC(=O)/C(=C/c2cnn3c(NC4CC4)nc(N[C@H]4CC[C@H](NS(=O)(=O)CCC(F)(F)F)CC4)nc23)N1]
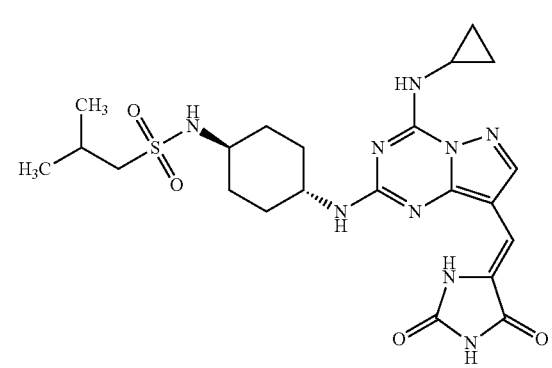 [SMILES: CC(C)CS(=O)(=O)N[C@H]1CC[C@H](Nc2nc(NC3CC3)n3ncc(/C=C4\NC(=O)NC4=O)c3n2)CC1]
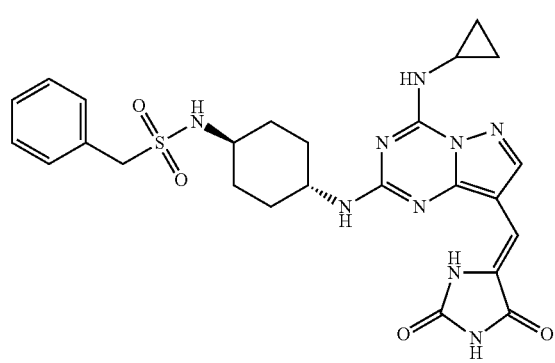 [SMILES: O=C1NC(=O)/C(=C/c2cnn3c(NC4CC4)nc(N[C@H]4CC[C@H](NS(=O)(=O)Cc5ccccc5)CC4)nc23)N1]

503
TABLE 41A-continued
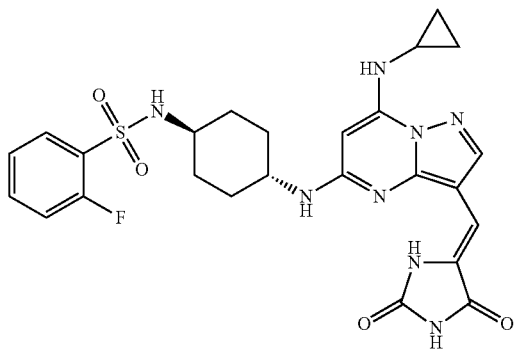 [SMILES: O=C1NC(=O)/C(=C/c2cnn3c(NC4CC4)cc(N[C@H]4CC[C@H](NS(=O)(=O)c5ccccc5F)CC4)nc23)N1]
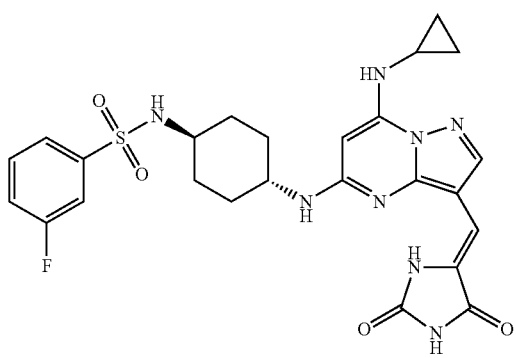 [SMILES: O=C1NC(=O)/C(=C/c2cnn3c(NC4CC4)cc(N[C@H]4CC[C@H](NS(=O)(=O)c5cccc(F)c5)CC4)nc23)N1]
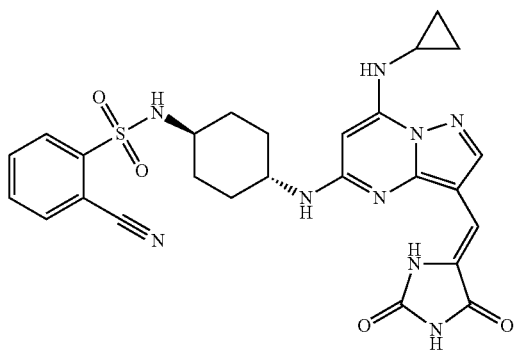 [SMILES: N#Cc1ccccc1S(=O)(=O)N[C@H]1CC[C@H](Nc2cc(NC3CC3)n3ncc(/C=C4\NC(=O)NC4=O)c3n2)CC1]
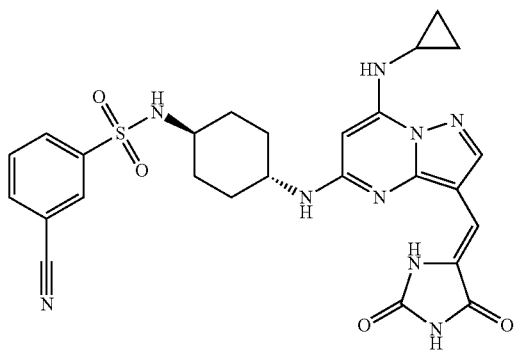 [SMILES: N#Cc1cccc(S(=O)(=O)N[C@H]2CC[C@H](Nc3cc(NC4CC4)n4ncc(/C=C5\NC(=O)NC5=O)c4n3)CC2)c1]
504
TABLE 41A-continued
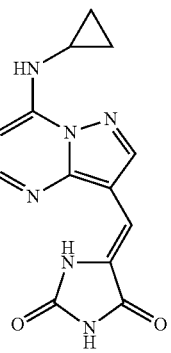
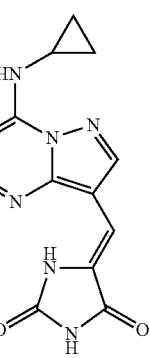
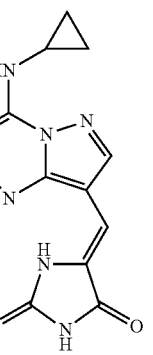
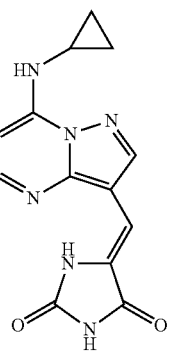

TABLE 41A-continued
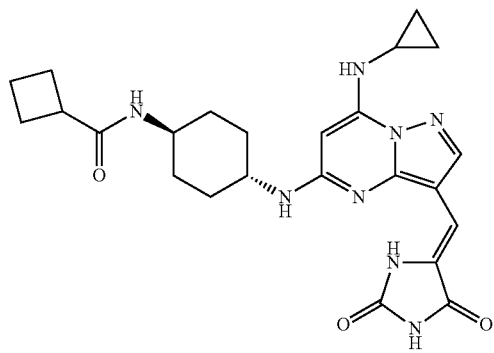 [SMILES: O=C1NC(=O)/C(=C/c2cnn3c(NC4CC4)cc(N[C@H]4CC[C@H](NC(=O)C5CCC5)CC4)nc23)N1]
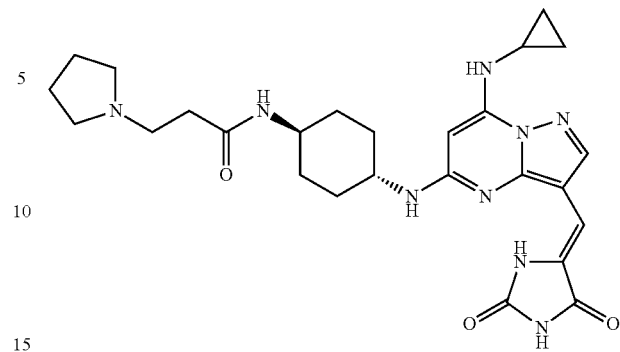
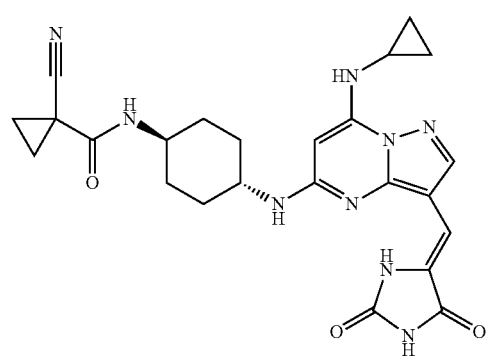 [SMILES: N#CC1(C(=O)N[C@H]2CC[C@H](Nc3cc(NC4CC4)n4ncc(/C=C5\NC(=O)NC5=O)c4n3)CC2)CC1]
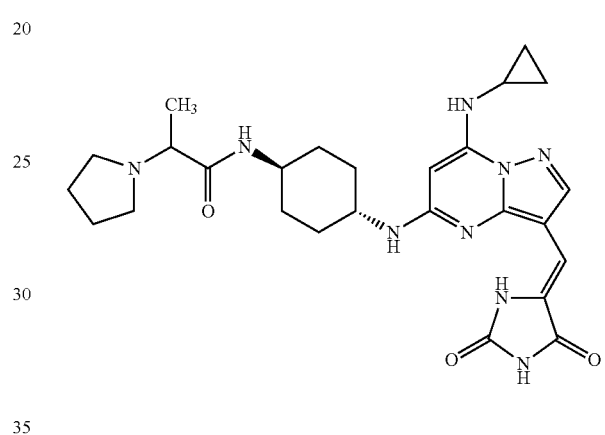
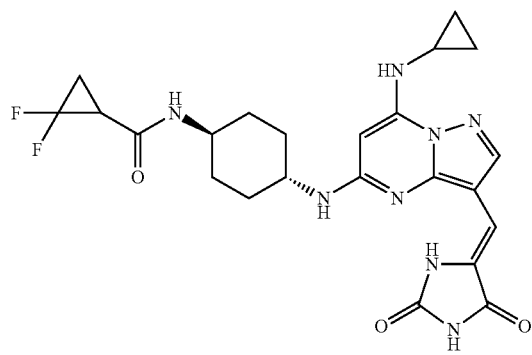 [SMILES: O=C1NC(=O)/C(=C/c2cnn3c(NC4CC4)cc(N[C@H]4CC[C@H](NC(=O)C5CC5(F)F)CC4)nc23)N1]
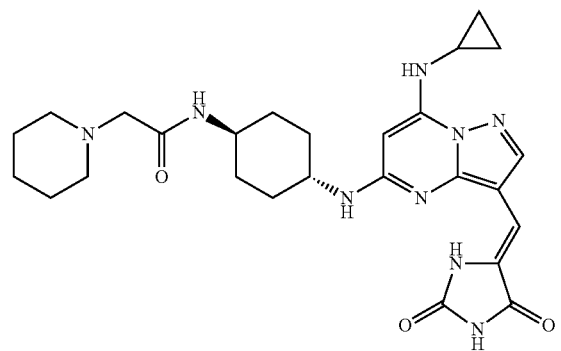 [SMILES: O=C1NC(=O)/C(=C/c2cnn3c(NC4CC4)cc(N[C@H]4CC[C@H](NC(=O)CN5CCCCC5)CC4)nc23)N1]
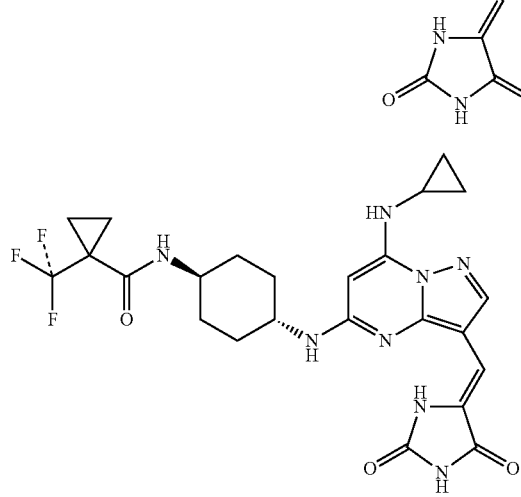

TABLE 41A-continued
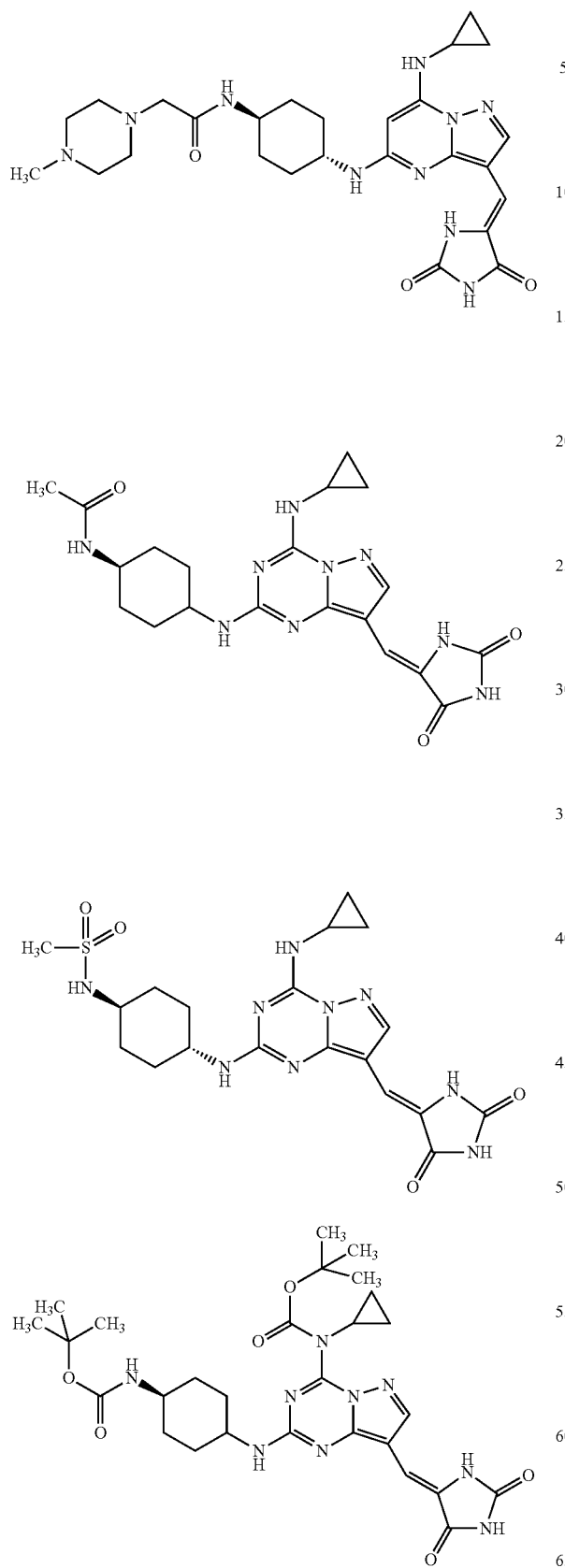
TABLE 41A-continued
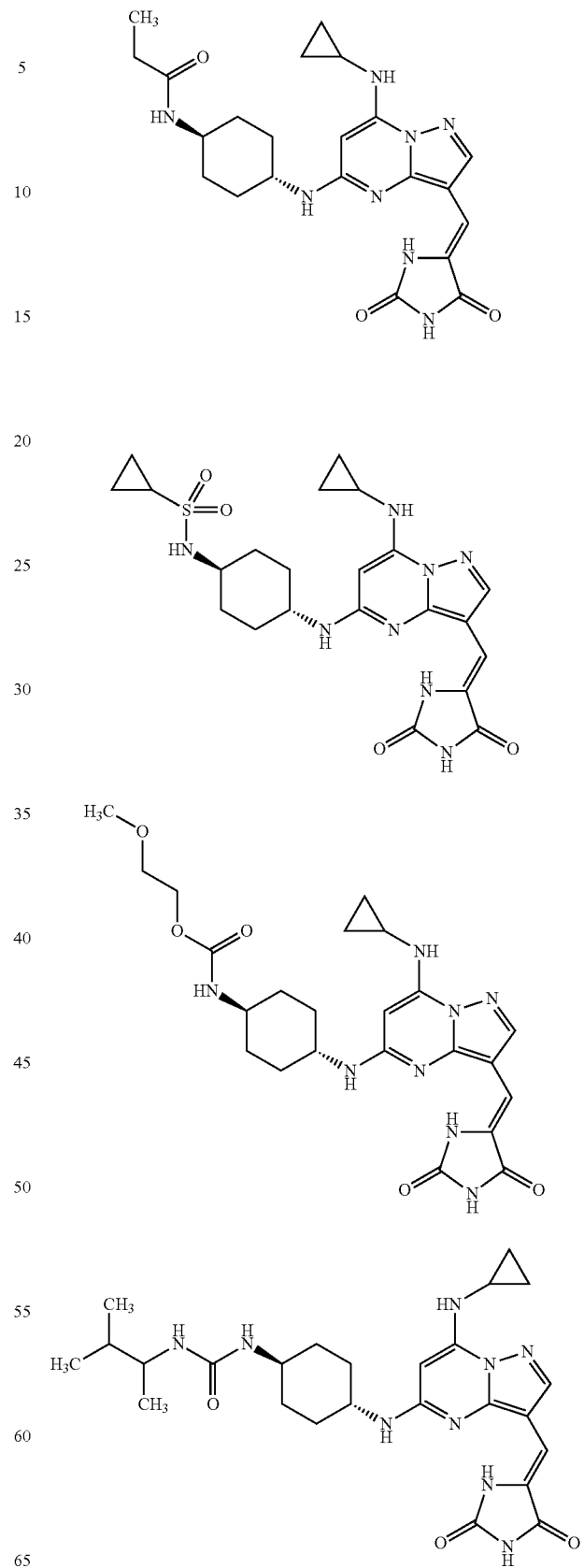

TABLE 41A-continued
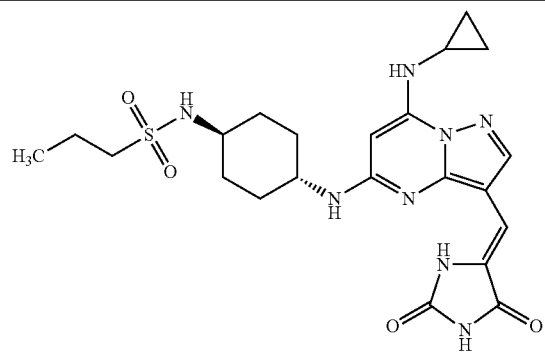
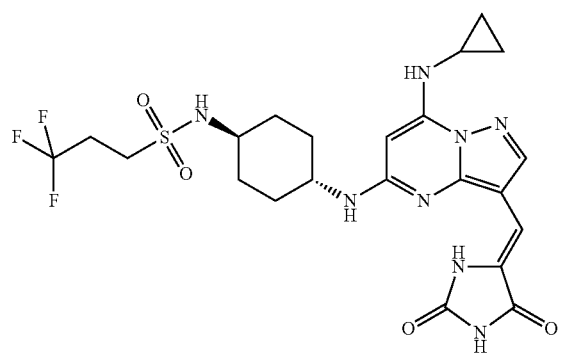 [SMILES: O=C1NC(=O)/C(=C/c2cnn3c(NC4CC4)cc(N[C@H]4CC[C@H](NS(=O)(=O)CCC(F)(F)F)CC4)nc23)N1]
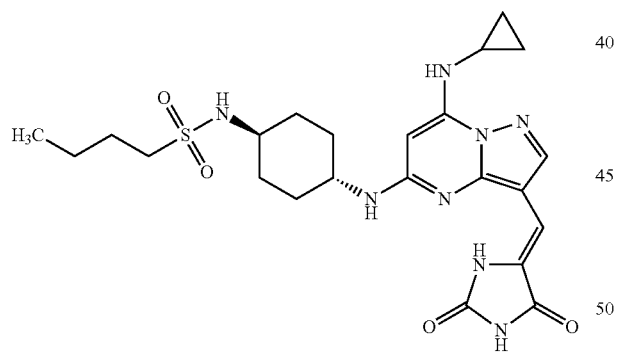
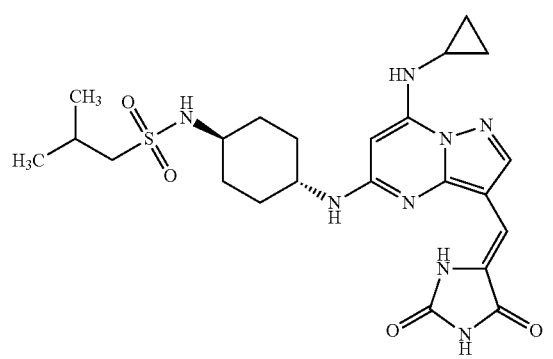 [SMILES: CC(C)CS(=O)(=O)N[C@H]1CC[C@H](Nc2cc(NC3CC3)n3ncc(/C=C4\NC(=O)NC4=O)c3n2)CC1]
TABLE 41A-continued
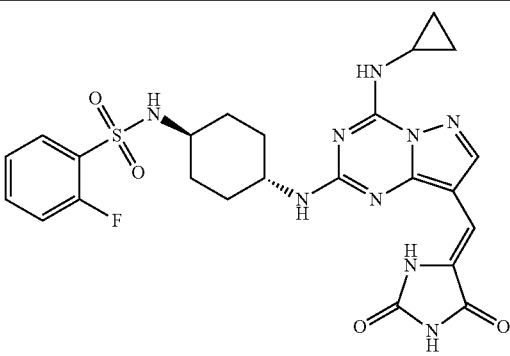
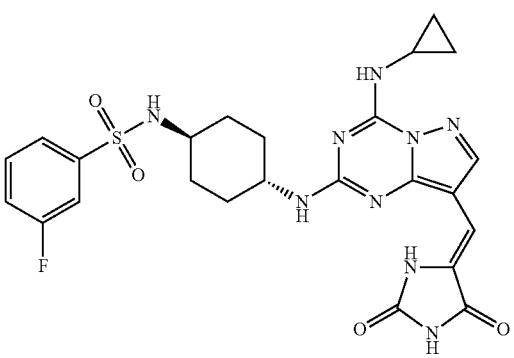
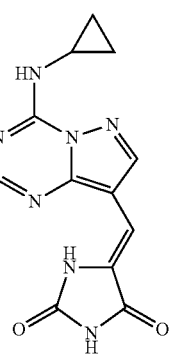

TABLE 41A-continued
511
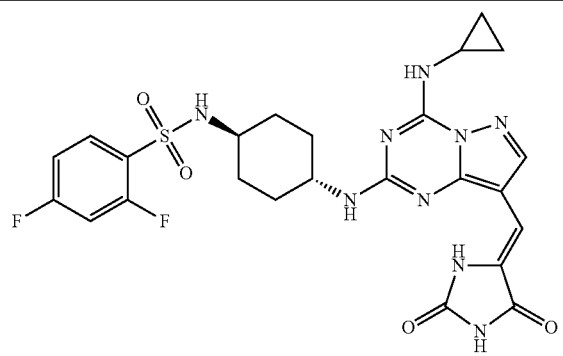
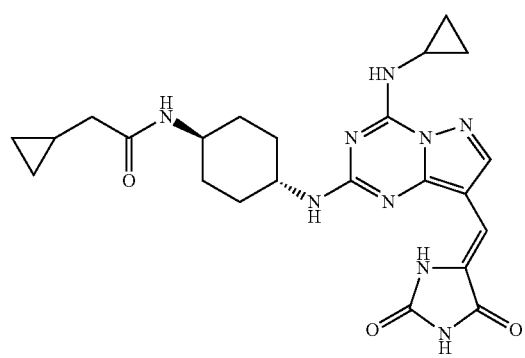 [SMILES: O=C1NC(=O)/C(=C/c2cnn3c(NC4CC4)nc(N[C@H]4CC[C@H](NC(=O)CC5CC5)CC4)nc23)N1]
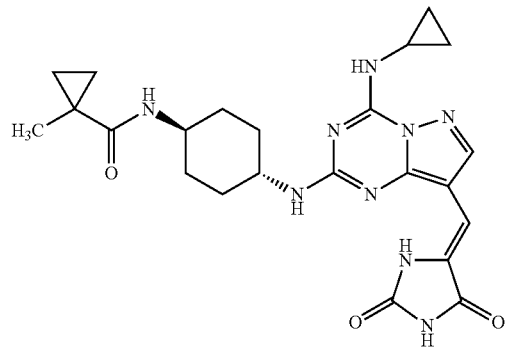 [SMILES: CC1(C(=O)N[C@H]2CC[C@H](Nc3nc(NC4CC4)n4ncc(/C=C5\NC(=O)NC5=O)c4n3)CC2)CC1]
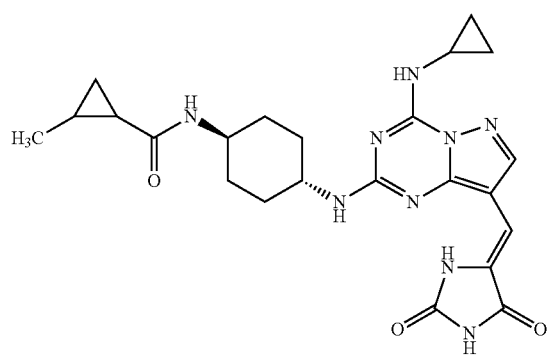 [SMILES: CC1CC1C(=O)N[C@H]1CC[C@H](Nc2nc(NC3CC3)n3ncc(/C=C4\NC(=O)NC4=O)c3n2)CC1]
TABLE 41A-continued
512
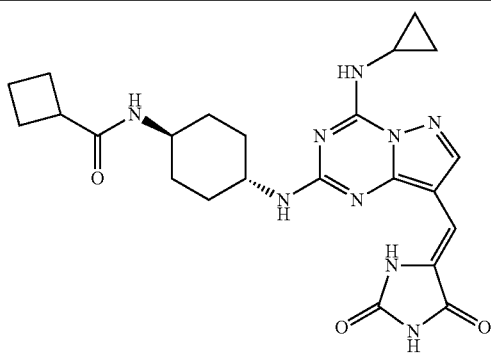
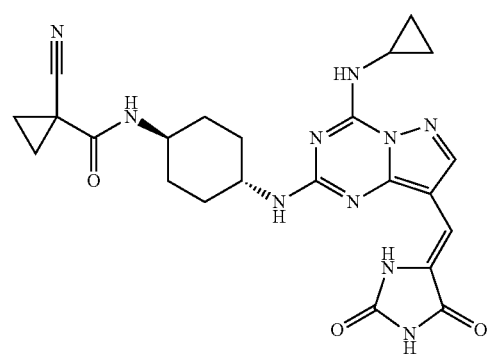 [SMILES: N#CC1(C(=O)N[C@H]2CC[C@H](Nc3nc(NC4CC4)n4ncc(/C=C5\NC(=O)NC5=O)c4n3)CC2)CC1]
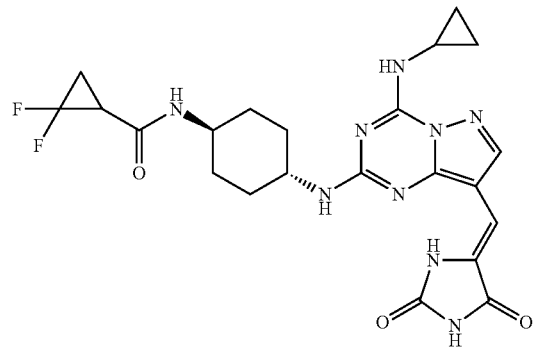 [SMILES: O=C1NC(=O)/C(=C/c2cnn3c(NC4CC4)nc(N[C@H]4CC[C@H](NC(=O)C5CC5(F)F)CC4)nc23)N1]
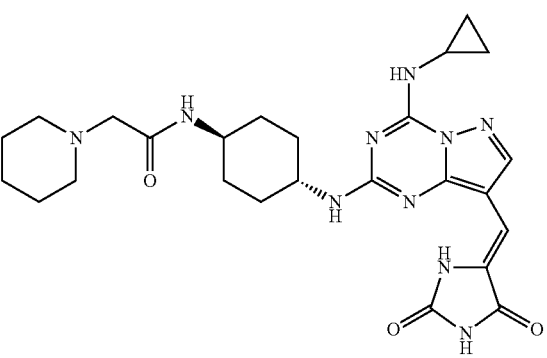 [SMILES: O=C1NC(=O)/C(=C/c2cnn3c(NC4CC4)nc(N[C@H]4CC[C@H](NC(=O)CN5CCCCC5)CC4)nc23)N1]

TABLE 41A-continued
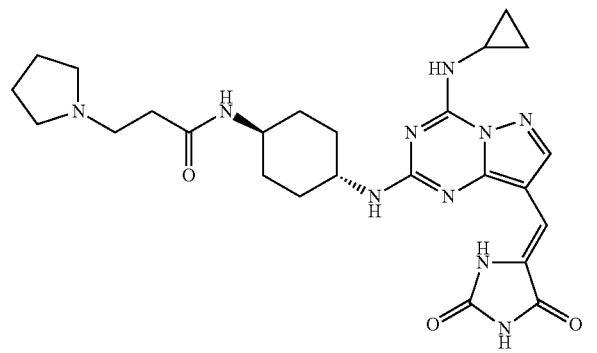 [SMILES: O=C1NC(=O)/C(=C/c2cnn3c(NC4CC4)nc(N[C@H]4CC[C@H](NC(=O)CCN5CCCC5)CC4)nc23)N1]
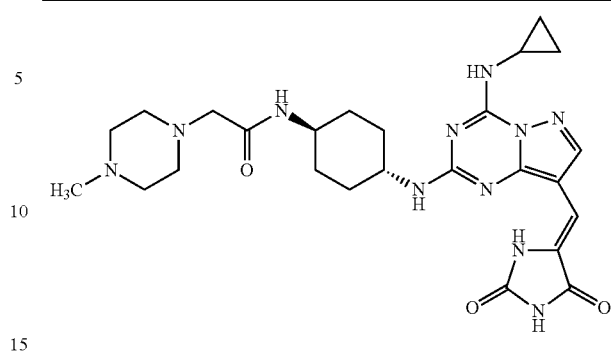
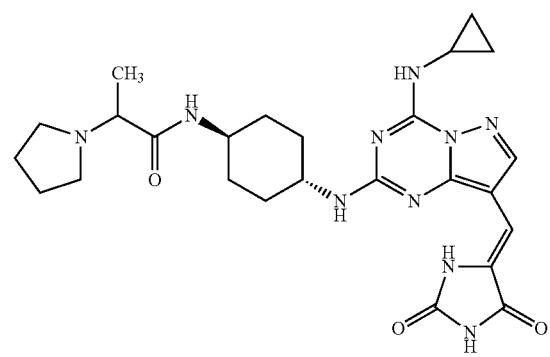 [SMILES: CC(C(=O)N[C@H]1CC[C@H](Nc2nc(NC3CC3)n3ncc(/C=C4\NC(=O)NC4=O)c3n2)CC1)N1CCCC1]
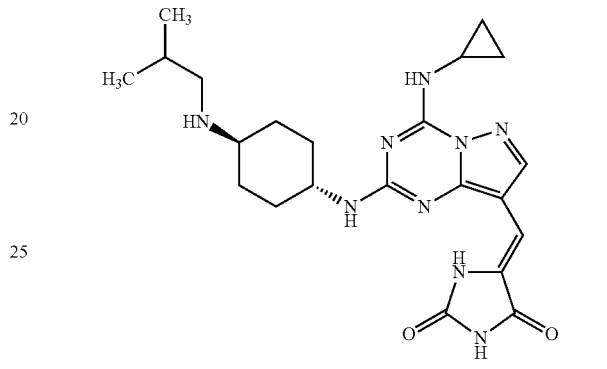
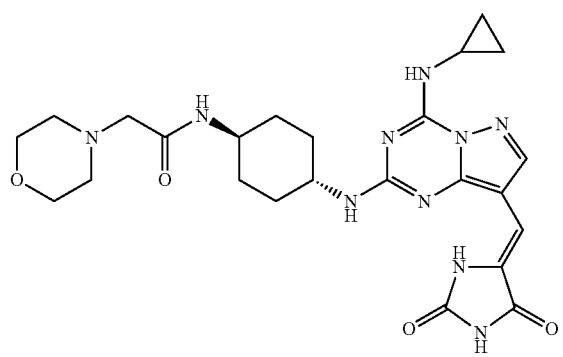 [SMILES: O=C1NC(=O)/C(=C/c2cnn3c(NC4CC4)nc(N[C@H]4CC[C@H](NC(=O)CN5CCOCC5)CC4)nc23)N1]
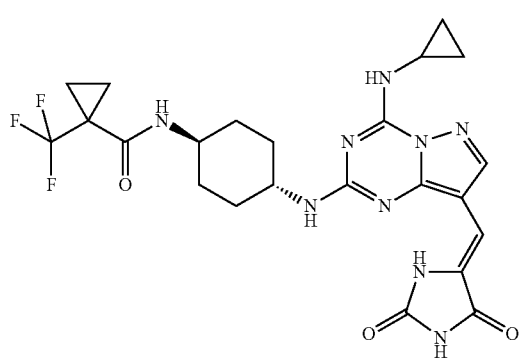 [SMILES: O=C1NC(=O)/C(=C/c2cnn3c(NC4CC4)nc(N[C@H]4CC[C@H](NC(=O)C5(C(F)(F)F)CC5)CC4)nc23)N1]
TABLE 41B
| Compound | CK2: IC50 (μM) | PIM2: IC50 (μM) | AB: MDAMB453 (μM) | AB: BxPC3 (μM) |
|---|---|---|---|---|
| O36 | <0.01 | 0.2532 | 0.154 | 4.467 |
| P36 | <0.01 | >2.5000 | 8.254 | >30 |
| Q36 | <0.01 | 0.6791 | 2.093 | 19.089 |
| R36 | <0.01 | 0.476 | 2.505 | 25.76 |
| S36 | <0.01 | >2.5000 | 0.404 | 4.396 |
| T36 | <1 | >2.5 | | |
| U36 | <0.01 | >1.0 | 1.47 | 10.84 |
| V36 | <0.01 | >2.5 | 1.929 | 10.172 |
| W36 | <0.01 | >1.0 | 2.95 | 14.11 |
| X36 | <0.01 | >2.5 | 1.646 | 13.758 |
| Y36 | <0.01 | >1.0 | 0.85 | 10.28 |
| Z36 | <0.01 | >2.5 | 0.647 | 10.871 |
| A37 | <0.01 | >1.0 | 8.10 | >30 |
| B37 | <0.01 | >2.5 | 2.031 | >30 |
| C37 | <0.01 | >1.0 | 2.49 | 13.79 |
| D37 | <0.01 | >2.5 | 1.189 | 11.567 |
| E37 | <0.01 | >1.0 | 2.85 | 11.65 |
| F37 | <0.1 | >2.5 | 1.306 | 13.099 |
| G37 | <0.01 | >1.0 | 1.76 | 13.92 |
| H37 | <0.1 | >2.5 | 3.413 | 18.066 |
| I37 | <0.01 | >1.0 | 3.23 | 19.35 |
| J37 | <0.01 | >2.5 | 1.48 | 15.81 |
| K37 | <0.01 | >1.0 | 4.48 | 12.63 |
| L37 | <0.01 | >1.0 | 1.25 | 6.39 |
| M37 | <0.01 | >2.5 | 0.792 | 5.473 |
| N37 | <0.01 | >1.0 | 2.16 | 4.37 |
| O37 | <0.01 | >2.5 | 1.91 | 7.035 |
| P37 | <0.01 | >1.0 | 3.02 | 9.44 |
| Q37 | <0.01 | >2.5 | 1.92 | 9.776 |
| R37 | <0.01 | >1.0 | 3.13 | 4.93 |
| S37 | <0.01 | >2.5 | 1.46 | 11.298 |
| T37 | <0.01 | >1.0 | 0.94 | 3.23 |
| U37 | <0.01 | >2.5 | 1.014 | 4.694 |
| V37 | <0.01 | >1.0 | 1.72 | 9.92 |
| W37 | <0.01 | >2.5 | 1.22 | 10.565 |
| X37 | <0.01 | >1.0 | 2.91 | 18.34 |
| Y37 | <0.01 | >2.5 | 5.154 | 19.647 |

TABLE 41B-continued

| Compound | CK2: IC50 (µM) | PIM2: IC50 (µM) | AB: MDAMB453 (µM) | AB: BxPC3 (µM) |
|---|---|---|---|---|
| Z37 | <0.01 | >1.0 | 1.30 | 7.61 |
| A38 | <0.01 | >2.5 | 1.487 | 9.152 |
| B38 | <0.01 | >1.0 | 1.90 | 9.73 |
| C38 | <0.01 | >2.5 | 1.228 | 10.5 |
| D38 | <0.01 | >1.0 | 1.25 | 8.76 |
| E38 | <0.01 | >2.5 | 0.949 | 7.851 |
| F38 | <0.01 | >1.0 | 1.91 | 10.83 |
| G38 | <0.01 | >2.5 | 1.166 | 9.948 |
| H38 | <0.01 | >1.0 | 1.30 | 10.80 |
| I38 | <0.01 | >2.5 | 0.784 | 9.886 |
| J38 | <0.01 | >1.0 | 3.46 | >30 |
| K38 | <0.01 | >2.5 | 5.929 | >30 |
| L38 | <0.01 | >1.0 | 1.85 | 15.78 |
| M38 | <0.01 | >2.5 | 1.519 | 17.331 |
| N38 | <0.01 | >1.0 | 3.41 | >30 |
| O38 | <0.01 | >2.5 | 2.696 | >30 |
| P38 | <0.01 | >1.0 | 1.78 | 11.19 |
| Q38 | <0.01 | >2.5 | 2.403 | 19.332 |
| R38 | <0.01 | >1.0 | 5.50 | >30 |
| S38 | <0.01 | >2.5 | 3.695 | >30 |
| T38 | <0.01 | >1.0 | | |

Example 236

Synthesis of (Z)-5-((5-(3-chlorophenoxy)-7-(cyclopropylamino)pyrazolo[1,5-a]pyrimidin-3-yl)methylene)imidazolidine-2,4-dione

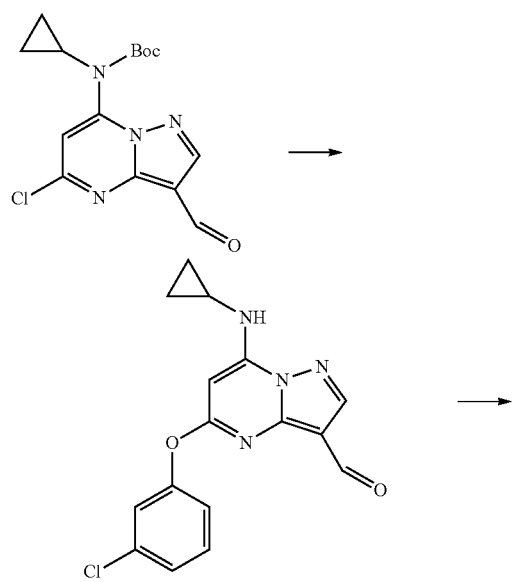

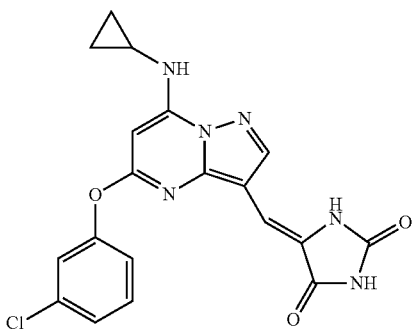

Tert-butyl 5-chloro-3-formylpyrazolo[1,5-a]pyrimidin-7-yl(cyclopropyl)carbamate (1.0 eq, 49 mg, 0.145 mmol) was mixed in a vial with NMP (0.2 ml), 3-chlorophenol (5.0 eq, 93 mg, 0.274 mmol) and potassium carbonate (5.0 eq, 100 mg, 0.723 mmol). The reaction mixture was stirred at room temperature for one hour. Water was added and the resulting gummy material was extracted with methylene chloride. The organic phase was dried over $Na_2SO_4$ and the volatiles removed in vacuo. The resulting NMP solution was reacted with a HCl 4N solution in dioxane (5 ml) at room temperature for one hour, at which time LCMS monitoring indicated completion of the reaction. The reaction was treated with water and 6N NaOH and stirred overnight at room temperature. The solid was filtered and dried to afford crude 5-(3-chlorophenoxy)-7-(cyclopropylamino)pyrazolo[1,5-a]pyrimidine-3-carbaldehyde as a solid (31 mg). The material was heated with hydantoin (30 mg), piperidine (30 uL) in Ethanol (1 ml) in a vial at 90° C. for seven hours. Water was added and the material was filtered, washed with ethanol, ethanol/water and dried. (Z)-5-((5-(3-chlorophenoxy)-7-(cyclopropylamino)pyrazolo[1,5-a]pyrimidin-3-yl)methylene)imidazolidine-2,4-dione was isolated as solid (43 mg, 38% over 2 steps).). LCMS (ES):>95% pure, m/z 411 [M+H]$^+$.

The following compounds were prepared using chemistry described in Example 236. Table 42B shows the biological activities of the compounds listed in Table 42A.

TABLE 42A

TABLE 42A-continued

[Structure: pyrazolopyrimidine with cyclopropylamino, cyanochlorophenoxy, and hydantoin substituents]

TABLE 42B

| Compound | CK2: IC50 (μM) | PIM2: IC50 (μM) | AB: MDAMB453 (μM) | AB: BxPC3 (μM) |
|---|---|---|---|---|
| U38 | <0.01 | >2.5 | 10.724 | 20.865 |
| V38 | <0.01 | >2.5 | 1.377 | 5.205 |

Example 237

Synthesis of 4-(2-(2-chloro-3-nitrophenoxy)ethyl)morpholine

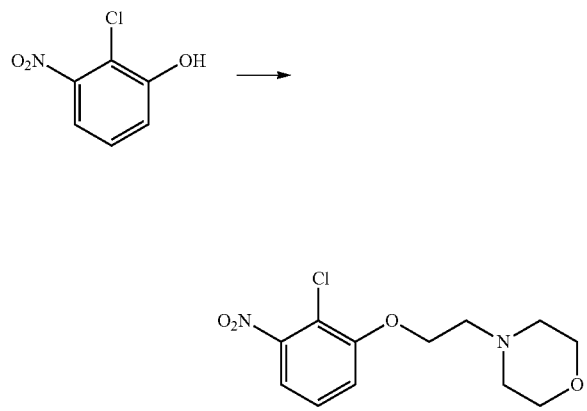

2-chloro-3-nitrophenol (1 g, 5.8 mmol) was dissolved in DMF (6 mL). $K_2CO_3$ (1.6 g, 11.5 mmol) was added and the solution changed from yellow to red. 4-(2-chloroethyl)morpholine hydrochloride (1.07 g, 5.8 mmol) was added and the solution was allowed to stir for 15 h. The reaction was poured into $H_2O$ (30 mL) and extracted with EtOAc (3×30 mL). The organics were washed with 1N NaOH (100 mL) and brine (100 mL) and then dried over $MgSO_4$, filtered, and concentrated in vacuo to provide 4-(2-(2-chloro-3-nitrophenoxy)ethyl)morpholine (1.4 g, 87%) as a golden oil.

The compounds described in the following table were prepared using chemistries similar to those exemplified in Example 237. All compounds were characterized by LCMS.

| Compound | Yield |
|---|---|
| [Structure: 2-chloro-1-nitro-3-(2-(pyrrolidin-1-yl)ethoxy)benzene] | 37 |
| [Structure: 2-chloro-1-nitro-3-(3-(dimethylamino)propoxy)benzene] | 30 |

Example 238

Synthesis of 2-chloro-3-(2-morpholinoethoxy)aniline

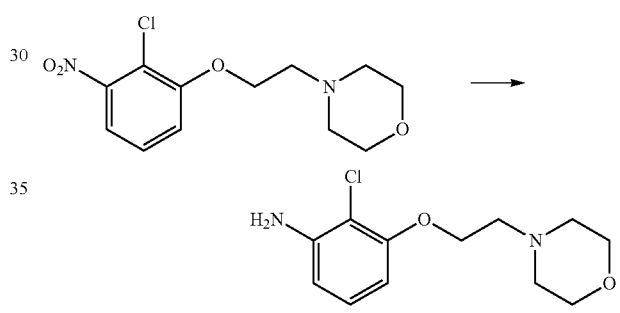

4-(2-(2-chloro-3-nitrophenoxy)ethyl)morpholine (873 mg, 3.1 mmol) was dissolved in toluene (12 mL). Ammonium formate (866 mg, 13.7 mmol) was dissolved in $H_2O$ (12 mL) and added. Iron powder (<10 micron, 766 mg, 13.7 mmol) was added and the reaction was placed in a 120° C. oil bath. After 1.25 h, the solution was cooled to 23° C. and filtered over a pad of celite eluting with 10% MeOH/dichloromethane (250 mL). The filtrate was concentrated in vacuo and the residue was purified via flash column chromatography to give 2-chloro-3-(2-morpholinoethoxy)aniline (503 mg, 75%) as a golden oil.

The compounds described in the following table were prepared using chemistries similar to those exemplified in Example 238. All compounds were characterized by LCMS.

| Structure | Yield |
|---|---|
| [Structure: 2-chloro-3-(2-(pyrrolidin-1-yl)ethoxy)aniline] | 90 |

-continued

| Structure | Yield |
|---|---|
| 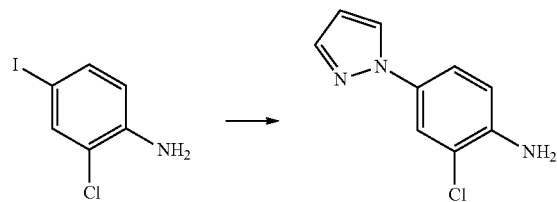 [SMILES: Nc1ccc(I)cc1Cl ; Nc1ccc(-n2cccn2)cc1Cl] | 76 |

Example 239

Synthesis of 2-chloro-4-(1H-pyrazol-1-yl)aniline 2-chloro-4-iodoaniline (760 mg, 3 mmol), N,N'-dimethylethylenediamine (96 µl, 0.9 mmol), 1H-pyrazole (430 mg, 6.3 mmol) were dissolved in DMF (3.8 mL). Cs$_2$CO$_3$ (1.86 g, 5.7 mmol) and CuI (57 mg, 0.3 mmol) were added and the reaction was placed in a 140° C. oil bath. After 3 h, the volatiles were removed in vacuo. The residue was diluted with dichloromethane and purified via flash column chromatography (1% MeOH/dichloromethane) to furnish 2-chloro-4-(1H-pyrazol-1-yl)aniline (540 mg, 93%) as a golden brown oil which crystallized overnight at −20° C.

The compounds described in the following table were prepared using chemistries similar to those exemplified in Example 239. All compounds were characterized by LCMS.

| Structure | Yield |
|---|---|
| 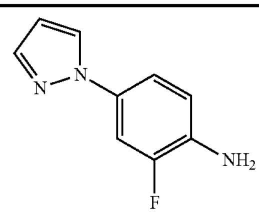 | 93 |
| 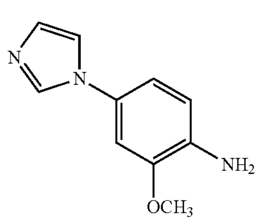 [SMILES: COc1cc(-n2ccnc2)ccc1N] | 89 |
| | 90 |
| | 58 |

Example 240

Synthesis of 1-(3-chloro-4-nitrophenyl)-4-methylpiperazine

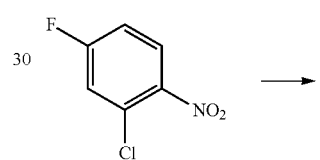

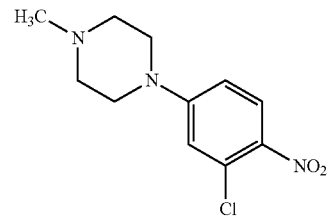

2-chloro-4-fluoronitrobenzene (1 g, 5.7 mmol) was dissolved in DMF (10 mL). 1-methylpiperazine (760 µL, 6.8 mmol) and then K$_2$CO$_3$ (1.57 g, 11.4 mmol) were added and the reaction was placed in a 100° C. oil bath. After 1 h, the solution was cooled to 23° C., then added to H$_2$O (75 mL). The precipitate was filtered, washed with H$_2$O (≈25 mL), then dried overnight (50° C., 25 mmHg) to provide 1-3-chloro-4-nitrophenyl)-4-methylpiperazine (1.28 g, 88%) as a maize colored solid.

The compounds described in the following table were prepared using chemistries similar to those exemplified in Example 240. All compounds were characterized by LCMS.

| Structure | Yield |
|---|---|
| (morpholine-Cl-nitrobenzene structure) | 97 |

| Structure | Yield |
|---|---|
| (morpholine-Cl-aniline structure) | 89 |

Example 241

Synthesis of 2-chloro-4-(4-methylpiperazin-1-yl)aniline

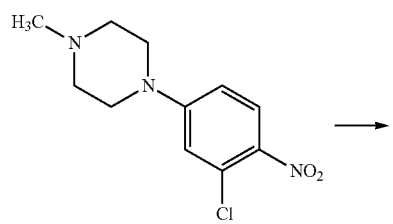

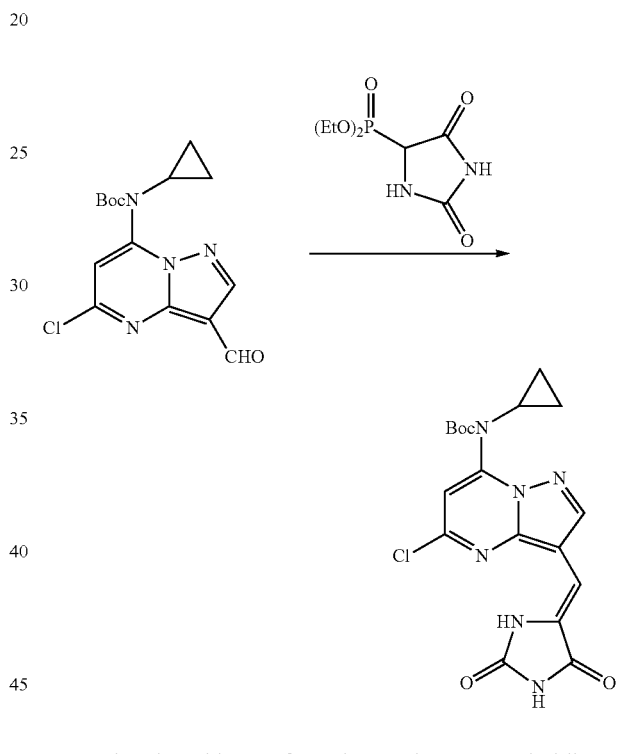

1-3-chloro-4-nitrophenyl)-4-methylpiperazine (414 mg, 1.62 mmol)was dissolved in toluene (6.5 mL). Ammonium formate (461 mg, 7.3 mmol) was dissolved in H$_2$O (6.5 mL) and added. Iron powder (<10 micron, 408 mg, 7.3 mmol) was added and the reaction was placed in a 120° C. oil bath. After 1.25 h, the solution was cooled to 23° C. and filtered over a pad of celite eluting with 10% MeOH/dichloromethane (250 mL). The filtrate was concentrated in vacuo and the residue was partitioned between H$_2$O (25 mL) and EtOAc (25 mL). The aqueous layer was further extracted with EtOAc (6×25 mL) and then dichloromethane (3×25 mL). The organics were dried over MgSO$_4$, filtered, and concentrated in vacuo to afford 2-chloro-4-(4-methylpiperazin-1-yl)aniline (157 mg, 43%) as a light brown solid.

The compounds described in the following table were prepared using chemistries similar to those exemplified in Example 241. All compounds were characterized by LCMS.

Example 242

Synthesis of (Z)-tert-butyl 5-chloro-3-(2,5dioxoimidazolidin-4-ylidine)methyl)pyrazolo[1,5-a]pyrimidine-7-yl(cyclopropyl)carbamate Tert-butyl 5-chloro-3-formylpyrazolo[1,5-a]pyrimidin-7-yl(cyclopropyl)carbamate (5.05 g, 15 mmol) was dissolved in anhydrous THF (100 mL). Diethyl 2,5-dioxoimidazolidin-4-ylphosphonate (5.33 g, 22.5 mmol) and NaOt-bu (1.87 g, 19.5 mmol) were then added. After stirring for 3 d at 23° C., additional diethyl 2,5-dioxoimidazolidin-4-ylphosphonate (3.5 g) and NaOt-bu (1.44 g) were added. After stirring an additional 24 h, the volatiles were removed in vacuo. The residue was stirred for 4 h in i-PrOH (50 mL) and water (250 mL) and then filtered to afford crude tert-butyl 5-chloro-3-((2,5-dioxoimidazolidin-4-ylidine)methyl)pyrazolo[1,5-a]pyrimidine-7-yl(cyclopropyl)carbamate (5.64 g, 90%) as a mixture of Z:E isomers (5.3:1). The crude solid was diluted with i-PrOH (110 mL) and heated to reflux. The solution was filtered and then allowed to cool to afford (Z)-tert-butyl 5-chloro-34(2,5-dioxoimidazolidin-4-ylidine)methyl)pyrazolo[1,5-a]pyrimidine-7-yl(cyclopropyl)carbamate (3.58 g, 57%) as a bright orange solid in two crops. $^1$H NMR (CDCl$_3$, 400 MHz) δ: 10.37 (bs, 1H), 8.17 (s, 1H), 8.02 (bs, 1H), 6.81 (s, 1H), 6.60 (s, 1H), 3.26 (dddd, 1H, J=6.8, 6.8, 3.2, 3.2 Hz), 1.43 (s, 9H), 0.87-0.94 (m, 2H), 0.62-0.68 (m, 2H). LCMS (ES): >90% pure, m/z 419 [M+1]+.

Diethyl 2,5-dioxoimidazolidin-4-ylphosphonate was prepared according to the procedure of Meanwell, et al. *J. Org. Chem.* 1991, 56, 6897.

Example 243

Synthesis of (Z)-5-((5-chloro-7-(cyclopropylamino)pyrazolo[1,5-a]pyrimidine-3-yl)methylene)imidazolidine-2,4-dione

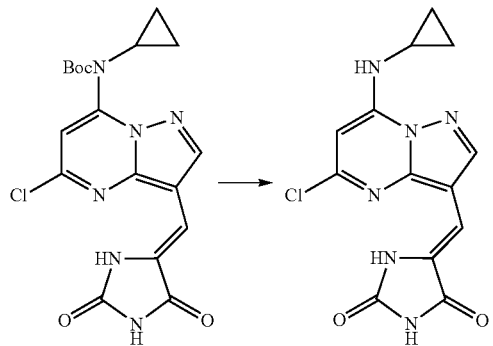 [SMILES: CC(C)(C)OC(=O)N(c1cc(Cl)nc2c(/C=C3\NC(=O)NC3=O)cnn12)C1CC1 ; O=C1NC(=O)/C(=C/c2cnn3c(NC4CC4)cc(Cl)nc23)N1]

(Z)-tert-butyl 5-chloro-3-((2,5-dioxoimidazolidin-4-ylidine)methyl)pyrazolo[1,5-a]pyrimidine-7-yl(cyclopropyl)carbamate (3.20 g, 7.66 mmol) was suspended in dichloromethane (30 mL). Trifluoroacetic acid (30 mL) was added slowly and the solution became homogeneous. After 1 h, the volatiles were removed in vacuo. The residue was triturated in Et$_2$O (100 mL) and the bright yellow solid was filtered off to afford (Z)-5-((5-chloro-7-(cyclopropylamino)pyrazolo[1,5-a]pyrimidin-3-yl)methylene)imidazolidine-2,4-dione (2.42 g, 99%). LCMS (ES): >90% pure, m/z 319 [M+1]+.

Example 244

Synthesis of (Z)-N-(3-(7-(cyclopropylamino)-3-((2,5-dioxoimidazolidin-4-ylidene)methyl)pyrazolo[1,5-a]pyrimidin-5-ylamino)phenyl)acetamide

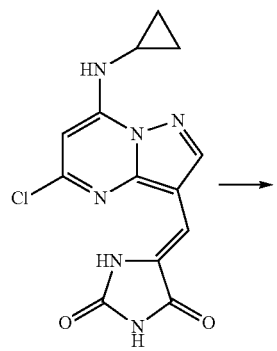

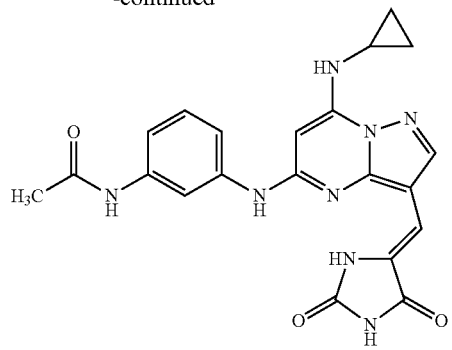

(Z)-5-((5-chloro-7-(cyclopropylamino)pyrazolo[1,5-a]pyrimidin-3-yl)methylene)imidazolidine-2,4-dione (75 mg, 0.23 mmol) was suspended in 1,4-dioxane (1.6 mL).N-(3-aminophenyl)acetamide (52 mg, 0.35 mmol), Cs$_2$CO$_3$ (105 mg, 0.32 mmol), (±)-BINAP (9 mg, 0.06 mmol) and palladium(II) acetate (7 mg, 0.04 mmol) were then added. The mixture was sealed and irradiated at 120° C. for 30 min in the microwave. H$_2$O (8 mL) was added and the precipitate was filtered off and dried. The crude residue was purified via flash column chromatography (2.5-3.5% MeOH/dichloromethane) to yield (Z)-N-(3-(7-(cyclopropylamino)-3-((2,5-dioxoimidazolidin-4-ylidene)methyl)pyrazolo[1,5-a]pyrimidin-5-ylamino)phenyl)acetamide (12 mg, 12%) as a bright yellow solid. LCMS (ES): >90% pure, m/z 433 [M+1]+.

The compounds described in the following table were prepared using chemistries similar to those exemplified in Examples 242 to 244. All compounds were characterized by LCMS. Table 43B shows the biological activities of the compounds listed in Table 43A.

TABLE 43A

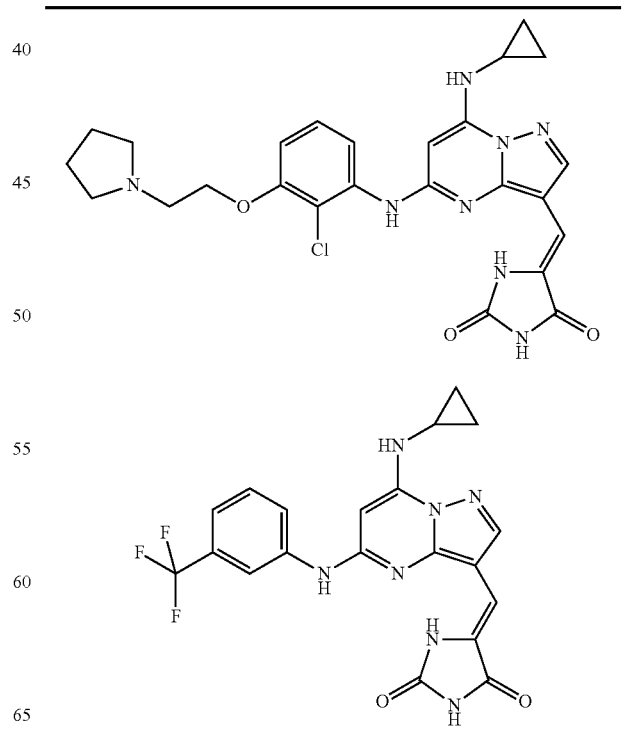

TABLE 43A-continued
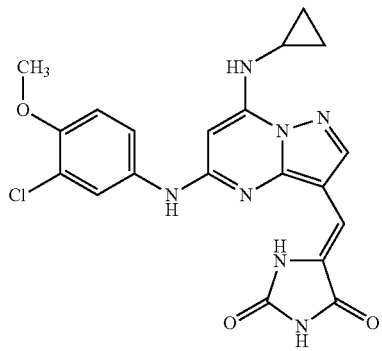 [SMILES: COc1ccc(Nc2cc(NC3CC3)n3ncc(/C=C4\NC(=O)NC4=O)c3n2)cc1Cl]
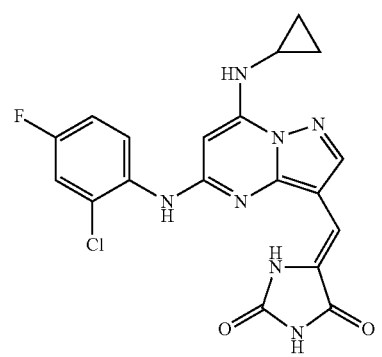
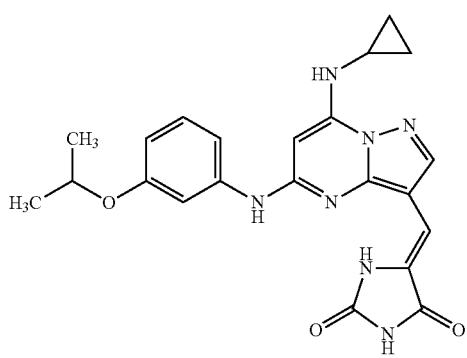 [SMILES: CC(C)Oc1cccc(Nc2cc(NC3CC3)n3ncc(/C=C4\NC(=O)NC4=O)c3n2)c1]
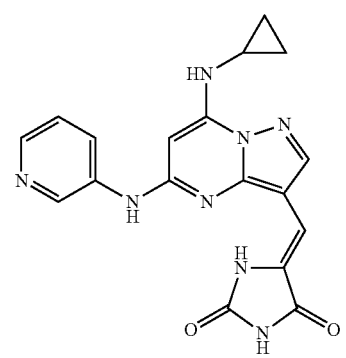 [SMILES: O=C1NC(=O)/C(=C/c2cnn3c(NC4CC4)cc(Nc4cccnc4)nc23)N1]
TABLE 43A-continued
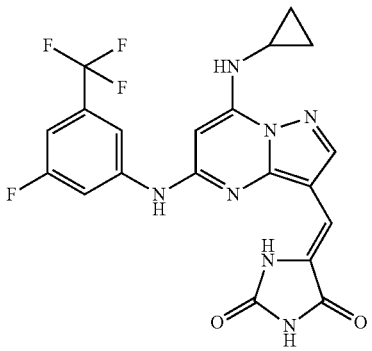 [SMILES: O=C1NC(=O)/C(=C/c2cnn3c(NC4CC4)cc(Nc4cc(F)cc(C(F)(F)F)c4)nc23)N1]
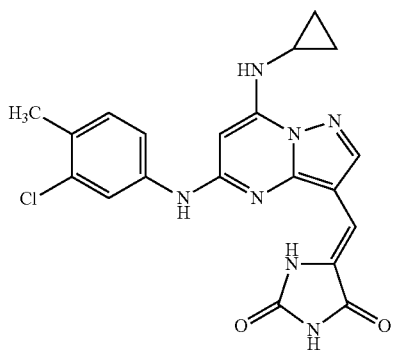 [SMILES: Cc1ccc(Nc2cc(NC3CC3)n3ncc(/C=C4\NC(=O)NC4=O)c3n2)cc1Cl]
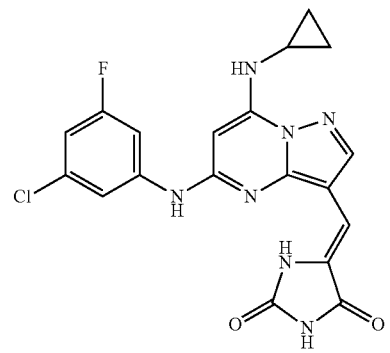 [SMILES: O=C1NC(=O)/C(=C/c2cnn3c(NC4CC4)cc(Nc4cc(F)cc(Cl)c4)nc23)N1]
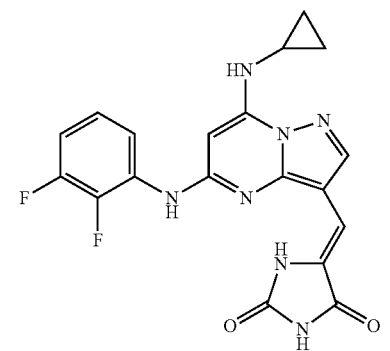

TABLE 43A-continued
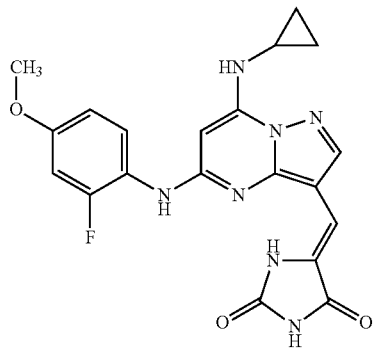 [SMILES: COc1ccc(Nc2cc(NC3CC3)n3ncc(/C=C4\NC(=O)NC4=O)c3n2)c(F)c1]
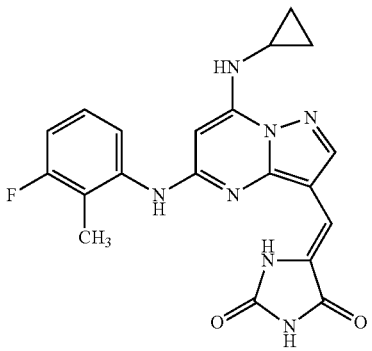
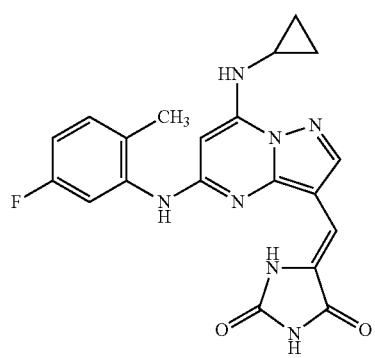 [SMILES: Cc1ccc(F)cc1Nc1cc(NC2CC2)n2ncc(/C=C3\NC(=O)NC3=O)c2n1]
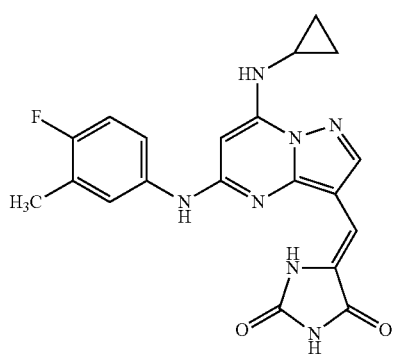
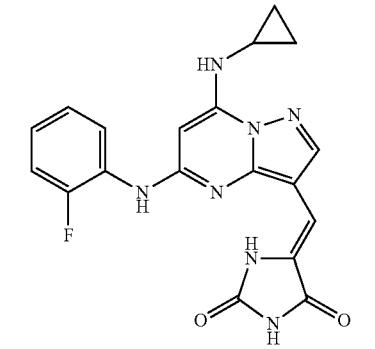
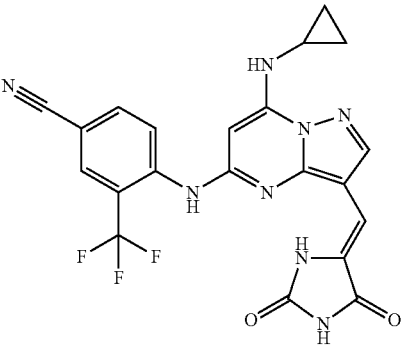
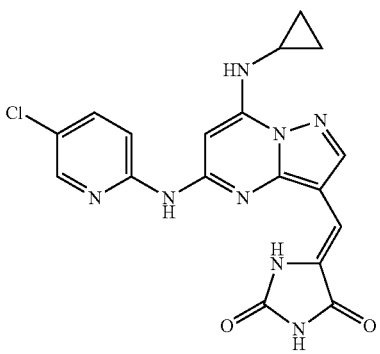 [SMILES: O=C1NC(=O)/C(=C/c2cnn3c(NC4CC4)cc(Nc4ccc(Cl)cn4)nc23)N1]
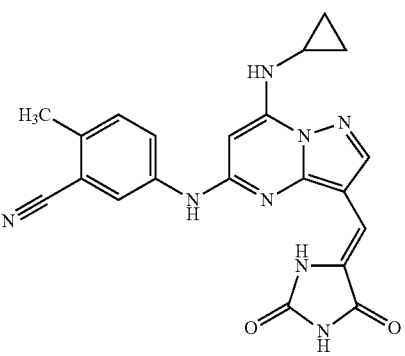 [SMILES: Cc1ccc(Nc2cc(NC3CC3)n3ncc(/C=C4\NC(=O)NC4=O)c3n2)cc1C#N]

TABLE 43A-continued
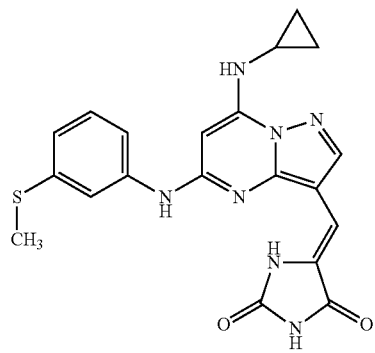 [SMILES: CSc1cccc(Nc2cc(NC3CC3)n3ncc(/C=C4\NC(=O)NC4=O)c3n2)c1]
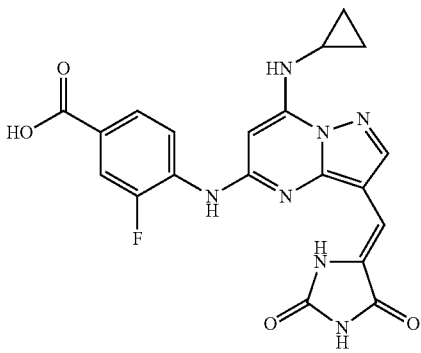
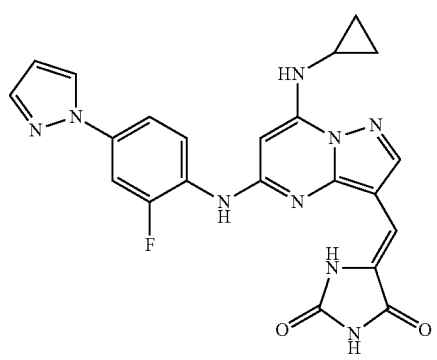 [SMILES: O=C1NC(=O)/C(=C/c2cnn3c(NC4CC4)cc(Nc4ccc(-n5cccn5)cc4F)nc23)N1]
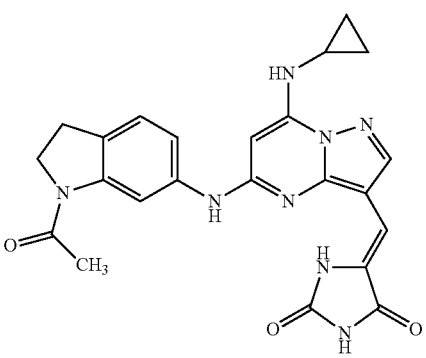 [SMILES: CC(=O)N1CCc2ccc(Nc3cc(NC4CC4)n4ncc(/C=C5\NC(=O)NC5=O)c4n3)cc21]

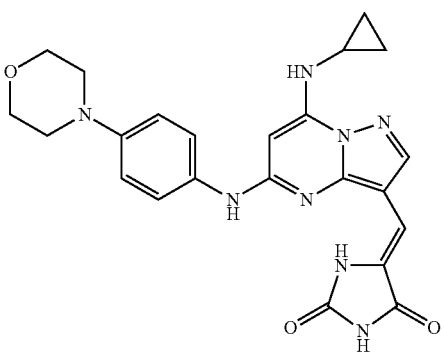 [SMILES: O=C1NC(=O)/C(=C/c2cnn3c(NC4CC4)cc(Nc4ccc(N5CCOCC5)cc4)nc23)N1]
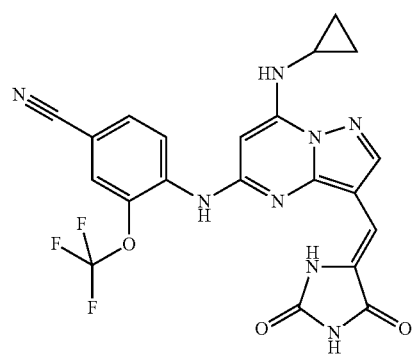
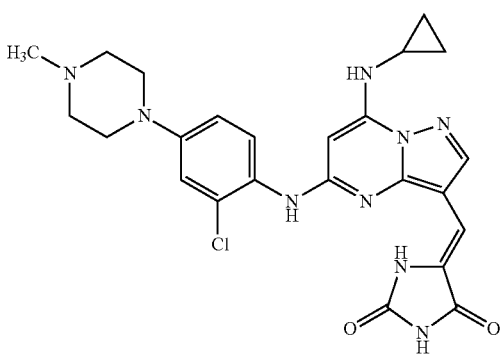 [SMILES: CN1CCN(c2ccc(Nc3cc(NC4CC4)n4ncc(/C=C5\NC(=O)NC5=O)c4n3)c(Cl)c2)CC1]

TABLE 43A-continued
531
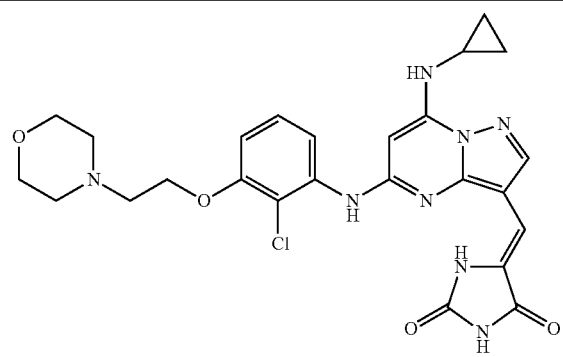
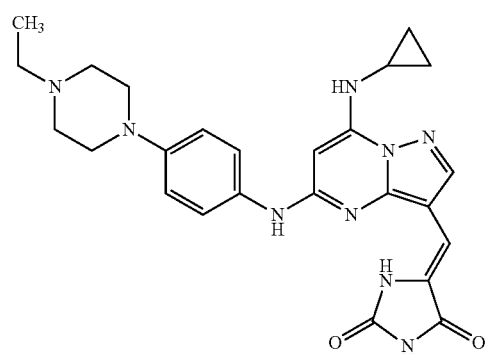
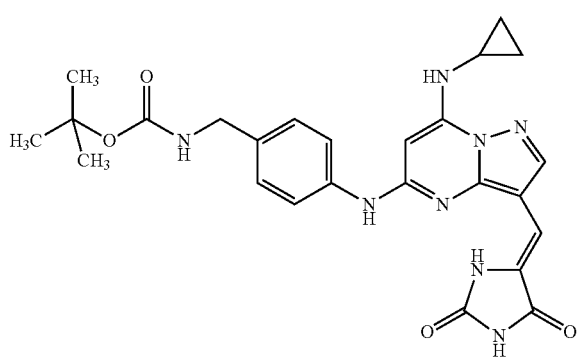 [SMILES: CC(C)(C)OC(=O)NCc1ccc(Nc2cc(NC3CC3)n3ncc(/C=C4\NC(=O)NC4=O)c3n2)cc1]
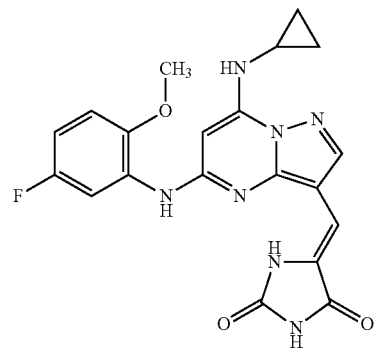 [SMILES: COc1ccc(F)cc1Nc1cc(NC2CC2)n2ncc(/C=C3\NC(=O)NC3=O)c2n1]
532
TABLE 43A-continued
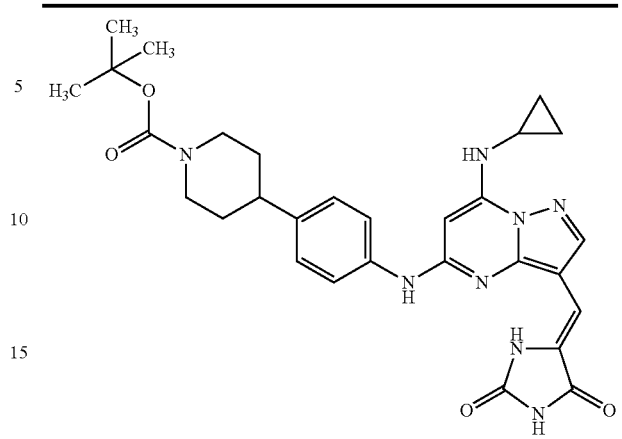
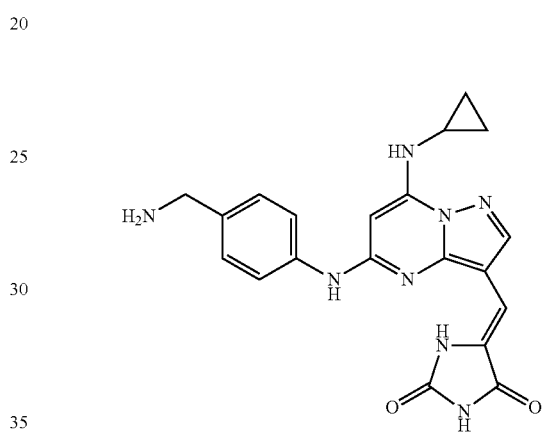
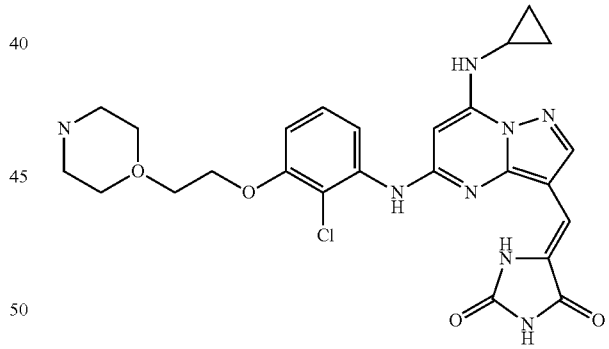
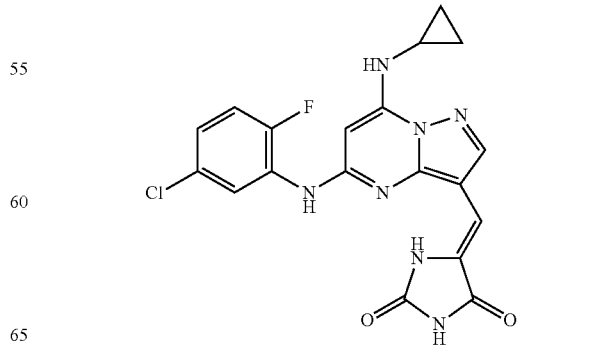

TABLE 43A-continued
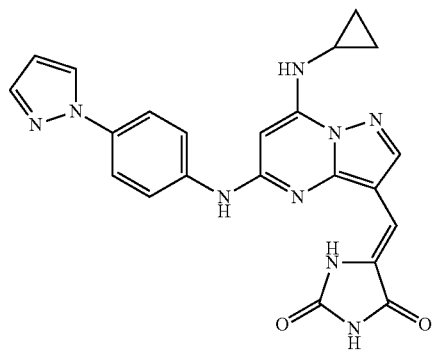 [SMILES: O=C1NC(=O)/C(=C/c2cnn3c(NC4CC4)cc(Nc4ccc(-n5cccn5)cc4)nc23)N1]
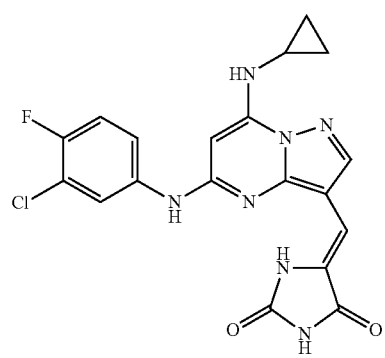 [SMILES: O=C1NC(=O)/C(=C/c2cnn3c(NC4CC4)cc(Nc4ccc(F)c(Cl)c4)nc23)N1]
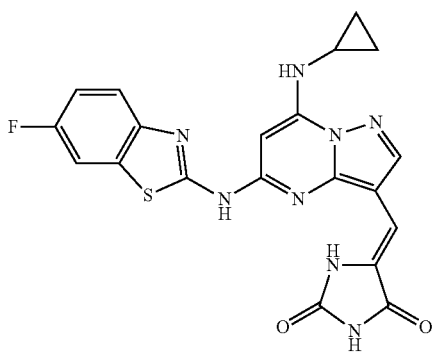 [SMILES: O=C1NC(=O)/C(=C/c2cnn3c(NC4CC4)cc(Nc4nc5ccc(F)cc5s4)nc23)N1]
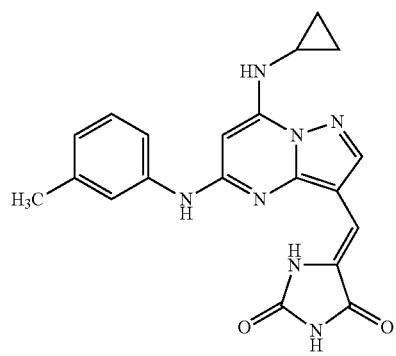
TABLE 43A-continued
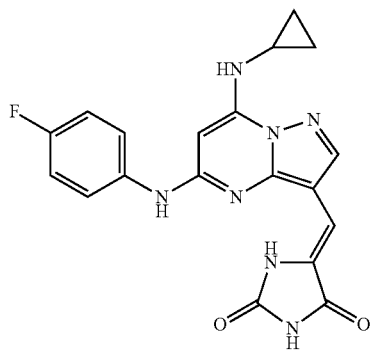
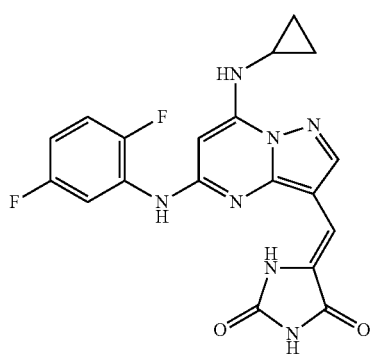
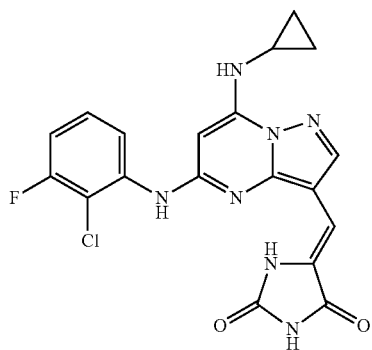
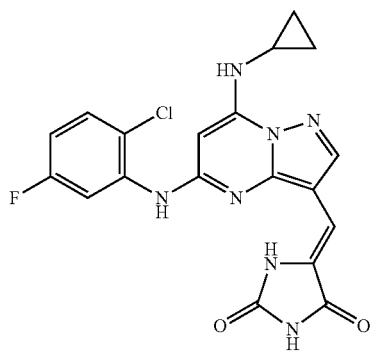

TABLE 43A-continued
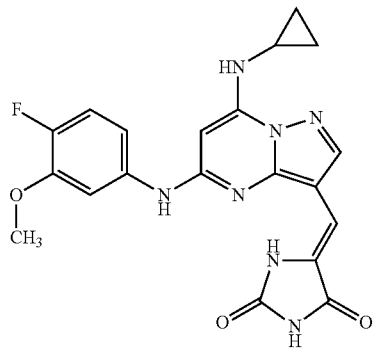 [SMILES: COc1cc(Nc2cc(NC3CC3)n3ncc(/C=C4\NC(=O)NC4=O)c3n2)ccc1F]
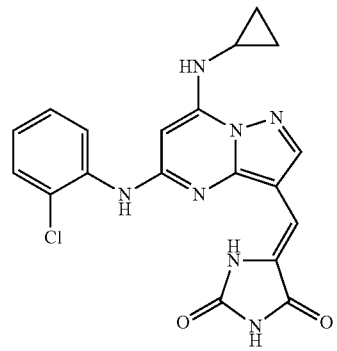
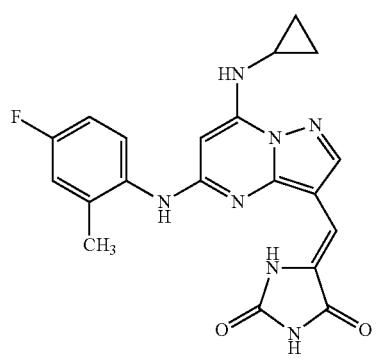
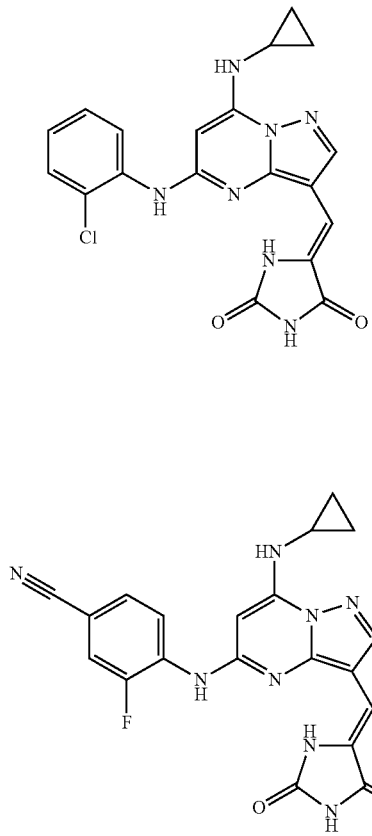
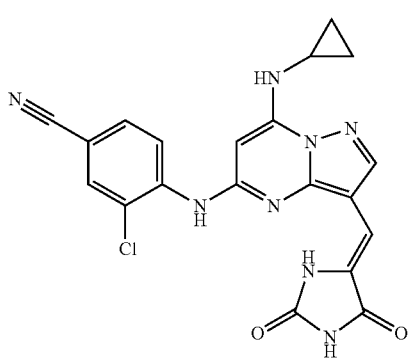
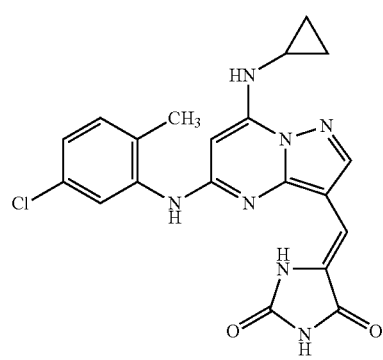 [SMILES: Cc1ccc(Cl)cc1Nc1cc(NC2CC2)n2ncc(/C=C3\NC(=O)NC3=O)c2n1]
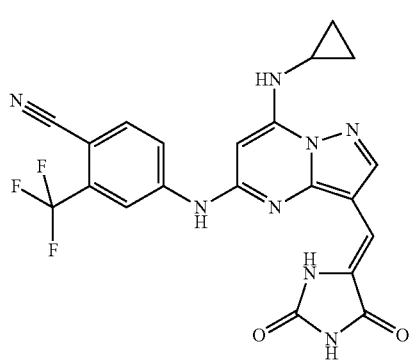
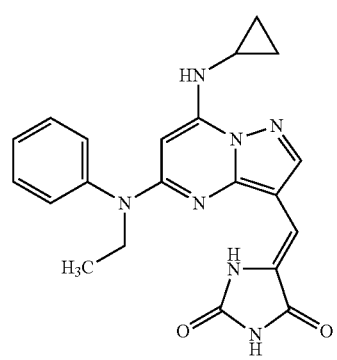 [SMILES: CCN(c1ccccc1)c1cc(NC2CC2)n2ncc(/C=C3\NC(=O)NC3=O)c2n1]

537
TABLE 43A-continued
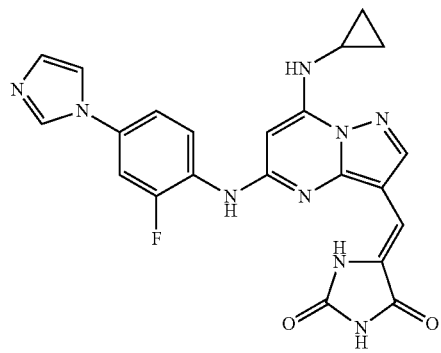
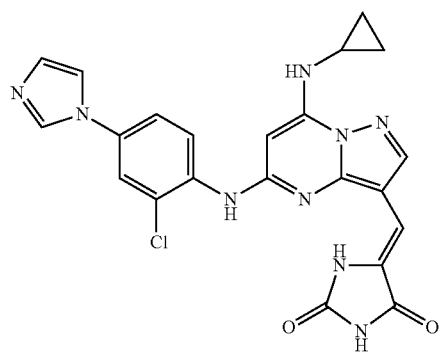
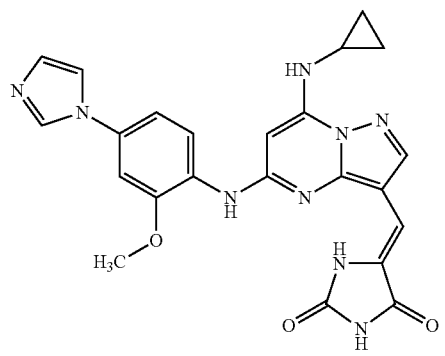 [SMILES: COc1cc(-n2ccnc2)ccc1Nc1cc(NC2CC2)n2ncc(/C=C3\NC(=O)NC3=O)c2n1]
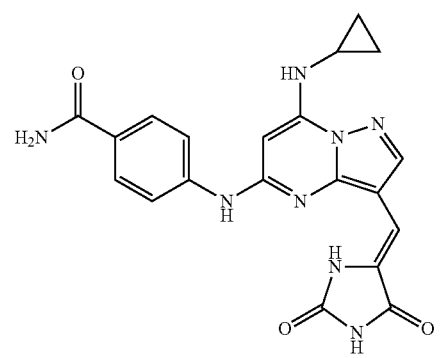
538
TABLE 43A-continued
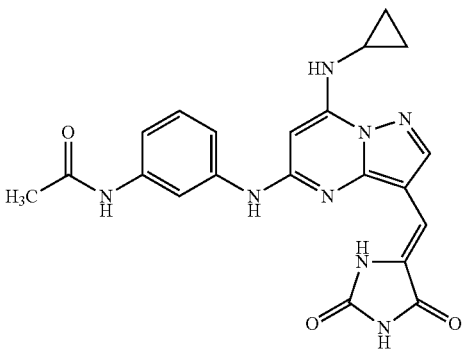 [SMILES: CC(=O)Nc1cccc(Nc2cc(NC3CC3)n3ncc(/C=C4\NC(=O)NC4=O)c3n2)c1]
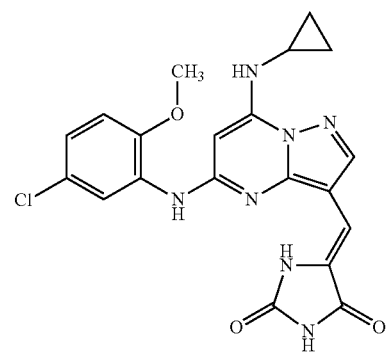
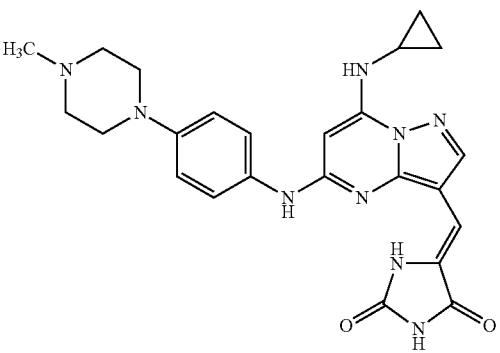 [SMILES: CN1CCN(c2ccc(Nc3cc(NC4CC4)n4ncc(/C=C5\NC(=O)NC5=O)c4n3)cc2)CC1]
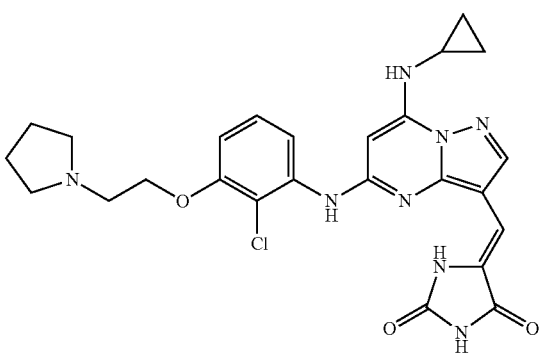 [SMILES: O=C1NC(=O)/C(=C/c2cnn3c(NC4CC4)cc(Nc4cccc(OCCN5CCCC5)c4Cl)nc23)N1]

TABLE 43A-continued
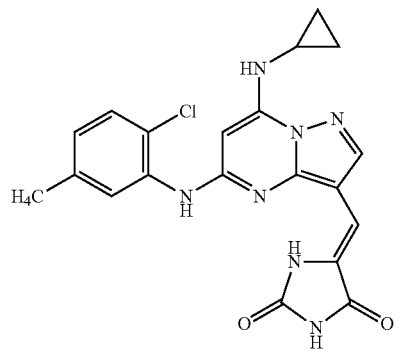
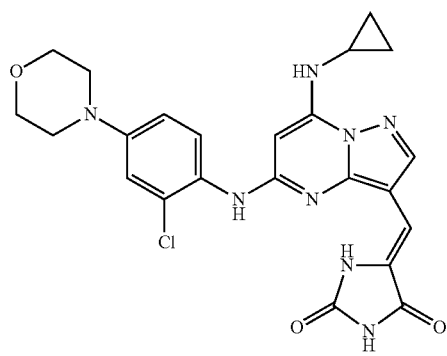 [SMILES: O=C1NC(=O)/C(=C/c2cnn3c(NC4CC4)cc(Nc4ccc(N5CCOCC5)cc4Cl)nc23)N1]
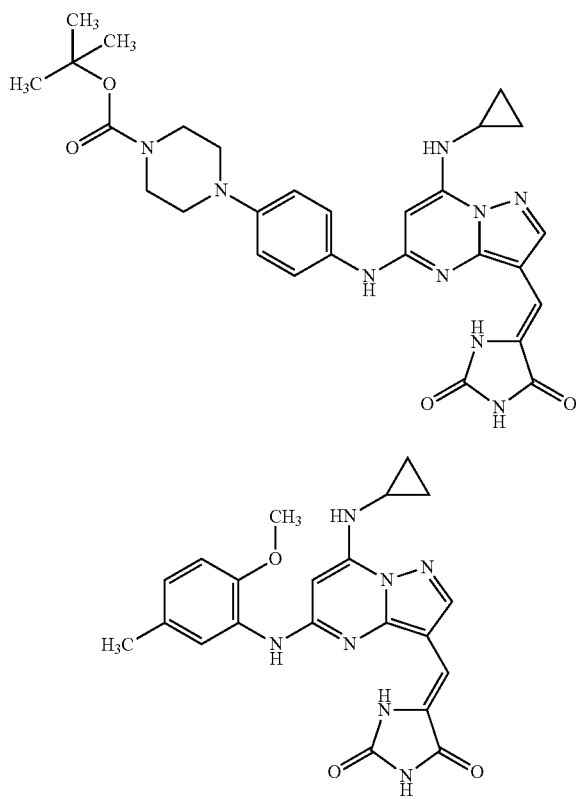
TABLE 43A-continued
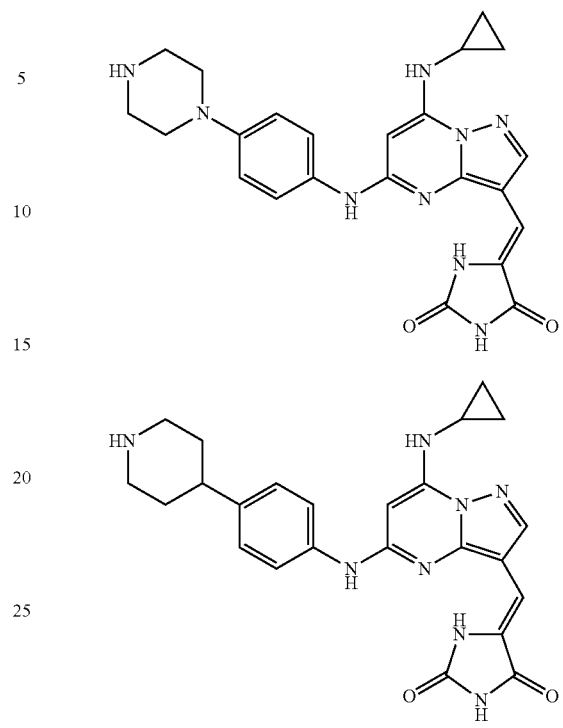
TABLE 43B
| Compound | CK2: IC50 (μM) | PIM2: % inh 2.5 μM | AB: MDAMB453 IC50 (μM) | AB: BxPC3 IC50 (μM) |
|---|---|---|---|---|
| W38 | <0.01 | 12.679 | 0.503 | 3.401 |
| X38 | <0.01 | −14.929 | 0.817 | 7.128 |
| Y38 | <0.01 |  | 6.404 | >30 |
| Z38 | <0.01 | 5.11 | 0.363 | 2.273 |
| A39 | <0.01 | −5.524 | 1.483 | 3.348 |
| B39 | <0.01 | 42.988 | 2.309 | 2.183 |
| C39 | <0.01 |  | 4.463 | 27.171 |
| D39 | <0.01 |  | 2.776 | 6.141 |
| E39 | <0.01 | 12.058 | 1.745 | 2.347 |
| F39 | <0.01 | 29.369 | 24.684 | >30 |
| G39 | <0.01 | 38.351 | 9.58 | 13.05 |
| H39 | <0.01 | 32.314 | 1.187 | 5.5 |
| I39 | <0.01 | −19.596 | 3.914 | 13.069 |
| J39 | <0.01 | 19.119 | 2.462 | 4.126 |
| K39 | <0.01 | −2.822 | 1.179 | 14.376 |
| L39 | <0.01 | 53.751 | 1.132 | 4.028 |
| M39 | <0.01 | −12.471 | 1.824 | 20.033 |
| N39 | <0.01 |  | 1.334 | 2.178 |
| O39 | <0.01 |  | 2.901 | 5.71 |
| P39 | <0.01 |  | 1.012 | 3.518 |
| Q39 | <0.01 | 50.224 | 0.568 | 2.448 |
| R39 | <0.01 |  | 7.228 | 15.996 |
| S39 | <0.1 |  | 3.118 | 5.462 |
| T39 | <0.01 |  | 5.657 | 13.157 |
| U39 | <0.01 |  | 16.983 | 13.301 |
| V39 | <0.01 | 15.34 | 0.503 | 3.722 |
| W39 | <0.01 | 20.319 | <0.12 | <0.12 |
| X39 | <0.1 | 23.241 | 3.558 | 0.409 |
| Y39 | <0.01 | 45.658 | 1.685 | 5.123 |
| Z39 | <0.01 | 32.912 | 10.761 | 11.535 |
| A40 | <0.01 | 61.33 | 1.214 | 4.211 |
| B40 | <0.01 | 27.322 | 8.026 | >30 |
| C40 | <0.01 | 54.631 | 0.568 | 0.427 |
| D40 | <0.01 | 56.161 | 3.885 | 4.838 |
| E40 | <0.01 | 45.415 | 10.016 | 7.671 |
| F40 | <0.01 | 74.699 | 1.487 | 2.566 |
| G40 | <0.01 | 74.328 | 16.589 | 14.183 |

TABLE 43B-continued

| Compound | CK2: IC50 (μM) | PIM2: % inh 2.5 μM | AB: MDAMB453 IC50 (μM) | AB: BxPC3 IC50 (μM) |
|---|---|---|---|---|
| H40 | <0.01 | 55.726 | 1.099 | 4.157 |
| I40 | <0.01 | 67.726 | 0.882 | 2.795 |
| J40 | <0.01 | 69.269 | 14.73 | 5.949 |
| K40 | <0.01 | 66.943 | 1.042 | 3.053 |
| L40 | <0.01 | 37.998 | 6.073 | 1.762 |
| M40 | <0.01 | 26.534 | 2.111 | 1.273 |
| N40 | <0.1 | 23.553 | 3.706 | 1.379 |
| O40 | <0.01 | 60.445 | 16.119 | >30 |
| P40 | <0.01 | 56.901 | 28.665 | >30 |
| Q40 | <0.01 | 41.399 | 2.892 | 5.65 |
| R40 | <0.01 | 30.569 | 3.021 | 4.466 |
| S40 | <0.01 | 33.343 | 3.273 | 13.798 |
| T40 | <0.01 | 64.565 | 0.656 | 1.485 |
| U40 | <0.01 | 39.619 | 2.736 | 3.191 |
| V40 | <0.01 | 63.083 | 1.997 | 3.383 |
| W40 | <0.01 | 12.679 | 0.503 | 3.401 |
| X40 | <0.01 | −14.929 | 0.817 | 7.128 |
| Y40 | <0.01 | 55.807 | 0.248 | 9.761 |
| Z40 | <0.01 | 55.427 | 0.999 | 3.866 |
| A41 | <0.01 | 41.66 | 2.511 | 22.3 |
| B41 | <0.01 | 35.147 | 0.764 | 2.282 |
| C41 | <0.01 | 24.356 | 5.447 | 12.691 |
| D41 | <0.01 | −6.887 | 3.168 | 3.25 |
| E41 | <0.01 | −12.19 | 1.04 | 1.794 |
| F41 | <0.01 | 19.291 | 15.678 | 26.981 |
| G41 | <0.01 | 73.187 | 0.803 | 9.037 |
| H41 | <0.01 | 76.943 | 0.852 | 5.263 |
| I41 | <0.01 | 59.089 | 0.776 | 9.983 |

Example 245

Synthesis of (Z)-4-(7-(cyclopropylamino)-3-((2,5-dioxoimidazolidin-4-ylidene)methyl)pyrazolo[1,5-a]pyrimidin-5-ylamino)-N-(2-(diethylamino)ethyl)-3-fluorobenzamide 2,2,2,-trifluoroacetate

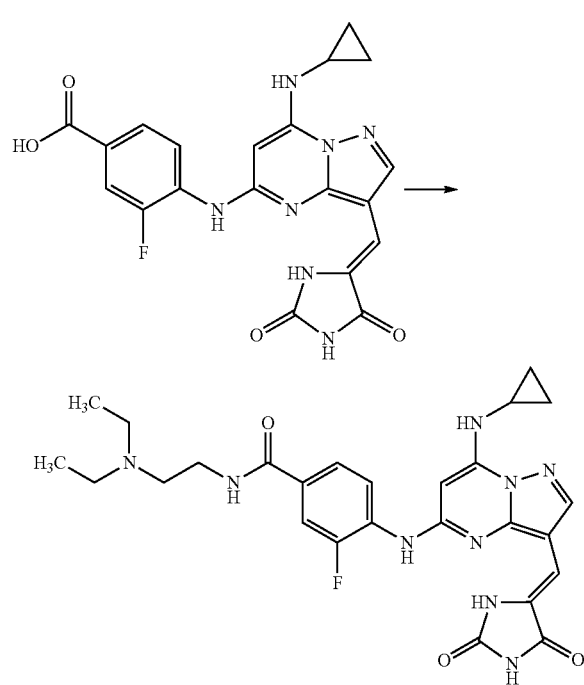 [SMILES: O=C1NC(=O)/C(=C/c2cnn3c(NC4CC4)cc(Nc4ccc(C(=O)O)cc4F)nc23)N1 ; CCN(CC)CCNC(=O)c1ccc(Nc2cc(NC3CC3)n3ncc(/C=C4\NC(=O)NC4=O)c3n2)c(F)c1]

(Z)-4-(7-(cyclopropylamino)-3-((2,5-dioxoimidazolidin-4-ylidene)methyl)pyrazolo[1,5-a]pyrimidin-5-ylamino)-3-fluorobenzoic acid (25 mg, 0.06 mmol) was suspended in DMF (0.2 mL). EDCI (13 mg, 0.7 mmol), HOBt (11 mg, 0.7 mmol), triethylamine (10 μL, 0.7 mmol), and N,N-diethylethylenediamine (8 μL, 0.7 mmol) were added sequentially. The reaction was heated to 65° C. After 1 h, the solution was diluted with DMSO (1 mL) and purified by reverse phase HPLC to yield (Z)-4-(7-(cyclopropylamino)-3-(2,5-dioxoimidazolidin-4-ylidene)methyl)pyrazolo[1,5-a]pyrimidin-5-ylamino)-N-(2-(diethylamino)ethyl)-3-fluorobenzamide 2,2,2-trifluoroacetate (29 mg, 76%). LCMS (ES): >90% pure, m/z 536 [M+1]$^+$.

The compounds described in the following table were prepared using chemistries similar to those exemplified in Example 245. All compounds were characterized by LCMS. Table 44B shows the biological activities of the compounds listed in Table 44A.

TABLE 44A

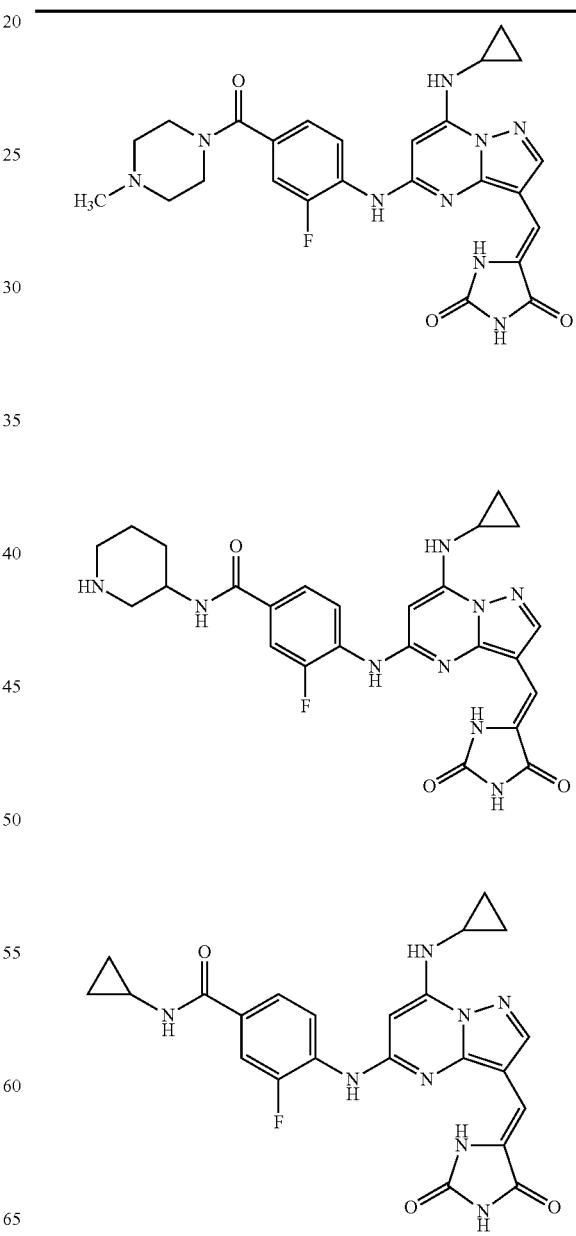

TABLE 44A-continued

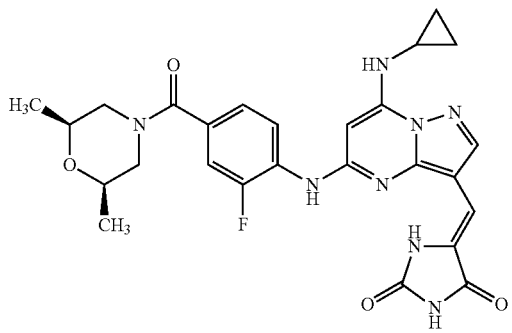 [SMILES: C[C@@H]1CN(C(=O)c2ccc(Nc3cc(NC4CC4)n4ncc(/C=C5\NC(=O)NC5=O)c4n3)c(F)c2)C[C@H](C)O1]

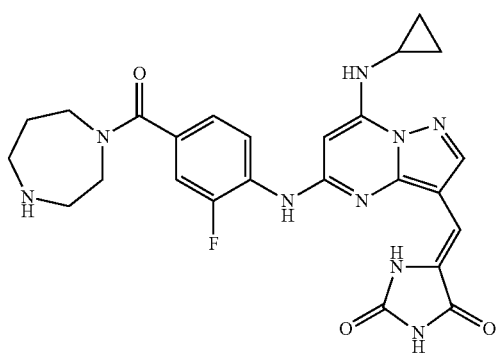 [SMILES: O=C1NC(=O)/C(=C/c2cnn3c(NC4CC4)cc(Nc4ccc(C(=O)N5CCCNCC5)cc4F)nc23)N1]

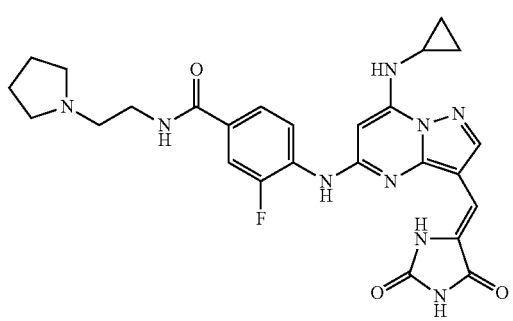 [SMILES: O=C1NC(=O)/C(=C/c2cnn3c(NC4CC4)cc(Nc4ccc(C(=O)NCCN5CCCC5)cc4F)nc23)N1]

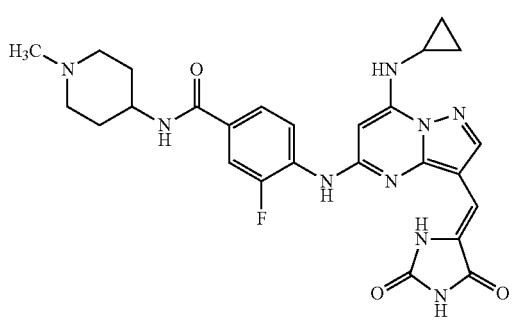 [SMILES: CN1CCC(NC(=O)c2ccc(Nc3cc(NC4CC4)n4ncc(/C=C5\NC(=O)NC5=O)c4n3)c(F)c2)CC1]

TABLE 44A-continued

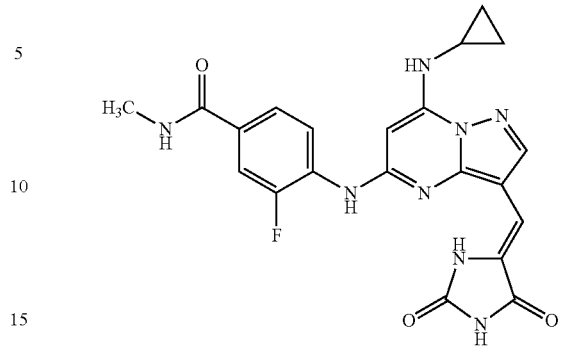

TABLE 44B

| Compound | CK2: IC50 (um) | PIM2: % inh 2.5 uM | AB: MDAMB453 (uM) | AB: BxPC3 (uM) |
|---|---|---|---|---|
| J41 | <0.01 | 33.546 | 1.288 | 10.863 |
| K41 | <0.01 | 55.606 | 5.536 | >30 |
| L41 | <0.01 | 55.104 | 8.434 | 13.38 |
| M41 | <0.01 | 19.242 | 7.402 | >30 |
| N41 | <0.1 | 75.247 | 2.764 | >30 |
| O41 | <0.01 | 57.4 | 3.155 | >30 |
| P41 | <0.1 | 45.679 | 3.578 | 22.618 |
| Q41 | <0.01 | 31.821 | 16.205 | 5.914 |

Example 246

Synthesis of 4-(7-(cyclopropylamino)pyrazolo[1,5-a]pyrimidin-5-ylamino)benzonitrile hydrochloride

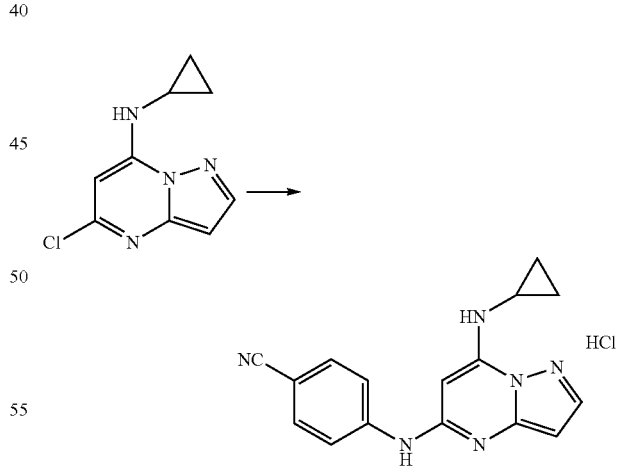

5-chloro-N-cyclopropylpyrazolo[1,5-a]pyrimidin-7-amine (208 mg, 1 mmol) was suspended in EtOH (1 mL). 4-aminobenzonitrile (236 mg, 2 mmol) and then conc. HCl (125 μL, 1.5 mmol) were added and the reaction was placed in a 95° C. oil bath. After 24 h, additional conc. HCl was added (62 μL). After an additional 24 h, the reaction was cooled to 23° C. and the filter cake was washed with EtOH (2 mL) to afford 4-(7-(cyclopropylamino)pyrazolo[1,5-a]pyrimidin-5- ylamino)benzonitrile hydrochloride (205 mg, 63%) as a light brown solid. LCMS (ES): >90% pure, m/z 291 [M+1]⁺.

Example 247

Synthesis of 4-(7-(cyclopropylamino)-3-formylpyrazolo[1,5-a]pyrimidin-5-ylamino)benzonitrile

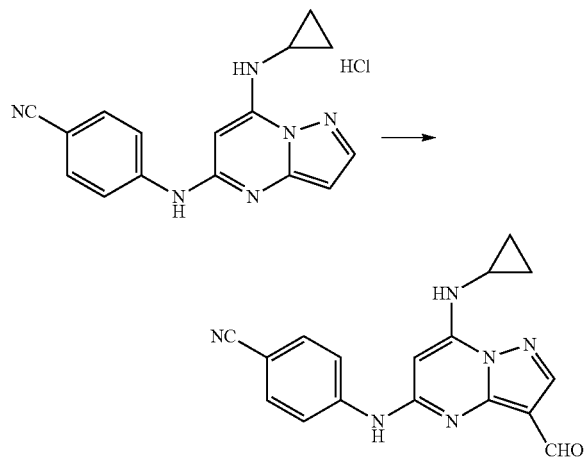

4-(7-(cyclopropylamino)pyrazolo[1,5-a]pyrimidin-5-ylamino)benzonitrile hydrochloride (205 mg, 0.62 mmol) was dissolved in anhydrous DMF (1 mL) and the solution was cooled to 0° C. by an external ice bath. POCl₃ (115 μL, 1.25 mmol) was added dropwise keeping the internal temperature <5° C. After addition, the ice bath was removed. After 5 h, the solution was poured into H₂O (20 mL) and the pH was adjusted to 11 by the addition of 6N NaOH. The solution was allowed to stir for 1 h, and the precipitate was filtered off. The crude product was triturated with EtOH (7 mL), filtered, and dried under high vacuum (1 mmHg) to provide 4-(7-(cyclopropylamino)-3-formylpyrazolo[1,5-a]pyrimidin-5-ylamino)benzonitrile (129 mg, 64%) as an orange solid. LCMS (ES): >90% pure, m/z 319 [M+1]⁺.

Example 248

Synthesis of (Z)-4-(7-(cyclopropylamino)-3-((2,5-dioxoimidazolidin-4-ylidene)methyl)pyrazolo[1,5-a]pyrimidin-5-ylamino)benzonitrile

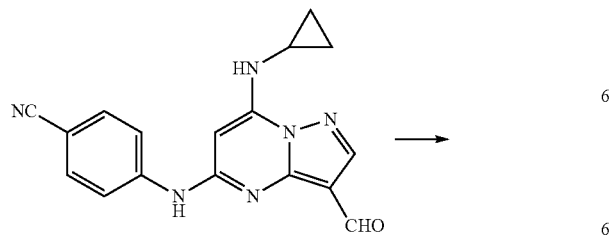

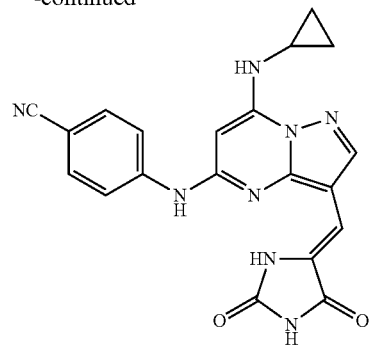

4-(7-(cyclopropylamino)-3-formylpyrazolo[1,5-a]pyrimidin-5-ylamino)benzonitrile (75 mg, 0.24 mmol) was suspended in EtOH (2.4 mL). Hydantoin (36 mg, 0.35 mmol) and piperidine (36 μL, 0.35 mmol) were added and the reaction was heated to 80° C. After 15 h, the solution was filtered while warm and the filter cake was washed with warm EtOH (3 mL) to give (Z)-4-(7-(cyclopropylamino)-3-((2,5-dioxoimidazolidin-4-ylidene)methyl)pyrazolo[1,5-a]pyrimidin-5-ylamino)benzonitrile (76 mg, 80%) as a bright yellow solid. LCMS (ES): >90% pure, m/z 401 [M+1]⁺.

The compounds described in the following table were prepared using chemistries similar to those exemplified in Examples 246 to 248. All compounds were characterized by LCMS. Table 45B shows the biological activities of the compounds listed in Table 45A.

TABLE 45A

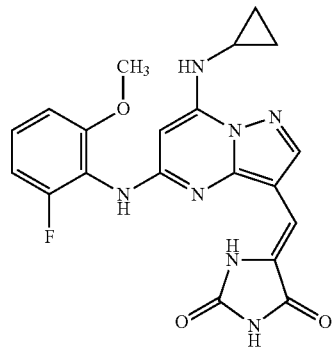 [SMILES: COc1cccc(F)c1Nc1cc(NC2CC2)n2ncc(/C=C3\NC(=O)NC3=O)c2n1]

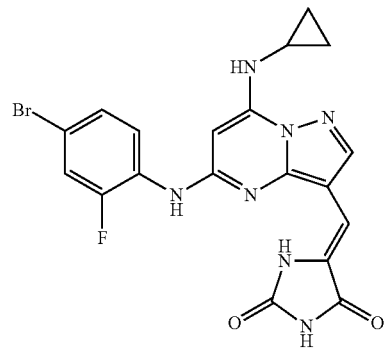 [SMILES: O=C1NC(=O)/C(=C/c2cnn3c(NC4CC4)cc(Nc4ccc(Br)cc4F)nc23)N1]

TABLE 45A-continued

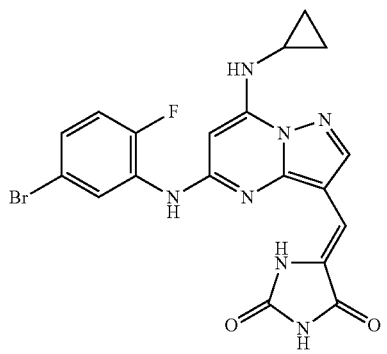 [SMILES: O=C1NC(=O)/C(=C/c2cnn3c(NC4CC4)cc(Nc4cc(Br)ccc4F)nc23)N1]

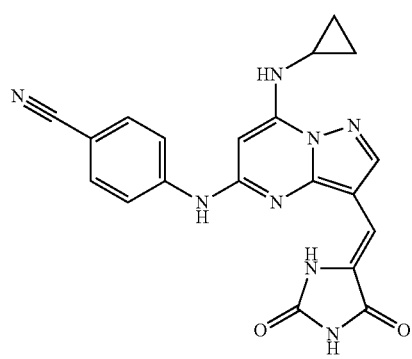 [SMILES: N#Cc1ccc(Nc2cc(NC3CC3)n3ncc(/C=C4\NC(=O)NC4=O)c3n2)cc1]

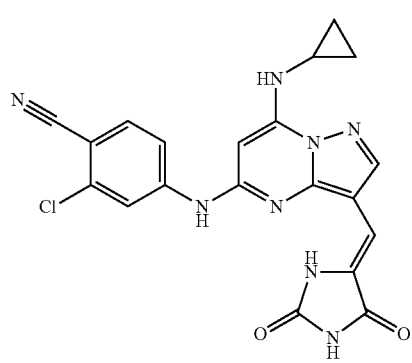 [SMILES: N#Cc1ccc(Nc2cc(NC3CC3)n3ncc(/C=C4\NC(=O)NC4=O)c3n2)cc1Cl]

TABLE 45B

| Compound | CK2: IC50 (uM) | PIM2: % inh 2.5 uM | AB: MDAMB453 (uM) | AB: BxPC3 (uM) |
|---|---|---|---|---|
| R41 | <0.1 | 55.09 | 0.8 | 1.179 |
| S41 | <0.01 | −33.889 | 1.525 | >30 |
| T41 | <0.01 | 43.69 | 1.96 | 1.901 |
| U41 | <0.01 | 57.088 | 1.019 | 1.56 |
| V41 | <0.01 | 16.198 | 0.352 | 3.08 |

Example 249

Synthesis of tert-butyl 5-(2-bromo-4-cyanophenylamino)-3-formylpyrazolo[1,5-a]pyrimidin-7-yl(cyclopropyl)carbamate

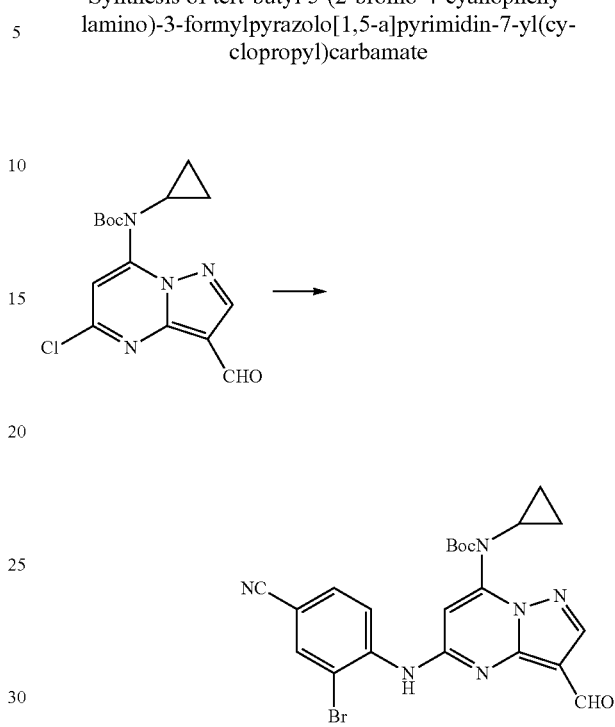

Tert-butyl 5-chloro-3-formylpyrazolo[1,5-a]pyrimidin-7-yl(cyclopropyl)carbamate (225 mg, 0.67 mmol) and 4-amino-3-bromobenzonitrile (197 mg, 1 mmol) were dissolved in anhydrous THF (4.5 mL). Sodium tert-butoxide (96 mg, 1 mmol) was added in one portion. After 1.5 h, the reaction was poured into H₂O (25 mL) and extracted with EtOAc (3×30 mL). The organics were washed with brine (1×100 mL), dried over MgSO₄, filtered and concentrated in vacuo. The tan solid was purified via flash column chromatography (30% EtOAc/hexanes) to provide tert-butyl 5-(2-bromo-4-cyanophenylamino)-3-formylpyrazolo[1,5-a]pyrimidin-7-yl(cyclopropyl)carbamate (106 mg, 32%) as a pale yellow solid. LCMS (ES): >90% pure, m/z 497 [M+1]⁺.

Example 250

Synthesis of 3-bromo-4-(7-(cyclopropylamino)-3-formylpyrazolo[1,5-a]pyrimidin-5-ylamino)benzonitrile

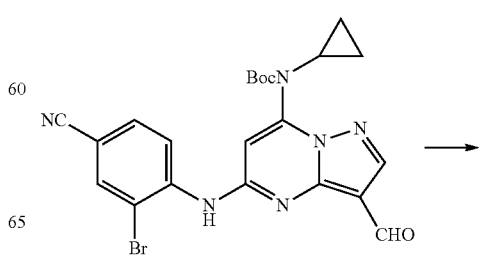

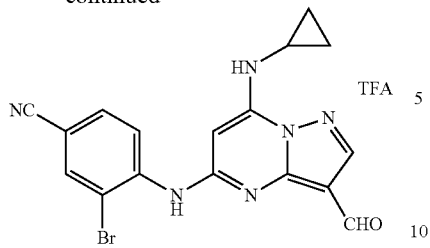

Tert-butyl 5-(2-bromo-4-cyanophenylamino)-3-formylpyrazolo[1,5-a]pyrimidin-7-yl(cyclopropyl)carbamate (105 mg, 0.21 mmol) was dissolved in dichloromethane (2 mL) and trifluoroacetic acid (2 mL) was added. After 1 h, the reaction was concentrated to dryness and the residue was triturated with Et₂O. The yellow solid was collected and dried to give 3-bromo-4-(7-(cyclopropylamino)-3-formylpyrazolo[1,5-a]pyrimidin-5-ylamino)benzonitrile 2,2,2-trifluoroacetate (72 mg, 67%).

Example 251

Synthesis of (Z)-3-bromo-4-(7-(cyclopropylamino)-3-(2,5-dioxoimidazolidin-4-ylidene)methyl)pyrazolo[1,5-a]pyrimidin-5-ylamino)benzonitrile

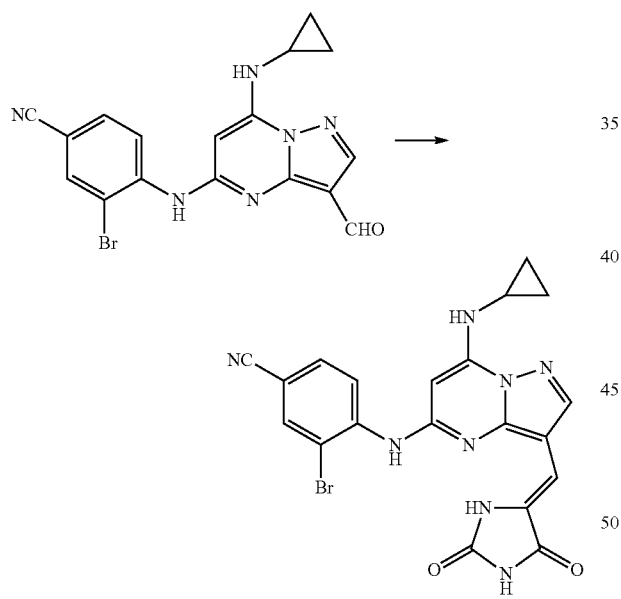

4-(7-(cyclopropylamino)-3-formylpyrazolo[1,5-a]pyrimidin-5-ylamino)benzonitrile 2,2,2-trifluoroacetate (72 mg, 0.14 mmol) was suspended in EtOH (2.4 mL). Hydantoin (17 mg, 0.17 mmol) and piperidine (33 µL, 0.34 mmol) were added and the reaction was heated to 80° C. After 15 h, the solution was filtered while warm and the filter cake was washed with warm EtOH (3 mL) to give (Z)-3-bromo-4-(7-(cyclopropylamino)-3-((2,5-dioxoimidazolidin-4-ylidene)methyl)pyrazolo[1,5-a]pyrimidin-5-ylamino)benzonitrile (60 mg, 89%) as a bright yellow solid. LCMS (ES): >90% pure, m/z 479 [M+1]⁺.

The compounds described in the following table were prepared using chemistries similar to those exemplified in Examples 249 to 251. All compounds were characterized by LCMS. Table 46B shows the biological activities of the compounds listed in Table 46A.

TABLE 46A

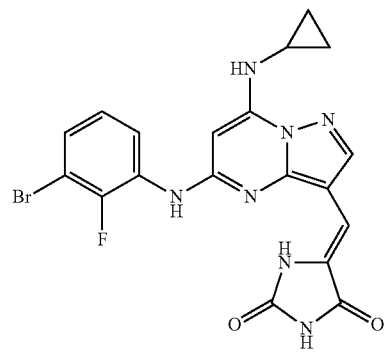

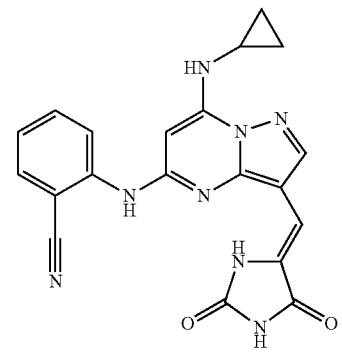 [SMILES: N#Cc1ccccc1Nc1cc(NC2CC2)n2ncc(/C=C3\NC(=O)NC3=O)c2n1]

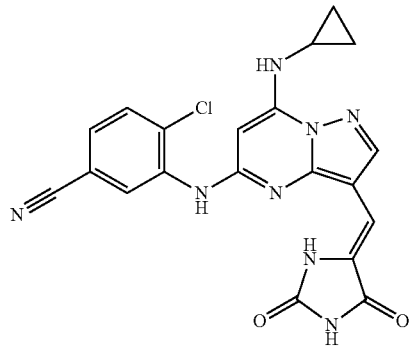 [SMILES: N#Cc1ccc(Cl)c(Nc2cc(NC3CC3)n3ncc(/C=C4\NC(=O)NC4=O)c3n2)c1]

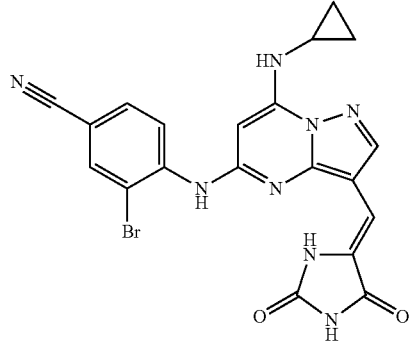 [SMILES: N#Cc1ccc(Nc2cc(NC3CC3)n3ncc(/C=C4\NC(=O)NC4=O)c3n2)c(Br)c1]

TABLE 46A-continued

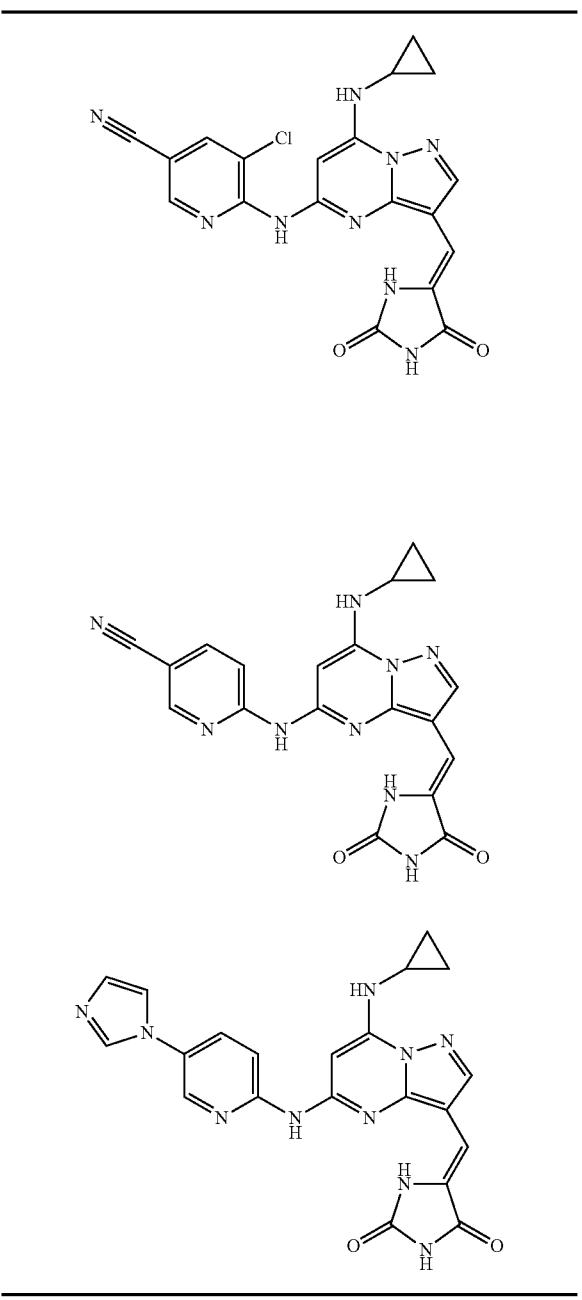

TABLE 46B

| Compound | CK2: IC50 (uM) | PIM2: % inh 2.5 uM | AB: MDAMB453 (uM) | AB: BxPC3 (uM) |
|---|---|---|---|---|
| W41 | <0.01 | 45.045 | 0.162 | 2.047 |
| X41 | <0.01 | 76.955 | 3.875 | 1.245 |
| Y41 | <0.01 | 60.279 | 0.617 | 2.272 |
| Z41 | <0.01 | 44.216 | 0.331 | 0.136 |
| A42 | <0.01 | 43.425 | 0.457 | 0.446 |
| B42 | <0.01 | 22.74 | 2.455 | 0.235 |
| C42 | <0.01 | 10.041 | 1.798 | 1.206 |

Example 252

Synthesis of (Z)-4-(7-(cyclopropylamino)-3-((1-methyl-2,5-dioxoimidazolidin-4-ylidene)methyl)pyrazolo[1,5-a]pyrimidin-5-ylamino)benzonitrile

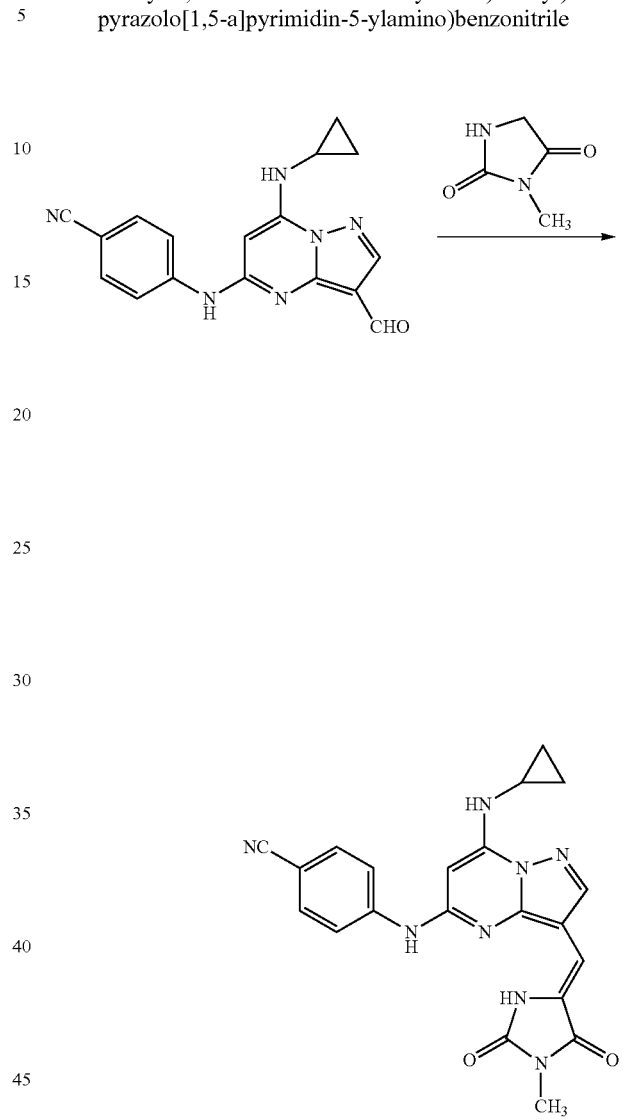

3-methylimidazolidine-2,4-dione was prepared according to the literature procedure setforth in Eur. JOC 2002, 1763.

4-(7-(cyclopropylamino)-3-formylpyrazolo[1,5-a]pyrimidin-5-ylamino)benzonitrile (51 mg, 0.16 mmol) was suspended in EtOH (1.6 mL). 3-methylimidazolidine-2,4-dione (28 mg, 0.24 mmol) and piperidine (24 μL, 0.24 mmol) were added and the reaction was heated to 80° C. After 15 h, the solution was diluted with $H_2O$ (2 mL) and filtered. The filter cake was washed with 50% H2O/50% EtOH (3 mL) and then dried in vacuo (~1 mmHg) to furnish (Z)-4-(7-(cyclopropylamino)-3-((1-methyl-2,5-dioxoimidazolidin-4-ylidene)methyl)pyrazolo[1,5-a]pyrimidin-5-ylamino)benzonitrile (45 mg, 68%) as a bright yellow solid. LCMS (ES): >90% pure, tm/z 415 [M+1]+.

The compounds described in the following table were prepared using chemistries similar to those exemplified in Example 252. All compounds were characterized by LCMS. Table 47B shows the biological activities of the compounds listed in Table 47A.

TABLE 47A

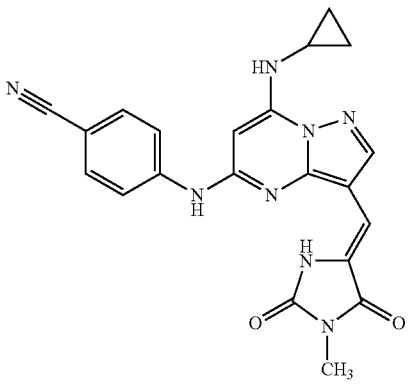 [SMILES: CN1C(=O)N/C(=C\c2cnn3c(NC4CC4)cc(Nc4ccc(C#N)cc4)nc23)C1=O]

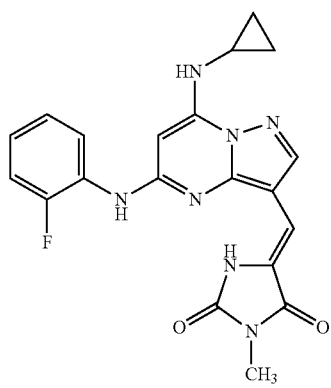 [SMILES: CN1C(=O)N/C(=C\c2cnn3c(NC4CC4)cc(Nc4ccccc4F)nc23)C1=O]

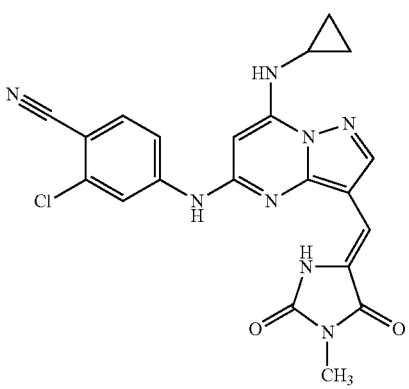 [SMILES: CN1C(=O)N/C(=C\c2cnn3c(NC4CC4)cc(Nc4ccc(C#N)c(Cl)c4)nc23)C1=O]

TABLE 47B

| Compound | CK2: IC50 (μM) | PIM2: % inh 2.5 μM | AB: MDAMB453 (μM) | AB: BxPC3 (μM) |
|---|---|---|---|---|
| D42 | <0.1 | −39.275 | 0.693 | 2.805 |
| E42 | <0.1 | −72.498 | 1.286 | 1.971 |
| F42 | <0.1 | −17.549 | 29.071 | >30 |

Example 253

Synthesis of (Z)-3-chloro-4-(7-(cyclopropylamino)-3-((2,5-dioxoimidazolidin-4-ylidene)methyl)pyrazolo[1,5-a]pyrimidin-5-yloxy)benzonitrile

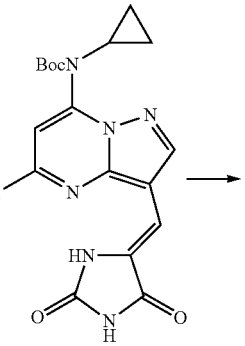

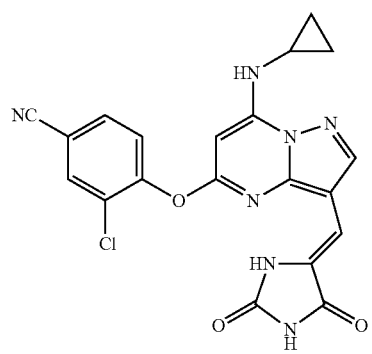

(Z)-tert-butyl 5-chloro-3-((2,5-dioxoimidazolidin-4-ylidene)methyl)pyrazolo[1,5-a]pyrimidin-7-yl(cyclopropyl)carbamate (75 mg, 0.18 mmol) was dissolved in anhydrous DMF (0.6 mL). 3-chloro-4-hydroxybenzonitrile (41 mg, 0.27 mmol) and $K_2CO_3$ (75 mg, 0.54 mmol) were added. After 24 h, $H_2O$ (3.5 mL) was added to the reaction and the bright yellow precipitate was filtered and dried. The crude solid was dissolved in dichloromethane (1 mL) and trifluoroacetic acid (1 mL). After 1 h, the reaction was concentrated to dryness and the residue was triturated with $Et_2O$ (3 mL) and filtered to provide (Z)-3-chloro-4-(7-(cyclopropylamino)-3-((2,5-dioxoimidazolidin-4-ylidene)methyl)pyrazolo[1,5-a]pyrimidin-5-yloxy)benzonitrile (45 mg, 57% over two steps) as a bright yellow solid.

Example 254

Synthesis of (Z)-5-((5-(5-chloro-2-fluorophenylamino)-7-(cyclopropylamino)pyrazolo[1,5-a]pyrimidin-3-yl)methylene)-3-(hydroxymethyl)imidazolidine-2,4-dione

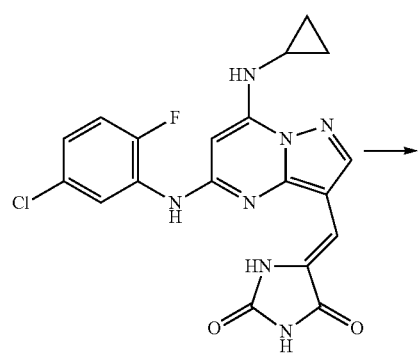

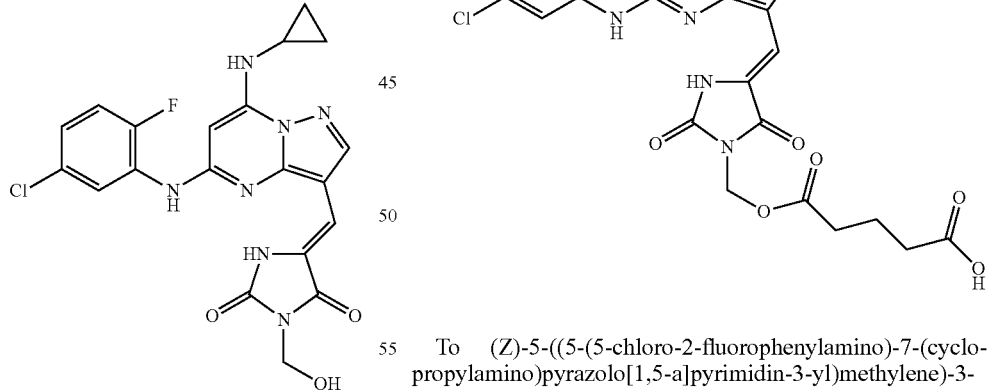

To (Z)-5-((5-(5-chloro-2-fluorophenylamino)-7-(cyclopropylamino)pyrazolo[1,5-a]pyrimidin-3-yl)methylene)imidazolidine-2,4-dione (500 mg, 1.17 mmol) in acetonitrile (15 mL) and pyridine (1.5 mL) was added formaldehyde (37% aq) (5.0 mL). The reaction mixture was stirred at 65° C. for 5 minutes. Cooled to room temperature and filtered off the resulting solid. Washed with water and dried under vacuum to provide 450 mg (84%) of (Z)-5-((5-(5-chloro-2-fluorophenylamino)-7-(cyclopropylamino)pyrazolo[1,5-a]pyrimidin-3-yl)methylene)-3-(hydroxymethyl)imidazolidine-2,4-dione as a yellow solid. LCMS (ES): >95% pure, m/z 458 [M+1]$^+$.

Example 255

Synthesis of (Z)-5-((4-((5-(5-chloro-2-fluorophenylamino)-7-(cyclopropylamino)pyrazolo[1,5-a]pyrimidin-3-yl)methylene)-2,5-dioxoimidazolidin-1-yl)methoxy)-5-oxopentanoic acid

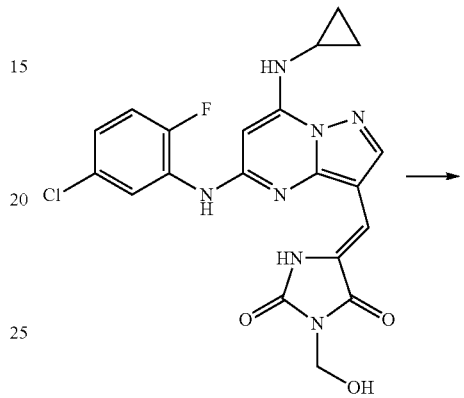

To (Z)-5-((5-(5-chloro-2-fluorophenylamino)-7-(cyclopropylamino)pyrazolo[1,5-a]pyrimidin-3-yl)methylene)-3-(hydroxymethyl)imidazolidine-2,4-dione (100 mg, 0.218 mmol) in pyridine (4.5 mL) was added glutaric anhydride (125 mg, 1.095 mmol), and DMAP (3 mg, 0.022 mmol). The reaction mixture was stirred at 75° C. overnight after which the reaction was not complete. Added glutaric anhydride (125 mg, 1.095 mmol) and DMAP (3 mg, 0.022 mmol) and stirred an additional 16 hours at 75° C. Cooled to 0° C. in ice bath and added 6M HCl until pH was less than 3 by pH paper. Filtered off the solid and washed with 0.1M HCl. Dried under vacuum to provide 40 mg (32%) of (Z)-5-((4-((5-(5-chloro-2-fluorophenylamino)-7-(cyclopropylamino)pyrazolo[1,5-a]pyrimidin-3-yl)methylene)-2,5-dioxoimidazolidin-1-yl)methoxy)-5-oxopentanoic acid as a yellow solid. LCMS (ES): >95% pure, m/z 572 [M+1]$^+$.

Example 256

Synthesis of (Z)-(4-((5-(5-chloro-2-fluorophenylamino)-7-(cyclopropylamino)pyrazolo[1,5-a]pyrimidin-3-yl)methylene)-2,5-dioxoimidazolidin-1-yl) methyl 3-(4-methylpiperazin-1-yl)propanoate

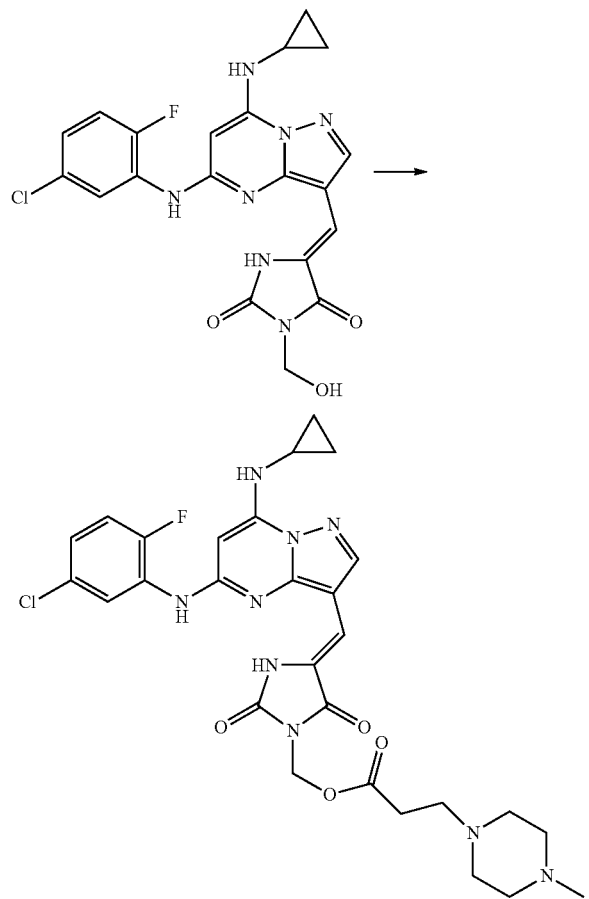

To (Z)-5-((5-chloro-2-fluorophenylamino)-7-(cyclopropylamino)pyrazolo[1,5-a]pyrimidin-3-yl)methylene)-3-(hydroxymethyl)imidazolidine-2,4-dione (100 mg, 0.218 mmol) in DMF (3 mL) was added 3-(4-methylpiperazin-1-yl)propanoic acid (75 mg, 0.436 mmol), dicyclohexylcarbodiimide (90 mg, 0.436 mmol), and DMAP (4.0 mg, 0.33 mmol). The reaction mixture was stirred at room temperature overnight and then diluted with ethyl acetate and washed 1× water, 3× brine. The organic layer was dried with MgSO$_4$, filtered and adsorbed onto silica gel. The crude material was purified by column chromatography eluting with 0-10% MeOH/CH$_2$Cl$_2$ gradient. Pure fractions were combined and the solvent was removed. This material was crystallized from ethyl acetate and hexane to provide 35 mg (26%) of (Z)-(4-((5-(5-chloro-2-fluorophenylamino)-7-(cyclopropylamino)pyrazolo[1,5-a]pyrimidin-3-yl)methylene)-2,5-dioxoimidazolidin-1-yl) methyl 3-(4-methylpiperazin-1-yl)propanoate as a yellow solid. LCMS (ES): >95% pure, m/z 612 [M+1]$^+$.

Example 257

Synthesis of (Z)-(4-((5-(5-chloro-2-fluorophenylamino)-7-(cyclopropylamino)pyrazolo[1,5-a]pyrimidin-3-yl)methylene)-2,5-dioxoimidazolidin-1-yl) methyl 2-aminoacetate

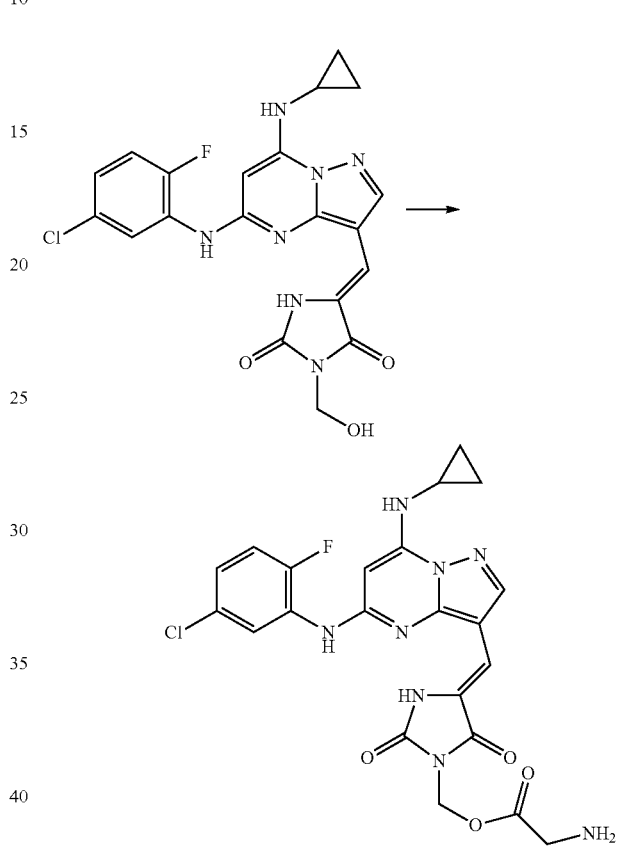

To (Z)-5-((5-(5-chloro-2-fluorophenylamino)-7-(cyclopropylamino)pyrazolo[1,5-a]pyrimidin-3-yl)methylene)-3-(hydroxymethyl)imidazolidine-2,4-dione (100 mg, 0.218 mmol) in DMF (3 mL) was added Boc-Gly-OH (153 mg, 0.873 mmol), dicyclohexylcarbodiimide (180 mg, 0.873 mmol), and DMAP (13 mg, 0.109 mmol). The reaction mixture was stirred at room temperature overnight, then diluted with ethyl acetate and washed 1× with 1M HCl followed by 3× brine. The organic layer was dried with MgSO$_4$, filtered and adsorbed onto silica gel. The crude material was purified by column chromatography eluting with 5-15% EtOAc/CH$_2$Cl$_2$ gradient. Pure fractions were combined and the solvent was removed. To the residue was added 4M HCl/dioxane (4 mL) and stirred at room temperature for 2 h. Removed excess HCl/dioxane. To the residue was added diethyl ether and the suspension was sonicated. The resulting solid was filtered off and washed with diethyl ether. Dried under vacuum to provide 23 mg (21%) of (Z)-(4-((5-(5-chloro-2-fluorophenylamino)-7-(cyclopropylamino)pyrazolo[1,5-a]pyrimidin-3-yl)methylene)-2,5-dioxoimidazolidin-1-yl)methyl 2-aminoacetate hydrogen chloride as a yellow solid. (LCMS (ES): >95% pure, m/z 515 [M+1]$^+$.

The following molecules were prepared using chemistries similar to synthesis in examples above. All compounds were TABLE 48A
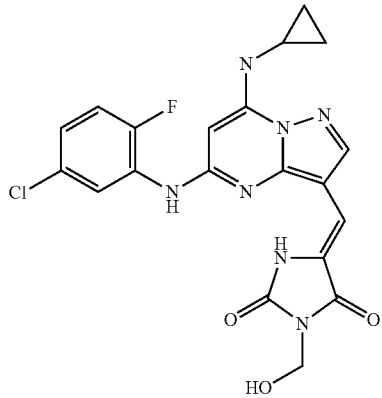 [SMILES: O=C1N/C(=C\c2cnn3c(NC4CC4)cc(Nc4cc(Cl)ccc4F)nc23)C(=O)N1CO]
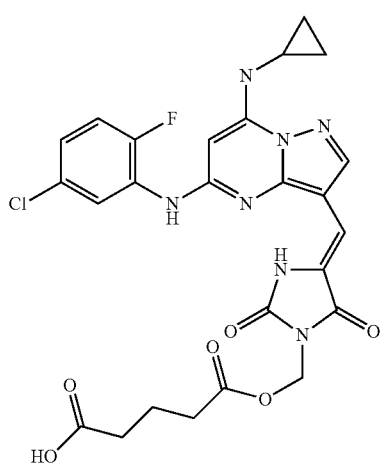 [SMILES: O=C(O)CCCC(=O)OCN1C(=O)N/C(=C\c2cnn3c(NC4CC4)cc(Nc4cc(Cl)ccc4F)nc23)C1=O]
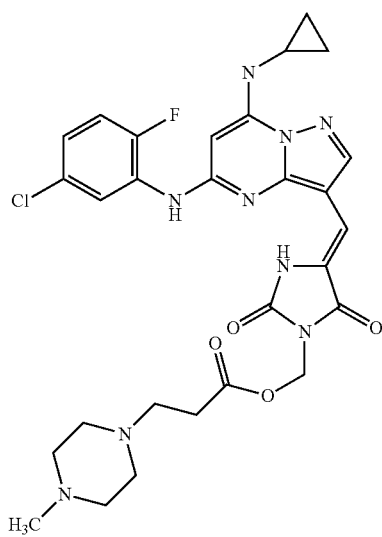 [SMILES: CN1CCN(CCC(=O)OCN2C(=O)N/C(=C\c3cnn4c(NC5CC5)cc(Nc5cc(Cl)ccc5F)nc34)C2=O)CC1]
TABLE 48A-continued
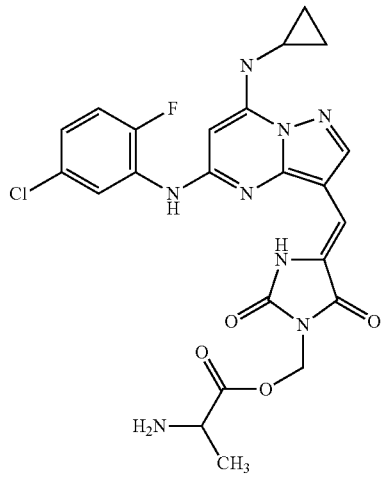 [SMILES: CC(N)C(=O)OCN1C(=O)N/C(=C\c2cnn3c(NC4CC4)cc(Nc4cc(Cl)ccc4F)nc23)C1=O]
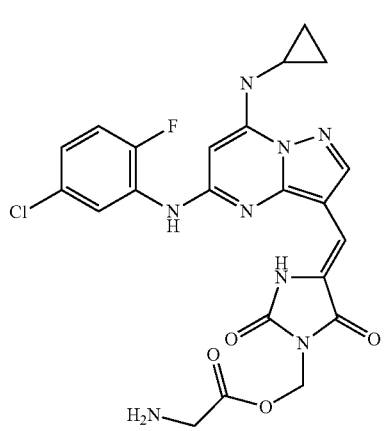 [SMILES: NCC(=O)OCN1C(=O)N/C(=C\c2cnn3c(NC4CC4)cc(Nc4cc(Cl)ccc4F)nc23)C1=O]
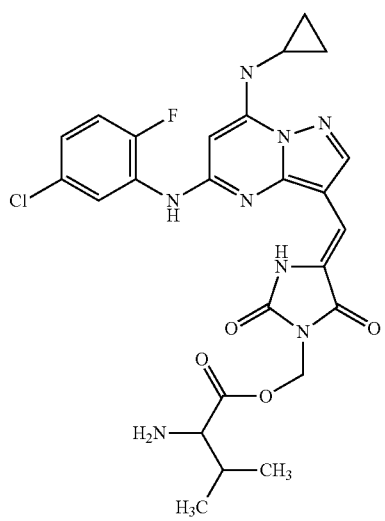 [SMILES: CC(C)C(N)C(=O)OCN1C(=O)N/C(=C\c2cnn3c(NC4CC4)cc(Nc4cc(Cl)ccc4F)nc23)C1=O]

TABLE 48A-continued

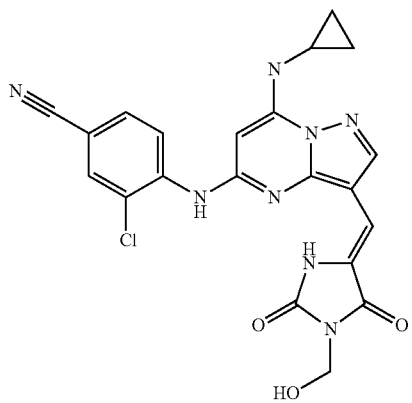 [SMILES: N#Cc1ccc(Nc2cc(NC3CC3)n3ncc(/C=C4\NC(=O)N(CO)C4=O)c3n2)c(Cl)c1]

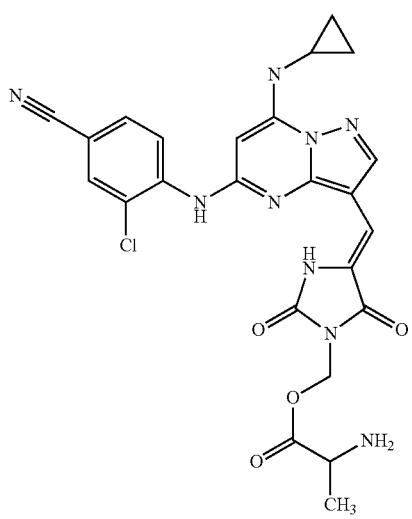 [SMILES: CC(N)C(=O)OCN1C(=O)N/C(=C\c2cnn3c(NC4CC4)cc(Nc4ccc(C#N)cc4Cl)nc23)C1=O]

TABLE 48B

| Compound | CK2: IC50 (uM) | PIM2: % inh 2.5 uM | AB: MDAMB453 IC50 (uM) | AB: BxPC3 IC50 (uM) |
|---|---|---|---|---|
| G42 | <0.01 | 65.361 | 0.232 | 1.104 |
| H42 | <0.01 | 19.196 | 0.291 | 1.989 |
| I42 | <0.01 | 42.049 | 0.25 | 1.143 |
| J42 | <0.1 | 42.889 | | |
| K42 | <0.1 | −6.849 | | |
| L42 | <0.01 | 79.506 | 0.898 | 0.946 |
| M42 | <0.1 | 60.348 | 0.172 | 0.43 |
| N42 | <0.01 | 23.501 | 0.222 | 0.539 |
| O42 | <0.1 | 3.674 | | |
| P42 | <0.1 | 13.383 | | |
| Q42 | <0.01 | −20.619 | 0.28 | 0.207 |
| R42 | <0.1 | | | |

Example 258

Synthesis of 5-((5-(4-(1H-pyrazol-1-yl)phenylamino)-7-(cyclopropylamino)pyrazolo[1,5-a]pyrimidin-3-yl)methyl)imidazolidine-2,4-dione

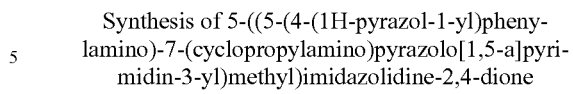

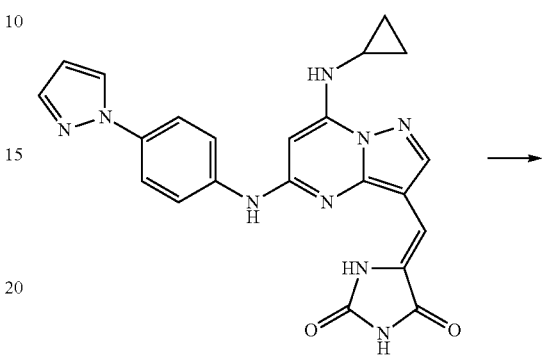

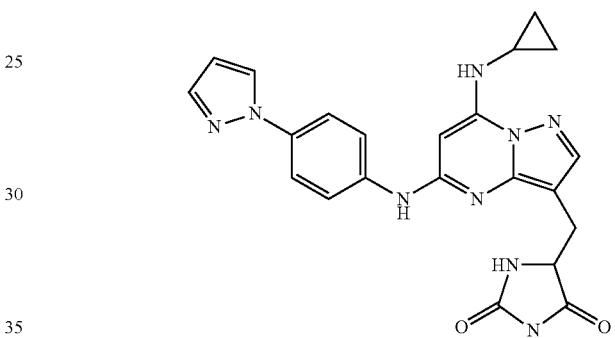

To (Z)-5-((5-(4-(1H-pyrazol-1-yl)phenylamino)-7-(cyclopropylamino)pyrazolo[1,5-a]pyrimidin-3-yl)methylene)imidazolidine-2,4-dione (40 mg, 0.091 mmol) in a Parr pressure reaction vessel was added acetic acid (6.0 mL) and 10% Pd/C (20 mg). The reaction vessel was placed on the Parr shaker at 55 psi for 3 days. Filtered through celite and purified by mass-directed LC/MS to provide 5-((5-(4-(1H-pyrazol-1-yl)phenylamino)-7-(cyclopropylamino)pyrazolo[1,5-a]pyrimidin-3-yl)methyl)imidazolidine-2,4-dione as the TFA salt. LCMS (ES): >95% pure, m/z 444 [M+1]$^+$.

Example 259

Synthesis of 2-chloro-4-(7-(cyclopropylamino)pyrazolo[1,5-a]pyrimidin-5-ylamino)phenol

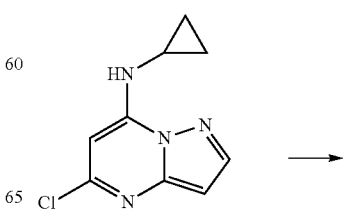

-continued

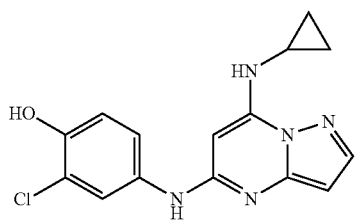

To 5-chloro-N-cyclopropylpyrazolo[1,5-a]pyrimidin-7-amine (500 mg, 2.396 mmol) in EtOH (10 mL) was added 4-amino-2-chlorophenol (516 mg, 3.59 mmol) followed by concentrated HCl (0.218 mL, 2.64 mmol). The reaction mixture was stirred at reflux temperature for 4 days. Removed 5 mL of EtOH on rotavap followed by addition of 5 mL of diethyl ether. The resulting solid was filtered off and rinsed with diethyl ether. Dried under nitrogen to provide 582 mg (77%) of 2-chloro-4-(7-(cyclopropylamino)pyrazolo[1,5-a]pyrimidin-5-ylamino)phenol as the HCl salt. LCMS (ES): >95% pure, m/z 316 [M+1]+.

Example 260

Synthesis of 5-(3-chloro-4-hydroxyphenylamino)-7-(cyclopropylamino)pyrazolo[1,5-a]pyrimidine-3-carbaldehyde

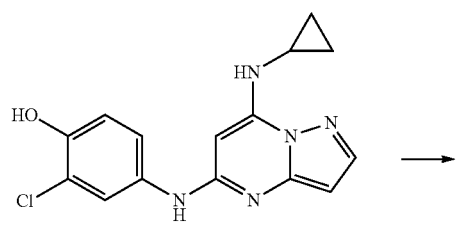

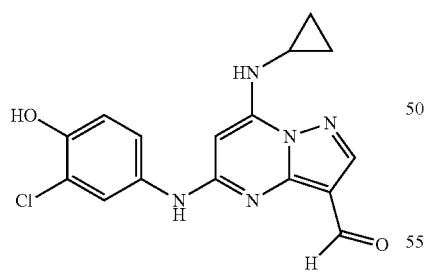

To 2-chloro-4-(7-(cyclopropylamino)pyrazolo[1,5-a]pyrimidin-5-ylamino)phenol (582 mg, 1.84 mmol) in DMF (4.5 mL) cooled to 0° C. was added phosphorous oxychloride (0.514 mL, 5.52 mmol) dropwise. The reaction mixture was stirred while warming to 45° C. over 3 h. This was cooled down to 0° C. and added slowly to an ice-cold solution of 2M NaOH while stirring. Upon completion, the mixture was stirred at room temperature for 1 h. The resulting solid was filtered off and washed with water to provide 412 mg (65%) of 5-(3-chloro-4-hydroxyphenylamino)-7-(cyclopropylamino)pyrazolo[1,5-a]pyrimidine-3-carbaldehyde. LCMS (ES): >95% pure, m/z 344 [M+1]+.

Example 261

Synthesis of 5-(3-chloro-4-(3-(dimethylamino)propoxy)phenylamino)-7-(cyclopropylamino)pyrazolo[1,5-a]pyrimidine-3-carbaldehyde

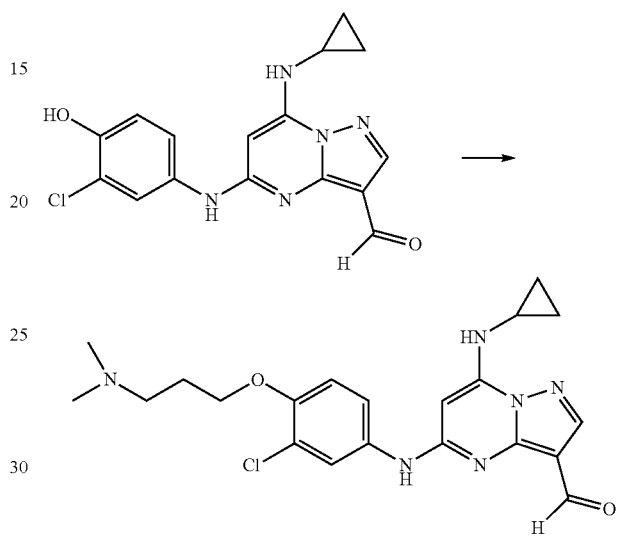

To 5-(3-chloro-4-hydroxyphenylamino)-7-(cyclopropylamino)pyrazolo[1,5-a]pyrimidine-3-carbaldehyde (100 mg, 0.291 mmol) in DMF (3 mL) was added $K_2CO_3$ (100 mg, 0.727 mmol). The reaction mixture was stirred at 80° C. for 16 h. Diluted with EtOAc and extracted into 2M HCl. The aqueous layer was basified to pH of 14 with 2M NaOH and extracted 2× with EtOAc. The organic layer was washed 3× with brine and dried with $MgSO_4$. Filtered and purified by column chromatography eluting with 10%-30% MeOH/EtOAc gradient. Combined pure fractions to provide 45 mg (36%) of 5-(3-chloro-4-(3-(dimethylamino)propoxy)phenylamino)-7-(cyclopropylamino)pyrazolo[1,5-a]pyrimidine-3-carbaldehyde LCMS (ES): m/z 429 [M+1]+.

Example 262

Synthesis of (Z)-5-((5-(3-chloro-4-(3-(dimethylamino)propoxy)phenylamino)-7-(cyclopropylamino) pyrazolo[1,5-a]pyrimidin-3-yl)methylene) imidazolidine-2,4-dione

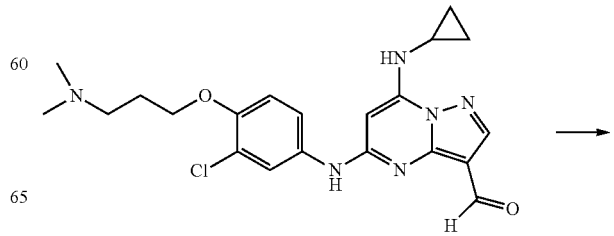

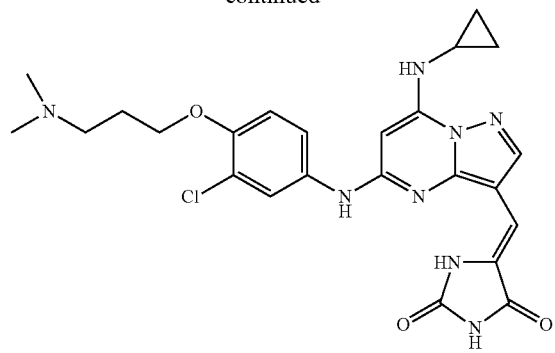

To 5-(3-chloro-4-(3-(dimethylamino)propoxy)phenylamino)-7-(cyclopropylamino)pyrazolo[1,5-a]pyrimidine-3-carbaldehyde (79 mg, 0.184 mmol) in EtOH (3 mL) was added piperidine (22 uL 0.221 mmol) followed by hydantoin (21 mg, 0.202 mmol). The reaction mixture was stirred at 85° C. for 6 h. The solvent was removed by rotary evaporation and the residue was diluted with 3 mL of water. The suspension was sonicated and the resulting solid was filtered off and washed with water followed by a 1:1 mixture of EtOH/water. The material was Dried under vacuum to provide 62 mg of (Z)-5-((5-(3-chloro-4-(3-(dimethylamino)propoxy)phenylamino)-7-(cyclopropylamino)pyrazolo[1,5-a]pyrimidin-3-yl)methylene)imidazolidine-2,4-dione LCMS (ES): m/z 511 [M+1]$^+$.

The compounds listed in Table 49A were prepared according to the procedures described above. Table 49B shows the biological activities of the compounds listed in Table 49A.

TABLE 49A

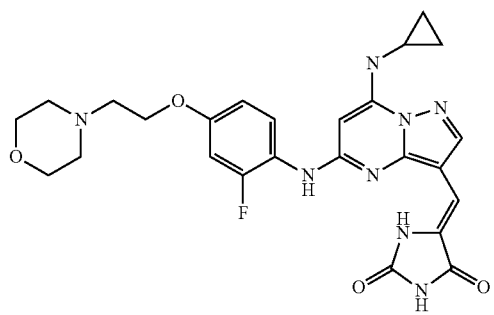 [SMILES: O=C1NC(=O)/C(=C/c2cnn3c(NC4CC4)cc(Nc4ccc(OCCN5CCOCC5)cc4F)nc23)N1]

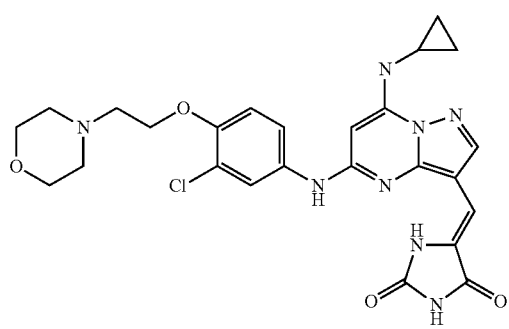 [SMILES: O=C1NC(=O)/C(=C/c2cnn3c(NC4CC4)cc(Nc4ccc(OCCN5CCOCC5)c(Cl)c4)nc23)N1]

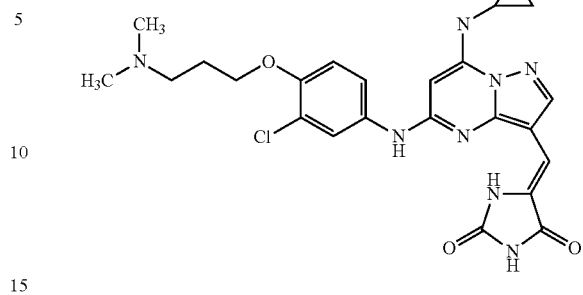

TABLE 49B

| Compound | CK2: IC50 (uM) | PIM2: % inh 2.5 uM | AB: MDAMB453 IC50 (uM) | AB: BxPC3 IC50 (uM) |
| --- | --- | --- | --- | --- |
| S42 | <0.01 | 44.49 | 2.739 | 5.005 |
| T42 | <0.01 | 44.33 | 2.094 | 5.332 |
| U42 | <0.01 | 48.912 | 1.087 | 2.463 |

Example 263

Synthesis of 7-(cyclopropylamino)-5-(methylthio)pyrazolo[1,5-a]pyrimidine-3-carbaldehyde

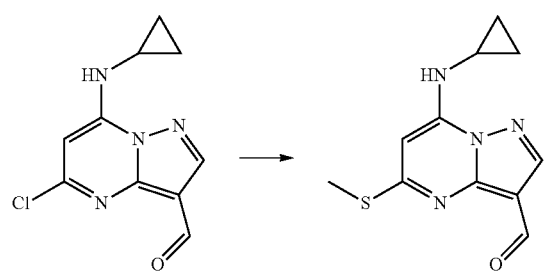 [SMILES: O=Cc1cnn2c(NC3CC3)cc(Cl)nc12 ; CSc1cc(NC2CC2)n2ncc(C=O)c2n1]

To 5-chloro-7-(cyclopropylamino) pyrazolo[1,5-a]pyrimidine-3-carbaldehyde (4.0 g, 16.87 mmol) in dimethylformamide was added sodium thiomethoxide (3.54 g, 50.5 mmol) and the reaction mixture was heated to 80° C. for 2 hrs. Cooled the reaction mixture, added water, stirred for 15 minutes and filtered white precipitate, dried to yield 7-(cyclopropylamino)-5-(methylthio)pyrazolo[1,5-a]pyrimidine-3-carbaldehyde (3.60 g, 86% yield). LCMS (M+1=249)

Example 264

Synthesis of (Z)-5-((7-(cyclopropylamino)-5-(methylthio)pyrazolo[1,5-a]pyrimidin-3-yl)methylene)imidazolidine-2,4-dione

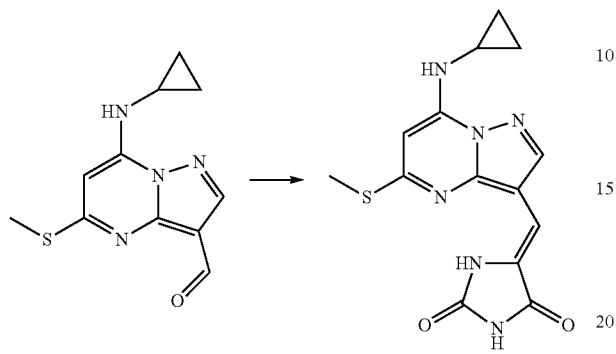

The above product 7-(cyclopropylamino)-5-(methylthio)pyrazolo[1,5-a]pyrimidine-3-carbaldehyde was dissolved in 20.0 mL ethanol, added hydantoin (2.82 g, 28.17 mmol) and piperidine (2.70 mL). The reaction was heated to 80° C. for overnight. Cooled the reaction mixture and yellow precipitate was filtered, washed with ethanol, dried to yield (Z)-5-((7-(cyclopropylamino)-5-(methylthio) pyrazolo[1,5-a]pyrimidin-3-yl)methylene) imidazolidine-2,4-dione 4.18 g (90% yield). LCMS (M+1=331)

Example 265

Synthesis of (Z)-5-((7-(cyclopropylamino)-5-methylsulfonyl)pyrazolo[1,5-a]pyrimidin-3-yl)methylene)imidazolidine-2,4-dione

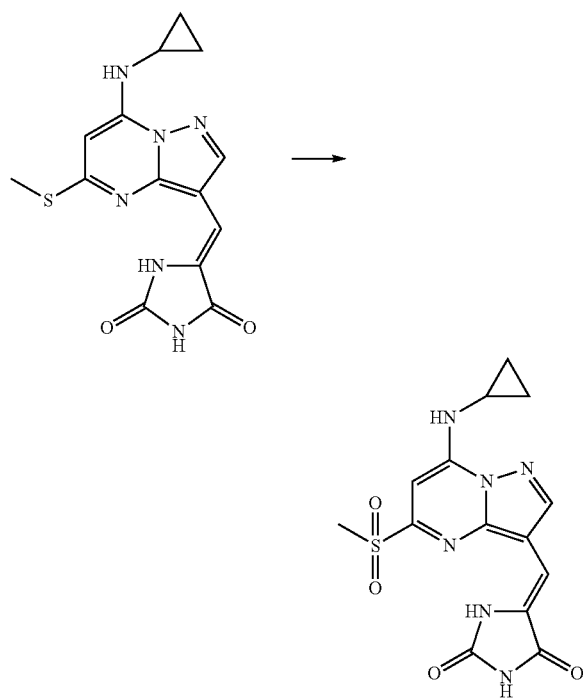

To (Z)-5-((7-(cyclopropylamino)-5-(methylthio) pyrazolo[1,5-a]pyrimidin-3-yl) methylene) imidazolidine-2,4-dione (step b) (4.2 g, 12.68 mmol) in 40.0 mL dichloromethane, was added meta-Chloroperoxybenzoic acid (8.75 g, 50.7 mmols) and the reaction mixture was stirred at room temperature overnight. Added another 10.0 mL of dichloromethane, sonicated for 10 minutes and then filtered the yellow precipitate to yield (Z)-5-((7-(cyclopropylamino)-5-(methylsulfonyl)pyrazolo[1,5-a]pyrimidin-3-yl)methylene) imidazolidine-2,4-dione (3.7 g, 73% yield). LCMS (M+1=363)

Example 266

Synthesis of (S,Z)-5-((5-(1-(3-chlorophenyl)ethylamino)-7-(cyclopropylamino)pyrazolo[1,5-a]pyrimidin-3-yl)methylene)imidazolidine-2,4-dione

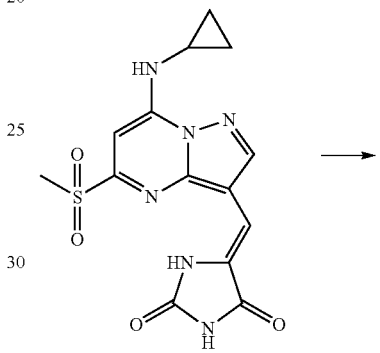

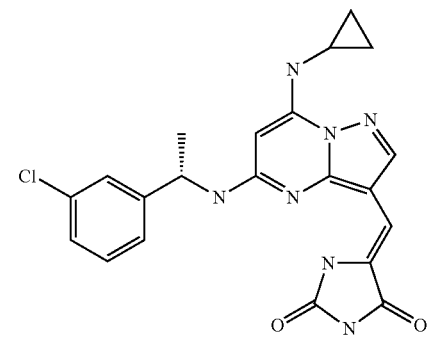

To (Z)-5-((7-(cyclopropylamino)-5-(methylsulfonyl) pyrazolo[1,5-a]pyrimidin-3-yl)methylene) imidazolidine-2, 4-dione (step c) (10 mg, 0.0275 mmol) in 200 uL NMP, was added (S)-1-(3-chlorophenyl)ethanamine (23.2 ul, 0.165 mmols) and the reaction mixture was heated in the microwave at 120° C. for 20 minutes. The mixture was concentrated and diluted with MeOH and purified by preparative HPLC to yield (S,Z)-5-((5-(1-(3-chlorophenyl)ethylamino)-7-(cyclopropylamino)pyrazolo[1,5-a]pyrimidin-3-yl)methylene)imidazolidine-2,4-dione LCMS (M+1=438)

The benzyl amine analogs shown below were prepared using procedures exemplified above or methods previously described in Examples 27, 28, and 29. Table 50B shows the biological activities of the compounds listed in Table 50A.

TABLE 50A
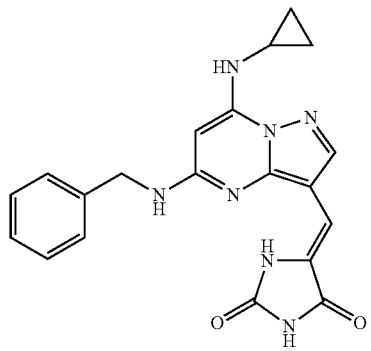 [SMILES: O=C1NC(=O)/C(=C/c2cnn3c(NC4CC4)cc(NCc4ccccc4)nc23)N1]
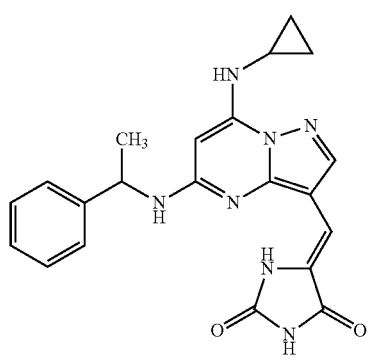 [SMILES: CC(Nc1cc(NC2CC2)n2ncc(/C=C3\NC(=O)NC3=O)c2n1)c1ccccc1]
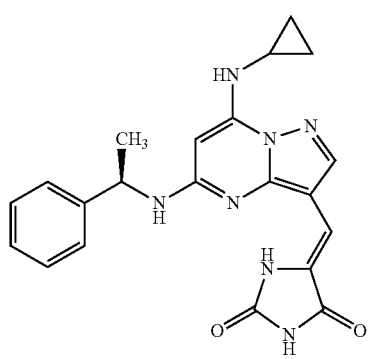 [SMILES: C[C@@H](Nc1cc(NC2CC2)n2ncc(/C=C3\NC(=O)NC3=O)c2n1)c1ccccc1]
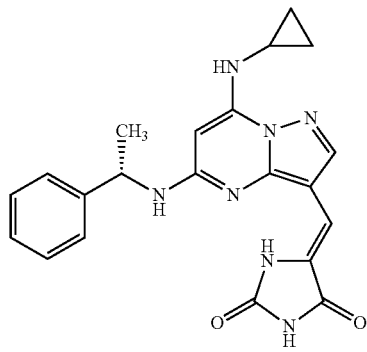 [SMILES: C[C@H](Nc1cc(NC2CC2)n2ncc(/C=C3\NC(=O)NC3=O)c2n1)c1ccccc1]
TABLE 50A-continued
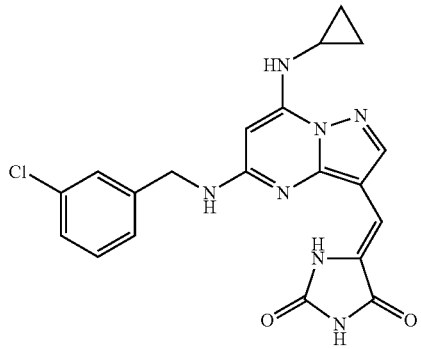 [SMILES: O=C1NC(=O)/C(=C/c2cnn3c(NC4CC4)cc(NCc4cccc(Cl)c4)nc23)N1]
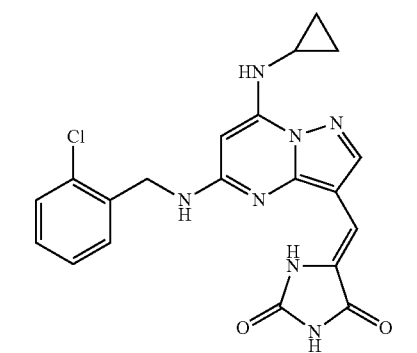 [SMILES: O=C1NC(=O)/C(=C/c2cnn3c(NC4CC4)cc(NCc4ccccc4Cl)nc23)N1]
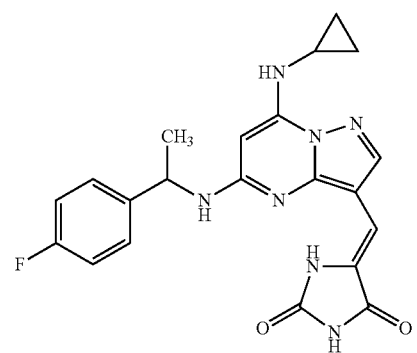 [SMILES: CC(Nc1cc(NC2CC2)n2ncc(/C=C3\NC(=O)NC3=O)c2n1)c1ccc(F)cc1]
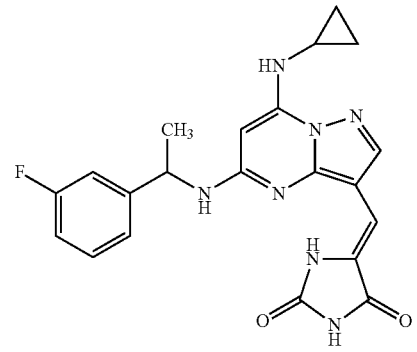 [SMILES: CC(Nc1cc(NC2CC2)n2ncc(/C=C3\NC(=O)NC3=O)c2n1)c1cccc(F)c1]

TABLE 50A-continued
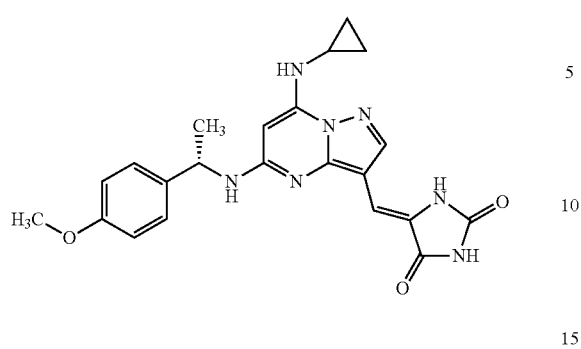
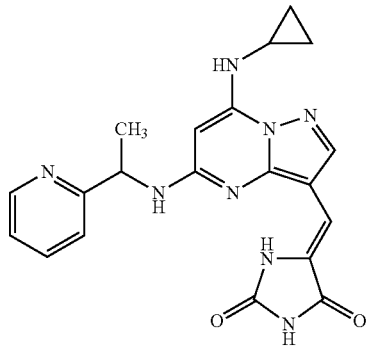 [SMILES: CC(Nc1cc(NC2CC2)n2ncc(/C=C3\NC(=O)NC3=O)c2n1)c1ccccn1]
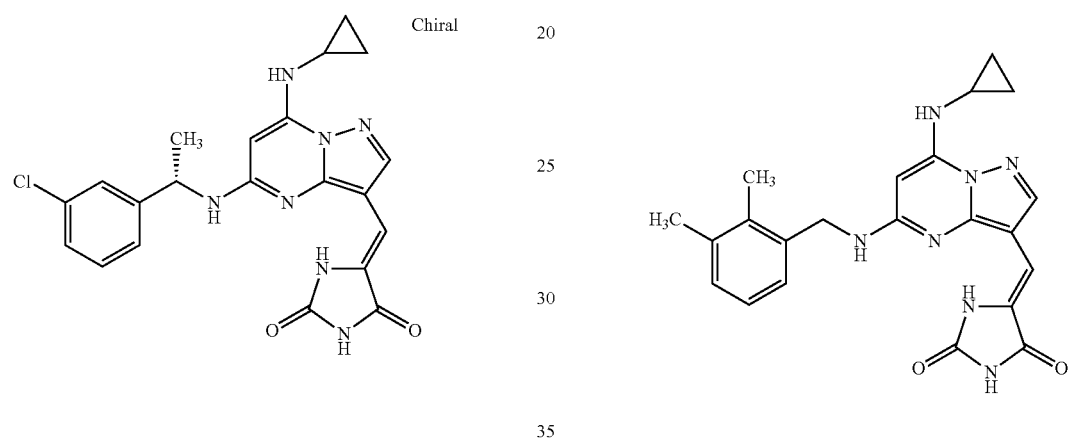
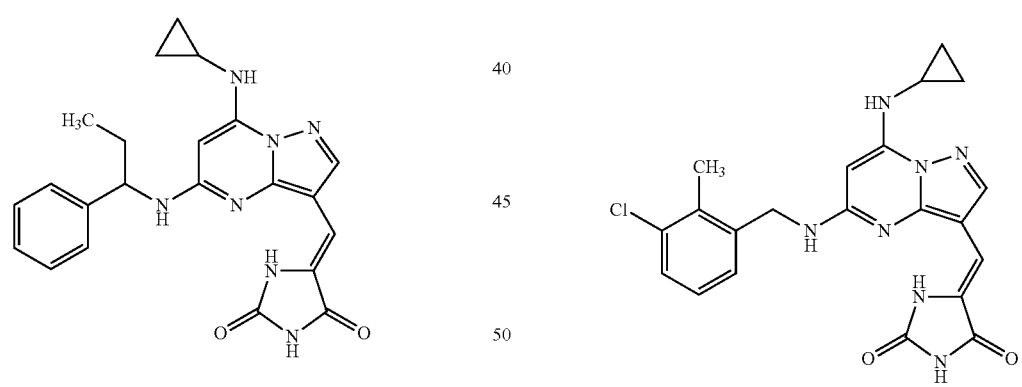
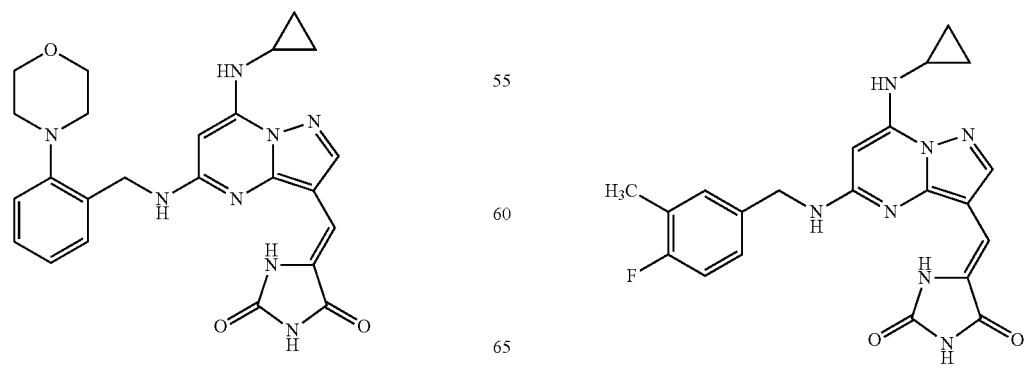

TABLE 50A-continued
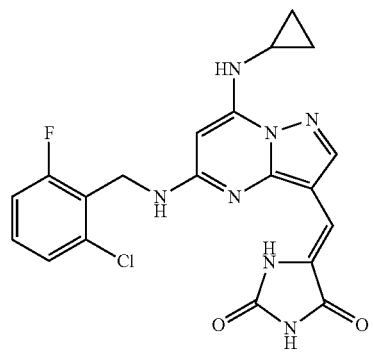 [SMILES: O=C1NC(=O)/C(=C/c2cnn3c(NC4CC4)cc(NCc4c(F)cccc4Cl)nc23)N1]
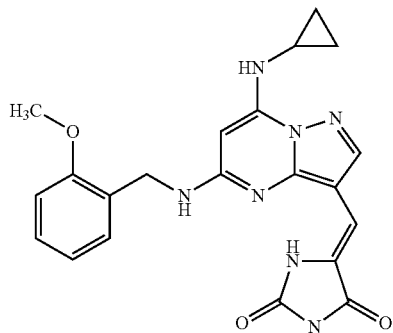
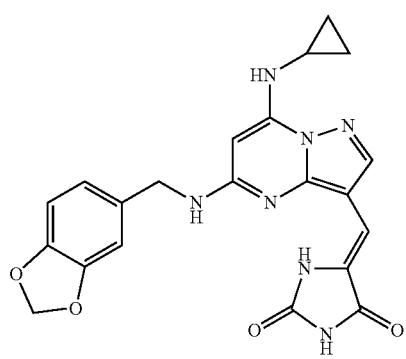 [SMILES: O=C1NC(=O)/C(=C/c2cnn3c(NC4CC4)cc(NCc4ccc5c(c4)OCO5)nc23)N1]
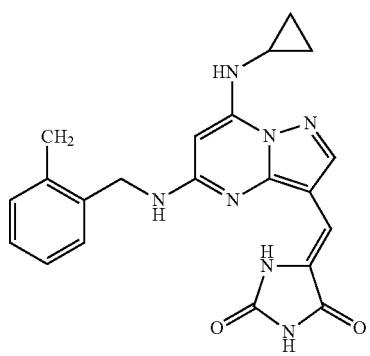
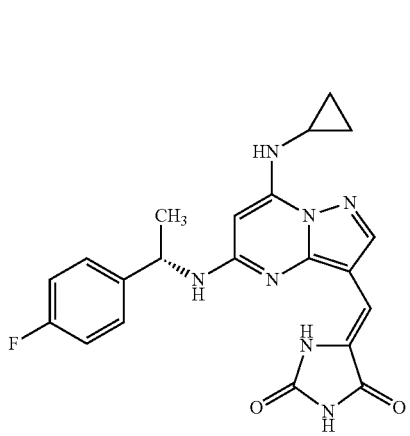 [SMILES: C[C@H](Nc1cc(NC2CC2)n2ncc(/C=C3\NC(=O)NC3=O)c2n1)c1ccc(F)cc1]
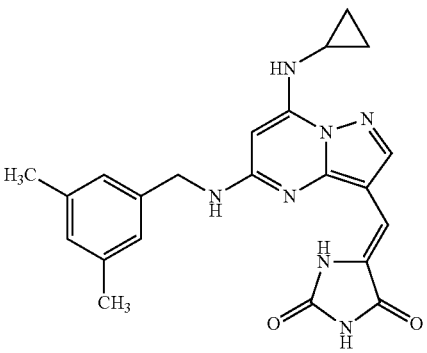
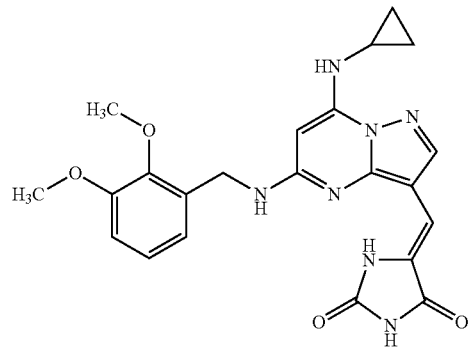 [SMILES: COc1cccc(CNc2cc(NC3CC3)n3ncc(/C=C4\NC(=O)NC4=O)c3n2)c1OC]
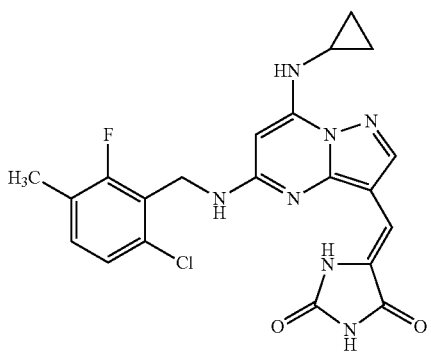 [SMILES: Cc1ccc(Cl)c(CNc2cc(NC3CC3)n3ncc(/C=C4\NC(=O)NC4=O)c3n2)c1F]

TABLE 50A-continued
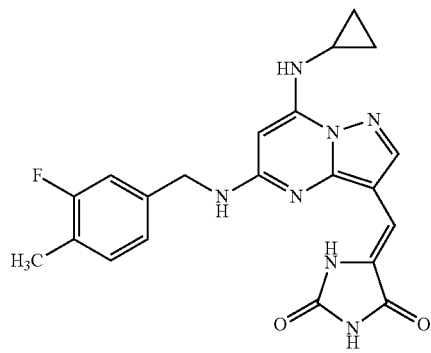 [SMILES: Cc1ccc(CNc2cc(NC3CC3)n3ncc(/C=C4\NC(=O)NC4=O)c3n2)cc1F]
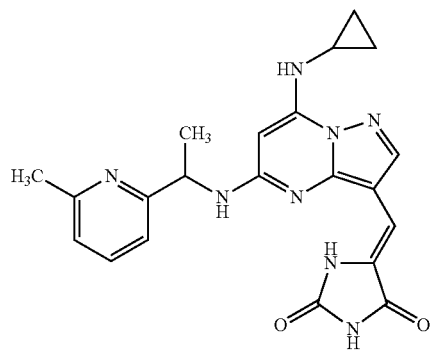
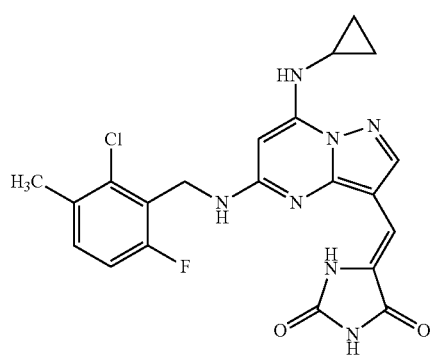 [SMILES: Cc1ccc(F)c(CNc2cc(NC3CC3)n3ncc(/C=C4\NC(=O)NC4=O)c3n2)c1Cl]
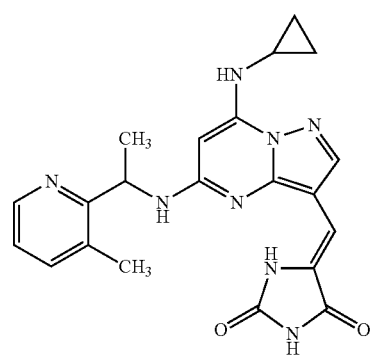
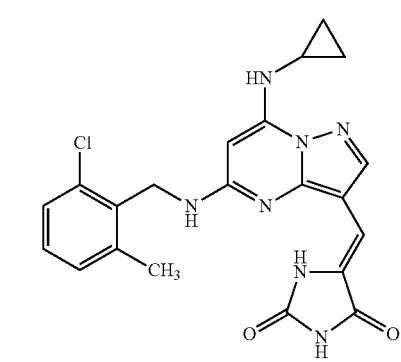 [SMILES: Cc1cccc(Cl)c1CNc1cc(NC2CC2)n2ncc(/C=C3\NC(=O)NC3=O)c2n1]
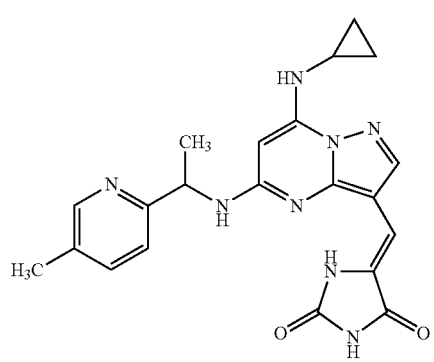
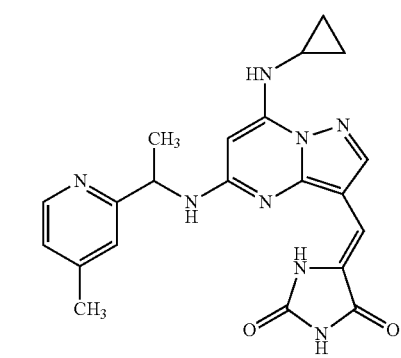 [SMILES: Cc1ccnc(C(C)Nc2cc(NC3CC3)n3ncc(/C=C4\NC(=O)NC4=O)c3n2)c1]
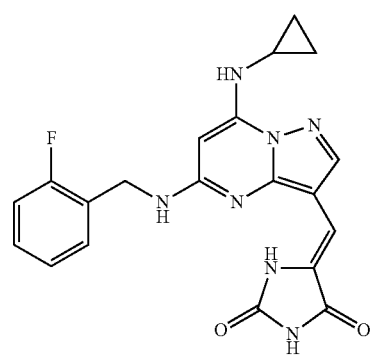

TABLE 50A-continued
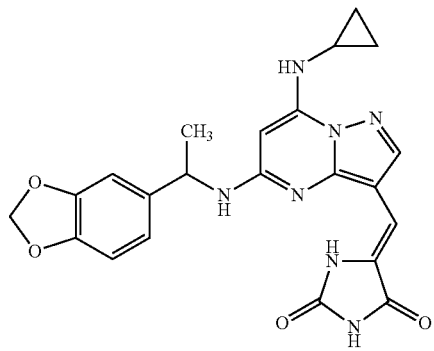 [SMILES: CC(Nc1cc(NC2CC2)n2ncc(/C=C3\NC(=O)NC3=O)c2n1)c1ccc2c(c1)OCO2]
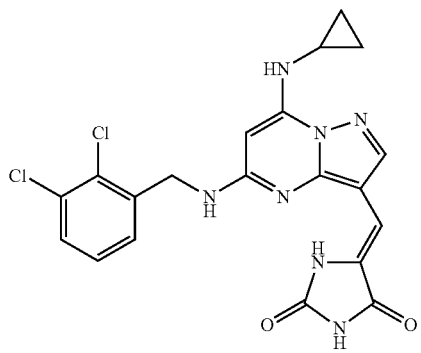
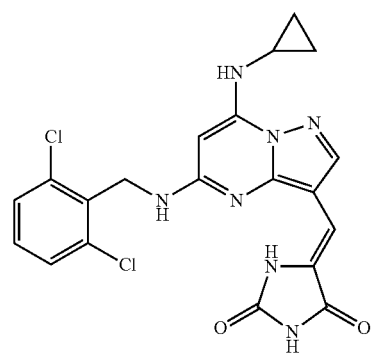 [SMILES: O=C1NC(=O)/C(=C/c2cnn3c(NC4CC4)cc(NCc4c(Cl)cccc4Cl)nc23)N1]
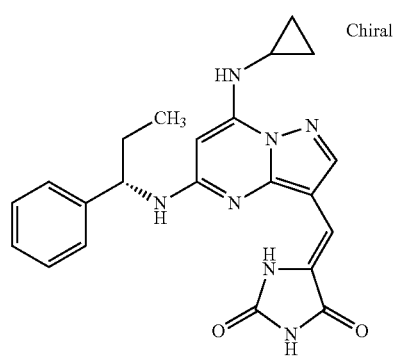 [SMILES: CC[C@H](Nc1cc(NC2CC2)n2ncc(/C=C3\NC(=O)NC3=O)c2n1)c1ccccc1]
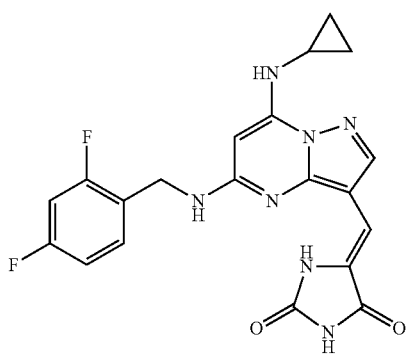
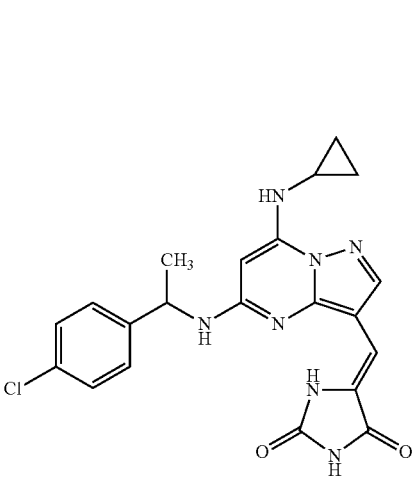 [SMILES: CC(Nc1cc(NC2CC2)n2ncc(/C=C3\NC(=O)NC3=O)c2n1)c1ccc(Cl)cc1]
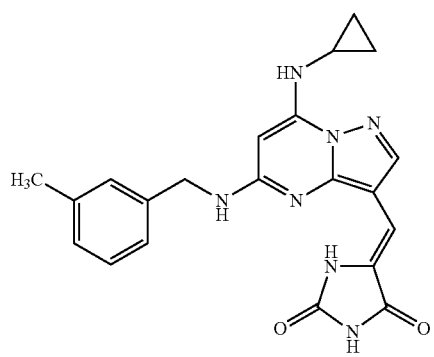
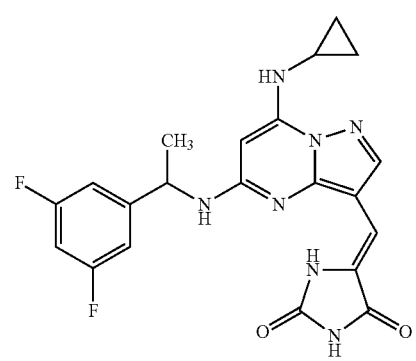

TABLE 50A-continued
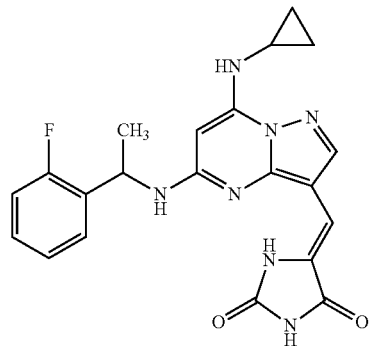 [SMILES: CC(Nc1cc(NC2CC2)n2ncc(/C=C3\NC(=O)NC3=O)c2n1)c1ccccc1F]
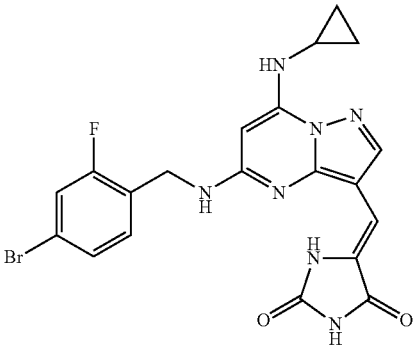
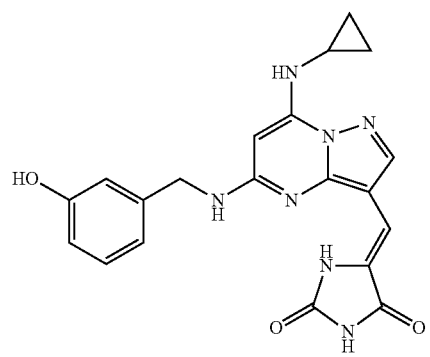 [SMILES: O=C1NC(=O)/C(=C/c2cnn3c(NC4CC4)cc(NCc4cccc(O)c4)nc23)N1]
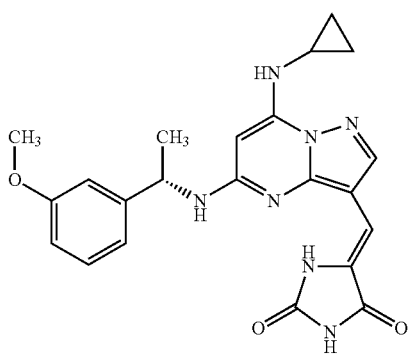 [SMILES: COc1cccc([C@H](C)Nc2cc(NC3CC3)n3ncc(/C=C4\NC(=O)NC4=O)c3n2)c1]
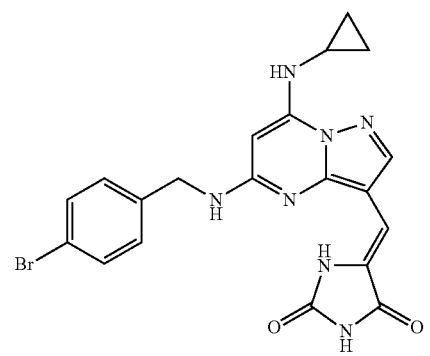
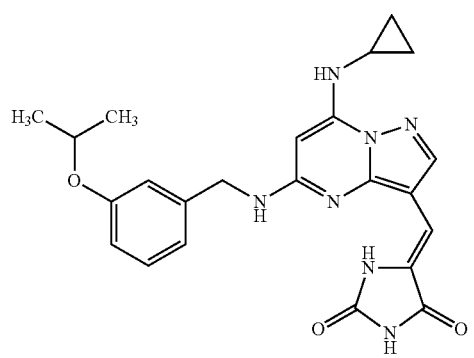 [SMILES: CC(C)Oc1cccc(CNc2cc(NC3CC3)n3ncc(/C=C4\NC(=O)NC4=O)c3n2)c1]
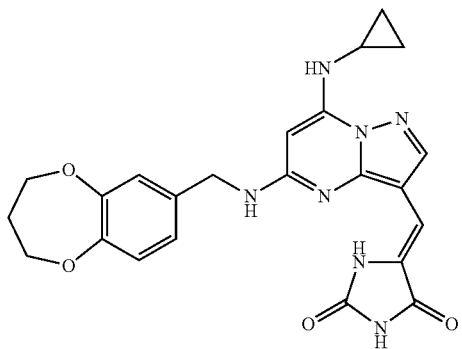
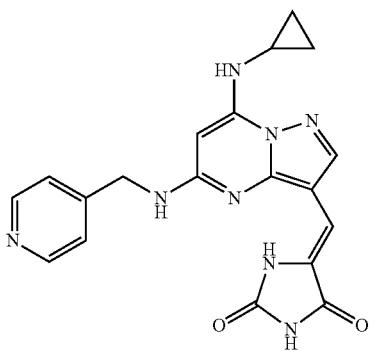 [SMILES: O=C1NC(=O)/C(=C/c2cnn3c(NC4CC4)cc(NCc4ccncc4)nc23)N1]

TABLE 50A-continued
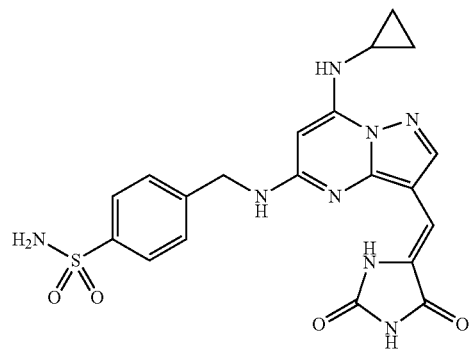 [SMILES: NS(=O)(=O)c1ccc(CNc2cc(NC3CC3)n3ncc(/C=C4\NC(=O)NC4=O)c3n2)cc1]
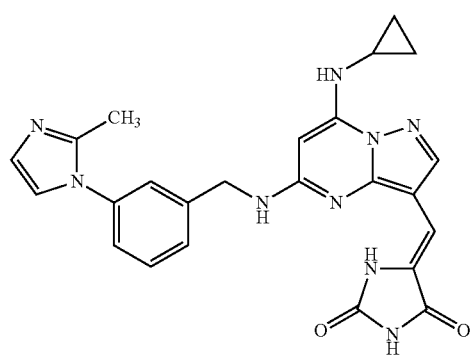 [SMILES: Cc1nccn1-c1cccc(CNc2cc(NC3CC3)n3ncc(/C=C4\NC(=O)NC4=O)c3n2)c1]
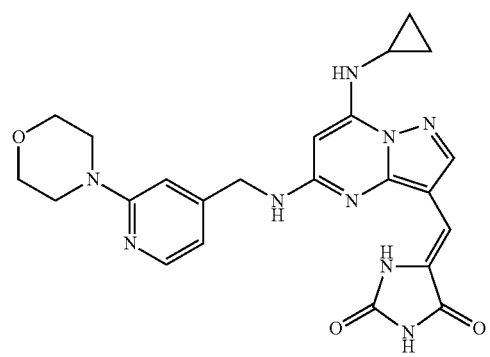 [SMILES: O=C1NC(=O)/C(=C/c2cnn3c(NC4CC4)cc(NCc4ccnc(N5CCOCC5)c4)nc23)N1]
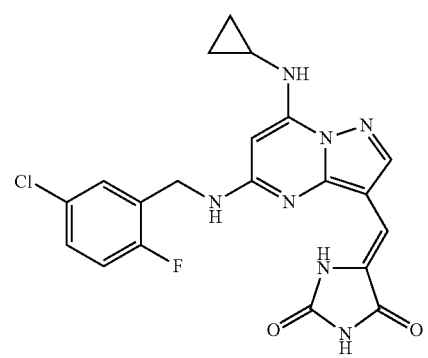 [SMILES: O=C1NC(=O)/C(=C/c2cnn3c(NC4CC4)cc(NCc4cc(Cl)ccc4F)nc23)N1]
TABLE 50A-continued
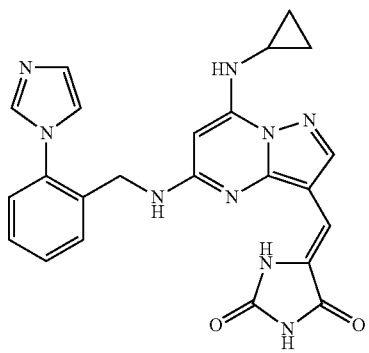 [SMILES: O=C1NC(=O)/C(=C/c2cnn3c(NC4CC4)cc(NCc4ccccc4-n4ccnc4)nc23)N1]
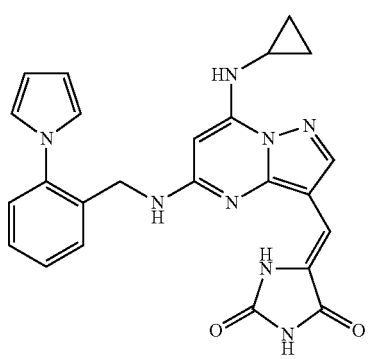 [SMILES: O=C1NC(=O)/C(=C/c2cnn3c(NC4CC4)cc(NCc4ccccc4-n4cccc4)nc23)N1]
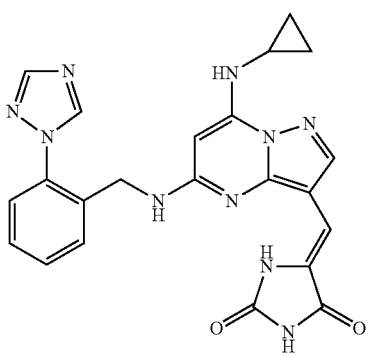
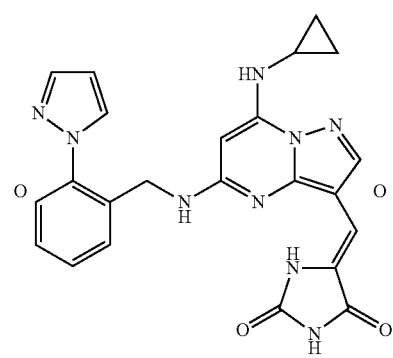

TABLE 50A-continued
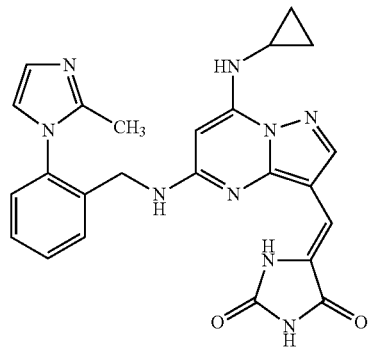 [SMILES: Cc1nccn1-c1ccccc1CNc1cc(NC2CC2)n2ncc(/C=C3\NC(=O)NC3=O)c2n1]
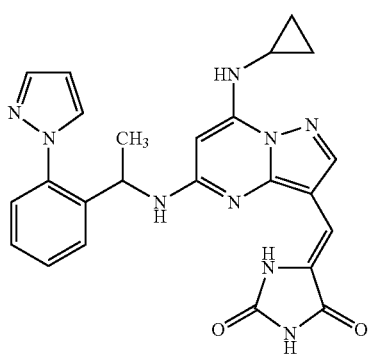 [SMILES: CC(Nc1cc(NC2CC2)n2ncc(/C=C3\NC(=O)NC3=O)c2n1)c1ccccc1-n1cccn1]
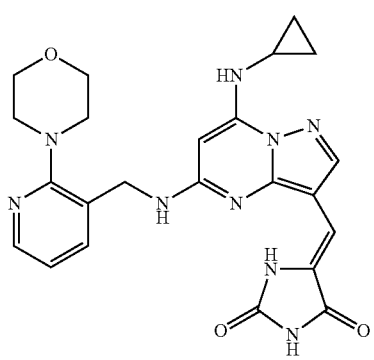 [SMILES: O=C1NC(=O)/C(=C/c2cnn3c(NC4CC4)cc(NCc4cccnc4N4CCOCC4)nc23)N1]
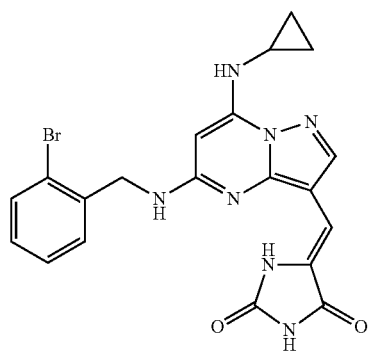 [SMILES: O=C1NC(=O)/C(=C/c2cnn3c(NC4CC4)cc(NCc4ccccc4Br)nc23)N1]
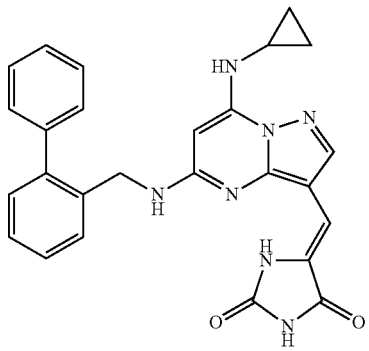 [SMILES: O=C1NC(=O)/C(=C/c2cnn3c(NC4CC4)cc(NCc4ccccc4-c4ccccc4)nc23)N1]
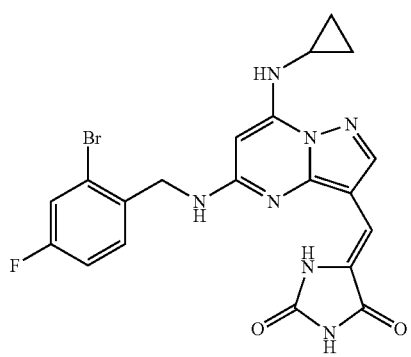 [SMILES: O=C1NC(=O)/C(=C/c2cnn3c(NC4CC4)cc(NCc4ccc(F)cc4Br)nc23)N1]
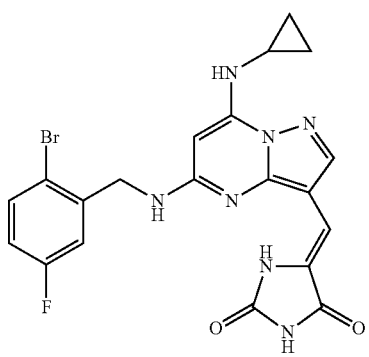 [SMILES: O=C1NC(=O)/C(=C/c2cnn3c(NC4CC4)cc(NCc4cc(F)ccc4Br)nc23)N1]
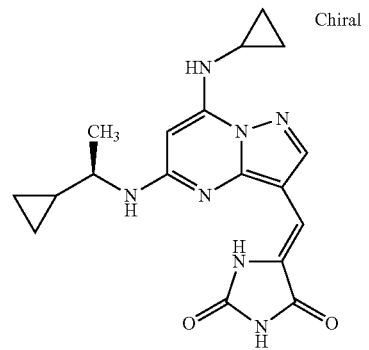 [SMILES: C[C@@H](Nc1cc(NC2CC2)n2ncc(/C=C3\NC(=O)NC3=O)c2n1)C1CC1]

TABLE 50A-continued
585
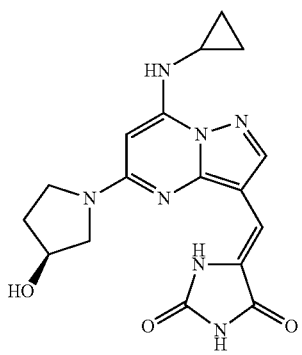 [SMILES: O=C1NC(=O)/C(=C/c2cnn3c(NC4CC4)cc(N4CC[C@H](O)C4)nc23)N1]
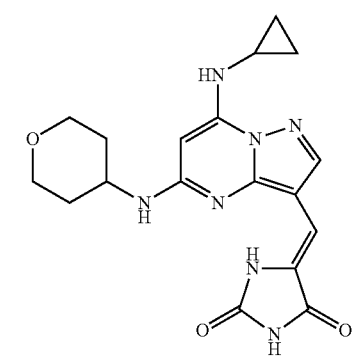 [SMILES: O=C1NC(=O)/C(=C/c2cnn3c(NC4CC4)cc(NC4CCOCC4)nc23)N1]
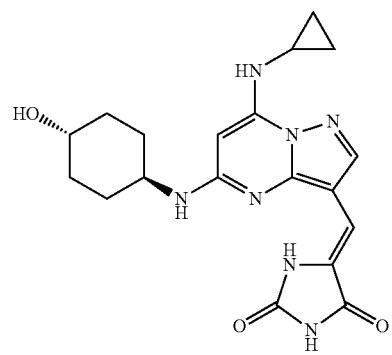 [SMILES: O=C1NC(=O)/C(=C/c2cnn3c(NC4CC4)cc(N[C@H]4CC[C@H](O)CC4)nc23)N1]
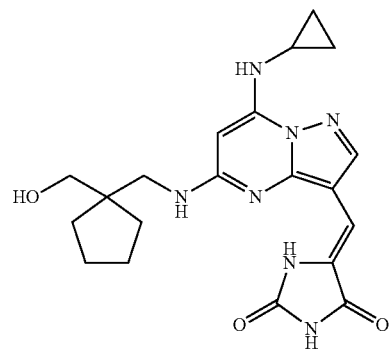 [SMILES: O=C1NC(=O)/C(=C/c2cnn3c(NC4CC4)cc(NCC4(CO)CCCC4)nc23)N1]
586
TABLE 50A-continued
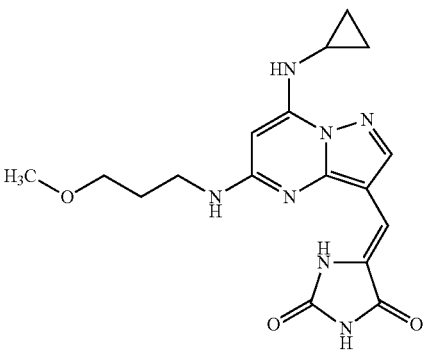 [SMILES: COCCCNc1cc(NC2CC2)n2ncc(/C=C3\NC(=O)NC3=O)c2n1]
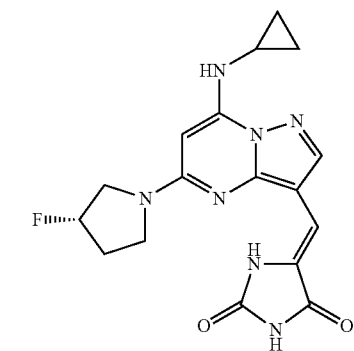 [SMILES: O=C1NC(=O)/C(=C/c2cnn3c(NC4CC4)cc(N4CC[C@H](F)C4)nc23)N1]
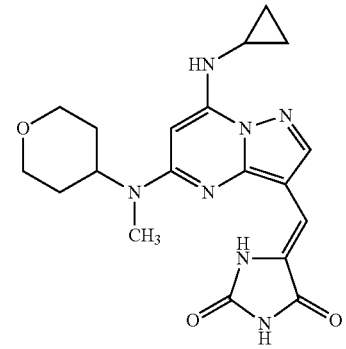 [SMILES: CN(c1cc(NC2CC2)n2ncc(/C=C3\NC(=O)NC3=O)c2n1)C1CCOCC1]
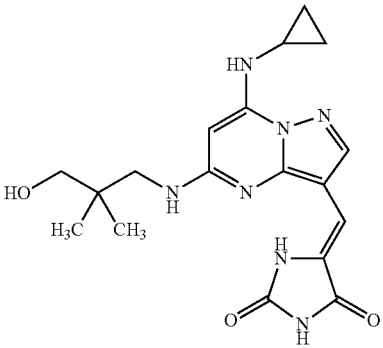 [SMILES: CC(C)(CO)CNc1cc(NC2CC2)n2ncc(/C=C3\NC(=O)NC3=O)c2n1]

TABLE 50A-continued
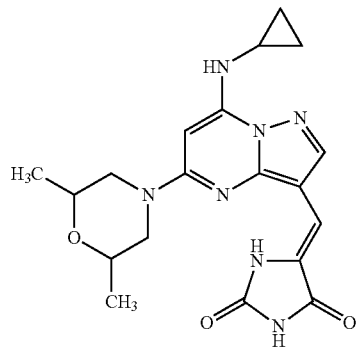 [SMILES: CC1CN(c2cc(NC3CC3)n3ncc(/C=C4\NC(=O)NC4=O)c3n2)CC(C)O1]
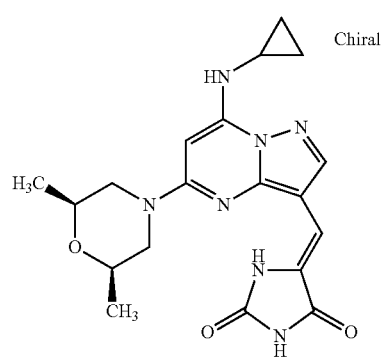 [SMILES: C[C@@H]1CN(c2cc(NC3CC3)n3ncc(/C=C4\NC(=O)NC4=O)c3n2)C[C@H](C)O1]
Chiral
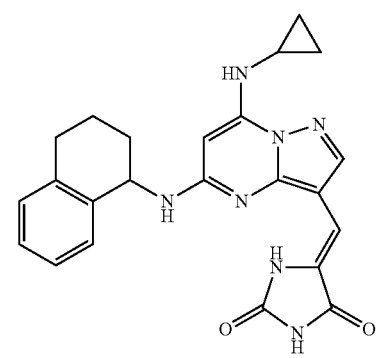 [SMILES: O=C1NC(=O)/C(=C/c2cnn3c(NC4CC4)cc(NC4CCCc5ccccc54)nc23)N1]
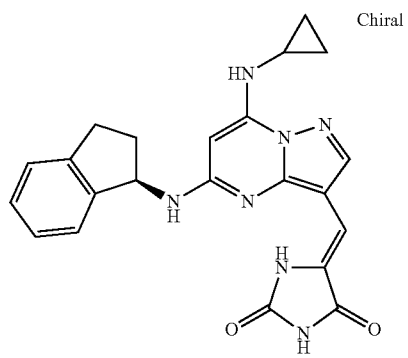 [SMILES: O=C1NC(=O)/C(=C/c2cnn3c(NC4CC4)cc(N[C@@H]4CCc5ccccc54)nc23)N1]
Chiral
TABLE 50A-continued
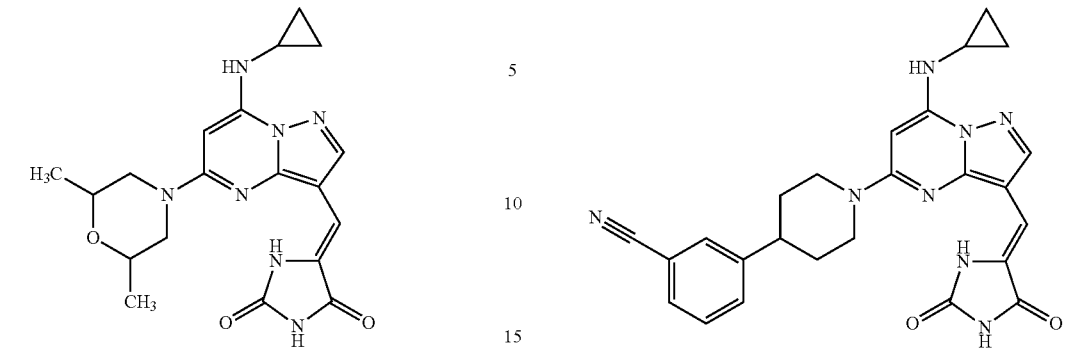
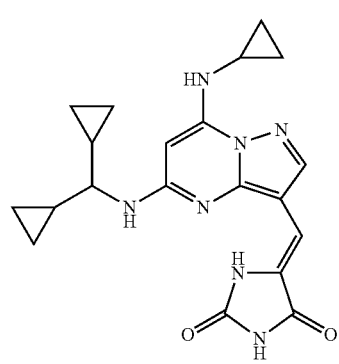 [SMILES: O=C1NC(=O)/C(=C/c2cnn3c(NC4CC4)cc(NC(C4CC4)C4CC4)nc23)N1]
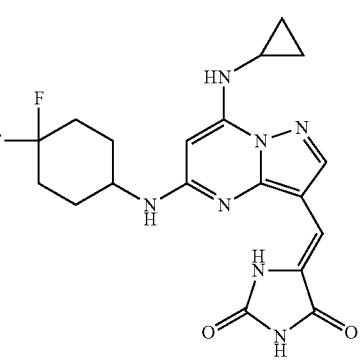
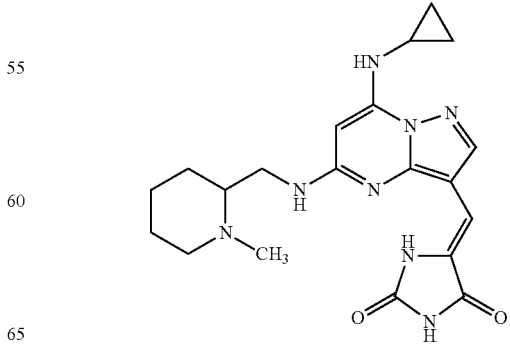

TABLE 50A-continued
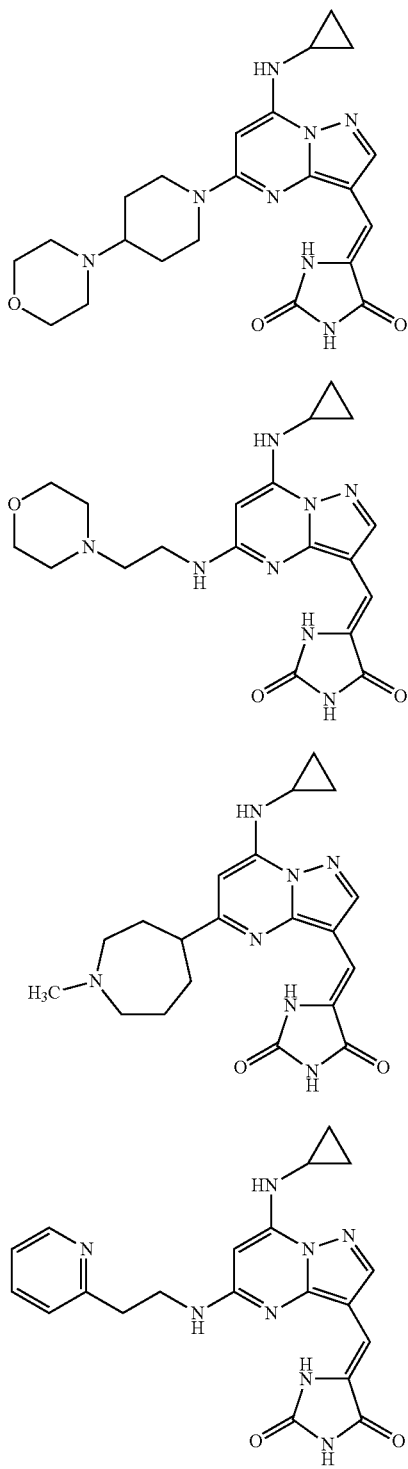
TABLE 50B
| Compound | CK2: IC50 (uM) | PIM2: % inh 2.5 uM | AB: MDAMB453 IC50 (uM) | AB: BxPC3 IC50 (uM) |
|---|---|---|---|---|
| V42 | <0.01 | 8.514 | 7.253 | 7.753 |
| W42 | <0.01 | 41.144 | 3.451 | 6.982 |
TABLE 50B-continued
| Compound | CK2: IC50 (uM) | PIM2: % inh 2.5 uM | AB: MDAMB453 IC50 (uM) | AB: BxPC3 IC50 (uM) |
|---|---|---|---|---|
| X42 | <0.01 | 24.082 | 5.335 | 7.883 |
| Y42 | <0.1 | 7.179 | 12.507 | 5.798 |
| Z42 | <0.1 | 46.188 | 3.333 | 6.124 |
| A43 | <0.1 | 51.937 | 5.542 | 11.672 |
| B43 | <0.1 | 57.05 | | |
| C43 | <0.01 | 46.18 | 3.788 | 10.91 |
| D43 | <0.1 | 46.258 | 18.532 | 21.512 |
| E43 | <0.1 | 35.462 | 3.442 | 7.676 |
| F43 | <0.1 | 47.13 | 5.127 | 11.302 |
| G43 | <0.1 | 40.238 | 0.25 | 0.311 |
| H43 | <0.01 | 70.122 | 1.575 | 7.156 |
| I43 | <0.1 | 44.879 | | |
| J43 | <0.1 | 54.24 | | |
| K43 | <0.1 | 59.084 | | |
| L43 | <0.01 | 54.602 | 7.624 | 11.881 |
| M43 | <0.01 | 58.527 | 6.073 | 4.019 |
| N43 | <0.01 | 53.361 | 3.747 | 5.688 |
| O43 | <0.1 | 39.481 | 7.183 | 13.677 |
| P43 | <0.01 | 30.394 | 7.84 | 10.566 |
| Q43 | <0.01 | 20.98 | 7.9 | 11.155 |
| R43 | <0.1 | 13.354 | 6.761 | 13.999 |
| S43 | <0.1 | 37.578 | 14.925 | 25.375 |
| T43 | <0.1 | 8.871 | | |
| U43 | <0.01 | 37.958 | 14.447 | 23.012 |
| V43 | <0.01 | 31.461 | 5.943 | 8.756 |
| W43 | <0.01 | 45.881 | 4.407 | 21.36 |
| X43 | <0.1 | 18.114 | 4.988 | 24.742 |
| Y43 | <0.1 | 37.959 | 4.445 | 15.629 |
| Z43 | <0.01 | 36.842 | 4.787 | 22.226 |
| A44 | <0.01 | | 22.798 | 20.301 |
| B44 | <0.1 | 24.036 | 22.599 | >30 |
| C44 | <0.01 | 43.464 | 4.882 | 6.246 |
| D44 | <0.1 | 48.152 | 16.668 | 14 |
| E44 | <0.1 | 46.863 | 10.367 | 10.084 |
| F44 | <0.1 | 20.409 | | |
| G44 | <0.01 | 24.063 | 1.604 | 7.202 |
| H44 | <0.1 | 28.124 | 4.276 | 8.203 |
| I44 | <0.1 | 31.932 | 6.52 | 14.085 |
| J44 | <0.1 | 35.323 | 6.219 | 17.199 |
| K44 | <0.01 | 84.937 | 3.914 | 3.632 |
| L44 | <0.1 | 40.527 | | |
| M44 | <0.01 | 31.316 | 5.907 | 10.674 |
| N44 | <0.1 | 24.588 | 4.282 | 5.226 |
| O44 | <0.1 | 18.817 | | |
| P44 | <0.1 | 14.088 | | |
| Q44 | <0.1 | 26.537 | | |
| R44 | <0.01 | 41.193 | 22.212 | 20.611 |
| S44 | <0.1 | 12.628 | 12.315 | 20.837 |
| T44 | <0.1 | 9.802 | | |
| U44 | <0.1 | 34.87 | | |
| V44 | <0.1 | 14.908 | 5.184 | 10.102 |
| W44 | <0.01 | −10.252 | 0.172 | 0.242 |
| X44 | <0.01 | 20.632 | 6.096 | 10.292 |
| Y44 | <0.01 | 36.847 | 2.301 | 1.384 |
| Z44 | <0.01 | 42.536 | 1.528 | 4.51 |
| A45 | <0.01 | 28.395 | 1.067 | 4.558 |
| B45 | <0.01 | 12.045 | 1.004 | 1.612 |
| C45 | <0.1 | −25.739 | 5.504 | 9.198 |
| D45 | <0.1 | −9.176 | <0.12 | <0.12 |
| E45 | <0.01 | 11.678 | 3.938 | 11.216 |
| F45 | <0.1 | −19.013 | 5.844 | 7.288 |
| G45 | <0.01 | | 2.857 | 4.311 |
| H45 | <0.01 | 45.857 | 16.617 | 13.54 |
| I45 | <0.01 | | 2.447 | 7.898 |
| J45 | <0.1 | 77.85 | 0.573 | 3.391 |
| K45 | <0.01 | 30.57 | 5.471 | 9.4 |
| L45 | <0.01 | 54.081 | 4.999 | 3.386 |
| M45 | <0.01 | 75.785 | 5.792 | 28.828 |
| N45 | <0.01 | 62.228 | 5.556 | 13.076 |
| O45 | <0.1 | 46.251 | | |
| P45 | <0.01 | 74.254 | 2.905 | 10.582 |
| Q45 | <0.1 | 74.048 | 14.792 | >30 |
| R45 | <0.01 | 28.85 | 3.477 | 5.733 |
| S45 | <0.01 | 32.937 | 2.98 | 7.511 |
| T45 | <0.1 | −6.871 | 21.079 | 14.555 |
| U45 | <0.1 | 38.332 | 1.063 | 1.443 |

TABLE 50B-continued

| Compound | CK2: IC50 (uM) | PIM2: % inh 2.5 uM | AB: MDAMB453 IC50 (uM) | AB: BxPC3 IC50 (uM) |
|---|---|---|---|---|
| V45 | <0.1 | 17.03 | 3.83 | 19.496 |
| W45 | <0.1 | 57.926 | 2.214 | 15.246 |
| X45 | <0.1 | 33.091 | | |
| Y45 | <0.1 | 20.409 | | |
| Z45 | <0.1 | 48.01 | | |
| A46 | <0.1 | 41.388 | 11.35 | 3.499 |

Example 267

Synthesis of 5,7-dichloro-6-methylpyrazolo[1,5-a]pyrimidine

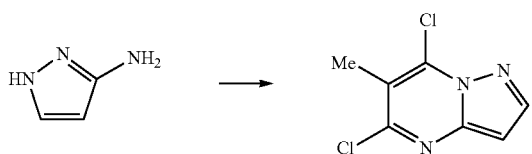 [SMILES: Nc1cc[nH]n1 ; Cc1c(Cl)nc2ccnn2c1Cl]

Under nitrogen gas atmosphere, sodium (3.5 g, 151 mmol) was added to ethanol (125 mL) in small portions and stirred at room temperature until all the sodium had dissolved. A solution of 3-aminopyrazole (12.5 g, 150 mmol) in ethanol (20 mL) and diethyl methylmalonate (26 mL, 153 mmol) were dropped, successively, to the above solution. The mixture was refluxed at 90° C. for 10 hours, cooled to room temperature, and filtered under vacuum. To the solid, cold 5N HCl was added and the resulting solid was collected by filtration under vacuum. The intermediate, 6-methylpyrazolo[1,5-a]pyrimidine-5,7-diol, was recovered as an off-white solid in 72% yield (17.9 g). This material was used for the next step without further purification. LCMS (M+1=166)

Under nitrogen gas atmosphere, phosphorous oxychloride (160 mL, 1.72 mol) and dimethylaniline (16 mL, 132 mmol) was added successively to the intermediate prepared above (16 g, 97 mmol). The mixture was heated at 110° C. for 4 hours then excess POCl₃ was removed under vacuum. The residue was made basic with 3N NaOH solution (pH=9-10) and extracted with ethyl acetate (3×). The combined organic layers were dried over anhydrous Na₂SO₄, filtered, and concentrated under vacuum. The residue was purified by silica gel chromatography (100% DCM) to provide 15.8 grams of the solid yellow product, 5,7-dichloro-6-methylpyrazolo[1,5-a]pyrimidine (81% yield). LCMS (M+1=203)

Example 268

Synthesis of 5-chloro-7-(cyclopropylamino)-6-methylpyrazolo[1,5-a]pyrimidine-3-carbaldehyde

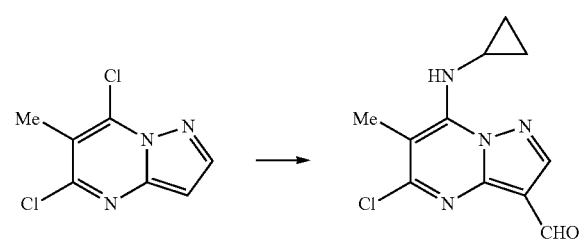 [SMILES: Cc1c(Cl)nc2ccnn2c1Cl ; Cc1c(Cl)nc2c(C=O)cnn2c1NC1CC1]

To the reaction flask, 5,7-dichloro-6-methylpyrazolo[1,5-a]pyrimidine (5 g, 25 mmol) was added along with cyclopropyl amine (1.8 mL, 25 mmol), triethylamine (3.5 mL, 25 mmol), and acetonitrile (87 mL). The reaction was stirred at room temperature for 3 hours then heated at 85° C. for an additional 6 hours. The mixture was cooled to room temperature, diluted with water, filtered and washed with water. The intermediate, 5-chloro-N-cyclopropyl-6-methylpyrazolo[1,5-a]pyrimidin-7-amine, was further purified by silica gel chromatography (10% ethyl acetate/hexanes) to provide 4.8 grams of a white solid (86% yield). LCMS (M+1=223)

To the intermediate (3.6 g, 16 mmol) isolated above in DMF (59 mL) was added phosphorous oxychloride (9 mL, 96 mmol) slowly at room temperature. The reaction mixture was allowed to stir at room temperature for 10 hours then quenched by addition to 6N NaOH solution. The pH of the mixture was adjusted with 6N HCl to pH=7-9. The solid was recovered by filtration and washed with water. The product, 5-chloro-7-(cyclopropylamino)-6-methylpyrazolo[1,5-a]pyrimidine-3-carbaldehyde, was purified by recrystallization from ethyl acetate/hexanes to yield a white solid in 73% yield (2.9 g). LCMS (M+1=251)

Example 269

Synthesis of tert-butyl 5-chloro-3-formyl-6-methylpyrazolo[1,5-a]pyrimidin-7-yl(cyclopropyl)carbamate

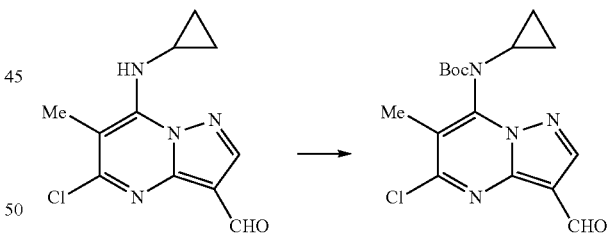

To 5-chloro-7-(cyclopropylamino)-6-methylpyrazolo[1,5-a]pyrimidine-3-carbaldehyde (2.9 g, 11.7 mmol) in methylene chloride (22 mL) was added triethylamine (2 mL, 14 mmol), dimethylaminopyridine (100 mg, 0.8 mmol), and di-t-butyldicarbonate (3.1 g, 14 mmol). The mixture was stirred at room temperature for 10 hours. The reaction mixture was transferred to a separatory funnel, washed 1× with H₂O, 2× with brine, dried over MgSO₄, filtered, and evaporated to dryness to provide an oily residue. The crude material was purified by silica gel chromatography (25% ethyl acetate/hexanes) to yield a light orange solid (3.6 g, 88% yield), tert-butyl 5-chloro-3-formyl-6-methylpyrazolo[1,5-a]pyrimidin-7-yl(cyclopropyl)carbamate. LCMS (M+1=351)

Example 270

Synthesis of 3-chloro-4-(7-(cyclopropylamino)-3-formyl-6-methylpyrazolo[1,5-a]pyrimidin-5-ylamino)benzonitrile

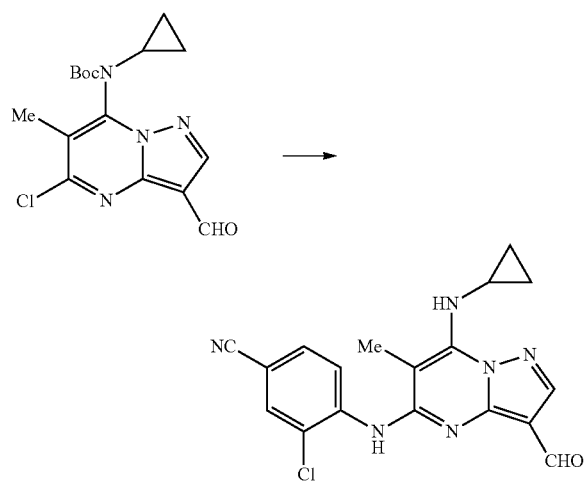

To 4-amino-3-chlorobenzonitrile (52 mg, 0.34 mmol), $Cs_2CO_3$ (130 mg, 0.4 mmol) were added to tert-butyl 5-chloro-3-formyl-6-methylpyrazolo[1,5-a]pyrimidin-7-yl(cyclopropyl)carbamate (100 mg, 0.29 mmol) dissolved in 1,4-dioxane (1.1 mL). Racemic BINAP (11 mg, 0.017 mmol) and palladium(II) acetate (8 mg, 0.011 mmol) were then added. The mixture was sealed and irradiated at 110° C. for 60 min in the microwave. $Et_2O$ (3 mL) was added and the solution was filtered. The filtrate was concentrated in vacuo. The crude residue was dissolved in dichloromethane (1.5 mL) and trifluoroacetic acid (1.5 mL). After stirring at room temperature for 1 hour, the solution was concentrated under a stream of air. The crude material was purified by silica gel chromatography (3% acetone/dichloromethane) to yield the product, 3-chloro-4-(7-(cyclopropylamino)-3-formyl-6-methylpyrazolo[1,5-a]pyrimidin-5-ylamino)benzonitrile (34 mg, 33% yield). LCMS (M+1=367)

Example 271

Synthesis of 3-chloro-4-(7-(cyclopropylamino)-3-((2,5-dioxoimidazolidin-4-ylidene)methyl)-6-methylpyrazolo[1,5-a]pyrimidin-5-ylamino)benzonitrile

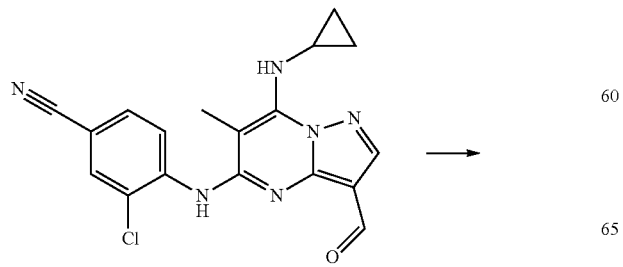

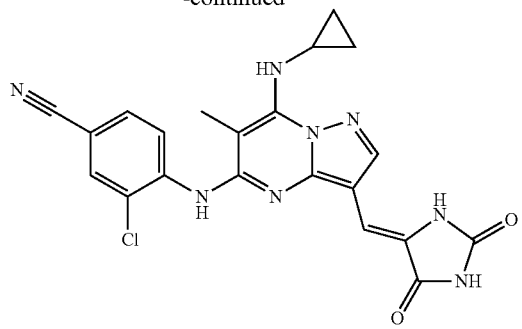

Hydantoin (2.7 mg, 0.027 mmol) and 3-chloro-4-(7-(cyclopropylamino)-3-formyl-6-methylpyrazolo[1,5-a]pyrimidin-5-ylamino)benzonitrile (10 mg, 0.027 mmol) were dissolved in ethanol (0.4 mL) along with piperidine (3 uL, 0.03 mmol). The reaction was heated at 80° C. After 10 hours, the reaction was cooled to r.t., diluted with water, and the precipitate was collected and washed with water, 1:1 ethanol:water, then ethanol. The bright yellow solid was dried in vacuo to give 3-chloro-4-(7-(cyclopropylamino)-3-((2,5-dioxoimidazolidin-4-ylidene)methyl)-6-methylpyrazolo[1,5-a]pyrimidin-5-ylamino)benzonitrile (7 mg, 58% yield). LCMS (M+1=449)

The following molecules were prepared using chemistries similar to synthesis in examples above. All compounds were characterized by LCMS. Table 51B shows the biological activities of the compounds listed in Table 51A.

TABLE 51A

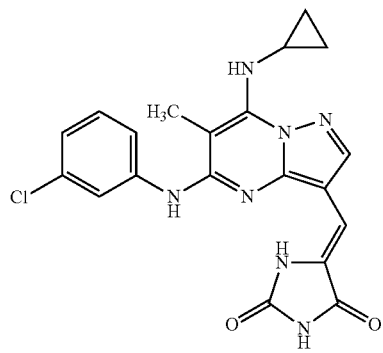 [SMILES: Cc1c(Nc2cccc(Cl)c2)nc2c(/C=C3\NC(=O)NC3=O)cnn2c1NC1CC1]

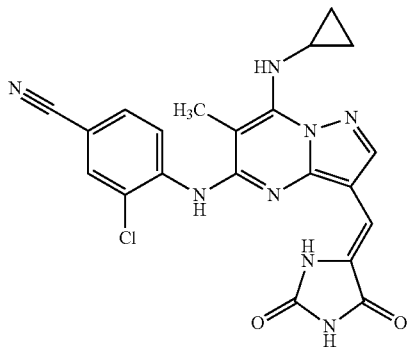 [SMILES: Cc1c(Nc2ccc(C#N)cc2Cl)nc2c(/C=C3\NC(=O)NC3=O)cnn2c1NC1CC1]

TABLE 51A-continued

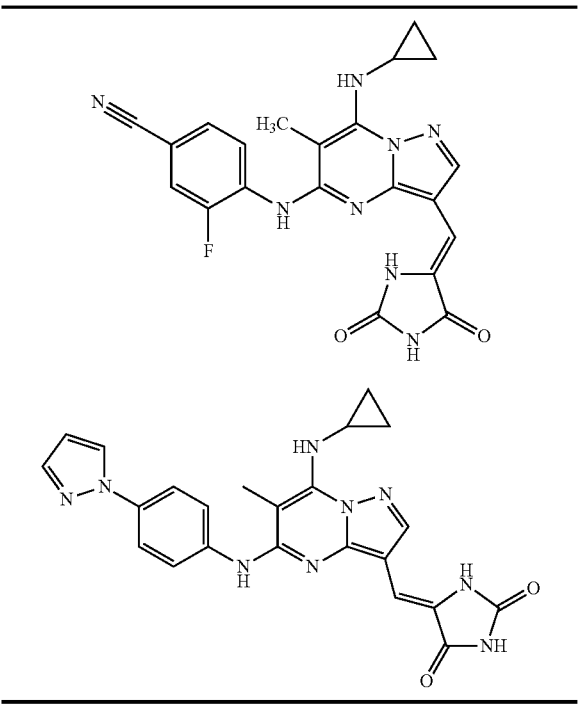

TABLE 51B

| Compound | CK2:<br>IC50<br>(uM) | PIM2:<br>% inh<br>2.5 uM | AB:<br>MDAMB453<br>IC50 (uM) | AB:<br>BxPC3<br>IC50 (uM) |
|---|---|---|---|---|
| B46 | <0.01 | 47.606 | 24.21 | >30 |
| C46 | <0.01 | 59.266 | 6.288 | 15.231 |
| D46 | <0.01 | 53.934 | 6.244 | 29.919 |
| E46 | <0.1 | 49.545 | 16.63 | 20.921 |

Example 272

Synthesis of 5-chloro-7-(cyclopropylamino)-2-methylpyrazolo[1,5-a]pyrimidine-3-carbaldehyde

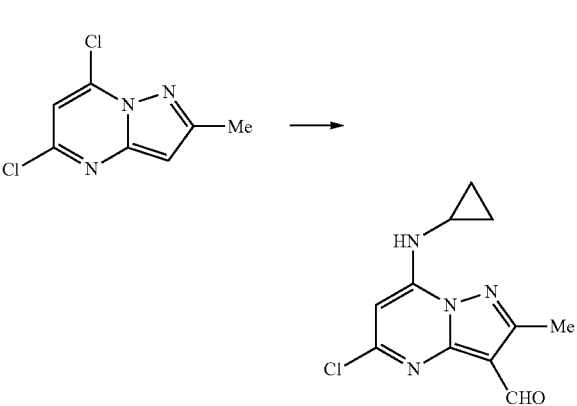

To the reaction flask, 5,7-dichloro-2-methylpyrazolo[1,5-a]pyrimidine (2 g, 10 mmol) was added along with cyclopropyl amine (0.7 mL, 10 mmol), triethylamine (1.4 mL, 10 mmol), and acetonitrile (30 mL). The reaction was stirred at room temperature for 8 hours then cooled to room temperature, diluted with water, filtered and washed with water. The intermediate, 5-chloro-N-cyclopropyl-2-methylpyrazolo[1,5-a]pyrimidin-7-amine, was dried under vacuum to provide 1.85 grams of a white solid (83% yield). LCMS (M+1=223)

To the intermediate (1.9 g, 8.3 mmol) isolated above in DMF (31 mL) was added phosphorous oxychloride (4.6 mL, 49.7 mmol) slowly at room temperature. The reaction mixture was allowed to stir at room temperature for 10 hours then quenched by addition to 6N NaOH solution. The pH of the mixture was adjusted with 6N HCl to pH=7-9. The solid was recovered by filtration and washed with water. The product, 5-chloro-7-(cyclopropylamino)-2-methylpyrazolo[1,5-a]pyrimidine-3-carbaldehyde, was obtained as a white solid in 80% yield (1.7 g). LCMS (M+1=251)

Example 273

Synthesis of tert-butyl 5-chloro-3-formyl-2-methylpyrazolo[1,5-a]pyrimidin-7-yl(cyclopropyl)carbamate

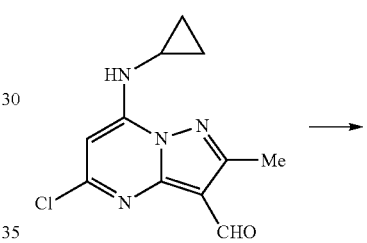

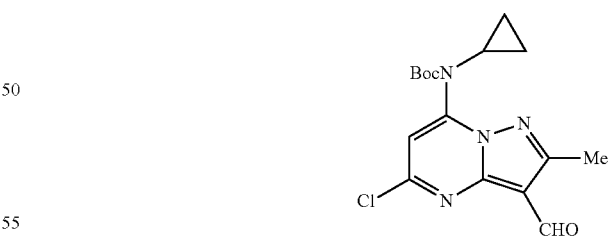

To 5-chloro-7-(cyclopropylamino)-2-methylpyrazolo[1,5-a]pyrimidine-3-carbaldehyde (1.7 g, 6.7 mmol) in methylene chloride (13 mL) was added triethylamine (1.1 mL, 8 mmol), dimethylaminopyridine (100 mg, 0.8 mmol), and di-t-butyl-dicarbonate (1.8 g, 8 mmol). The mixture was stirred at room temperature for 10 hours. The reaction mixture was transferred to a separatory funnel, washed 1× with H$_2$O, 2× with brine, dried over MgSO$_4$, filtered, and evaporated to dryness to provide an oily residue which solidified on standing. The product, tert-butyl 5-chloro-3-formyl-2-methylpyrazolo[1,5- a]pyrimidin-7-yl(cyclopropyl)carbamate, was recovered as an off-white solid in 82% yield (1.9 g). LCMS (M+1=351)

Example 274

Synthesis of 5-(4-(1H-pyrazol-1-yl)phenylamino)-7-(cyclopropylamino)-2-methylpyrazolo[1,5-a]pyrimidine-3-carbaldehyde

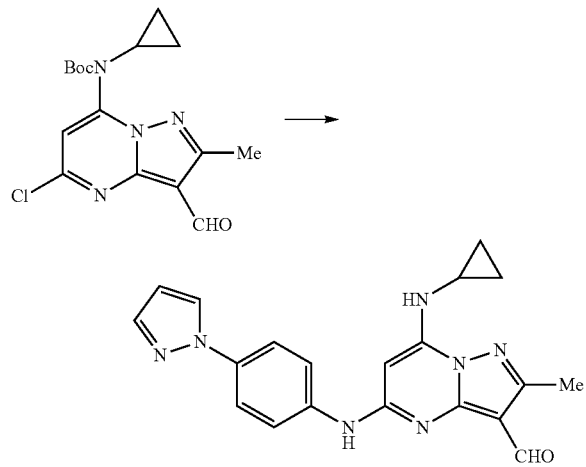

To 4-(1H-pyrazol-1-yl)aniline (54 mg, 0.34 mmol), Cs$_2$CO$_3$ (130 mg, 0.4 mmol) were added to tert-butyl 5-chloro-3-formyl-2-methylpyrazolo[1,5-a]pyrimidin-7-yl(cyclopropyl)carbamate (100 mg, 0.29 mmol) dissolved in 1,4-dioxane (1.1 mL). Racemic BINAP (11 mg, 0.017 mmol) and palladium(II) acetate (8 mg, 0.011 mmol) were then added. The mixture was sealed and irradiated at 110° C. for 60 min in the microwave. Et$_2$O (3 mL) was added and the solution was filtered. The filtrate was concentrated in vacuo. The crude residue was dissolved in dichloromethane (1.5 mL) and trifluoroacetic acid (1.5 mL). After stirring at room temperature for 1 hour, the solution was concentrated under a stream of air. The crude material was purified by silica gel chromatography (15% acetone/dichloromethane) to yield the product, 5-(4-(1H-pyrazol-1-yl)phenylamino)-7-(cyclopropylamino)-2-methylpyrazolo[1,5-a]pyrimidine-3-carbaldehyde (24 mg, 23% yield). LCMS (M+1=374)

Example 275

Synthesis of 5-((5-(4-(1H-pyrazol-1-yl)phenylamino)-7-(cyclopropylamino)-2-methylpyrazolo[1,5-a]pyrimidin-3-yl)methylene)imidazolidine-2,4-dione

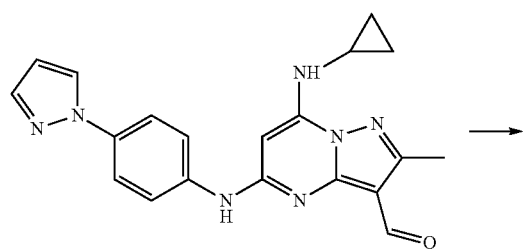

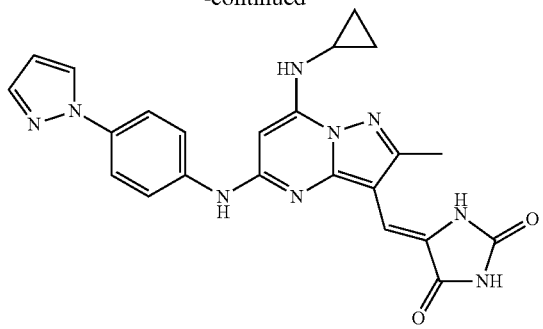

Hydantoin (3 mg, 0.03 mmol) and 5-(4-(1H-pyrazol-1-yl)phenylamino)-7-(cyclopropylamino)-2-methylpyrazolo[1,5-a]pyrimidine-3-carbaldehyde (12 mg, 0.03 mmol) were dissolved in ethanol (0.4 mL) along with piperidine (3 uL, 0.03 mmol). The reaction was heated at 80° C. in the microwave for 2 hours. The reaction was then cooled to r.t., diluted with water, and the precipitate was collected and washed with water, 1:1 ethanol:water, then ethanol. The yellow solid was dried in vacuo to give 5-((5-(4-(1H-pyrazol-1-yl)phenylamino)-7-(cyclopropylamino)-2-methylpyrazolo[1,5-a]pyrimidin-3-yl)methylene)imidazolidine-2,4-dione (9.5 mg, 65% yield). LCMS (M+1=456)

TABLE 52

| Biological Activies of Example 275: | |
| --- | --- |
| CK2: IC50 (µM) | PIM2: % inh (2.5 µM) |
| >1 | 43.426 |

Example 276

Synthesis of 7-chloro-5-(methylthio)pyrazolo[1,5-a]pyrimidine-6-carbonitrile

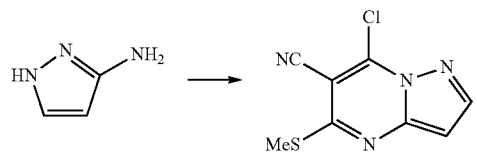 [SMILES: Nc1cc[nH]n1 ; CSc1nc2ccnn2c(Cl)c1C#N]

Under nitrogen gas atmosphere, 2-cyano-3,3-bismethylthio-2-propenoic methyl ester (6 g, 29.5 mmol) was added to ethanol (40 mL) along with 3-aminopyrazole (2.6 g, 31 mmol) and the mixture was refluxed for 2.5 hours. The reaction was then cooled to room temperature and precipitate was collected by filtration under vacuum. The solid was washed with ethanol and dried under vacuum to give 7-hydroxy-5-(methylthio)pyrazolo[1,5-a]pyrimidine-6-carbonitrile in 67% yield (4.1 g). This material was used for the next step without further purification. LCMS (M+1=207)

Under nitrogen gas atmosphere, phosphorous oxychloride (9.4 mL, 101.3 mmol) and dimethylaniline (2.6 mL, 20.3 mmol) was added successively to the intermediate, 7-hydroxy-5-(methylthio)pyrazolo[1,5-a]pyrimidine-6-carbonitrile, prepared above (4.1 g, 19.7 mmol). The mixture was heated at 110° C. for 4 hours then excess POCl$_3$ was removed under vacuum. The residue was made basic with 3N NaOH solution (pH=9-10) and extracted with ethyl acetate (3×). The combined organic layers were dried over anhydrous Na$_2$SO$_4$, filtered, and concentrated under vacuum. The residue was purified by recrystallization from ethyl acetate hexanes to provide the product, 7-chloro-5-(methylthio)pyrazolo[1,5-a] pyrimidine-6-carbonitrile (80% yield). LCMS (M+1=225)

Example 277

Synthesis of 7-(cyclopropylamino)-3-formyl-5-(methylthio)pyrazolo[1,5-a]pyrimidine-6-carbonitrile

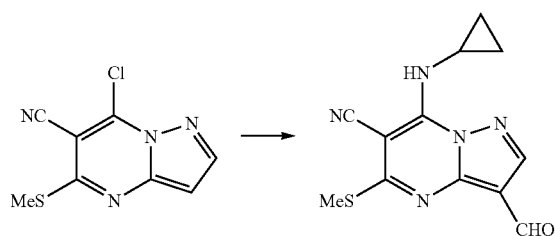 [SMILES: CSc1nc2ccnn2c(Cl)c1C#N ; CSc1nc2c(C=O)cnn2c(NC2CC2)c1C#N]

To the reaction flask, 7-chloro-5-(methylthio)pyrazolo[1,5-a]pyrimidine-6-carbonitrile (3.1 g, 13.7 mmol) was added along with cyclopropyl amine (0.96 mL, 13.7 mmol), triethylamine (1.9 mL, 13.7 mmol), and acetonitrile (30 mL). The reaction was stirred at 85° C. for 10 hours then the mixture was cooled to room temperature, diluted with water, filtered and washed with water. The intermediate, 7-(cyclopropylamino)-5-(methylthio)pyrazolo[1,5-a]pyrimidine-6-carbonitrile, was further purified by recrystallization from ethyl acetate hexanes to provide 3 grams in 89% yield. LCMS (M+1=246)

To the intermediate (3 g, 12.2 mmol) isolated above in DMF (45 mL) was added phosphorous oxychloride (13.7 mL, 146 mmol) slowly at room temperature. The reaction mixture was allowed to stir at 70° C. for 10 hours, cooled to room temperature, and quenched by addition to 6N NaOH solution. The pH of the mixture was adjusted with 6N HCl to pH=7-9. The solid was recovered by filtration and washed with water. The product, 7-(cyclopropylamino)-3-formyl-5-(methylthio)pyrazolo[1,5-a]pyrimidine-6-carbonitrile, was obtained as a solid in 38% yield (1.28 g). LCMS (M+1=274)

Example 278

Synthesis of 7-(cyclopropylamino)-3-((2,5-dioxoimidazolidin-4-ylidene)methyl)-5-(methylsulfinyl)pyrazolo[1,5-a]pyrimidine-6-carbonitrile and 7-(cyclopropylamino)-3-((2,5-dioxoimidazolidin-4-ylidene)methyl)-5-(methylsulfonyl)pyrazolo[1,5-a]pyrimidine-6-carbonitrile

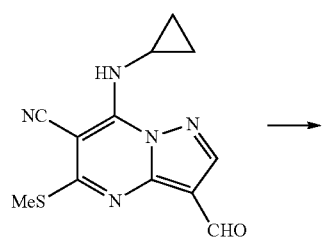

-continued

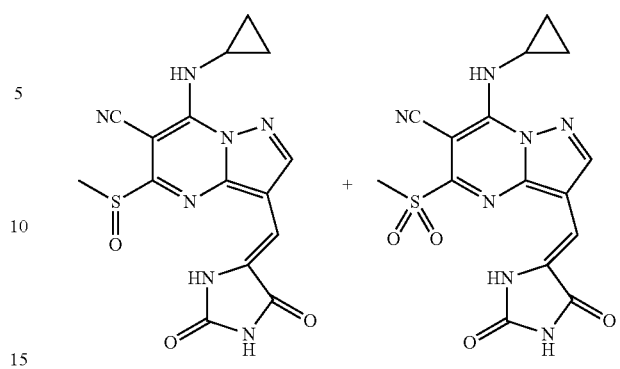

Hydantoin (366 mg, 3.7 mmol) and 7-(cyclopropylamino)-3-formyl-5-(methylthio)pyrazolo[1,5-a]pyrimidine-6-carbonitrile (1 g, 3.7 mmol) were dissolved in ethanol (18.5 mL) along with piperidine (3.7 mL, 3.7 mmol). The reaction was heated at 80° C. After 10 hours, the reaction was cooled to r.t., diluted with water, and the precipitate was collected and washed with water, 1:1 ethanol:water, then ethanol. The yellow solid was dried in vacuo to give the intermediate, 7-(cyclopropylamino)-3-((2,5-dioxoimidazolidin-4-ylidene)methyl)-5-(methylthio)pyrazolo[1,5-a]pyrimidine-6-carbonitrile (1.1 g, 83% yield). LCMS (M+1=356)

The intermediate (1.1 g, 3.04 mmol) was mixed with m-chloroperbenzoic acid (1.9 g, 7.6 mmol) in dichloromethane (12 mL). The mixture was allowed to stir at room temperature for 12 hours. The solid was collected by filtration, washed dichloromethane then dried under vacuum overnight. The products, 7-(cyclopropylamino)-3-((2,5-dioxoimidazolidin-4-ylidene)methyl)-5-(methylsulfonyl) pyrazolo[1,5-a]pyrimidine-6-carbonitrile and 7-(cyclopropylamino)-3-((2,5-dioxoimidazolidin-4-ylidene) methyl)-5-(methylsulfinyl)pyrazolo[1,5-a]pyrimidine-6-carbonitrile, were recovered as a yellow solid in quantitative yield. LCMS (M+1=372) and LCMS (M+1=388)

Example 279

Synthesis of 5-(1-(3-chlorophenyl)ethylamino)-7-(cyclopropylamino)-3-((2,5-dioxoimidazolidin-4-ylidene)methyl)pyrazolo[1,5-a]pyrimidine-6-carbonitrile

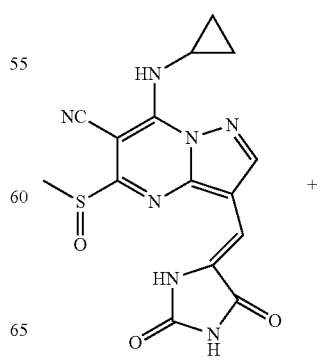

-continued

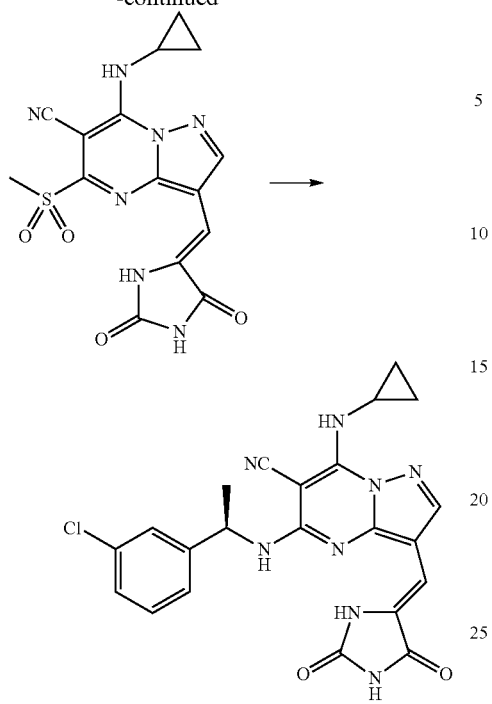

The mixture of 7-(cyclopropylamino)-3-((2,5-dioxoimidazolidin-4-ylidene)methyl)-5-(methylsulfonyl)pyrazolo[1,5-a]pyrimidine-6-carbonitrile and 7-(cyclopropylamino)-3-((2,5-dioxoimidazolidin-4-ylidene)methyl)-5-(methylsulfinyl)pyrazolo[1,5-a]pyrimidine-6-carbonitrile (20 mg) was mixed with (R)-1-(3-chlorophenyl)ethanamine (33 mg) in i-propanol (0.5 mL). The reaction mixture was heated at 90° C. in the microwave for 1 hour. The reaction was cooled to room temperature and concentrated under vacuum. The residue was diluted with water, filtered and washed with water followed by 20% ethanol/water mixture. The solid was dried under high vacuum to give 2 mg of the product, 5-(1-(3-chlorophenyl)ethylamino)-7-(cyclopropylamino)-3-((2,5-dioxoimidazolidin-4-ylidene)methyl)pyrazolo[1,5-a]pyrimidine-6-carbonitrile. LCMS (M+1=463)

The following molecules were prepared using chemistries similar to synthesis in examples above. All compounds were characterized by LCMS. Table 53B shows the biological activities of the compounds listed in Table 53A.

TABLE 53A

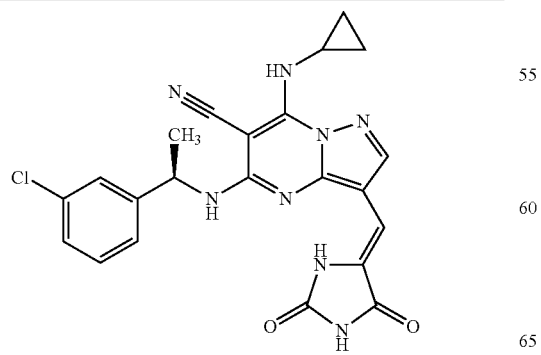

TABLE 53A-continued

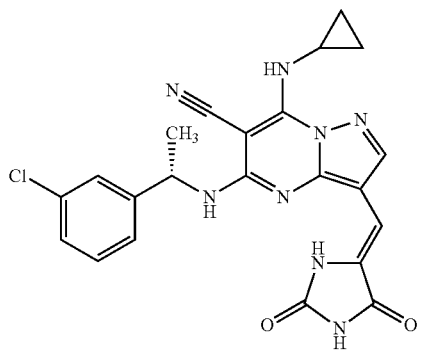 [SMILES: C[C@H](Nc1nc2c(/C=C3\NC(=O)NC3=O)cnn2c(NC2CC2)c1C#N)c1cccc(Cl)c1]

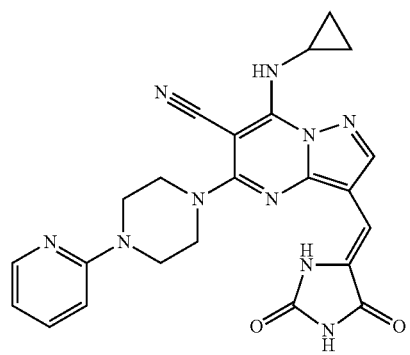 [SMILES: N#Cc1c(N2CCN(c3ccccn3)CC2)nc2c(/C=C3\NC(=O)NC3=O)cnn2c1NC1CC1]

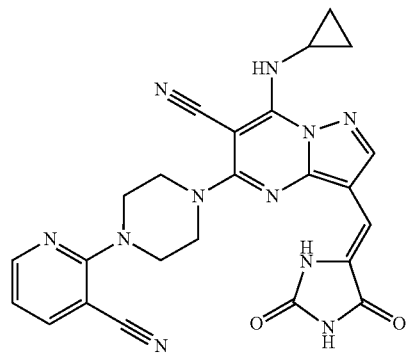 [SMILES: N#Cc1cccnc1N1CCN(c2nc3c(/C=C4\NC(=O)NC4=O)cnn3c(NC3CC3)c2C#N)CC1]

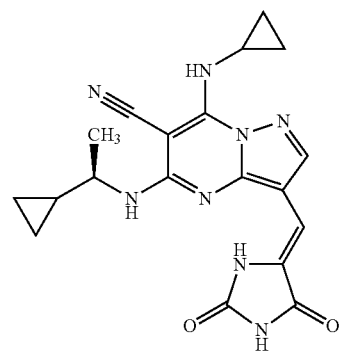 [SMILES: C[C@@H](Nc1nc2c(/C=C3\NC(=O)NC3=O)cnn2c(NC2CC2)c1C#N)C1CC1]

TABLE 53A-continued

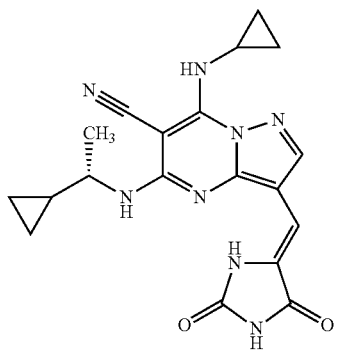 [SMILES: C[C@H](Nc1nc2c(/C=C3\NC(=O)NC3=O)cnn2c(NC2CC2)c1C#N)C1CC1]

TABLE 53B

| Compound | CK2: IC50 (uM) | PIM2: % inh 2.5 uM | AB: MDAMB453 IC50 (uM) | AB: BxPC3 IC50 (uM) |
|---|---|---|---|---|
| F46 | <0.1 | 39.402 | | |
| G46 | <0.1 | 71.368 | 9.41 | 16.174 |
| H46 | <0.1 | 41.888 | >30 | >30 |
| I46 | <0.1 | 84.757 | 25.494 | 2.698 |
| J46 | <0.1 | 57.881 | 7.76 | 6.299 |
| K46 | <0.1 | 69.233 | 6.41 | 2.989 |

Example 280

Synthesis of 2-(4-(7-(cyclopropylamino)-3-formylpyrazolo[1,5-a]pyrimidin-5-yl)piperazin-1-yl)nicotinonitrile

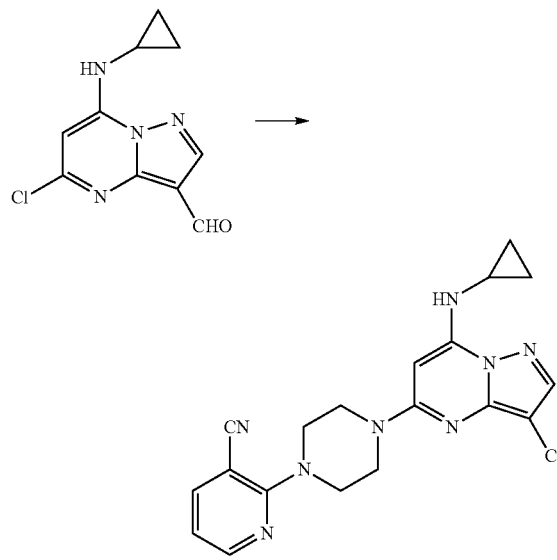

In a reaction flask, 2-(piperazin-1-yl)nicotinonitrile (22 mg, 0.11 mmol) was mixed with 5-chloro-7-(cyclopropylamino)pyrazolo[1,5-a]pyrimidine-3-carbaldehyde (27 mg, 0.11 mmol) in DMF (0.5 mL) along with potassium carbonate (32 mg, 0.23 mmol). The reaction was heated at 95° C. for 12 hours then partitioned between water and ethyl acetate. The organic layer was washed with water then saturated NaCl solution. The ethyl acetate layer was isolated, dried of anhydrous sodium sulfate, filtered, and evaporated to dryness. The product, 2-(4-(7-(cyclopropylamino)-3-formylpyrazolo[1,5-a]pyrimidin-5-yl)piperazin-1-yl)nicotinonitrile, was recovered in 35% yield (16 mg) after recrystallization from ethyl acetate/hexanes. LCMS (M+1=389)

Example 281

Synthesis of 2-(4-(7-(cyclopropylamino)-3-((2,5-dioxoimidazolidin-4-ylidene)methyl)pyrazolo[1,5-a]pyrimidin-5-yl)piperazin-1-yl)nicotinonitrile

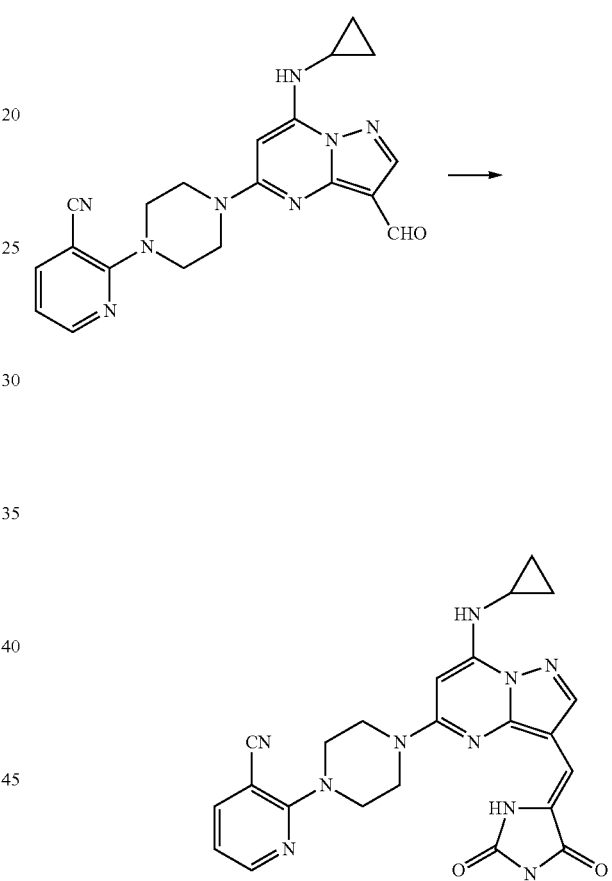

Hydantoin (4 mg, 0.04 mmol) and 2-(4-(7-(cyclopropylamino)-3-formylpyrazolo[1,5-a]pyrimidin-5-yl)piperazin-1-yl)nicotinonitrile (16 mg, 0.04 mmol) were dissolved in ethanol (0.5 mL) along with piperidine (4 uL, 0.04 mmol). The reaction was heated at 80° C. for 12 hours. The reaction was then cooled to r.t., diluted with water, and the precipitate was collected and washed with water, 1:1 ethanol:water, then ethanol. The yellow solid was further purified by recrystallization from ethyl acetate/hexanes and dried in vacuo to give 2-(4-(7-(cyclopropylamino)-3-((2,5-dioxoimidazolidin-4-ylidene)methyl)pyrazolo[1,5-a]pyrimidin-5-yl)piperazin-1-yl)nicotinonitrile (2 mg, 21% yield). LCMS (M+1=471)

The following molecules were prepared using chemistries similar to synthesis in examples above. All compounds were characterized by LCMS. Table 54B shows the biological activities of the compounds listed in Table 54A.

TABLE 54A

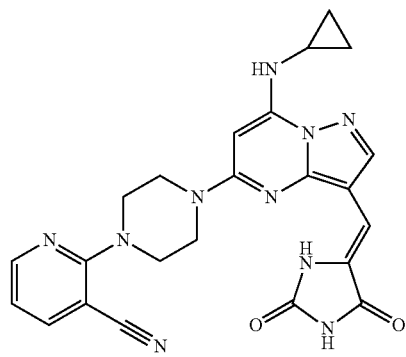 [SMILES: N#Cc1cccnc1N1CCN(c2cc(NC3CC3)n3ncc(/C=C4\NC(=O)NC4=O)c3n2)CC1]

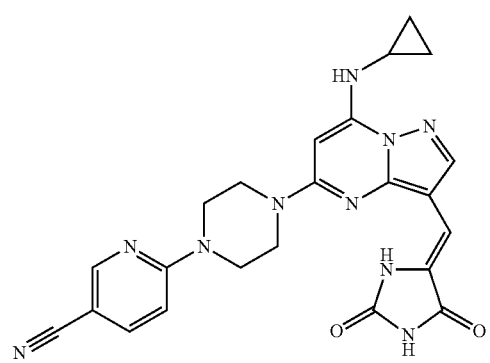 [SMILES: N#Cc1ccc(N2CCN(c3cc(NC4CC4)n4ncc(/C=C5\NC(=O)NC5=O)c4n3)CC2)nc1]

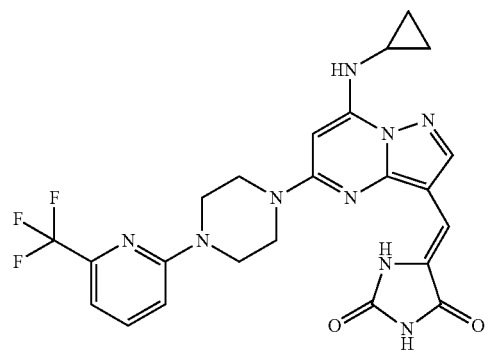 [SMILES: O=C1NC(=O)/C(=C/c2cnn3c(NC4CC4)cc(N4CCN(c5cccc(C(F)(F)F)n5)CC4)nc23)N1]

TABLE 54A-continued

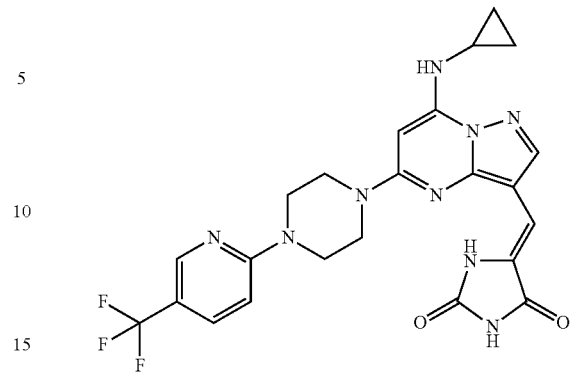

TABLE 54B

| Compound | CK2: IC50 (uM) | PIM2: % inh 2.5 uM | AB: MDAMB453 IC50 (uM) | AB: BxPC3 IC50 (uM) |
|---|---|---|---|---|
| L46 | <0.01 | 47.249 | 1.082 | 3.701 |
| M46 | <0.1 | 60.945 | | |
| N46 | <0.1 | 32.984 | 19.188 | 7.441 |
| O46 | <0.1 | 12.231 | | |
| P46 | <0.1 | −39.422 | | |

Example 282

Synthesis of 2-(4-(7-(cyclopropylamino)-3-formyl-6-methylpyrazolo[1,5-a]pyrimidin-5-yl)piperazin-1-yl)nicotinonitrile

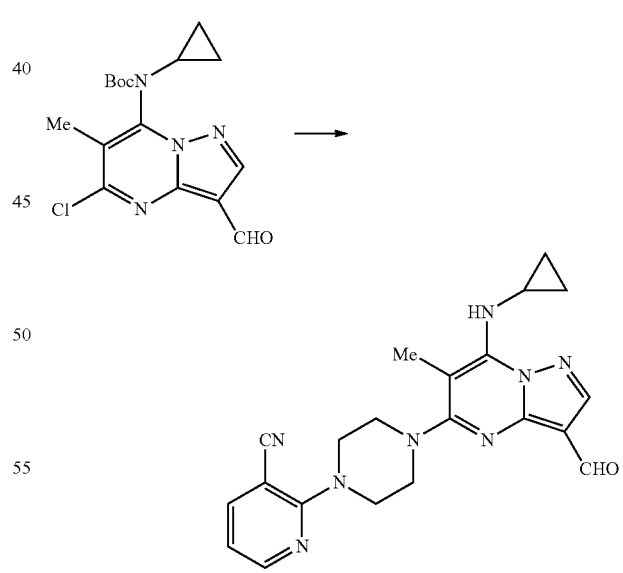

Tert-butyl 5-chloro-3-formyl-6-methylpyrazolo[1,5-a]pyrimidin-7-yl(cyclopropyl)carbamate (60 mg, 0.17 mmol) was mixed with 2-(piperazin-1-yl)nicotinonitrile (64 mg, 0.34 mmol) in i-propanol (1 mL). The reaction mixture was heated at 90° C. in the microwave for 1 hour. The reaction was cooled to room temperature and concentrated under vacuum. The residue was dissolved in (1:1) TFA/DCM (4 mL) and stirred at room temperature for 1 hour. The reaction was evaporated to dryness, quenched with 3N NaOH, filtered, washed with water, and dried under vacuum The product, 2-(4-(7-(cyclopropylamino)-3-formyl-6-methylpyrazolo[1,5-a]pyrimidin-5-yl)piperazin-1-yl)nicotinonitrile, was further purified by preparative TLC using 5% acetone/dichloromethane as the eluent (40 mg, 58% yield). LCMS (M+1=403)

Example 283

Synthesis of 2-(4-(7-(cyclopropylamino)-3-((2,5-dioxoimidazolidin-4-ylidene)methyl)-6-methylpyrazolo[1,5-a]pyrimidin-5-yl)piperazin-1-yl)nicotinonitrile

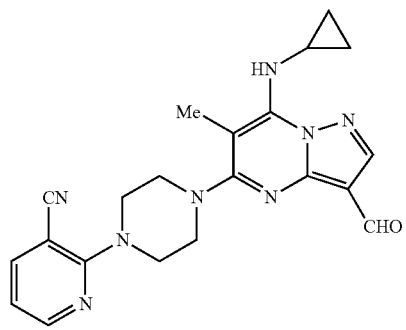

Hydantoin (7.5 mg, 0.08 mmol) and 2-(4-(7-(cyclopropylamino)-3-formyl-6-methylpyrazolo[1,5-a]pyrimidin-5-yl)piperazin-1-yl)nicotinonitrile (15 mg, 0.04 mmol) were dissolved in ethanol (0.5 mL) along with piperidine (8 uL, 0.08 mmol). The reaction was heated at 80° C. for 1 hour in the microwave. The reaction was then cooled to r.t., diluted with water, and the precipitate was collected and washed with water, 1:1 ethanol:water, then ethanol. The yellow solid was dried in vacuo to give 2-(4-(7-(cyclopropylamino)-3-((2,5-dioxoimidazolidin-4-ylidene)methyl)-6-methylpyrazolo[1,5-a]pyrimidin-5-yl)piperazin-1-yl)nicotinonitrile (3 mg, 17% yield). LCMS (M+1=485)

Example 284

Synthesis of 2-(4-(7-(cyclopropylamino)-3-((2,4-dioxothiazolidin-5-ylidene)methyl)-6-methylpyrazolo[1,5-a]pyrimidin-5-yl)piperazin-1-yl)nicotinonitrile

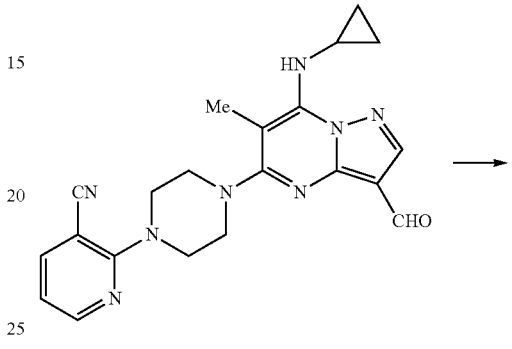

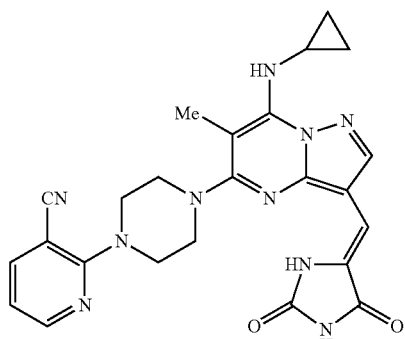

In a reaction flask, thiazolidine-2,4-dione (9 mg, 0.08 mmol) and 2-(4-(7-(cyclopropylamino)-3-formyl-6-methylpyrazolo[1,5-a]pyrimidin-5-yl)piperazin-1-yl)nicotinonitrile (15 mg, 0.04 mmol) were dissolved in ethanol (0.5 mL) along with piperidine (8 uL, 0.08 mmol). The reaction was heated at 80° C. for 1 hour in the microwave. The reaction was then cooled to r.t., diluted with water, and the precipitate was collected and washed with water, 1:1 ethanol:water, then ethanol. The yellow solid was dried in vacuo to give 2-(4-(7-(cyclopropylamino)-3-((2,4-dioxothiazolidin-5-ylidene)methyl)-6-methylpyrazolo[1,5-a]pyrimidin-5-yl)piperazin-1-yl)nicotinonitrile (10 mg, 54% yield). LCMS (M+1=502)

The following molecules were prepared using chemistries similar to synthesis in examples above. All compounds were characterized by LCMS. Table 55B shows the biological activities of the compounds listed in Table 55A.

609

TABLE 55A

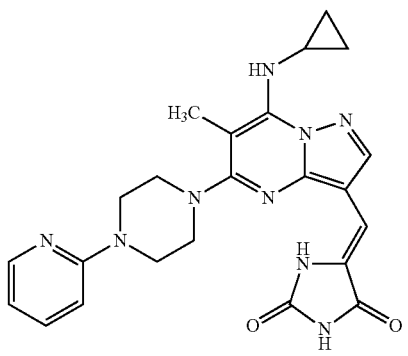 [SMILES: Cc1c(N2CCN(c3ccccn3)CC2)nc2c(/C=C3\NC(=O)NC3=O)cnn2c1NC1CC1]

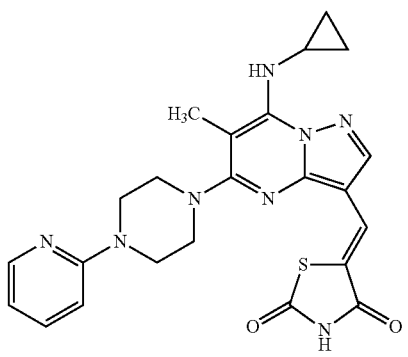 [SMILES: Cc1c(N2CCN(c3ccccn3)CC2)nc2c(/C=C3\SC(=O)NC3=O)cnn2c1NC1CC1]

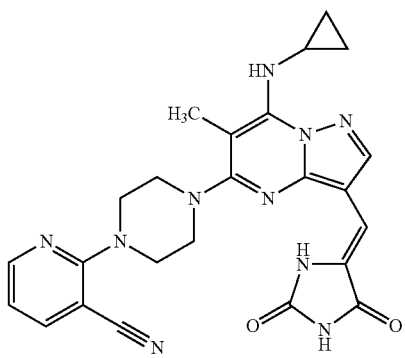 [SMILES: Cc1c(N2CCN(c3ncccc3C#N)CC2)nc2c(/C=C3\NC(=O)NC3=O)cnn2c1NC1CC1]

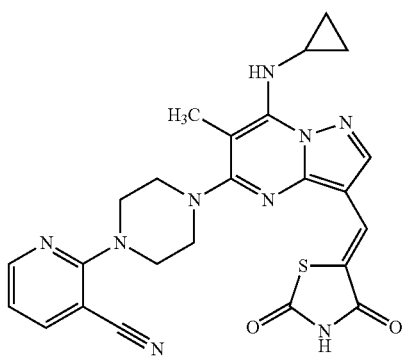 [SMILES: Cc1c(N2CCN(c3ncccc3C#N)CC2)nc2c(/C=C3\SC(=O)NC3=O)cnn2c1NC1CC1]

TABLE 55B

| Compound | CK2: IC50 (uM) | PIM2: % inh 2.5 uM | AB: MDAMB453 IC50 (uM) | AB: BxPC3 IC50 (uM) |
|---|---|---|---|---|
| Q46 | <0.01 | 13.151 | >30 | >30 |
| R46 | <1 | 68.545 | | |

610

TABLE 55B-continued

| Compound | CK2: IC50 (uM) | PIM2: % inh 2.5 uM | AB: MDAMB453 IC50 (uM) | AB: BxPC3 IC50 (uM) |
|---|---|---|---|---|
| S46 | <1 | −19.761 | | |
| T46 | <1 | 50.998 | | |

Example 285

Synthesis of tert-butyl 5-chloropyrazolo[1,5-a]pyrimidin-7-yl(2-morpholinopropyl)carbamate

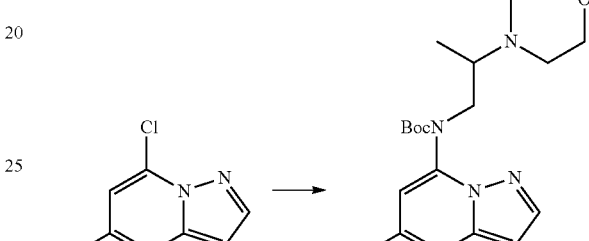

To the reaction flask, 5,7-dichloropyrazolo[1,5-a]pyrimidine (3.2 g, 17 mmol) was added along with 2-morpholinopropan-1-amine (2.4 g, 17 mmol), triethylamine (2.3 mL, 17 mmol), and acetonitrile (56 mL). The reaction was stirred at 85° C. for 12 hours then cooled to room temperature, diluted with water, filtered and washed with water. The intermediate, 5-chloro-N-(2-morpholinopropyl)pyrazolo[1,5-a]pyrimidin-7-amine, was dried under vacuum to provide 3.8 grams of an off-white solid (77% yield). LCMS (M+1=296)

To 5-chloro-N-(2-morpholinopropyl)pyrazolo[1,5-a]pyrimidin-7-amine (3.8 g, 13 mmol) in methylene chloride (50 mL) was added triethylamine (2.1 mL, 15 mmol), dimethylaminopyridine (200 mg, 1.6 mmol), and di-t-butyldicarbonate (3.3 g, 15 mmol). The mixture was stirred at room temperature for 10 hours. The reaction mixture was transferred to a separatory funnel, washed 1× with $H_2O$, 2× with brine, dried over $MgSO_4$, filtered, and evaporated to dryness to provide an oily residue which solidified on standing. The product, tert-butyl 5-chloropyrazolo[1,5-a]pyrimidin-7-yl(2-morpholinopropyl)carbamate, was recovered as an off-white solid in 39% yield (5.1 mmol). LCMS (M+1=396)

Example 286

Synthesis of N5-(5-chloro-2-fluorophenyl)-N7-(2-morpholinopropyl)pyrazolo[1,5-a]pyrimidine-5,7-diamine

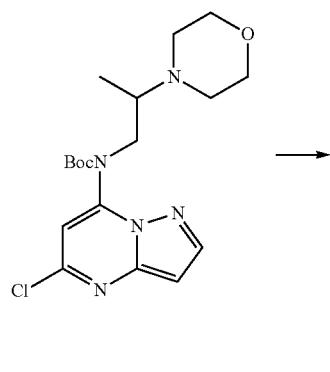

To tert-butyl 5-chloropyrazolo[1,5-a]pyrimidin-7-yl(2-morpholinopropyl)carbamate (396 mg, 1 mmol), 5-chloro-2-fluoroaniline (145 uL, 1.2 mmol), and LiHMDS (2.2 mL, 2.2 mmol, 1M in THF) was added X-Phos (11 mg, 0.024 mmol) and tris(dibenzylideneacetone)dipalladium(0) (18 mg, 0.02 mmol). The mixture was sealed and irradiated at 65° C. for 60 min in the microwave. The reaction was quenched with 1N HCL (2 mL) and then neutralized with saturated sodium bicarbonate solution. The mixture was extracted with ethyl acetate and washed with saturated sodium chloride solution. The organic layer was collected, dried over anhydrous sodium sulfate, filtered, and evaporated to dryness. The crude residue was dissolved in dichloromethane (2 mL) and trifluoroacetic acid (2 mL). After stirring at room temperature for 1 hour, the solution was concentrated under a stream of nitrogen. The crude material was neutralized with saturated sodium bicarbonate solution then purified by silica gel chromatography (75% ethyl acetate/hexanes) to yield the product, N5-(5-chloro-2-fluorophenyl)-N-7-(2-morpholinopropyl)pyrazolo[1,5-a]pyrimidine-5,7-diamine (84 mg, 21% yield). LCMS (M+1=405)

Example 287

Synthesis of 5-(5-chloro-2-fluorophenylamino)-7-(2-morpholinopropylamino)pyrazolo[1,5-a]pyrimidine-3-carbaldehyde

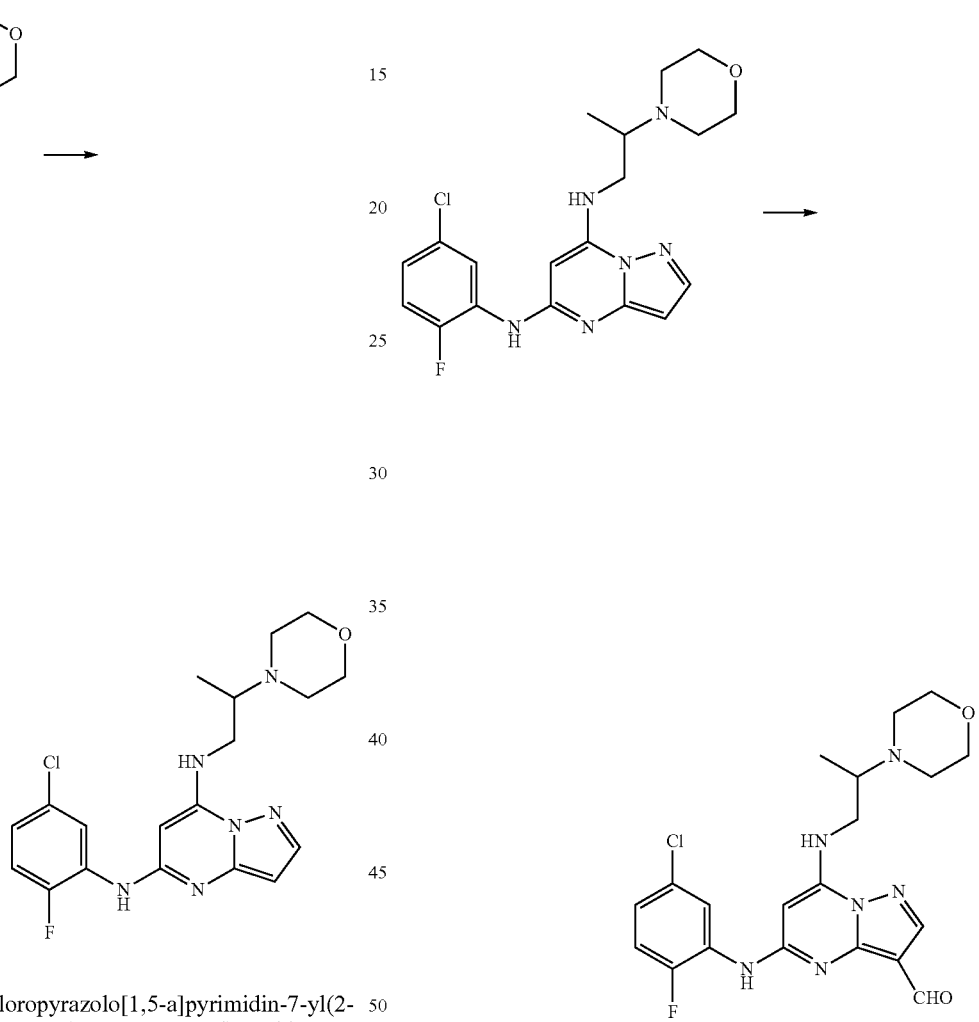

In a reaction flask, N5-(5-chloro-2-fluorophenyl)-N7-(2-morpholinopropyl)pyrazolo[1,5-a]pyrimidine-5,7-diamine (84 mg, 0.21 mmol) was dissolved in DMF (0.9 mL) then phosphorous oxychloride (58 uL, 0.62 mmol) was added slowly at room temperature. The reaction mixture was allowed to stir at room temperature for 2 days then quenched by addition to 6N NaOH solution. The pH of the mixture was adjusted with 6N HCl to pH=7-9. The solid was recovered by filtration and washed with water. The product, 5-(5-chloro-2-fluorophenylamino)-7-(2-morpholinopropylamino)pyrazolo[1,5-a]pyrimidine-3-carbaldehyde, was purified by prepara-

Example 288

Synthesis of 5-((5-(5-chloro-2-fluorophenylamino)-7-(2-morpholinopropylamino)pyrazolo[1,5-a]pyrimidin-3-yl)methylene)imidazolidine-2,4-dione

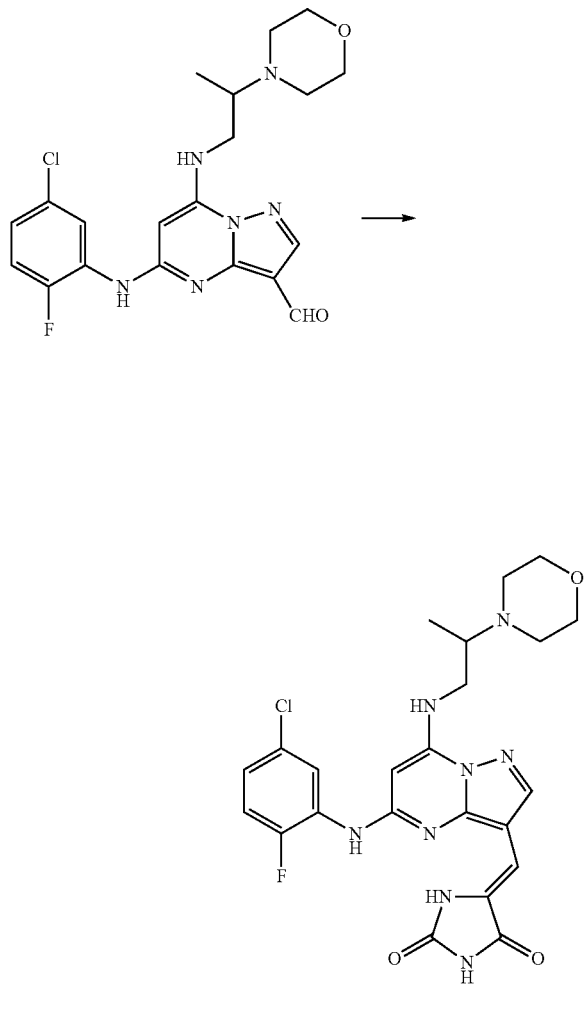

Hydantoin (7 mg, 0.07 mmol) and 5-(5-chloro-2-fluorophenylamino)-7-(2-morpholinopropylamino)pyrazolo[1,5-a]pyrimidine-3-carbaldehyde (15 mg, 0.035 mmol) were dissolved in ethanol (0.5 mL) along with piperidine (7 uL, 0.07 mmol). The reaction was heated at 80° C. for 1 hour in the microwave. The reaction was then cooled to r.t., diluted with water, and the precipitate was collected and washed with water, 1:1 ethanol:water, then ethanol. The yellow solid was dried in vacuo to give 5-((5-(5-chloro-2-fluorophenylamino)-7-(2-morpholinopropylamino)pyrazolo[1,5-a]pyrimidin-3-yl)methylene)imidazolidine-2,4-dione (5 mg, 28% yield). LCMS (M+1=515)

The following molecules were prepared using chemistries similar to synthesis in examples above. All compounds were characterized by LCMS. Table 56B shows the biological activities of the compounds listed in Table 56A.

TABLE 56A

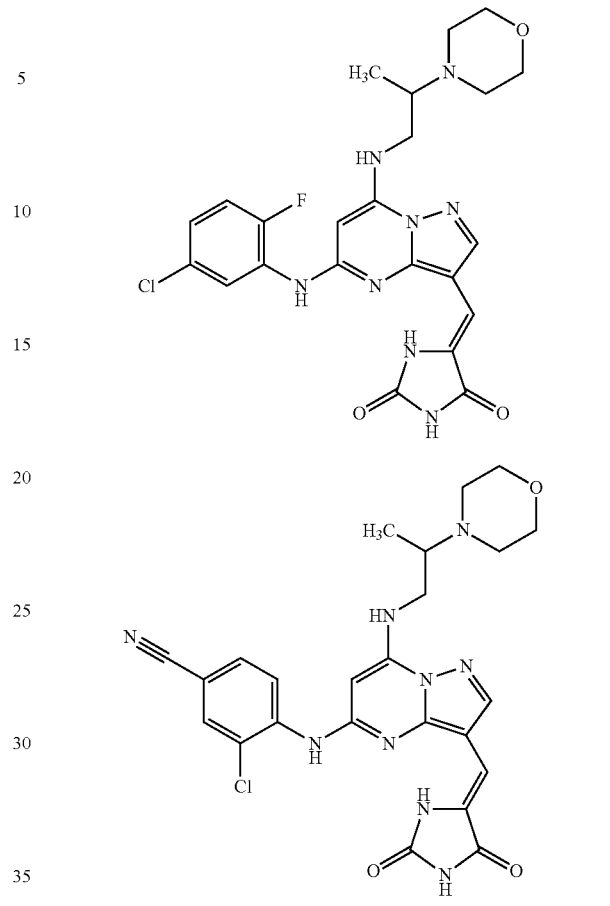

TABLE 56B

| LCMS m/z [M + 1]+ | CK2: IC50 (μM) | PIM2: IC50 (μM) | AB: MDAMB453 (μM) | AB: BxPC3 (μM) |
|---|---|---|---|---|
| 515 | <0.01 | | | |
| 522 | <0.01 | | 1.522 | 10.361 |

Example 289

Synthesis of tert-butyl 4-(7-(cyclopropylamino)-3-formylpyrazolo[1,5-a]pyrimidin-5-yl)piperazine-1-carboxylate

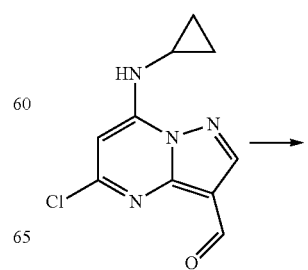

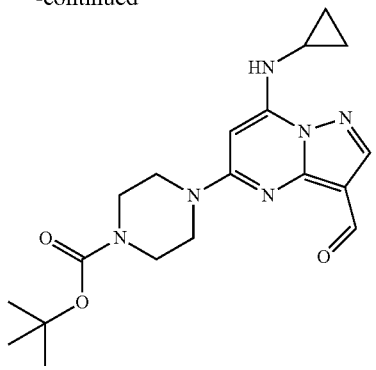

To 5-chloro-7-(cyclopropylamino) pyrazolo[1,5-a]pyrimidine-3-carbaldehyde (500 mg, 2.11 mmol) in dimethylformamide was added 1-Boc-piperazine (1.17 g, 6.33 mmol), potassium carbonate (583 mg, 4.21 mmol) and diisopropyl ethylamine (0.41 mL, 2.5 mmol). The mixture was heated to 80° C. for overnight. Cooled the reaction mixture, added water and filtered the white precipitate to yield tert-butyl 4-(7-(cyclopropylamino)-3-formylpyrazolo[1,5-a]pyrimidin-5-yl)piperazine-1-carboxylate (655 mg, 80% yield). LCMS (M+1=387)

Example 290

Synthesis of (Z)-5-((7-(cyclopropylamino)-5-(piperazin-1-yl)pyrazolo[1,5-a]pyrimidin-3-yl)methylene) imidazolidine-2,4-dione

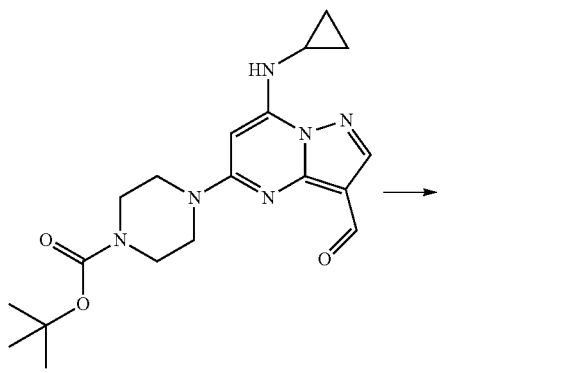

The above product tert-butyl 4-(7-(cyclopropylamino)-3-formylpyrazolo[1,5-a]pyrimidin-5-yl)piperazine-1-carboxylate (250 mg, 0.645 mmol) was dissolved in 2.0 mL ethanol, added hydantoin (129 mg, 1.288 mmol) and piperidine (127 ul). The reaction was heated to 80° C. for three hours. Cooled the reaction mixture and yellow precipitate was filtered, washed with ethanol, dried to yield (Z)-tert-butyl 4-(7-(cyclopropylamino)-3-((2,5-dioxoimidazolidin-4-ylidene)methyl)pyrazolo[1,5-a]pyrimidin-5-yl)piperazine-1-carboxylate (264 mg, 87% yield). The above product was further dissolved in 1:1 mixture of DCM: TFA and stirred at room temperature for 30 minutes. Mixture was concentrated and dried to yield yellow solid of (Z)-5((7-(cyclopropylamino)-5-(piperazin-1-yl)pyrazolo[1,5-a]pyrimidin-3-yl) methylene) imidazolidine-2,4-dione. LCMS (M+1=369)

Example 291

Synthesis of (Z)-5-((5-(4-(2-cyclopropylacetyl)piperazin-1-yl)-7-(cyclopropylamino)pyrazolo[1,5-a]pyrimidin-3-yl)methylene)imidazolidine-2,4-dione

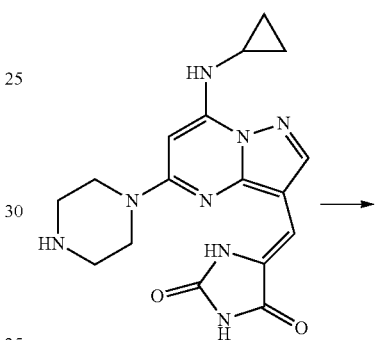

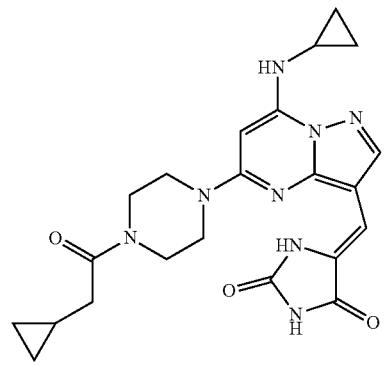

To (Z)-5((7-(cyclopropylamino)-5-(piperazin-1-yl)pyrazolo[1,5-a]pyrimidin-3-yl) methylene) imidazolidine-2,4-dione (step b) (10 mg, 0.027 mmol) in 50.0 uL NMP, was added HOBT (4.4 mg, 0.032 mmol), cyclopropyl acetic acid (60 ul in 0.02M NMP solution), DIPEA (9.5 ul, 0.067 mmol) and EDC (7.8 mg, 0.040 mmol). The reaction mixture was stirred at room temperature for one hour. Diluted the reaction mixture with methanol and prepared by HPLC to yield (Z)-5-((5-(4-(2-cyclopropylacetyl)piperazin-1-yl)-7-(cyclopropylamino)pyrazolo[1,5-a]pyrimidin-3-yl)methylene) imidazolidine-2,4-dione. LCMS (M+1=451)

The compounds listed in the following Table 57A were prepared according to the procedures as described above. Table 57B shows the biological activities of the compounds listed in Table 57A.

TABLE 57A
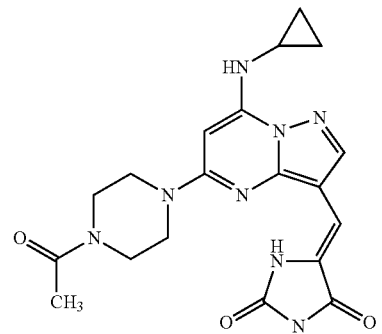
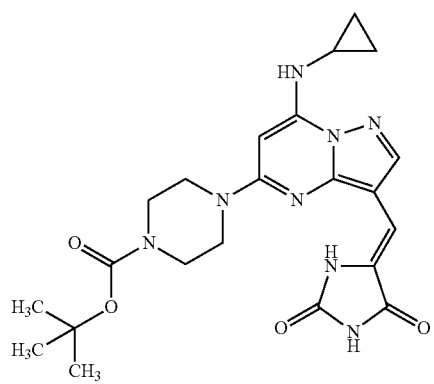 [SMILES: CC(C)(C)OC(=O)N1CCN(c2cc(NC3CC3)n3ncc(/C=C4\NC(=O)NC4=O)c3n2)CC1]
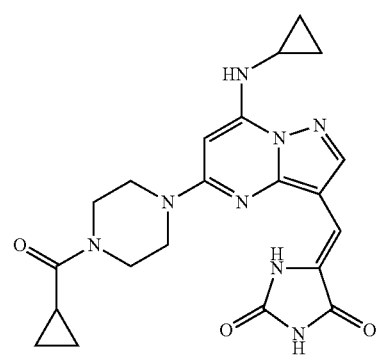 [SMILES: O=C1NC(=O)/C(=C/c2cnn3c(NC4CC4)cc(N4CCN(C(=O)C5CC5)CC4)nc23)N1]
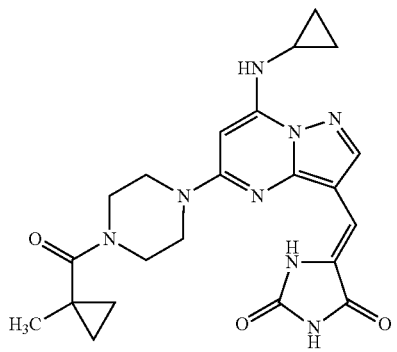 [SMILES: CC1(C(=O)N2CCN(c3cc(NC4CC4)n4ncc(/C=C5\NC(=O)NC5=O)c4n3)CC2)CC1]
TABLE 57A-continued
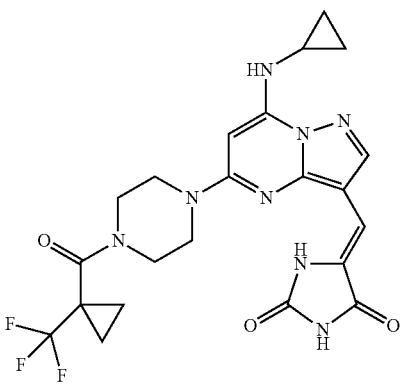 [SMILES: O=C1NC(=O)/C(=C/c2cnn3c(NC4CC4)cc(N4CCN(C(=O)C5(C(F)(F)F)CC5)CC4)nc23)N1]
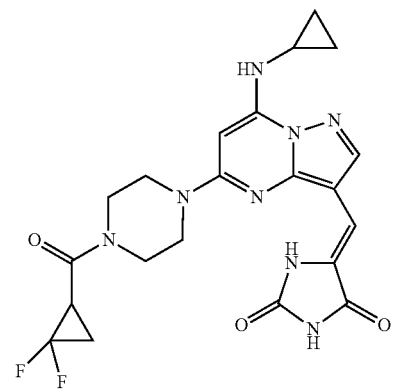 [SMILES: O=C1NC(=O)/C(=C/c2cnn3c(NC4CC4)cc(N4CCN(C(=O)C5CC5(F)F)CC4)nc23)N1]
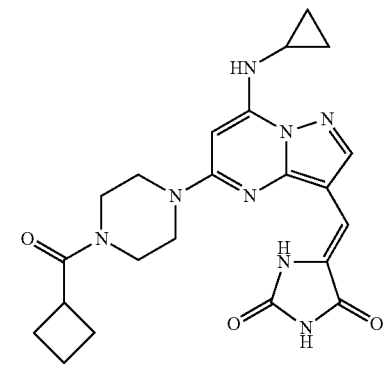 [SMILES: O=C1NC(=O)/C(=C/c2cnn3c(NC4CC4)cc(N4CCN(C(=O)C5CCC5)CC4)nc23)N1]
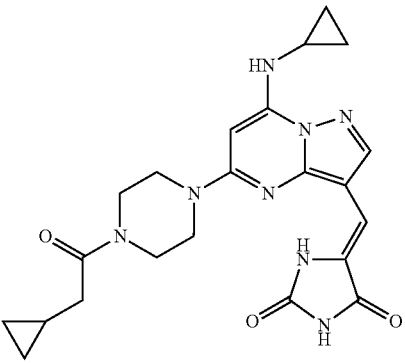 [SMILES: O=C1NC(=O)/C(=C/c2cnn3c(NC4CC4)cc(N4CCN(C(=O)CC5CC5)CC4)nc23)N1]

TABLE 57A-continued

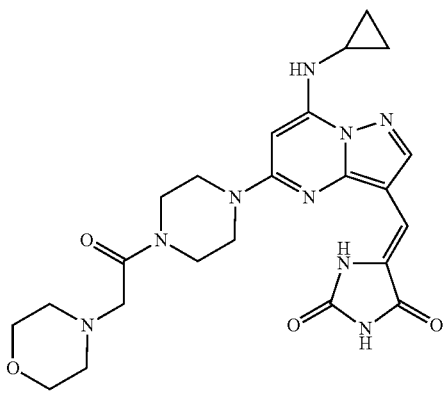 [SMILES: O=C1NC(=O)/C(=C/c2cnn3c(NC4CC4)cc(N4CCN(C(=O)CN5CCOCC5)CC4)nc23)N1]

TABLE 57B

| Compound | CK2: IC50 (μM) | PIM2: IC50 (μM) | AB: MDAMB453 (μM) | AB: BxPC3 (μM) |
|---|---|---|---|---|
| U46 | <0.1 | 42.842 | 5.375 | 10.85 |
| V46 | <0.01 | 38.513 | 8.682 | >30 |
| W46 | <0.01 | 70.354 | 20.4 | 5.92 |
| X46 | <0.01 | 41.17 | 0.899 | 11.126 |
| Y46 | <0.01 | 52.82 | 0.773 | 16.427 |
| Z46 | <0.01 | 51.843 | 1.187 | 8.643 |
| A47 | <0.01 | 60.724 | 5.638 | >30 |
| B47 | <0.01 | 41.017 | 2.584 | 6.843 |
| C47 | <0.01 | 3.668 | 8.715 | >30 |

Example 292

Synthesis of tert-butyl 5-azido-3-formylpyrazolo[1,5-a]pyrimidin-7-yl(cyclopropyl)carbamate

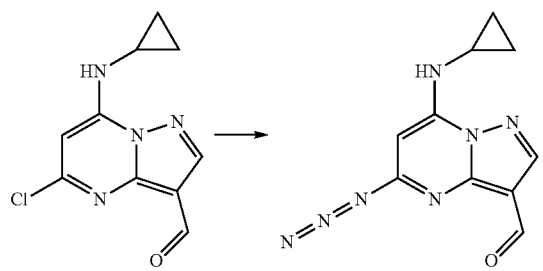

To 5-chloro-7-(cyclopropylamino) pyrazolo[1,5-a]pyrimidine-3-carbaldehyde (4.0 g, 16.87 mmol) in dimethylformamide was added sodium azide (1.56 g, 23.9 mmol) and the reaction mixture was heated at 80° C. for 8 hrs. Cooled the reaction mixture, added water and white precipitate filtered and dried to yield 5-azido-7-(cyclopropylamino) pyrazolo[1,5-a]pyrimidine-3-carbaldehyde (2.95 g, 75% yield). LCMS (M+1=244)

Example 293

Synthesis of 5-amino-7-(cyclopropylamino)pyrazolo[1,5-a]pyrimidine-3-carbaldehyde

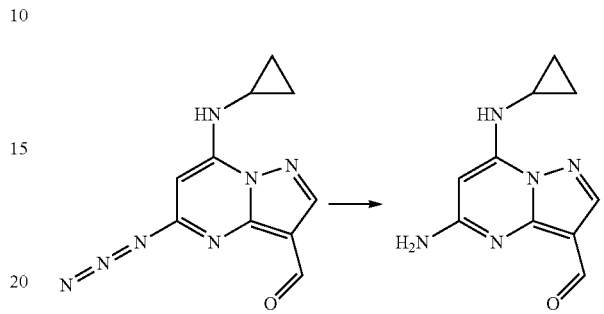

The above product 5-azido-7-(cyclopropylamino) pyrazolo[1,5-a]pyrimidine-3-carbaldehyde (1.09 g, 4.46 mmol) was subjected to hydrogenation using 10% wt palladium on carbon in ethanol. The reaction was stirred under hydrogen for 6 hours. The mixture was filtered through celite and sonicated with 1:1 mixture of ethyl acetate and hexane. The light yellow solid was filtered and dried to yield 5-amino-7-(cyclopropylamino) pyrazolo[1,5-a]pyrimidine-3-carbaldehyde as product 750 mg (85% yield). LCMS (M+1=218)

Example 294

Synthesis of (Z)-N-(7-(cyclopropylamino)-3-((2,5-dioxoimidazolidin-4-ylidene)methyl)pyrazolo[1,5-a]pyrimidin-5-yl)-2-fluorobenzamide

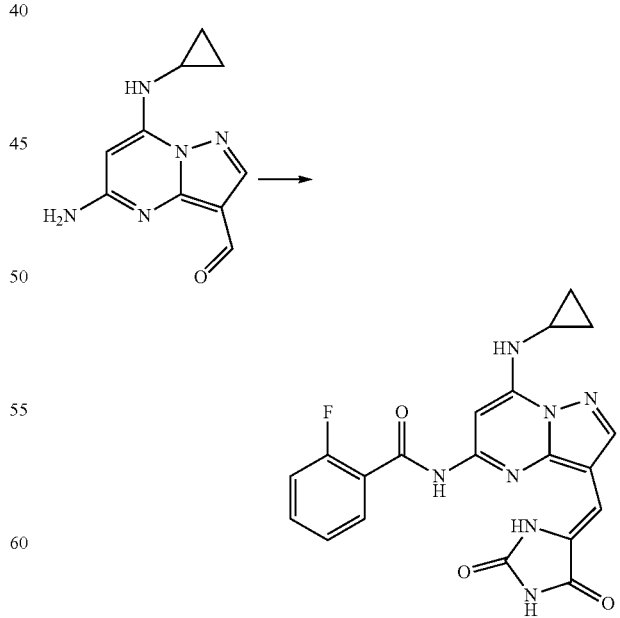

To 5-amino-7-(cyclopropylamino) pyrazolo[1,5-a]pyrimidine-3-carbaldehyde (step b) (30 mg, 0.138 mmol) in 1.0 mL tetrahydrofuran, stirring under nitrogen, was added 2-fluoro benzoyl chloride (33 ul, 0.275 mmol) and DIPEA (28.8 ul). The reaction mixture was stirred at room temperature for one hour. The reaction was then partitioned between ethyl acetate and water, the organic layer was dried under sodium sulfate concentrated on high vacuum to yield N-(7-(cyclopropylamino)-3-formylpyrazolo[1,5-a]pyrimidin-5-yl)-2-fluorobenzamide. The crude product was further dissolved in 1.0 mL ethanol, added hydantoin (41.2 mg, 0.411 mmol) and pipperdine (40.0 ul). The reaction was heated to 80° C. for three hours. Cooled the reaction mixture and yellow precipitate was filtered, washed with ethanol to yield 10 mg (40% yield, two steps) (Z)-N-(7-(cyclopropylamino)-3-((2,5-dioxoimidazolidin-4-ylidene)methyl)pyrazolo[1,5-a]pyrimidin-5-yl)-2-fluorobenzamide. LCMS (M+1=422)

Example 295

Synthesis of (Z)-4-cyano-N-(7-(cyclopropylamino)-3-((2,5-dioxoimidazolidin-4-ylidene)methyl)pyrazolo[1,5-a]pyrimidin-5-yl)benzamide

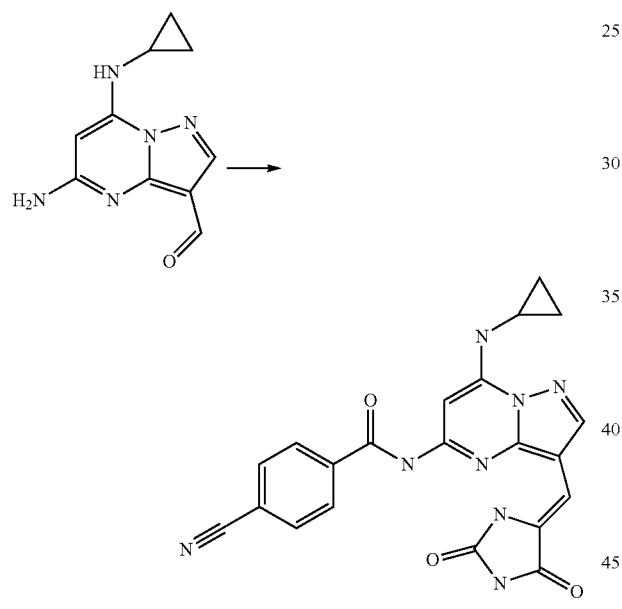

To 5-amino-7-(cyclopropylamino) pyrazolo[1,5-a]pyrimidine-3-carbaldehyde (step b) (30 mg, 0.138 mmol) in 1.0 mL acetonitrile was added HATU (104 mg, 0.273 mmol), 3-cyano benzoic acid (30 mg, 0.203 mmol) and DIPEA (48.0 up. The reaction mixture was heated to 80° C. for five hours. Cooled the reaction mixture and light yellow precipitate was filtered, washed With acetonitrile to yield 4-cyano-N-(7-(cyclopropylamino)-3-formylpyrazolo[1,5-a]pyrimidin-5-yl) benzamide. The crude product was further dissolved in 1.0 mL ethanol, added hydantoin (10 mg, 0.01 mmol) and pipperdine (9.5 ul). The reaction was heated to 80° C. for three hours. Cooled the reaction mixture and precipitate was filtered, washed with ethanol to yield 7 mg (40% yield, two steps) (Z)-4-cyano-N-(7-(cyclopropylamino)-3-((2,5-dioxoimidazolidin-4-ylidene)methyl)pyrazolo[1,5-a]pyrimidin-5-yl)benzamide. LCMS (M+1=429)

The following compounds were prepared using chemistries similar to synthesis in examples above with the corresponding acids, chloroformates, or isocyanates. All compounds were characterized by LCMS. Table 58B shows the biological activities of the compounds listed in Table 58A.

TABLE 58A

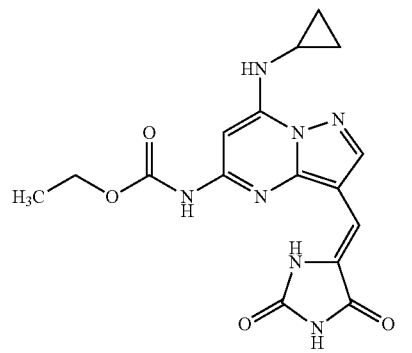 [SMILES: CCOC(=O)Nc1cc(NC2CC2)n2ncc(/C=C3\NC(=O)NC3=O)c2n1]

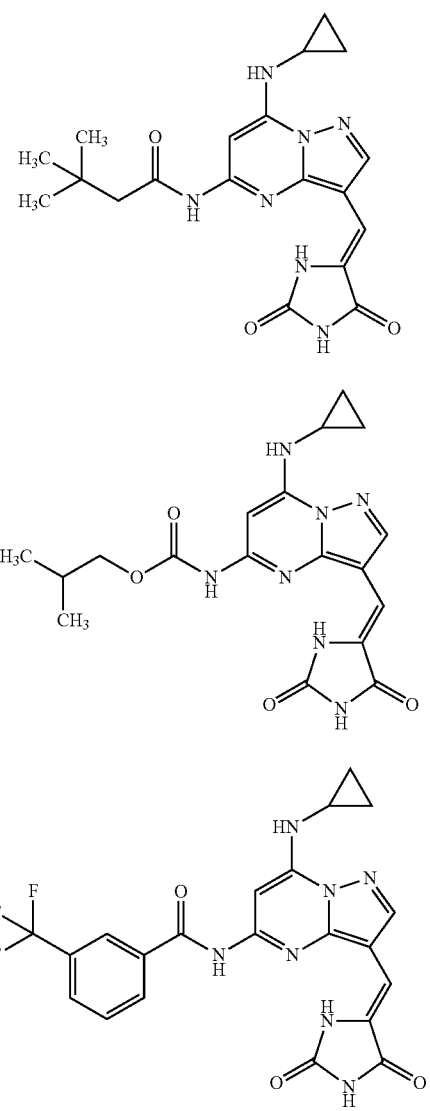

US 8,575,177 B2
623
TABLE 58A-continued
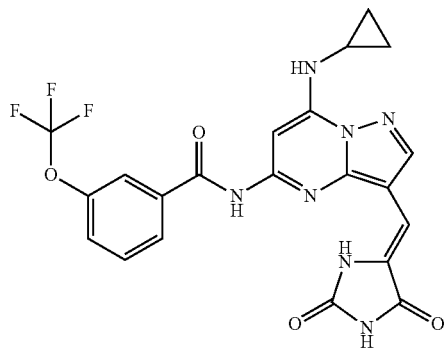 [SMILES: O=C1NC(=O)/C(=C/c2cnn3c(NC4CC4)cc(NC(=O)c4cccc(OC(F)(F)F)c4)nc23)N1]
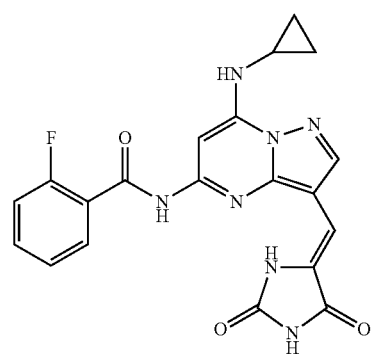 [SMILES: O=C1NC(=O)/C(=C/c2cnn3c(NC4CC4)cc(NC(=O)c4ccccc4F)nc23)N1]
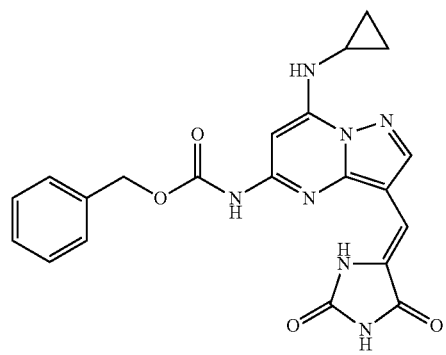 [SMILES: O=C1NC(=O)/C(=C/c2cnn3c(NC4CC4)cc(NC(=O)OCc4ccccc4)nc23)N1]
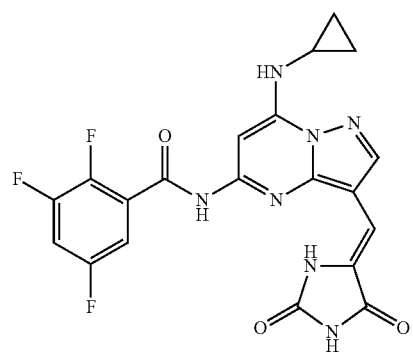 [SMILES: O=C1NC(=O)/C(=C/c2cnn3c(NC4CC4)cc(NC(=O)c4cc(F)cc(F)c4F)nc23)N1]
624
TABLE 58A-continued
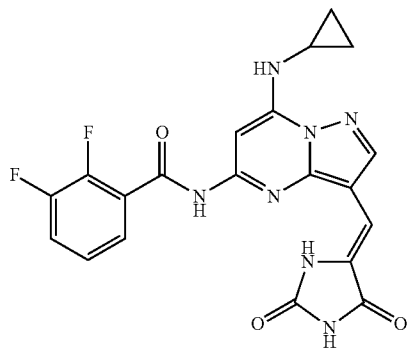 [SMILES: O=C1NC(=O)/C(=C/c2cnn3c(NC4CC4)cc(NC(=O)c4cccc(F)c4F)nc23)N1]
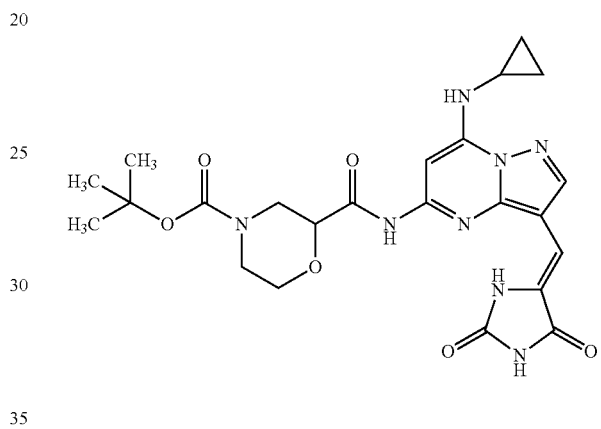
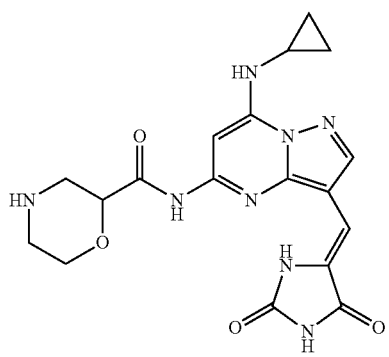 [SMILES: O=C1NC(=O)/C(=C/c2cnn3c(NC4CC4)cc(NC(=O)C4CNCCO4)nc23)N1]
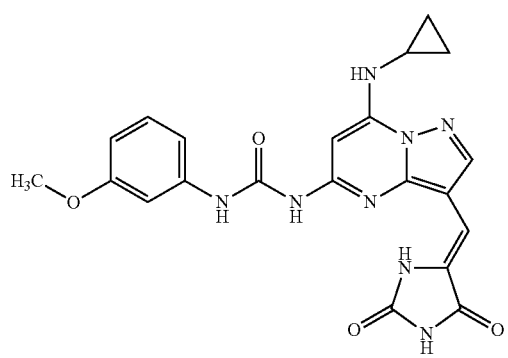 [SMILES: COc1cccc(NC(=O)Nc2cc(NC3CC3)n3ncc(/C=C4\NC(=O)NC4=O)c3n2)c1]

TABLE 58A-continued
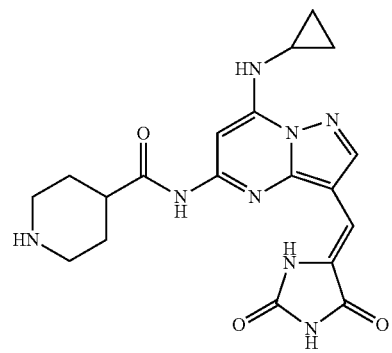 [SMILES: O=C1NC(=O)/C(=C/c2cnn3c(NC4CC4)cc(NC(=O)C4CCNCC4)nc23)N1]
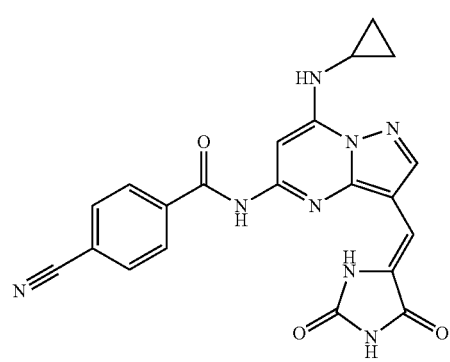 [SMILES: N#Cc1ccc(C(=O)Nc2cc(NC3CC3)n3ncc(/C=C4\NC(=O)NC4=O)c3n2)cc1]
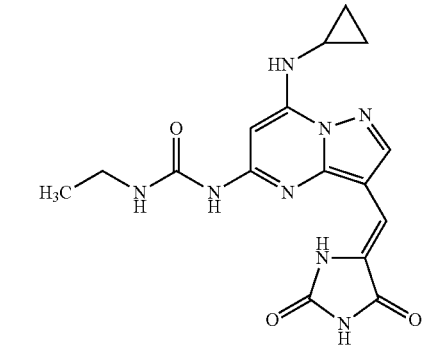 [SMILES: CCNC(=O)Nc1cc(NC2CC2)n2ncc(/C=C3\NC(=O)NC3=O)c2n1]
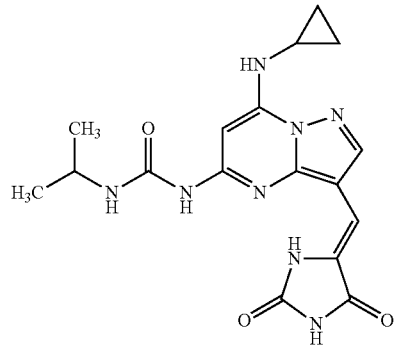 [SMILES: CC(C)NC(=O)Nc1cc(NC2CC2)n2ncc(/C=C3\NC(=O)NC3=O)c2n1]
TABLE 58A-continued
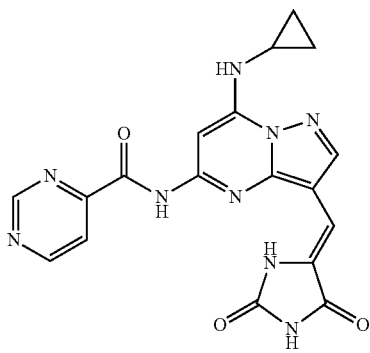 [SMILES: O=C1NC(=O)/C(=C/c2cnn3c(NC4CC4)cc(NC(=O)c4ccncn4)nc23)N1]
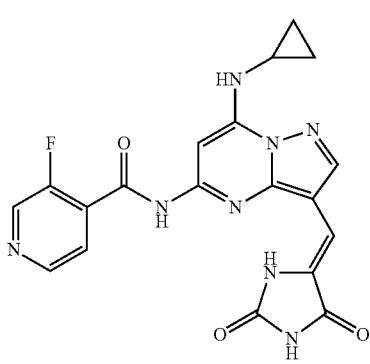 [SMILES: O=C1NC(=O)/C(=C/c2cnn3c(NC4CC4)cc(NC(=O)c4ccncc4F)nc23)N1]
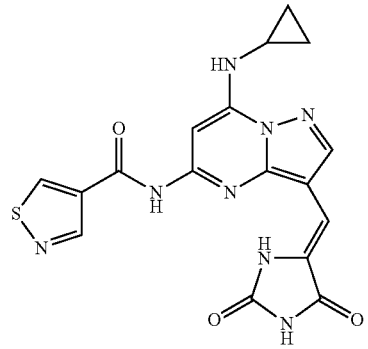 [SMILES: O=C1NC(=O)/C(=C/c2cnn3c(NC4CC4)cc(NC(=O)c4cnsc4)nc23)N1]
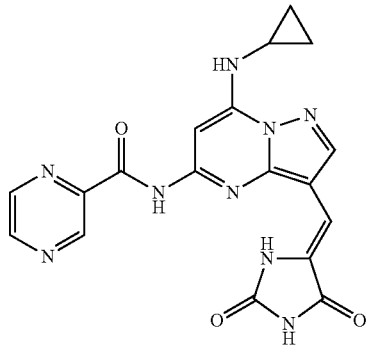 [SMILES: O=C1NC(=O)/C(=C/c2cnn3c(NC4CC4)cc(NC(=O)c4cnccn4)nc23)N1]

TABLE 58A-continued
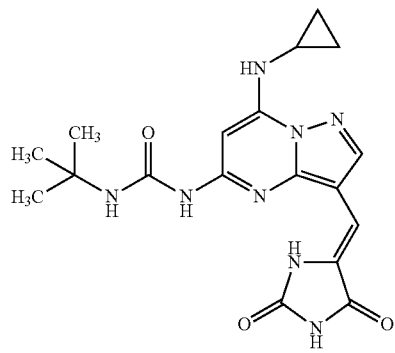 [SMILES: CC(C)(C)NC(=O)Nc1cc(NC2CC2)n2ncc(/C=C3\NC(=O)NC3=O)c2n1]
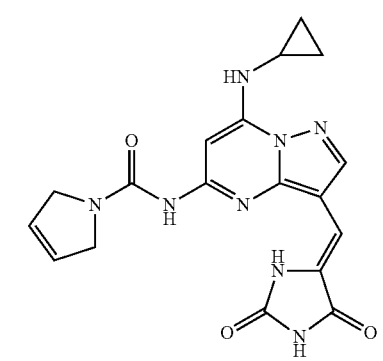 [SMILES: O=C1NC(=O)/C(=C/c2cnn3c(NC4CC4)cc(NC(=O)N4CC=CC4)nc23)N1]
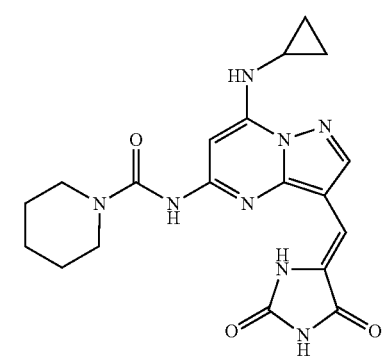 [SMILES: O=C1NC(=O)/C(=C/c2cnn3c(NC4CC4)cc(NC(=O)N4CCCCC4)nc23)N1]
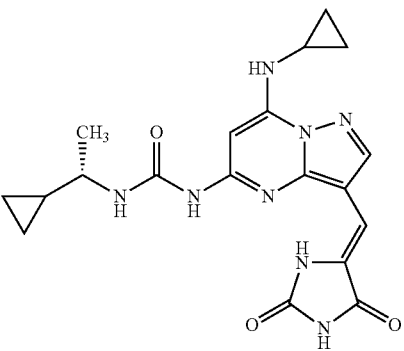 [SMILES: C[C@H](NC(=O)Nc1cc(NC2CC2)n2ncc(/C=C3\NC(=O)NC3=O)c2n1)C1CC1]
TABLE 58A-continued
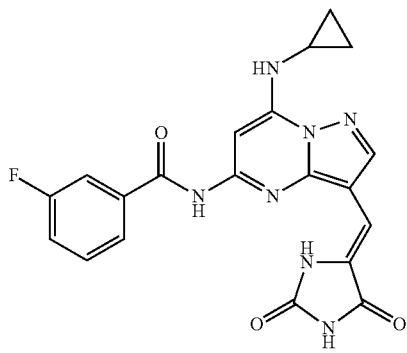 [SMILES: O=C1NC(=O)/C(=C/c2cnn3c(NC4CC4)cc(NC(=O)c4cccc(F)c4)nc23)N1]
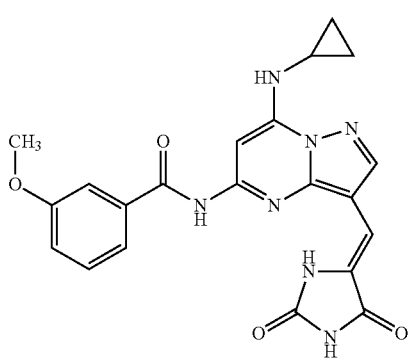 [SMILES: COc1cccc(C(=O)Nc2cc(NC3CC3)n3ncc(/C=C4\NC(=O)NC4=O)c3n2)c1]
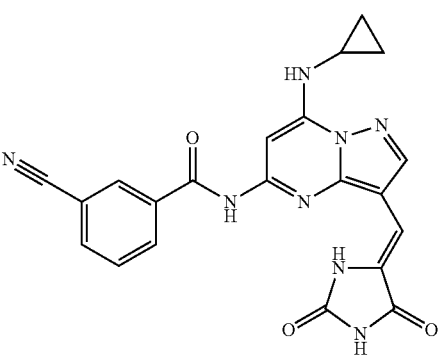 [SMILES: N#Cc1cccc(C(=O)Nc2cc(NC3CC3)n3ncc(/C=C4\NC(=O)NC4=O)c3n2)c1]
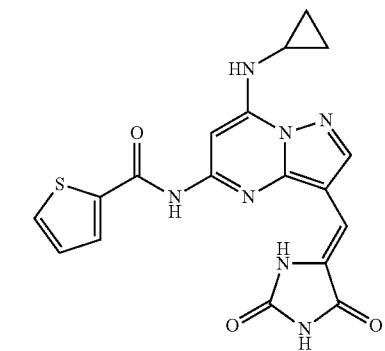 [SMILES: O=C1NC(=O)/C(=C/c2cnn3c(NC4CC4)cc(NC(=O)c4cccs4)nc23)N1]

TABLE 58A-continued
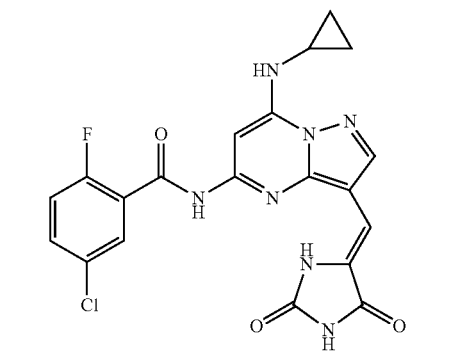 [SMILES: O=C1NC(=O)/C(=C/c2cnn3c(NC4CC4)cc(NC(=O)c4cc(Cl)ccc4F)nc23)N1]
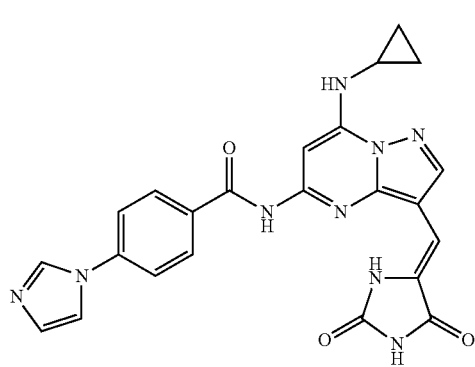 [SMILES: O=C1NC(=O)/C(=C/c2cnn3c(NC4CC4)cc(NC(=O)c4ccc(-n5ccnc5)cc4)nc23)N1]
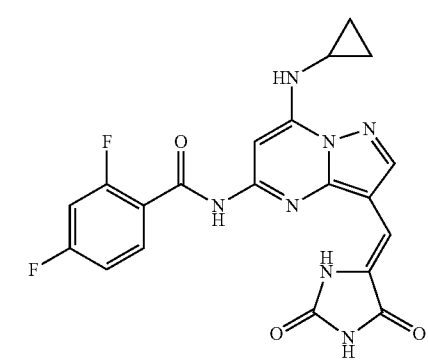 [SMILES: O=C1NC(=O)/C(=C/c2cnn3c(NC4CC4)cc(NC(=O)c4ccc(F)cc4F)nc23)N1]
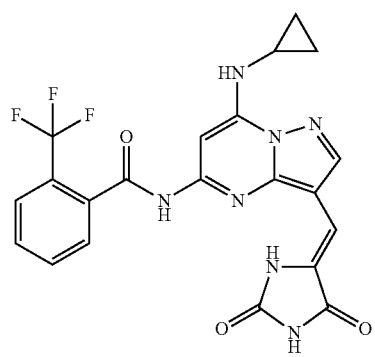 [SMILES: O=C1NC(=O)/C(=C/c2cnn3c(NC4CC4)cc(NC(=O)c4ccccc4C(F)(F)F)nc23)N1]
TABLE 58A-continued
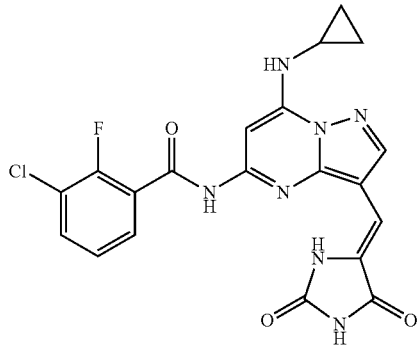 [SMILES: O=C1NC(=O)/C(=C/c2cnn3c(NC4CC4)cc(NC(=O)c4cccc(Cl)c4F)nc23)N1]
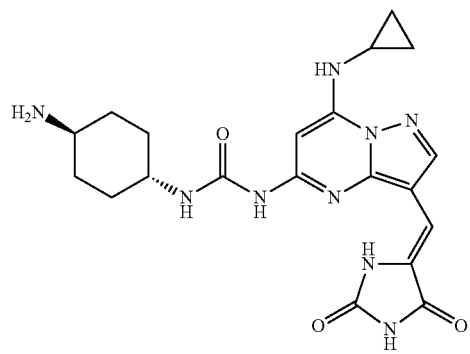 [SMILES: N[C@H]1CC[C@H](NC(=O)Nc2cc(NC3CC3)n3ncc(/C=C4\NC(=O)NC4=O)c3n2)CC1]
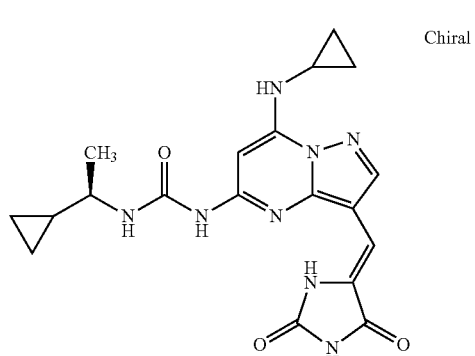
Chiral
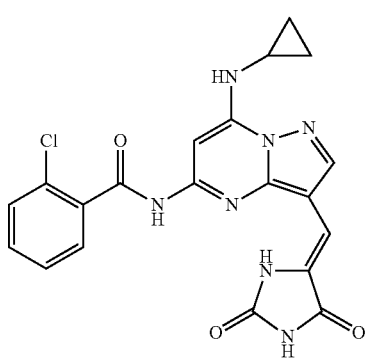 [SMILES: O=C1NC(=O)/C(=C/c2cnn3c(NC4CC4)cc(NC(=O)c4ccccc4Cl)nc23)N1]

TABLE 58A-continued
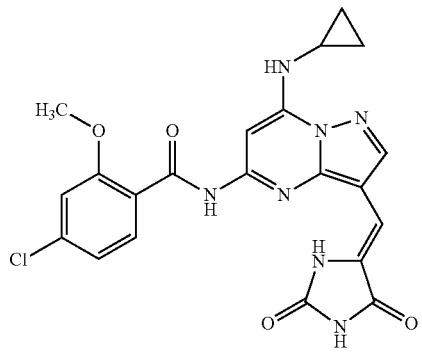 [SMILES: COc1cc(Cl)ccc1C(=O)Nc1cc(NC2CC2)n2ncc(/C=C3\NC(=O)NC3=O)c2n1]
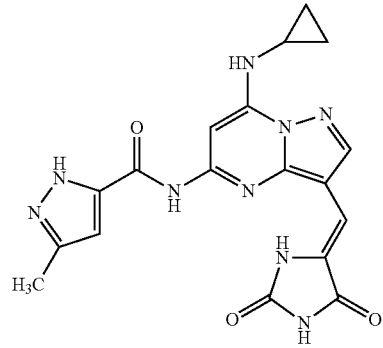 [SMILES: Cc1cc(C(=O)Nc2cc(NC3CC3)n3ncc(/C=C4\NC(=O)NC4=O)c3n2)[nH]n1]
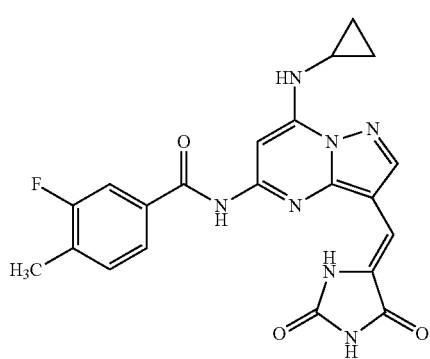 [SMILES: Cc1ccc(C(=O)Nc2cc(NC3CC3)n3ncc(/C=C4\NC(=O)NC4=O)c3n2)cc1F]
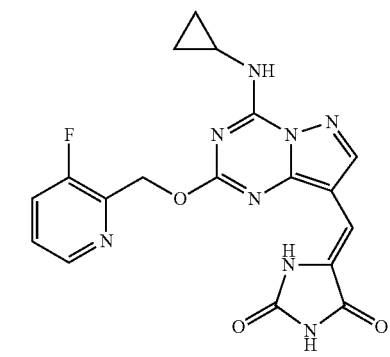 [SMILES: O=C1NC(=O)/C(=C/c2cnn3c(NC4CC4)nc(OCc4ncccc4F)nc23)N1]
TABLE 58A-continued
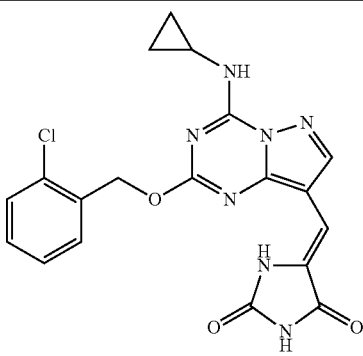
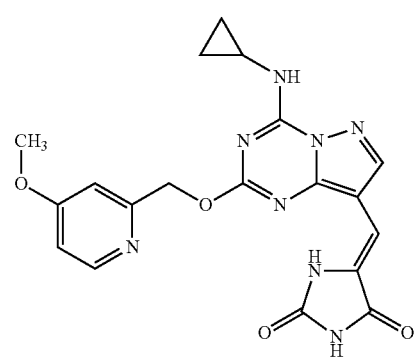 [SMILES: COc1ccnc(COc2nc(NC3CC3)n3ncc(/C=C4\NC(=O)NC4=O)c3n2)c1]
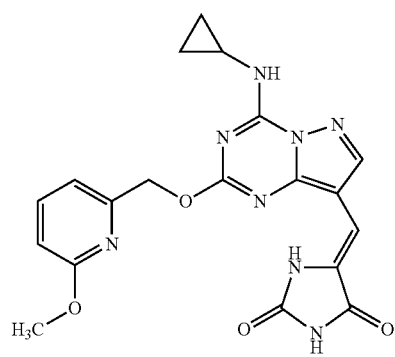 [SMILES: COc1cccc(COc2nc(NC3CC3)n3ncc(/C=C4\NC(=O)NC4=O)c3n2)n1]

TABLE 58A-continued
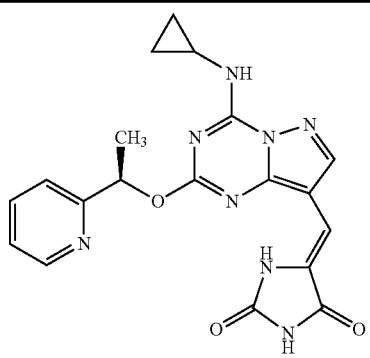
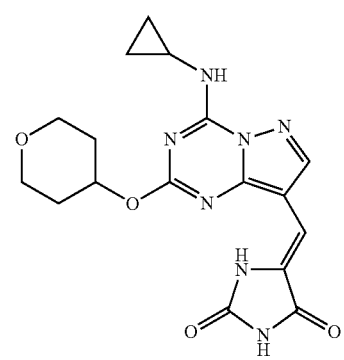 [SMILES: O=C1NC(=O)/C(=C/c2cnn3c(NC4CC4)nc(OC4CCOCC4)nc23)N1]
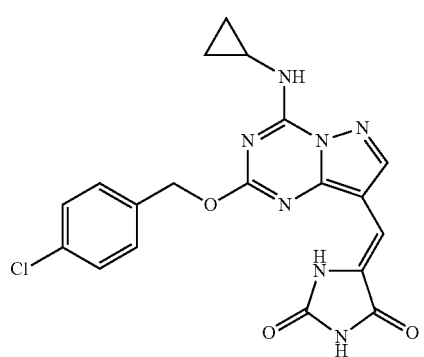 [SMILES: O=C1NC(=O)/C(=C/c2cnn3c(NC4CC4)nc(OCc4ccc(Cl)cc4)nc23)N1]
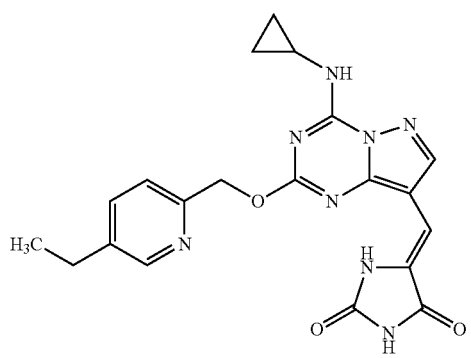
TABLE 58A-continued
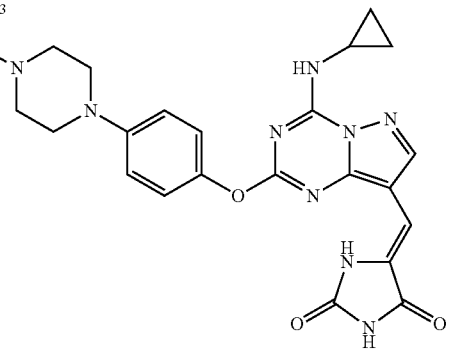
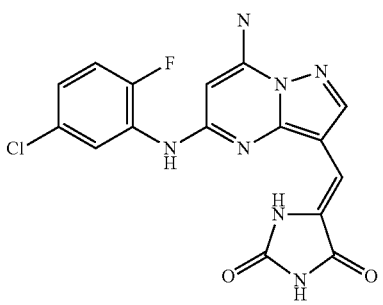 [SMILES: Nc1cc(Nc2cc(Cl)ccc2F)nc2c(/C=C3\NC(=O)NC3=O)cnn12]
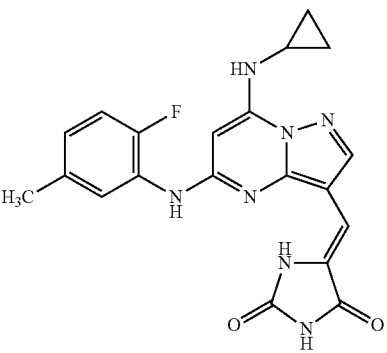 [SMILES: Cc1ccc(F)c(Nc2cc(NC3CC3)n3ncc(/C=C4\NC(=O)NC4=O)c3n2)c1]

| 635 | 636 |
|---|---|
| TABLE 58A-continued | TABLE 58A-continued |
| 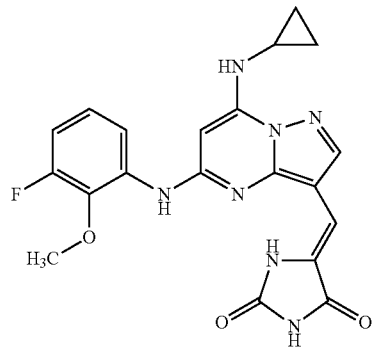 | 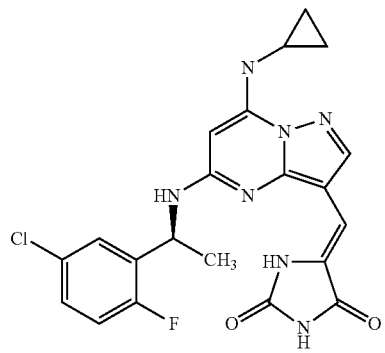  Chiral |
| 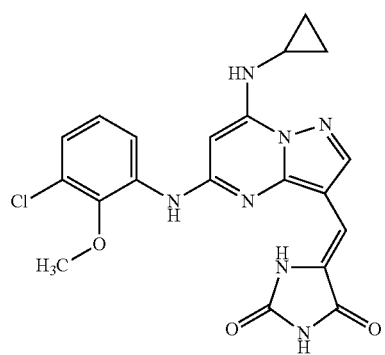 [SMILES: COc1c(Cl)cccc1Nc1cc(NC2CC2)n2ncc(/C=C3\NC(=O)NC3=O)c2n1] | 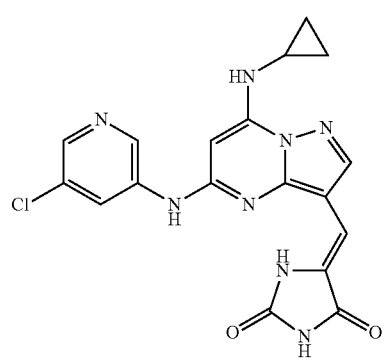 [SMILES: O=C1NC(=O)/C(=C/c2cnn3c(NC4CC4)cc(Nc4cncc(Cl)c4)nc23)N1] |
| 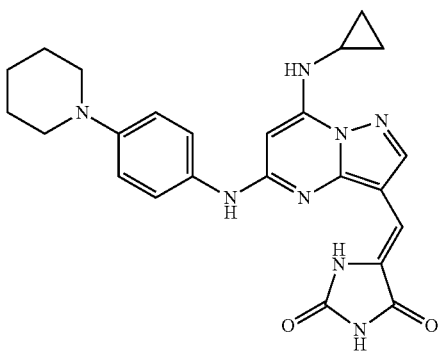 | 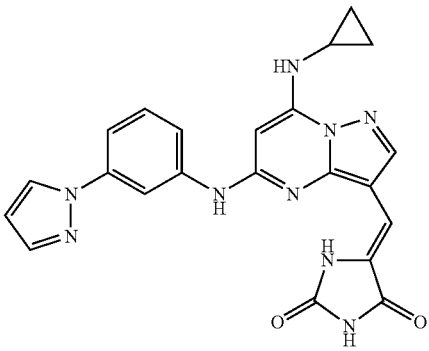 [SMILES: O=C1NC(=O)/C(=C/c2cnn3c(NC4CC4)cc(Nc4cccc(-n5cccn5)c4)nc23)N1] |
| 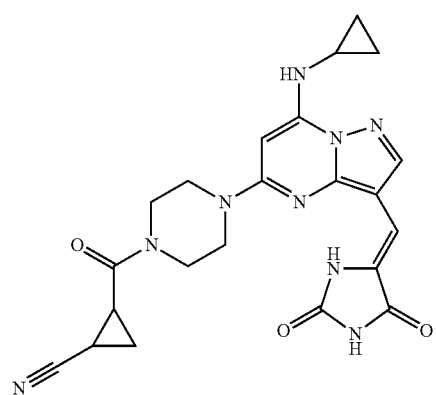 | 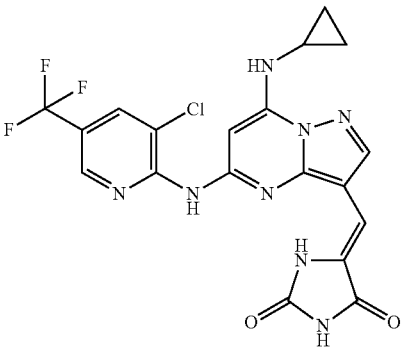 [SMILES: O=C1NC(=O)/C(=C/c2cnn3c(NC4CC4)cc(Nc4ncc(C(F)(F)F)cc4Cl)nc23)N1] |

TABLE 58A-continued
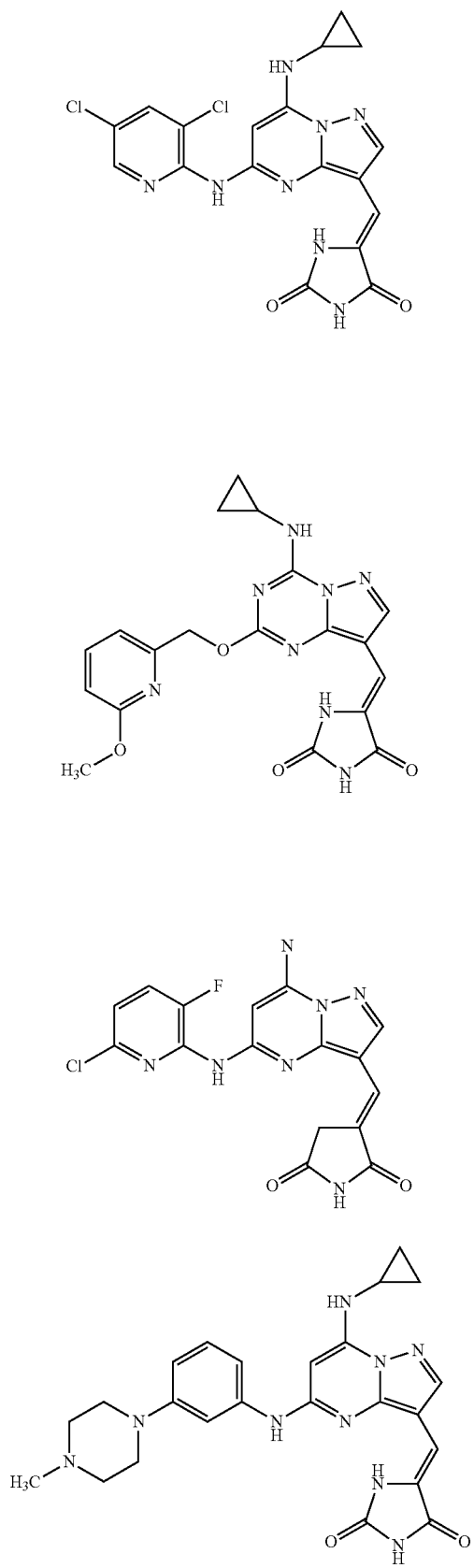
TABLE 58B
| Compound | CK2: IC50 (µM) | PIM2: IC50 (µM) | AB: MDAMB453 (µM) | AB: BxPC3 (µM) |
|---|---|---|---|---|
| D47 | <0.01 | | >30 | 9.159 |
| E47 | <0.01 | | >30 | 13.301 |
| F47 | <0.01 | | 8.426 | 6.12 |
| G47 | <0.01 | | 3.966 | 1.261 |
| H47 | <0.01 | | 10.968 | 5.493 |
| I47 | <0.01 | 45.534 | 2.681 | 2.072 |
| J47 | <0.01 | | 6.214 | 8.323 |
| K47 | <0.01 | 24.91 | 2.632 | 3.408 |
| L47 | <0.01 | 34.04 | 1.358 | 0.462 |
| M47 | <0.1 | 8.709 | 4.483 | 13.992 |
| N47 | <1 | −3.824 | | |
| O47 | <0.1 | | | |
| P47 | <0.1 | 19.381 | | |
| Q47 | <0.01 | −3.745 | >30 | 10.923 |
| R47 | <0.01 | 35.033 | 6.348 | 3.024 |
| S47 | <0.01 | 23.66 | 10.188 | 6.687 |
| T47 | <0.1 | 2.891 | | |
| U47 | <0.1 | 19.928 | 24.406 | 2.473 |
| V47 | <0.01 | 29.314 | 8.961 | 1.499 |
| W47 | <0.01 | 41.784 | 15.923 | 3.845 |
| X47 | <0.1 | −19.744 | 6.48 | 2.609 |
| Y47 | <0.1 | 39.441 | 9.161 | 5.819 |
| Z47 | <0.1 | 28.144 | 7.944 | 6.871 |
| A48 | <0.01 | 11.381 | 3.624 | 3.507 |
| B48 | <0.01 | 65.249 | 2.288 | 9.991 |
| C48 | <0.01 | 80.785 | 1.571 | 14.323 |
| D48 | <0.01 | 47.119 | 2.875 | 9.111 |
| E48 | <0.01 | 21.326 | 1.478 | 0.817 |
| F48 | <0.01 | 26.323 | 9.984 | 0.479 |
| G48 | <0.01 | −17.316 | >30 | >30 |
| H48 | <0.01 | 36.311 | 1.753 | 1.068 |
| I48 | <0.01 | 6.687 | 4.714 | 4.008 |
| J48 | <0.01 | −4.732 | 1.276 | 1.915 |
| K48 | <0.1 | 25.886 | 25.328 | >30 |
| L48 | <0.01 | 12.626 | 4.558 | 6.99 |
| M48 | <0.01 | 10.818 | 2.091 | 1.194 |
| N48 | <0.01 | 6.252 | 9.495 | 1.3 |
| O48 | <0.01 | 28.649 | 5.485 | 4.79 |
| P48 | <0.01 | −31.641 | 2.964 | 2.068 |
The following compounds were prepared using chemistries described in the present disclosure. Table 59B shows the biological activities of the compounds listed in Table 59A.

TABLE 59A
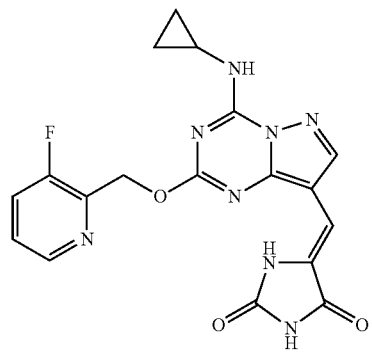 [SMILES: O=C1NC(=O)/C(=C/c2cnn3c(NC4CC4)nc(OCc4ncccc4F)nc23)N1]
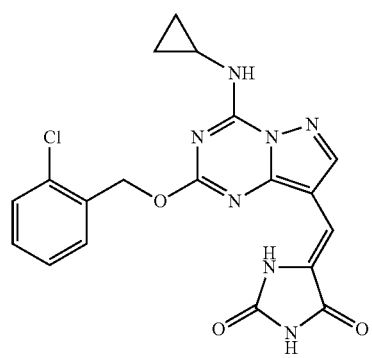 [SMILES: O=C1NC(=O)/C(=C/c2cnn3c(NC4CC4)nc(OCc4ccccc4Cl)nc23)N1]
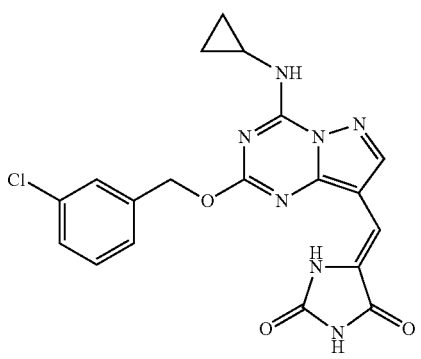 [SMILES: O=C1NC(=O)/C(=C/c2cnn3c(NC4CC4)nc(OCc4cccc(Cl)c4)nc23)N1]
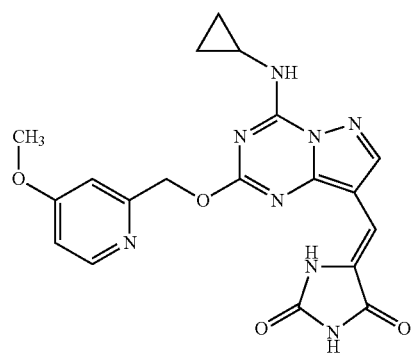 [SMILES: COc1ccnc(COc2nc(NC3CC3)n3ncc(/C=C4\NC(=O)NC4=O)c3n2)c1]
TABLE 59A-continued
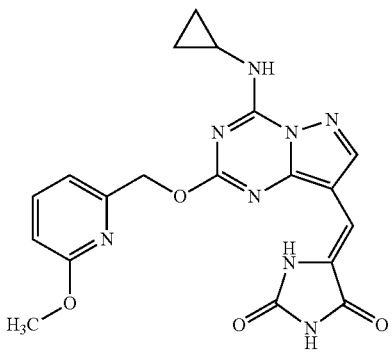 [SMILES: COc1cccc(COc2nc(NC3CC3)n3ncc(/C=C4\NC(=O)NC4=O)c3n2)n1]
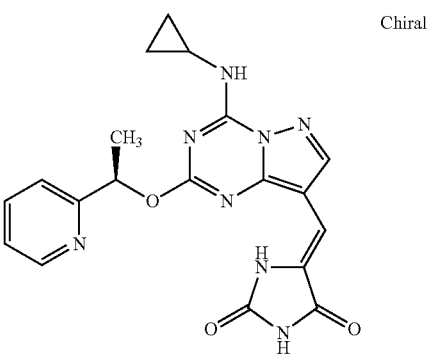 [SMILES: C[C@@H](Oc1nc(NC2CC2)n2ncc(/C=C3\NC(=O)NC3=O)c2n1)c1ccccn1 ; "Chiral"]
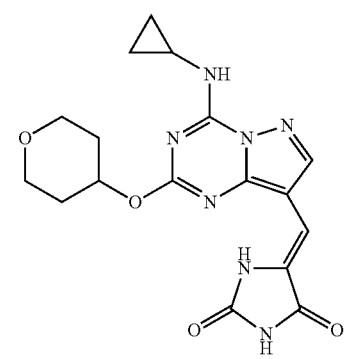 [SMILES: O=C1NC(=O)/C(=C/c2cnn3c(NC4CC4)nc(OC4CCOCC4)nc23)N1]
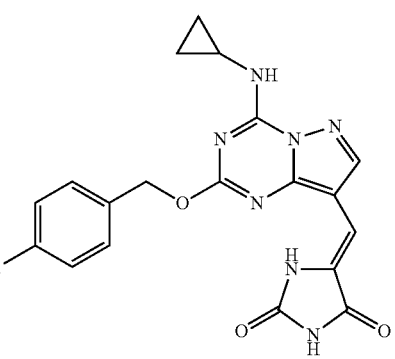

TABLE 59A-continued
641
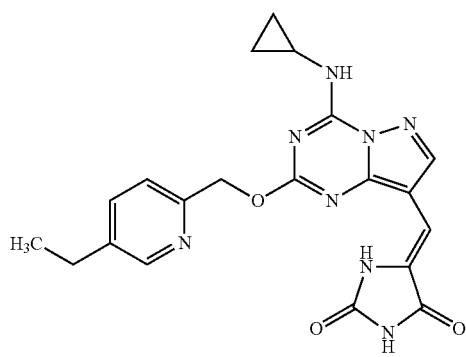 [SMILES: CCc1ccc(COc2nc(NC3CC3)n3ncc(/C=C4\NC(=O)NC4=O)c3n2)nc1]
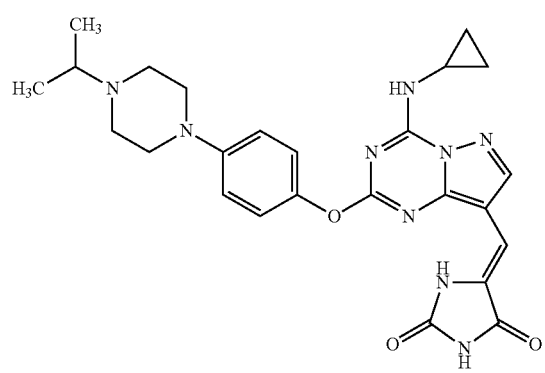 [SMILES: CC(C)N1CCN(c2ccc(Oc3nc(NC4CC4)n4ncc(/C=C5\NC(=O)NC5=O)c4n3)cc2)CC1]
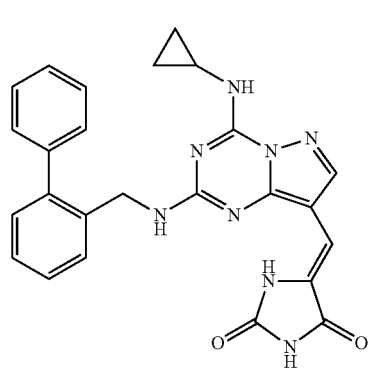 [SMILES: O=C1NC(=O)/C(=C/c2cnn3c(NC4CC4)nc(NCc4ccccc4-c4ccccc4)nc23)N1]
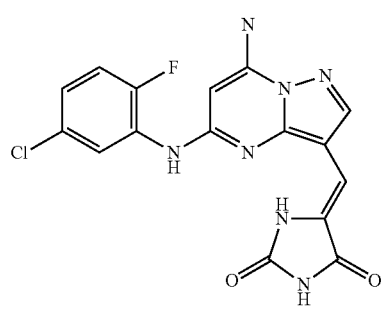 [SMILES: Nc1cc(Nc2cc(Cl)ccc2F)nc2c(/C=C3\NC(=O)NC3=O)cnn12]
642
TABLE 59A-continued
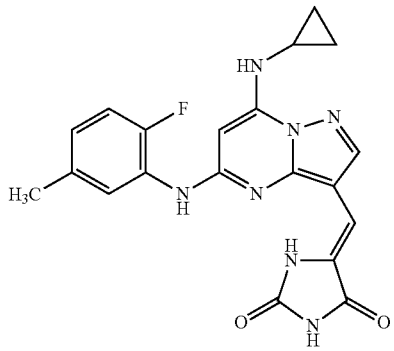 [SMILES: Cc1ccc(F)c(Nc2cc(NC3CC3)n3ncc(/C=C4\NC(=O)NC4=O)c3n2)c1]
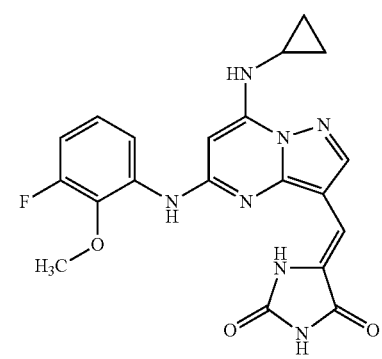 [SMILES: COc1c(F)cccc1Nc1cc(NC2CC2)n2ncc(/C=C3\NC(=O)NC3=O)c2n1]
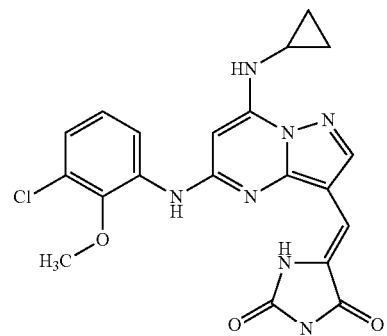
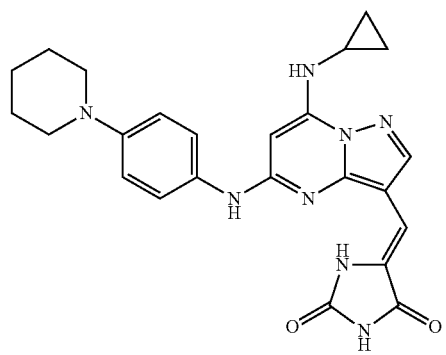 [SMILES: O=C1NC(=O)/C(=C/c2cnn3c(NC4CC4)cc(Nc4ccc(N5CCCCC5)cc4)nc23)N1]

TABLE 59A-continued
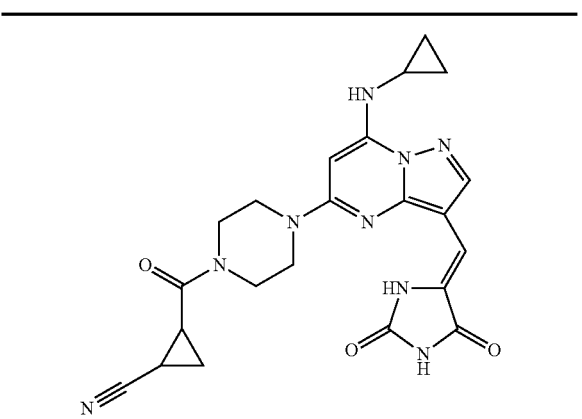
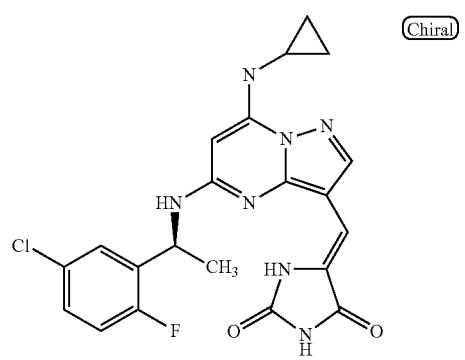 [SMILES: C[C@H](Nc1cc(NC2CC2)n2ncc(/C=C3\NC(=O)NC3=O)c2n1)c1cc(Cl)ccc1F ; "Chiral"]
(Chiral)
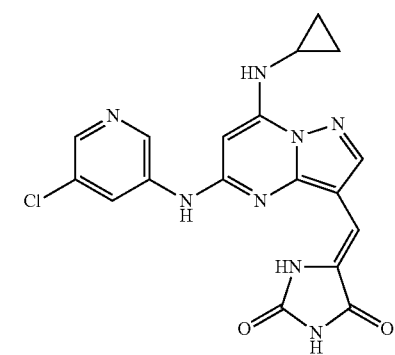 [SMILES: O=C1NC(=O)/C(=C/c2cnn3c(NC4CC4)cc(Nc4cncc(Cl)c4)nc23)N1]
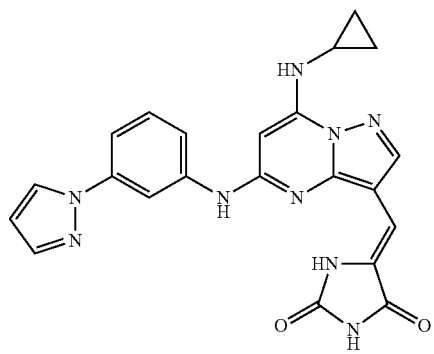 [SMILES: O=C1NC(=O)/C(=C/c2cnn3c(NC4CC4)cc(Nc4cccc(-n5cccn5)c4)nc23)N1]
TABLE 59A-continued
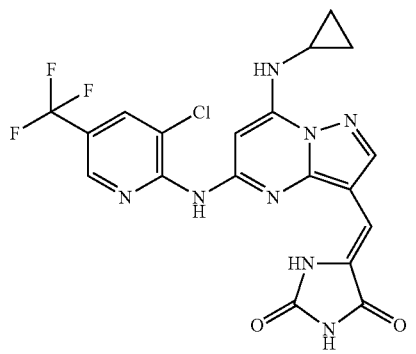 [SMILES: O=C1NC(=O)/C(=C/c2cnn3c(NC4CC4)cc(Nc4ncc(C(F)(F)F)cc4Cl)nc23)N1]
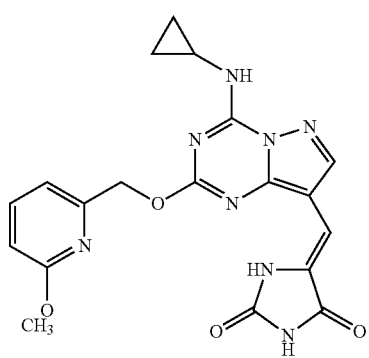 [SMILES: COc1cccc(COc2nc(NC3CC3)n3ncc(/C=C4\NC(=O)NC4=O)c3n2)n1]
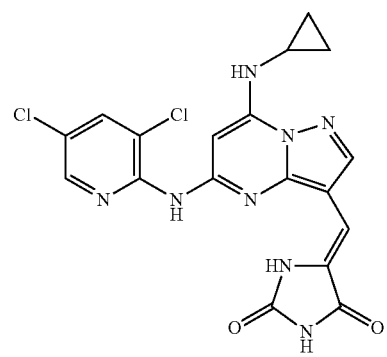 [SMILES: O=C1NC(=O)/C(=C/c2cnn3c(NC4CC4)cc(Nc4ncc(Cl)cc4Cl)nc23)N1]
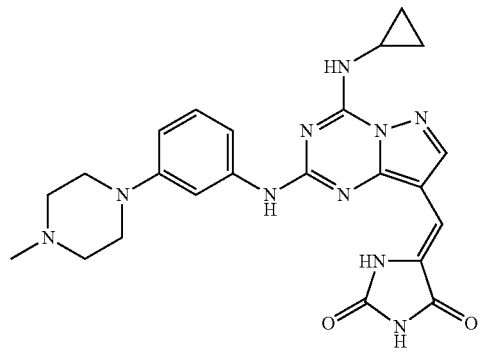 [SMILES: CN1CCN(c2cccc(Nc3nc(NC4CC4)n4ncc(/C=C5\NC(=O)NC5=O)c4n3)c2)CC1]

TABLE 59A-continued
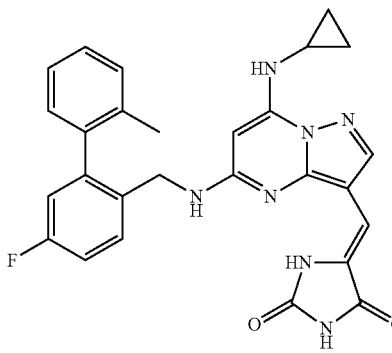
TABLE 59B
| Compound | CK2: IC50 (μM) | PIM2: IC50 (μM) | AB: MDAMB453 (μM) | AB: BxPC3 (μM) |
| --- | --- | --- | --- | --- |
| Q48 | <0.1 | | | |
| R48 | <0.01 | | | |
| S48 | <0.01 | | | |
| T48 | <0.1 | | | |
| U48 | <0.01 | | | |
| V48 | <0.01 | | | |
| W48 | <0.1 | | | |
| X48 | <0.1 | | | |
| Y48 | <0.1 | 2.026 | 11.928 | 12.73 |
| Z48 | <0.1 | | | |
| A49 | <0.01 | 87.627 | 0.709 | 6.265 |
| B49 | <0.01 | 26.245 | | >30 |
| C49 | <0.01 | | 0.529 | 1.688 |
| D49 | <0.01 | | 0.988 | 1.191 |
| E49 | <0.01 | | 2.855 | 6.613 |
| F49 | <0.01 | 49.17 | 2.401 | 14.078 |
| G49 | <0.01 | −32.822 | 13.256 | 29.23 |
| H49 | <0.01 | | | |
| I49 | <0.01 | | | |
| J49 | <0.01 | | | |
| K49 | <0.01 | | | |
| L49 | <0.01 | | | |
| M49 | <0.01 | | | |
| N49 | <0.01 | | | |
| O49 | <0.1 | | | |
The following compounds in Table 60 can be prepared using chemistries described in the present disclosure:
TABLE 60
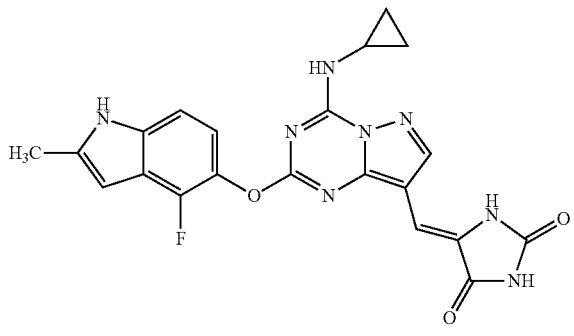 [SMILES: Cc1cc2c(F)c(Oc3nc(NC4CC4)n4ncc(/C=C5\NC(=O)NC5=O)c4n3)ccc2[nH]1]
TABLE 60-continued
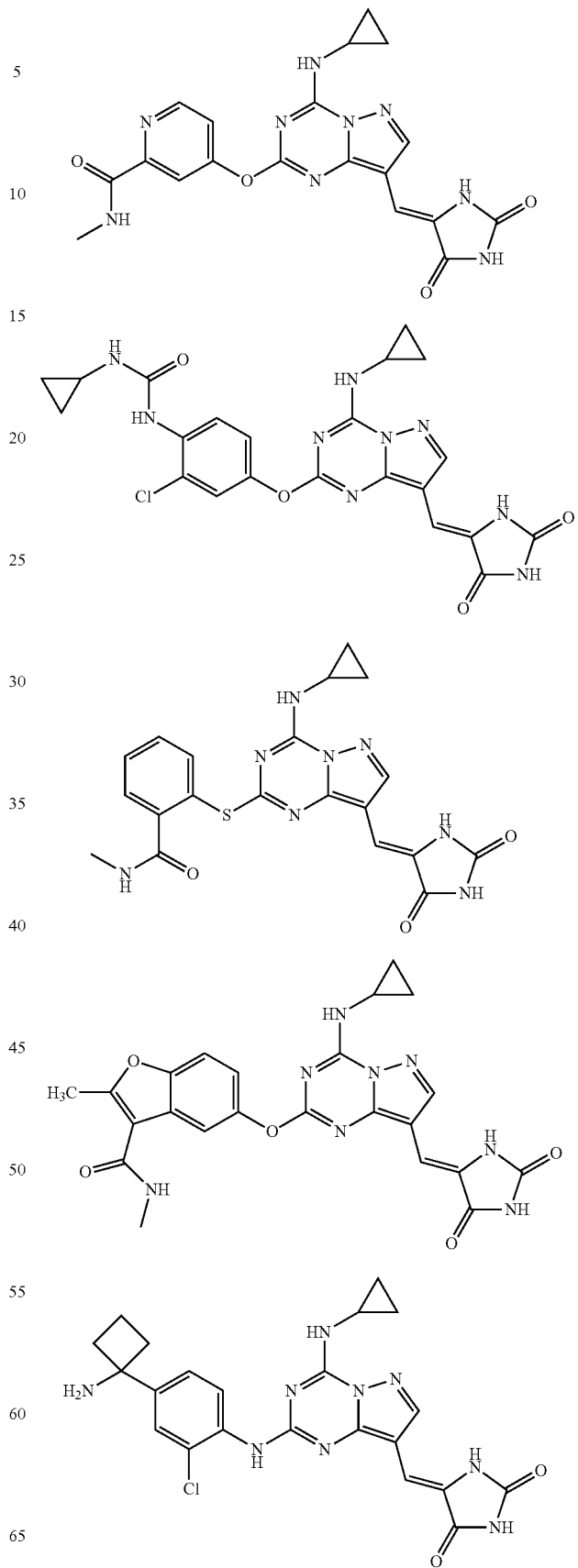

TABLE 60-continued
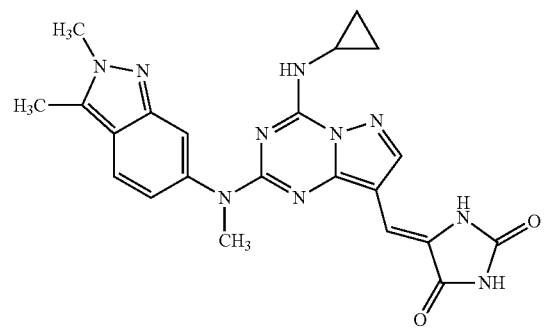
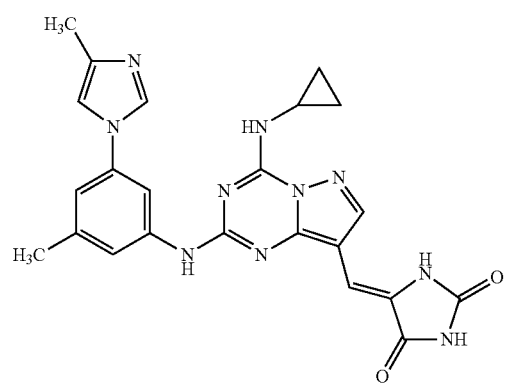 [SMILES: Cc1cc(Nc2nc(NC3CC3)n3ncc(/C=C4\NC(=O)NC4=O)c3n2)cc(-n2cnc(C)c2)c1]
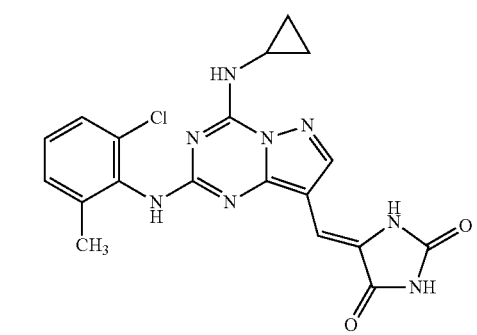 [SMILES: Cc1cccc(Cl)c1Nc1nc(NC2CC2)n2ncc(/C=C3\NC(=O)NC3=O)c2n1]
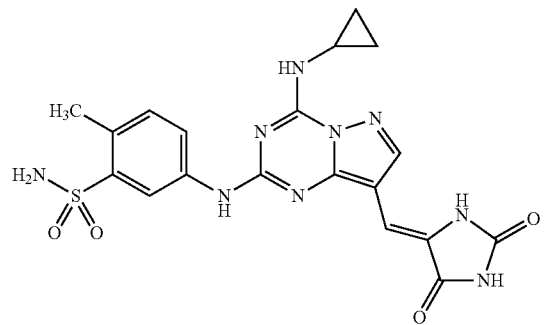 [SMILES: Cc1ccc(Nc2nc(NC3CC3)n3ncc(/C=C4\NC(=O)NC4=O)c3n2)cc1S(N)(=O)=O]
TABLE 60-continued
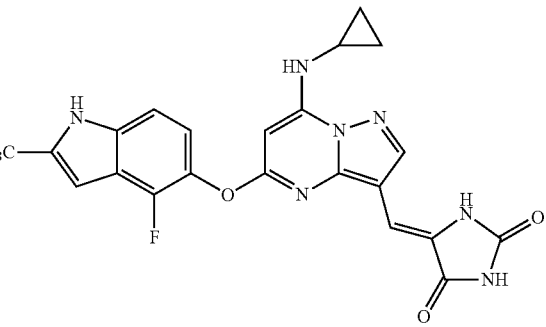
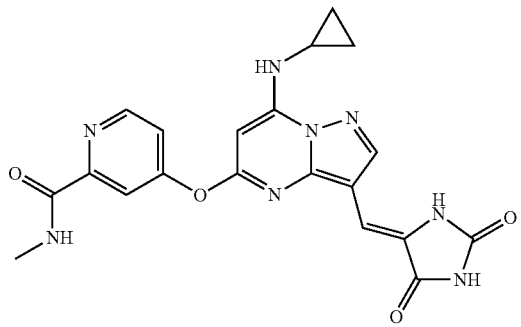 [SMILES: CNC(=O)c1cc(Oc2cc(NC3CC3)n3ncc(/C=C4\NC(=O)NC4=O)c3n2)ccn1]
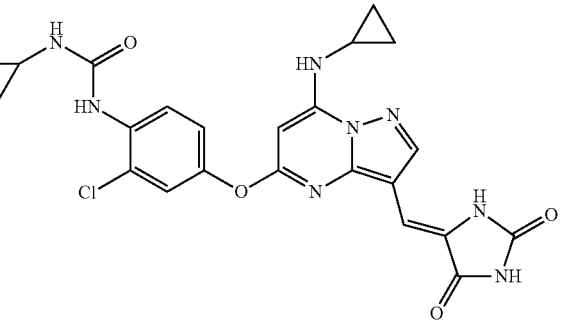
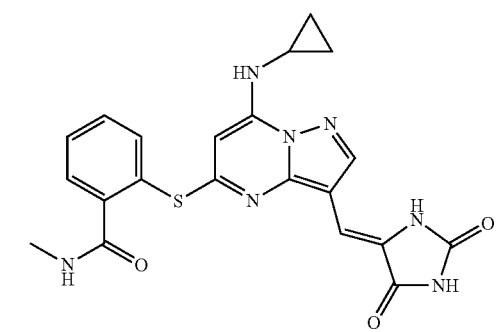 [SMILES: CNC(=O)c1ccccc1Sc1cc(NC2CC2)n2ncc(/C=C3\NC(=O)NC3=O)c2n1]
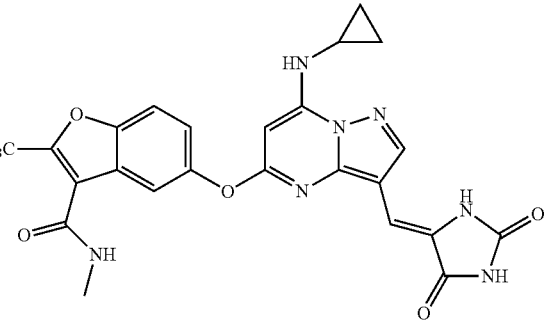

TABLE 60-continued
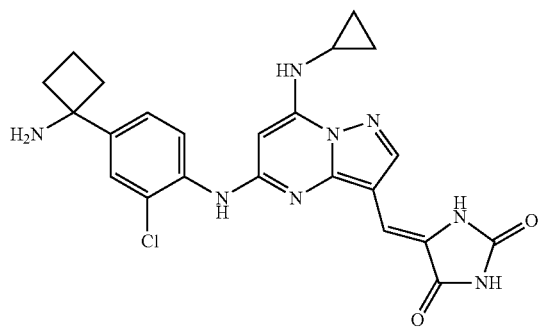 [SMILES: NC1(c2ccc(Nc3cc(NC4CC4)n4ncc(/C=C5\NC(=O)NC5=O)c4n3)c(Cl)c2)CCC1]
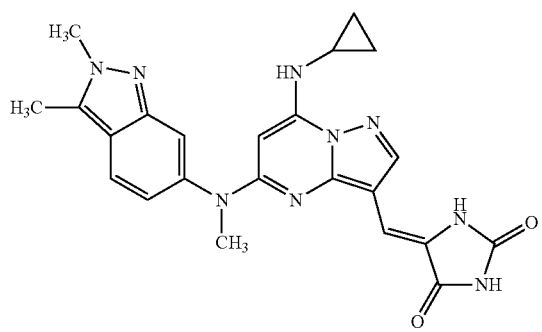 [SMILES: Cc1c2ccc(N(C)c3cc(NC4CC4)n4ncc(/C=C5\NC(=O)NC5=O)c4n3)cc2nn1C]
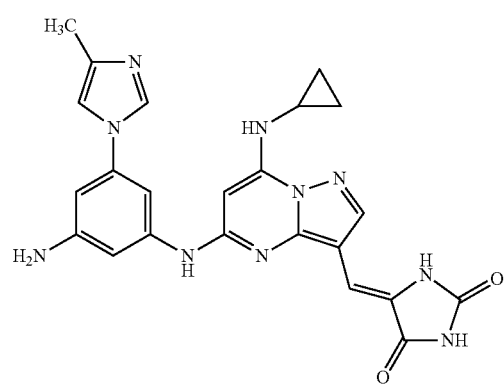 [SMILES: Cc1cn(-c2cc(N)cc(Nc3cc(NC4CC4)n4ncc(/C=C5\NC(=O)NC5=O)c4n3)c2)cn1]
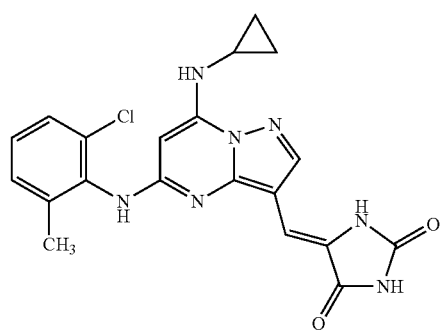 [SMILES: Cc1cccc(Cl)c1Nc1cc(NC2CC2)n2ncc(/C=C3\NC(=O)NC3=O)c2n1]
TABLE 60-continued
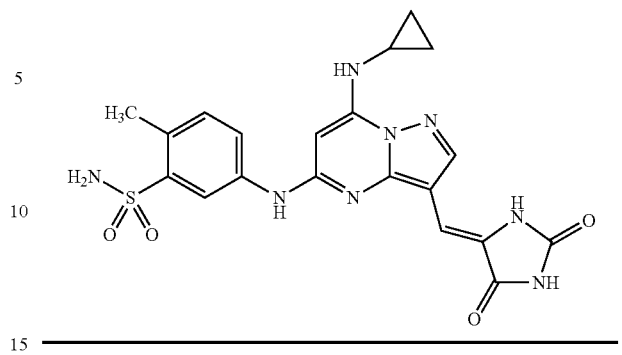
Compound 3 were prepared by reaction compound 1 with boronic acid 2 using Suzuki coupling reaction conditions as shown below (Scheme 2).
Scheme 2
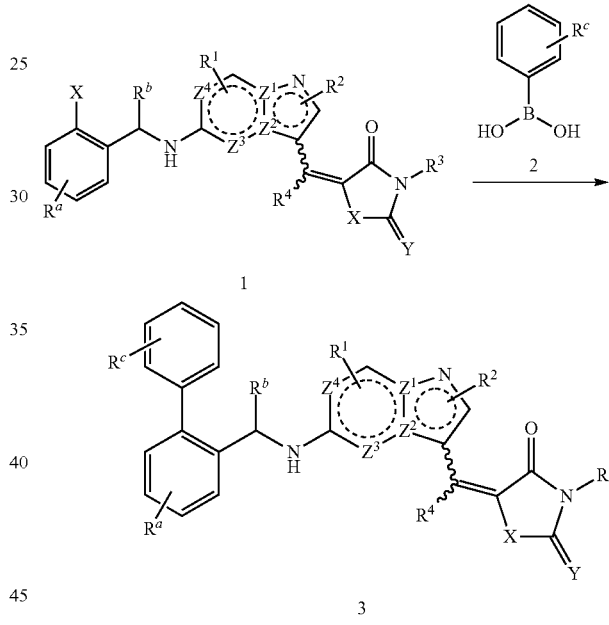
X = I, Br
The following compounds can be prepin Table 61 can be prepared by using chemistry described in Scheme 2.
TABLE 61
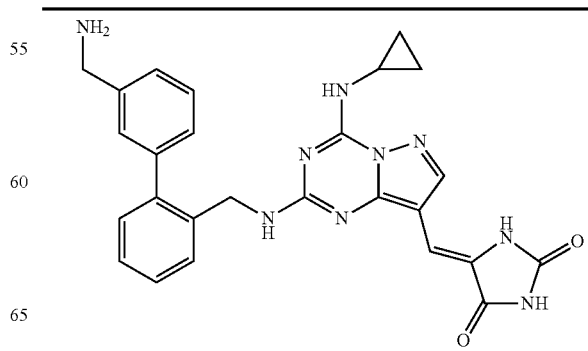

TABLE 61-continued
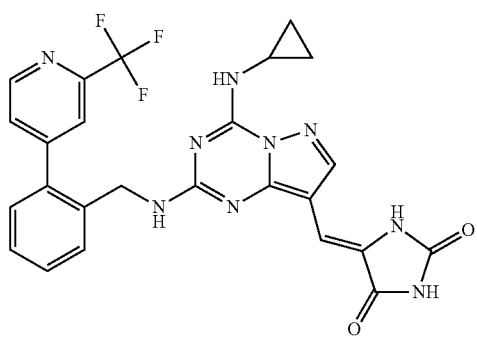 [SMILES: O=C1NC(=O)/C(=C/c2cnn3c(NC4CC4)nc(NCc4ccccc4-c4ccnc(C(F)(F)F)c4)nc23)N1]
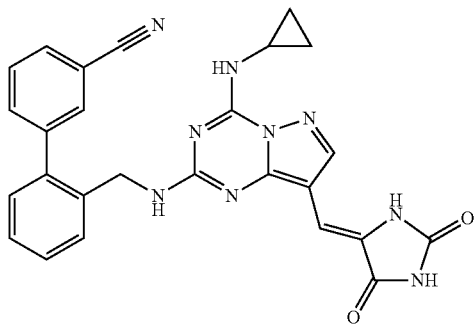
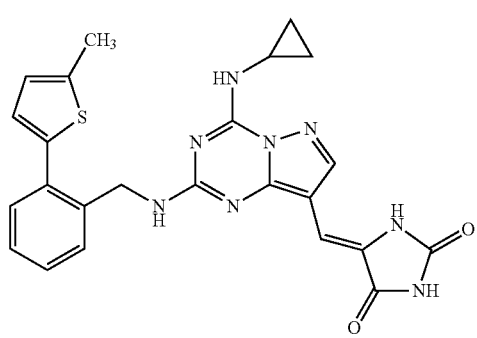 [SMILES: Cc1ccc(-c2ccccc2CNc2nc(NC3CC3)n3ncc(/C=C4\NC(=O)NC4=O)c3n2)s1]
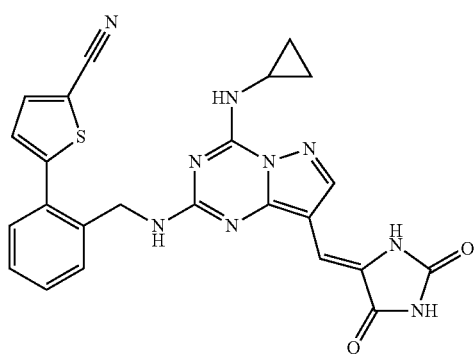
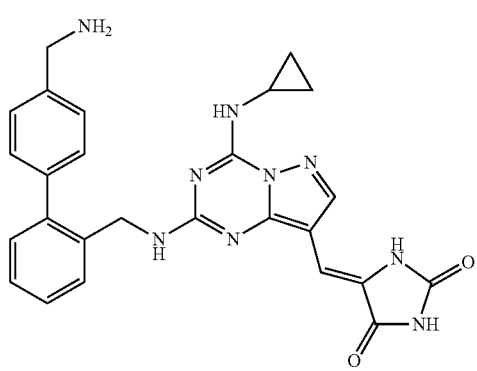 [SMILES: NCc1ccc(-c2ccccc2CNc2nc(NC3CC3)n3ncc(/C=C4\NC(=O)NC4=O)c3n2)cc1]
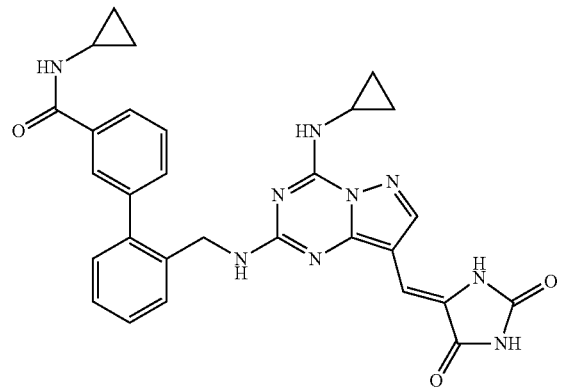
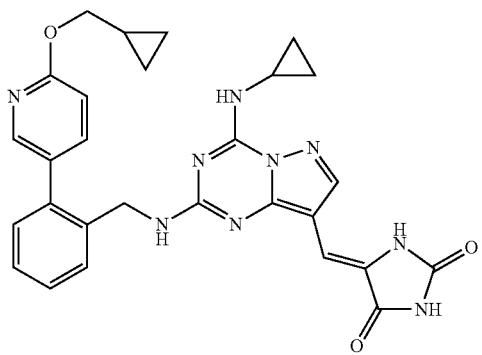 [SMILES: O=C1NC(=O)/C(=C/c2cnn3c(NC4CC4)nc(NCc4ccccc4-c4ccc(OCC5CC5)nc4)nc23)N1]
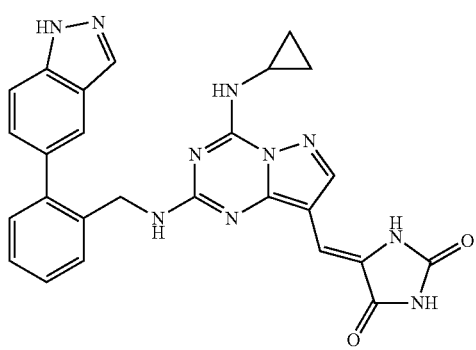 [SMILES: O=C1NC(=O)/C(=C/c2cnn3c(NC4CC4)nc(NCc4ccccc4-c4ccc5[nH]ncc5c4)nc23)N1]

TABLE 61-continued
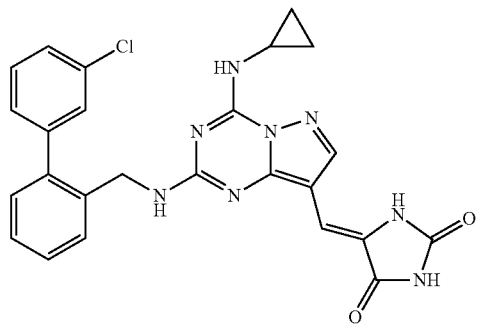 [SMILES: O=C1NC(=O)/C(=C/c2cnn3c(NC4CC4)nc(NCc4ccccc4-c4cccc(Cl)c4)nc23)N1]
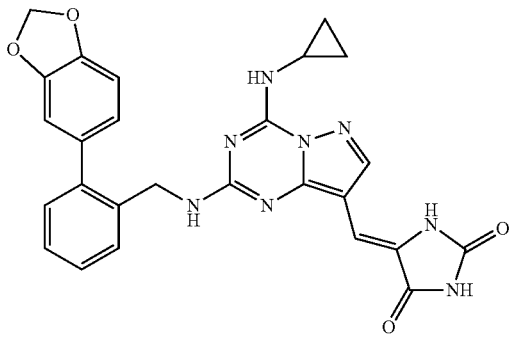
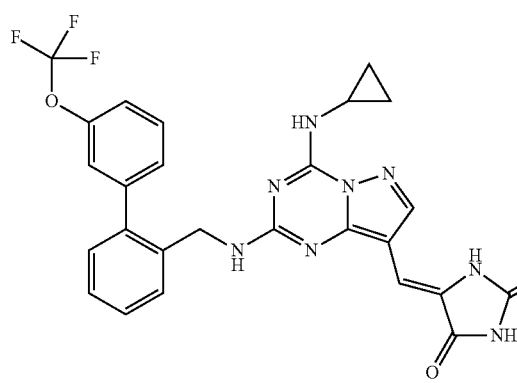
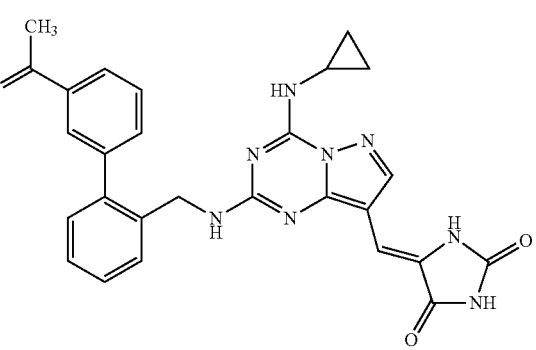
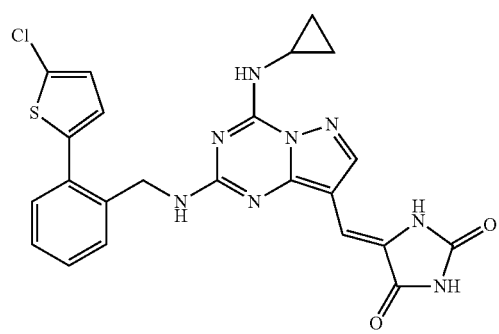 [SMILES: O=C1NC(=O)/C(=C/c2cnn3c(NC4CC4)nc(NCc4ccccc4-c4ccc(Cl)s4)nc23)N1]
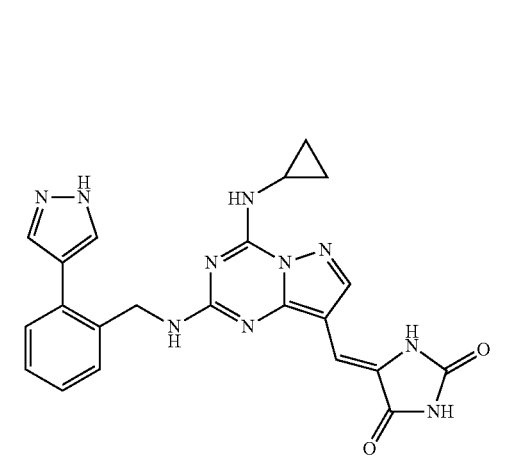
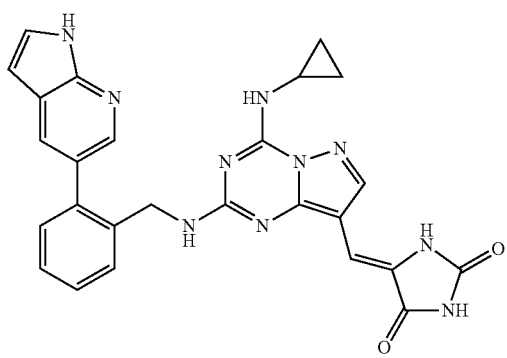 [SMILES: O=C1NC(=O)/C(=C/c2cnn3c(NC4CC4)nc(NCc4ccccc4-c4cnc5[nH]ccc5c4)nc23)N1]
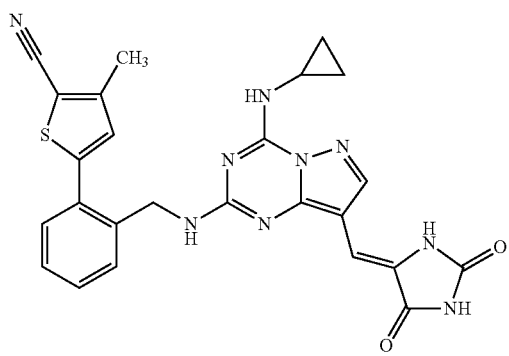 [SMILES: Cc1cc(-c2ccccc2CNc2nc(NC3CC3)n3ncc(/C=C4\NC(=O)NC4=O)c3n2)sc1C#N]

TABLE 61-continued
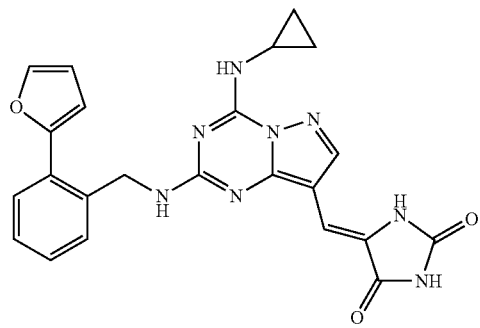 [SMILES: O=C1NC(=O)/C(=C/c2cnn3c(NC4CC4)nc(NCc4ccccc4-c4ccco4)nc23)N1]
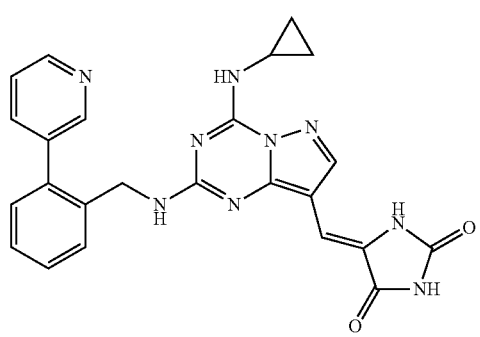 [SMILES: O=C1NC(=O)/C(=C/c2cnn3c(NC4CC4)nc(NCc4ccccc4-c4cccnc4)nc23)N1]
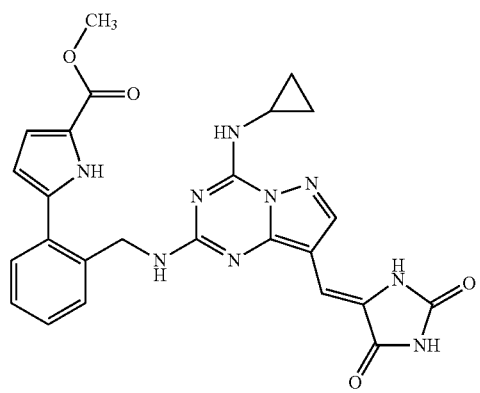 [SMILES: COC(=O)c1ccc(-c2ccccc2CNc2nc(NC3CC3)n3ncc(/C=C4\NC(=O)NC4=O)c3n2)[nH]1]
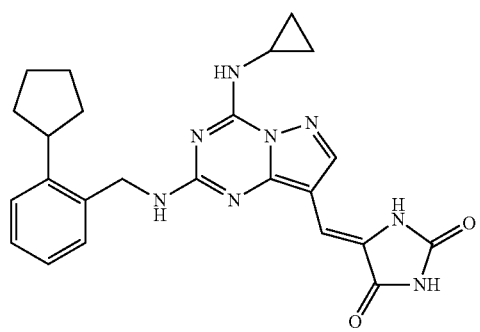 [SMILES: O=C1NC(=O)/C(=C/c2cnn3c(NC4CC4)nc(NCc4ccccc4C4CCCC4)nc23)N1]
TABLE 61-continued
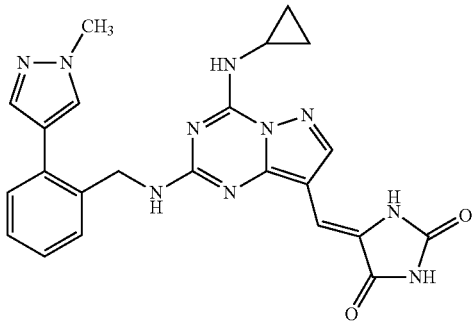 [SMILES: Cn1cc(-c2ccccc2CNc2nc(NC3CC3)n3ncc(/C=C4\NC(=O)NC4=O)c3n2)cn1]
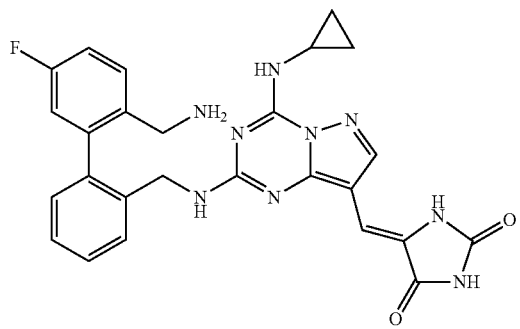 [SMILES: NCc1ccc(F)cc1-c1ccccc1CNc1nc(NC2CC2)n2ncc(/C=C3\NC(=O)NC3=O)c2n1]
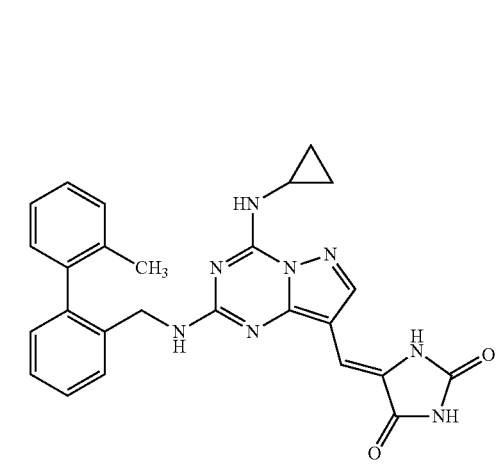 [SMILES: Cc1ccccc1-c1ccccc1CNc1nc(NC2CC2)n2ncc(/C=C3\NC(=O)NC3=O)c2n1]
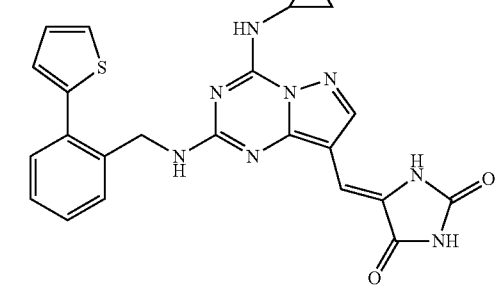

TABLE 61-continued
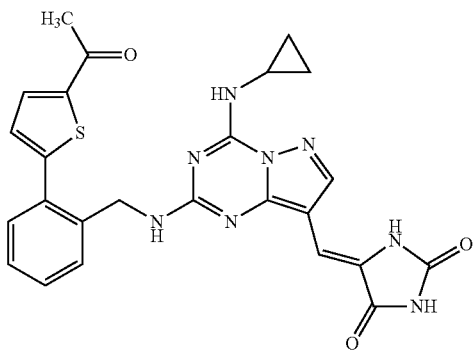 [SMILES: CC(=O)c1ccc(-c2ccccc2CNc2nc(NC3CC3)n3ncc(/C=C4\NC(=O)NC4=O)c3n2)s1]
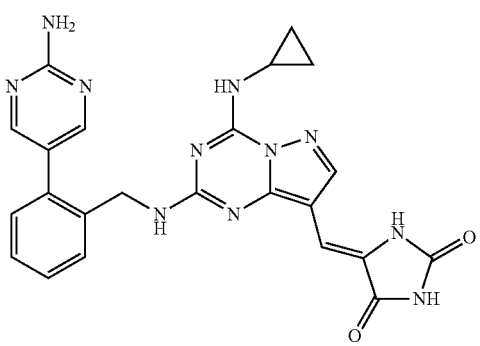 [SMILES: Nc1ncc(-c2ccccc2CNc2nc(NC3CC3)n3ncc(/C=C4\NC(=O)NC4=O)c3n2)cn1]
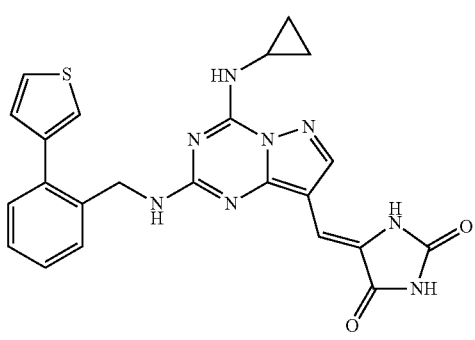 [SMILES: O=C1NC(=O)/C(=C/c2cnn3c(NC4CC4)nc(NCc4ccccc4-c4ccsc4)nc23)N1]
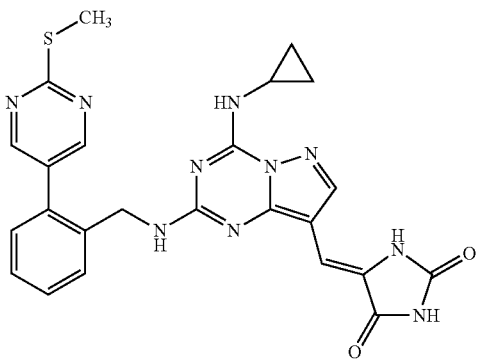 [SMILES: CSc1ncc(-c2ccccc2CNc2nc(NC3CC3)n3ncc(/C=C4\NC(=O)NC4=O)c3n2)cn1]
TABLE 61-continued
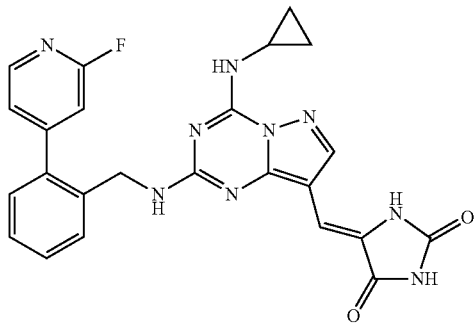 [SMILES: O=C1NC(=O)/C(=C/c2cnn3c(NC4CC4)nc(NCc4ccccc4-c4ccnc(F)c4)nc23)N1]
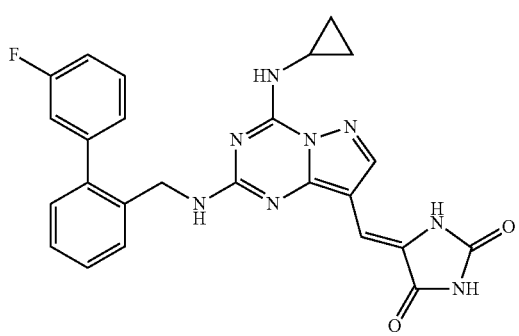 [SMILES: O=C1NC(=O)/C(=C/c2cnn3c(NC4CC4)nc(NCc4ccccc4-c4cccc(F)c4)nc23)N1]
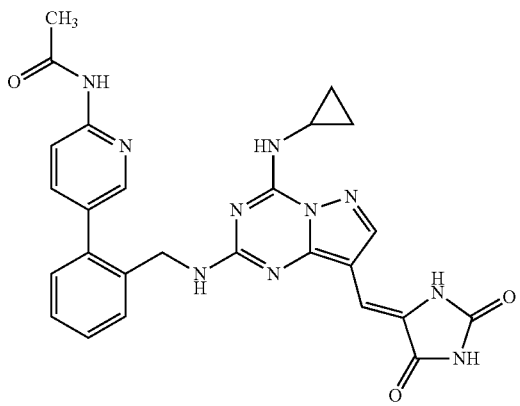 [SMILES: CC(=O)Nc1ccc(-c2ccccc2CNc2nc(NC3CC3)n3ncc(/C=C4\NC(=O)NC4=O)c3n2)cn1]
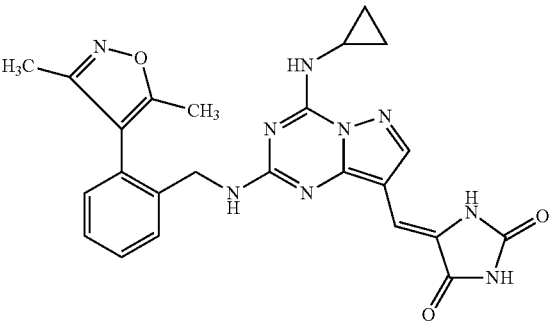 [SMILES: Cc1noc(C)c1-c1ccccc1CNc1nc(NC2CC2)n2ncc(/C=C3\NC(=O)NC3=O)c2n1]

TABLE 61-continued

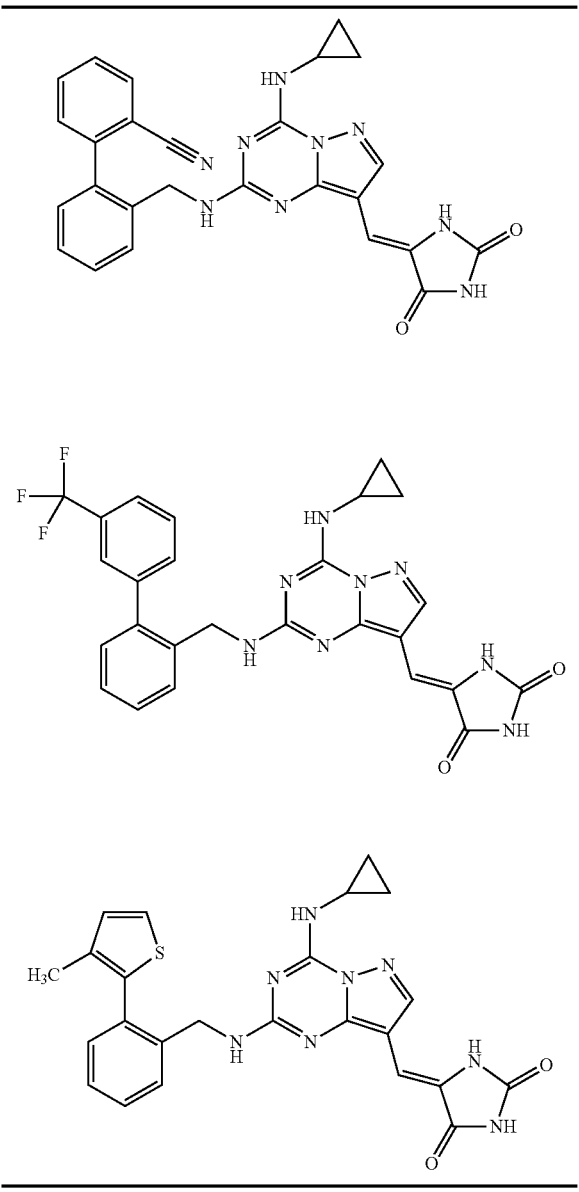

Compound 5 (as shown in Scheme 3 below) were prepared from compound 4 using chemistries described in patent application US2004/0019058. Compound 5 can be converted to molecule 6 using intermediates and chemistries described above. Deprotection of 6 using reagents such as N,N-dimethylbarbituric acid and a palladium catalyst can lead to 7.

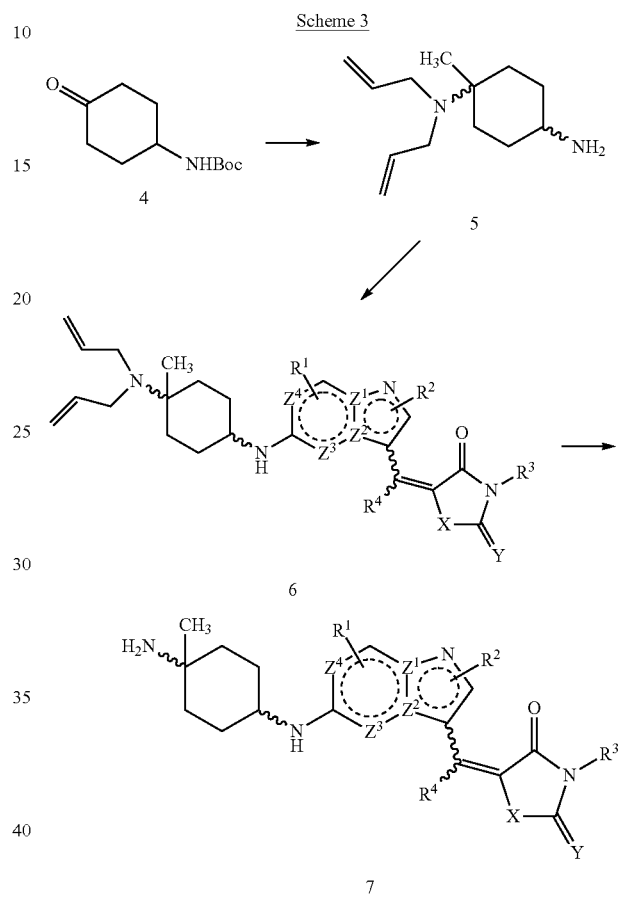

Compound 7 (as shown in Scheme 4 below) can be converted to molecules 8, 9, 10, 11 and 12 using chemistries known to a person skilled in the art.

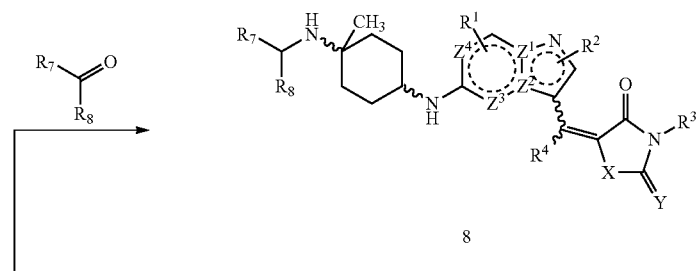

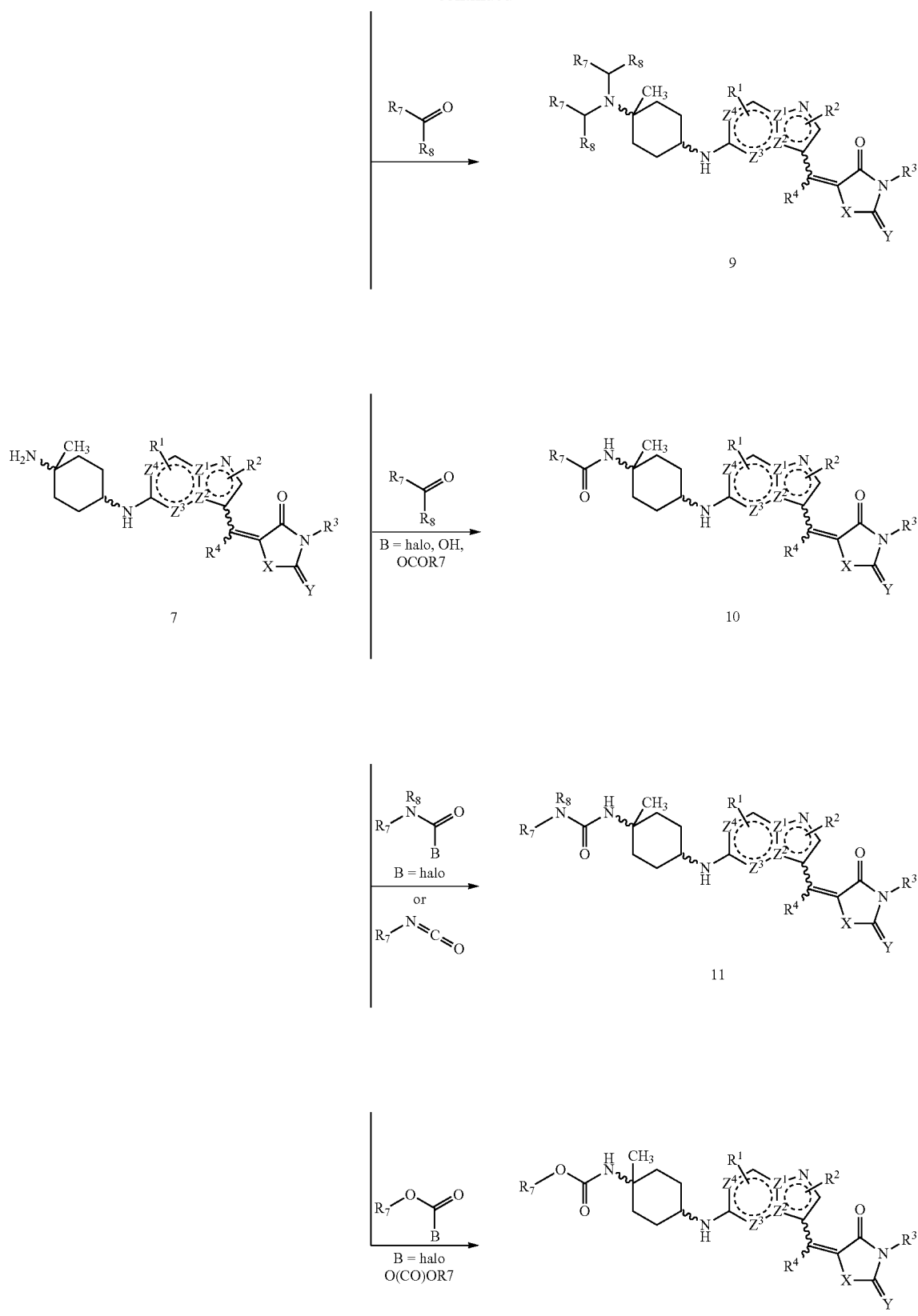

The following compounds in Table 62 can be prepared using chemistries described in the present disclosure:
TABLE 62
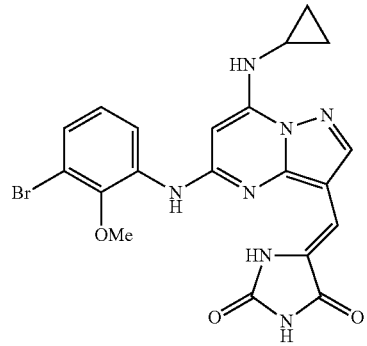 [SMILES: COc1c(Br)cccc1Nc1cc(NC2CC2)n2ncc(/C=C3\NC(=O)NC3=O)c2n1]
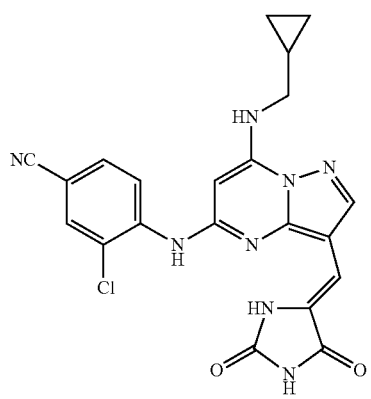 [SMILES: N#Cc1ccc(Nc2cc(NCC3CC3)n3ncc(/C=C4\NC(=O)NC4=O)c3n2)c(Cl)c1]
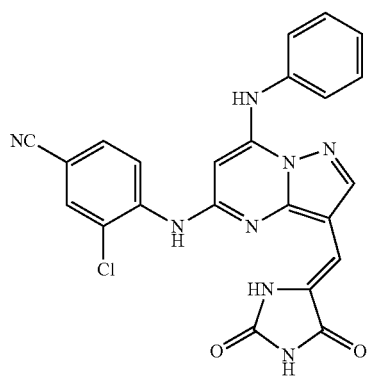 [SMILES: N#Cc1ccc(Nc2cc(Nc3ccccc3)n3ncc(/C=C4\NC(=O)NC4=O)c3n2)c(Cl)c1]
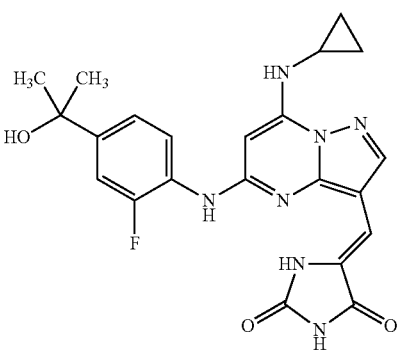 [SMILES: CC(C)(O)c1ccc(Nc2cc(NC3CC3)n3ncc(/C=C4\NC(=O)NC4=O)c3n2)c(F)c1]
TABLE 62-continued
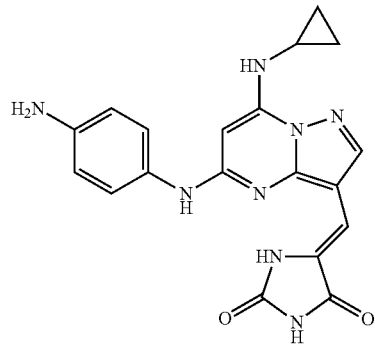 [SMILES: Nc1ccc(Nc2cc(NC3CC3)n3ncc(/C=C4\NC(=O)NC4=O)c3n2)cc1]
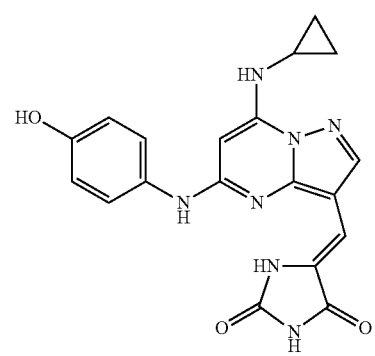 [SMILES: O=C1NC(=O)/C(=C/c2cnn3c(NC4CC4)cc(Nc4ccc(O)cc4)nc23)N1]
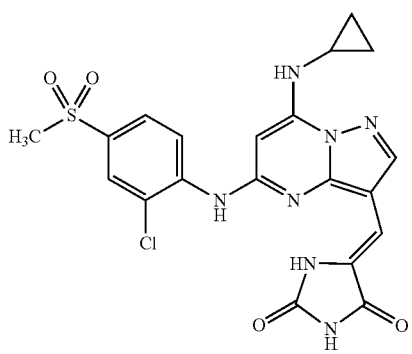 [SMILES: CS(=O)(=O)c1ccc(Nc2cc(NC3CC3)n3ncc(/C=C4\NC(=O)NC4=O)c3n2)c(Cl)c1]
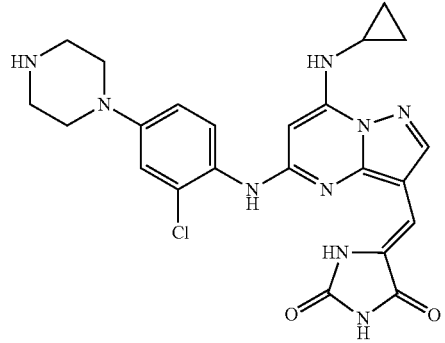 [SMILES: O=C1NC(=O)/C(=C/c2cnn3c(NC4CC4)cc(Nc4ccc(N5CCNCC5)cc4Cl)nc23)N1]

665
TABLE 62-continued
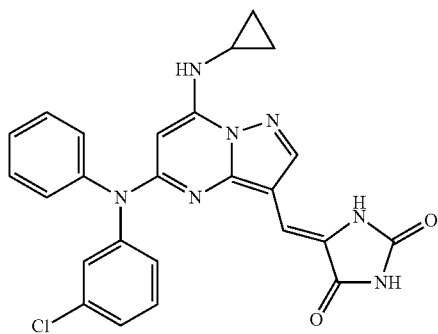 [SMILES: O=C1NC(=O)/C(=C/c2cnn3c(NC4CC4)cc(N(c4ccccc4)c4cccc(Cl)c4)nc23)N1]
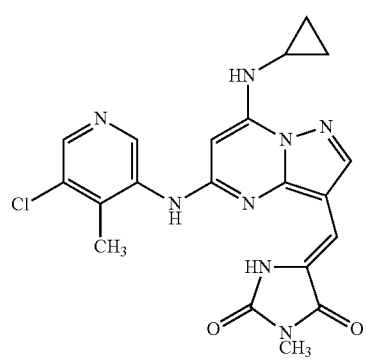 [SMILES: Cc1c(Cl)cncc1Nc1cc(NC2CC2)n2ncc(/C=C3\NC(=O)N(C)C3=O)c2n1]
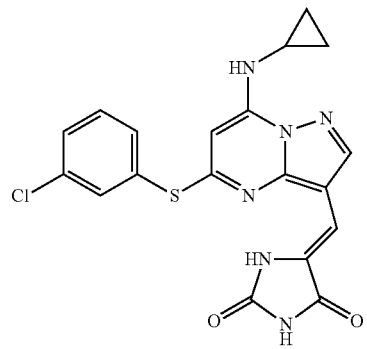 [SMILES: O=C1NC(=O)/C(=C/c2cnn3c(NC4CC4)cc(Sc4cccc(Cl)c4)nc23)N1]
Compound 3 were prepared by reaction compound 1 with boronic acid 2 using Suzuki coupling reaction conditions (as shown in Scheme 5 below).
Scheme 5
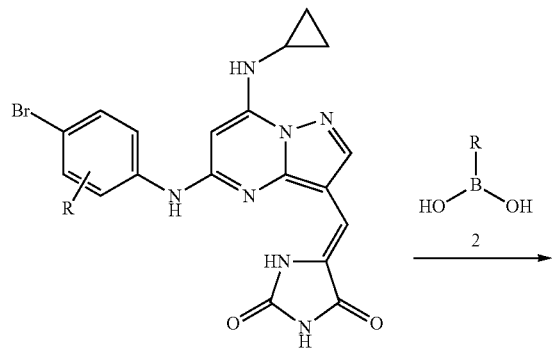
666
-continued
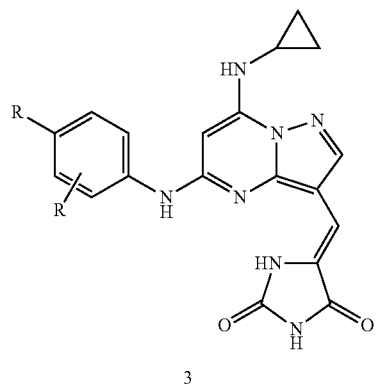
3
The following compounds in Table 63 can be prepared using chemistry described on Scheme 5:
TABLE 63
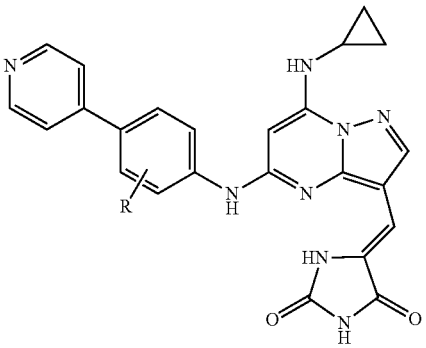
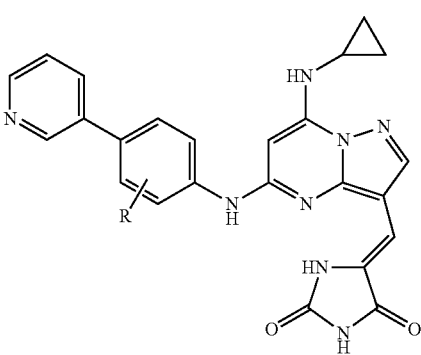
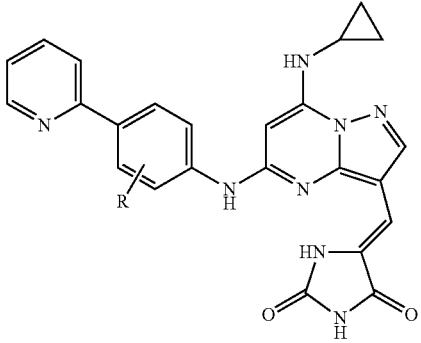

TABLE 63-continued
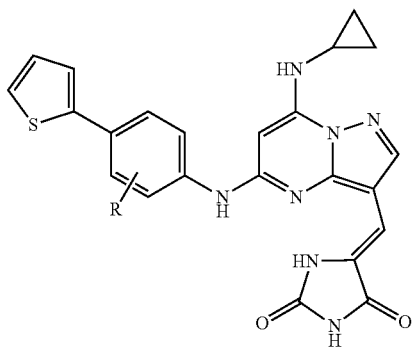
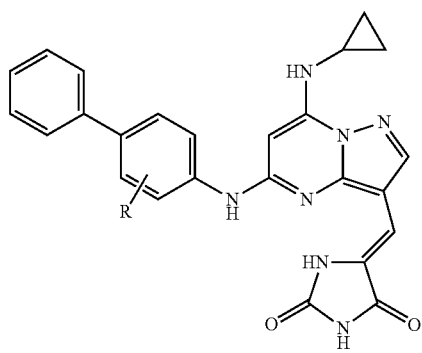
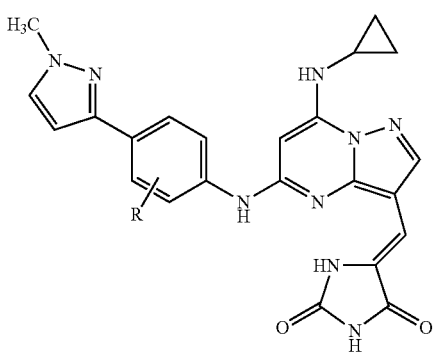
TABLE 63-continued
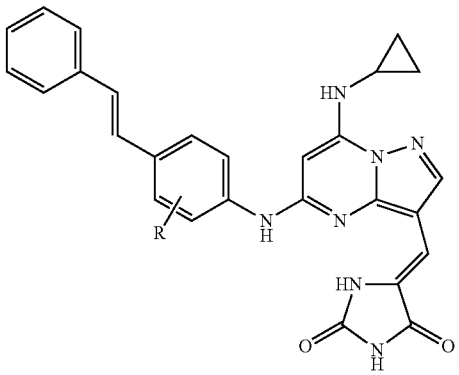
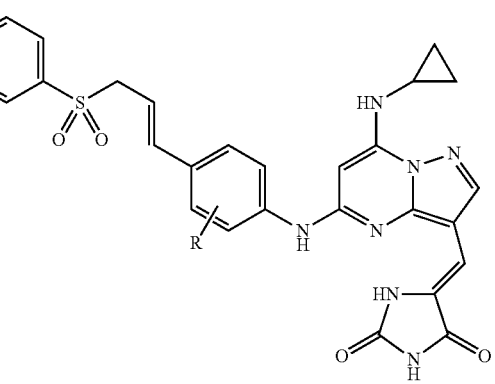
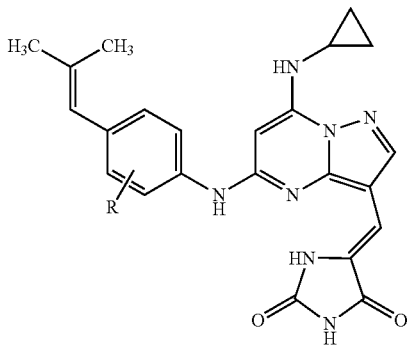
Compound 2 were prepared by reaction compound 1 using reductive amination conditions (as shown in Scheme 6 below).

Scheme 6
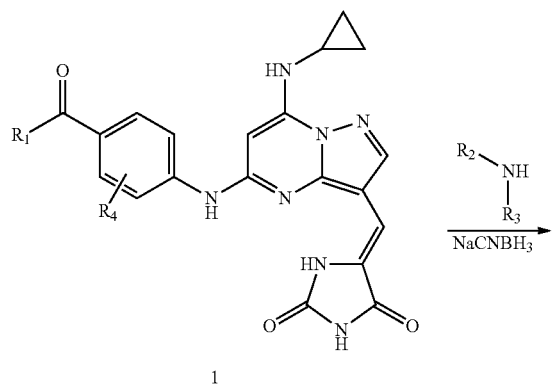
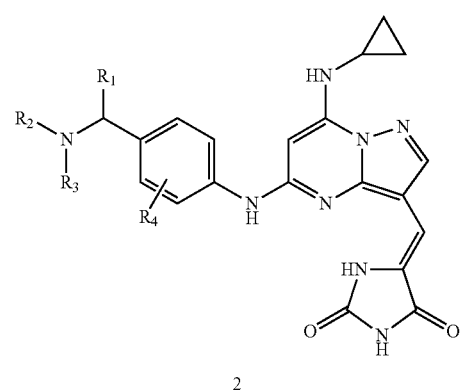
$R_1$ = H, alkyl
The following compounds in Table 64 can be prepared using chemistry described on Scheme 6:
TABLE 64
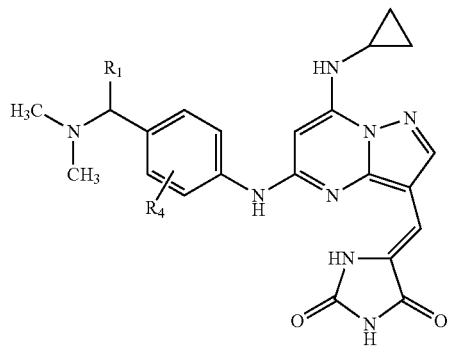
TABLE 64-continued
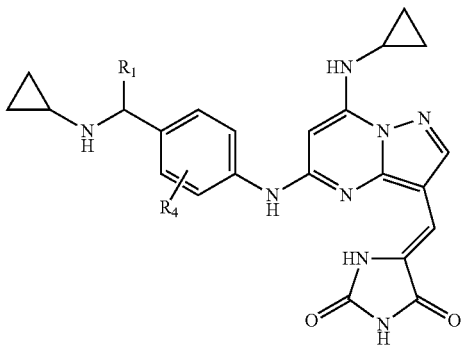
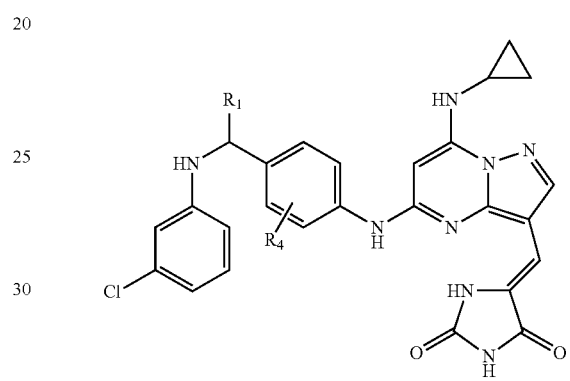
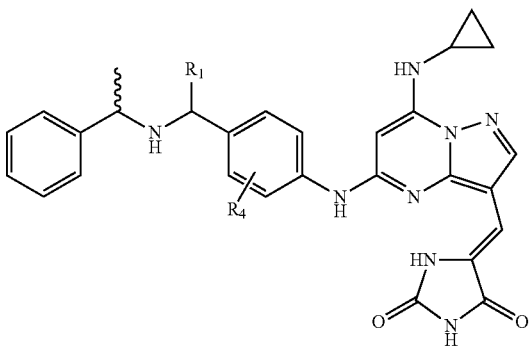
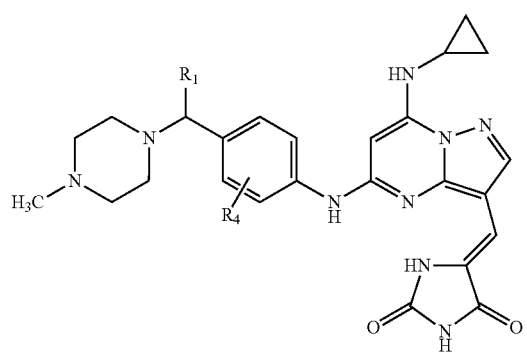

TABLE 64-continued

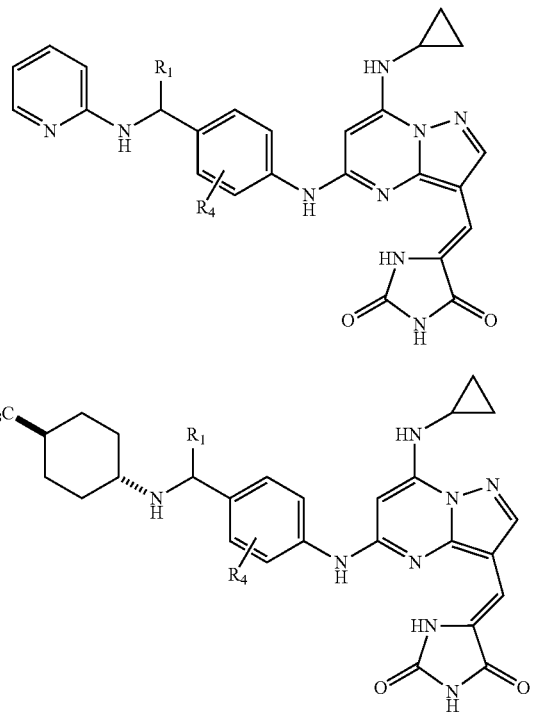

Biological Test Methods:

Biological Example A

CK2 Assay Method

Modulatory activity of compounds described herein was assessed in vitro in cell-free CK2 assays by the following method.

In a final reaction volume of 50 μl, CK2 ααββ (4 ng, 8.5 mU) was incubated with various concentrations of test compounds in DMSO (1 ul, 2% by volume), 20 mM MOPS pH 7.2, 10 mM EGTA, 0.15 M NaCl, 10 mM DTT, 0.002% Brij-35, 200 μM RRRDDDSDDD (SEQ ID NO.: 4), 10 mM MgAcetate, ATP 15 uM and 0.33% (by volume) ([γ-33P] ATP: Stock 1 mCi/100 μl; 3000Ci/mmol (Perkin Elmer)). Reactions were maintained for 40 min at 23° C. The reactions were quenched with 100 ul of 0.75% Phosphoric acid, then transferred to and filtered through a Phosphocellulose filter plate (Millipore, MSPH-N6B-50). After washing each well 4 times with 0.75% Phosphoric acid, scintillation fluid (20 uL) was added to each well and the residual radioactivity was measured using a Wallac luminescence counter.

Biological Example B

PIM-1 Assay Method

The following procedure was used to assay the PIM-1 kinase activity of compounds of the invention. Other methods for assaying PIM-1 and other PIM kinases, as well as methods to assay for activity against the various kinases for the kinase panel mentioned in FIGS. 1 and 2, are known in the art.

In a final reaction volume of 50 ul, recombinant PIM-1 (1 ng) was incubated with 12 mM MOPS pH 7.0, 0.4 mM EDTA, glycerol 1%, brij 35 0.002%, 2-mercaptoethanol 0.02%, BSA 0.2 mg/ml, 100 uM KKRNRTLTK (SEQ ID NO.: 5), 10 mM MgAcetate, 15 uM ATP, [γ-$^{33}$P-ATP] (specific activity approx. 500 cpm/pmol), DMSO 4% and test inhibitor compound at the required concentration. The reaction was initiated by the addition of the Magnesium ATP mixture. After 40 min incubation at 23° C., the reactions were quenched by the addition of 100 ul 0.75% Phosphoric acid, and the labeled peptide collected by filtration through a phosphocellulose filter plate. The plate was washed 4 times with 0.075% phosphoric acid (100 ul per well) and then, after the addition of scintillation fluid (20 ul per well), the counts were measured by a scintillation counter.

Biological Example C

PIM-2 Assay Method

Test compounds dissolved and diluted in DMSO (2 μl) were added to a reaction mixture comprising 10 μl of 5× Reaction Buffer (40 mM MOPS pH 7.0, 5 mM EDTA), 10 μl of recombinant human PIM2 solution (4 ng PIM-2 dissolved in dilution buffer (20 mM MOPS pH 7.0; EDTA 1 mM; 5% Glycerol; 0.01% Brij 35; 0.1%; 0.1% 2-mercaptoethanol; 1 mg/ml BSA)) and 8 ul of water. Reactions were initiated by the addition of 10 ul of ATP Solution (49% (15 mM MgCl$_2$; 75 uM ATP) 1% ([γ-$^{33}$]ATP: Stock 1 mCi/100μl; 3000 Ci/mmol (Perkin Elmer)) and 10 ul of substrate peptide solution (RSRSSYPAGT (SEQ ID NO.: 6), dissolved in water at a concentration of 1 mM), Reactions were maintained for 10 min at 30° C. The reactions were quenched with 100 ul of 0.75% Phosphoric acid, then transferred to and filtrered through a Phosphocellulose filter plate (Millipore, MSPH-N6B-50). After washing each well 4 times with 0.75% Phosphoric acid, scintillation fluid (20 uL) was added to each well and the residual radioactivity was measured using a Wallac luminescence counter.

Biological Example D

Cell Proliferation Modulatory Activity

A representative cell-proliferation assay protocol using Alamar Blue dye (stored at 4° C., use 20 ul per well) is described hereafter.

96-Well Plate Setup and Compound Treatment a. Split and trypsinize cells.
b. Count cells using hemocytometer.
c. Plate 4,000-5,000 cells per well in 100 μl of medium and seed into a 96-well plate according to the following plate layout. Add cell culture medium only to wells B10 to B12. Wells B1 to B9 have cells but no compound added.

|   | 1 2 3 | 4 5 6 | 7 8 9 | 10 11 12 |   |
|---|---|---|---|---|---|
| A |   | EMPTY |   |   |   |
| B |   | NO COMPOUND ADDED |   | Medium Only |   |
| C | 10 nM | 100 nM | 1 uM | 10 uM | Control |
| D | 10 nM | 100 nM | 1 uM | 10 uM | Comp 1 |
| E | 10 nM | 100 nM | 1 uM | 10 uM | Comp 2 |
| F | 10 nM | 100 nM | 1 uM | 10 uM | Comp 3 |
| G | 10 nM | 100 nM | 1 uM | 10 uM | Comp 4 |
| H |   | EMPTY |   |   |   | d. Add 100 μl of 2× drug dilution to each well in a concentration shown in the plate layout above. At the same time, add 100 μl of media into the control wells (wells B10 to B12). Total volume is 200 μl /well.

e. Incubate four (4) days at 37° C., 5% $CO_2$ in a humidified incubator.

f. Add 20 μl Alamar Blue reagent to each well.

g. Incubate for four (4) hours at 37° C., 5% $CO_2$ in a humidified incubator.

h. Record fluorescence at an excitation wavelength of 544 nm and emission wavelength of 590 nm using a microplate reader.

In the assays, cells are cultured with a test compound for approximately four days, the dye is then added to the cells and fluorescence of non-reduced dye is detected after approximately four hours. Different types of cells can be utilized in the assays (e.g., HCT-116 human colorectal carcinoma cells, PC-3 human prostatic cancer cells, MDA-MB231 human breast cancer cells, K-562 human chronic myelogenous leukemia (CML) cells, MiaPaca human pancreatic carcinoma cells, MV-4 human acute myeloid leukemia cells, and BxPC3 human pancreatic adenocarcinoma cells).

Activity of compounds of the present invention tested in these in vitro and cellular assays are summarized in Tables 1A and 2A below. The compounds listed in Tables 1A and 2A are the Examples and species as described above.

TABLE A1

Bioactivity Data for Some Compounds of Formula II and Formula II'.

| Compound | AB: MV-4-11 | AB: MDAMB453 | AB: K-562 | AB: BxPC3 | AB: SUM-149PT | CK2: IC50 (uM) | PIM1: IC50 (uM) | PIM2: IC50 (uM) |
|---|---|---|---|---|---|---|---|---|
| P49 | 0.185 | 1.958 | 0.437 | 4.945 | 4.495 | <0.01 | 0.6565 | >2.5000 |
| Q49 |  |  |  |  |  | 0.1647 | 2.0638 | 1.6438 |
| R49 | 3.608 | 7.7 | 5.129 | 9.45 | 4.6 | <0.01 | 2.0575 | 1.8456 |
| S49 |  |  |  |  |  | 0.1367 | 0.9177 | 1.3934 |
| T49 |  |  |  |  |  | 0.1739 | >2.5000 | 1.4327 |
| U49 |  |  |  |  |  | <0.01 | 1.4455 | 1.4379 |
| V49 |  |  |  |  |  | 0.2072 | >2.5000 | >2.5000 |
| W49 |  |  |  |  |  | 0.0513 | 1.2533 | >2.5000 |
| X49 |  |  |  |  |  | 0.7502 | >2.5000 | >2.5000 |
| Y49 | 1.759 | 1.069 | 1.723 | 7.592 | 1.693 | <0.01 | 0.4414 | 0.5759 |
| Z49 | >10 | 14.3 | >10 | 26.465 | >30 | <0.01 | >2.5000 | >2.5000 |
| A50 |  |  |  |  |  | 0.764 | 0.5235 | 1.0907 |

TABLE A2

Bioactivity Data for Some Compounds of Formula II and Formula II'

| Compound | AB: MDAMB453 | AB: BxPC3 | AB: SUM-149PT | CK2: IC50 (Brij 15 um ATP) | PIM2: IC50 (5 um ATP) |
|---|---|---|---|---|---|
| B50 | 1.047 | 2.341 | 1.043 | 0.00072 |  |
| C50 | 1.552 | 1.564 | 1.922 | 0.00216 | >2.5000 |
| D50 | <0.12 | <0.12 | 0.154 | 0.00038 |  |
| E50 | 0.842 | 3.96 | 1.595 | 0.00081 | >2.5000 |
| F50 | 3.459 | 2.958 | 2.054 | 0.00663 |  |
| G50 | 1.483 | 1.626 | 2.073 | 0.00359 | 1.3652 |
| H50 | 3.507 | 3.876 | 4.996 | 0.00412 | 1.2984 |

Citation of the above patents, patent applications, publications and documents is not an admission that any of the foregoing is pertinent prior art, nor does it constitute any admission as to the contents or date of these publications or documents. Furthermore, the contents of the patents, patent applications, publications and documents cited herein are incorporated by reference in their entirety for all purposes to the same extent as each and everyone of them is incorporated by references specifically.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention.

We claim:

1. A compound of Formula (II):

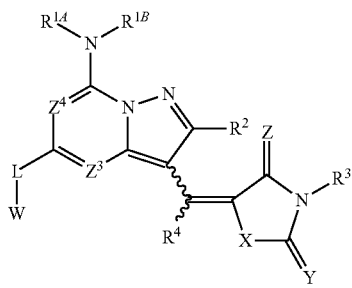

(II)

or a pharmaceutically acceptable salt or solvate thereof;
wherein:
$Z^3$ is N; and $Z^4$ is $CR^5$ or CH;
$R^5$ is selected from halo, —CN, —R, —OR, —S(O)$_n$R, —COOR, —CONR$_2$, and —NR$_2$,
wherein each R is independently selected from H and optionally substituted C1-C4 alkyl, or alternatively, the two R groups, taken together with the nitrogen atom to which they are attached, form an optionally substituted 5 or 6 membered heterocyclic ring that optionally contains one or more additional heteroatom selected from N, O and S as a ring member;

$R^2$, $R^3$ and $R^4$ are each independently selected from H and optionally substituted C1-C10 alkyl;
X represents O, S, or NR$^2$;
Y is O or S or NR$^{10}$;
where $R^{10}$ is selected from H, CN, optionally substituted C1-C4 alkyl, optionally substituted C2-C4 alkenyl, optionally substituted C2-C4 alkynyl, optionally substituted C1-C4 alkoxy, and —NR$^7$R$^8$,
Z is O or S;
L is a bond, —CR$^7$=CR$^8$—, —C≡C—, —NR$^7$—, —O—, —S(O)$_n$—, —(CR$^7$R$^8$)$_m$—, —(CR$^7$R$^8$)$_m$—NR$^7$—, —(CR$^7$R$^8$)$_m$—O—, or —(CR$^7$R$^8$)$_m$—S(O)$_n$—;
W is optionally substituted C1-C10 alkyl, optionally substituted C1-C10 heteroalkyl, optionally substituted aryl, optionally substituted heteroaryl, —NR$^7$R$^8$, —OR$^7$, —S(O)$_n$R$^7$, —CONR$^7$R$^8$, optionally substituted heterocyclyl, optionally substituted carbocyclyl, optionally substituted C2-C10 alkenyl, optionally substituted C2-C10 alkynyl, or —CR$^7$R$^8$R$^9$;
where each R$^7$ and R$^8$ and R$^9$ is independently selected from H, optionally substituted C1-C10 alkyl, optionally substituted heteroalkyl, optionally substituted carbocyclyl, optionally substituted heterocyclyl, optionally substituted carbocyclylalkyl, optionally substituted heterocyclylalkyl, optionally substituted aryl, optionally substituted arylalkyl, optionally substituted heteroaryl, and optionally substituted heteroarylalkyl;
or R$^8$ and R$^9$, taken together with the carbon atom to which they are attached, form =O (oxo) or =N—OR$^7$ or =N—CN;

or $R^7$ and $R^8$, taken together on a single carbon atom or on adjacent connected carbon atoms of $(CR^7R^8)_m$ whether alone or as part of another group, form a 3 to 8 membered carbocyclic ring or heterocyclic ring;

or $R^7$ and $R^8$, taken together with the nitrogen atom to which they are attached, form an optionally substituted 5 to 10 membered heterocyclic or heteroaryl ring that optionally contains one or more additional heteroatom selected from N, O and S as a ring member;

provided that no more than one of or $R^7$ and $R^8$ in —$NR^7R^8$ is selected from the group consisting of alkoxy, alkylamino, dialkylamino and heterocyclyl;

each n is independently is 0, 1 or 2;

each m is independently 1, 2, 3 or 4; and $R^{1A}$ and $R^{1B}$ are each independently selected from H, optionally substituted C1-C10 alkyl, optionally substituted heteroalkyl, optionally substituted heterocyclyl, optionally substituted carbocyclyl, optionally substituted carbocyclylalkyl, optionally substituted heterocyclylalkyl, optionally substituted aryl, optionally substituted arylalkyl, optionally substituted heteroaryl, or optionally substituted heteroarylalkyl;

or $R^{1A}$ and $R^{1B}$, taken together with the nitrogen atom to which they are attached, form an optionally substituted 5- to 8-membered monocyclic or 5- to 10-membered bicyclic heteroaryl or heterocyclic ring containing up to two additional heteroatoms selected from N, O and S as ring members.

2. The compound of claim 1, wherein $R^3$ and $R^4$ are both H.

3. The compound of claim 1, wherein $R^2$ is H, —$CH_3$, halo, $OCH_3$, or $CF_3$.

4. The compound of claim 1, wherein Y is O or S.

5. The compound of claim 1, wherein Z is O.

6. The compound of claim 1, wherein X is NH.

7. The compound of claim 1, wherein X is O or S.

8. The compound of claim 1, wherein
the optionally substituted carbocyclyl is an optionally substituted C3-C8 cycloalkyl;
the optionally substituted carbocyclylalkyl is an optionally substituted C4-C10 cycloalkylalkyl; and
the optionally substituted heteroalkyl is an optionally substituted C1-C6 alkoxy, optionally substituted C1-C6 alkylamino, or optionally substituted C1-C6 dialkylamino.

9. The compound of claim 1, wherein L is a bond or NH.

10. The compound of claim 1, wherein W is optionally substituted phenyl, optionally substituted phenylalkyl, optionally substituted cycloalkylalkyl, or optionally substituted heterocyclyl.

11. The compound of 1, wherein
-L-W is —$NHR^7$, —$OR^7$, or —$S(O)_nR^7$;
n is 0, 1, or 2; and
$R^7$ is optionally substituted C1-C10 alkyl, optionally substituted heteroalkyl, optionally substituted aryl, optionally substituted heteroaryl, optionally substituted arylalkyl, optionally substituted heteroarylalkyl, optionally substituted carbocyclyl, optionally substituted heterocyclyl, optionally substituted carbocyclylalkyl, or optionally substituted heterocyclylalkyl.

12. The compound of claim 1, wherein
-L-W is —$NR^7R^8$; and
$R^7$ and $R^8$, taken together with the nitrogen atom to which they are attached, form an optionally substituted heterocyclyl which optionally contains one or more additional heteroatom as ring members.

13. The compound of claim 1, wherein
-L-W is optionally substituted aryl, optionally substituted heteroaryl, optionally substituted carbocyclyl, or optionally substituted heterocyclyl.

14. The compound of claim 1, wherein $R^{1A}$ is H and $R^{1B}$ is optionally substituted C1-C10 alkyl, optionally substituted heterocyclyl, optionally substituted cycloalkyl, optionally substituted cycloalkylalkyl, optionally substituted heterocyclylalkyl, optionally substituted arylalkyl, or an optionally substituted 5-6 membered aryl ring containing up to two heteroatoms as ring members.

15. The compound of claim 1, which has the structural Formula (IIa):

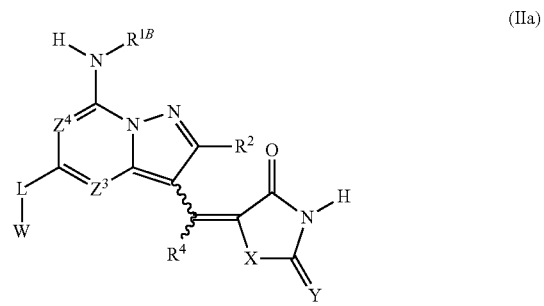

(IIa)

wherein
$R^2$ is H, $CH_3$ or $CF_3$;
$Z^3$ is N; and $Z^4$ is $CR^5$ or CH;
where $R^5$ is selected from halo, —CN, —R, —OR, —$S(O)_n$R, —COOR, —$CONR^2$, and —$NR_2$,
wherein each R is independently selected from H and optionally substituted C1-C4 alkyl, or the two R groups, taken together with the nitrogen atom to which they are attached, form an optionally substituted 5- or 6-membered heterocyclic ring which contains one or more additional heteroatom selected from N, O or S as a ring member;
$R^4$ is H, $CH_3$ or $CF_3$;
X is O, S or NH;
Y is O or S;
$R^{1B}$ is selected from H, optionally substituted C1-C10 alkyl, optionally substituted heteroalkyl, optionally substituted heterocyclyl, optionally substituted cycloalkyl, optionally substituted cycloalkylalkyl, optionally substituted heterocyclylalkyl, optionally substituted arylalkyl, or an optionally substituted heteroaryl;
L is a bond, —$NR^7$—, —O—, —$S(O)_n$—, $(CR^7R^8)_m$, or —$(CR^7R^8)_m$—$NR^7$—;
m is 1, 2, 3, or 4;
n is 0, 1, or 2;
W is selected from optionally substituted aryl, optionally substituted heteroaryl, and —$NR^7R^8$, where each $R^7$ and $R^8$ is independently selected from H, optionally substituted C1-C6 alkoxy, optionally substituted C1-C6 alkylamino, optionally substituted C1-C6 dialkylamino, optionally substituted heterocyclyl, optionally substituted C1-C10 alkyl, optionally substituted C3-C8 cycloalkyl, optionally substituted C4-C10 cycloalkylalkyl, optionally substituted aryl, optionally substituted arylalkyl, optionally substituted heteroaryl, and optionally substituted heteroarylalkyl;
and $R^7$ and $R^8$, taken together on a single carbon atom or on adjacent connected carbon atoms of $(CR^7R^8)_m$ whether alone or as part of another group, form a 3- to 8-membered ring that contains one or more heteroatoms as ring members;

or $R^7$ and $R^8$, taken together with the nitrogen atom to which they are attached, form an optionally substituted 5- to 10-membered heterocyclic or heteroaryl ring system that optionally contains an additional heteroatom selected from N, O and S as a ring member; and provided that no more than one of or $R^7$ and $R^8$ in —$NR^7R^8$ is selected from the group consisting of alkoxy, alkylamino, dialkylamino and heterocyclyl.

16. The compound of claim 15, wherein $R^2$, $R^4$ and $R^5$ are each H.

17. The compound of claim 15, wherein X is NH and Y is O.

18. The compound of claim 15, wherein $R^{1B}$ is C3-C8 cycloalkyl or C4-C8 cycloalkylalkyl.

19. The compound of claim 15, wherein L is NH.

20. The compound of claim 15, wherein W is optionally substituted phenyl or optionally substituted thienyl.

21. The compound of claim 15, wherein W is optionally substituted phenylalkyl, optionally substituted cycloalkylalkyl, or optionally substituted heterocyclyl.

22. The compound of claim 15, wherein
-L-W is —$NHR^7$, —$OR^7$, or —$S(O)_nR^7$;
n is 0, 1, or 2; and
$R^7$ is optionally substituted C1-C10 alkyl, optionally substituted heteroalkyl, optionally substituted aryl, optionally substituted heteroaryl, optionally substituted arylalkyl, optionally substituted heteroarylalkyl, optionally substituted carbocyclyl, optionally substituted heterocyclyl, optionally substituted carbocyclylalkyl, or optionally substituted heterocyclylalkyl.

23. The compound of claim 15, wherein
-L-W is —$NR^7R^8$; and
$R^7$ and $R^8$, taken together with the nitrogen atom to which they are attached, form an optionally substituted heterocyclyl which optionally contains one or more additional heteroatom as ring members.

24. The compound of claim 15, wherein
-L-W is optionally substituted aryl, optionally substituted heteroaryl, optionally substituted carbocyclyl, or optionally substituted heterocyclyl.

25. The compound of claim 15, which has the structural Formula (II-Th):

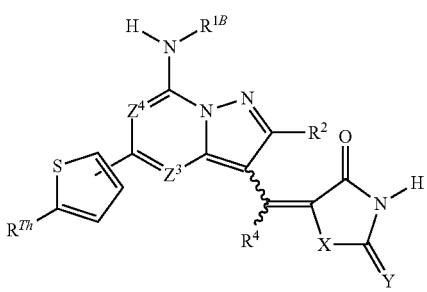

(II-Th)

wherein
$R^{Th}$ is selected from H, halo, optionally substituted C1-C6 alkyl, CN, $S(O)_{0-2}R$, —$SO_2NR_2$, COOR, $CONR_2$, and C(O)R,
where each R is independently H, halo, CN, or an optionally substituted member selected from the group consisting of C1-C6 alkyl, C1-C6 alkoxy, C1-C6 alkylamino, di(C1-C6)alkylamino, C3-C8 cycloalkyl, C4-C10 cycloalkylalkyl, C5-C8 heterocyclyl, C6-C10 heterocyclylalkyl, aryl, arylalkyl, C5-C6 heteroalkyl, and C6-C10 heteroalkylalkyl; and two R on the same atom or adjacent connected atoms can form an optionally substituted heterocyclic ring that can contain an additional heteroatom selected from N, O and S as a ring member.

26. The compound of claim 25, wherein Y is O, and X is NH or S.

27. The compound of claim 25, wherein $R^2$ and $R^4$ are each H.

28. The compound of claim 25, wherein $R^{TH}$ is $CONR_2$.

29. The compound of claim 25, wherein $R^{1B}$ is cyclopropyl or cyclopropylmethyl.

30. The compound of claim 1, which has the structural Formula (IIb):

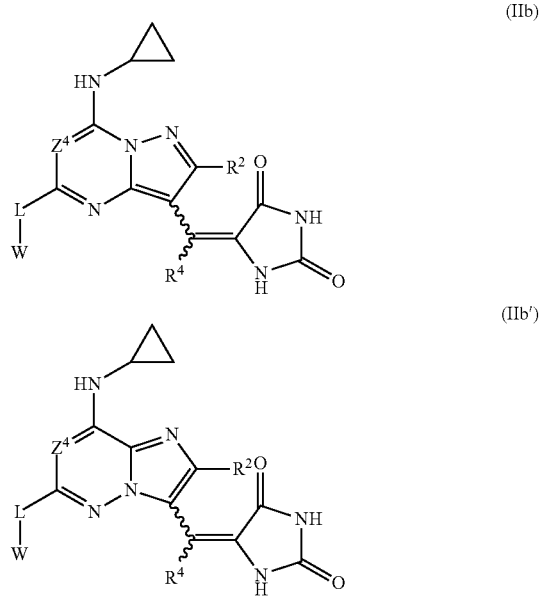

wherein
$R^2$ and $R^4$ are independently H, $CH_3$ or $CF_3$;
$Z^4$ is N or CH;
-L-W is —$NR^{8A}R^7$, —$NHR^7$, —$OR^7$, or —$S(O)_nR^7$;
n is 0, 1, or 2; and
$R^7$ is optionally substituted C1-C10 alkyl, optionally substituted heteroalkyl, optionally substituted aryl, optionally substituted heteroaryl, optionally substituted arylalkyl, optionally substituted heteroarylalkyl, optionally substituted carbocyclyl, optionally substituted heterocyclyl, optionally substituted carbocyclylalkyl, or optionally substituted heterocyclylalkyl, optionally substituted aryl, optionally substituted heteroaryl, optionally substituted carbocyclyl, or optionally substituted heterocyclyl; or
$R^7$ and $R^{8A}$, taken together with the nitrogen atom to which they are attached, form an optionally substituted heterocyclyl which optionally contains one or more additional heteroatom as ring members.

31. The compound of claim 1, which has the structural Formula (IIc):

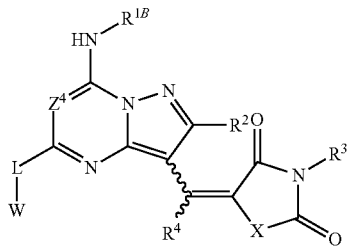

(IIc)

wherein,

X is O, S, or NR²;

R³ is —(CH₂)—X^C;

X^C is hydroxyl or a group having structural formula (a), (b), (c), or (d):

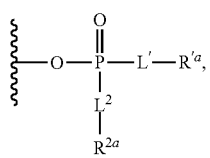

(a)

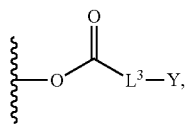

(b)

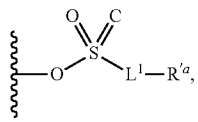

(c)

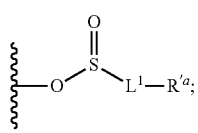

(d)

$L^1$ and $L^2$ are each independently a covalent bond, —O—, or —NR^{3a}—;

$R^{1a}$ and $R^{2a}$ are each independently hydrogen, alkyl, heteroalkyl, heteroaryl, heterocyclyl, alkenyl, alkynyl, arylalkyl, heteroarylalkyl, heterocyclylalkyl, -alkylene-C(O)—O—R^{4a}, or -alkylene-O—C(O)—O—R^{4a}; and $R^{3a}$ and $R^{4a}$ are each independently hydrogen, alkyl, heteroalkyl, cyclylalkyl, heterocyclyl, aryl, heteroaryl, alkenyl, alkynyl, arylalkyl, heterocyclylalkyl, or heteroarylalkyl;

$L^3$ is a covalent bond or alkylene;

Y is $OR^{5a}$, $NR^{5a}R^{6a}$, or $C(O)OR^{7a}$, provided that when Y is $C(O)OR^{7a}$, then $L^3$ is not a covalent bond; and $R^{5a}$, $R^{6a}$, and $R^{7a}$ are each independently hydrogen, alkyl, arylalkyl, aryl, heteroalkyl, alkylheteroaryl, heterocyclyl, or heteroaryl; or alternatively, $R^{5a}$ and $R^{6a}$, taken together with the nitrogen atom to which they are attached, form a hetercyclyl ring optionally containing one or more additional heteroatom independently selected from N, O, and S.

32. The compound of claim 31, wherein

X is NR²;

R³ is —(CH₂)—X^C;

X^C is hydroxyl or a group having structural formula (b):

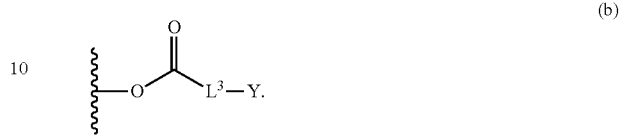

(b)

33. The compound of claim 31, wherein R² and R⁴ are hydrogen.

34. The compound of claim 31, wherein $R^{1B}$ is an optionally substituted C1-C10 alkyl, cycloalkyl, or cycloalkylalkyl.

35. The compound of claim 31, wherein -L-W is —OR⁷ or —NR⁷R⁸.

36. The compound of claim 35, wherein R⁷ is optionally substituted aryl or optionally substituted heteroaryl; and R⁸ is H.

37. The compound of claim 36, wherein R⁸ is optionally substituted phenyl.

38. The compound of claim 32, wherein $L^3$ is a covalent bond; and Y is $OR^{5a}$ or $NR^{5a}R^{6a}$.

39. The compound of claim 1, which is selected from the group consisting of

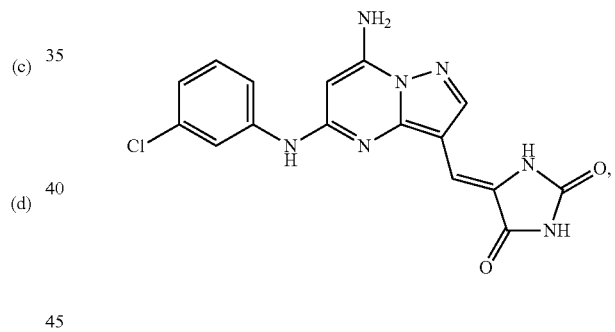

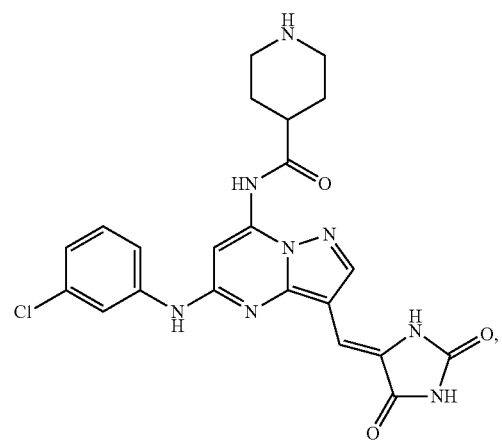

689
-continued
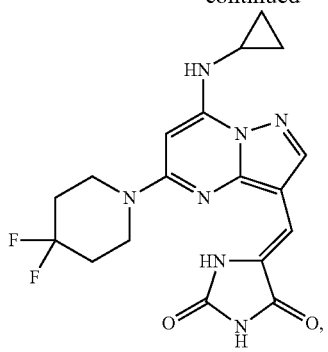
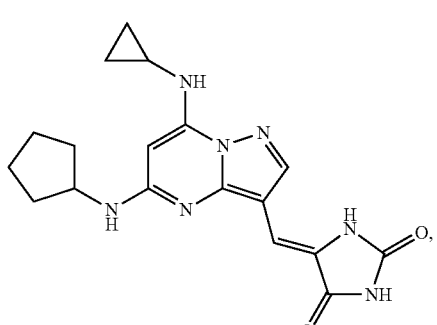
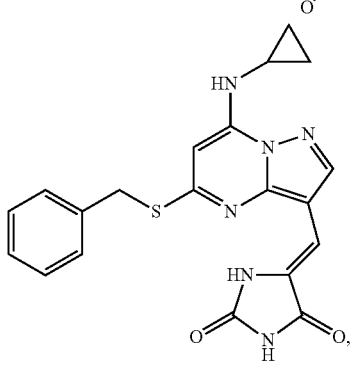
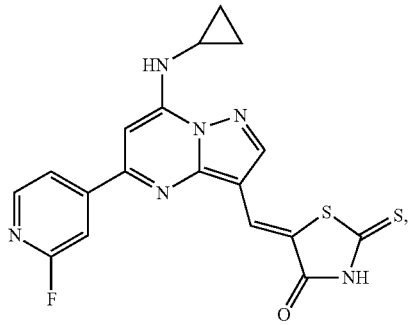
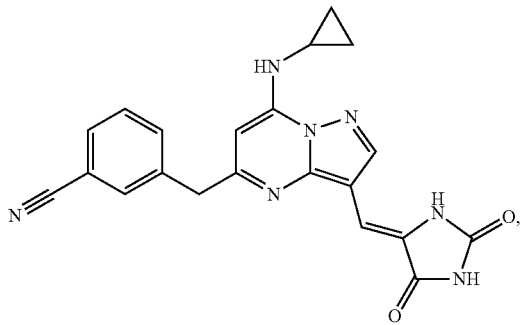
690
-continued
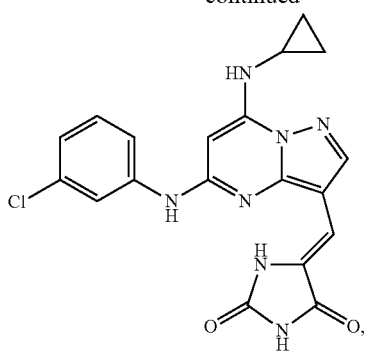
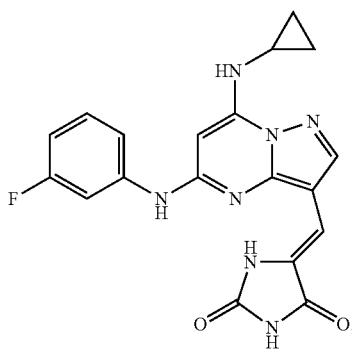
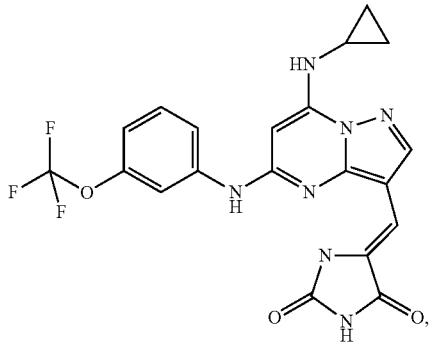
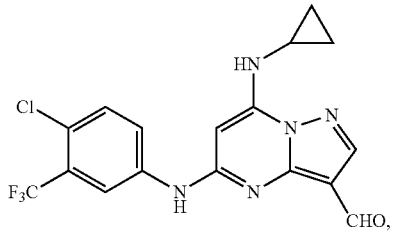

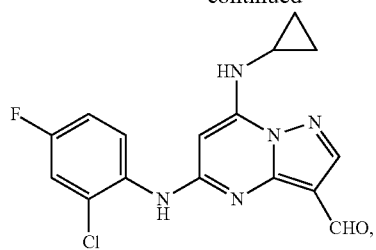
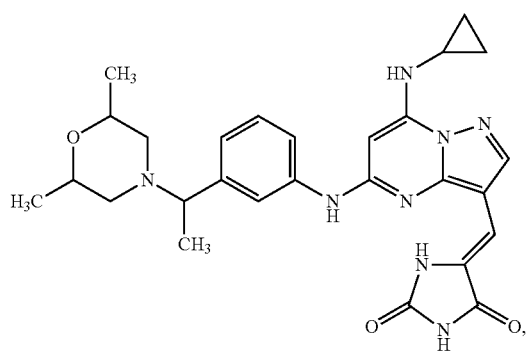
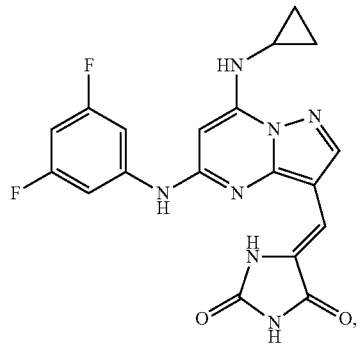
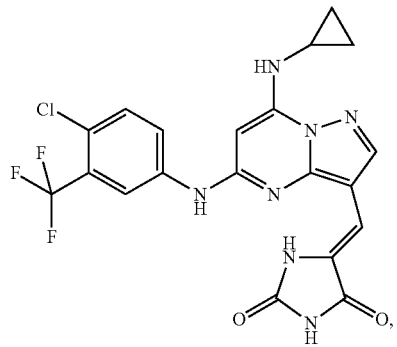
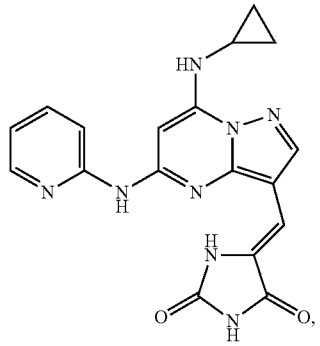
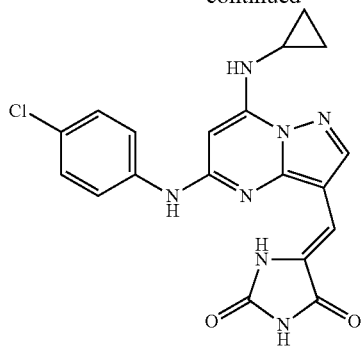
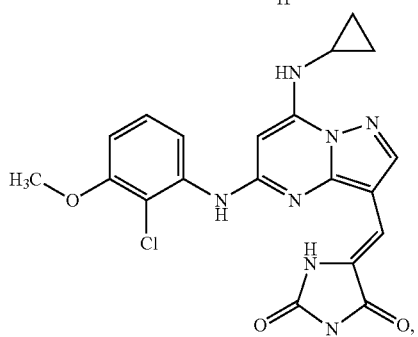
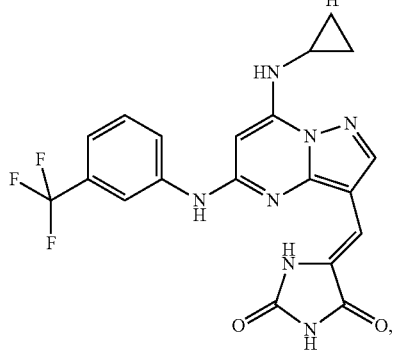
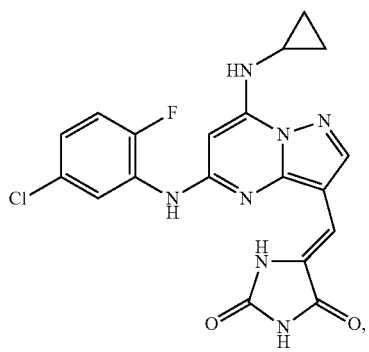
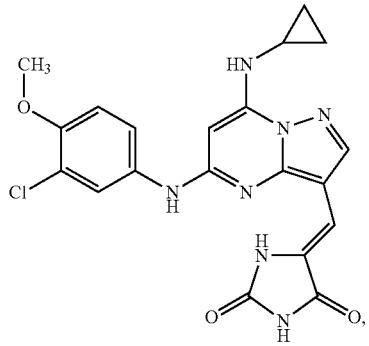

693
-continued
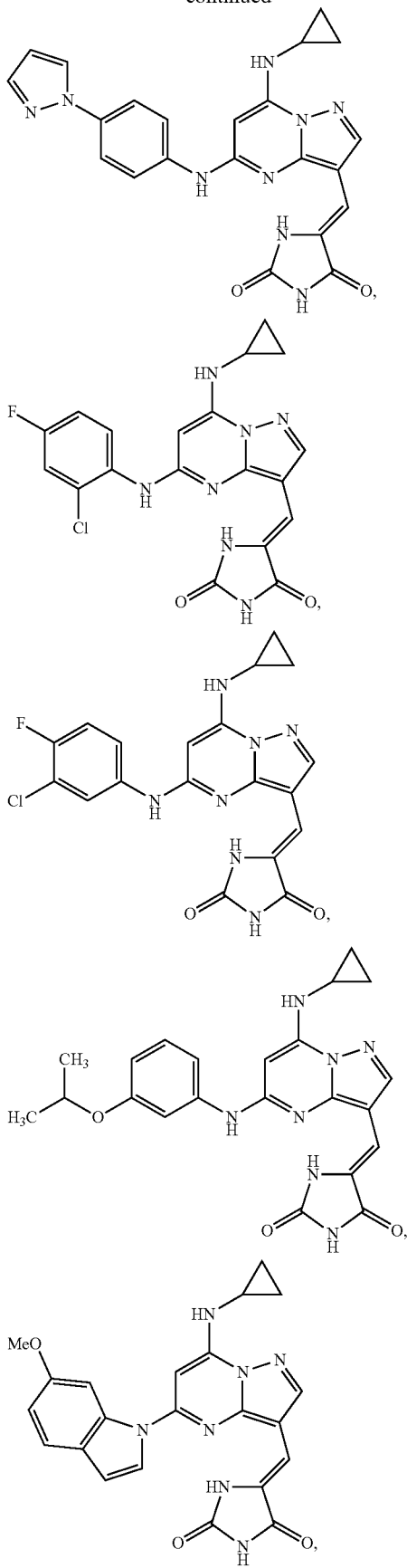
694
-continued
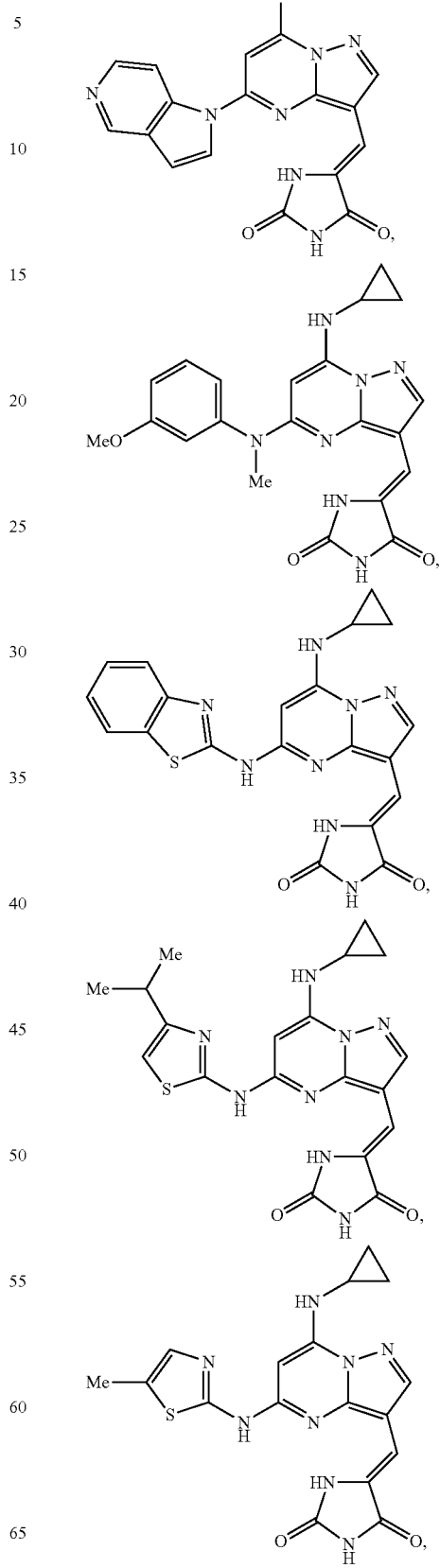

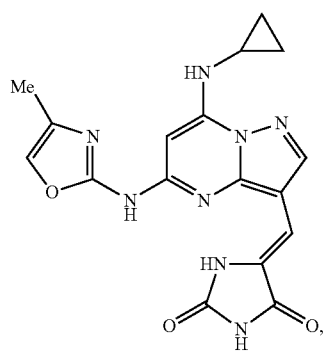
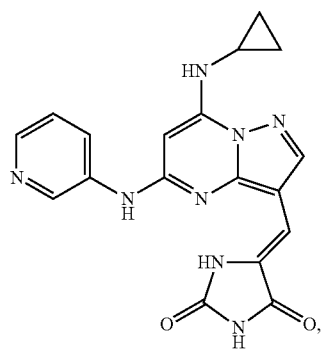
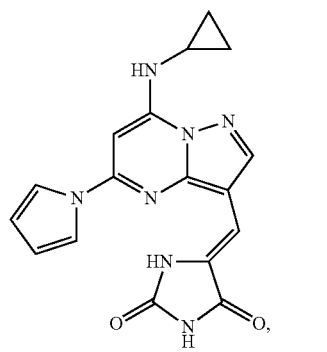
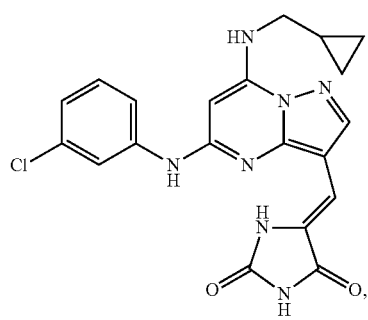
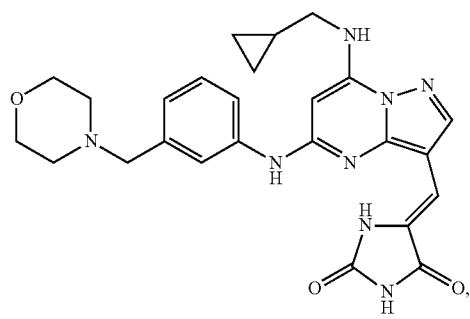
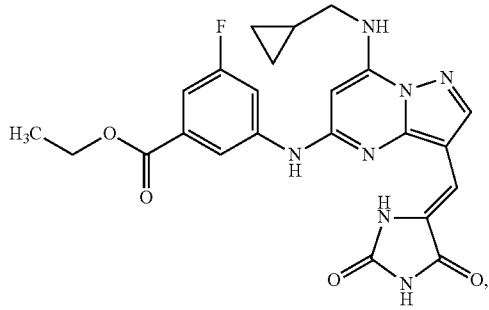
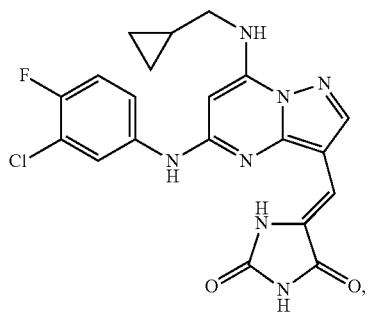
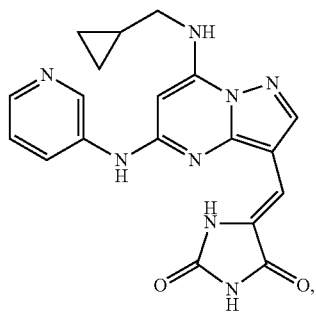
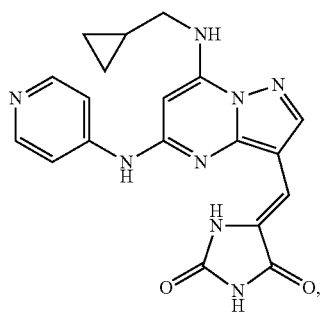
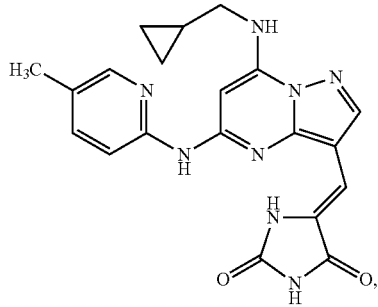

697
-continued
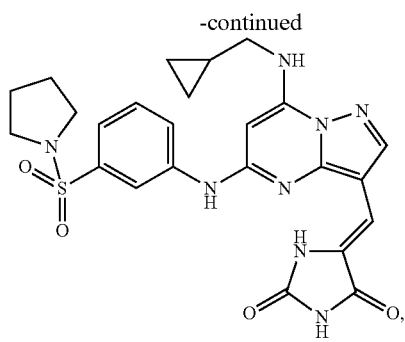
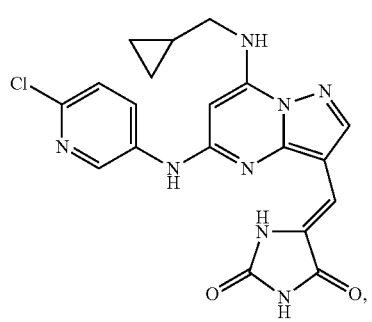
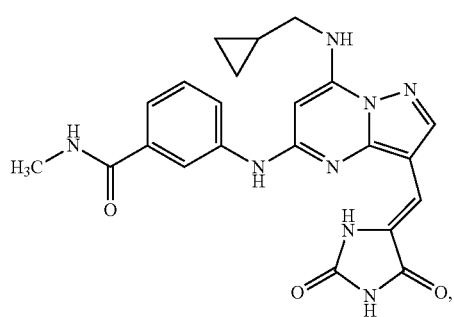
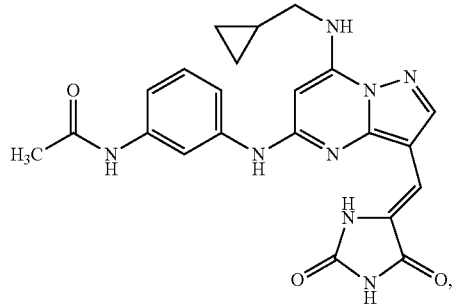
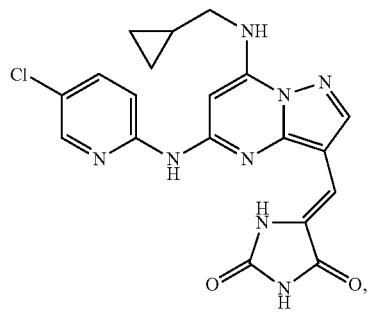
698
-continued
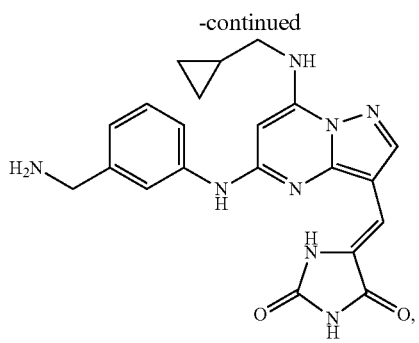
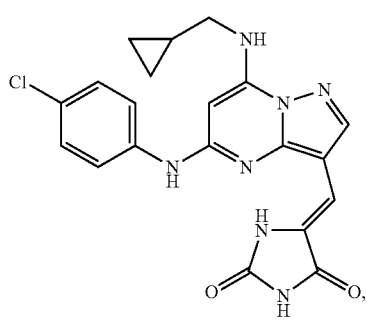
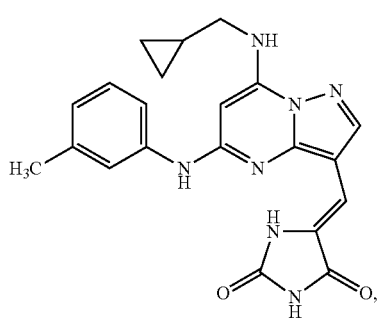
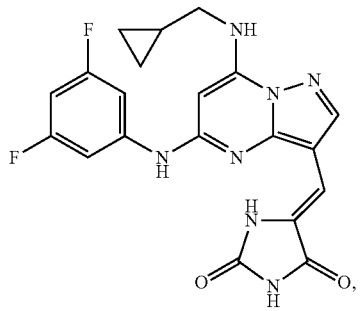
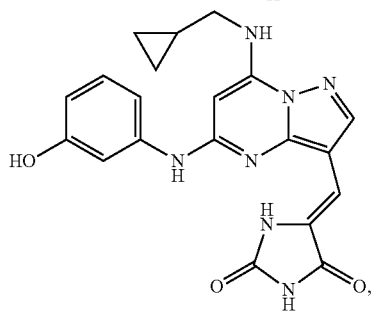

| 699 -continued | 700 -continued |
|---|---|
| 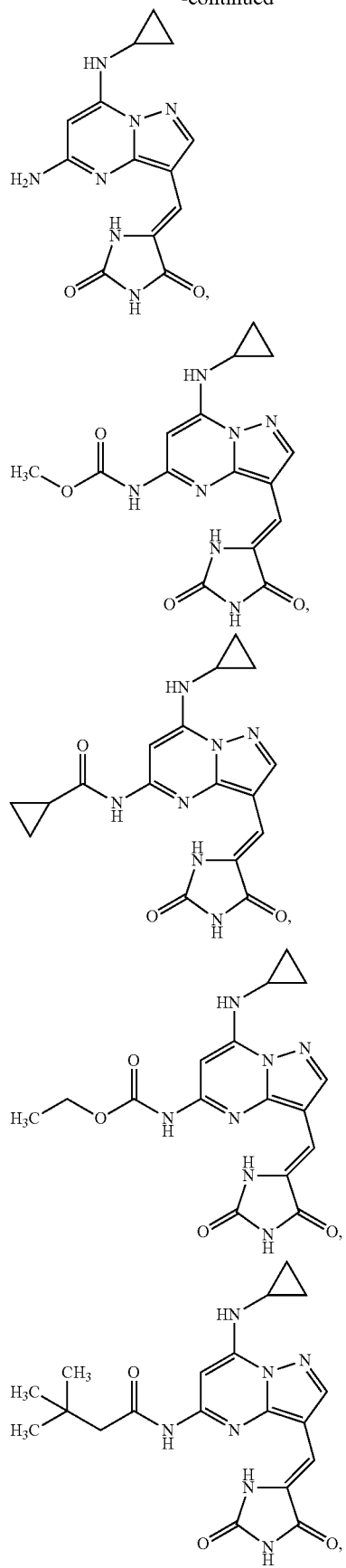 | 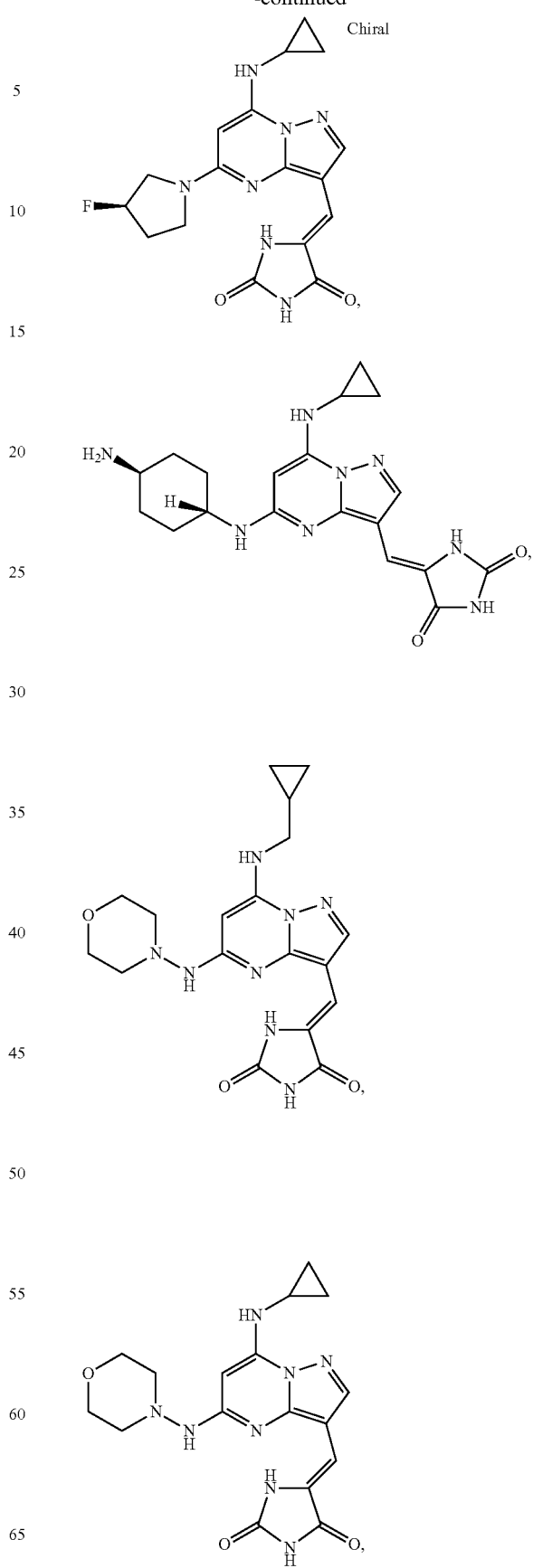 |

701
-continued
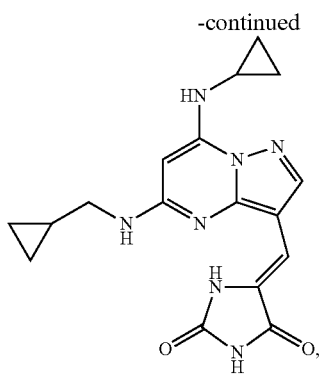
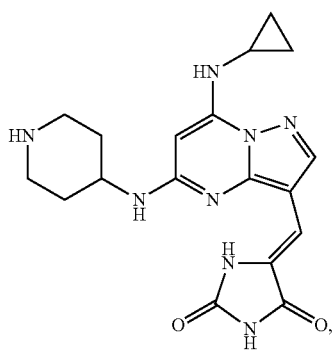
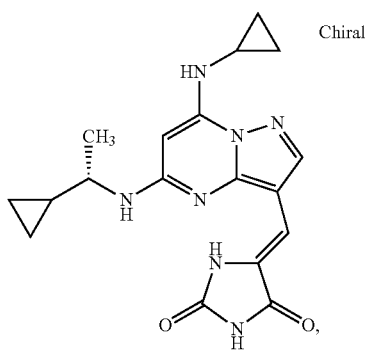
Chiral
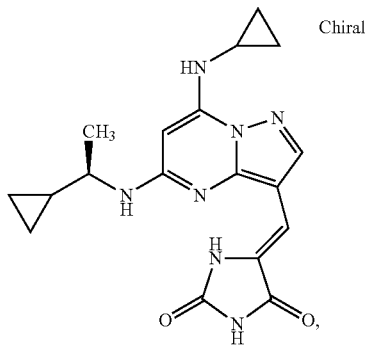
Chiral
702
-continued
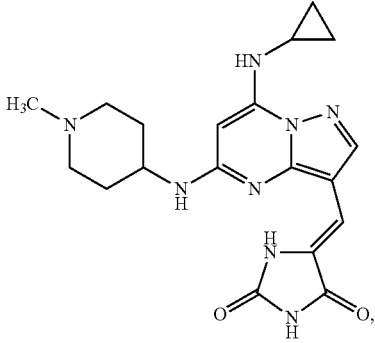
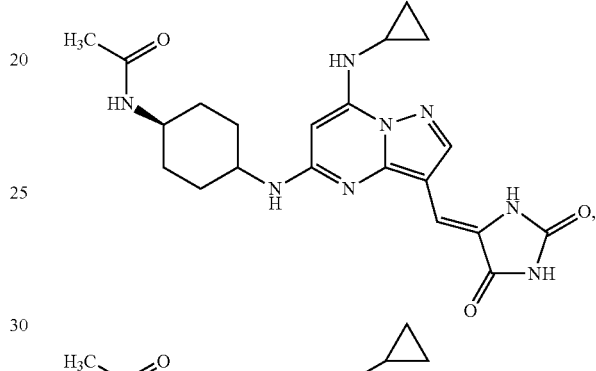
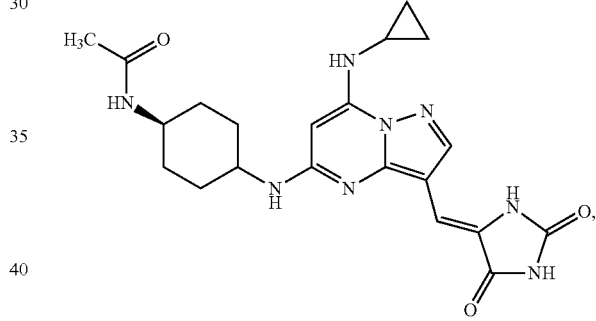
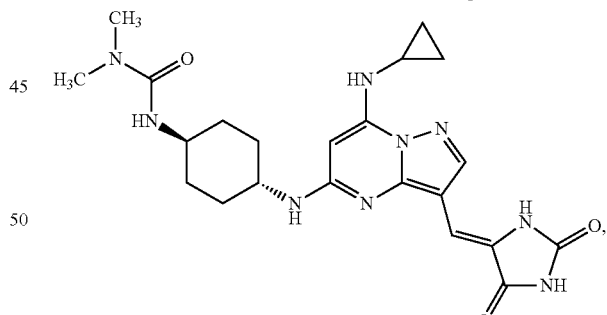
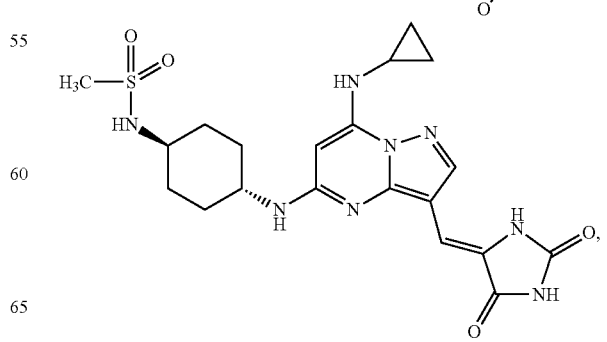

703
-continued
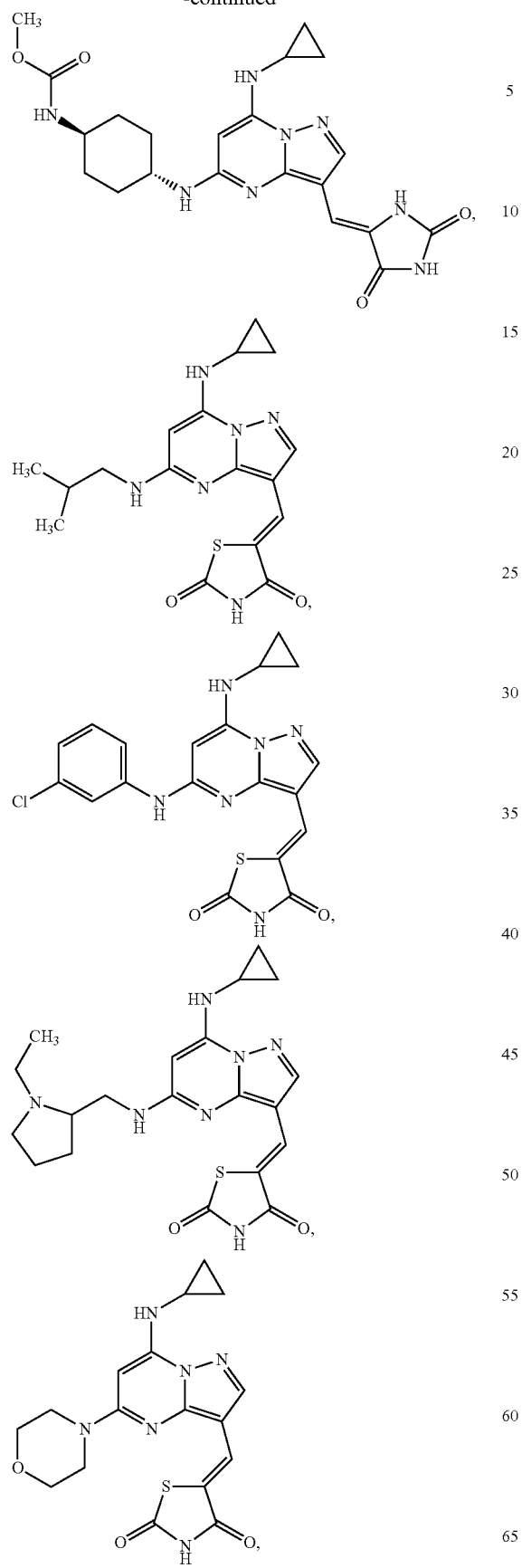
704
-continued
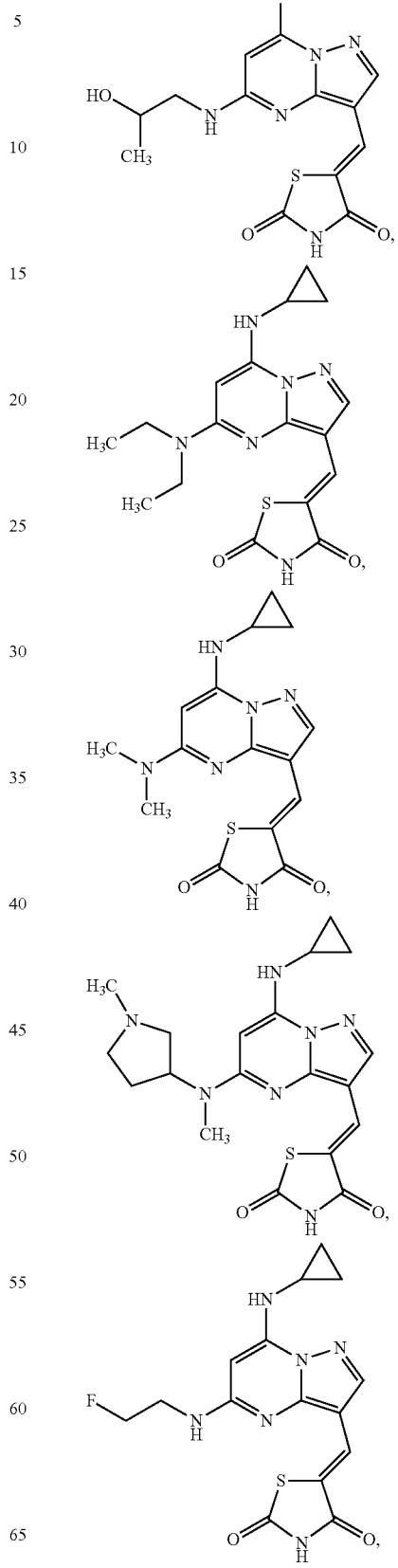

705
-continued
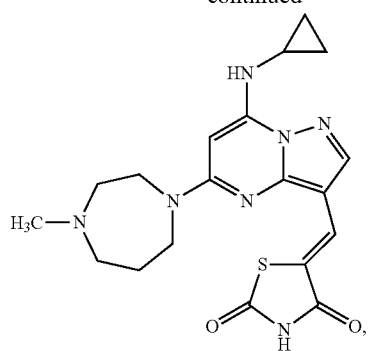
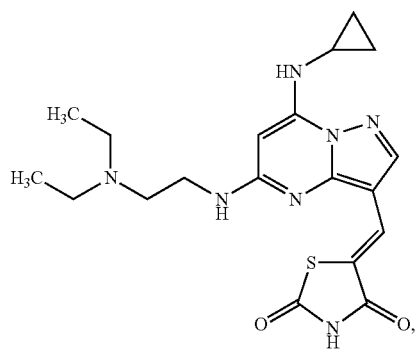
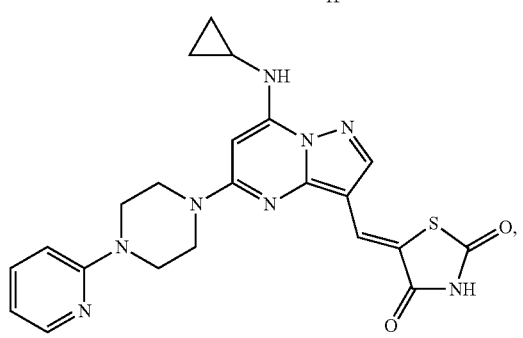
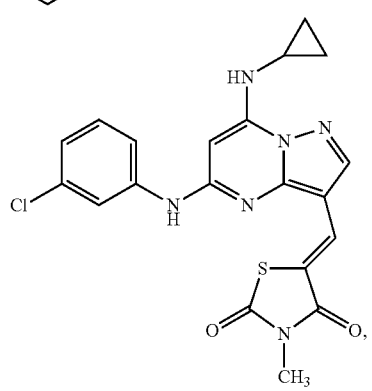
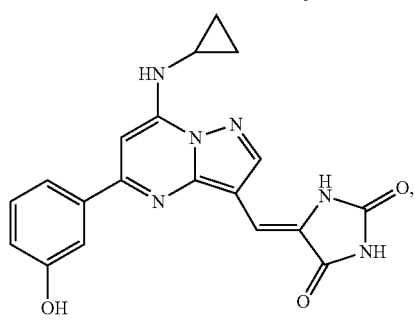
706
-continued
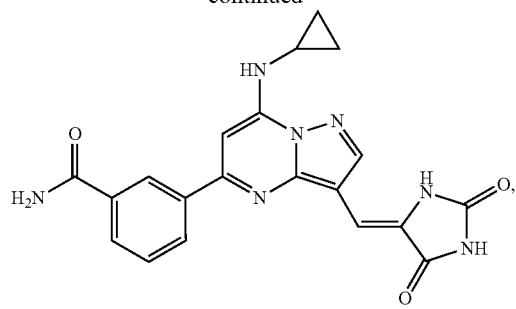
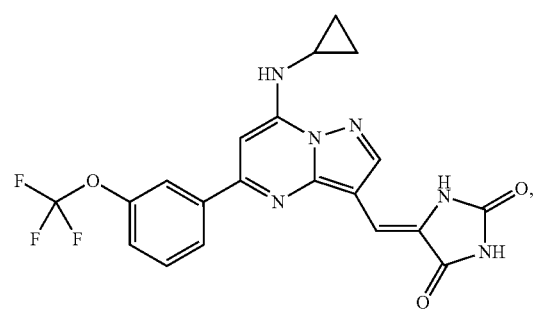
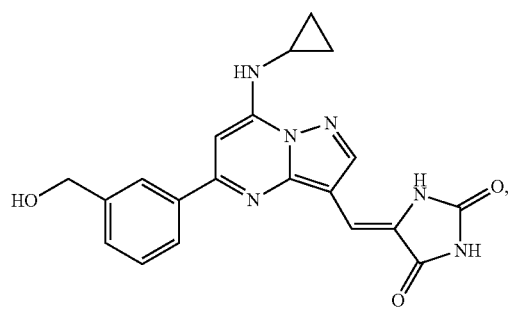
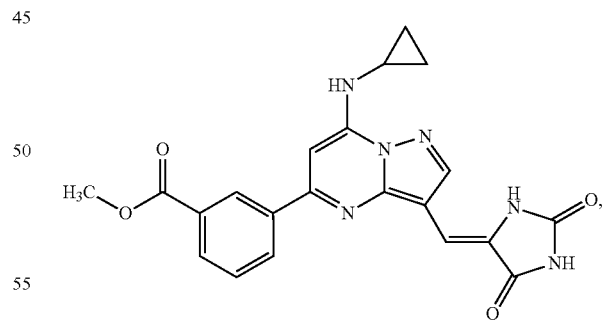
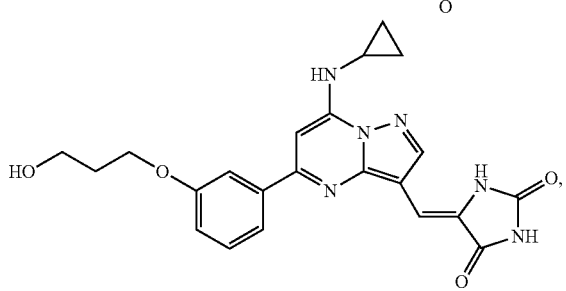

707
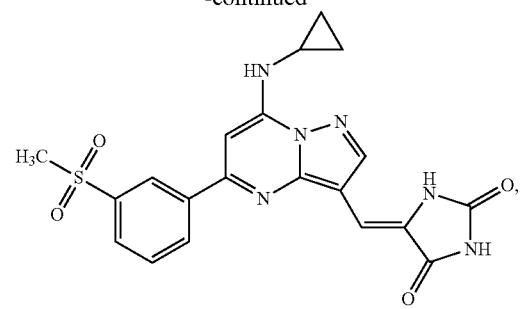
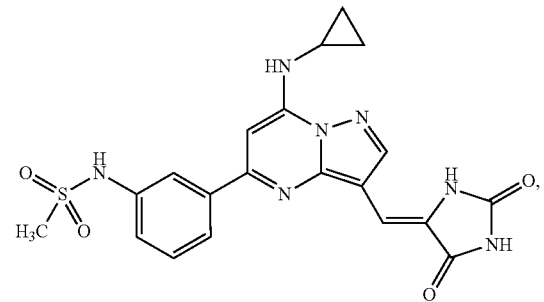
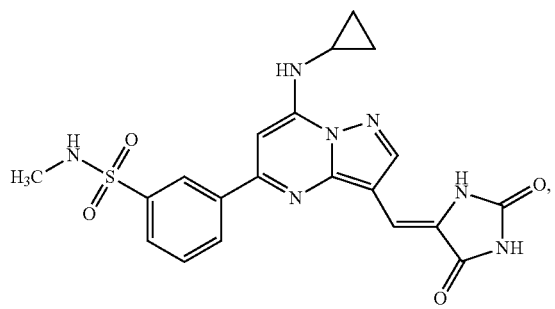
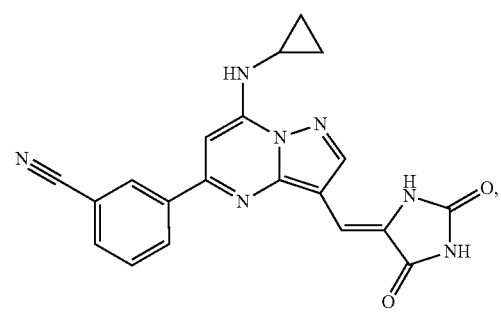
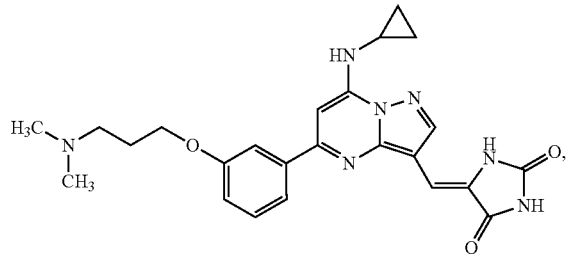
708
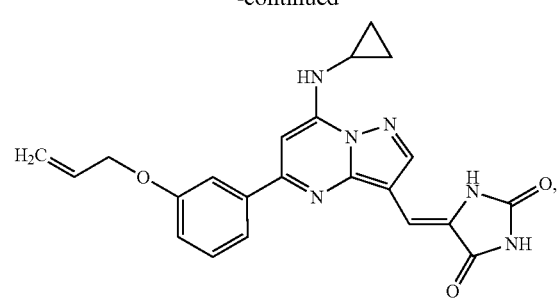
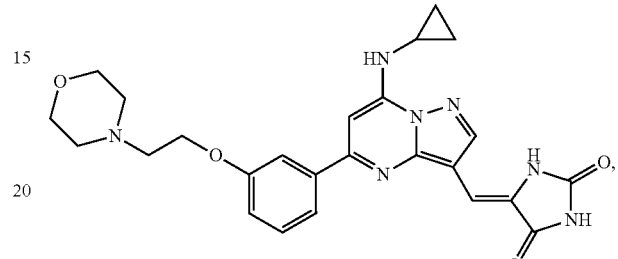
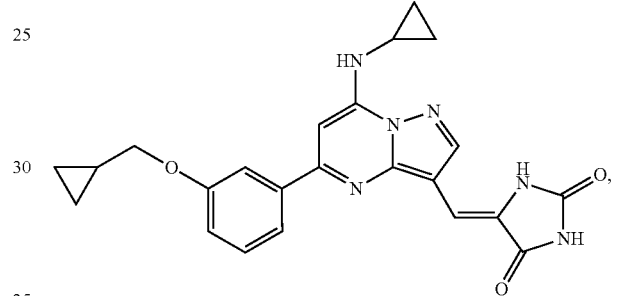
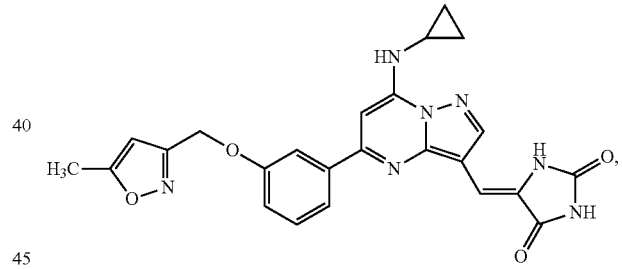
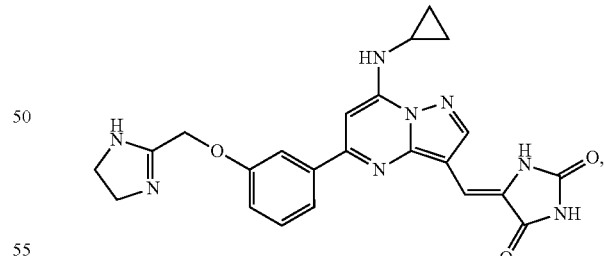
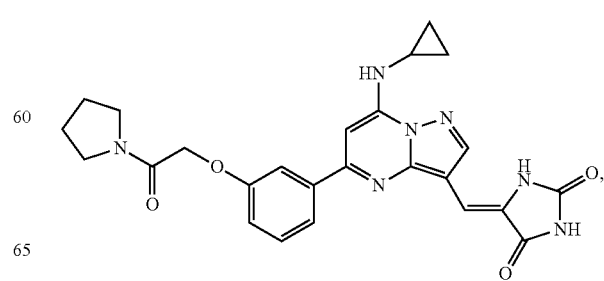

709
-continued
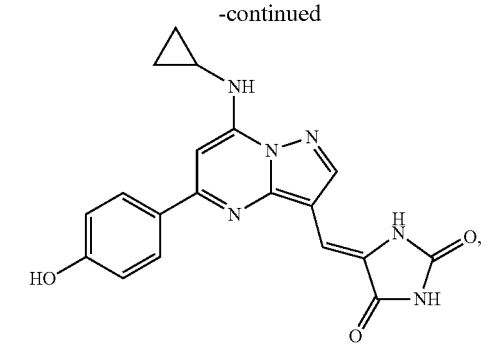
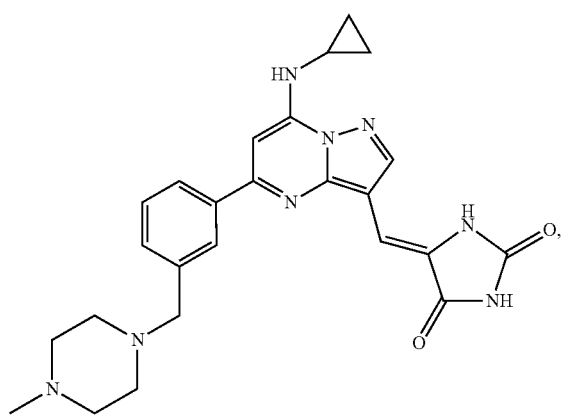
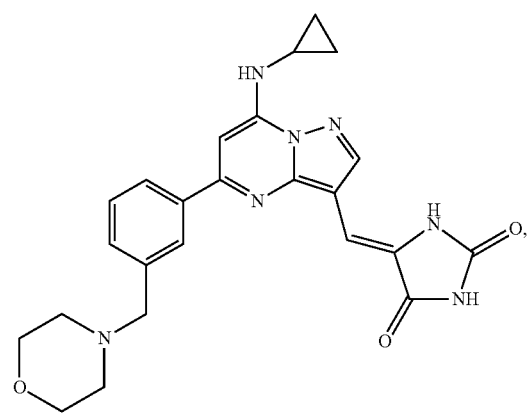
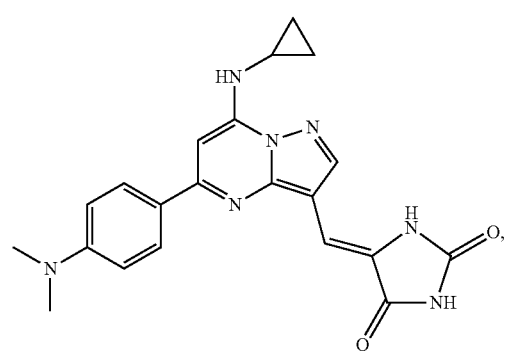
710
-continued
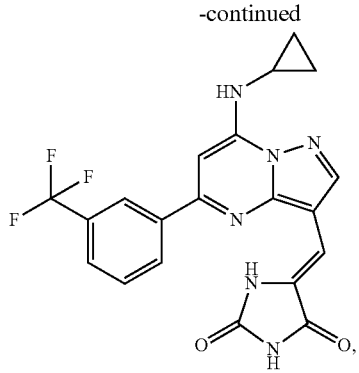
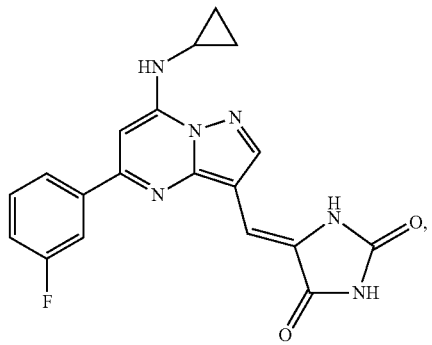
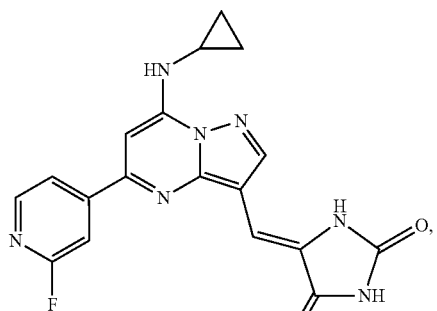
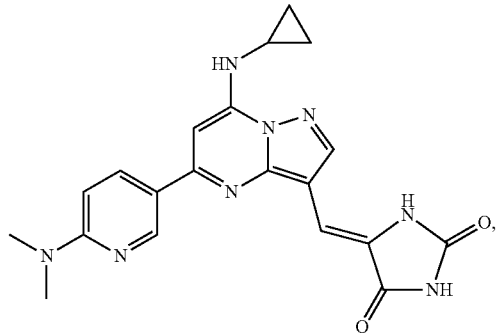
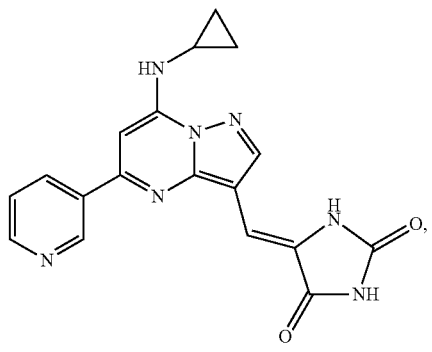

711
-continued
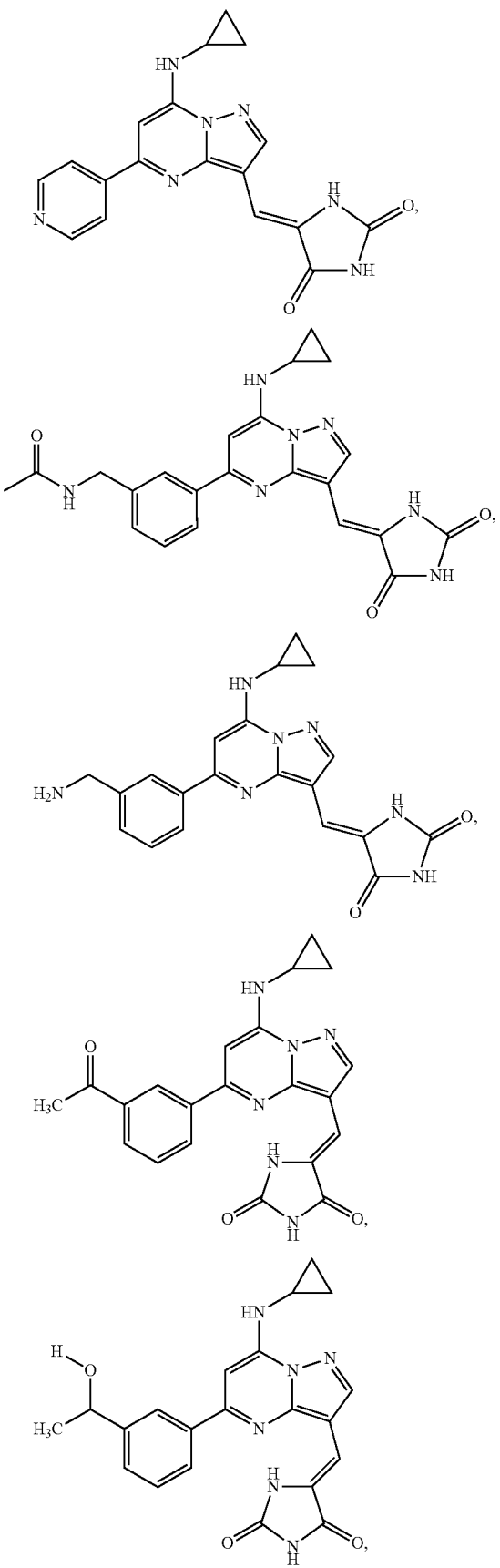
712
-continued
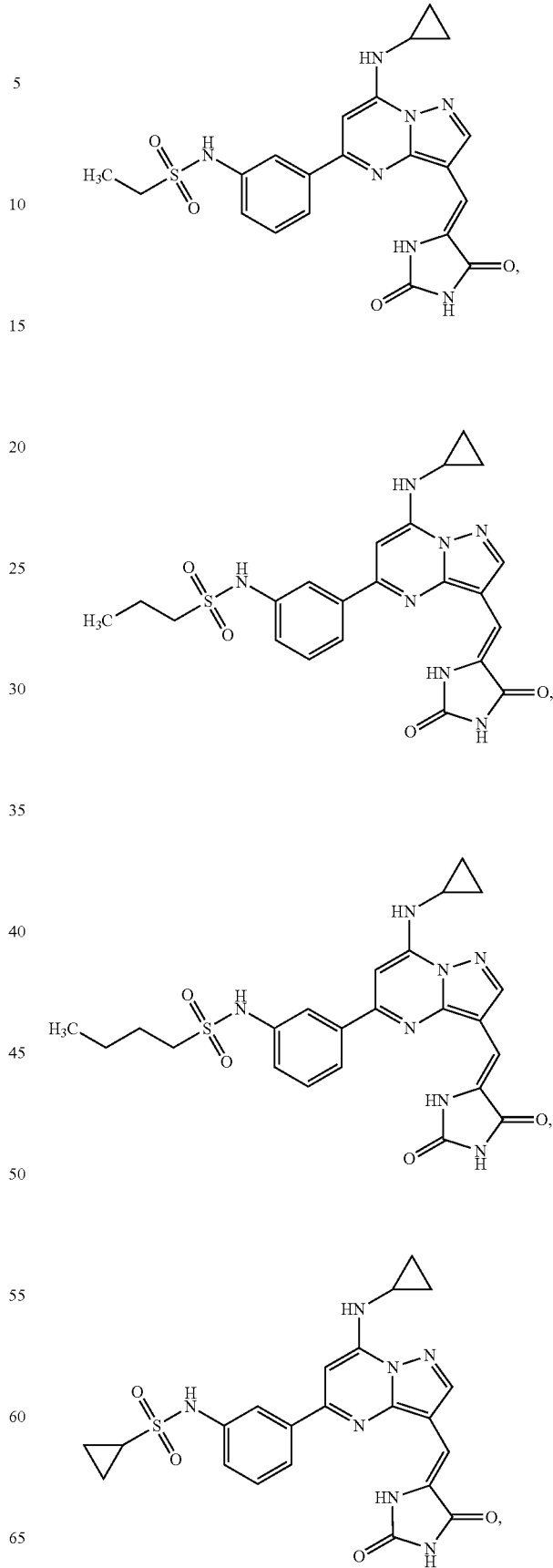

713
-continued
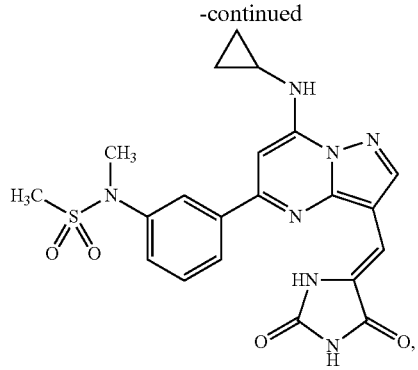
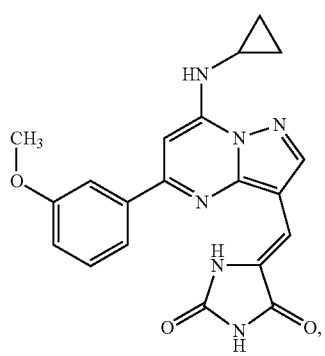
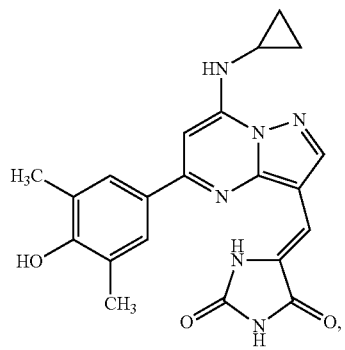
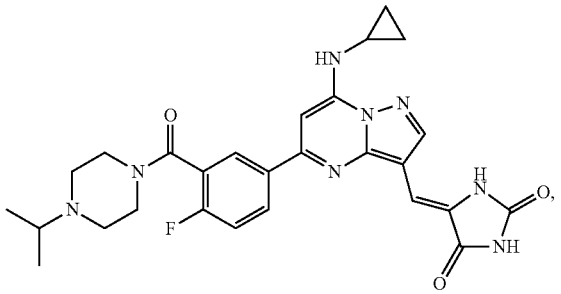
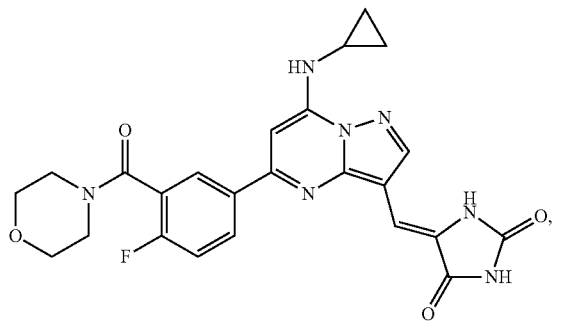
714
-continued
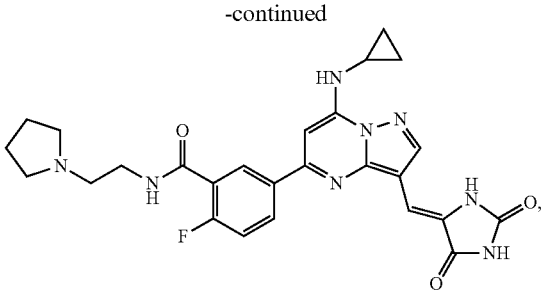
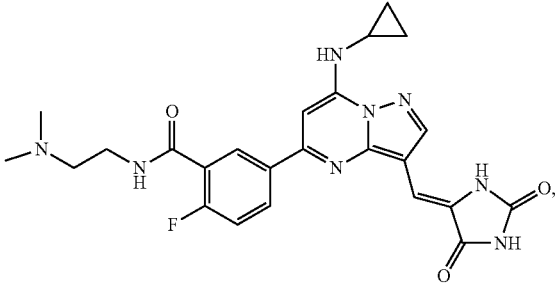
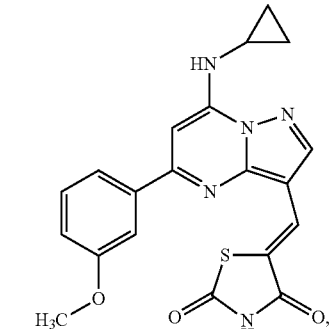
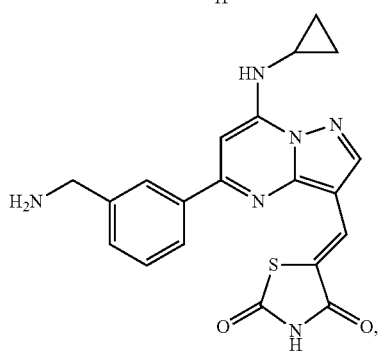
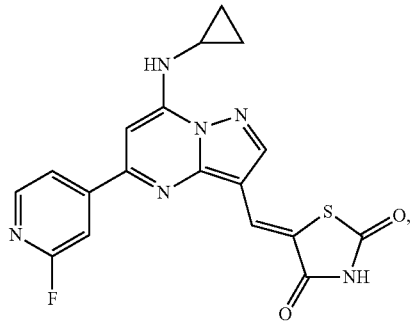

715
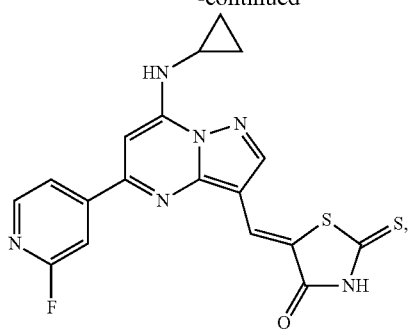
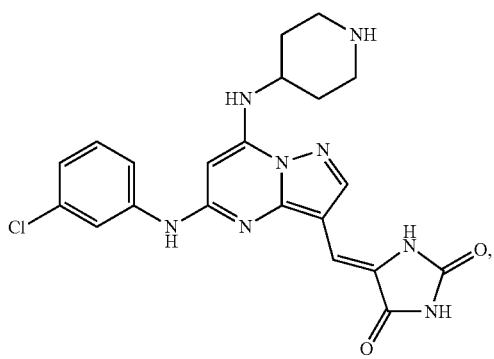
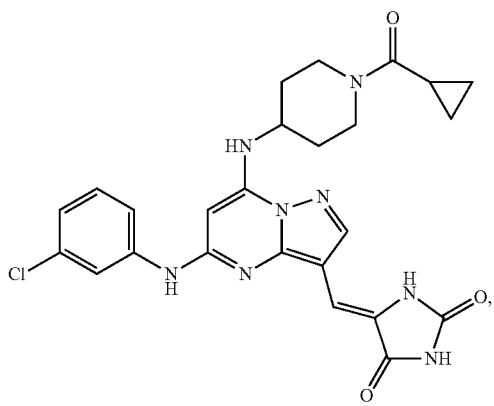
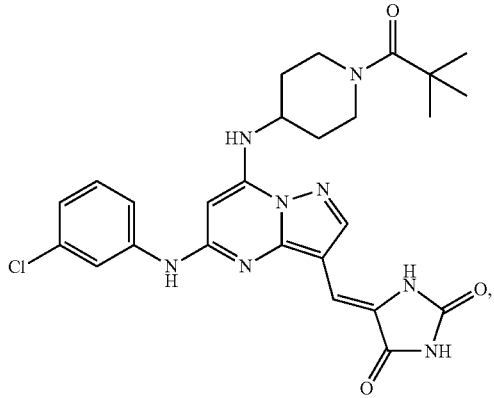
716
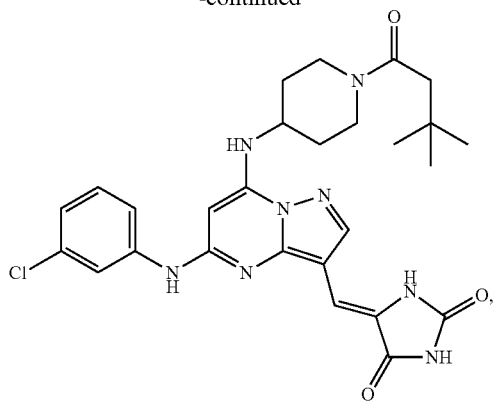
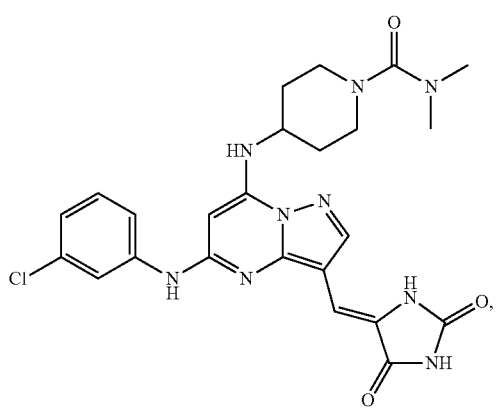
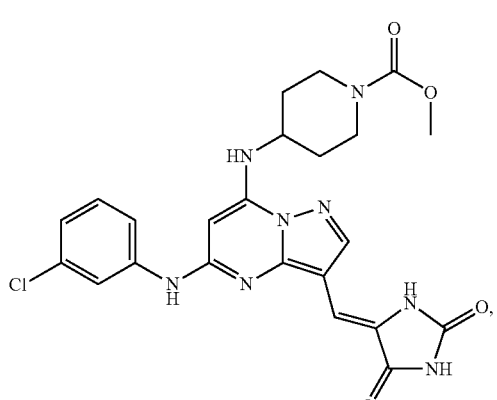
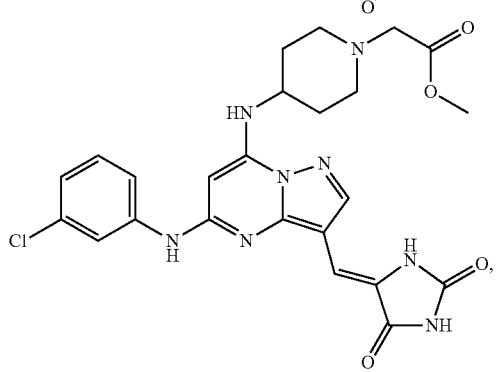

717 -continued

718 -continued

719
-continued
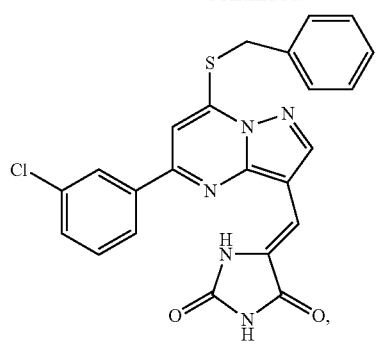
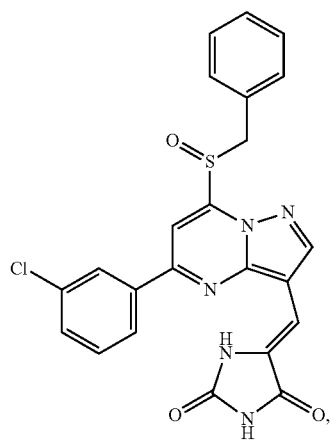
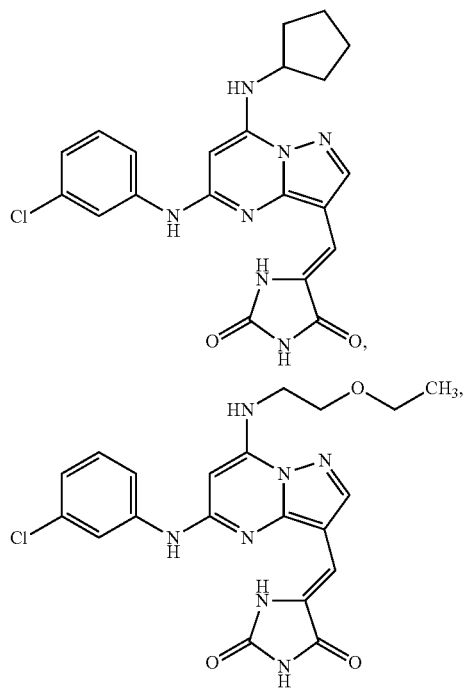
720
-continued
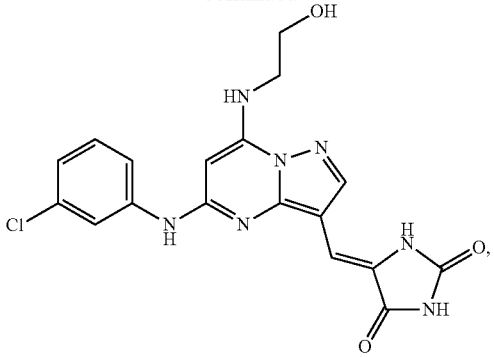
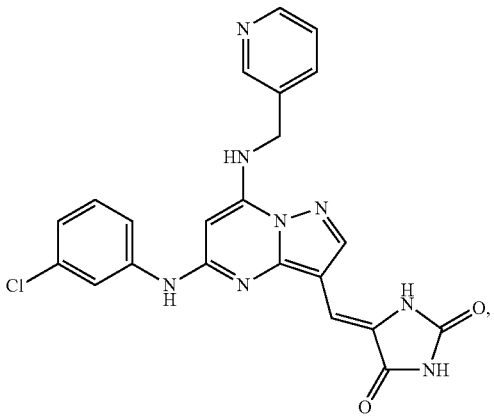
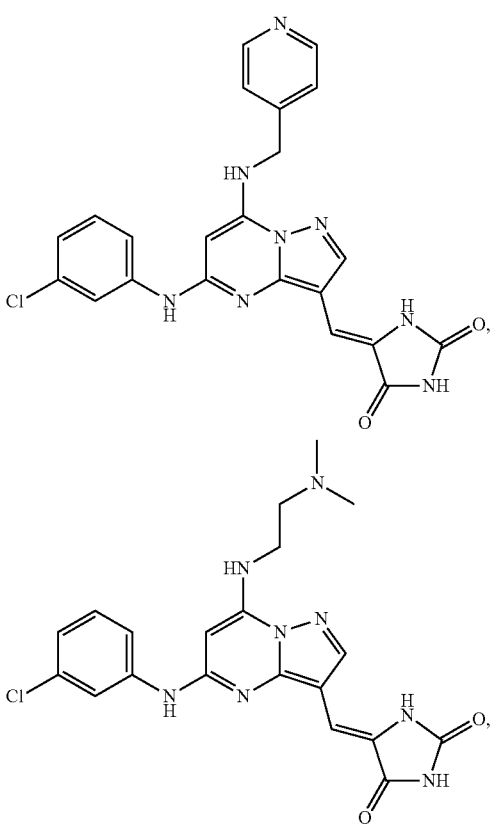

721
-continued
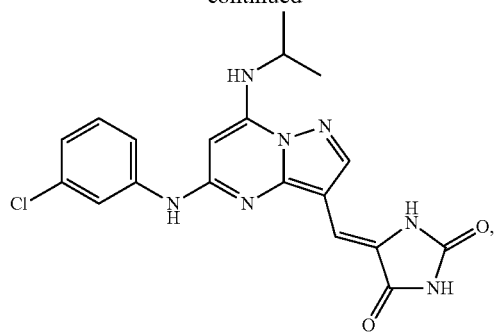
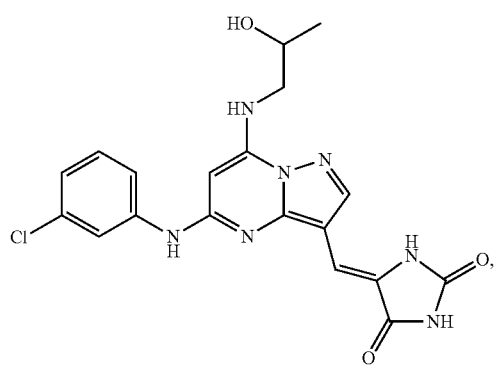
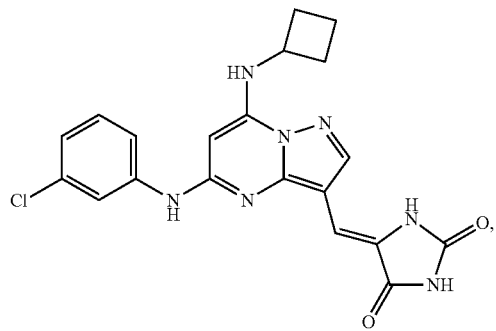
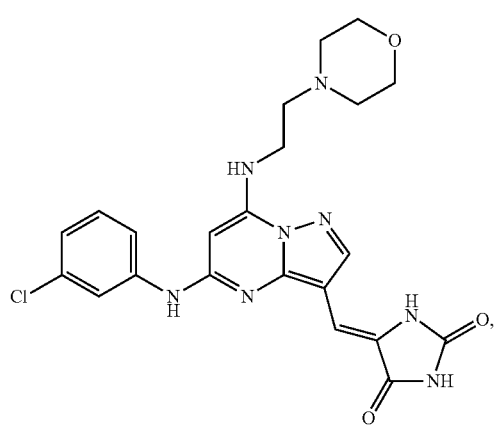
722
-continued
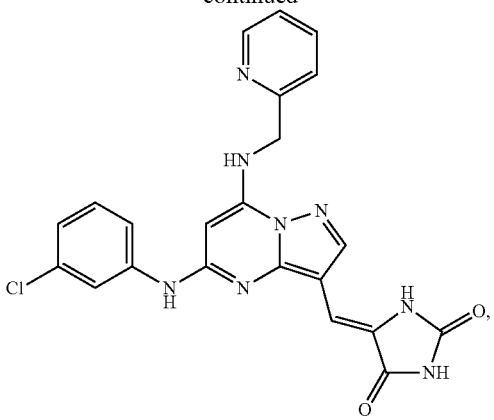
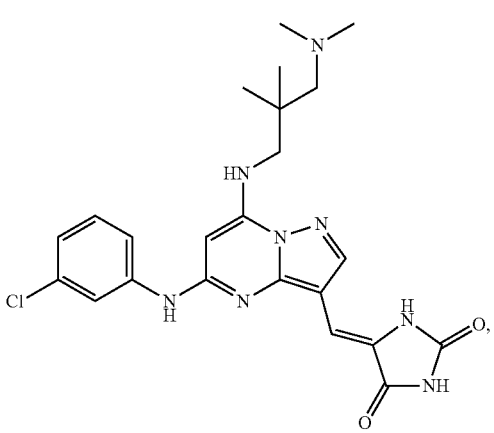
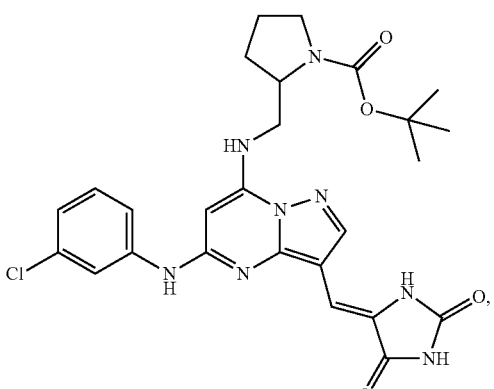
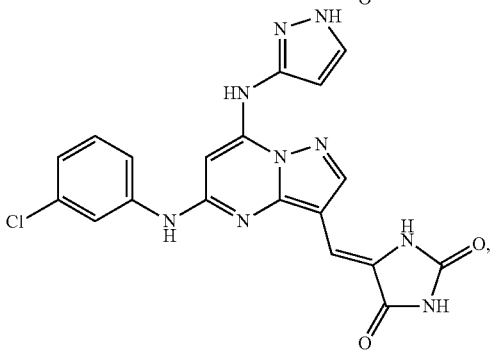

723
-continued
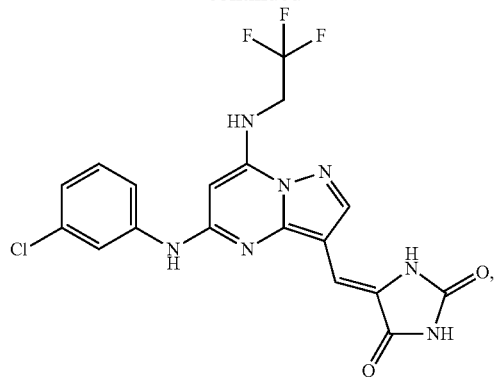
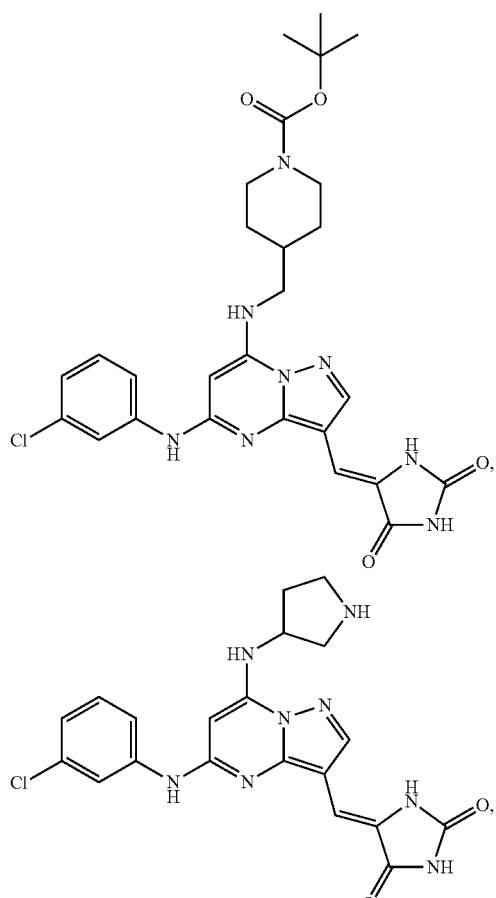
724
-continued
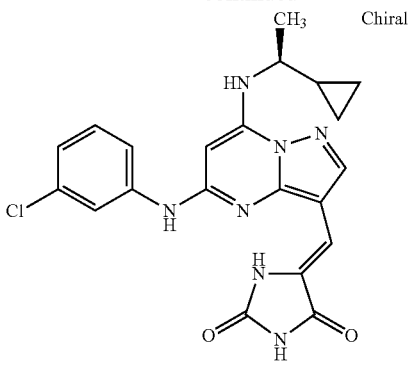
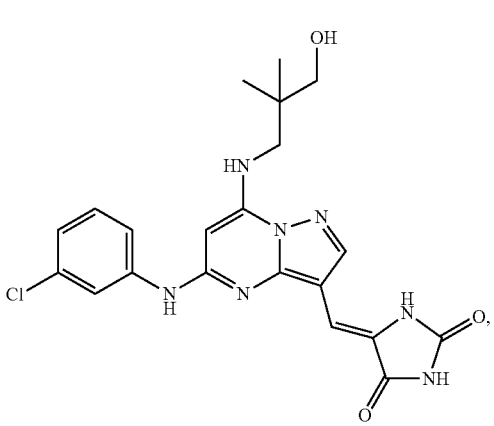
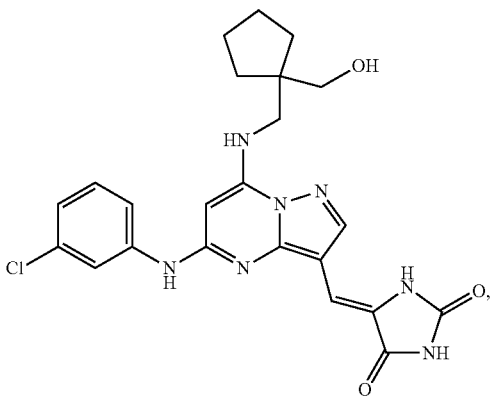
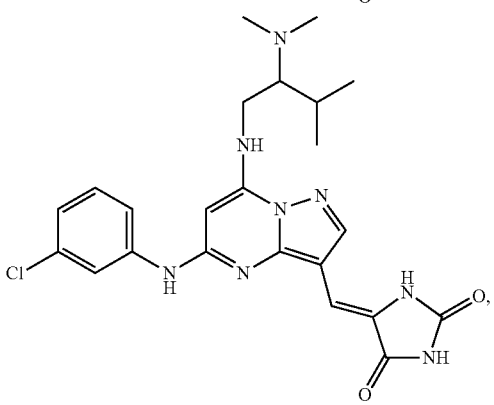

725
-continued
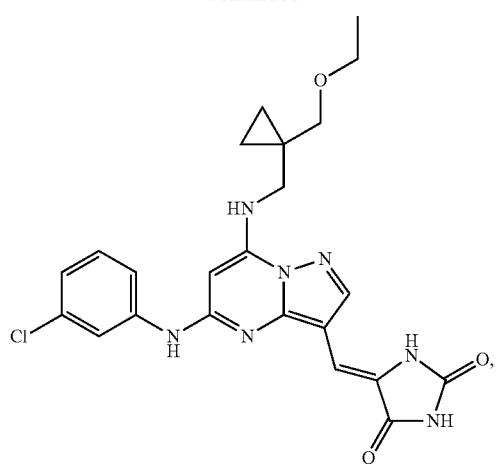
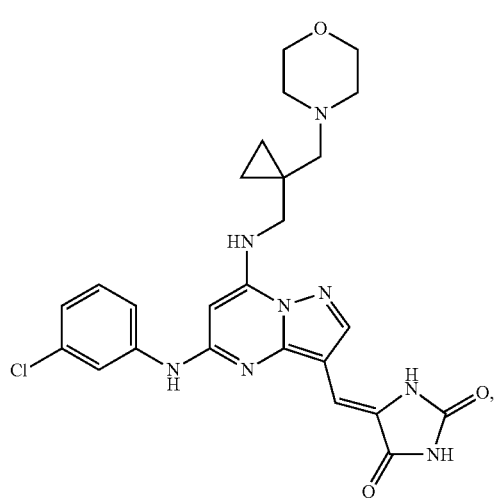
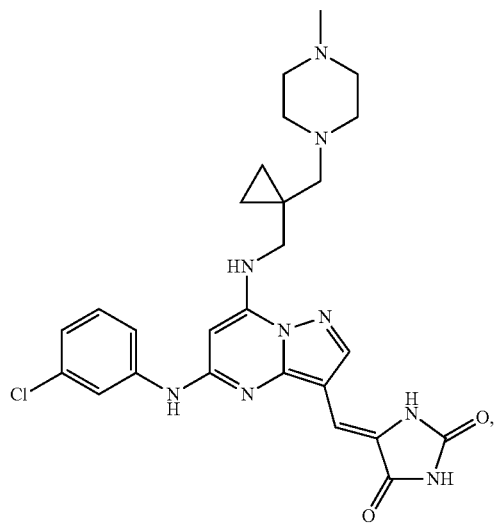
726
-continued
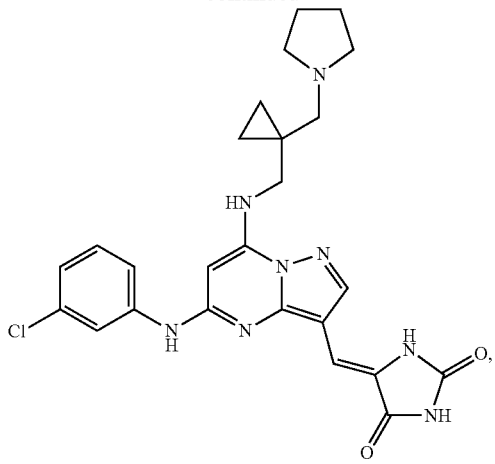
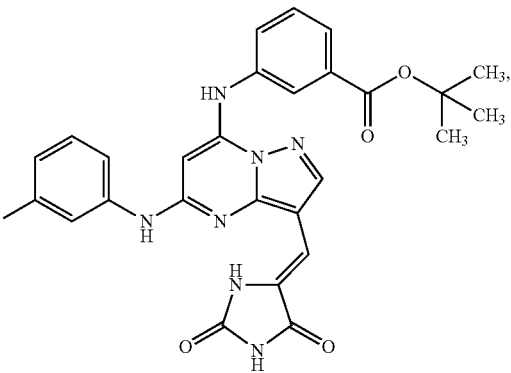
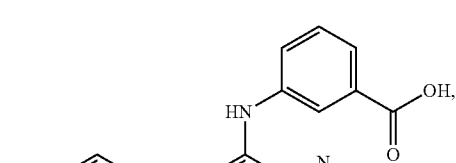
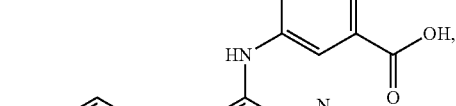

727
-continued
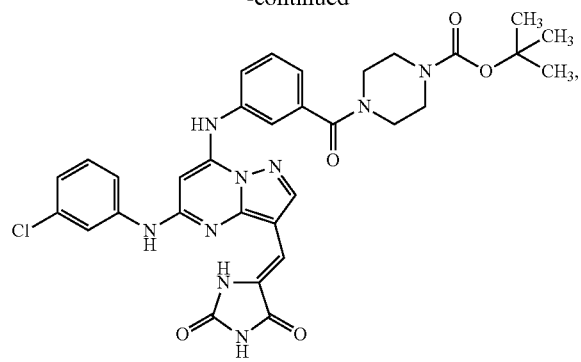
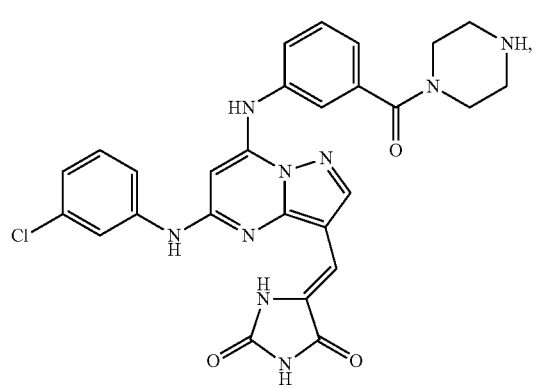
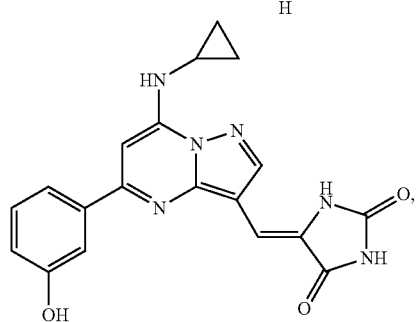
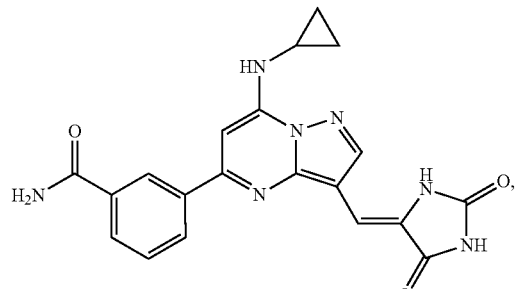
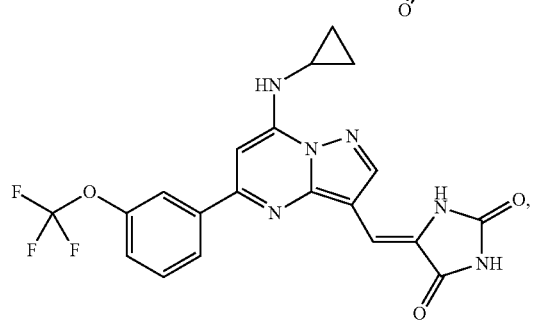
728
-continued
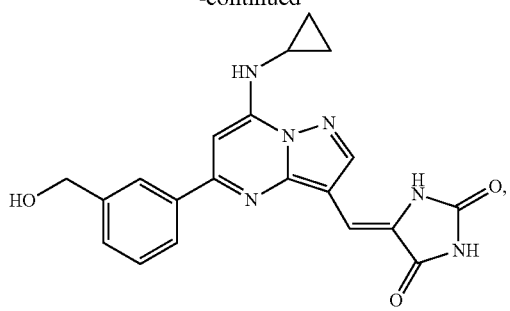
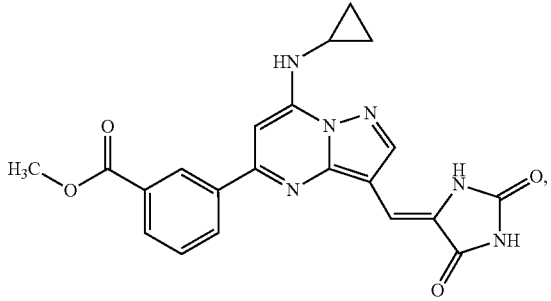
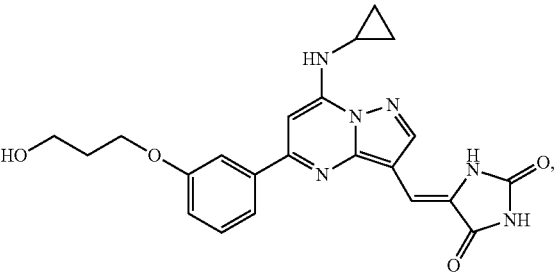
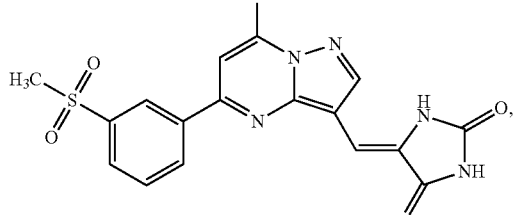
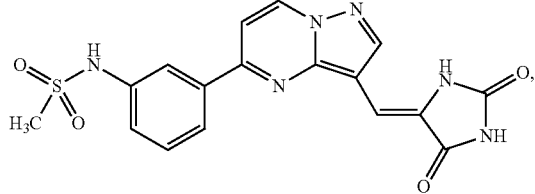

729
-continued
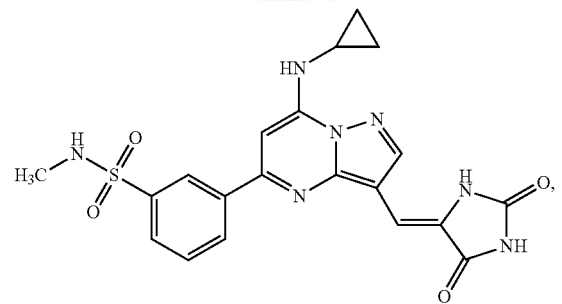
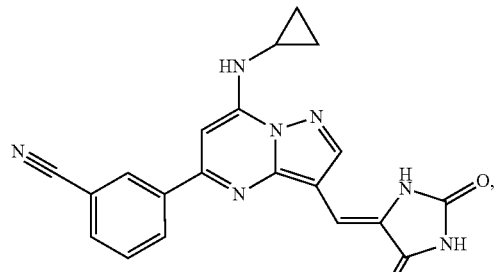
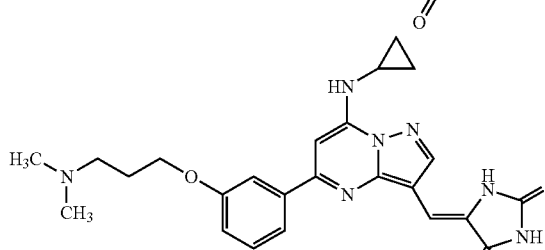
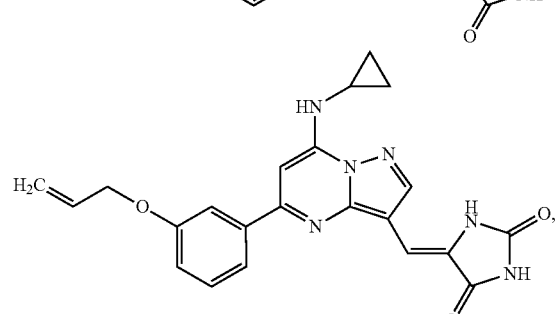
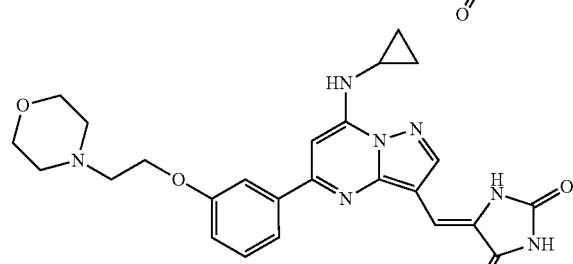
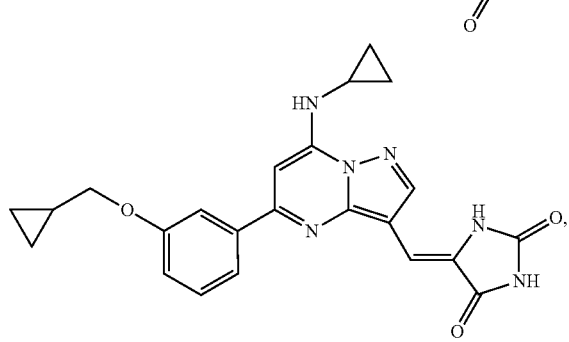
730
-continued
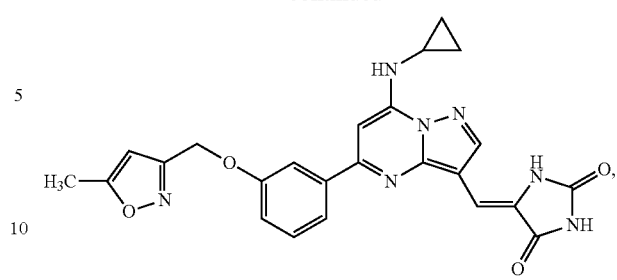
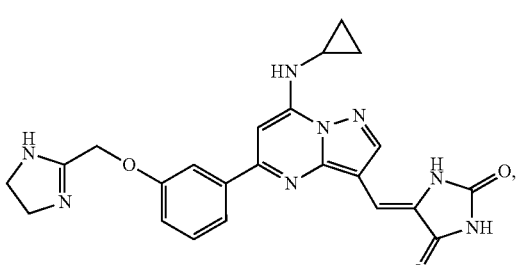
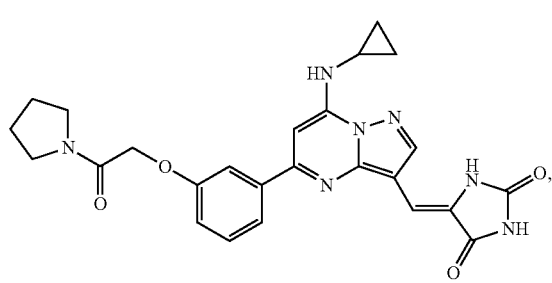
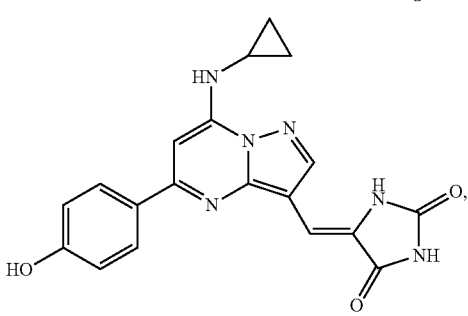
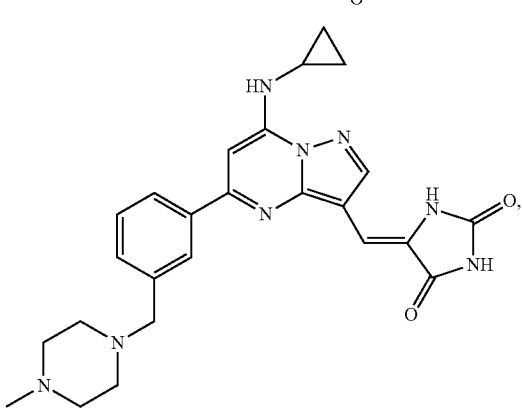

731
-continued
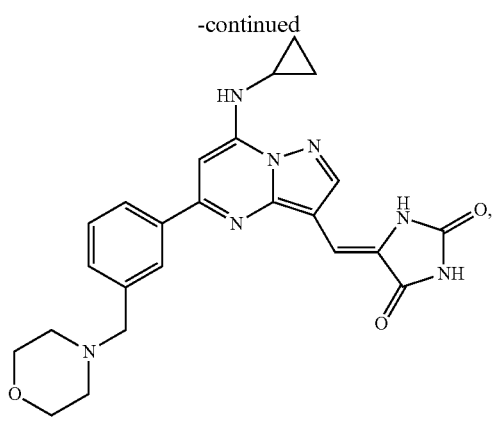
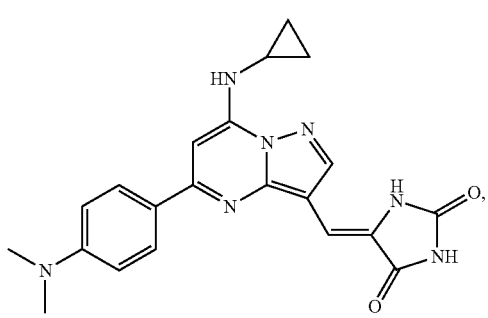
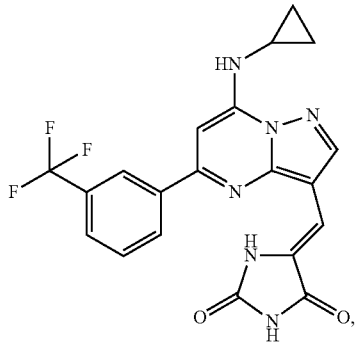
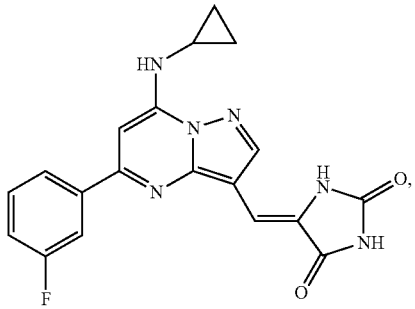
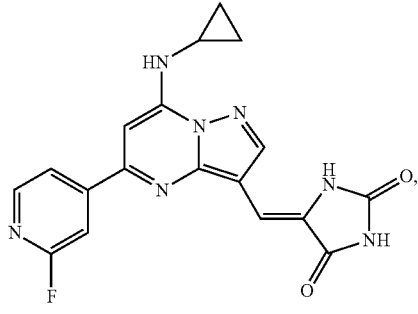
732
-continued
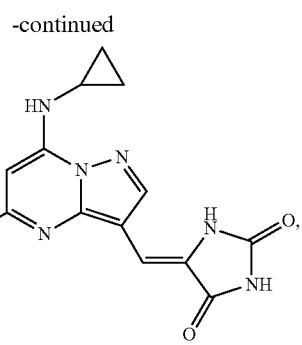
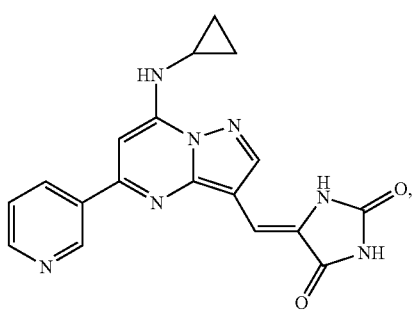
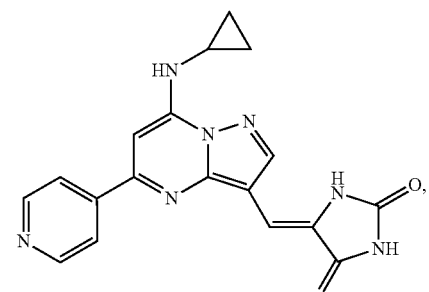
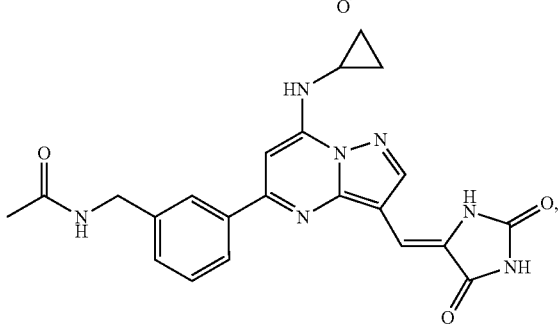
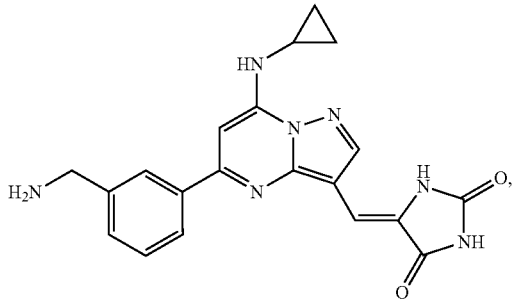

733
-continued
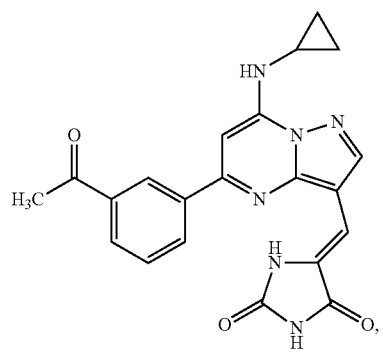
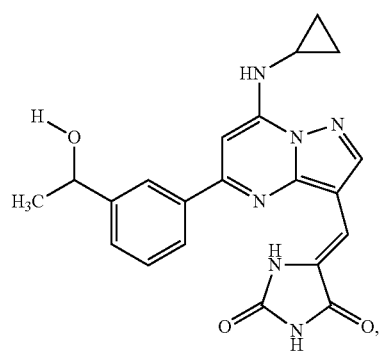
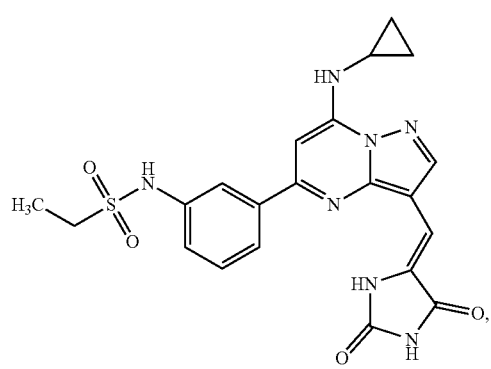
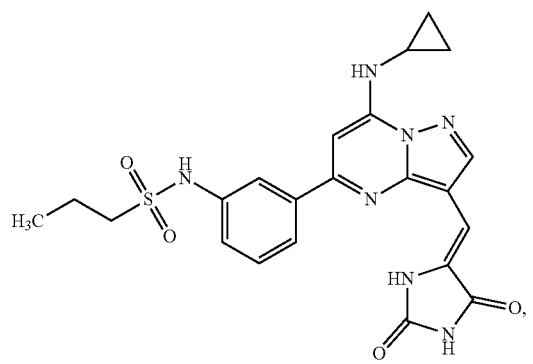
734
-continued
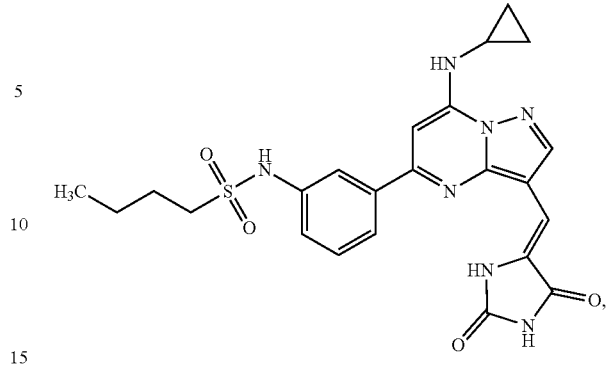
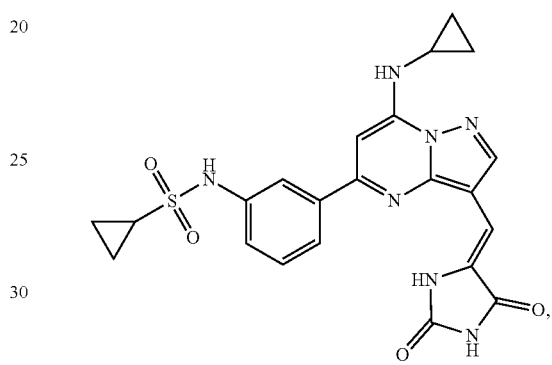
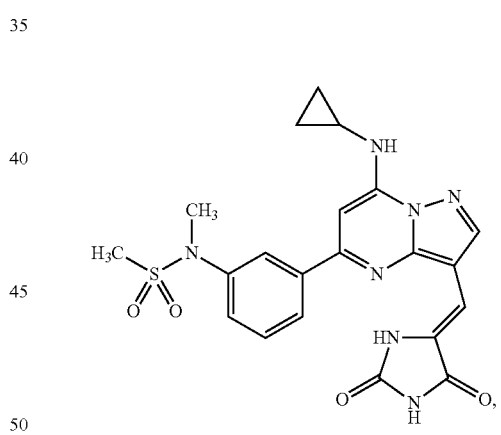
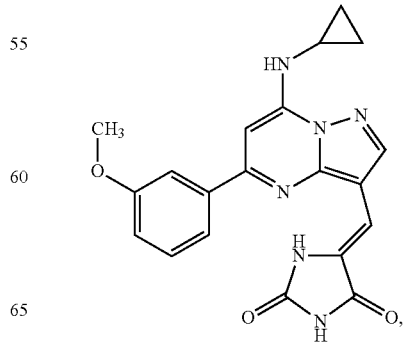

735
-continued
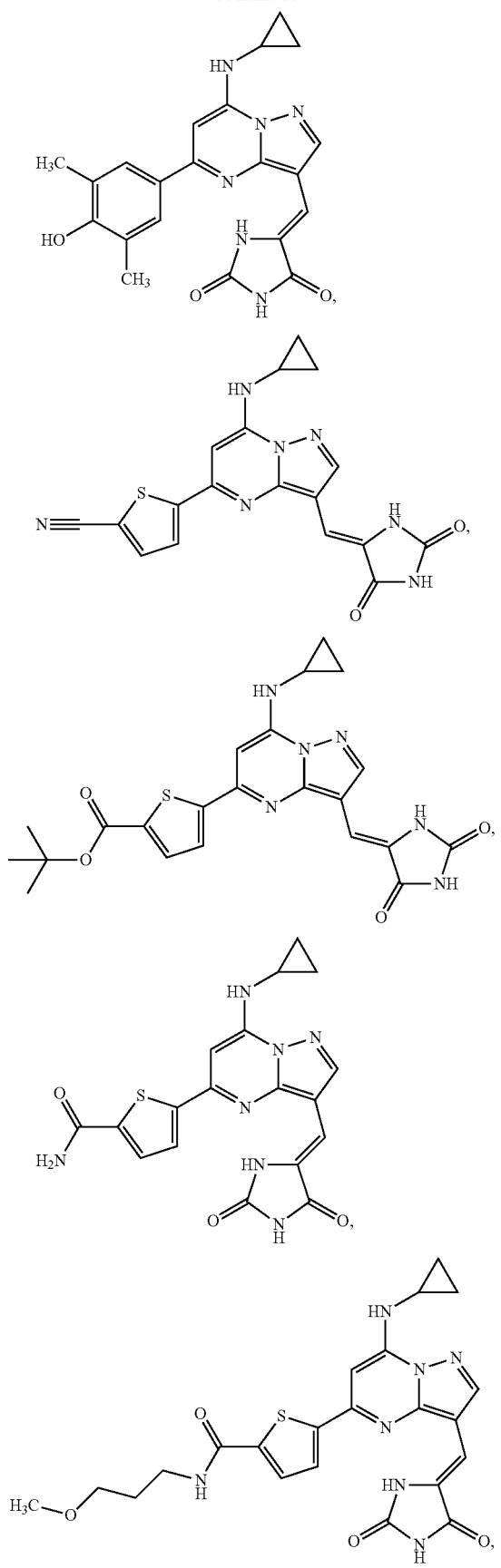
736
-continued
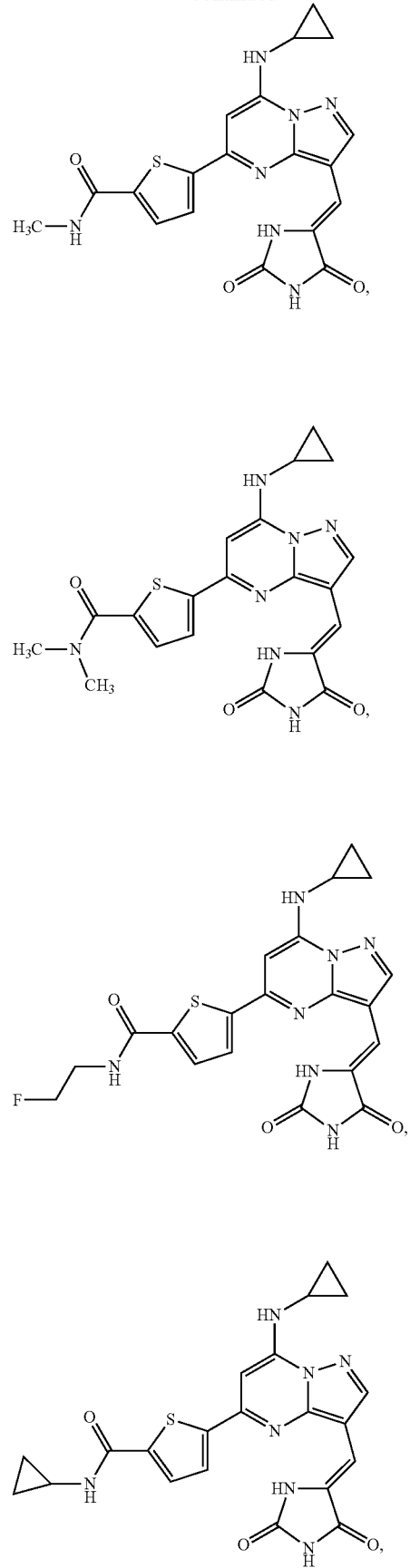

| 737 | 738 |
|---|---|
| -continued | -continued |
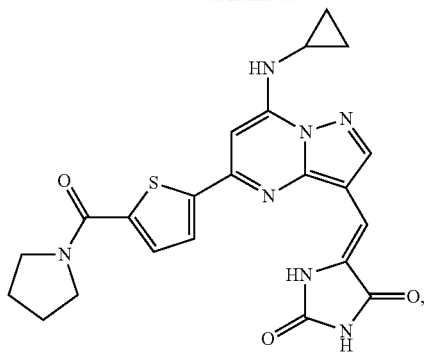
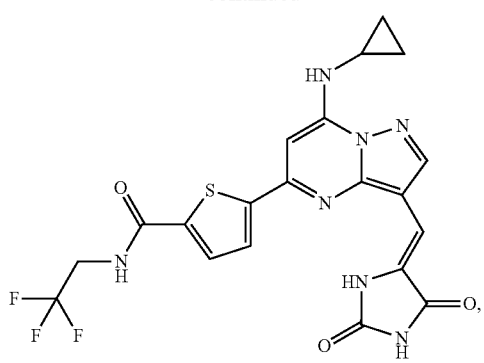
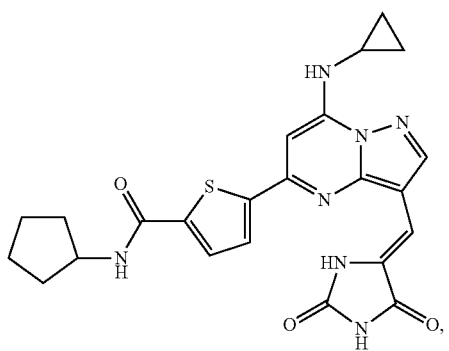
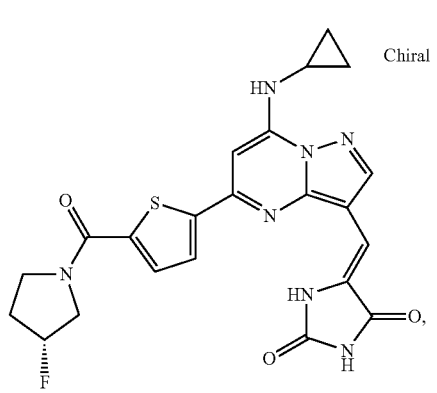
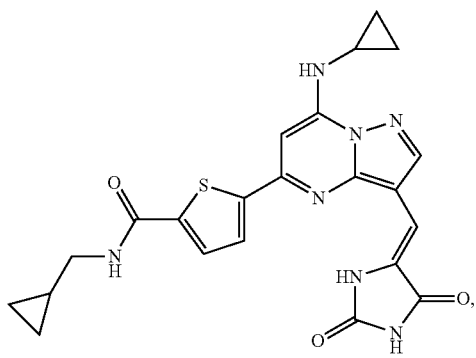
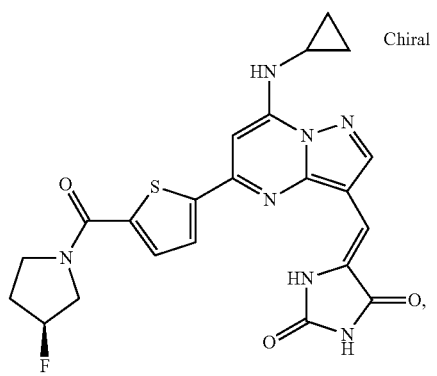
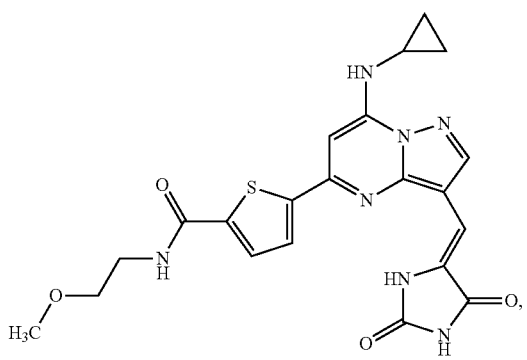
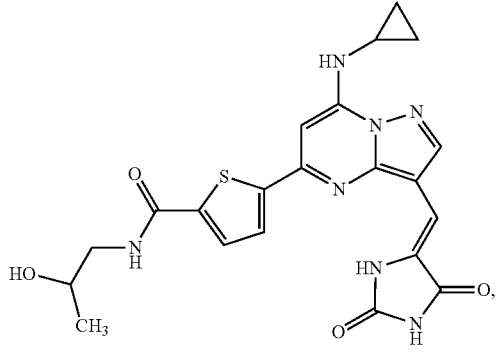

739
-continued
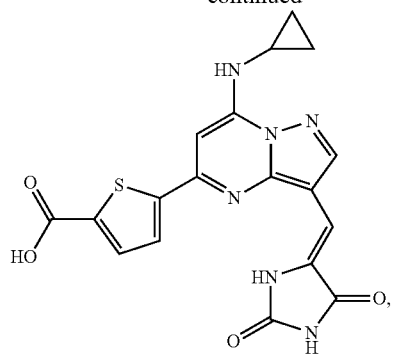
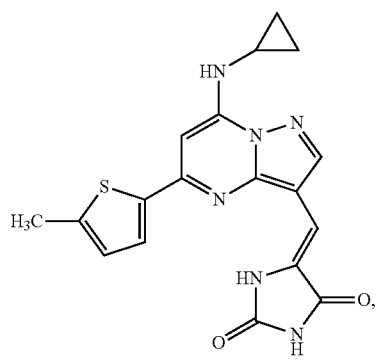
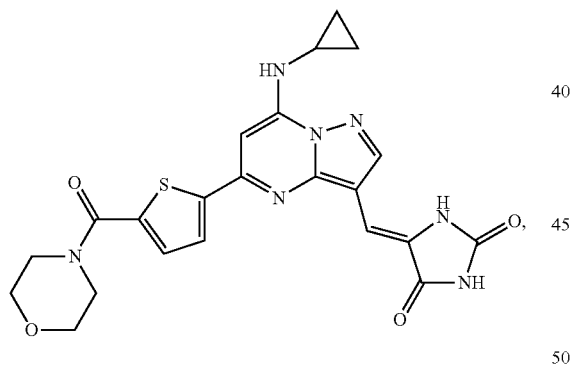
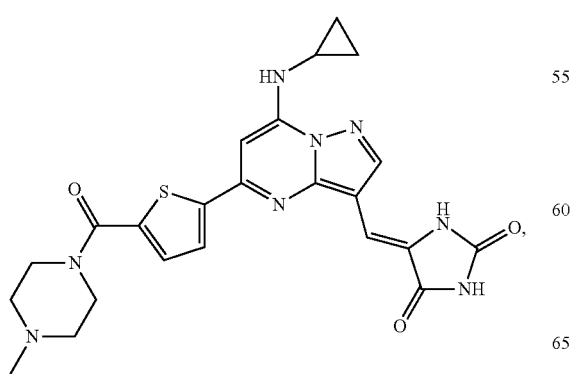
740
-continued
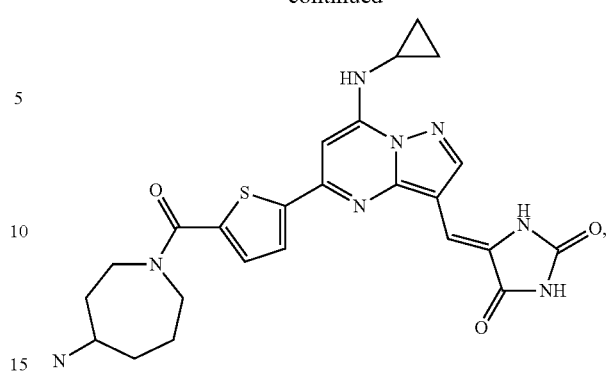
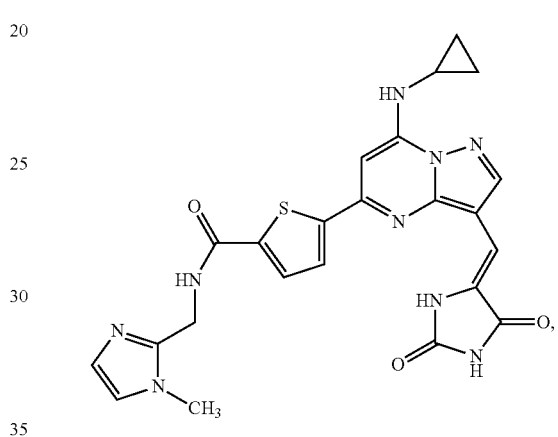
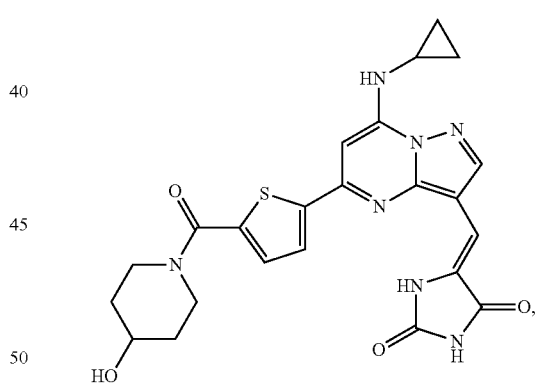
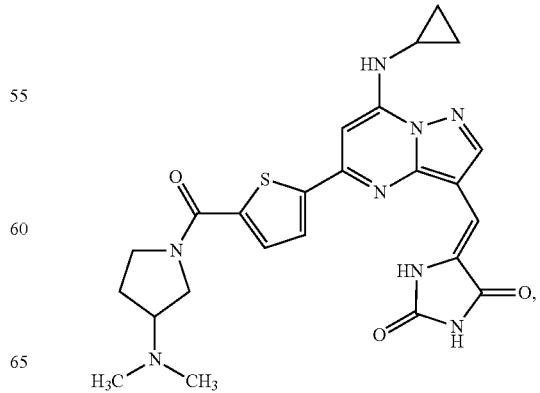

741
-continued
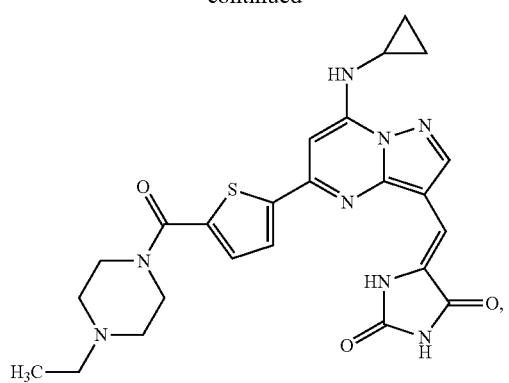
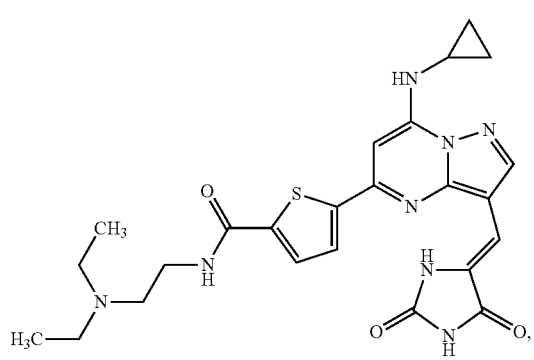
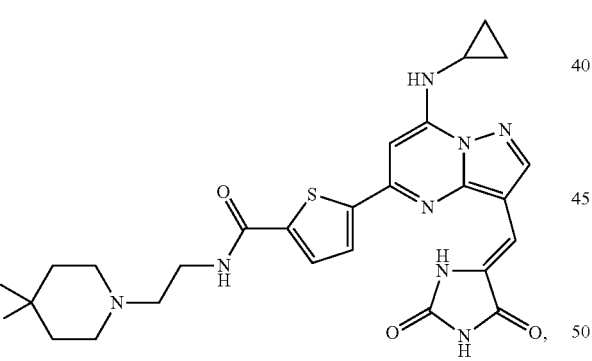
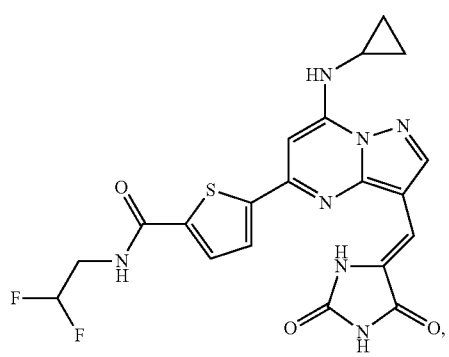
742
-continued
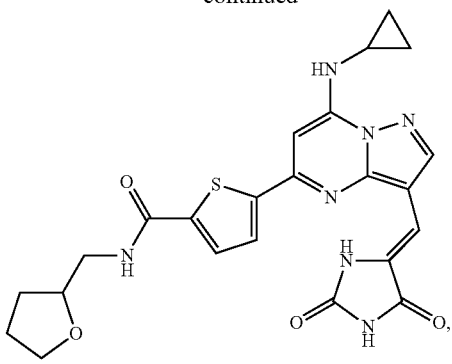
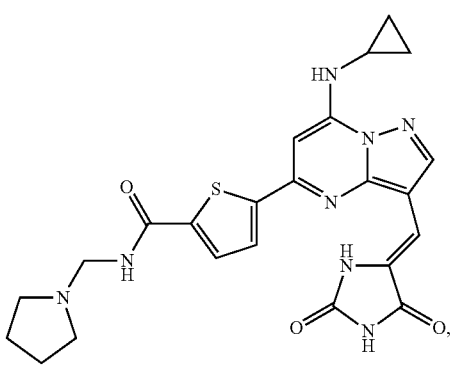
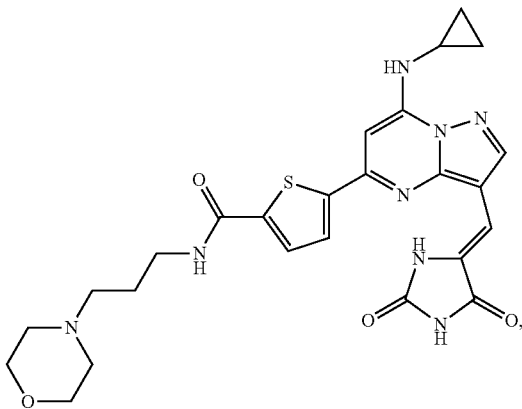
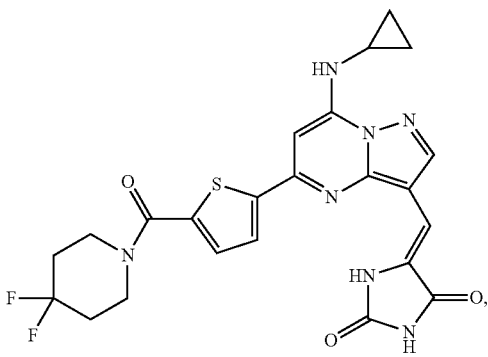

743
-continued
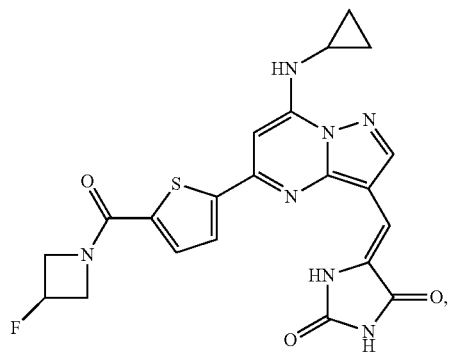
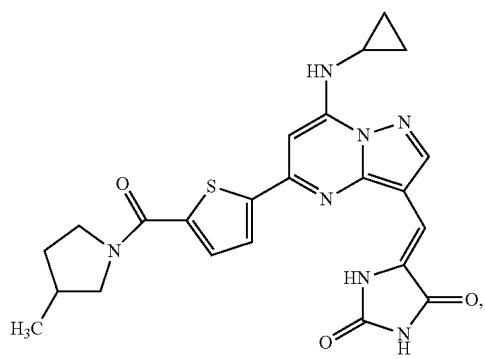
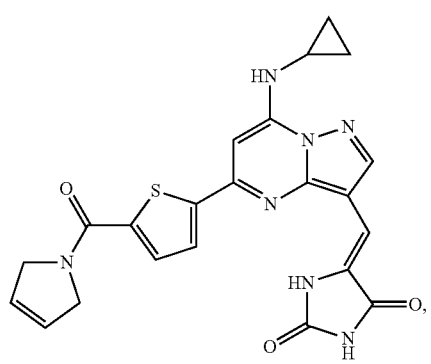
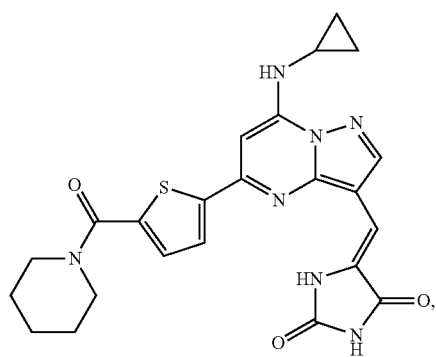
744
-continued
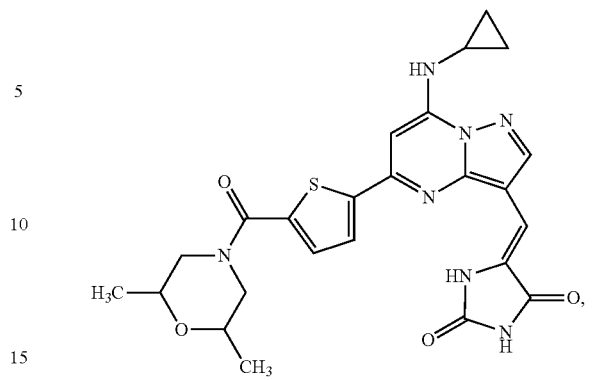
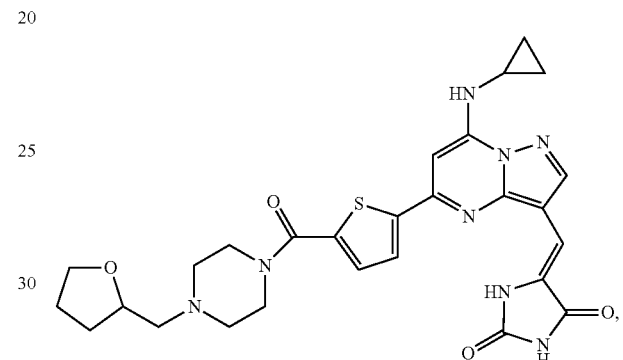
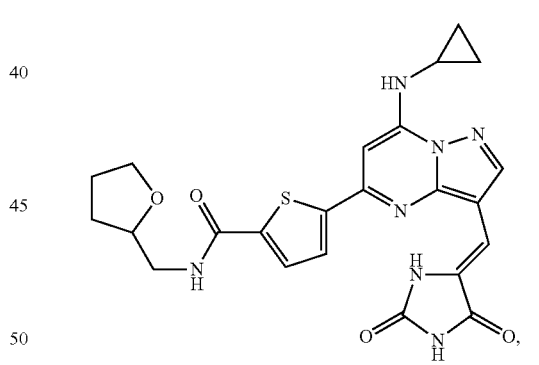
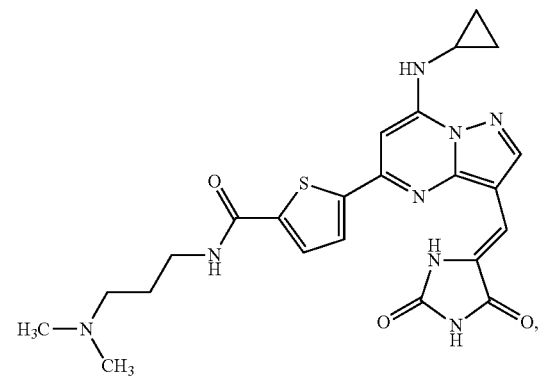

745
-continued
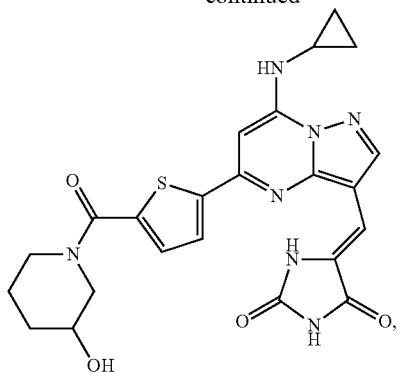
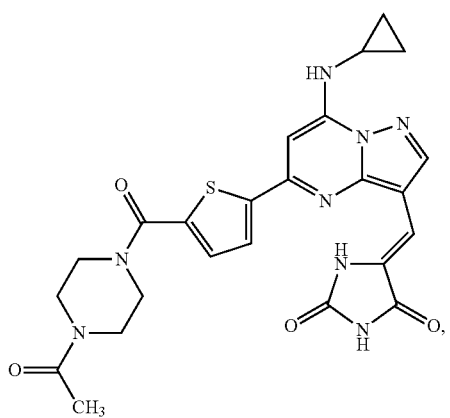
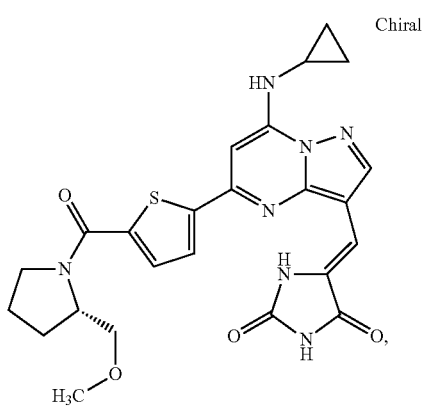
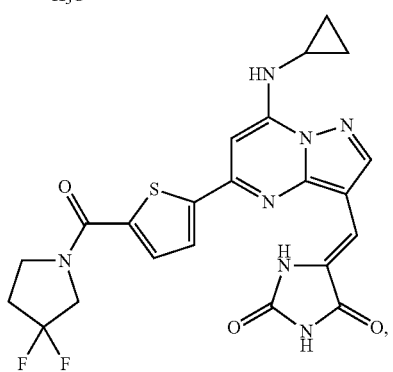
746
-continued
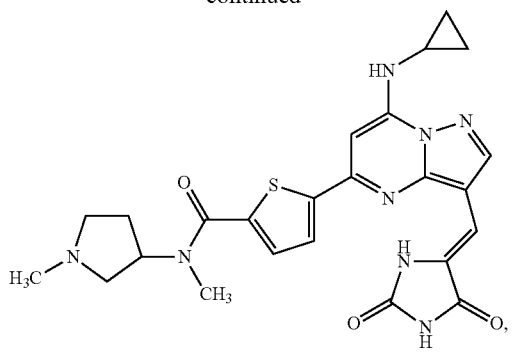
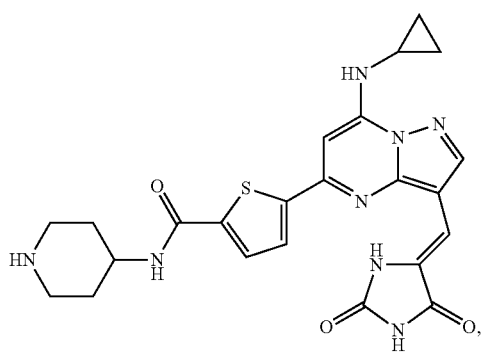
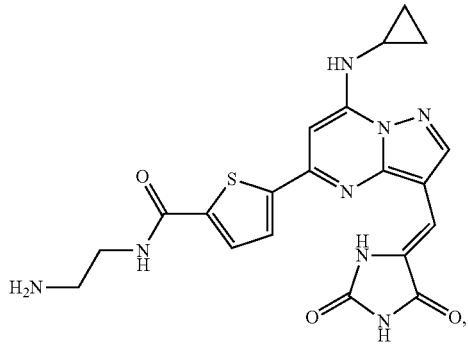
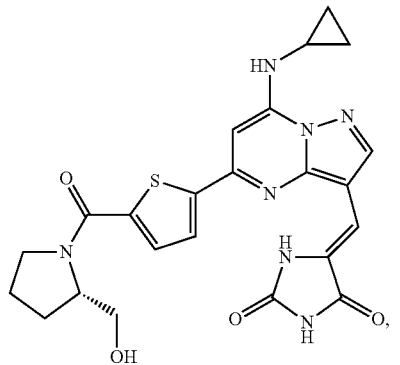

747
-continued
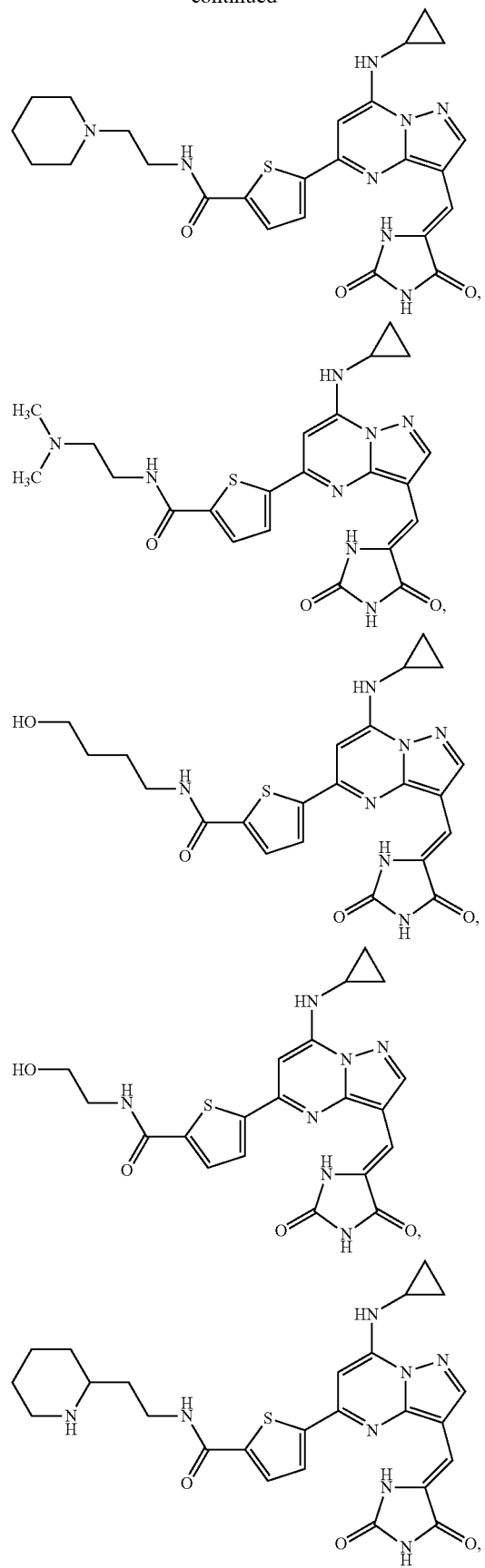
748
-continued
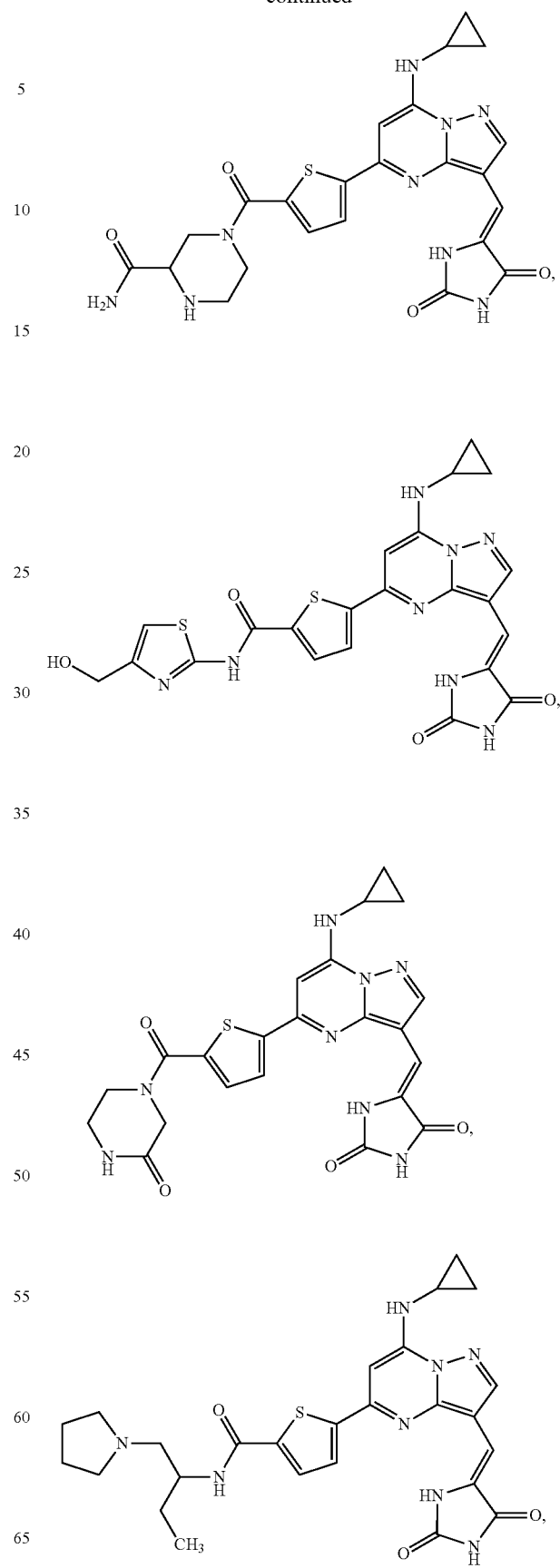

749
-continued
750
-continued
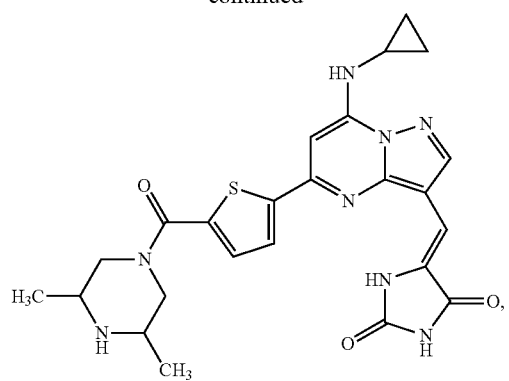
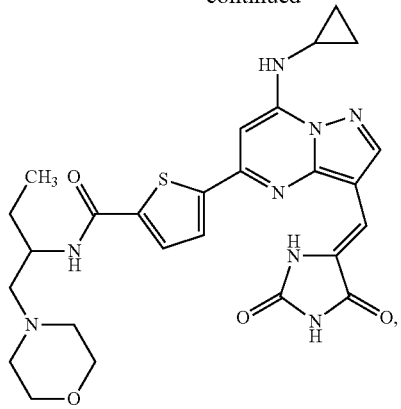
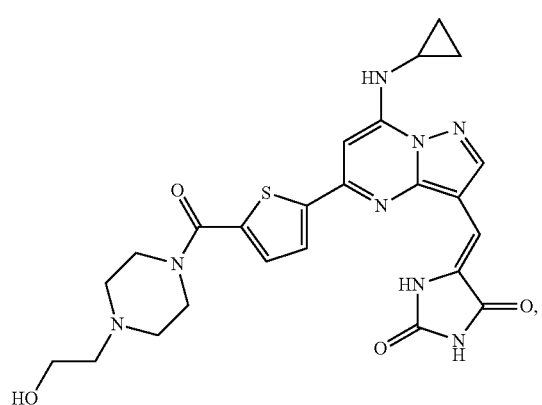
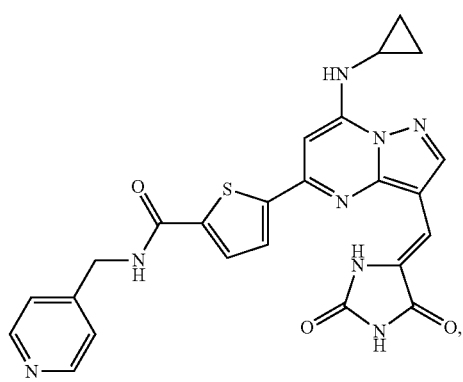
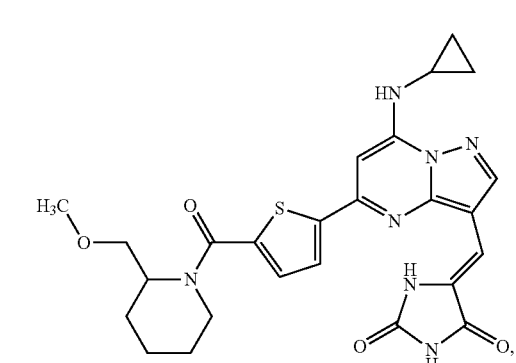
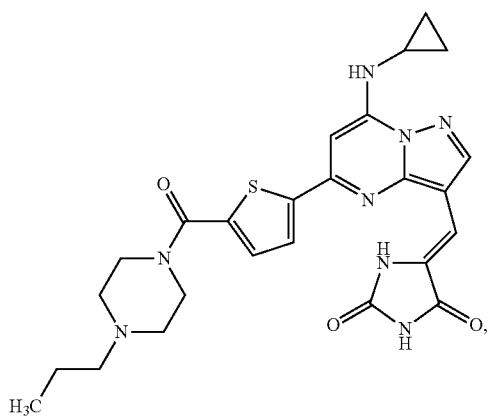
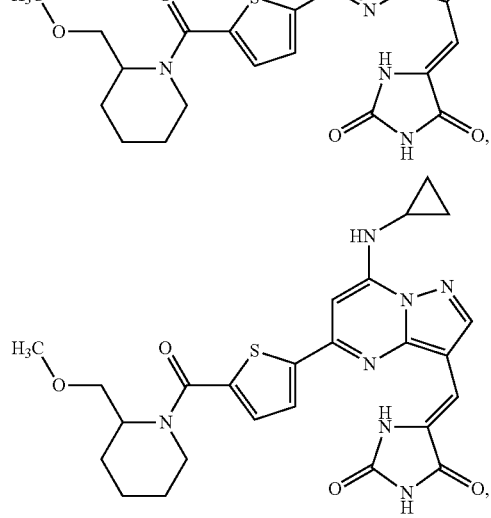
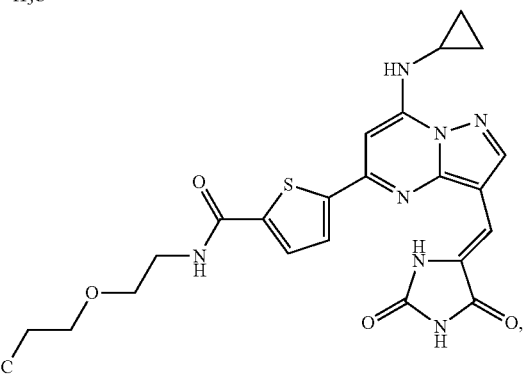

751
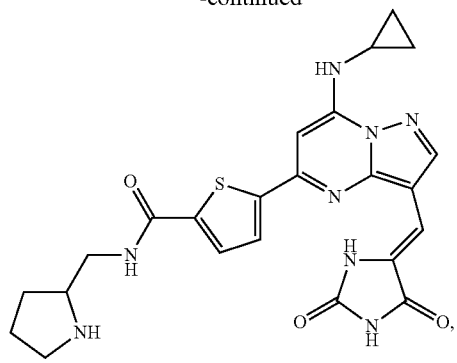
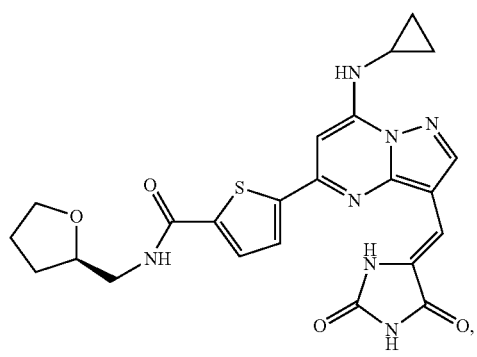
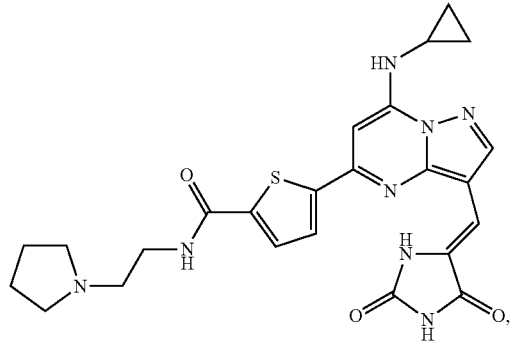
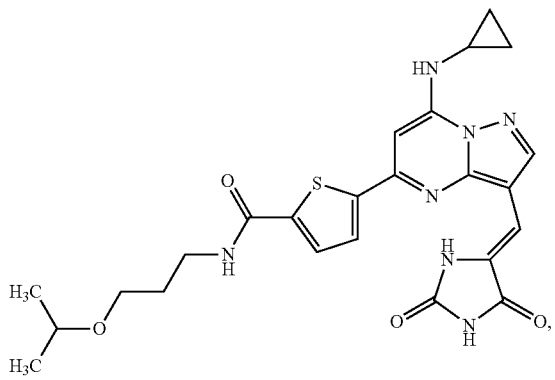
752
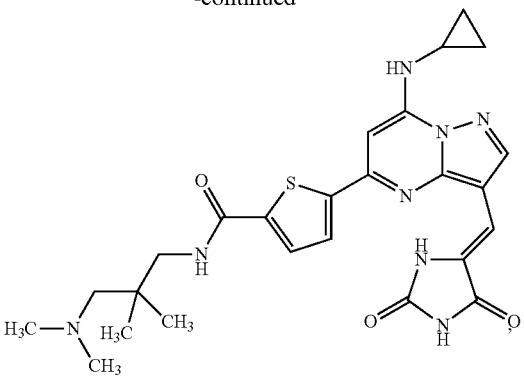
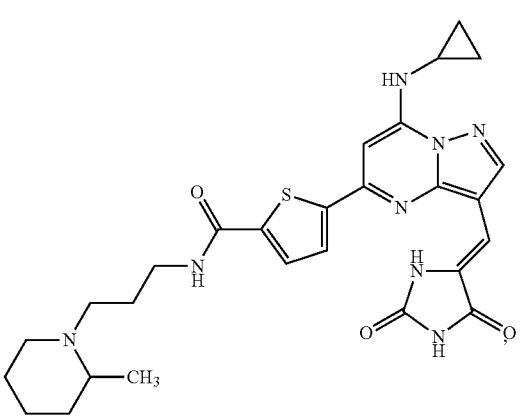
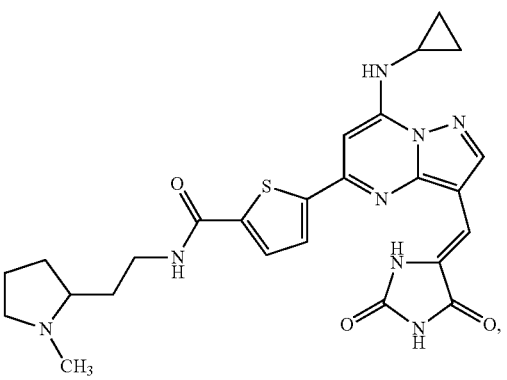
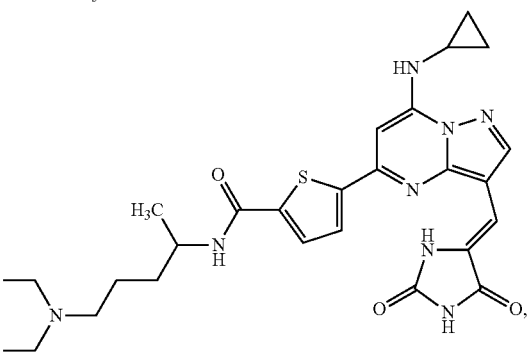

753
-continued
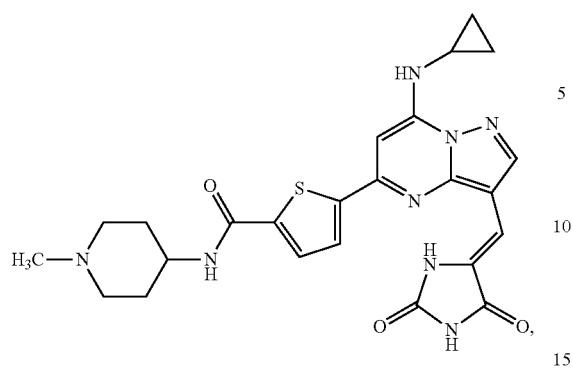
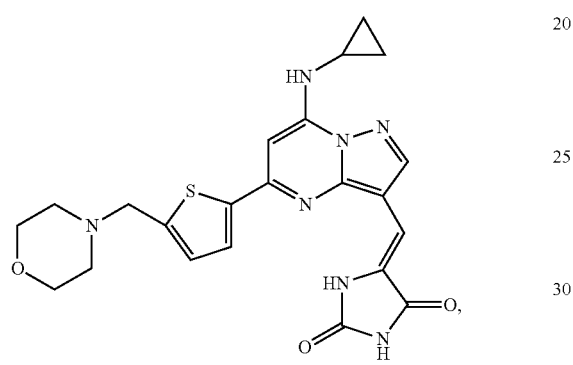
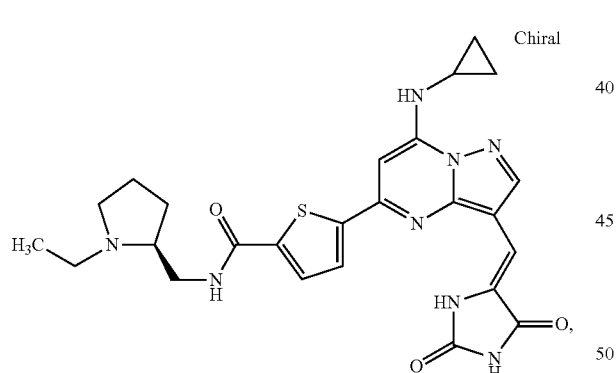
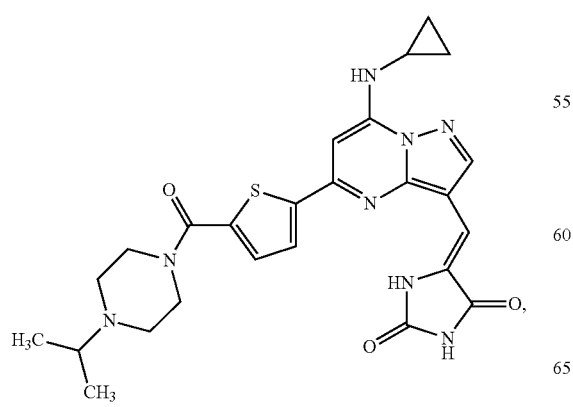
754
-continued
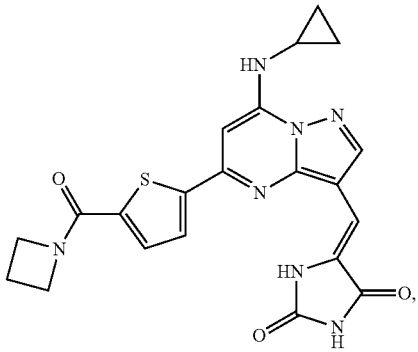
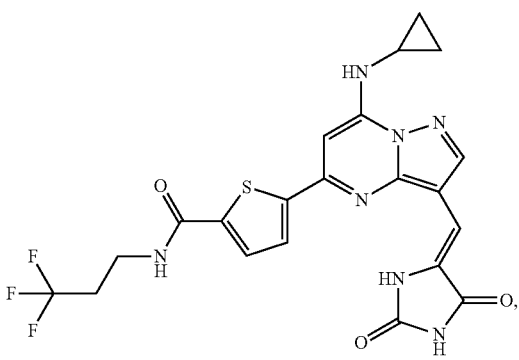
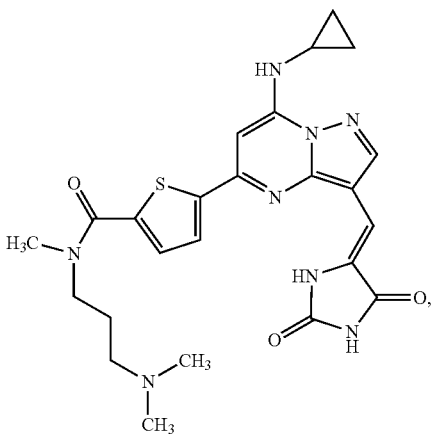
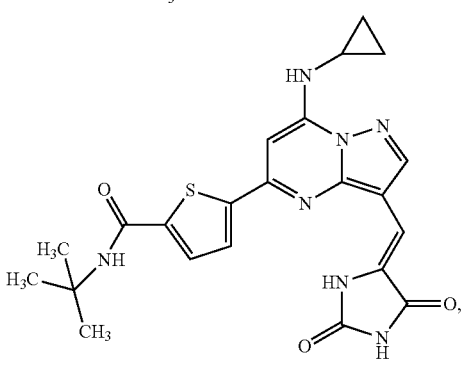

755
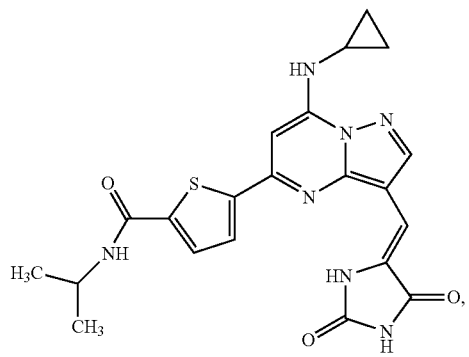
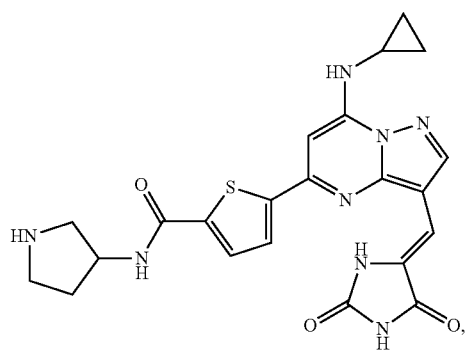
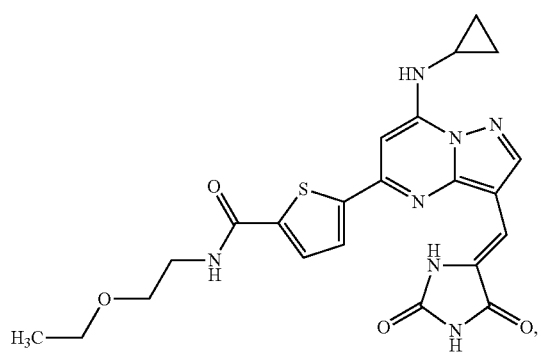
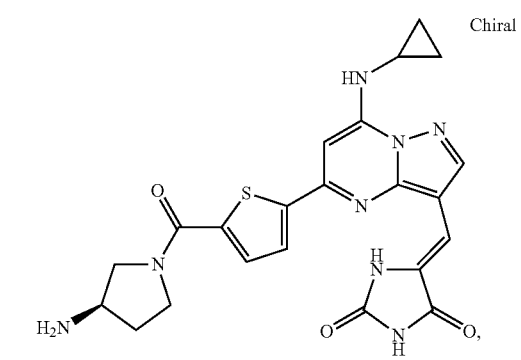
756
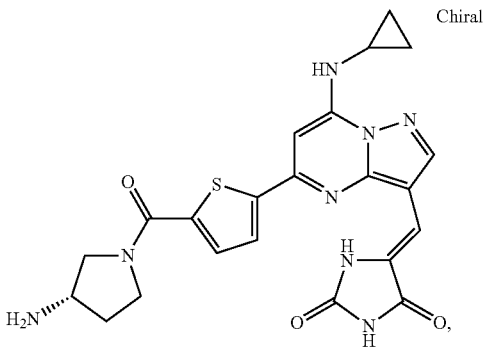
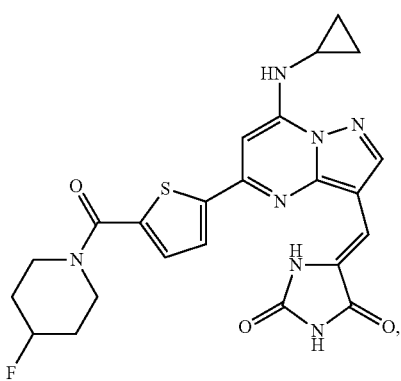
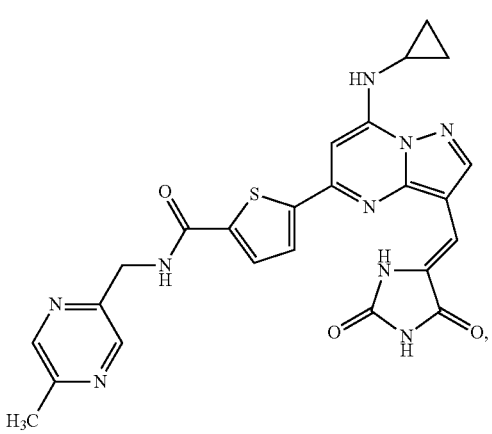
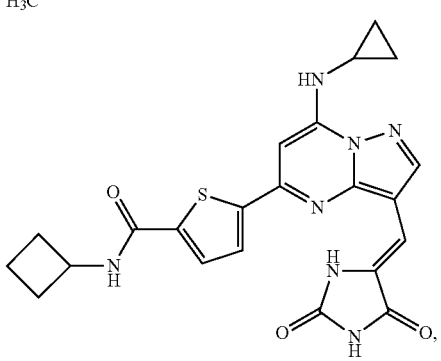

757
-continued
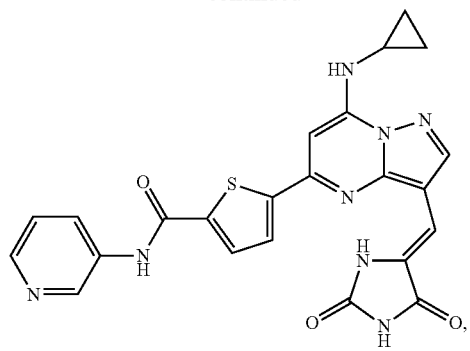
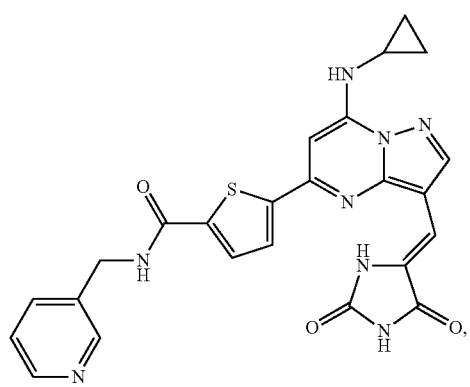
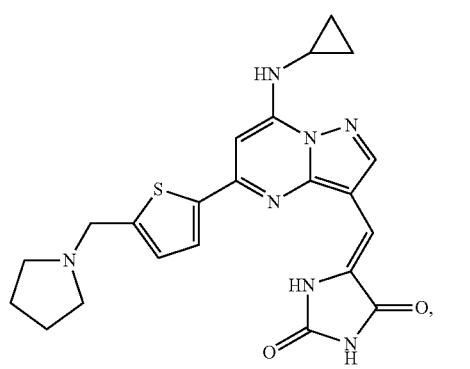
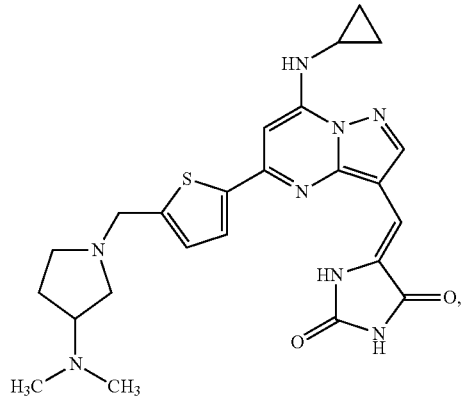
758
-continued
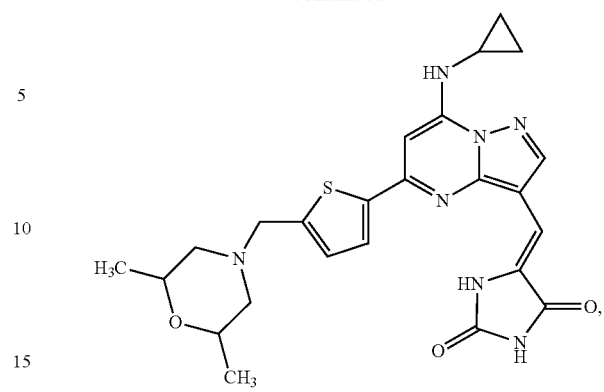
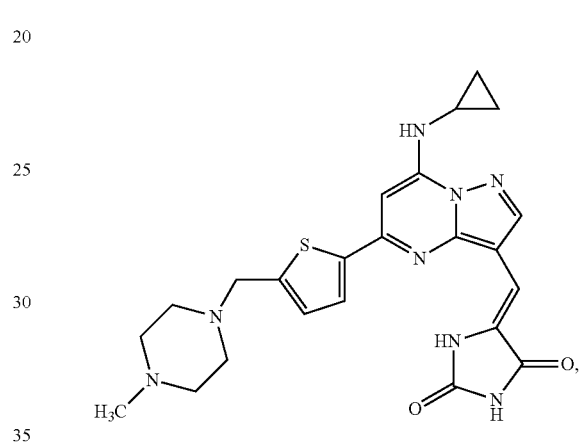
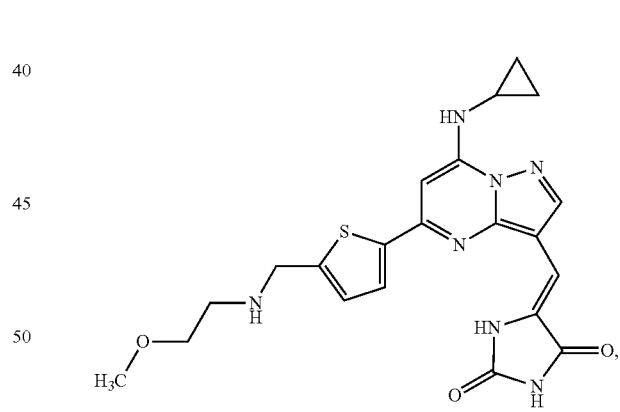
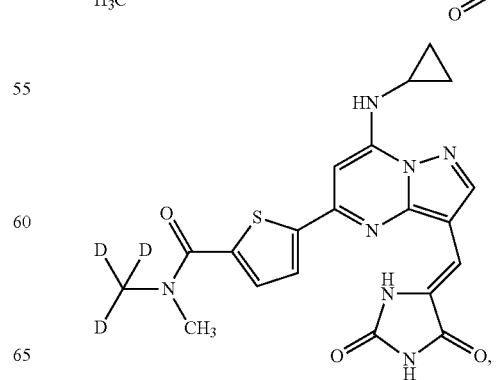

759
-continued
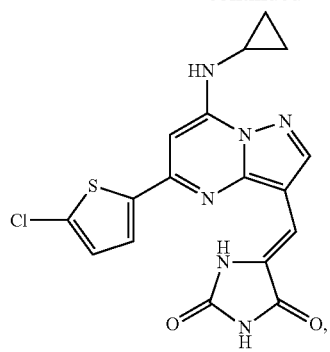
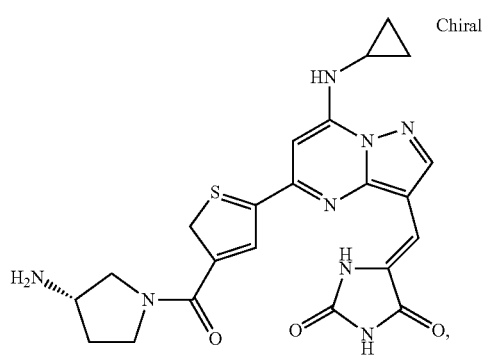
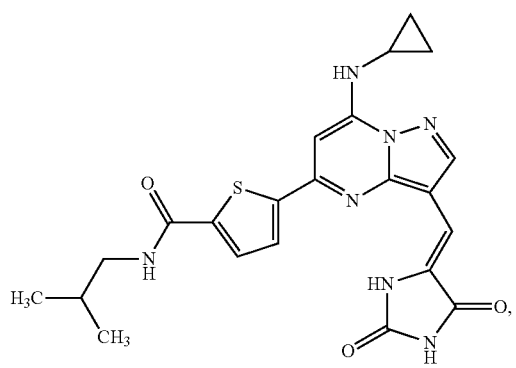
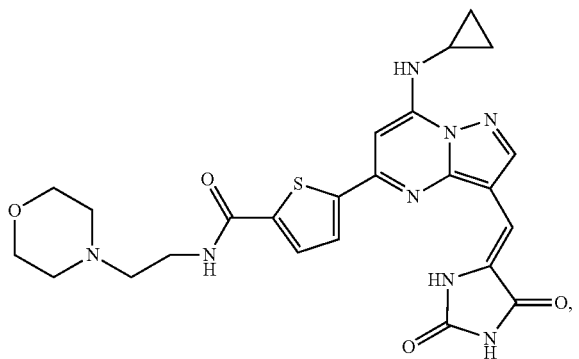
760
-continued
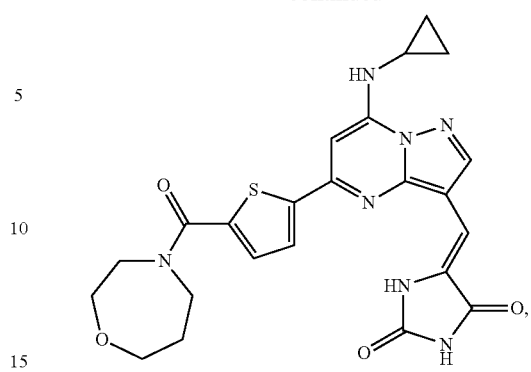
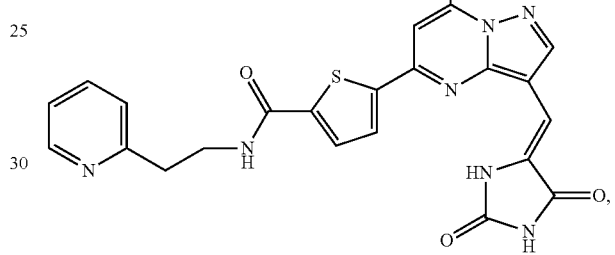
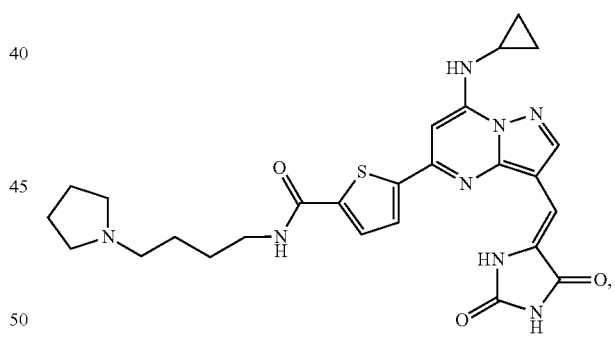
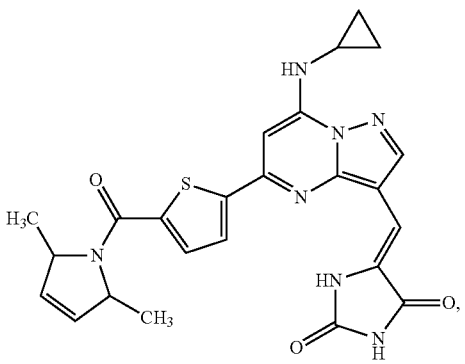

761
-continued
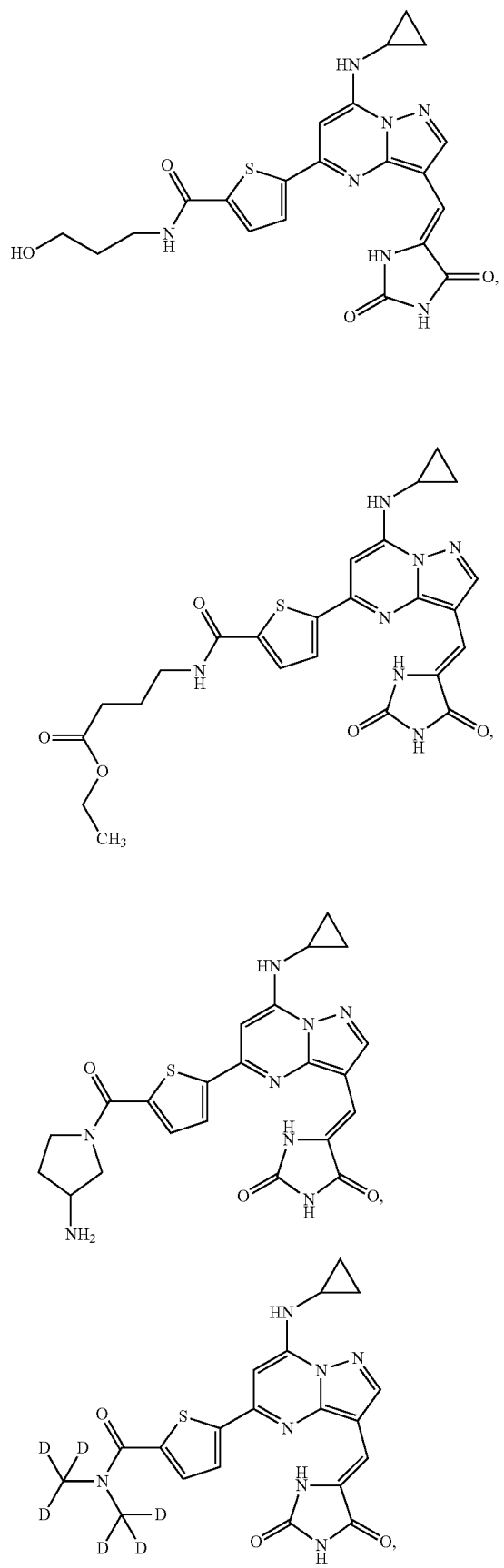
762
-continued
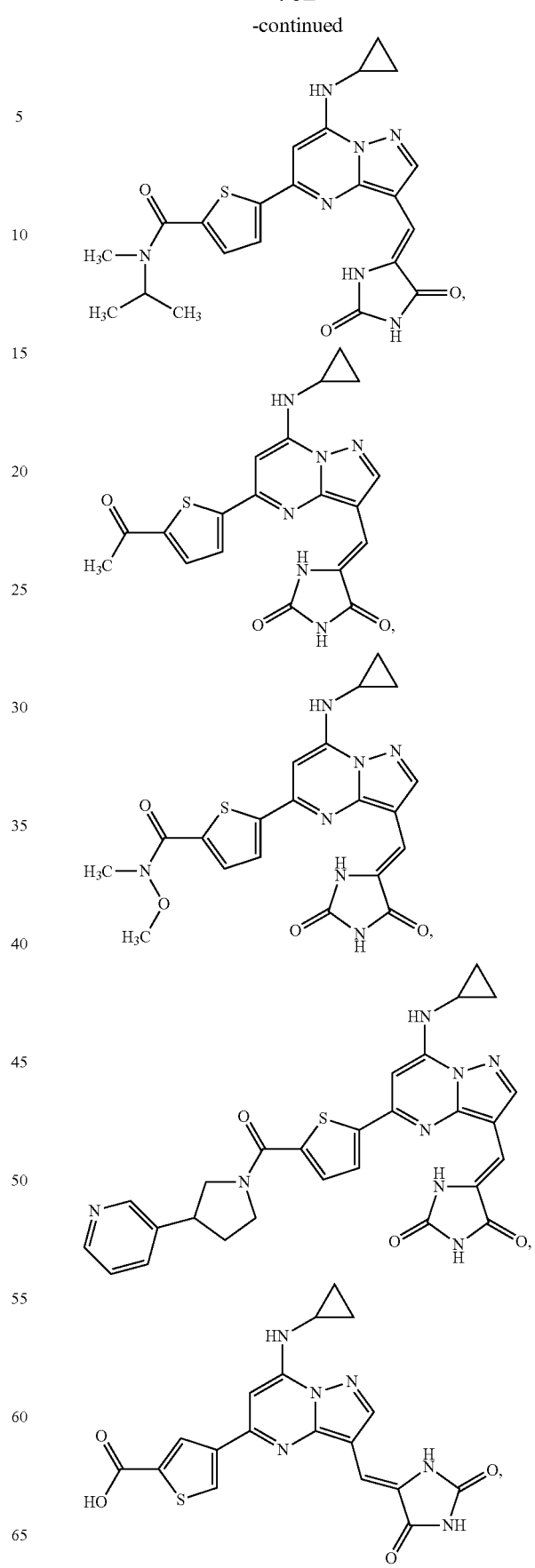

763
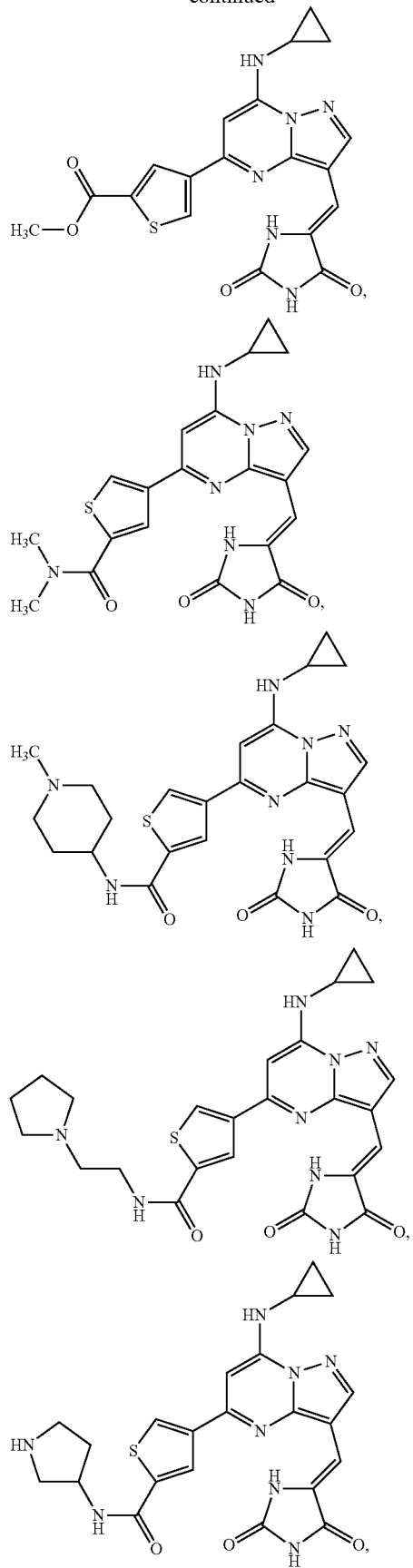
764
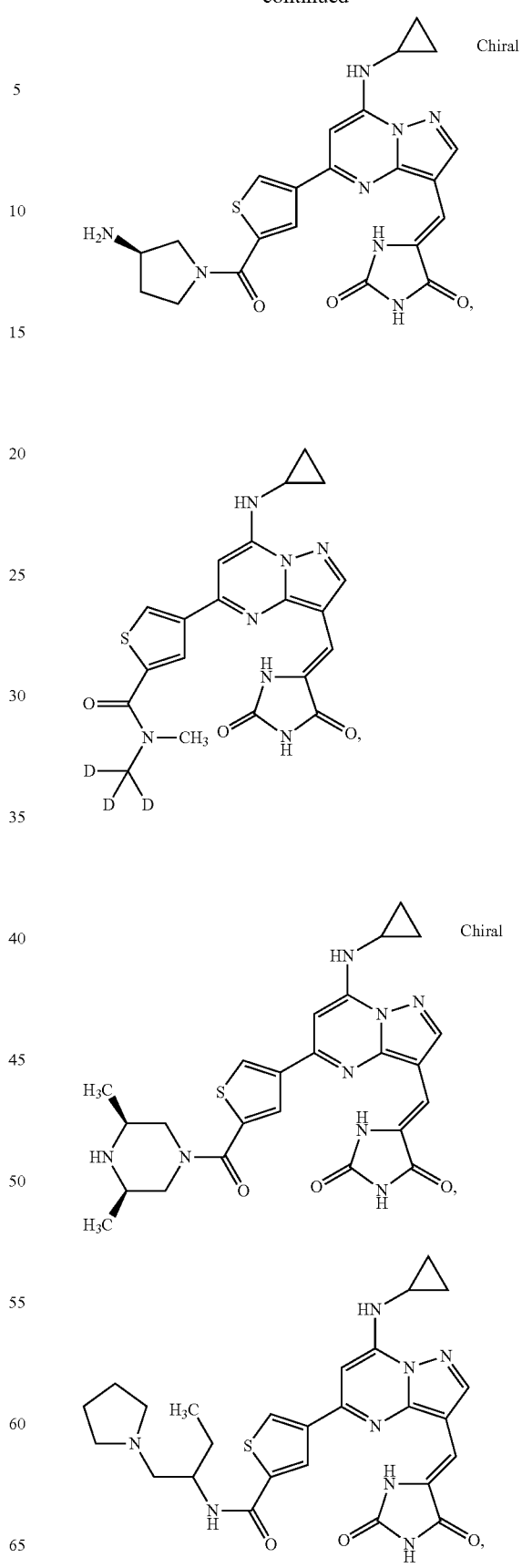

765
-continued
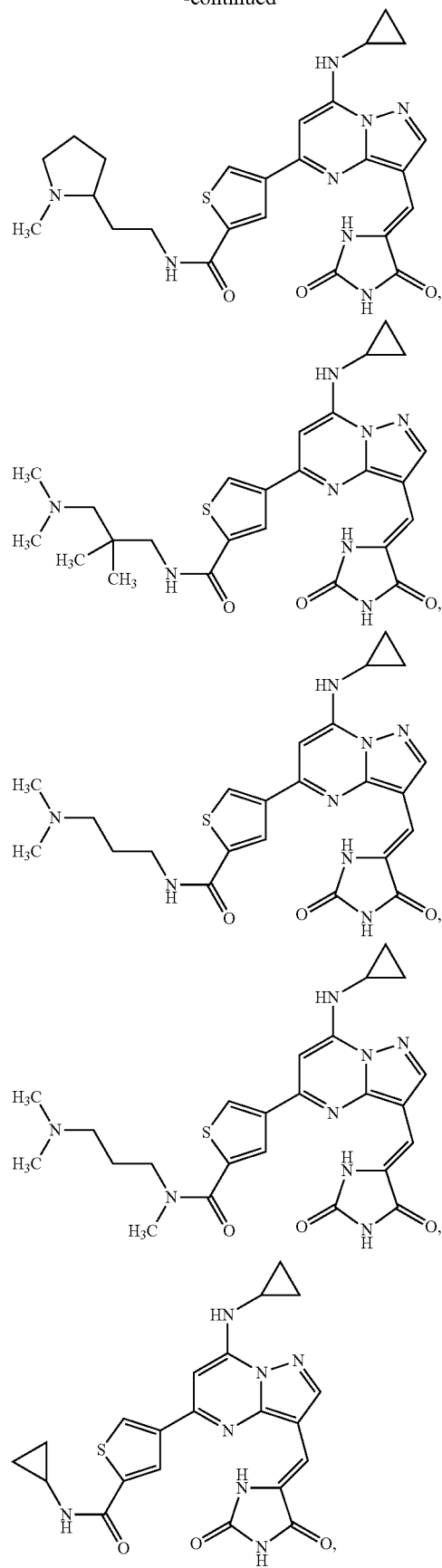
766
-continued
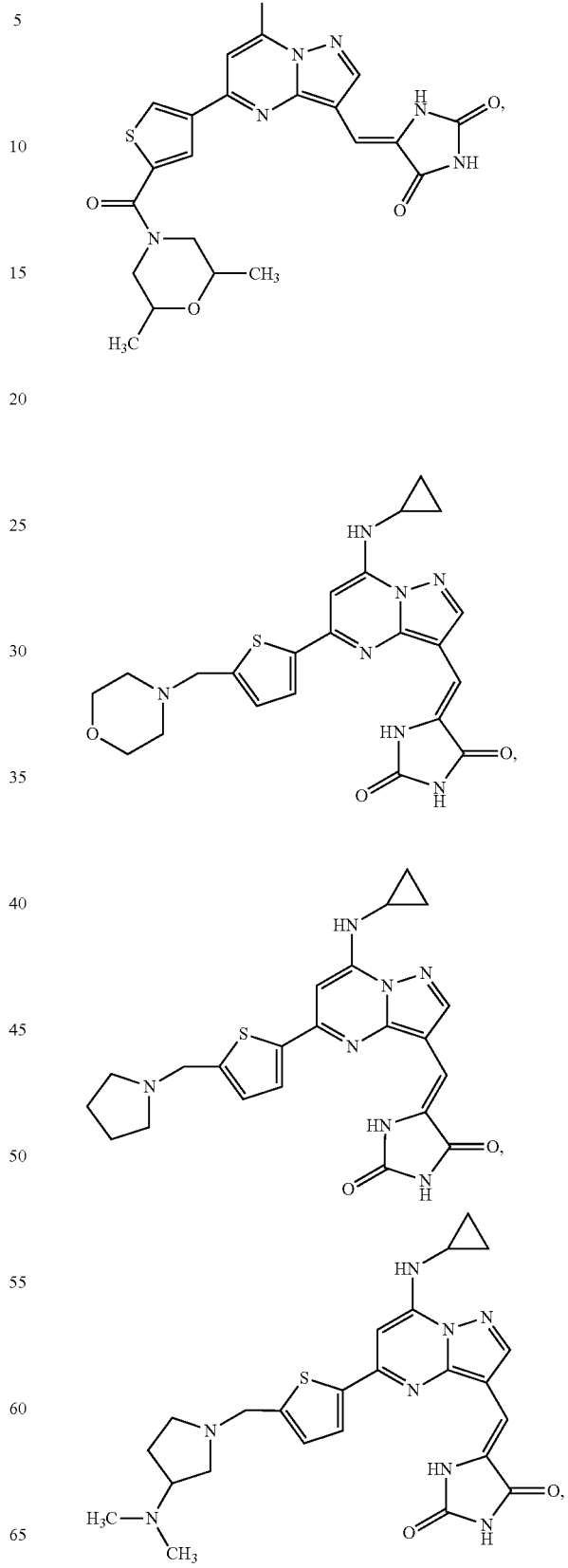

767
-continued
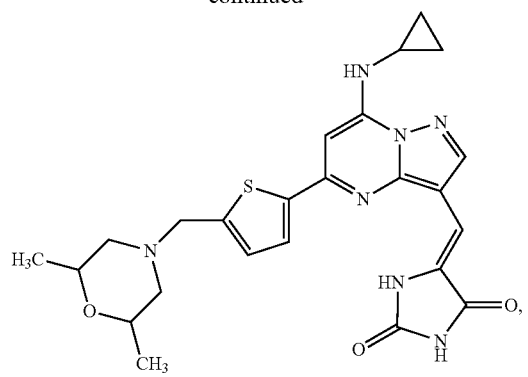
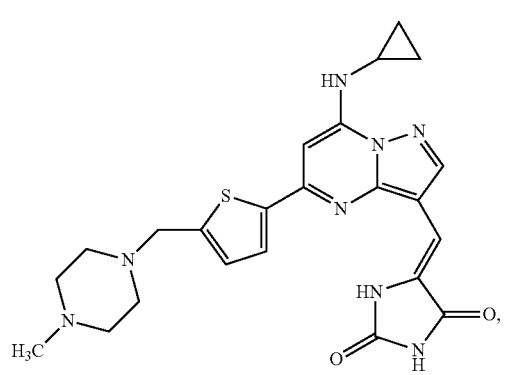
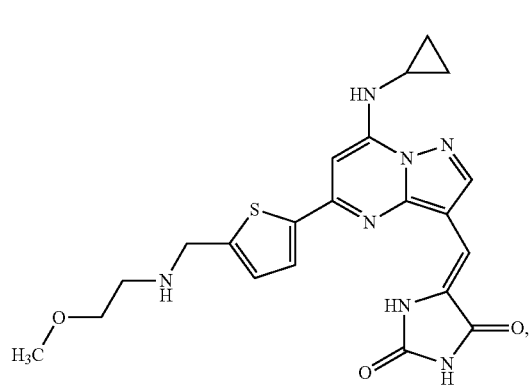
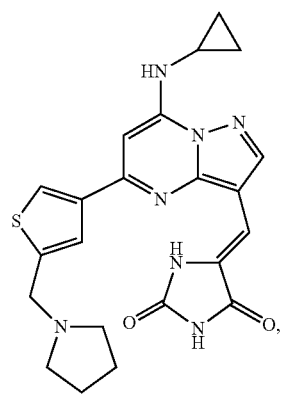
768
-continued
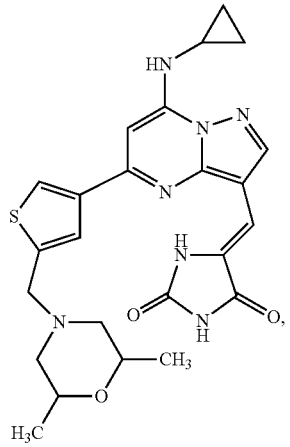
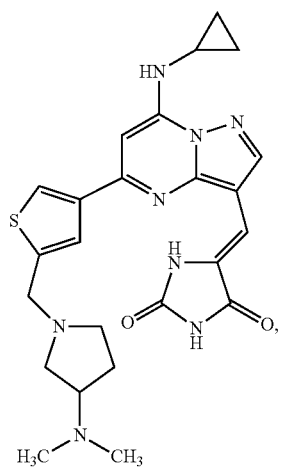
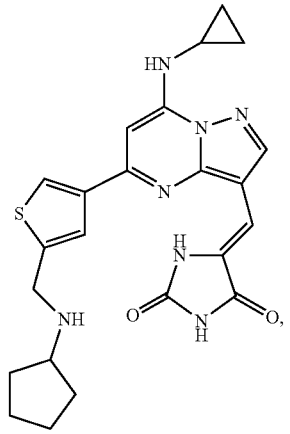
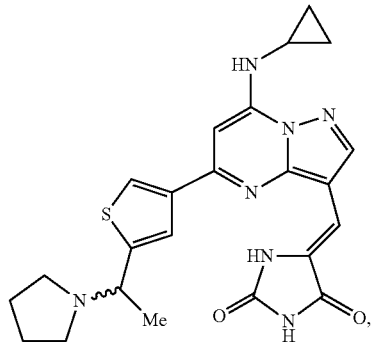

769
-continued
770
-continued
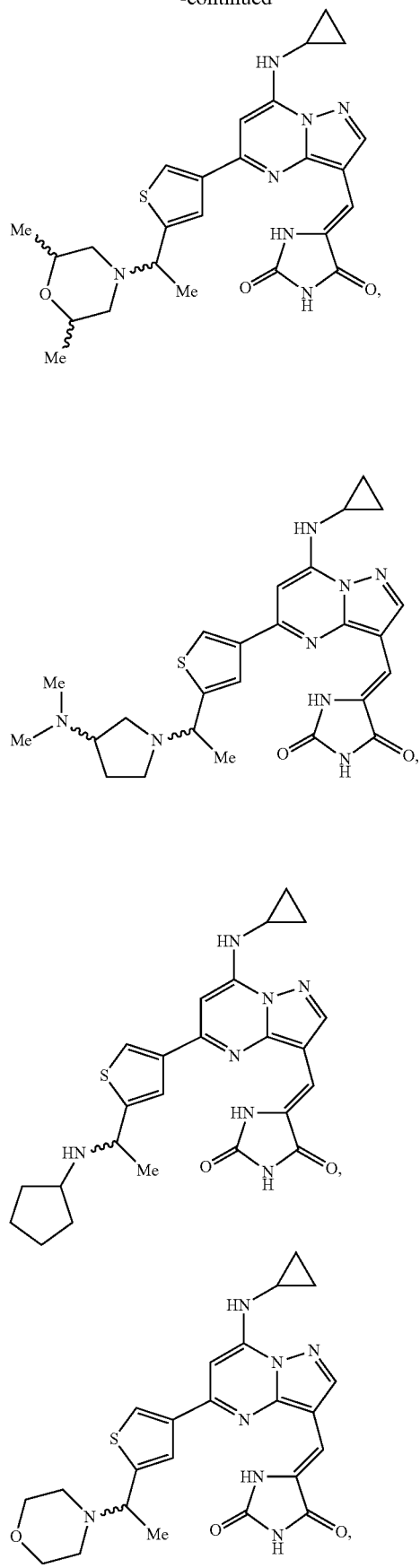
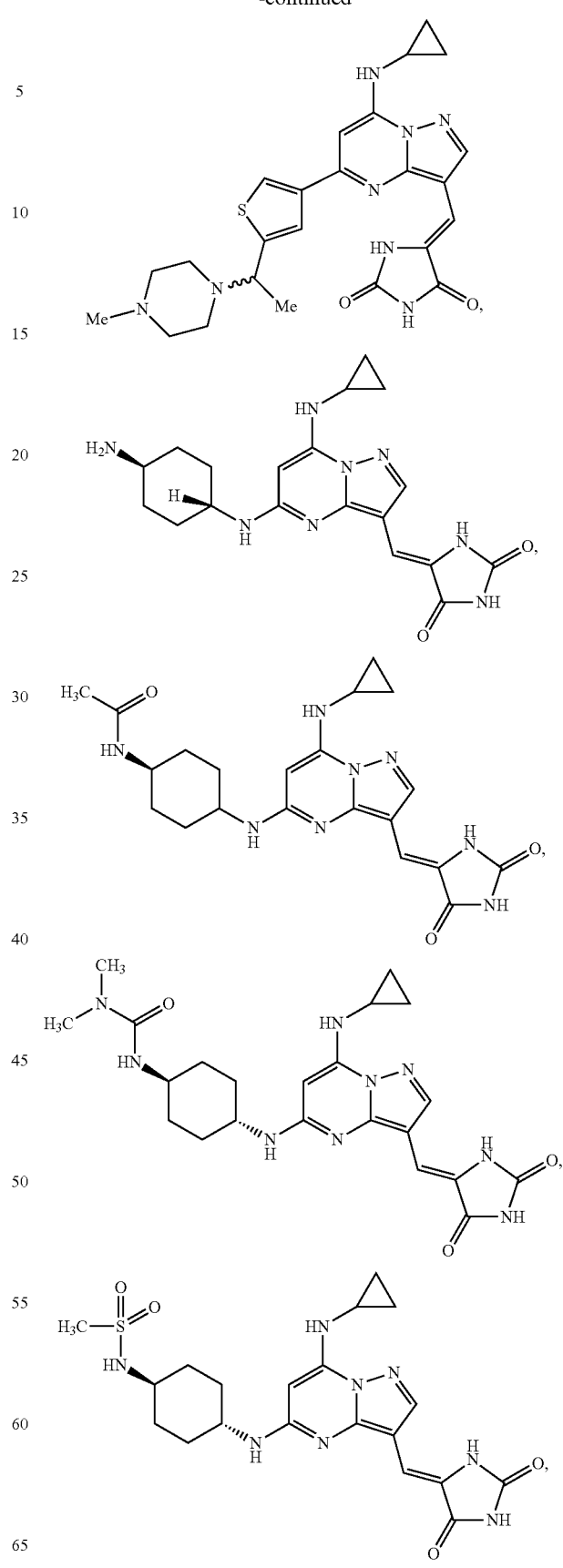

771
-continued
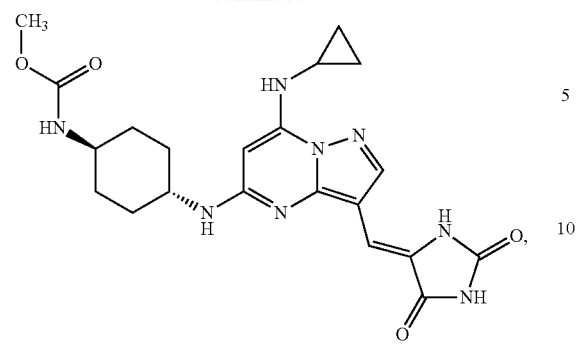
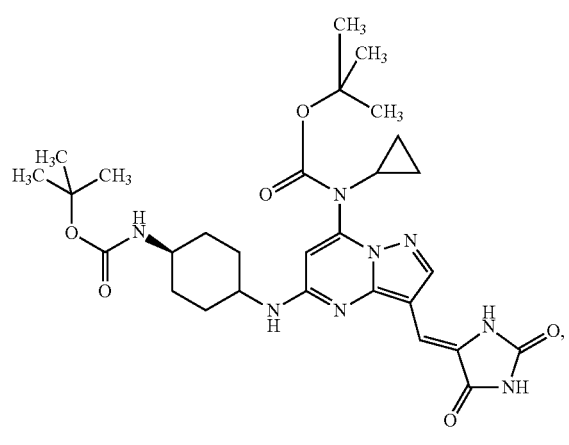
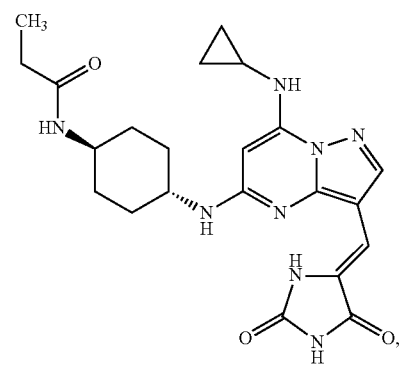
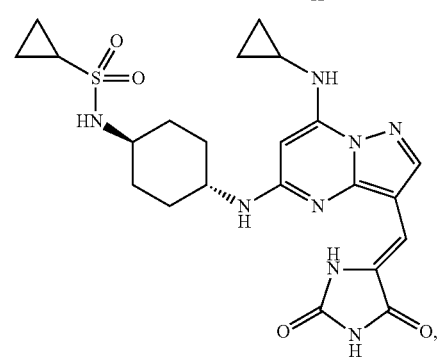
772
-continued
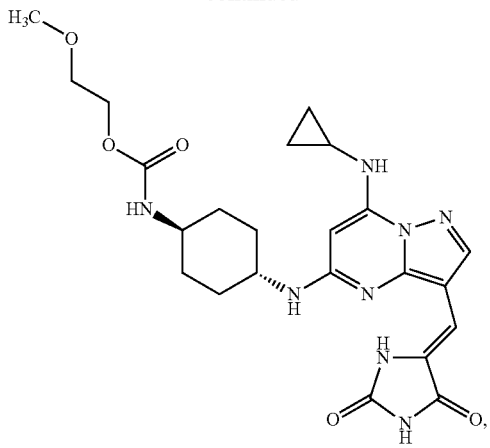
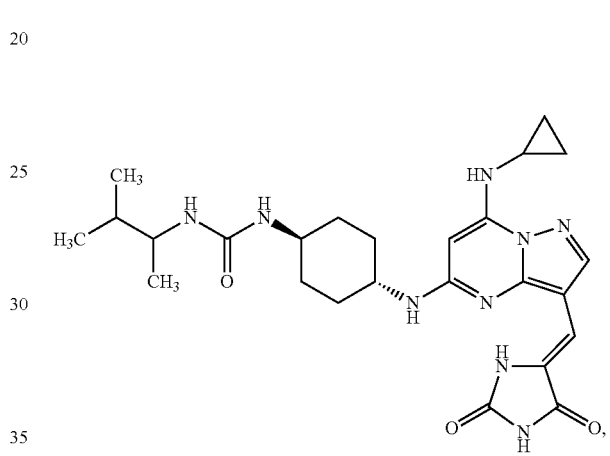
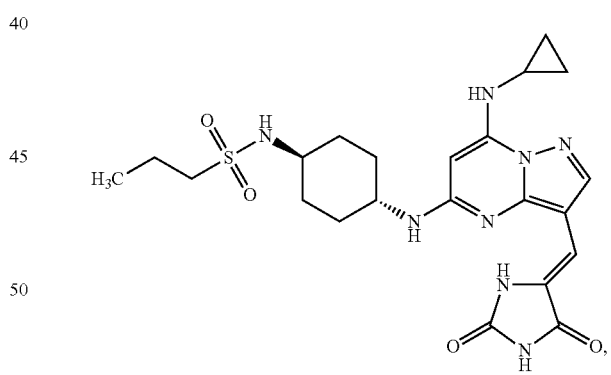
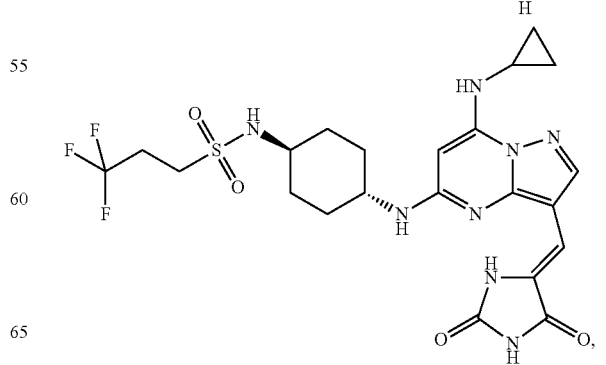

773
-continued
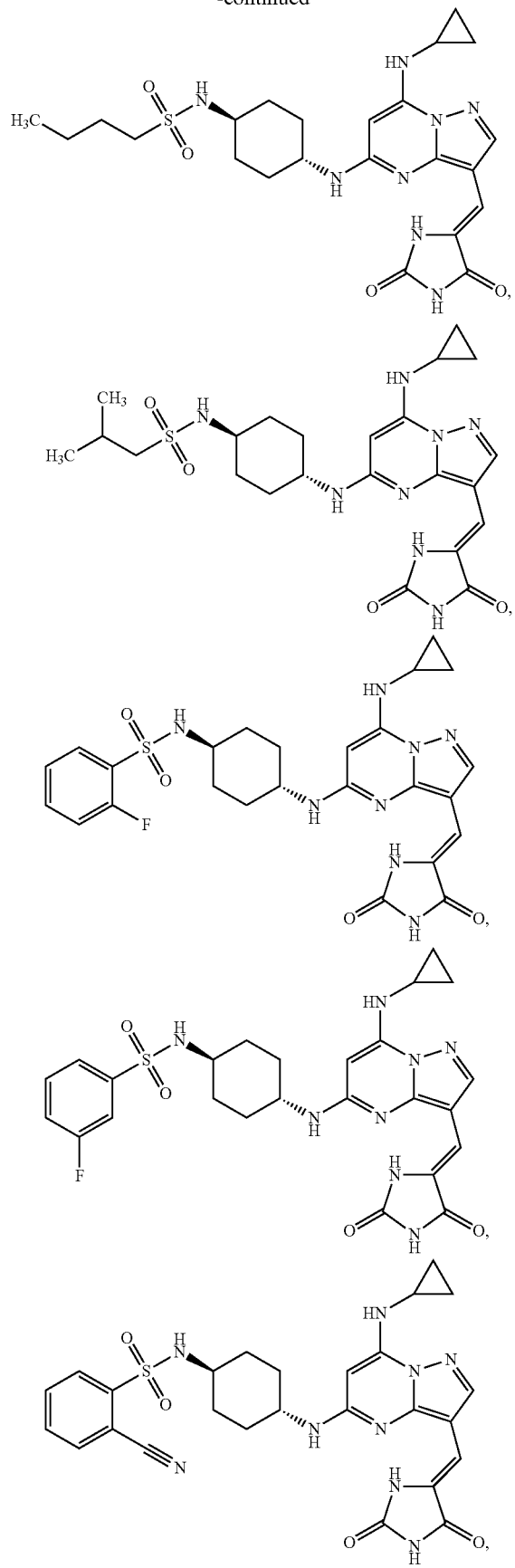
774
-continued
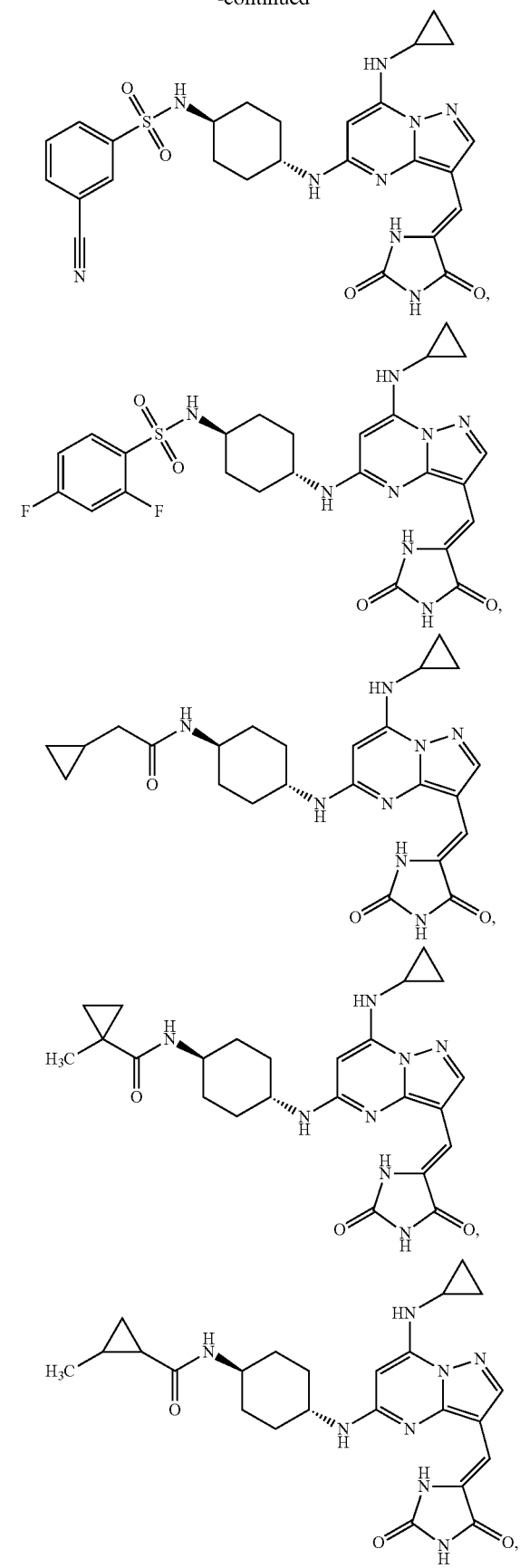

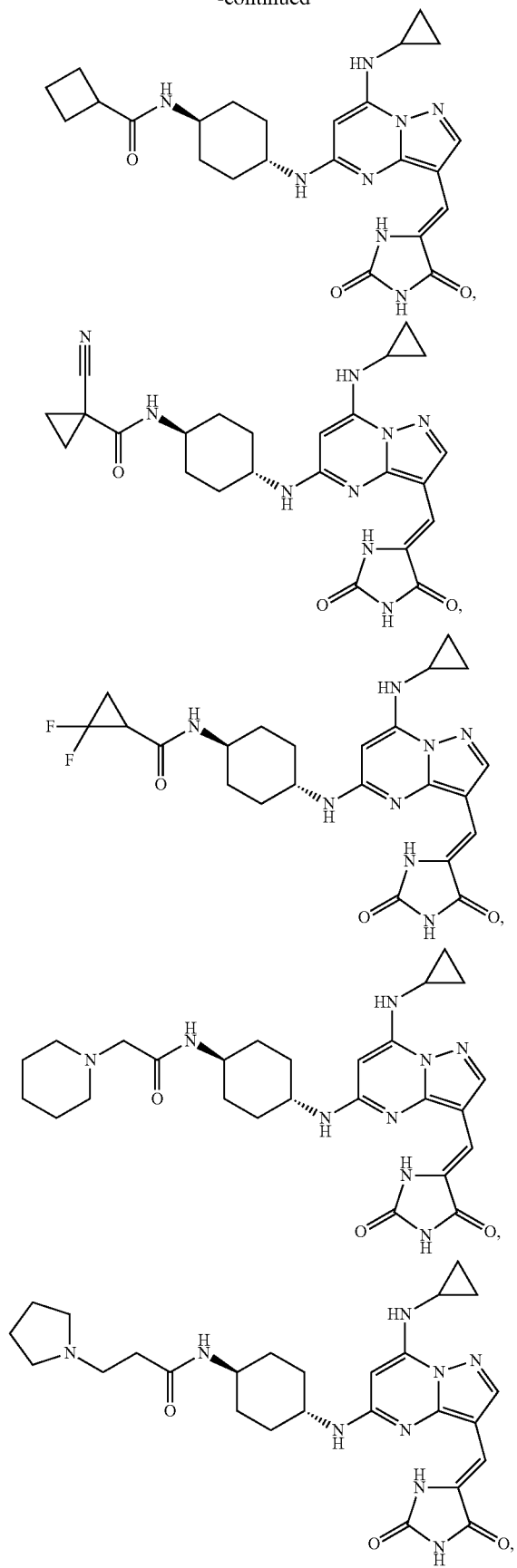
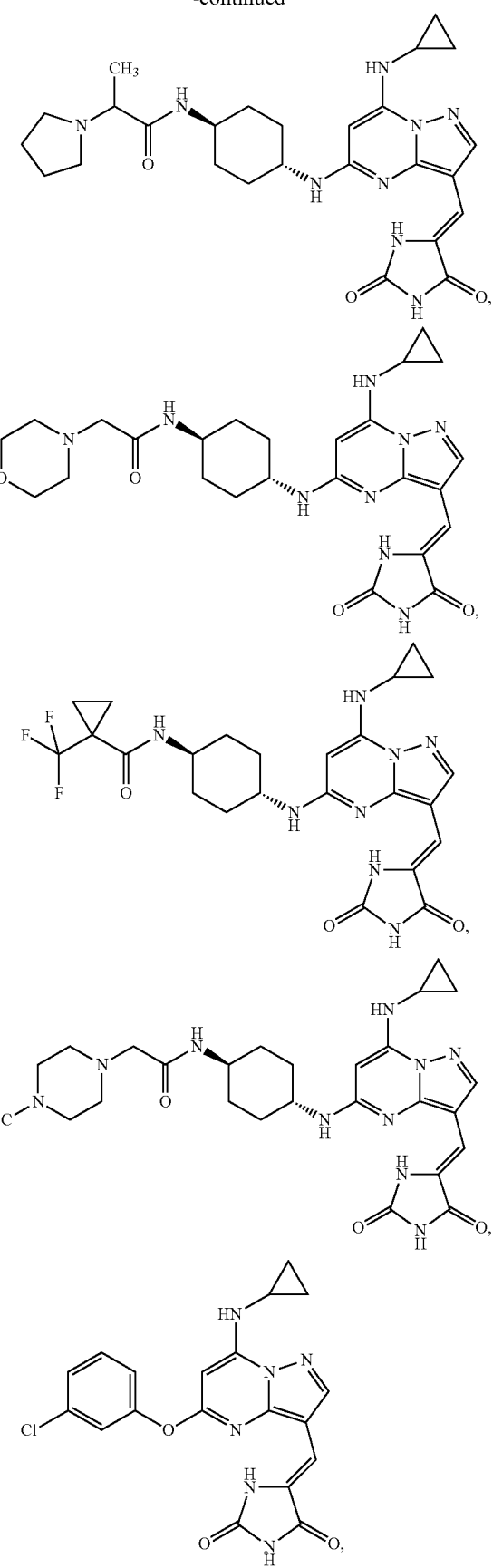

777
-continued
778
-continued
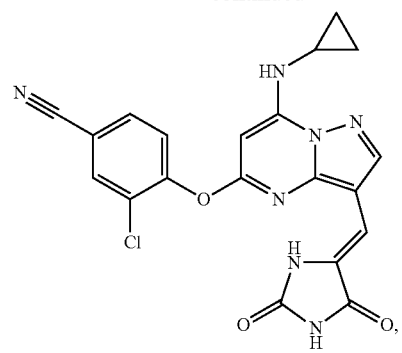
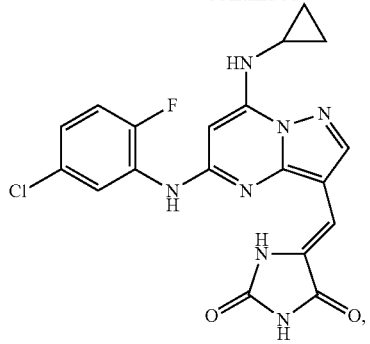
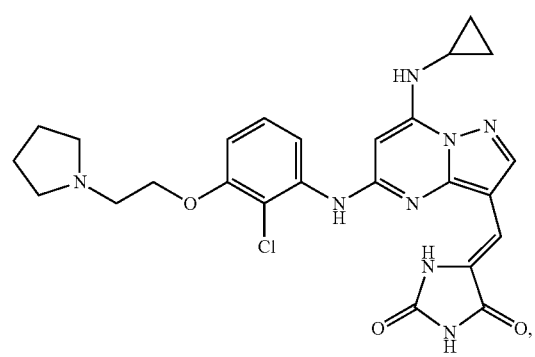
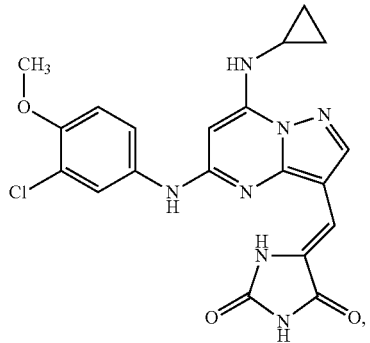
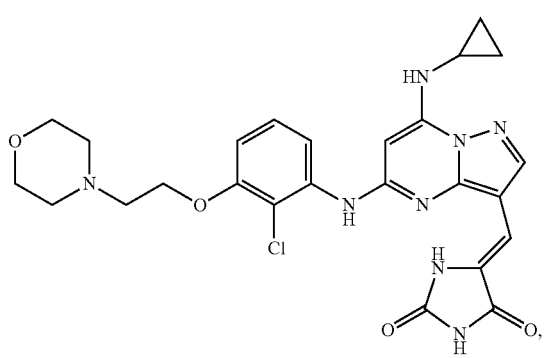
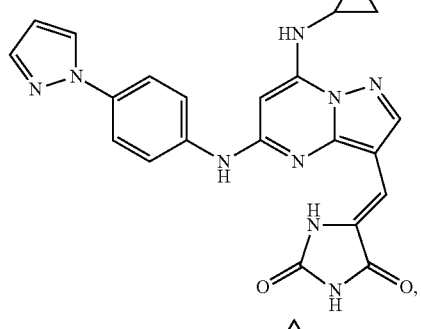
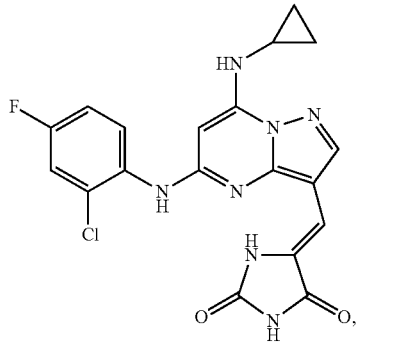
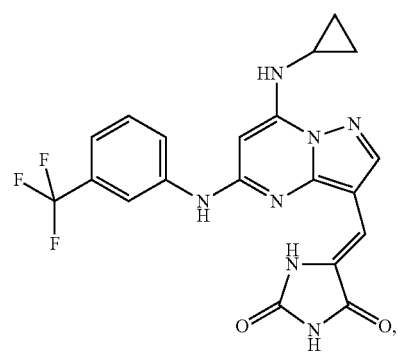
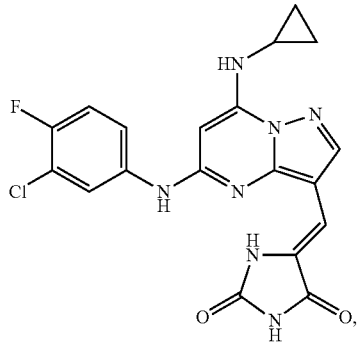

779
-continued
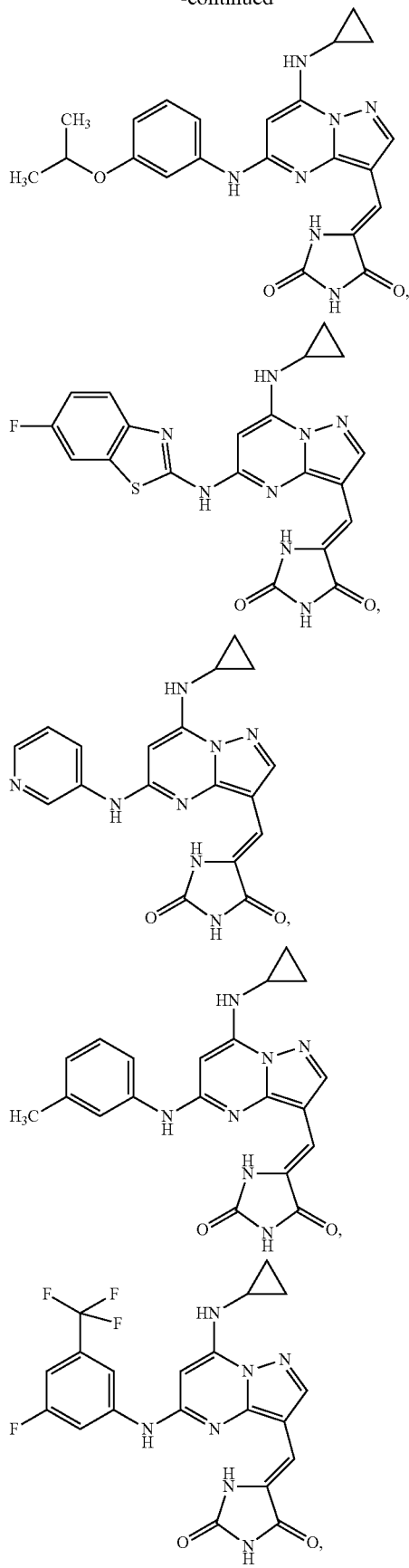
780
-continued
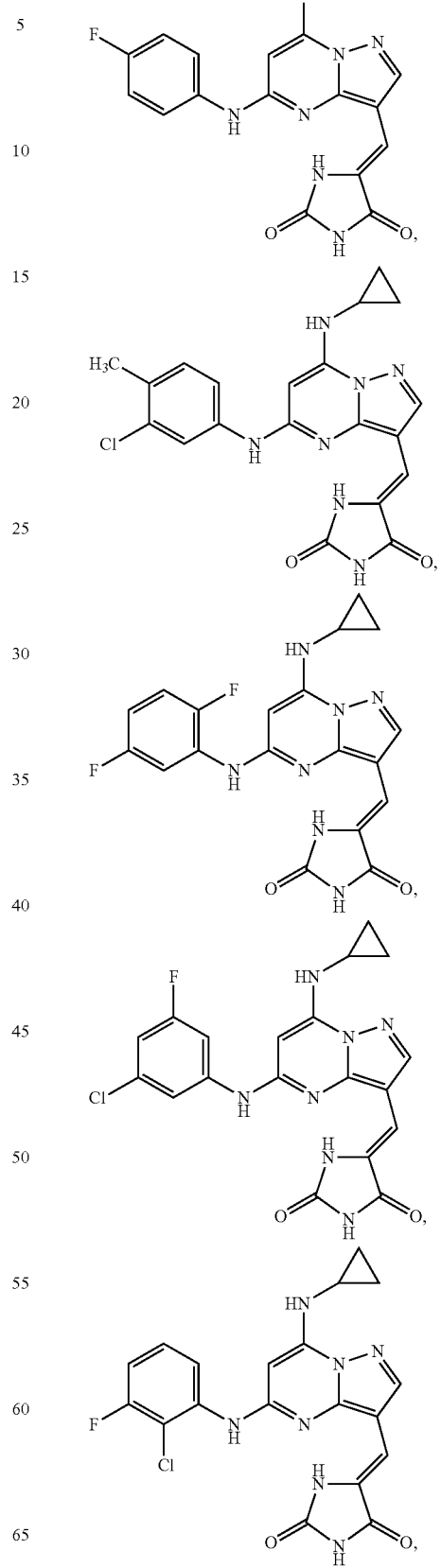

781
-continued
782
-continued
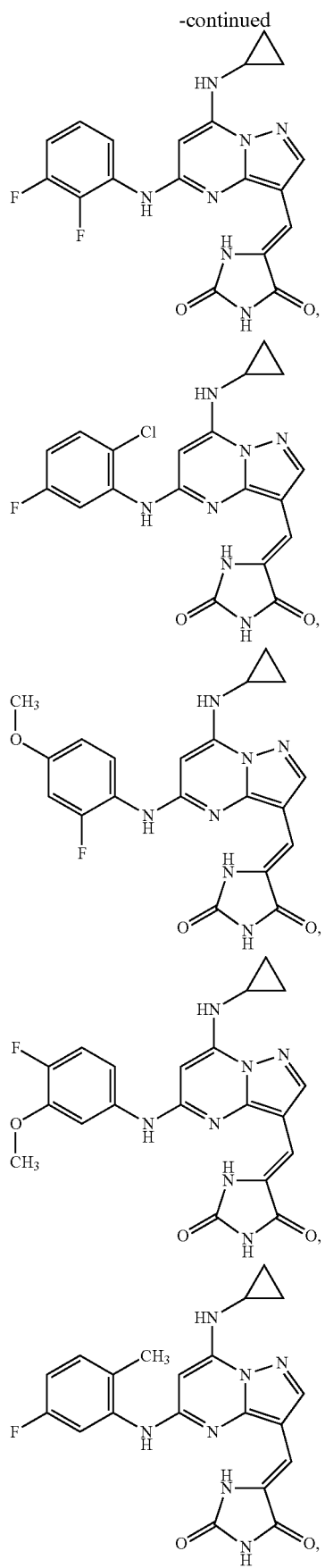
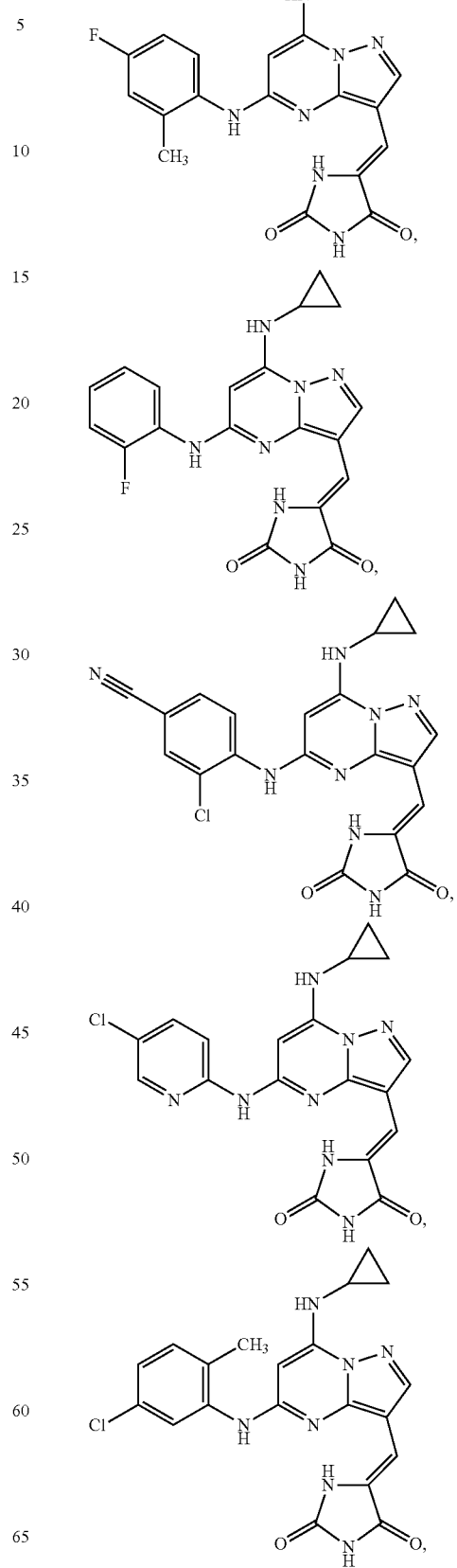

783 -continued
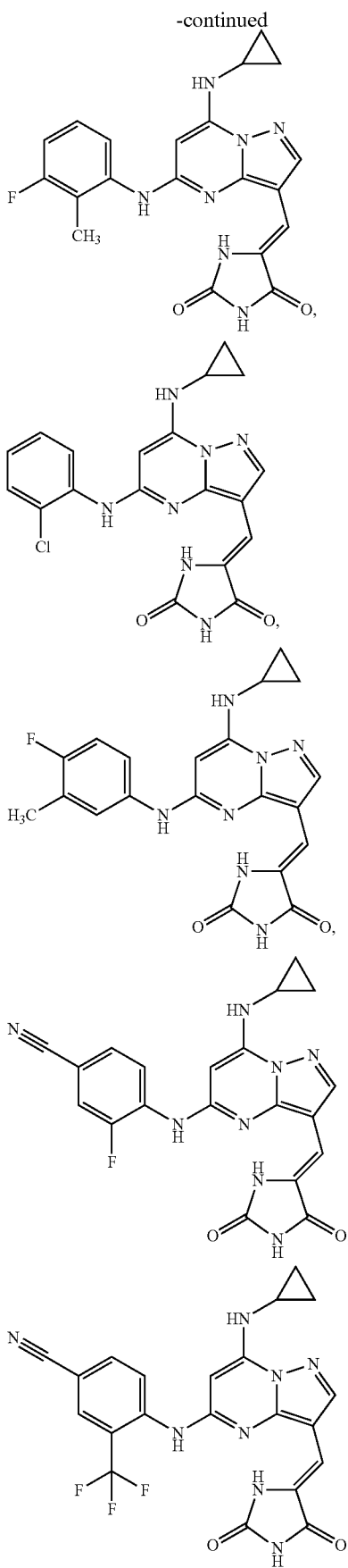
784 -continued
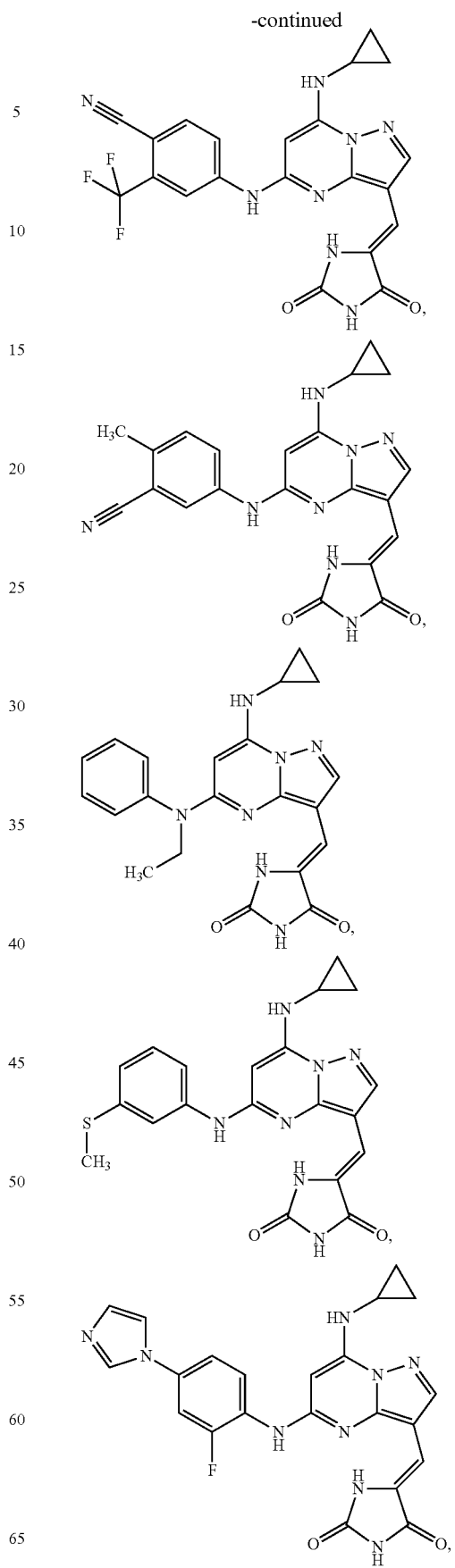

785
-continued
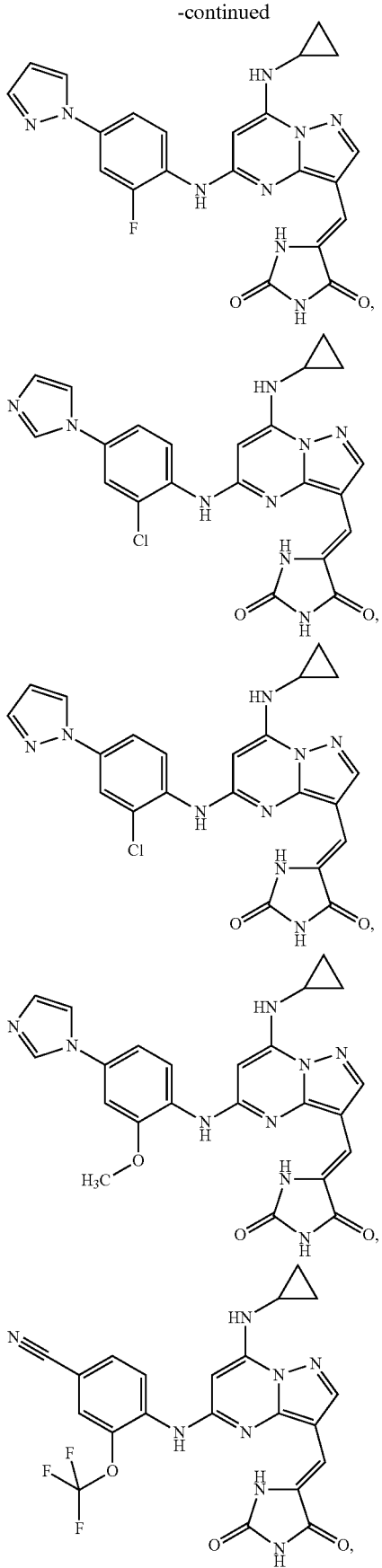
786
-continued
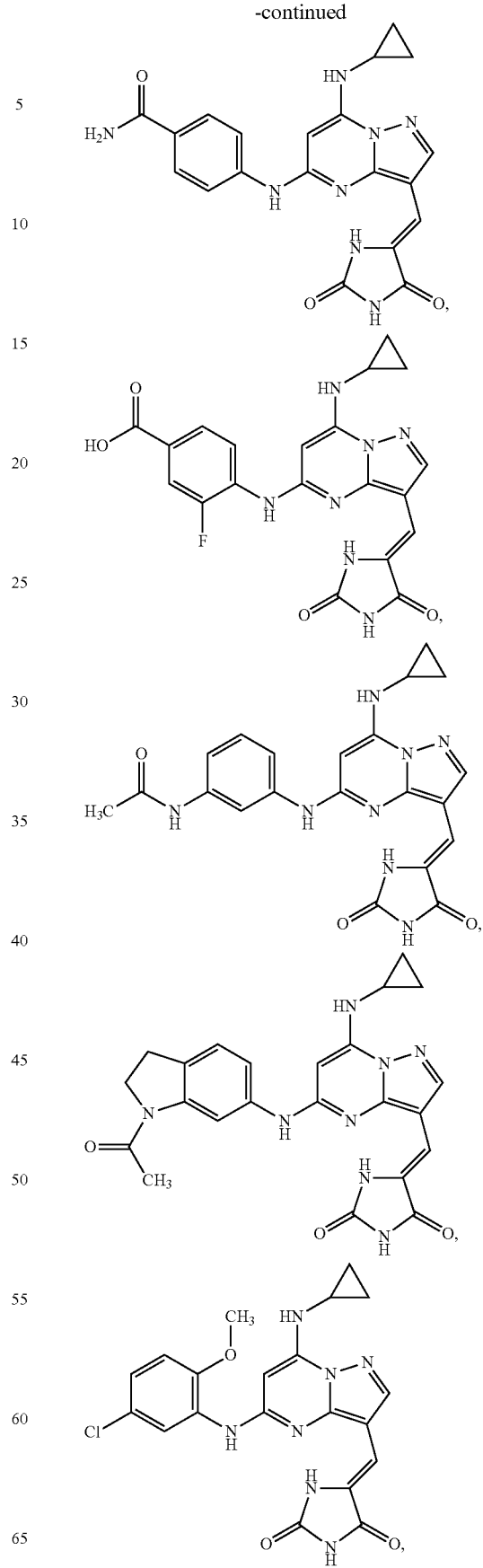

787
-continued
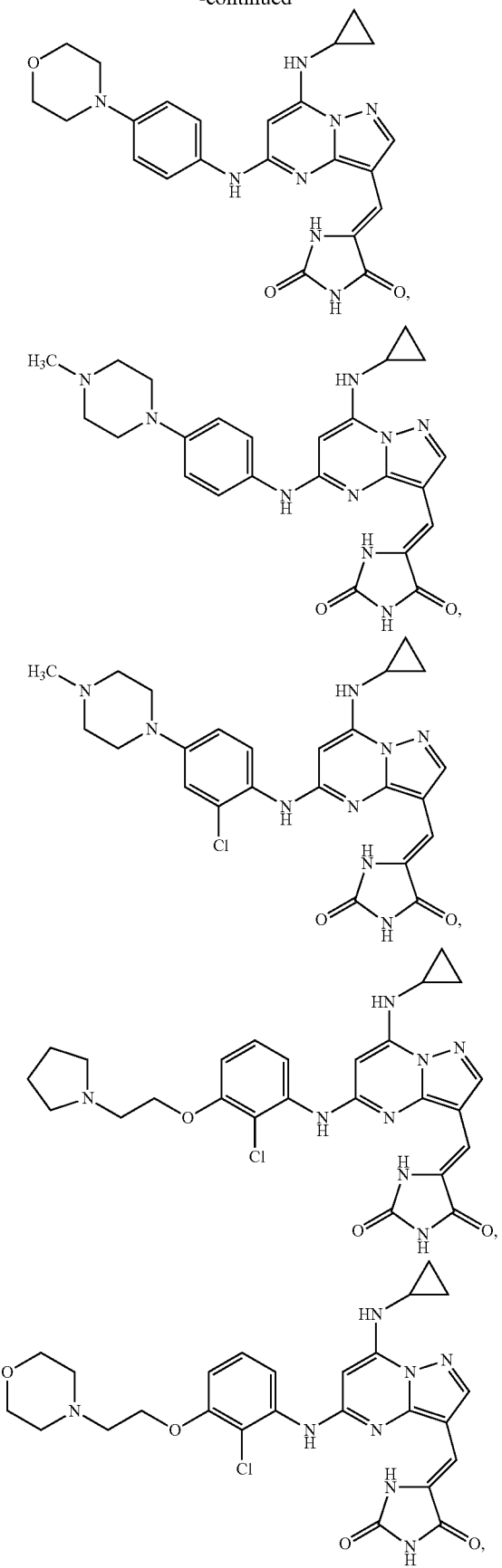
788
-continued
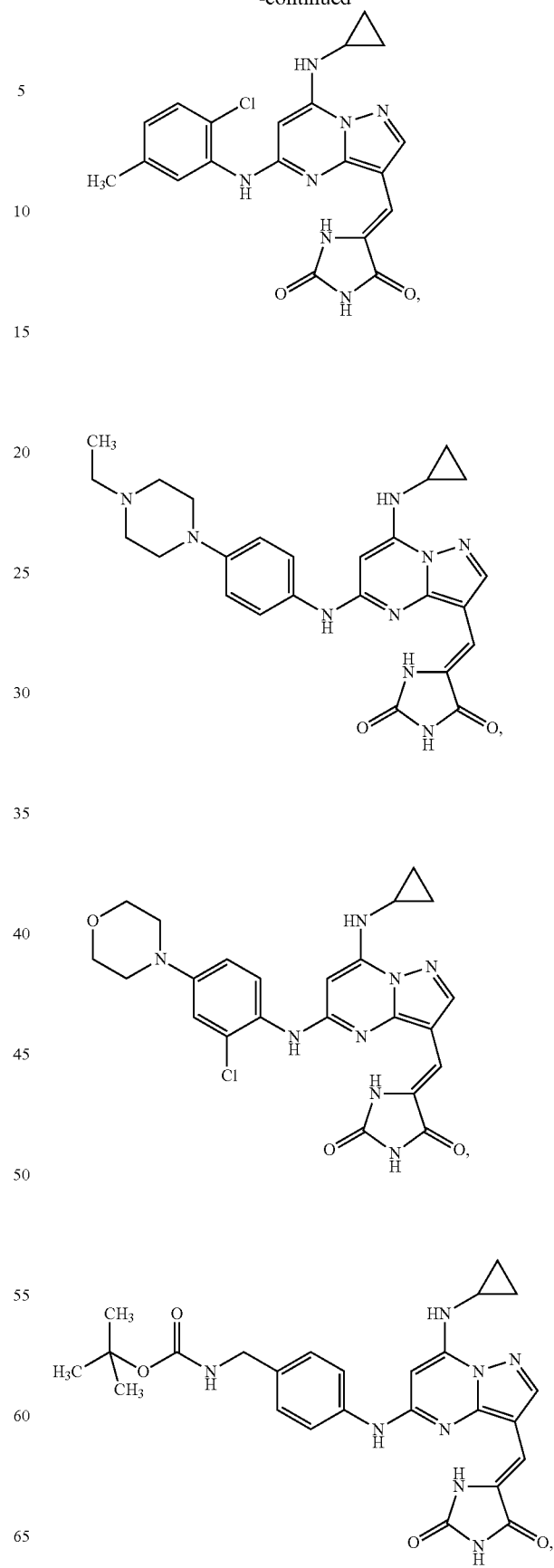

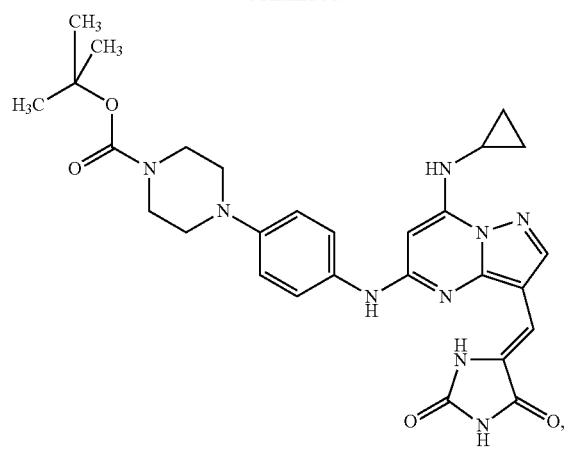
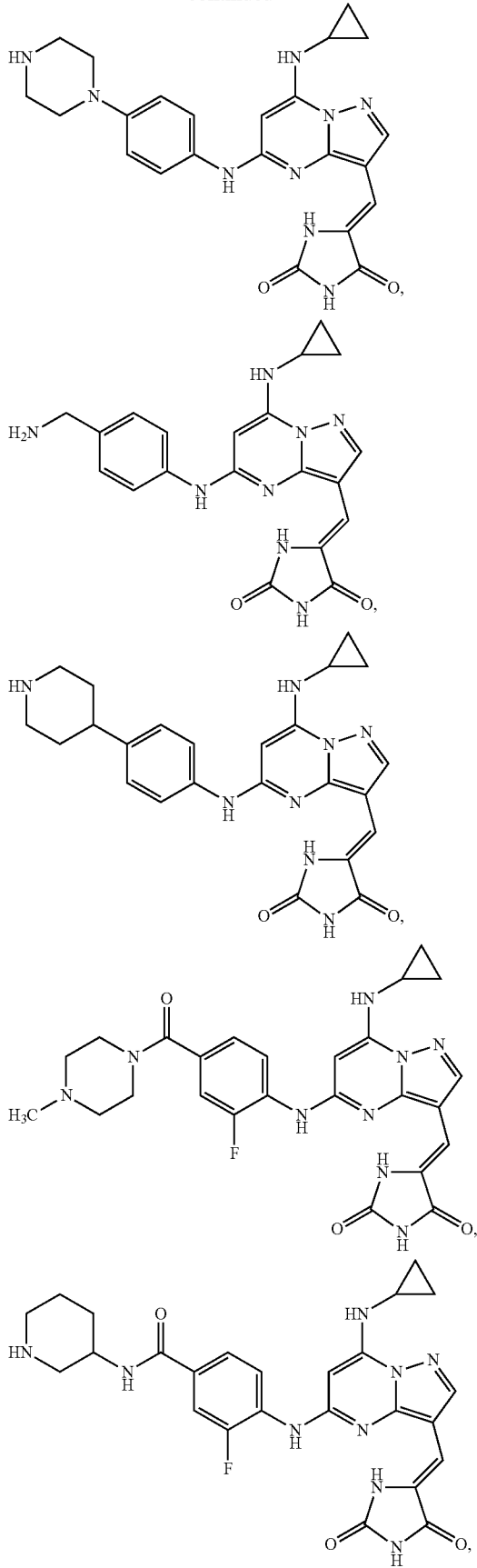

791
-continued
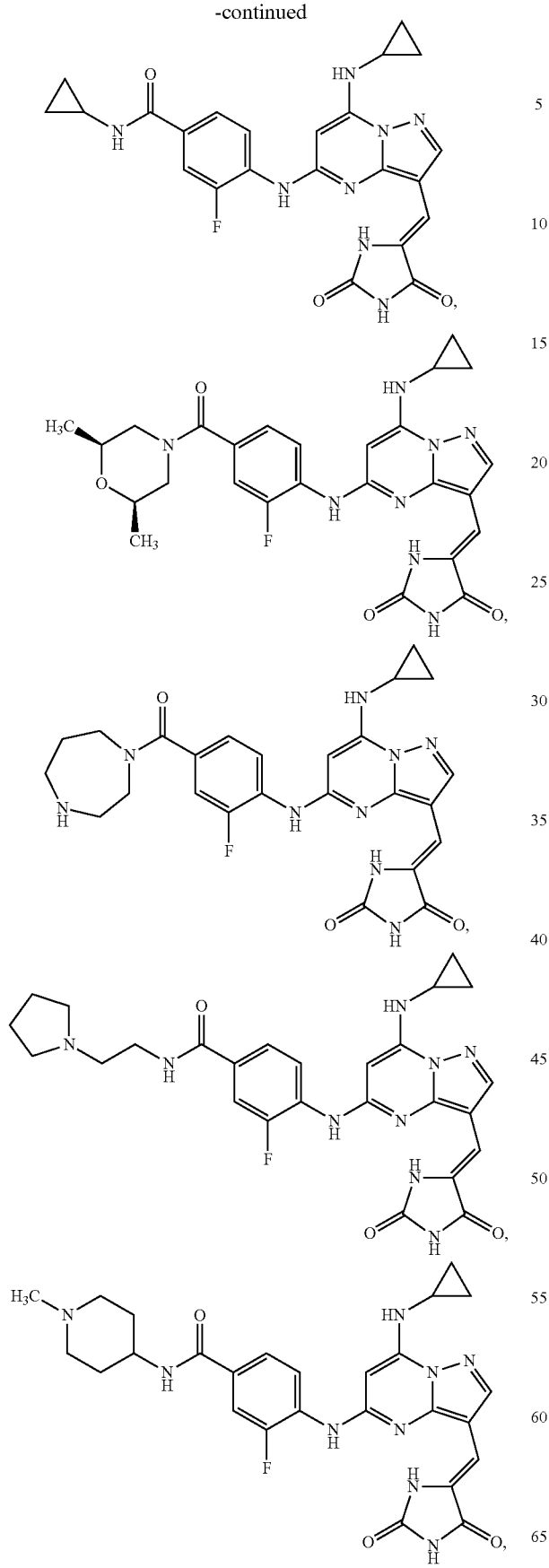
792
-continued
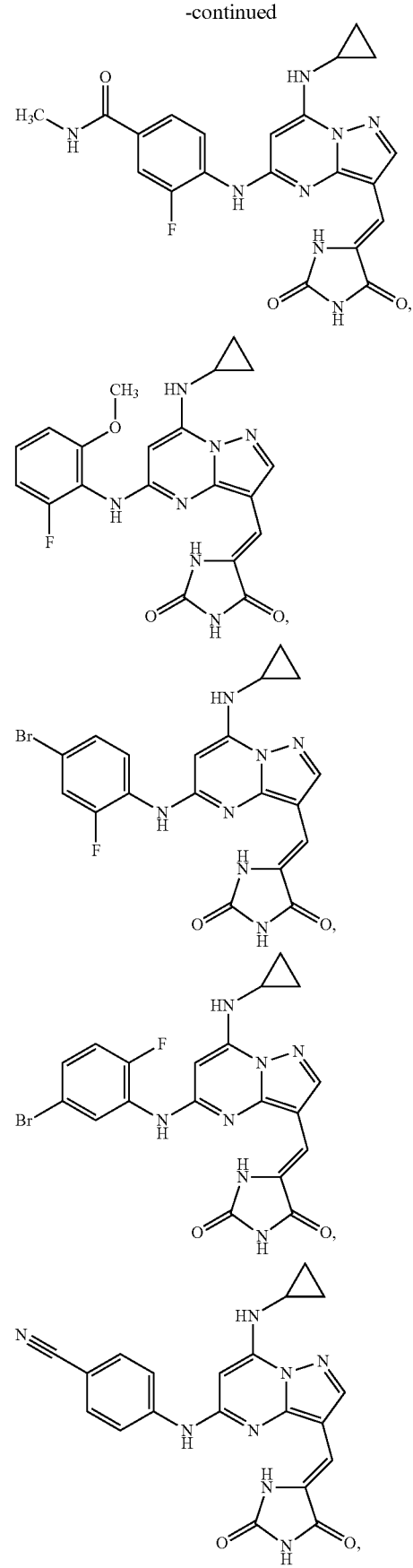

793
-continued
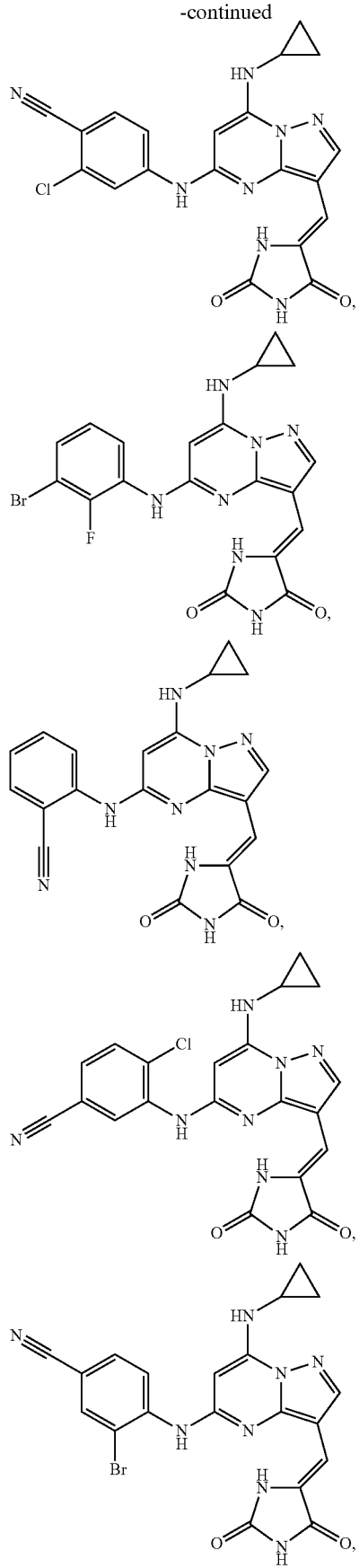
794
-continued
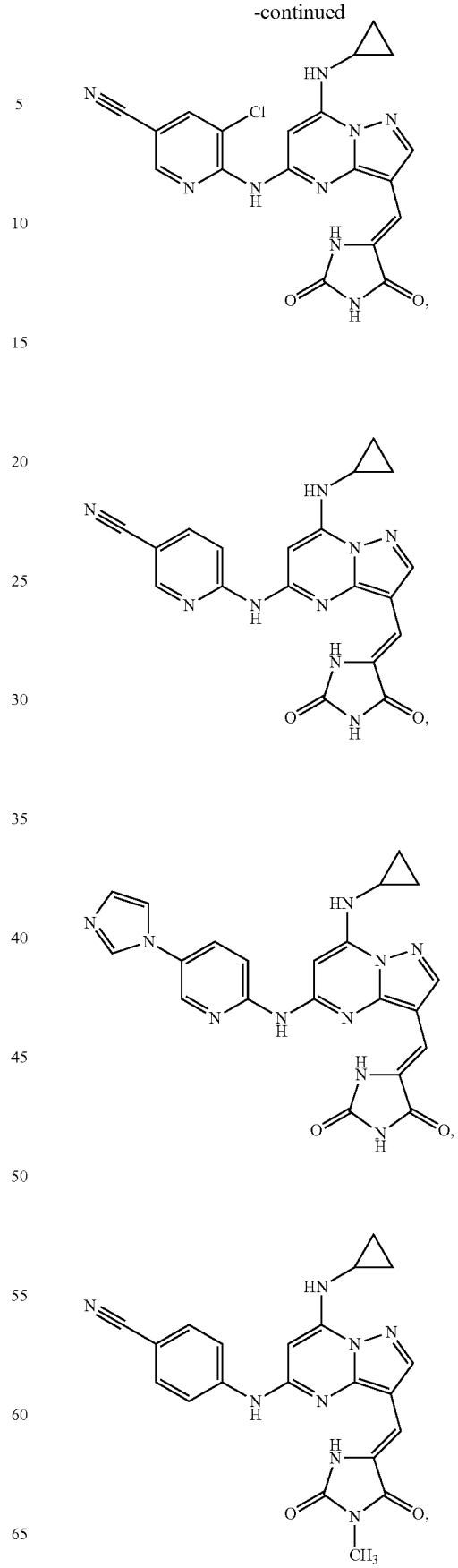

795                                                 796
-continued                                          -continued 797
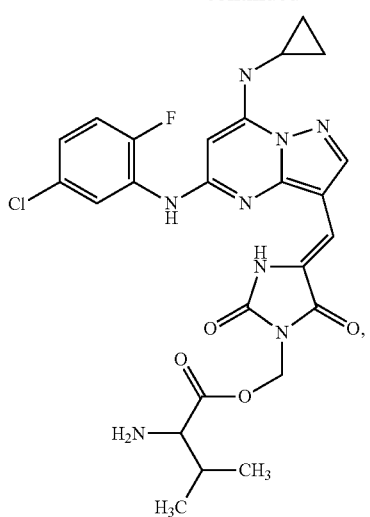
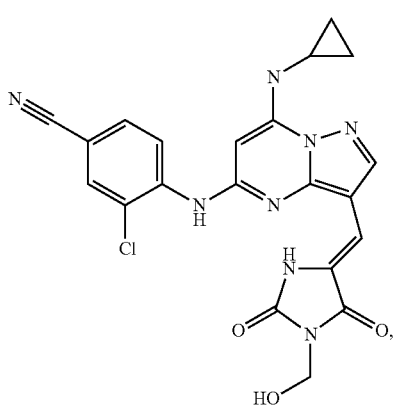
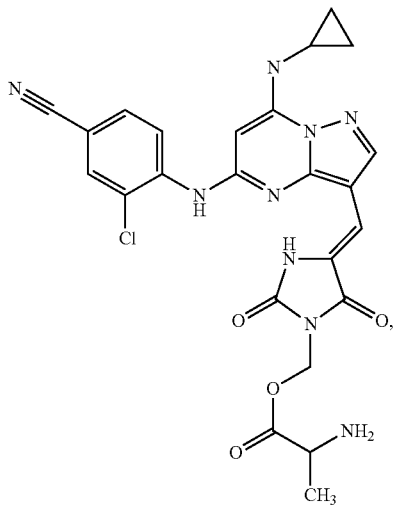
798
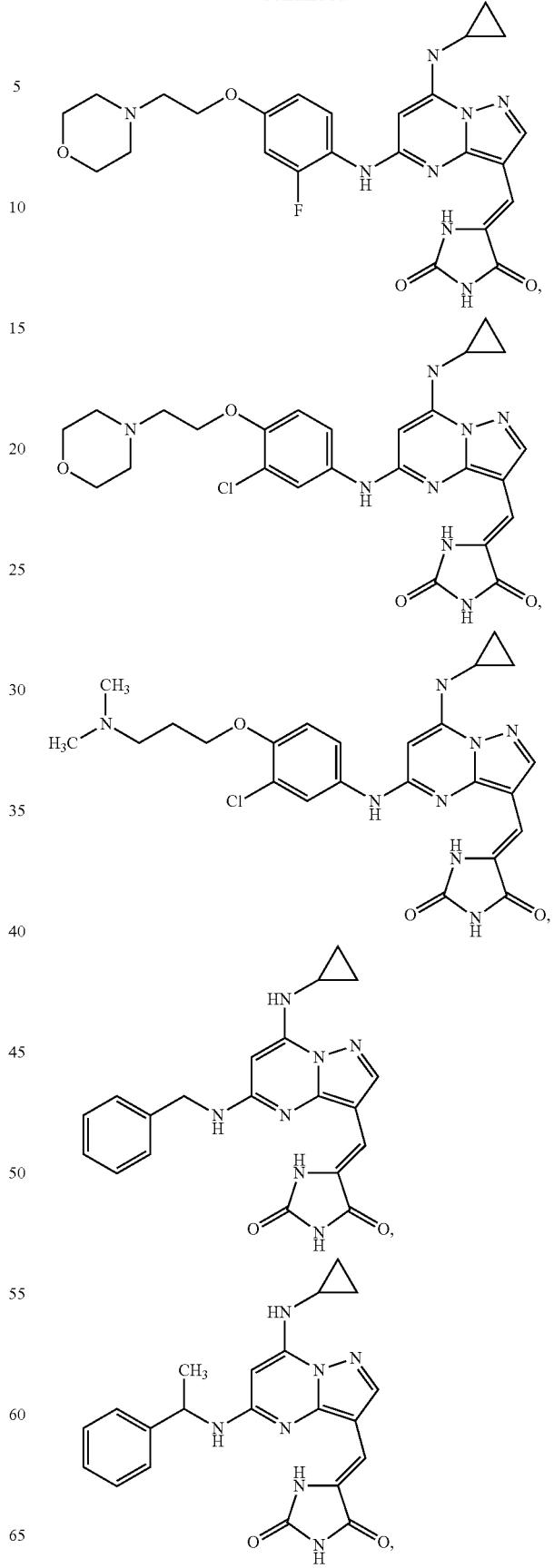

799
-continued
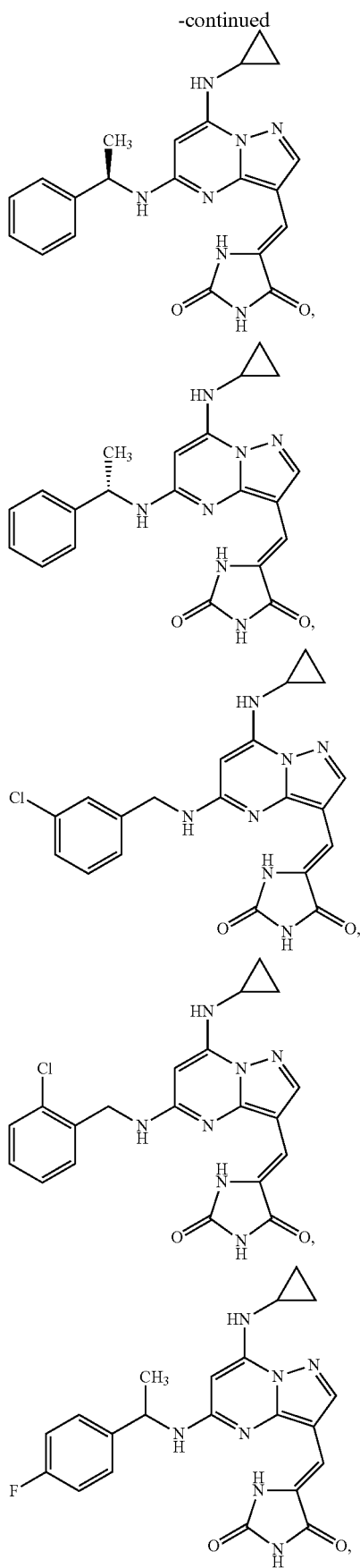
800
-continued
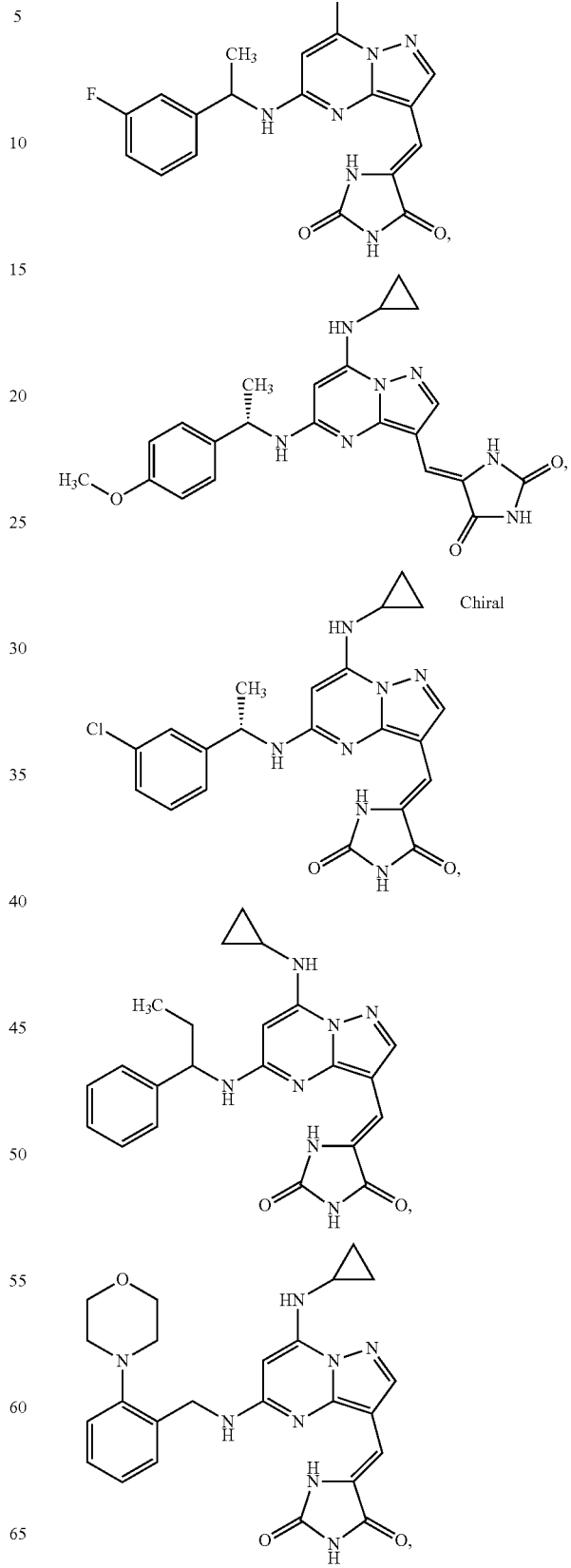

801
-continued
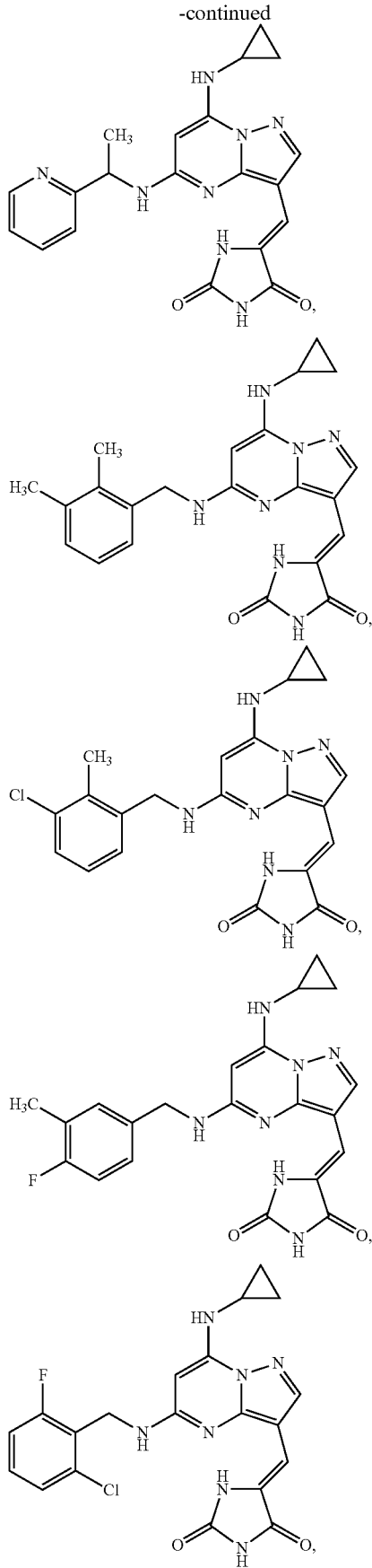
802
-continued
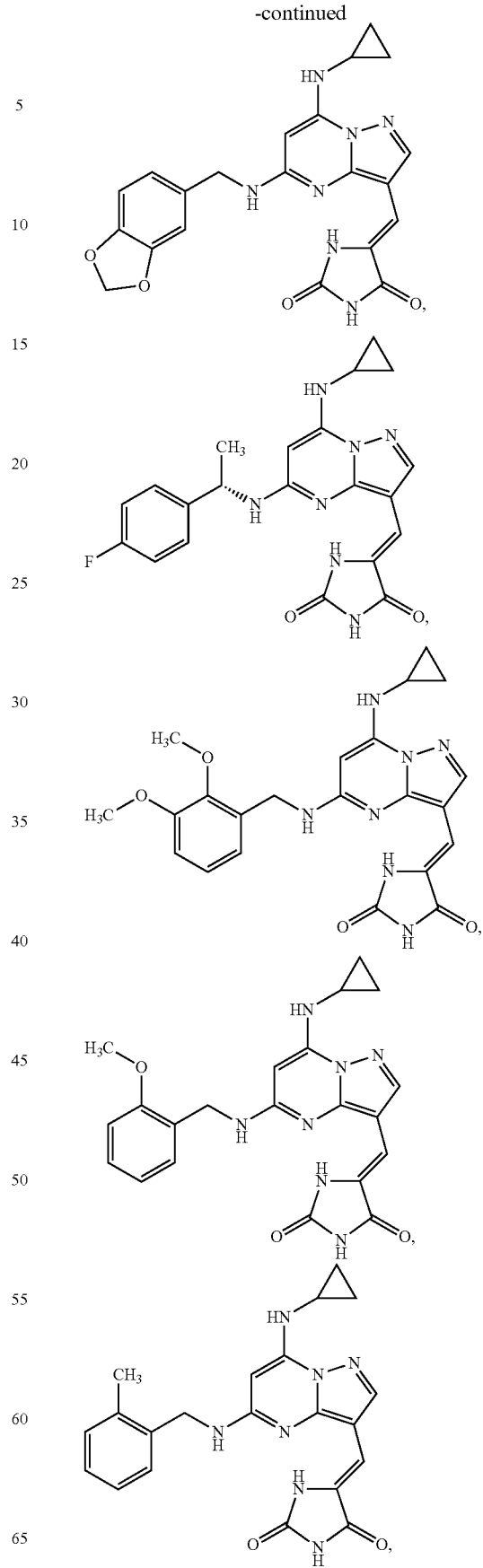

803
-continued
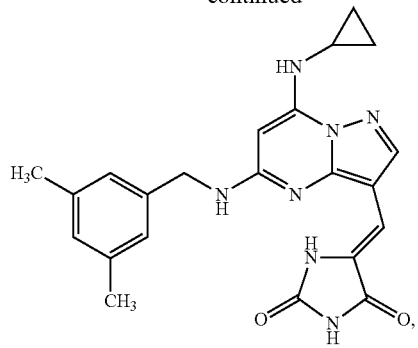
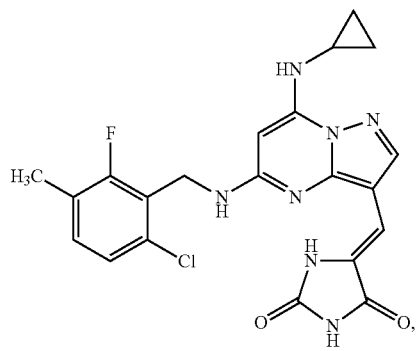
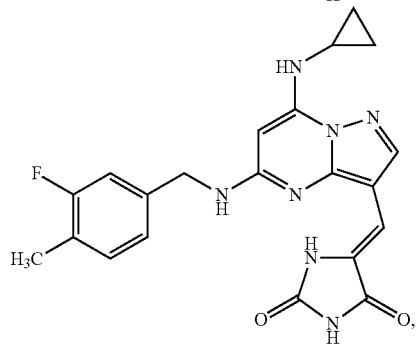
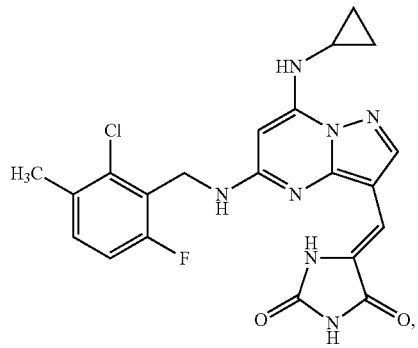
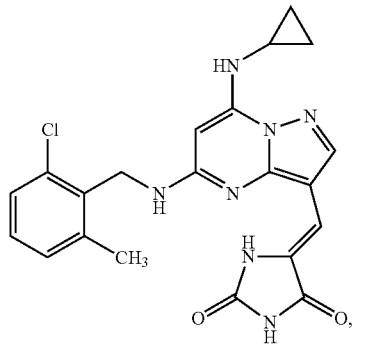
804
-continued
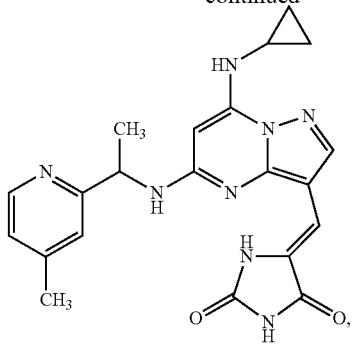
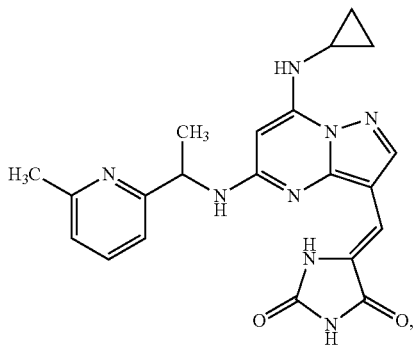
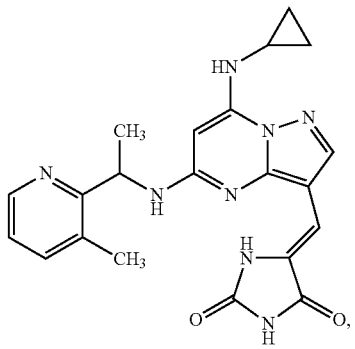
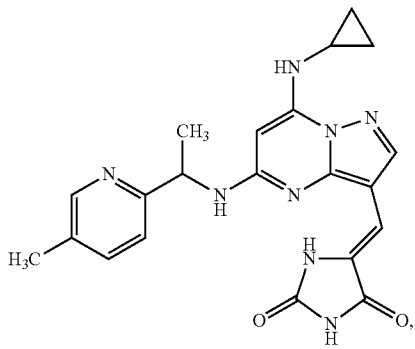
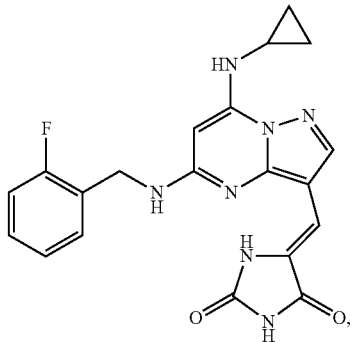

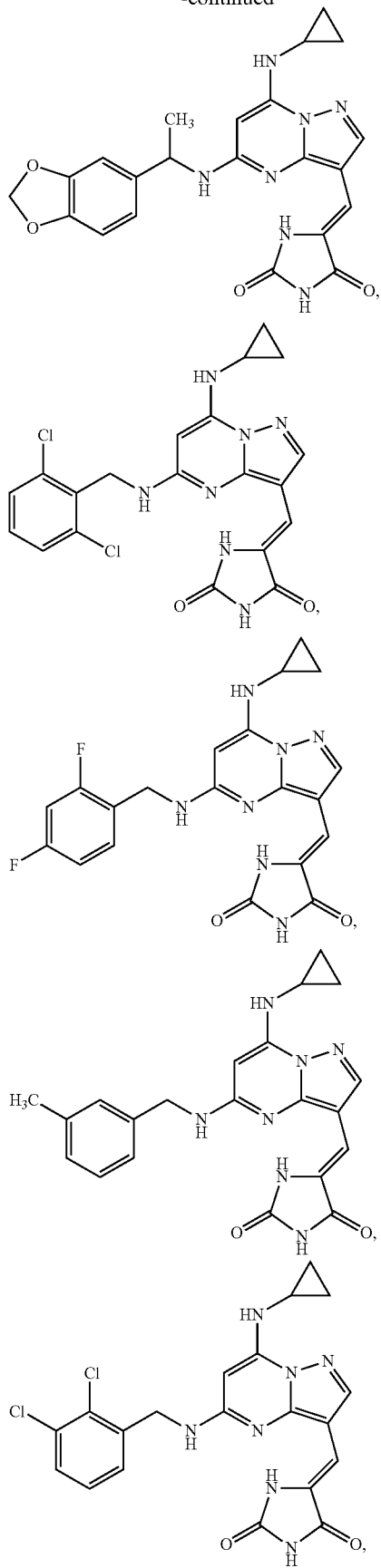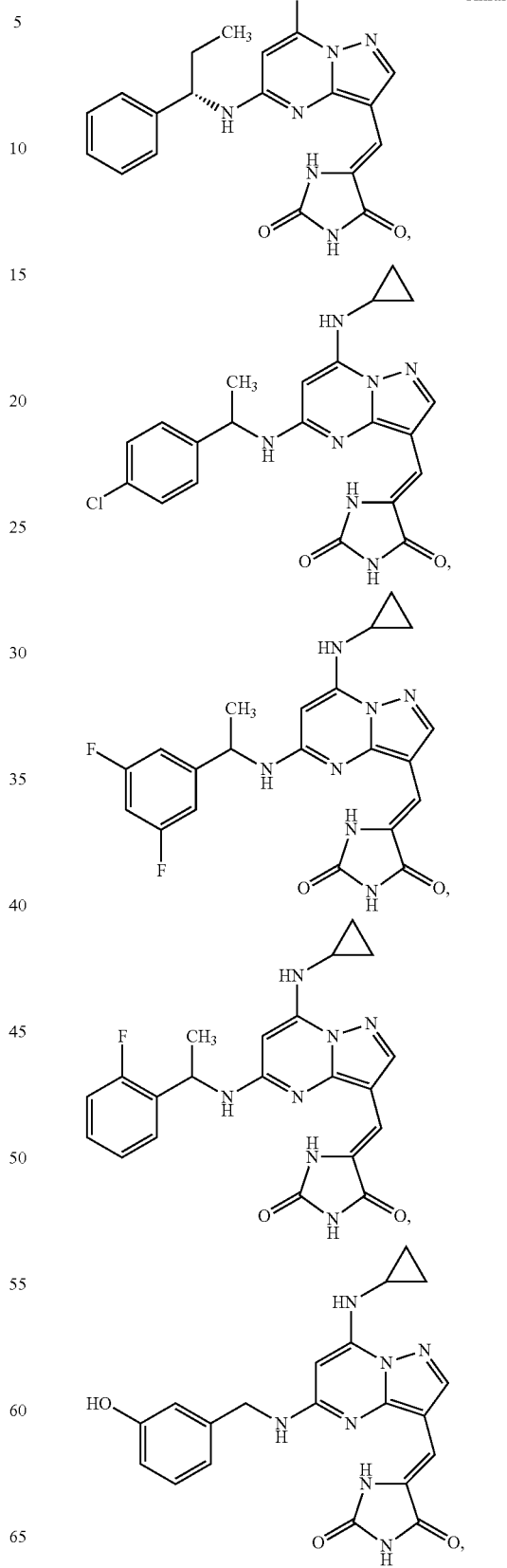

807
-continued
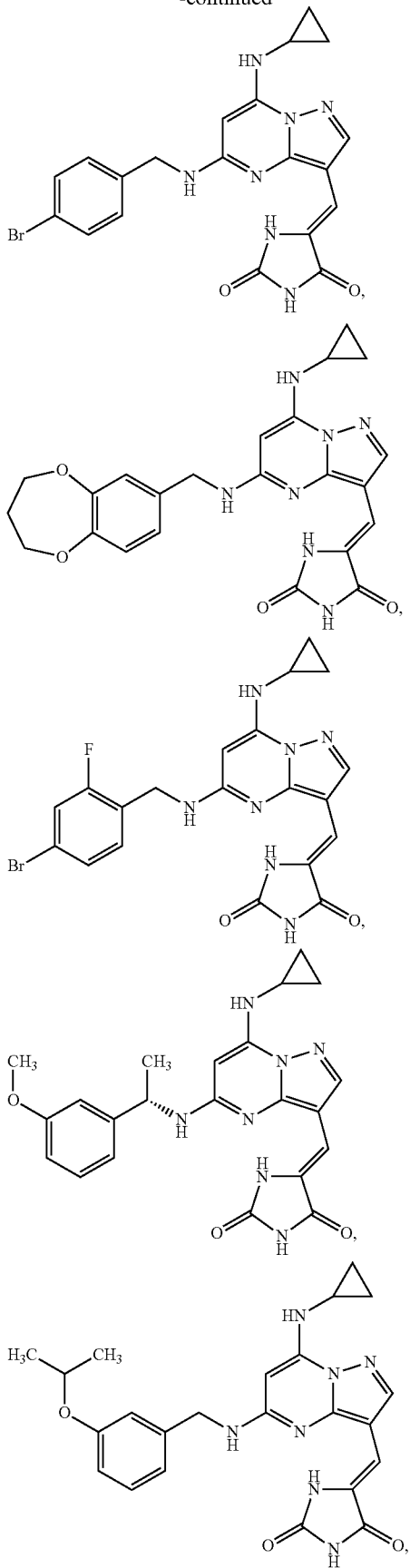
808
-continued
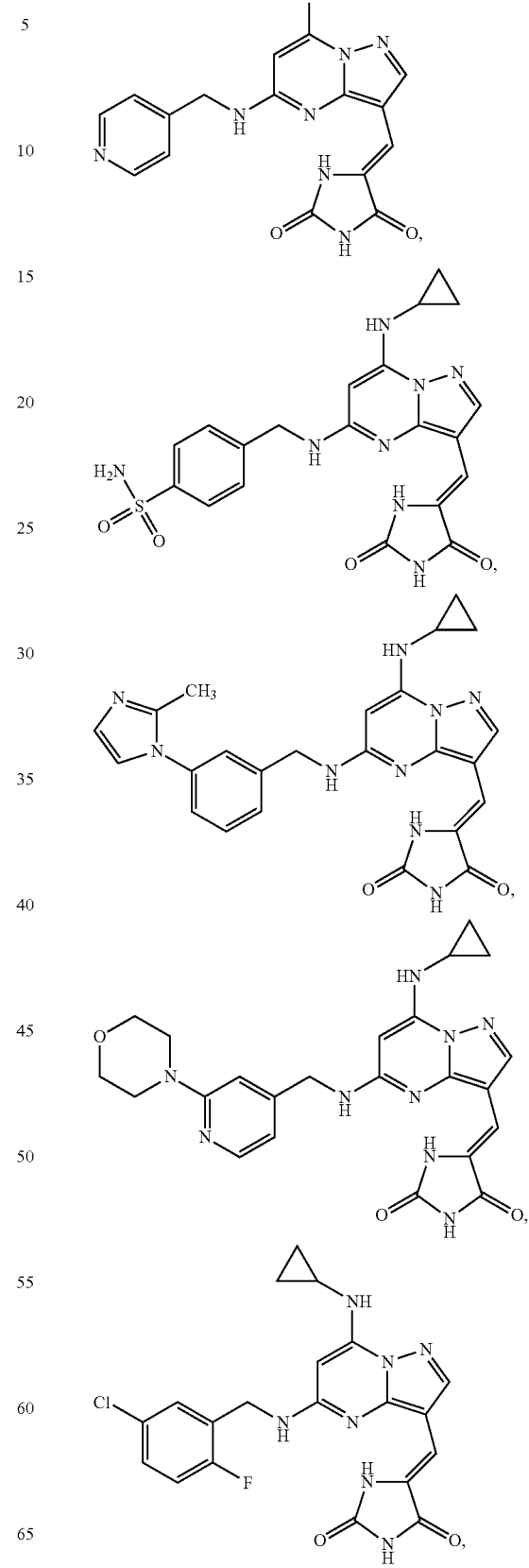

809
-continued
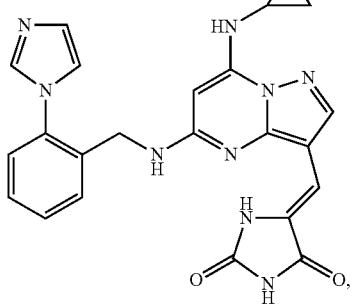
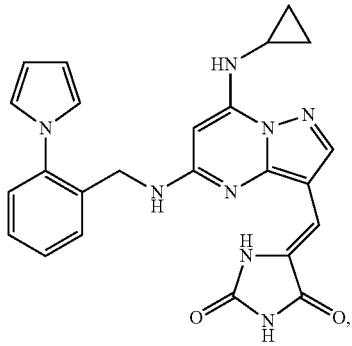
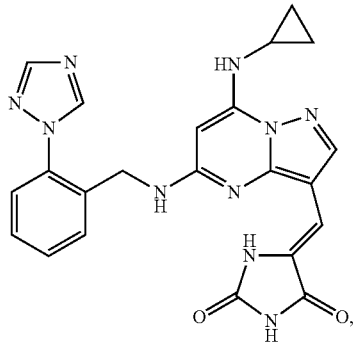
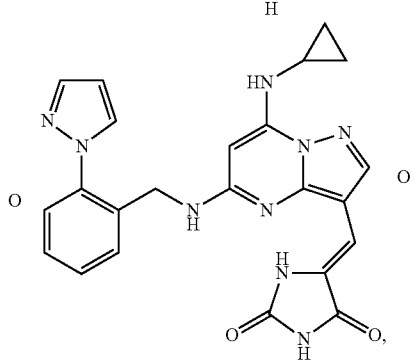
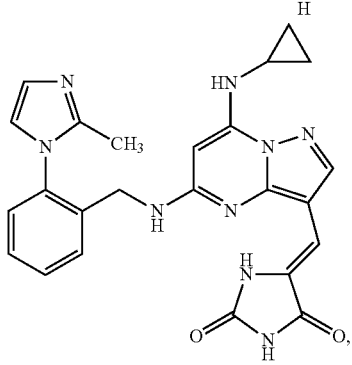
810
-continued
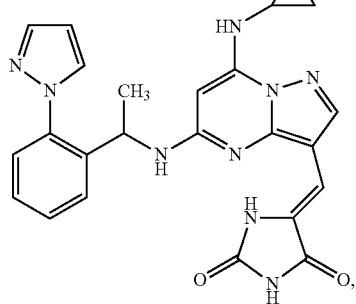
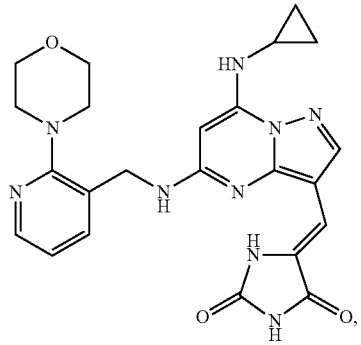
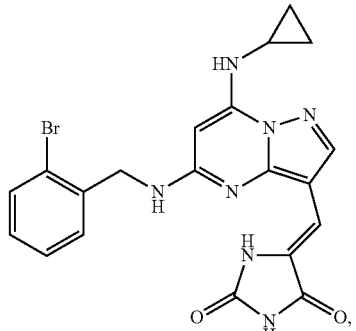
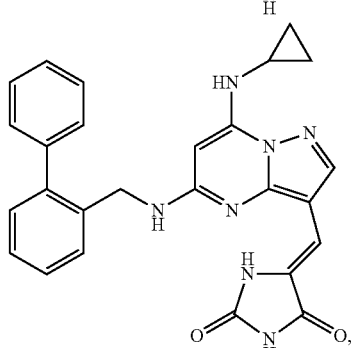
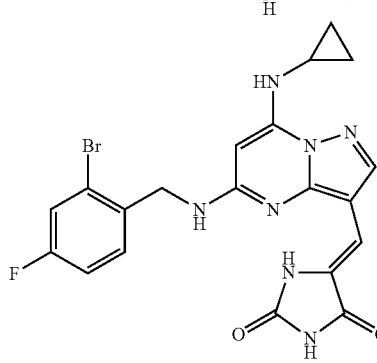

811
-continued
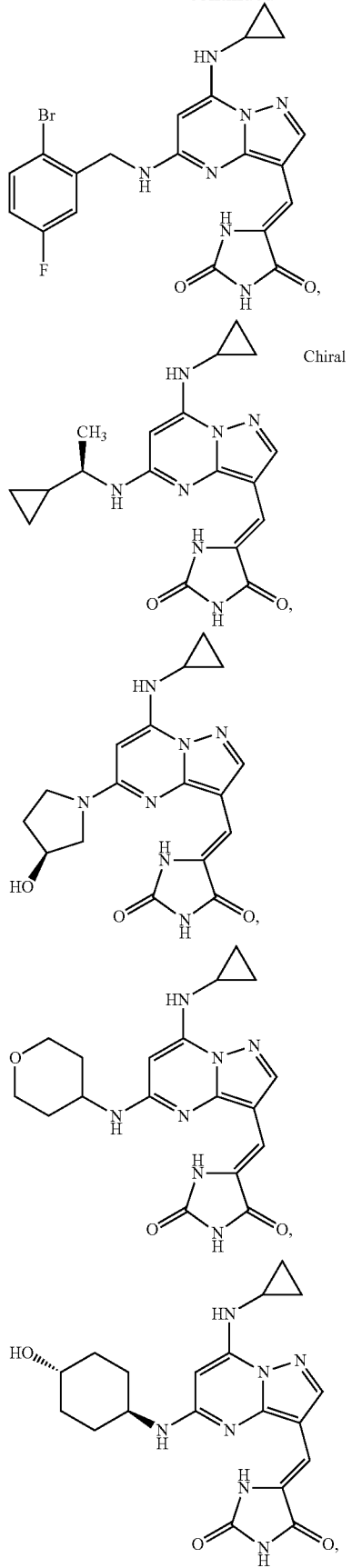
812
-continued
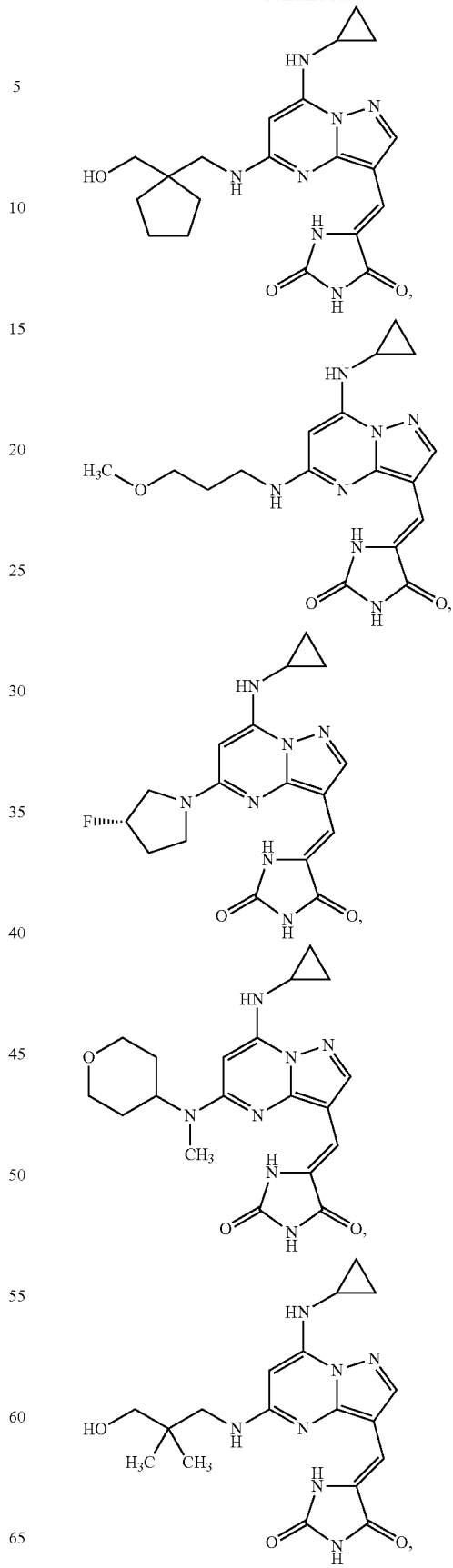

813
-continued
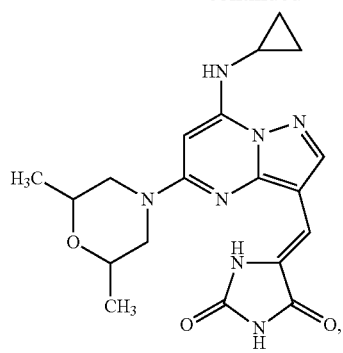
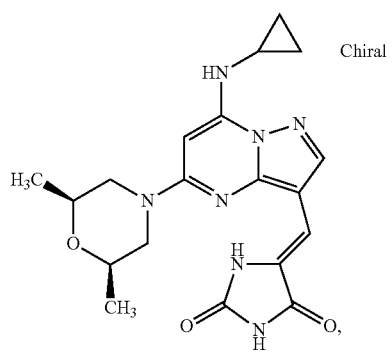
Chiral
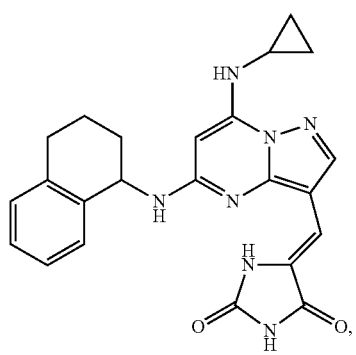
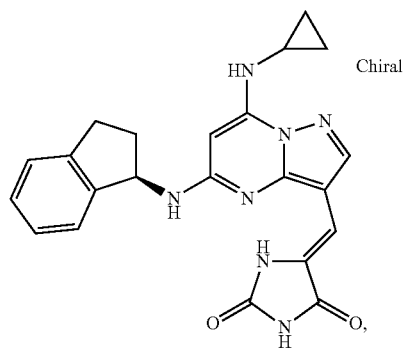
Chiral
814
-continued
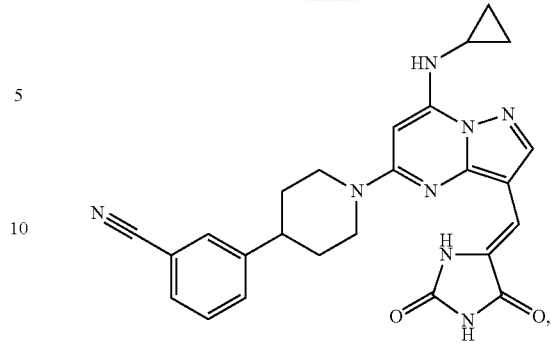
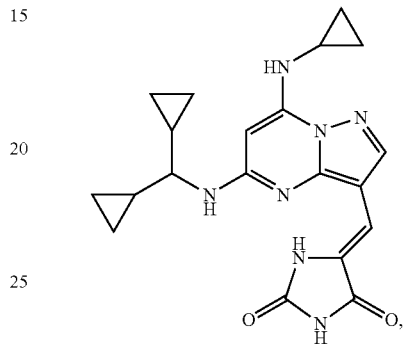
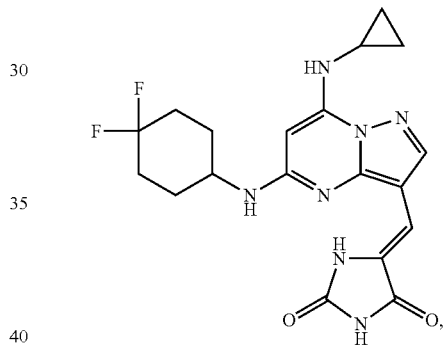
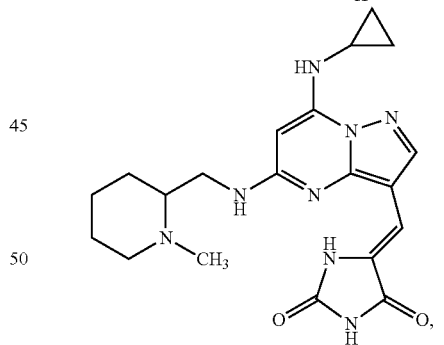
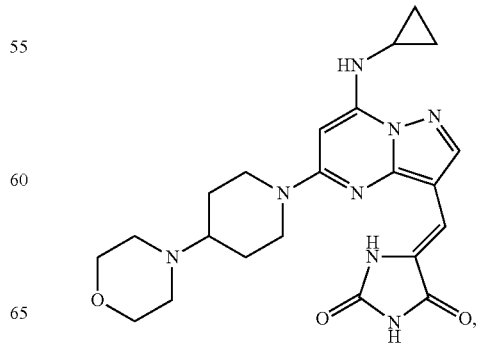

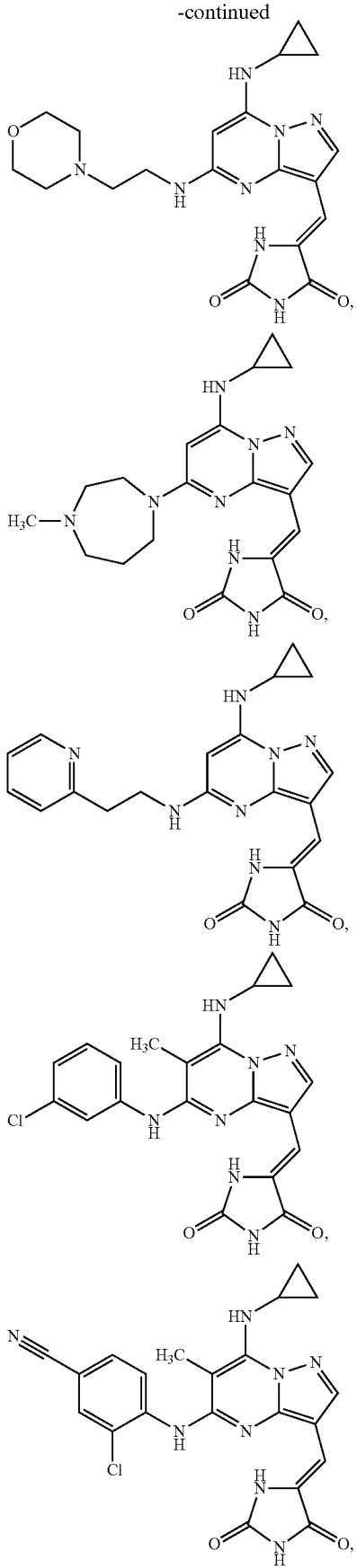
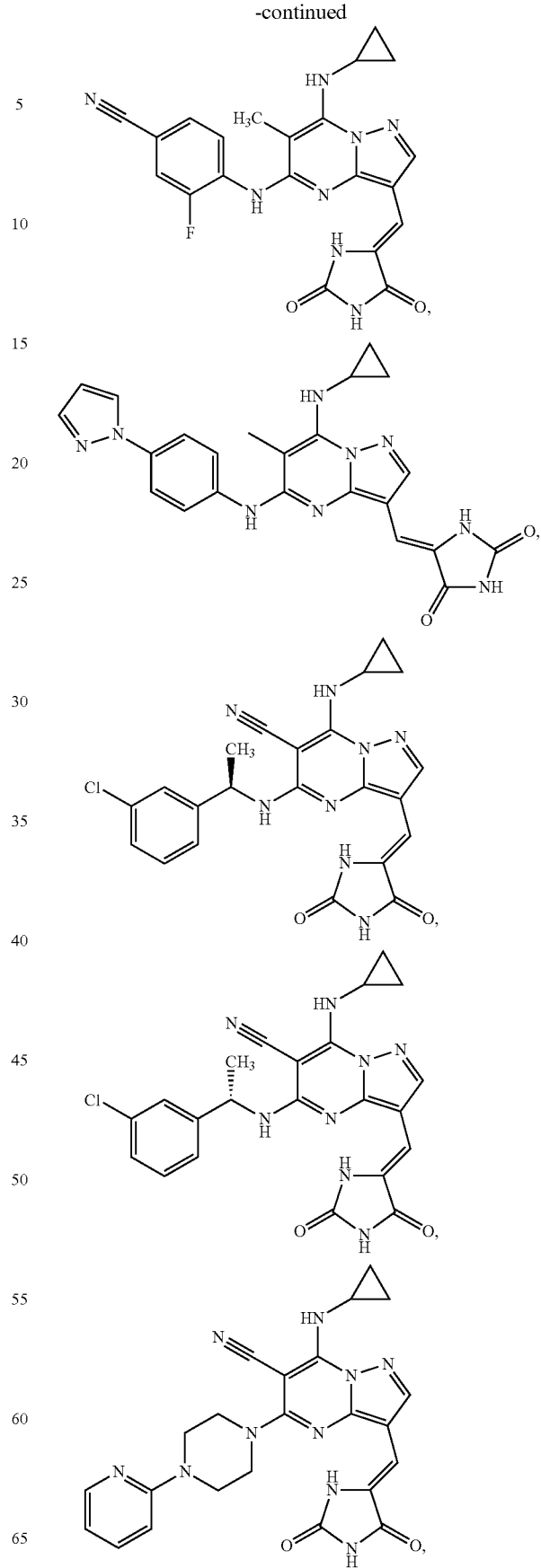

817 -continued
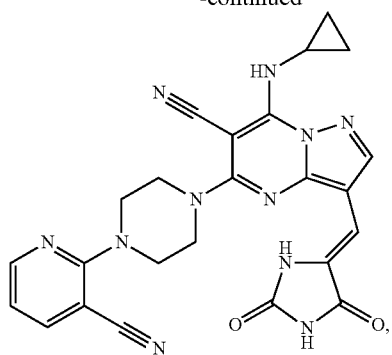
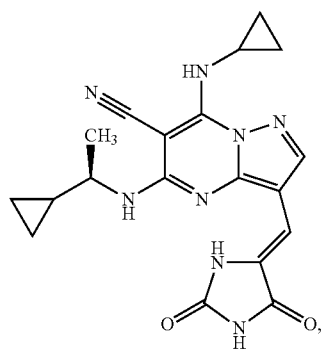
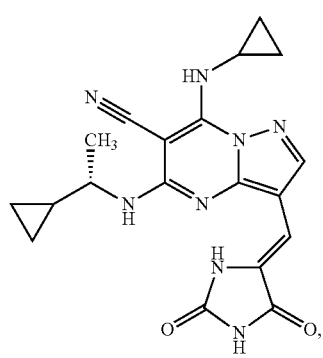
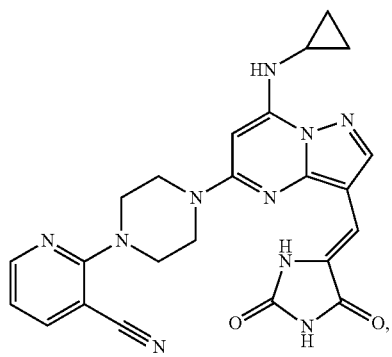
818 -continued
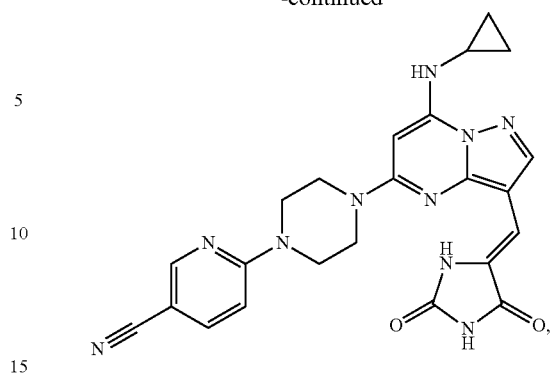
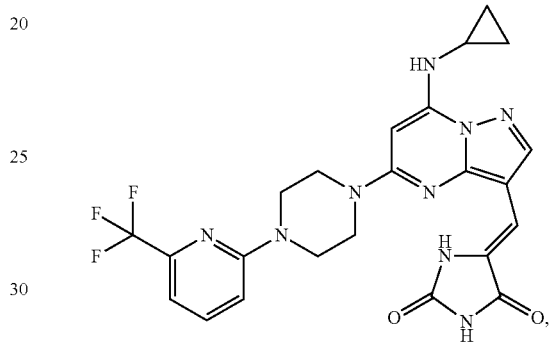
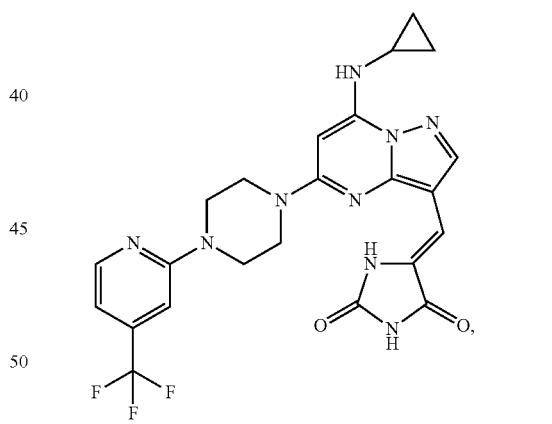
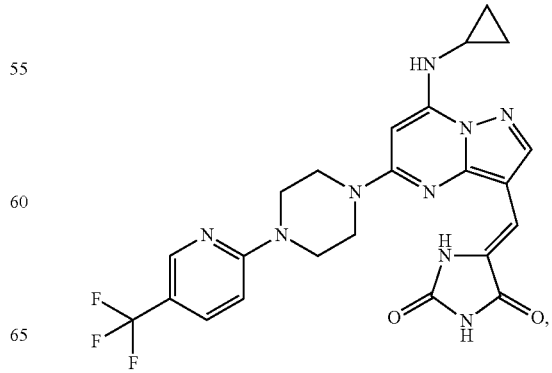

819
-continued
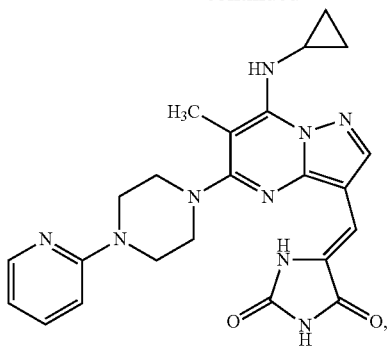
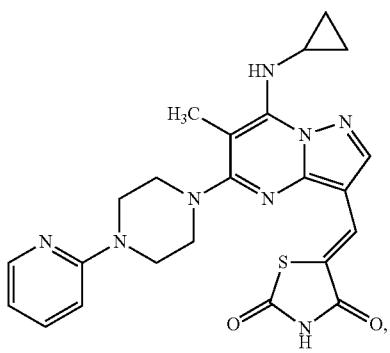
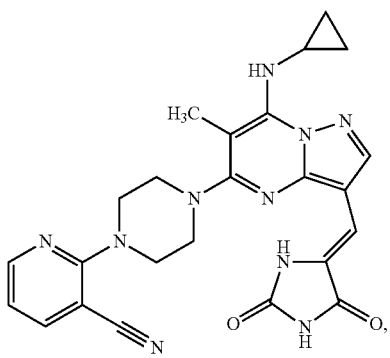
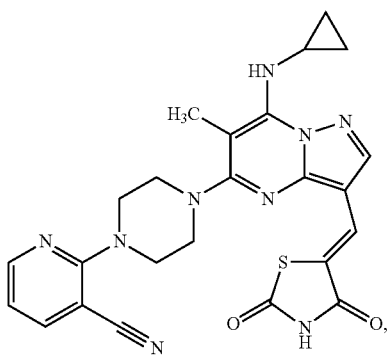
820
-continued
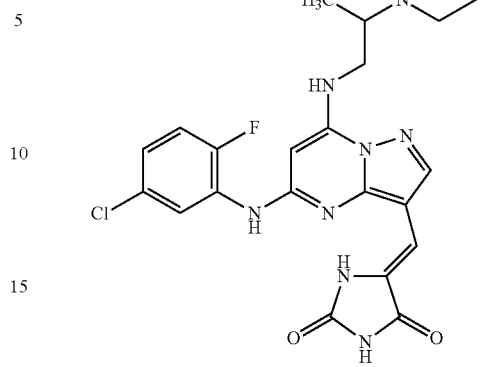
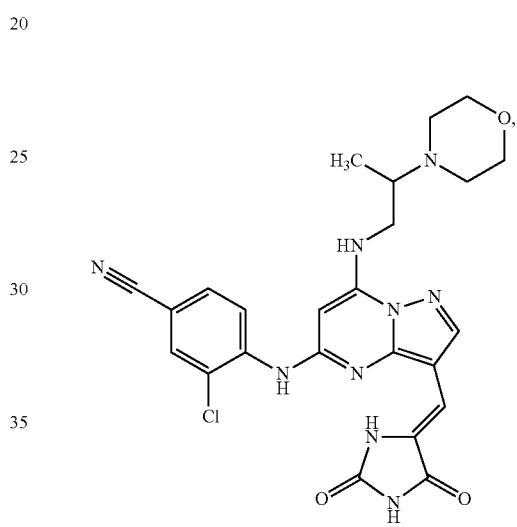
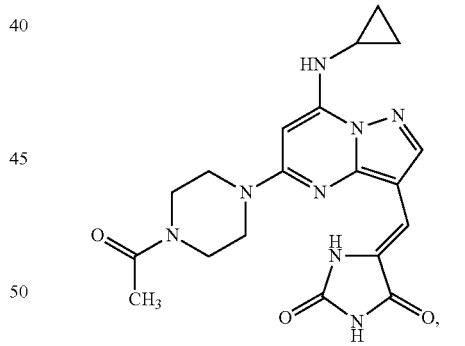
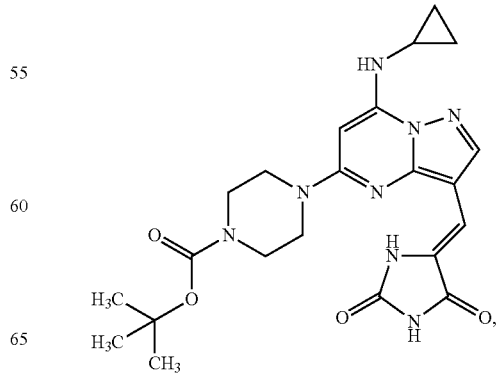

821
-continued
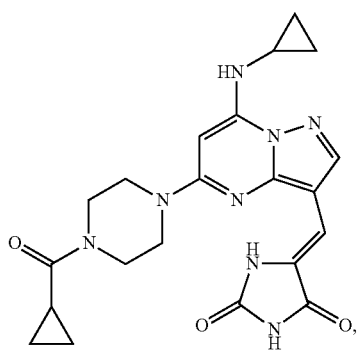
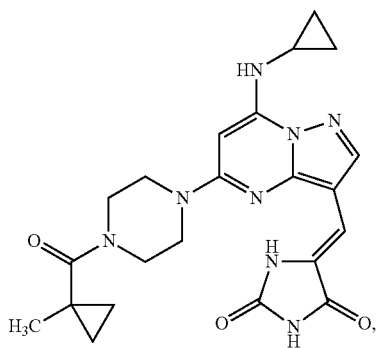
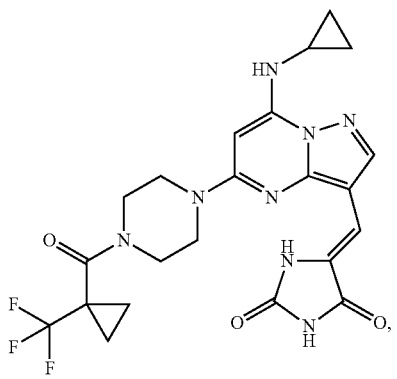
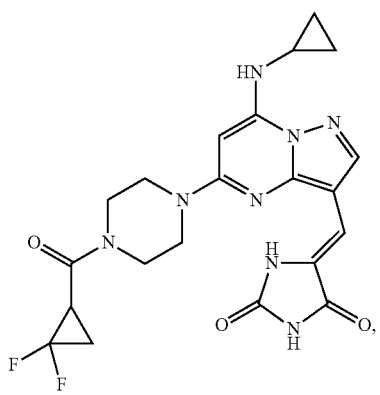
822
-continued
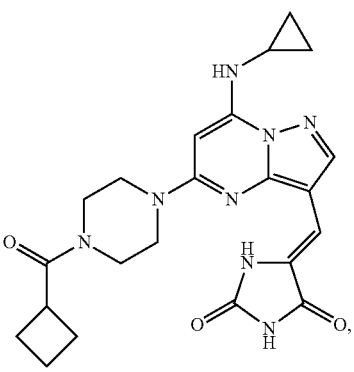
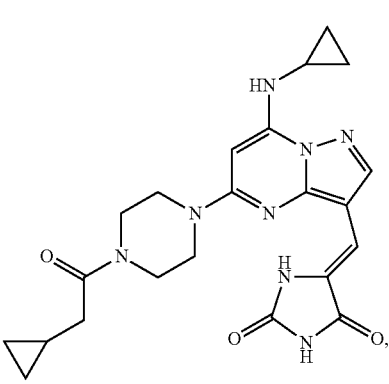
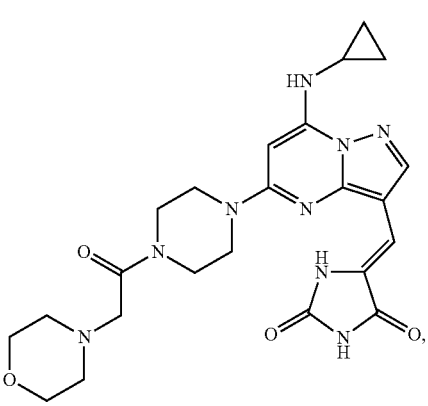
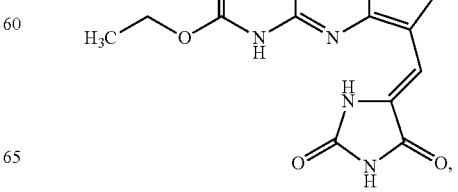

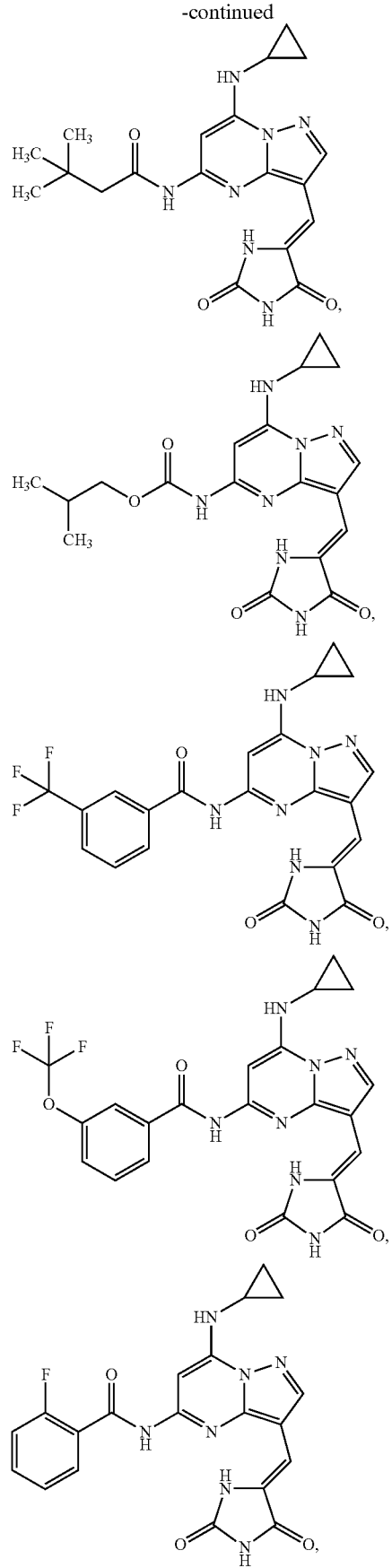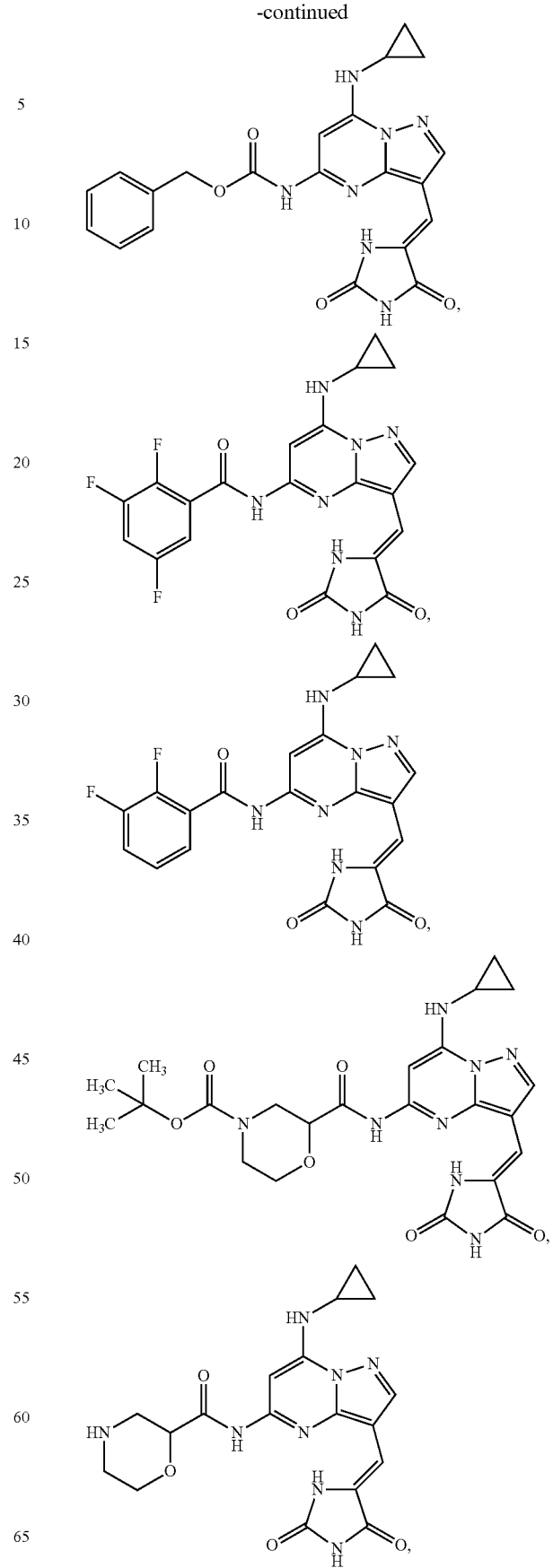

825
-continued
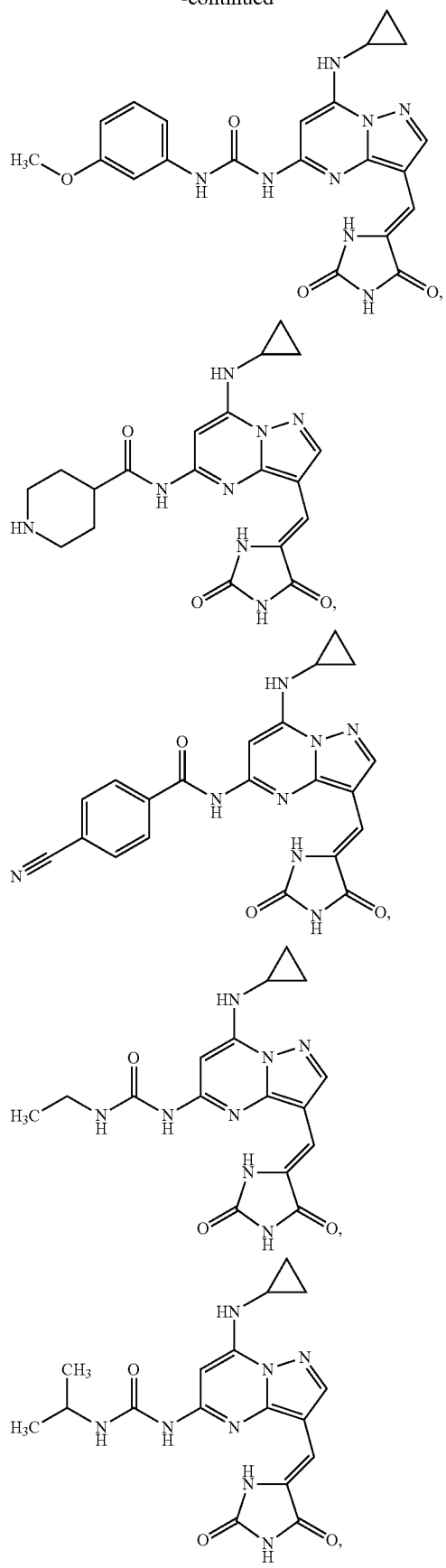
826
-continued
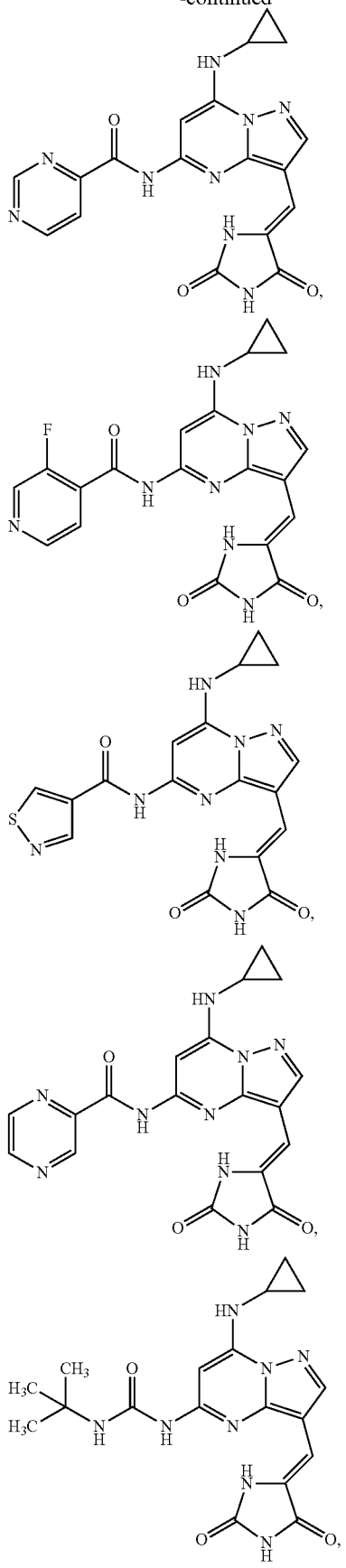

827
-continued
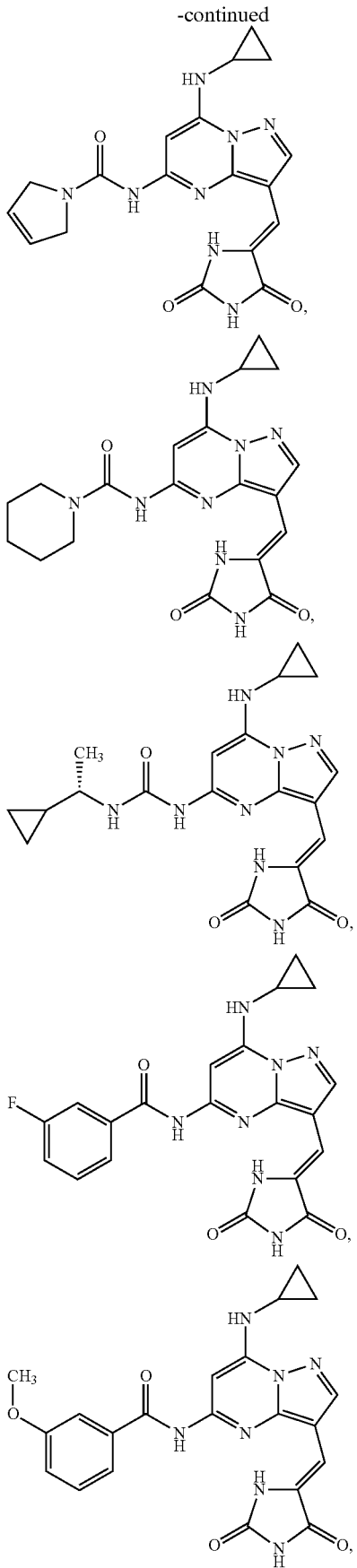
828
-continued
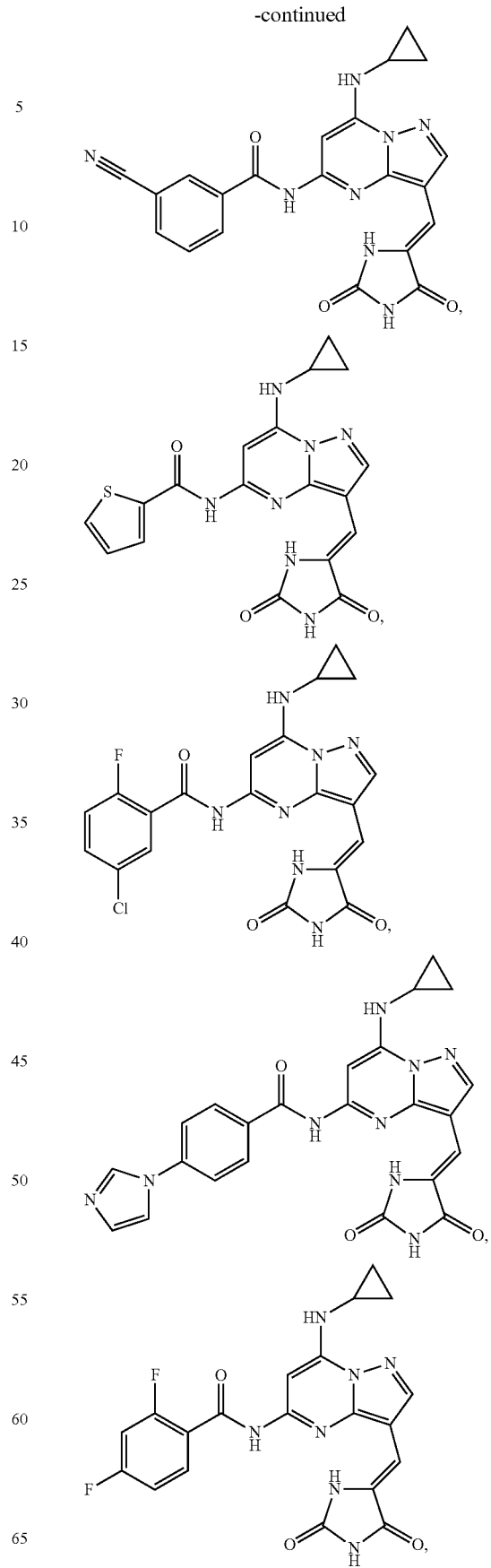

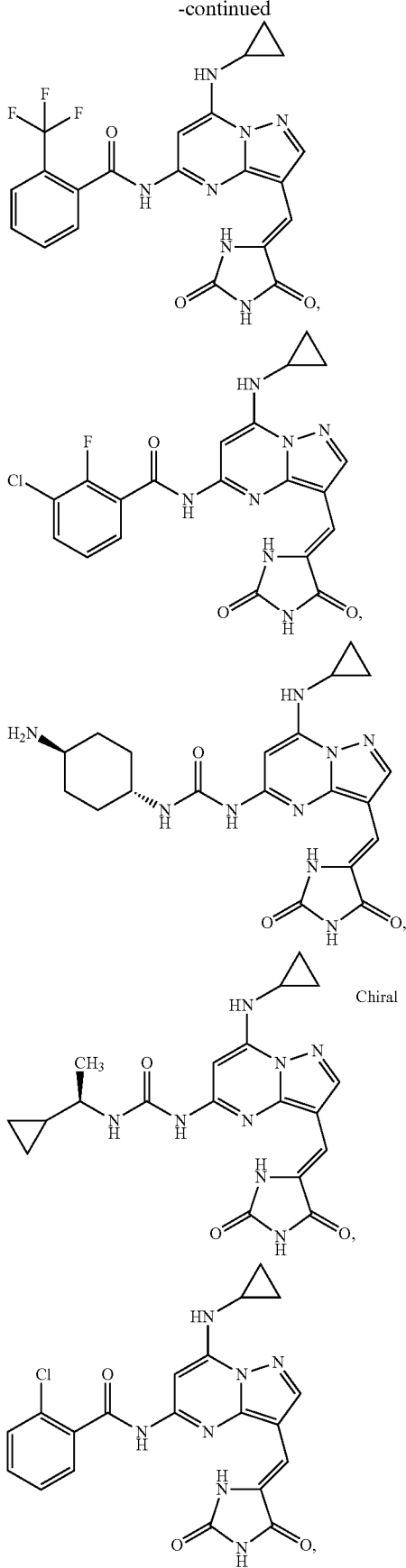
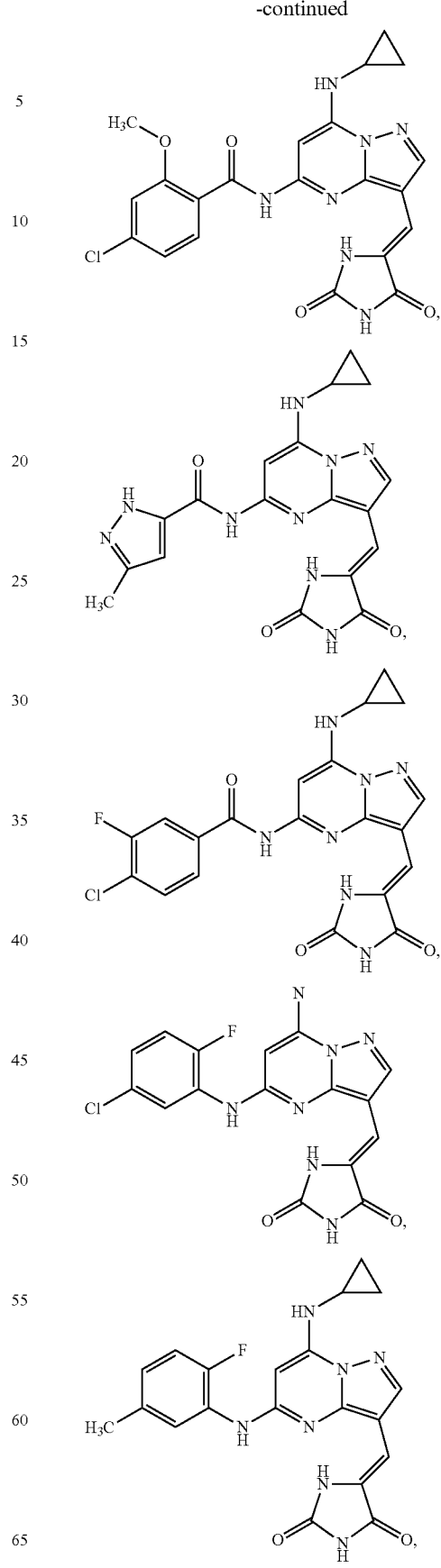

831
-continued
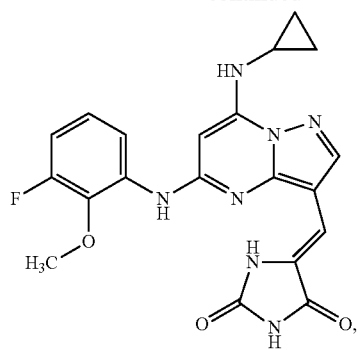
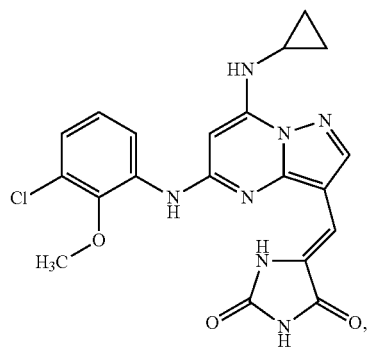
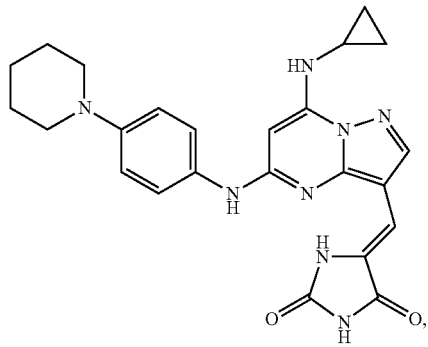
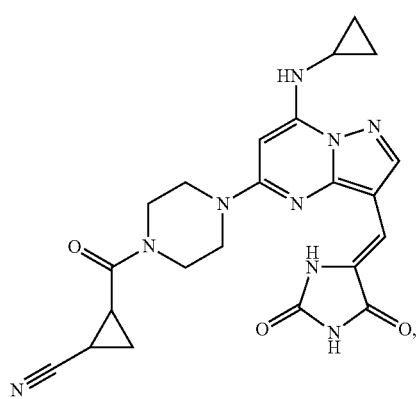
832
-continued
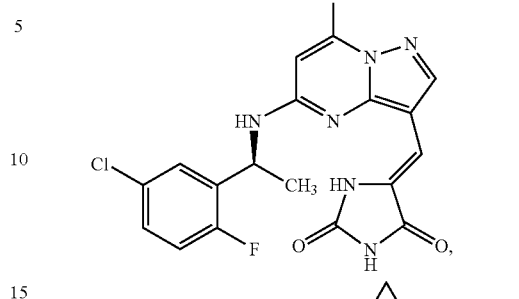
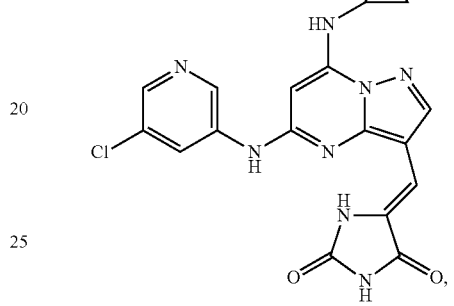
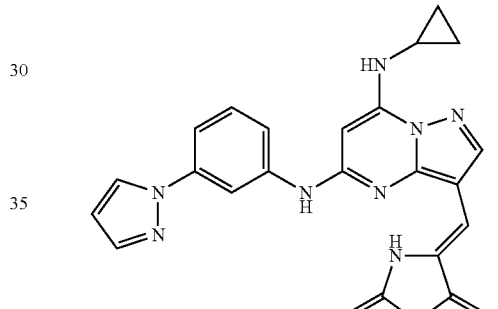
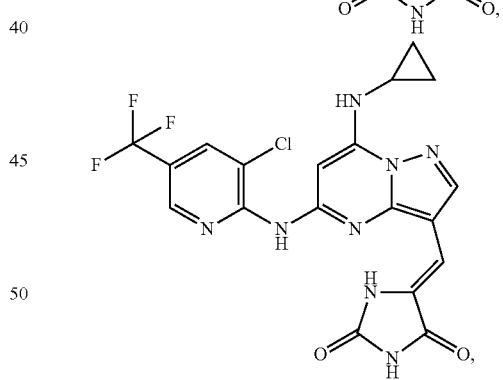
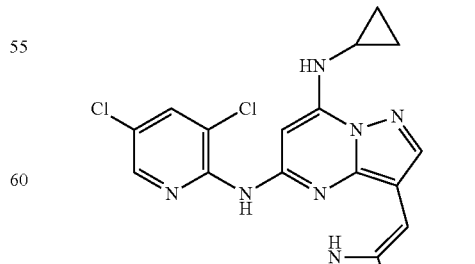

833
-continued
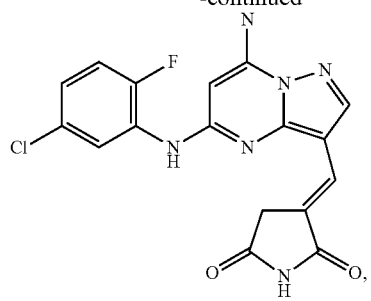
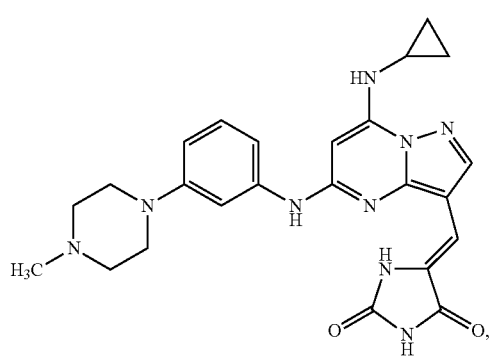
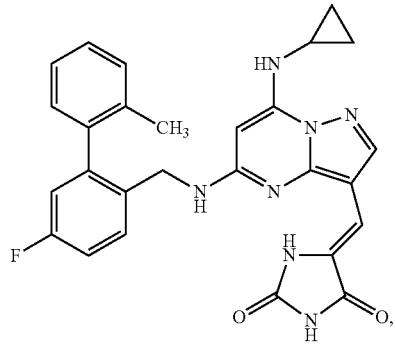
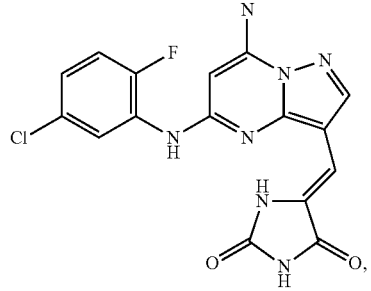
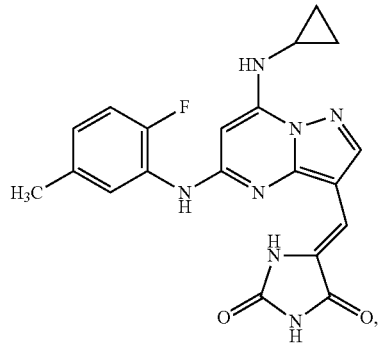
834
-continued
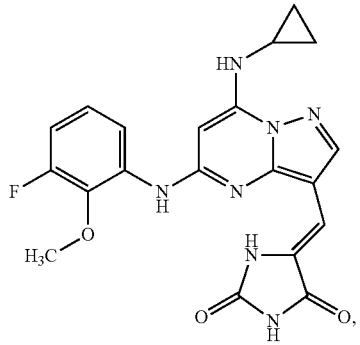
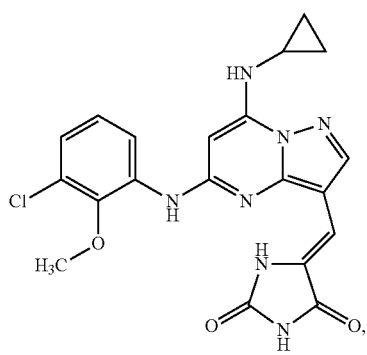
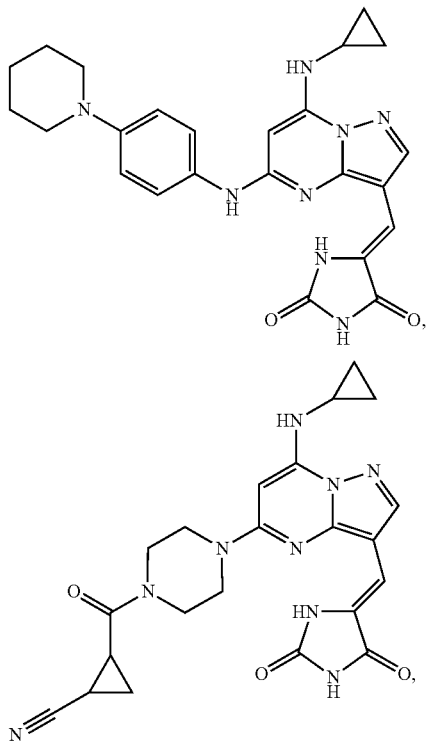

835
-continued
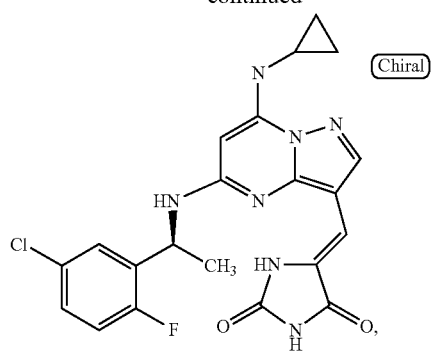
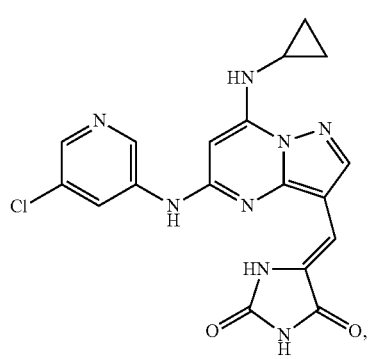
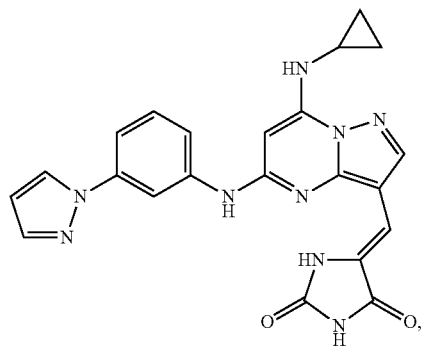
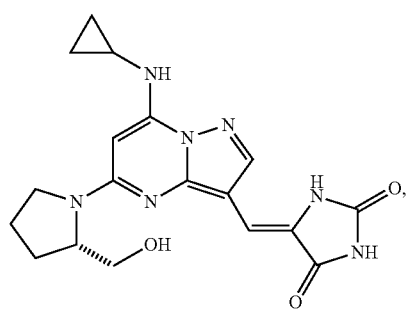
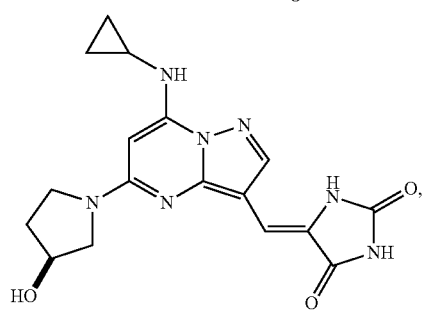
836
-continued
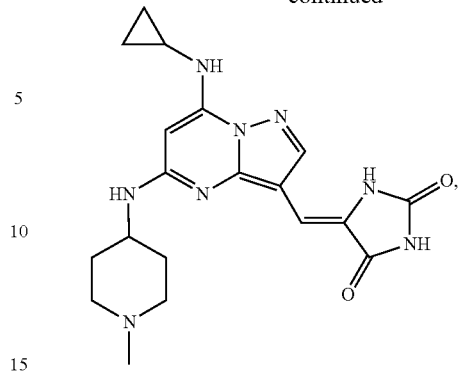
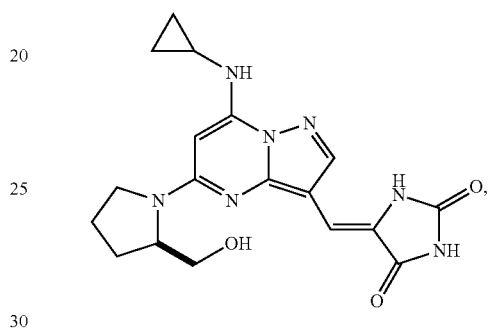
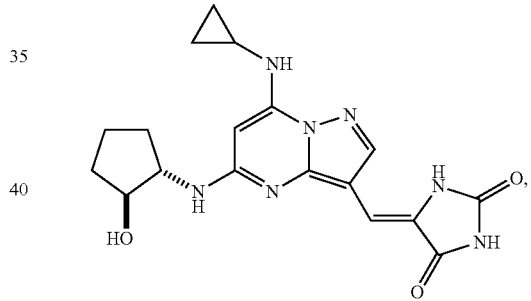
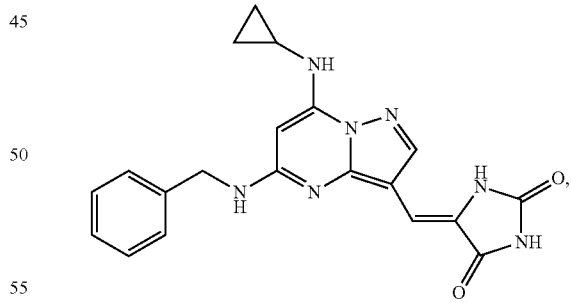
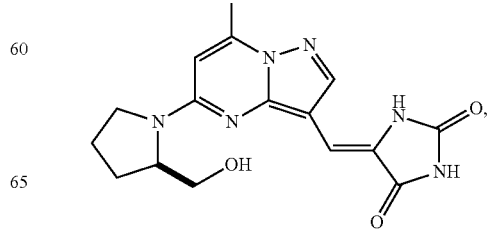

837
-continued
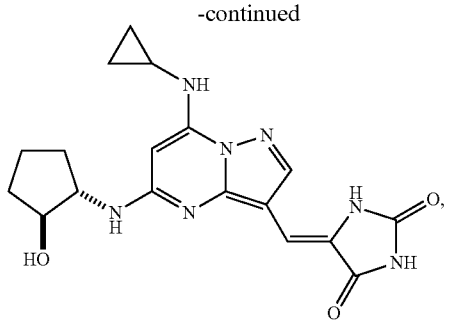
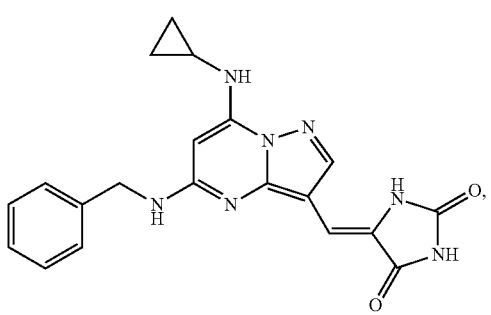
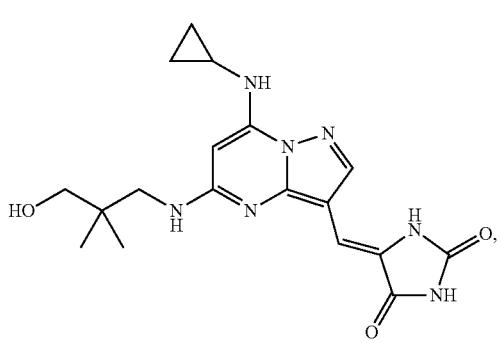
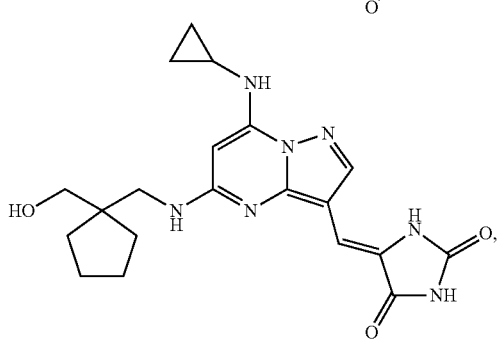
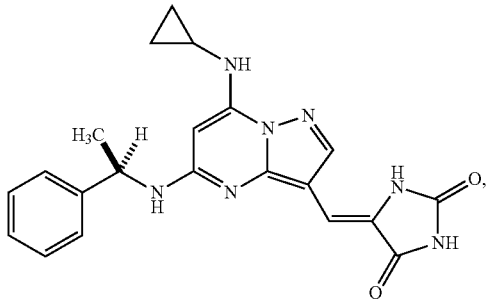
838
-continued
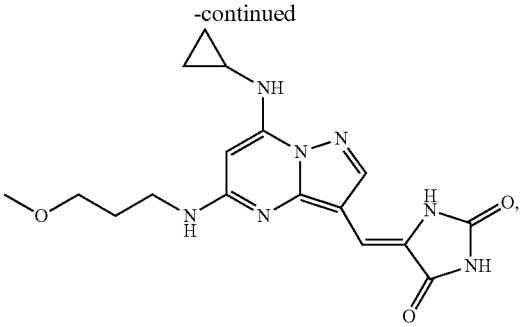
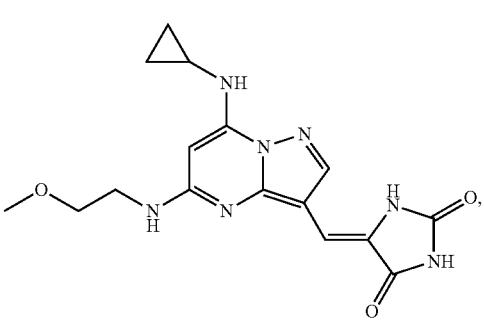
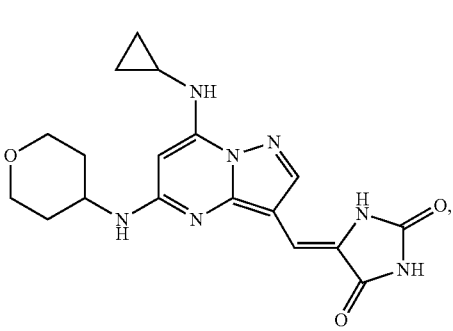
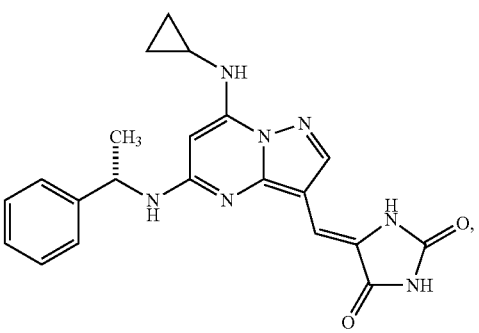
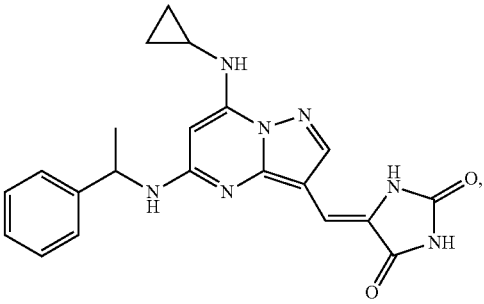

839
-continued
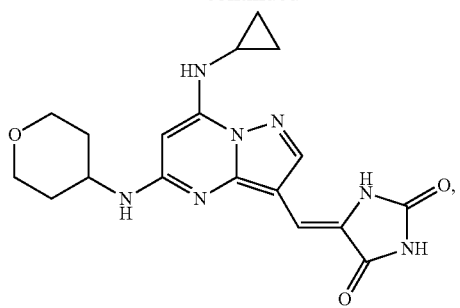
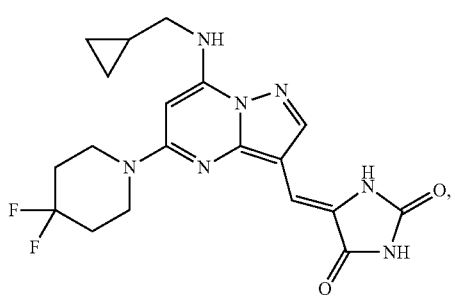
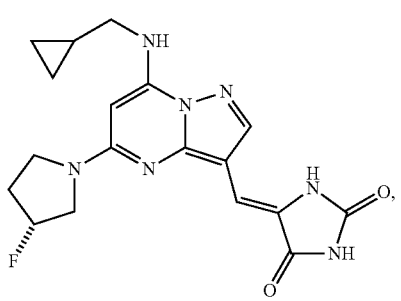
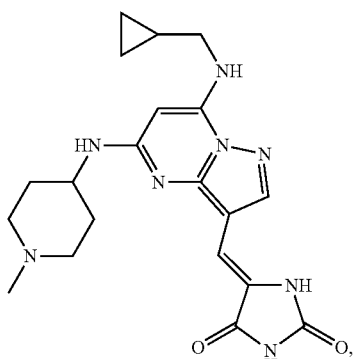
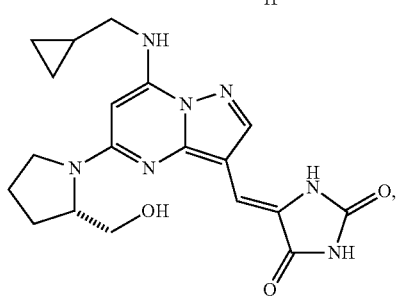
840
-continued
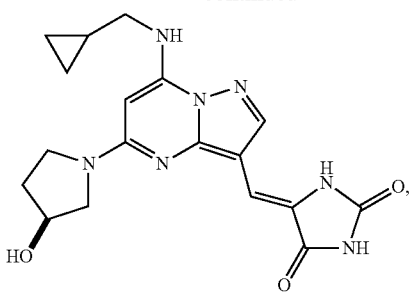
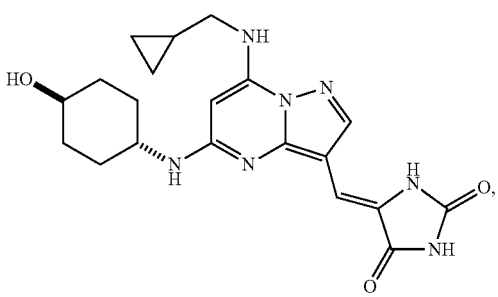
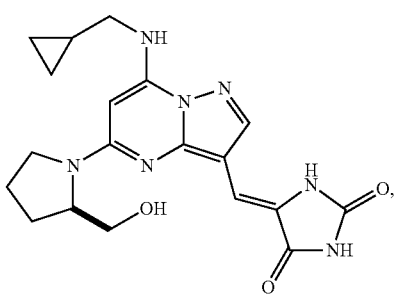
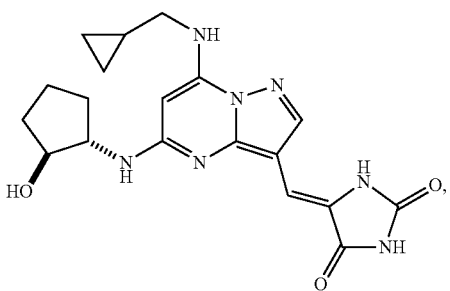
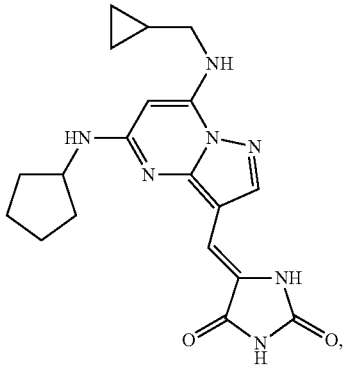

841
-continued
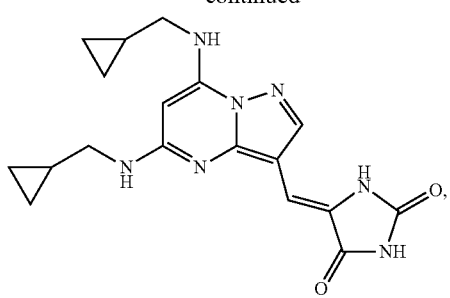
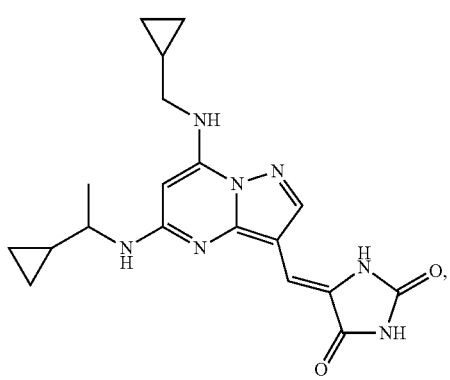
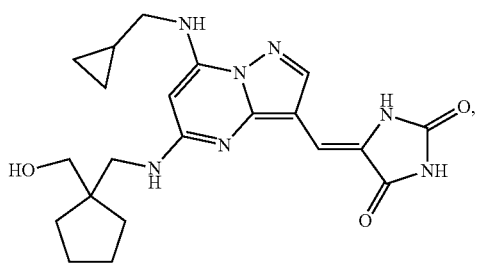
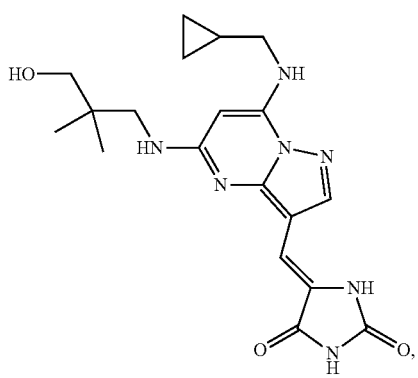
842
-continued
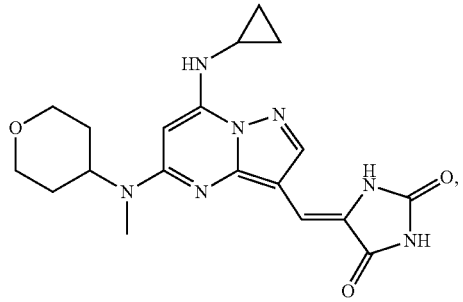
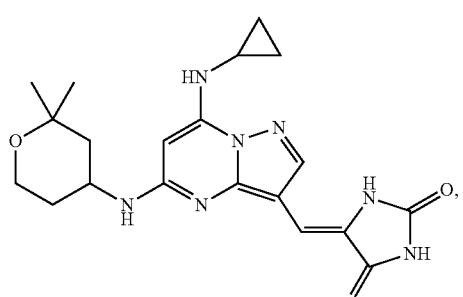
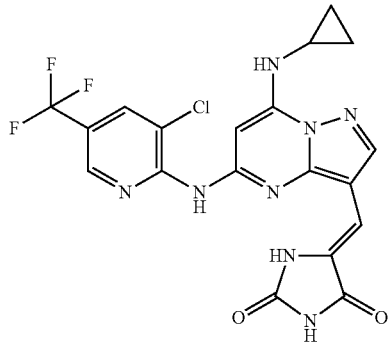
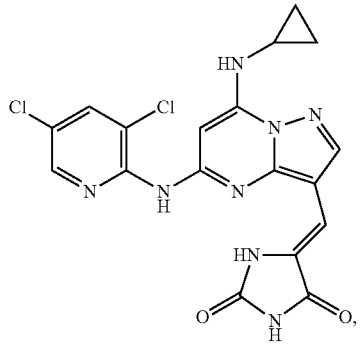
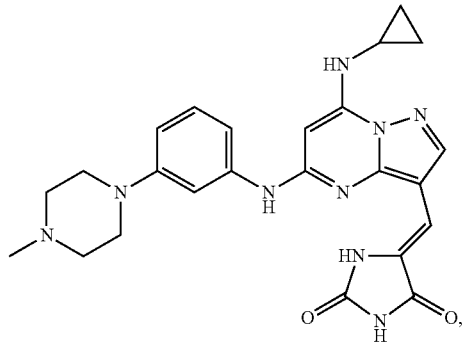
and -continued
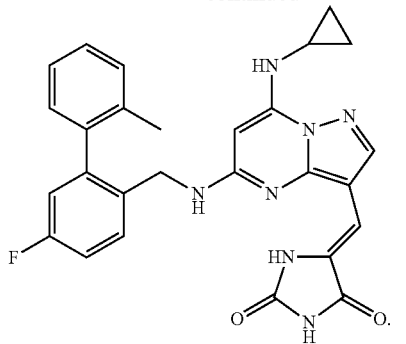
40. A pharmaceutical composition comprising
a compound of claim 1; and
at least one pharmaceutically acceptable excipient.
* * * * *